United States Patent
Cottrell et al.

(10) Patent No.: US 7,964,624 B1
(45) Date of Patent: *Jun. 21, 2011

(54) INHIBITORS OF SERINE PROTEASES

(75) Inventors: Kevin M. Cottrell, Cambridge, MA (US); John Maxwell, Hingham, MA (US); Qing Tang, Acton, MA (US); Anne-Laure Grillot, Somerville, MA (US); Arnaud Le Tiran, Lexington, MA (US); Emanuele Perola, Brookline, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 526 days.

This patent is subject to a terminal disclaimer.

(21) Appl. No.: 11/711,845

(22) Filed: Feb. 27, 2007

Related U.S. Application Data

(63) Continuation-in-part of application No. 11/511,109, filed on Aug. 28, 2006.

(60) Provisional application No. 60/711,530, filed on Aug. 26, 2005.

(51) Int. Cl.
| | |
|---|---|
| A61K 31/42 | (2006.01) |
| A61K 31/4245 | (2006.01) |
| A61K 31/4439 | (2006.01) |
| A61K 31/454 | (2006.01) |
| A61K 31/4725 | (2006.01) |
| C07D 498/10 | (2006.01) |
| C07D 261/04 | (2006.01) |
| C07D 413/04 | (2006.01) |

(52) U.S. Cl. ........ 514/378; 514/274; 514/256; 514/278; 548/240; 548/243; 548/244; 546/15; 546/209; 546/144; 546/272.1; 544/230; 544/333

(58) Field of Classification Search ................. 548/240, 548/243, 244; 514/378, 274, 256, 278; 546/15, 546/209, 144, 272.1; 544/230, 333
See application file for complete search history.

(56) References Cited

U.S. PATENT DOCUMENTS

| | | |
|---|---|---|
| 4,499,082 A | 2/1985 | Shenvi et al. |
| 4,720,484 A | 1/1988 | Vincent et al. |
| 4,880,780 A | 11/1989 | Trainor et al. |
| 5,053,519 A | 10/1991 | Teetz et al. |
| 5,231,084 A | 7/1993 | Hock et al. |
| 5,371,072 A | 12/1994 | Webb et al. |
| 5,384,410 A | 1/1995 | Kettner |
| 5,468,858 A | 11/1995 | Berlin et al. |
| 5,484,801 A | 1/1996 | Al-Razzak et al. |
| 5,496,927 A | 3/1996 | Kolb et al. |
| 5,502,061 A | 3/1996 | Hui et al. |
| 5,559,158 A | 9/1996 | Al-Razzak et al. |
| 5,610,193 A | 3/1997 | Al-Razzak et al. |
| 5,656,600 A | 8/1997 | Abelman et al. |
| 5,656,627 A | 8/1997 | Bemis et al. |
| 5,672,582 A | 9/1997 | Veber et al. |
| 5,716,929 A | 2/1998 | Bemis et al. |
| 5,725,878 A | 3/1998 | Al-Razzak et al. |
| 5,736,520 A | 4/1998 | Bey et al. |
| 5,756,466 A | 5/1998 | Bemis et al. |
| 5,760,029 A | 6/1998 | Jadhav et al. |
| 5,807,876 A | 9/1998 | Armistead et al. |
| 5,847,135 A | 12/1998 | Bemis et al. |
| 5,849,866 A | 12/1998 | Kolb |
| 5,861,267 A | 1/1999 | Su |
| 5,866,684 A | 2/1999 | Attwood et al. |
| 5,948,436 A | 9/1999 | Al-Razzak et al. |
| 5,973,111 A | 10/1999 | Bemis et al. |
| 5,990,276 A | 11/1999 | Zhang et al. |
| 6,018,020 A | 1/2000 | Attwood et al. |
| 6,025,147 A | 2/2000 | Bemis et al. |
| 6,025,516 A | 2/2000 | Ramaswamy et al. |
| 6,037,157 A | 3/2000 | Norbeck |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bemis et al. |
| 6,117,639 A | 9/2000 | Germann et al. |
| 6,130,315 A | 10/2000 | Kolb |
| 6,143,715 A | 11/2000 | Llinas-Brunet et al. |

(Continued)

FOREIGN PATENT DOCUMENTS

DE 3211676 10/1983

(Continued)

OTHER PUBLICATIONS

PCT International Search Report, PCT/US2006/033770, Feb. 15, 2007.

(Continued)

*Primary Examiner* — Jason M Nolan

(74) *Attorney, Agent, or Firm* — Honigman, Miller, Schwartz and Cohn; Kathryn D. Soulier; Jonathan P. O'Brien

(57) ABSTRACT

The present invention relates to compounds of formula (I):

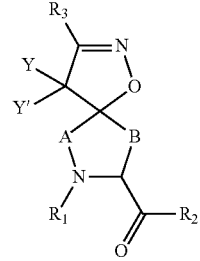

or a pharmaceutically acceptable salt thereof. These compounds inhibit serine protease, particularly the hepatitis C virus NS3-NS4A protease.

27 Claims, No Drawings

U.S. PATENT DOCUMENTS

| | | | |
|---|---|---|---|
| 6,153,579 | A | 11/2000 | Kim et al. |
| 6,172,077 | B1 | 1/2001 | Curtis et al. |
| 6,183,121 | B1 | 2/2001 | Kim et al. |
| 6,211,338 | B1 | 4/2001 | Malcolm et al. |
| 6,225,320 | B1 | 5/2001 | Kulagowski et al. |
| 6,251,583 | B1 | 6/2001 | Zhang et al. |
| 6,265,380 | B1 | 7/2001 | Tung et al. |
| 6,268,207 | B1 | 7/2001 | Bailey |
| 6,274,613 | B1 | 8/2001 | Plant et al. |
| 6,303,287 | B1 | 10/2001 | Kim et al. |
| 6,323,180 | B1 | 11/2001 | Llinas-Brunet et al. |
| 6,329,379 | B1 | 12/2001 | Llinas-Brunet et al. |
| 6,329,417 | B1 | 12/2001 | Llinas-Brunet et al. |
| 6,344,465 | B1 | 2/2002 | Armistead et al. |
| 6,348,608 | B1 | 2/2002 | Shi |
| 6,399,771 | B1 | 6/2002 | Plant et al. |
| 6,410,531 | B1 | 6/2002 | Llinas-Brunet et al. |
| 6,420,380 | B2 | 7/2002 | Llinas-Brunet et al. |
| 6,420,522 | B1 | 7/2002 | Bemis et al. |
| 6,498,178 | B2 | 12/2002 | Stamos et al. |
| 6,528,276 | B1 | 3/2003 | Germann et al. |
| 6,534,523 | B1 | 3/2003 | Llinas-Brunet et al. |
| 6,541,496 | B1 | 4/2003 | Armistead et al. |
| 6,548,555 | B1 | 4/2003 | Curatolo et al. |
| 6,608,027 | B1 | 8/2003 | Tsantrizos et al. |
| 6,608,067 | B1 | 8/2003 | Tung et al. |
| 6,617,309 | B2 | 9/2003 | Tung et al. |
| 6,653,127 | B1 | 11/2003 | Taremi et al. |
| 6,653,295 | B2 | 11/2003 | Glunz et al. |
| 6,699,855 | B2 | 3/2004 | Zhang et al. |
| 6,727,366 | B2 | 4/2004 | Han et al. |
| 6,767,991 | B1 | 7/2004 | Llinas-Brunet et al. |
| 6,774,212 | B2 | 8/2004 | Han |
| 6,800,434 | B2 | 10/2004 | Saksena et al. |
| 6,824,769 | B2 | 11/2004 | Chaturvedi et al. |
| 6,833,442 | B2 | 12/2004 | Shibasaki et al. |
| 6,838,475 | B2 | 1/2005 | Arasappan et al. |
| 6,846,802 | B2 | 1/2005 | Chen et al. |
| 6,846,806 | B2 | 1/2005 | Priestley |
| 6,867,284 | B1 | 3/2005 | Matassa et al. |
| 6,872,805 | B2 | 3/2005 | Campbell et al. |
| 6,909,000 | B2 | 6/2005 | Farmer et al. |
| 6,911,428 | B2 | 6/2005 | Zhu et al. |
| 6,914,122 | B2 | 7/2005 | Venkatraman et al. |
| 6,919,423 | B2 | 7/2005 | Llinas-Brunet |
| 6,939,692 | B2 | 9/2005 | Bathe et al. |
| 6,939,854 | B2 | 9/2005 | Priestley |
| 7,012,066 | B2 | 3/2006 | Saksena et al. |
| 7,034,178 | B2 | 4/2006 | Faber et al. |
| 7,091,184 | B2 | 8/2006 | Llinas-Brunet et al. |
| 7,105,302 | B2 | 9/2006 | Bathe et al. |
| 7,109,172 | B2 | 9/2006 | Britt et al. |
| 7,119,073 | B2 | 10/2006 | Colarusso et al. |
| 7,122,627 | B2 | 10/2006 | Priestley |
| 7,169,760 | B2 | 1/2007 | Saksena et al. |
| 7,208,600 | B2 | 4/2007 | Cottrell et al. |
| 7,241,796 | B2 | 7/2007 | Farmer et al. |
| 7,244,721 | B2 | 7/2007 | Saksena et al. |
| 7,250,520 | B2 | 7/2007 | Wallace |
| 7,273,885 | B2 | 9/2007 | Pitlik et al. |
| 7,288,624 | B2 | 10/2007 | Bemis et al. |
| 7,365,092 | B2 | 4/2008 | Cottrell et al. |
| 7,371,372 | B2 | 5/2008 | Chaturvedi et al. |
| 7,378,422 | B2 | 5/2008 | Perni et al. |
| 7,381,827 | B2 | 6/2008 | Tanoury et al. |
| 7,388,017 | B2 | 6/2008 | Tung et al. |
| 7,504,378 | B2 | 3/2009 | Llinas-Brunet et al. |
| 7,592,316 | B2 | 9/2009 | Njoroge et al. |
| 2002/0016294 | A1 | 2/2002 | Venkatraman et al. |
| 2002/0016442 | A1 | 2/2002 | Llinas-Brunet et al. |
| 2002/0032175 | A1 | 3/2002 | Tung et al. |
| 2002/0037998 | A1 | 3/2002 | Llinas-Brunet et al. |
| 2002/0042046 | A1 | 4/2002 | Kim et al. |
| 2002/0045729 | A1 | 4/2002 | Kerres et al. |
| 2002/0065248 | A1 | 5/2002 | Zhang et al. |
| 2002/0068702 | A1 | 6/2002 | Lim-Wilby et al. |
| 2002/0102235 | A1 | 8/2002 | Arasappan et al. |
| 2002/0107181 | A1 | 8/2002 | Chen et al. |
| 2002/0111378 | A1 | 8/2002 | Stamos et al. |
| 2002/0123468 | A1 | 9/2002 | Han |
| 2002/0142449 | A1 | 10/2002 | Kwong et al. |
| 2002/0147160 | A1 | 10/2002 | Bhat et al. |
| 2002/0160962 | A1 | 10/2002 | Saksena et al. |
| 2002/0177725 | A1 | 11/2002 | Priestley |
| 2002/0183249 | A1 | 12/2002 | Taylor et al. |
| 2002/0187488 | A1 | 12/2002 | Lin et al. |
| 2003/0008828 | A1 | 1/2003 | Priestley et al. |
| 2003/0036501 | A1 | 2/2003 | Saksena et al. |
| 2003/0064962 | A1 | 4/2003 | Glunz et al. |
| 2003/0068369 | A1 | 4/2003 | McAllister et al. |
| 2003/0083467 | A1 | 5/2003 | Germann et al. |
| 2003/0100768 | A1 | 5/2003 | Han et al. |
| 2003/0119752 | A1 | 6/2003 | Farmer et al. |
| 2003/0144257 | A1 | 7/2003 | Biggadike et al. |
| 2003/0153788 | A1 | 8/2003 | Kobayashi et al. |
| 2003/0181363 | A1 | 9/2003 | Llinas-Brunet et al. |
| 2003/0186895 | A1 | 10/2003 | Llinas-Brunet et al. |
| 2003/0186952 | A1 | 10/2003 | Crew et al. |
| 2003/0187018 | A1 | 10/2003 | Llinas-Brunet et al. |
| 2003/0191067 | A1 | 10/2003 | Llinas-Brunet et al. |
| 2003/0195362 | A1 | 10/2003 | Kempf et al. |
| 2003/0216325 | A1 | 11/2003 | Saksena et al. |
| 2003/0236242 | A1 | 12/2003 | Perni et al. |
| 2004/0006237 | A1 | 1/2004 | Dolitzky et al. |
| 2004/0018986 | A1 | 1/2004 | Pitlik et al. |
| 2004/0048774 | A1 | 3/2004 | Saunders et al. |
| 2004/0058982 | A1 | 3/2004 | Harris |
| 2004/0067901 | A1 | 4/2004 | Bhat et al. |
| 2004/0072788 | A1 | 4/2004 | Bhat et al. |
| 2004/0077600 | A1 | 4/2004 | Tung et al. |
| 2004/0082574 | A1 | 4/2004 | Wang et al. |
| 2004/0105820 | A1 | 6/2004 | Weers et al. |
| 2004/0110747 | A1 | 6/2004 | Altman |
| 2004/0142876 | A1 | 7/2004 | Colarusso et al. |
| 2004/0171626 | A1 | 9/2004 | Beaulieu et al. |
| 2004/0180815 | A1 | 9/2004 | Nakajima et al. |
| 2004/0186125 | A1 | 9/2004 | Poupart et al. |
| 2004/0224900 | A1 | 11/2004 | Bailey et al. |
| 2004/0229817 | A1 | 11/2004 | Duggal et al. |
| 2004/0229818 | A1 | 11/2004 | Llinas-Brunet |
| 2004/0266731 | A1 | 12/2004 | Tung et al. |
| 2005/0020503 | A1 | 1/2005 | Llinas-Brunet et al. |
| 2005/0049220 | A1 | 3/2005 | Stuyver et al. |
| 2005/0059606 | A1 | 3/2005 | Saksena et al. |
| 2005/0062522 | A1 | 3/2005 | Haider et al. |
| 2005/0080005 | A1 | 4/2005 | Llinas-Brunet et al. |
| 2005/0080017 | A1 | 4/2005 | Cottrell et al. |
| 2005/0090450 | A1 | 4/2005 | Farmer et al. |
| 2005/0107304 | A1 | 5/2005 | Britt et al. |
| 2005/0112093 | A1 | 5/2005 | Ette et al. |
| 2005/0119189 | A1 | 6/2005 | Cottrell et al. |
| 2005/0119318 | A1 | 6/2005 | Hudyma et al. |
| 2005/0120398 | A1 | 6/2005 | Kalkeri et al. |
| 2005/0136400 | A1 | 6/2005 | Lin et al. |
| 2005/0137139 | A1 | 6/2005 | Perni et al. |
| 2005/0153877 | A1 | 7/2005 | Miao et al. |
| 2005/0187165 | A1 | 8/2005 | Scola et al. |
| 2005/0187192 | A1 | 8/2005 | Fleming et al. |
| 2005/0192212 | A1 | 9/2005 | Llinas-Brunet et al. |
| 2005/0197299 | A1 | 9/2005 | Babine et al. |
| 2005/0197301 | A1 | 9/2005 | Njoroge et al. |
| 2005/0215486 | A1 | 9/2005 | Cottrell et al. |
| 2005/0222236 | A1 | 10/2005 | Tsantrizos et al. |
| 2005/0249702 | A1 | 11/2005 | Njoroge et al. |
| 2005/0287514 | A1 | 12/2005 | Byrn |
| 2006/0003317 | A1 | 1/2006 | Perni et al. |
| 2006/0003942 | A1 | 1/2006 | Tung et al. |
| 2006/0046956 | A1 | 3/2006 | Sannigrahi et al. |
| 2006/0089385 | A1 | 4/2006 | Cui et al. |
| 2006/0105978 | A1 | 5/2006 | Chu et al. |
| 2006/0205672 | A1 | 9/2006 | Saksena et al. |
| 2006/0211629 | A1 | 9/2006 | Britt et al. |
| 2007/0087973 | A1 | 4/2007 | Tanoury |
| 2007/0105781 | A1 | 5/2007 | Lyons et al. |
| 2007/0161789 | A1 | 7/2007 | Cottrell et al. |
| 2007/0179167 | A1 | 8/2007 | Cottrell et al. |
| 2007/0191381 | A1 | 8/2007 | Tung |

| | | |
|---|---|---|
| 2007/0212683 A1 | 9/2007 | Connelly |
| 2007/0218012 A1 | 9/2007 | Bittorf et al. |
| 2007/0218138 A1 | 9/2007 | Bittorf et al. |
| 2007/0225297 A1 | 9/2007 | Perni et al. |
| 2007/0231262 A1 | 10/2007 | Lin et al. |
| 2007/0243166 A1 | 10/2007 | Llinas-Brunet et al. |
| 2007/0244334 A1 | 10/2007 | Tanoury et al. |
| 2007/0292933 A1 | 12/2007 | Pitlik et al. |
| 2008/0045480 A1 | 2/2008 | Farmer et al. |
| 2008/0070972 A1 | 3/2008 | Kadiyala et al. |
| 2008/0125376 A1 | 5/2008 | Cottrell et al. |
| 2008/0167480 A1 | 7/2008 | Wallace |
| 2008/0267915 A1 | 10/2008 | Lin et al. |
| 2008/0311079 A1 | 12/2008 | Perni et al. |
| 2009/0022688 A1 | 1/2009 | Farmer et al. |
| 2009/0143312 A1 | 6/2009 | Tung et al. |
| 2009/0191555 A1 | 7/2009 | Lin et al. |
| 2009/0247468 A1 | 10/2009 | Bittorf et al. |

FOREIGN PATENT DOCUMENTS

| | | |
|---|---|---|
| EP | 0417721 | 3/1991 |
| EP | 0675112 | 10/1995 |
| JP | 09124691 | 5/1997 |
| WO | WO 92/12140 | 7/1992 |
| WO | WO 93/25574 | 12/1993 |
| WO | WO 94/14436 | 7/1994 |
| WO | WO 95/09614 | 7/1994 |
| WO | WO 95/07696 | 3/1995 |
| WO | WO 96/11697 | 4/1996 |
| WO | WO 97/17364 | 5/1997 |
| WO | WO 97/40028 | 10/1997 |
| WO | WO 97/43310 | 11/1997 |
| WO | WO 98/13365 | 4/1998 |
| WO | WO 98/17679 | 4/1998 |
| WO | WO 98/22496 | 5/1998 |
| WO | WO 98/40381 | 9/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/09558 | 2/2000 |
| WO | WO-0009543 A2 | 2/2000 |
| WO | WO 00/23421 | 4/2000 |
| WO | WO 00/31129 | 6/2000 |
| WO | WO 00/56331 | 9/2000 |
| WO | WO-0059929 | 10/2000 |
| WO | WO 01/02424 | 1/2001 |
| WO | WO 01/07407 | 2/2001 |
| WO | WO 01/32691 | 5/2001 |
| WO | WO 01/40262 | 6/2001 |
| WO | WO 01/40266 | 6/2001 |
| WO | WO 01/58929 | 8/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/07761 | 1/2002 |
| WO | WO 02/08187 | 1/2002 |
| WO | WO 02/08198 | 1/2002 |
| WO | WO 02/08244 | 1/2002 |
| WO | WO 02/08251 | 1/2002 |
| WO | WO 02/08256 | 1/2002 |
| WO | WO 00/09588 | 2/2002 |
| WO | WO 02/18369 | 3/2002 |
| WO | WO 02/48116 | 6/2002 |
| WO | WO 02/48157 | 6/2002 |
| WO | WO-0248172 | 6/2002 |
| WO | WO 02/060926 | 8/2002 |
| WO | WO 02/079234 | 10/2002 |
| WO | WO 03/003804 | 1/2003 |
| WO | WO 03/006490 | 1/2003 |
| WO | WO 03/020298 | 3/2003 |
| WO | WO 03/062228 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/087092 | 10/2003 |
| WO | WO 2004/026896 | 4/2004 |
| WO | WO 2004/030670 | 4/2004 |
| WO | WO 2004/032827 | 4/2004 |
| WO | WO 2004/037855 | 5/2004 |
| WO | WO 2004/039833 | 5/2004 |
| WO | WO 2004/072243 | 8/2004 |
| WO | WO 2004/089974 | 10/2004 |
| WO | WO 2004/092161 | 10/2004 |
| WO | WO 2004/093798 | 11/2004 |
| WO | WO 2004/094452 | 11/2004 |
| WO | WO 2004/103996 | 12/2004 |
| WO | WO 2004/113365 | 12/2004 |
| WO | WO 2005/007681 | 1/2005 |
| WO | WO 2005/010029 | 2/2005 |
| WO | WO 2005/021584 | 3/2005 |
| WO | WO 2005/028501 | 3/2005 |
| WO | WO 2005/028502 | 3/2005 |
| WO | WO 2005/030796 | 4/2005 |
| WO | WO 2005/035525 | 4/2005 |
| WO | WO 2005/037214 | 4/2005 |
| WO | WO 2005/037860 | 4/2005 |
| WO | WO 2005/042570 | 5/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/058821 | 6/2005 |
| WO | WO 2005/070955 | 8/2005 |
| WO | WO 2005/073195 | 8/2005 |
| WO | WO 2005/073216 | 8/2005 |
| WO | WO 2005/077969 | 8/2005 |
| WO | WO 2005/085242 | 9/2005 |
| WO | WO 2005/085275 | 9/2005 |
| WO | WO 2005/087721 | 9/2005 |
| WO | WO 2005/087725 | 9/2005 |
| WO | WO 2005/087731 | 9/2005 |
| WO | WO 2005/095403 | 10/2005 |
| WO | WO 2005 107745 | 11/2005 |
| WO | WO 2005/113581 | 12/2005 |
| WO | WO 2005/123076 | 12/2005 |
| WO | WO 2006/000085 | 1/2006 |
| WO | WO 2006/007448 | 1/2006 |
| WO | WO 2006/007700 | 1/2006 |
| WO | WO 2006/007708 | 1/2006 |
| WO | WO 2007/016589 | 2/2007 |
| WO | WO 2007/025307 | 3/2007 |
| WO | WO 2008/106058 | 9/2008 |

OTHER PUBLICATIONS

Cheng, Wei-Chieh, et al., *Journal of Organic Chemistry*, "Stereoselective Synthesis of unnatural Spiroisoxazolinoproline-Based Amino Acids and Derivatives," pp. 5673-5677 (2002).
Akahoshi, F., "Chymase Inhibitors and their Therapeutic Potential", Drugs of the Future, 27(8) (2002), pp. 765-770.
Anonymous, VPI internet press release Sep. 7, 2004.
Anonymous, newsrx internet article, May 31, 2004.
Arasappan, A., "Hepatitis C Virus NS3-4A Serine Protease Inhibitors: SAR of P'2 Moiety with Improved Potency", Bioorg. & Med. Chem. Let., vol. 15, (2005), pp. 4180-4184.
Bastos, M., "Inhibitors of Human Heart Chymase Based on a Peptide Library", Proc. Natl. Acad. Sci. USA, vol. 92 (1995), pp. 6738-6742.
Beak, P., "Complex Induced Proximity Effects: Enantioselective Syntheses Based on Asymmetric Deprotonations of N-Boc-Pyrrolidines", J. Amer. Chem. Soc., vol. 116 (1994), pp. 3231-3239.
Behrens, C., "Selective Transformations of 2,3-Epoxy Alcohols and Related Derivatives. Strategies for Nucleophilic Attack at Carbon-3 or Carbon-2", J. Org.Chem., vol. 50 (1985), pp. 5696-5704.
Bergmeier, S.C., "Synthesis of Bicyclic Proline Analogs Using a formal [3=2] Intramolecular Aziridine-Allylsilane Cycloaddition Reaction", Tetrahedron, vol. 55, No. 26 (1999), pp. 8025-8038.
Blair, W., "5th Antiviral Drug Discovery and Development Summit," Expert opinion on investigational drugs (2004), 13(8), pp. 1065-1069.
Blankley, C.J., "Synthesis and Structure-Activity Relationships of Potent New Abgiotensin Converting Enzyme Inhibitors Containing Saturated Bicyclic Amino Acids", J. Of Medicinal Chem., vol. 30 (1987).

Cacciola, J., "The Synthesis of Lysine a-Ketoamide Thrombin Inhibitors via an Epoxy Amide Ring Opening", Tetrahedron Let., vol. 38, No. 33 (1997), pp. 5741-5744.

Chawla, et al., "Challenges in Polymorphism of Pharmaceuticals", CRIPS vol. 5, No. 1, Jan.-Mar. 2004, 4 pages.

Chen, S., "Synthesis and Evaluation of Tripeptidyl a-Ketoamides as Human Rhinovirus 3C Protease Inhibitors", Bioorg. & Med. Chem. Letters, vol. 13, No. 20 (2003), pp. 3531-3536.

Chen, S., "Discovery of Small-Molecule Inhibitors of HCV NS3-4A Protease as Potential Therapeutic Agents against HCV Infection," Current Medicinal Chemistry (2005), 12(20), pp. 2317-2342.

Chen, S., "P1 and P1' Optimization of [3,4]-Bicycloproline P2 Incorporated Tetrapeptidyl a-ketoamide Based HCV Protease Inhibitors," Letters in Drug Design and Discovery (2005), 2(2), pp. 118-123.

Collado, I., "Stereocontrolled Synthesis of 4-Substituted (±)-Kainic Acids", Journal of Organic Chem., vol. 63 (1998).

Davis, G. "Future Options for the Management of Hepatitis C", Seminars in Liver Disease, vol. 19, Supp. 1 (1999), pp. 103-112.

Dixon, S. M., "A Spiroisoazolinoproline-based Amino Acid Scaffold for Solid Phase and One-Bead—One-Compound Library Synthesis" Journal of Combinatorial Chemistry, 9 (2007) pp. 143-157.

Dunsdon, R., "Solid Phase Synthesis of Aminoboronic Acids: Potent Inhibitors of the Hepatitis C Virus NS3 Proteinase", Bioorganic & Medicinal Chemistry Letters, 10 (2000), pp. 1577-1579.

Elemes, Synthesis of enantiopure a-deuteriated Boc-L-amino acids, J. Chem. Soc., Perkin Trans., vol. 1 (1995), pp. 537-540.

Esch, P.M., "Reductive Cyclization of Carbon-Centered Glycine Radicals; A Novel Synthetic route to Cyclic a-Amino Acids", Tetrahedron, vol. 48, No. 22 (1992), pp. 4659-4676.

Farmer, L., "Inhibitors of Hepatitis C Virus NS3-4A Protease: P2 Proline Variants," Letters in Drug Design and Discovery (2005), 2, pp. 497-502.

Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.

Gallagher, D., "Complex-Induced Proximity Effects: Evidence for a Prelithiation Complex and a Rate-Determining Deprotonation in the Asymmetric Lithiation of Boc-Pyrrolidine by an -PrLi/(-) Sparteine Complex", J. Org. Chem., vol. 60 (1995), pp. 7092-7093.

Gallagher, D., "Chiral Organolithium Complexes: The Effect of Ligand Structure on the Enantioselective Deprotonation of Boc-Pyrrolidine", J. Org. Chem., vol. 60 (1995), pp. 8148-8154.

Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(1H-Imidazol-1-yl)benzoyl]-7-isopropyl-3,7-diazabicyclo[3.3.1]nonane Dihydroperchlorate", J. Med. Chem, vol. 39, No. 13 (1996), pp. 2559-2570.

Golina, S., "Vulcanisation of Poly(diethyl-n-butylamino) Phosphazenes", Internat'l Polymer Science & Tech., vol. 18, No. 3 (1991), pp. T20-T22.

Han, W., "a-Ketoamides, a-Ketoesters and a-Diketones as HCV NS3 Protease Inhibitors", Bioorganic & Medicinal Chemistry Letters 10 (2000), pp. 711-713.

Janssen, H.L.A., "Suicide Associated with Alfa-Interferon Therapy for Chronic Viral Hepatitis", J. Hepatol., 21 (1994), pp. 241-243.

Johansson, A., "Acyl Sulfonamides as Potent Protease Inhibitors of the Hepatitis C Virus Full-Length NS3 (Protease-Helicase/NTPase): A comparative Study of Different C-Terminals", Bioorganic & Medicinal Chemistry, 11 (2003), pp. 2551-2568.

Johansson, P., "Potent inhibitors of the hepatitis C virus NS3 protease: Use of a novel P2 cyclopentane-derived template," Bioorganic & Medicinal Chemistry (2006), 14, pp. 5136-5151.

Kakei, H., "Catalytic Asymmetric Epoxidation of a, β-Unsaturated Esters Using an Yttrium-Biphenyldiol Complex", J. Am. Chem. Soc., vol. 127 (2005), pp. 8962-8963.

Kalkeri, G., "Expression of HCV Protease in the Liver of Mice Results in Liver Injury Which can be Inhibited by VX-950, A Vertex HCV Protease Inhibitor," AALSD Abstracts, Hepatology (2004), 40(1), pp. 281A.

Kamandi, E., "Die Synthese von β-Phenyl-Isoserinen Durch Ammonolyse von β-Phenyl-Glycidestern, I.", Archiv de Pharmazie, vol. 307 No. 11 (1974), pp. 871-878.

Kao, J.H., "Efficacy of Consensus Interferon in the Treatment of Chronic Hepatitis", J. Gastroenterol. Hepatol, 15 (2000), pp. 1418-1423.

Kieffer, Genetic Heterogeneity in the HCV Ns3 Protease of Untreated Genotype 1 Patients Has Little Effect on the Sensitivity of the VX-950, 12th Internat'l Conf. on Hep. C Virus and Related Viruses, Montreal, Canada, Oct. 2-6, 2005.

Kieffer, T., "Genetic Heterogeneity in the HCV NS3 Protease of Untreated Genotype 1 Patients has Little Effect on the Sensitivity to VX-950", Hepatol, vol. 42 (2005), p. 537A.

Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.

Kieffer, T., "Combination of Telaprevir (VX-950) and Peg-Ifn-Alfa Suppresses both Wild-Type Virus and Resistance Variants in HCV Genotype 1-Infected Patients in a 14-Day Phase 1B Study", Hepatol. 44, Supp.2 (2006), p. 222A.

Kerrick, S., "Asymmetric Deprotonations: Enantioselective Syntheses of 2-Substituted (tert-Butoxycarbonyl) pyrrolldines", J. Amer. Chem. Soc., vol. 113 (1991), pp. 9703-9710.

Kim, J., "Hepatitis C Virus NS3 RNA Helicase Domain with a bound Oligonucleotide: The Crystal Structure Provides Insights into the Mode of Unwinding", Structure, vol. 6, No. 1, (1998), pp. 89-100.

Kim, J., "Crystal structure of the hepatitis C virus NS3 protease domain complexed with a synthetic NS4A cofactor peptide," Cell, vol. 87, 1996, pp. 343-355 [and Kim, J. "Erratum," Cell, vol. 89, No. 1 (1997), p. 159.

Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.

Reesink, H., "Final Results of a Phase 1B, Multiple-Dose Study of VX-950, a Hepatitis C Virus Protease Inhibitor", Hepatology, vol. 42, No. 4, Supp. 1 (2005), pp. 234A-235A.

Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.

Renault, P.F., "Side Effects of Alpha Interferon", Seminars in Liver disease, 9 (1989), pp. 273-277.

Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.

Sagnard, I., "Enantioselective Synthesis of Cyclopropane a-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-3152.

Schneider, "Enhanced Plasma Concentration by Selective Deuteration of Rofecoxib in Rats", Arzneim.-Forsch.,Drug Res., vol. 56, No. 4, (2006), pp. 295-300.

Taber, D., "Asymmetric Nucleophillic Epoxidation", Org. Chem. Highlights, (2004).

Takamizawa, A., "Structure and Organization of the Hepatitis C Virus Genome Isolated from Human Carriers", J. Virol., 65 (1991), pp. 1105-1113.

Taliani, M., "A continuous Assay of Hepatitis C Virus Protease Based on Resonance Energy Transfer Depsipeptide Substrates", Anal. Biochem., vol. 240 (1996), pp. 60-67.

Tan, S., "Strategies for Hepatitis C Therapeutic Intervention: Now and Next", Current Op. in Pharmacology, vol. 4, No. 5 (2004), pp. 465-470.

Tazulakhova, E.B., "Russian Experience in Screening, Analysis and Clinical Application of Novel Interferon Inducers", J. Interferon Cytokine Res., 21 (2001), pp. 65-73.

Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.

Toom, L., "Microwave-Assisted Raney Nickel Reduction of Bispidinone Thioketals to N,N'-Dialkylbispidines", Synthesis, vol. 12 (2006), pp. 2064-2068.

Udding, J.H., "Transition Metal-Catalyzed Chlorine Transfer Cyclizations of Carbon-Centered Glycine Radicals; A Novel Synthetic Route to Cyclic a-Amino Acids", Tetrahedron, vol. 50, No. 6 (1994), pp. 1907-1918.

Victor, F. "P1 and P3 optimization of novel bicycloproline P2 bearing tetrapeptidyl alpha-ketoamide based HCV protease inhibitors", Bioorganic & Medicinal Chemistry Letters, 14 (2004) pp. 257-261.

Vishweshwar, P., "Pharmaceutical Co-Crystals", J. Pharm. Sci., vol. 95, No. 3 (2006), pp. 499-516.

Walker, M.A., "Hepatitis C Virus: An Overview of Current Approaches and Progress", DDT, 4 (1999), pp. 518-529.

Wang, Z., "Asymmetric Epoxidation of trans-β-Methylstyrene and 1-Phenylcyclohexene Using a D-Fructose-Derived. Ketone: (R,R)-trans-β-Methylstyrene Oxide and (R,R)-1-Phenylcyclohexene Oxide", Org. Syntheses, vol. 80 (2003), p. 9.

Weiland, O., "Interferon Therapy in Chronic Hepatitis C Virus Infection", FEMS Microiol. Rev., 14 (1994), pp. 279-288.

White, P.W. "Blunting the Swiss Army Knife of Hepatitis C Virus: Inhibitors of NS3/4A Protease" Progress in Medicinal Chemistry 44 (2006), pp. 65-107.

Yao, N., "Molecular views of viral polyprotein processing revealed by the crystal structure of the hepatitis C virus bifunctional protease-helicase," Structure (1999), 7, pp. 1353-1363.

Yasuda, M., "Synthesis of Conformationally Defined Glutamic Acid Analogues from Readily Available Diels-Alder Adducts", Chem. and Pharm. Bulletin (1995).

Yip, Y., "Discovery of a Novel Bicycloproline P2 Bearing Peptidyl a-Ketoamide LY514962 as HCV Protease Inhibitor", Bio. & Med. Chem. Let., vol. 14, No. 1 (2005), pp. 251-256.

Yip, Y., "P4 and P1' Optimization of Bicycloproline P2 Bearing Tetrapeptidyl a-Ketoamides as HCV Protease Inhibitors", Bio. & Med. Chem. Let., vol. 14, No. 9 (2004), pp. 5007-5011.

Yun, C. "Oxidation of the antihistaminic drug terfenadine in human liver microsomes: Role of Cytochrome P-450 3A(4) in N-dealkylation and C-hydroxylation", Drug metabolism and Disposition, 21(3) (1993) pp. 403-409.

PCT ISR PCT/US07/64294 dated Nov. 16, 2007.
PCT ISR for PCT/US01/26008, Feb. 5, 2002.
PCT ISR for PCT/US05/039240, Dec. 6, 2006.
ISR dated Dec. 27, 2007 from PCT/US2006/032481.
ISR dated Jul. 23, 2007 from PCT/US2007/006320.
ISR dated Aug. 3, 2001 from PCT/US2007/004995.
ISR dated Jan. 16, 2009 from PCT/US2008/002395.
ISR for PCT US 2008 002541, Jul. 7, 2008.

Kwong, A.D., "Structure and Function of Hepatitis C Virus NS3 Helicase", Top Microbiol. Immunol., vol. 242, (2000), pp. 171-196.

Kwong, A.D., "Erratum to 'Hepatitis C Virus NS3/4A Protease' [Antiviral Res. 41 (1998) 1-18]", Antiviral Res., vol. 41 (1999), pp. 1-18.

Kwong, A.D., "Hepatitis C Virus NS3/4A Protease", Antiviral Res., vol. 41 (1999), pp. 67-84.

Kwong, A.D., "An Orally Bioavailable Inhibitor of the HCV NS3-4a Protease; a Potential HCV Therapeutic", 5th Antivir. Drug Disc. and Devel. Summit, (2004).

Kwong, HCV Protease Inhibitors: Activity and Resistance, 13th Conference on Retroviruses and Opp. Infections (CROI), Denver, Co, Feb. 5-8, 2006.

Kwong, A.D., "Beyond Interferon and Ribavirin: Antiviral Therapies for Hepatitis C Virus", Drug Disc. Today: Ther. Strategies, vol. 3 (2006), pp. 211-220.

Kwong, A.D., "A Novel Hepatitis C Protease Inhibitor", HepDART (2005).

Lamar, J., "Novel P4 Truncated Tripeptidyl a-ketoamides as HCV Protease Inhibitors", Bio. & Med. Chem. Let, vol. 14 No. 1 (2004), pp. 263-266.

Landro, J.A. "Mechanistic Role of an NS4A Peptide Cofactor with the Truncated NS3 Protease of Hepatitis C Virus: Elucidation of the NS4A Stimulatory Effect via Kintetic Analysis and Inhibitor Mapping", Biochemistry, 36 (1997) pp. 9340-9348.

Laplante, S., "NMR Line-Broadening and Transferred NOESY as a Medicinal Chemistry Tool for Studying Inhibitors of the Hepatitis C Virus NS3 Protease Domain", Bioorganic & Medicinal Chemistry Letters, 10 (2000), pp. 2271-2274.

Lavanchy, D., "Global Surveillance and control of Hepatitis C", J. Viral Hepatitis, 6 (1999), pp. 35-47.

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Internat'l Symposium on Viral Hep. and Liver Dis., (2006).

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol., vol. 131, No. 3 (2006), pp. 950-951.

Lehmann, Über die chemischen and biologischen Eigenschaften einiger a-Aminoketone, Helvetica Chimica Acta., vol. 33 (1950), pp. 1217-1226.

Lin, C., "Structure-Based Mutagenesis Study of Hepatitis C Virus NS3 Helicase", J. Virol., vol. 73, No. 10 (1999), pp. 8798-8807.

Lin, K., "Combination of a Hepatitis C Virus NS3-NS4A Protease Inhibitor and Alph Interferon Synergistically Inhibits Viral RNA Replication and Facilitates Viral RNA Clearance in Replicon Cells", Antimicrob. Agents Chemo, vol. 48 (2004), pp. 4784-4792.

Lin, K., "VX-950, a Novel Hepatitis C Virus (HCV) NS3-4A Protease Inhibitor, Exhibits Potent Antiviral Activities in HCV Replicon Cells", Antimicrob. Agents Chemo, vol. 50, No. 5 (2006), pp. 1813-1822.

Lin, K., "Vx-950: A Tight-Binding HCV Protease Inhibitor with a Superior Sustained Inhibitory Response in HCV Replicon Cells", Hepatol, vol. 38 (2003), p. 222A.

Lin, C., "Discovery and Development of VX-950, a Novel, Covalent and Reversible Inhibitor of Hepatitis C Virus NS3-4A Serine Protease", Infect. disord. Drug Targets, vol. 6, No, 1 (2006), pp. 3-16.

Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.

Llinàs-Brunet, M., "Highly Potent and Selective Peptide-Based Inhibitors of the Hepatitis C Virus Serine Protease: Towards Smaller Inhibitors", Bioorganic & Medicinal Chemistry Letters, 10 (2000), pp. 2267-2270.

Llinàs-Brunet, M., "Peptide-Based Inhibitors of the Hepatitis C Virus Serine Protease", Bioorganic & Medicinal Chemistry Letters, 8 (1998), pp. 1713-1718.

Llinàs-Brunet, M., "Studies on the C-Terminal of Hexapeptide Inhibitors of the Hepatitis C virus Serine Protease", Bioorganic & Medicinal Chemistry Letters, 8 (1998), 2719-2724.

Lohmann, F. "Replication of Subgenomic Hepatitis C Virus RNAs in a Hepatoma Cell Line", Science, 285.5454 (1999) p. 110.

Marigo, M., "Asymmetric Organocatalytic Epoxidation of a,β-Unsaturated Aldehydes with Hydrogen Peroxide", J. Am. Chem. Soc., vol. 127, No. 19 (2005), pp. 6964-6965.

Markland, W., "Broad-Sprectrum Antiviral Activity of the IMP Dehydrogenase Inhibitor VX-497: a Comparison with Ribavirin and Demonstration of Antiviral Additivity with Alph Interferon", Antimicrob. Ag. Chem. (2004), vol. 44, No. 4.

McLaren, R., "Infrared observations of circumstellar ammonia in OH/IR supergiants," Astrophysical Journal (1980), 240(3, Pt. 2), pp. L159-L163.

Mehdi, The Inbibition of Human Neutrophil Elastase and Cathepsin G by Peptidyl 1,2-Dicarbonyl Derivatives, Biochem & Biophys. Res. Comm., vol. 166, No. 2 (1990), pp. 595-660.

Monn, J., "A Concise, Stereocontrolled Thiazolium Ylide Approach to Kainic Acid", J. Organic Chem., vol. 59, No. 10 (1994), pp. 2773-2778.

Moradpour, D., "Current and Evolving Therapies for Hepatitis C", Eur. J. Gastroenterol. Hepatol., vol. 11 (1999), pp. 1199-1202.

Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Virol., vol. 71, No. 5 (1997), pp. 3767-3775.

Newman, A., "Solid-state Analysis of the Active Pharmaceutical Ingredient in Drug Products", vol. 8, No. 19 (2003), pp. 898-905.

Patent Abstracts of Japan, vol. 1997, No. 9, Sep. 30, 1997.

Perni, R., "NS3-4A Protease as a Target for Interfering with Hepatitis C Virus Replication", Drug News Perspect., vol. 13, No. 2 (2000), pp. 69-77.

Perni, R.B., "Inhibitors of Hepatitis C Virus NS3-4A Protease 1. Non-Charged Tetrapeptide Variants", Bioorganic & Medicinal Chemistry Letters, 13 (2003), pp. 4059-4063.

Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.

Perni, R., "VX-950: The Discovery of an Inhibitor of the Hepatitis C NS3-4A Protease and a Potential Hepatitis C Virus Therapeutic", Hepatology, vol. 38 (2003) p. 624A.

Perni, R.B., "Inhibitors of Hepatitis C Virus NS3-4A Protease 2. Warhead SAR and Optimization", Bioorganic & Medicinal Chemistry Letters, 14 (2004), pp. 1441-1446.

Perni, R.B., "Inhibitors of Hepatitis C Virus NS3-4A Part 3: P2 Proline Variants", Bioorganic & Medicinal Chemistry Letters, 14 (2004), pp. 1939-1942.

Perni, R., "The Design of Inhibitors of the HCV NS3-4A Protease: The Identification of a Clinical Development Candidate, VX-950," ACS National Medicinal Chemistry Symposium, Madison, WI, Jun. 2004 (2004).

Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.

Perni, R., "Toward Smaller HCV NS3-4A Protease Inhibitors: 3-Substituted Proline-based Tripeptide Scaffolds," Abstracts of Papers, 229th ACS National Meeting, San Diego, CA, United States, Mar. 13-17, 2005 (2005), MEDI-350.

Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.

Pippel, D., "Complex-Induced Proximity Effects: Steroselective Carbon-Carbon Bond Formation in Chiral Auxiliary Mediated β-Lithiation-Substitution Sequences of β-Substituted Secondary Carboxamides", J. Org. Chem., vol. 63 (1998), pp. 2-3.

Poliakov, A., "Structure-Activity Relationships for the Selectivity of Hepatitis C Virus NS3 Protease Inhibitors", ,Biochimica et Biophysica Acta, 1672 (2004), pp. 51-59.

Ramachandran, R., "Anti-Viral Activity of VX-950 Resolves Expression of an HCV-Associated Gene Signature", J. Hepatol, vol. 44, Supp. 2 (2006), p. S223.

Reesink, H., "Initial Results of a Phase 1B, Multiple-Dose Study of VX-950, a Hepatitis C Virus Protease Inhibitor", Gastroent., vol. 128, No. 4, Supp. 2 (2005), pp. A696-A697.

Reesink, H., "Rapid Decline of Viral RNA in Hepatitis C Patients Treated with VX-950: A Phase Ib, Placebo-Controlled Randomized Study", Gastroenterol., vol. 131, No. 4 (2006), pp. 997-1002.

SEQUENCE LISTING

<160> NUMBER OF SEQ ID NOS: 6

<210> SEQ ID NO 1
<211> LENGTH: 695
<212> TYPE: PRT
<213> ORGANISM: Hepatitis C virus
<220> FEATURE:
<221> NAME/KEY: MISC_FEATURE
<222> LOCATION: (1)..(10)
<223> OTHER INFORMATION: Histidine tag

<400> SEQUENCE: 1

Met Ser His His His His His Ala Met Ala Pro Ile Thr Ala Tyr
1               5                   10                  15

Ala Gln Gln Thr Arg Gly Leu Leu Gly Cys Ile Ile Thr Ser Leu Thr

```
              20                  25                  30
Gly Arg Asp Lys Asn Gln Val Glu Gly Glu Val Gln Ile Val Ser Thr
             35                  40                  45
Ala Thr Gln Thr Phe Leu Ala Thr Cys Ile Asn Gly Val Cys Trp Thr
             50                  55                  60
Val Tyr His Gly Ala Gly Thr Arg Thr Ile Ala Ser Pro Lys Gly Pro
65                  70                  75                  80
Val Ile Gln Met Tyr Thr Asn Val Asp Gln Asp Leu Val Gly Trp Pro
                 85                  90                  95
Ala Pro Gln Gly Ser Arg Ser Leu Thr Pro Cys Thr Cys Gly Ser Ser
                100                 105                 110
Asp Leu Tyr Leu Val Thr Arg His Ala Asp Val Ile Pro Val Arg Arg
                115                 120                 125
Arg Gly Asp Ser Arg Gly Ser Leu Leu Ser Pro Arg Pro Ile Ser Tyr
            130                 135                 140
Leu Lys Gly Ser Ser Gly Gly Pro Leu Leu Cys Pro Ala Gly His Ala
145                 150                 155                 160
Val Gly Leu Phe Arg Ala Ala Val Cys Thr Arg Gly Val Thr Lys Ala
                165                 170                 175
Val Asp Phe Ile Pro Val Glu Asn Leu Glu Thr Thr Met Arg Ser Pro
                180                 185                 190
Val Phe Thr Asp Asn Ser Ser Pro Pro Ala Val Pro Gln Ser Phe Gln
                195                 200                 205
Val Ala His Leu His Ala Pro Thr Gly Ser Gly Lys Ser Thr Lys Val
                210                 215                 220
Pro Ala Ala Tyr Ala Ala Gln Gly Tyr Lys Val Leu Val Leu Asn Pro
225                 230                 235                 240
Ser Val Ala Ala Thr Leu Gly Phe Gly Ala Tyr Met Ser Lys Ala His
                245                 250                 255
Gly Val Asp Pro Asn Ile Arg Thr Gly Val Arg Thr Ile Thr Thr Gly
                260                 265                 270
Ser Pro Ile Thr Tyr Ser Thr Tyr Gly Lys Phe Leu Ala Asp Gly Gly
                275                 280                 285
Cys Ser Gly Gly Ala Tyr Asp Ile Ile Ile Cys Asp Glu Cys His Ser
                290                 295                 300
Thr Asp Ala Thr Ser Ile Leu Gly Ile Gly Thr Val Leu Asp Gln Ala
305                 310                 315                 320
Glu Thr Ala Gly Ala Arg Leu Val Val Leu Ala Thr Ala Thr Pro Pro
                325                 330                 335
Gly Ser Val Thr Val Ser His Pro Asn Ile Glu Glu Val Ala Leu Ser
                340                 345                 350
Thr Thr Gly Glu Ile Pro Phe Tyr Gly Lys Ala Ile Pro Leu Glu Val
            355                 360                 365
Ile Lys Gly Gly Arg His Leu Ile Phe Cys His Ser Lys Lys Lys Cys
            370                 375                 380
Asp Glu Leu Ala Ala Lys Leu Val Ala Leu Gly Ile Asn Ala Val Ala
385                 390                 395                 400
Tyr Tyr Arg Gly Leu Asp Val Ser Val Ile Pro Thr Asn Gly Asp Val
                405                 410                 415
Val Val Val Ser Thr Asp Ala Leu Met Thr Gly Phe Thr Gly Asp Phe
                420                 425                 430
Asp Ser Val Ile Asp Cys Asn Thr Cys Val Thr Gln Thr Val Asp Phe
                435                 440                 445
```

```
Ser Leu Asp Pro Thr Phe Thr Ile Glu Thr Thr Leu Pro Gln Asp
    450                 455                 460

Ala Val Ser Arg Thr Gln Arg Arg Gly Arg Thr Gly Arg Gly Lys Pro
465                 470                 475                 480

Gly Ile Tyr Arg Phe Val Ala Pro Gly Glu Arg Pro Ser Gly Met Phe
                485                 490                 495

Asp Ser Ser Val Leu Cys Glu Cys Tyr Asp Ala Gly Cys Ala Trp Tyr
            500                 505                 510

Glu Leu Met Pro Ala Glu Thr Thr Val Arg Leu Arg Ala Tyr Met Asn
        515                 520                 525

Thr Pro Gly Leu Pro Val Cys Gln Asp His Leu Glu Phe Trp Glu Gly
    530                 535                 540

Val Phe Thr Gly Leu Thr His Ile Asp Ala His Phe Leu Ser Gln Thr
545                 550                 555                 560

Lys Gln Ser Gly Glu Asn Phe Pro Tyr Leu Val Ala Tyr Gln Ala Thr
                565                 570                 575

Val Cys Ala Arg Ala Gln Ala Pro Pro Pro Ser Trp Asp Gln Met Trp
            580                 585                 590

Lys Cys Leu Ile Arg Leu Lys Pro Thr Leu His Gly Pro Thr Pro Leu
        595                 600                 605

Leu Tyr Arg Leu Gly Ala Val Gln Asn Glu Val Thr Leu Thr His Pro
    610                 615                 620

Ile Thr Lys Tyr Ile Met Thr Cys Met Ser Ala Asp Leu Glu Val Val
625                 630                 635                 640

Thr Ser Thr Trp Val Leu Val Gly Gly Val Leu Ala Ala Leu Ala Ala
                645                 650                 655

Tyr Cys Leu Ser Thr Gly Cys Val Val Ile Val Gly Arg Ile Val Leu
            660                 665                 670

Ser Gly Lys Pro Ala Ile Ile Pro Asp Arg Glu Val Leu Tyr Gln Glu
        675                 680                 685

Phe Asp Glu Met Glu Glu Cys
    690                 695

<210> SEQ ID NO 2
<211> LENGTH: 10
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: (alpha) aminobutyric acid

<400> SEQUENCE: 2

Glu Asp Val Val Xaa Cys Ser Met Ser Tyr
1               5                   10

<210> SEQ ID NO 3
<211> LENGTH: 16
<212> TYPE: PRT
<213> ORGANISM: Artificial
<220> FEATURE:
<223> OTHER INFORMATION: Synthetically generated peptide

<400> SEQUENCE: 3

Lys Lys Gly Ser Val Val Ile Val Gly Arg Ile Val Leu Ser Gly Lys
1               5                   10                  15

<210> SEQ ID NO 4
```

-continued

```
<211> LENGTH: 23
<212> TYPE: PRT
<213> ORGANISM: Artificial
<220> FEATURE:
<223> OTHER INFORMATION: Synthetically generated peptide

<400> SEQUENCE: 4

Lys Lys Gly Ser Val Val Ile Val Gly Arg Ile Val Leu Ser Gly Lys
1               5                   10                  15

Pro Ala Ile Ile Pro Lys Lys
            20

<210> SEQ ID NO 5
<211> LENGTH: 15
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: (alpha) aminobutyric acid
<220> FEATURE:
<221> NAME/KEY: MOD_RES
<222> LOCATION: (12)..(12)
<223> OTHER INFORMATION: Asp(EDANS)

<400> SEQUENCE: 5

Glu Asp Val Val Xaa Cys Ser Met Ser Tyr Thr Asp Lys Lys Lys
1               5                   10                  15

<210> SEQ ID NO 6
<211> LENGTH: 14
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: FITC-2-aminohexanoic acid
<220> FEATURE:
<221> NAME/KEY: MOD_RES
<222> LOCATION: (6)..(6)
<223> OTHER INFORMATION: (alpha) aminobutyric acid

<400> SEQUENCE: 6

Xaa Glu Asp Val Val Xaa Cys Ser Met Ser Tyr Thr Lys Lys
1               5                   10
```

INHIBITORS OF SERINE PROTEASES

CROSS-REFERENCE

This application is a continuation-in-part of U.S. patent application Ser. No. 11/511,109 filed on Aug. 28, 2006, which claims the benefit of U.S. provisional Patent Application No. 60/711,530, filed on Aug. 26, 2005, both of which are hereby incorporated by reference.

FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States," Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently HCV NS3 serine protease is also an attractive target for drug discovery.

There are not currently any satisfactory anti-HCV agents or treatments. Until recently, the only established therapy for HCV disease was interferon treatment. However, interferons have significant side effects [M. A. Walker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (≈25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

This invention relates to compounds of formula (I)

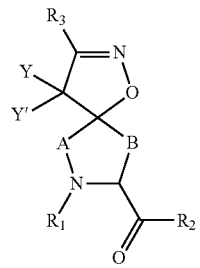

or a pharmaceutically acceptable salt thereof wherein, each A is $—(CX_1X_2)_a—$;
each B is $—(CX_1X_2)_b—$;
each $X_1$ is independently hydrogen, halo, amino, sulfanyl, optionally substituted aliphatic, optionally substituted aryl, or $—O—X_{1A}$;
each $X_2$ is independently hydrogen, halo, amino, sulfanyl, optionally substituted aliphatic, optionally substituted aryl, or $—O—X_{1B}$;
$X_{1A}$ and $X_{1B}$ are each independently an optionally substituted aliphatic, an optionally substituted cycloaliphatic, an optionally substituted heterocycloaliphatic, an optionally substituted aryl, or an optionally substituted heteroaryl;
or, $X_1$ and $X_2$ together form an oxo group;
each $R_1$ is $—Z^AR_4$, wherein each $Z^A$ is independently a bond or an optionally substituted aliphatic wherein up to three carbon units of $Z^A$ are optionally and independently replaced by $—C(O)—$, $—C(S)—$, $—C(O)NR^A—$, $—C(O)NR^ANR^A—$, $—C(O)O—$, $—NR^AC(O)O—$, $—O—$, $—NR^AC(O)NR^A—$, $—NR^ANR^A—$, $—S—$, $—SO—$, $—SO_2—$, $—NR^A—$, $—SO_2NR^A—$, or $—NR^ASO_2NR^A—$ provided that $—NR^ANR^A—$, $—NR^AC(O)NR^A—$, or $—NR^ASO_2NR^A—$ is not directly bound to the nitrogen ring atom of formula (I);
each $R_4$ is independently $R^A$, halo, $—OH$, $—CN$, $—NO_2$, $—NH_2$, or $—OCF_3$;
each $R^A$ is independently hydrogen, an optionally substituted aliphatic, an optionally substituted cycloaliphatic, an optionally substituted heterocycloaliphatic, an optionally substituted aryl, or an optionally substituted heteroaryl;
each $R_2$ is $—Z^BR_5$, wherein each $Z^B$ is independently a bond or an optionally substituted aliphatic wherein up to three carbon units of $Z^B$ are optionally and independently replaced by $—C(O)—$, $—C(S)—$, $—C(O)NR^B—$, $—C(O)NR^B-NR^B—$, $—C(O)O—$, $—NR^BC(O)O—$, $—NR^BC(O)NR^B—$, $—NR^BNR^B—$, $—S—$, $—SO—$, $—SO_2—$, $—NR^B—$, $—SO_2NR^B—$, or $—NR^BSO_2NR^B—$, provided that $—SO—$, $—SO_2—$, or $—SO_2NR^B—$ is not directly bound to the carbonyl of formula (I);
each $R_5$ is independently $R^B$, halo, $—OH$, $—CN$, $—NO_2$, $—NH_2$, alkoxy, or haloalkoxy;
Each $R^B$ is independently hydrogen, an optionally substituted aliphatic, an optionally substituted cycloaliphatic, an optionally substituted aryl, or an optionally substituted heteroaryl;
or, $R_1$ and $R_2$, together with the atoms to which they are attached, form an optionally substituted heterocycloaliphatic ring;
each $R_3$ is an optionally substituted aliphatic, amino, sulfonyl, sulfanyl, sulfinyl, sulfonamide, sulfamide, sulfo, $—O—R_{3A}$, an optionally substituted cycloaliphatic, an optionally substituted heterocycloaliphatic, an optionally substituted aryl, or an optionally substituted heteroaryl;
each $R_{3A}$ is independently an optionally substituted aliphatic, an optionally substituted cycloaliphatic, an optionally substituted heterocycloaliphatic, an optionally substituted aryl, or an optionally substituted heteroaryl;
each Y and Y' is independently $—Z^DR_7$, wherein each $Z^D$ is independently a bond or an optionally substituted straight or branched $C_{1-6}$ aliphatic chain wherein up to two carbon units of $Z^D$ are optionally and independently replaced by $—C(O)—$, $—C(S)—$, $—C(O)NR^D—$, $—C(O)NR^DNR^D—$, $—C(O)O—$, $—NR^DC(O)O—$, $—O—$, $—NR^DC(O)NR^D—$, $—NR^DNR^D—$, $—S—$, $—SO—$, $—SO_2—$, $—NR^D—$, $—SO_2NR^D—$, $—NR^DSO_2—$, or $—NR^DSO_2NR^D—$, or Y and Y' together form $=O$ or $=S$;
each $R_7$ is independently $R^D$, halo, $—OH$, $—CN$, $—NO_2$, $—NH_2$, or $—OCF_3$;
each $R^D$ is independently hydrogen, or optionally substituted aryl; and
each of a and b is independently 0, 1, 2, or 3, provided that the sum of a and b is 2 or 3.

The invention also relates to compounds of formula (I) below.

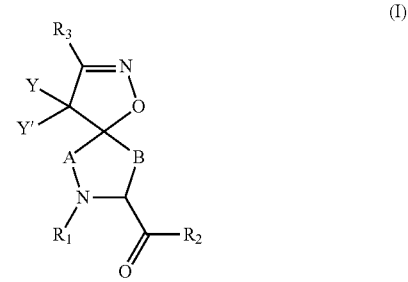

In this formula, each A is $—CH_2—$;
each B is $—CH_2—$;
each $R_1$ is $—Z^AR_4$, wherein each $Z^A$ is $—C(O)—$, $—C(S)—$, $—C(O)NR^A—$, $—C(O)NR^ANR^A—$, $—C(O)O—$, $—NR^AC(O)O—$, $—O—$, $—S—$, $—SO—$, $—SO_2—$, $—NR^A—$, or $—SO_2NR^A—$;
each $R_4$ is independently $R^A$, halo, $—OH$, $—CN$, $—NO_2$, $—NH_2$, alkoxy, or haloalkoxy;
each $R^A$ is independently hydrogen, an optionally substituted aliphatic, an optionally substituted cycloaliphatic, an optionally substituted heterocycloaliphatic, an optionally substituted aryl, or an optionally substituted heteroaryl;
each $R_2$ is $—Z^BR_5$, wherein each $Z^B$ is independently a bond or an optionally substituted aliphatic wherein up to four carbon units of $Z^B$ are optionally and independently replaced by $—C(O)—$, $—C(S)—$, $—C(O)NR^B—$, $—C(O)NR^B-NR^B—$, $—C(O)O—$, $—C(O)C(O)—NR^B—$, $—NR^BC(O)O—$, $—NR^BC(O)NR^B—$, $—NR^BNR^B—$, $—S—$, $—SO—$, $—SO_2—$, $—NR^B—$, $—SO_2NR^B—$, or $—NR^BSO_2NR^B—$, provided that $—SO—$, $—SO_2—$, or $—SO_2NR^B—$ is not directly bound to the carbonyl in formula (I);
each $R_5$ is independently $R^B$, halo, $—OH$, $—CN$, $—NO_2$, $—NH_2$, alkoxy, or haloalkoxy;
each $R^B$ is independently hydrogen, an optionally substituted aliphatic, an optionally substituted cycloaliphatic, an optionally substituted aryl, or an optionally substituted heteroaryl;

or, $R_1$ and $R_2$, together with the atoms to which they are attached, form an optionally substituted heterocycloaliphatic ring;

each $R_3$ is an optionally substituted aliphatic, amino, sulfonyl, sulfanyl, sulfinyl, sulfonamide, sulfamide, sulfo, —O—$R_{3A}$, an optionally substituted cycloaliphatic, an optionally substituted heterocycloaliphatic, an optionally substituted aryl, or an optionally substituted heteroaryl;

each $R_{3A}$ is independently an optionally substituted aliphatic, an optionally substituted cycloaliphatic, an optionally substituted heterocycloaliphatic, an optionally substituted aryl, or an optionally substituted heteroaryl; and each of Y and Y' is H.

In some aspects, the invention features a pharmaceutical composition comprising a compound of formula (I) or a pharmaceutically acceptable salt thereof in an amount effective to inhibit a serine protease; and an acceptable carrier, adjuvant or vehicle. The composition may include an additional agent selected from an immunomodulatory agent; an antiviral agent; a second inhibitor of HCV protease; an inhibitor of another target in the HCV life cycle; and a cytochrome P-450 inhibitor; or combinations thereof. The immunomodulatory agent is α-, β-, or γ-interferon or thymosin; said antiviral agent is ribavirin, amantadine, or telbivudine; or said inhibitor of another target in the HCV life cycle is an inhibitor of HCV helicase, polymerase, or metalloprotease. Cytochrome P-450 inhibitor may be ritonavir.

In other aspects, a method of inhibiting the activity of a serine protease comprising the step of contacting said serine protease with a compound of formula (I). The serine protease may be an HCV NS3 protease. The methods also include treating an HCV infection in a patient by administering a compound of formula (I). The method may also include administering to said patient an additional agent selected from an immunomodulatory agent; an antiviral agent; a second inhibitor of HCV protease; an inhibitor of another target in the HCV life cycle; or combinations thereof; wherein said additional agent is administered to said patient in the same dosage form as the serine protease inhibitor or as a separate dosage form. The immunomodulatory agent is α-, β-, or γ-interferon or thymosin; said antiviral agent is ribavarin or amantadine; or said inhibitor of another target in the HCV life cycle is an inhibitor of HCV helicase, polymerase, or metalloprotease.

In still other aspects, a method of eliminating or reducing HCV contamination of a biological sample or medical or laboratory equipment includes the step of contacting said biological sample or medical or laboratory equipment with a compound of formula (I). The sample or equipment may be selected from blood, other body fluids, biological tissue, a surgical instrument, a surgical garment, a laboratory instrument, a laboratory garment, a blood or other body fluid collection apparatus; a blood or other body fluid storage material.

The compounds of the invention, as described herein, also exhibit advantageous PK properties and/or increased potency.

The invention also relates to compositions that comprise the above compounds and the use thereof; methods of preparing compounds of formula (I), and methods of assaying compounds for serine protease activity. Such compositions may be used to pre-treat devices that are to be inserted into a patient, to treat biological samples, and for direct administration to a patient. In each case, the composition will be used to lessen the risk of or the severity of the HCV infection.

Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1 to 12 (e.g., 1 to 10, 1 to 8, 1 to 6, or 1 to 4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, or heterocycloaliphaticamino), sulfonyl (e.g., aliphatic-$SO_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2 to 12 (e.g., 2 to 8, 2 to 6, or 2 to 4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, heterocycloaliphaticamino, or aliphaticsulfonylamino), sulfonyl (e.g., alkyl-$SO_2$—, cycloaliphatic-$SO_2$—, or aryl-$SO_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2 to 12 (e.g., 2 to 8, 2 to 6, or 2 to 4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl (e.g., aliphaticsulfanyl or cycloaliphaticsulfanyl), sulfinyl (e.g., aliphaticsulfinyl or cycloaliphaticsulfinyl), sulfonyl (e.g., aliphatic-$SO_2$—, aliphaticamino-$SO_2$—, or cycloaliphatic-$SO_2$—), amido (e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl), urea, thiourea, sulfamoyl, sulfamide, alkoxycarbonyl, alkylcarbonyloxy, cycloaliphatic, heterocycloaliphatic, aryl, heteroaryl, acyl (e.g., (cycloaliphatic)carbonyl or (heterocycloaliphatic)carbonyl), amino (e.g., aliphaticamino), sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl, (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di-(such as p,m-dihaloaryl), and tri-(such as halo) aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic (e.g., alkyl, alkenyl, or alkynyl, including carboxyalkyl, hydroxyalkyl, or haloalkyl such as trifluoromethyl); cycloaliphatic (e.g., cycloalkyl or cycloalkenyl); (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido (e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino); cyano; halo; hydroxy; acyl; mercapto; alkylsulfanyl; sulfoxy; urea; thiourea; sulfamoyl; sulfamide; oxo; or carbamoyl.

As used herein, a "bicyclic ring system" includes 8- to 12- (e.g., 9, 10, or 11) membered structures that form two rings, wherein the two rings have at least one atom in common (e.g., 1 atom or 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-12 (e.g., 5-12) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, spiro[5.5]undecanyl, spiro[2.5]octanyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic mono- or bicyclic ring of 3 to 12 (e.g., 4 to 8) carbon atoms having one or more double bonds. Examples of cycloalkenyl groups include cyclopentenyl, 1,4-cyclohexa-di-enyl, cycloheptenyl, cyclooctenyl, hexahydroindenyl, octahydro-naphthyl, cyclohexenyl, cyclopentenyl, spiro[5.5]undec-3-enyl, spiro[2.5]oct-5-enyl, bicyclo[2.2.2]octenyl, or bicyclo[3.3.1]nonenyl.

A cycloalkyl or cycloalkenyl group can be optionally substituted with one or more substituents such as phosphor; aliphatic (e.g., alkyl, alkenyl, or alkynyl); cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido (e.g., (aliphatic)carbonylamino, (cycloaliphatic)carbonylamino, ((cycloaliphatic)aliphatic)carbonylamino, (aryl)carbonylamino, (araliphatic) carbonylamino, (heterocycloaliphatic)carbonylamino, ((heterocycloaliphatic)aliphatic)carbonylamino, (heteroaryl) carbonylamino, or (heteroaraliphatic)carbonylamino); nitro; carboxy (e.g., HOOC—, alkoxycarbonyl, or alkylcarbonyloxy); acyl (e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl); cyano; halo; hydroxy; mercapto; sulfonyl (e.g., alkyl-$SO_2$— and aryl-$SO_2$—); sulfinyl (e.g., alkyl-S(O)—); sulfanyl (e.g., alkyl-S—); sulfoxy; urea; thiourea; sulfamoyl; sulfamide; oxo; or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-12 membered mono- or bicylic (fused or bridged) (e.g., 5- to 12-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, 3-oxaspiro[5.5]undec-3-enyl, 6-oxaspiro[2.5]oct-5-enyl, and 2,6-dioxa-tricyclo[3.3.1.0$^{3,7}$]nonyl.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S).

Monocyclic and bicycloheteroaliphatics are numbered according to standard chemical nomenclature. A heterocycloalkyl or heterocycloalkenyl group can be optionally substituted with one or more substituents such as phosphor; aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl]; nitro; cyano; halo; hydroxy; mercapto; sulfonyl [e.g., alkylsulfonyl or arylsulfonyl]; sulfinyl [e.g., alkylsulfinyl]; sulfanyl [e.g., alkylsulfanyl]; sulfoxy; urea; thiourea; sulfamoyl; sulfamide; oxo; or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, 1,2,3,4-tetrahydroisoquinoline, isoindoline, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl)heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be aliphatic, aryl, aralipatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$ when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, "cyclic group" or "cyclic moiety" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables A, B, R$_1$, R$_2$, R$_3$, Y and Y', and other variables contained in formulae described herein encompass specific groups, such as alkyl and aryl. Unless otherwise noted, each of the specific groups for the variables A, B, R$_1$, R$_2$, R$_3$, Y and Y', and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. Such compounds are useful, for example, as analytical tools or probes in biological assays, or as therapeutic agents.

In other aspects, the invention features certain compounds as described generically and specifically below. Such specific descriptions are illustrative only and are not meant to limit scope of the compounds or uses thereof.

DETAILED DESCRIPTION

I. Compounds

A. Generic Compounds

In some aspects, the invention provides compounds of formula (I) useful for inhibiting serine protease activity and methods of inhibiting serine protease activity. Compounds of formula (I) include:

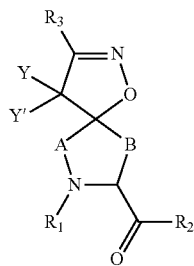

or a pharmaceutically acceptable salt thereof, wherein, each A is $-(CX_1X_2)_a-$;
each B is $-(CX_1X_2)_b-$;
each $X_1$ is independently hydrogen, halo, amino, sulfanyl, optionally substituted $C_{1-4}$ aliphatic, optionally substituted aryl, or $-O-X_{1A}$;
each $X_2$ is independently hydrogen, halo, amino, sulfanyl, optionally substituted $C_{1-4}$ aliphatic, optionally substituted aryl, or $-O-X_{1B}$;
$X_{1A}$ and $X_{1B}$ are each independently an optionally substituted aliphatic, an optionally substituted cycloaliphatic, an optionally substituted heterocycloaliphatic, an optionally substituted aryl, or an optionally substituted heteroaryl;
or, $X_1$ and $X_2$ together form an oxo group;
each $R_1$ is $-Z^A R_4$, wherein each $Z^A$ is independently a bond or an optionally substituted branched or straight $C_{1-12}$ aliphatic chain wherein up to three carbon units of $Z^A$ are optionally and independently replaced by $-C(O)-$, $-C(S)-$, $-C(O)NR^A-$, $-C(O)NR^ANR^A-$, $-C(O)O-$, $-NR^AC(O)O-$, $-O-$, $-NR^AC(O)NR^A-$, $-NR^ANR^A-$, $-S-$, $-SO-$, $-SO_2-$, $-NR^A-$, $-SO_2NR^A-$, or $-NR^ASO_2NR^A-$ provided that $-NR^ANR^A-$, $-NR^AC(O)NR^A-$, or $-NR^ASO_2NR^A-$ is not directly bound to the nitrogen ring atom of formula (I).
each $R_4$ is independently $R^A$, halo, $-OH$, $-CN$, $-NO_2$, $-NH_2$, or $-OCF_3$;
each $R^A$ is independently hydrogen, an optionally substituted aliphatic, an optionally substituted cycloaliphatic, an optionally substituted heterocycloaliphatic, an optionally substituted aryl, or an optionally substituted heteroaryl;
each $R_2$ is $-Z^BR_5$, wherein each $Z^B$ is independently a bond or an optionally substituted branched or straight $C_{1-12}$ aliphatic chain wherein up to three carbon units of $Z^B$ are optionally and independently replaced by $-C(O)-$, $-C(S)-$, $-C(O)NR^B-$, $-C(O)NR^BNR^B-$, $-C(O)O-$, $-NR^BC(O)O-$, $-NR^BC(O)NR^B-$, $-NR^BNR^B-$, $-S-$, $-SO-$, $-SO_2-$, $-NR^B-$, $-SO_2NR^B-$, or $-NR^BSO_2NR^B-$, provided that SO, $SO_2$, or $-SO_2NR^B-$ is not directly bound to the carbonyl of formula (I);
each $R_5$ is independently $R^B$, halo, $-OH$, $-CN$, $-NO_2$, $-NH_2$, or $-OCF_3$;
each $R^B$ is independently hydrogen, an optionally substituted aliphatic, an optionally substituted cycloaliphatic, an optionally substituted aryl, or an optionally substituted heteroaryl;
or, $R_1$ and $R_2$, together with the atoms to which they are attached, form an optionally substituted heterocycloaliphatic ring;
each $R_3$ is an optionally substituted aliphatic, amino, sulfonyl, sulfanyl, sulfinyl, sulfonamide, sulfamide, sulfo, $-O-R_{3A}$, an optionally substituted cycloaliphatic, an optionally substituted heterocycloaliphatic, an optionally substituted aryl, or an optionally substituted heteroaryl;
each $R_{3A}$ is independently an optionally substituted aliphatic, an optionally substituted cycloaliphatic, an optionally substituted heterocycloaliphatic, an optionally substituted aryl, or an optionally substituted heteroaryl;
each Y and Y' is independently $-Z^DR_7$, wherein each $Z^D$ is independently a bond or an optionally substituted straight or branched $C_{1-6}$ aliphatic chain wherein up to two carbon units of $Z^D$ are optionally and independently replaced by $-C(O)-$, $-C(S)-$, $-C(O)NR^D-$, $-C(O)NR^DNR^D-$, $-C(O)O-$, $-NR^DC(O)O-$, $-O-$, $-NR^DC(O)NR^D-$, $-NR^DNR^D-$, $-S-$, $-SO-$, $-SO_2-$, $-NR^D-$, $-SO_2NR^D-$, $-NR^DSO_2-$, or $-NR^DSO_2NR^D-$, or Y and Y' together form $=O$ or $=S$;
each $R_7$ is independently $R^D$, halo, $-OH$, $-CN$, $-NO_2$, $-NH_2$, or $-OCF_3$;
each $R^D$ is independently hydrogen, or optionally substituted aryl; and
each of a and b is independently 0, 1, 2, or 3; provided that the sum of a and b is 2 or 3.

B. Specific Compounds

1. Substituent $R_1$:

Each $R_1$ is $-Z^AR_4$, wherein each $Z^A$ is independently a bond or an optionally substituted branched or straight $C_{1-12}$ aliphatic chain wherein up to three carbon units of $Z^A$ are optionally and independently replaced by $-C(O)-$, $-C(S)-$, $-C(O)NR^A-$, $-C(O)NR^ANR^A-$, $-C(O)O-$, $-NR^AC(O)O-$, $-O-$, $-NR^AC(O)NR^A-$, $-NR^ANR^A-$, $-S-$, $-SO-$, $-SO_2-$, $-NR^A-$, $SO_2NR^A-$, or $-NR^ASO_2NR^A-$ provided that $-NR^ANR^A-$, $-NR^AC(O)NR^A-$, or $-NR^ASO_2NR^A-$ is not directly bound to the nitrogen ring atom of formula (I).

Each $R_4$ is independently $R^A$, halo, $-OH$, $-CN$, $-NO_2$, $-NH_2$, or $-OCF_3$.

Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

In several embodiments $R_1$ is optionally substituted with 1 to 4 substituents.

In certain embodiments, $R_1$ is $-Q_4-W_4-Q_3-W_3-Q_2-W_2-Q_1$; wherein each of $W_2$, $W_3$, and $W_4$ is independently a bond, $-C(O)-$, $-C(S)-$, $-C(O)N(Q_5)-$, $-C(O)O-$, $-O-$, $-N(Q_5)C(O)N(Q_s)-$, $-SO_2-$, $-N(Q_5)SO_2-$, $-S-$, $-N(Q_5)-$, $-SO-$, $-OC(O)-$, $-N(Q_5)C(O)O-$, or $-SO_2N(Q_5)-$; each of $Q_1$, $Q_2$, $Q_3$ and $Q_4$ is independently a bond, an optionally substituted $C_{1-4}$ aliphatic, an optionally substituted cycloaliphatic, an optionally substituted heterocycloaliphatic, an optionally substituted aryl, an optionally substituted heteroaryl, or a hydrogen when $Q_1$, $Q_2$, $Q_3$, or $Q_4$ is the terminal group of $R_f$; and each $Q_5$ is independently hydrogen or an optionally substituted aliphatic. In some specific embodiments, $Q_4$ is a bond.

In several embodiments, $R_1$ is an optionally substituted acyl group. In several examples, $R_1$ is an optionally substituted alkylcarbonyl. Additional examples of $R_1$ include (amino)alkylcarbonyl, (halo)alkylcarbonyl, (aryl)alkylcarbonyl, (cycloaliphatic)alkylcarbonyl, or (heterocycloaliphatic)alkylcarbonyl. Included in these examples are embodiments where $R_1$ is (heterocycloalkyl(oxy(carbonyl(amino))))alkylcarbonyl, (heteroaryl(carbonyl(amino(alkyl(carbonyl(amino)))))alkylcarbonyl, (bicycloaryl(sulfonyl(amino)))alkylcarbonyl, (aryl(alkoxy(carbonyl(amino))))alkylcarbonyl, (alkyl(carbonyl(amino)))alkylcarbonyl, (alkenyl(alkoxy(carbonyl(amino))))alkylcarbonyl, (cycloaliphatic(alkyl(amino(carbonyl(amino)))))alkylcarbonyl, (heteroaryl(carbonyl(amino(alkyl(carbonyl(amino))))))alkylcarbonyl, (alkyl(amino(carbonyl(amino))))alkylcarbonyl, or (bicycloaryl(amino(carbonyl(amino))))alkylcarbonyl, each of which is optionally substituted with 1-3 substituents.

In several embodiments, $R_1$ is an optionally substituted carboxy group. In one example, $R_1$ is optionally substituted alkoxycarbonyl. Another example of $R_1$ includes alkoxycarbonyl, or (tricyclic aryl)alkoxycarbonyl, each of which is optionally substituted with 1-3 substituents. Other carboxy groups include (aliphatic(oxy))carbonyl, a (heteroaralkyl(oxy))carbonyl, (heterocycloaliphatic(oxy)carbonyl, (aralkyl(oxy))carbonyl, each of which is optionally substituted with 1-3 of halo, alkoxy, aliphatic, cycloaliphatic, heterocycloaliphatic, aryl, heteroaryl, or combinations thereof.

In several embodiments, $R_1$ is optionally substituted aminocarbonyl. Examples of $R_1$ include (alkoxy(aryl(alkyl)))aminocarbonyl, (alkyl)aminocarbonyl, or (aryl(alkoxy(carbonyl(alkyl(amino(carbonyl(alkyl))))))aminocarbonyl, each of which is optionally substituted with 1-3 substituents.

In several embodiments, $R_1$ is optionally substituted heteroaryl. In one example, $R_1$ is an optionally substituted oxazolyl, pyrrolyl, furyl, thiophenyl, triazinyl, pyridinyl, pyrazinyl, pyrimidinyl, or pyridazinyl.

In several embodiments, $R_1$ is an alkylsulfonyl, aminosulfonyl, arylsulfonyl, heteroarylsulfonyl, cycloaliphaticsulfonyl, or heterocycloaliphaticsulfonyl, each of which is optionally substituted with 1-4 substituents.

In several embodiments, $R_1$ is an optionally substituted alkylsulfonyl. Examples of $R_1$ include (aryl)alkylsulfonyl, or (alkyl(amino))alkylsulfonyl, alkylsulfonyl, aminosulfonyl, arylsulfonyl, heteroarylsulfonyl, cycloaliphaticsulfonyl, or heterocycloaliphaticsulfonyl, each of which is optionally substituted 1-3 substituents. In certain embodiments, $R_1$ is an optionally substituted alkyl sulfonyl.

In several embodiments, $R_1$ is an (aryl)alkylsulfonyl, or (alkyl(amino))alkylsulfonyl, each of which is optionally substituted.

In some specific embodiments, $R_1$ is (amino)alkylcarbonyl, (halo)alkylcarbonyl, (aryl)alkylcarbonyl, (cycloaliphatic)alkylcarbonyl, or (heterocycloaliphatic)alkylcarbonyl, (heterocycloalkyl(oxy(carbonyl(amino))))alkylcarbonyl, (heteroaryl(carbonyl(amino(alkyl(carbonyl(amino)))))alkylcarbonyl, (bicycloaryl(sulfonyl(amino)))alkylcarbonyl, (aryl(alkoxy(carbonyl(amino))))alkylcarbonyl, (alkyl(carbonyl(amino)))alkylcarbonyl, (alkenyl(alkoxy(carbonyl(amino))))alkylcarbonyl, (cycloaliphatic(alkyl(amino(carbonyl(amino)))))alkylcarbonyl, (heteroaryl(carbonyl(amino(alkyl(carbonyl(amino))))))alkylcarbonyl, (alkyl(amino(carbonyl(amino))))alkylcarbonyl, or (bicycloaryl(amino(carbonyl(amino))))alkylcarbonyl, each of which is optionally substituted.

In other specific embodiments, $R_1$ is a heteroarylcarbonyl, a (cycloaliphatic(alkyl(amido(alkyl))))carbonyl, a (heterocycloaliphatic(oxy(amido(alkyl))))carbonyl, an (aryl(sulfonyl(amino(alkyl))))carbonyl, an (aralkyl(oxy(amido(alkyl))))carbonyl, an (aliphatic(oxy(amido(alkyl))))carbonyl, a (cycloaliphatic(alkyl(amido(alkyl))))carbonyl, a (heterocycloaliphatic)carbonyl, or a (heteroaryl(amido(alkyl(amido(alkyl))))carbonyl, each of which is optionally substituted with 1-4 of halo, aliphatic, cycloaliphatic, acyl, alkoxy, or combinations thereof.

In still other embodiments, $R_1$ is amido. For example, $R_1$ is (alkoxy(aryl(alkyl)))aminocarbonyl, (alkyl)aminocarbonyl, or (aryl(alkoxy(carbonyl(alkyl(amino(carbonyl(alkyl))))))aminocarbonyl, each of which is optionally substituted.

In several embodiments, $R_1$ is

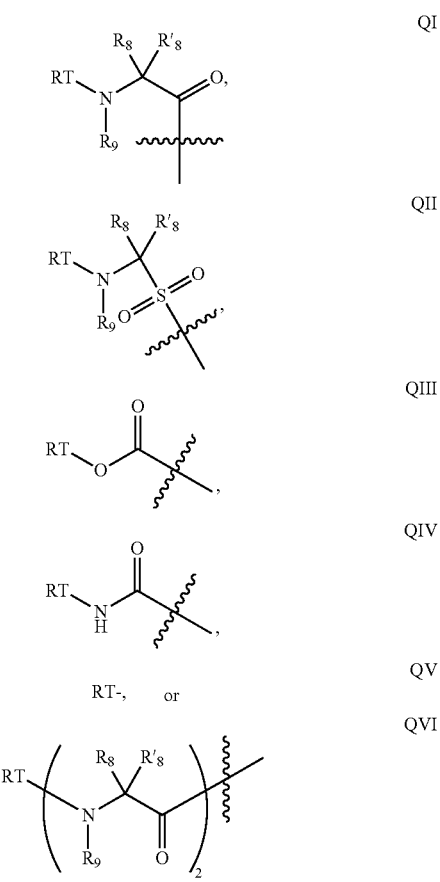

wherein T is a bond, —C(O)—, —OC(O)—, —NHC(O)—, —S(O)$_2$N(H)—, —C(O)C(O)— or —SO$_2$—; each R is independently hydrogen, amino, an optionally substituted aliphatic, an optionally substituted cycloaliphatic, an optionally substituted heterocycloaliphatic, an optionally substituted aryl, or an optionally substituted heteroaryl; each $R_8$ and $R'_8$ is independently hydrogen, an optionally substituted aliphatic, an optionally substituted cycloaliphatic, an optionally substituted heterocycloaliphatic, an optionally substituted aryl, or an optionally substituted heteroaryl; and each $R_9$ is independently hydrogen, an optionally substituted aliphatic, an optionally substituted heteroaryl, an optionally substituted phenyl, or $R_8$ and $R_9$, bound on adjacent atoms, taken together with the atoms to which they are attached form a 5 to 7 membered, optionally substituted monocyclic heterocycloaliphatic, or a 6 to 12 membered, optionally substituted bicyclic heterocycloaliphatic; or $R_8$ and $R'_8$, taken together with the atoms to which they are attached form an optionally substituted cycloaliphatic or an optionally substituted heterocycloaliphatic. For clarity, when $R_1$ is QVI, each of $R_8$, $R'_8$ and $R_9$ in each subunit can be independently selected as described above. The set of $R_8$, $R'_8$ and $R_9$ variables in one subunit need not necessarily be identical to the same set of $R_8$, $R'_8$ and $R_9$ variables in the other subunit.

In other embodiments, $R_1$ is QI or QII.

In some embodiments, R in the substituent in QI, QII, QIII, QIV, QV, or QVI is

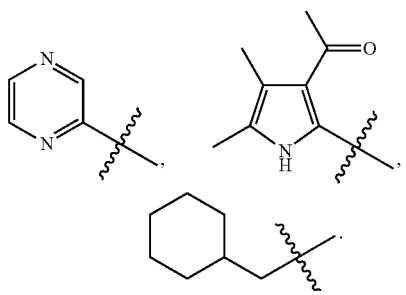

In other embodiments, $R_1$ is QVI and R is

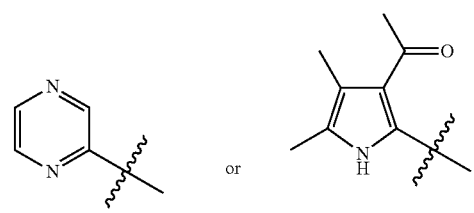

In other embodiments, R in the substituent QI, QII, QIII, QIV, QV, or QVI is

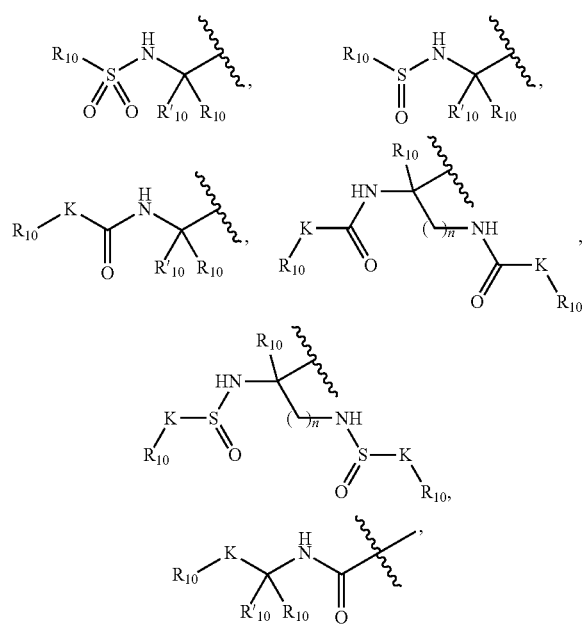

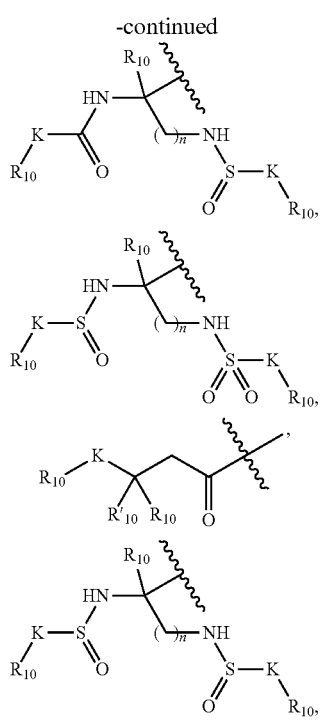

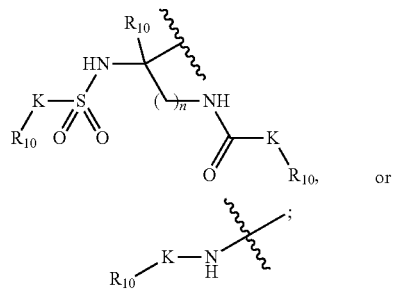

wherein each $R_{10}$ and $R'_{10}$ is independently hydrogen, optionally substituted aliphatic, optionally substituted aryl, optionally substituted heteroaryl, optionally substituted heterocycloaliphatic, or optionally substituted cycloaliphatic, or $R_{10}$ and $R'_{10}$ together with the atom to which they are both bound form an optionally substituted cycloaliphatic or an optionally substituted heterocycloaliphatic; and each K is independently a bond, $C_{1-12}$ aliphatic, —O—, —S—, —S(O)$_2$—, —NR$_{14}$—, —C(O)—, or —C(O)NR$_{14}$—, wherein $R_{14}$ is hydrogen or an optionally substituted $C_{1-12}$ aliphatic; and n is 1-3. For clarity, when more than one $R_{10}$ is present in QI, QII, QIII, QIV, QV, or QVI, each $R_{10}$ can be the same or different. In several embodiments, $R_{10}$ or $R'_{10}$ is [$C_{3-10}$ cycloalkyl or cycloalkenyl]-$C_{1-12}$ aliphatic, (3 to 10 membered)-heterocycloaliphatic, (3 to 10 membered)-heterocycloaliphatic-$C_{1-12}$ aliphatic-, (5 to 10 membered)-heteroaryl, or (5 to 10 membered)-heteroaryl-$C_{1-12}$ aliphatic-.

In still other embodiments, R in the substituent in QI, QII, QIII, QIV, QV, or QVI is

21
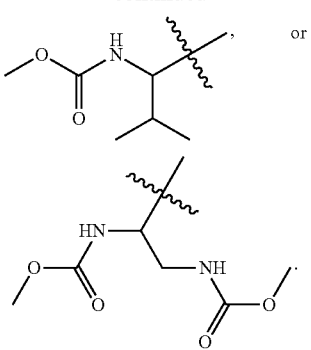
In further embodiments, R in the substituent in QI, QII, QIII, QIV, QV, or QVI is
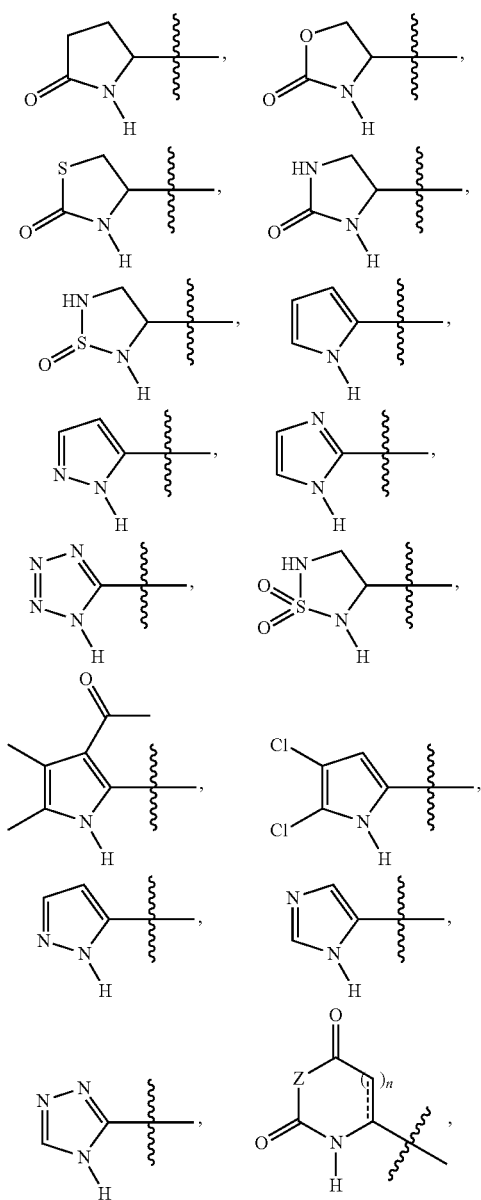
22
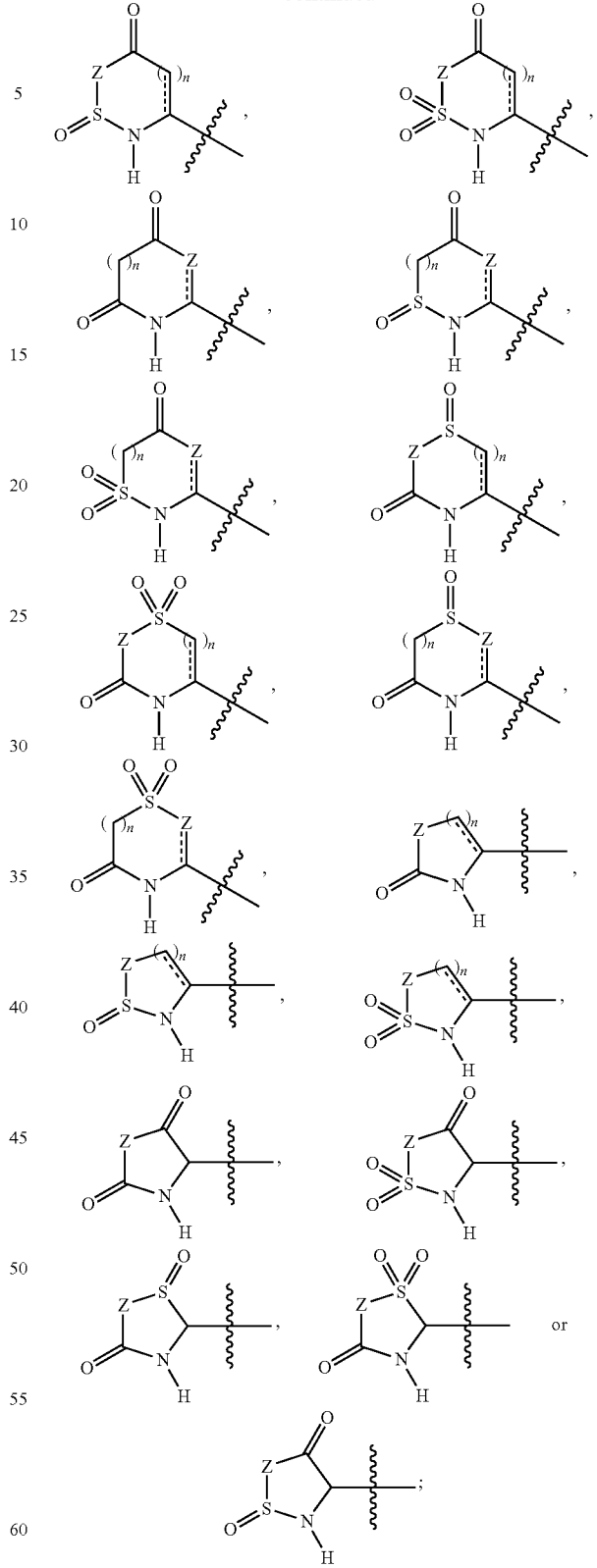
wherein each Z is independently —O—, —S—, —NR$_{50}$—, or —C(R$_{50}$)$_2$—, ===== is independently a single bond or a double bond, and each R$_{50}$ is independently hydrogen, optionally substituted aliphatic, optionally substituted aryl, optionally substituted heteroaryl, optionally substituted heterocycloaliphatic, or optionally substituted cycloaliphatic; and n is 1 or 2.

In several embodiments, $R_1$ is

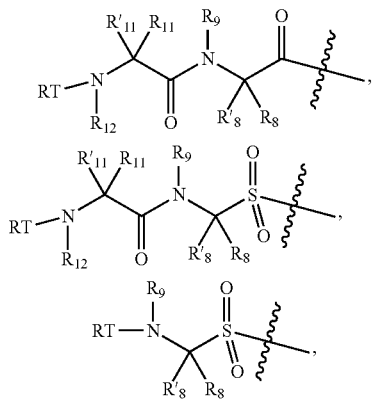

wherein T is a bond, —C(O)—, —OC(O)—, —NHC(O)—, —S(O)$_2$N(H)—, —C(O)C(O)— or —SO$_2$—; each R is independently hydrogen, amino, an optionally substituted aliphatic, an optionally substituted cycloaliphatic, an optionally substituted heterocycloaliphatic, an optionally substituted aryl, or an optionally substituted heteroaryl; each $R_8$ and $R'_8$ is independently hydrogen, an optionally substituted aliphatic, an optionally substituted cycloaliphatic, an optionally substituted heterocycloaliphatic, an optionally substituted aryl, or an optionally substituted heteroaryl; and each $R_9$ is independently hydrogen, an optionally substituted aliphatic, an optionally substituted heteroaryl, an optionally substituted phenyl, or $R_8$ and $R_9$, bound on adjacent atoms, taken together with the atoms to which they are attached form a 5 to 7 membered, optionally substituted monocyclic heterocycloaliphatic, or a 6 to 12 membered, optionally substituted bicyclic heterocycloaliphatic, in which each heterocycloaliphatic ring; or $R_8$ and $R'_8$, taken together with the atoms to which they are attached form an optionally substituted cycloaliphatic or an optionally substituted heterocycloaliphatic; each $R_{11}$ and $R'_{11}$ is independently hydrogen, an optionally substituted aliphatic, an optionally substituted heteroaryl, an optionally substituted phenyl, an optionally substituted cycloaliphatic, an optionally substituted heterocycloaliphatic; or $R_{11}$ and $R'_{11}$ together with the atom to which they are both attached form an optionally substituted 3 to 7 membered cycloaliphatic or heterocycloaliphatic ring; and each $R_{12}$ is independently hydrogen or a protecting group.

In some embodiments, $R_{11}$ and $R'_{11}$ together with the atom to which they are attached form a 3 to 7 membered ring. Non-limiting examples include

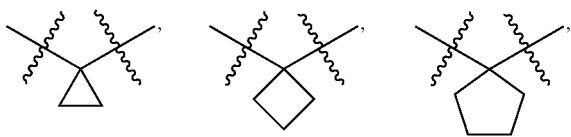

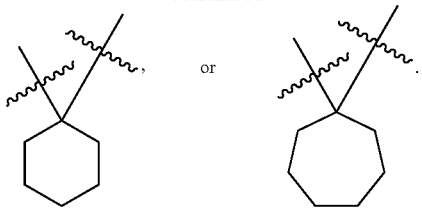

Non-limiting examples of $R_8$ and $R_{11}$ include

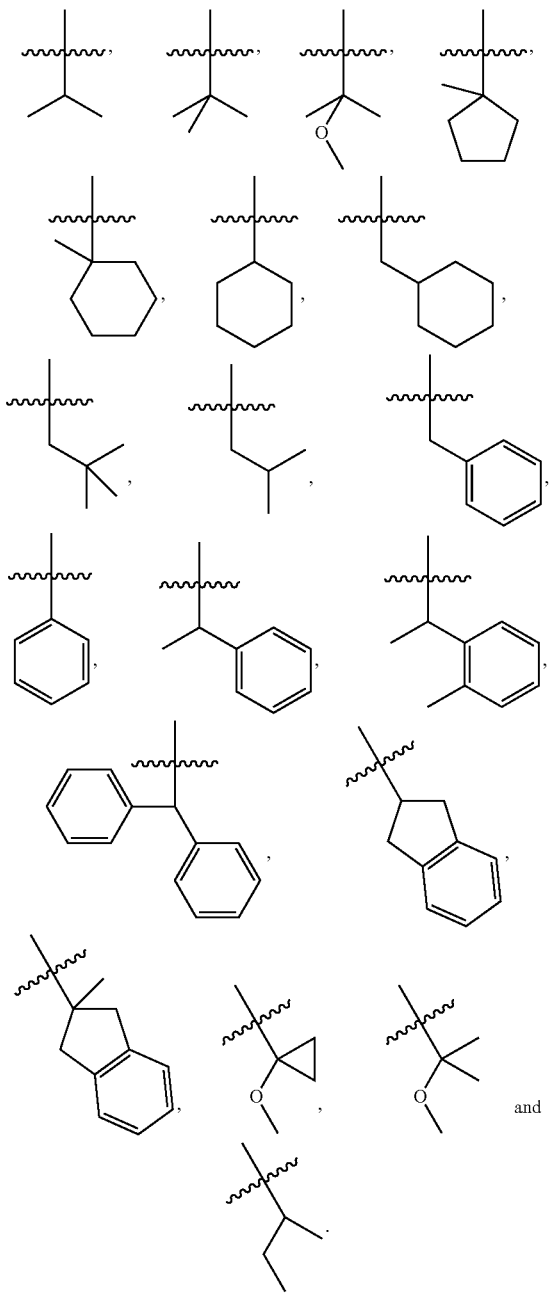

Alternatively, $R_8$ and $R_{11}$ together with the atoms to which they are attached may form an optionally substituted 5 to 7 membered monocyclic heterocycloaliphatic or an optionally substituted 6 to 12 membered bicyclic heterocycloaliphatic, in which each heterocycloaliphatic or aryl ring optionally contains an additional heteroatom selected from O, S and N.

Also, $R_8$ and $R_9$ together to with the atoms to which they are attached can form a ring, $R_7$ and the ring system formed by $R_8$ and $R_9$ form an optionally substituted 8 to 14 membered bicyclic fused ring system, wherein the bicyclic fused ring system is optionally further fused with an optionally substituted phenyl to form an optionally substituted 10 to 16 membered tricyclic fused ring system.

In several embodiments, $R_1$ is:

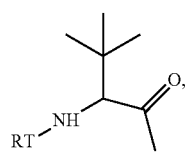

wherein T is —C(O)—, and R is

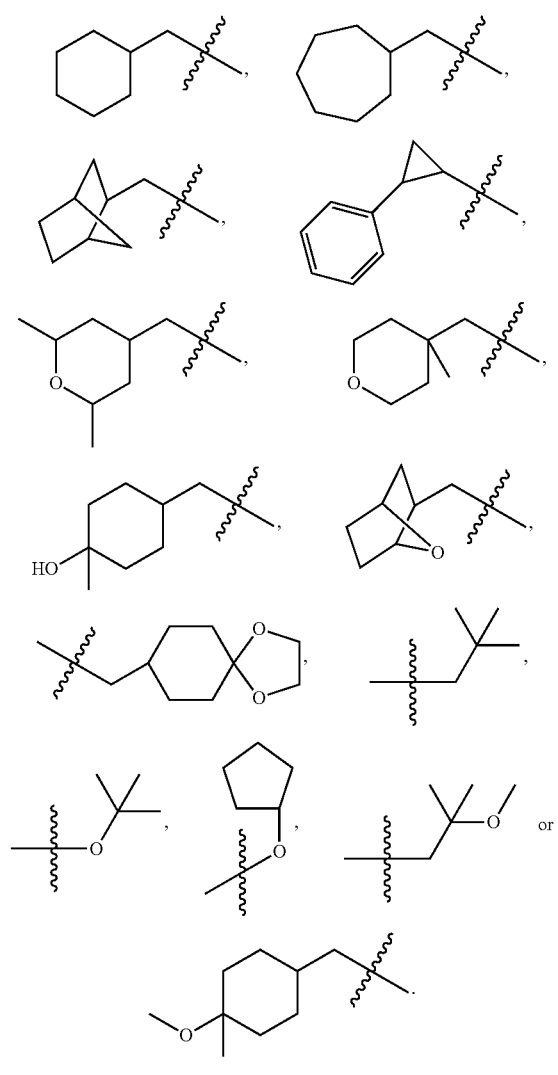

In several embodiments, $R_1$ is a group selected from:

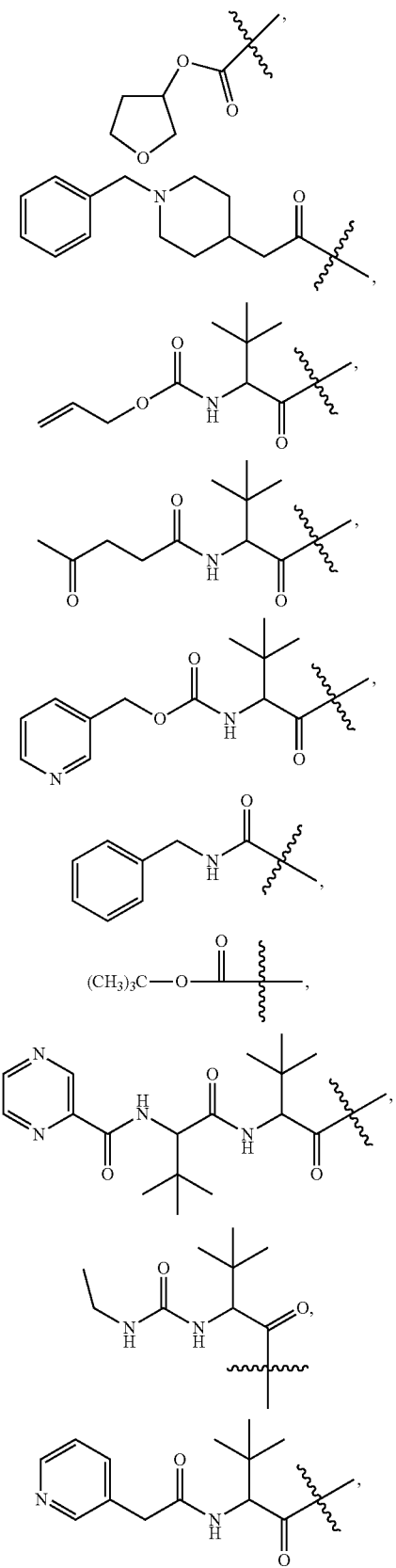

27
-continued
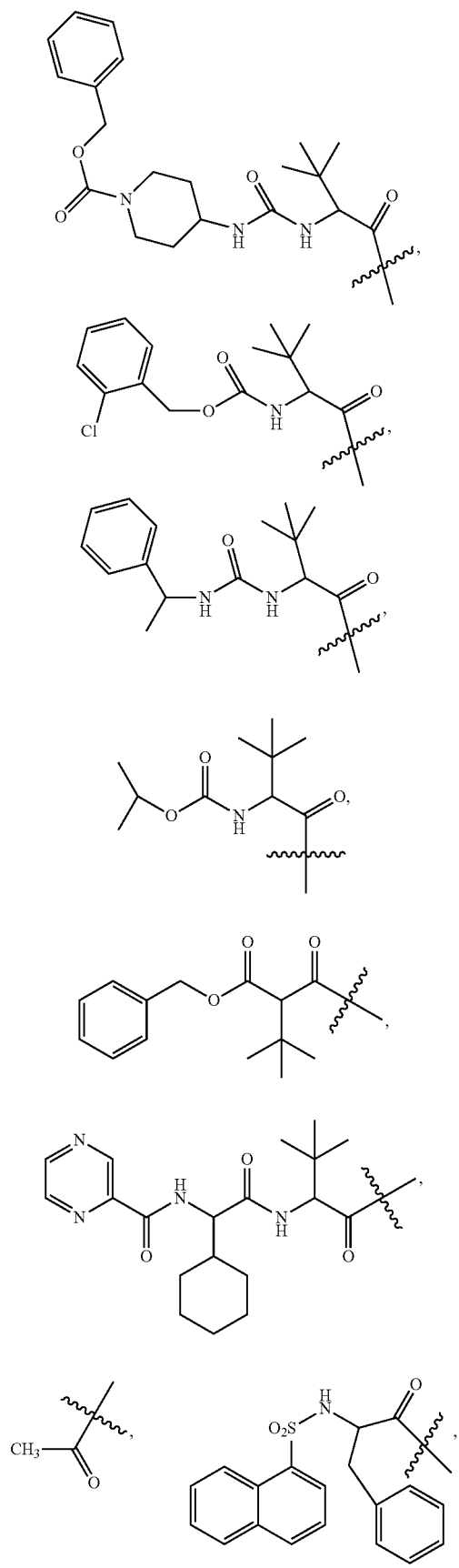
28
-continued
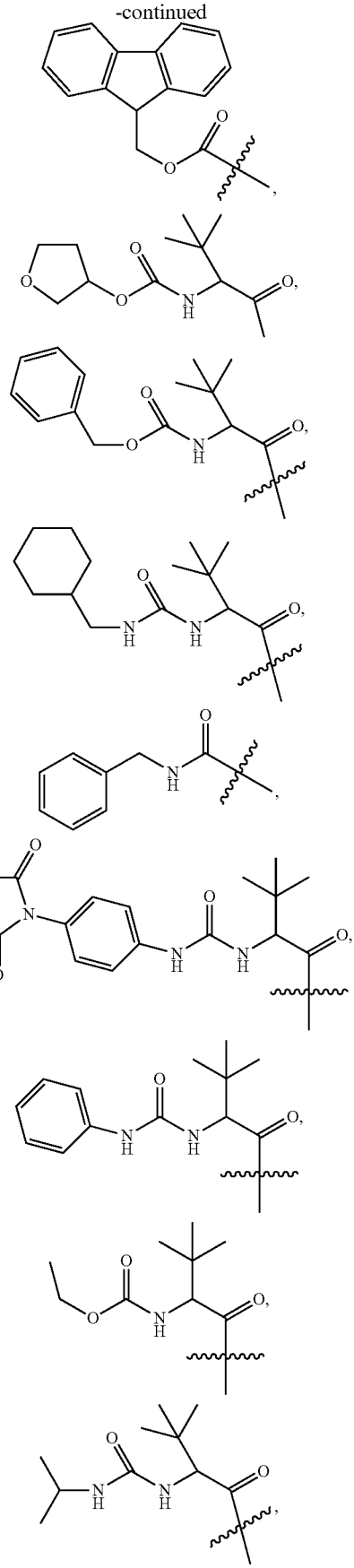

29
-continued
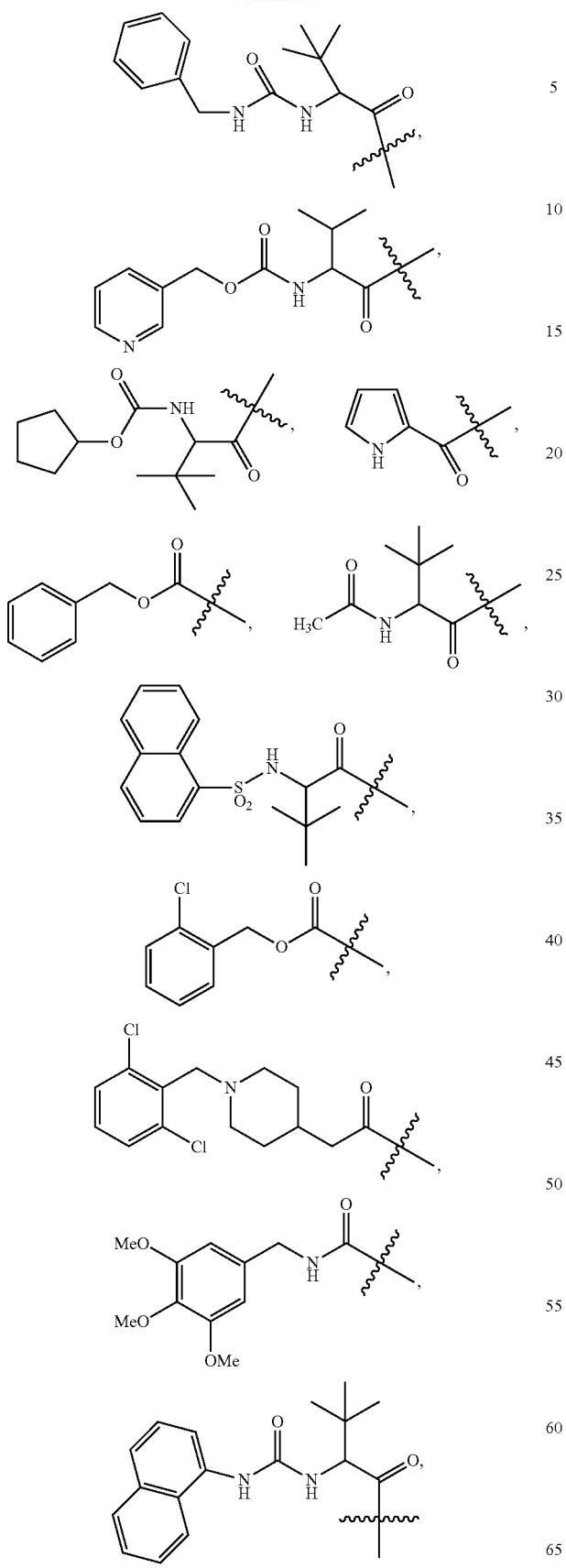
30
-continued
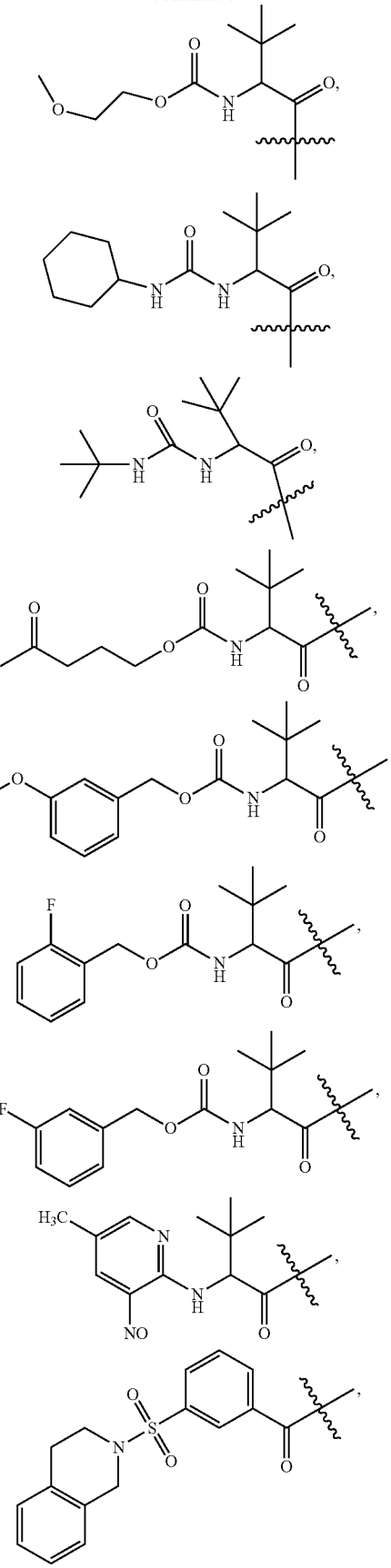

31
-continued
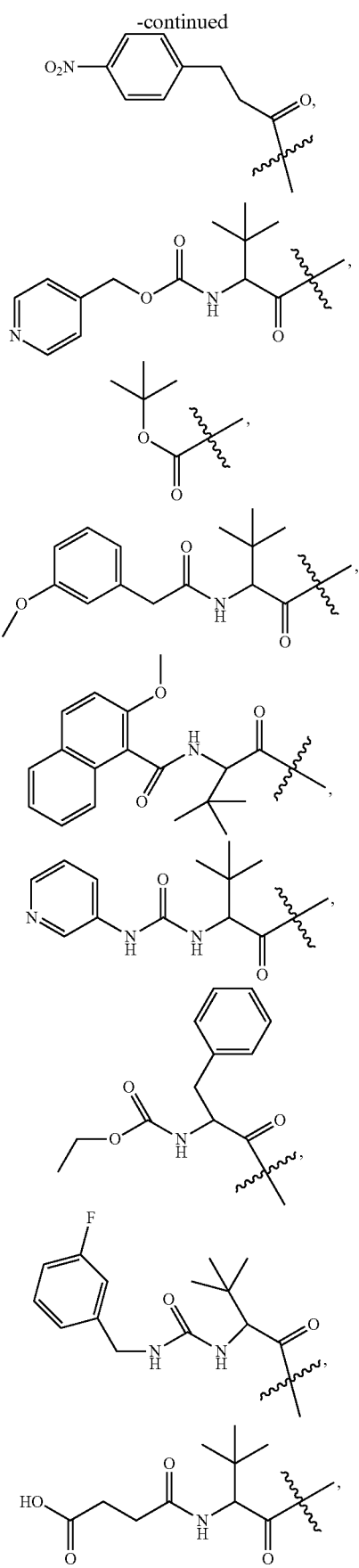
32
-continued
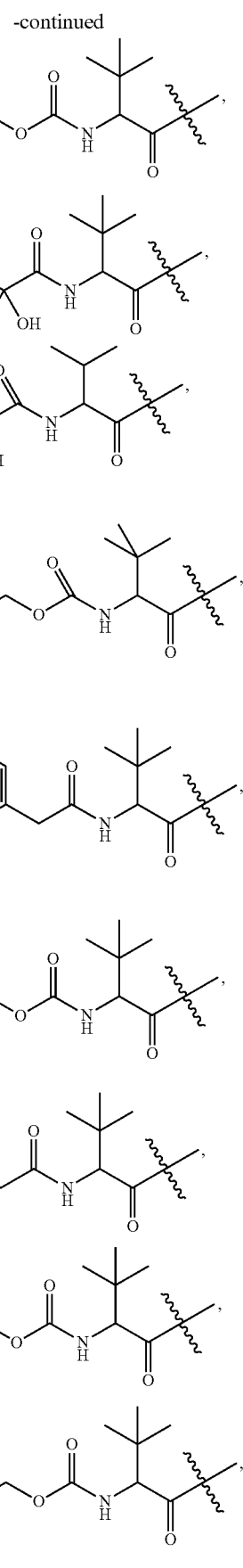

33
-continued
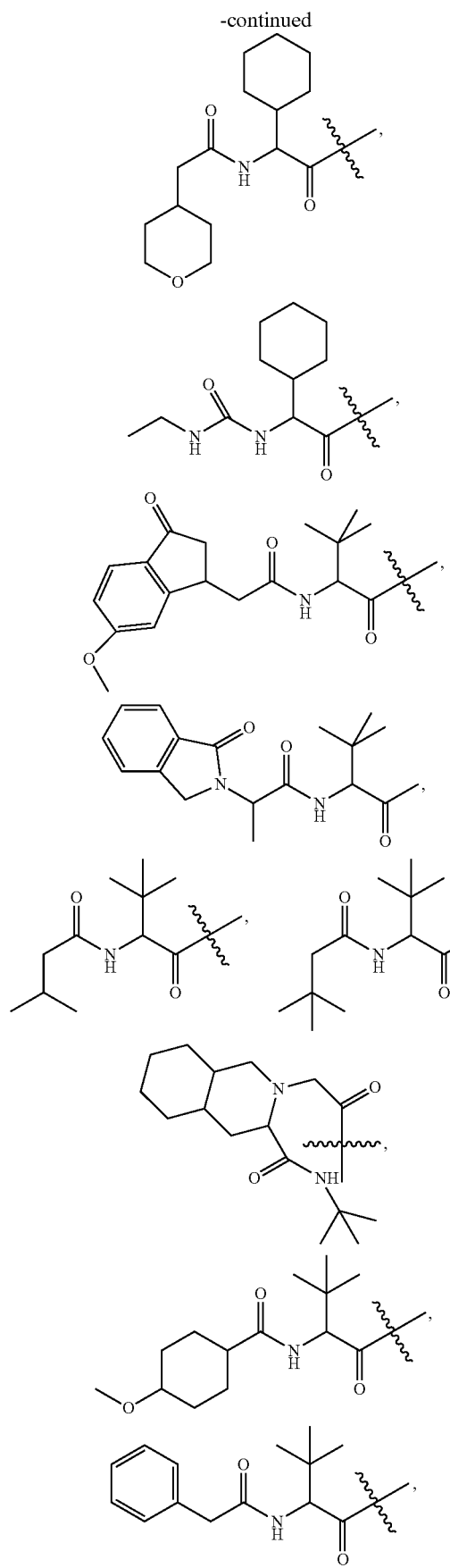
34
-continued
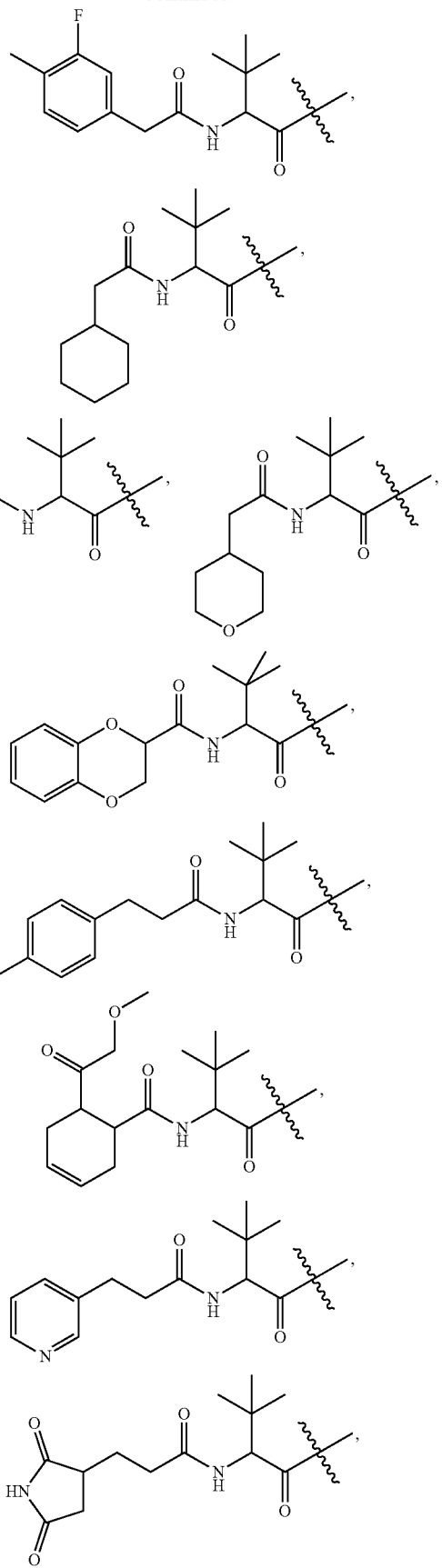

35
-continued
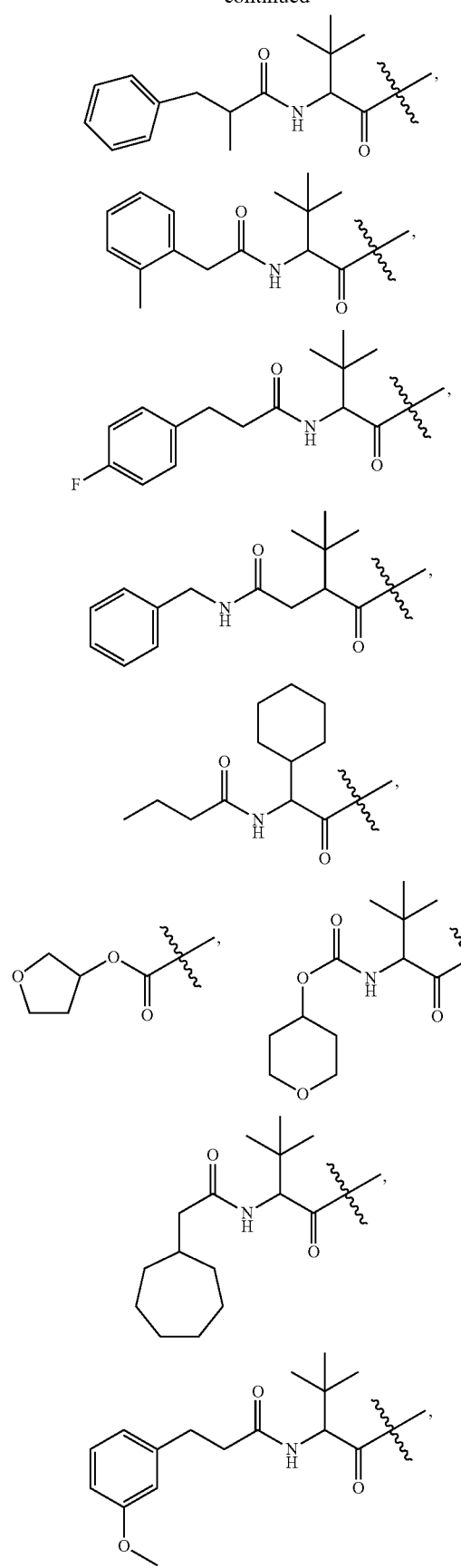
36
-continued
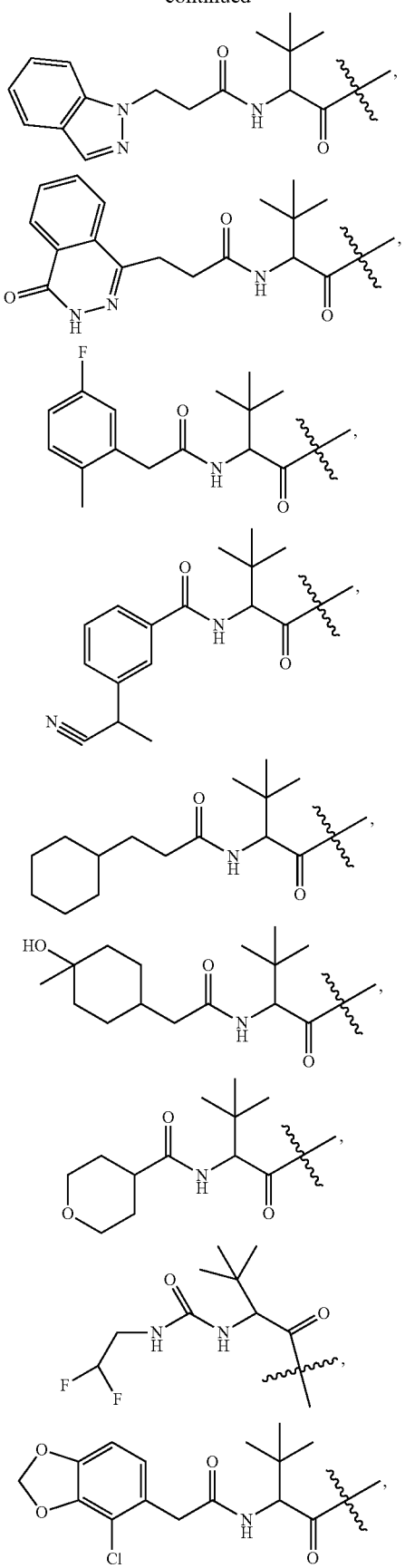

37
-continued
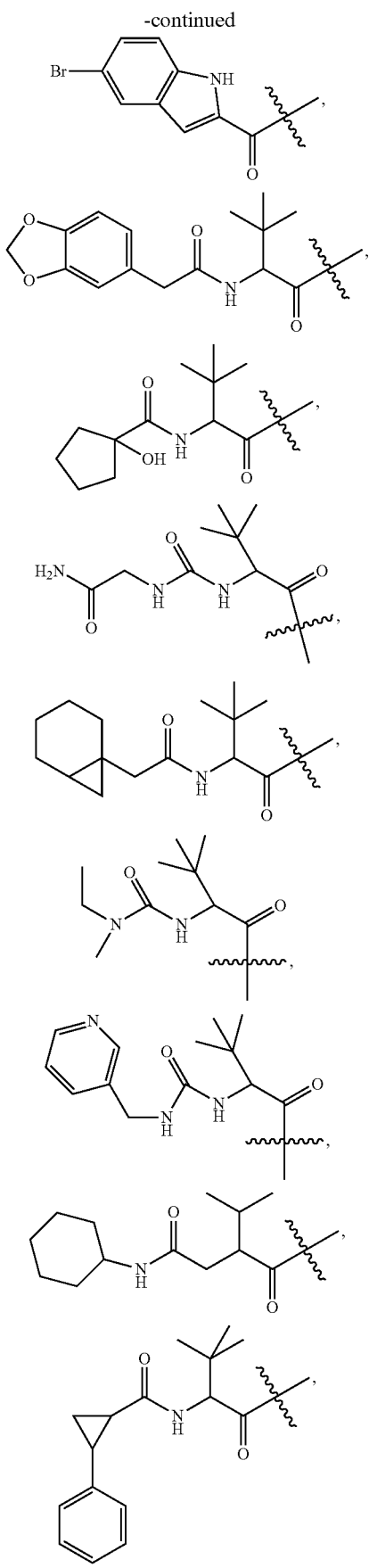
38
-continued
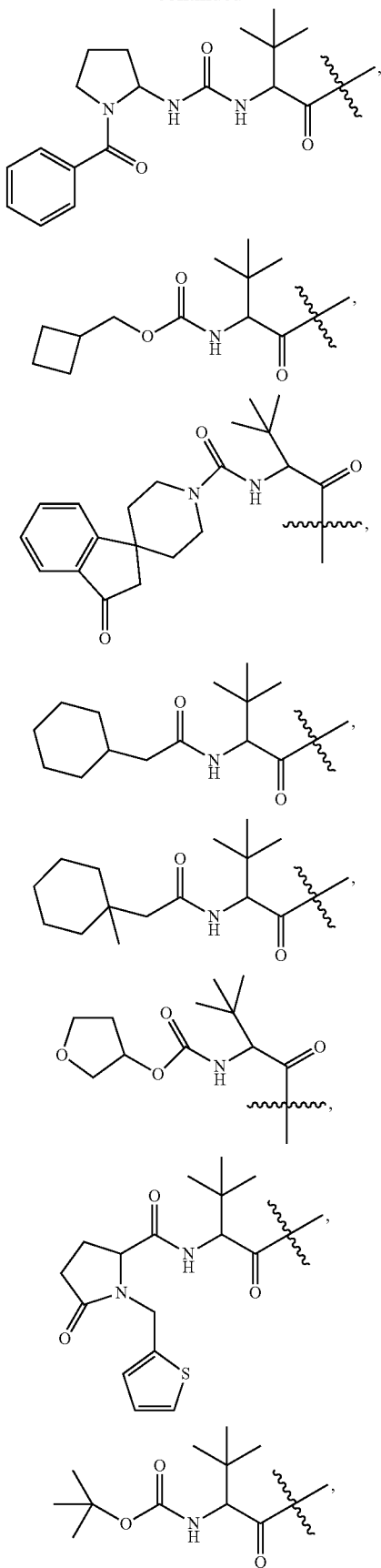

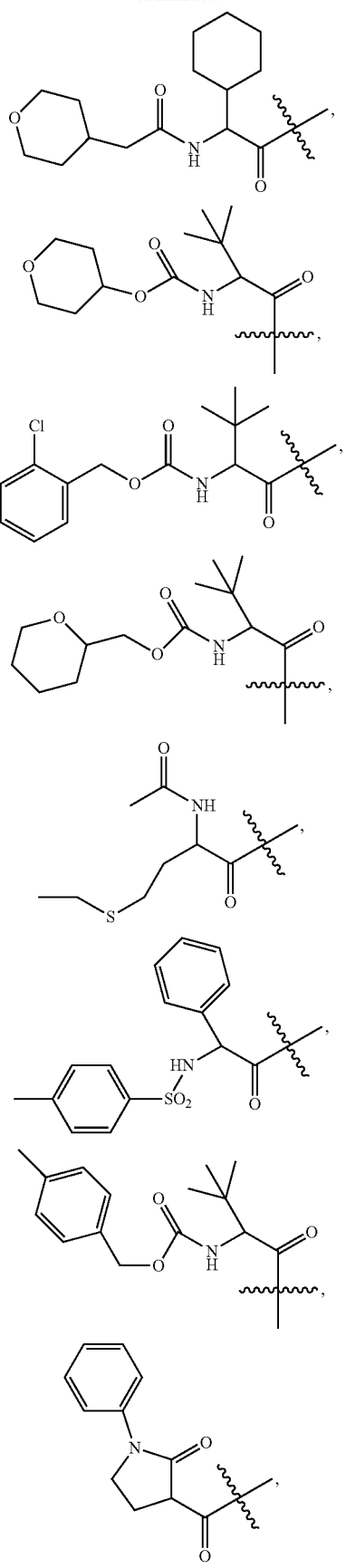
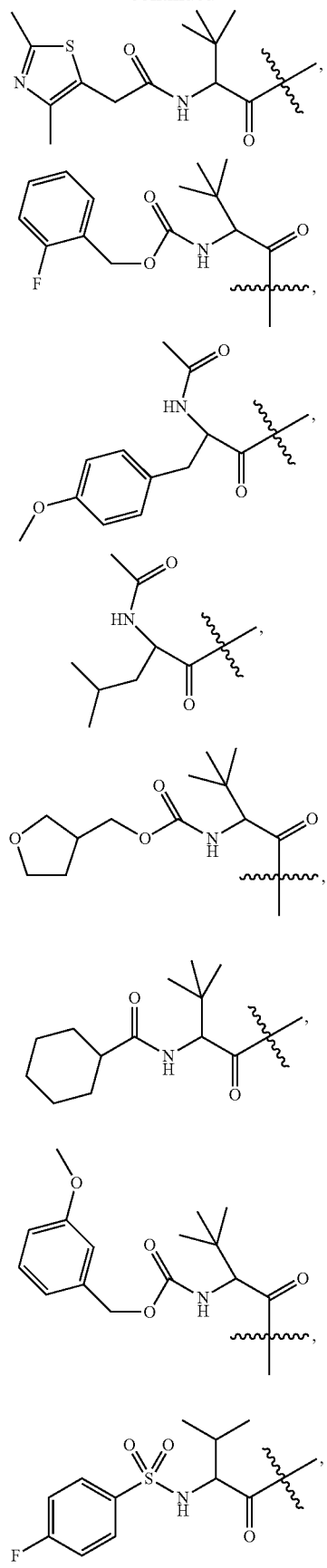

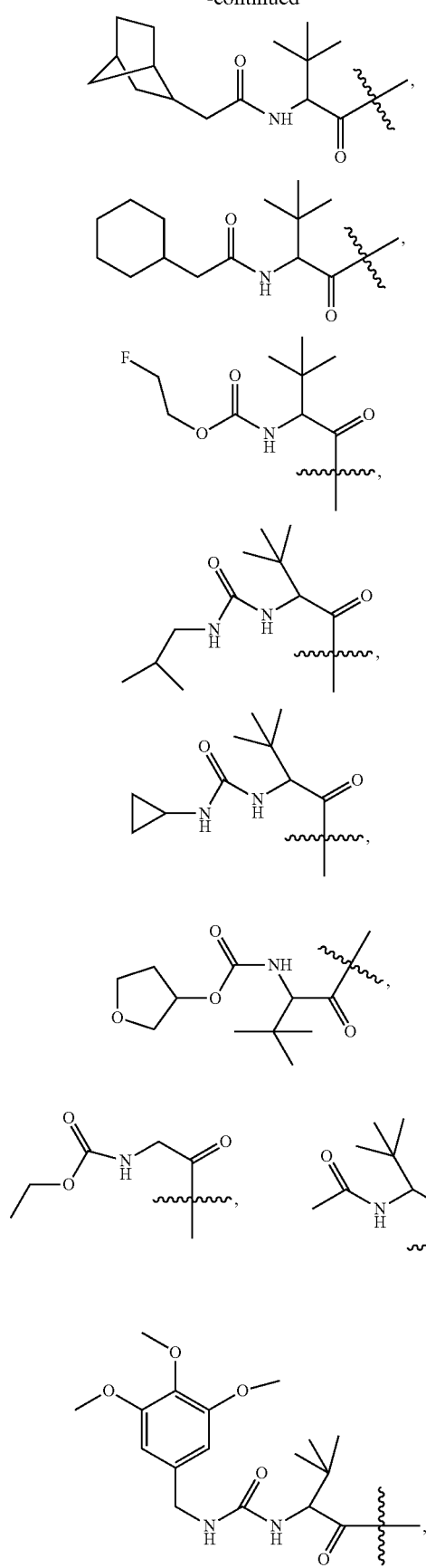
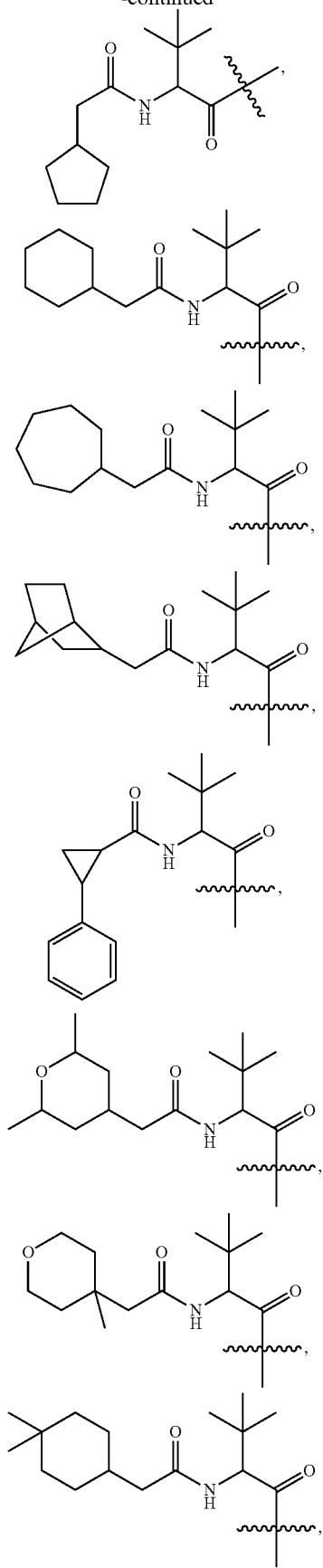

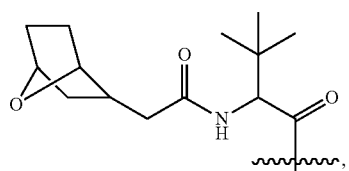
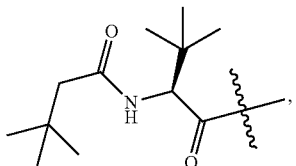
and
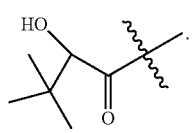
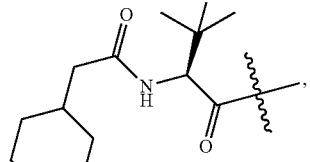
In several embodiments, $R_1$ is
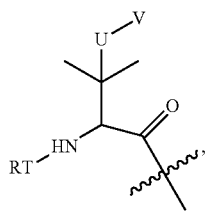
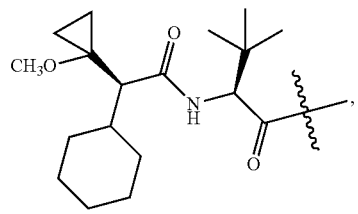
wherein U is a bond or —O—; V is an alkyl; T is —C(O)—; and R is an aliphatic, cycloaliphatic, heterocycloaliphatic, aryl, heteroaryl, alkoxy or cycloalkoxy. Examples of $R_1$ include
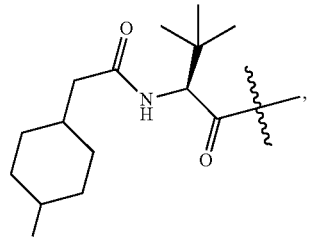
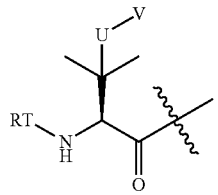
in which R, U, and V are as just defined.
In some embodiments, R is an aliphatic, cycloaliphatic or heterocycloaliphatic such that examples of $R_1$ include
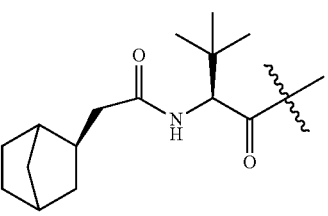
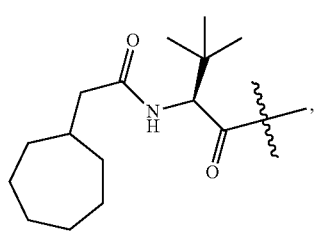
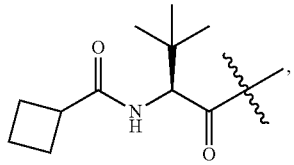
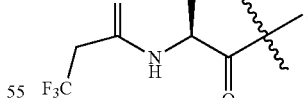 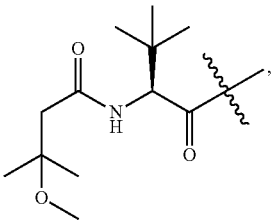
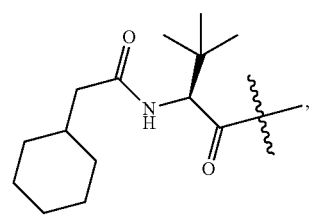
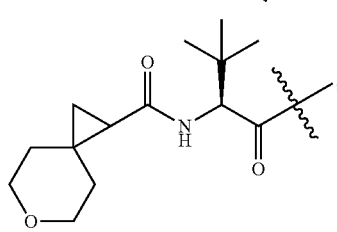

-continued
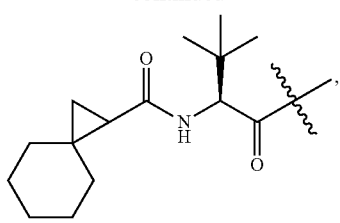
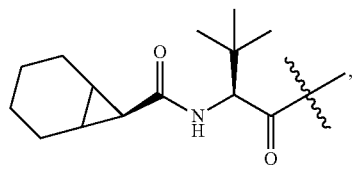
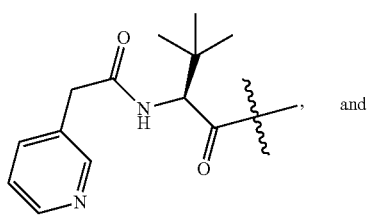
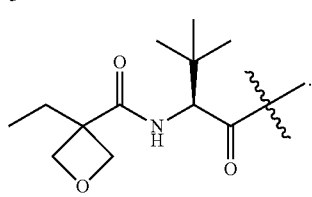
In other embodiments, R is an alkoxy or cycloalkoxy such that examples of $R_1$ include
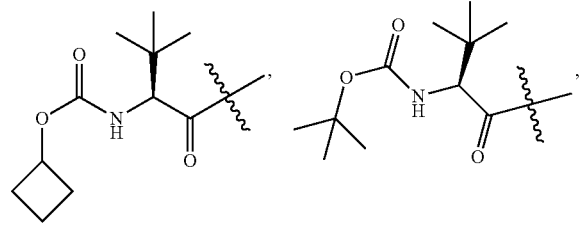
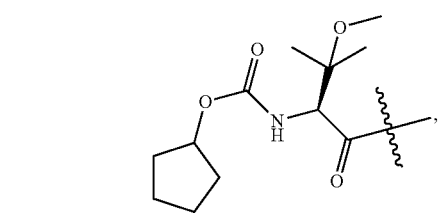
-continued
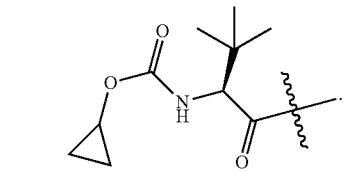
, and
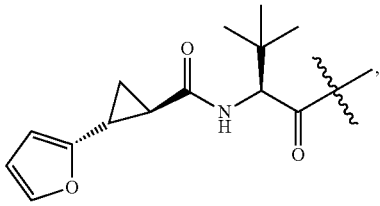
In further embodiments, R is cyclopropyl optionally substituted with cyano, halo, aliphatic, cycloaliphatic, heterocycloaliphatic, aryl, or heteroaryl such that $R_1$ is selected from the group consisting of:
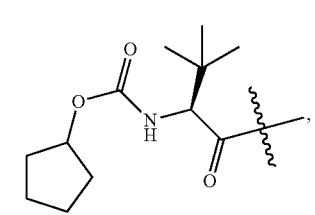
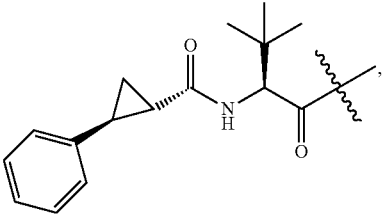

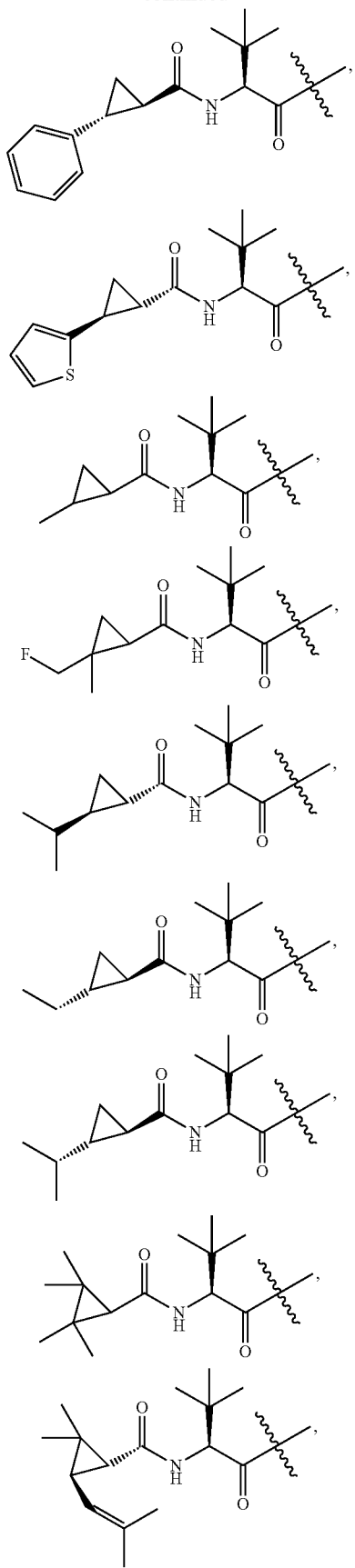
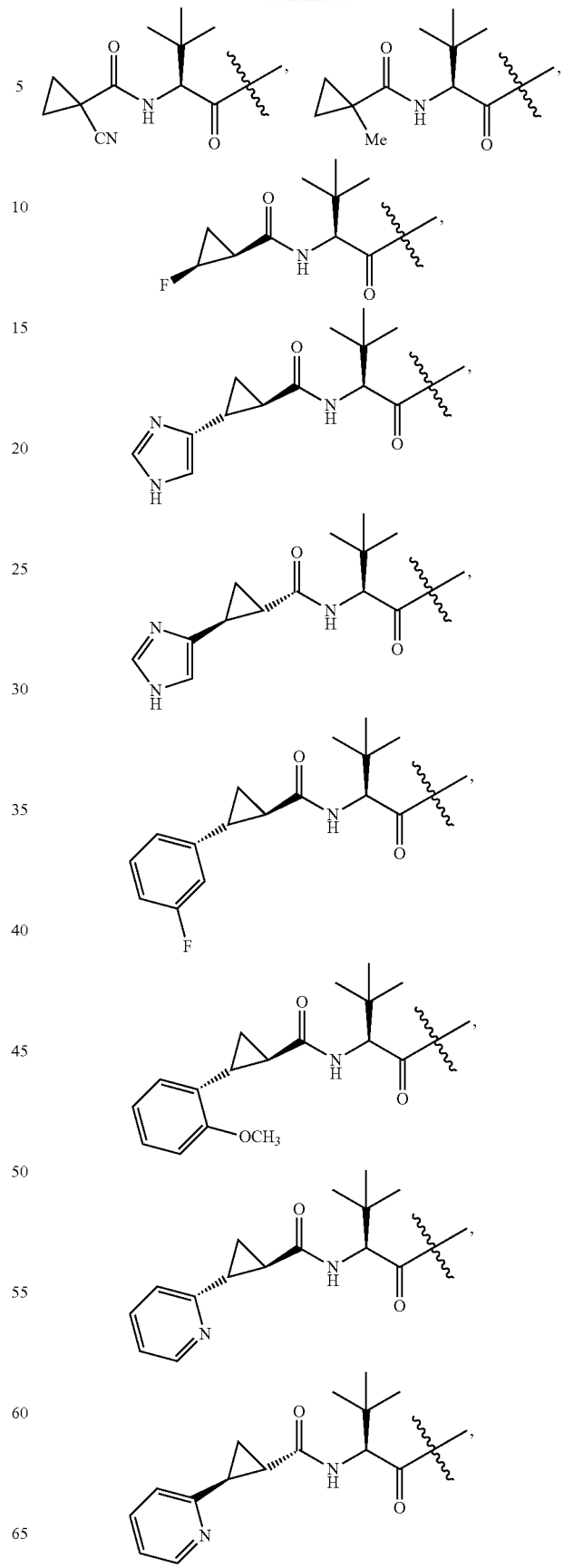

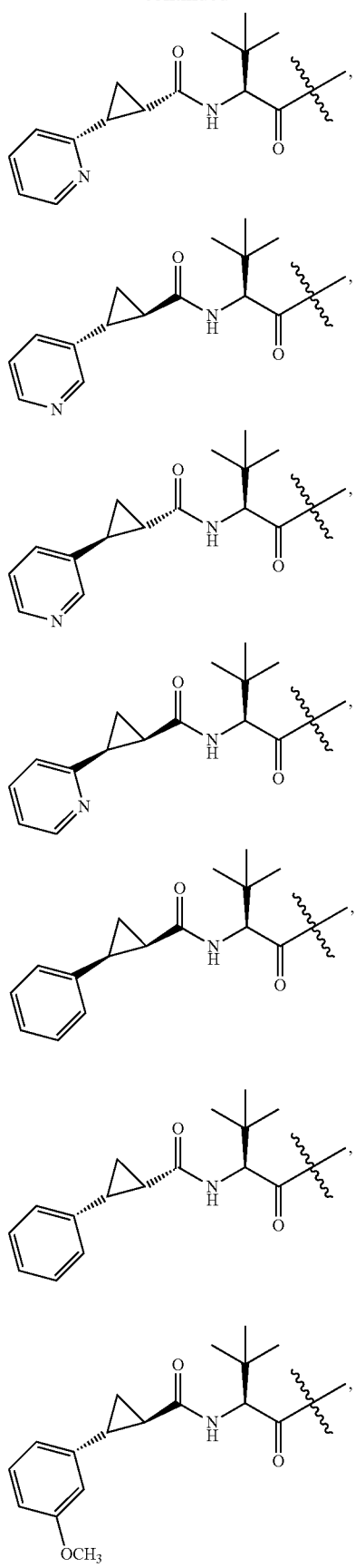
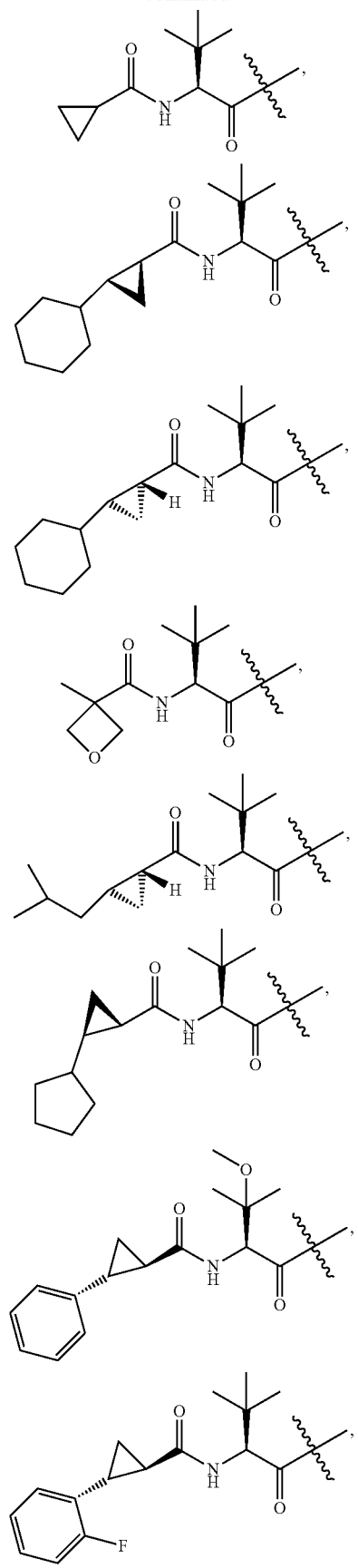

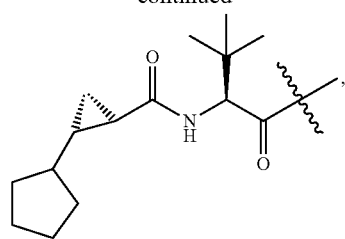
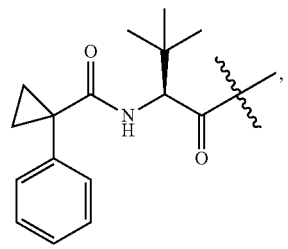
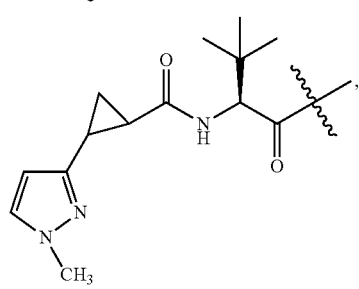
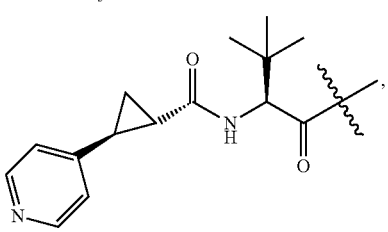
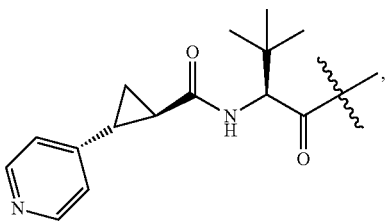
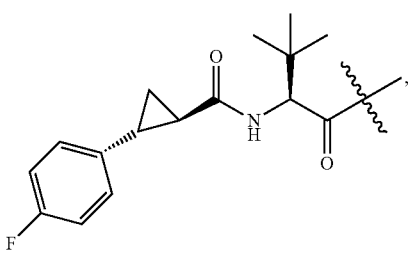
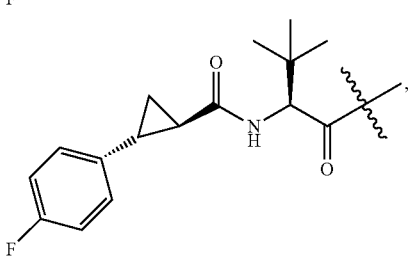
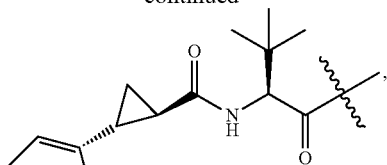
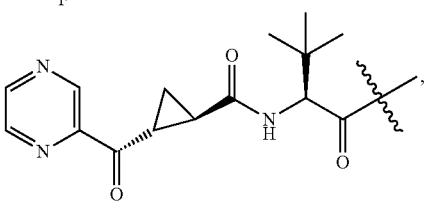
and
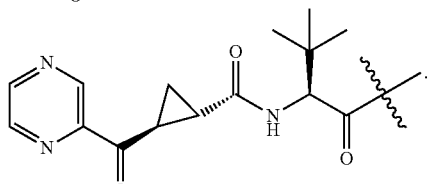
In some embodiments, $R_1$ is
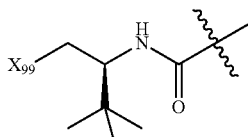
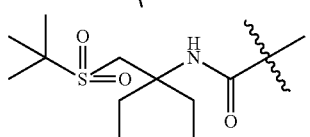
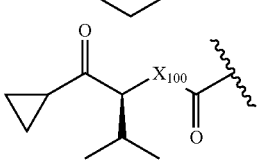
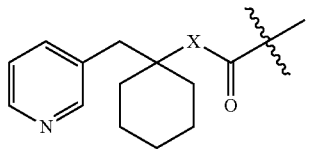
wherein $X_{99}$ is OR, OC(NH)R, or
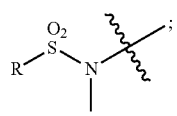
$X_{100}$ is NH, $CH_2$; and R is defined above.
Additional examples of $R_1$ are illustrated in PCT publications WO 2004/103996 A1, WO 2004/72243 A2, WO 03/064456 A1, WO 03/64455 A2, WO 03/064416 A1, and U.S. Patent Publication US 2005/0090450, as well as those 2. Substituent $R_2$:

In several embodiments, $R_2$ is —$Z^B R_5$, wherein each $Z^B$ is independently a bond or an optionally substituted branched or straight $C_{1-12}$ aliphatic chain wherein up to three carbon units of $Z^B$ are optionally and independently replaced by —C(O)—, —C(S)—, —C(O)NR$^B$—, —C(O)NR$^B$NR$^B$—, —C(O)O—, —NR$^B$C(O)O—, —NR$^B$C(O)NR$^B$—, —NR$^B$-NR$^B$—, —S—, —SO—, —SO$_2$—, —NR$^B$—, —SO$_2$NR$^B$—, or —NR$^B$SO$_2$NR$^B$—, provided that SO, SO$_2$, or —SO$_2$NR$^B$— is not directly bound to the carbonyl of formula (I). Each $R_5$ is independently $R^B$, halo, —OH, —CN, —NO$_2$, —NH$_2$, or —OCF$_3$. Each $R^B$ is independently hydrogen, an optionally substituted aliphatic, an optionally substituted cycloaliphatic, an optionally substituted aryl, or an optionally substituted heteroaryl.

In still further embodiments, $R_2$ is —$Z_1$—$V_1$—$Z_2$—$V_2$—$Z_3$—$V_3$ each of $V_1$, $V_2$, and $V_3$ is independently a bond, an optionally substituted aliphatic, an optionally substituted cycloaliphatic, an optionally substituted heterocycloaliphatic, an optionally substituted aryl, an optionally substituted heteroaryl, or a hydrogen when $V_1$, $V_2$, $V_3$ is the terminal group of $R_2$; each of $Z_1$, $Z_2$, and $Z_3$ is independently a bond, —C(O)—, —C(O)C(O)—, —C(S)—, —C(O)N(Q$_6$)-, —N(Q$_6$)C(O)—, —C(O)C(O)N(Q$_6$)-, —O—, SO—, —SO$_2$—, —N(Q$_6$)SO$_2$—, —N(Q$_6$)C(O)N(Q$_6$)-, —N(Q$_6$)C(S)N(Q$_6$)-, —N(Q$_6$)-, —N(Q$_6$)SO$_2$—, —SO$_2$N(Q$_6$)-, —C(O)N(Q$_6$)SO$_2$—, —SO$_2$N(Q$_6$)C(O)—, or hydrogen when $Z_1$, $Z_2$, or $Z_3$ is the terminal group of $R_2$; and each $Q_6$ is independently hydrogen, or an optionally substituted aliphatic.

In other embodiments, $R_2$ is an optionally substituted (aliphatic)amino wherein the aliphatic portion of $R_2$ is —$Z_2$—$V_2$—$Z_3$—$V_3$ or —$Z_3$—$V_3$ wherein each of $Z_2$ and $Z_3$ is independently a bond, —C(O)—, —N(Q$_5$)-, —CH(OH)—, —C(O)N(Q$_6$)-, or —C(O)C(O)N(Q$_6$)-; $V_2$ is independently a bond, an optionally substituted aliphatic, or an optionally substituted cycloaliphatic; and $V_3$ is hydrogen, an optionally substituted aliphatic, or an optionally substituted cycloaliphatic.

In still further embodiments, $Z_2$ is —CH(OH)—, $V_2$ is a bond, and $Z_3$ is —C(O)N(Q$_6$)- such that $R_2$ is —N(Q$_6$)-CH(OH)—C(O)—N(V$_3$)(Q$_6$).

In certain embodiments, $R_2$ is an optionally substituted (aliphatic)amino, optionally substituted (cycloaliphatic)amino, an optionally substituted alkoxy, or hydroxy.

In still another embodiment, $R_2$ is an alkoxy optionally substituted with 1-3 of halo, hydroxy, aliphatic, cycloaliphatic, or heterocycloaliphatic.

In several embodiments, $R_2$ is amino. Examples of $R_2$ include a mono-substituted amino. Additional examples of $R_2$ include (cycloaliphatic(carbonyl(carbonyl(alkyl))))amino (amino(carbonyl(carbonyl(aliphatic))))amino, (aliphatic(carbonyl(carbonyl(aliphatic))))amino, or (aryl(amino(carbonyl(carbonyl(aliphatic)))))amino, each of which is optionally substituted with 1 to 3 substituents.

In several embodiments, $R_2$ is —NR$_{2Z}$R'$_{2Z}$, —SR$_{2Y}$, or —NR$_{2Y}$—CR$_{2X}$R'$_{2X}$-L$_1$-NR$_{2Z}$—R$_{2W}$, wherein R$_{2Y}$ is independently hydrogen, an optionally substituted aliphatic, an optionally substituted cycloaliphatic, an optionally substituted heterocycloaliphatic, an optionally substituted aryl, or an optionally substituted heteroaryl; each R$_{2W}$ is independently hydrogen, optionally substituted aliphatic, optionally substituted aryl, optionally substituted heteroaryl, optionally substituted heterocycloaliphatic, or optionally substituted cycloaliphatic; each R$_{ex}$ and R'$_{2X}$ is independently hydrogen, an optionally substituted aliphatic, an optionally substituted heteroaryl, an optionally substituted phenyl, an optionally substituted cycloaliphatic, an optionally substituted heterocycloaliphatic; or R$_{2X}$ and R'$_{2X}$ together with the atom to which they are both attached form an optionally substituted 3 to 7 membered cycloaliphatic or heterocycloaliphatic ring; each L$_1$ is —CH$_2$—, —C(O)—, —C(O)C(O)—, —C(O)O—, —S(O)—, or —SO$_2$—; each R$_{2Z}$ or R'$_{2Z}$ is hydrogen, an optionally substituted aliphatic, an optionally substituted cycloaliphatic, an optionally substituted heterocycloaliphatic, an optionally substituted aryl, or an optionally substituted heteroaryl; or R$_{2Z}$ and R'$_{2Z}$ together with the nitrogen to which they are both attached may form an optionally substituted 3 to 7 membered heterocycloaliphatic ring.

In several embodiments, each R$_{2X}$ and R'$_{2X}$ is independently hydrogen, or optionally substituted aliphatic, optionally substituted cycloaliphatic, or optionally substituted (cycloaliphatic)aliphatic.

In several embodiments, L$_1$ is —C(O)C(O)— or —SO$_2$—.

In several other embodiments, each R$_{2W}$ is hydrogen or optionally substituted cycloaliphatic.

In several embodiments, R$_2$ is —NH—CHR$_{2X}$—C(O)—C(O)—N(R$_{2Z}$)R$_{2W}$.

In several embodiments, R$_2$ is —NH—CHR$_{2X}$—CH(OH)—C(O)—N(R$_{2Z}$)R$_{2W}$.

In several embodiments, R$_2$ is —NH—CHR$_{2X}$—C(O)—C(O)—NHR$_{2Z}$ wherein —NHR$_{2Z}$ is NH-cyclopropyl, —NH-Me, —NH-Et, —NH-iPr, —NH-nPr.

In several embodiments R$_2$ is —NR$_{2Z}$R'$_{2Z}$, —SR$_{2Z}$ wherein each R$_{2Z}$ and R'$_{2Z}$ is independently hydrogen, alkyl, cycloalkyl or aralkyl. Non-limiting examples of R$_{2Z}$ include methyl, ethyl, t-butyl, cyclopentyl, cyclohexyl and benzyl.

In other embodiments R$_2$ is (—NH—CR$_{2X}$R'$_{2X}$-L$_1$-C(O))$_i$-M; wherein each M is independently —OH, R$_{2X}$, —NR$_{2Z}$R'$_{2Z}$, or —OR$_{2X}$, each i is 1 or 2, and L$_1$, R$_{2Z}$, R$_{2X}$, and R'$_{2Z}$ are defined above.

In several embodiments R$_2$ is (—NH—CR$_{2Z}$R'$_{2Z}$— L$_1$-C(O))$_i$-M wherein L$_1$ is —C(O)—, i is 1, and M is independently R$_{2X}$, —N(R$_{2X}$R'$_{2X}$), —OR$_{2X}$, —NHSO$_2$R$_{2X}$, or —SR$_{2X}$.

In some embodiments, R'$_{2Z}$ is H and R$_{2Z}$ is an aliphatic, (aryl)aliphatic or cycloaliphatic. Non-limiting examples of R$_{2X}$ include hydrogen,

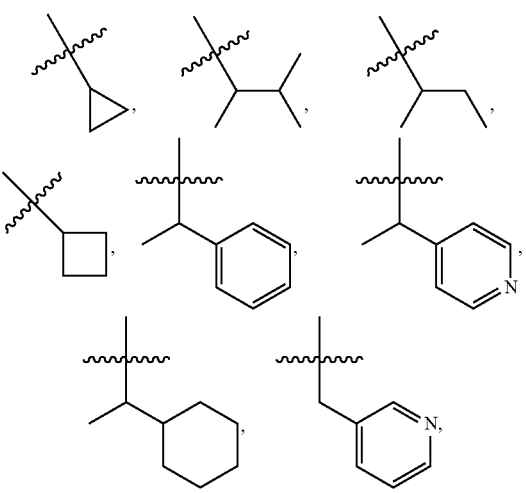

-continued

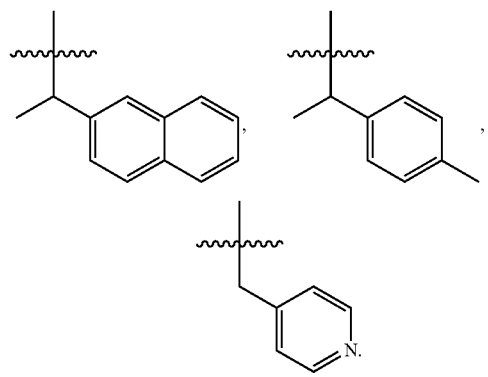

In some embodiments, R'$_{2X}$ is H and R$_{2X}$ is an optionally substituted aliphatic, optionally substituted aryl, optionally substituted aralkyl, optionally substituted heteroaliphatic or optionally substituted heteroaralkyl. Some non-limiting examples of R$_{2X}$ include

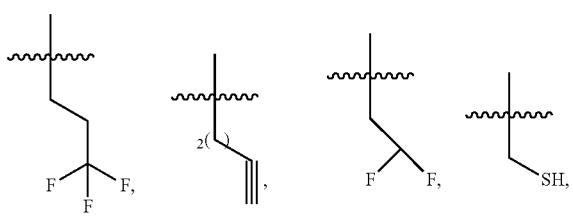

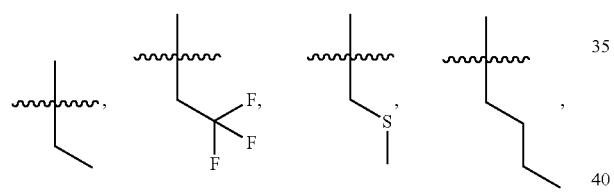

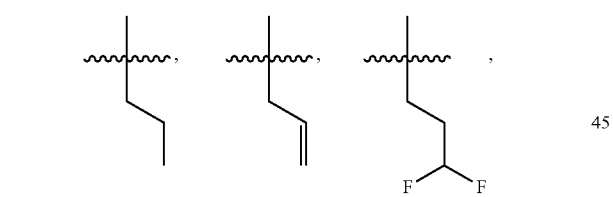

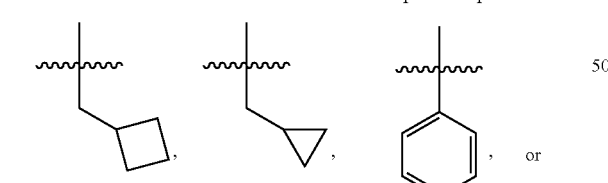

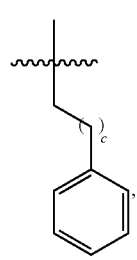

where c is 0-3.

In several embodiments, R$_2$ is

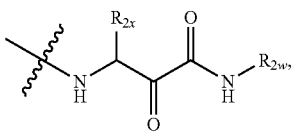

wherein R$_{2X}$ is

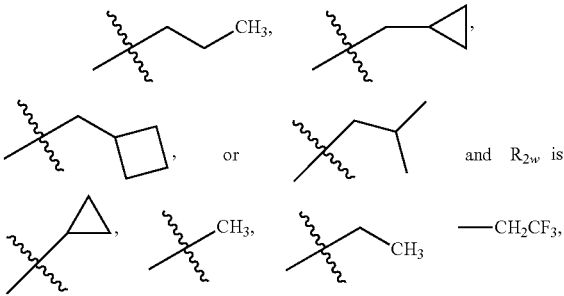

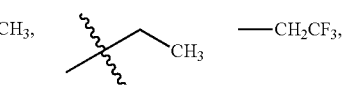

or hydrogen.

In some embodiments, R$_2$ is selected from the group consisting of

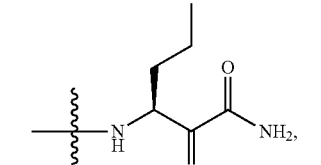

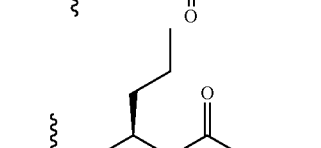

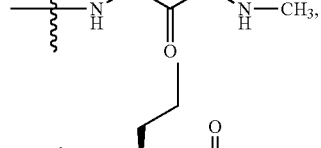

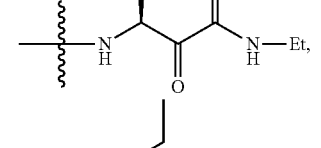

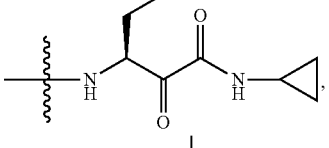

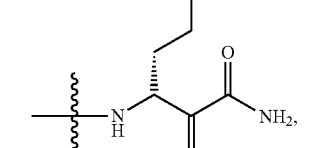

In some embodiments, $R_2$ is selected from the group consisting of:
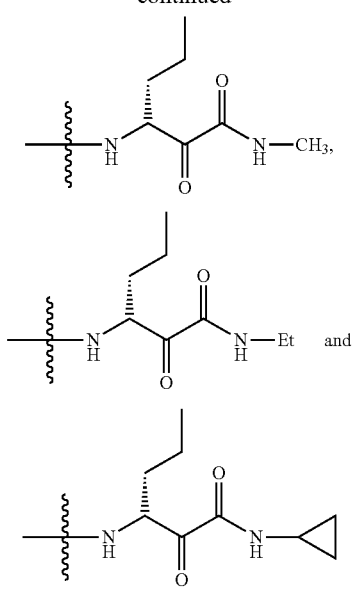
In some embodiments, $R_2$ is selected from the group consisting of:
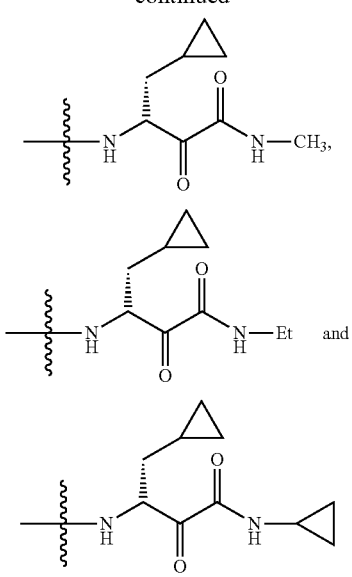

In some embodiments, $R_2$ is

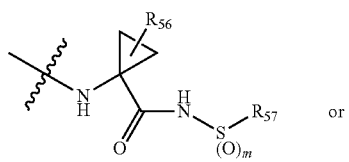

or

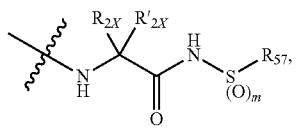

wherein each $R_{56}$ is independently optionally substituted $C_{1-6}$ aliphatic; optionally substituted aryl, optionally substituted heteraryl, optionally substituted cycloaliphatic, or optionally substituted heterocycloaliphatic; each $R_{57}$ is independently optionally substituted aliphatic, optionally substituted aryl, optionally substituted aliphatic, optionally substituted heteroaryl, optionally substituted aliphatic, optionally substituted cycloaliphatic or optionally substituted amino; and m is 1 or 2; and each $R_{2X}$ and $R'_{2X}$ is independently hydrogen, an optionally substituted aliphatic, an optionally substituted cycloaliphatic, an optionally substituted heterocycloaliphatic, an optionally substituted aryl, or an optionally substituted heteroaryl; or $R_{2X}$ and $R'_{2X}$ together with the atom to which they are both attached form an optionally substituted 3 to 7 membered cycloaliphatic or heterocycloaliphatic ring.

In some other embodiments, $R_2$ is

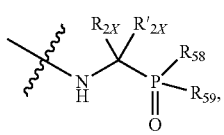

wherein $R_{58}$ and $R_{59}$ are each independently selected from optionally substituted aliphatic, optionally substituted alkoxy, optionally substituted aryloxy, optionally substituted heteroaryloxy, optionally substituted (cycloaliphatic)oxy, optionally substituted (heterocycloaliphatic)oxy optionally substituted aryl, optionally substituted heteroaryl, optionally substituted cycloaliphatic or optionally substituted amino; and each $R_{2X}$ and $R'_{2X}$ is independently hydrogen, an optionally substituted aliphatic, an optionally substituted cycloaliphatic, an optionally substituted heterocycloaliphatic, an optionally substituted aryl, or an optionally substituted heteroaryl; or $R_{2X}$ and $R'_{2X}$ together with the atom to which they are both attached form an optionally substituted 3 to 7 membered cycloaliphatic or heterocycloaliphatic ring.

In several embodiments, a portion of $R_1$ and a portion of $R_2$ together can form a cyclic structure, e.g., a 5- to 18-membered cycloheteroaliphatic ring. Some non-limiting example include

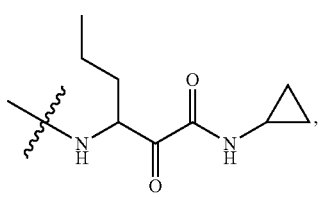

and

In several embodiments, $R_2$ is one selected from

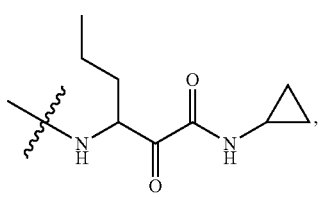

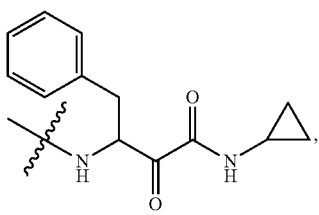

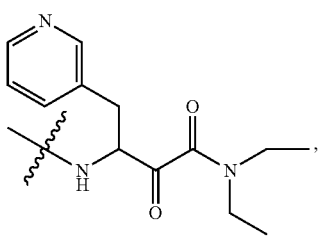

61
-continued
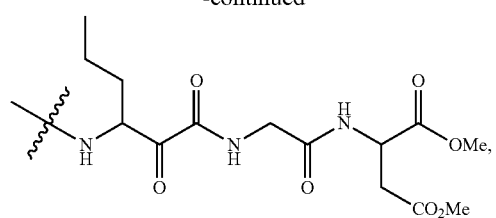
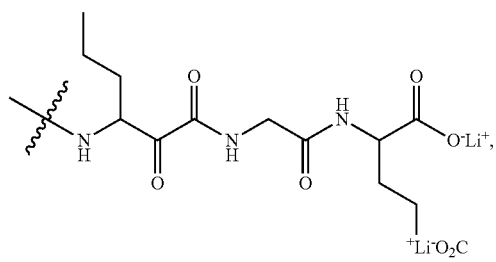
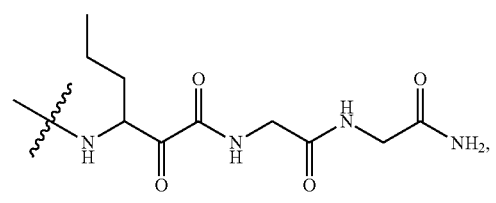
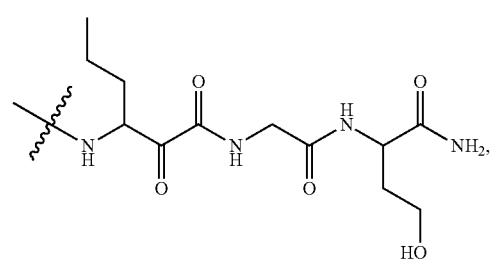
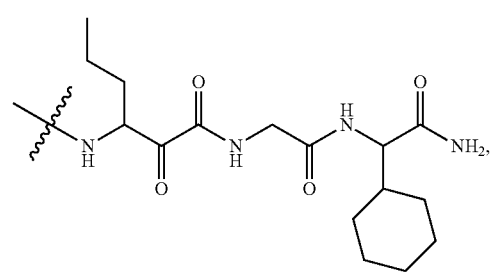
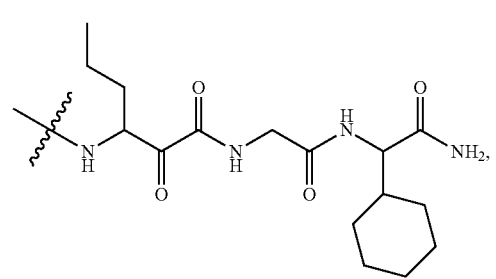
62
-continued
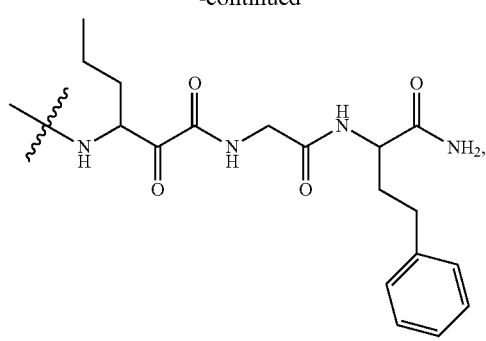
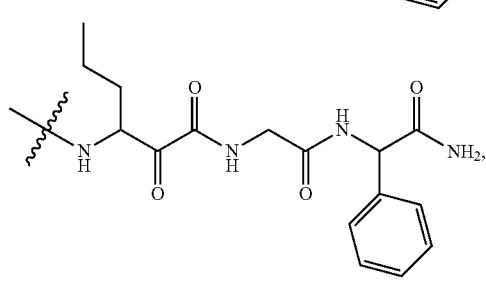
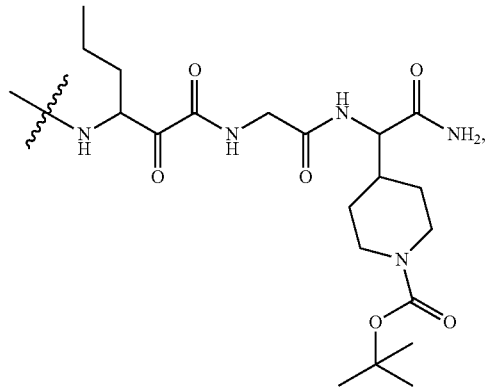
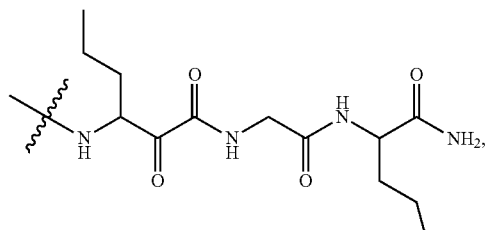
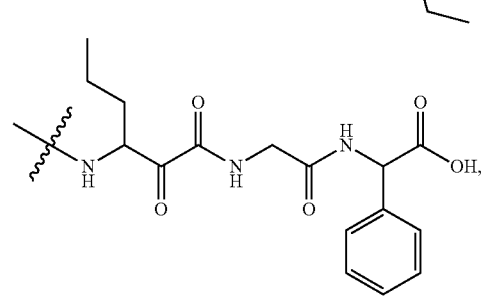
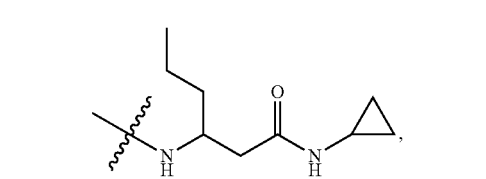

63
-continued
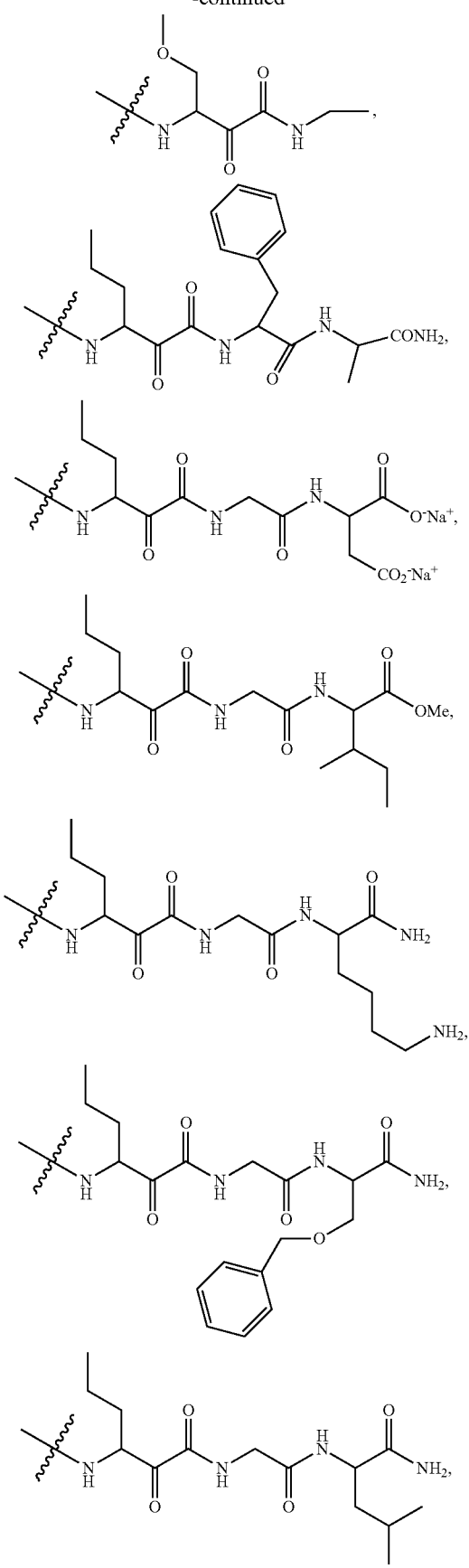
64
-continued
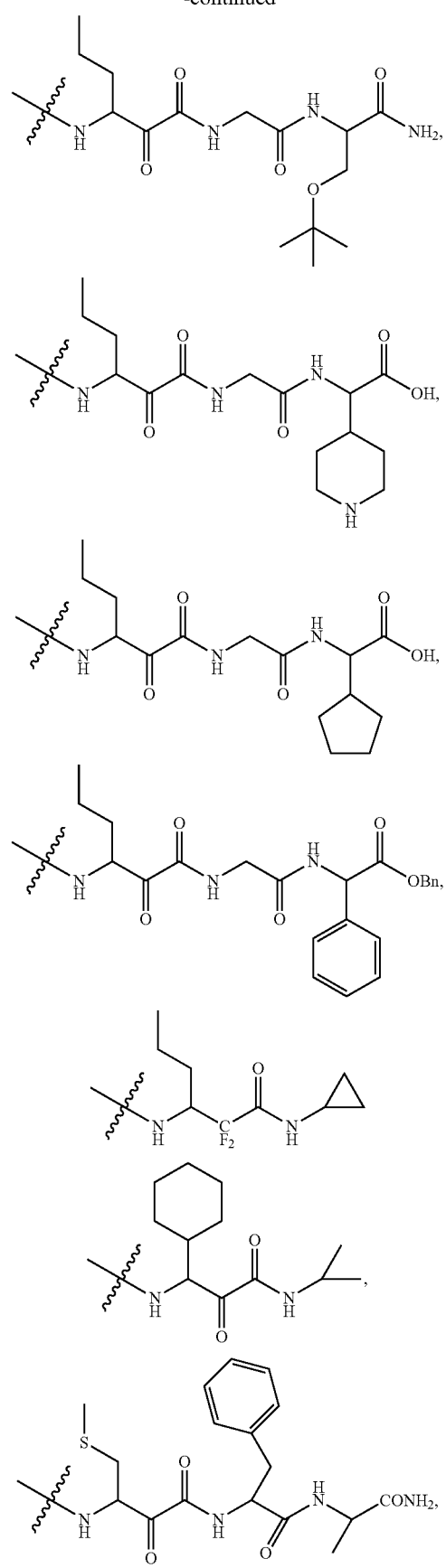

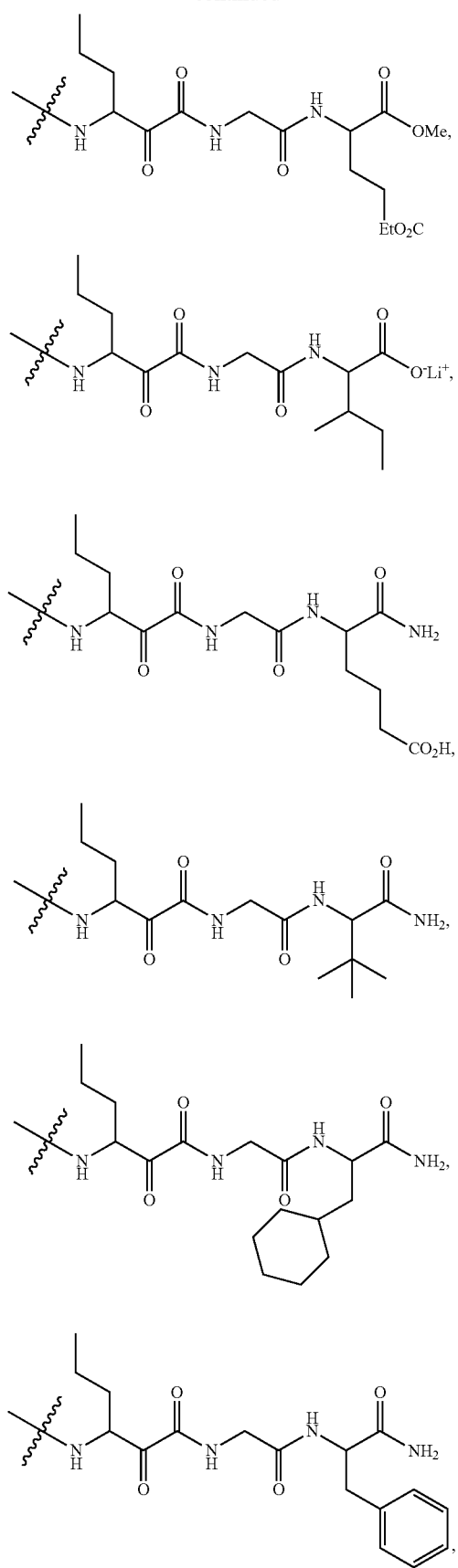
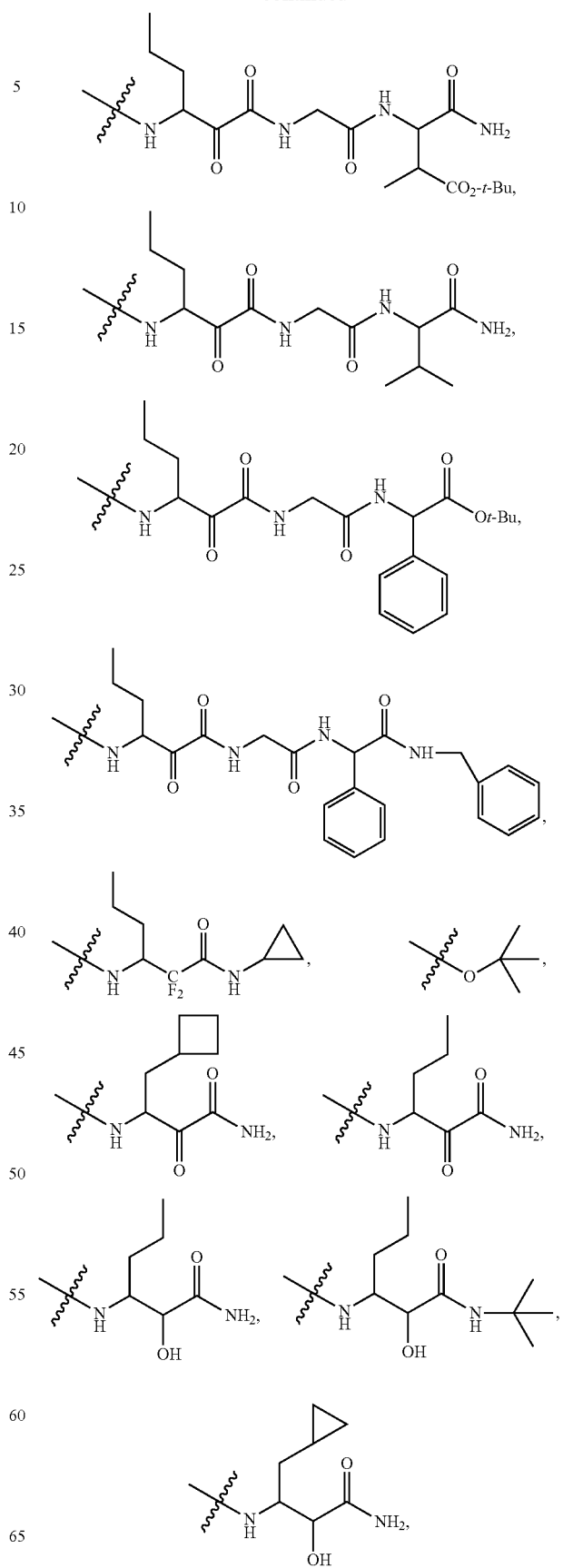

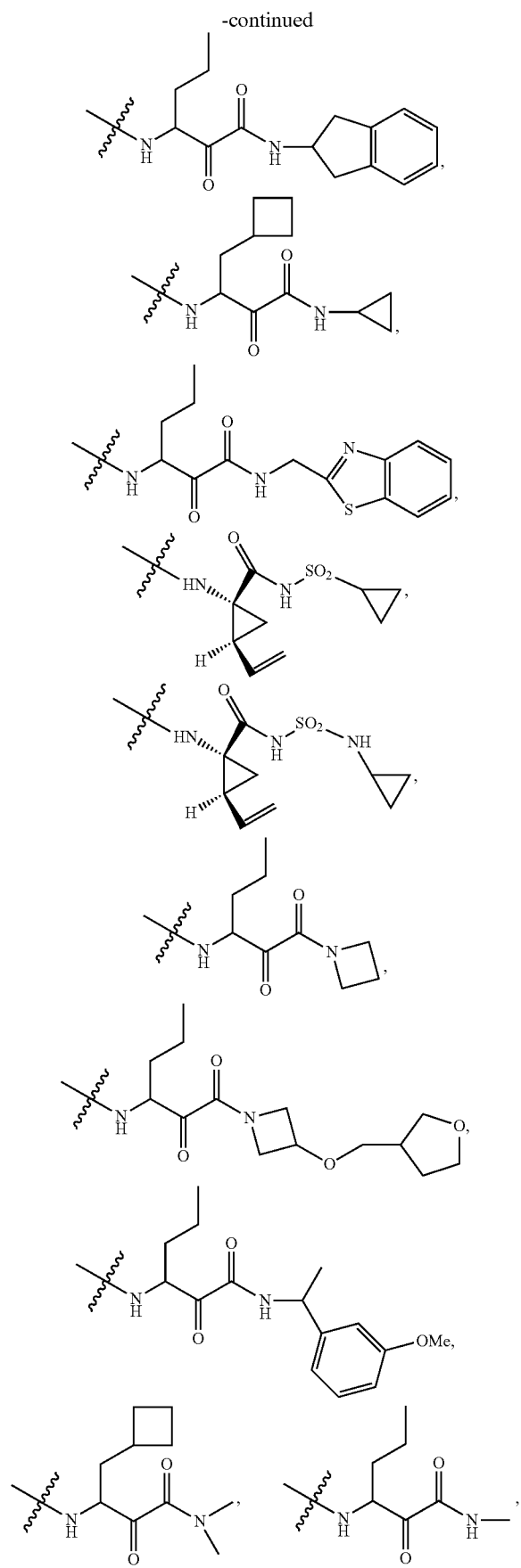
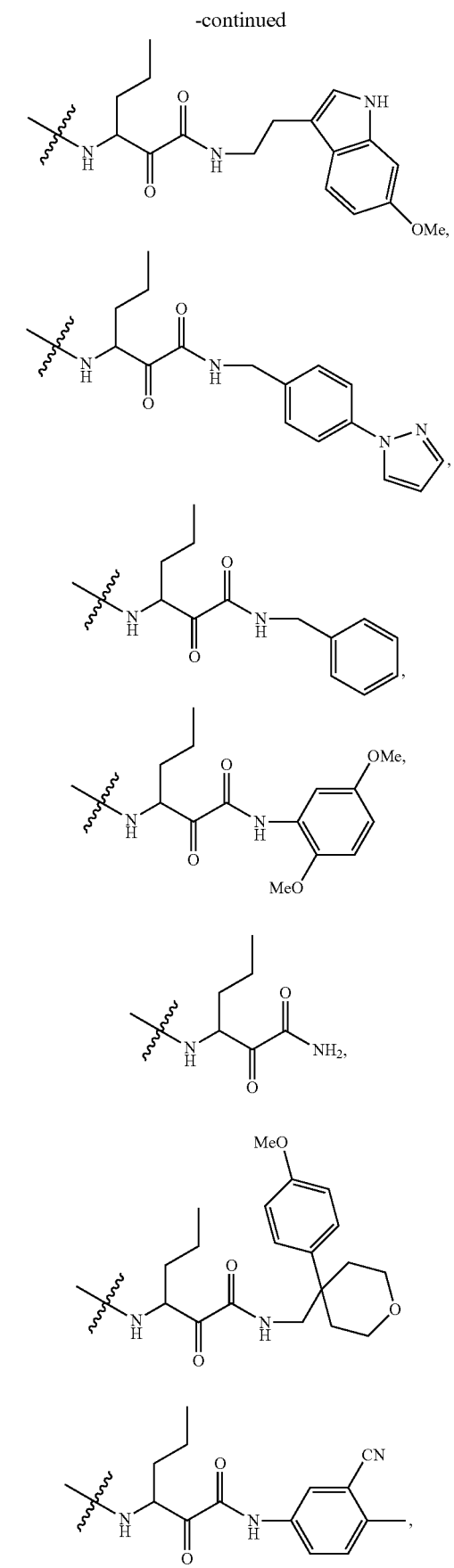

69
-continued
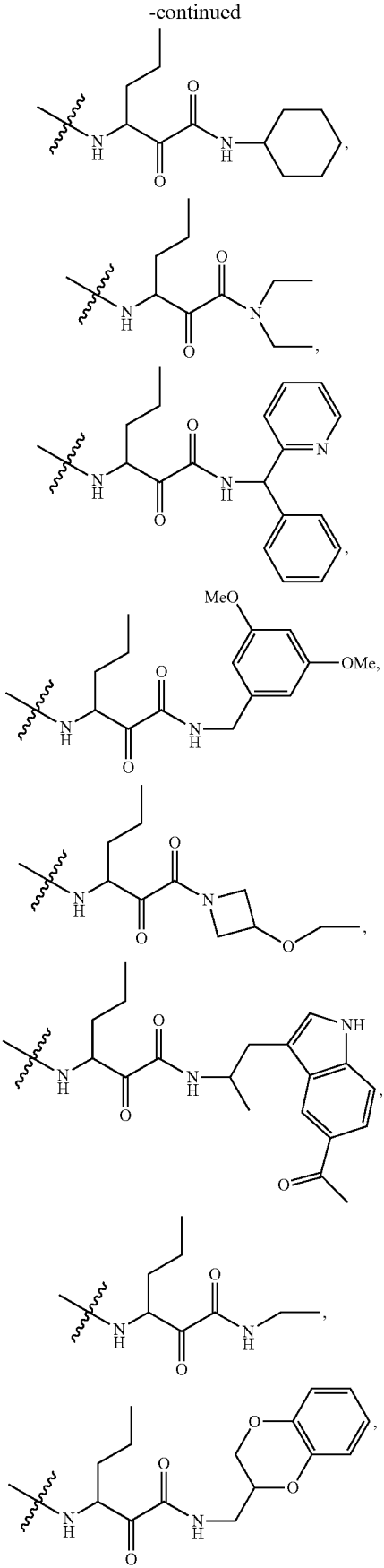
70
-continued
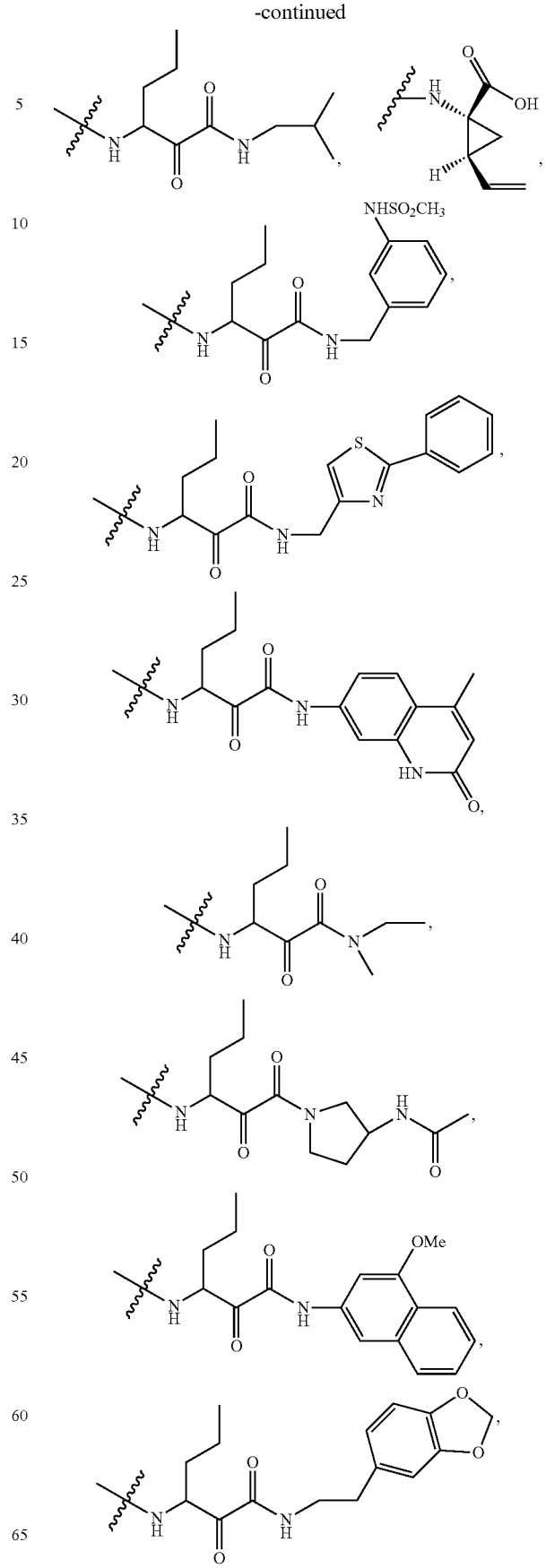

-continued
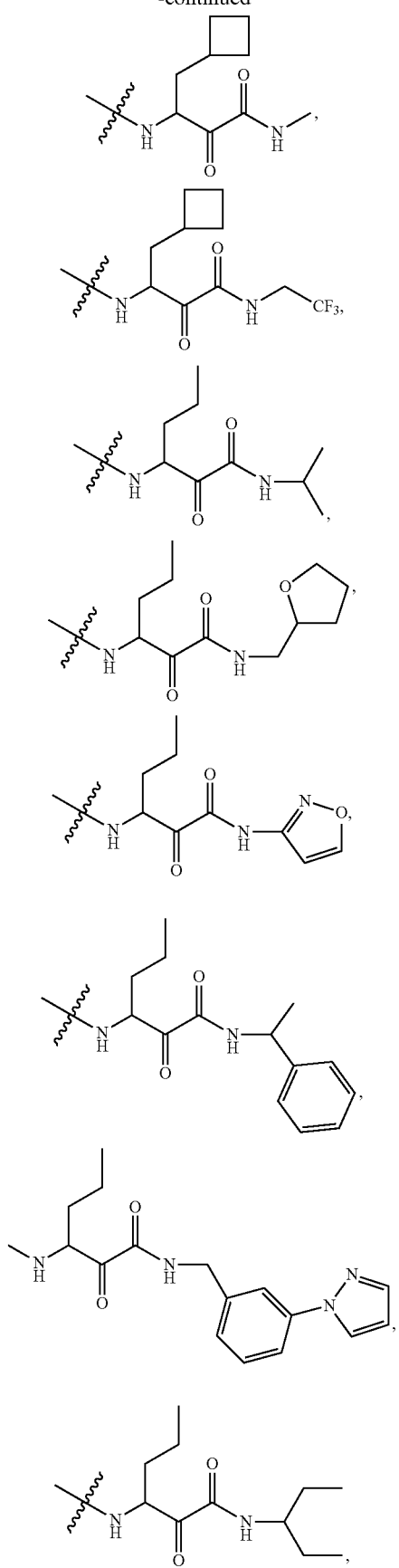
-continued
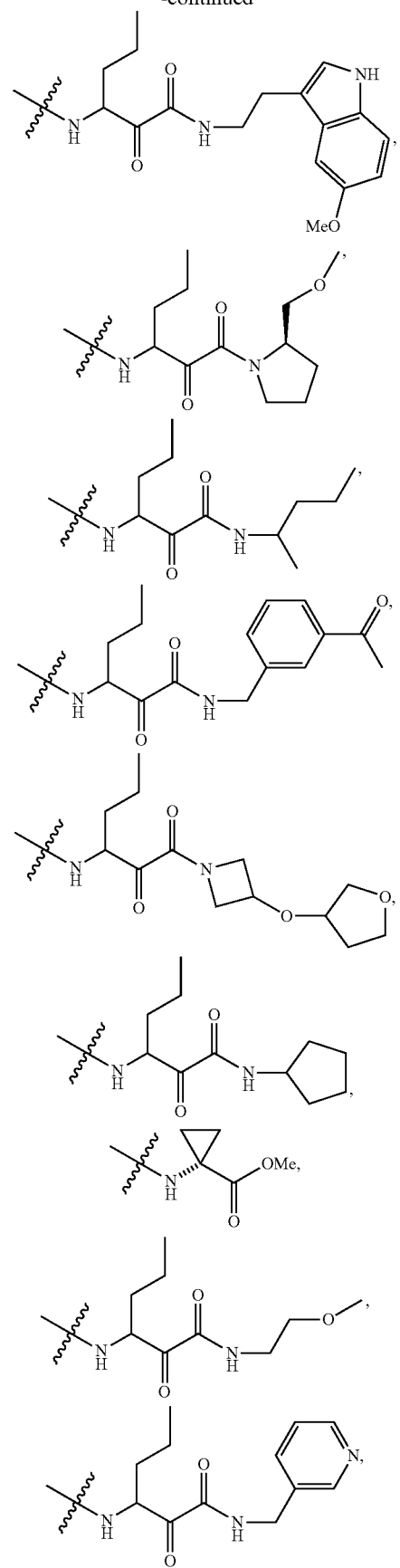

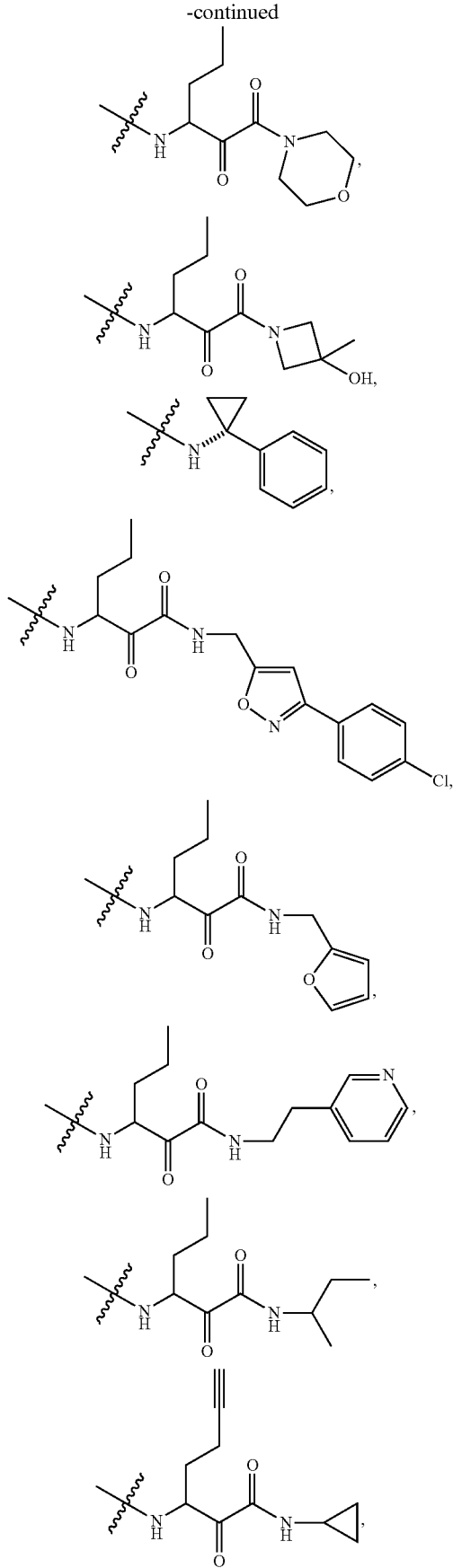
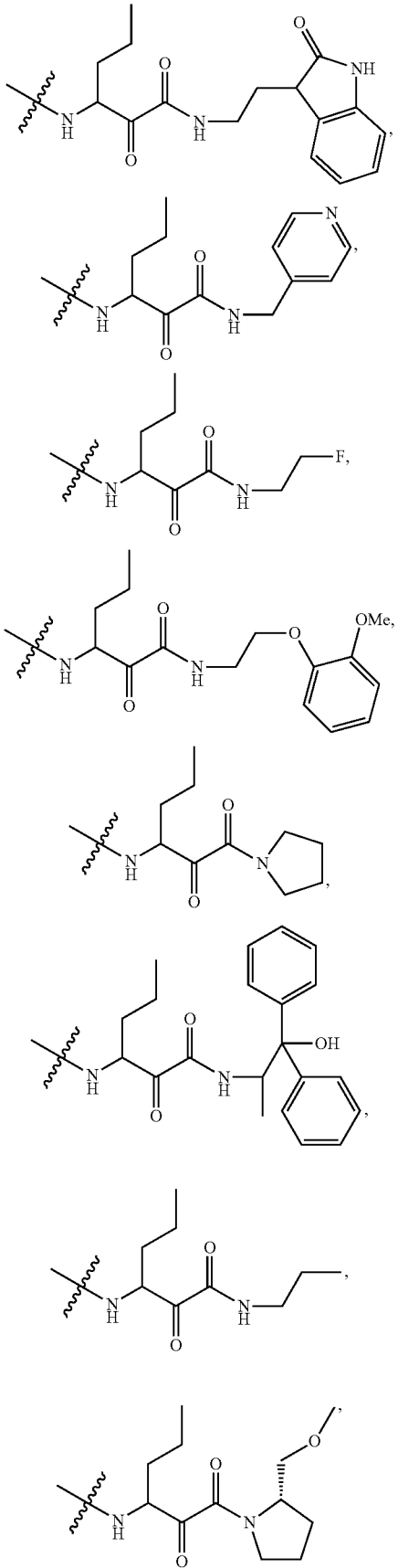

75
-continued
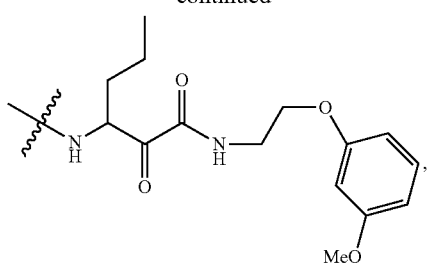
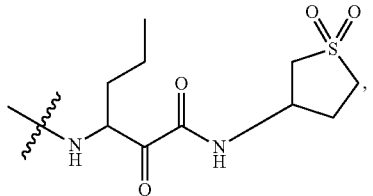
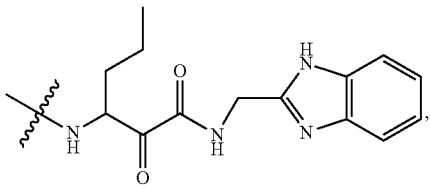
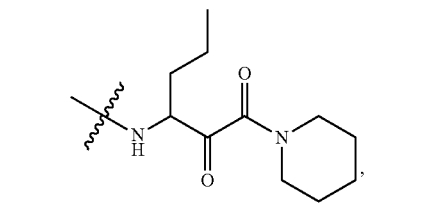
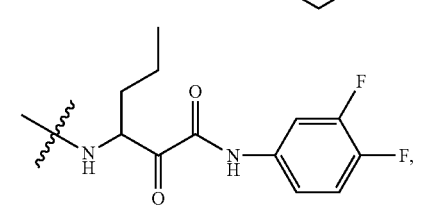
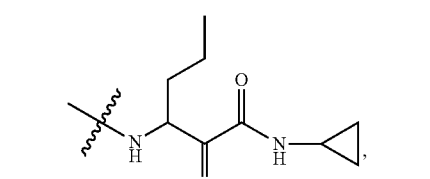
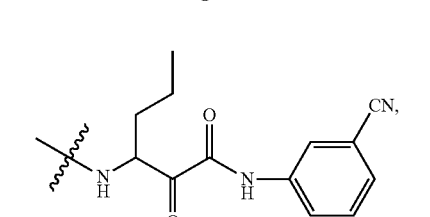
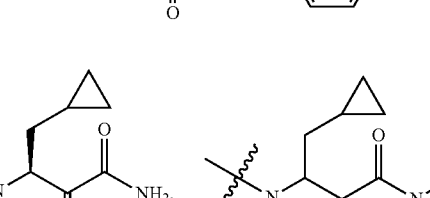
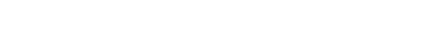
76
-continued
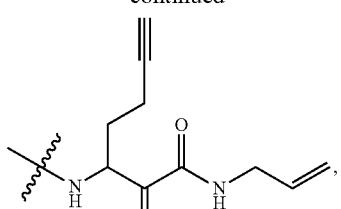
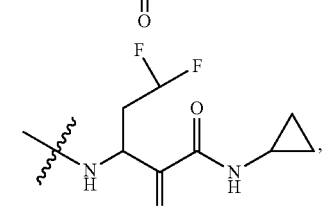
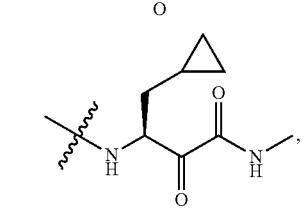
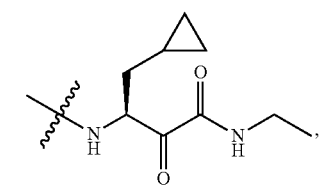
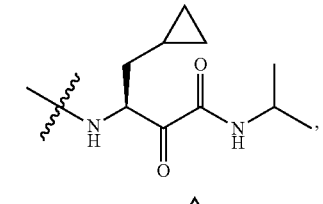
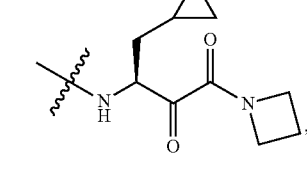
In some specific embodiments, $R_2$ is
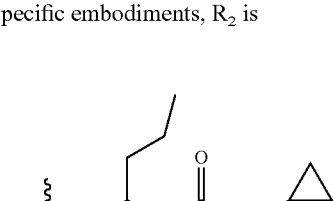
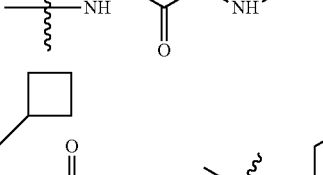
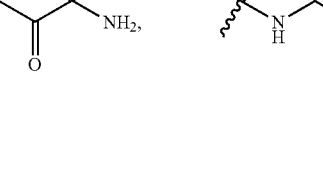

-continued

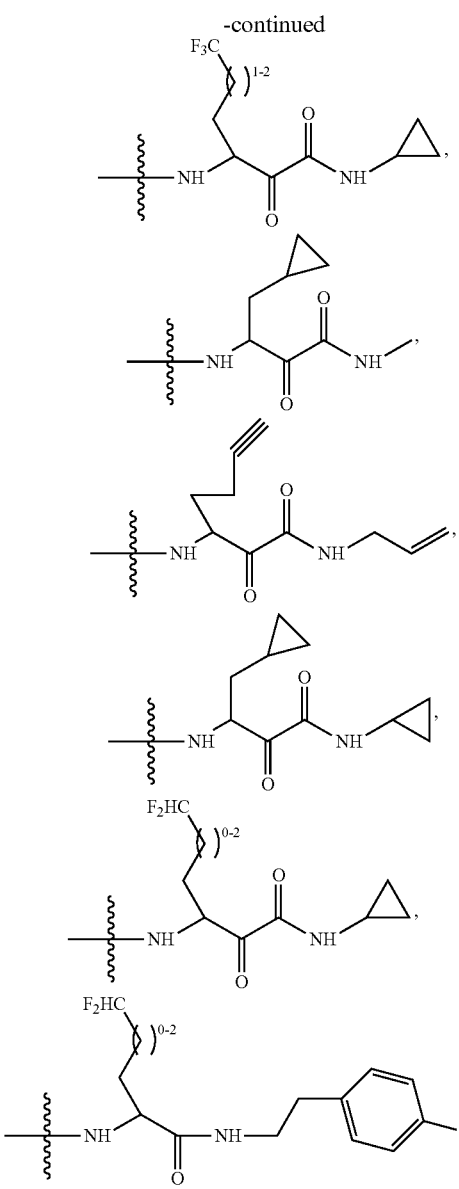

where X$_{200}$ is —OX$_{202}$ or —X$_{202}$, and X$_{202}$ is aliphatic, cycloaliphatic, heterocycloaliphatic, aryl, or heteroaryl.

In other embodiments, R$_2$ is

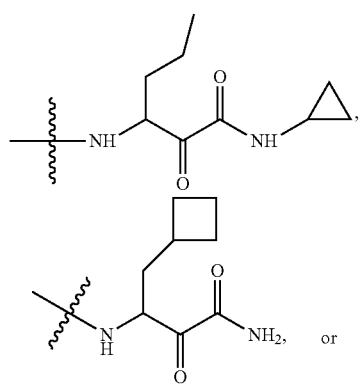

-continued

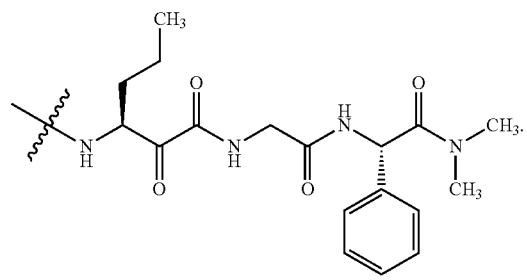

In some other embodiments, R$_2$ is

Additional examples of R$_2$ are illustrated in PCT publications WO 2004/103996 A1, WO 2004/72243 A2, WO 03/064456 A1, WO 03/64455 A2, WO 03/064416 A1, and U.S. Patent Publication US 2005/0090450, as well as those other publications referenced herein, each of which is incorporated in its entirety by reference.

3. Substituent R$_3$:

Each R$_3$ is an aliphatic, a cycloaliphatic, a heterocycloaliphatic, an aryl, or a heteroaryl, each of which is optionally substituted.

In several embodiments, each R$_3$ is independently —Z$^C$R$_6$, wherein each Z$^C$ is independently a bond or an optionally substituted aliphatic wherein up to two carbon units of Z$^C$ are optionally and independently replaced by —C(O)—, —CS—, —C(O)NR$^C$—, —C(O)NR$^C$NR$^C$—, —C(O)O—, —NR$^C$C(O)O—, —O—, —NR$^C$C(O)NR$^C$—, —NR$^C$NR$^C$—, —S—, —SO—, —SO$_2$—, —NR$^C$—, —SO$_2$NR$^C$—, or —NR$^C$SO$_2$NR$^C$—. Each R$_6$ is independently R$^C$, halo, —OH, —CN, —NO$_2$, —NH$_2$, alkoxy, or haloalkoxy. Each R$^C$ is independently hydrogen, an optionally substituted aliphatic group, an optionally substituted cycloaliphatic, an optionally substituted heterocycloaliphatic, an optionally substituted aryl, or an optionally substituted heteroaryl. However, in many embodiments, when Z$^C$ is a bond and R$_6$ is R$^C$, then R$^C$ is independently an optionally substituted aliphatic group, an optionally substituted cycloaliphatic, an optionally substituted heterocycloaliphatic, an optionally substituted aryl, or an optionally substituted heteroaryl.

In still other embodiments, each R$_3$ is an optionally substituted aliphatic, amino, sulfonyl, sulfanyl, sulfinyl, sulfonamide, sulfamide, sulfo, —O—R$_{3,4}$, an optionally substituted cycloaliphatic, an optionally substituted heterocycloaliphatic, an optionally substituted aryl, or an optionally substituted heteroaryl; and each R$_{3,4}$ is independently an optionally substituted aliphatic, an optionally substituted cycloaliphatic, an optionally substituted heterocycloaliphatic, an optionally substituted aryl, or an optionally substituted heteroaryl.

In several embodiments, R$_3$ is an optionally substituted aryl. In some examples, R$_3$ is a monocyclic, bicyclic, or tricyclic aryl, each of which is optionally substituted. For example, R$_3$ is an optionally substituted phenyl, an optionally substituted naphthyl, or an optionally substituted anthracenyl. In other examples, $R_3$ is a monocyclic, bicyclic, or tricyclic aryl, each of which is optionally substituted with 1 to 4 of halo, hydroxy, cyano, nitro, aliphatic, haloaliphatic, (aliphatic)oxy, (halo(aliphatic))oxy, (aliphatic(oxy(aryl)))oxy, aryl, heteroaryl, haloaryl, cycloaliphatic, heterocycloaliphatic, or combinations thereof. In several examples, $R_3$ is an optionally substituted fused bicyclic aryl. In several examples, $R_3$ is an optionally substituted fused tricyclic aryl.

In several embodiments, $R_3$ is an optionally substituted heteroaryl. In several examples, $R_3$ is a monocyclic or bicyclic heteroaryl, each of which is optionally substituted with 1 to 4 of halo, hydroxy, cyano, nitro, aliphatic, haloaliphatic, (aliphatic)oxy, (halo(aliphatic))oxy, (aliphatic(oxy(aryl))) oxy, aryl, heteroaryl, haloaryl, cycloaliphatic, heterocycloaliphatic, or combinations thereof.

In some embodiments, $R_3$ is optionally substituted aliphatic such as methyl, ethyl or propyl, each of which is optionally substituted.

According to other embodiments, $R_3$ is an optionally substituted aliphatic.

According to other embodiments, $R_3$ is an optionally substituted $C_{1-5}$ aliphatic.

In several examples, $R_3$ is

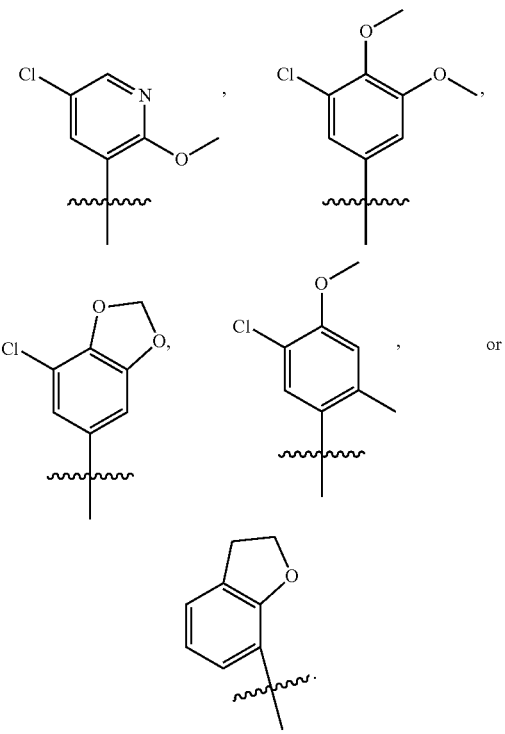

In several embodiments, $R_3$ is one selected from:

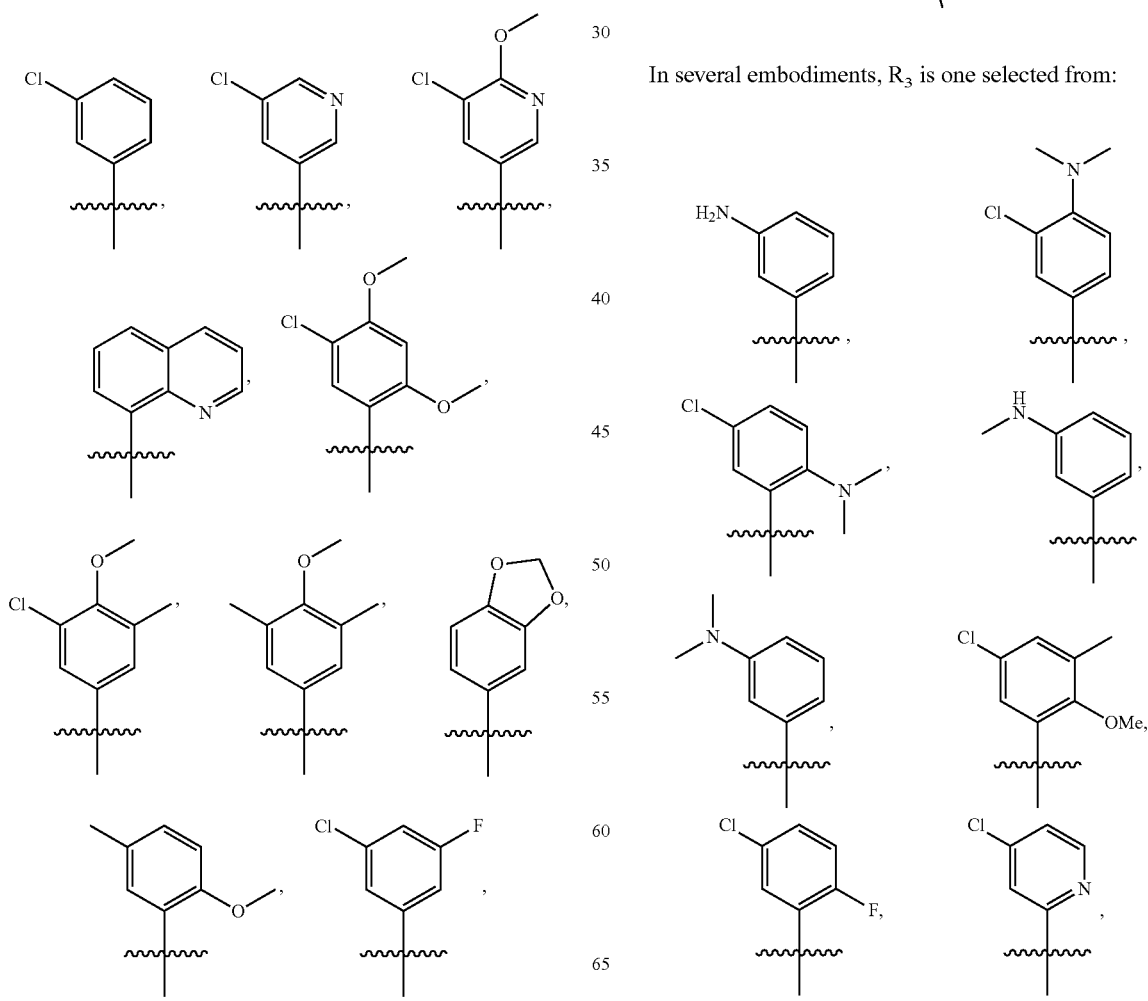

-continued
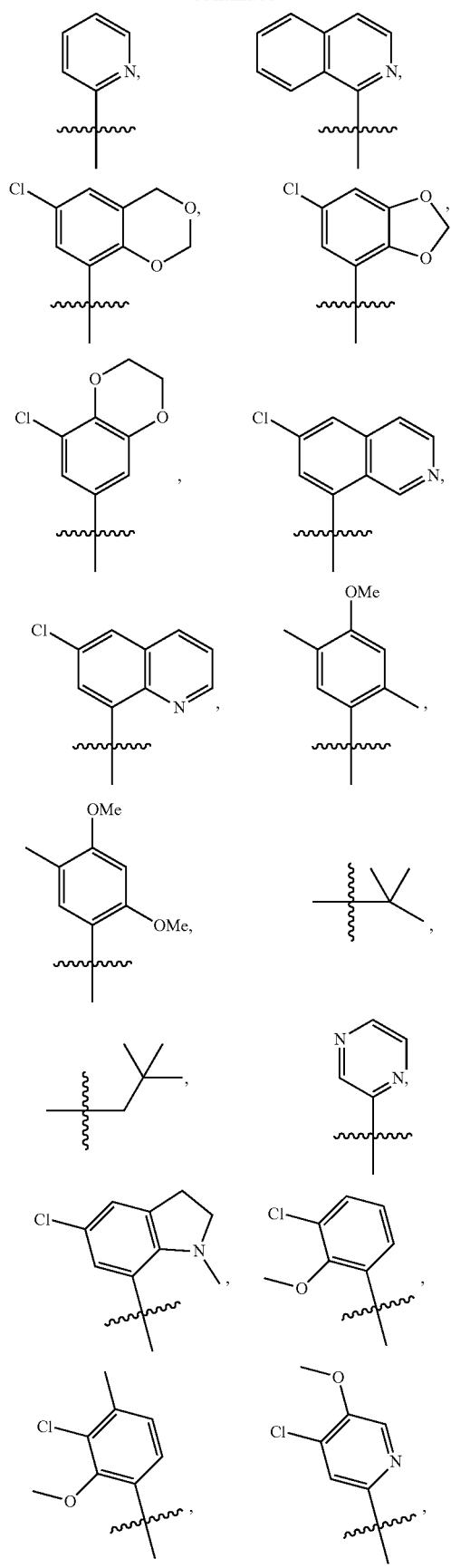
-continued
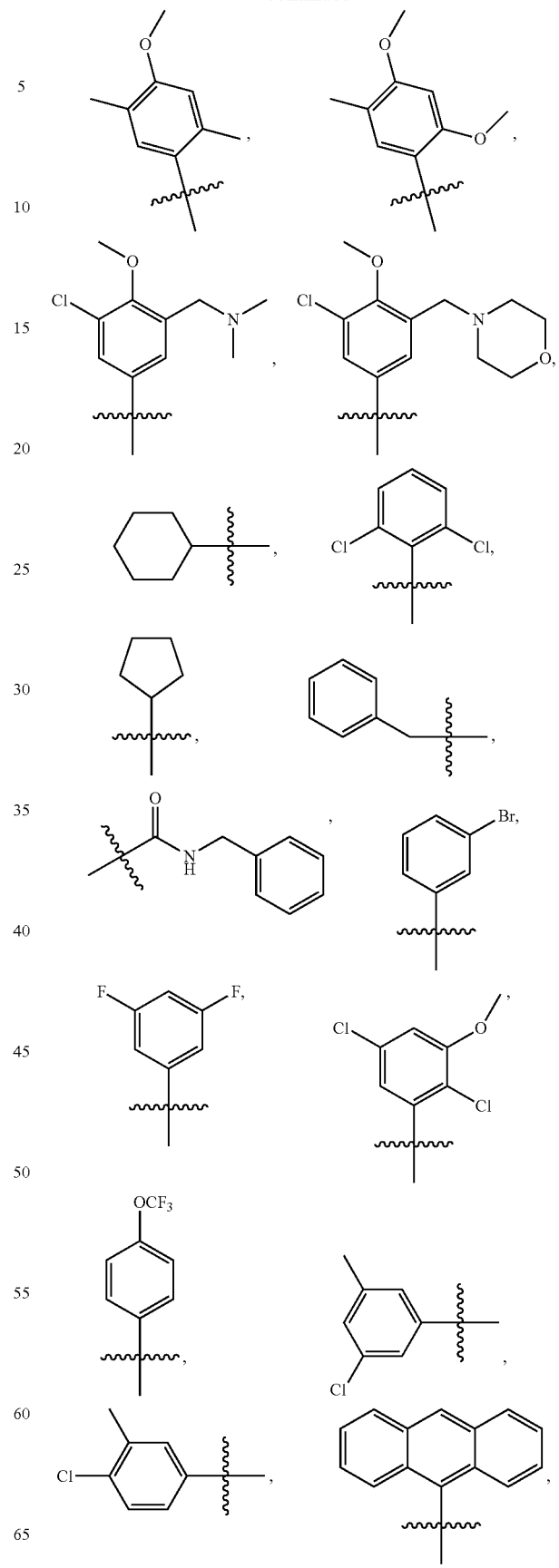

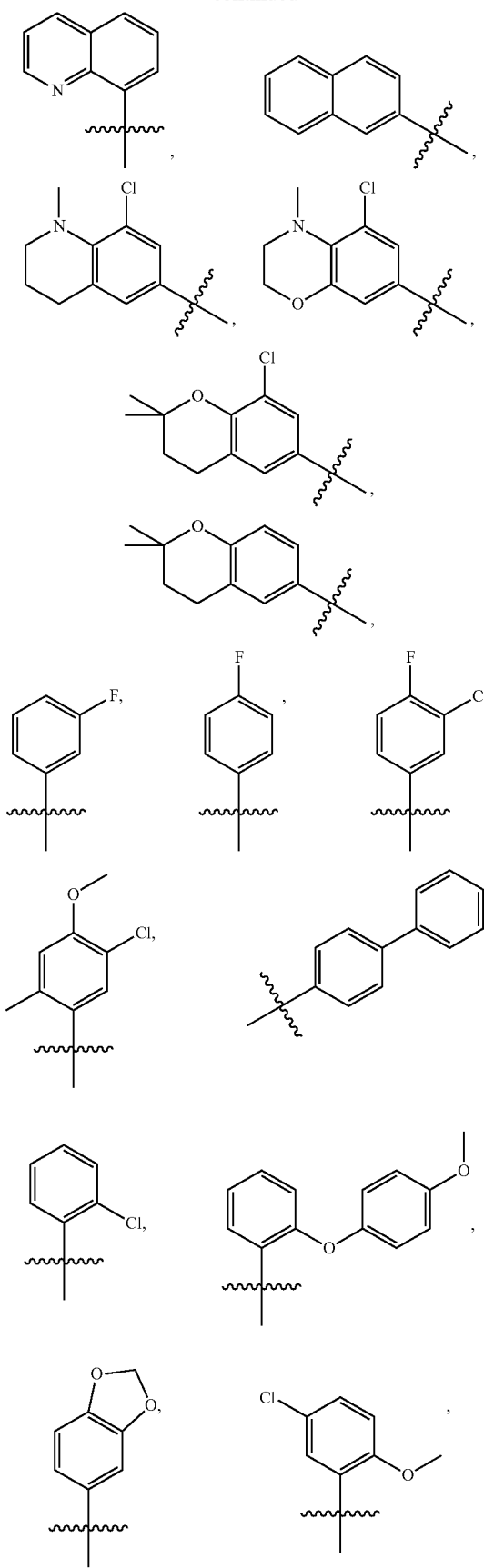
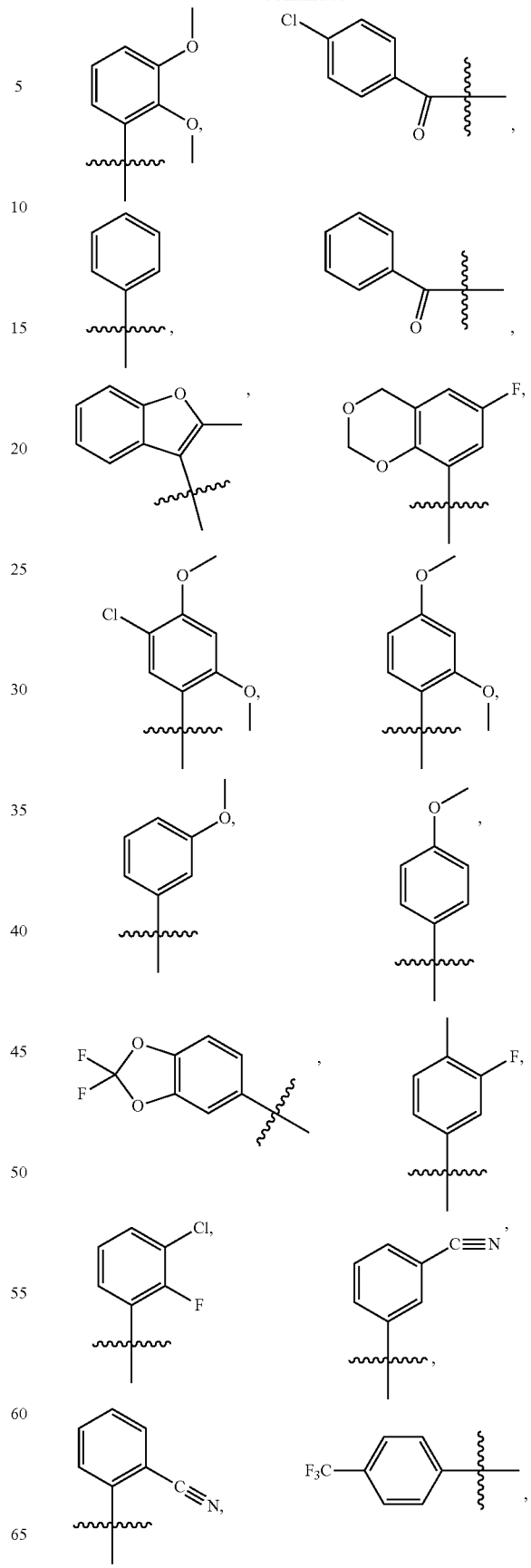

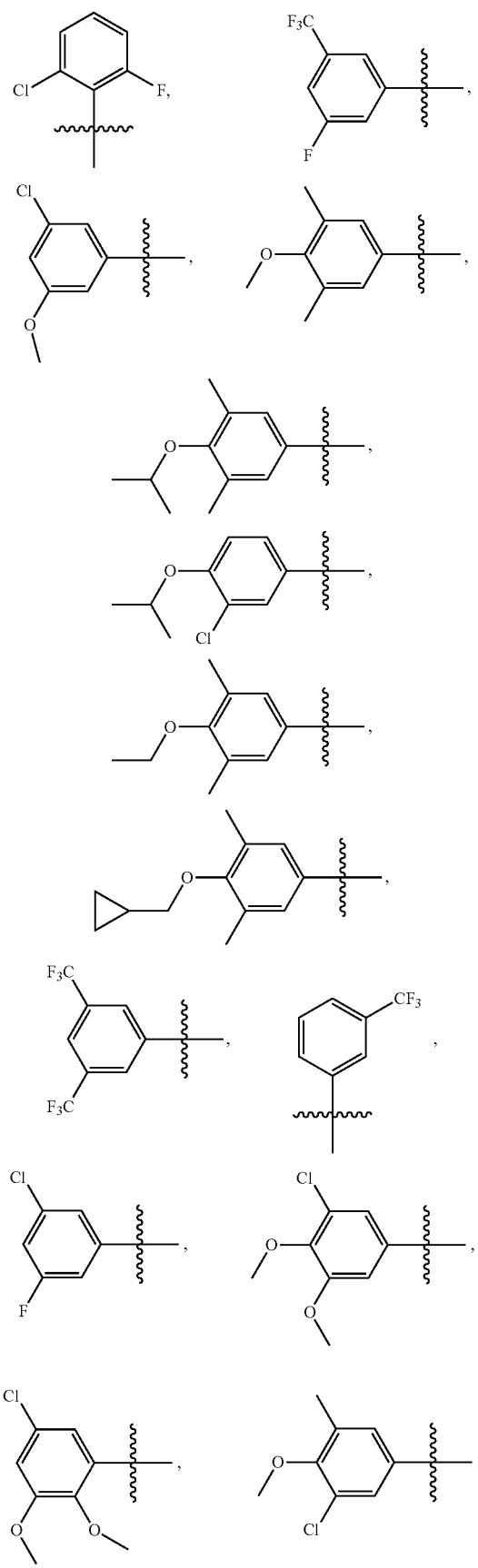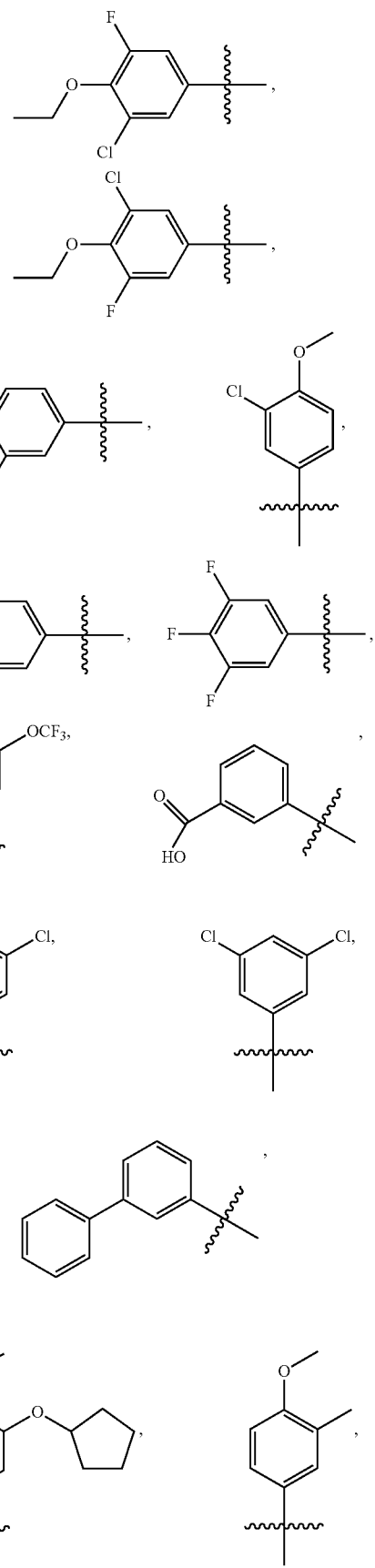

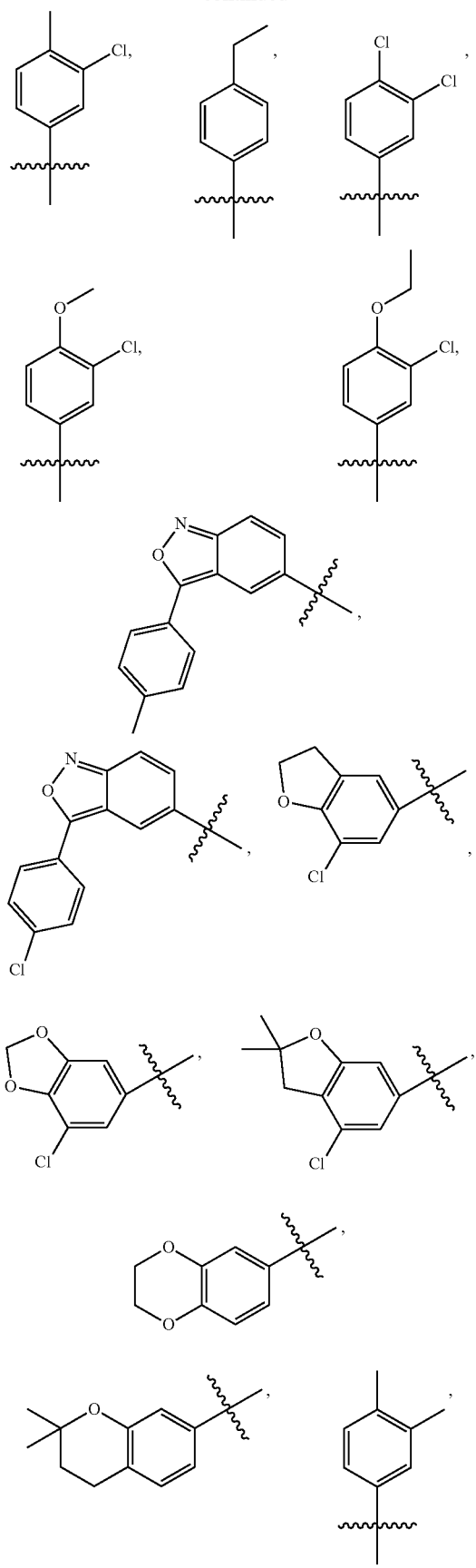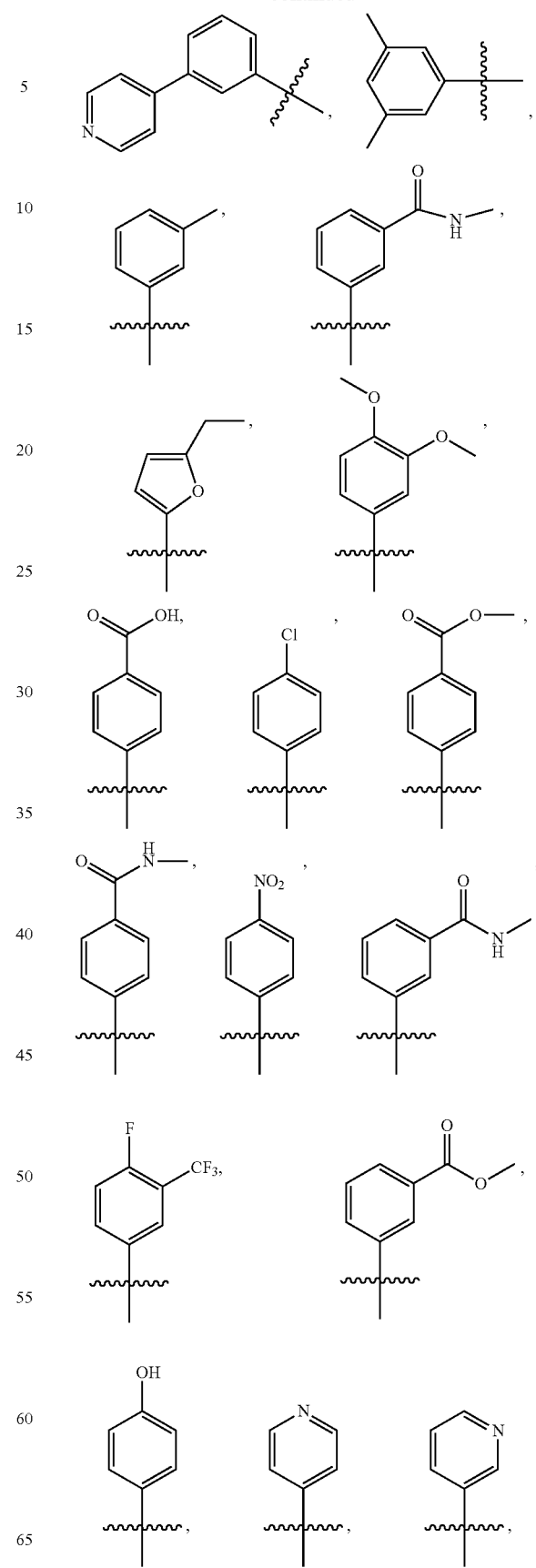

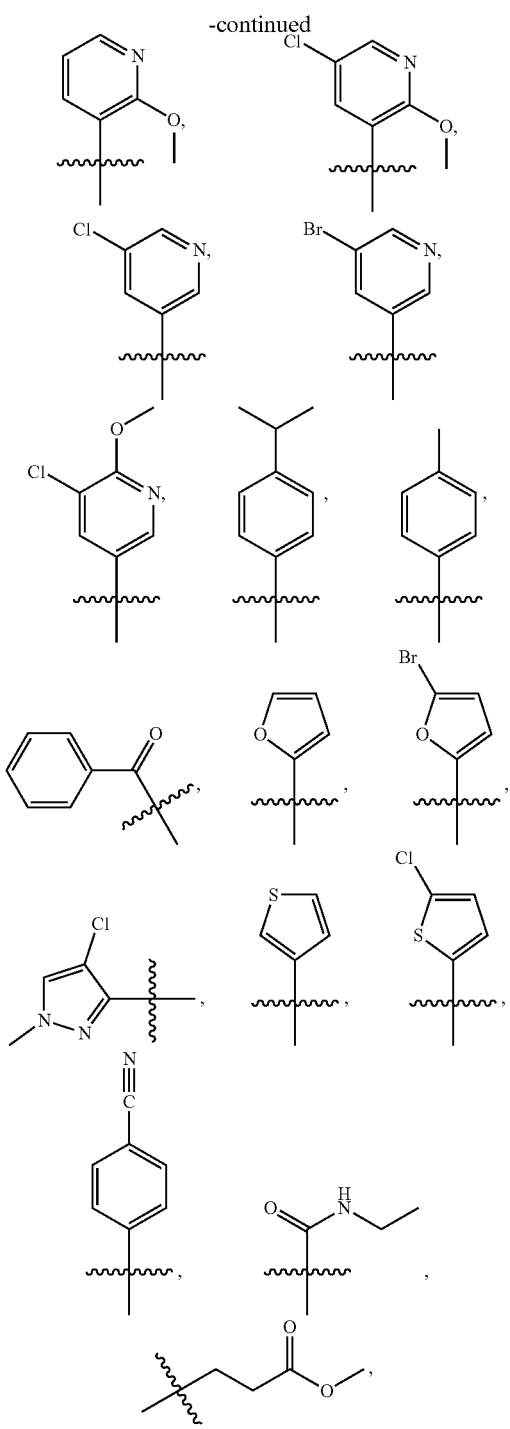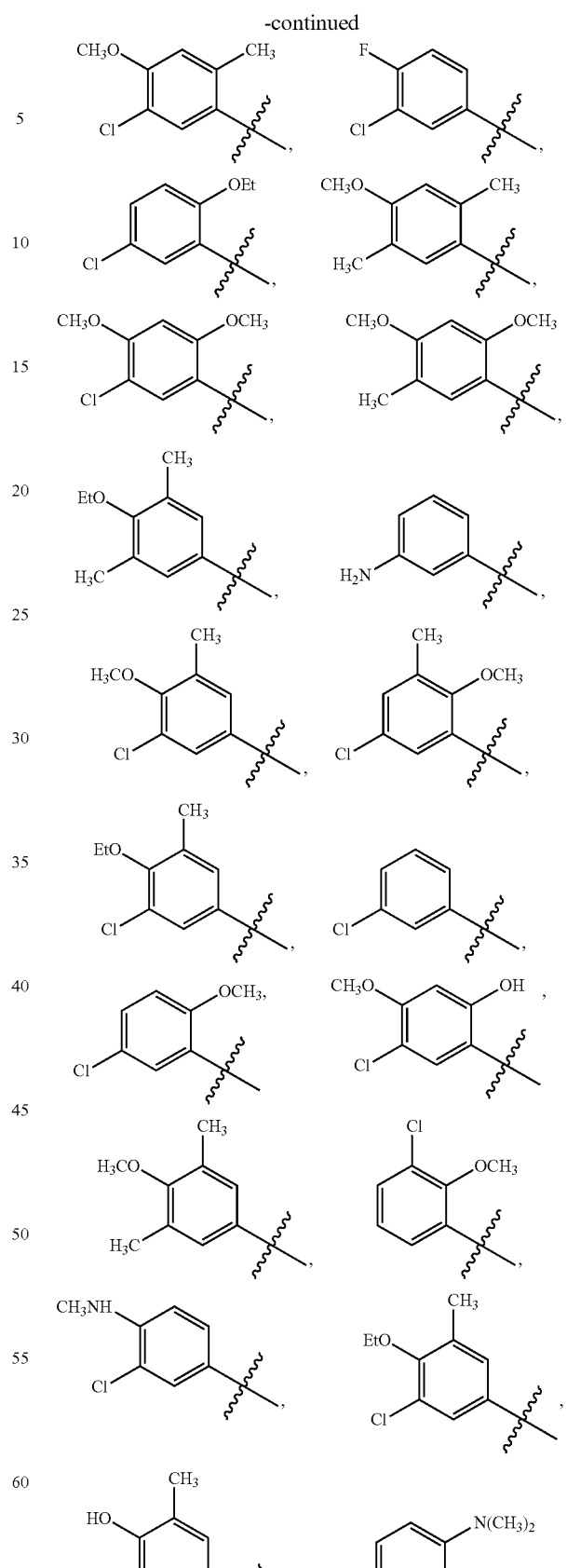
$CH_3-$, $CH_3CH_2-$, and $CH_3CH_2CH_2-$.
In some embodiments, $R_3$ is selected from the group consisting of:
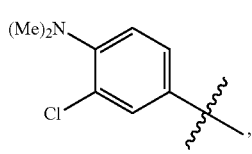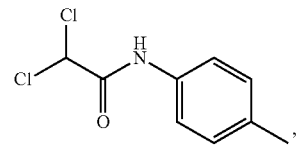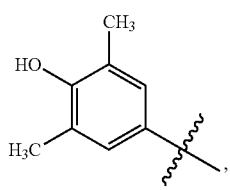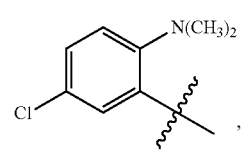

-continued

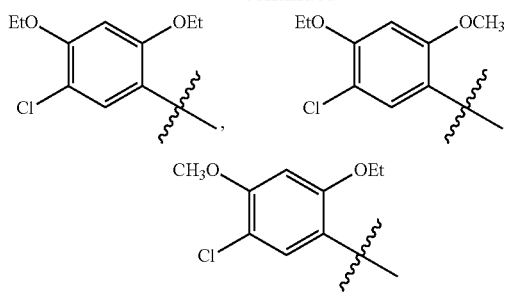

or

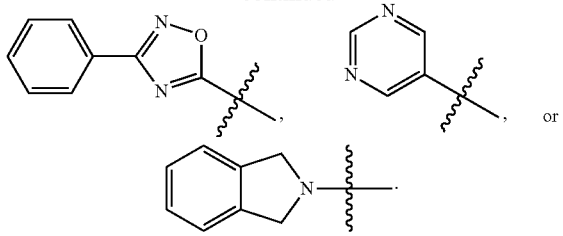

In some embodiments, R₃ is an optionally substituted monocyclic, bicyclic, or tricyclic heteroaryl, each of which is optionally substituted with 1-3 of halo, hydroxy, cyano, nitro, aliphatic, haloaliphatic, (aliphatic)oxy, (halo(aliphatic))oxy, (aliphatic(oxy(aryl)))oxy, aryl, heteroaryl, haloaryl, cycloaliphatic, heterocycloaliphatic, or combinations thereof.

In further embodiments, R₃ is selected from the group consisting of:

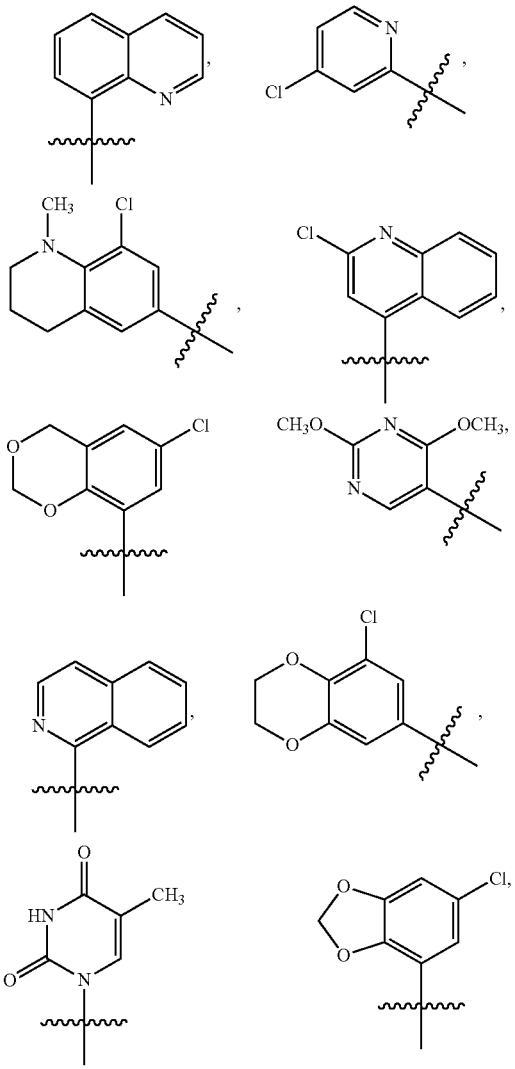

In other embodiments, R₃ is an optionally substituted amino or an optionally substituted aryloxy.

In some embodiments, R₃ is selected from the group consisting of

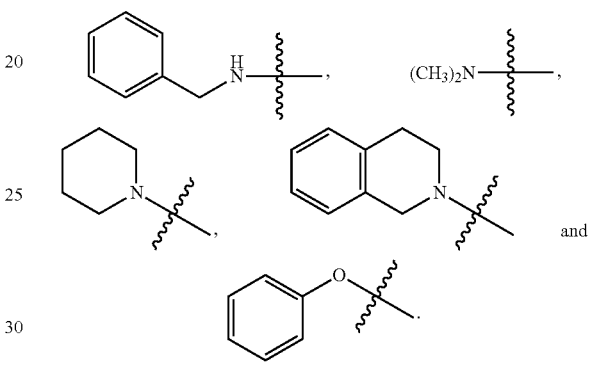

and

4. Group A:

Each A is $-(CX_1X_2)_a-$, wherein each $X_1$ and $X_2$ is independently hydrogen, optionally substituted $C_{1-4}$ aliphatic, or optionally substituted aryl; or $X_1$ and $X_2$ taken together form an oxo group; and each a is 0 to 3.

In several embodiments, $X_1$ or $X_2$ is hydrogen.

In several embodiments, $X_1$ or $X_2$ is optionally substituted $C_{1-4}$ aliphatic. Examples of $X_1$ or $X_2$ include trifluoromethyl, or optionally substituted ethyl, propyl, butyl, or isomers thereof.

In several embodiments, $X_1$ or $X_2$ is an optionally substituted aryl. Examples of $X_1$ or $X_2$ include optionally substituted phenyl, naphthyl, or azulenyl.

5. Group B:

Each B is $-(CX_1X_2)_b-$, wherein each $X_1$ and $X_2$ is independently hydrogen, optionally substituted $C_{1-4}$ aliphatic, or optionally substituted aryl; or $X_1$ and $X_2$ taken together form an oxo group; and each b is 0 to 3.

In several embodiments, $X_1$ or $X_2$ is hydrogen.

In several embodiments, $X_1$ or $X_2$ is optionally substituted $C_{1-4}$ aliphatic. Examples of $X_1$ or $X_2$ include trifluoromethyl, or optionally substituted ethyl, propyl, butyl, or isomers thereof. In several additional examples, $X_1$ or $X_2$ is an optionally substituted mono- or di-substituted (amino)-$C_{1-4}$ aliphatic.

In several embodiments, $X_1$ or $X_2$ is an optionally substituted aryl. Examples of $X_1$ or $X_2$ include optionally substituted phenyl, naphthyl, indenyl, or azulenyl.

6. Substituents Y and Y':

In several embodiments, each Y and Y' is independently hydrogen, optionally substituted aliphatic, or optionally substituted aryl.

Each Y and Y' is independently $-Z^DR_7$, wherein each $Z^D$ is independently a bond or an optionally substituted straight or branched ($C_{1-6}$)-aliphatic chain wherein up to two carbon units of $Z^D$ are optionally and independently replaced by —C(O)—, —CS—, —C(O)NR$^D$—, —C(O)NR$^D$NR$^D$—, —C(O)O—, —OC(O)—, —NR$^D$C(O)O—, —O—, —NR$^D$C(O)NR$^D$—, —OC(O)NR$^D$—, —NR$^D$NR$^D$—, —NR$^D$C(O)—, —S—, —SO—, —SO$_2$—, —NR$^D$—, —SO$_2$NR$^D$—, —NR$^D$SO$_2$—, or —NR$^D$SO$_2$NR$^D$—. Each $R_7$ is independently $R^D$, halo, —OH, —CN, —NO$_2$, —NH$_2$, or —OCF$_3$. Each $R^D$ is independently hydrogen, or optionally substituted aryl.

In several embodiments, one selected from Y and Y' is hydrogen.

In several embodiments, one selected from Y and Y' is optionally substituted aliphatic.

In several embodiments, one selected from Y and Y' is optionally substituted aryl.

In several embodiments, both Y and Y' are hydrogen.

In several embodiments, one of Y or Y' is hydrogen and the other is fluorine.

In several embodiments, both of Y and Y' are fluorine.

In additional of examples, one of Y or Y' is hydrogen and the other is methoxycarbonyl; one of Y or Y' is hydrogen and the other is hydroxy; or together, Y and Y' form an oxo group or form =S.

7. Exceptions:

In compounds of formula (I), the sum of a and b is 2 or 3. For example, a is 0 and b is 3; a is 1 and b is 2; a is 2 and b is 1; or a is 3 and b is 0.

C. Sub-Generic Compounds:

Another aspect of the present invention provides compounds of formula (I)a useful for inhibiting serine protease activity and methods inhibiting serine protease activity. Compounds of formula (Ia) include:

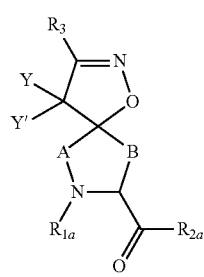

(Ia)

or a pharmaceutically acceptable salt thereof wherein $R_3$, A, B, Y, and Y' are defined above in formula (I).

Each $R_{ia}$ is -Q$_4$-W$_4$-Q$_3$-W$_3$-Q$_2$-W$_2$-Q$_1$; wherein each of W$_2$, W$_3$, and W$_4$ is independently a bond, —C(O)—, —C(S)—, —C(O)N(Q$_5$)-, —C(O)O—, —O—, —N(Q$_5$)C(O)N(Q$_5$)-, —SO$_2$—, —N(Q$_5$)SO$_2$—, —S—, —N(Q$_5$)-, —SO—, —N(Q$_5$)C(O)—, —OC(O)—, —N(Q$_5$)C(O)O—, or —SO$_2$N(Q$_5$)-; each of Q$_1$, Q$_2$, Q$_3$ and Q$_4$ is independently a bond, an optionally substituted $C_{1-4}$ aliphatic, an optionally substituted cycloaliphatic, an optionally substituted heterocycloaliphatic, an optionally substituted aryl, an optionally substituted heteroaryl, or a hydrogen when Q$_1$, Q$_2$, Q$_3$, or Q$_4$ is the terminal group of R$_1$; and each Q$_5$ is independently hydrogen or an optionally substituted aliphatic.

Each $R_{2a}$ is —Z$_1$—V$_1$—Z$_2$—V$_2$—Z$_3$—V$_3$ each of V$_1$, V$_2$, and V$_3$ is independently a bond, an optionally substituted aliphatic, an optionally substituted cycloaliphatic, an optionally substituted heterocycloaliphatic, an optionally substituted aryl, an optionally substituted heteroaryl, or a hydrogen when V$_1$, V$_2$, V$_3$ is the terminal group of R$_2$; each of Z$_1$, Z$_2$, and Z$_3$ is independently a bond, —C(O)—, —C(O)C(O)—, —C(S)—, —C(O)N(Q$_5$)-, —N(Q$_5$)C(O)—, —C(O)C(O)N (Q$_5$)-, —O—, SO—, —SO$_2$—, —N(Q$_5$)SO$_2$—, —N(Q$_5$)C(O)N(Q$_5$)-, —N(Q$_5$)C(S)N(Q$_5$)-, —N(Q$_5$)-, —N(Q$_5$)SO$_2$—, —SO$_2$N(Q$_5$)-, —C(O)N(Q$_5$)SO$_2$—, —SO$_2$N(Q$_5$)C(O)—, or hydrogen when Z$_1$, Z$_2$, or Z$_3$ is the terminal group of R$_2$; and each Q$_5$ is independently hydrogen, or an optionally substituted aliphatic.

In several examples, $R_{2a}$ is an optionally substituted (aliphatic)amino, an optionally substituted alkoxy, or hydroxy.

In several examples, $R_{2a}$ is an (aliphatic)amino wherein the nitrogen atom is optionally substituted with —Z$_2$—V$_2$—Z$_3$—V$_3$ or —Z$_3$—V$_3$ wherein each of Z$_2$ and Z$_3$ is independently a bond, —C(O)—, —N(Q$_5$)-, or —C(O)C(O)N(Q$_5$)-; and each of V$_2$ and V$_3$ is independently a bond, an optionally substituted aliphatic, or an optionally substituted cycloaliphatic.

Another aspect of the present invention provides compounds of formula (I)$_b$ useful for inhibiting serine protease activity and methods inhibiting serine protease activity. Compounds of formula (I)b include:

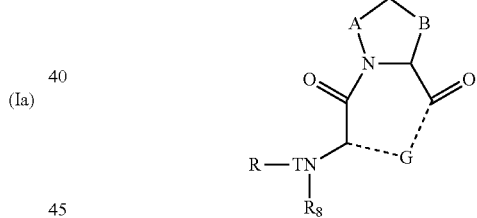

Ib or a pharmaceutically acceptable salt thereof, wherein $R_3$, $R_8$, R, T, A, B, Y and Y' are defined above in formula (I).

Each G is a 2 to 15 atom optionally substituted aliphatic chain optionally containing 1 to 3 heteroatoms selected from O, S and N.

Examples of compounds of formula (I)$_b$ include:

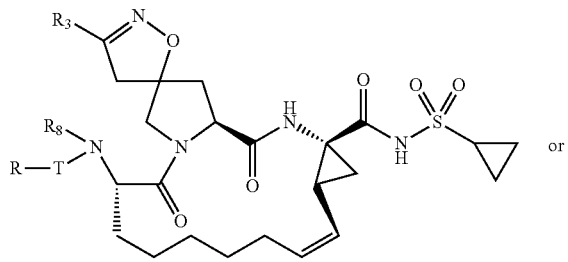

or

-continued

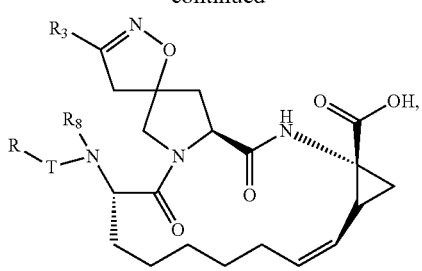

wherein T, R, and R₃ are defined above in formula (I).

Still other examples of formula (I)_b are

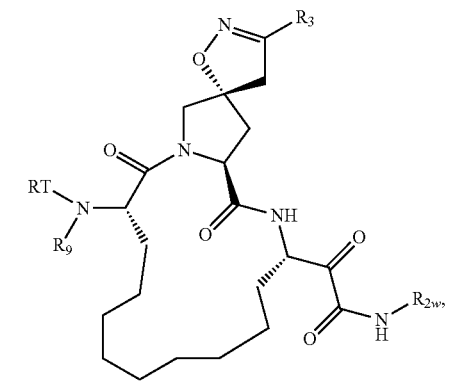

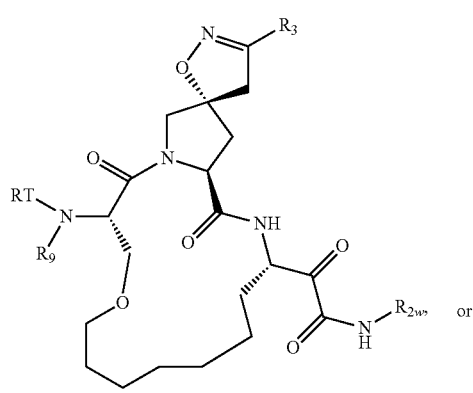

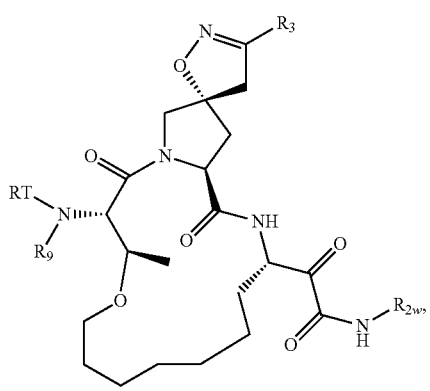

wherein each R_{2w} is independently

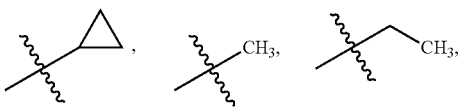

or hydrogen; each T is independently a bond, —C(O)—, —OC(O)—, —NHC(O)—, —S(O)₂N(H)—, —C(O)C(O)— or —SO₂—; each R is independently hydrogen, an optionally substituted aliphatic, an optionally substituted cycloaliphatic, an optionally substituted heterocycloaliphatic, an optionally substituted aryl, or an optionally substituted heteroaryl; and each R₉ is independently hydrogen, an optionally substituted aliphatic, an optionally substituted heteroaryl, an optionally substituted phenyl.

Further specific examples of compounds of formula (I)b are

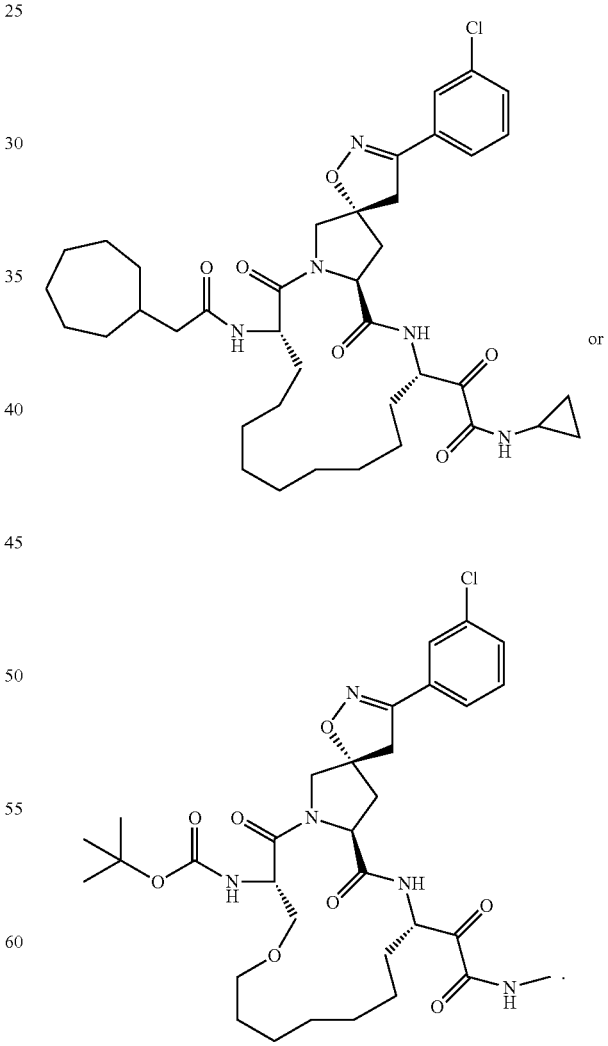

Other examples of compounds of formula (I)b include:

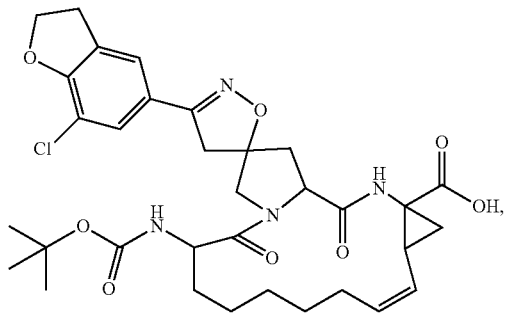

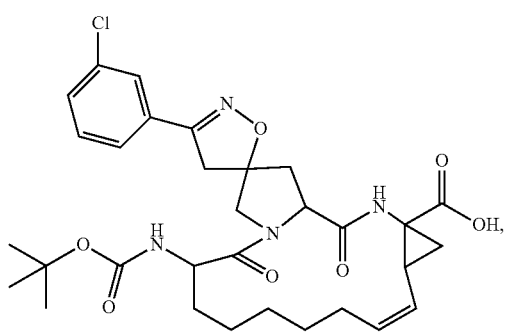

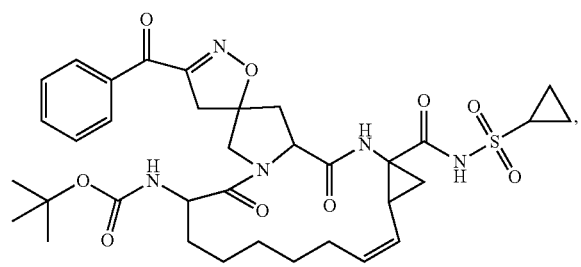

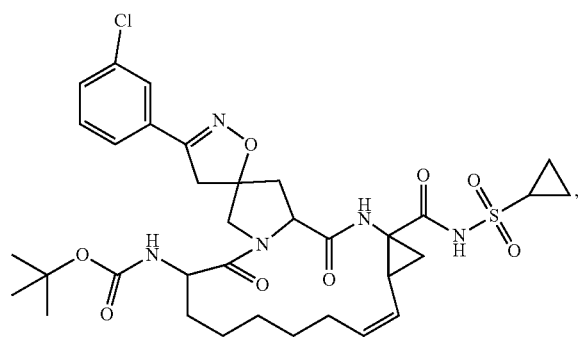

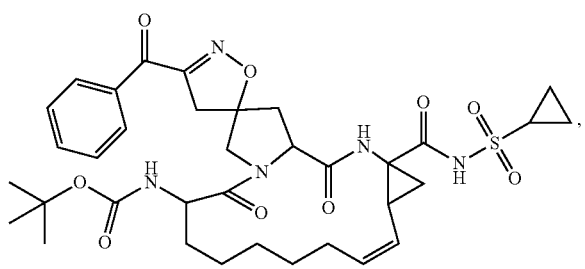

-continued

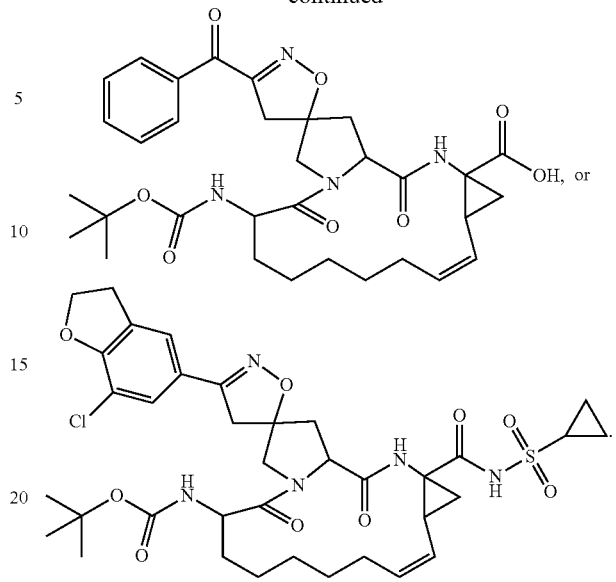

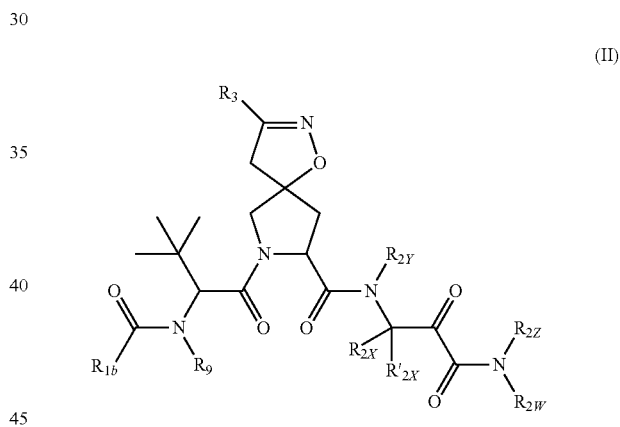

Another aspect of the present invention provides compounds of formula (I)I useful for inhibiting serine protease activity and methods inhibiting serine protease activity. Compounds of formula (II) include:

(II)

or a pharmaceutically acceptable salt thereof, wherein

Each $R_3$ is an optionally substituted aryl or an optionally substituted heteroaryl;

Each $R_{2Y}$ is independently hydrogen, an optionally substituted aliphatic, an optionally substituted cycloaliphatic, an optionally substituted heterocycloaliphatic, an optionally substituted aryl, or an optionally substituted heteroaryl;

Each $R_9$ is independently hydrogen, optionally substituted aliphatic, optionally substituted aryl, optionally substituted heteroaryl, optionally substituted heterocycloaliphatic, or optionally substituted cycloaliphatic;

Each $R_{2X}$ and $R'_{2X}$ is independently hydrogen, an optionally substituted aliphatic, an optionally substituted heteroaryl, an optionally substituted phenyl, an optionally substituted cycloaliphatic, an optionally substituted heterocycloaliphatic; or $R_{2X}$ and $R'_{2X}$ together with the atom to which they are both attached form an optionally substituted 3 to 7 membered cycloaliphatic or heterocycloaliphatic ring, or $R_{2X}$ and $R_{2Y}$ together with the atoms to which they are attached form an optionally substituted 5 to 7 membered heterocycloaliphatic ring;

Each $R_{1b}$ is —$Z^E R_{21}$, wherein $Z^E$ is —$CH_2$—, —NH—, —CH($R_{1Z}$)—, or —O—, and $R_{21}$ is optionally substituted 6-7 membered cycloaliphatic or optionally substituted tert-butyl;

Each $R_{1Z}$ is optionally substituted aliphatic, optionally substituted cycloaliphatic, optionally substituted heterocycloaliphatic, optionally substituted aryl, or optionally substituted heteroaryl;

Each $R_{2Z}$ is hydrogen, optionally substituted cycloaliphatic, optionally substituted heterocycloaliphatic, or optionally substituted aliphatic; and Each $R_{2W}$ is hydrogen, optionally substituted cycloaliphatic, optionally substituted heterocycloaliphatic, or optionally substituted aliphatic, or $R_{2Z}$ and $R_{2W}$, together with the nitrogen atom to which they are attached form an optionally substituted heterocycloaliphatic.

Another aspect of the present invention provides compounds of formula (I) II useful for inhibiting serine protease activity and methods inhibiting serine protease activity. Compounds of formula (III) include:

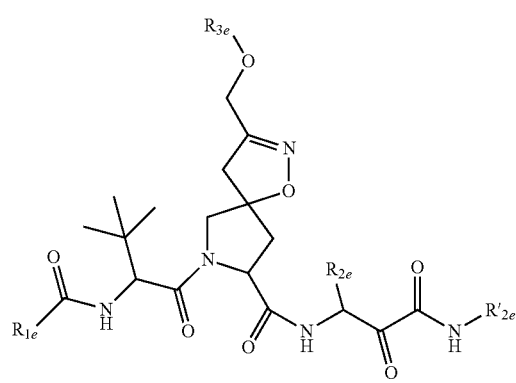

(III)

or a pharmaceutically acceptable salt thereof, wherein $R_{1e}$ is

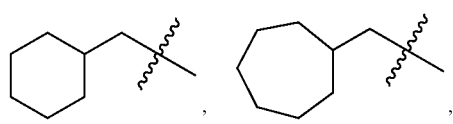

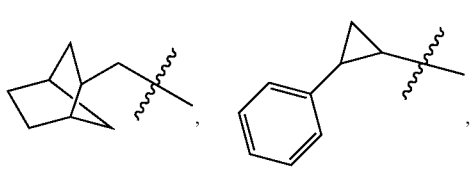

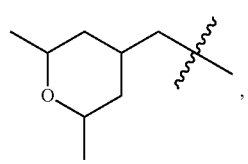

$R_{2e}$ is

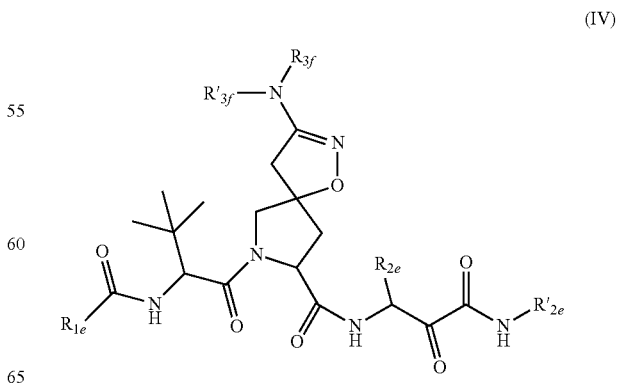

or hydrogen; and $R_{3e}$ is optionally substituted aryl or optionally substituted heteroaryl.

Another aspect of the present invention provides compounds of formula (I)V useful for inhibiting serine protease activity and methods inhibiting serine protease activity. Compounds of formula (IV) include:

(IV)

or a pharmaceutically acceptable salt thereof, wherein $R_{1e}$ is

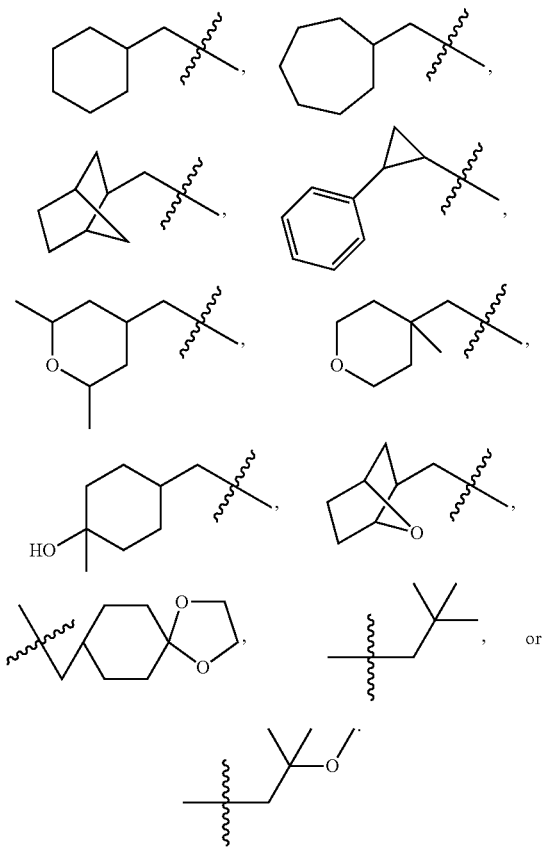

$R_{2e}$ is

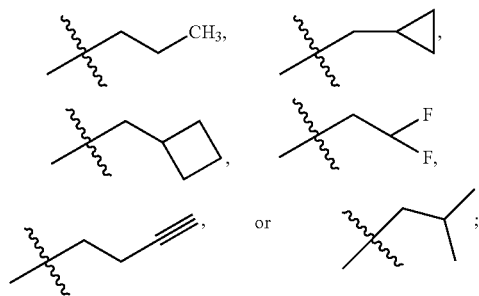

$R'_{2e}$ is

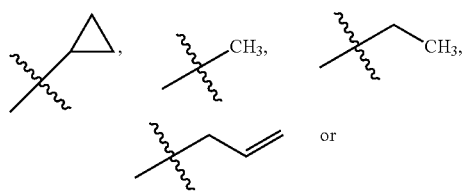

hydrogen; and

Each of $R_{3f}$ and $R'_{3f}$ is independently hydrogen, sulfonamide, sulfonyl, sulfinyl, optionally substituted acyl, optionally substituted aliphatic, optionally substituted cycloaliphatic, optionally substituted heterocycloaliphatic, optionally substituted aryl, or optionally substituted heteroaryl, or $R_{3f}$ and $R'_{3f}$ together with the nitrogen atom to which they are attached form an optionally substituted, saturated, partially unsaturated, or full unsaturated, 5-8 membered heterocycloaliphatic or heteroaryl.

Another aspect of the present invention provides compounds of formula V useful for inhibiting serine protease activity and methods inhibiting serine protease activity. Compounds of formula (V) include:

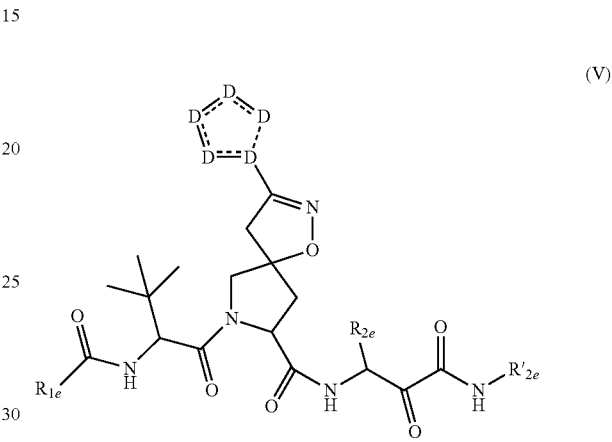

(V)

or a pharmaceutically acceptable salt thereof, wherein $R_{1e}$, $R_{2e}$, and $R'_{2e}$ are defined above in formula (III).

Each D is independently —$CR_8$—, N, S, or O, provided that no more than two D are independently, S, or O, and $R_8$ is defined above in formula (I).

Another aspect of the present invention provides compounds of formula VI useful for inhibiting serine protease activity and methods inhibiting serine protease activity. Compounds of formula (VI) include:

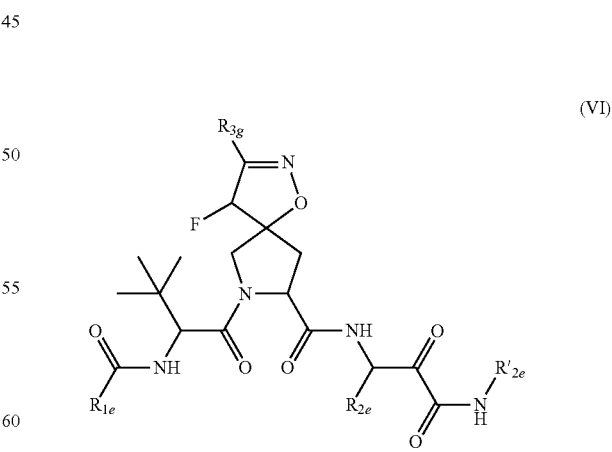

(VI)

or a pharmaceutically acceptable salt thereof, wherein $R_{1e}$, $R_{2e}$, and $R'_{2e}$ are defined above in formula (III).

Each $R_{3g}$ is a substituted aryl or a substituted heteroaryl. In some embodiments, $R_{3g}$ is

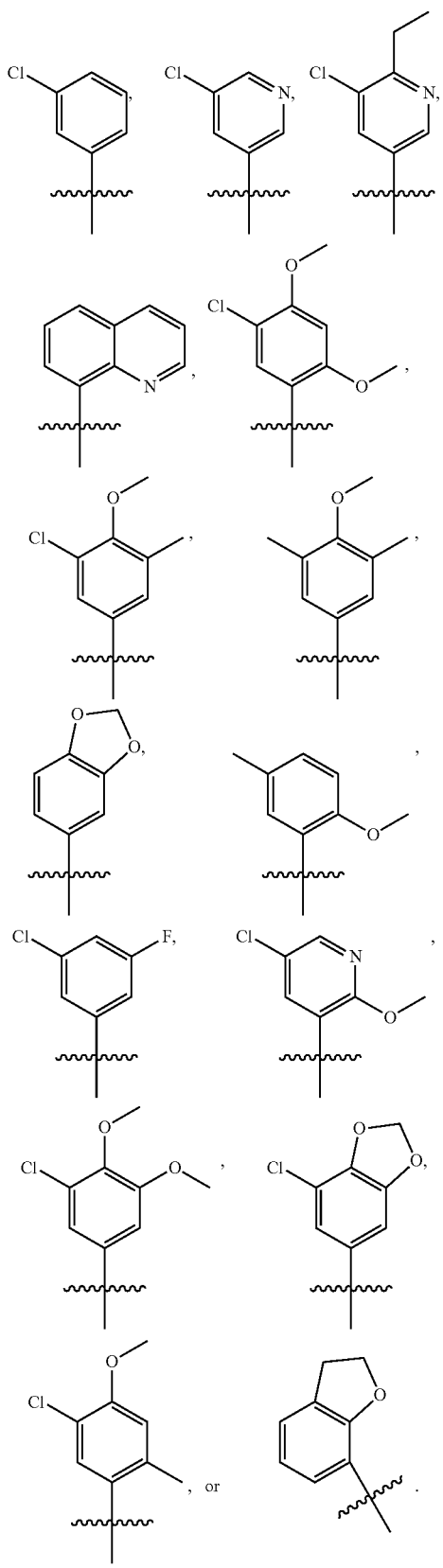

Another aspect of the present invention provides compounds of formula VII useful for inhibiting serine protease activity and methods inhibiting serine protease activity. Compounds of formula (VII) include:

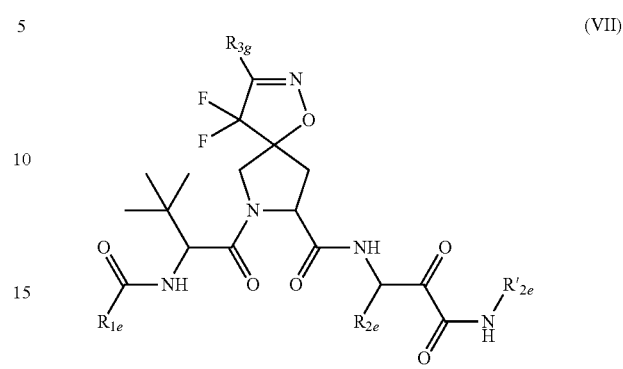

(VII)

or a pharmaceutically acceptable salt thereof, wherein $R_{1e}$, $R_{2e}$, and $R'_{2e}$ are defined above in formula (III), and $R_{3g}$ is defined in formula (VI).

Another aspect of the present invention provides compounds of formula VIII useful for inhibiting serine protease activity and methods inhibiting serine protease activity. Compounds of formula (VIII) include:

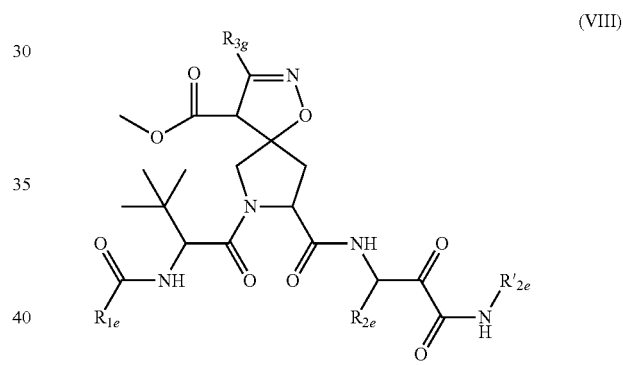

(VIII)

or a pharmaceutically acceptable salt thereof, wherein $R_{1e}$, $R_{2e}$, and $R'_{2e}$ are defined above in formula (I)II, and $R_{3g}$ is defined in formula VI.

Another aspect of the present invention provides compounds of formula (I)X useful for inhibiting serine protease activity and methods inhibiting serine protease activity. Compounds of formula (IX) include:

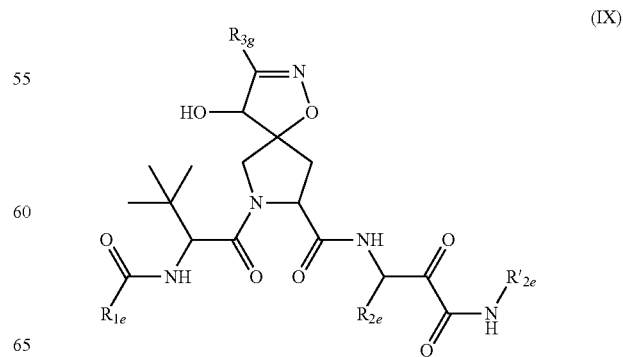

(IX)

or a pharmaceutically acceptable salt thereof, wherein $R_{1e}$, $R_{2e}$, and $R'_{2e}$ are defined above in formula (III), and $R_{3g}$ is defined in formula (VI).

Another aspect of the present invention provides compounds of formula (X) useful for inhibiting serine protease activity and methods inhibiting serine protease activity. Compounds of formula (X) include:

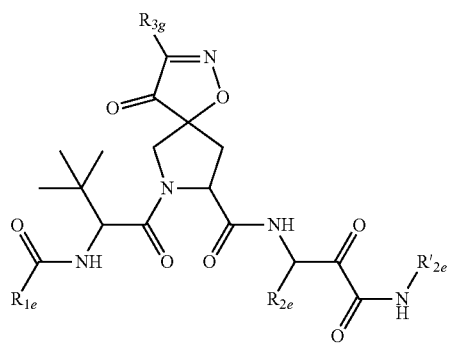

(X)

or a pharmaceutically acceptable salt thereof, wherein $R_{1e}$, $R_{2e}$, and $R'_{2e}$ are defined above in formula (III), and $R_{3g}$ is defined in formula (VI).

D. Combinations of Embodiments

Other embodiments include any combination of the aforementioned substituents $R_1$, $R_2$, $R_3$, A, B, Y, and Y'.

E. Exemplary Compounds

The invention is intended to include compounds wherein $R_1$ and $R_2$ contain structural elements of a serine protease inhibitor. Compounds having the structural elements of a serine protease inhibitor include, but are not limited to, the compounds of the following publications: WO 97/43310, US 20020016294, WO 01/81325, WO 01/58929, WO 01/32691, WO 02/08198, WO 01/77113, WO 02/08187, WO 02/08256, WO 02/08244, WO 03/006490, WO 01/74768, WO 99/50230, WO 98/17679, WO 02/48157, WO 02/08251, WO 02/07761, WO 02/48172, WO 02/08256, US 20020177725, WO 02/060926, US 20030008828, WO 02/48116, WO 01/64678, WO 01/07407, WO 98/46630, WO 00/59929, WO 99/07733, WO 00/09588, US 20020016442, WO 00/09543, WO 99/07734, U.S. Pat. No. 6,018,020, U.S. Pat. No. 6,265,380, U.S. Pat. No. 6,608,027, US 20020032175, US 20050080017, WO 98/22496, WO 05/028502, U.S. Pat. No. 5,866,684, WO 02/079234, WO 00/31129, WO 99/38888, WO 99/64442, WO 2004/072243, WO 02/18369, US 2006/046956, US 2005/197301, WO 2005058821, WO 2005051980, WO 2005030796, WO2005021584, WO2005113581, WO2005087731, WO2005087725, WO2005087721, WO2005085275, WO2005085242, US2003216325, WO2003062265, WO2003062228, WO2002008256, WO 2002008198, WO2002008187, WO 2002048172, WO 2001081325, WO 2001077113, U.S. Pat. No. 6,251,583, U.S. Pat. No. 5,990,276, US20040224900, US20040229818, WO2004037855, WO2004039833, WO200489974, WO2004103996, WO2004030670, WO2005028501, WO2006007700, WO2005070955, WO2006007708, WO2006000085, WO2005073195, WO2005073216, WO2004026896, WO2004072243, WO2004113365, WO2005010029, US20050153877, WO2004093798, WO2004094452, WO2005046712, WO2005051410, WO2005054430, WO2004032827, WO2005095403, WO2005077969, WO2005037860, WO2004092161, WO2005028502, WO2003087092, and WO2005037214, each of which is incorporated herein by reference.

Specific exemplary compounds of the invention are shown below in Table 1.

TABLE 1

Exemplary compounds of Formula (I).

| Structure | Compound No. |
| --- | --- |
| 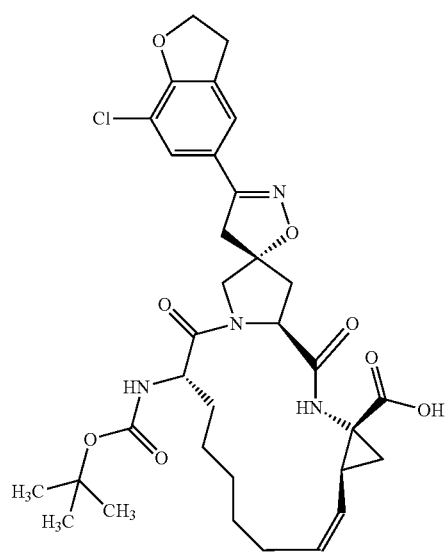 | 1 |

TABLE 1-continued

Exemplary compounds of Formula (I).

| Structure | Compound No. |
|---|---|
| 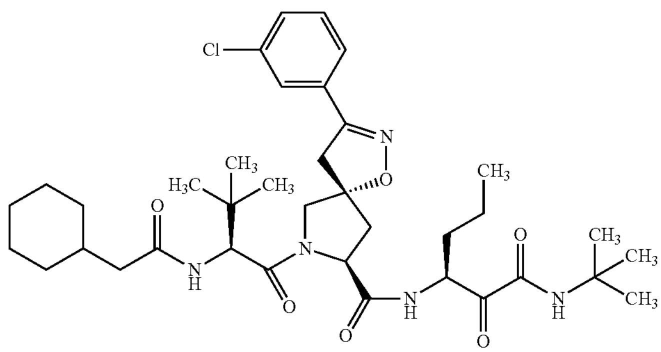 | 2 |
| 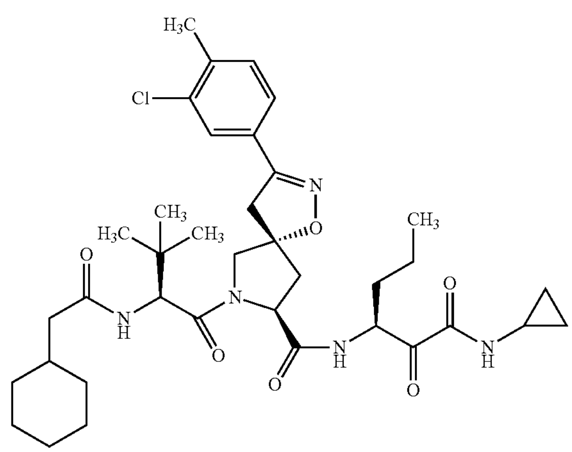 | 3 |
| 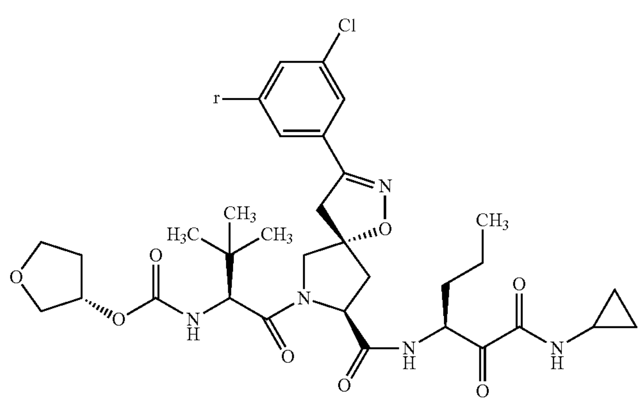 | 4 |

TABLE 1-continued

Exemplary compounds of Formula (I).

| Structure | Compound No. |
|---|---|
| 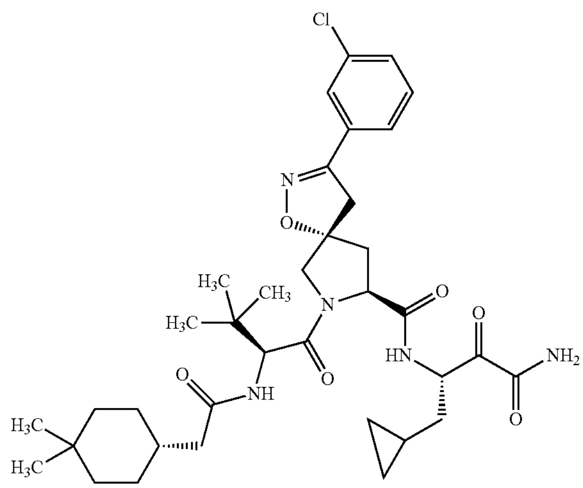 | 5 |
| 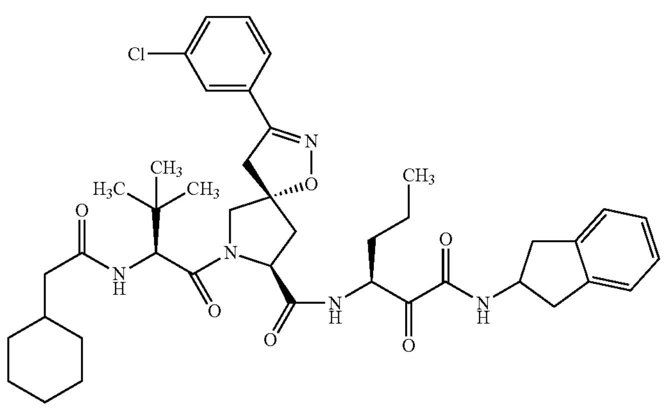 | 6 |
| 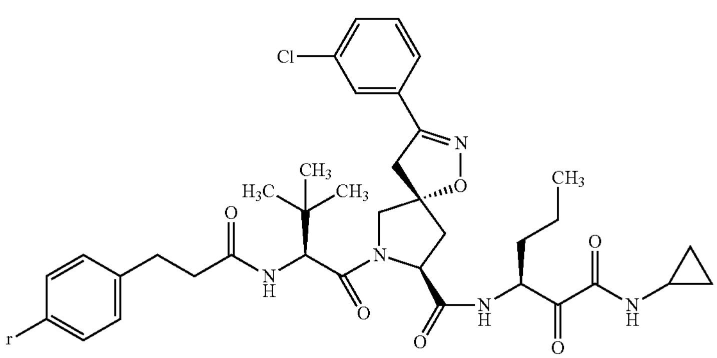 | 7 |

TABLE 1-continued

Exemplary compounds of Formula (I).

| Structure | Compound No. |
|---|---|
| 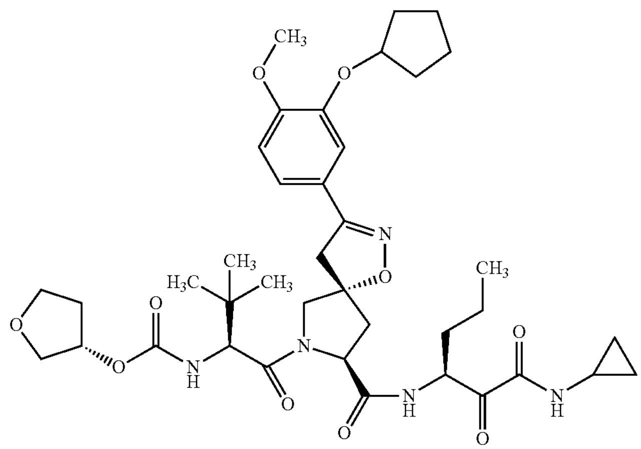 | 8 |
| 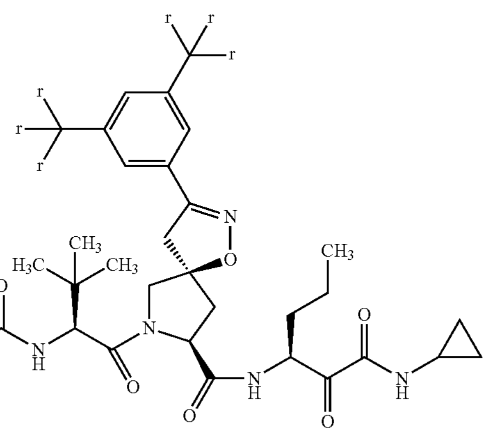 | 9 |
| 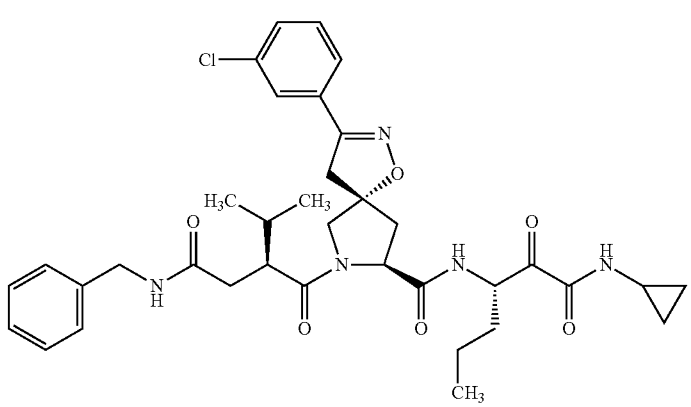 | 10 |

TABLE 1-continued

Exemplary compounds of Formula (I).

| Structure | Compound No. |
|---|---|
| 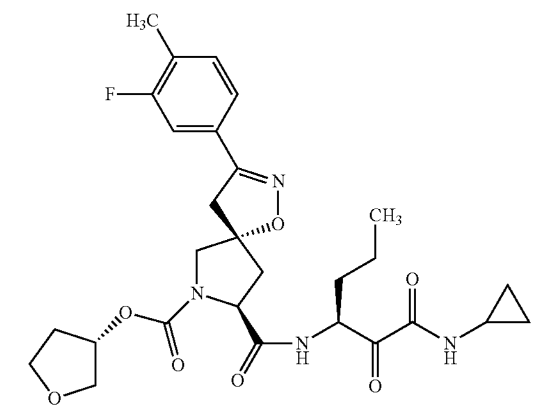 | 11 |
| 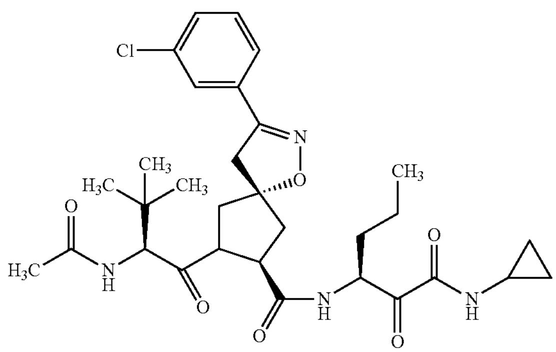 | 12 |
| 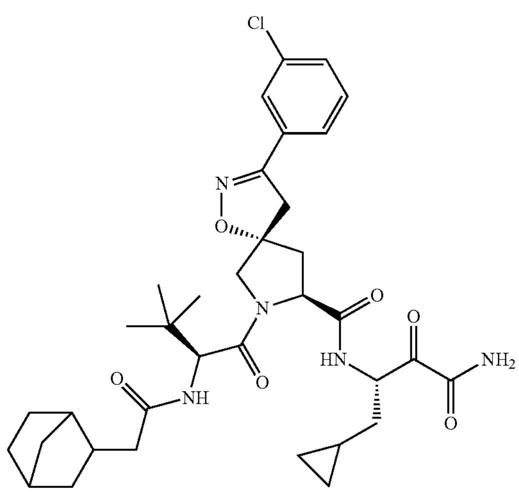 | 13 |

TABLE 1-continued
Exemplary compounds of Formula (I).
| Structure | Compound No. |
|---|---|
| 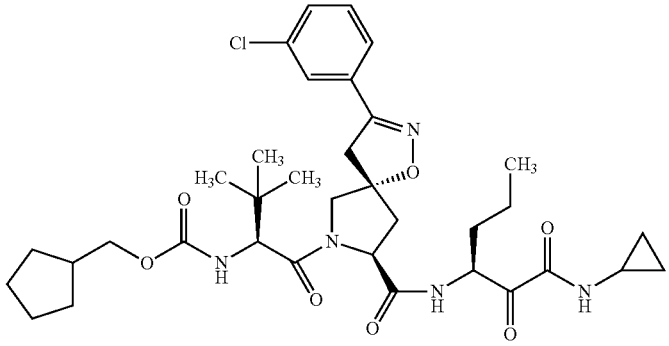 | 14 |
| 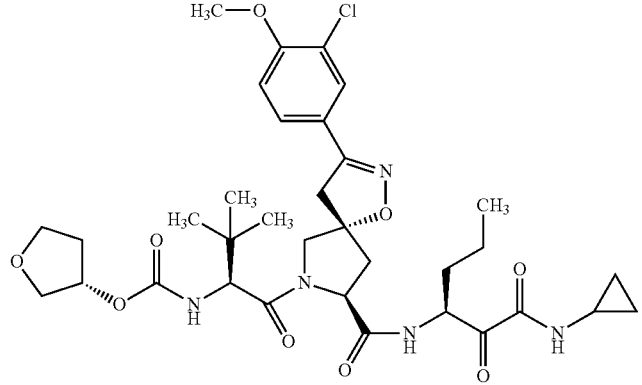 | 15 |
| 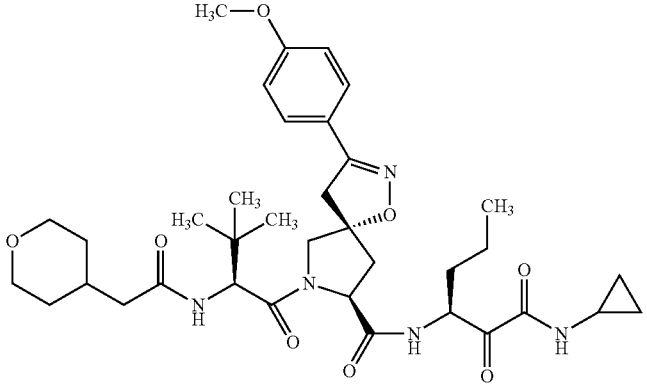 | 16 |
| 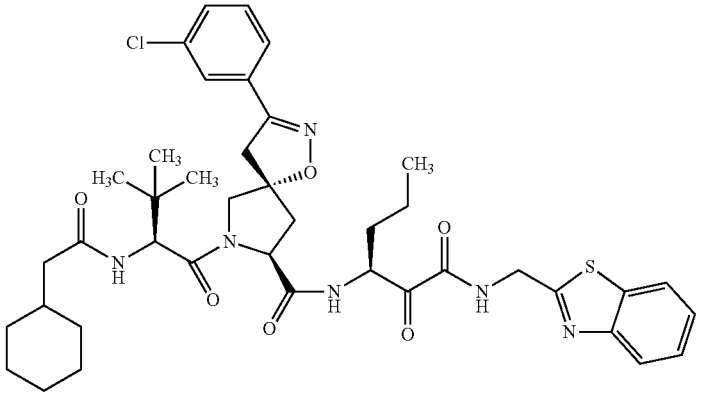 | 17 |

TABLE 1-continued

Exemplary compounds of Formula (I).

| Structure | Compound No. |
|---|---|
| 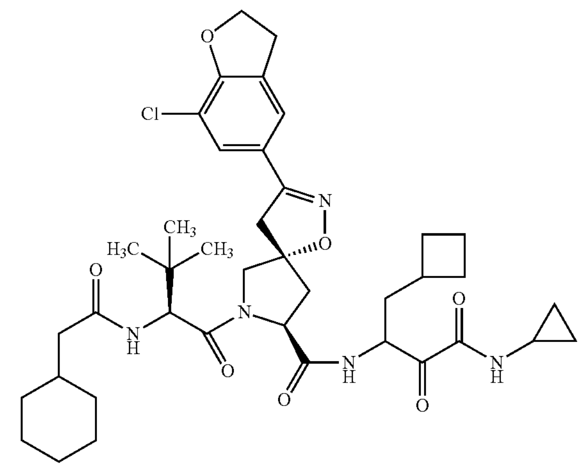 | 18 |
| 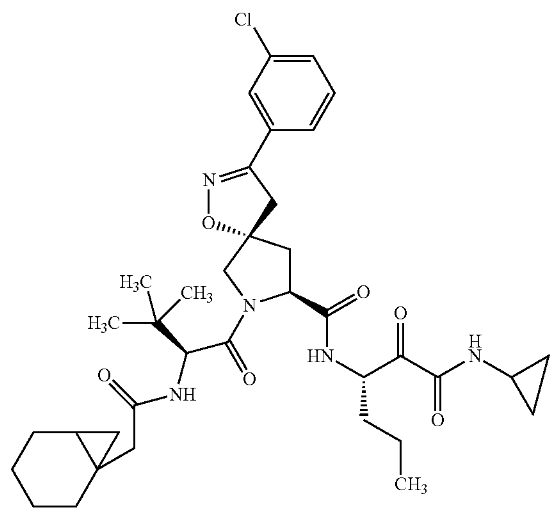 | 19 |
| 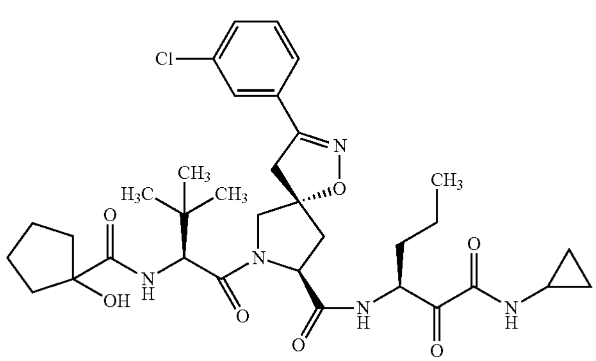 | 20 |

TABLE 1-continued

Exemplary compounds of Formula (I).

| Structure | Compound No. |
|---|---|
| 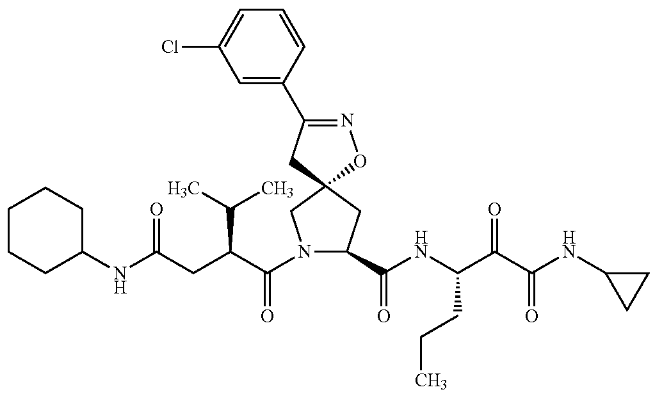 | 21 |
| 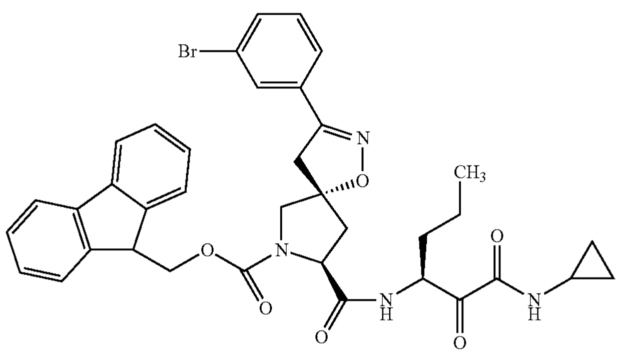 | 22 |
| 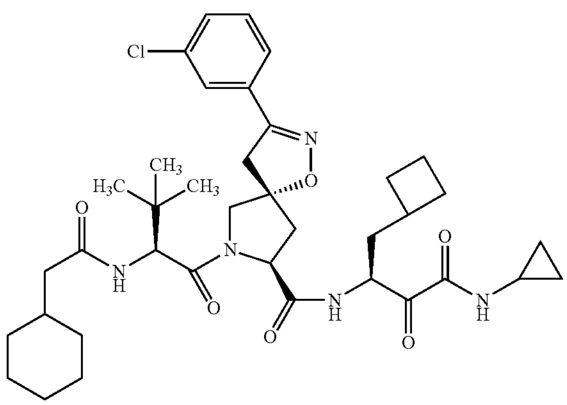 | 23 |
| 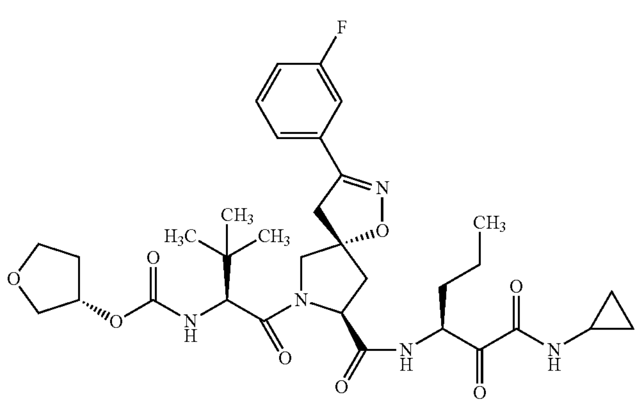 | 24 |

TABLE 1-continued

Exemplary compounds of Formula (I).

| Structure | Compound No. |
|---|---|
| 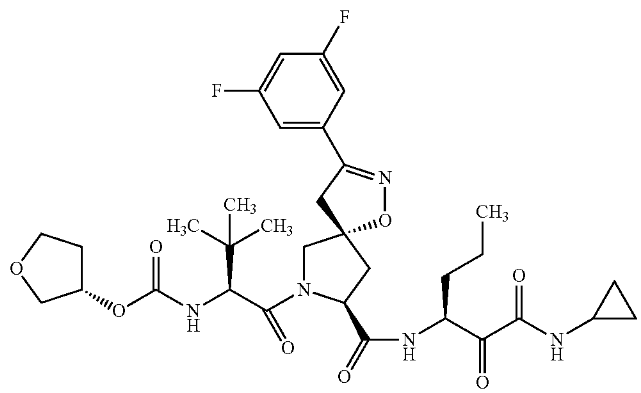 | 25 |
| 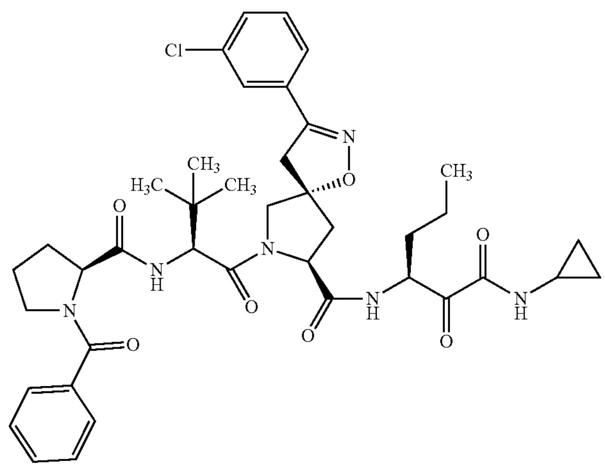 | 26 |
| 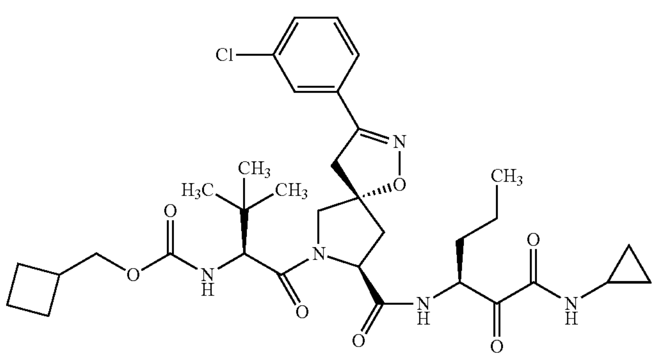 | 27 |

TABLE 1-continued

Exemplary compounds of Formula (I).

| Structure | Compound No. |
|---|---|
| 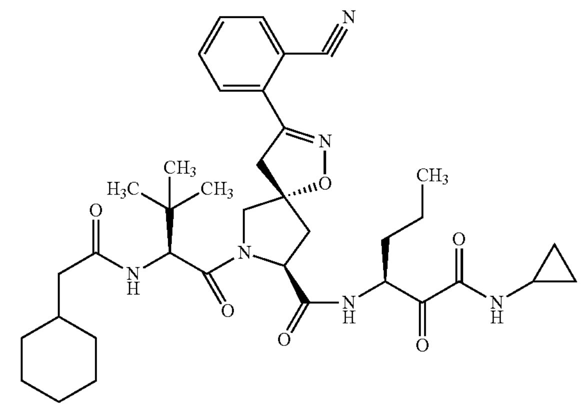 | 28 |
| 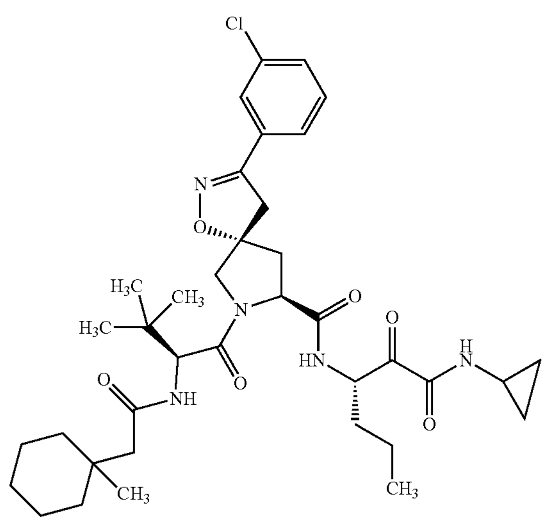 | 29 |
| 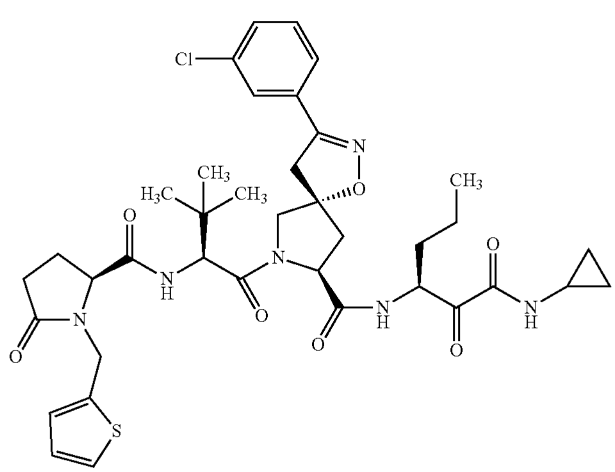 | 30 |

TABLE 1-continued

Exemplary compounds of Formula (I).

| Structure | Compound No. |
|---|---|
| 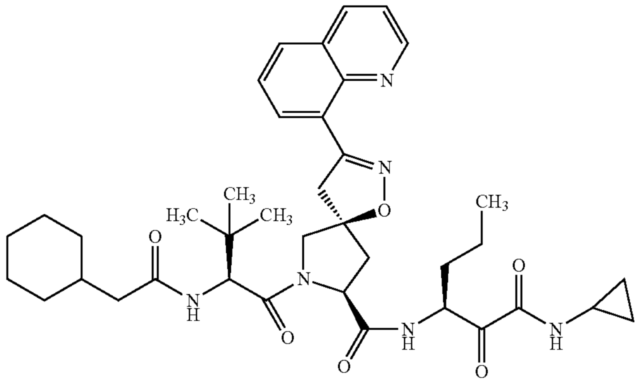 | 31 |
| 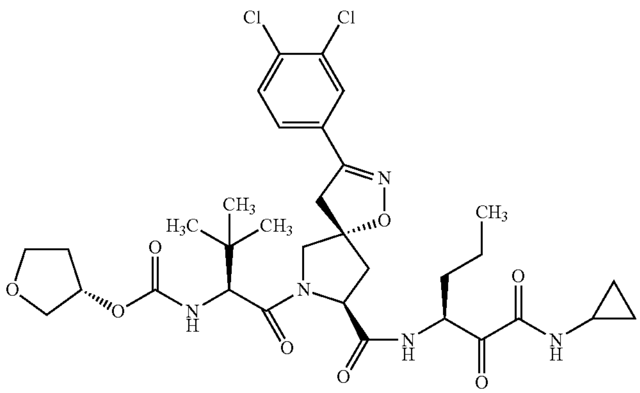 | 32 |
| 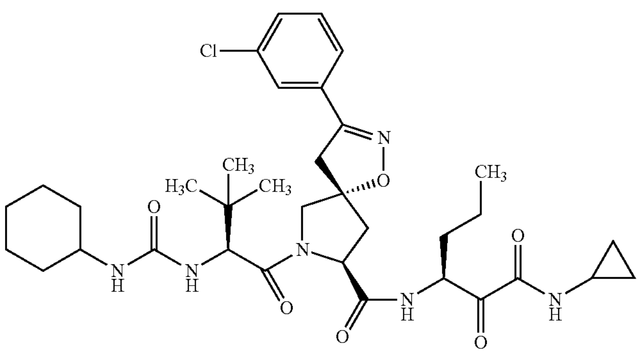 | 33 |
| 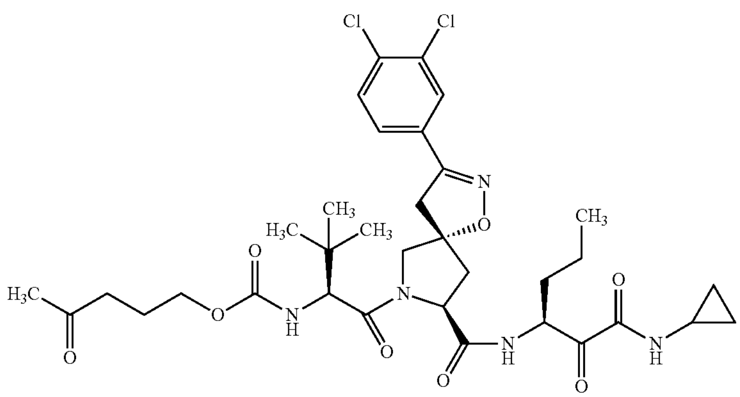 | 34 |

TABLE 1-continued

Exemplary compounds of Formula (I).

| Structure | Compound No. |
|---|---|
| 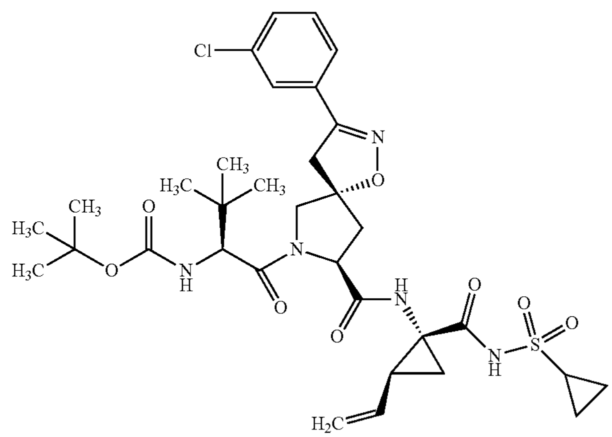 | 35 |
| 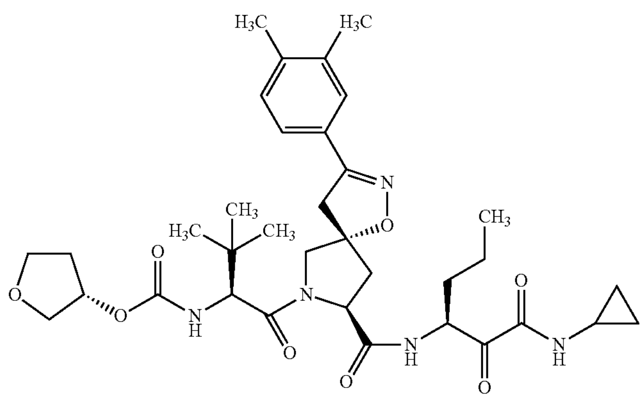 | 36 |
| 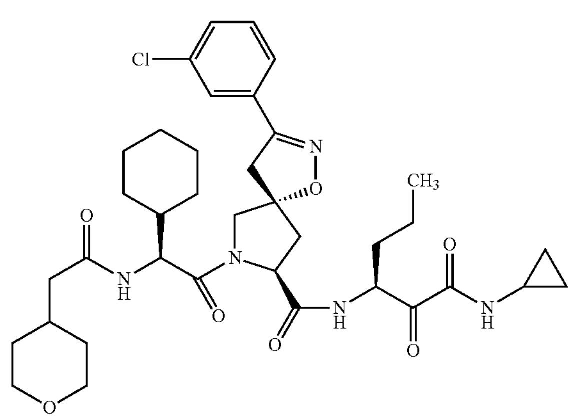 | 37 |

TABLE 1-continued

Exemplary compounds of Formula (I).

| Structure | Compound No. |
|---|---|
| 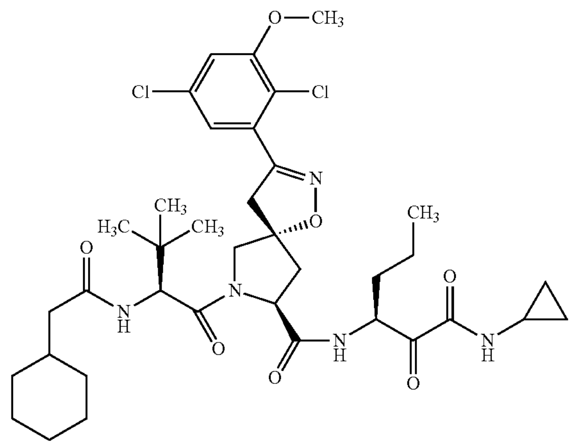 | 38 |
| 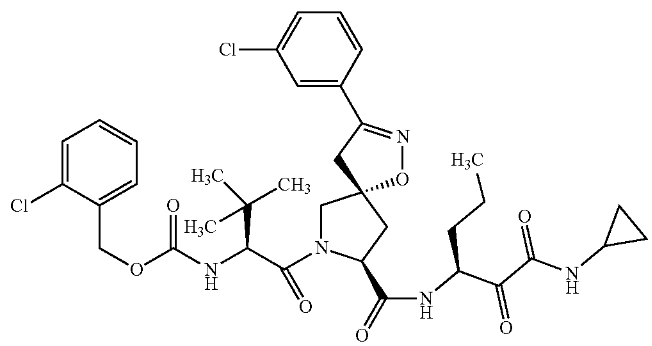 | 39 |
| 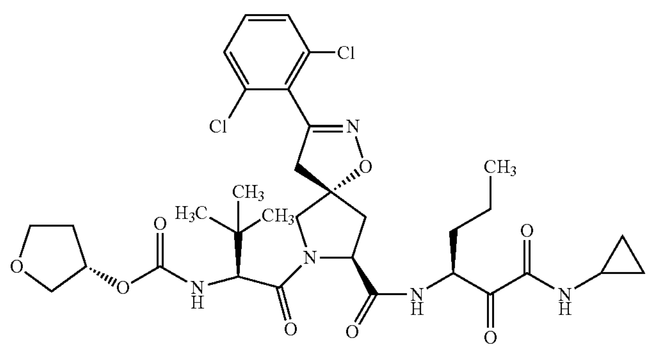 | 40 |
| 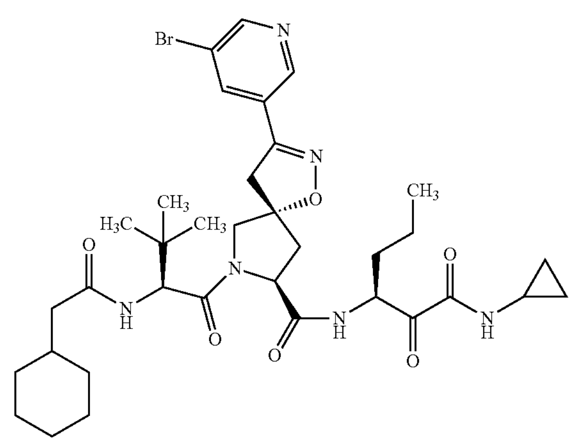 | 41 |

TABLE 1-continued
Exemplary compounds of Formula (I).
| Structure | Compound No. |
|---|---|
| 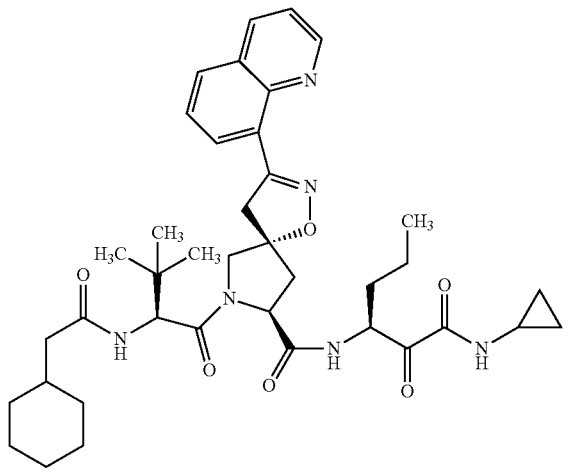 | 42 |
| 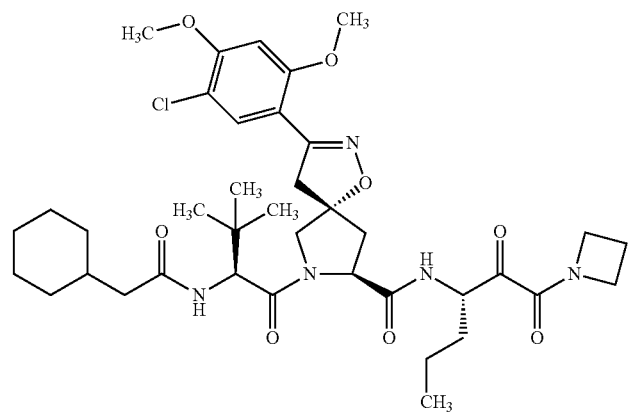 | 43 |
| 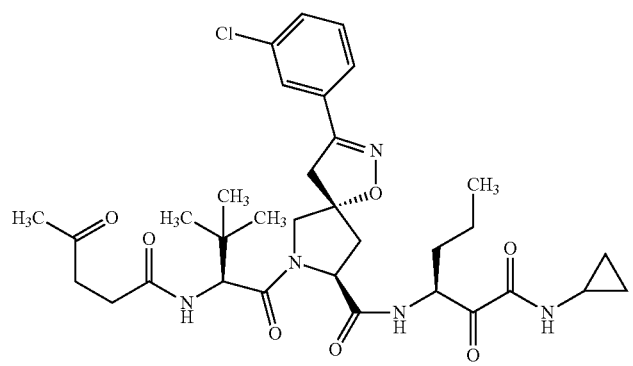 | 44 |

TABLE 1-continued

Exemplary compounds of Formula (I).

| Structure | Compound No. |
|---|---|
| 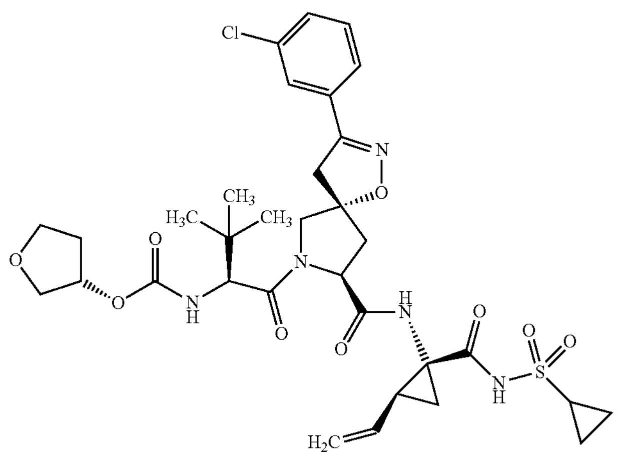 | 45 |
| 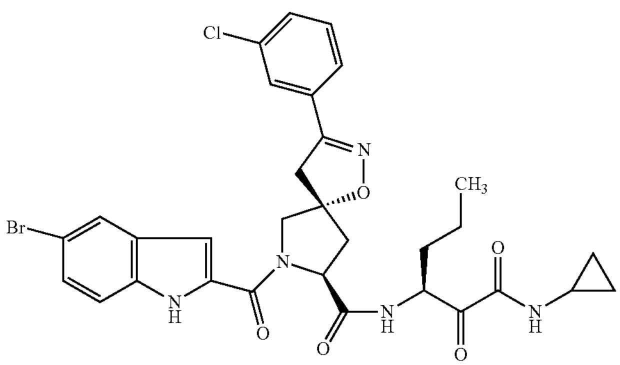 | 46 |
| 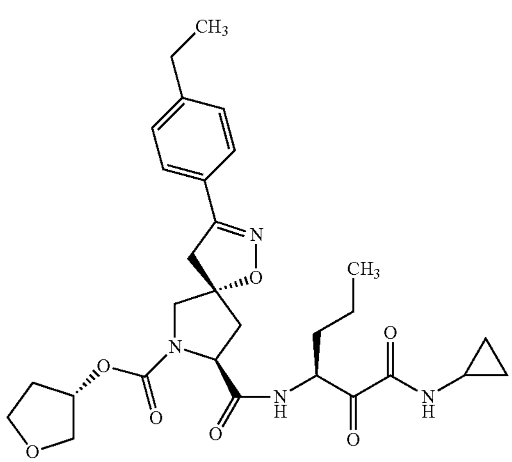 | 47 |

TABLE 1-continued

Exemplary compounds of Formula (I).

| Structure | Compound No. |
|---|---|
| 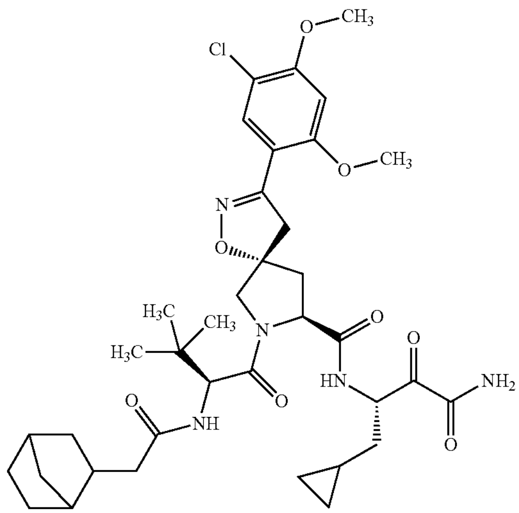 | 48 |
| 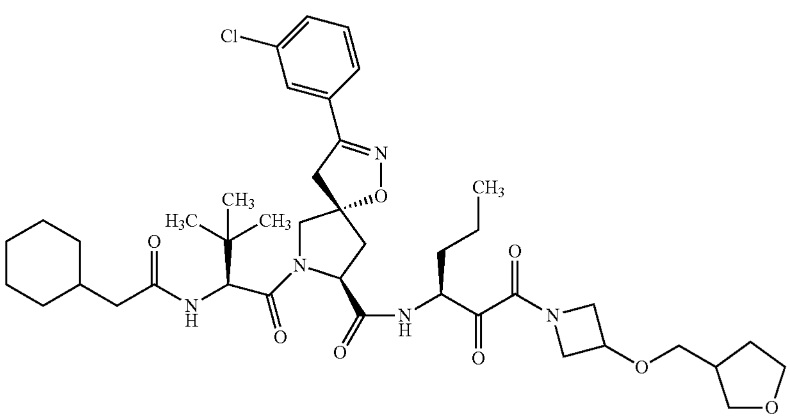 | 49 |
| 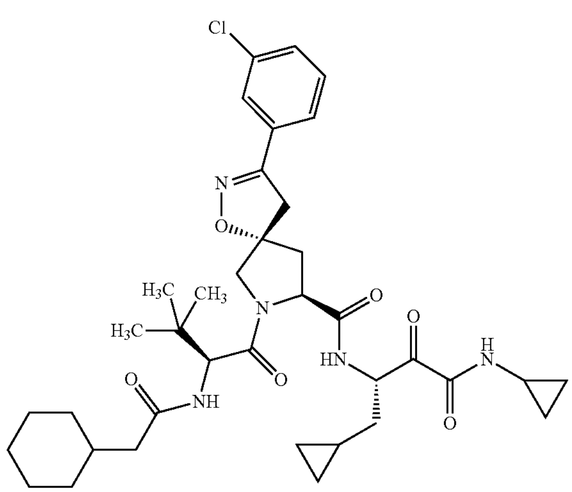 | 50 |

TABLE 1-continued

Exemplary compounds of Formula (I).

| Structure | Compound No. |
|---|---|
| 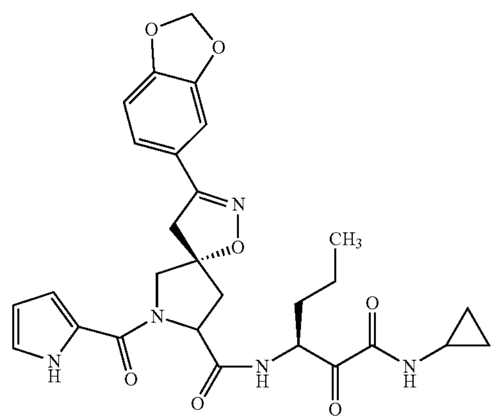 | 51 |
| 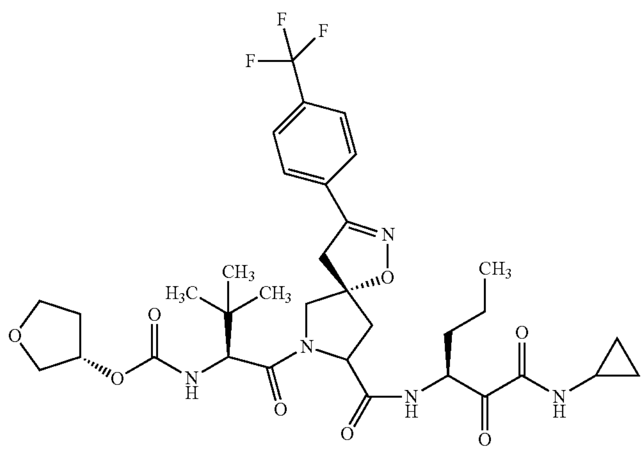 | 52 |
| 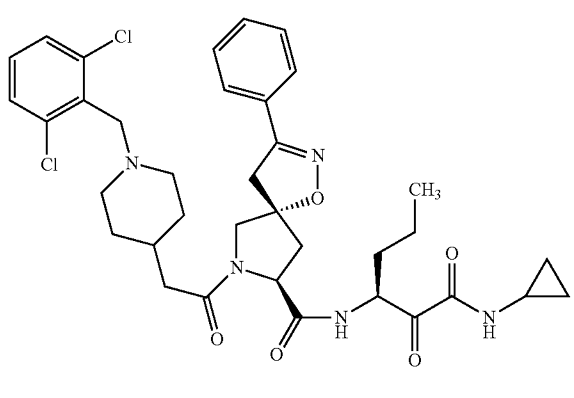 | 53 |

TABLE 1-continued
Exemplary compounds of Formula (I).
| Structure | Compound No. |
|---|---|
| 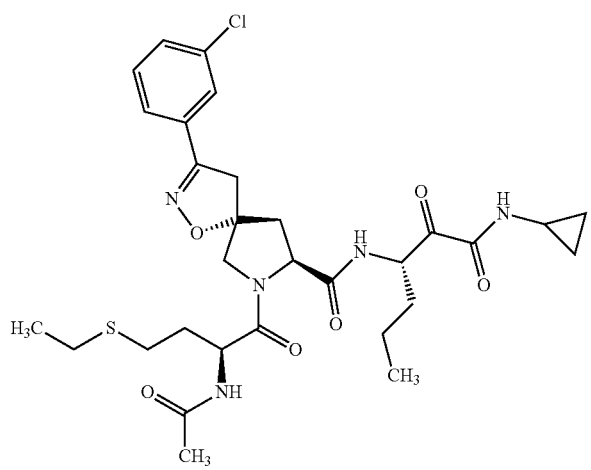 | 54 |
| 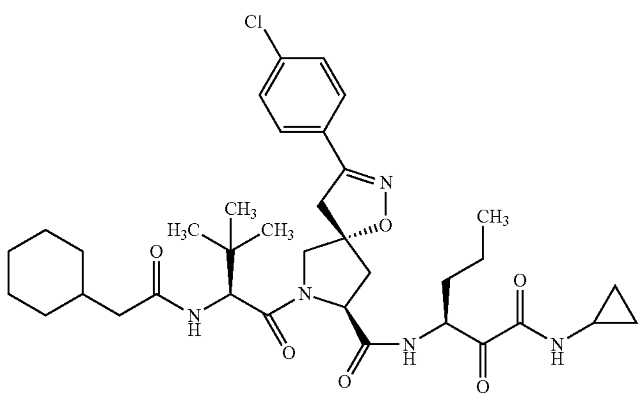 | 55 |
| 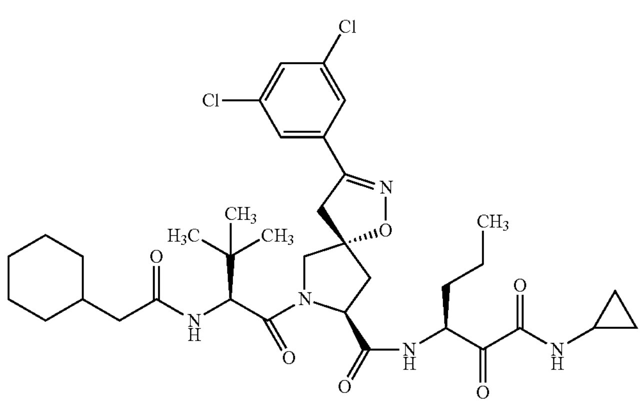 | 56 |

TABLE 1-continued
Exemplary compounds of Formula (I).
| Structure | Compound No. |
|---|---|
| 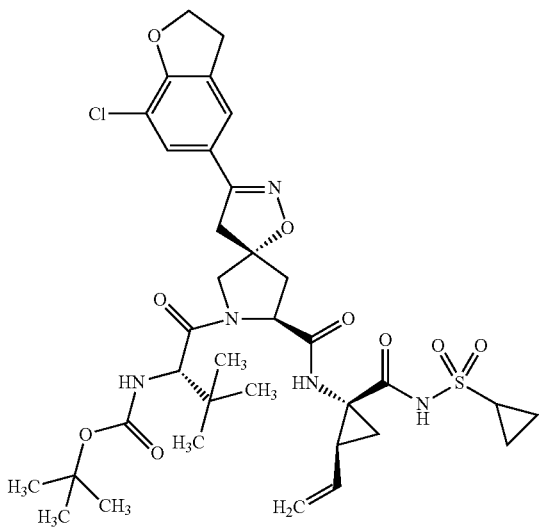 | 57 |
| 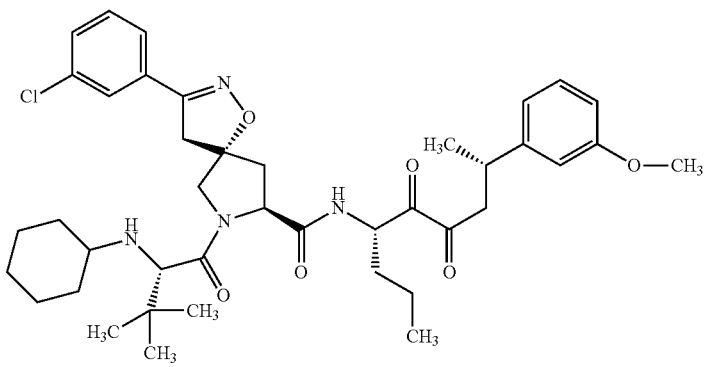 | 58 |
| 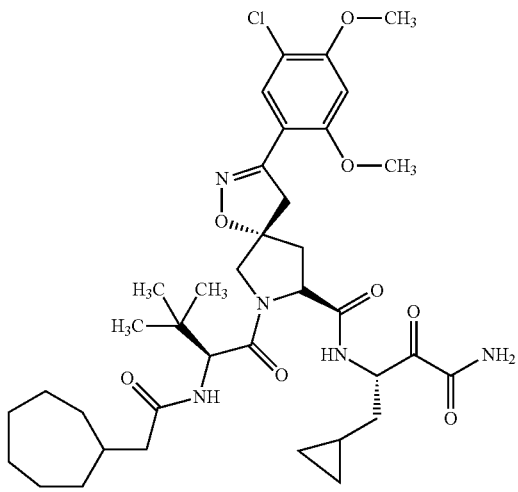 | 59 |

TABLE 1-continued

Exemplary compounds of Formula (I).

| Structure | Compound No. |
|---|---|
| 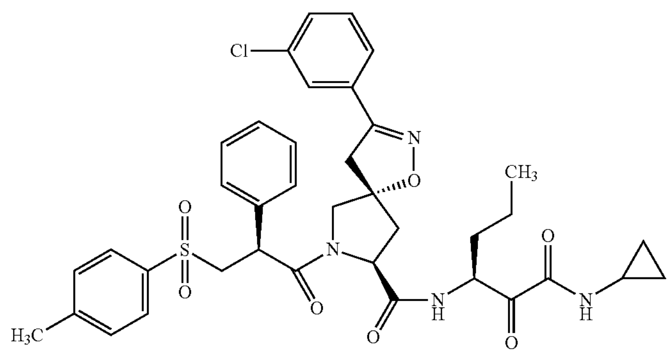 | 60 |
| 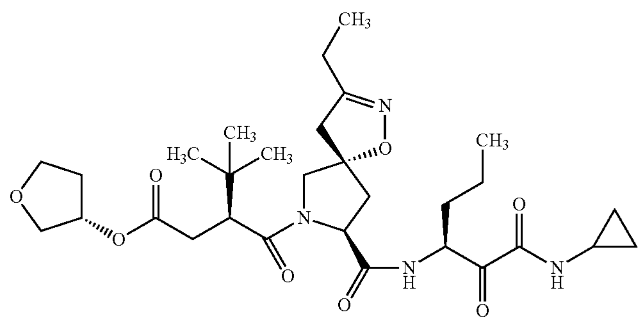 | 61 |
| 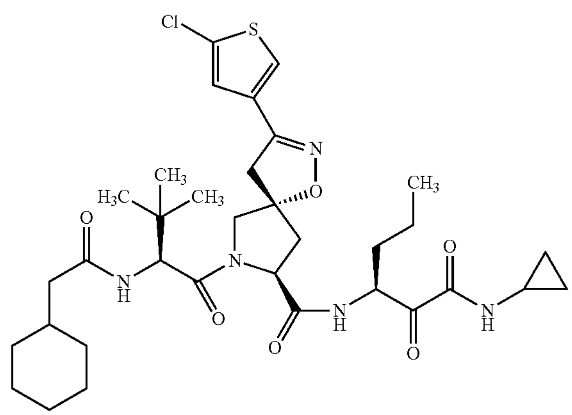 | 62 |
| 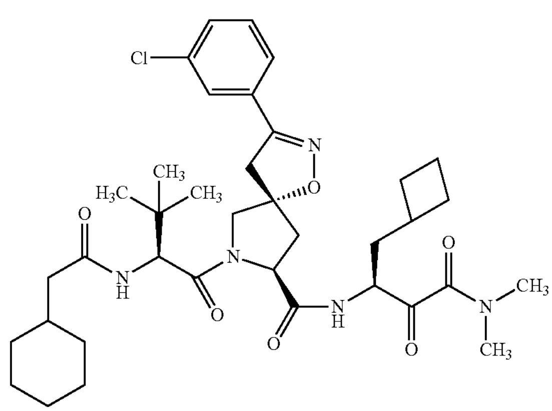 | 63 |

TABLE 1-continued

Exemplary compounds of Formula (I).

| Structure | Compound No. |
|---|---|
| 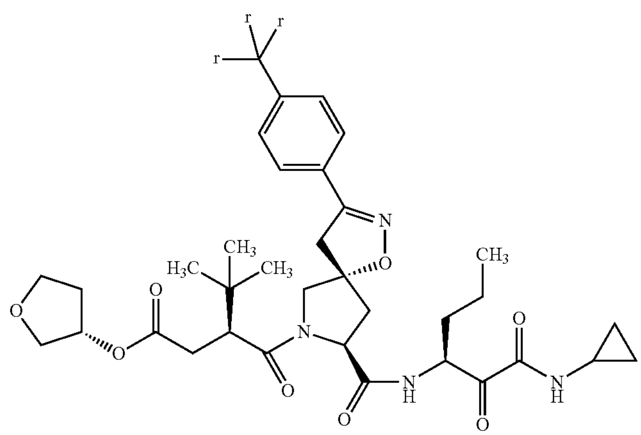 | 64 |
| 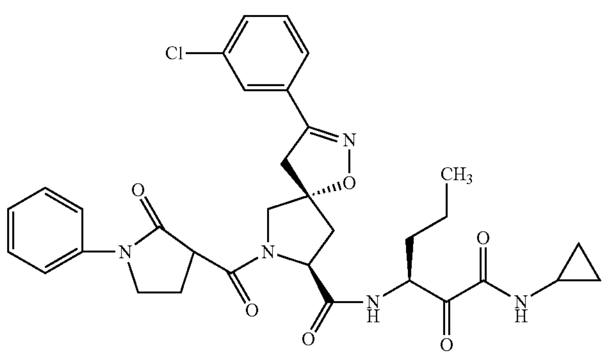 | 65 |
| 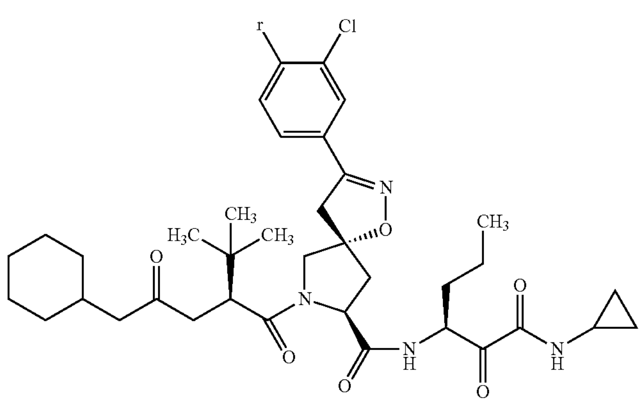 | 66 |

TABLE 1-continued
Exemplary compounds of Formula (I).
| Structure | Compound No. |
|---|---|
| 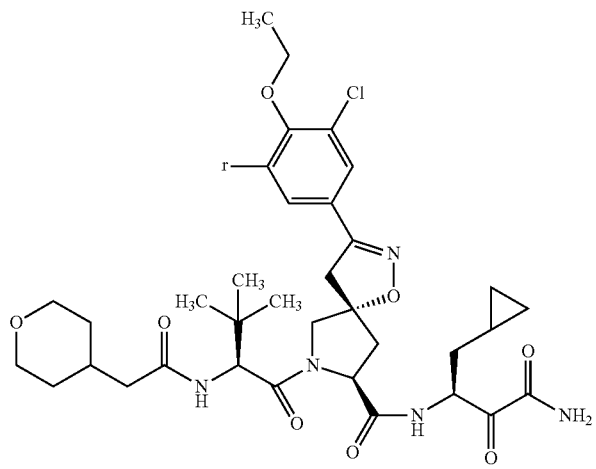 | 67 |
| 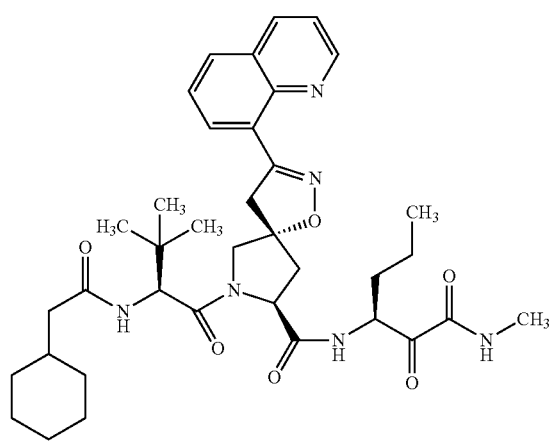 | 68 |
| 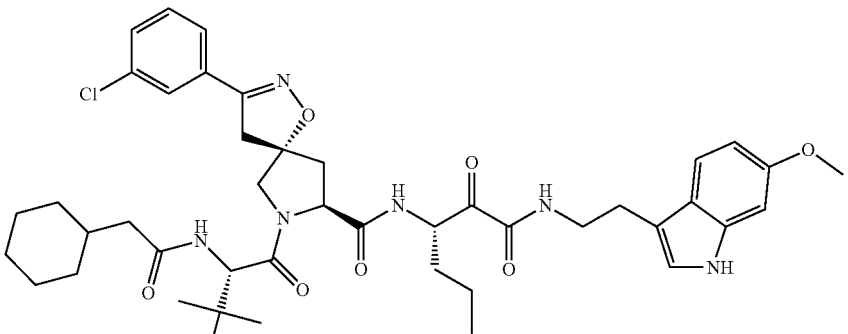 | 69 |

TABLE 1-continued

Exemplary compounds of Formula (I).

| Structure | Compound No. |
|---|---|
| 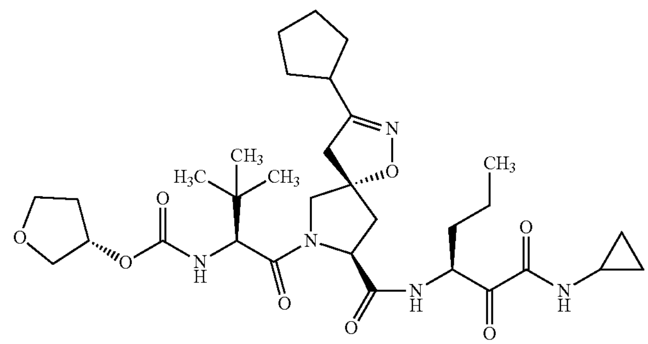 | 70 |
| 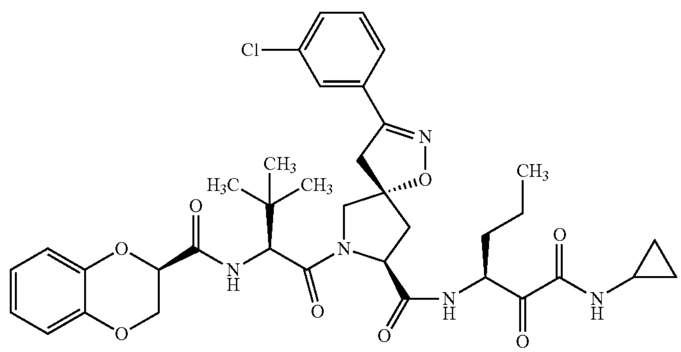 | 71 |
| 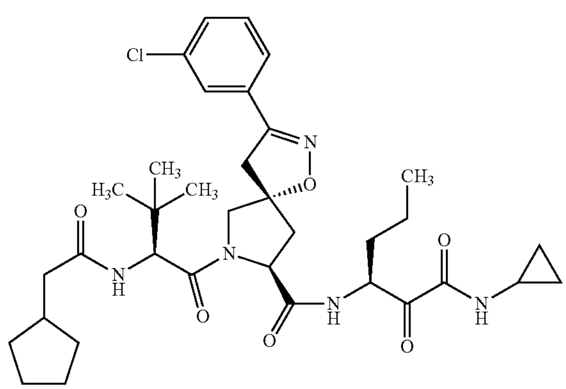 | 72 |
| 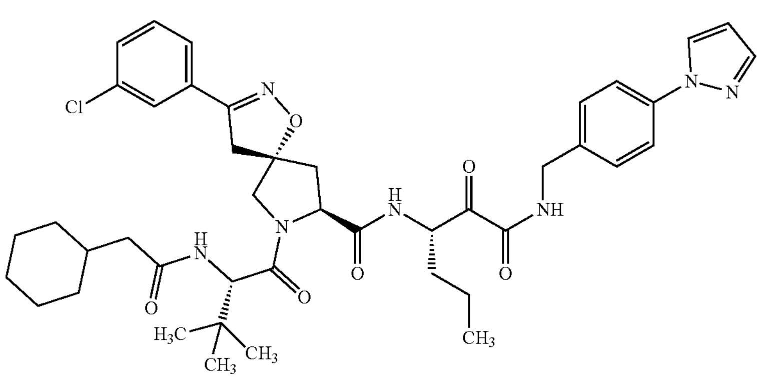 | 73 |

| Structure | Compound No. |
|---|---|
| 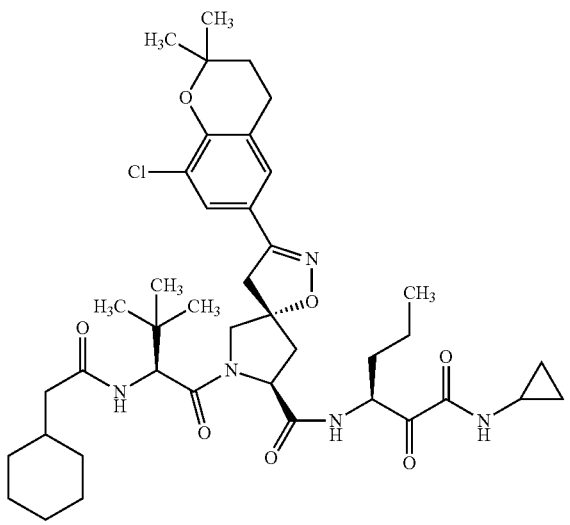 | 74 |
| 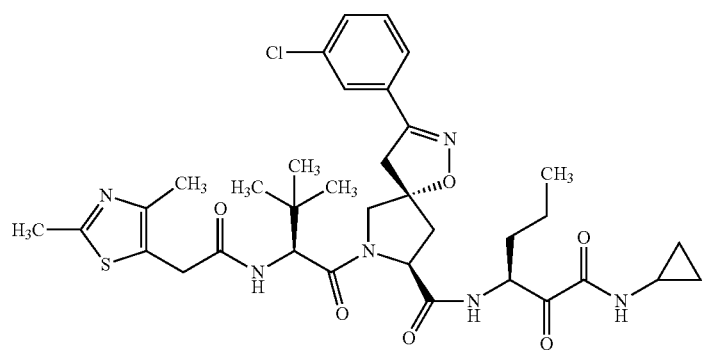 | 75 |
| 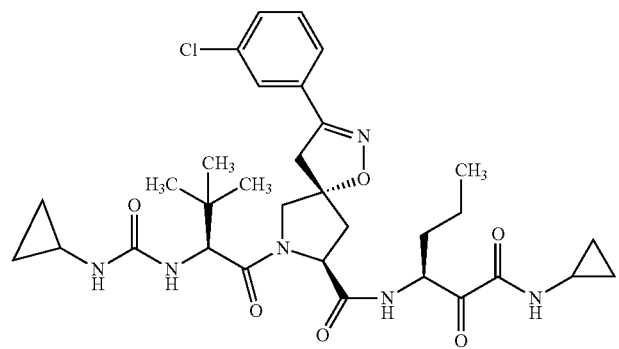 | 76 |

TABLE 1-continued

Exemplary compounds of Formula (I).

| Structure | Compound No. |
|---|---|
| 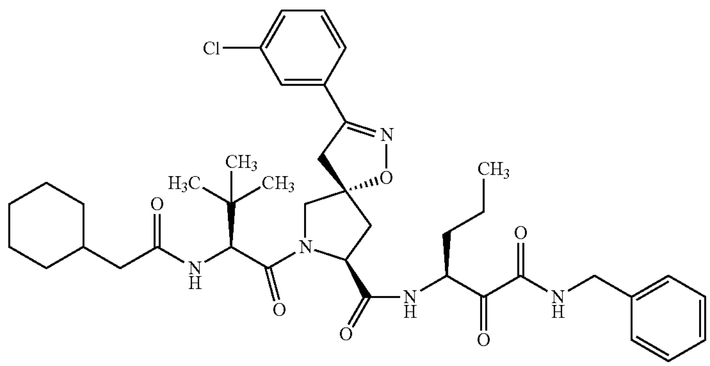 | 77 |
| 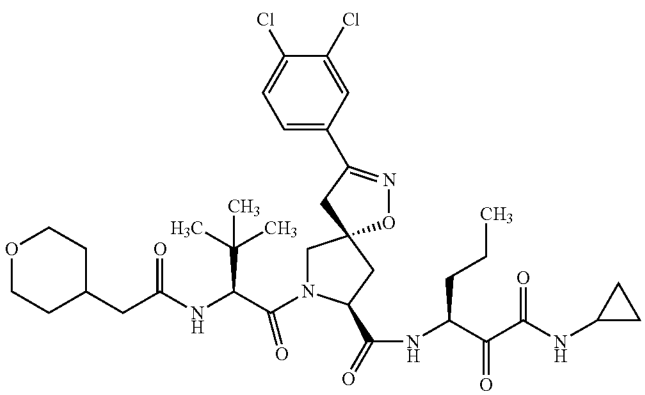 | 78 |
| 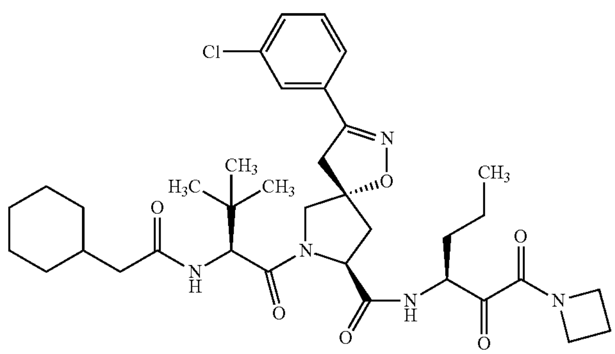 | 79 |
| 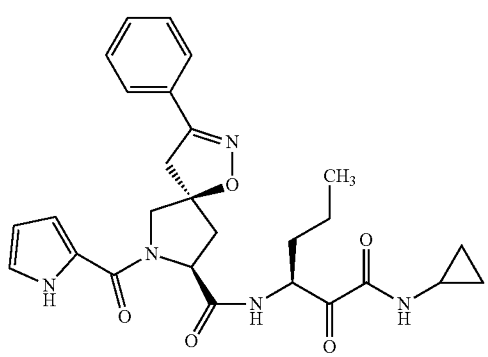 | 80 |

TABLE 1-continued

Exemplary compounds of Formula (I).

| Structure | Compound No. |
|---|---|
| 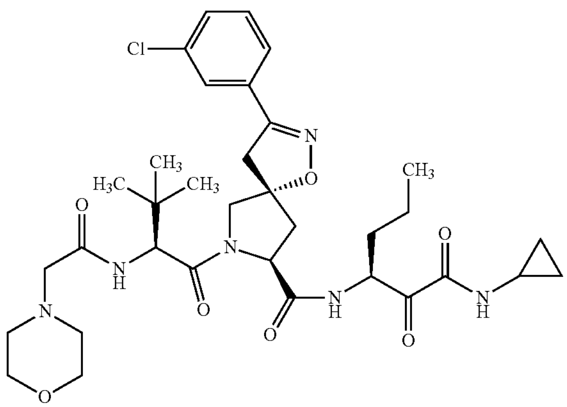 | 81 |
| 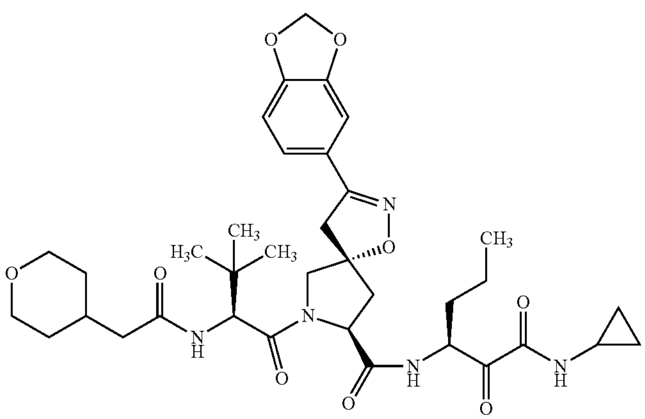 | 82 |
| 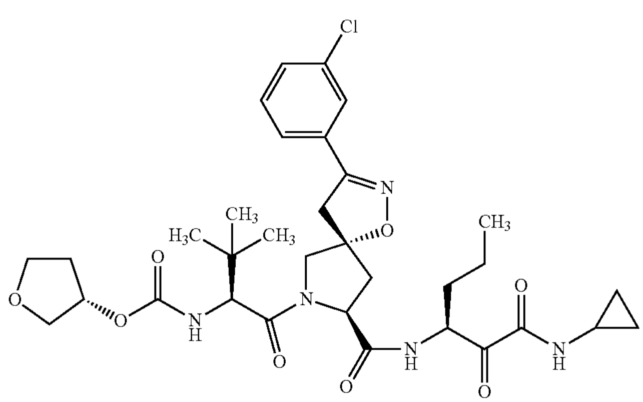 | 83 |

TABLE 1-continued

Exemplary compounds of Formula (I).

| Structure | Compound No. |
|---|---|
| 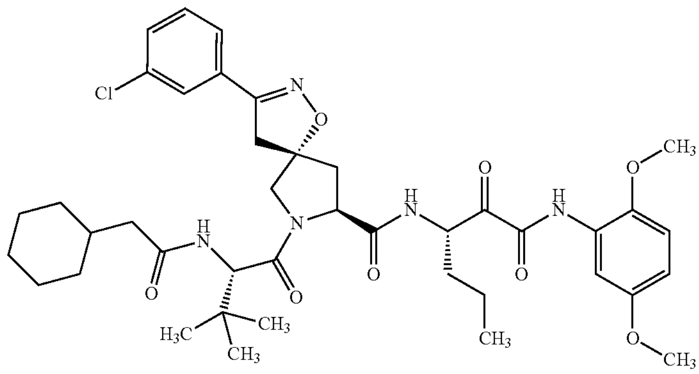 | 84 |
| 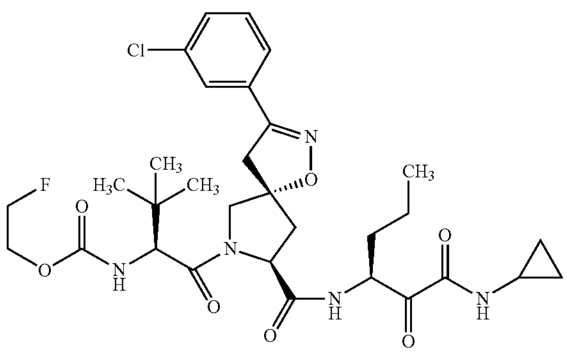 | 85 |
| 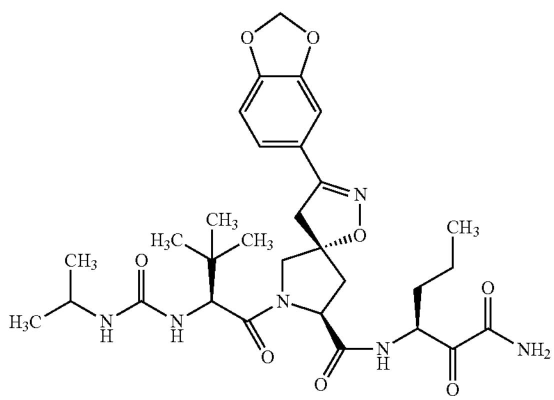 | 86 |
| 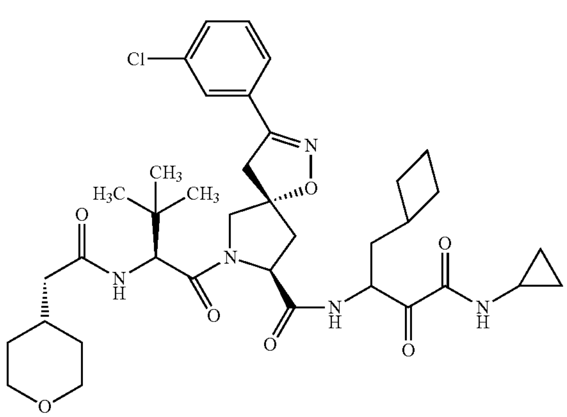 | 87 |

TABLE 1-continued
Exemplary compounds of Formula (I).
| Structure | Compound No. |
|---|---|
| 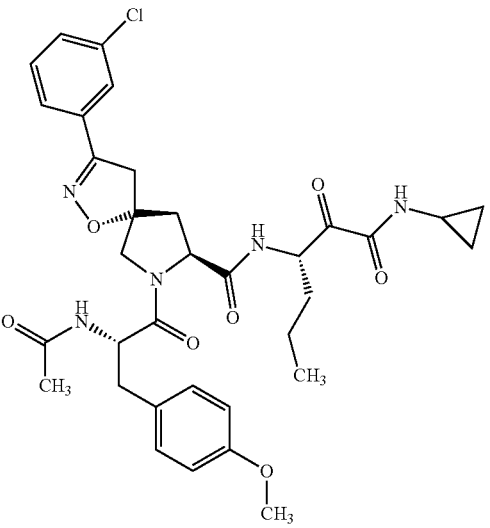 | 88 |
| 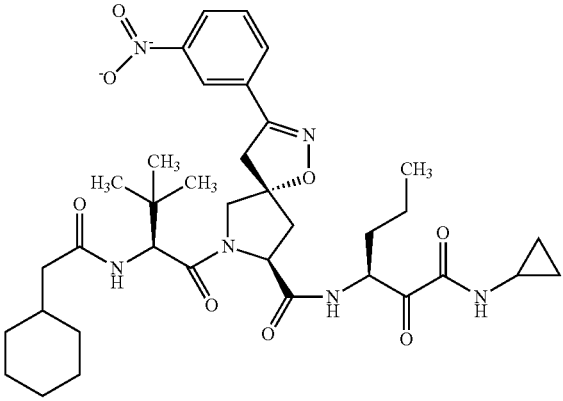 | 89 |
| 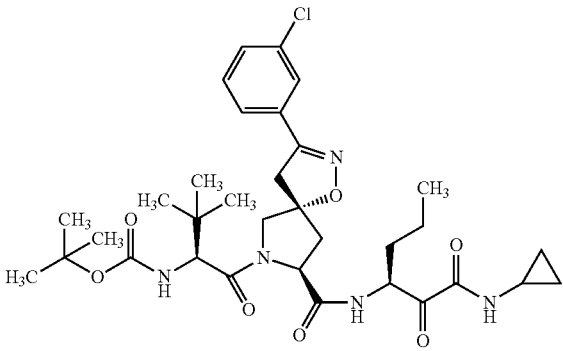 | 90 |

TABLE 1-continued

Exemplary compounds of Formula (I).

| Structure | Compound No. |
|---|---|
| 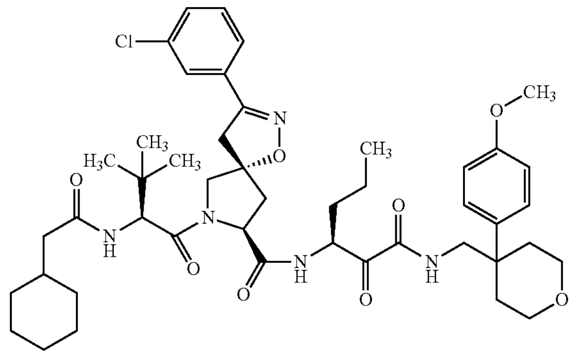 | 91 |
| 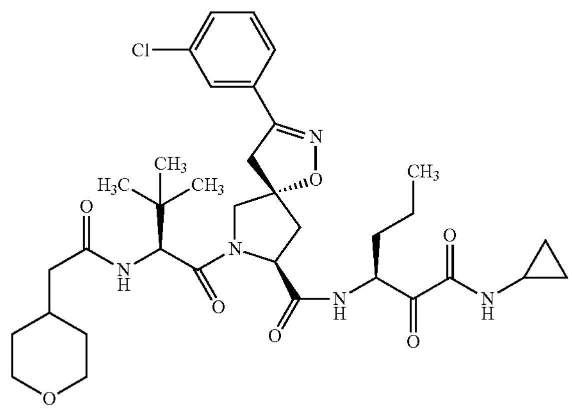 | 92 |
| 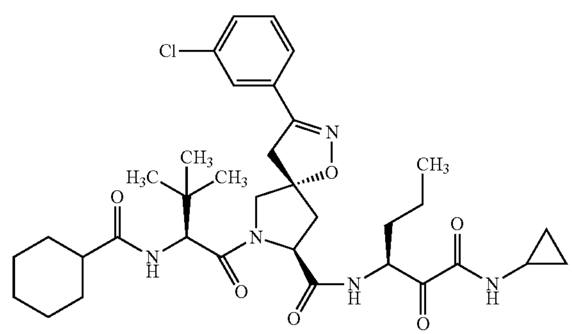 | 93 |
| 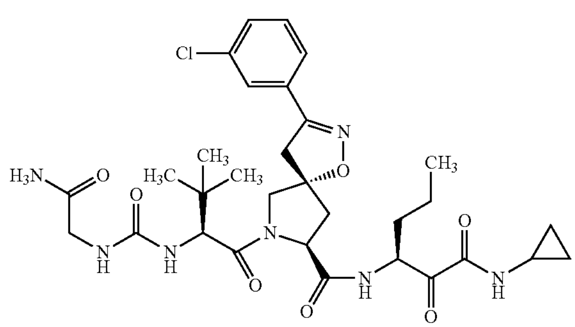 | 94 |

TABLE 1-continued

Exemplary compounds of Formula (I).

| Structure | Compound No. |
|---|---|
| 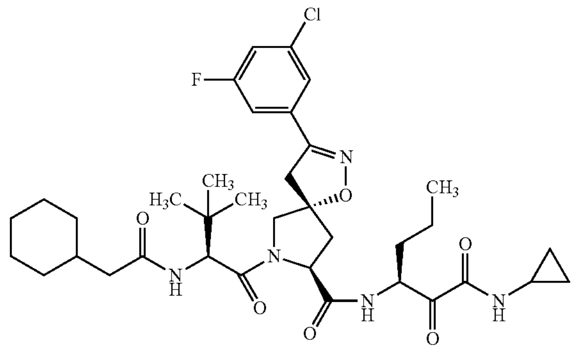 | 95 |
| 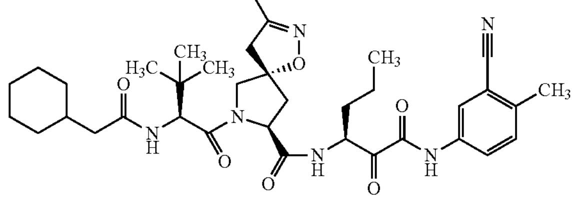 | 96 |
| 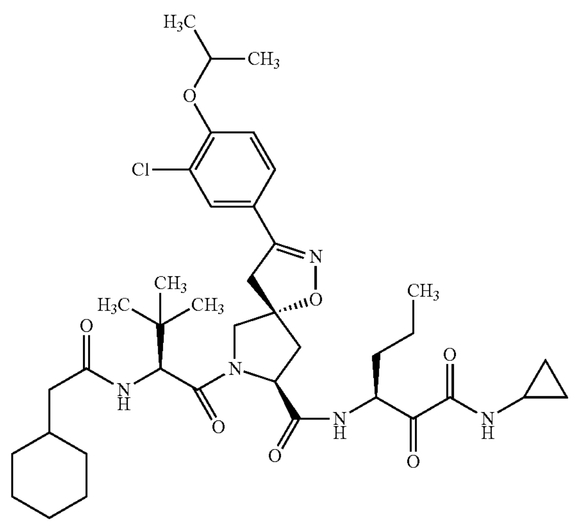 | 97 |
| 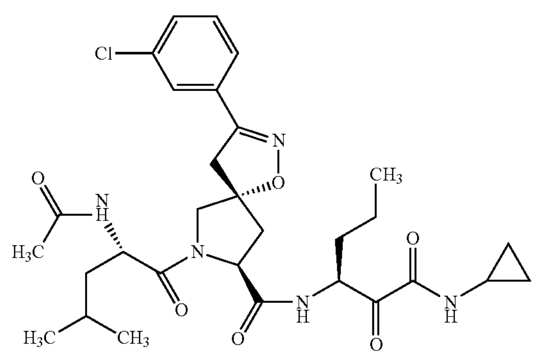 | 98 |

TABLE 1-continued

Exemplary compounds of Formula (I).

| Structure | Compound No. |
|---|---|
| 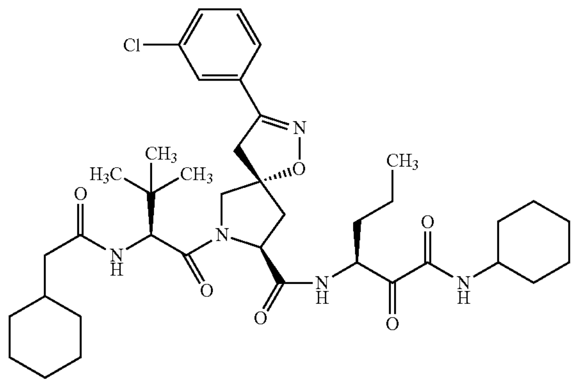 | 99 |
| 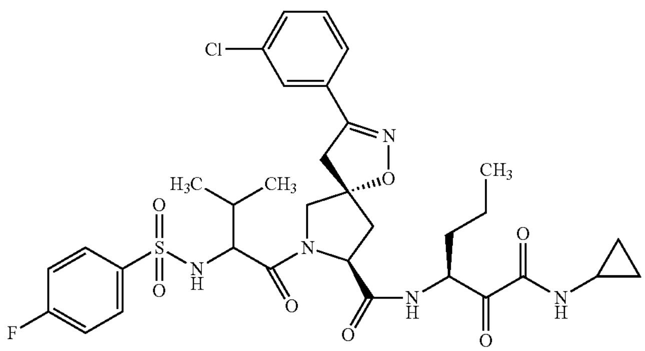 | 100 |
| 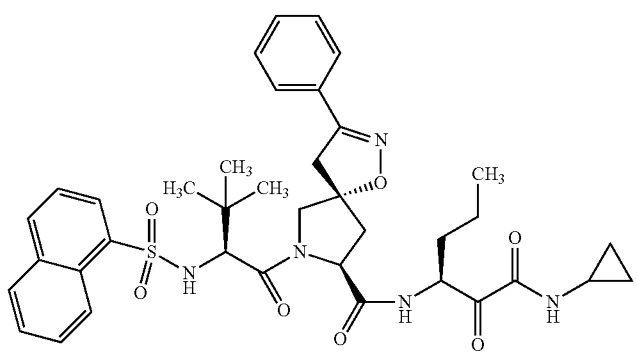 | 101 |
| 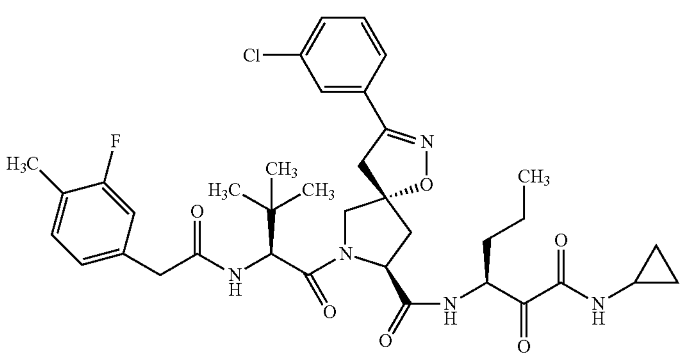 | 102 |

TABLE 1-continued

Exemplary compounds of Formula (I).

| Structure | Compound No. |
|---|---|
| 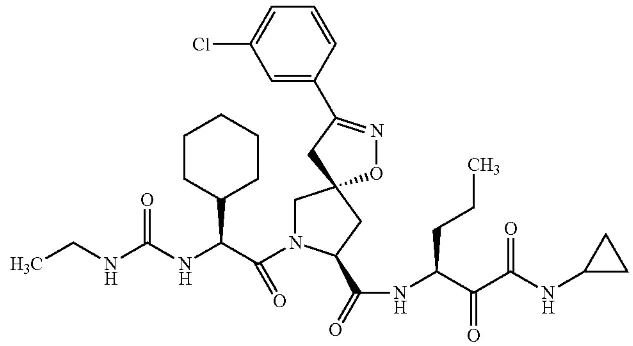 | 103 |
| 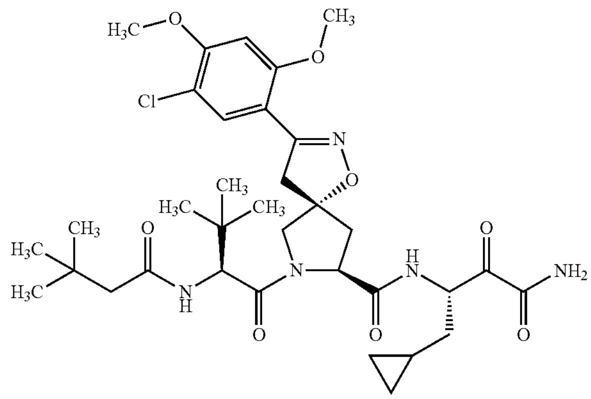 | 104 |
| 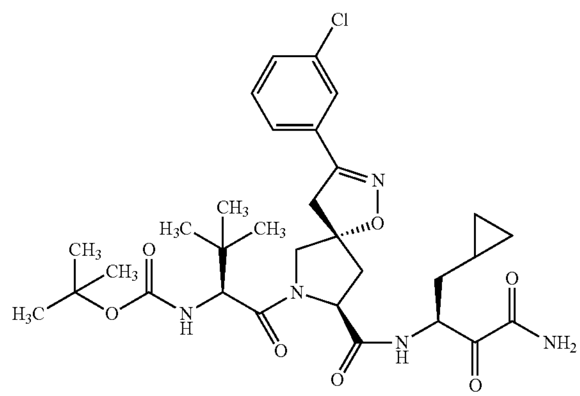 | 105 |
| 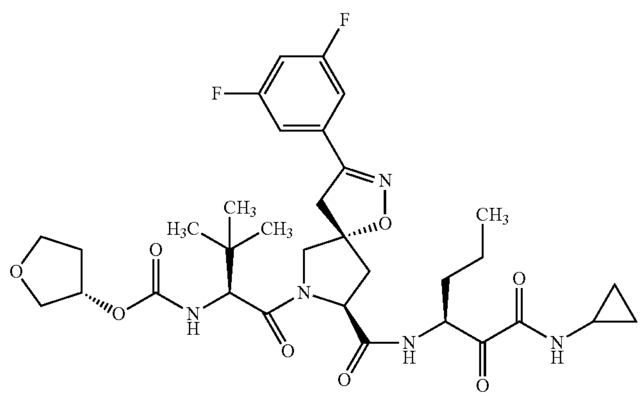 | 106 |

TABLE 1-continued

Exemplary compounds of Formula (I).

| Structure | Compound No. |
|---|---|
| 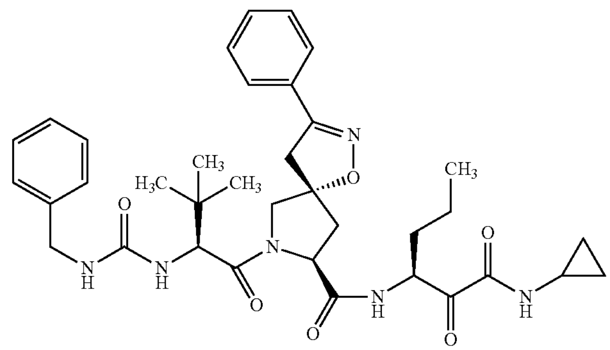 | 107 |
| 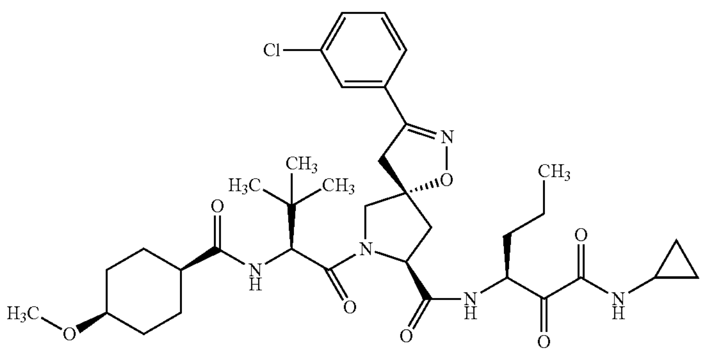 | 108 |
| 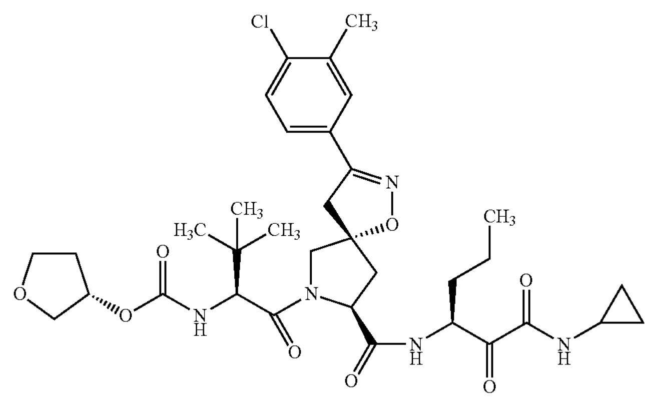 | 109 |
| 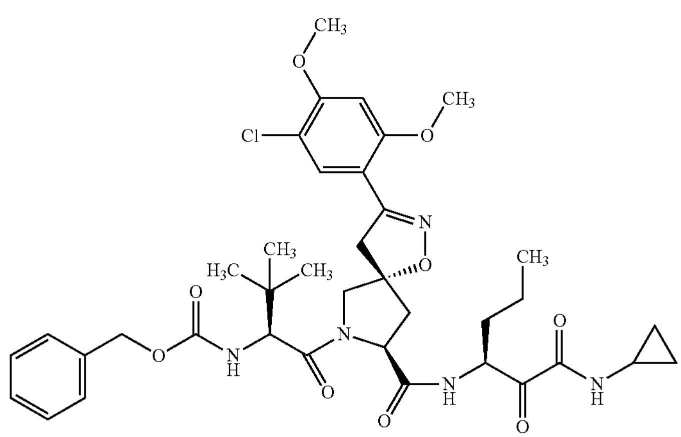 | 110 |

TABLE 1-continued

Exemplary compounds of Formula (I).

| Structure | Compound No. |
|---|---|
| 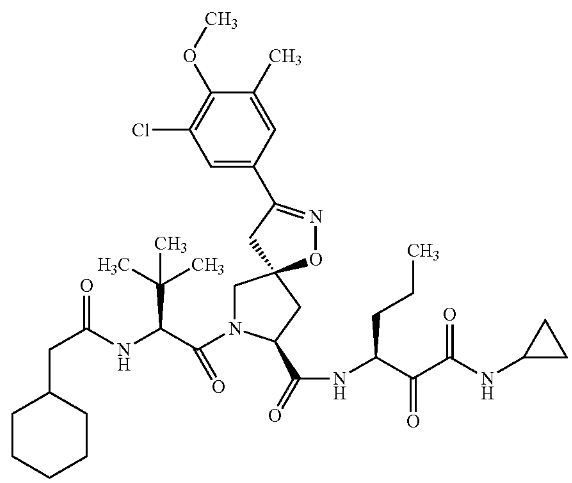 | 111 |
| 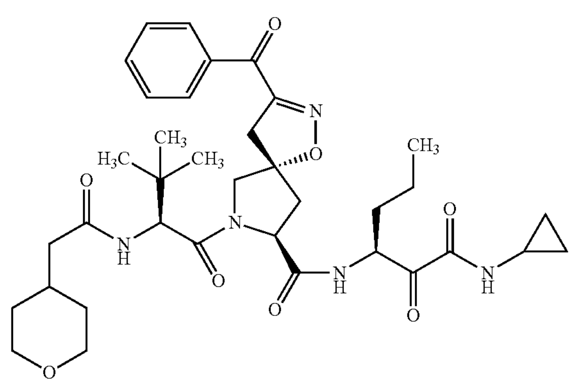 | 112 |
| 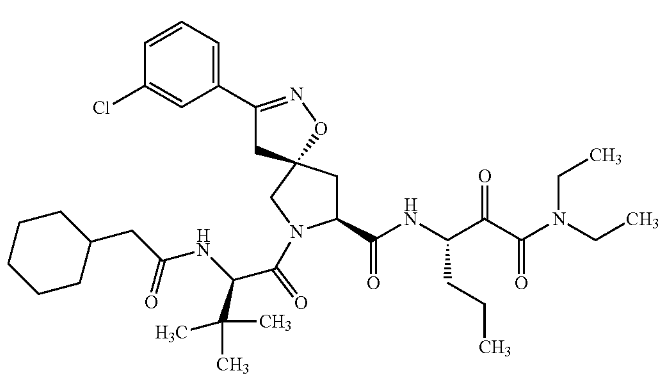 | 113 |

TABLE 1-continued

Exemplary compounds of Formula (I).

| Structure | Compound No. |
|---|---|
| 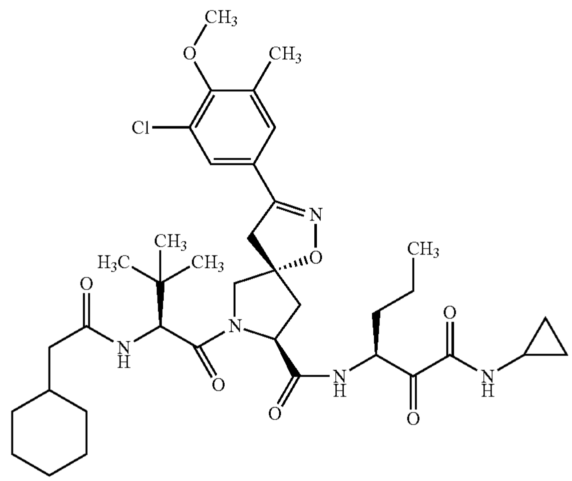 | 114 |
| 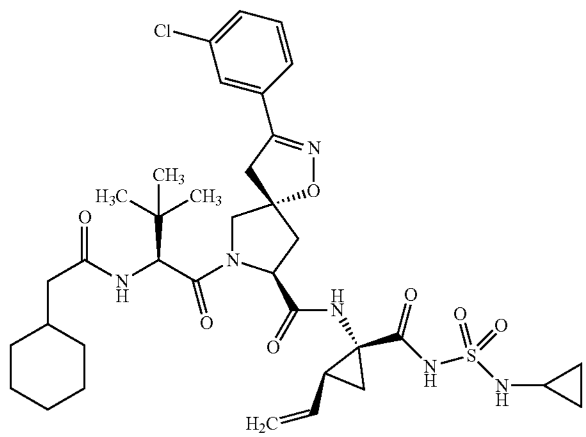 | 115 |
| 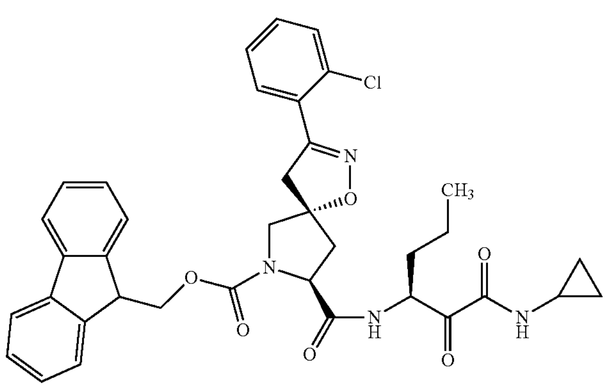 | 116 |

TABLE 1-continued

Exemplary compounds of Formula (I).

| Structure | Compound No. |
|---|---|
| 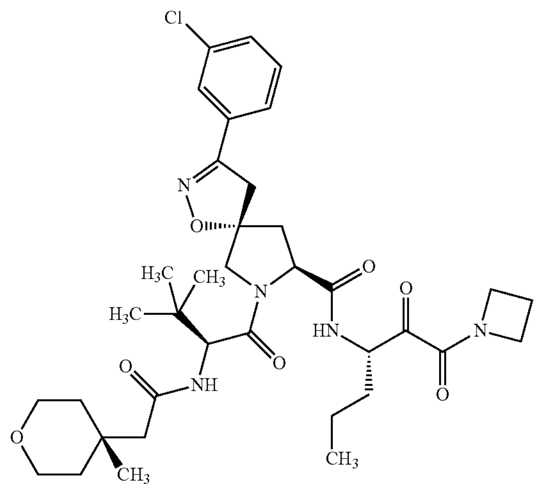 | 117 |
| 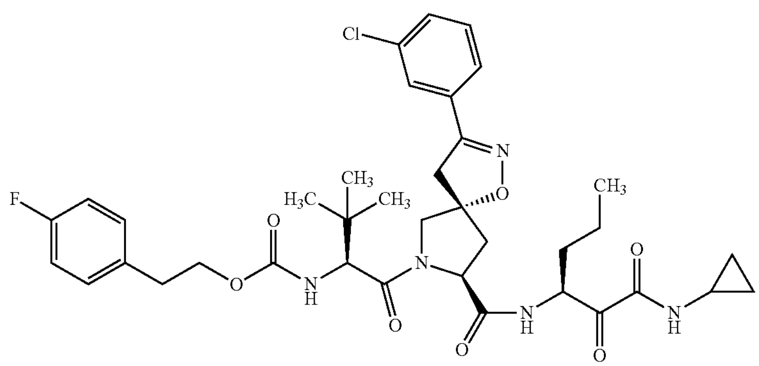 | 118 |
| 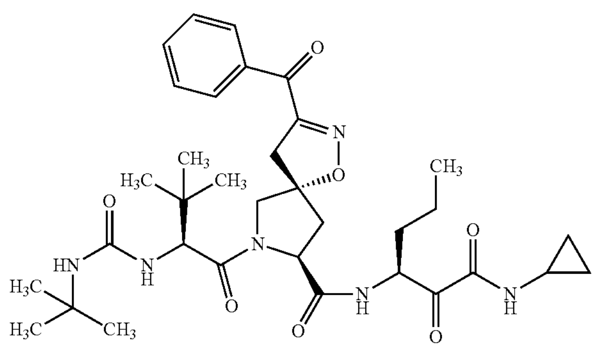 | 119 |
| 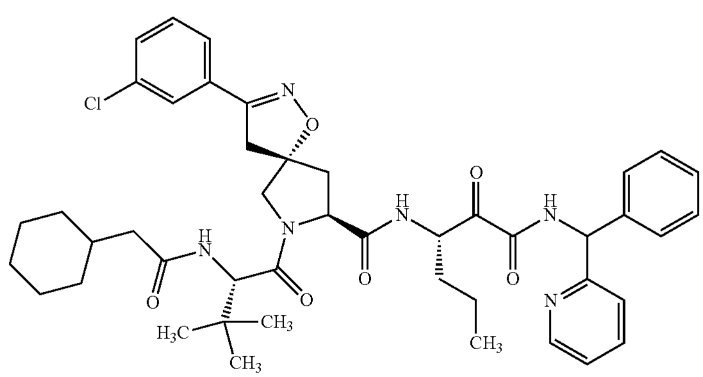 | 120 |

TABLE 1-continued
Exemplary compounds of Formula (I).
| Structure | Compound No. |
| --- | --- |
| 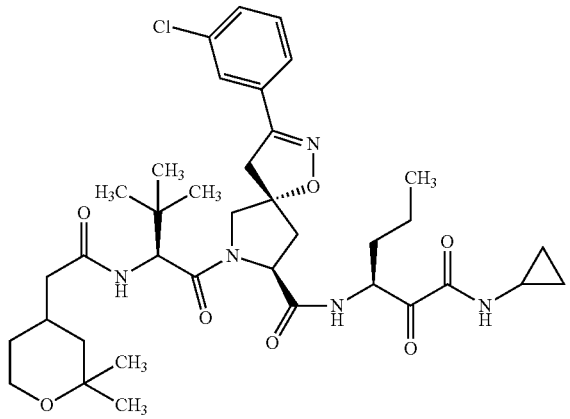 | 121 |
| 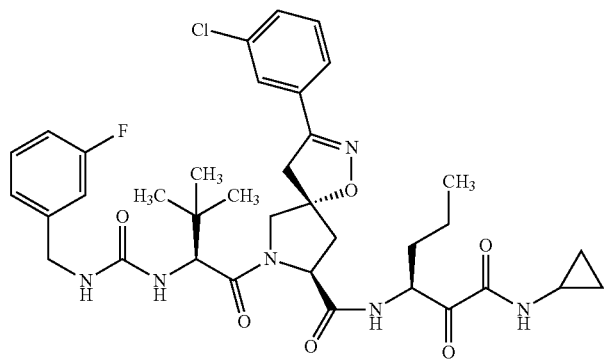 | 122 |
| 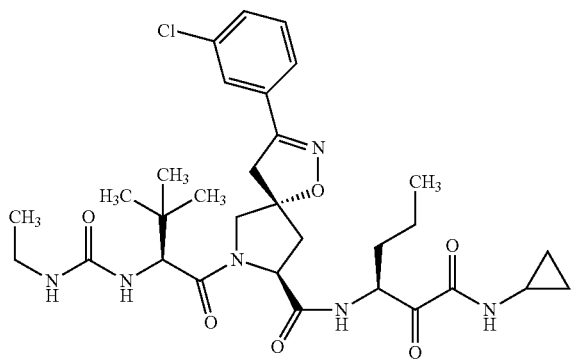 | 123 |

TABLE 1-continued

Exemplary compounds of Formula (I).

| Structure | Compound No. |
|---|---|
| 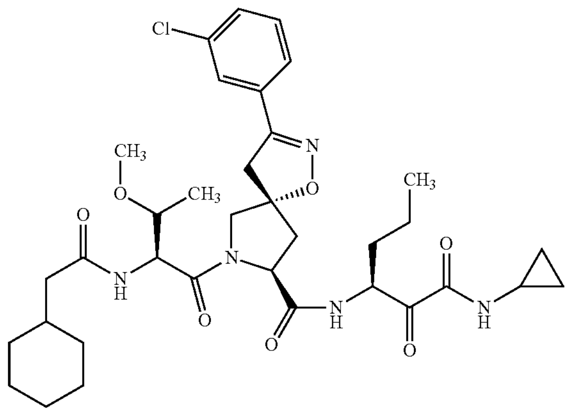 | 124 |
| 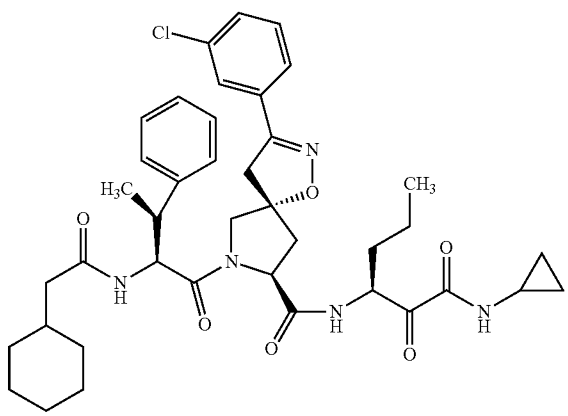 | 125 |
| 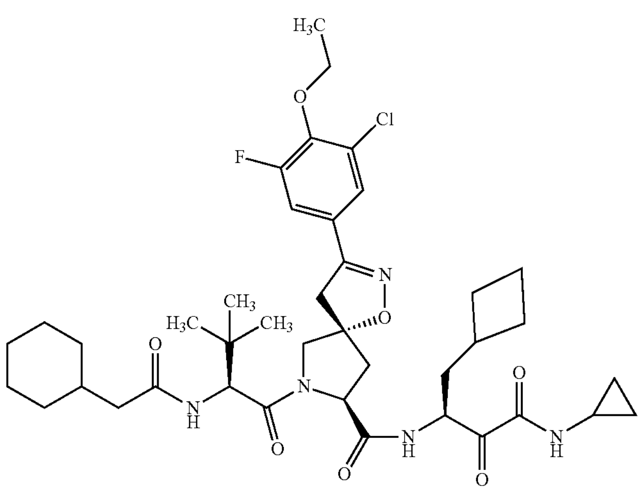 | 126 |

TABLE 1-continued

Exemplary compounds of Formula (I).

| Structure | Compound No. |
|---|---|
| 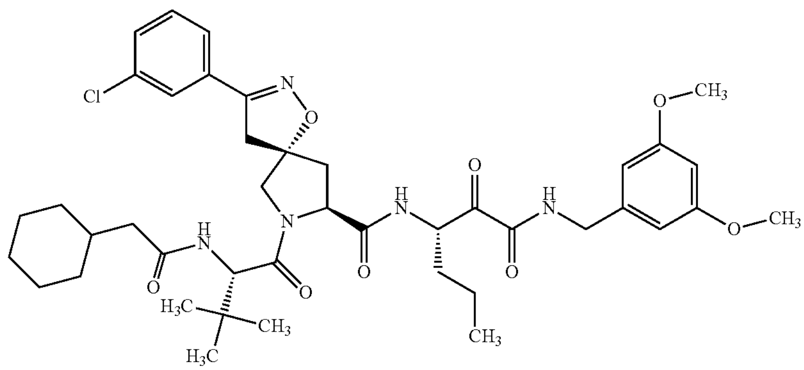 | 127 |
| 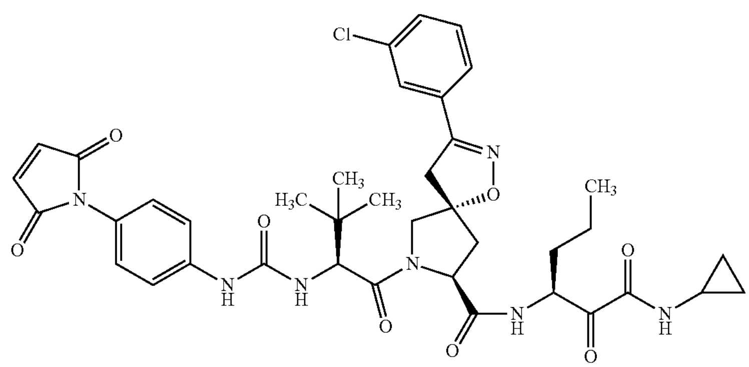 | 128 |
| 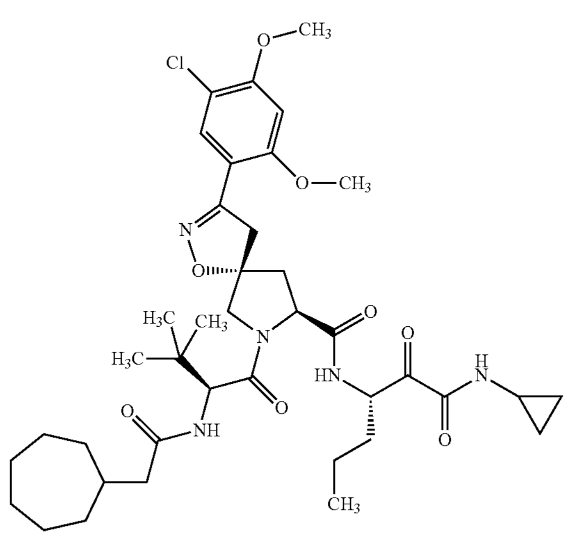 | 129 |

TABLE 1-continued

Exemplary compounds of Formula (I).

| Structure | Compound No. |
|---|---|
| 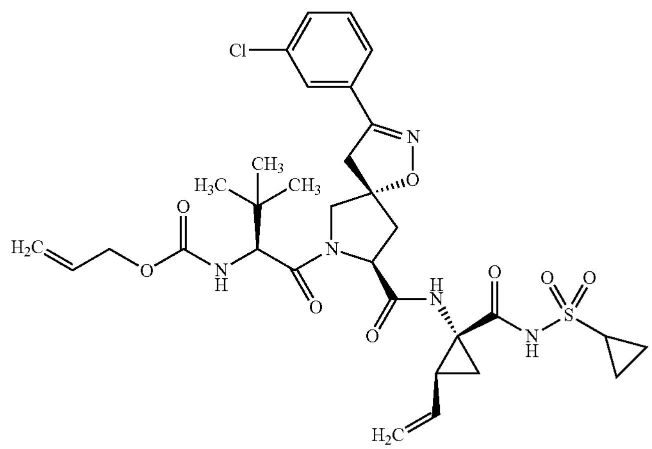 | 130 |
| 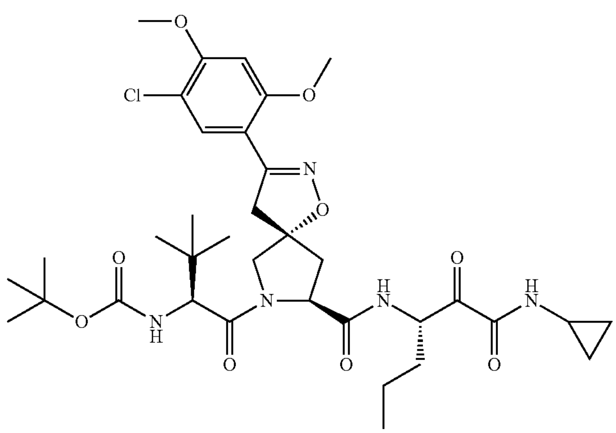 | 131 |
| 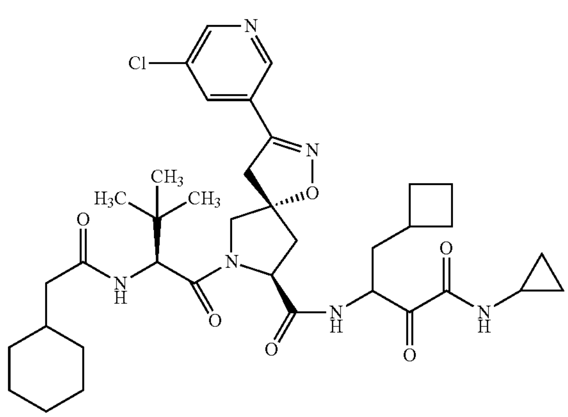 | 132 |

TABLE 1-continued

Exemplary compounds of Formula (I).

| Structure | Compound No. |
|---|---|
| 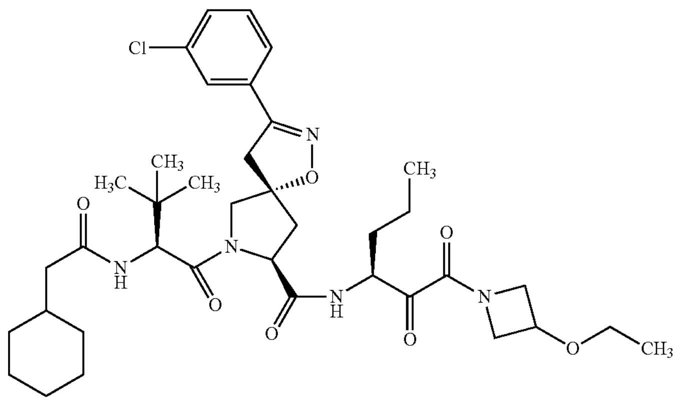 | 133 |
| 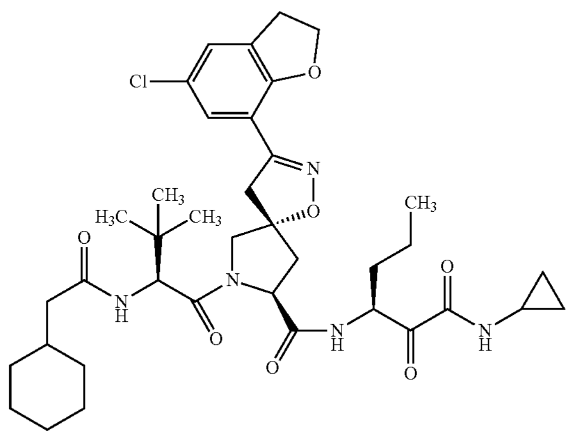 | 134 |
| 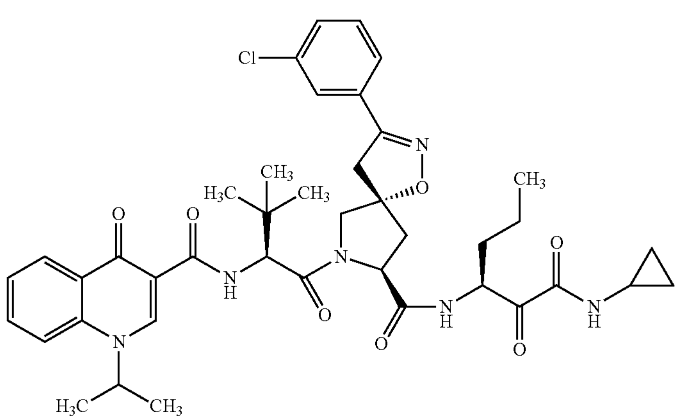 | 135 |

TABLE 1-continued

Exemplary compounds of Formula (I).

| Structure | Compound No. |
|---|---|
| 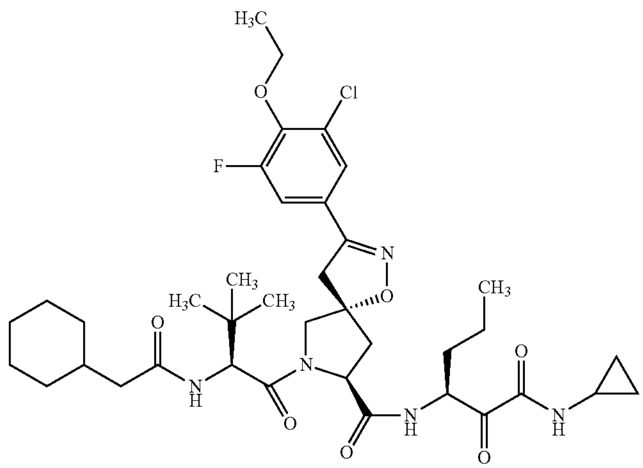 | 136 |
| 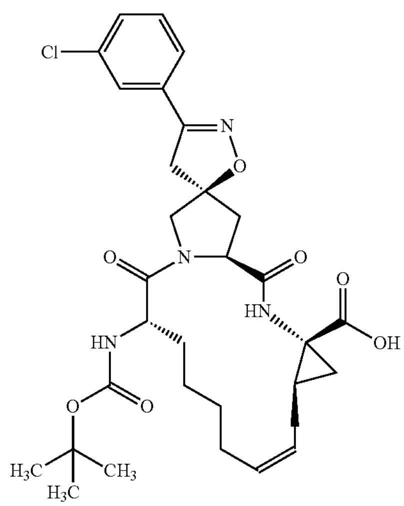 | 137 |
| 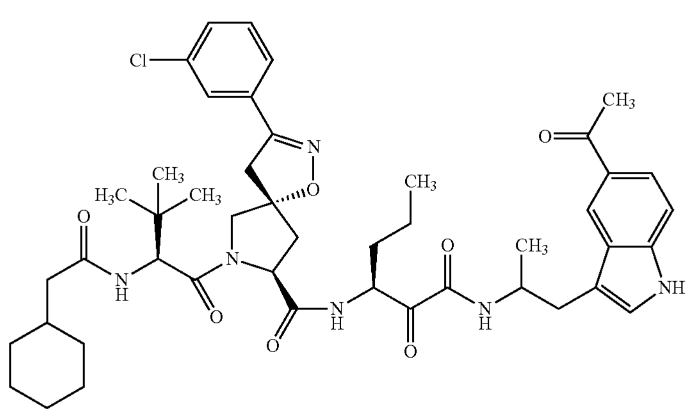 | 138 |

TABLE 1-continued

Exemplary compounds of Formula (I).

| Structure | Compound No. |
|---|---|
| 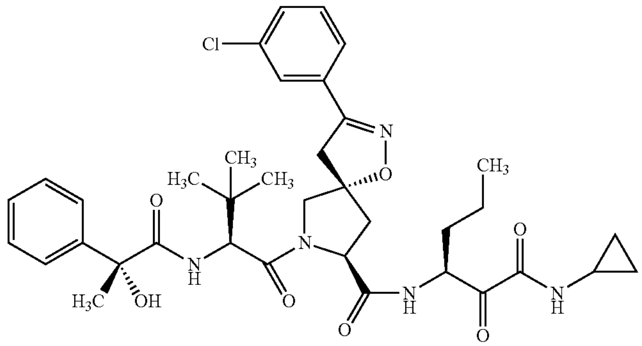 | 139 |
| 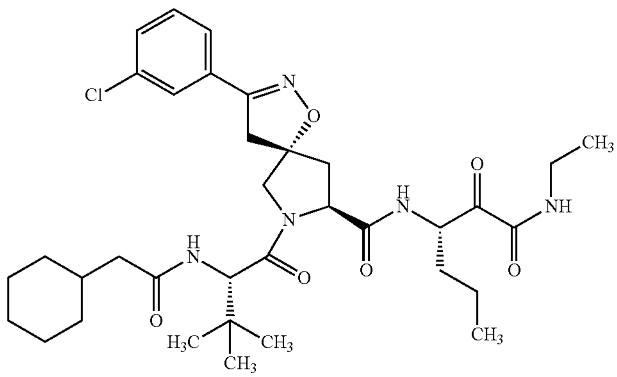 | 140 |
| 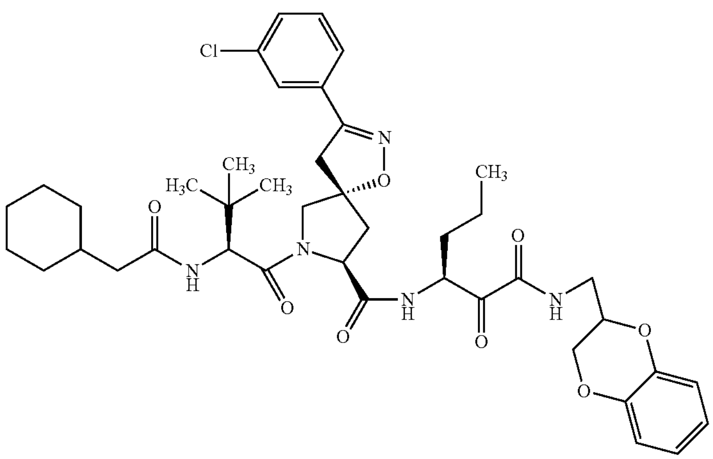 | 141 |
| 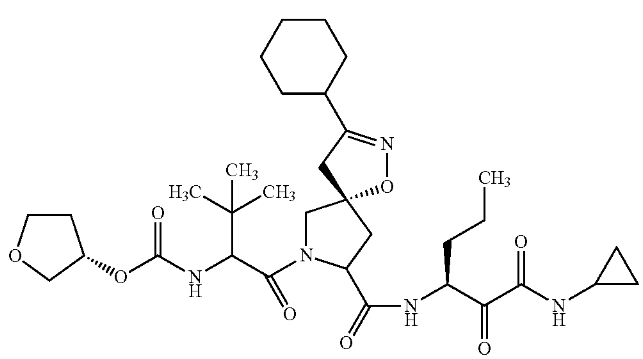 | 142 |

TABLE 1-continued

Exemplary compounds of Formula (I).

| Structure | Compound No. |
|---|---|
| 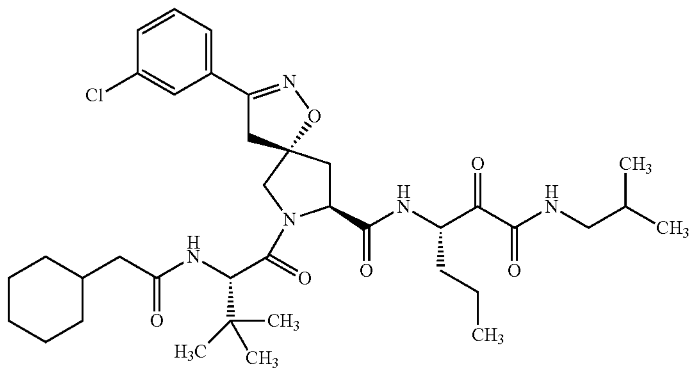 | 143 |
| 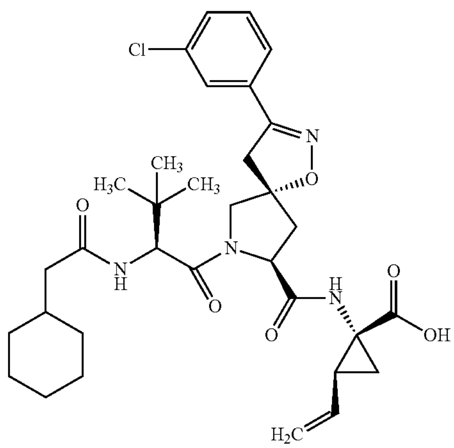 | 144 |
| 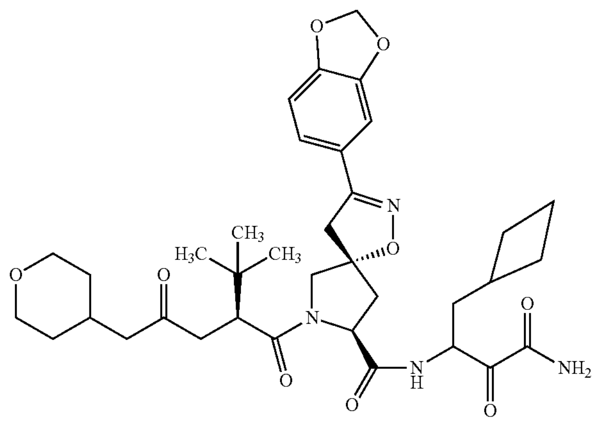 | 145 |
| 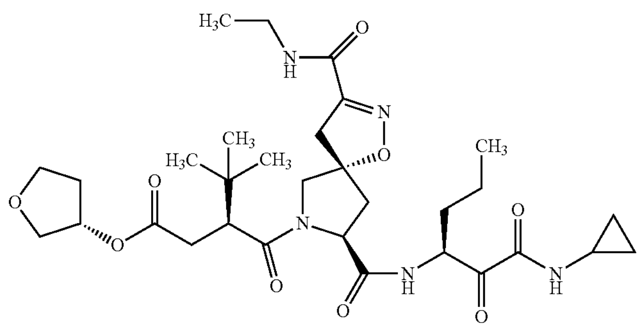 | 146 |

193
TABLE 1-continued
Exemplary compounds of Formula (I).
| Structure | Compound No. |
|---|---|
| 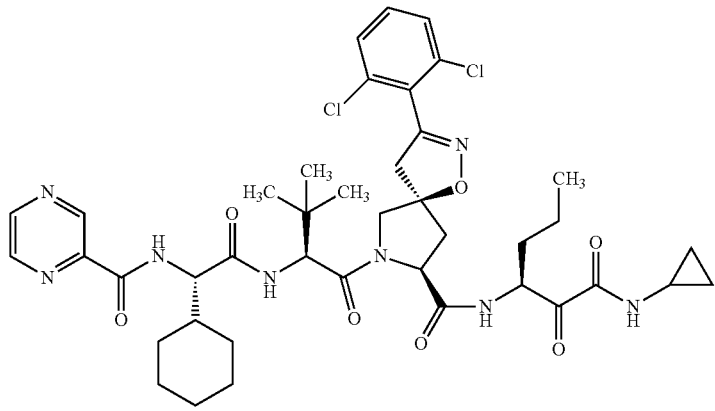 | 147 |
| 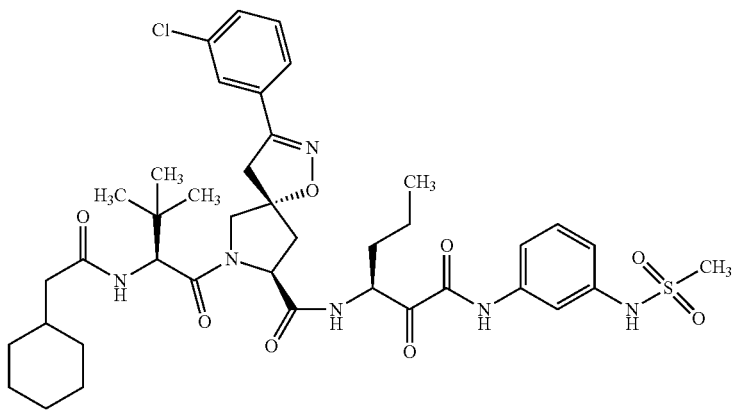 | 148 |
| 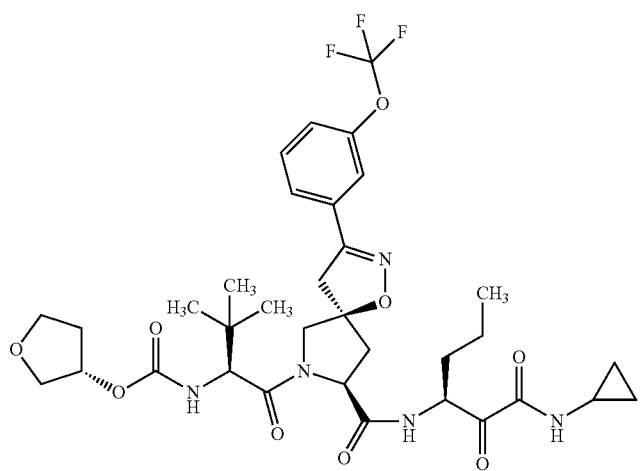 | 149 |

TABLE 1-continued
Exemplary compounds of Formula (I).
| Structure | Compound No. |
|---|---|
| 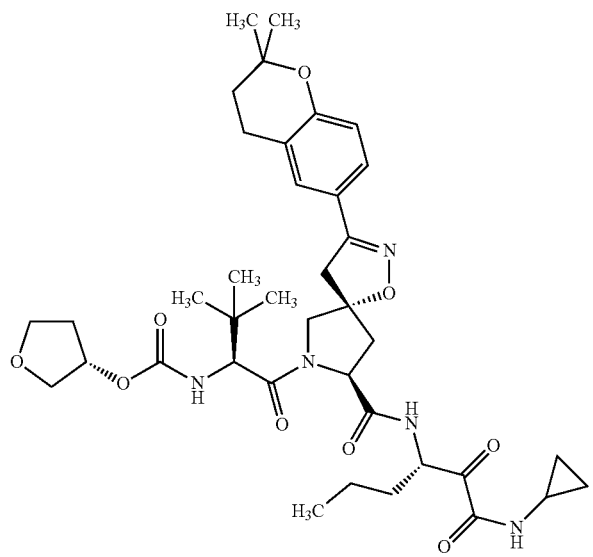 | 150 |
| 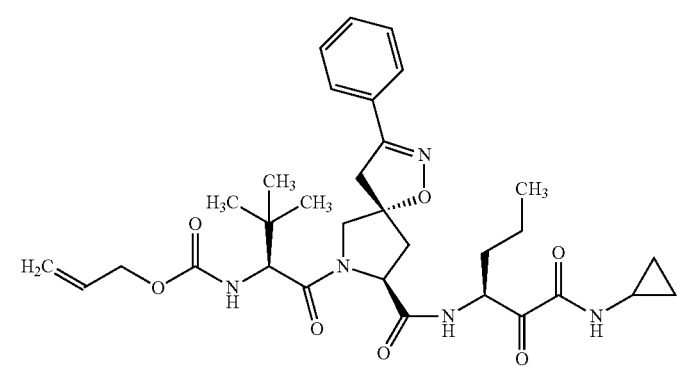 | 151 |
| 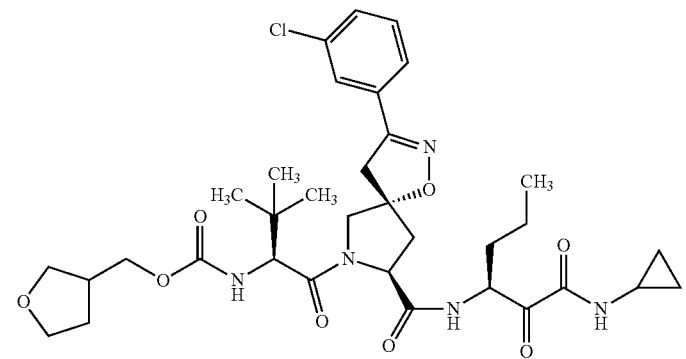 | 152 |

TABLE 1-continued

Exemplary compounds of Formula (I).

| Structure | Compound No. |
|-----------|--------------|
| 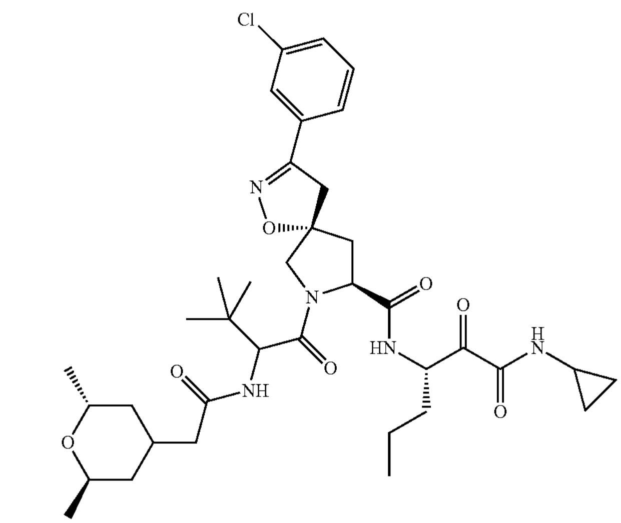          | 153 |
| 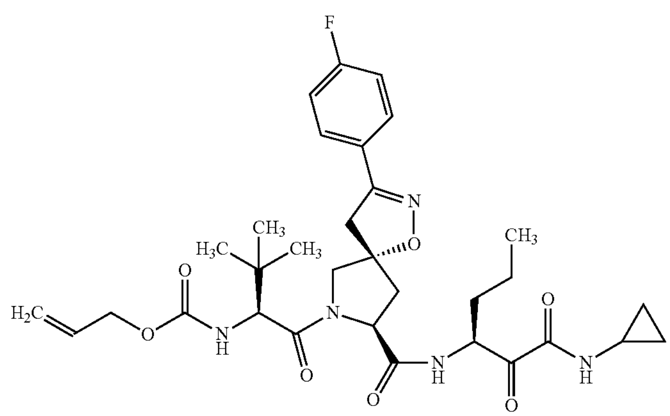          | 154 |
| 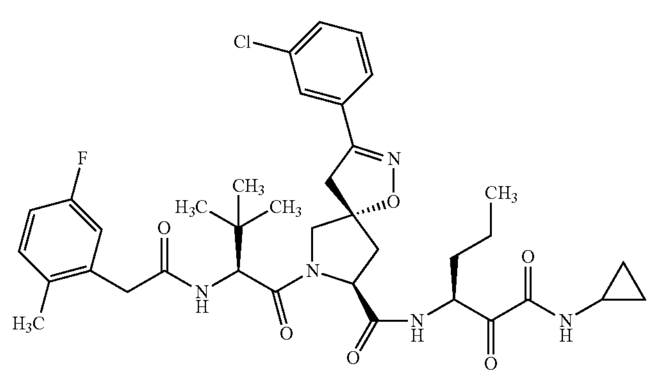          | 155 |

TABLE 1-continued

Exemplary compounds of Formula (I).

| Structure | Compound No. |
|---|---|
| 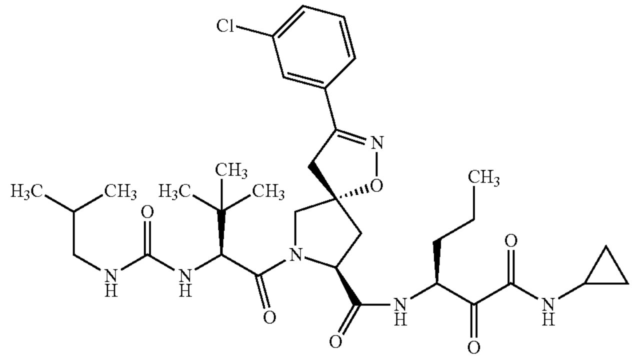 | 156 |
| 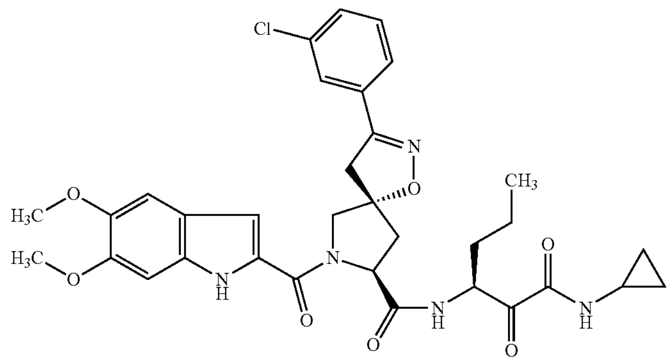 | 157 |
| 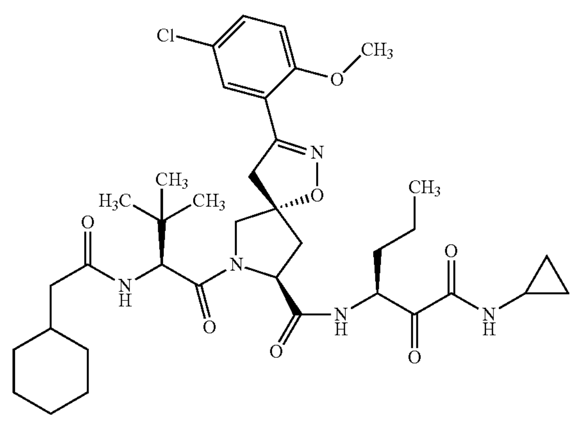 | 158 |
| 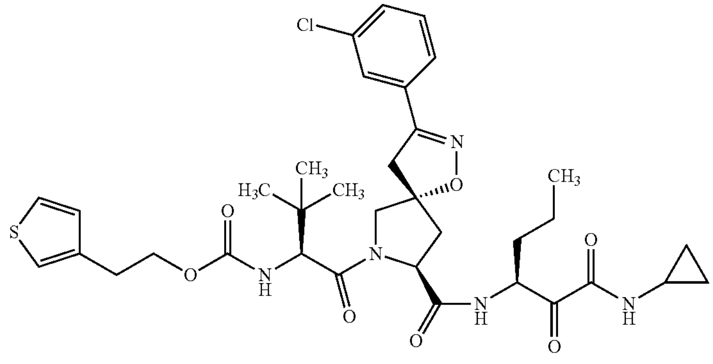 | 159 |

TABLE 1-continued

Exemplary compounds of Formula (I).

| Structure | Compound No. |
|---|---|
| 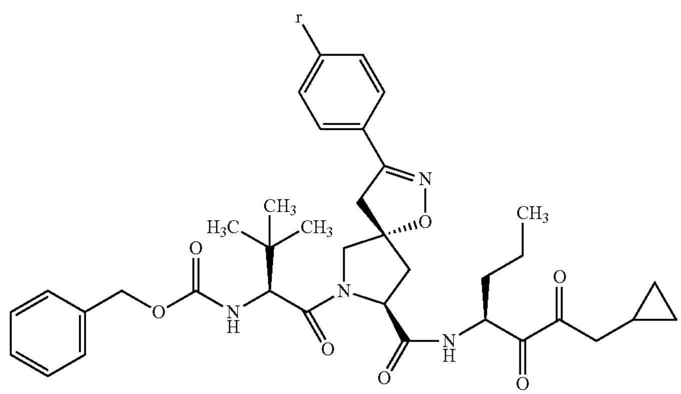 | 160 |
| 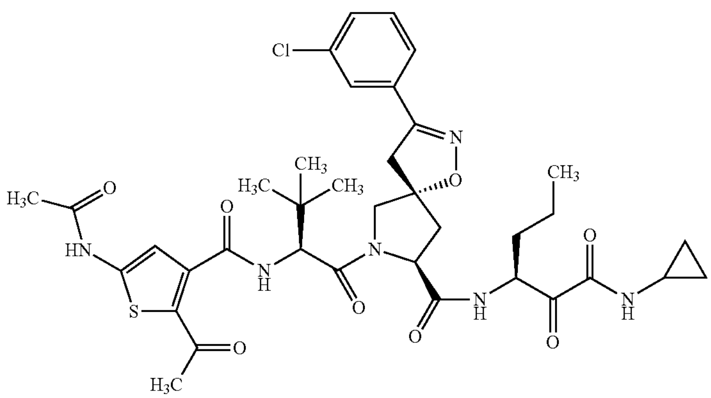 | 161 |
| 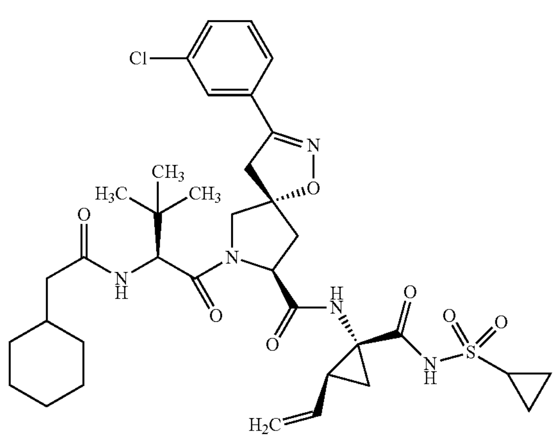 | 162 |

TABLE 1-continued

Exemplary compounds of Formula (I).

| Structure | Compound No. |
|---|---|
| 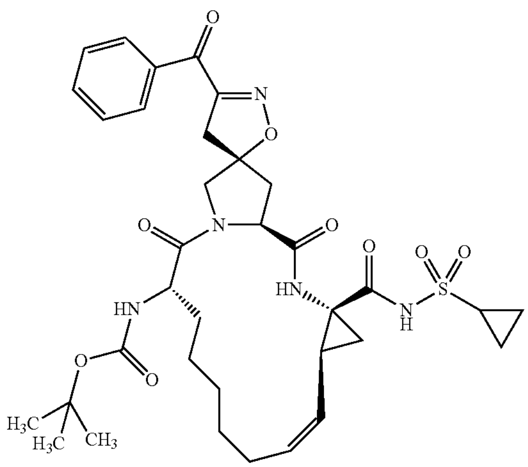 | 163 |
| 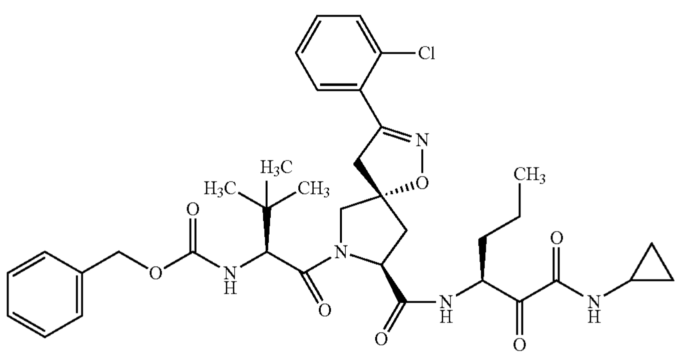 | 164 |
| 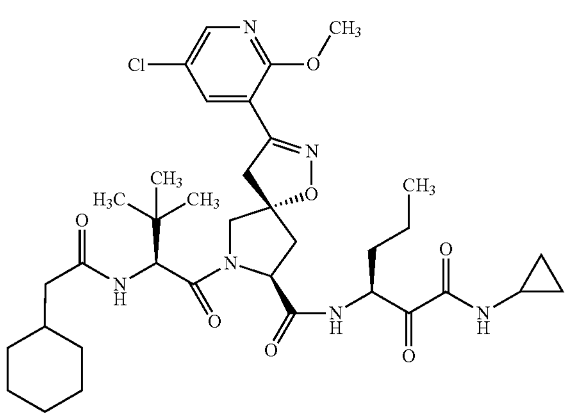 | 165 |

TABLE 1-continued

Exemplary compounds of Formula (I).

| Structure | Compound No. |
|---|---|
| 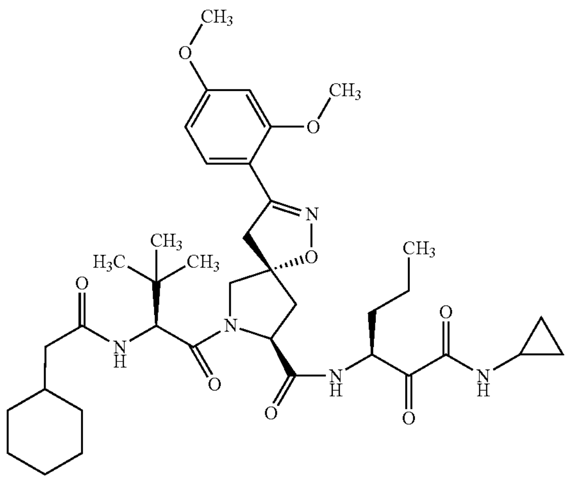 | 166 |
| 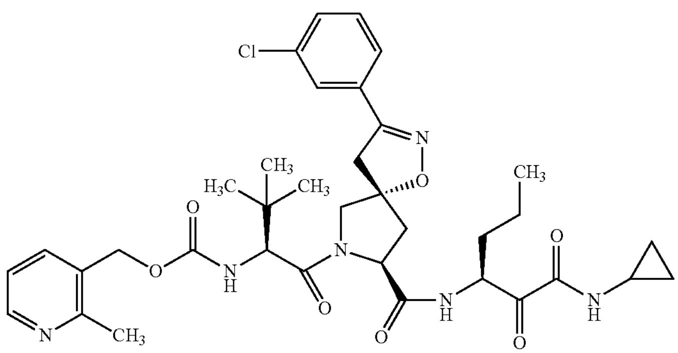 | 167 |
| 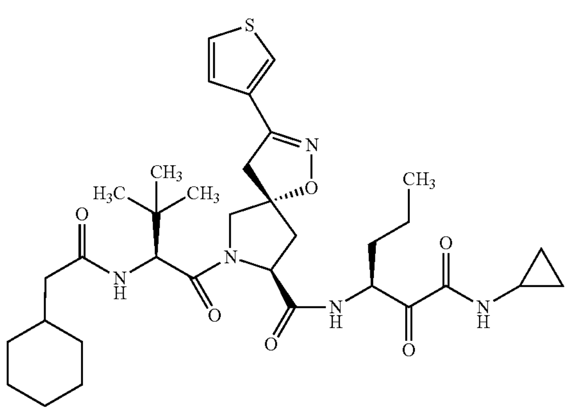 | 168 |

TABLE 1-continued

Exemplary compounds of Formula (I).

| Structure | Compound No. |
|---|---|
| 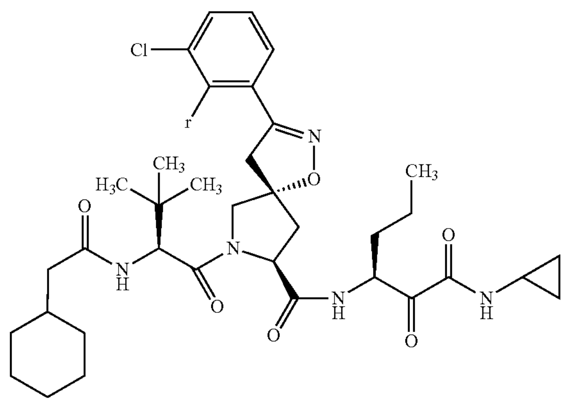 | 169 |
| 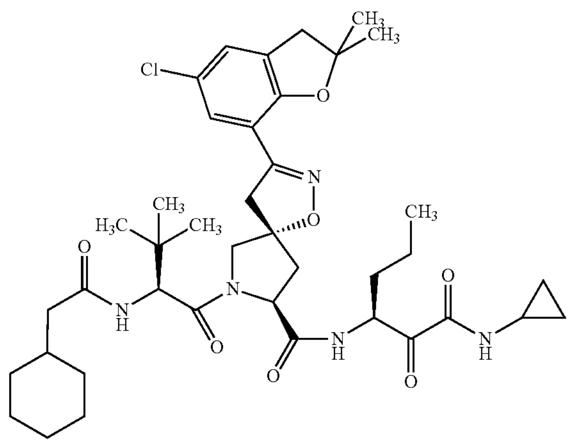 | 170 |
| 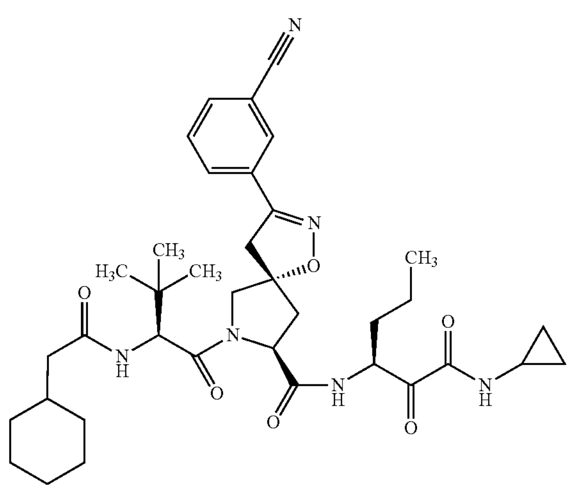 | 171 |

TABLE 1-continued

Exemplary compounds of Formula (I).

| Structure | Compound No. |
|---|---|
| 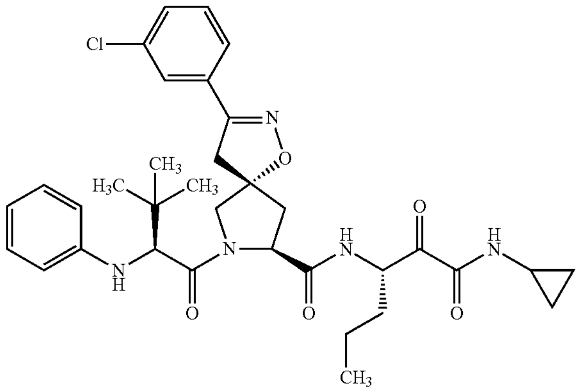 | 172 |
| 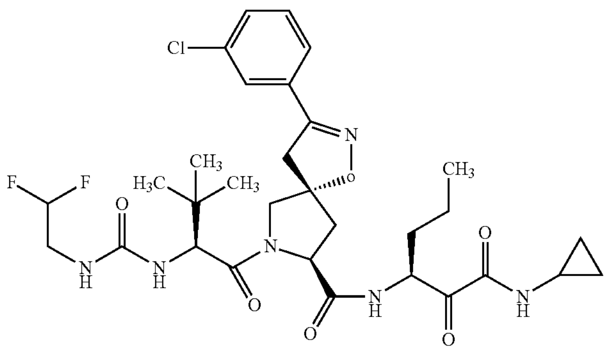 | 173 |
| 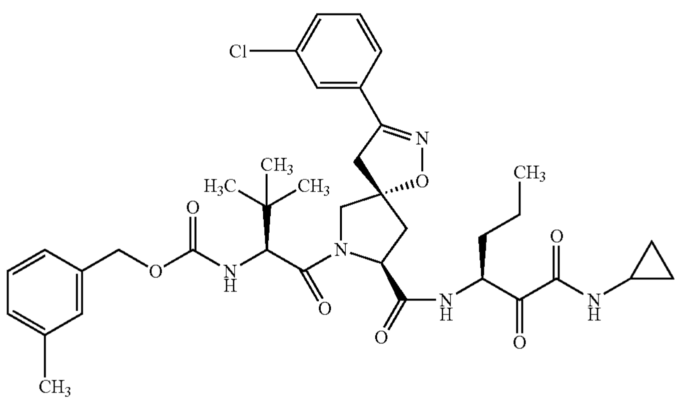 | 174 |
| 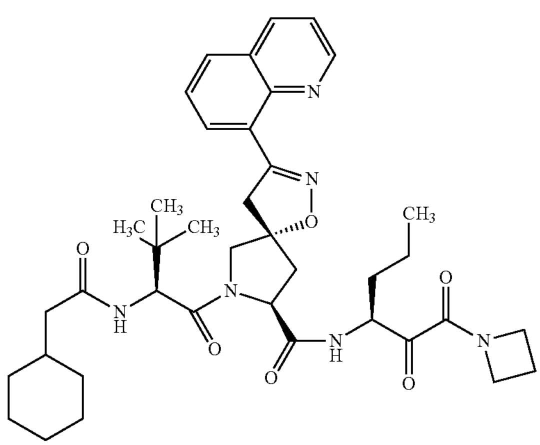 | 175 |

_211_ _212_
TABLE 1-continued
Exemplary compounds of Formula (I).
| Structure | Compound No. |
|---|---|
| 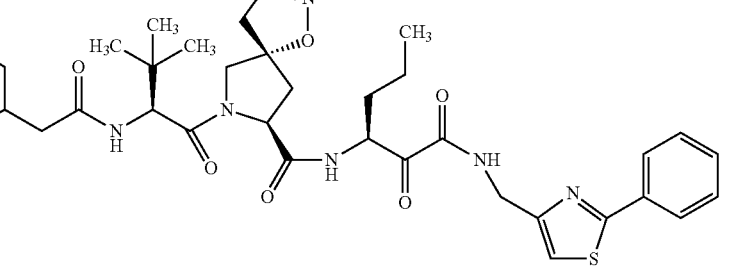 | 176 |
| 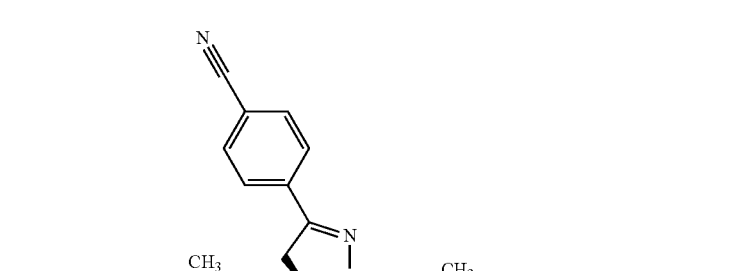 | 177 |
| 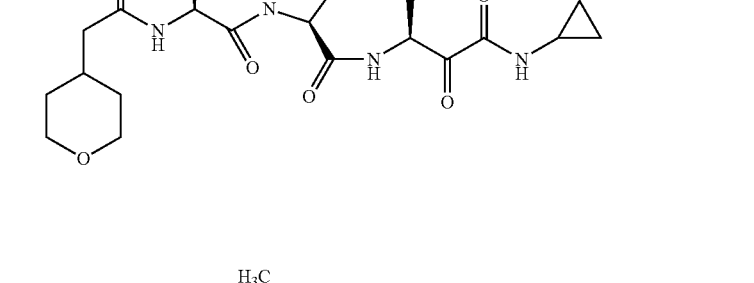 | 178 |

TABLE 1-continued

Exemplary compounds of Formula (I).

| Structure | Compound No. |
|---|---|
| 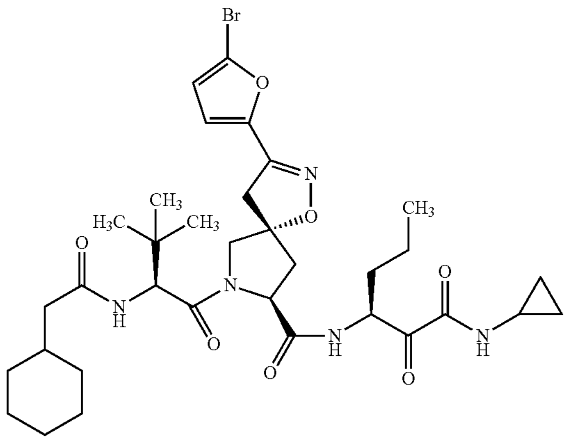 | 179 |
| 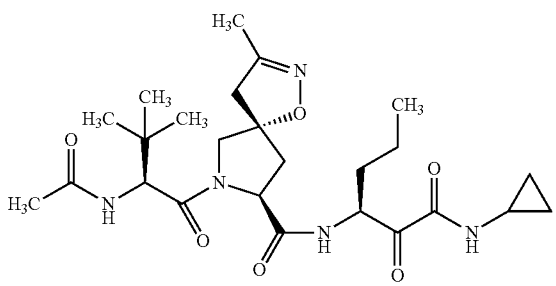 | 180 |
| 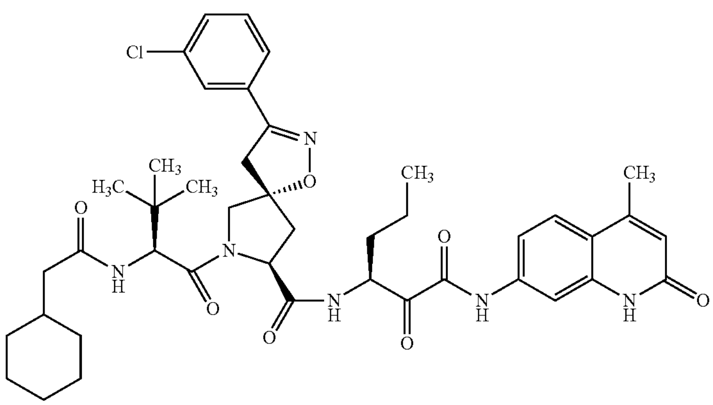 | 181 |
| 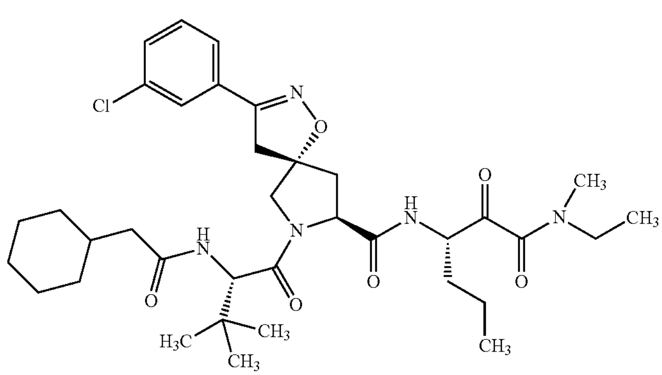 | 182 |

TABLE 1-continued

Exemplary compounds of Formula (I).

| Structure | Compound No. |
|---|---|
| 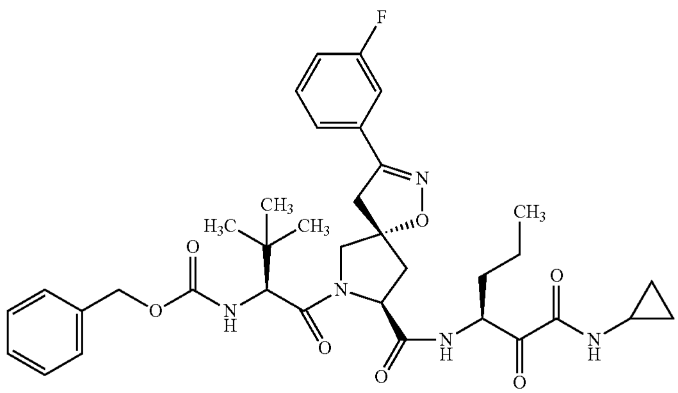 | 183 |
| 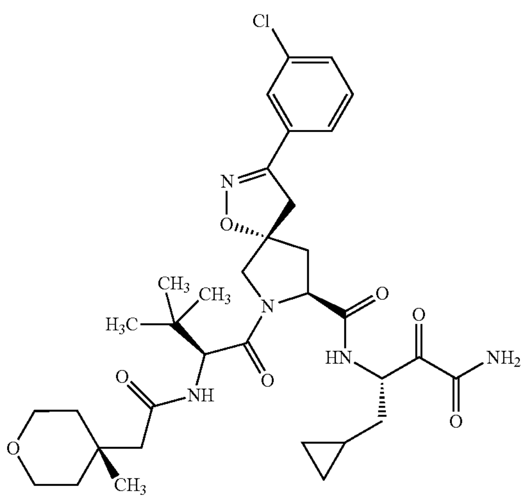 | 184 |
| 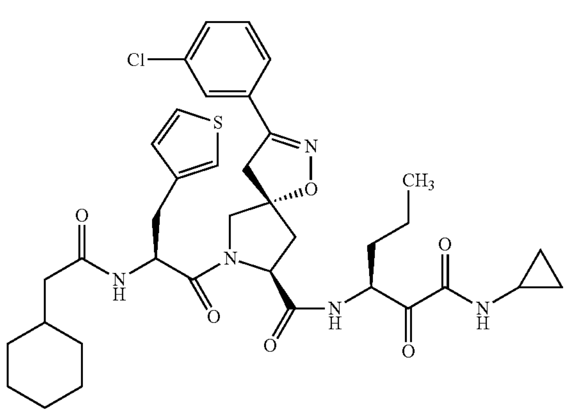 | 185 |

TABLE 1-continued

Exemplary compounds of Formula (I).

| Structure | Compound No. |
|---|---|
| 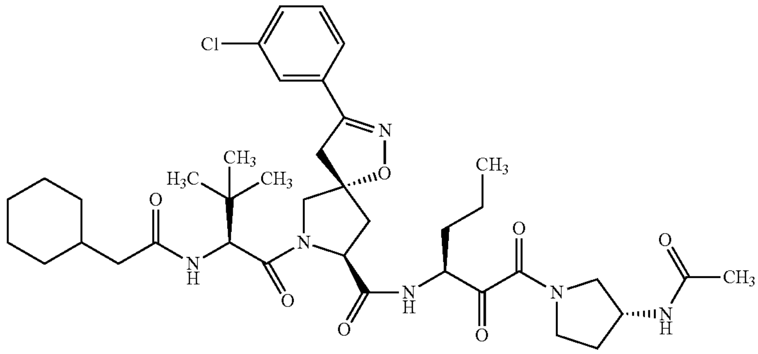 | 186 |
| 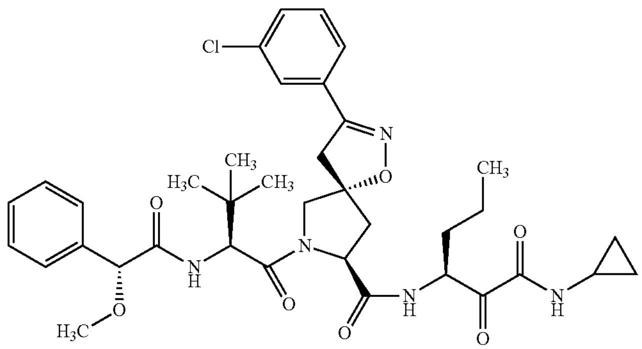 | 187 |
| 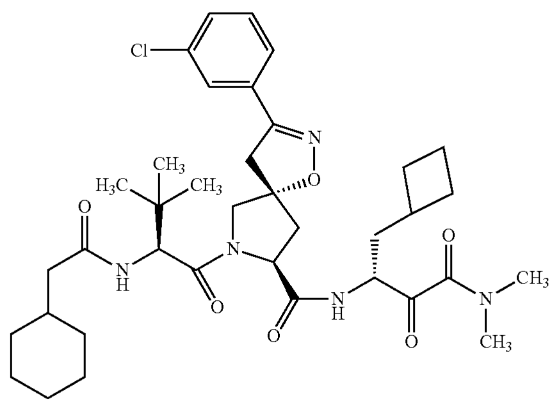 | 188 |
| 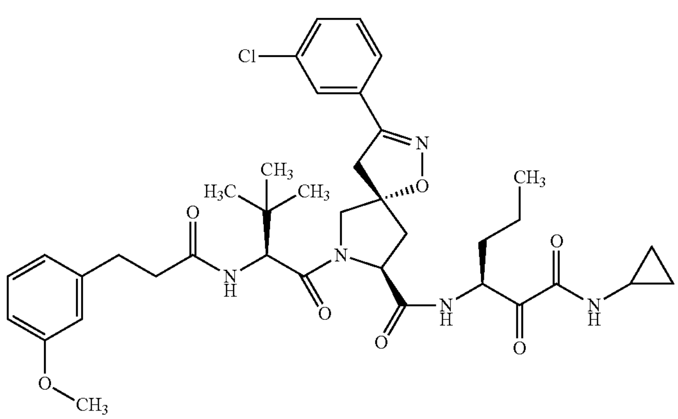 | 189 |

TABLE 1-continued

Exemplary compounds of Formula (I).

| Structure | Compound No. |
|---|---|
| 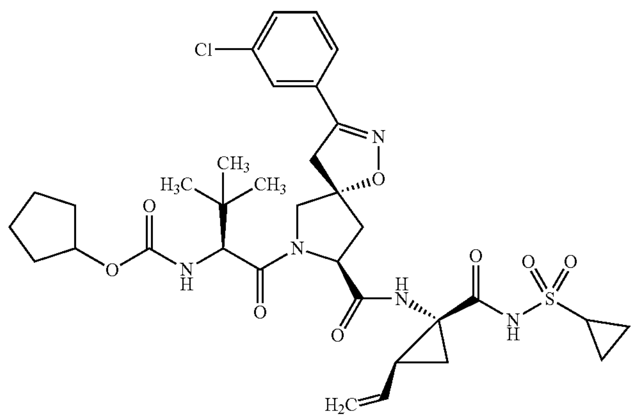 | 190 |
| 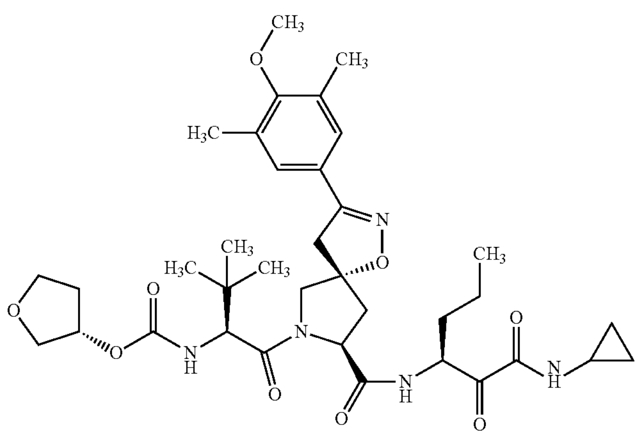 | 191 |
| 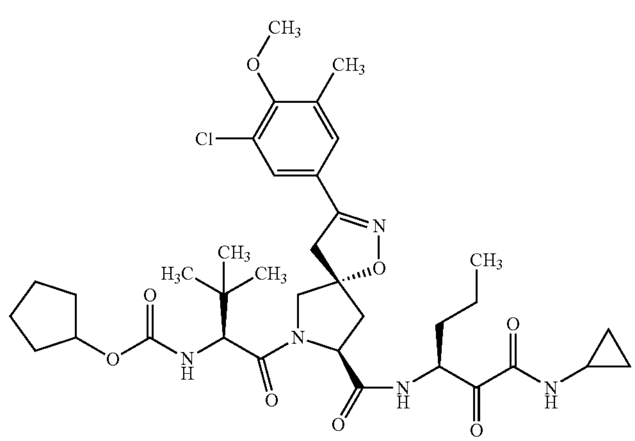 | 192 |

TABLE 1-continued

Exemplary compounds of Formula (I).

| Structure | Compound No. |
|---|---|
| 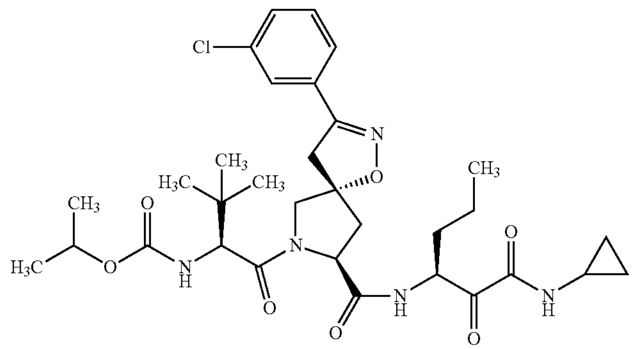 | 193 |
| 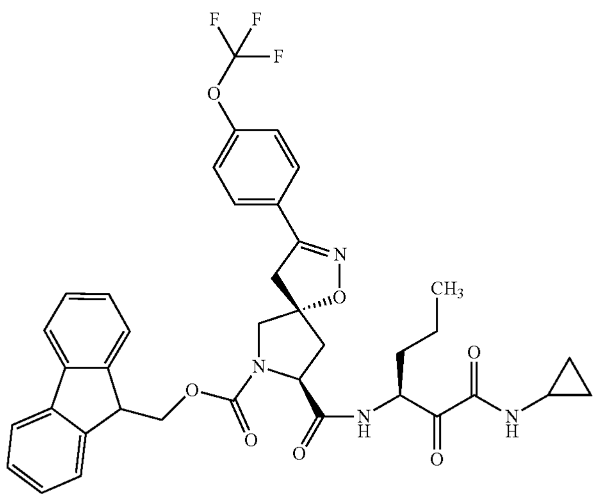 | 194 |
| 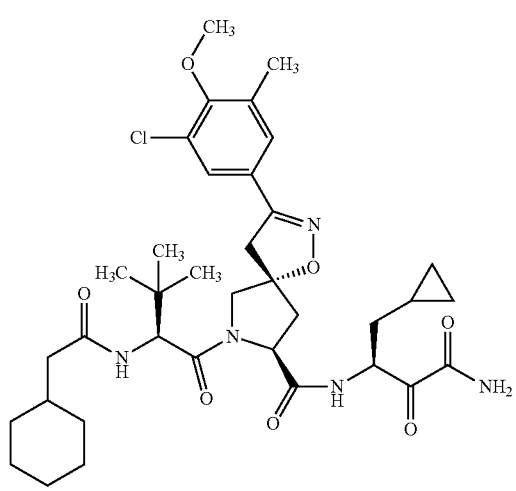 | 195 |

TABLE 1-continued

Exemplary compounds of Formula (I).

| Structure | Compound No. |
|---|---|
| 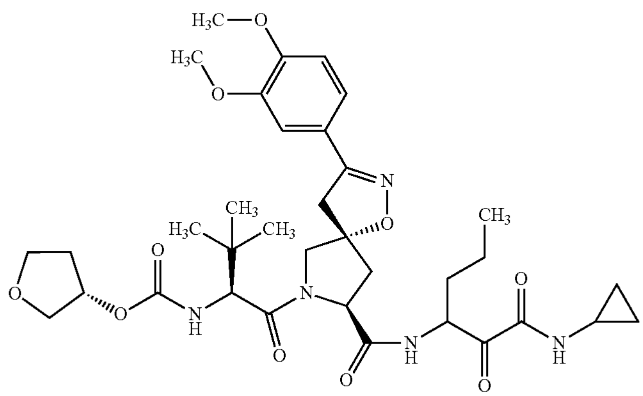 | 196 |
| 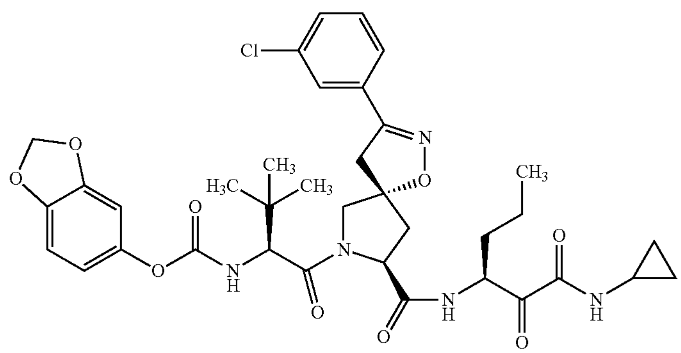 | 197 |
| 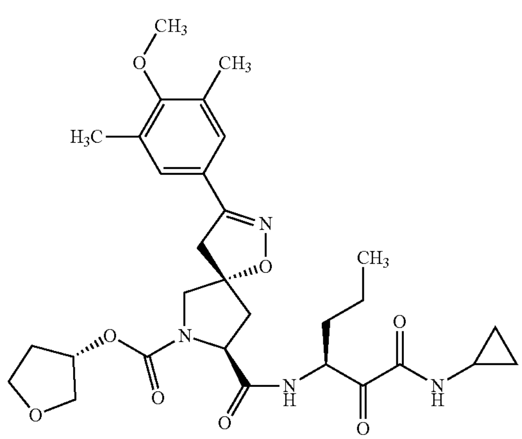 | 198 |

TABLE 1-continued

Exemplary compounds of Formula (I).

| Structure | Compound No. |
|---|---|
| 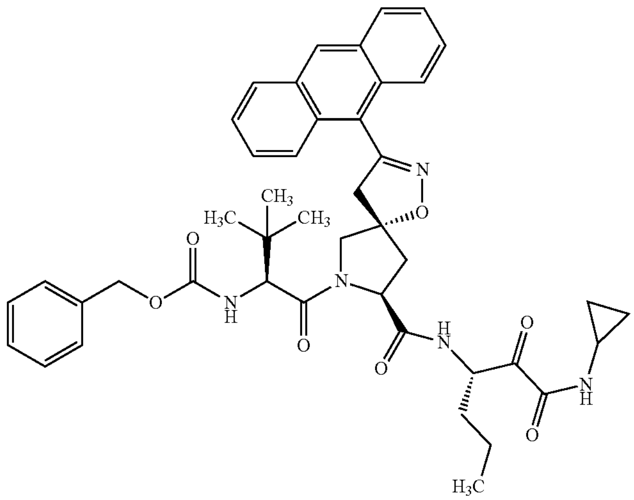 | 199 |
| 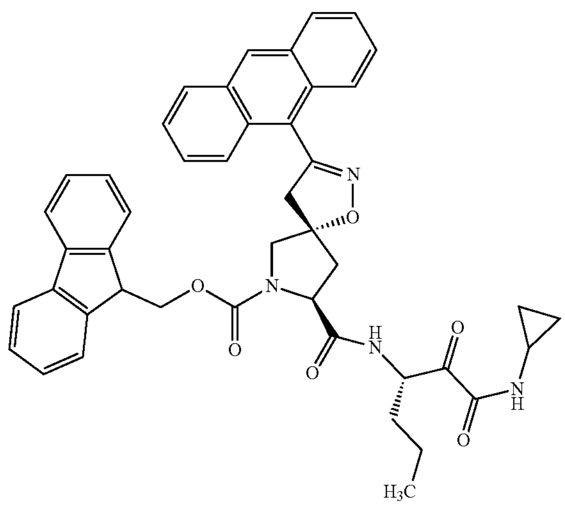 | 200 |
| 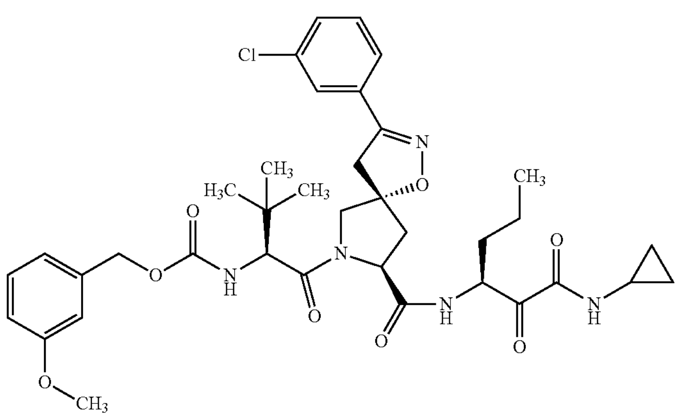 | 201 |

TABLE 1-continued

Exemplary compounds of Formula (I).

| Structure | Compound No. |
|---|---|
| 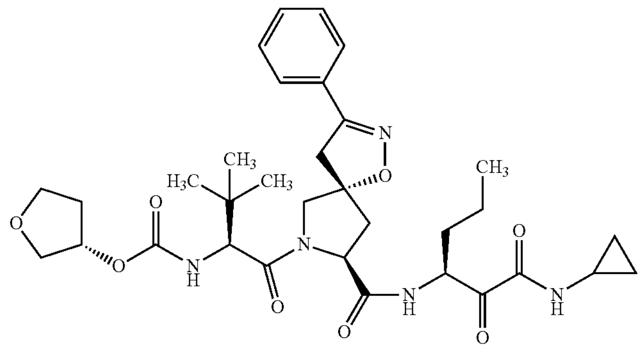 | 202 |
| 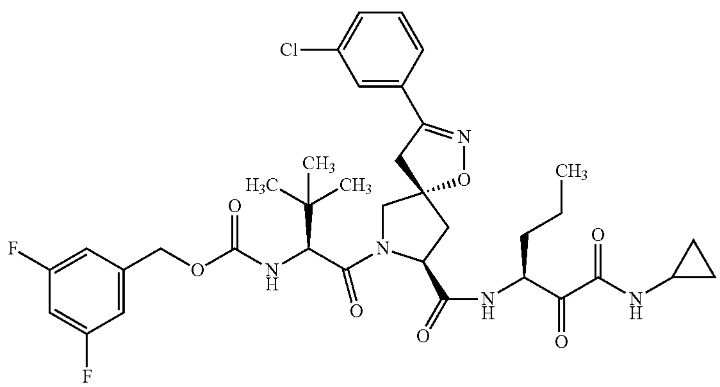 | 203 |
| 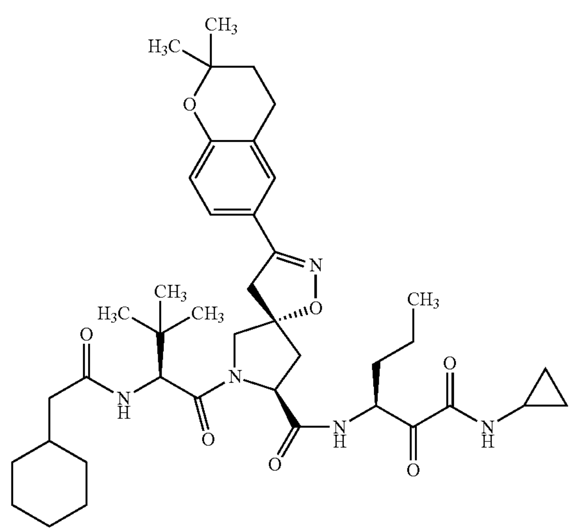 | 204 |

TABLE 1-continued

Exemplary compounds of Formula (I).

| Structure | Compound No. |
|---|---|
| 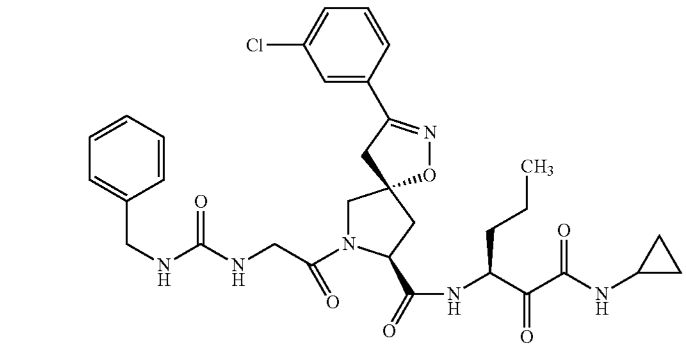 | 205 |
| 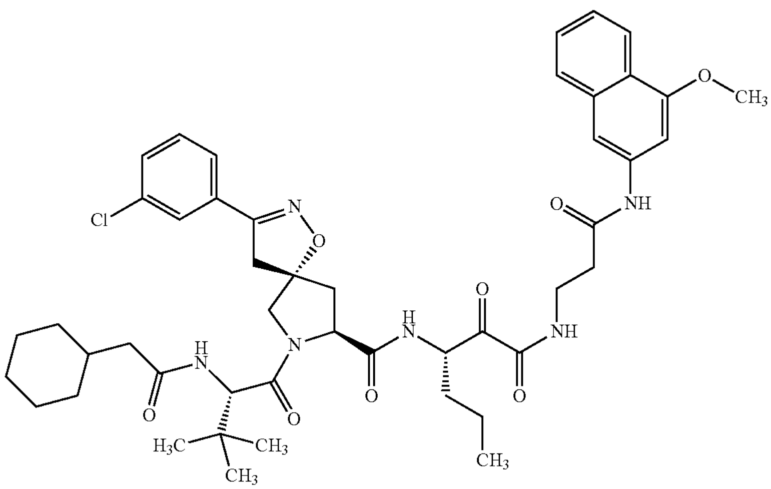 | 206 |
| 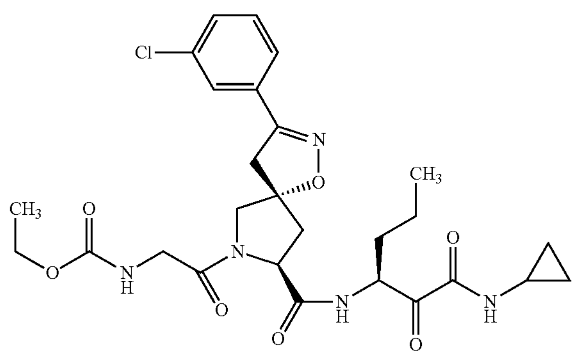 | 207 |
| 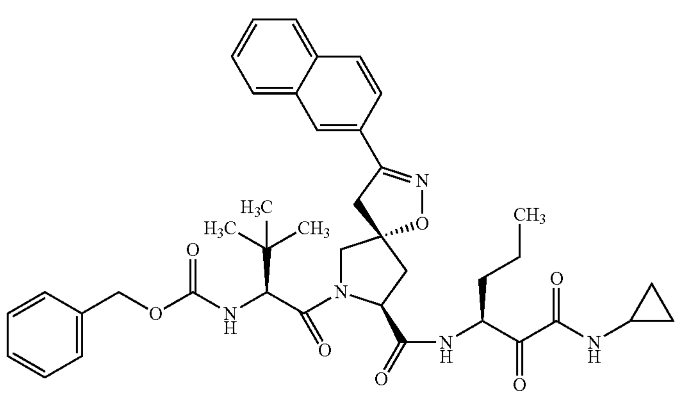 | 208 |

TABLE 1-continued
Exemplary compounds of Formula (I).
| Structure | Compound No. |
|---|---|
| 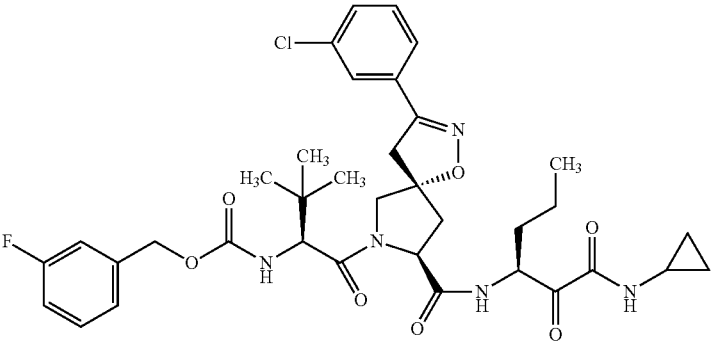 | 209 |
| 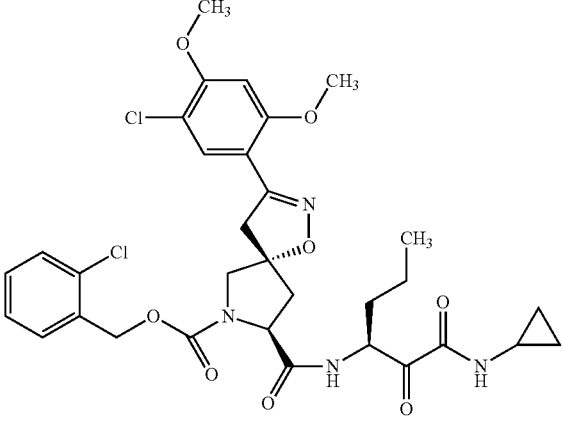 | 210 |
| 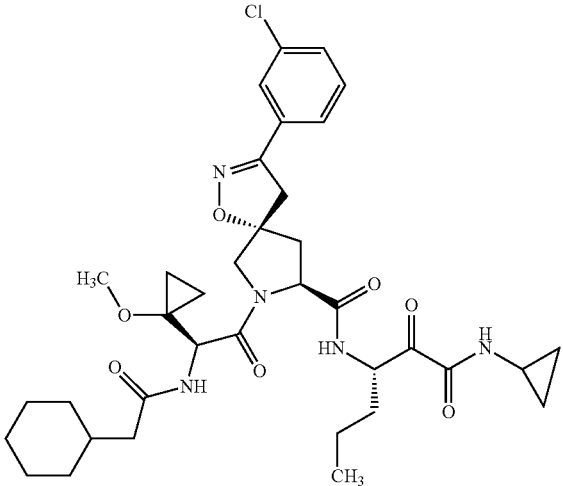 | 211 |

TABLE 1-continued

Exemplary compounds of Formula (I).

| Structure | Compound No. |
|---|---|
| 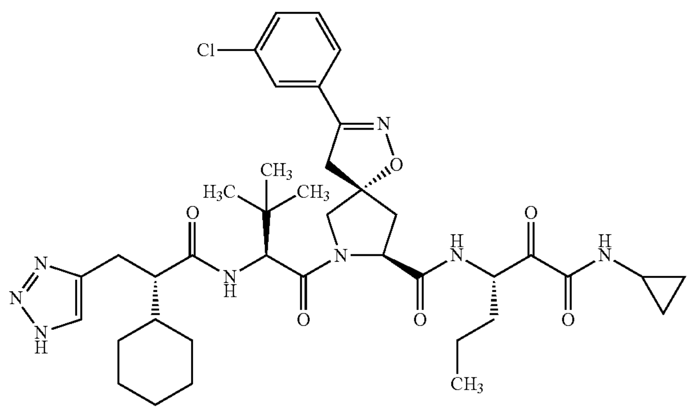 | 212 |
| 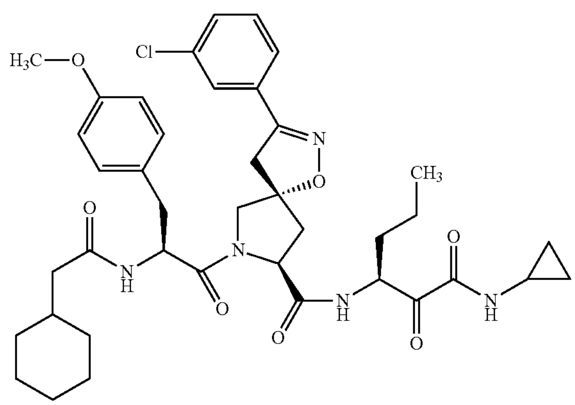 | 213 |
| 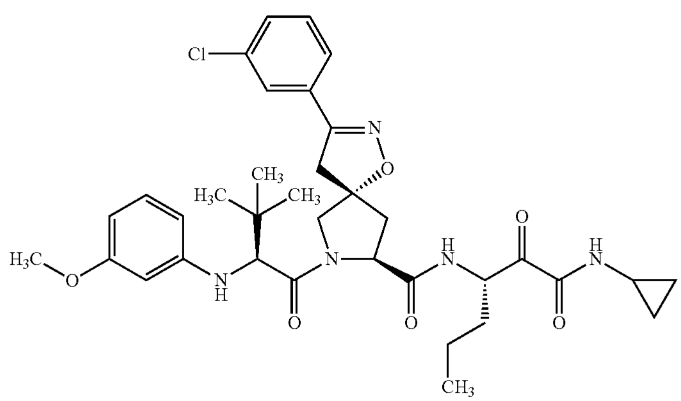 | 214 |

TABLE 1-continued

Exemplary compounds of Formula (I).

| Structure | Compound No. |
|---|---|
| 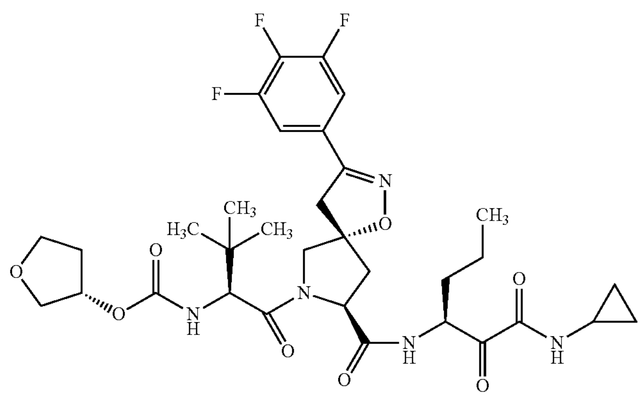 | 215 |
| 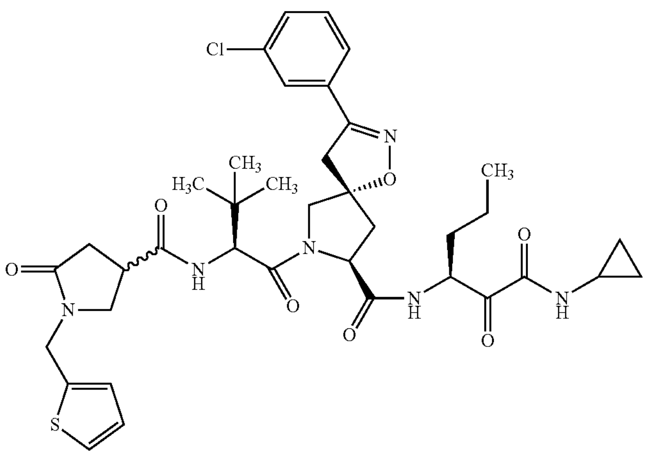 | 216 |
| 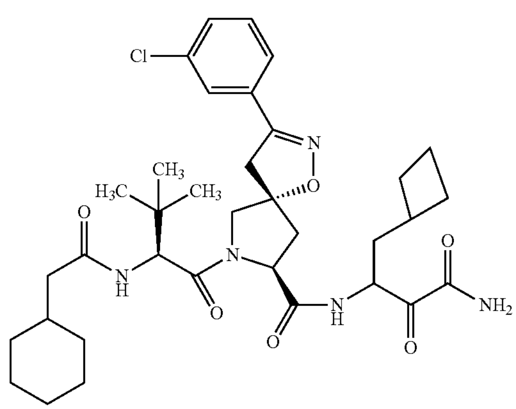 | 217 |

TABLE 1-continued

Exemplary compounds of Formula (I).

| Structure | Compound No. |
|---|---|
| 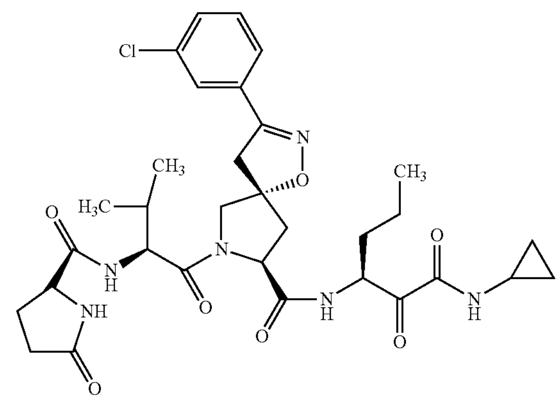 | 218 |
| 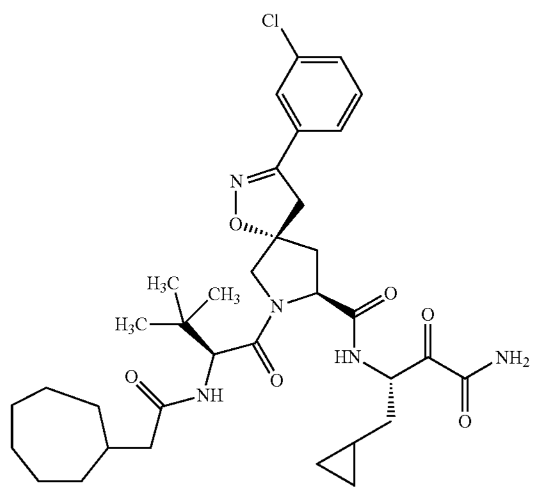 | 219 |
| 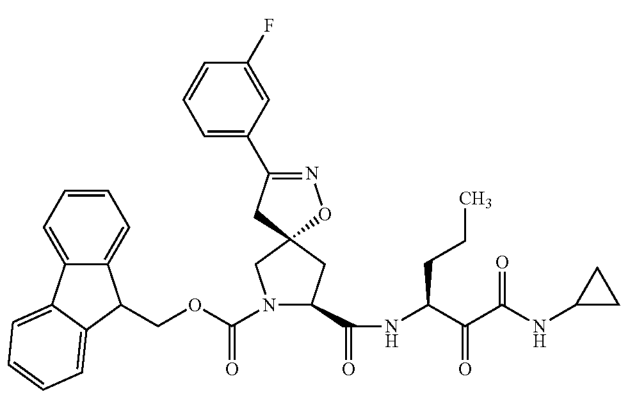 | 220 |

TABLE 1-continued
Exemplary compounds of Formula (I).
| Structure | Compound No. |
|---|---|
| 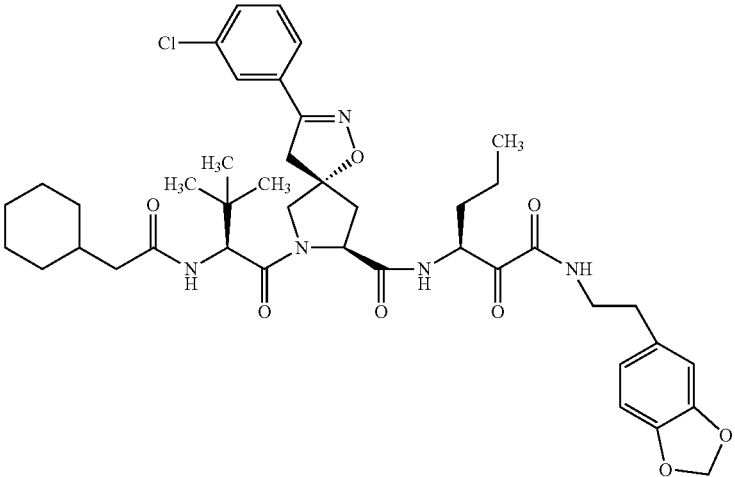 | 221 |
| 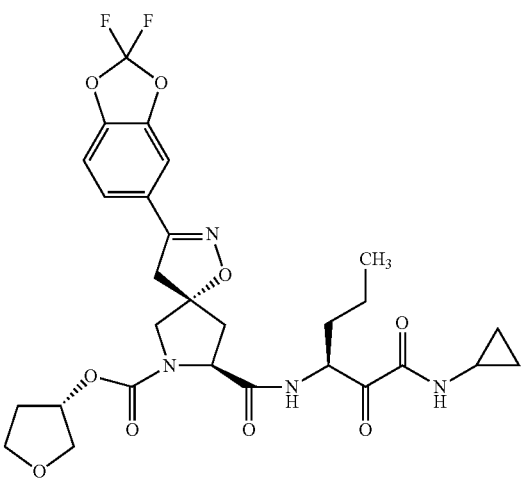 | 222 |
| 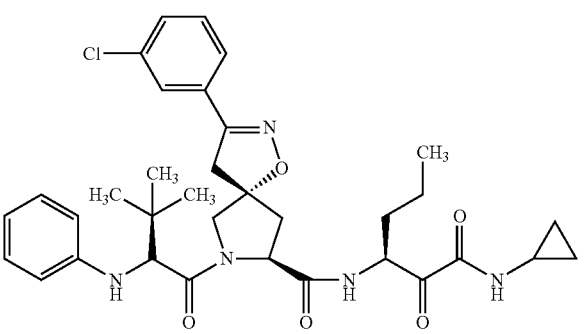 | 223 |

TABLE 1-continued

Exemplary compounds of Formula (I).

| Structure | Compound No. |
|---|---|
| 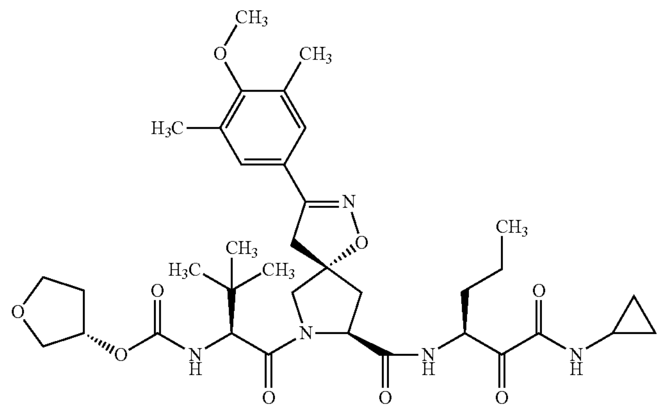 | 224 |
| 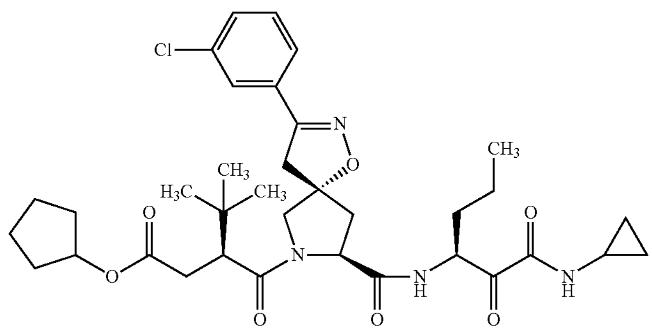 | 225 |
| 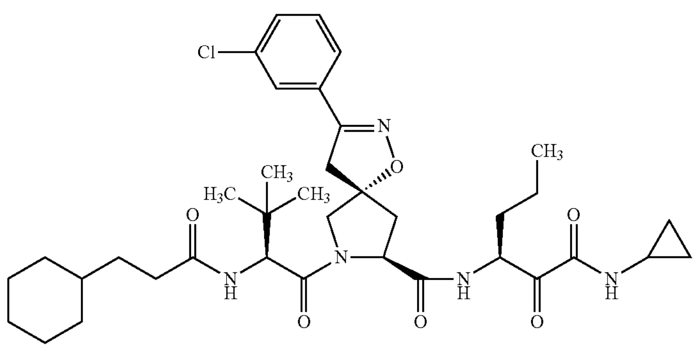 | 226 |
| 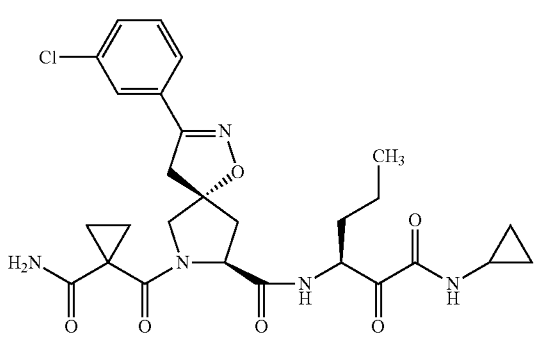 | 227 |

TABLE 1-continued

Exemplary compounds of Formula (I).

| Structure | Compound No. |
|---|---|
| 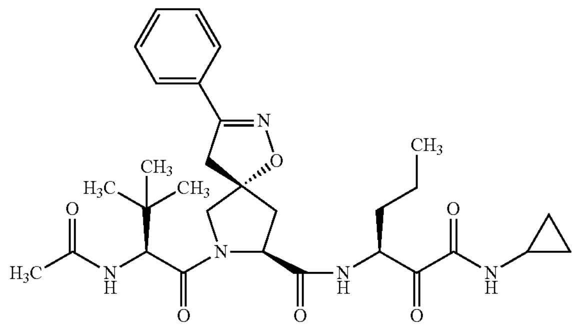 | 228 |
| 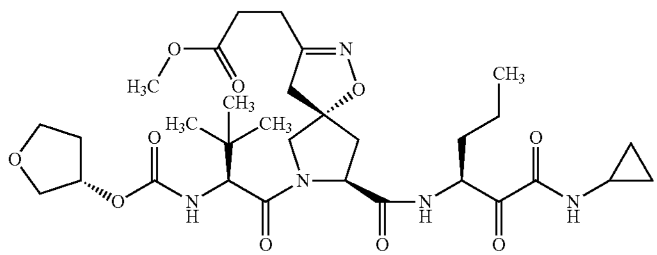 | 229 |
| 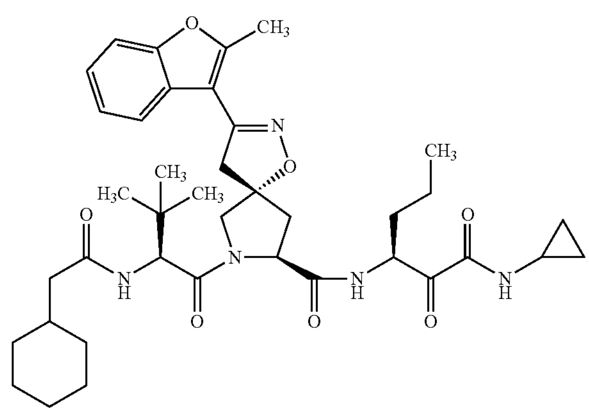 | 230 |
| 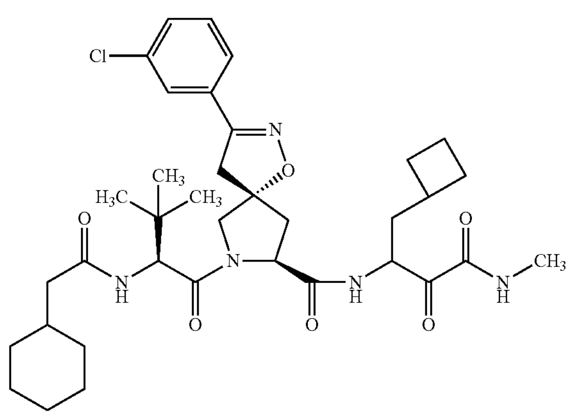 | 231 |

TABLE 1-continued

Exemplary compounds of Formula (I).

| Structure | Compound No. |
|---|---|
| 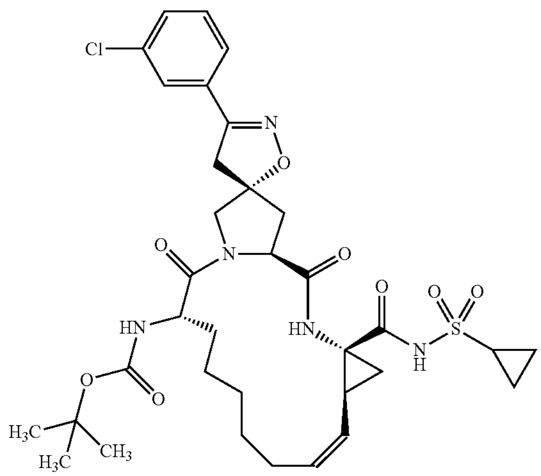 | 232 |
| 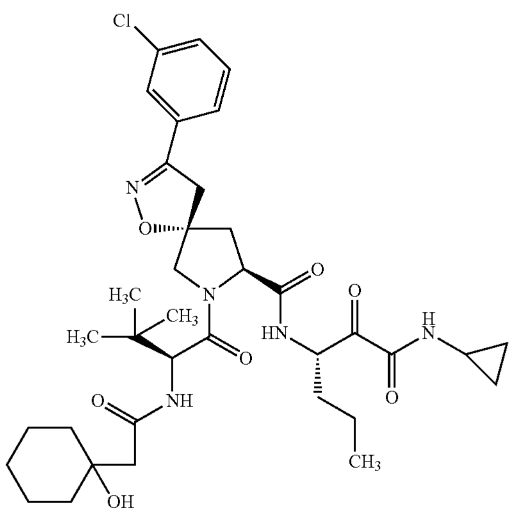 | 233 |
| 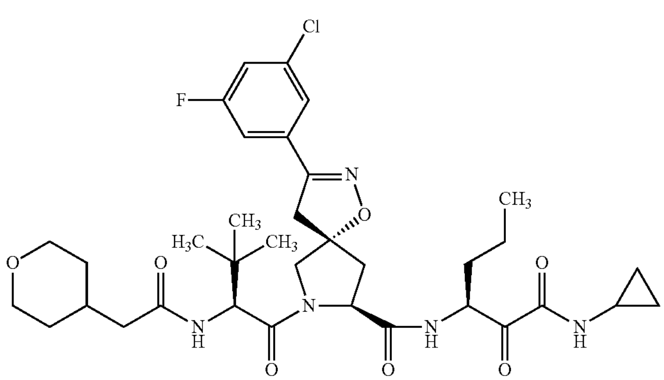 | 234 |

TABLE 1-continued
Exemplary compounds of Formula (I).
| Structure | Compound No. |
|---|---|
| 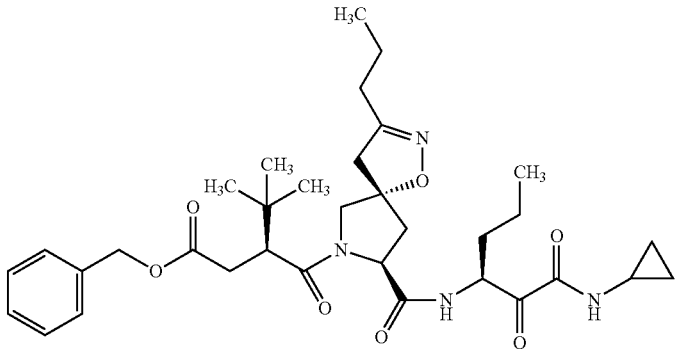 | 235 |
| 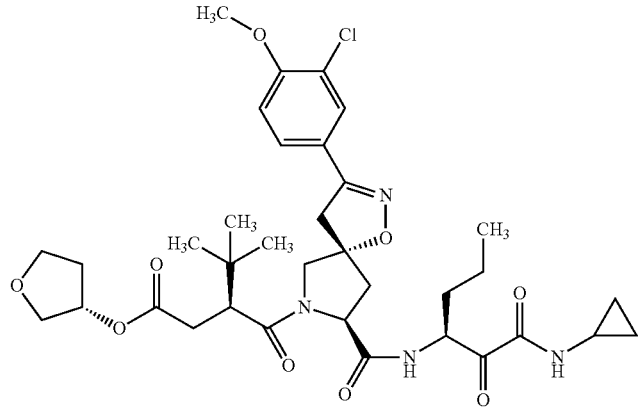 | 236 |
| 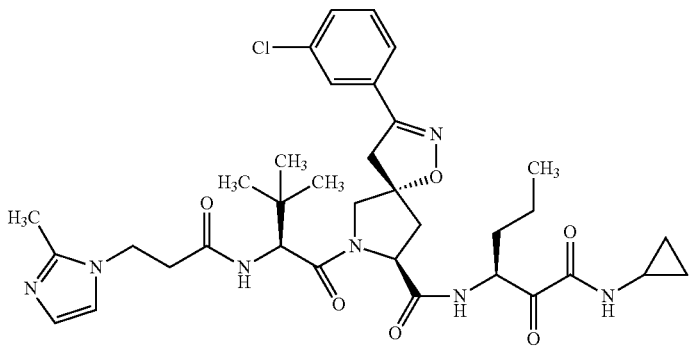 | 237 |
| 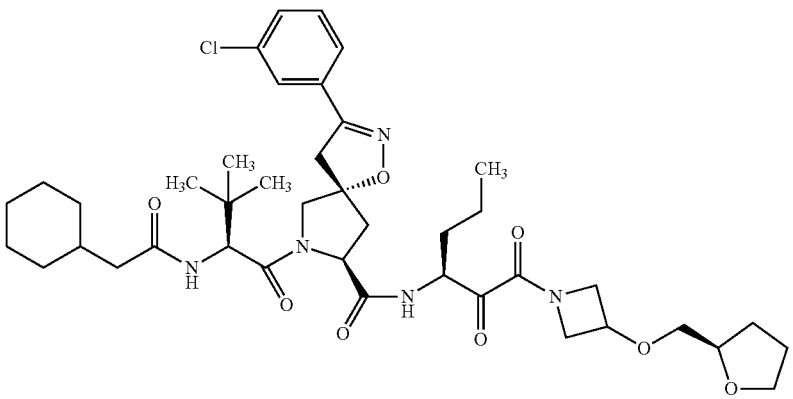 | 238 |

TABLE 1-continued
Exemplary compounds of Formula (I).
| Structure | Compound No. |
|---|---|
| 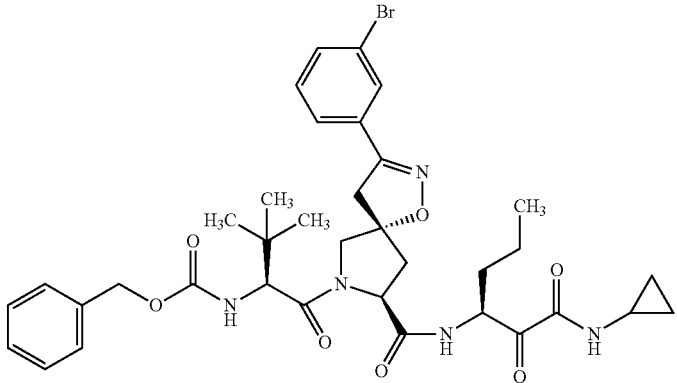 | 239 |
| 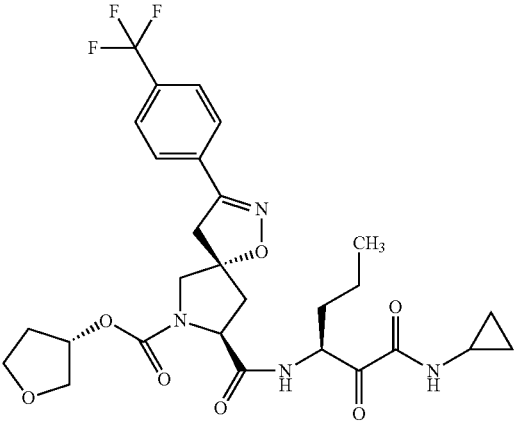 | 240 |
| 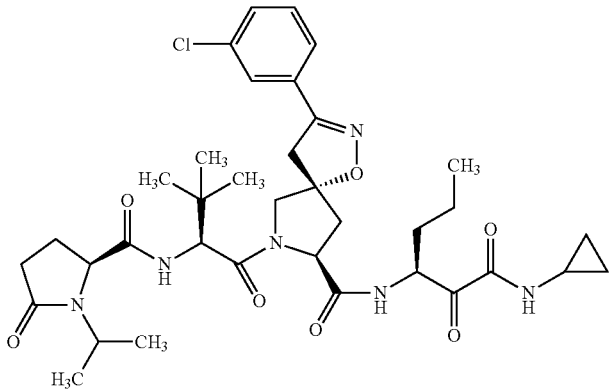 | 241 |

TABLE 1-continued

Exemplary compounds of Formula (I).

| Structure | Compound No. |
|---|---|
| 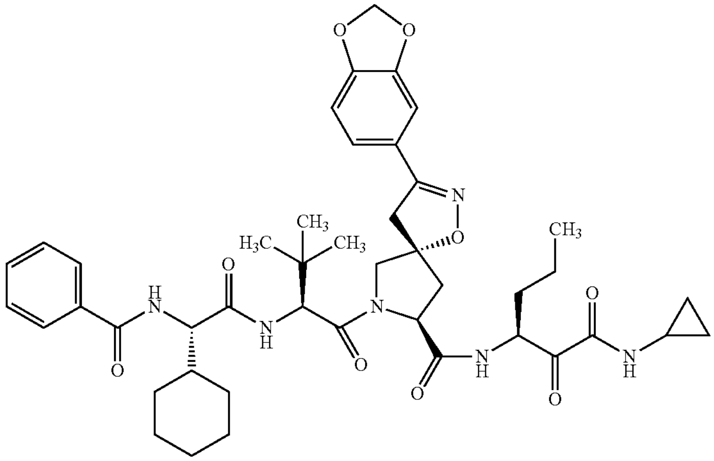 | 242 |
| 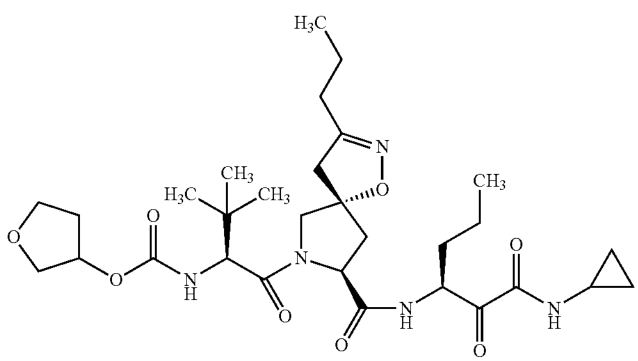 | 243 |
| 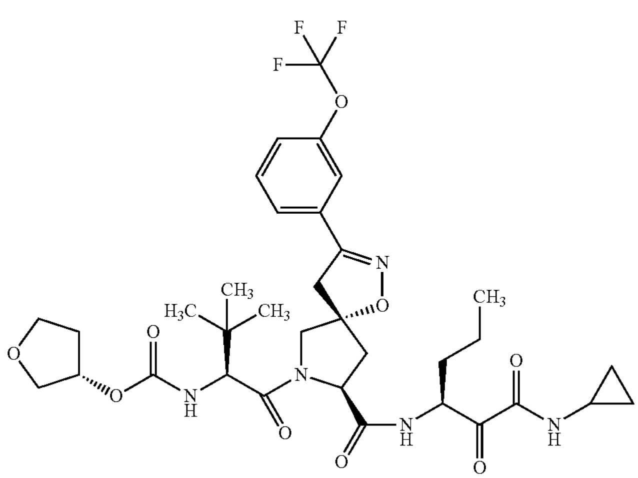 | 244 |

TABLE 1-continued
Exemplary compounds of Formula (I).
| Structure | Compound No. |
|---|---|
| 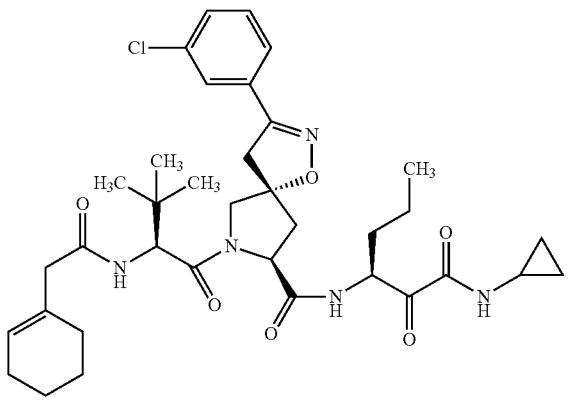 | 245 |
| 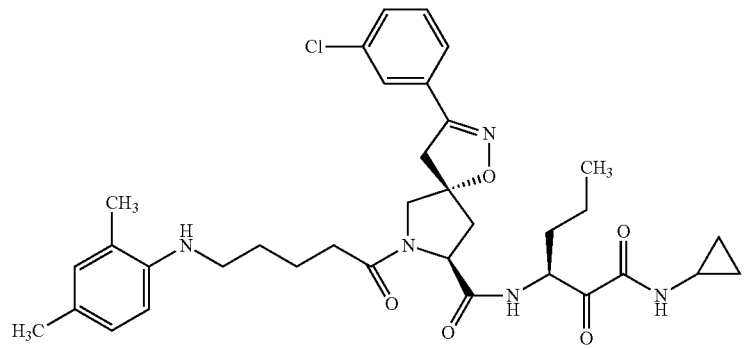 | 246 |
| 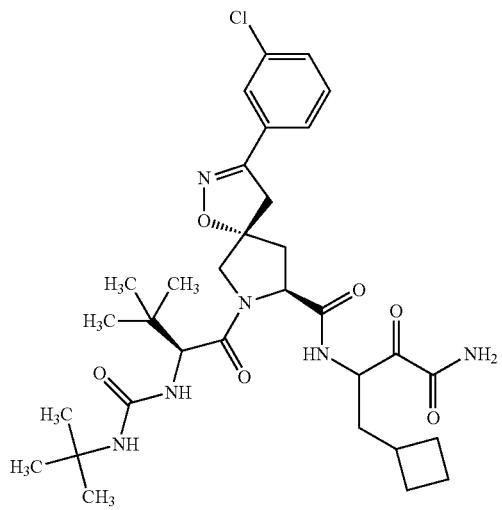 | 247 |

TABLE 1-continued
Exemplary compounds of Formula (I).
| Structure | Compound No. |
|---|---|
| 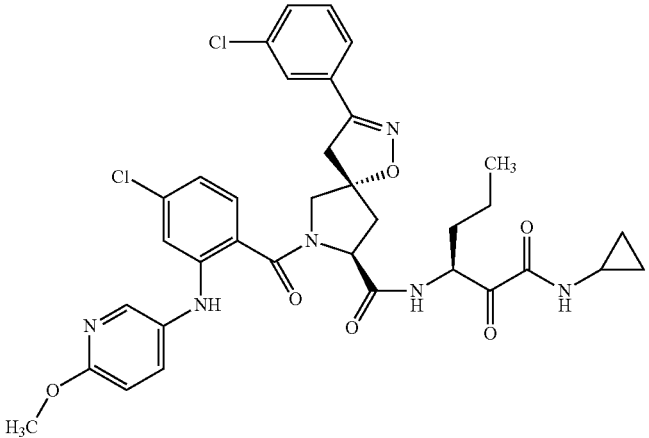 | 248 |
| 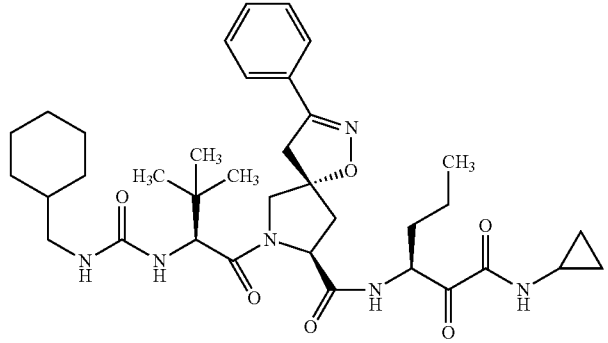 | 249 |
| 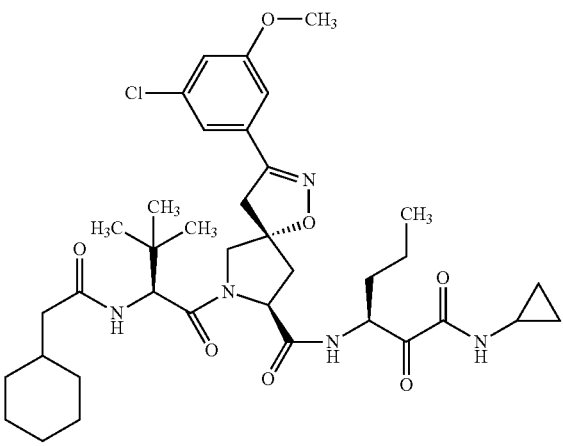 | 250 |

TABLE 1-continued

Exemplary compounds of Formula (I).

| Structure | Compound No. |
|---|---|
| 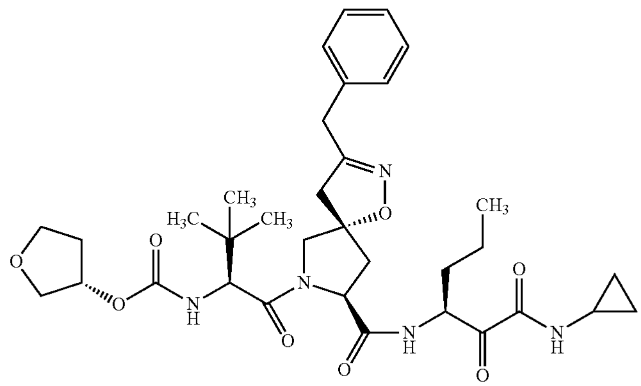 | 251 |
| 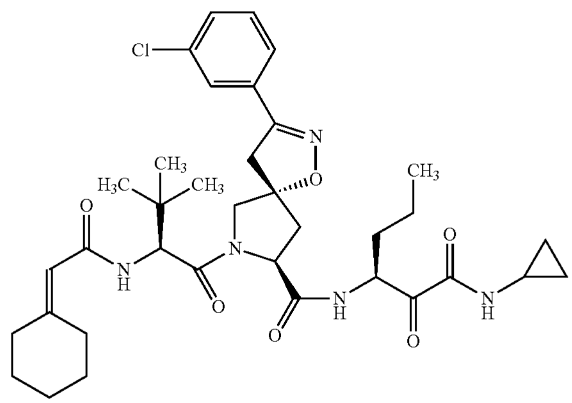 | 252 |
| 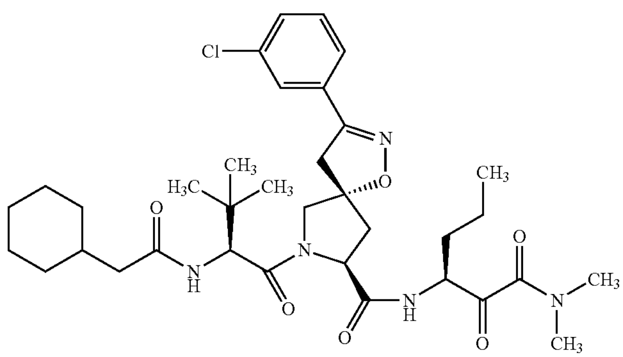 | 253 |
| 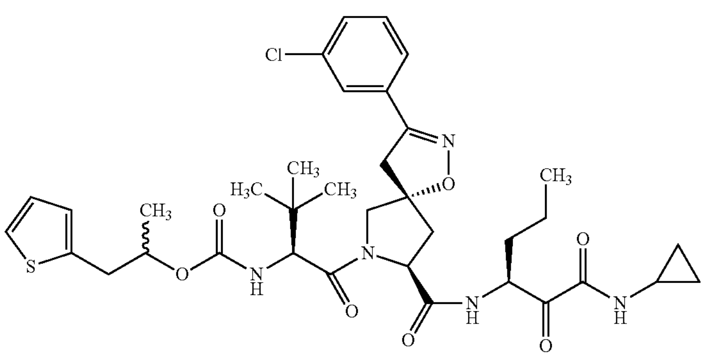 | 254 |

TABLE 1-continued

Exemplary compounds of Formula (I).

| Structure | Compound No. |
|---|---|
| 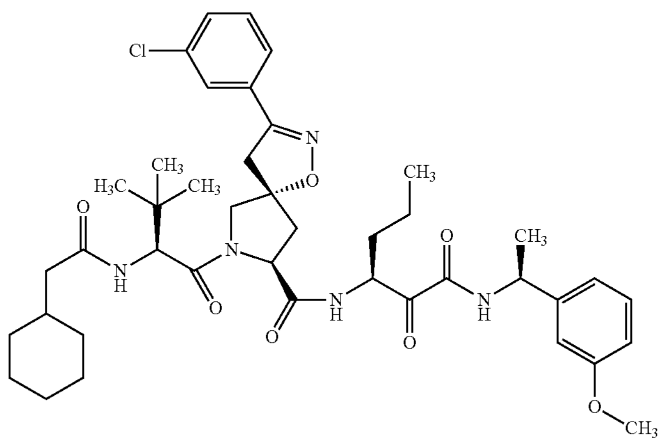 | 255 |
| 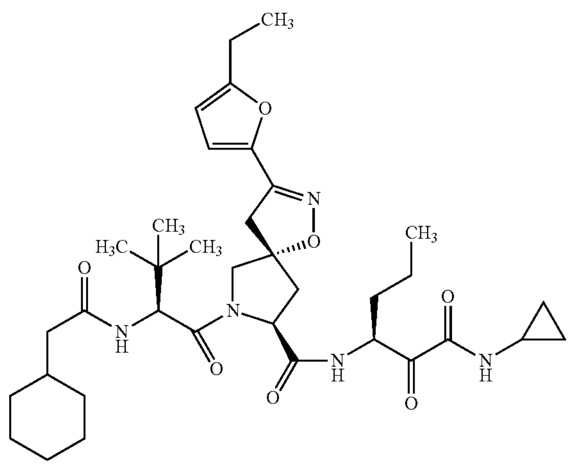 | 256 |
| 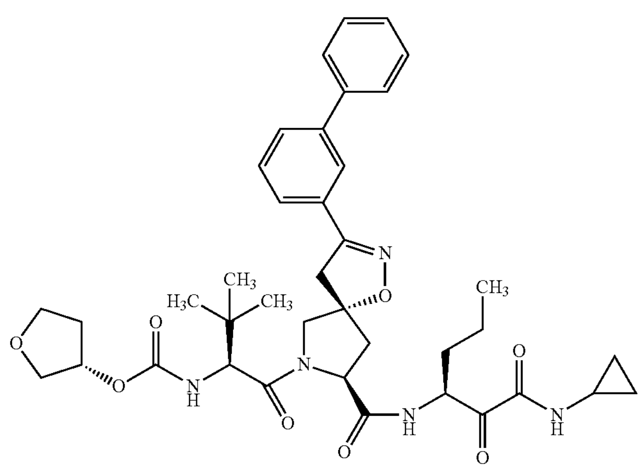 | 257 |

TABLE 1-continued

Exemplary compounds of Formula (I).

| Structure | Compound No. |
|---|---|
| 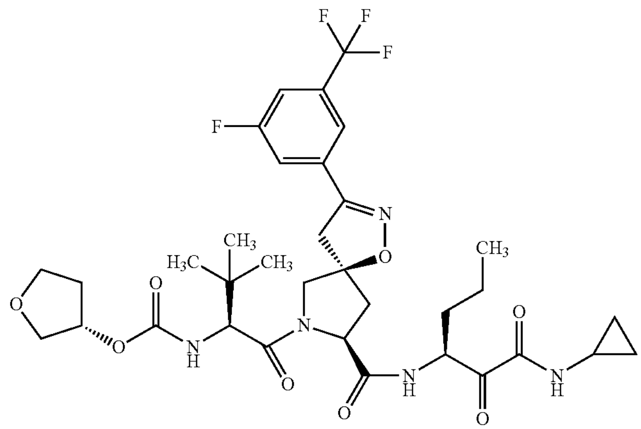 | 258 |
| 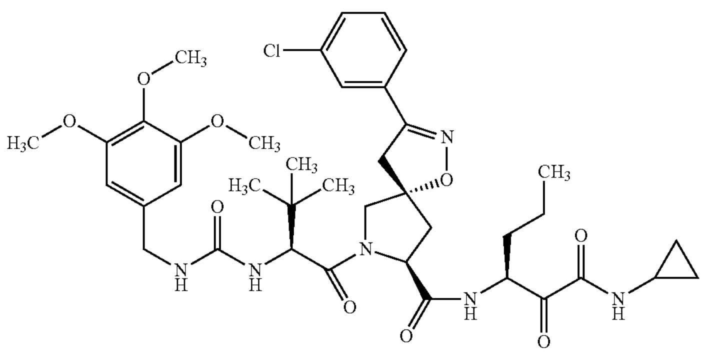 | 259 |
| 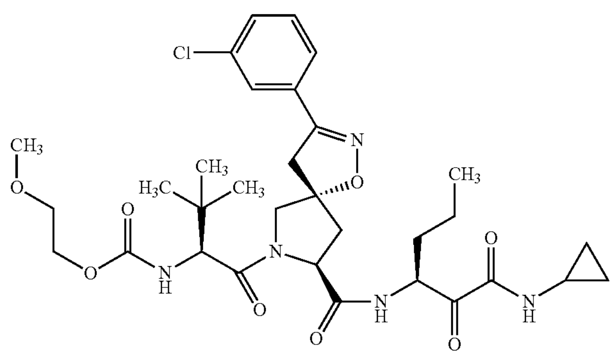 | 260 |
| 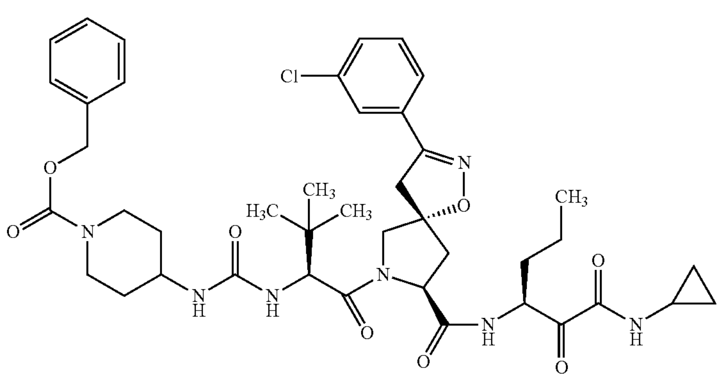 | 261 |

TABLE 1-continued

Exemplary compounds of Formula (I).

| Structure | Compound No. |
|---|---|
| 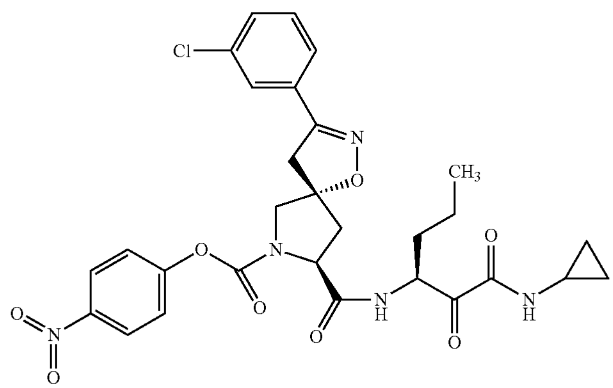 | 262 |
| 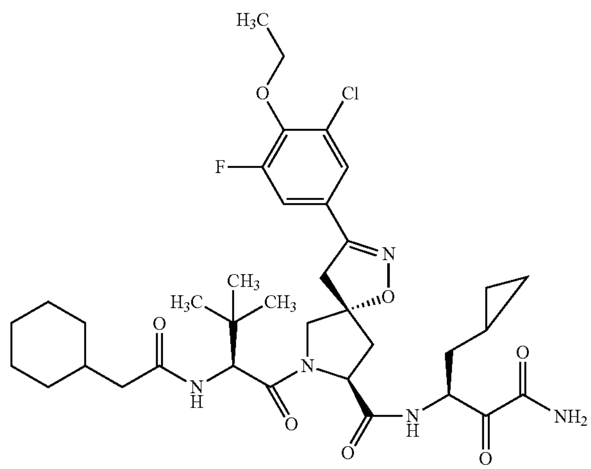 | 263 |
| 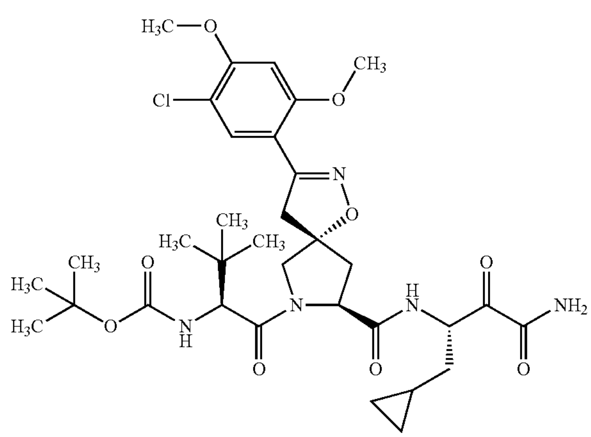 | 264 |

TABLE 1-continued

Exemplary compounds of Formula (I).

| Structure | Compound No. |
|---|---|
| 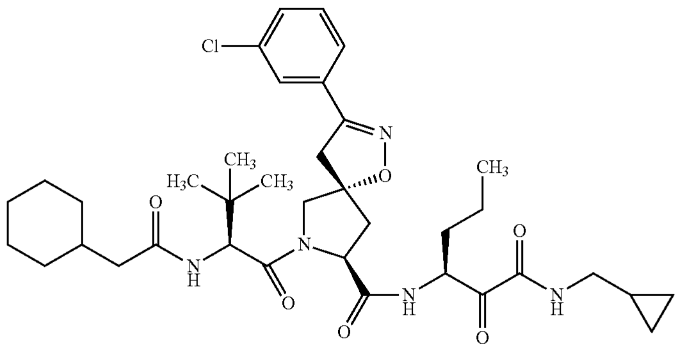 | 265 |
| 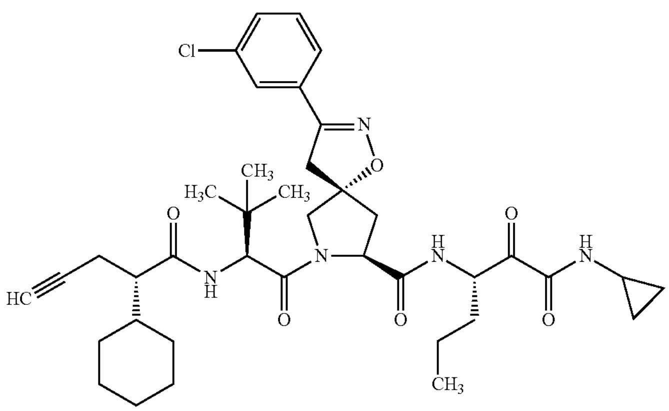 | 266 |
| 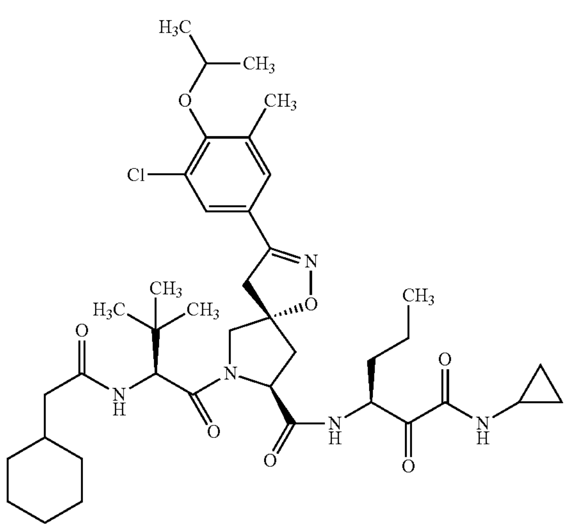 | 267 |

TABLE 1-continued

Exemplary compounds of Formula (I).

| Structure | Compound No. |
|---|---|
| 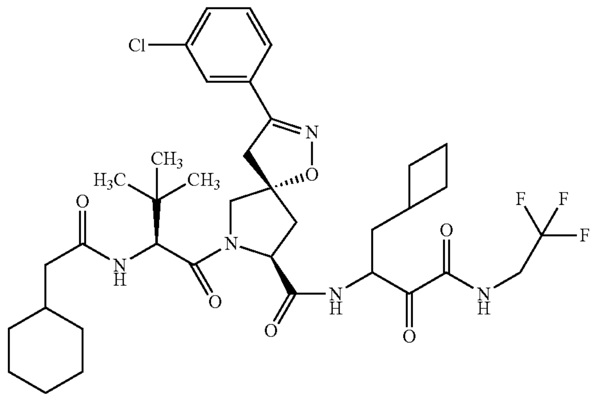 | 268 |
| 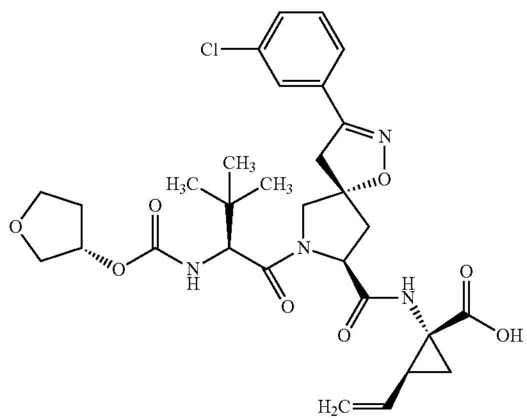 | 269 |
| 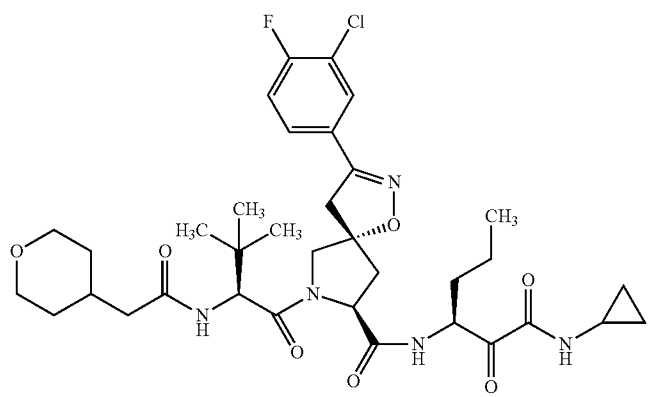 | 270 |
| 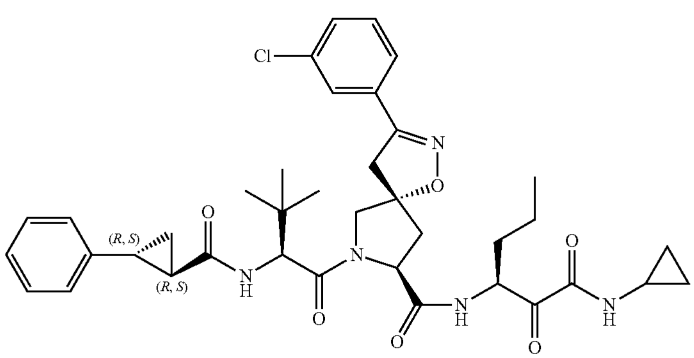 | 271 |

TABLE 1-continued
Exemplary compounds of Formula (I).
| Structure | Compound No. |
|---|---|
| 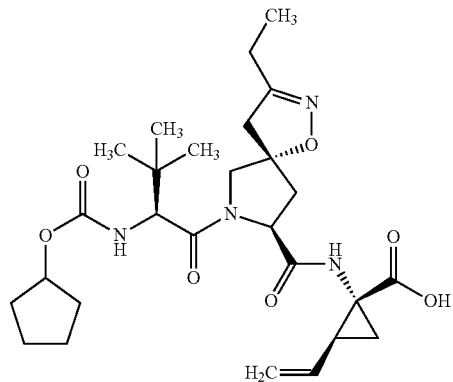 | 272 |
| 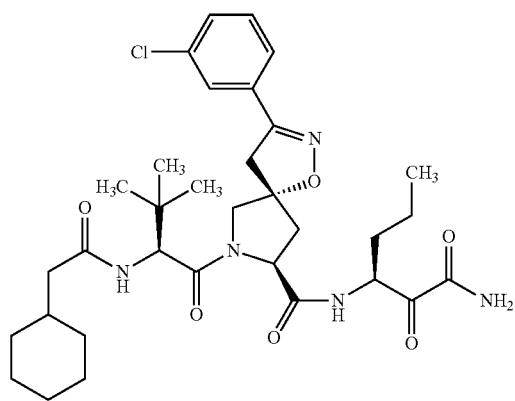 | 273 |
| 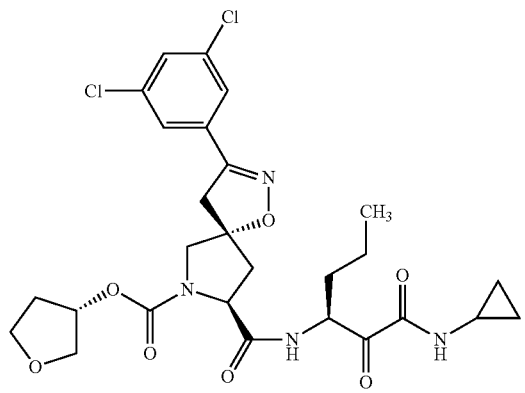 | 274 |

TABLE 1-continued
Exemplary compounds of Formula (I).
| Structure | Compound No. |
|---|---|
| 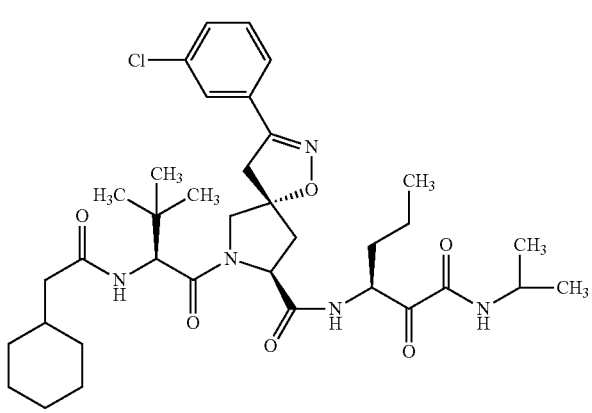 | 275 |
| 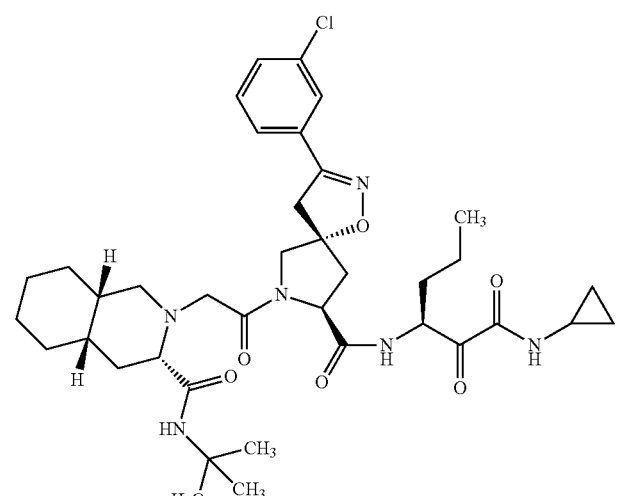 | 276 |
| 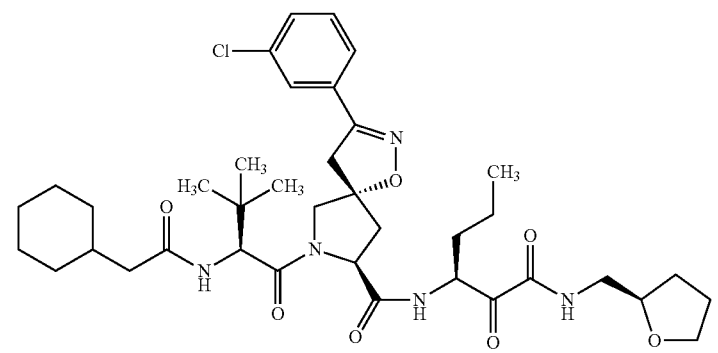 | 277 |

TABLE 1-continued
Exemplary compounds of Formula (I).
| Structure | Compound No. |
|---|---|
| 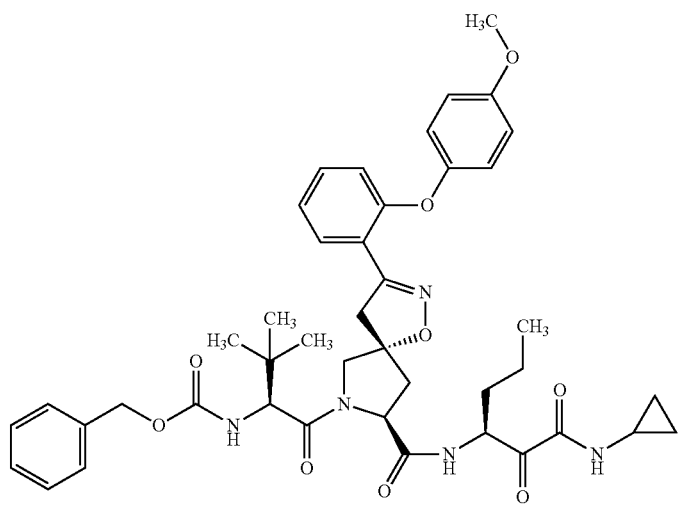 | 278 |
| 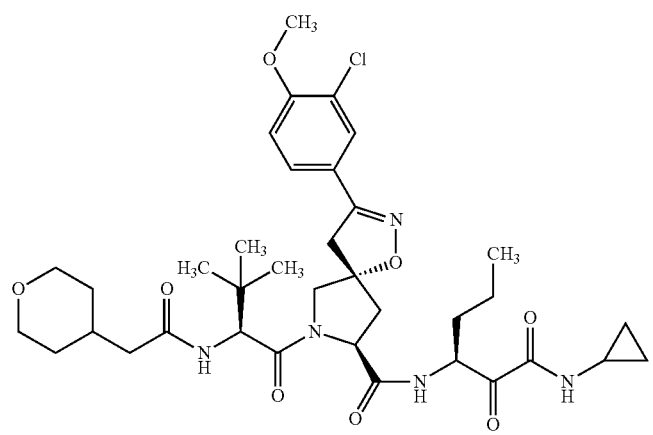 | 279 |
| 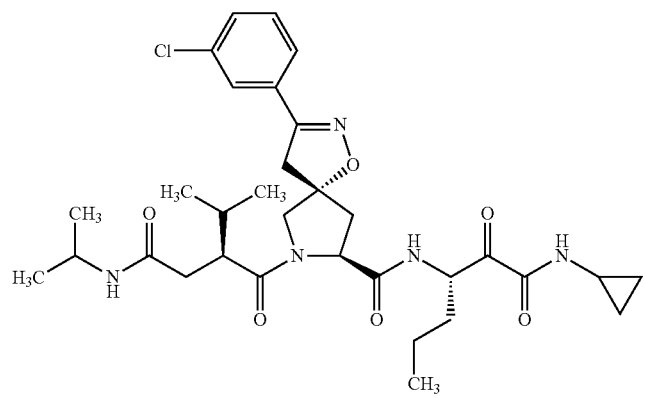 | 280 |

TABLE 1-continued
Exemplary compounds of Formula (I).
| Structure | Compound No. |
|---|---|
| 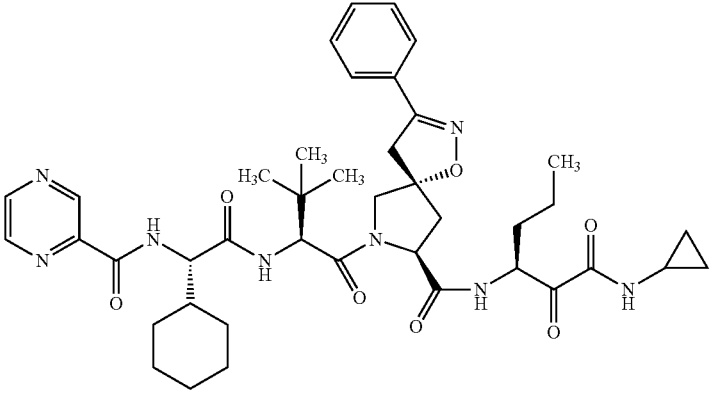 | 281 |
| 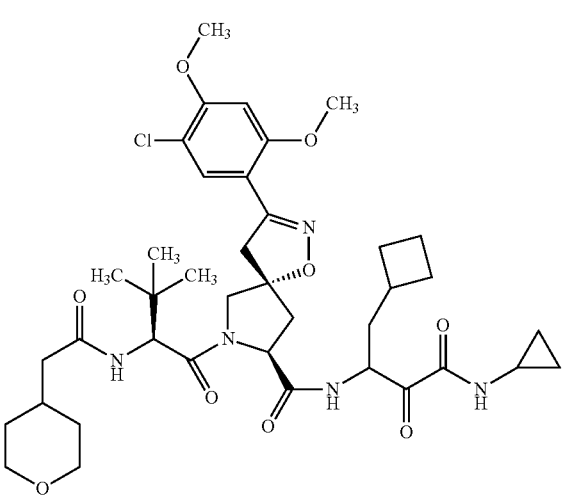 | 282 |
| 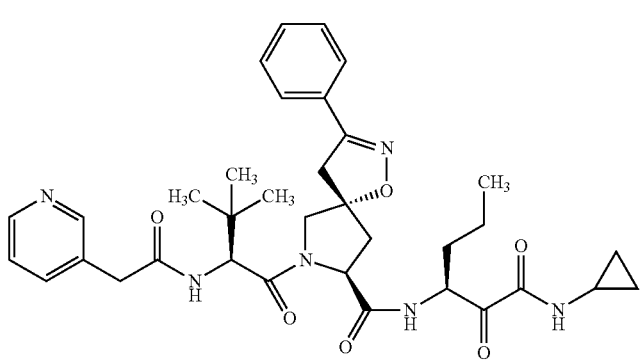 | 283 |

TABLE 1-continued

Exemplary compounds of Formula (I).

| Structure | Compound No. |
|---|---|
| 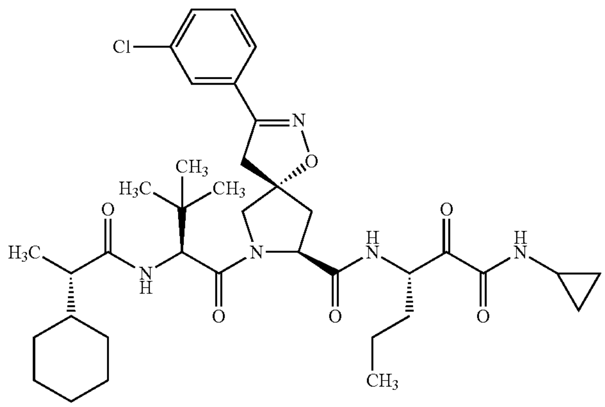 | 284 |
| 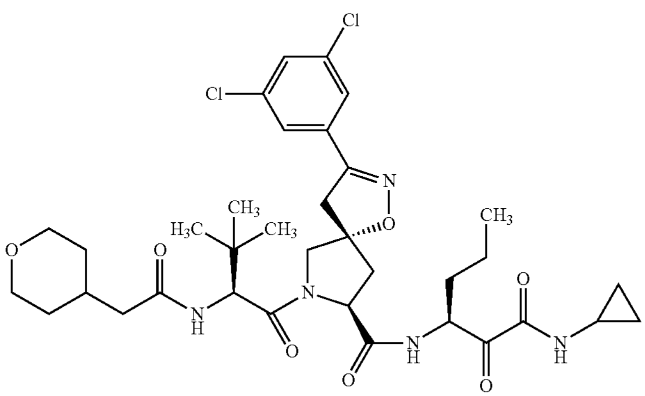 | 285 |
| 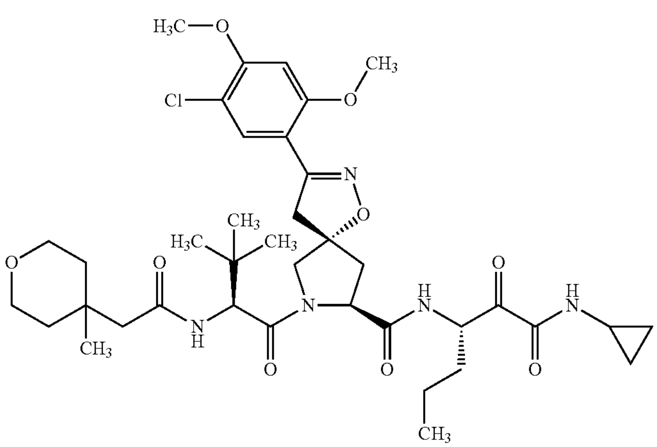 | 286 |

TABLE 1-continued
Exemplary compounds of Formula (I).
| Structure | Compound No. |
|---|---|
| 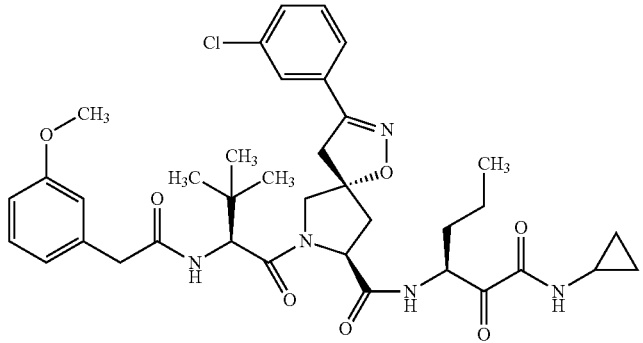 | 287 |
| 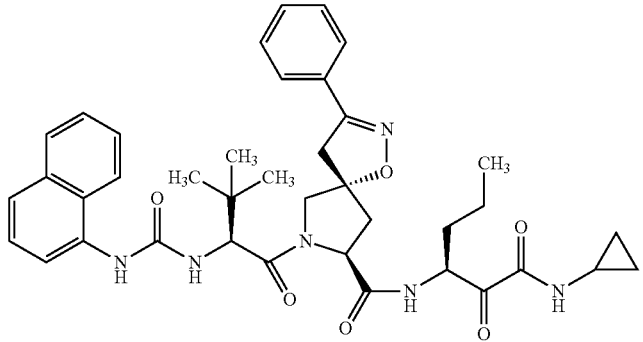 | 288 |
| 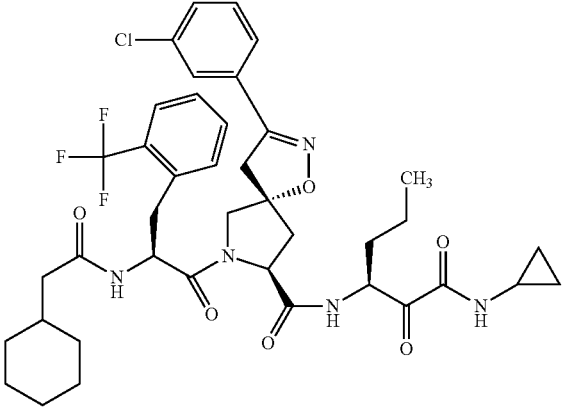 | 289 |
| 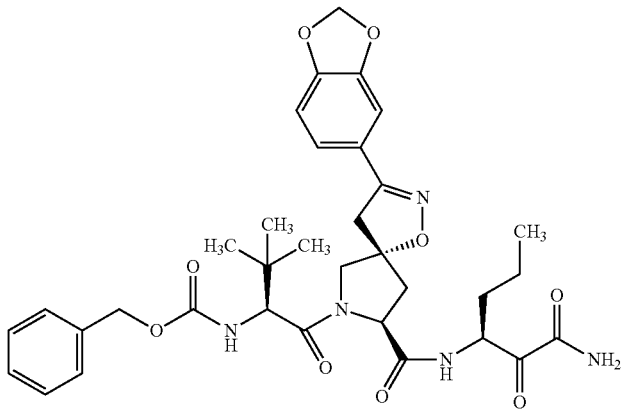 | 290 |

TABLE 1-continued
Exemplary compounds of Formula (I).
| Structure | Compound No. |
|---|---|
| 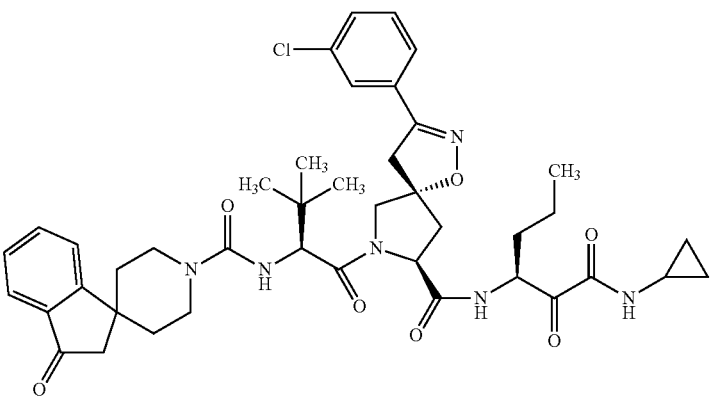 | 291 |
| 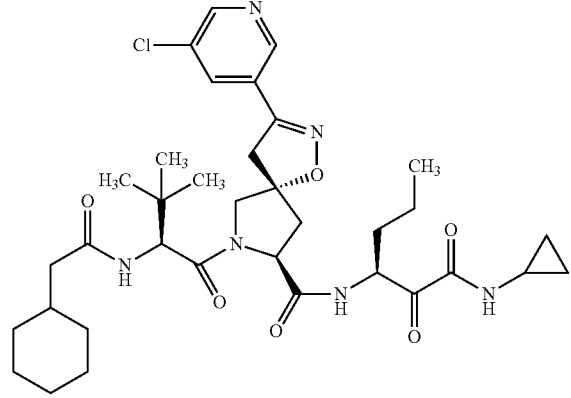 | 292 |
| 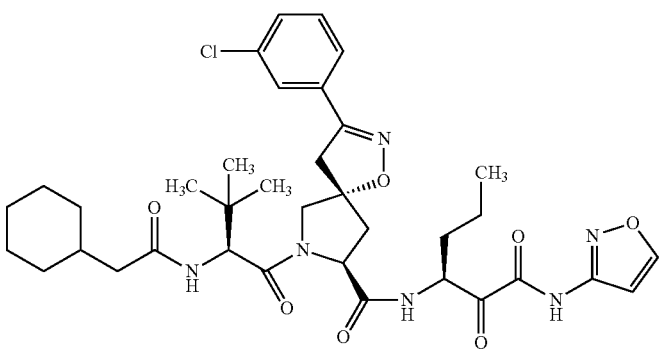 | 293 |
| 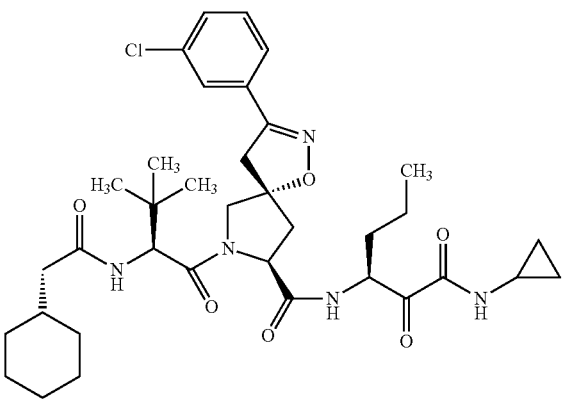 | 294 |

TABLE 1-continued

Exemplary compounds of Formula (I).

| Structure | Compound No. |
|---|---|
| 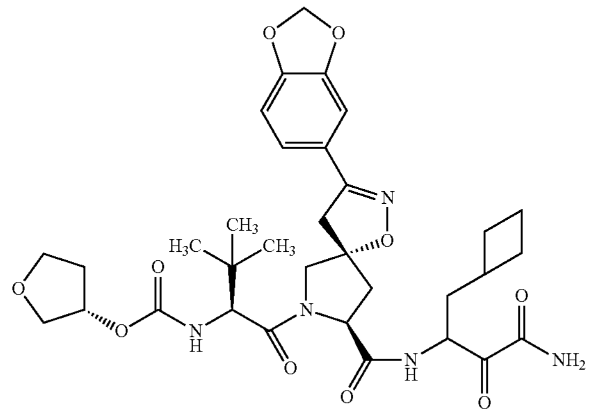 | 295 |
| 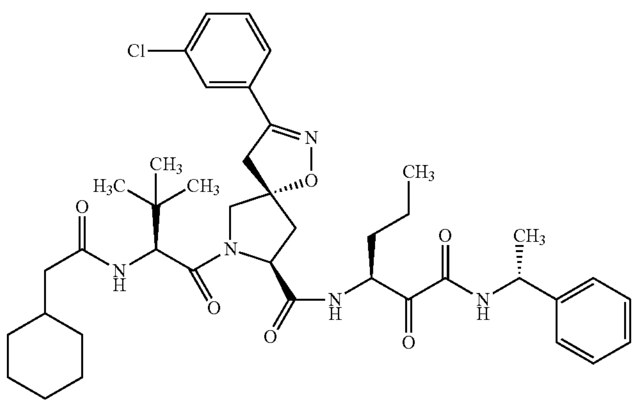 | 296 |
| 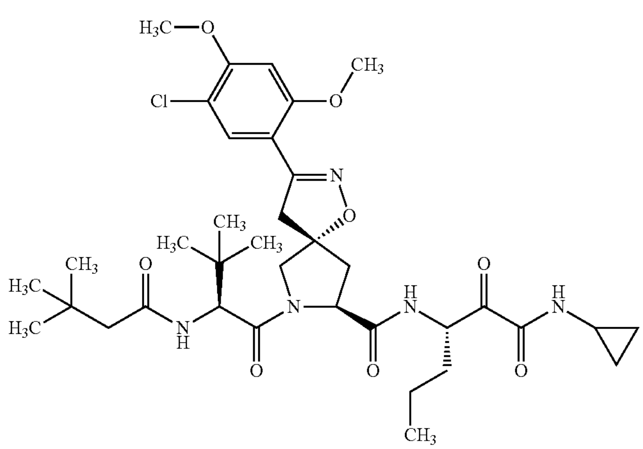 | 297 |

TABLE 1-continued

Exemplary compounds of Formula (I).

| Structure | Compound No. |
|---|---|
| 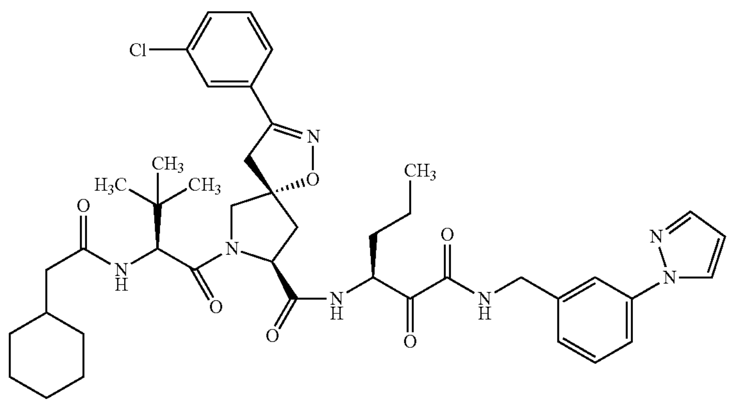 | 298 |
| 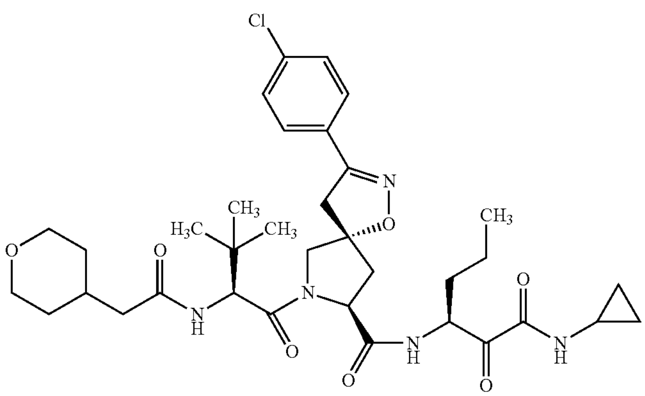 | 299 |
| 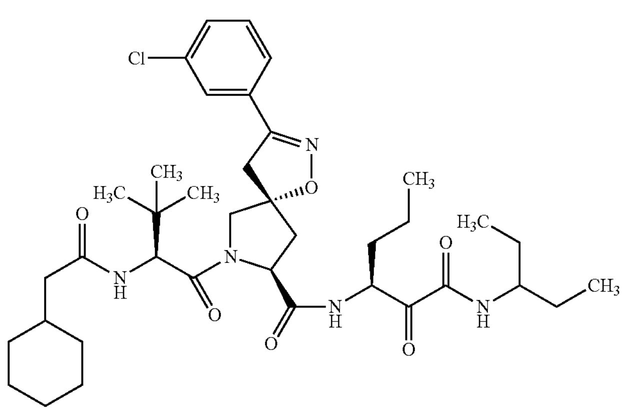 | 300 |

TABLE 1-continued

Exemplary compounds of Formula (I).

| Structure | Compound No. |
|---|---|
| 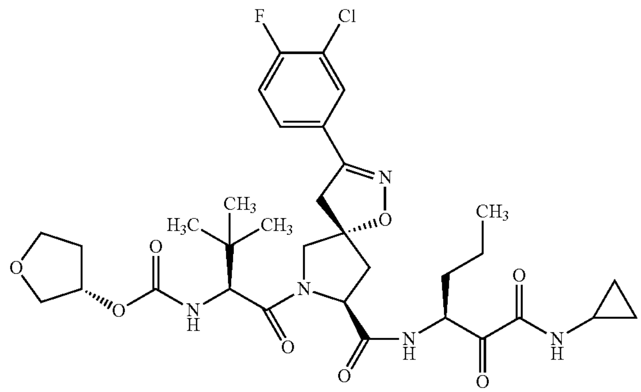 | 301 |
| 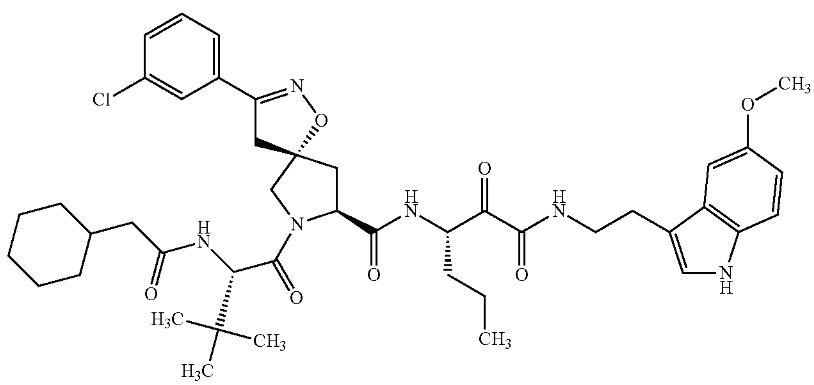 | 302 |
| 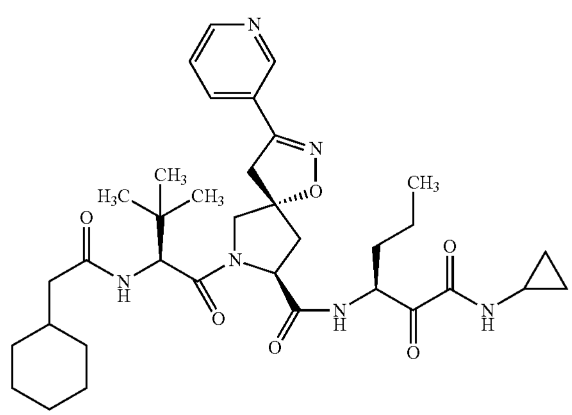 | 303 |
| 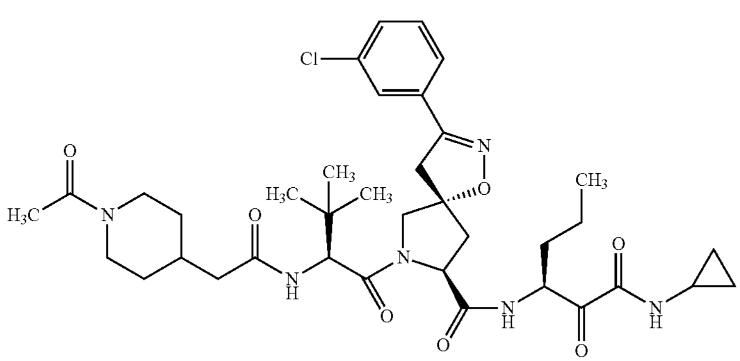 | 304 |

TABLE 1-continued

Exemplary compounds of Formula (I).

| Structure | Compound No. |
|---|---|
| 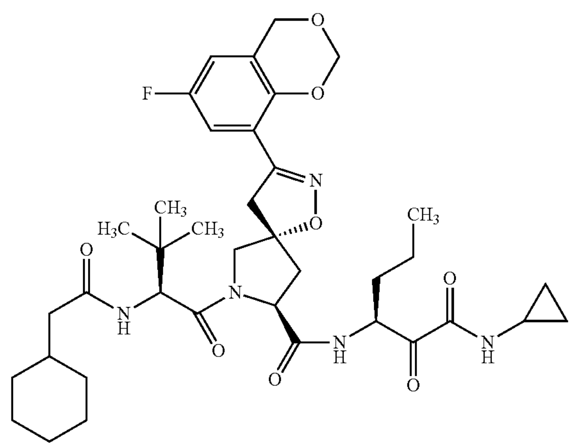 | 305 |
| 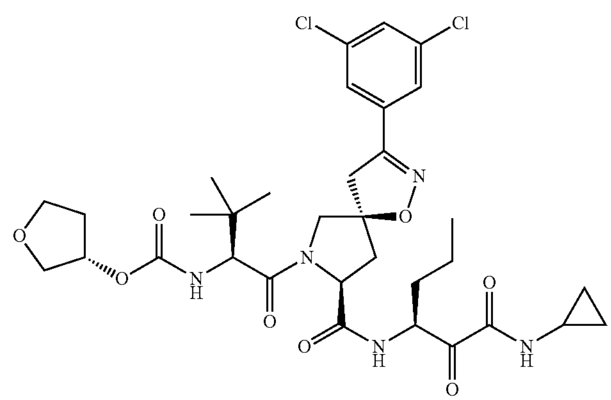 | 306 |
| 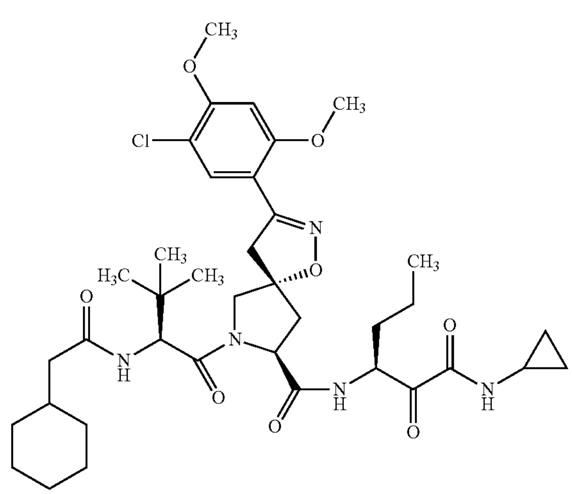 | 307 |

TABLE 1-continued

Exemplary compounds of Formula (I).

| Structure | Compound No. |
|---|---|
| 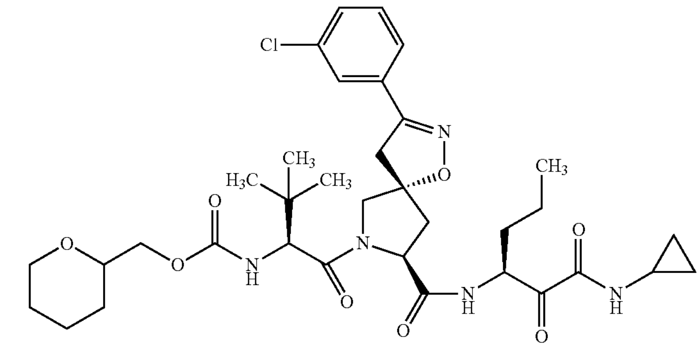 | 308 |
| 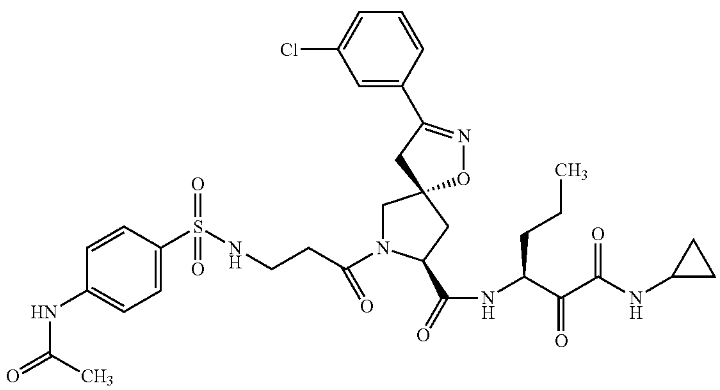 | 309 |
| 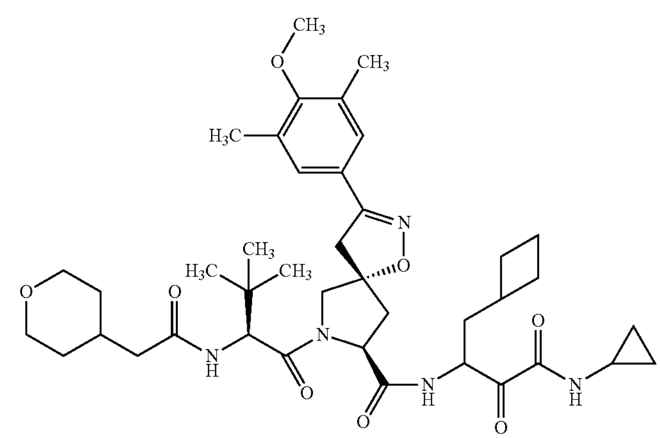 | 310 |
| 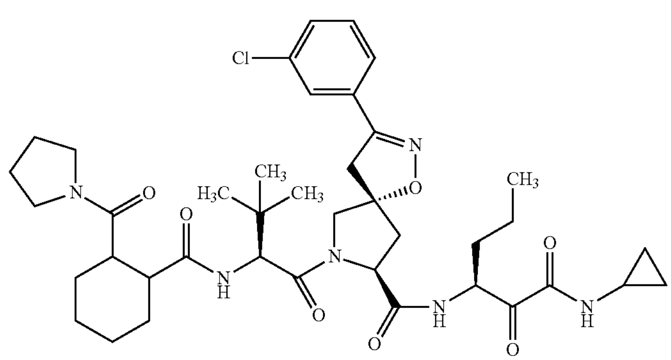 | 311 |

TABLE 1-continued
Exemplary compounds of Formula (I).
| Structure | Compound No. |
|---|---|
| 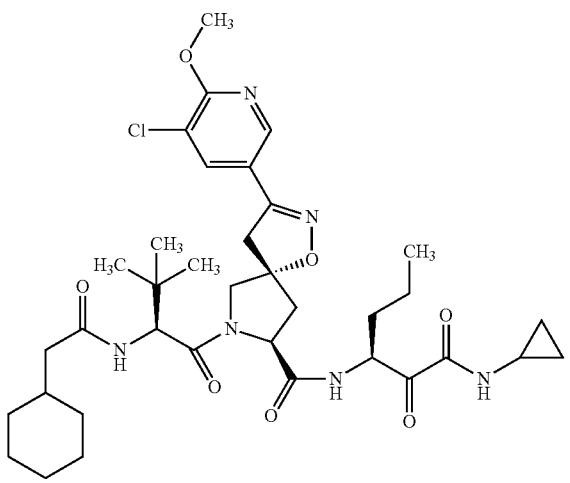 | 312 |
| 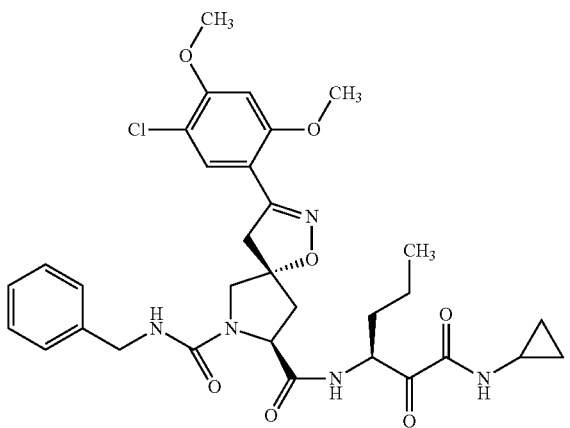 | 313 |
| 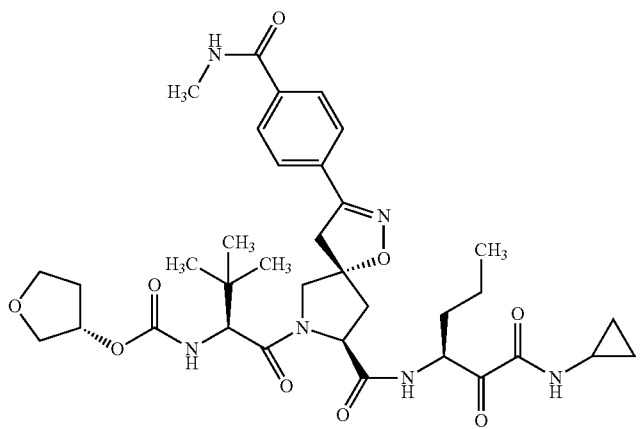 | 314 |

TABLE 1-continued

Exemplary compounds of Formula (I).

| Structure | Compound No. |
|---|---|
| 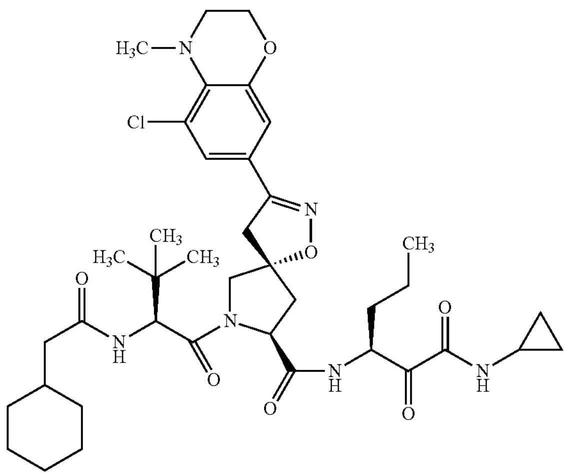 | 315 |
| 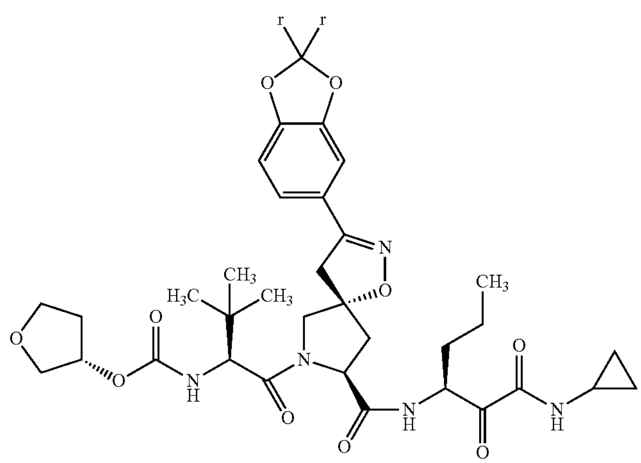 | 316 |
| 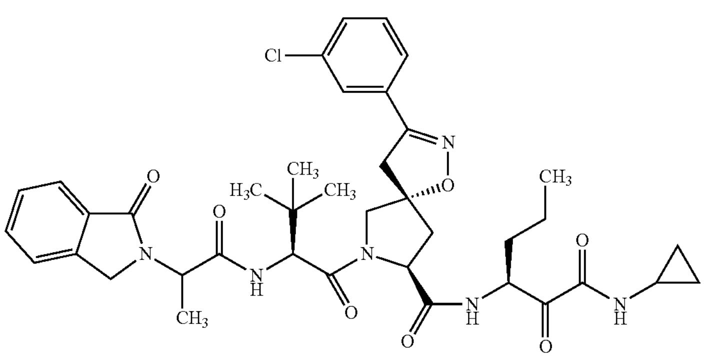 | 317 |

TABLE 1-continued
Exemplary compounds of Formula (I).
| Structure | Compound No. |
|---|---|
| 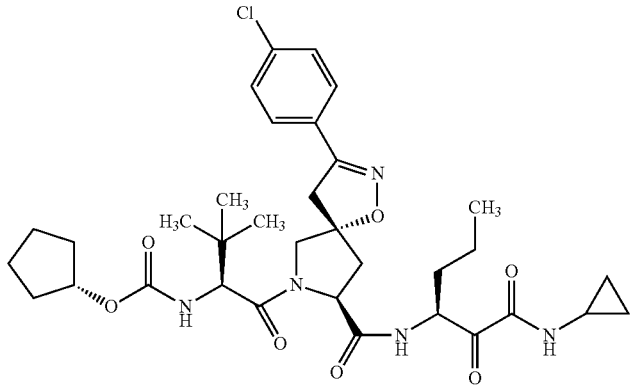 | 318 |
| 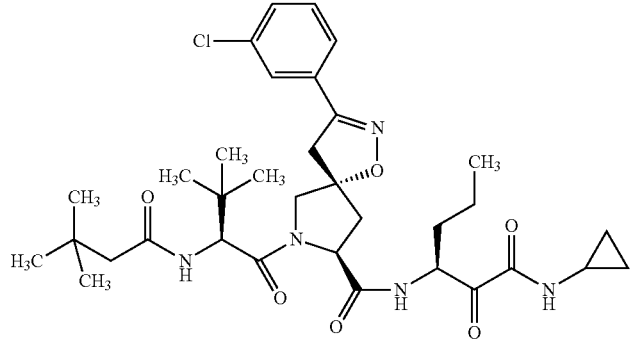 | 319 |
| 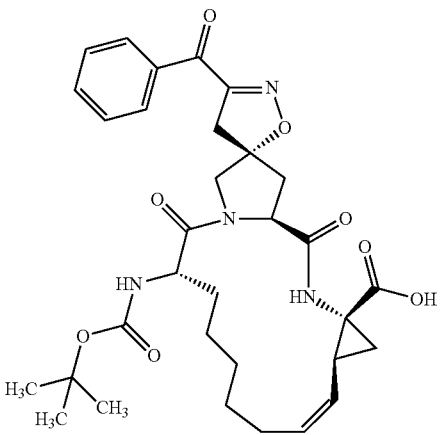 | 320 |

TABLE 1-continued
Exemplary compounds of Formula (I).
| Structure | Compound No. |
|---|---|
| 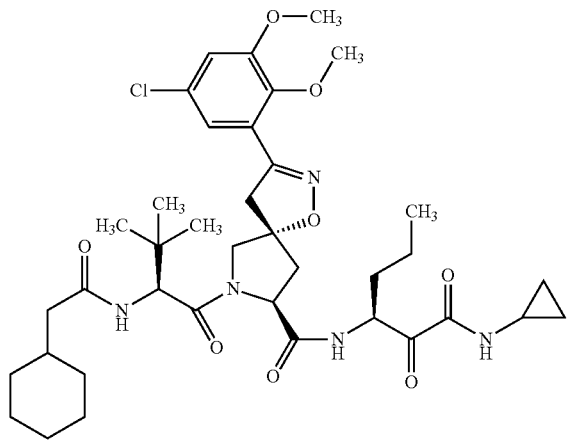 | 321 |
| 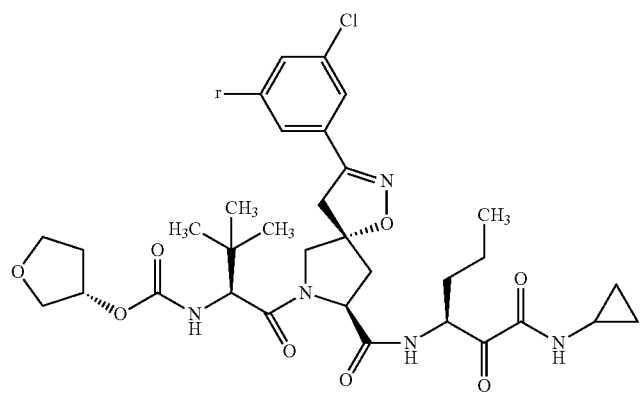 | 322 |
| 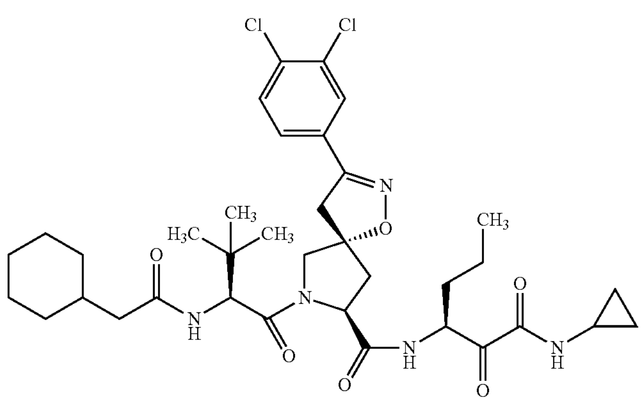 | 323 |

TABLE 1-continued

Exemplary compounds of Formula (I).

| Structure | Compound No. |
|---|---|
| 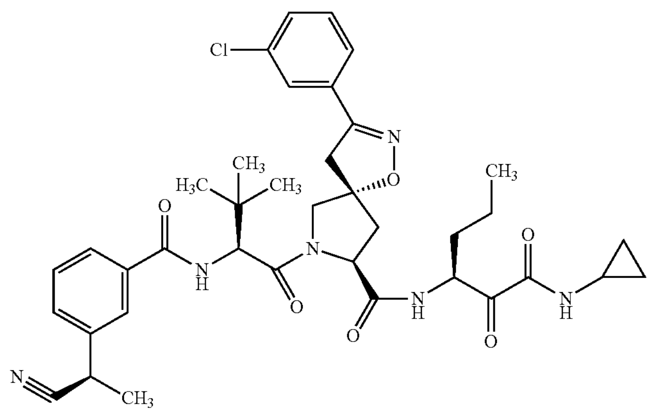 | 324 |
| 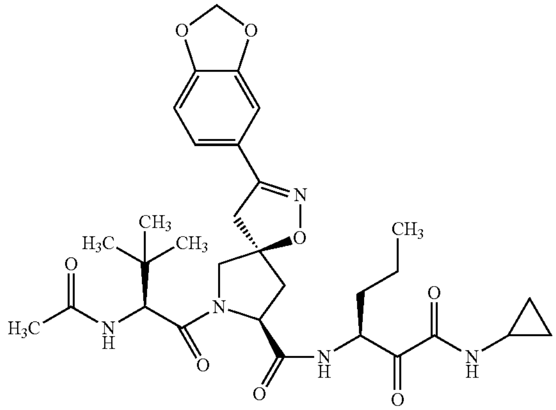 | 325 |
| 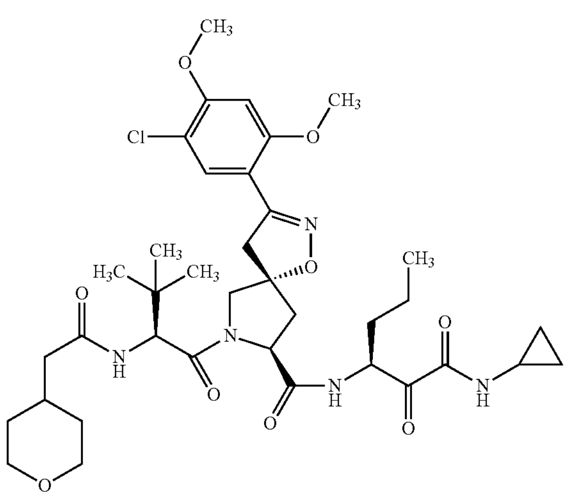 | 326 |

TABLE 1-continued

Exemplary compounds of Formula (I).

| Structure | Compound No. |
|---|---|
| 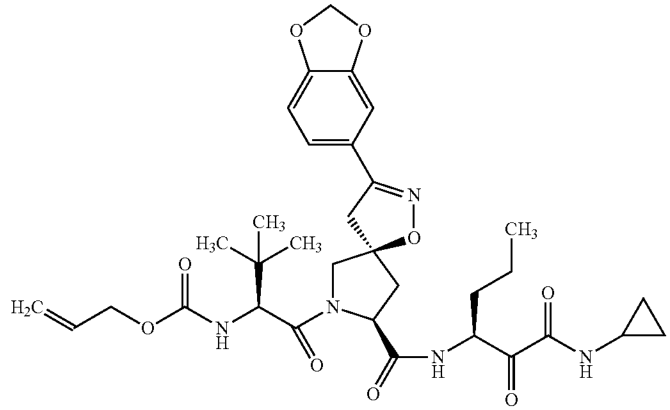 | 327 |
| 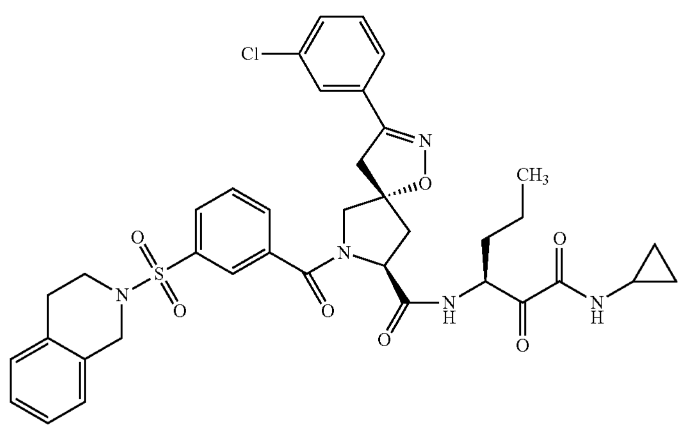 | 328 |
| 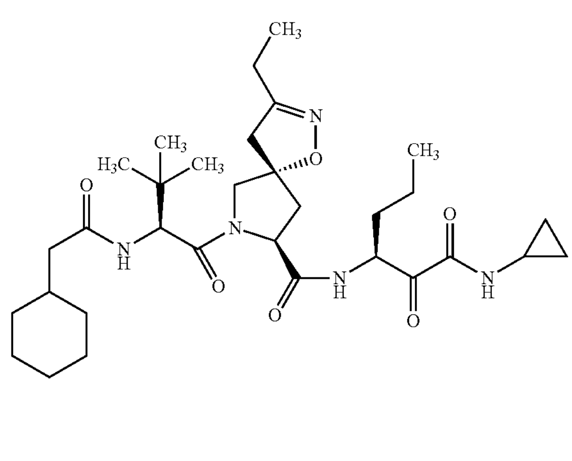 | 329 |

TABLE 1-continued

Exemplary compounds of Formula (I).

| Structure | Compound No. |
|---|---|
| 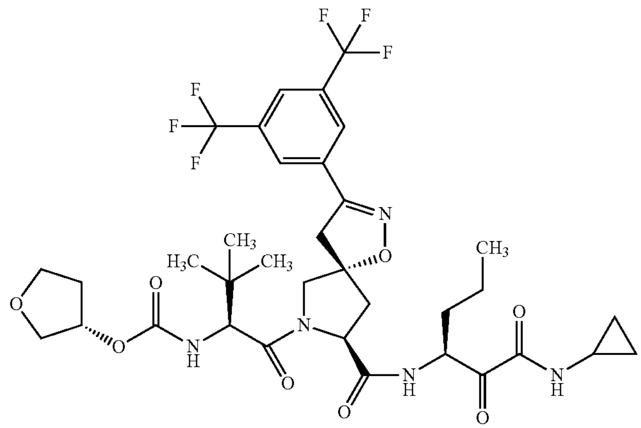 | 330 |
| 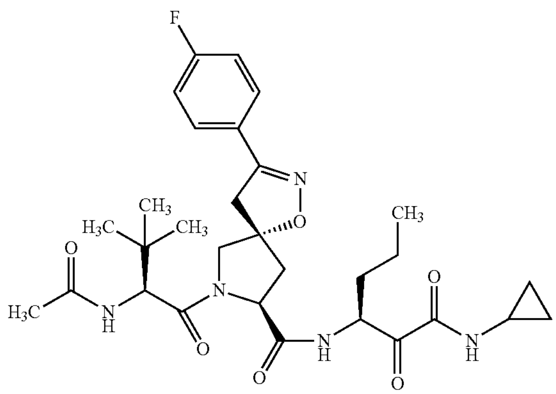 | 331 |
| 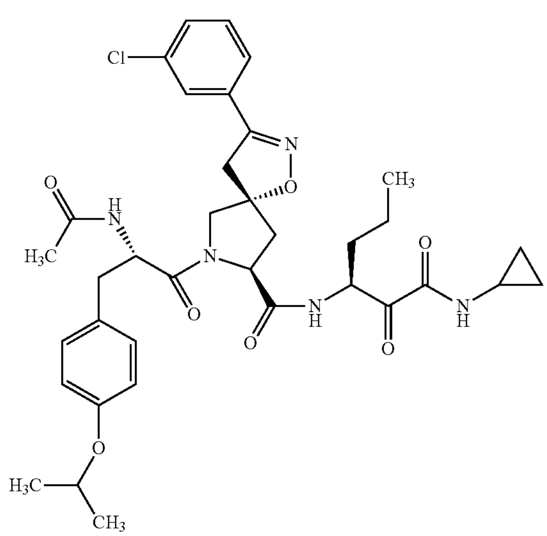 | 332 |

TABLE 1-continued

Exemplary compounds of Formula (I).

| Structure | Compound No. |
|---|---|
| 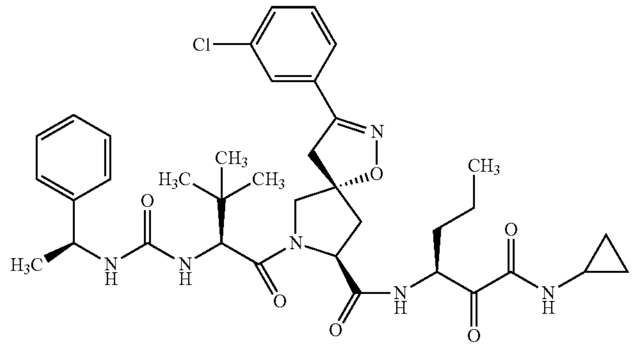 | 333 |
| 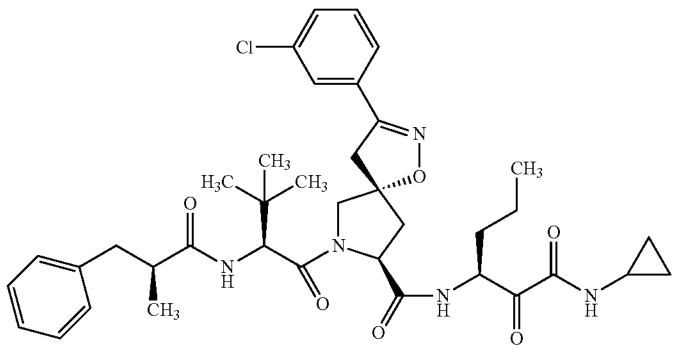 | 334 |
| 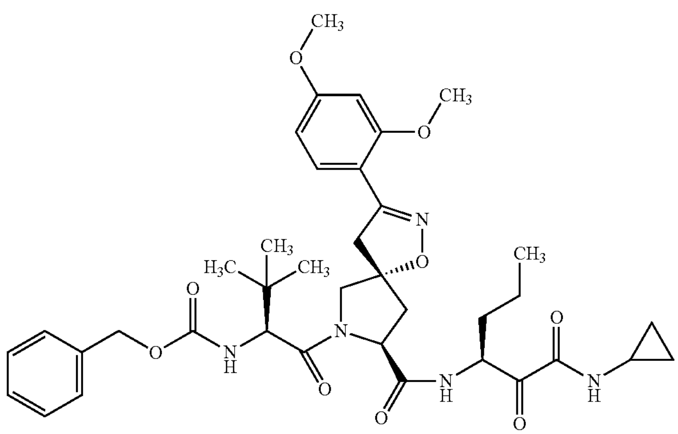 | 335 |
| 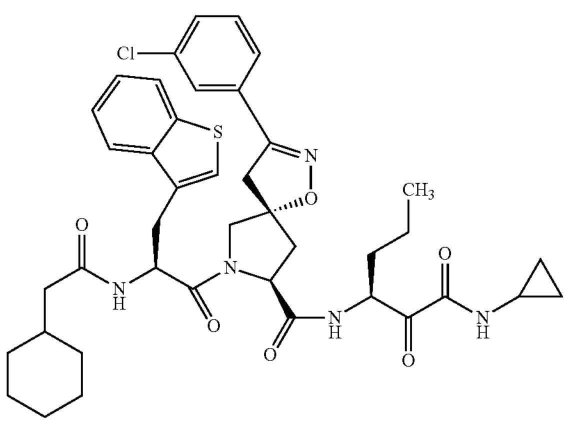 | 336 |

TABLE 1-continued

Exemplary compounds of Formula (I).

| Structure | Compound No. |
|---|---|
| 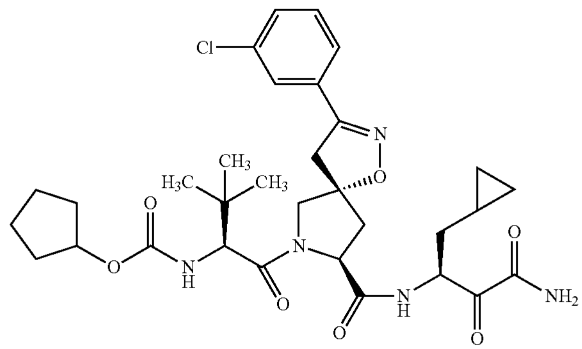 | 337 |
| 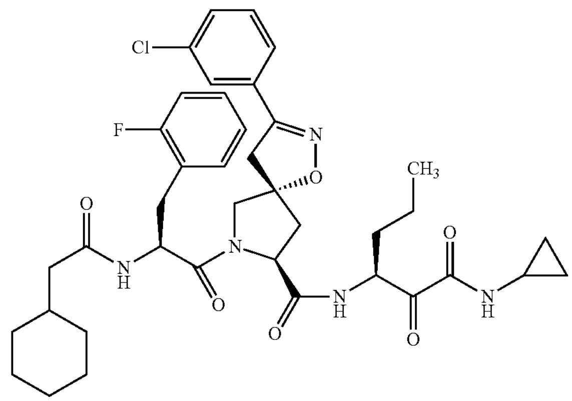 | 338 |
| 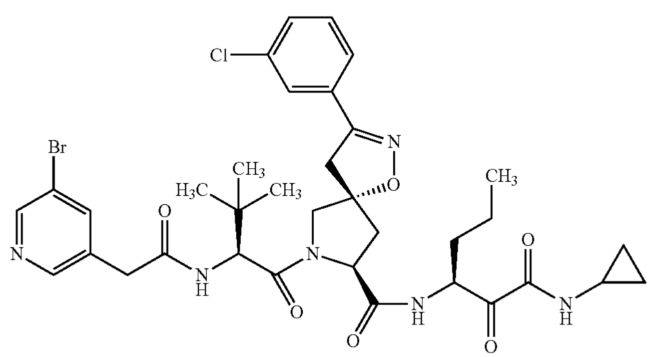 | 339 |
| 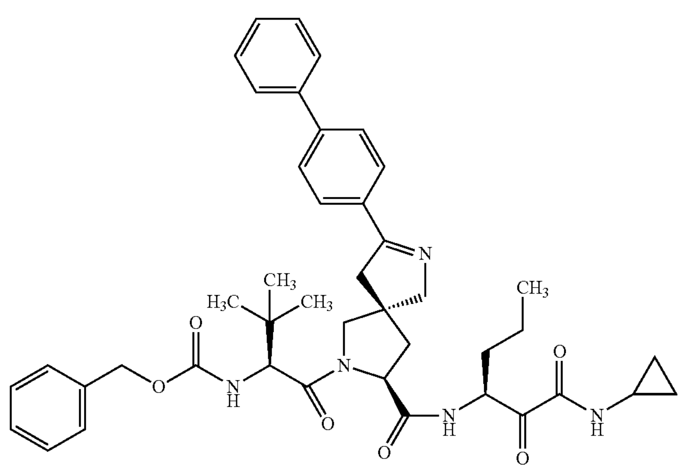 | 340 |

TABLE 1-continued

Exemplary compounds of Formula (I).

| Structure | Compound No. |
|---|---|
| 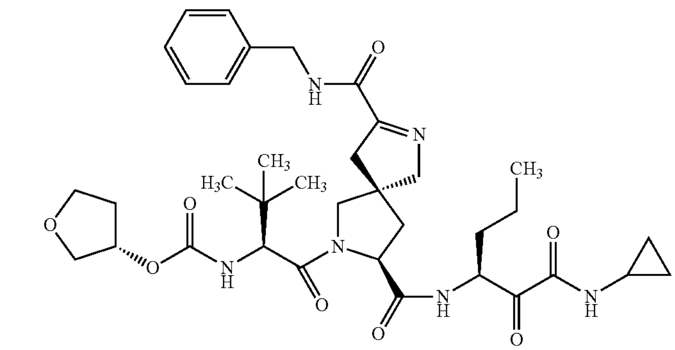 | 341 |
| 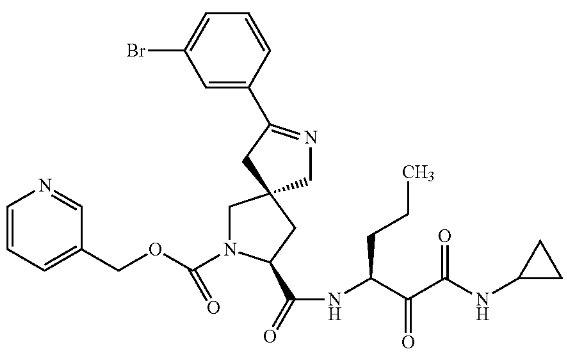 | 342 |
| 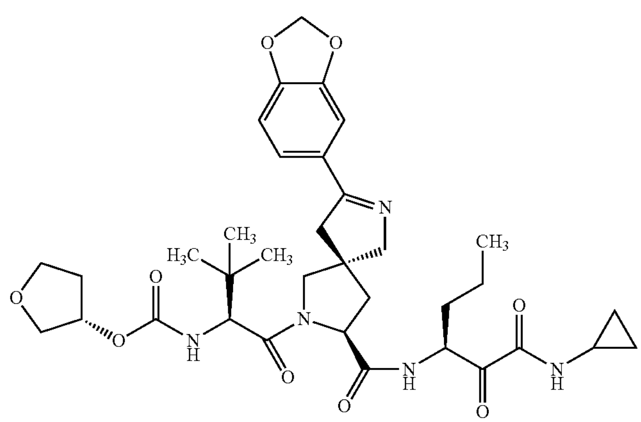 | 343 |
| 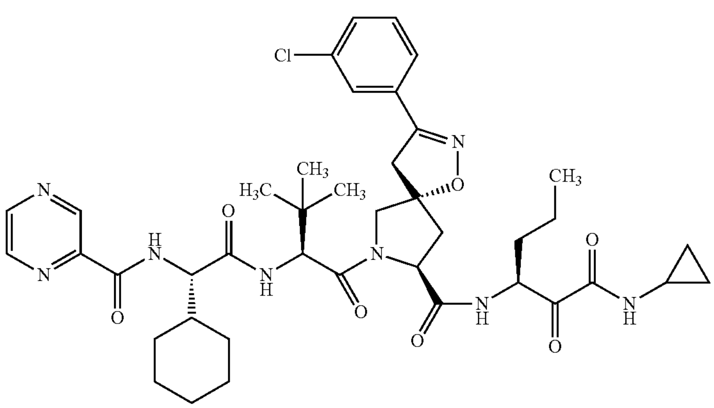 | 344 |

TABLE 1-continued

Exemplary compounds of Formula (I).

| Structure | Compound No. |
|---|---|
| 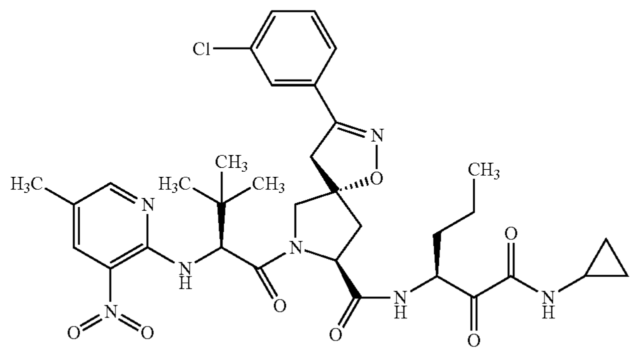 | 345 |
| 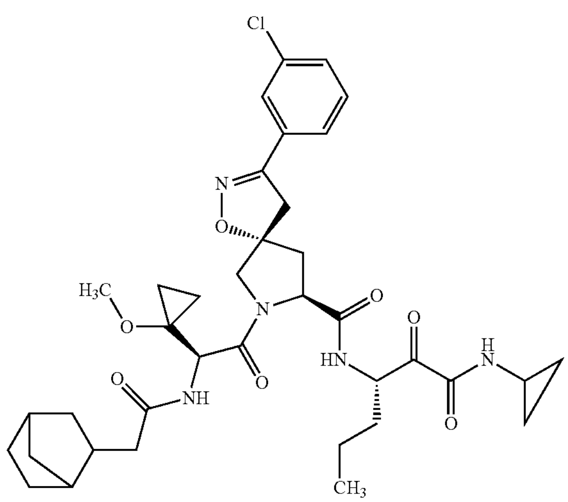 | 346 |
| 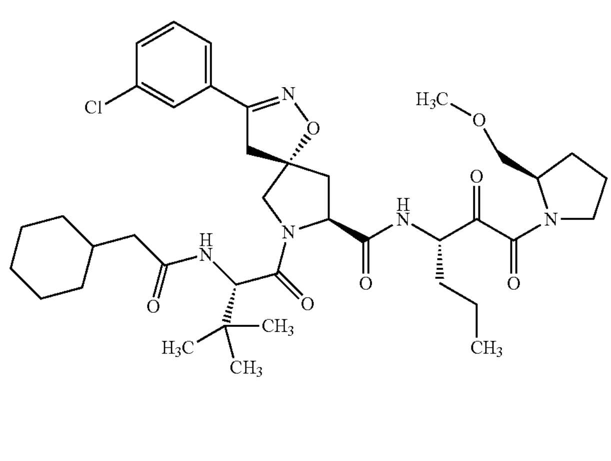 | 347 |

TABLE 1-continued

Exemplary compounds of Formula (I).

| Structure | Compound No. |
|---|---|
| 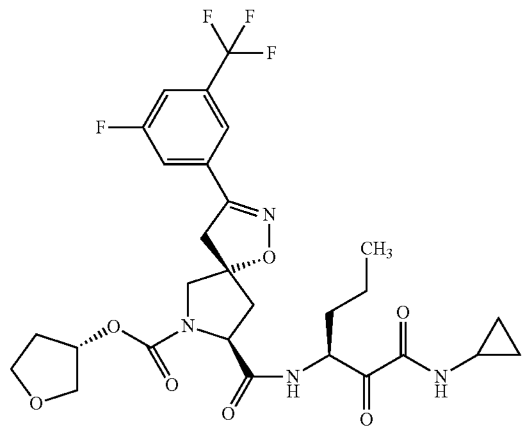 | 348 |
| 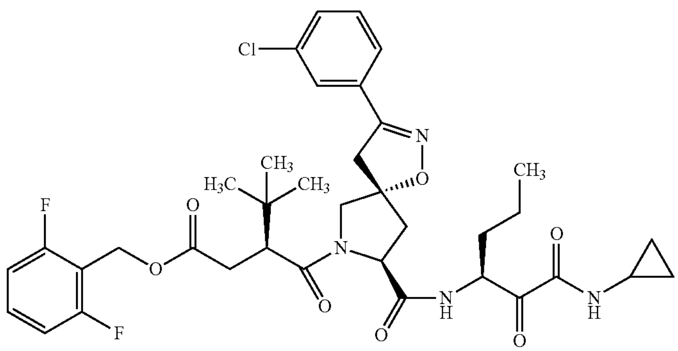 | 349 |
| 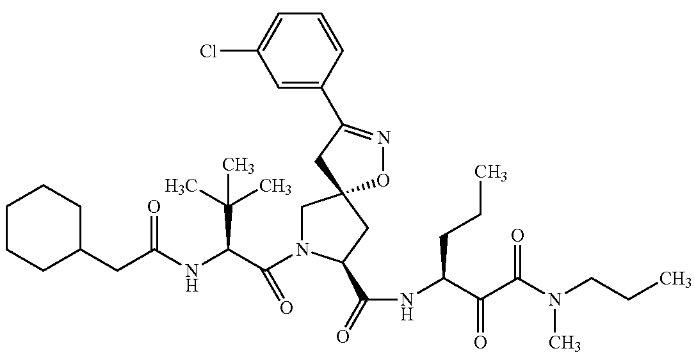 | 350 |
| 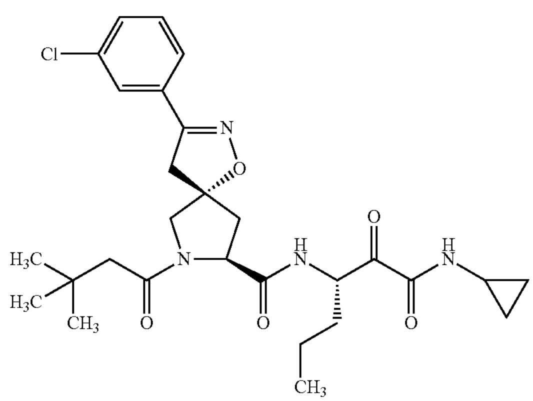 | 351 |

TABLE 1-continued

Exemplary compounds of Formula (I).

| Structure | Compound No. |
|---|---|
| 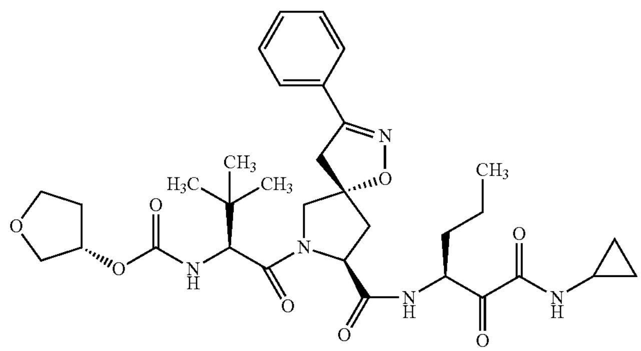 | 352 |
| 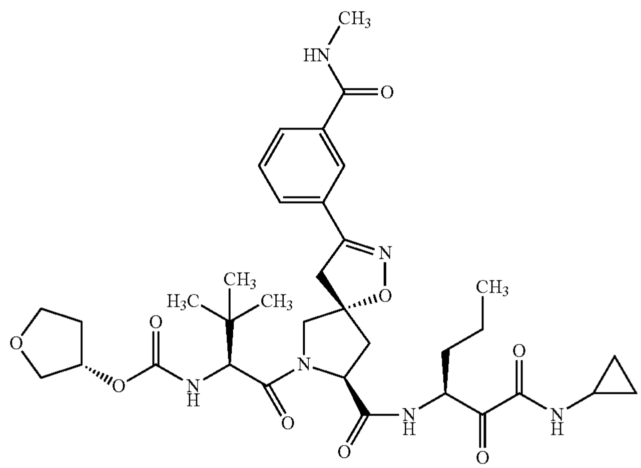 | 353 |
| 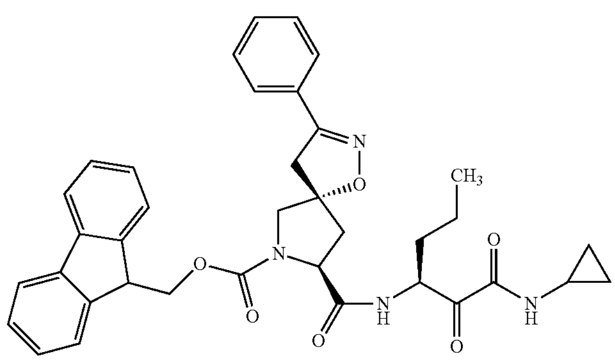 | 354 |
| 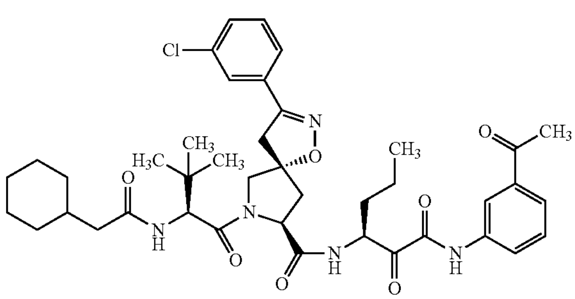 | 355 |

TABLE 1-continued

Exemplary compounds of Formula (I).

| Structure | Compound No. |
|---|---|
| 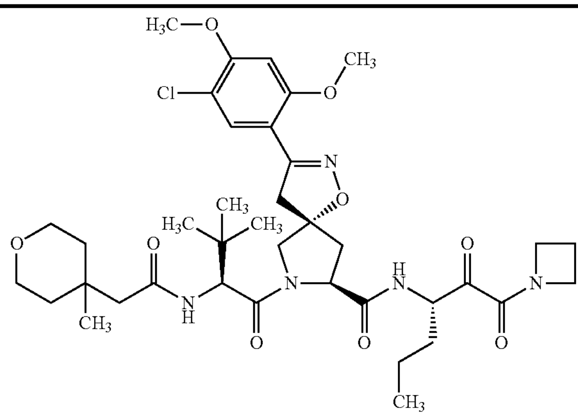 | 356 |
| 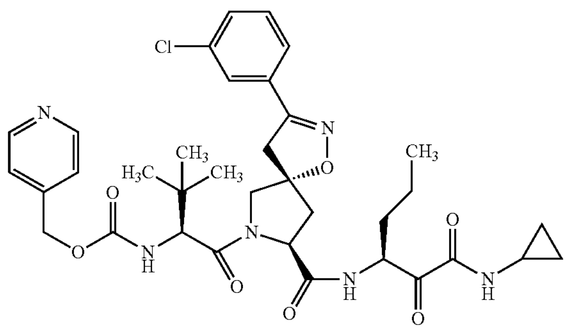 | 357 |
| 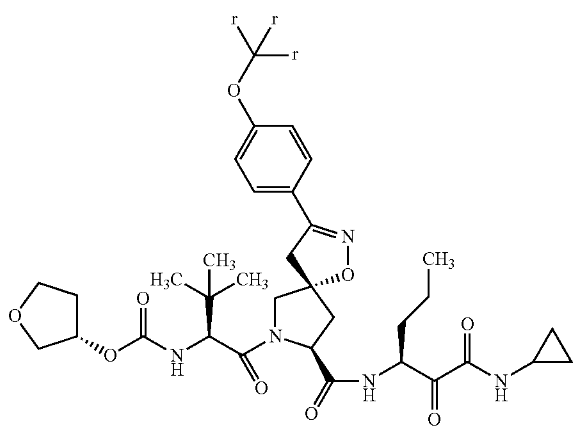 | 358 |
| 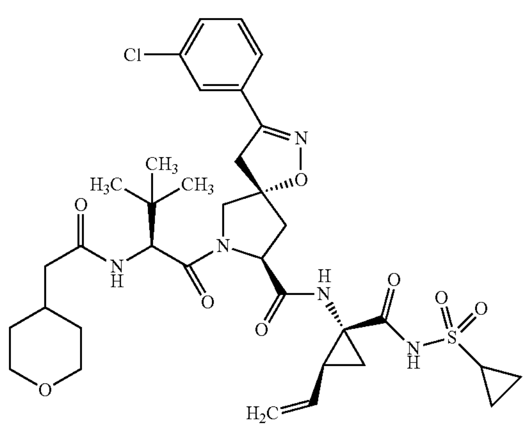 | 359 |

TABLE 1-continued

Exemplary compounds of Formula (I).

| Structure | Compound No. |
|---|---|
| 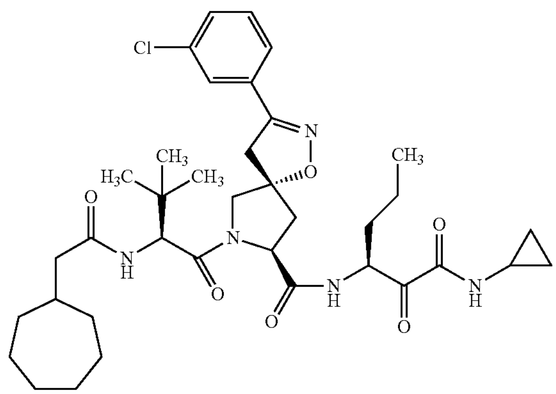 | 360 |
| 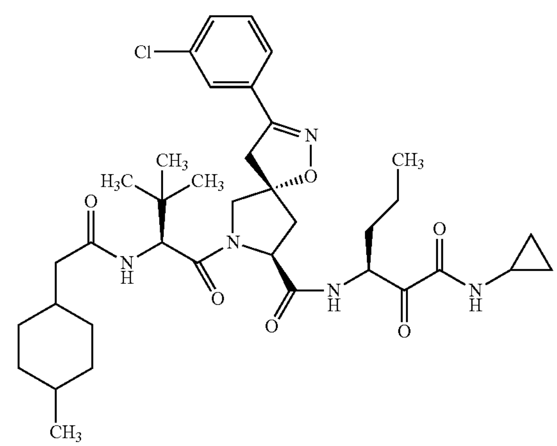 | 361 |
| 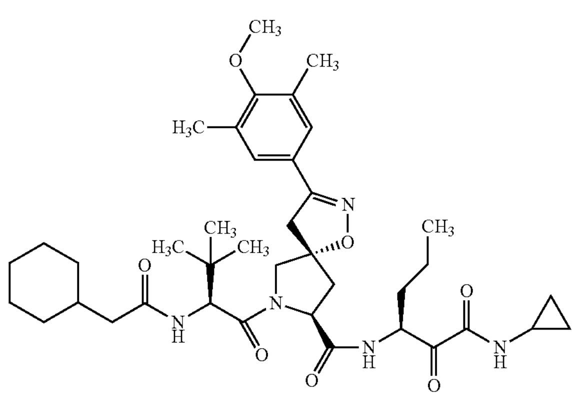 | 362 |

TABLE 1-continued

Exemplary compounds of Formula (I).

| Structure | Compound No. |
|---|---|
| 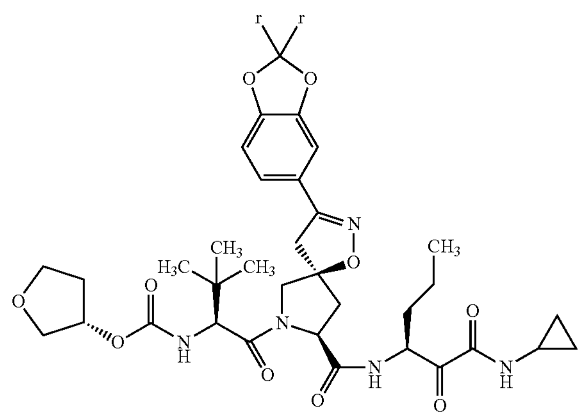 | 363 |
| 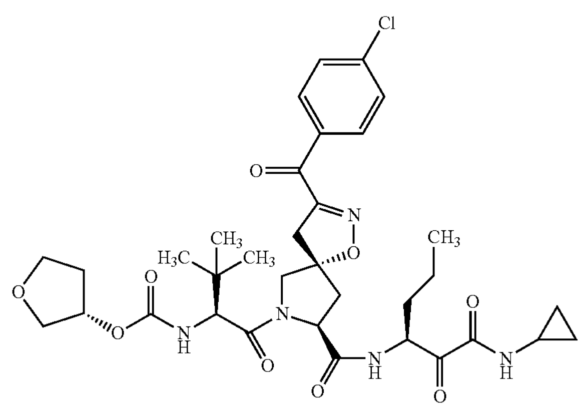 | 364 |
| 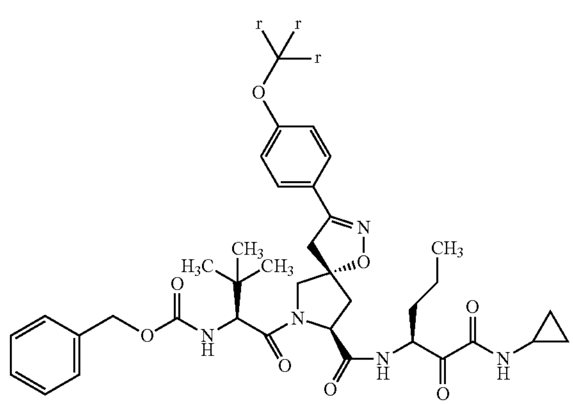 | 365 |

TABLE 1-continued

Exemplary compounds of Formula (I).

| Structure | Compound No. |
|---|---|
| 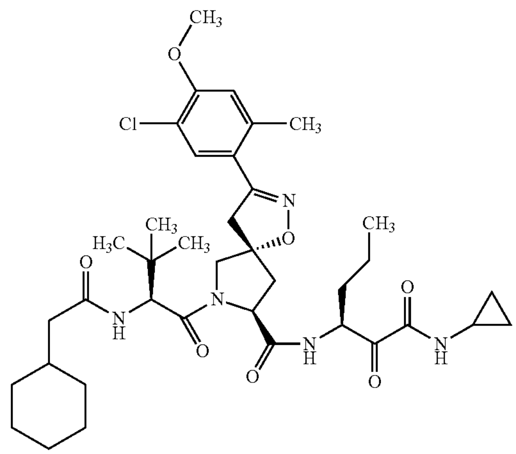 | 366 |
| 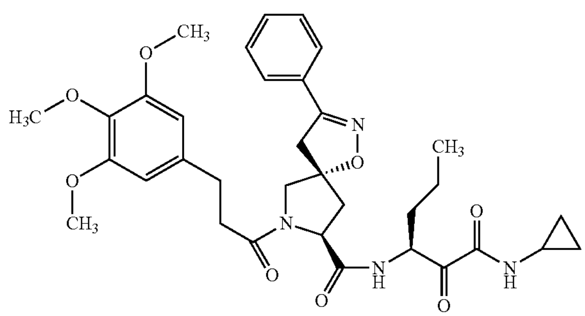 | 367 |
| 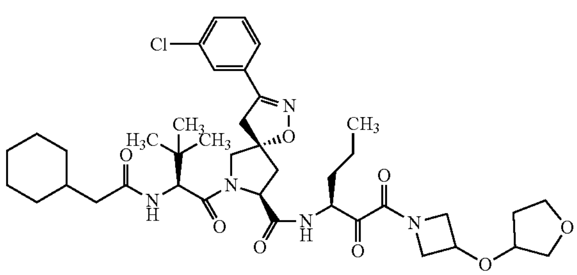 | 368 |
| 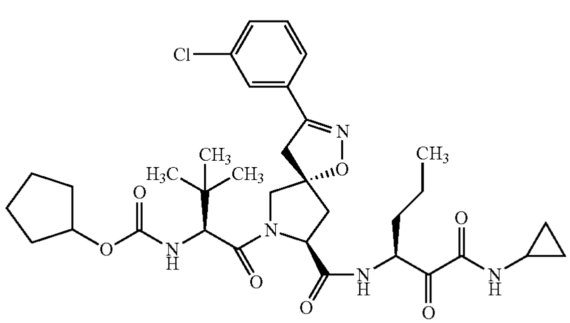 | 369 |

TABLE 1-continued

Exemplary compounds of Formula (I).

| Structure | Compound No. |
|---|---|
| 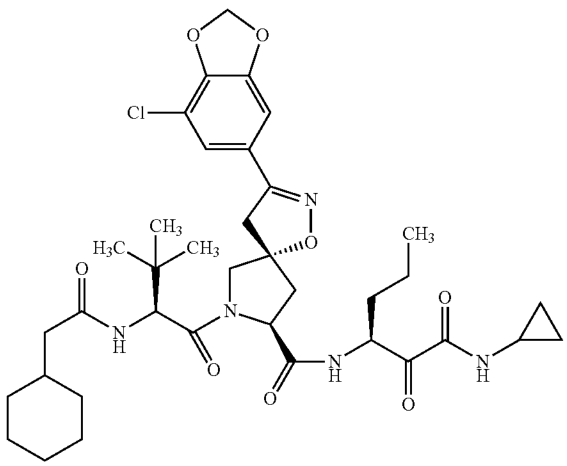 | 370 |
| 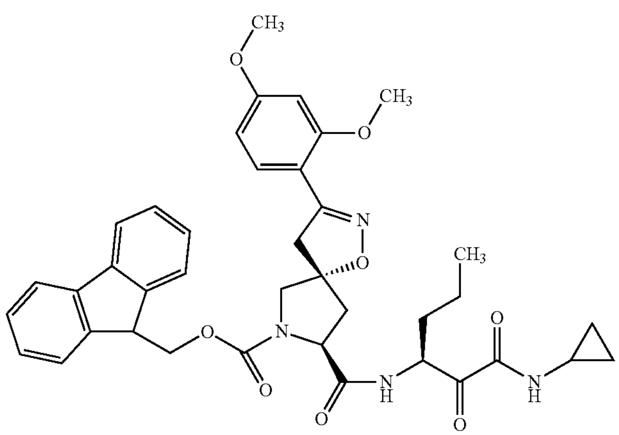 | 371 |
| 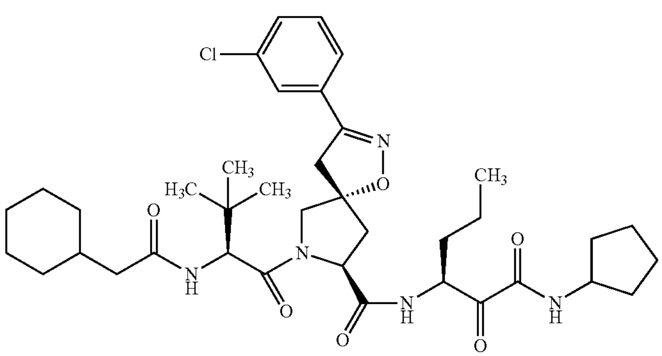 | 372 |

TABLE 1-continued

Exemplary compounds of Formula (I).

| Structure | Compound No. |
|---|---|
| 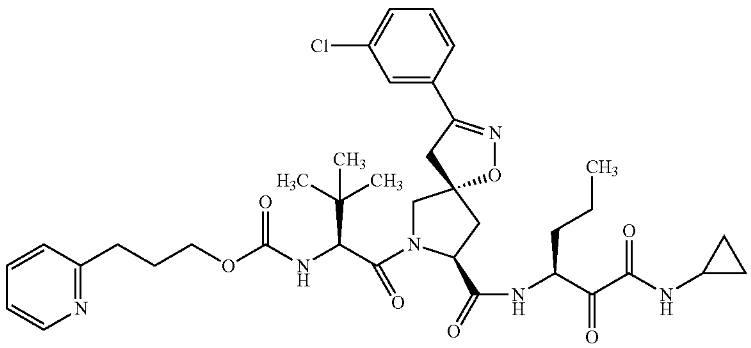 | 373 |
| 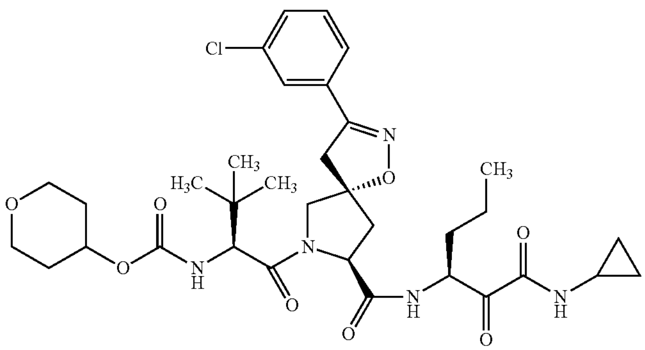 | 374 |
| 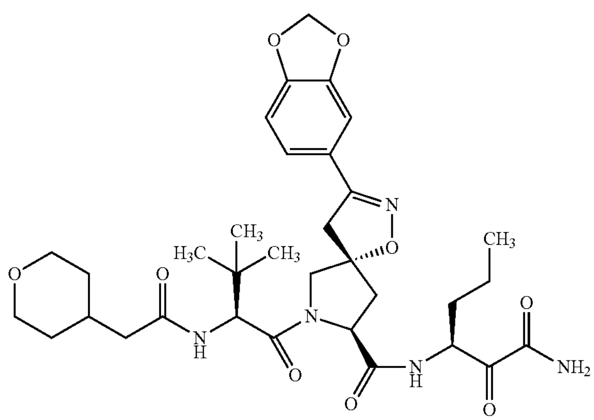 | 375 |
| 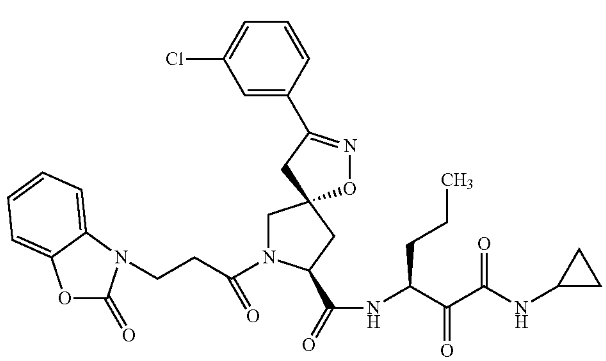 | 376 |

TABLE 1-continued
Exemplary compounds of Formula (I).
| Structure | Compound No. |
|---|---|
| 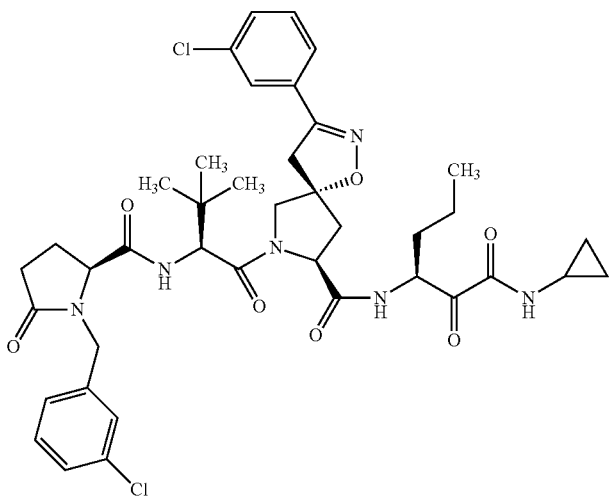 | 377 |
| 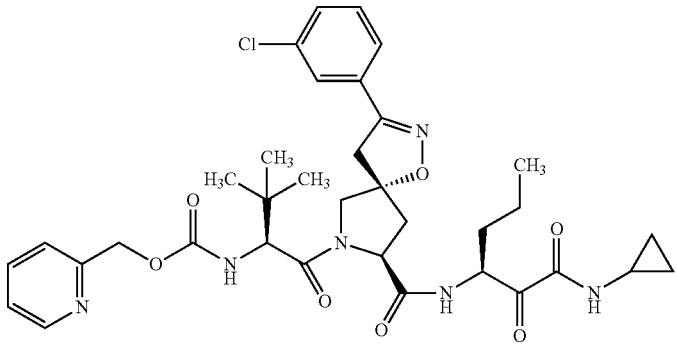 | 378 |
| 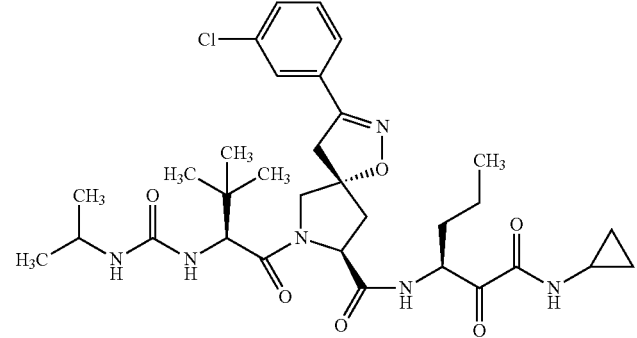 | 379 |
| 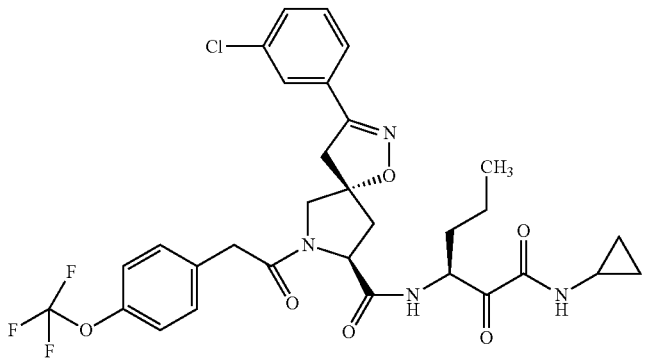 | 380 |

TABLE 1-continued

Exemplary compounds of Formula (I).

| Structure | Compound No. |
|---|---|
| 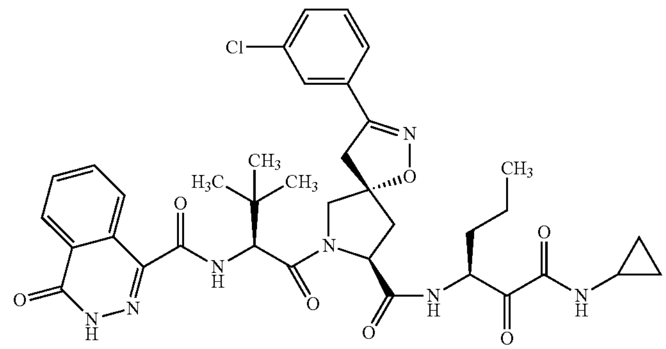 | 381 |
| 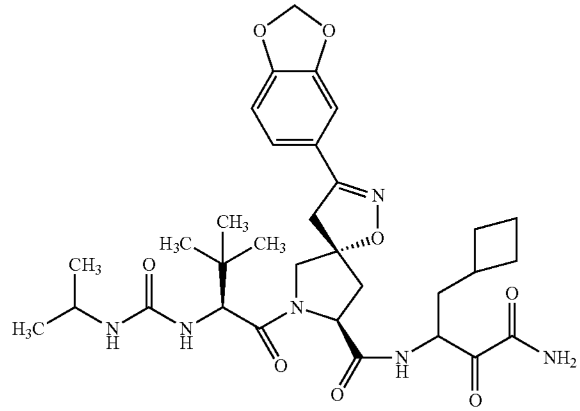 | 382 |
| 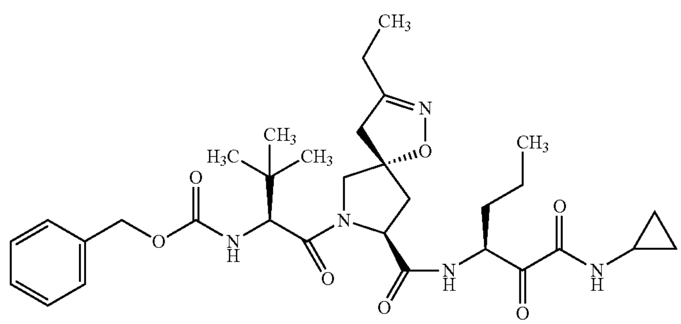 | 383 |
| 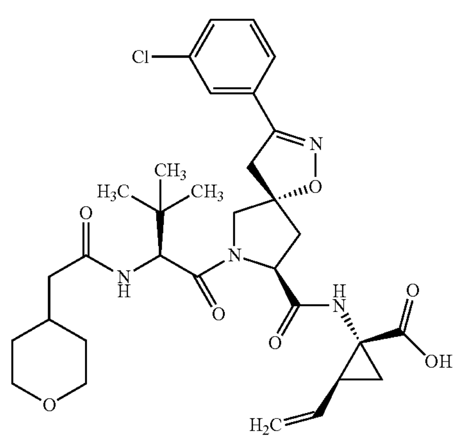 | 384 |

TABLE 1-continued

Exemplary compounds of Formula (I).

| Structure | Compound No. |
|---|---|
| 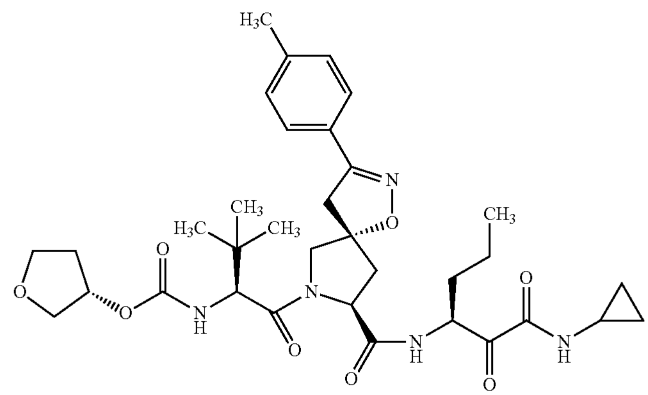 | 385 |
| 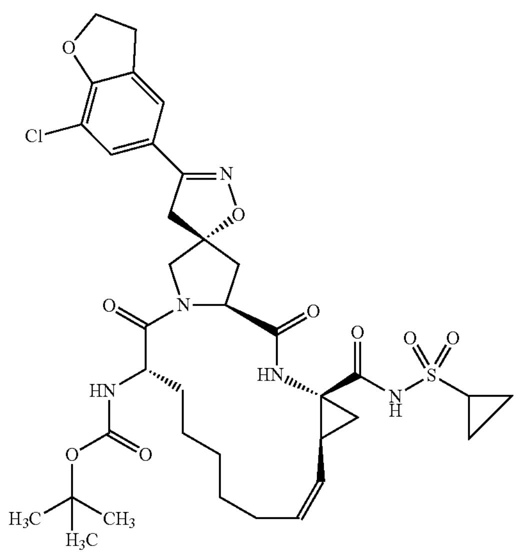 | 386 |
| 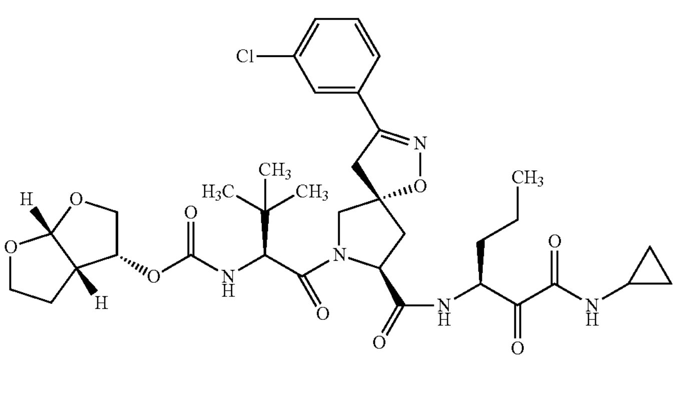 | 387 |

TABLE 1-continued

Exemplary compounds of Formula (I).

| Structure | Compound No. |
|---|---|
| 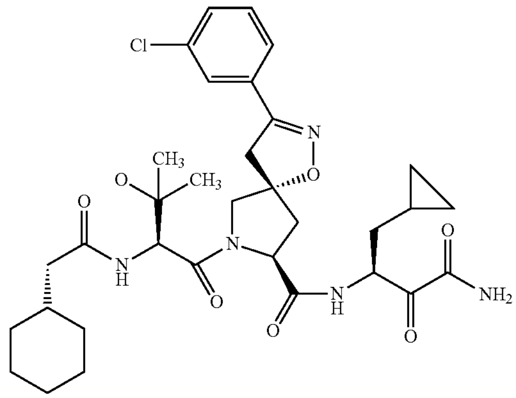 | 388 |
| 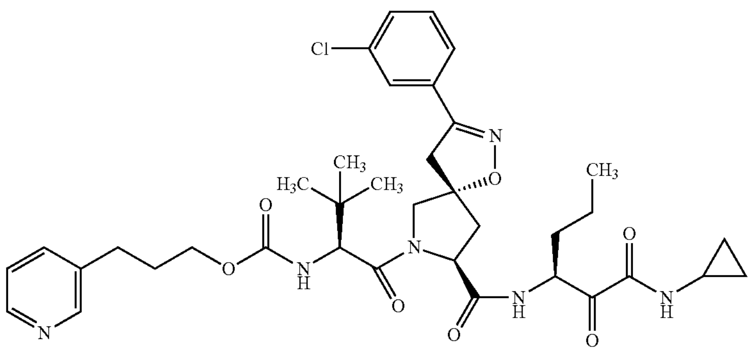 | 389 |
| 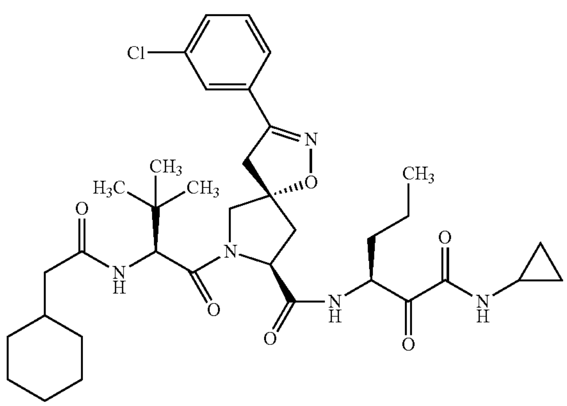 | 390 |
| 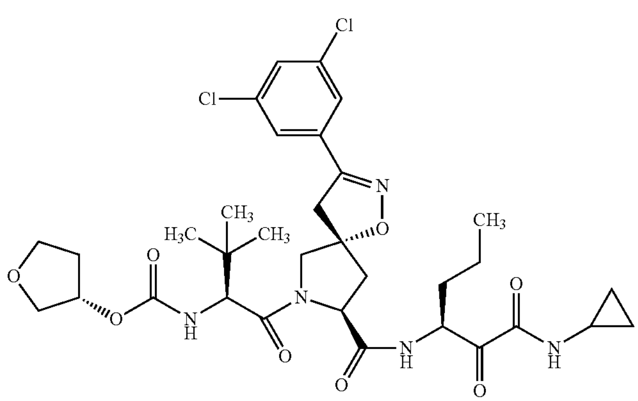 | 391 |

TABLE 1-continued
Exemplary compounds of Formula (I).
| Structure | Compound No. |
|---|---|
| 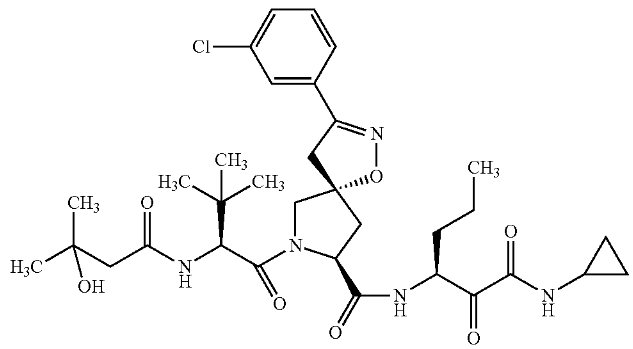 | 392 |
| 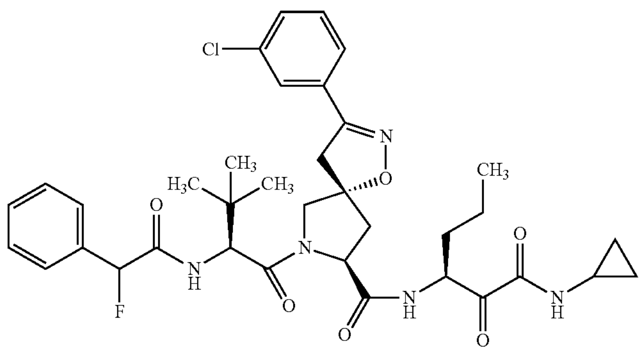 | 393 |
| 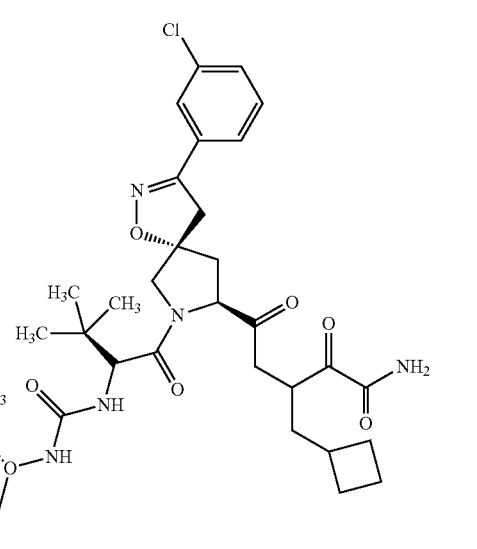 | 394 |

TABLE 1-continued
Exemplary compounds of Formula (I).
| Structure | Compound No. |
|---|---|
| 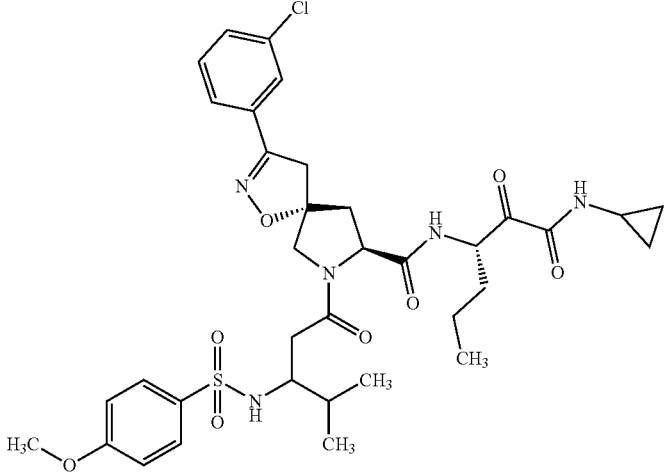 | 395 |
| 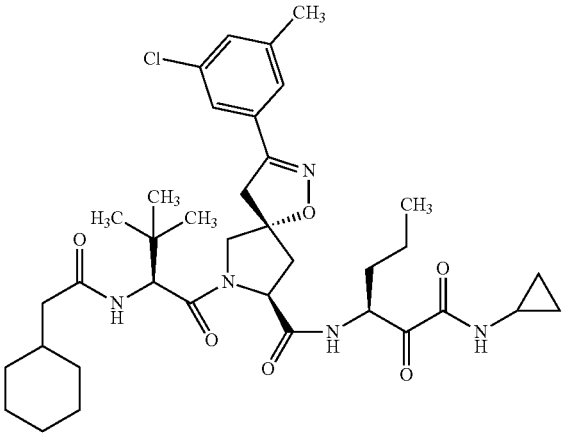 | 396 |
| 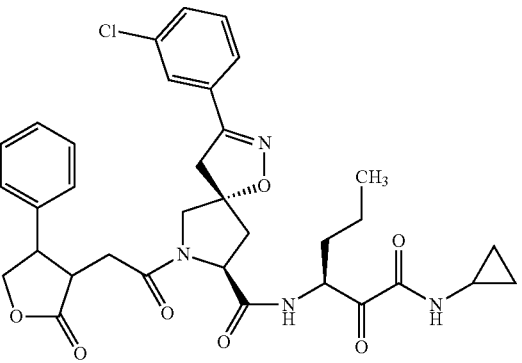 | 397 |

TABLE 1-continued
Exemplary compounds of Formula (I).
| Structure | Compound No. |
|---|---|
| 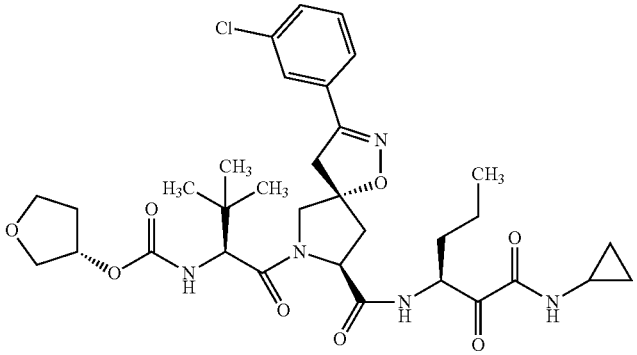 | 398 |
| 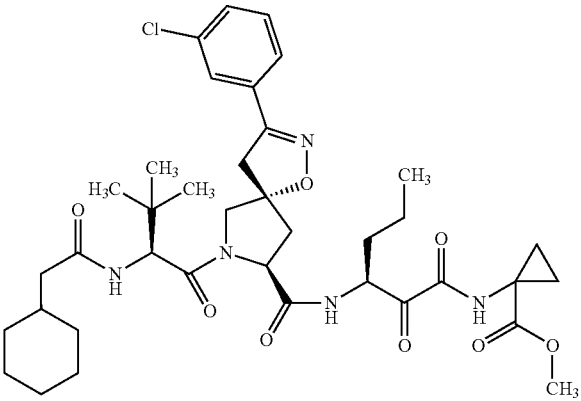 | 399 |
| 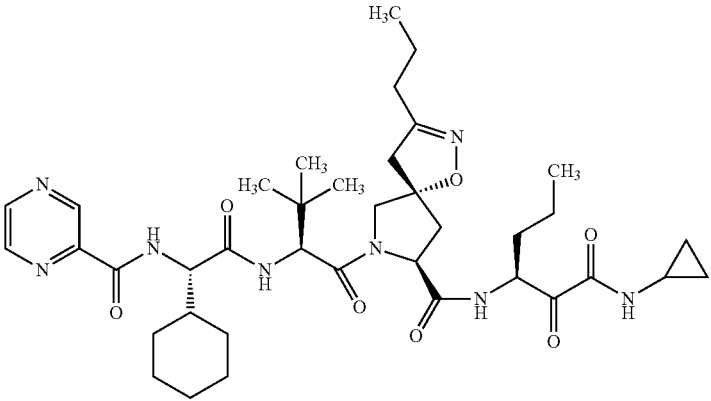 | 400 |
| 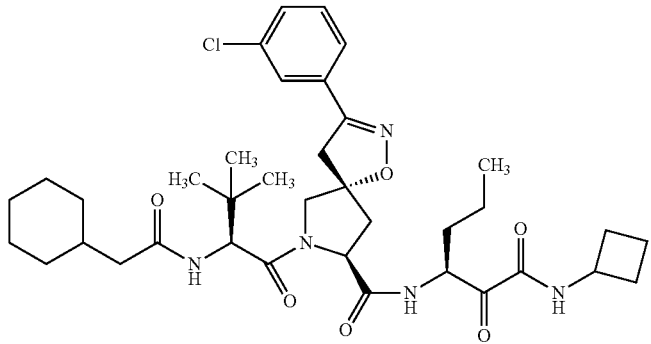 | 401 |

TABLE 1-continued

Exemplary compounds of Formula (I).

| Structure | Compound No. |
|---|---|
| 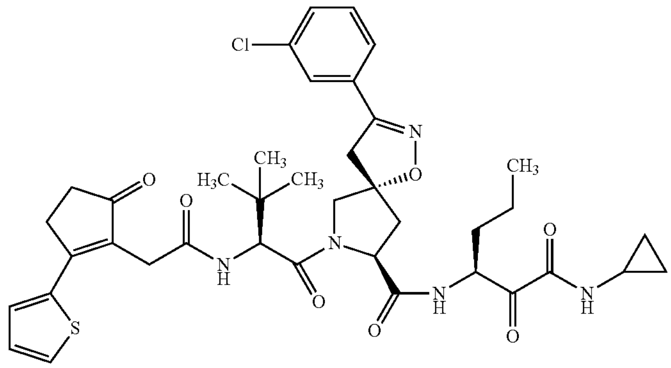 | 402 |
| 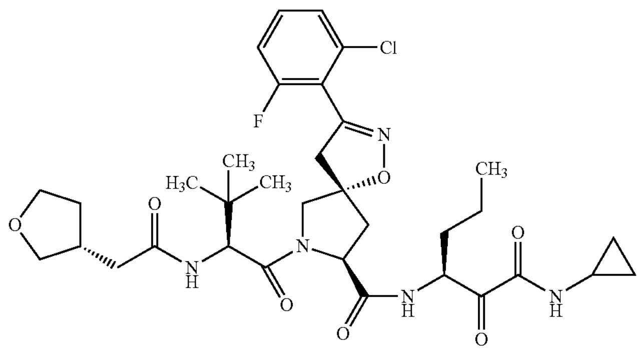 | 403 |
| 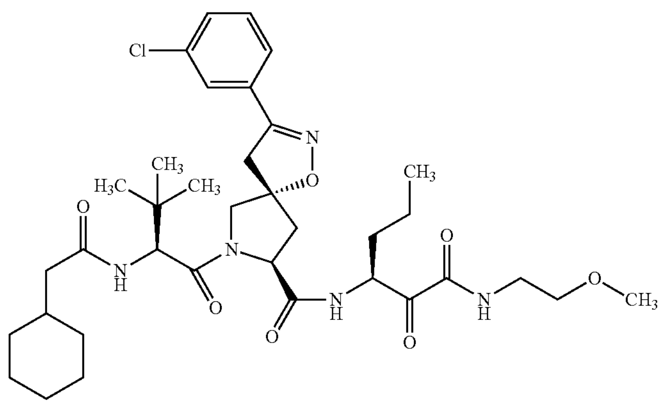 | 404 |
| 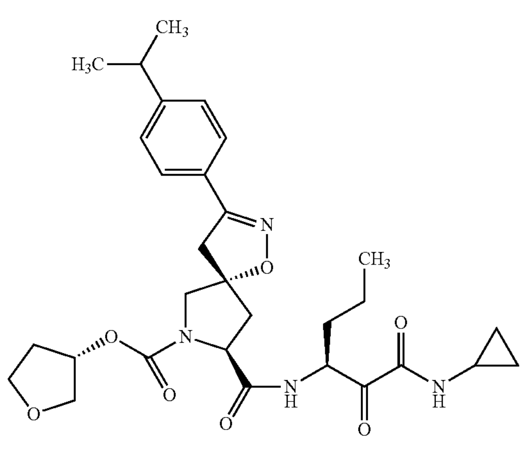 | 405 |

TABLE 1-continued
Exemplary compounds of Formula (I).
| Structure | Compound No. |
|---|---|
| 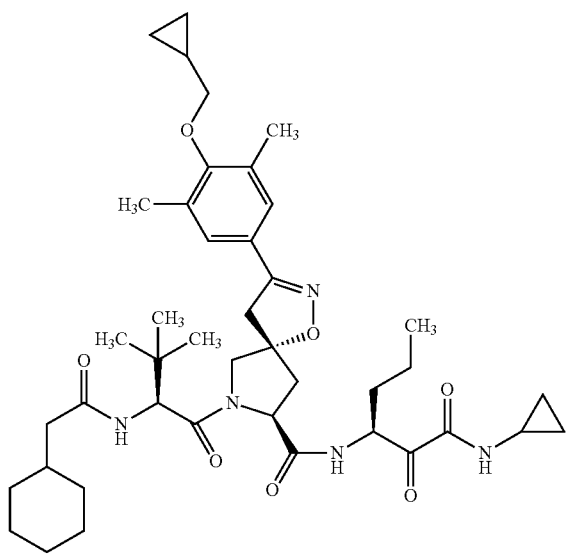 | 406 |
| 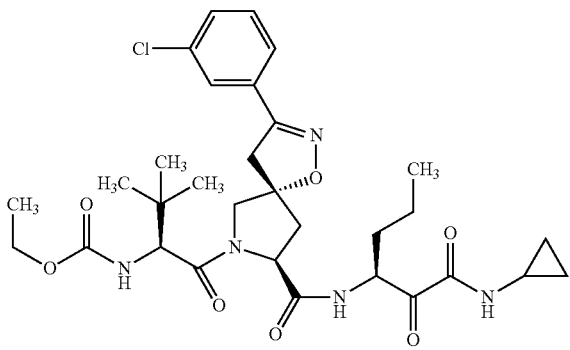 | 407 |
| 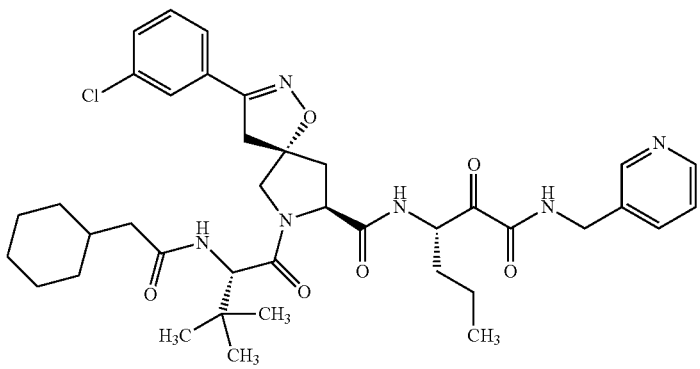 | 408 |

TABLE 1-continued
Exemplary compounds of Formula (I).
| Structure | Compound No. |
|---|---|
| 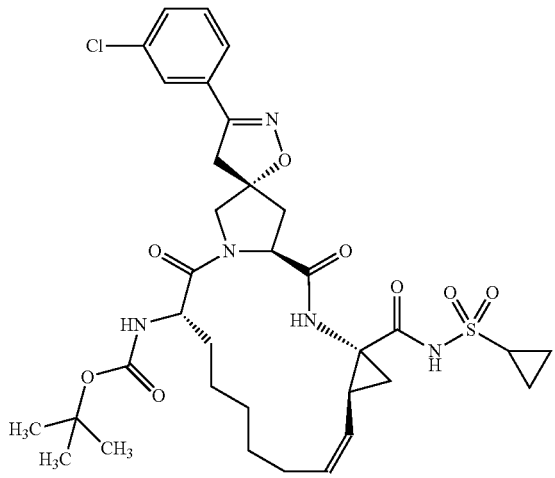 | 409 |
| 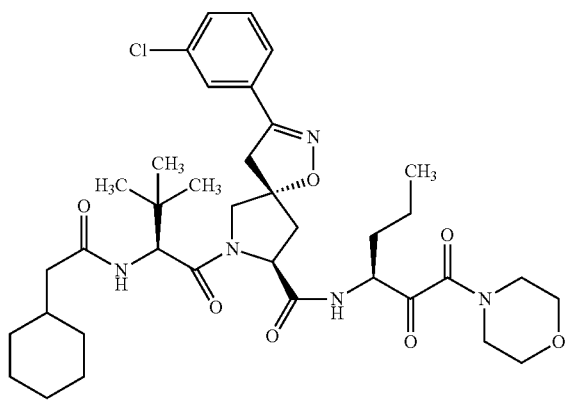 | 410 |
| 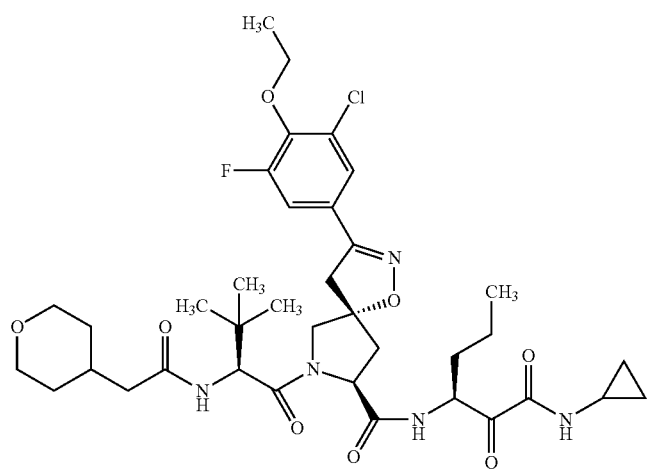 | 411 |

TABLE 1-continued
Exemplary compounds of Formula (I).
| Structure | Compound No. |
|---|---|
| 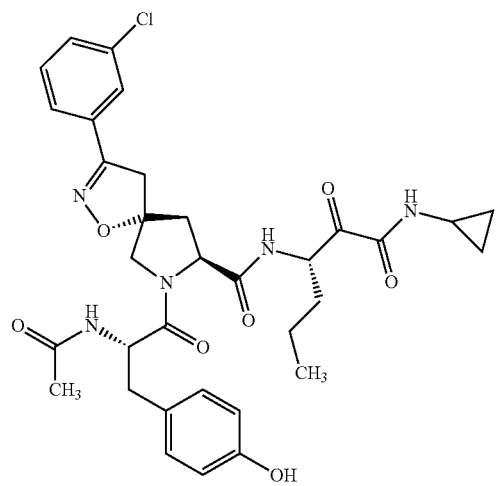 | 412 |
| 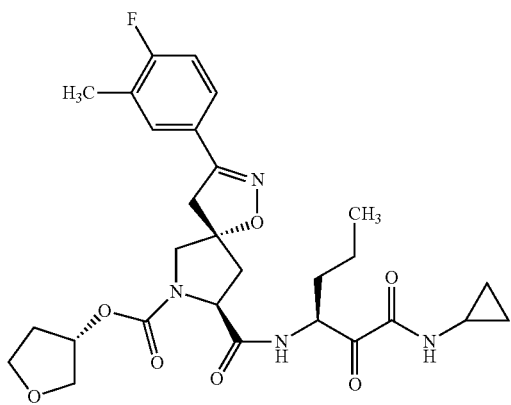 | 413 |
| 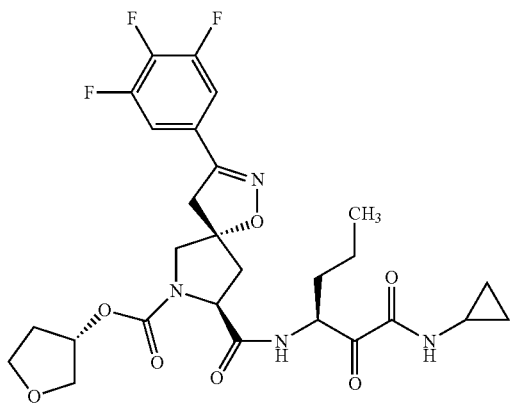 | 414 |

TABLE 1-continued

Exemplary compounds of Formula (I).

| Structure | Compound No. |
|---|---|
| 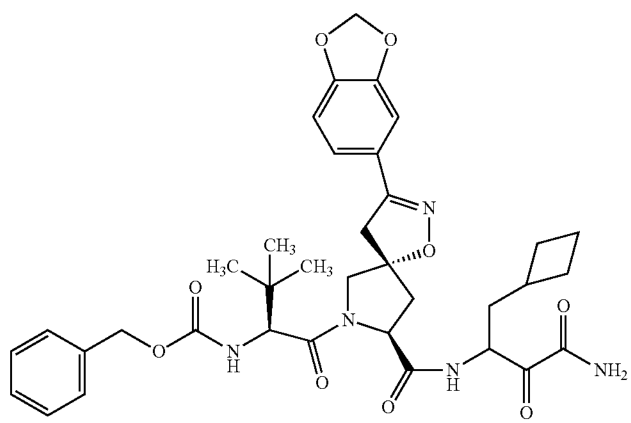 | 415 |
| 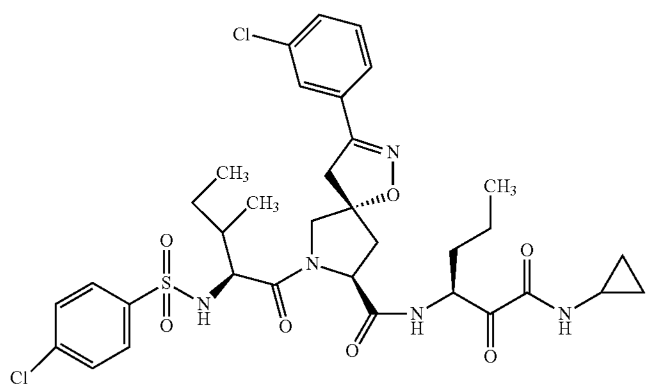 | 416 |
| 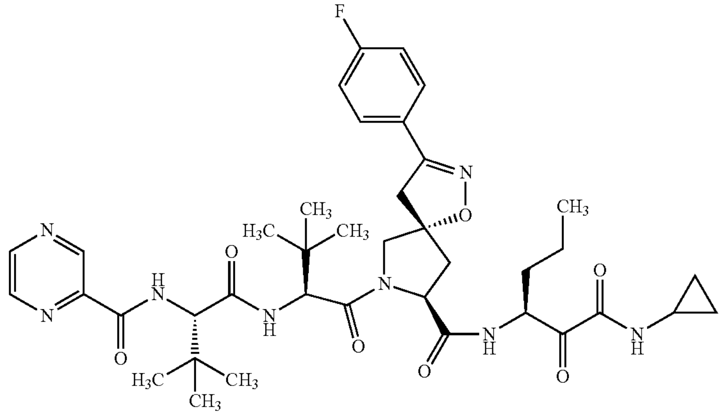 | 417 |

TABLE 1-continued
Exemplary compounds of Formula (I).
| Structure | Compound No. |
|---|---|
| 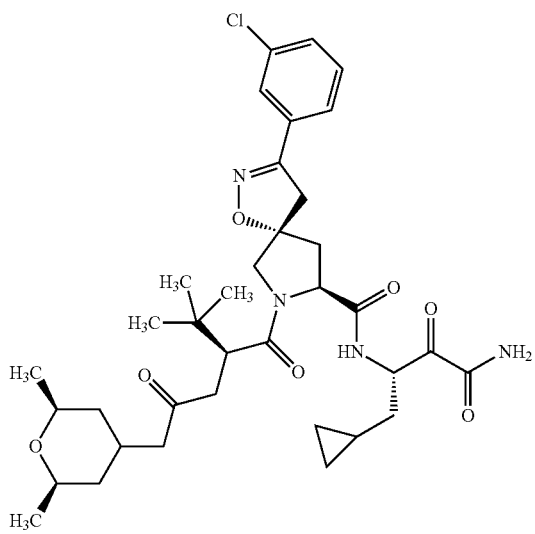 | 418 |
| 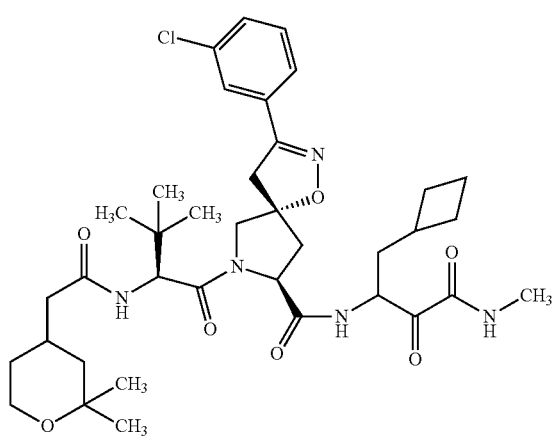 | 419 |
| 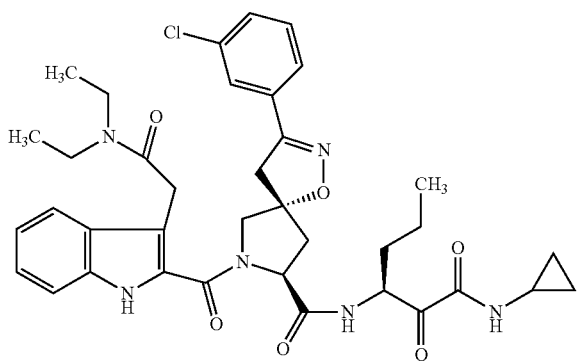 | 420 |

TABLE 1-continued

Exemplary compounds of Formula (I).

| Structure | Compound No. |
|---|---|
| 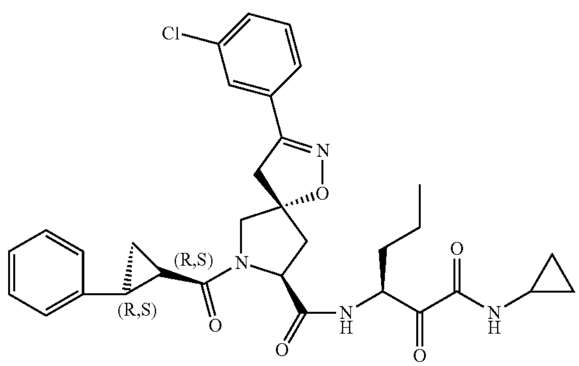 | 421 |
| 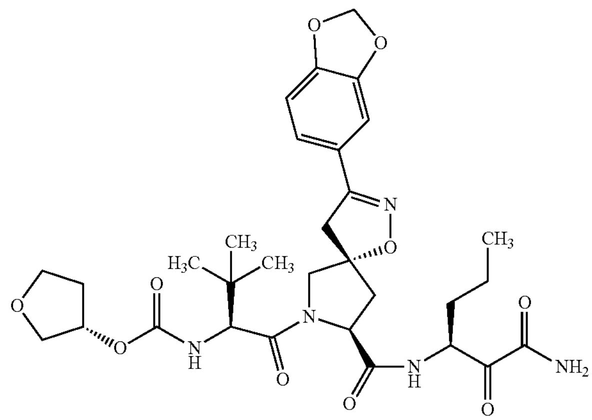 | 422 |
| 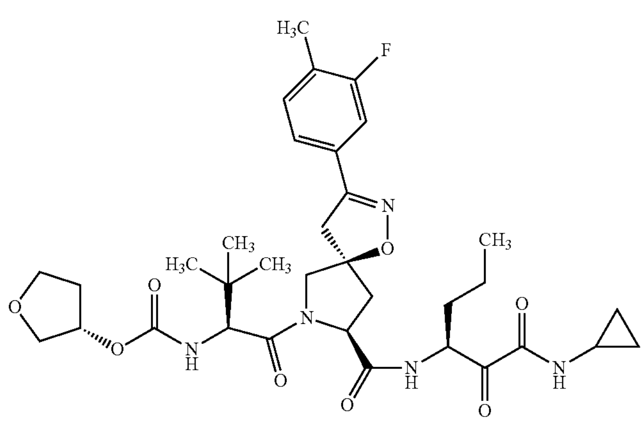 | 423 |

TABLE 1-continued
Exemplary compounds of Formula (I).
| Structure | Compound No. |
|---|---|
| 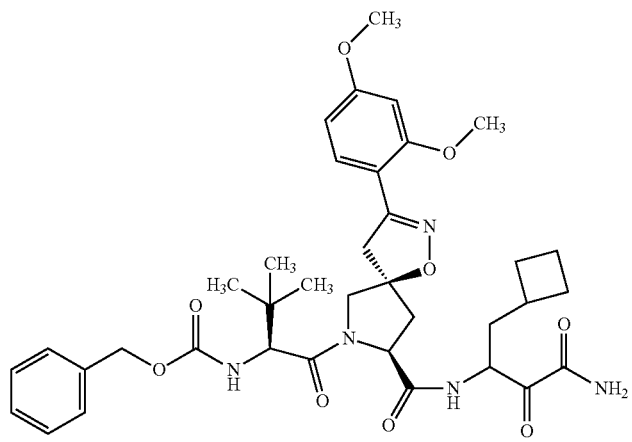 | 424 |
| 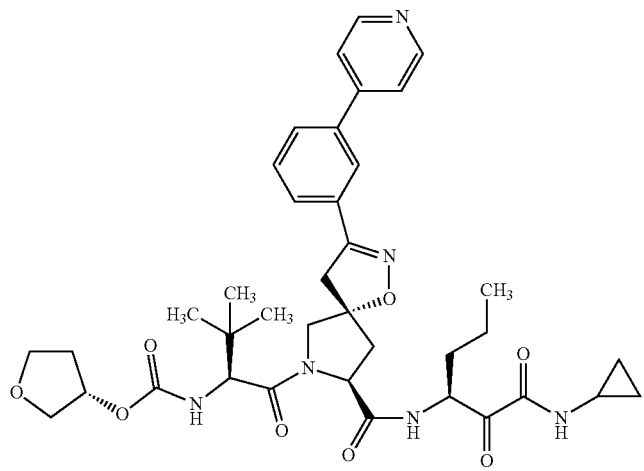 | 425 |
| 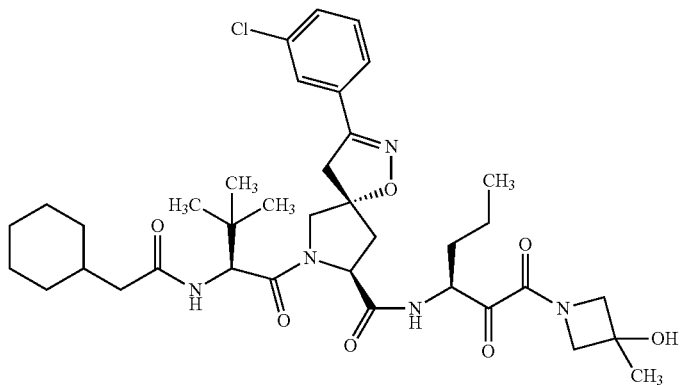 | 426 |

TABLE 1-continued

Exemplary compounds of Formula (I).

| Structure | Compound No. |
|---|---|
| 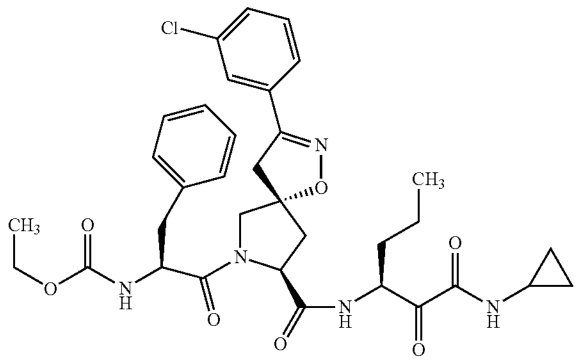 | 427 |
| 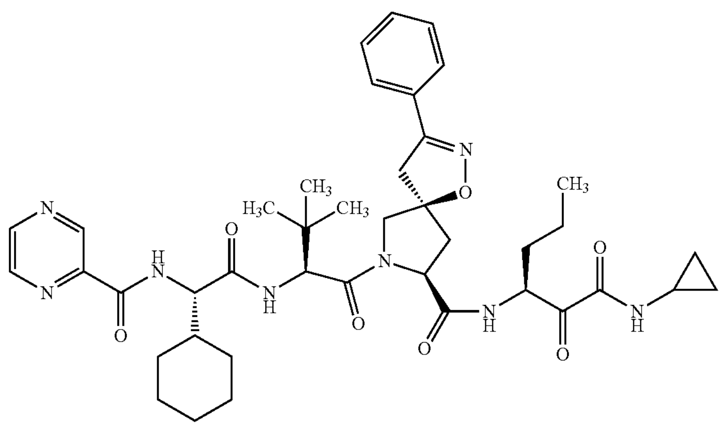 | 428 |
| 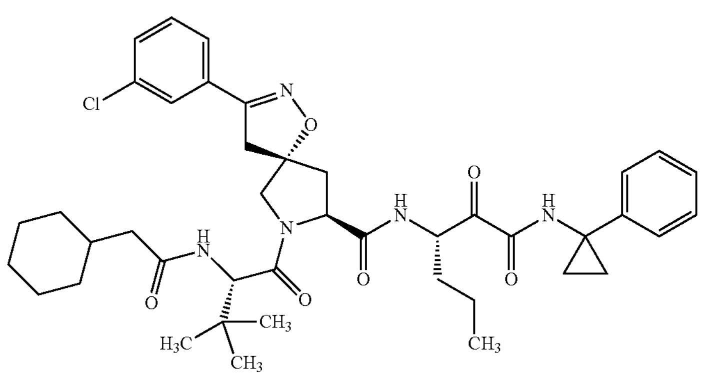 | 429 |

US 7,964,624 B1

363 364

TABLE 1-continued

Exemplary compounds of Formula (I).

| Structure | Compound No. |
|---|---|
| 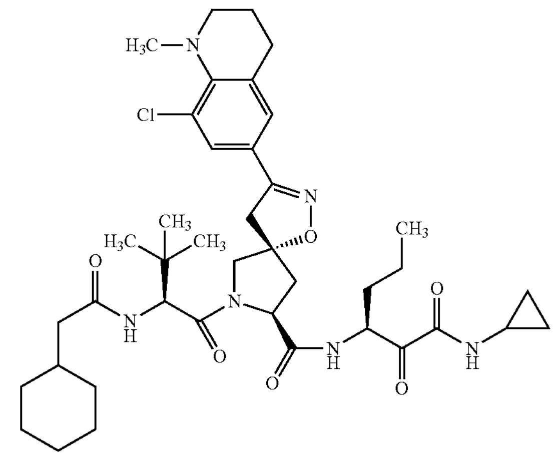 | 430 |
| 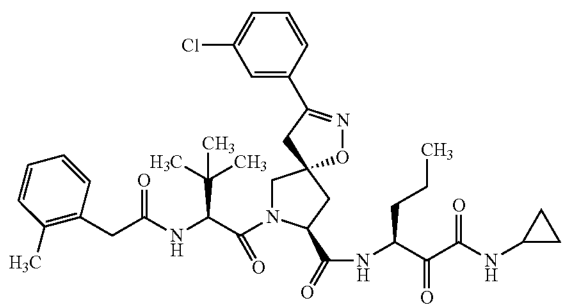 | 431 |
| 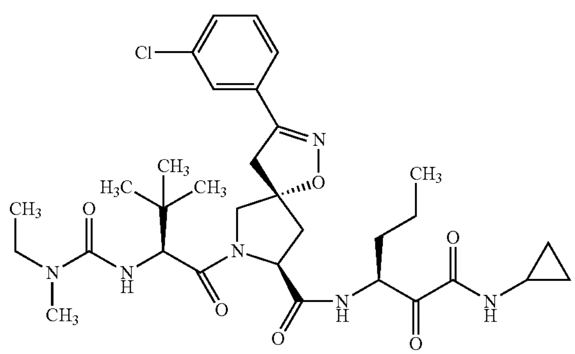 | 432 |
| 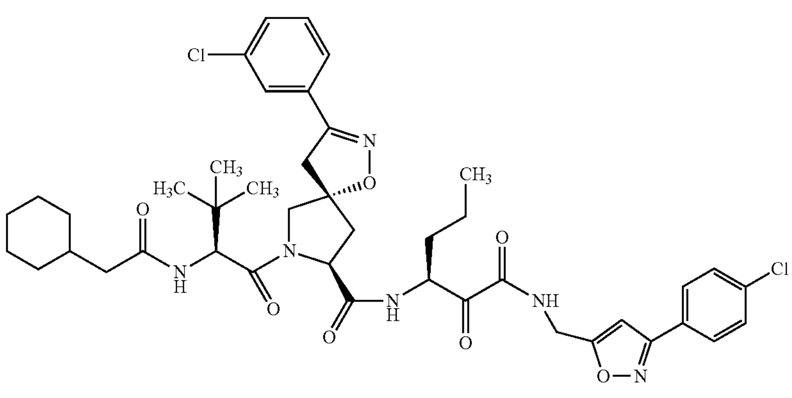 | 433 |

TABLE 1-continued

Exemplary compounds of Formula (I).

| Structure | Compound No. |
|---|---|
| 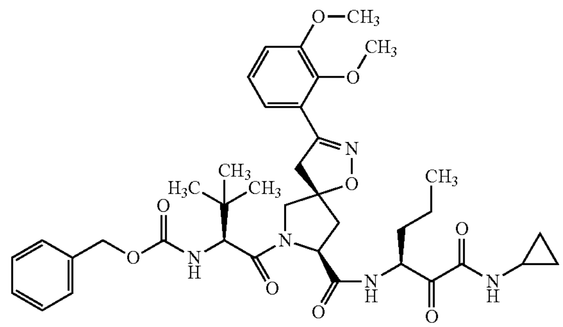 | 434 |
| 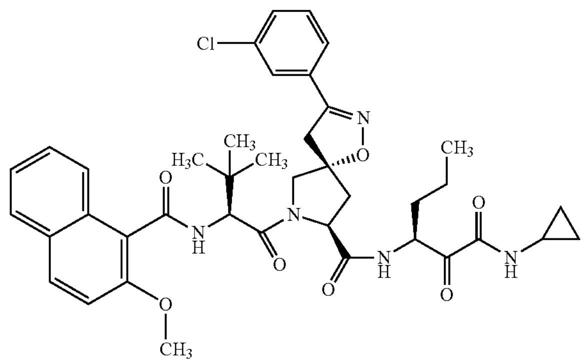 | 435 |
| 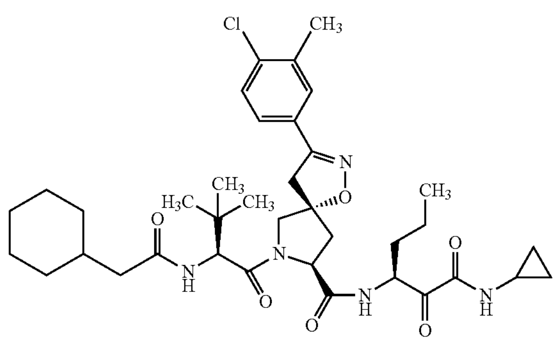 | 436 |
| 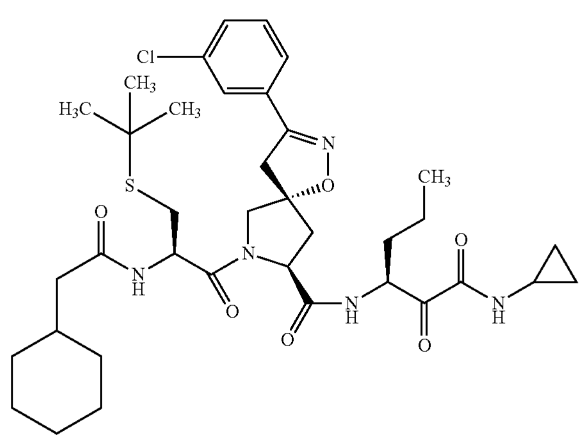 | 437 |

TABLE 1-continued

Exemplary compounds of Formula (I).

| Structure | Compound No. |
|---|---|
| 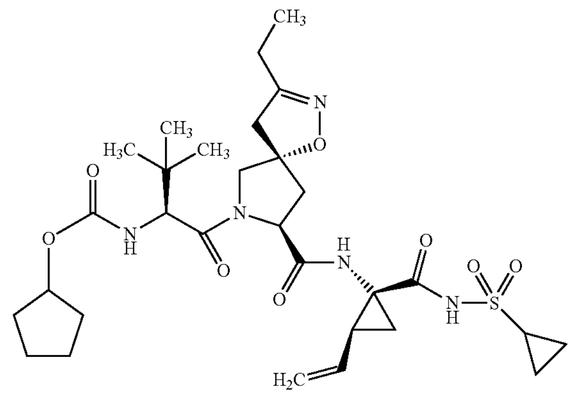 | 438 |
| 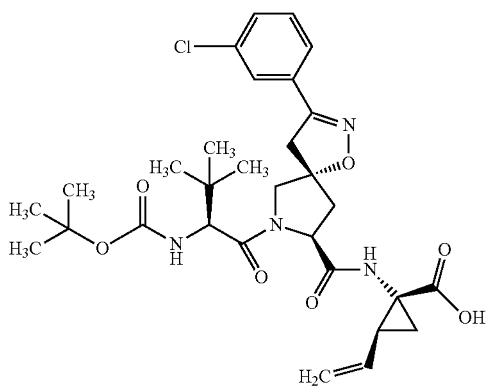 | 439 |
| 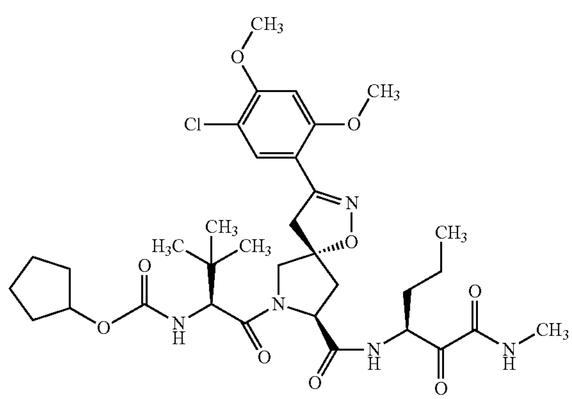 | 440 |
| 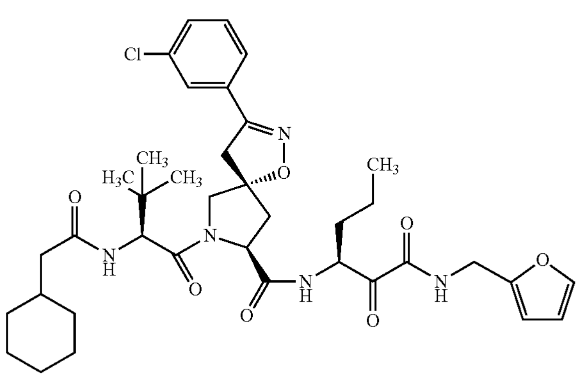 | 441 |

TABLE 1-continued
Exemplary compounds of Formula (I).
| Structure | Compound No. |
|---|---|
| 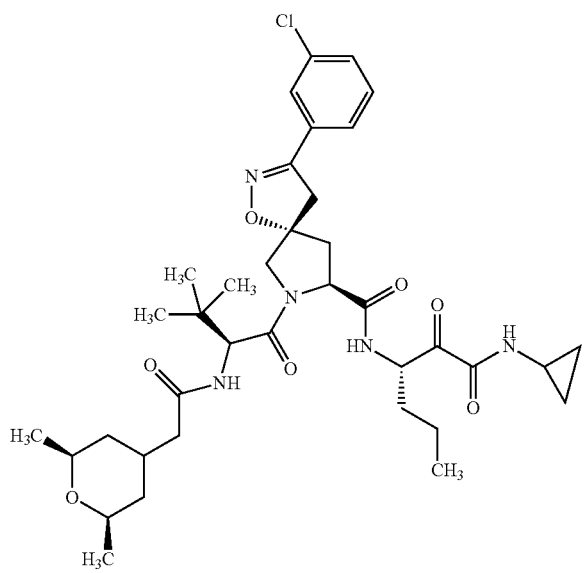 | 442 |
| 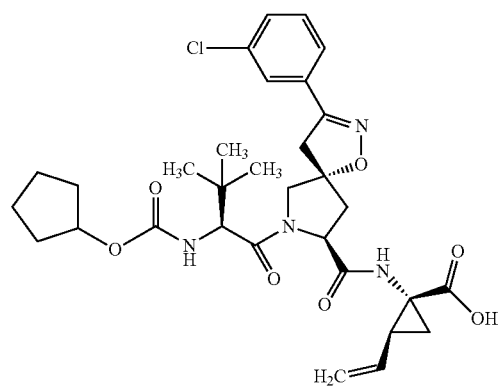 | 443 |
| 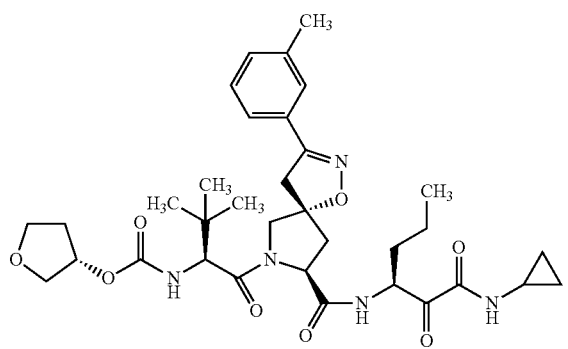 | 444 |

TABLE 1-continued

Exemplary compounds of Formula (I).

| Structure | Compound No. |
|---|---|
| 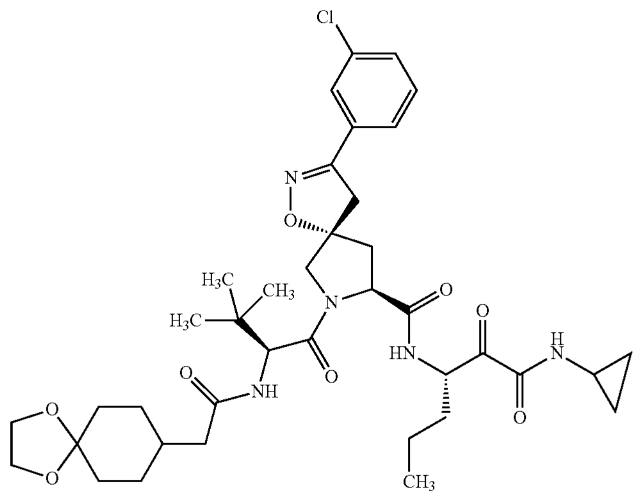 | 445 |
| 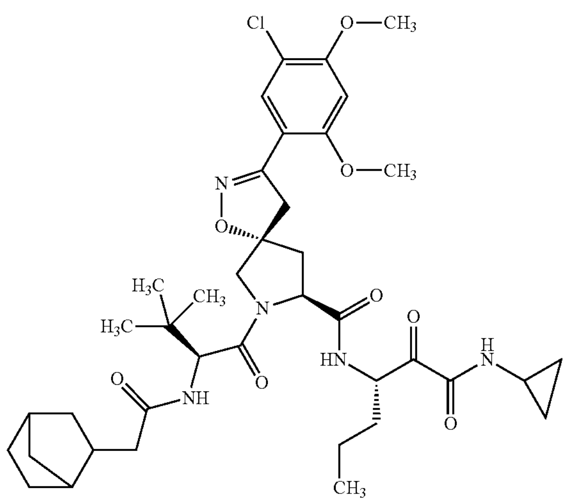 | 446 |
| 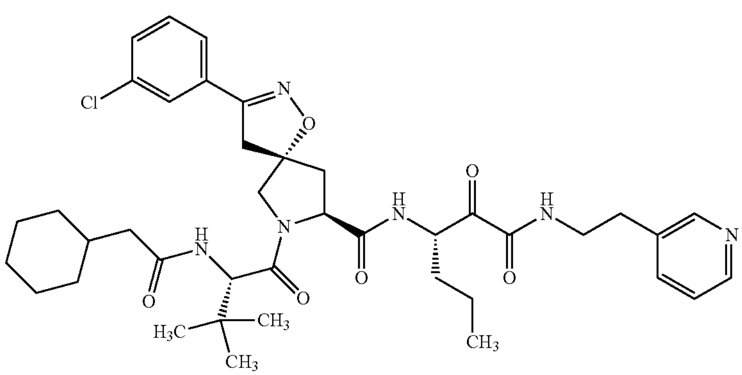 | 447 |

TABLE 1-continued

Exemplary compounds of Formula (I).

| Structure | Compound No. |
|---|---|
| 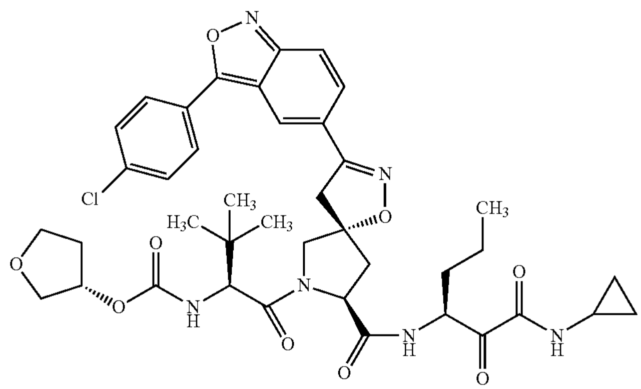 | 448 |
| 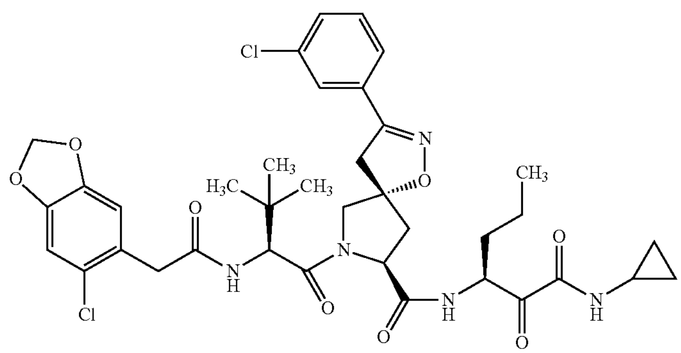 | 449 |
| 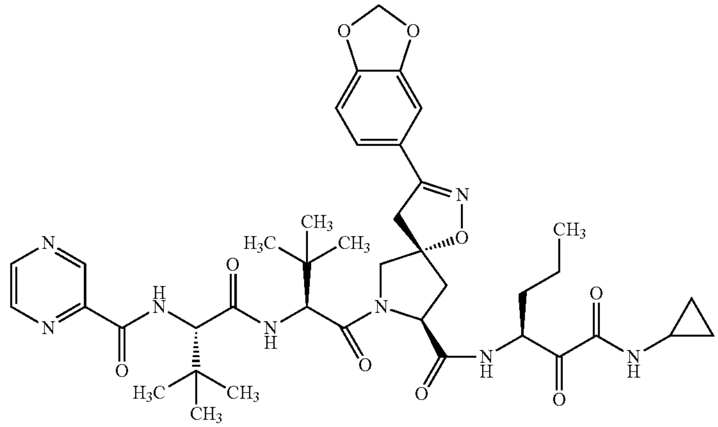 | 450 |

TABLE 1-continued

Exemplary compounds of Formula (I).

| Structure | Compound No. |
|---|---|
| 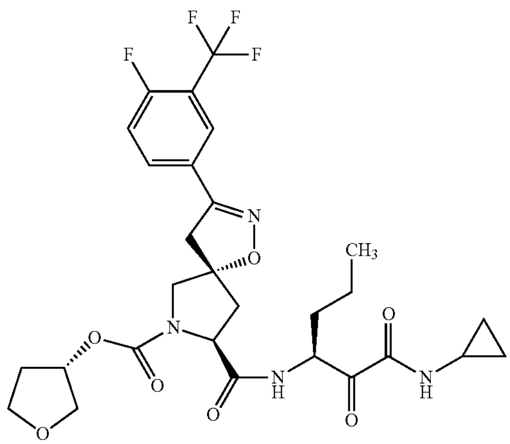 | 451 |
| 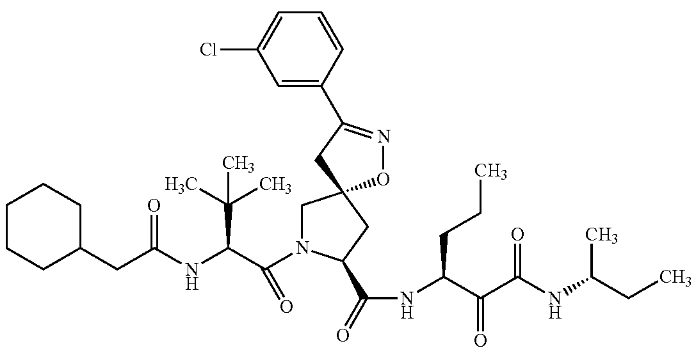 | 452 |
| 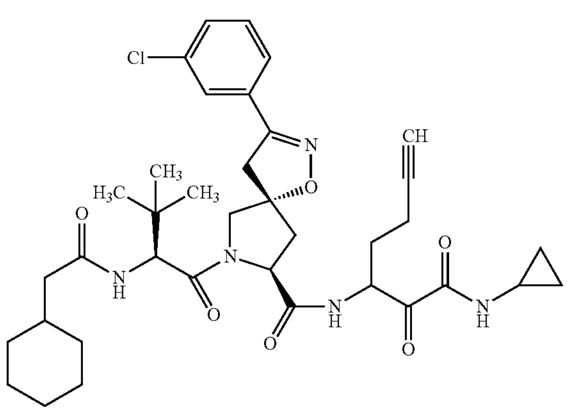 | 453 |

TABLE 1-continued
Exemplary compounds of Formula (I).
| Structure | Compound No. |
|---|---|
| 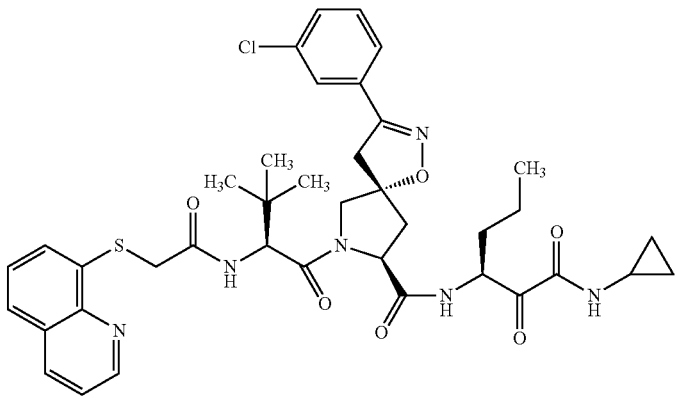 | 454 |
| 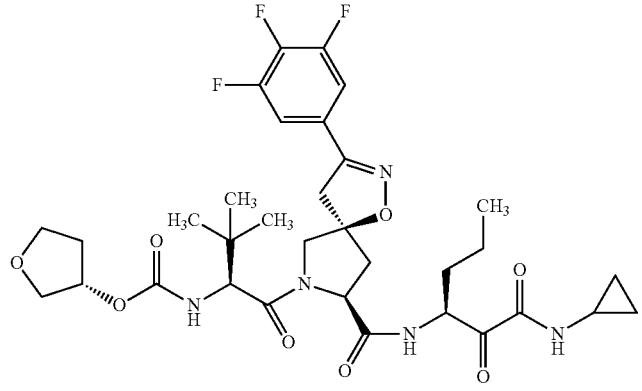 | 455 |
| 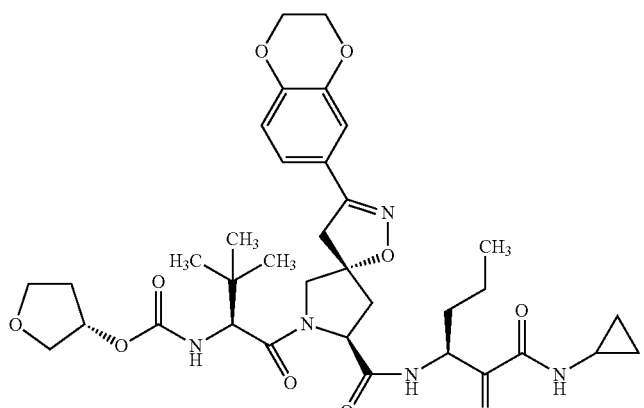 | 456 |

TABLE 1-continued

Exemplary compounds of Formula (I).

| Structure | Compound No. |
|---|---|
| 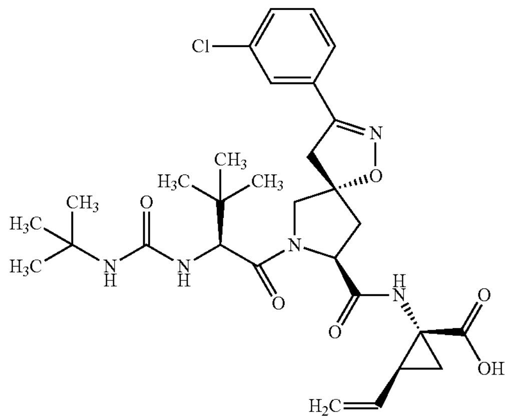 | 457 |
| 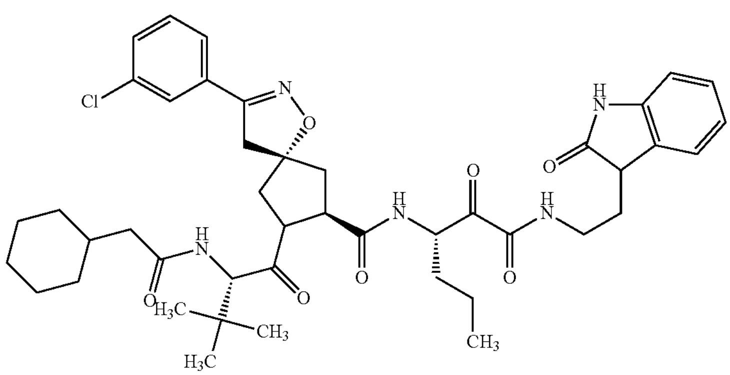 | 458 |
| 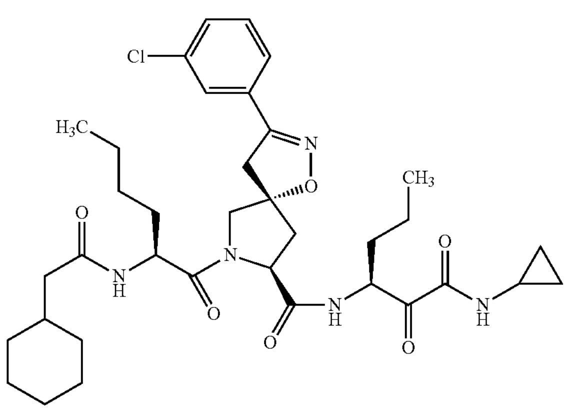 | 459 |

TABLE 1-continued

Exemplary compounds of Formula (I).

| Structure | Compound No. |
|---|---|
| 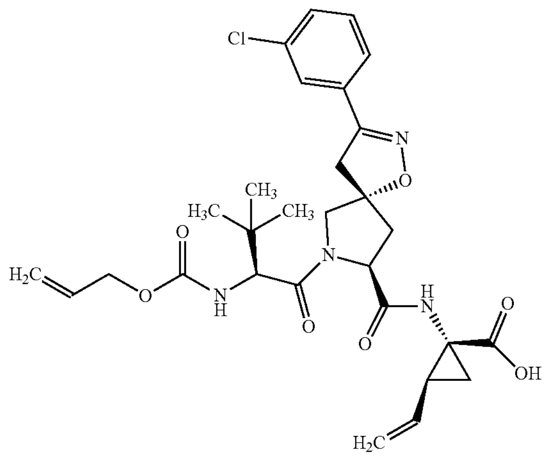 | 460 |
| 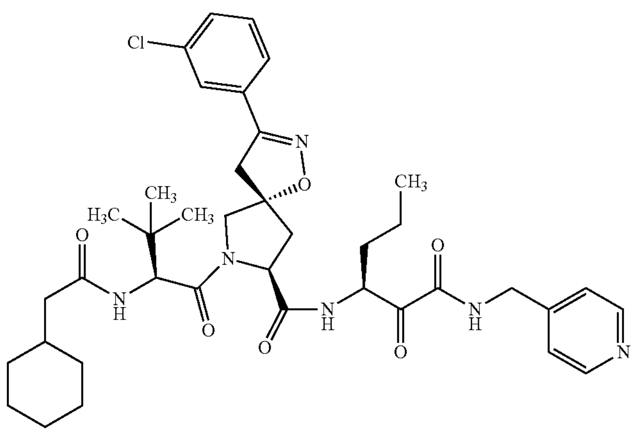 | 461 |
| 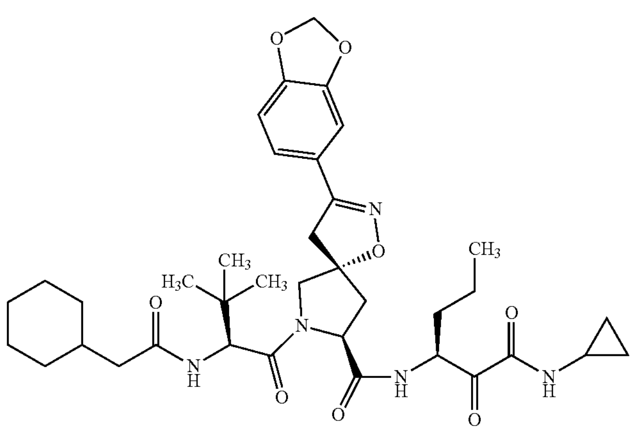 | 462 |

TABLE 1-continued

Exemplary compounds of Formula (I).

| Structure | Compound No. |
|---|---|
| 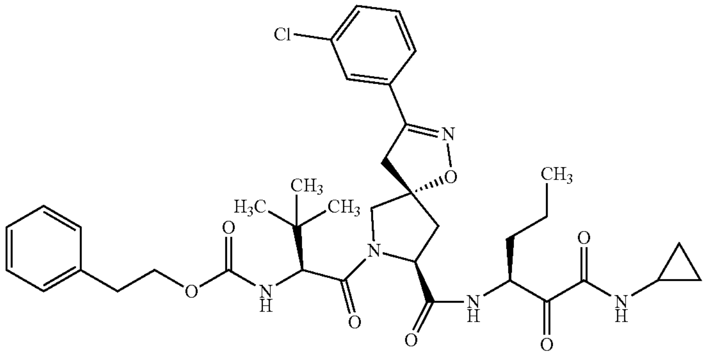 | 463 |
| 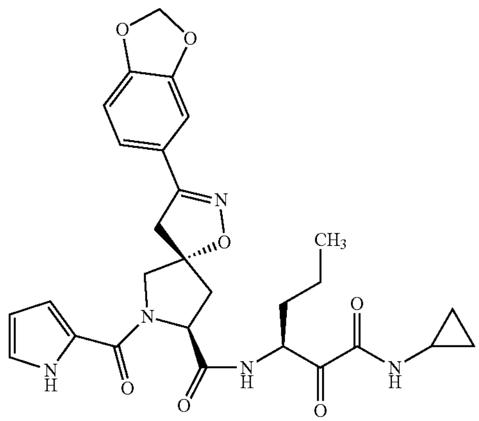 | 464 |
| 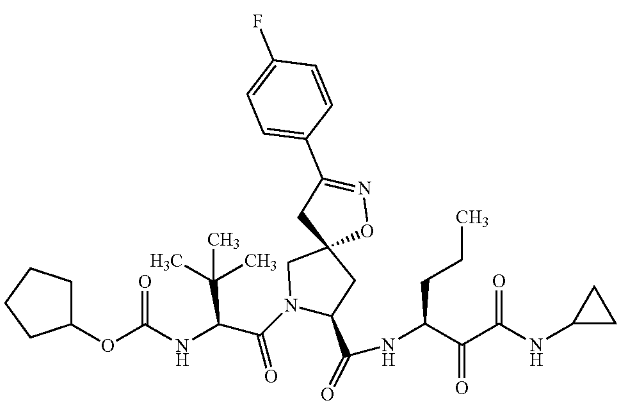 | 465 |
| 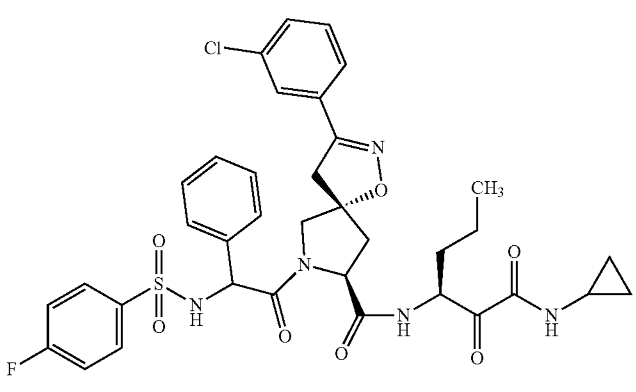 | 466 |

TABLE 1-continued

Exemplary compounds of Formula (I).

| Structure | Compound No. |
|---|---|
| 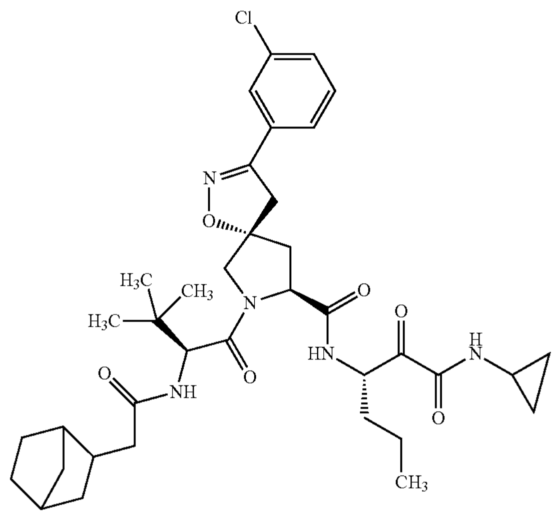 | 467 |
| 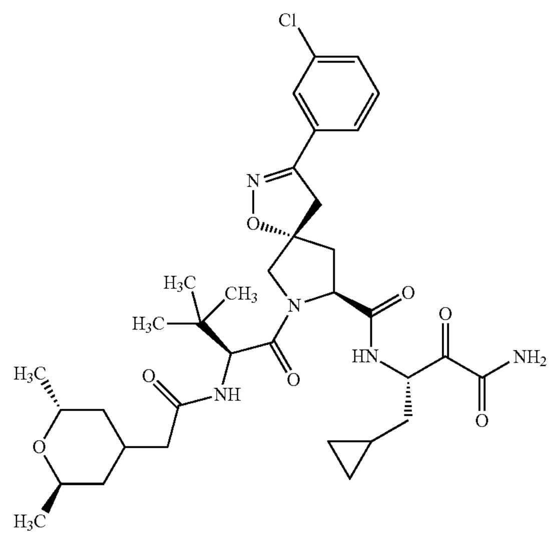 | 468 |
| 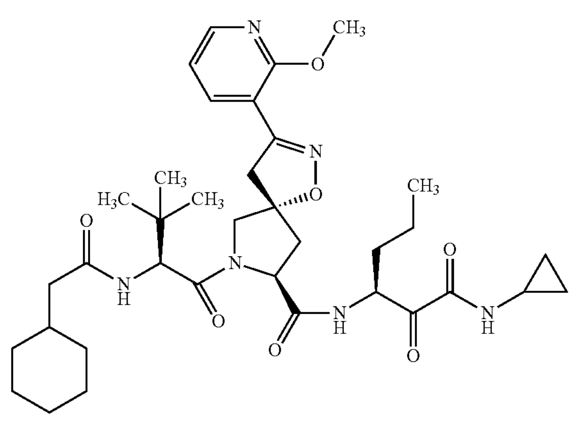 | 469 |

TABLE 1-continued

Exemplary compounds of Formula (I).

| Structure | Compound No. |
|---|---|
| 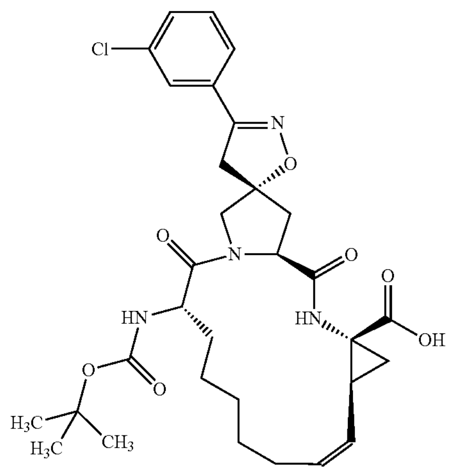 | 470 |
| 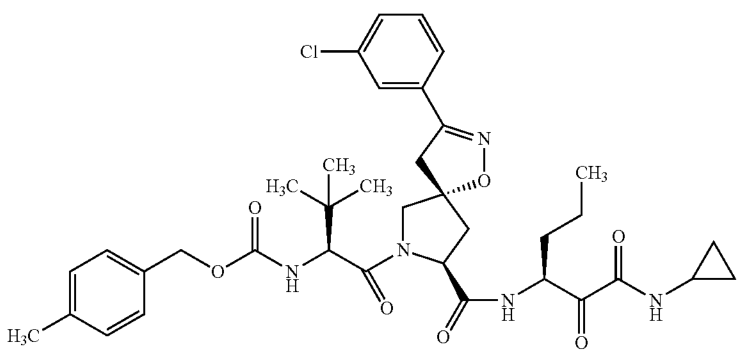 | 471 |
| 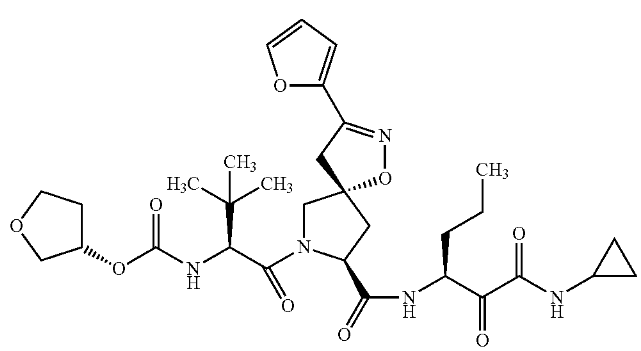 | 472 |

TABLE 1-continued

Exemplary compounds of Formula (I).

| Structure | Compound No. |
|---|---|
| 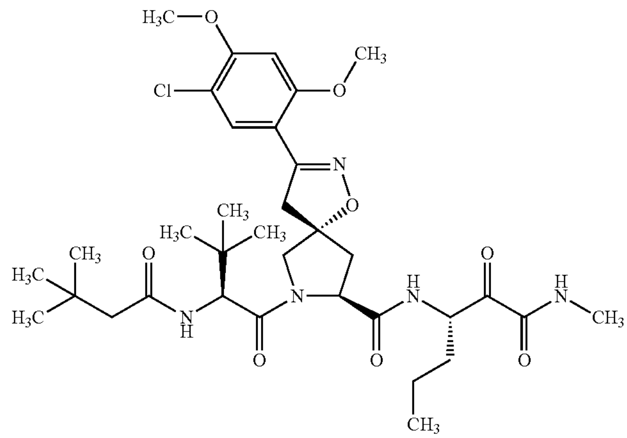 | 473 |
| 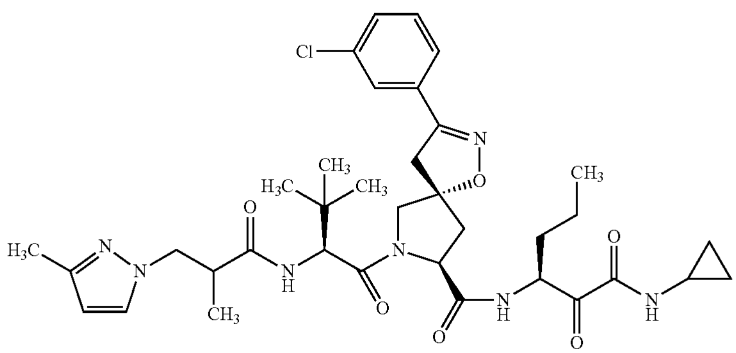 | 474 |
| 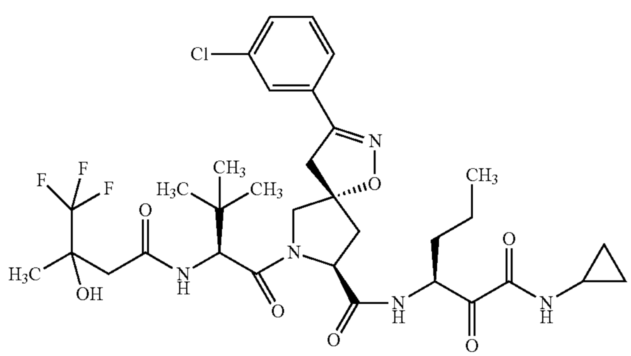 | 475 |
| 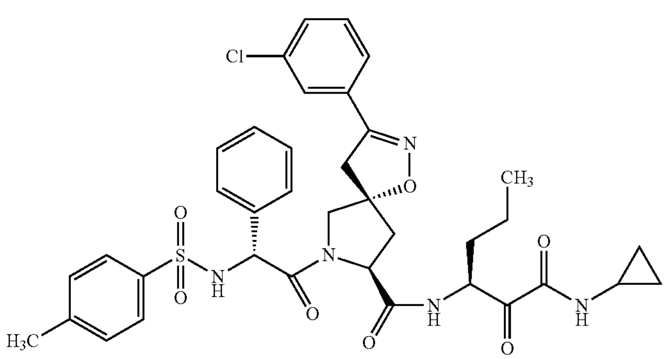 | 476 |

TABLE 1-continued

Exemplary compounds of Formula (I).

| Structure | Compound No. |
|---|---|
| 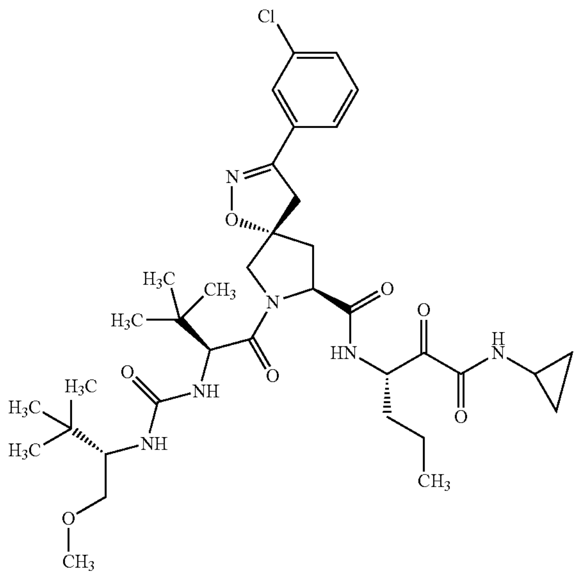 | 477 |
| 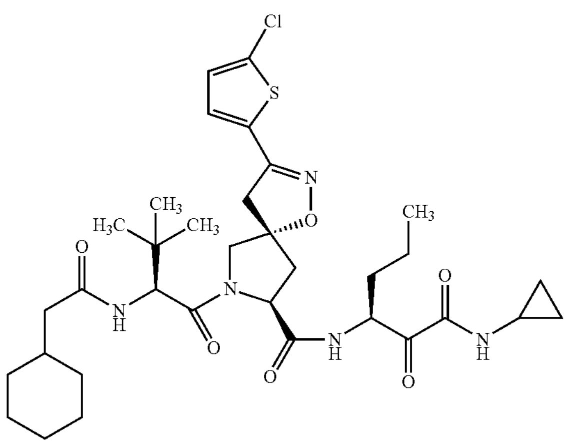 | 478 |
| 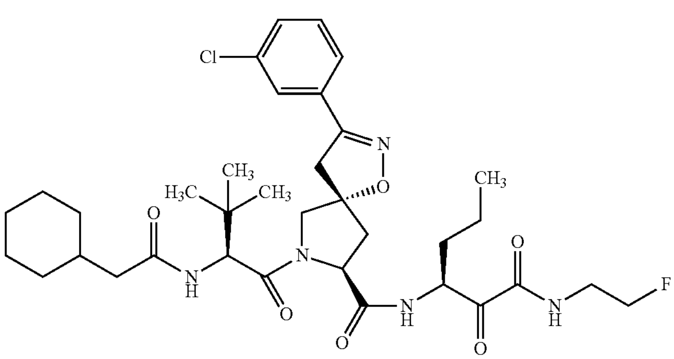 | 479 |

TABLE 1-continued
Exemplary compounds of Formula (I).
| Structure | Compound No. |
|---|---|
| 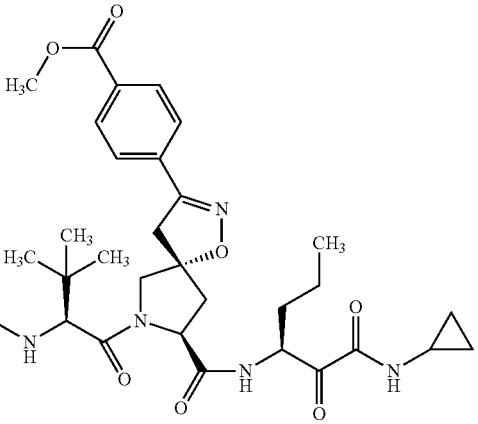 | 480 |
| 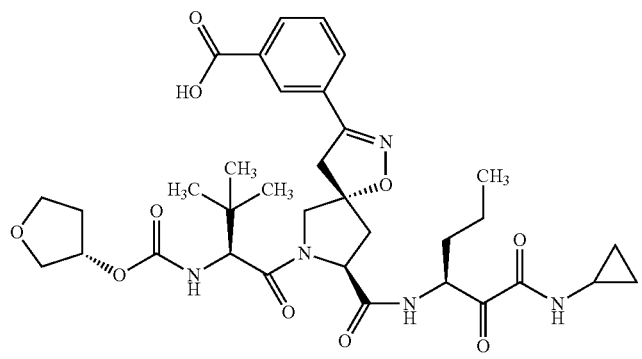 | 481 |
| 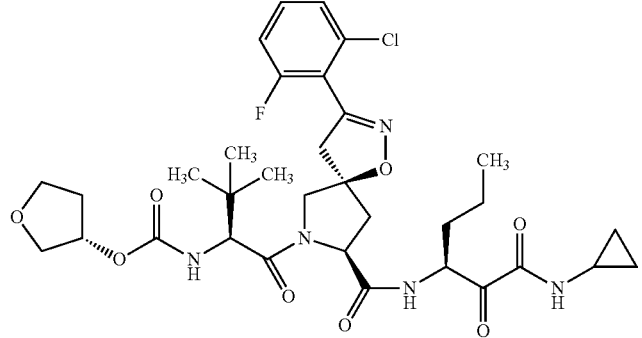 | 482 |
| 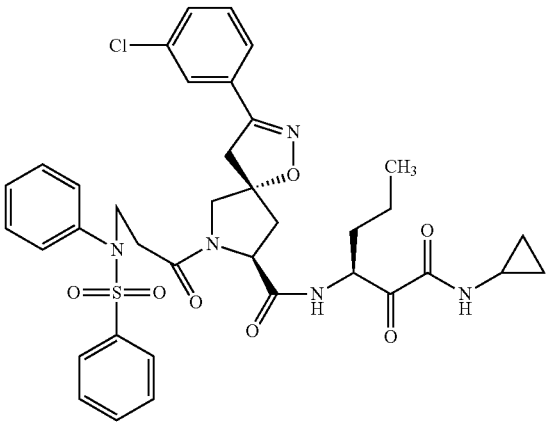 | 483 |

TABLE 1-continued

Exemplary compounds of Formula (I).

| Structure | Compound No. |
|---|---|
| 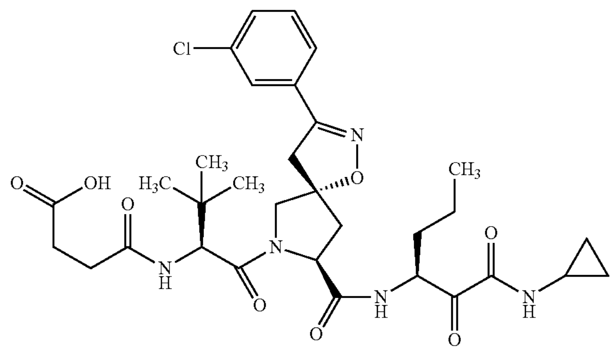 | 484 |
| 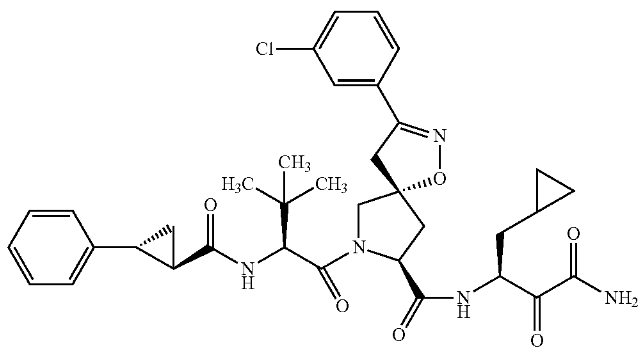 | 485 |
| 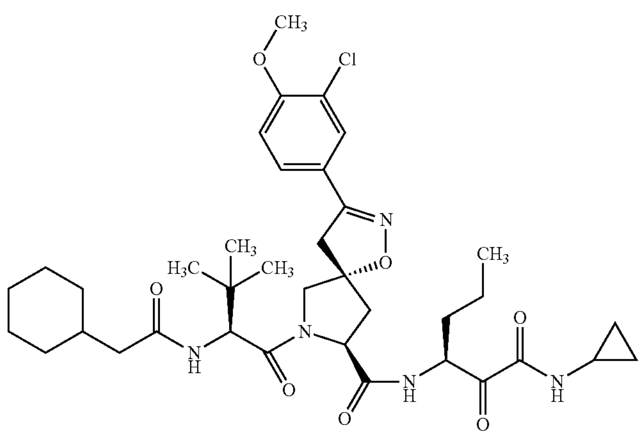 | 486 |
| 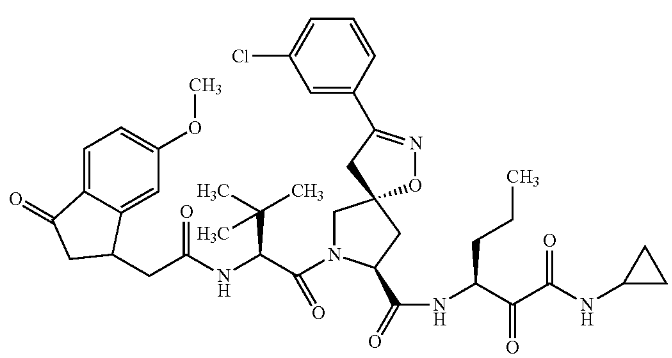 | 487 |

TABLE 1-continued
Exemplary compounds of Formula (I).
| Structure | Compound No. |
|---|---|
| 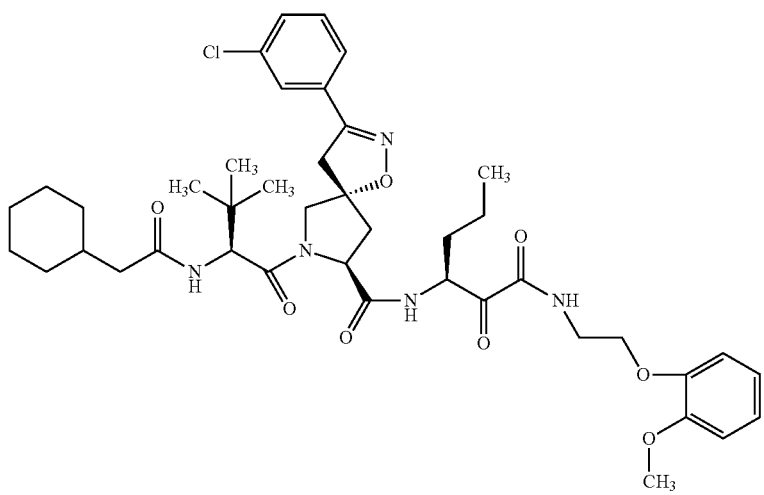 | 488 |
| 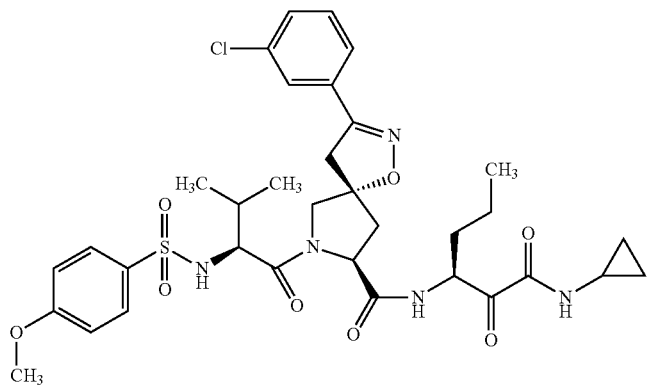 | 489 |
| 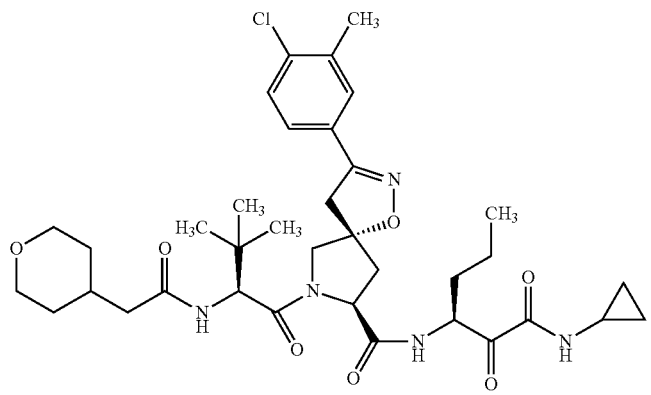 | 490 |

TABLE 1-continued

Exemplary compounds of Formula (I).

| Structure | Compound No. |
|---|---|
| 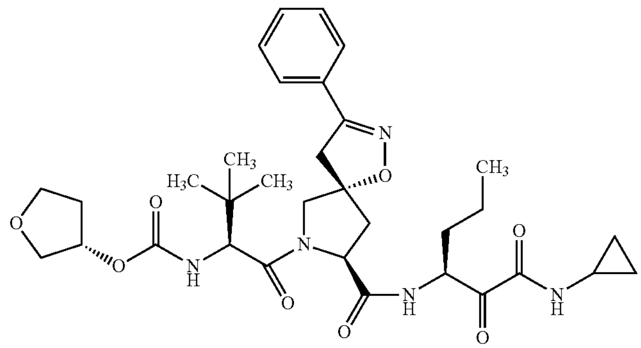 | 491 |
| 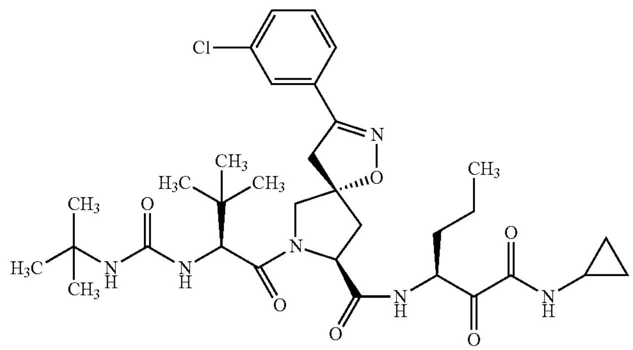 | 492 |
| 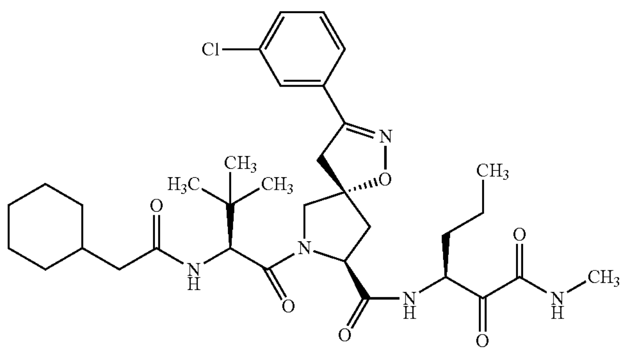 | 493 |
| 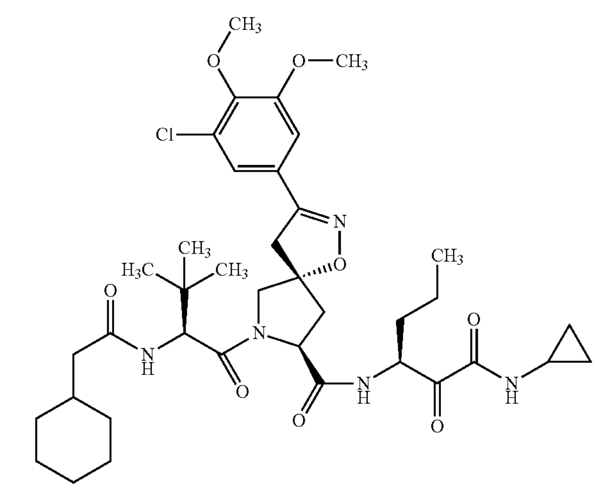 | 494 |

TABLE 1-continued

Exemplary compounds of Formula (I).

| Structure | Compound No. |
|---|---|
| 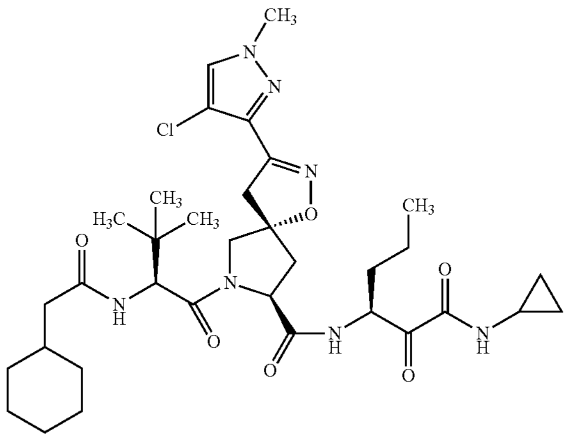 | 495 |
| 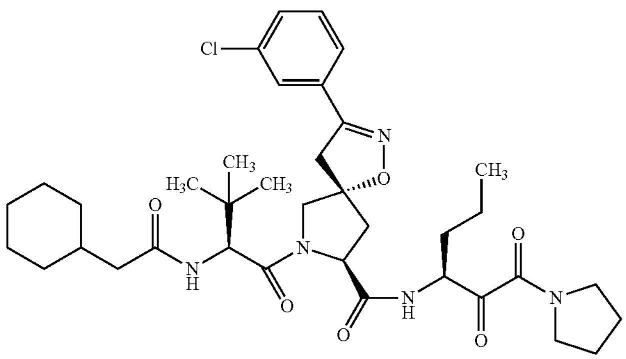 | 496 |
| 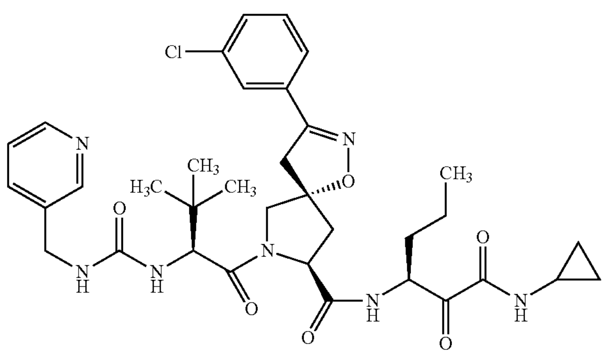 | 497 |
| 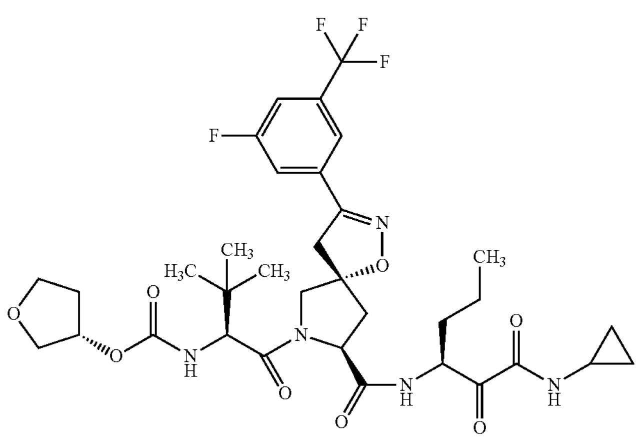 | 498 |

TABLE 1-continued

Exemplary compounds of Formula (I).

| Structure | Compound No. |
|---|---|
| 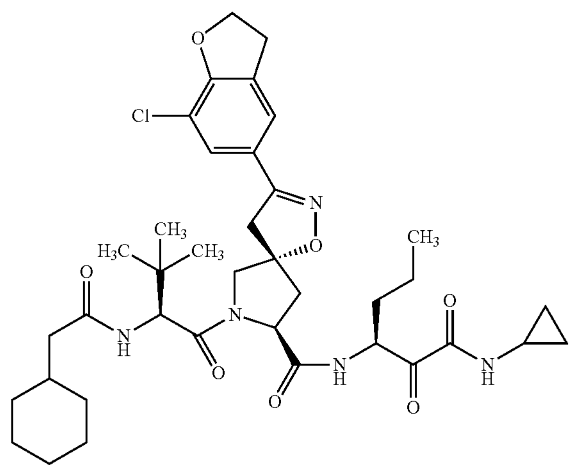 | 499 |
| 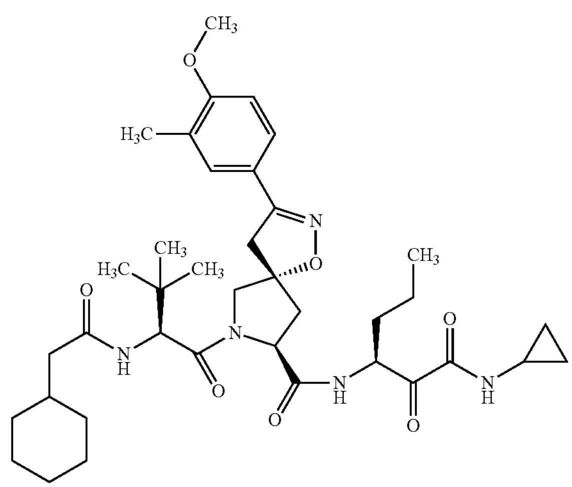 | 500 |
| 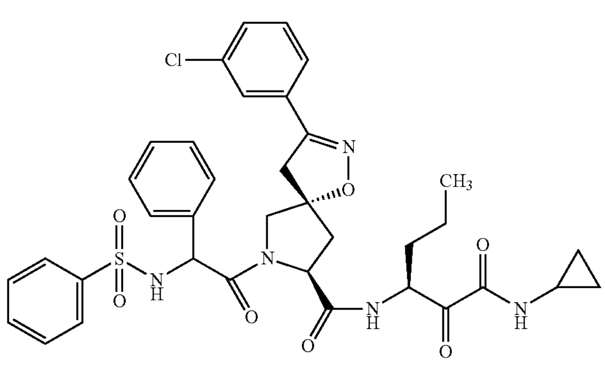 | 501 |

TABLE 1-continued

Exemplary compounds of Formula (I).

| Structure | Compound No. |
|---|---|
| 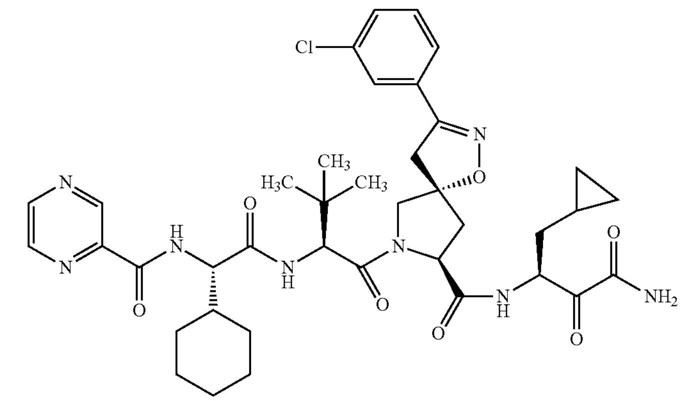 | 502 |
| 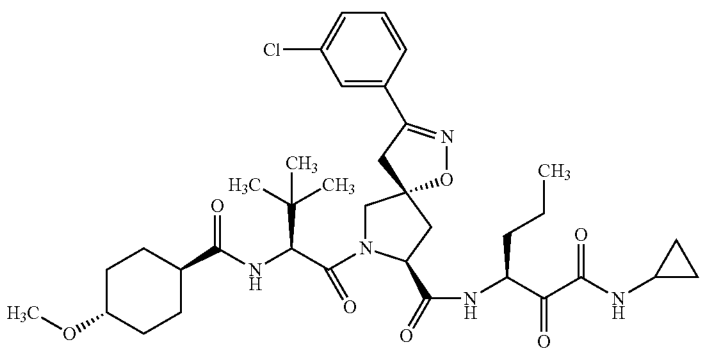 | 503 |
| 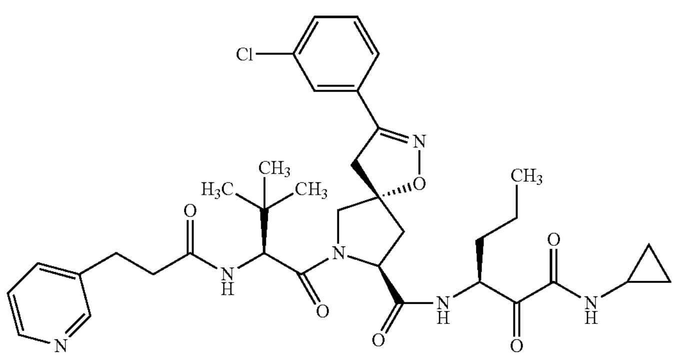 | 504 |
| 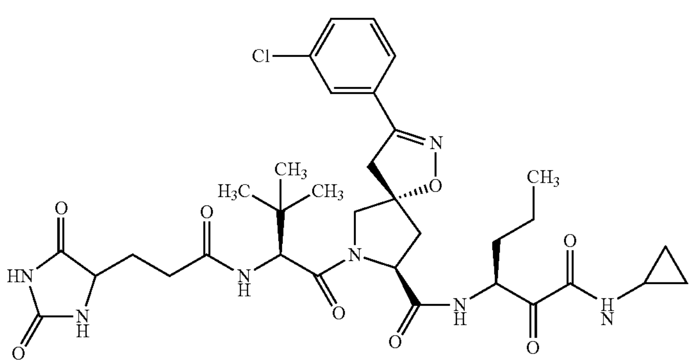 | 505 |

TABLE 1-continued

Exemplary compounds of Formula (I).

| Structure | Compound No. |
|---|---|
| 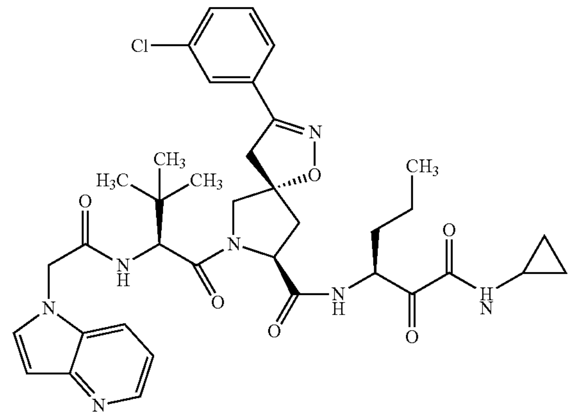 | 506 |
| 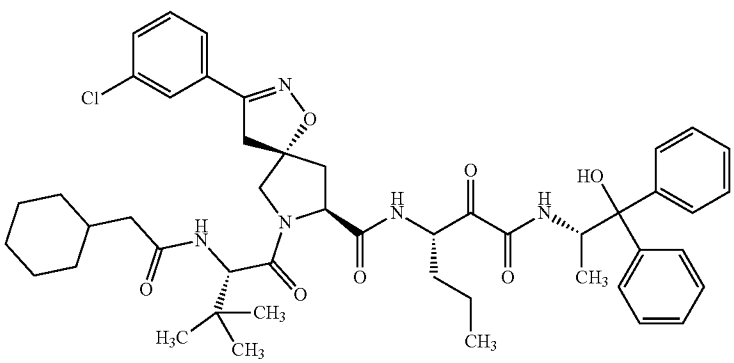 | 507 |
| 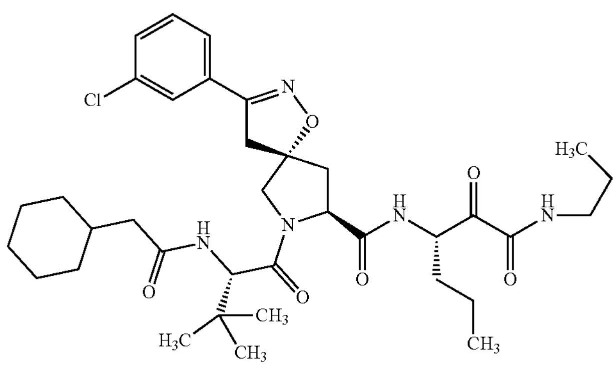 | 508 |
| 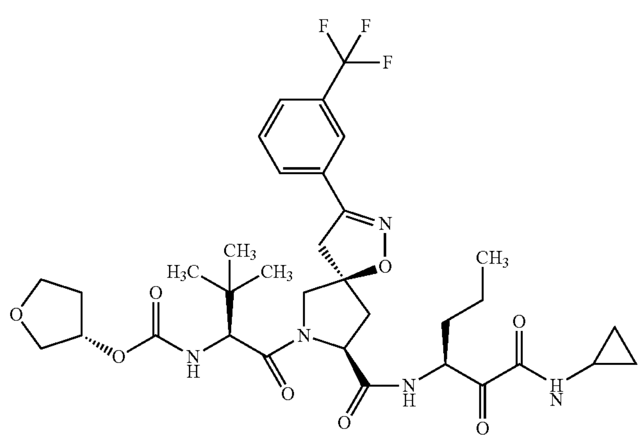 | 509 |

TABLE 1-continued
Exemplary compounds of Formula (I).
| Structure | Compound No. |
|---|---|
| 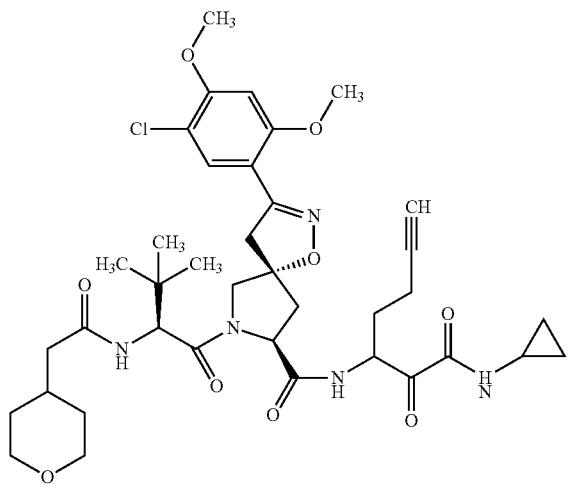 | 510 |
| 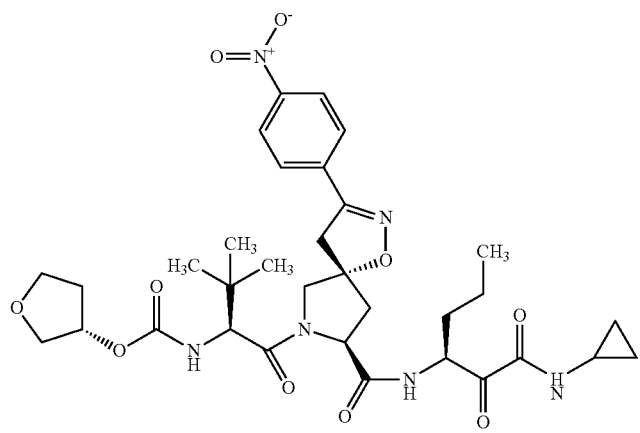 | 511 |
| 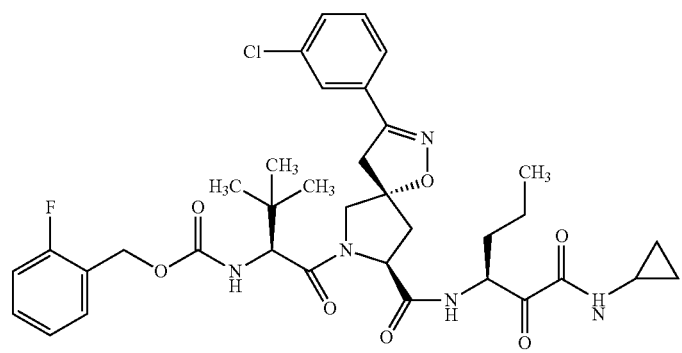 | 512 |

TABLE 1-continued

Exemplary compounds of Formula (I).

| Structure | Compound No. |
|---|---|
| 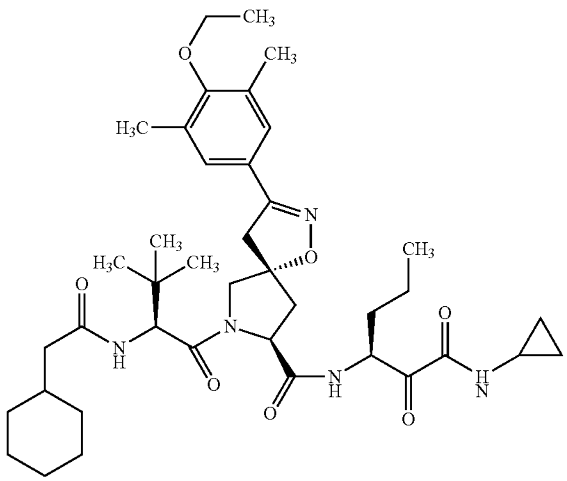 | 513 |
| 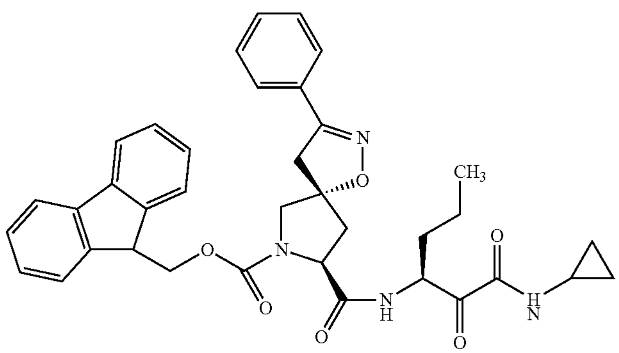 | 514 |
| 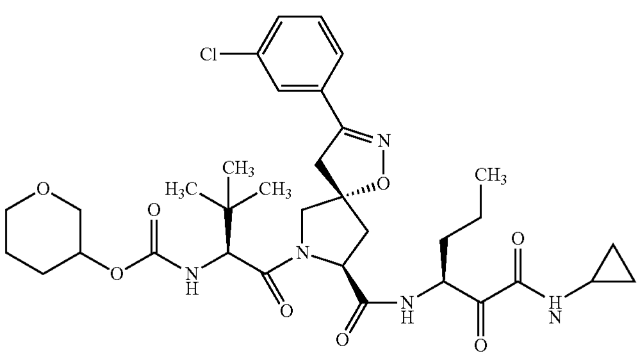 | 515 |

TABLE 1-continued
Exemplary compounds of Formula (I).
| Structure | Compound No. |
|---|---|
| 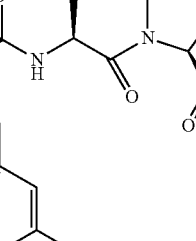 | 516 |
| 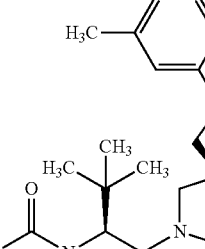 | 517 |
| 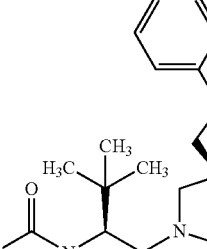 | 518 |
| 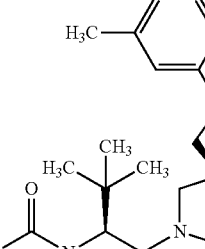 | 519 |

TABLE 1-continued

Exemplary compounds of Formula (I).

| Structure | Compound No. |
|---|---|
| 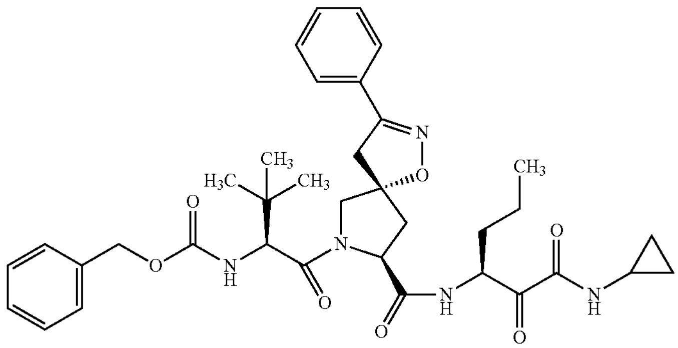 | 520 |
| 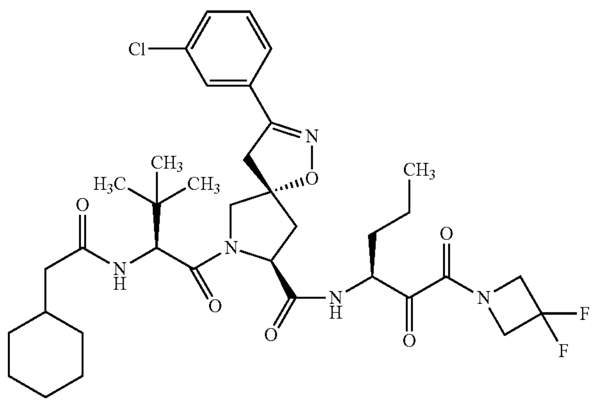 | 521 |
| 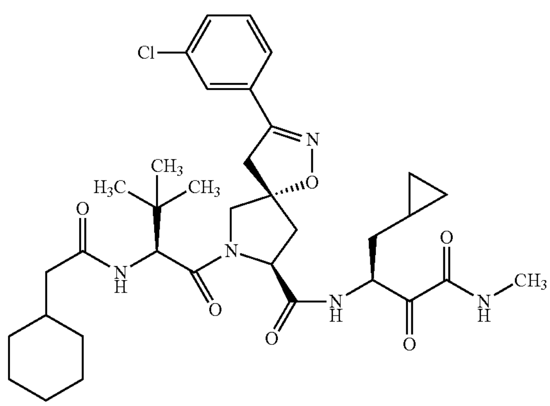 | 522 |
| 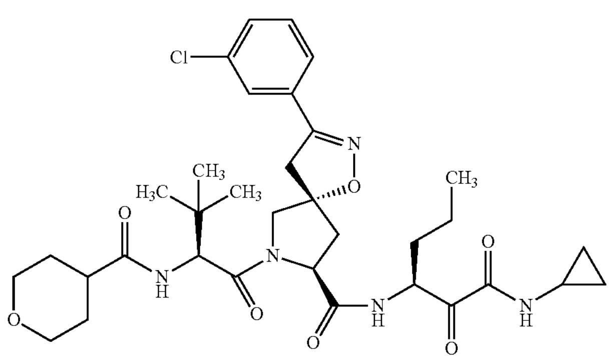 | 523 |

TABLE 1-continued

Exemplary compounds of Formula (I).

| Structure | Compound No. |
|---|---|
| 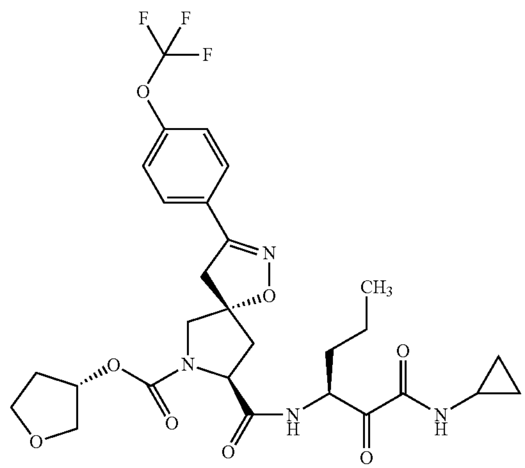 | 524 |
| 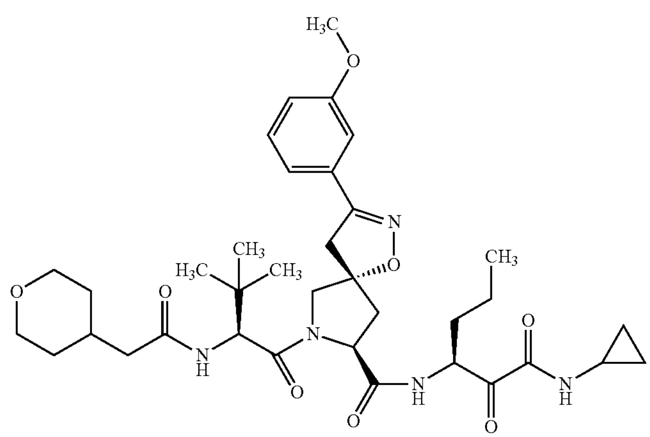 | 525 |
| 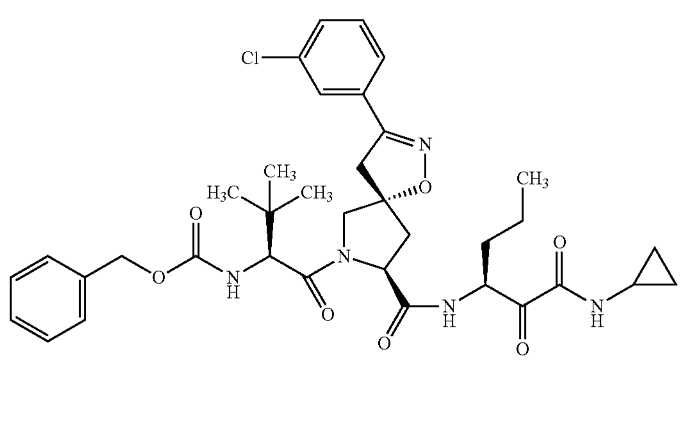 | 526 |

TABLE 1-continued

Exemplary compounds of Formula (I).

| Structure | Compound No. |
|---|---|
| 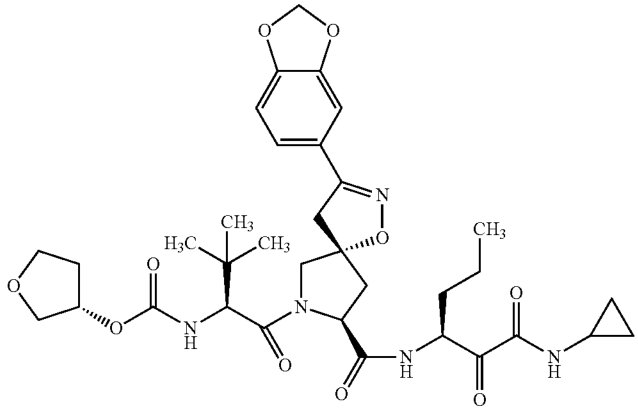 | 527 |
| 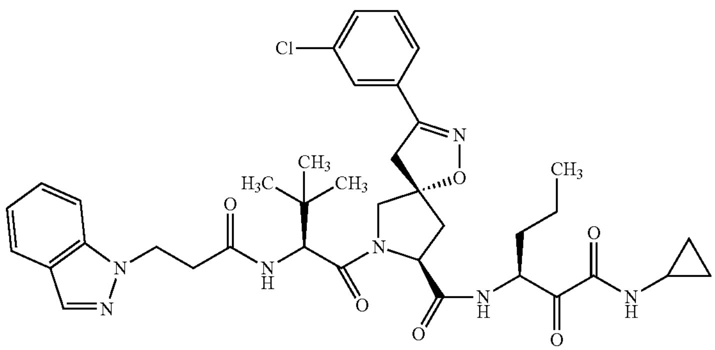 | 528 |
| 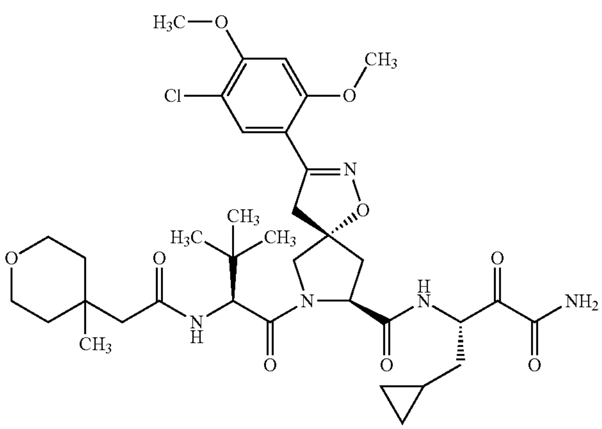 | 529 |
| 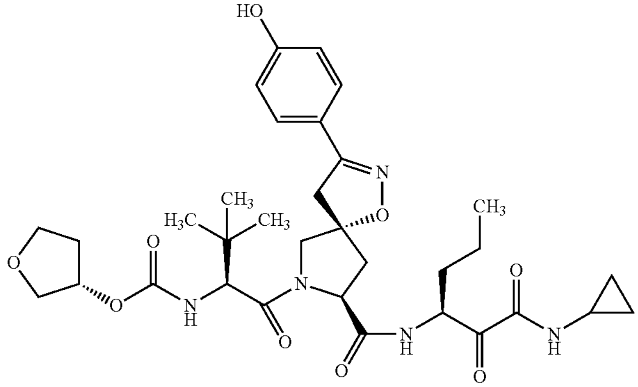 | 530 |

TABLE 1-continued
Exemplary compounds of Formula (I).
| Structure | Compound No. |
|---|---|
| 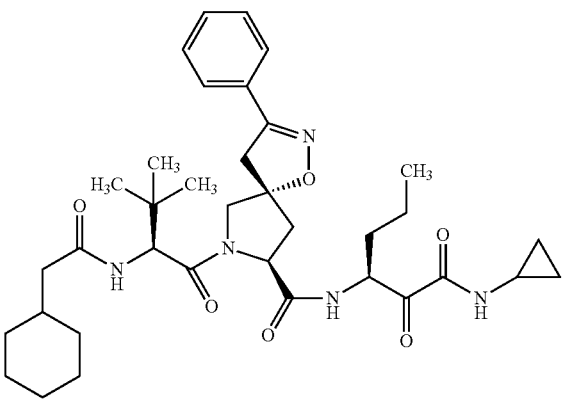 | 531 |
| 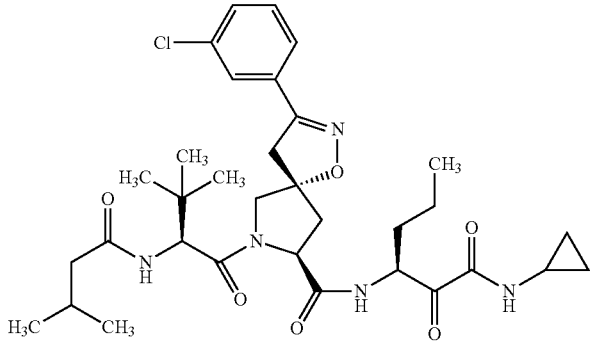 | 532 |
| 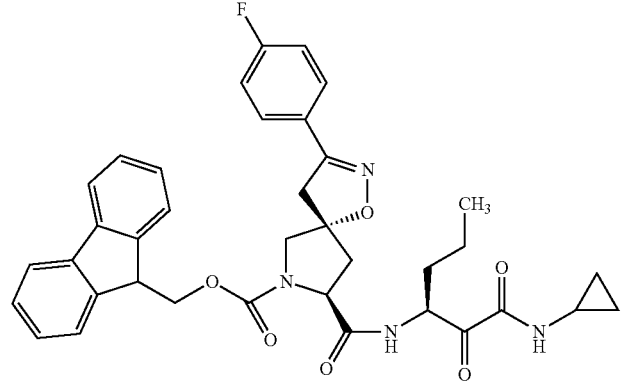 | 533 |
| 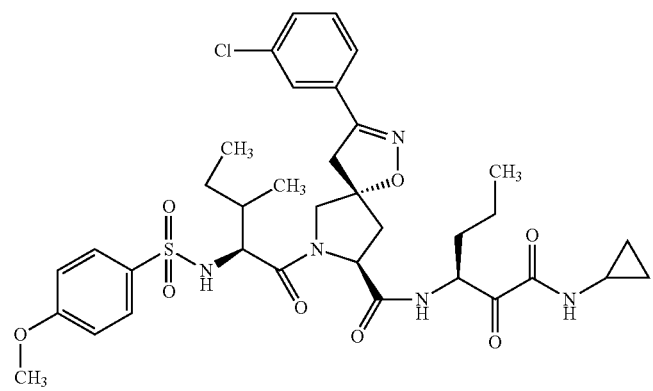 | 534 |

TABLE 1-continued

Exemplary compounds of Formula (I).

| Structure | Compound No. |
|---|---|
| 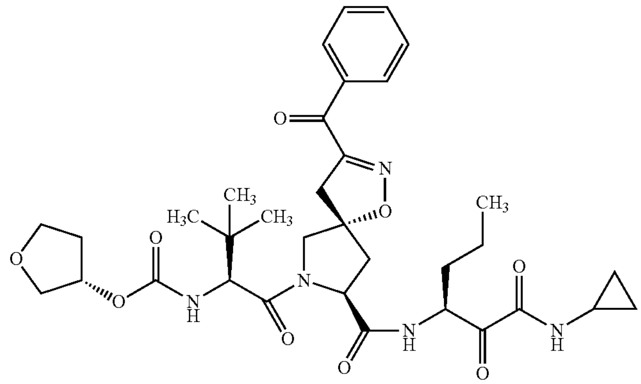 | 535 |
| 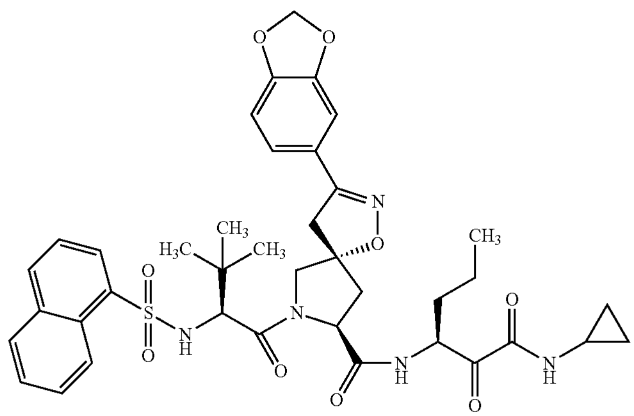 | 536 |
| 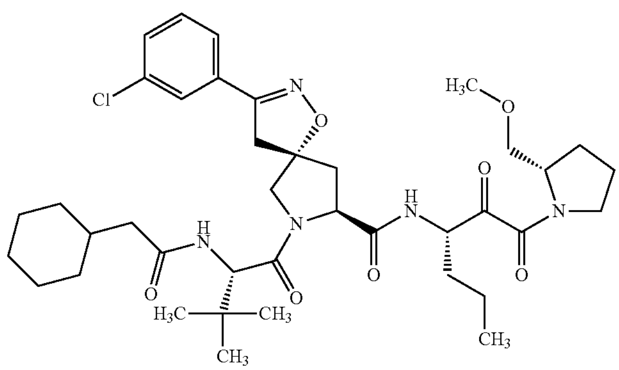 | 537 |
| 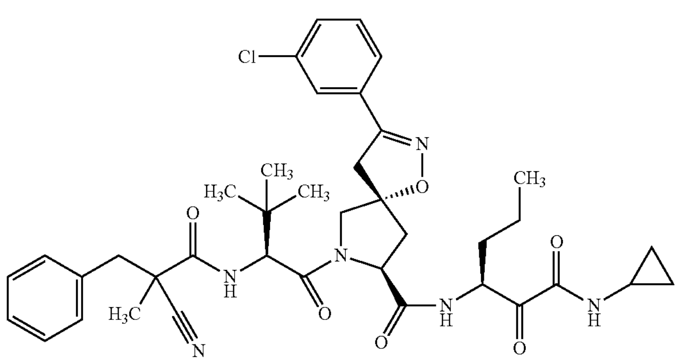 | 538 |

TABLE 1-continued

Exemplary compounds of Formula (I).

| Structure | Compound No. |
|---|---|
| 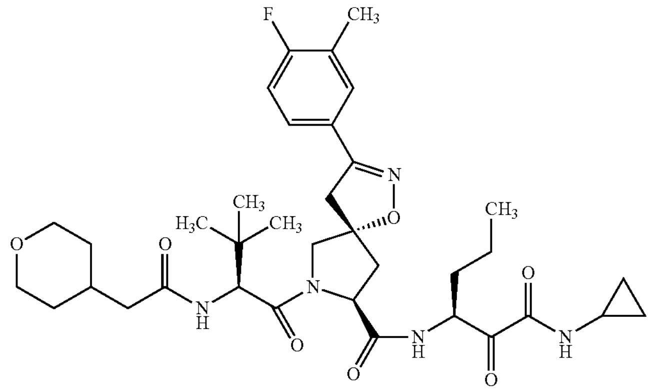 | 539 |
| 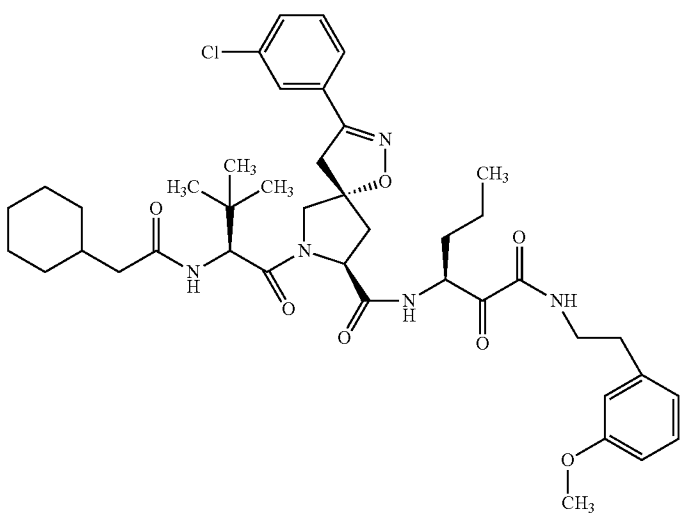 | 540 |
| 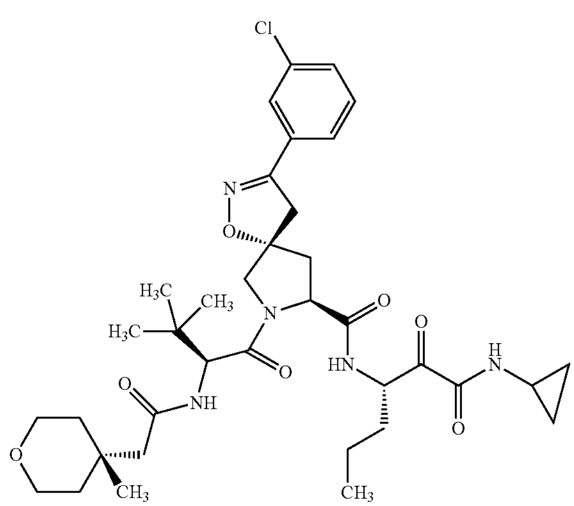 | 541 |

TABLE 1-continued

Exemplary compounds of Formula (I).

| Structure | Compound No. |
|---|---|
| 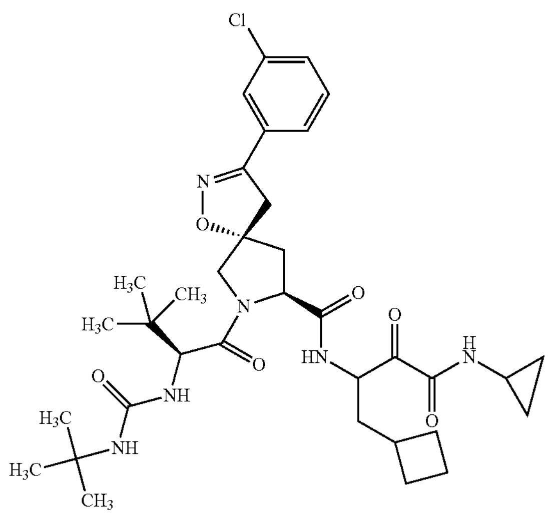 | 542 |
| 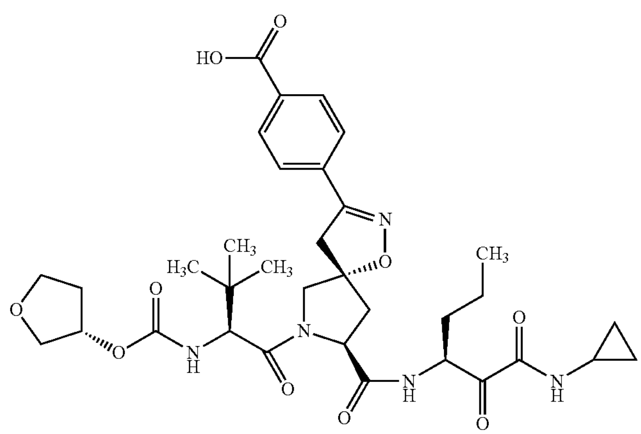 | 543 |
| 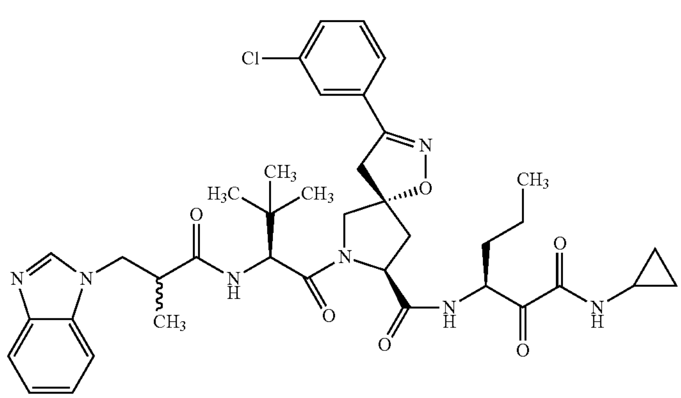 | 544 |

TABLE 1-continued
Exemplary compounds of Formula (I).
| Structure | Compound No. |
|---|---|
| 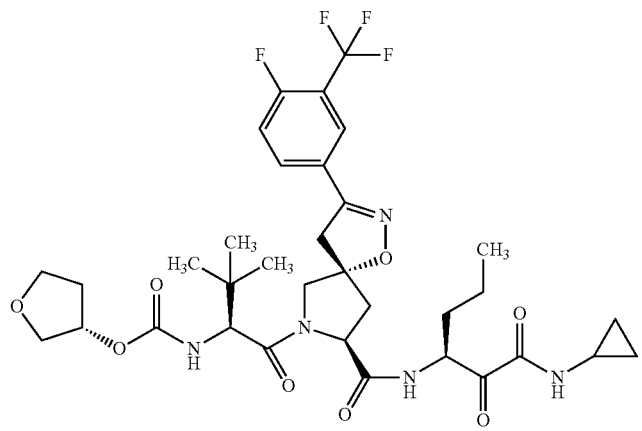 | 545 |
| 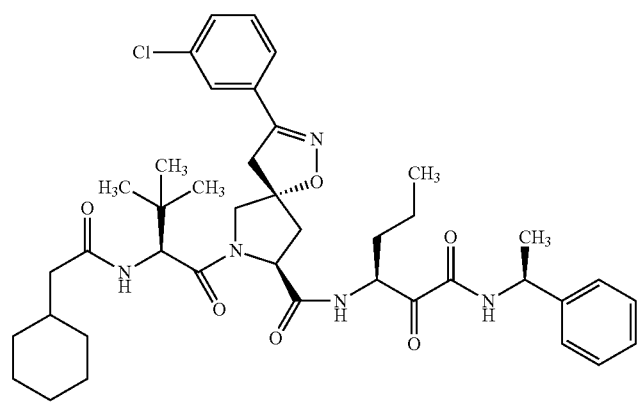 | 546 |
| 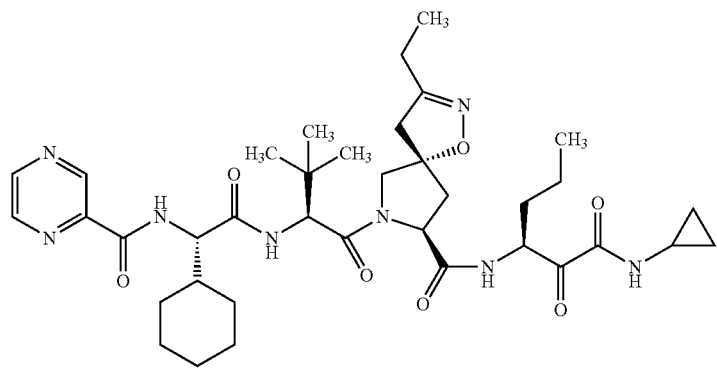 | 547 |

TABLE 1-continued

Exemplary compounds of Formula (I).

| Structure | Compound No. |
|---|---|
| 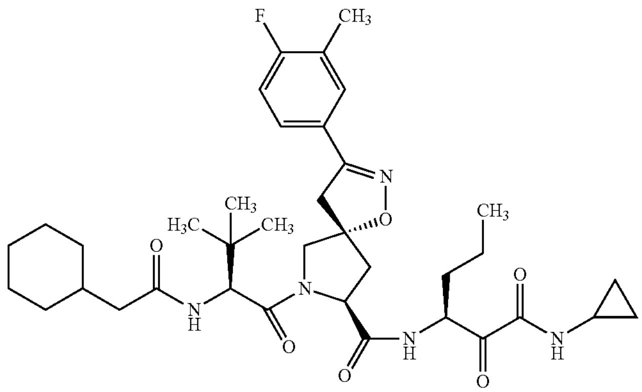 | 548 |
| 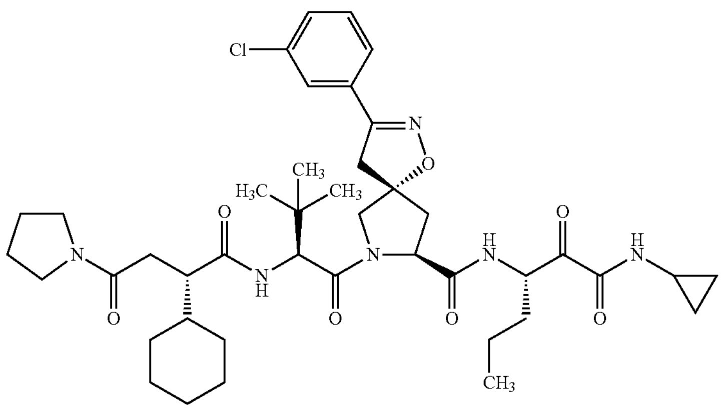 | 549 |
| 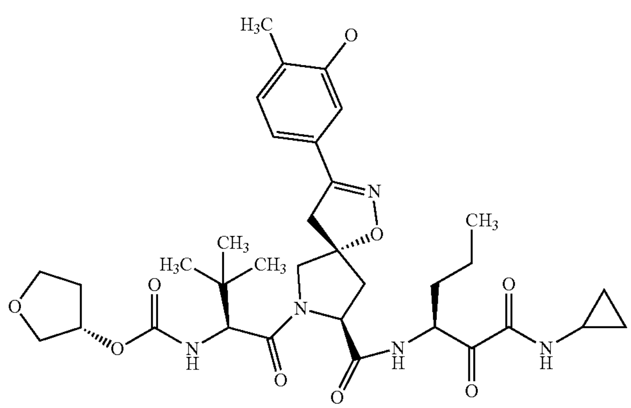 | 550 |
| 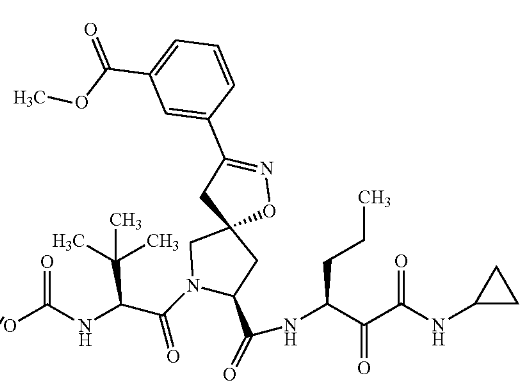 | 551 |

TABLE 1-continued

Exemplary compounds of Formula (I).

| Structure | Compound No. |
|---|---|
| 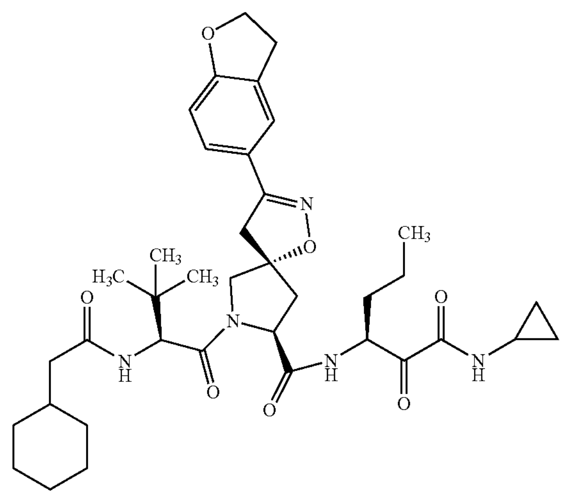 | 552 |
| 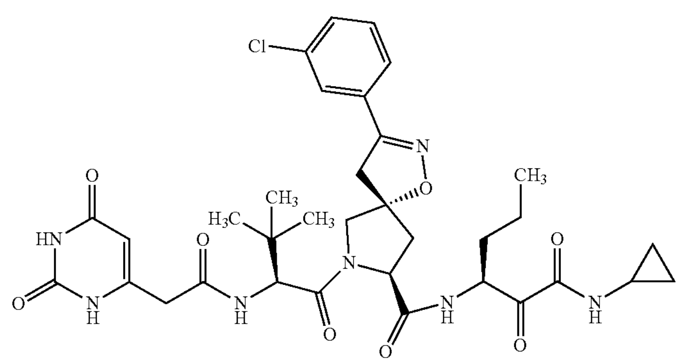 | 553 |
| 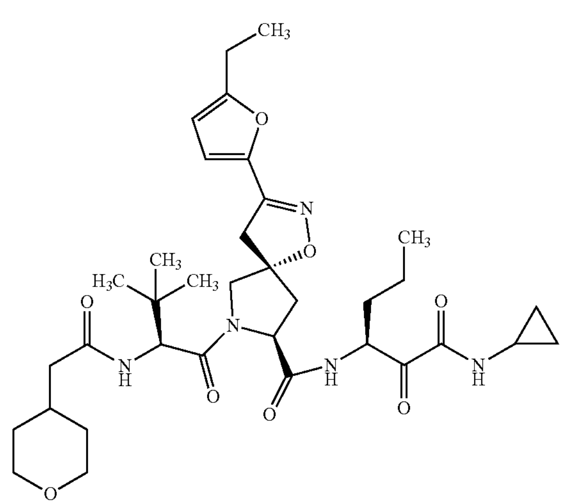 | 554 |

TABLE 1-continued

Exemplary compounds of Formula (I).

| Structure | Compound No. |
|---|---|
| 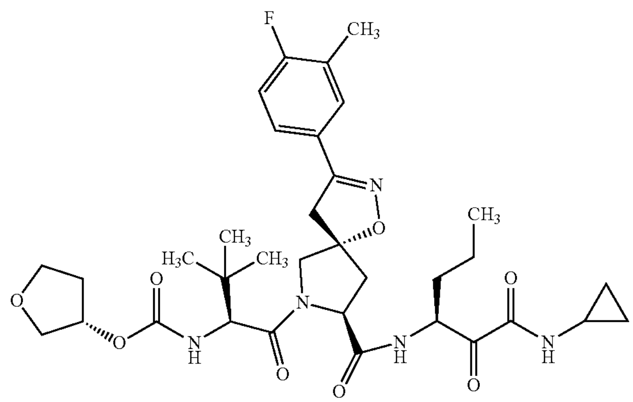 | 555 |
| 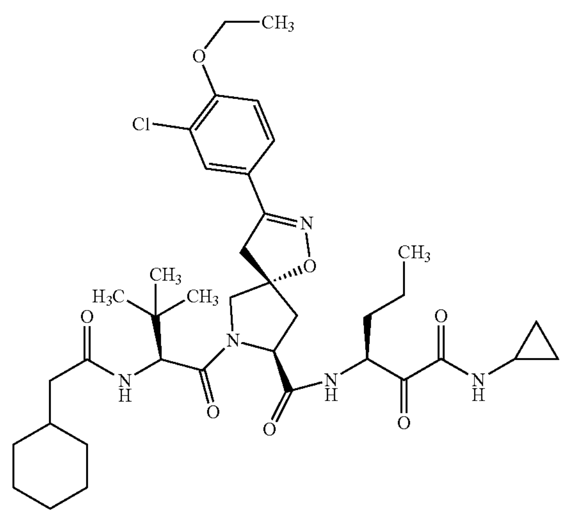 | 556 |
| 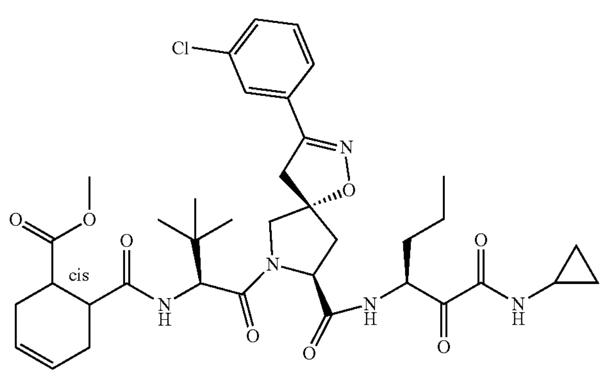 | 557 |

TABLE 1-continued

Exemplary compounds of Formula (I).

| Structure | Compound No. |
|---|---|
| 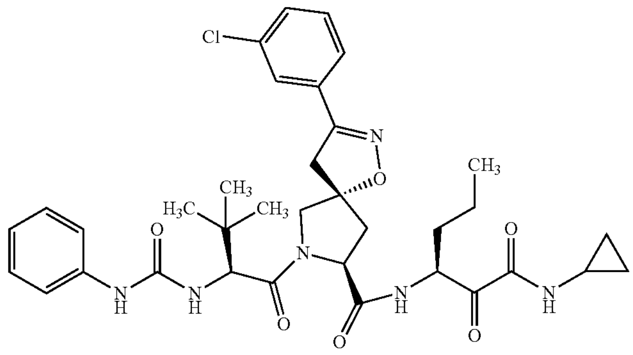 | 558 |
| 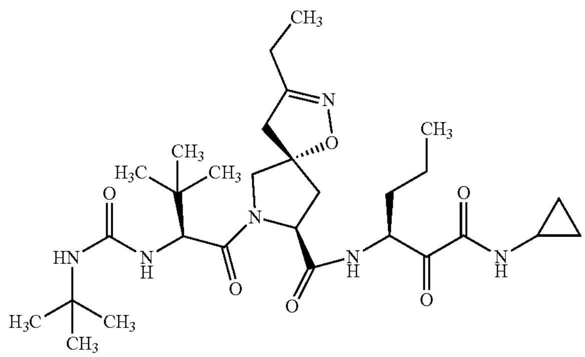 | 559 |
| 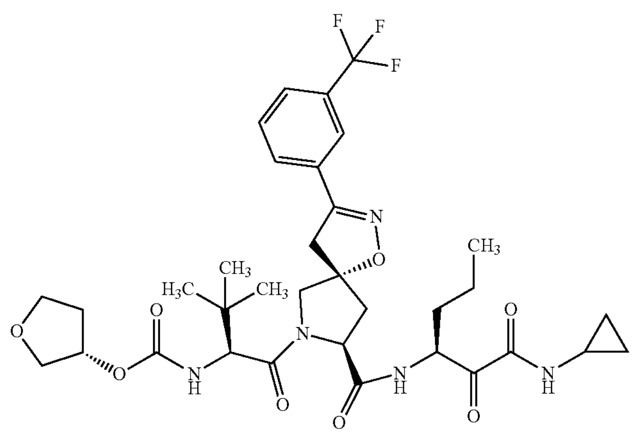 | 560 |
| 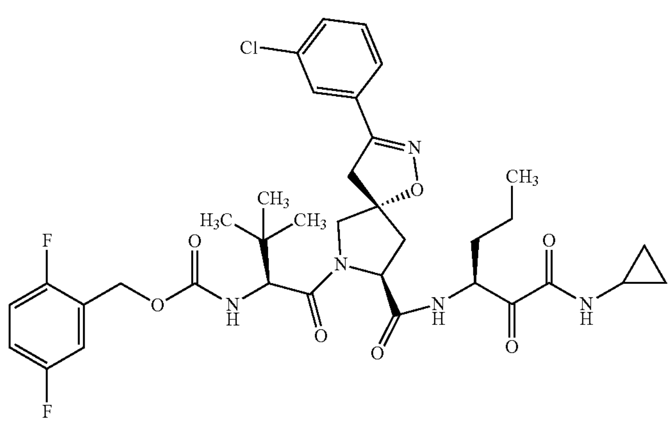 | 561 |

TABLE 1-continued

Exemplary compounds of Formula (I).

| Structure | Compound No. |
|---|---|
| 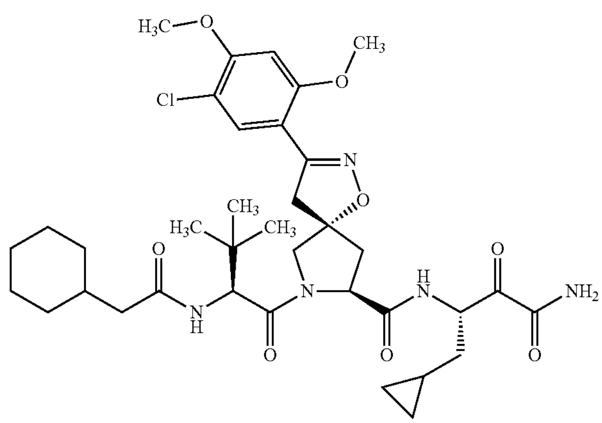 | 562 |
| 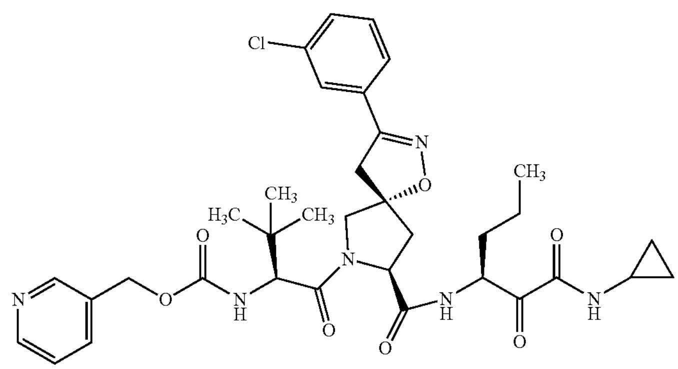 | 563 |
| 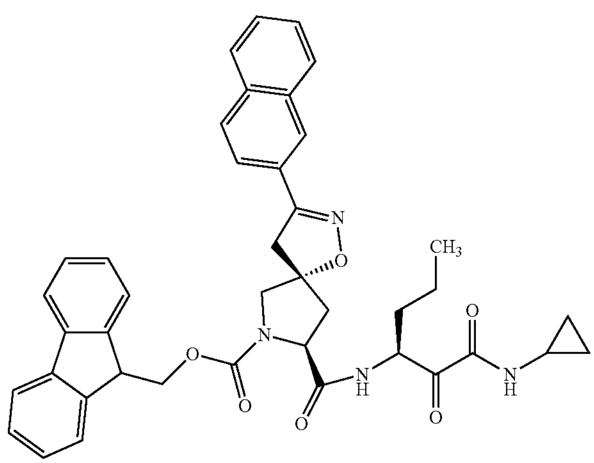 | 564 |

TABLE 1-continued

Exemplary compounds of Formula (I).

| Structure | Compound No. |
|---|---|
| 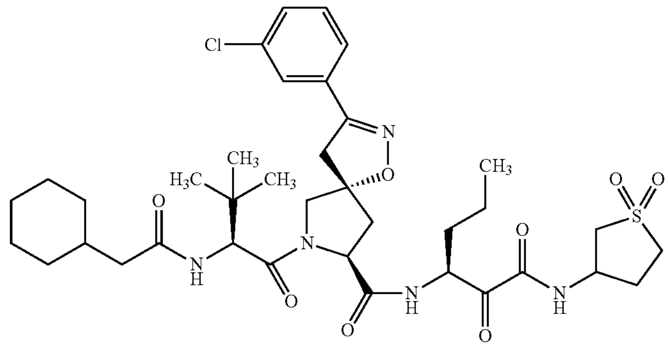 | 565 |
| 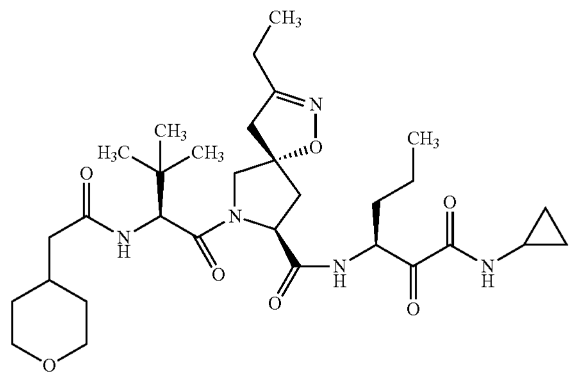 | 566 |
| 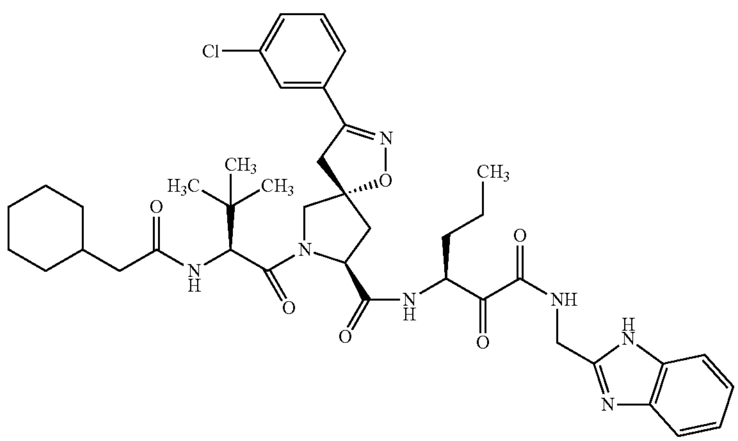 | 567 |
| 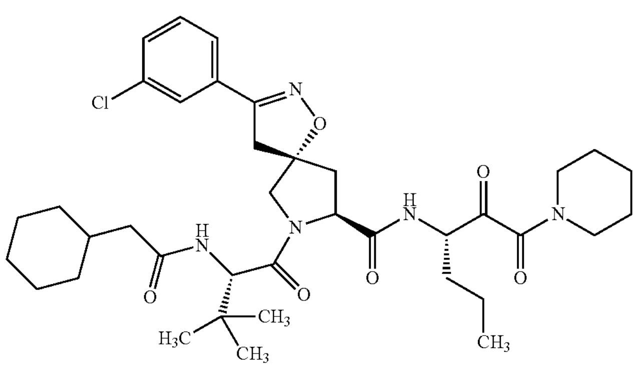 | 568 |

TABLE 1-continued

Exemplary compounds of Formula (I).

| Structure | Compound No. |
|---|---|
| 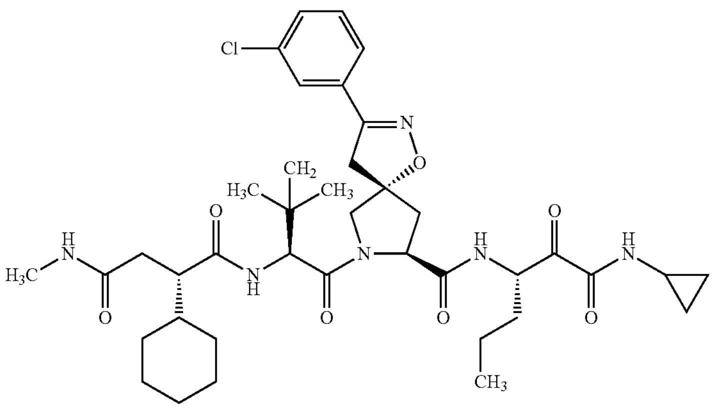 | 569 |
| 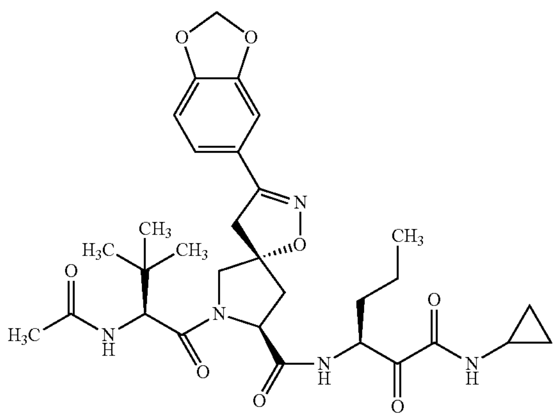 | 570 |
| 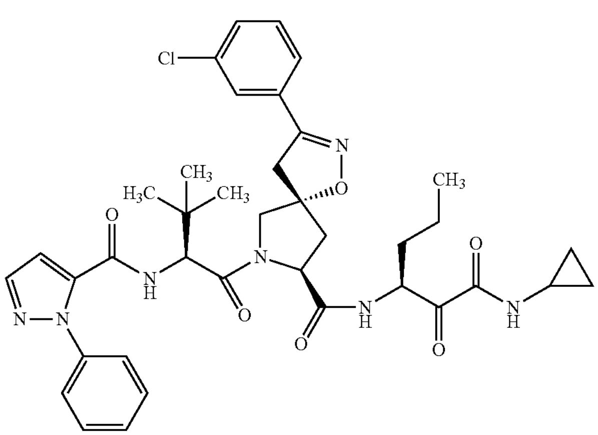 | 571 |

TABLE 1-continued

Exemplary compounds of Formula (I).

| Structure | Compound No. |
|---|---|
| 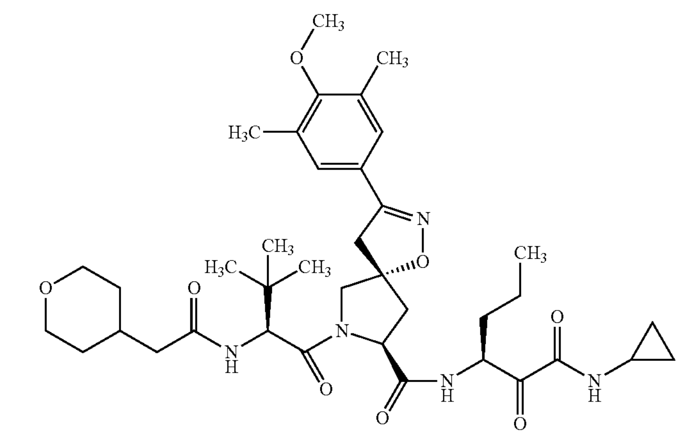 | 572 |
| 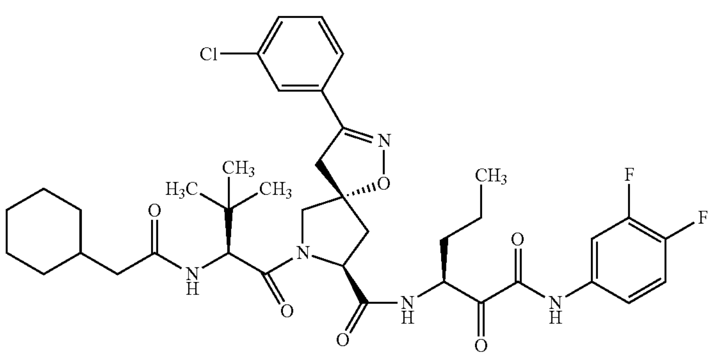 | 573 |
| 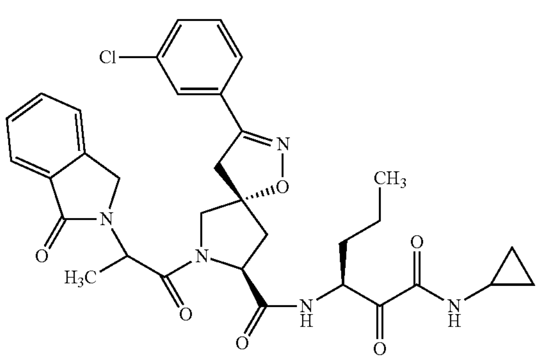 | 574 |

TABLE 1-continued

Exemplary compounds of Formula (I).

| Structure | Compound No. |
|---|---|
| 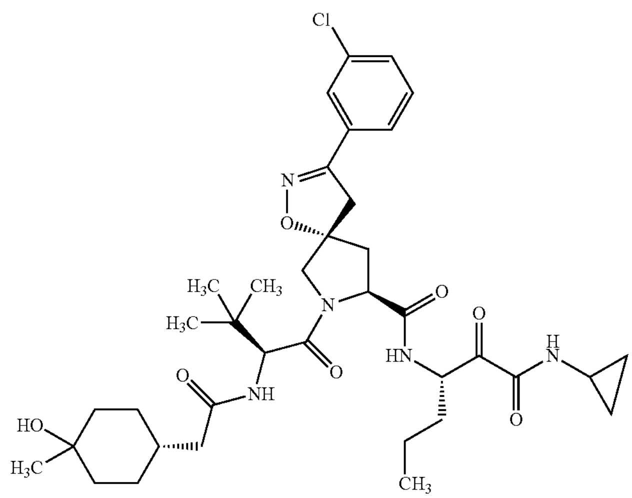 | 575 |
| 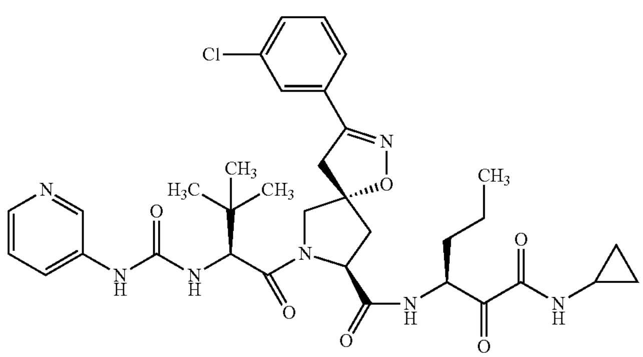 | 576 |
| 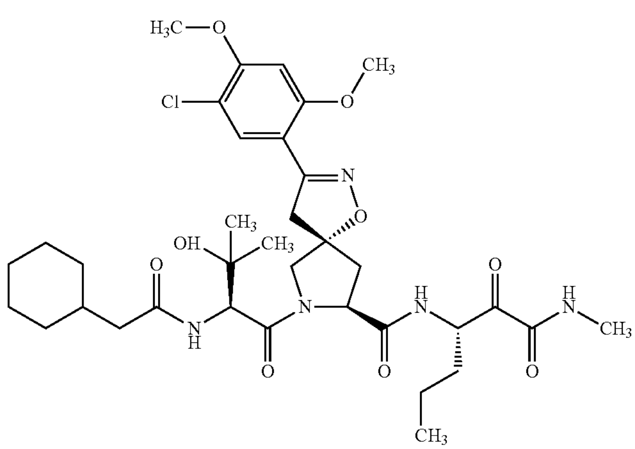 | 577 |

TABLE 1-continued

Exemplary compounds of Formula (I).

| Structure | Compound No. |
|---|---|
| 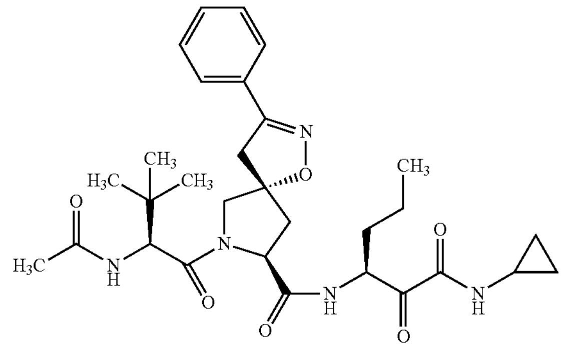 | 578 |
| 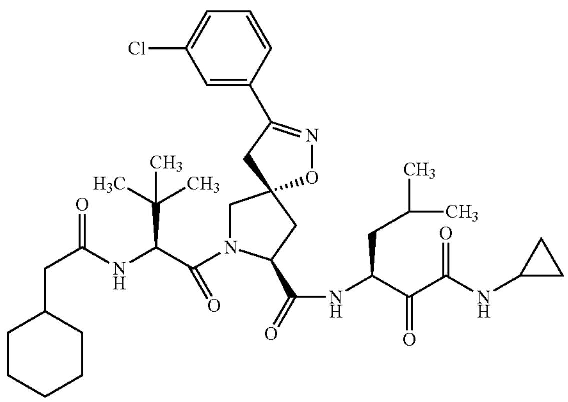 | 579 |
| 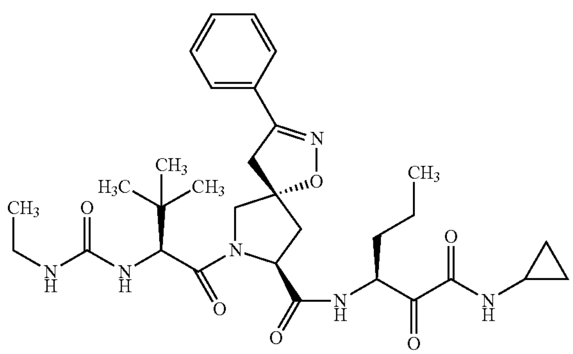 | 580 |
| 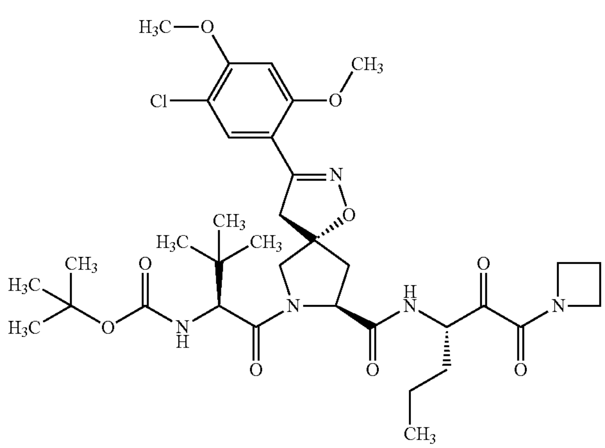 | 581 |

TABLE 1-continued

Exemplary compounds of Formula (I).

| Structure | Compound No. |
|---|---|
| 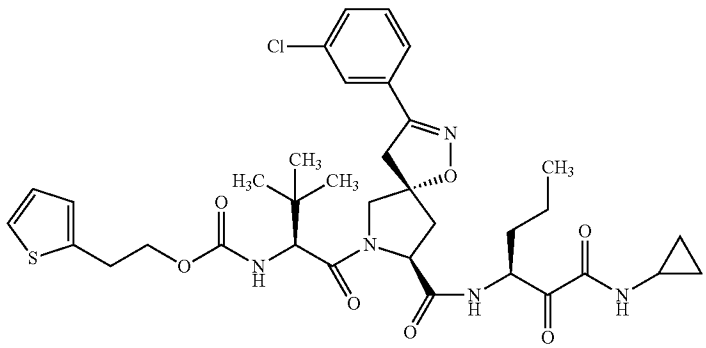 | 582 |
| 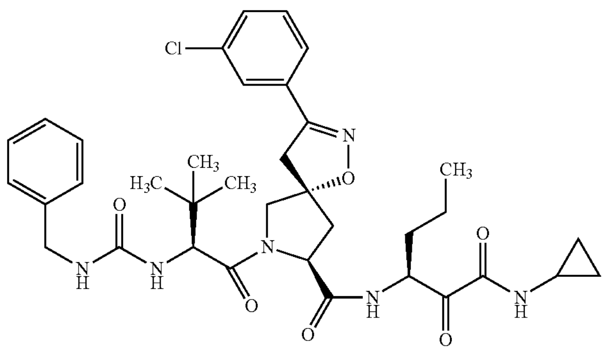 | 583 |
| 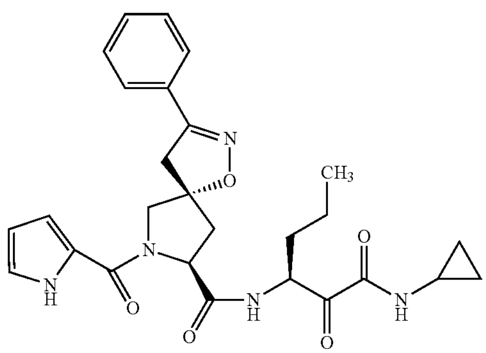 | 584 |
| 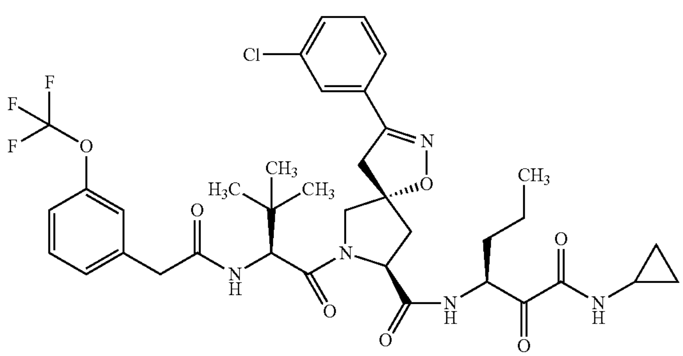 | 585 |

TABLE 1-continued

Exemplary compounds of Formula (I).

| Structure | Compound No. |
|---|---|
| 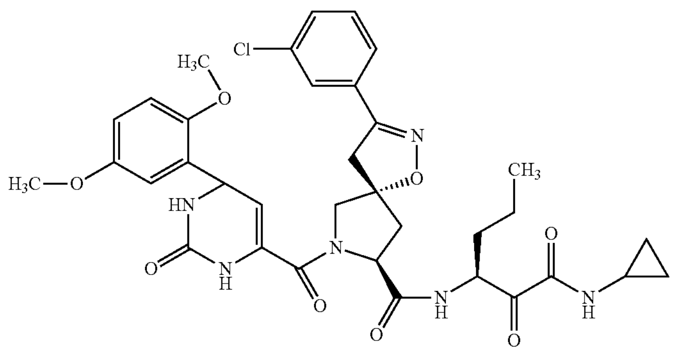 | 586 |
| 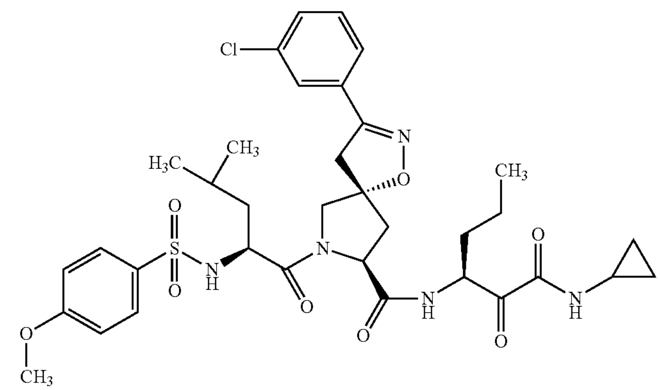 | 587 |
| 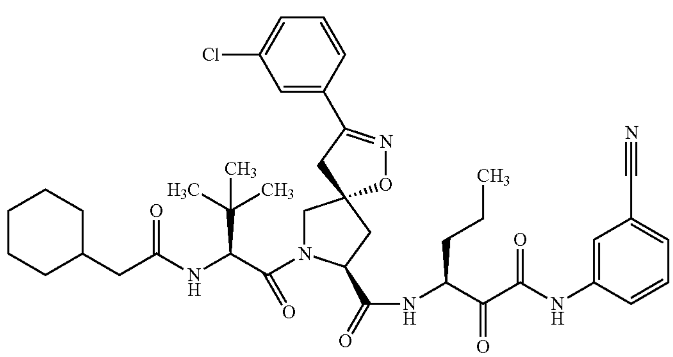 | 588 |
| 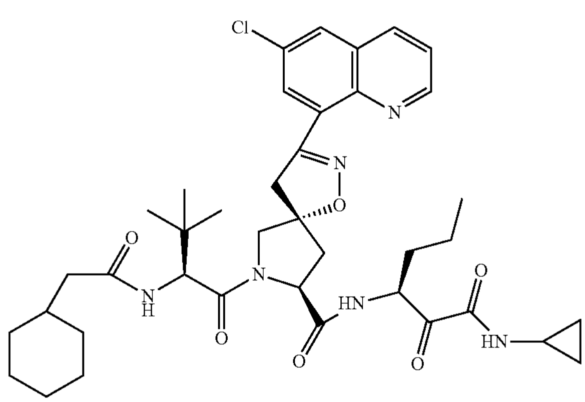 | 589 |

TABLE 1-continued

Exemplary compounds of Formula (I).

| Structure | Compound No. |
|---|---|
| 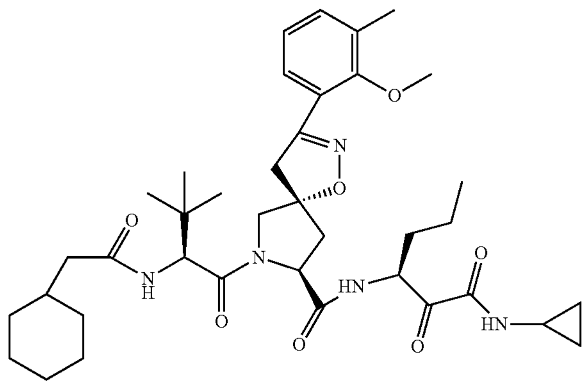 | 590 |
| 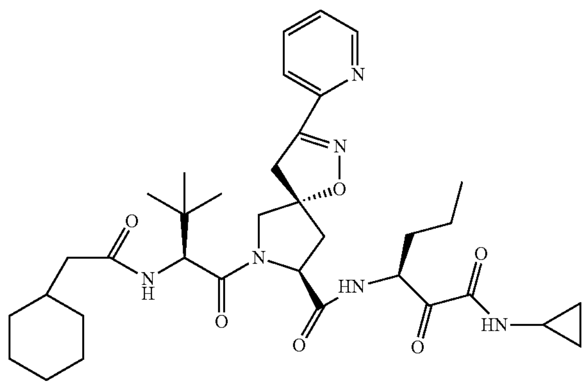 | 591 |
| 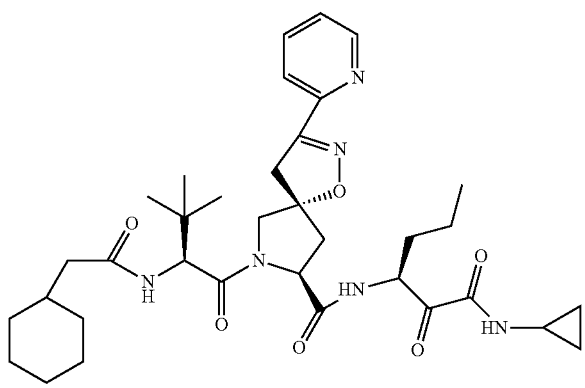 | 592 |
| 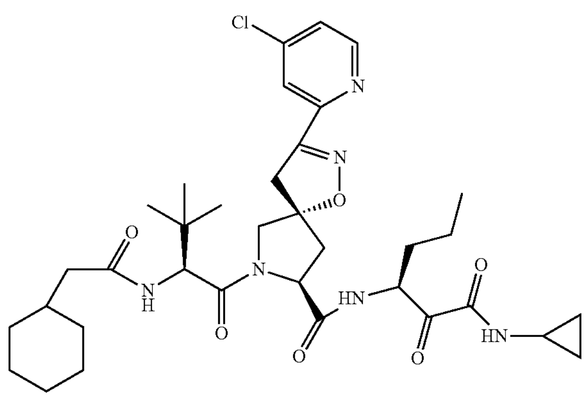 | 593 |

TABLE 1-continued
Exemplary compounds of Formula (I).
| Structure | Compound No. |
|---|---|
| 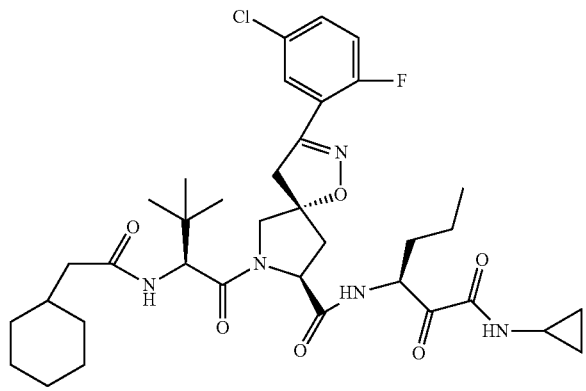 | 594 |
| 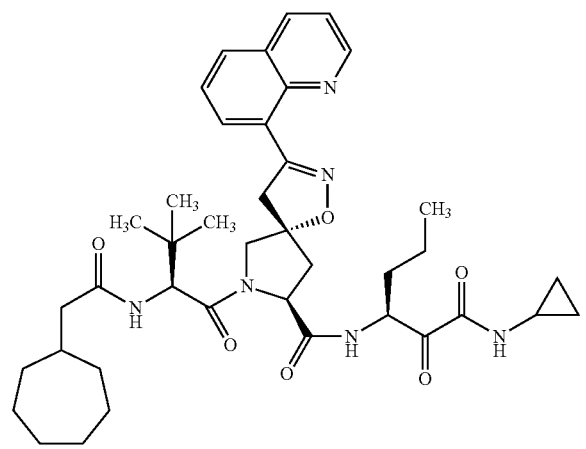 | 595 |
| 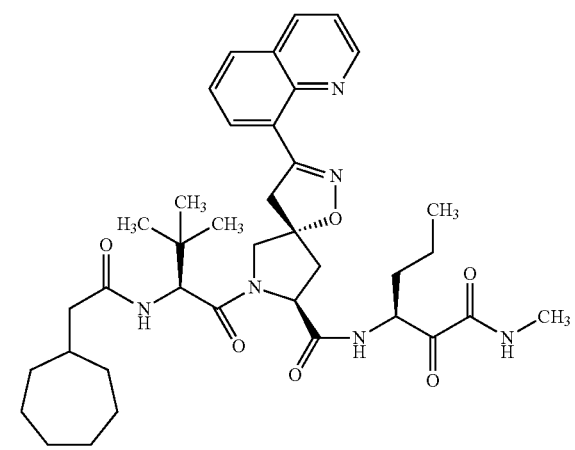 | 596 |

TABLE 1-continued

Exemplary compounds of Formula (I).

| Structure | Compound No. |
|---|---|
| 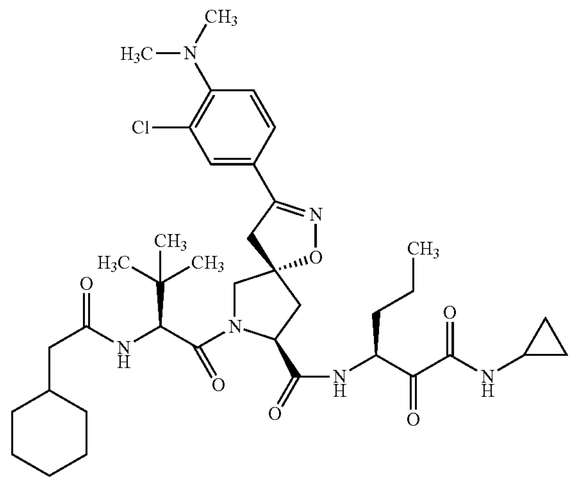 | 597 |
| 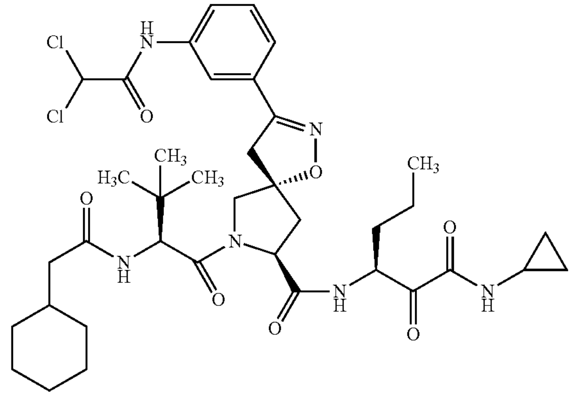 | 598 |
| 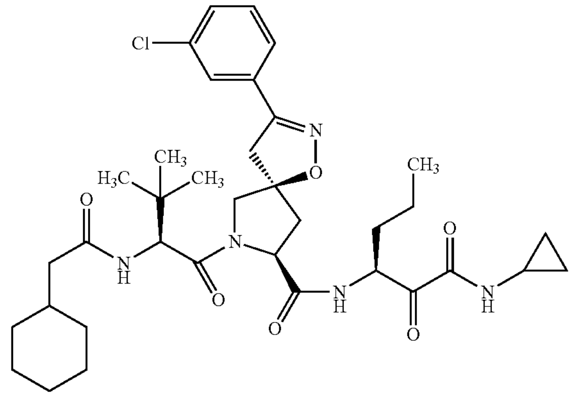 | 599 |

TABLE 1-continued

Exemplary compounds of Formula (I).

| Structure | Compound No. |
|---|---|
| 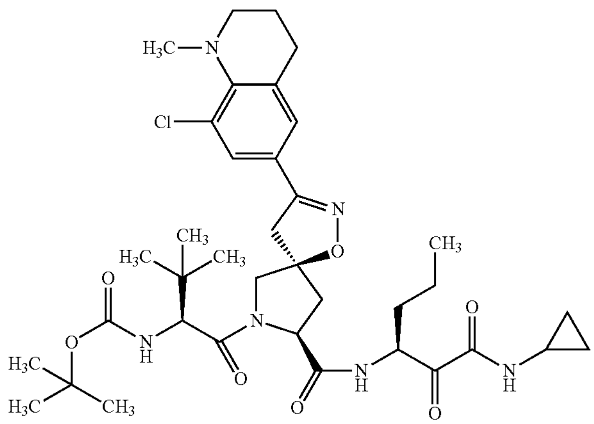 | 600 |
| 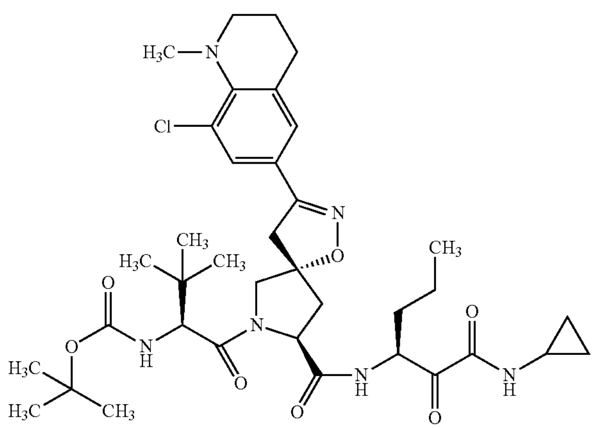 | 601 |
| 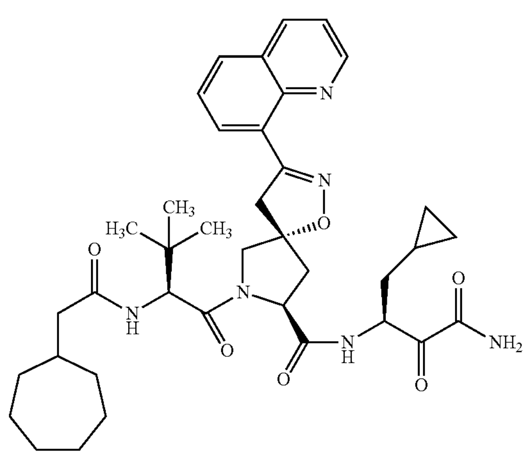 | 602 |

TABLE 1-continued

Exemplary compounds of Formula (I).

| Structure | Compound No. |
|---|---|
| 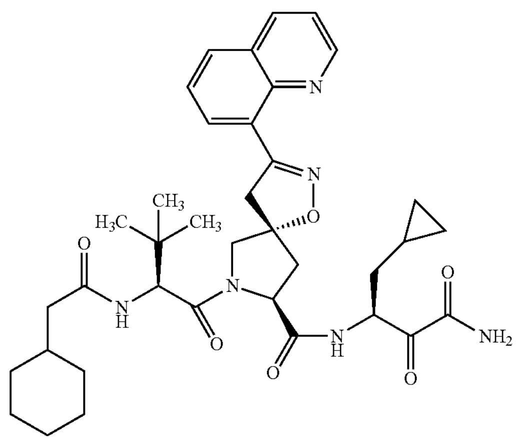 | 603 |
| 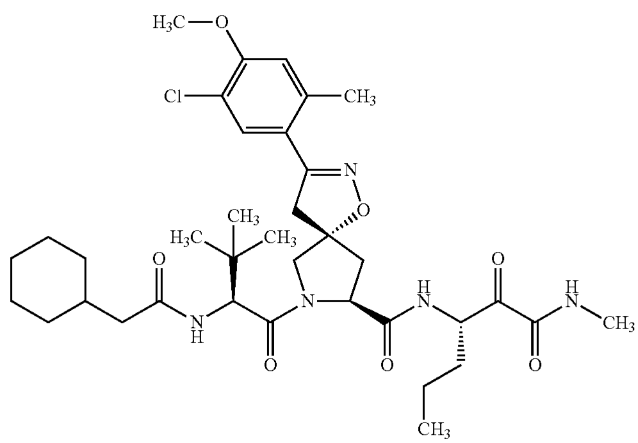 | 604 |
| 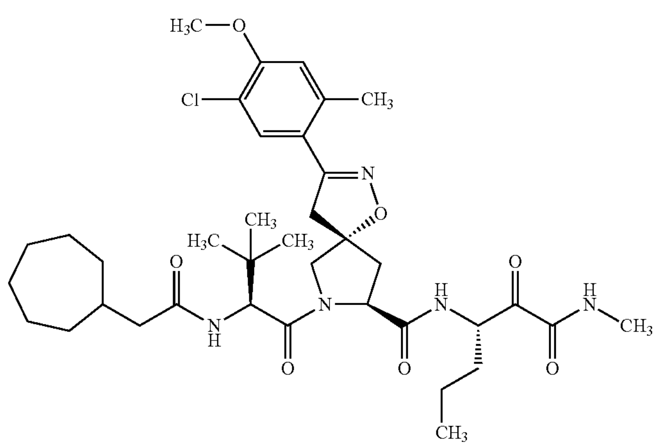 | 605 |

TABLE 1-continued

Exemplary compounds of Formula (I).

| Structure | Compound No. |
|---|---|
| 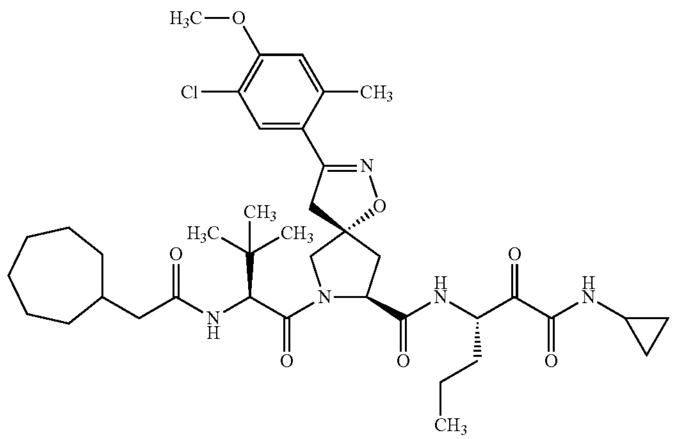 | 606 |
| 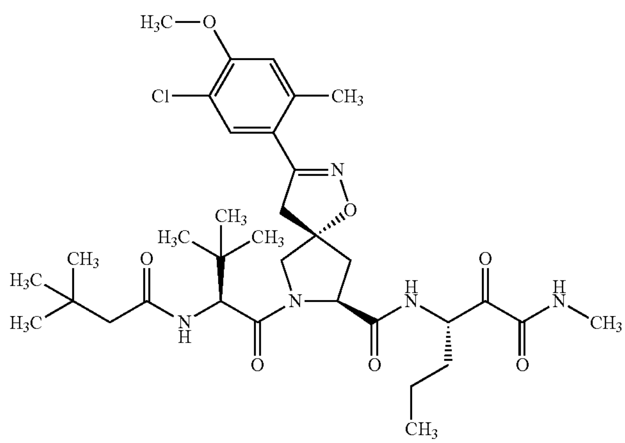 | 607 |
| 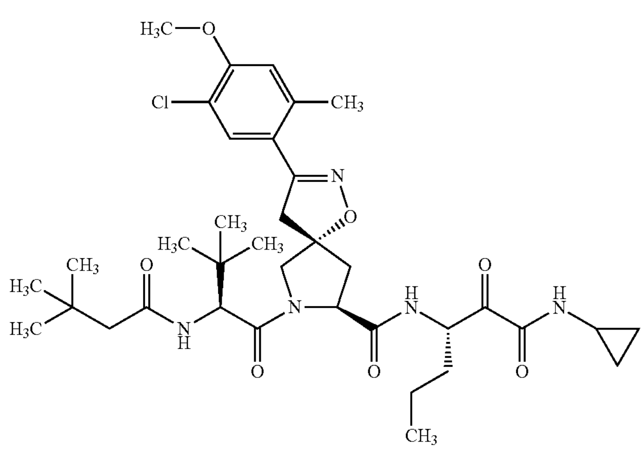 | 608 |

TABLE 1-continued

Exemplary compounds of Formula (I).

| Structure | Compound No. |
|---|---|
| 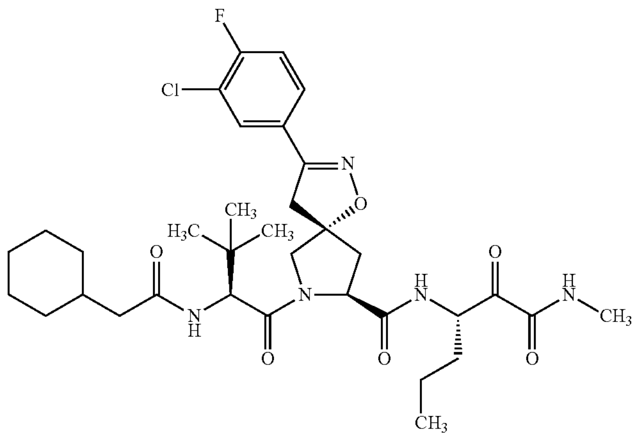 | 609 |
| 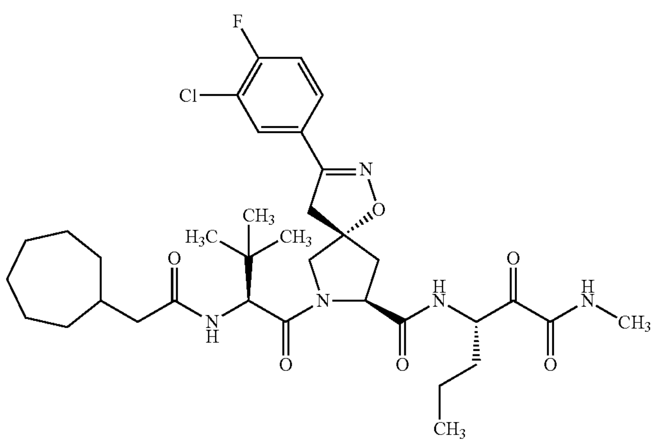 | 610 |
| 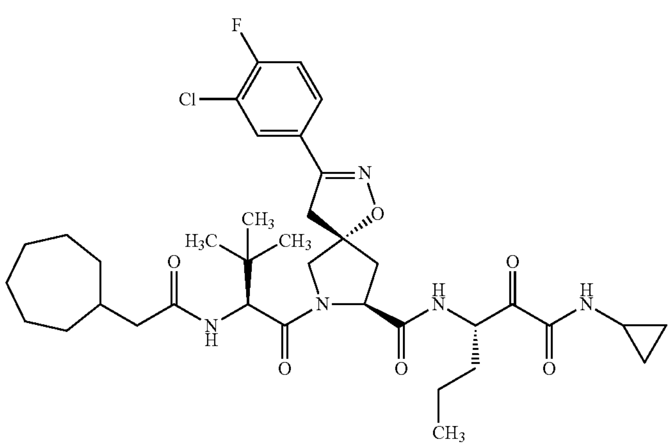 | 611 |

TABLE 1-continued

Exemplary compounds of Formula (I).

| Structure | Compound No. |
|---|---|
| 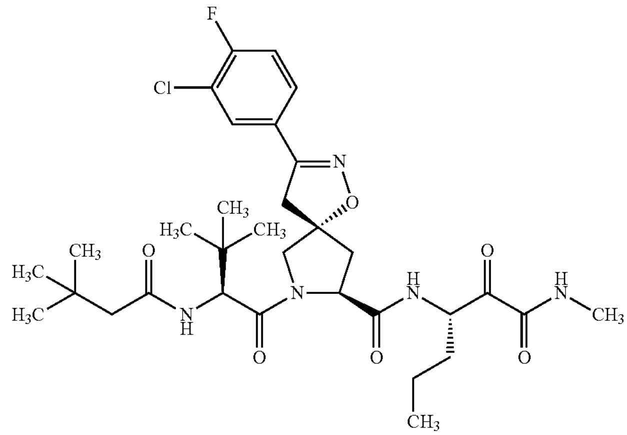 | 612 |
| 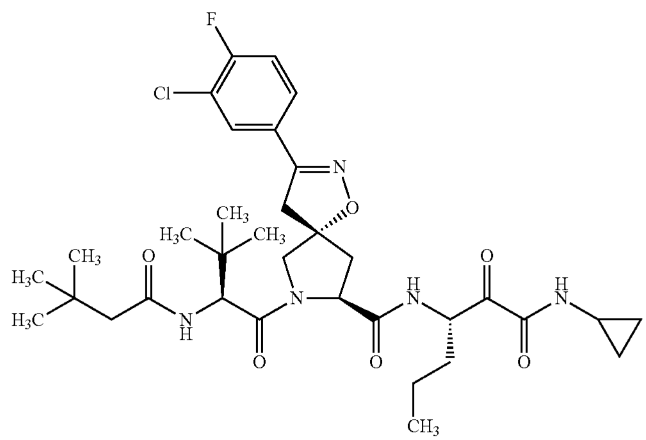 | 613 |
| 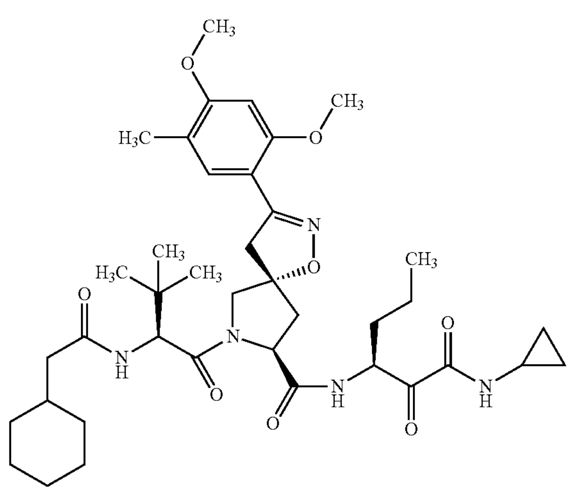 | 614 |

TABLE 1-continued

Exemplary compounds of Formula (I).

| Structure | Compound No. |
|---|---|
| 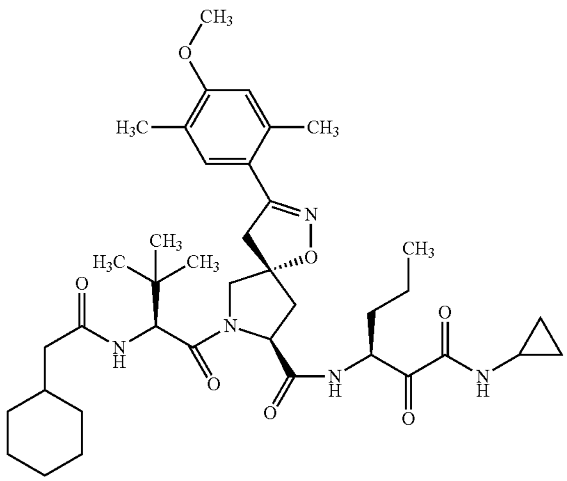 | 615 |
| 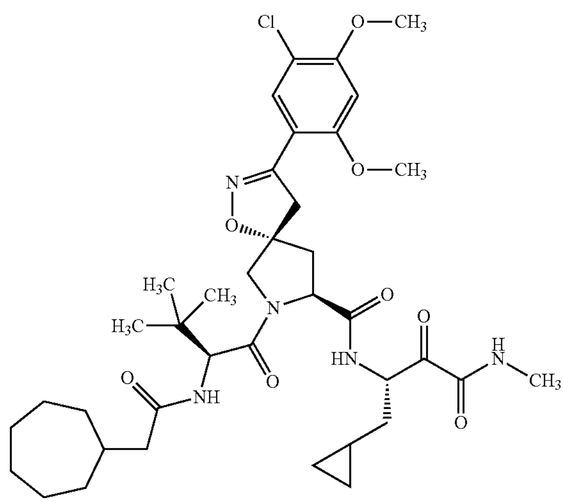 | 616 |
| 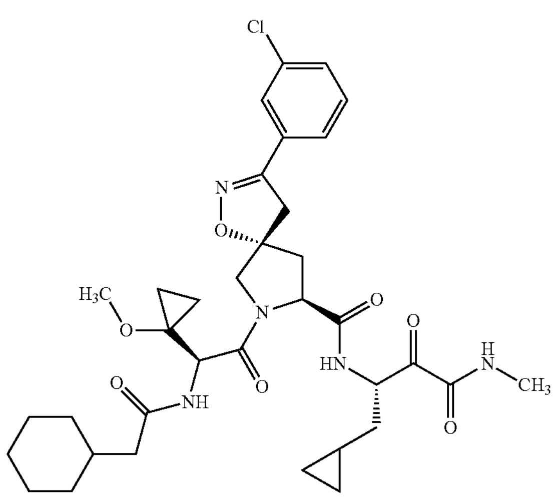 | 617 |

TABLE 1-continued

Exemplary compounds of Formula (I).

| Structure | Compound No. |
|---|---|
| 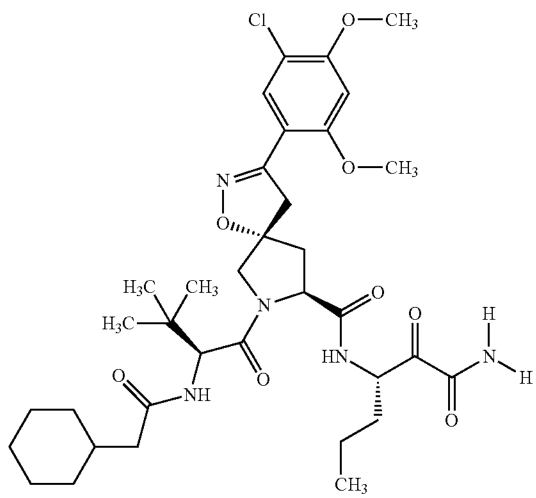 | 618 |
| 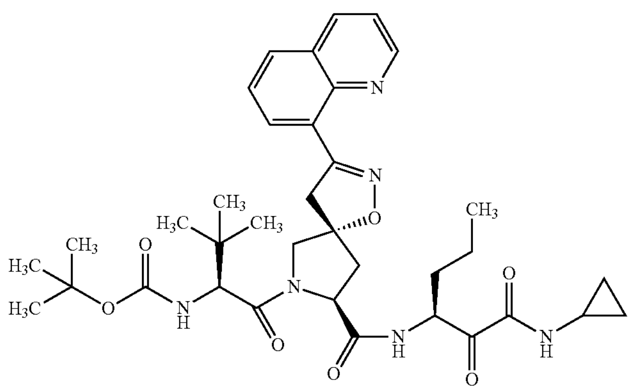 | 619 |
| 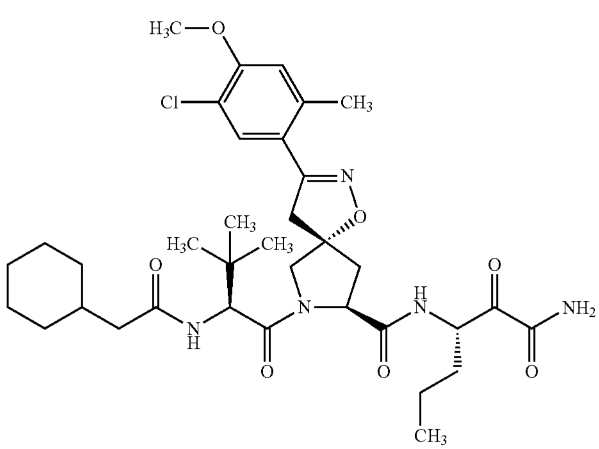 | 620 |

TABLE 1-continued

Exemplary compounds of Formula (I).

| Structure | Compound No. |
|---|---|
| 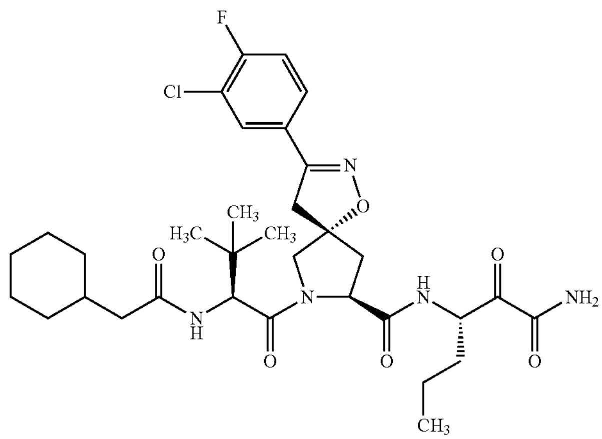 | 621 |
| 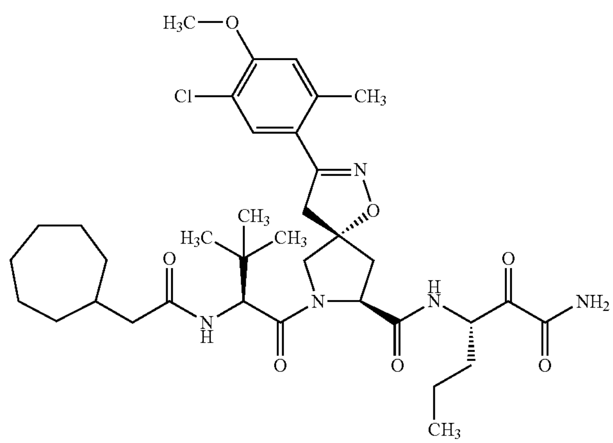 | 622 |
| 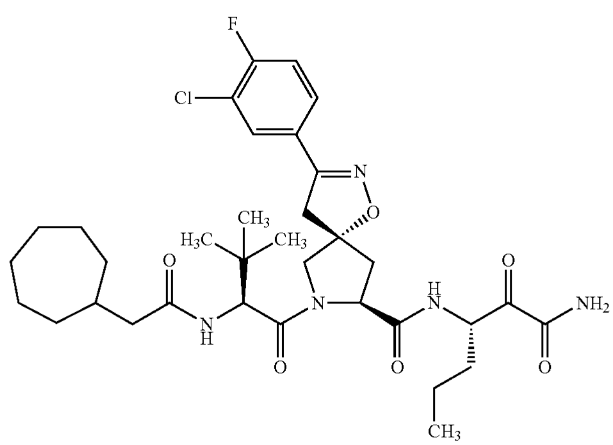 | 623 |

TABLE 1-continued

Exemplary compounds of Formula (I).

| Structure | Compound No. |
|---|---|
| 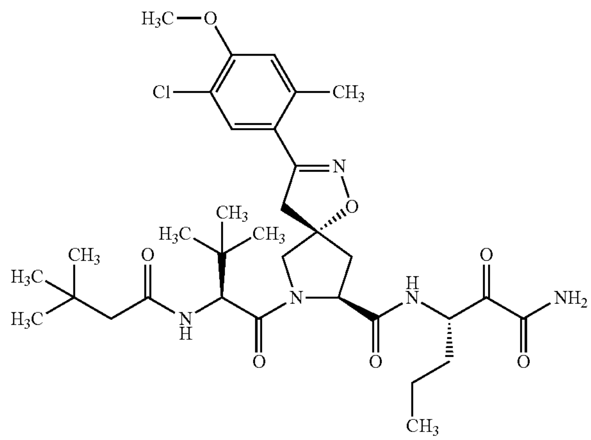 | 624 |
| 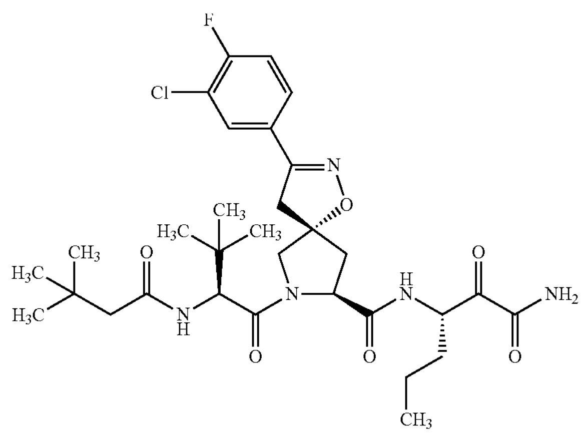 | 625 |
| 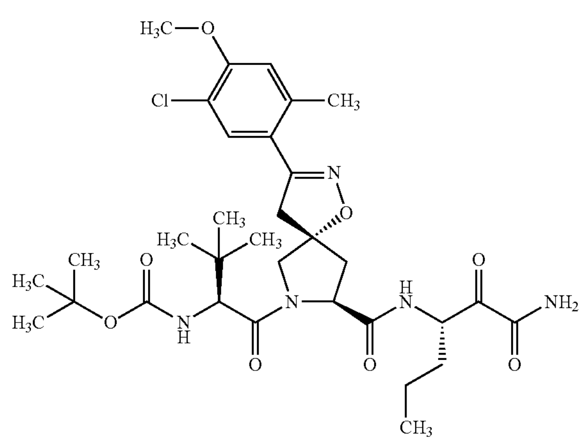 | 626 |

TABLE 1-continued

Exemplary compounds of Formula (I).

| Structure | Compound No. |
|---|---|
| 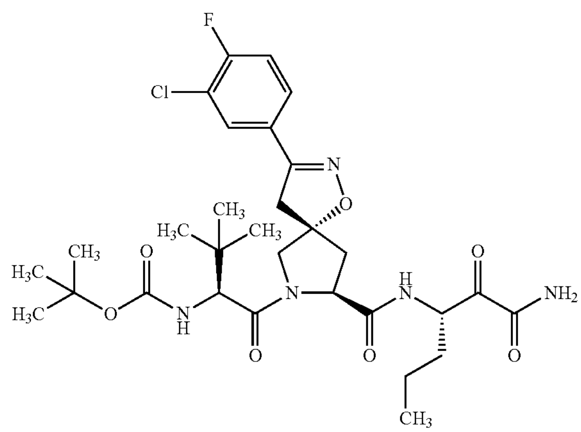 | 627 |
| 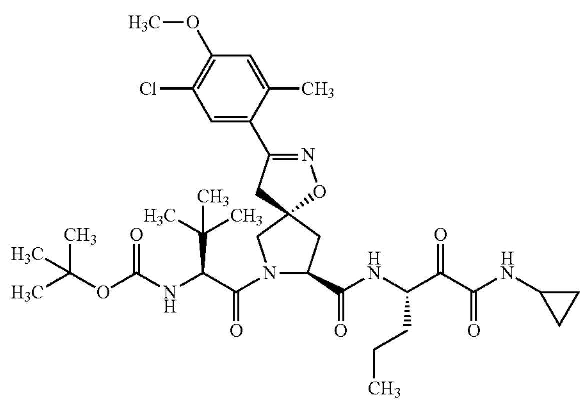 | 628 |
| 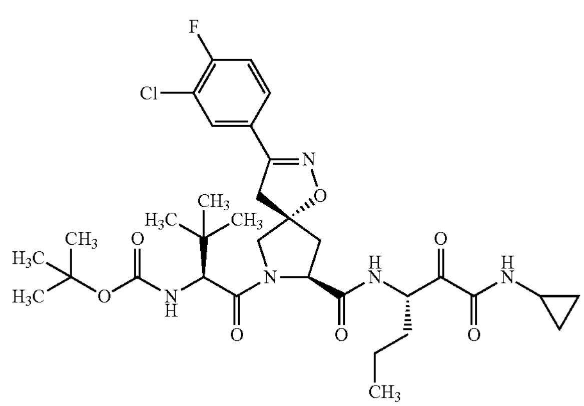 | 629 |

TABLE 1-continued
Exemplary compounds of Formula (I).
| Structure | Compound No. |
|---|---|
| 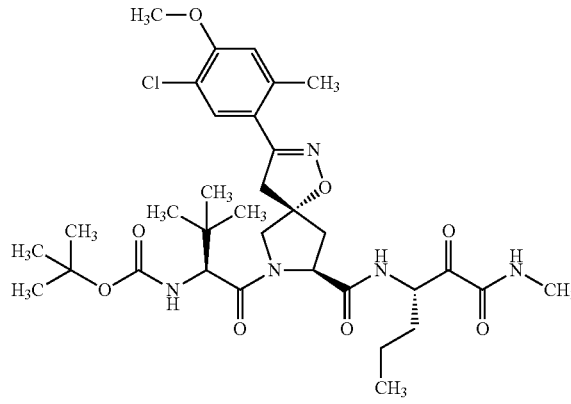 | 630 |
| 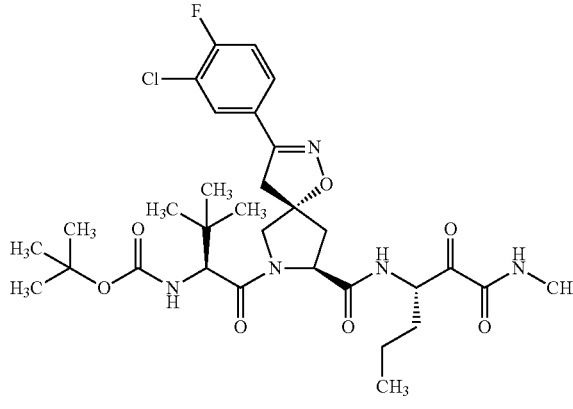 | 631 |
| 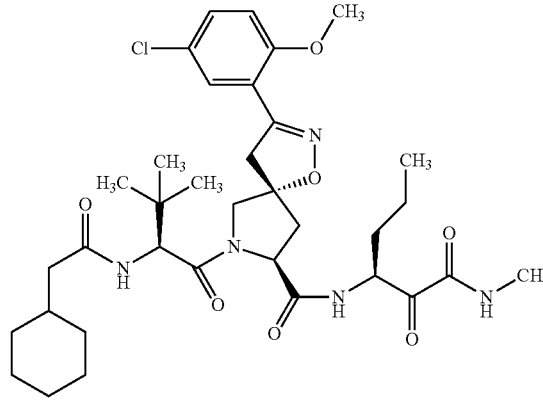 | 632 |

TABLE 1-continued

Exemplary compounds of Formula (I).

| Structure | Compound No. |
|---|---|
| 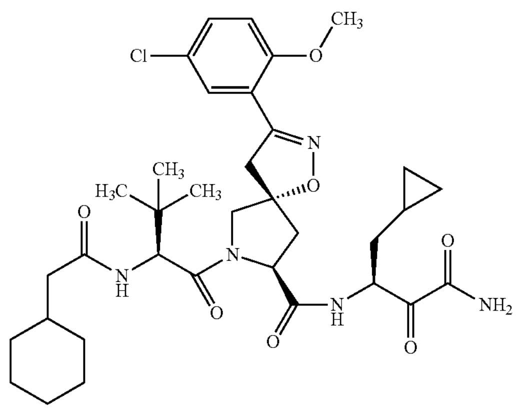 | 633 |
| 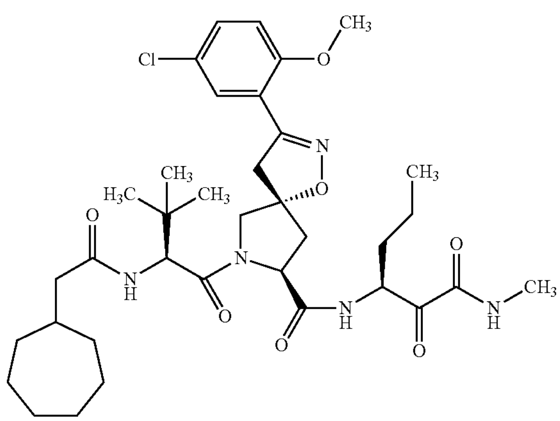 | 634 |
| 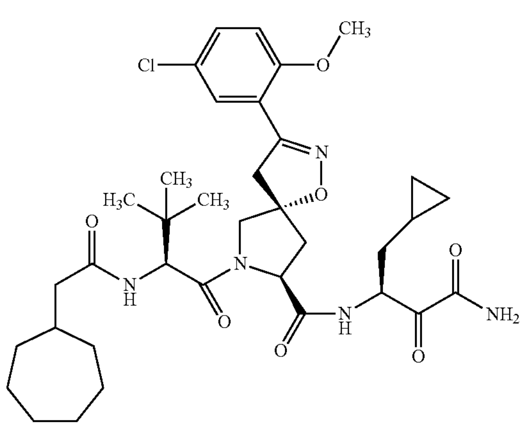 | 635 |

TABLE 1-continued

Exemplary compounds of Formula (I).

| Structure | Compound No. |
|---|---|
| 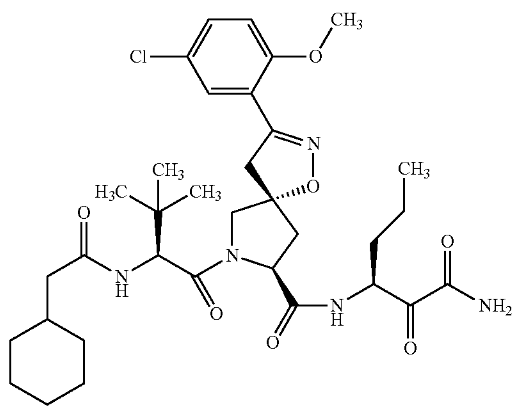 | 636 |
| 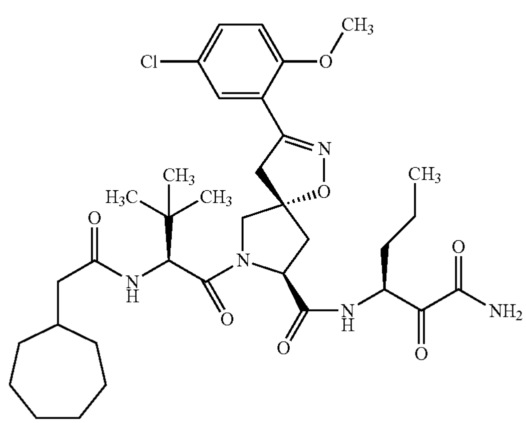 | 637 |
| 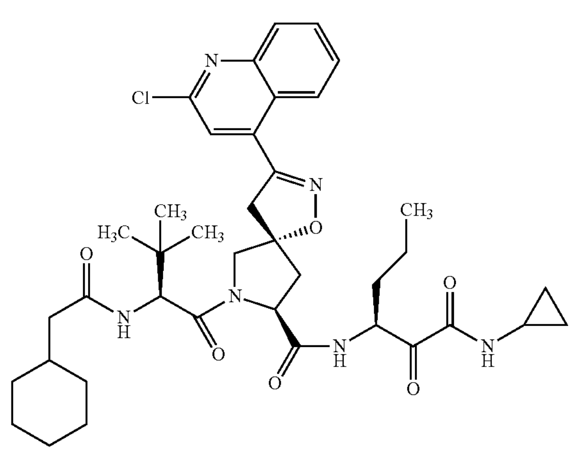 | 638 |

TABLE 1-continued

Exemplary compounds of Formula (I).

| Structure | Compound No. |
|---|---|
| 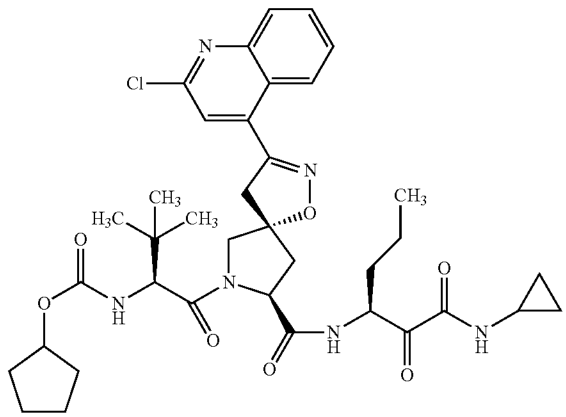 | 639 |
| 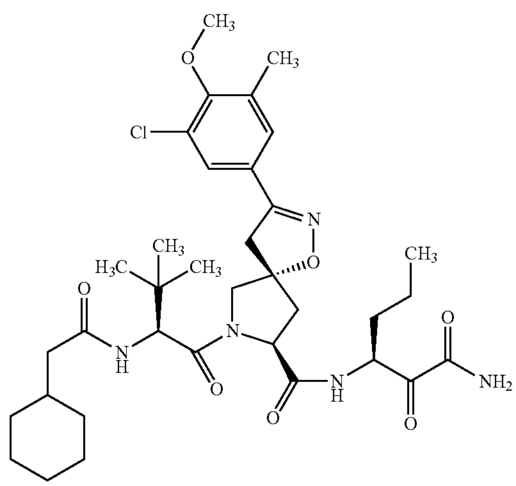 | 640 |
| 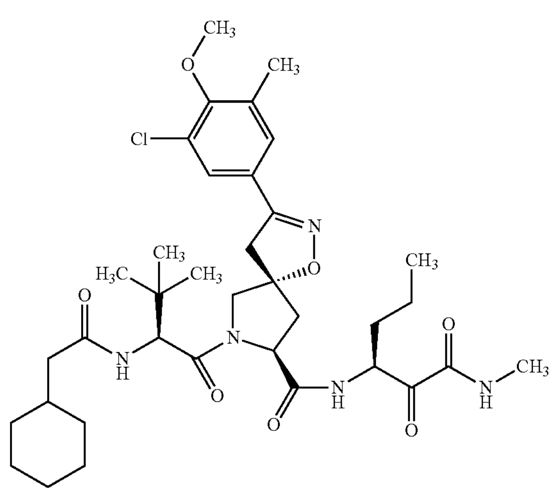 | 641 |

TABLE 1-continued
Exemplary compounds of Formula (I).
| Structure | Compound No. |
|---|---|
| 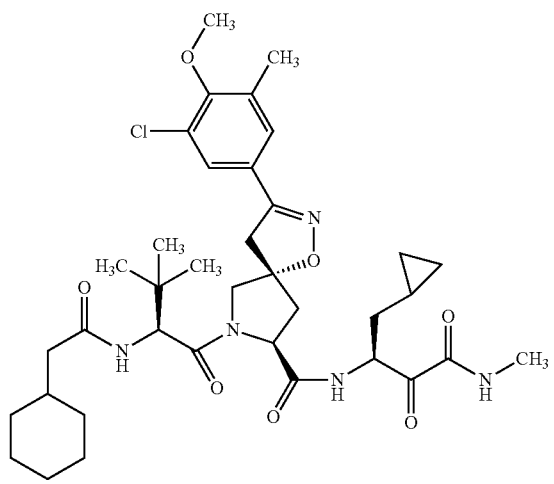 | 642 |
| 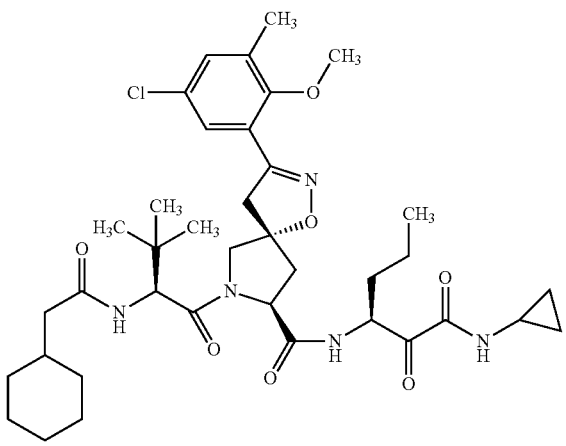 | 643 |
| 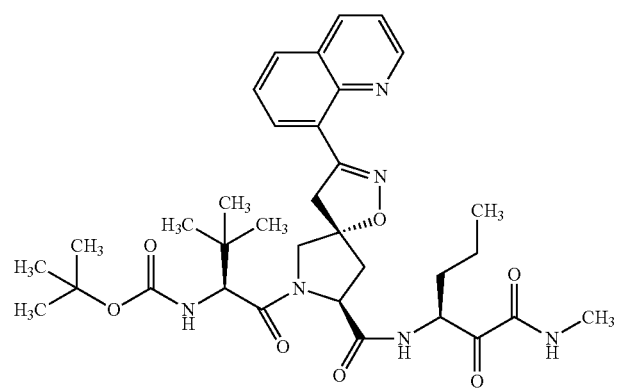 | 644 |

TABLE 1-continued
Exemplary compounds of Formula (I).
| Structure | Compound No. |
|---|---|
| 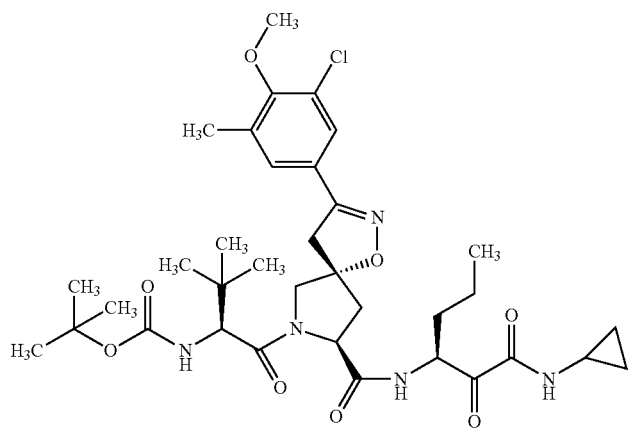 | 645 |
| 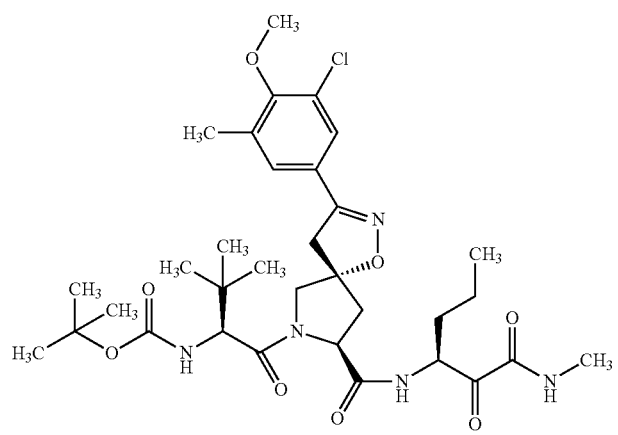 | 646 |
| 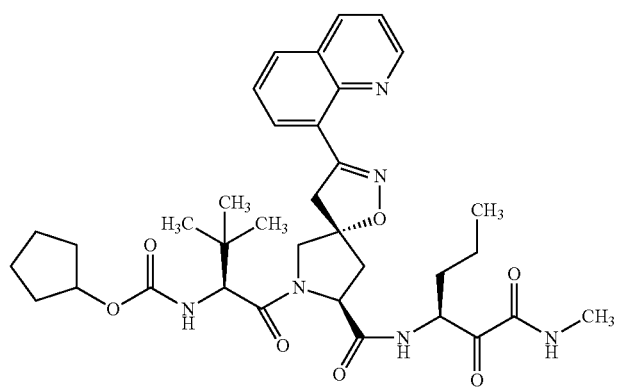 | 647 |

TABLE 1-continued

Exemplary compounds of Formula (I).

| Structure | Compound No. |
|---|---|
| 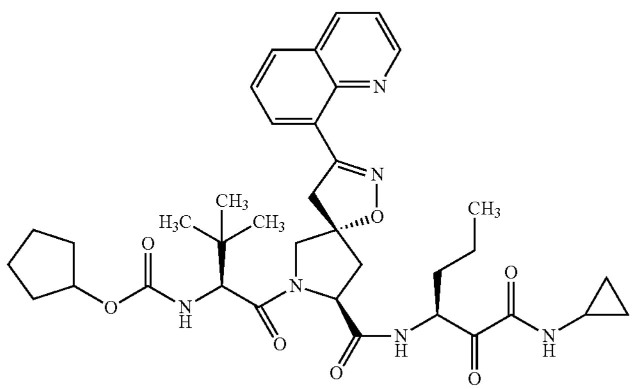 | 648 |
| 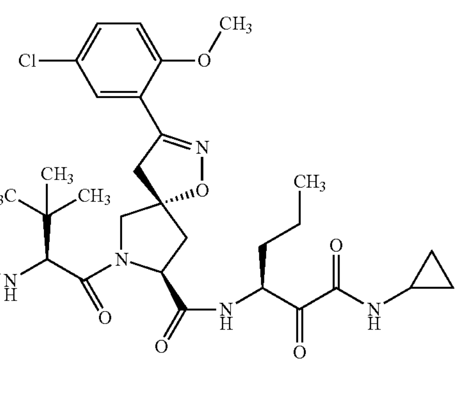 | 649 |
| 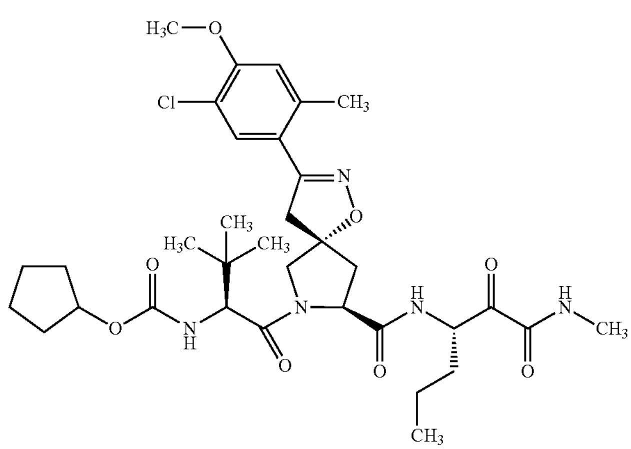 | 650 |

TABLE 1-continued
Exemplary compounds of Formula (I).
| Structure | Compound No. |
|---|---|
| 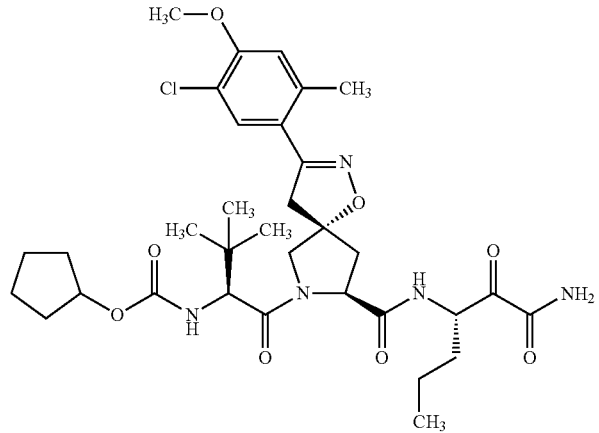 | 651 |
| 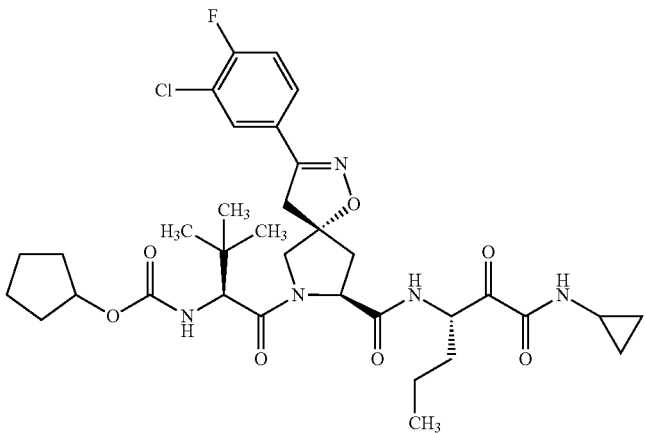 | 652 |
| 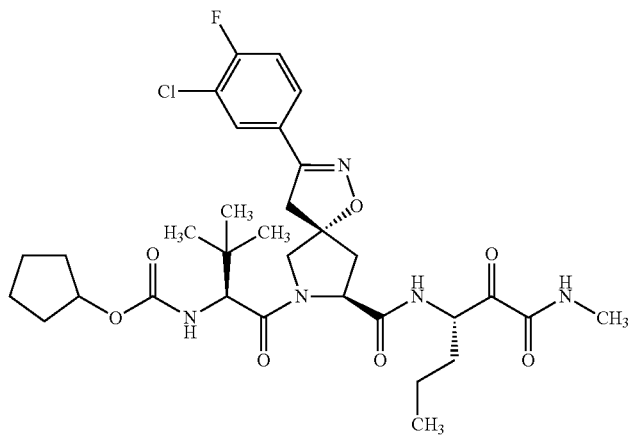 | 653 |

TABLE 1-continued

Exemplary compounds of Formula (I).

| Structure | Compound No. |
|---|---|
| 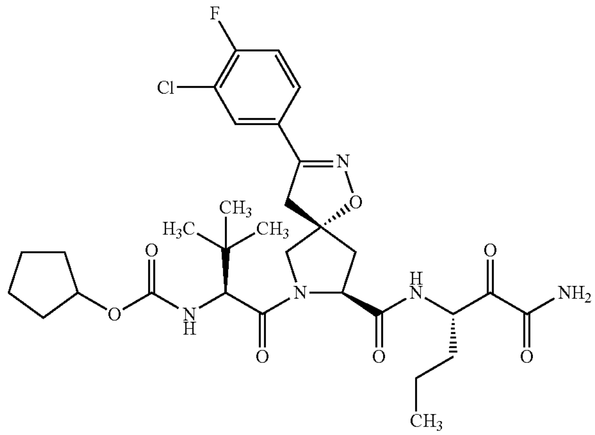 | 654 |
| 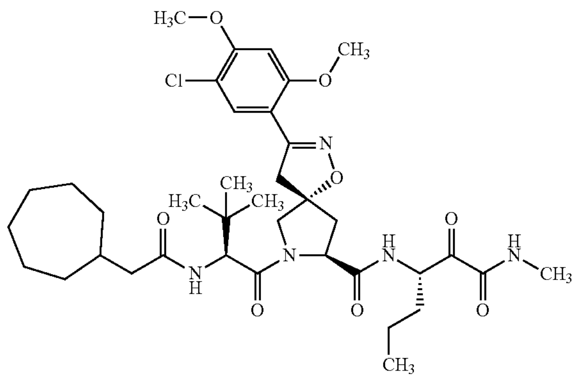 | 655 |
| 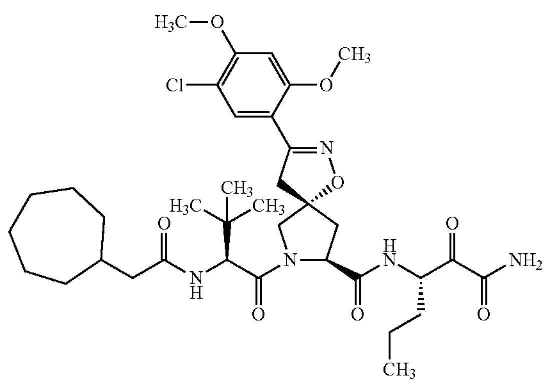 | 656 |
| 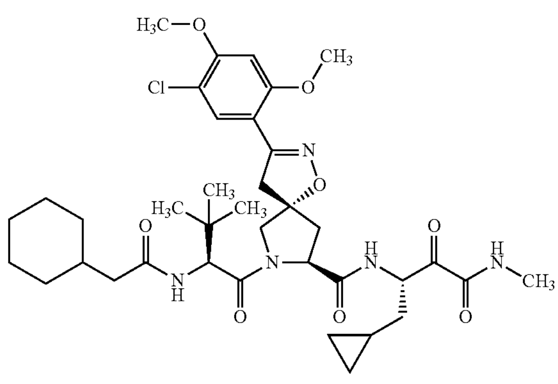 | 657 |

TABLE 1-continued

Exemplary compounds of Formula (I).

| Structure | Compound No. |
|---|---|
| 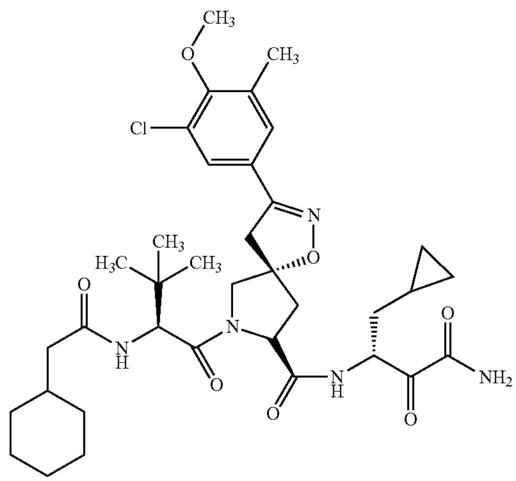 | 658 |
| 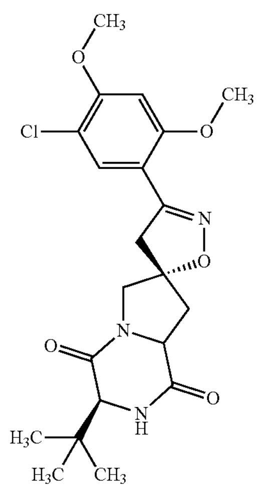 | 659 |
| 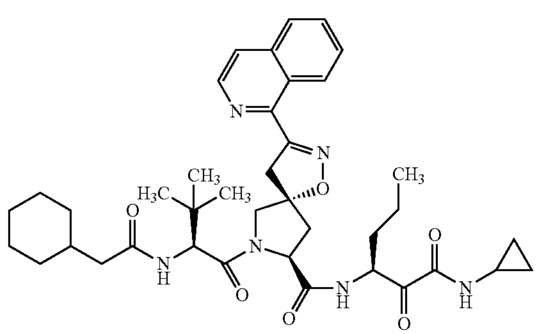 | 660 |

TABLE 1-continued

Exemplary compounds of Formula (I).

| Structure | Compound No. |
|---|---|
| 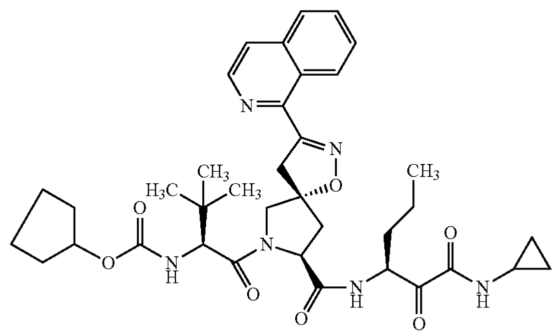 | 661 |
| 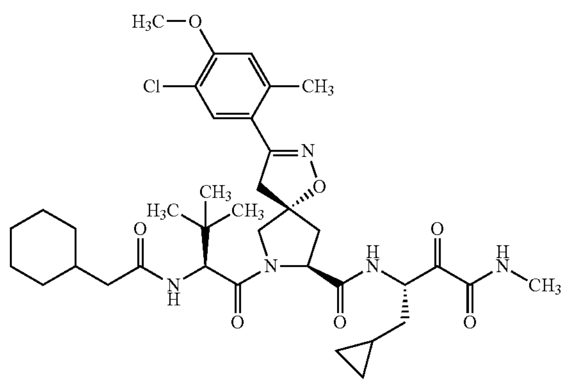 | 662 |
| 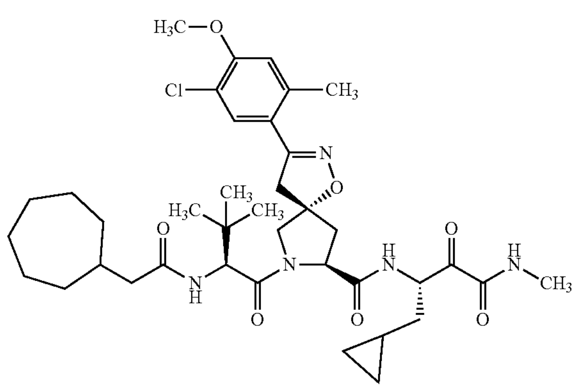 | 663 |
| 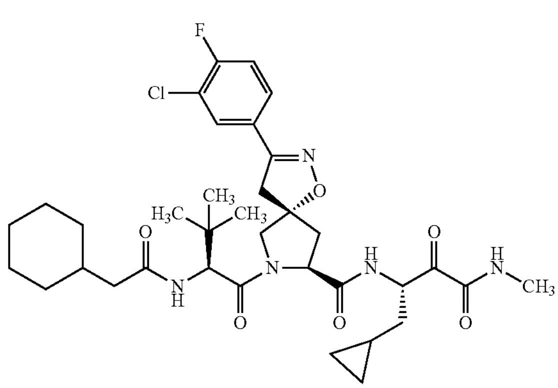 | 664 |

TABLE 1-continued

Exemplary compounds of Formula (I).

| Structure | Compound No. |
|---|---|
| 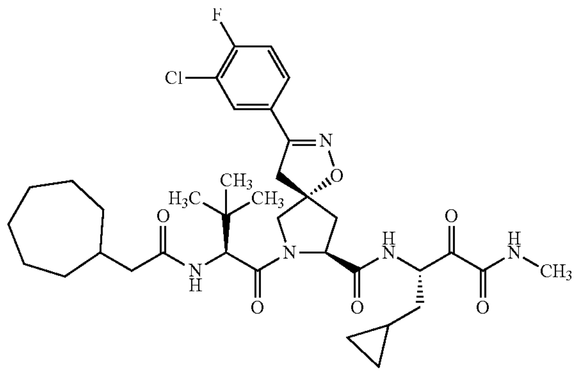 | 665 |
| 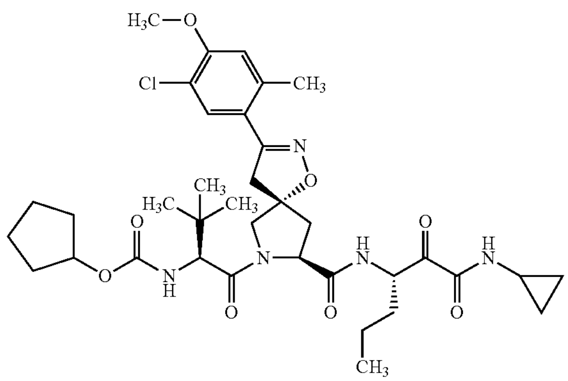 | 666 |
| 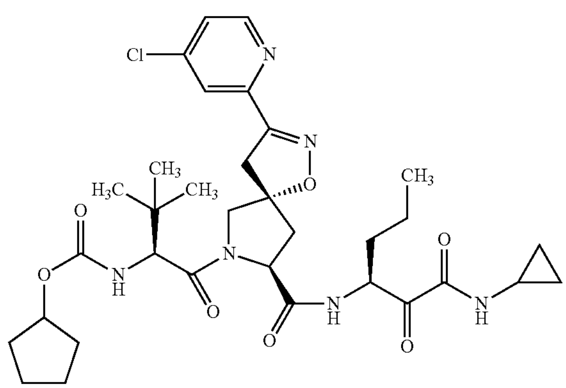 | 667 |
| 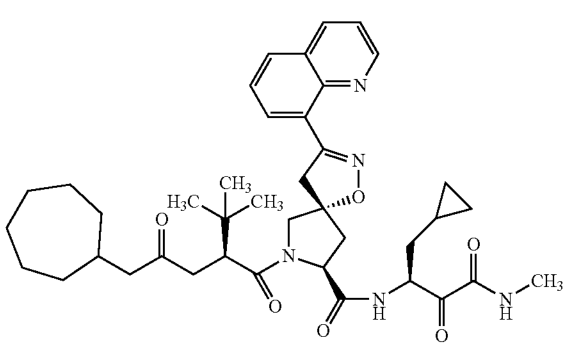 | 668 |

TABLE 1-continued
Exemplary compounds of Formula (I).
| Structure | Compound No. |
|---|---|
| 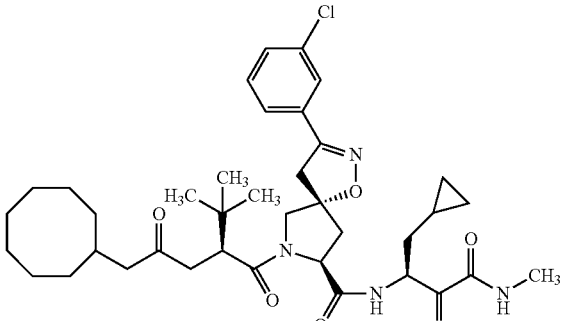 | 669 |
| 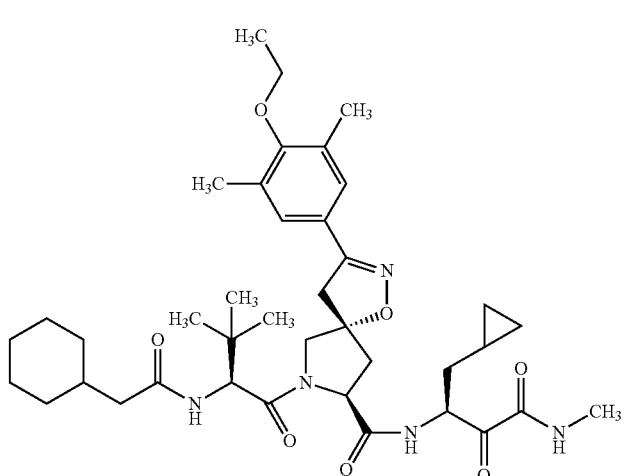 | 670 |
| 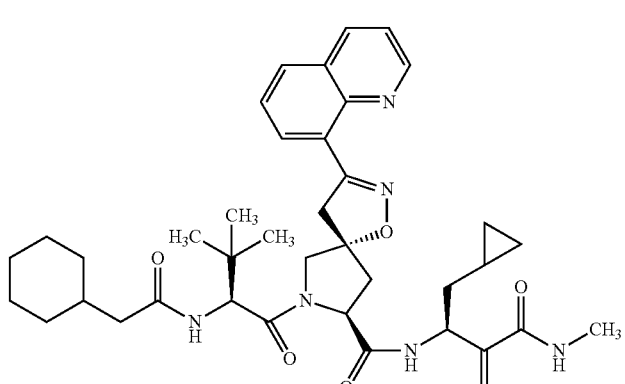 | 671 |
| 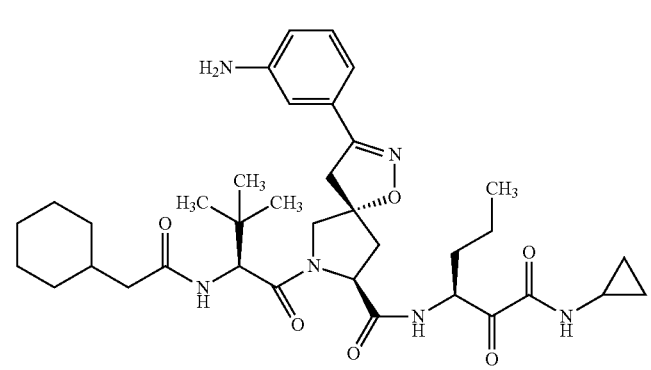 | 672 |

TABLE 1-continued

Exemplary compounds of Formula (I).

| Structure | Compound No. |
|---|---|
| 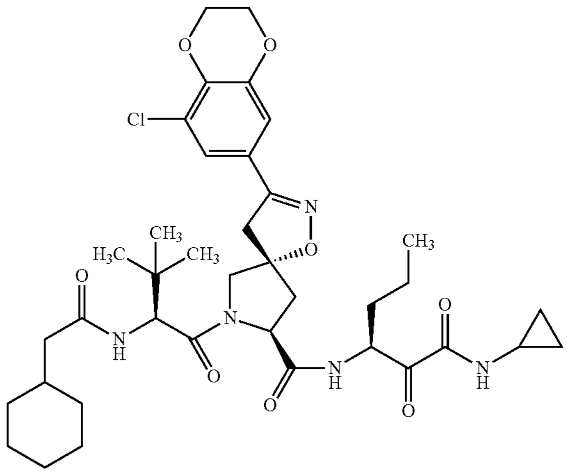 | 673 |
| 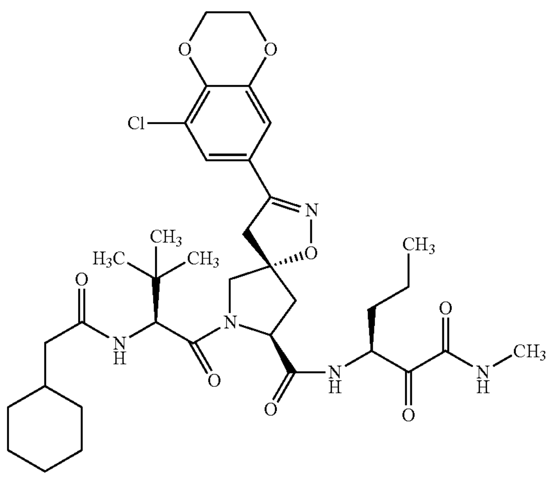 | 674 |
| 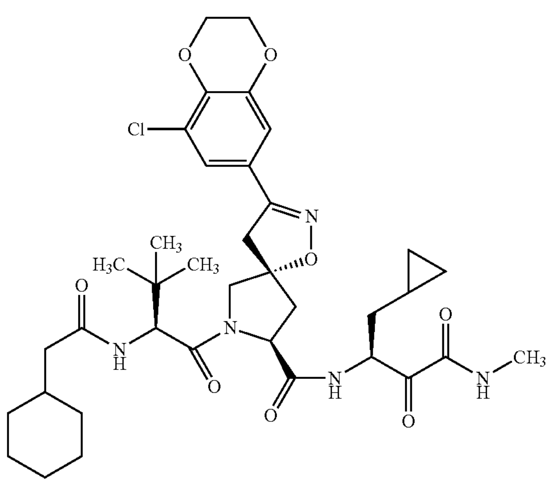 | 675 |

TABLE 1-continued

Exemplary compounds of Formula (I).

| Structure | Compound No. |
|---|---|
| 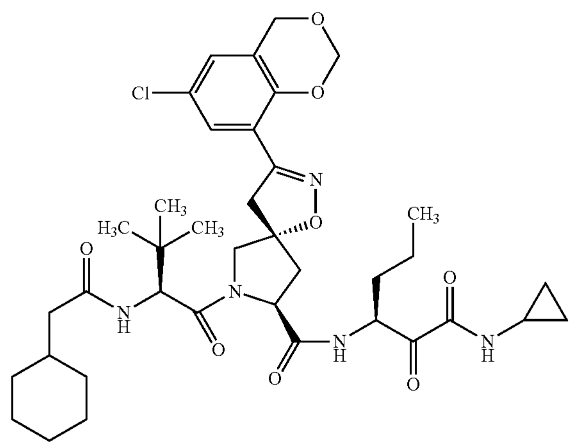 | 676 |
| 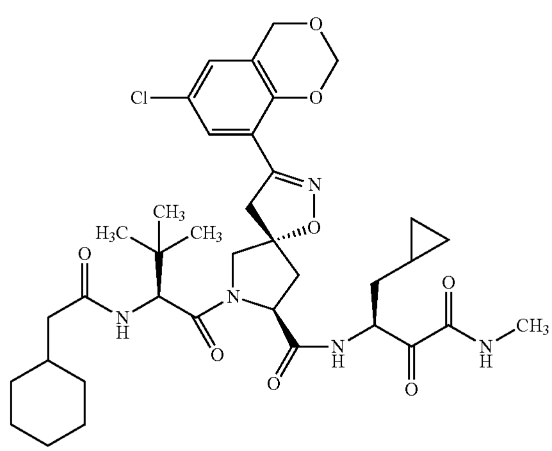 | 677 |
| 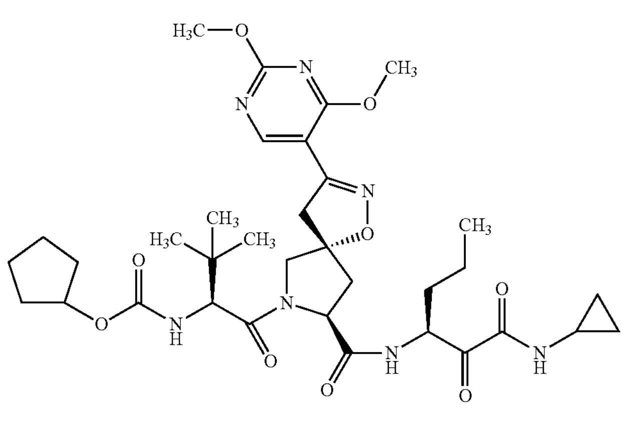 | 678 |

TABLE 1-continued

Exemplary compounds of Formula (I).

| Structure | Compound No. |
|---|---|
| 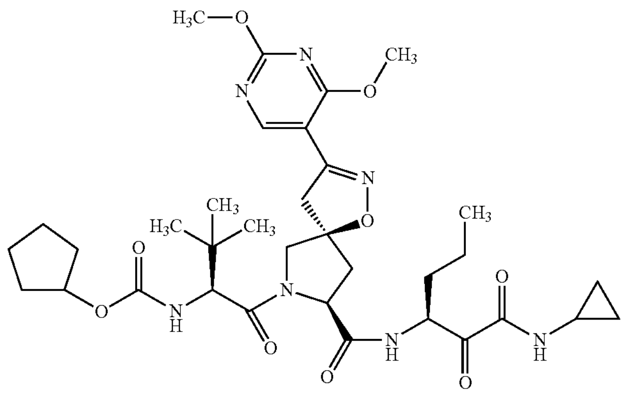 | 679 |
| 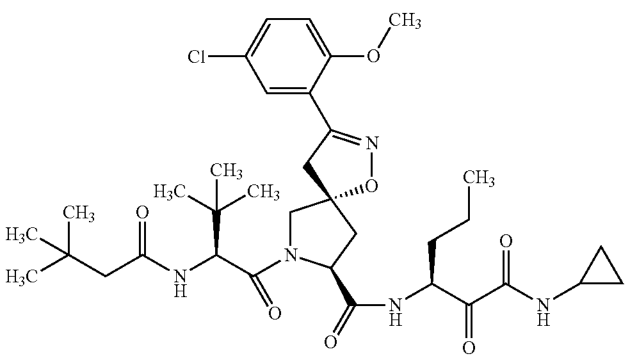 | 680 |
| 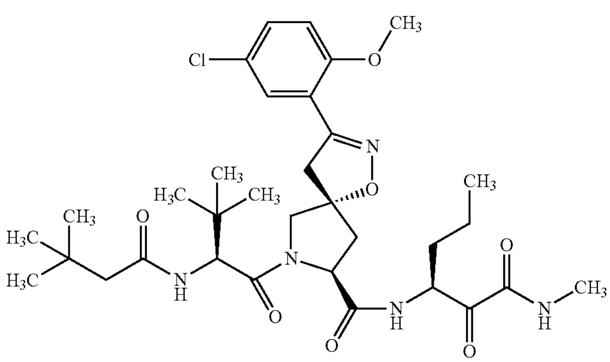 | 681 |
| 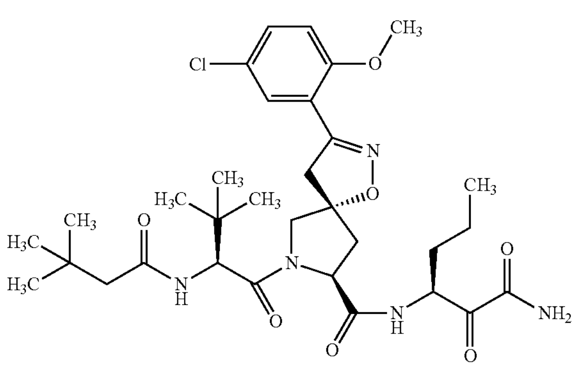 | 682 |

TABLE 1-continued

Exemplary compounds of Formula (I).

| Structure | Compound No. |
|---|---|
| 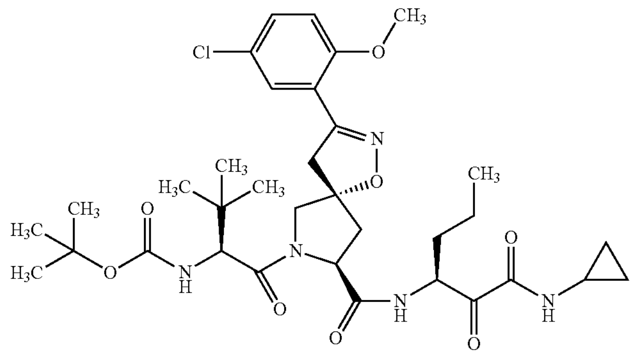 | 683 |
| 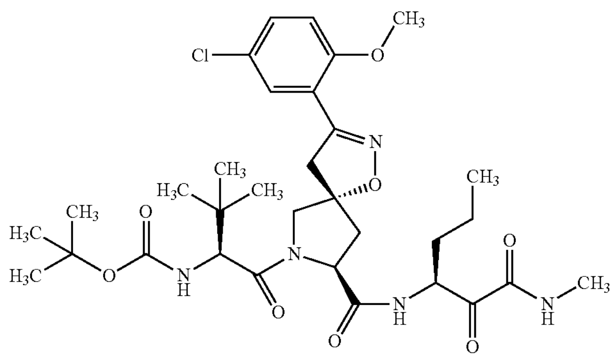 | 684 |
| 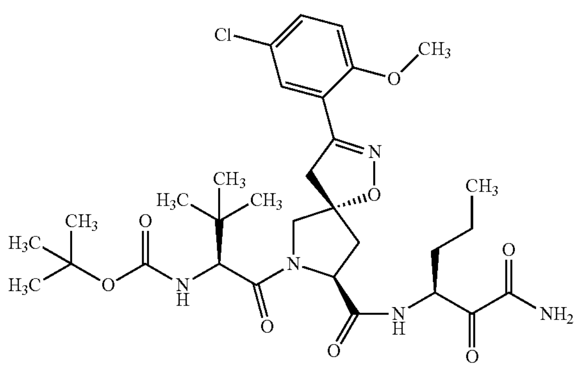 | 685 |
| 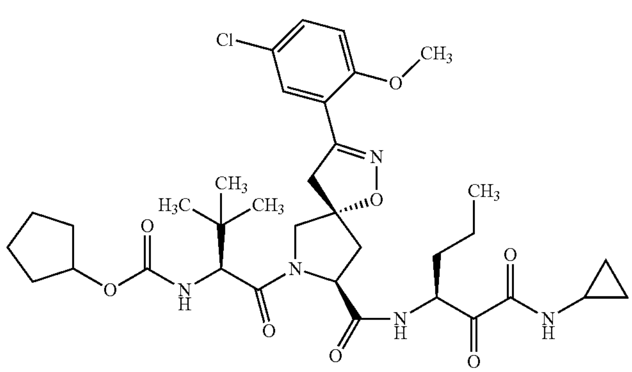 | 686 |

TABLE 1-continued

Exemplary compounds of Formula (I).

| Structure | Compound No. |
|---|---|
| 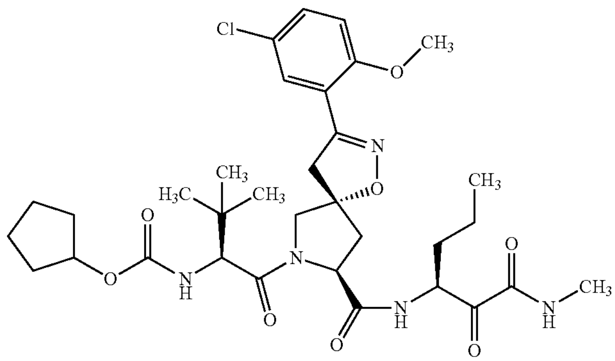 | 687 |
| 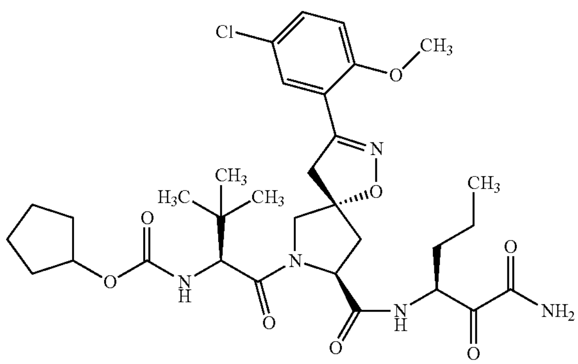 | 688 |
| 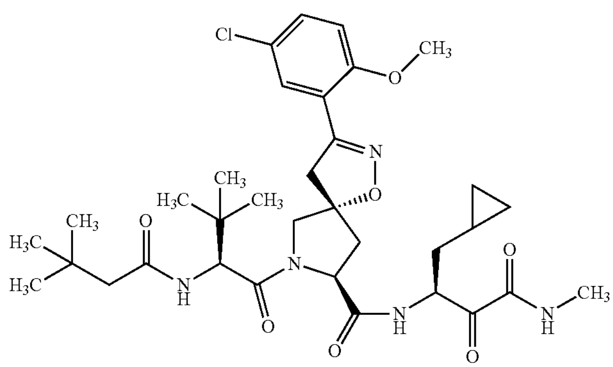 | 689 |
| 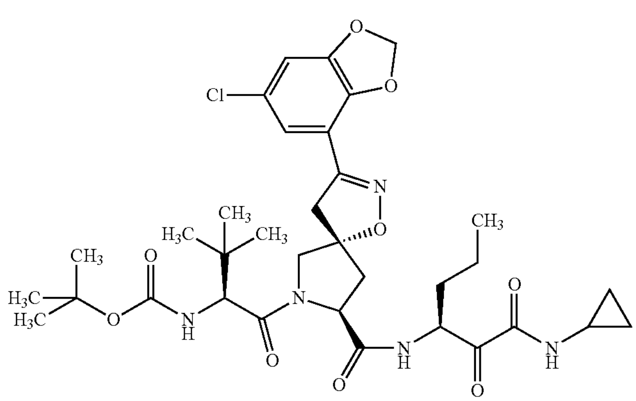 | 690 |

TABLE 1-continued

Exemplary compounds of Formula (I).

| Structure | Compound No. |
|---|---|
| 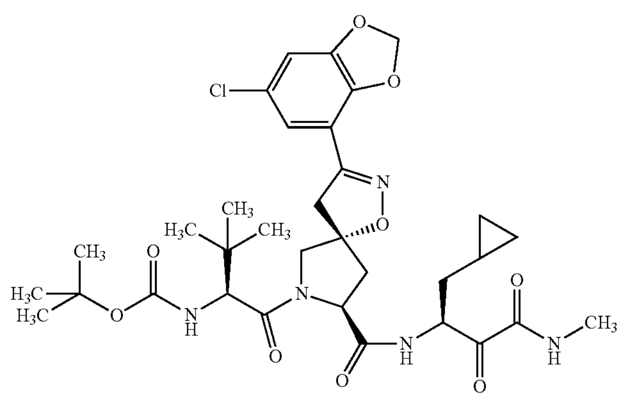 | 691 |
| 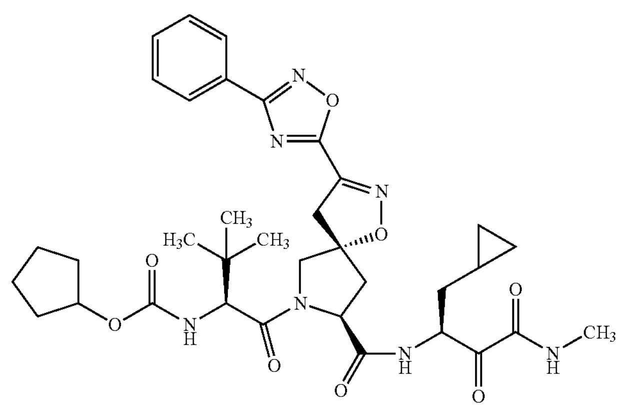 | 692 |
| 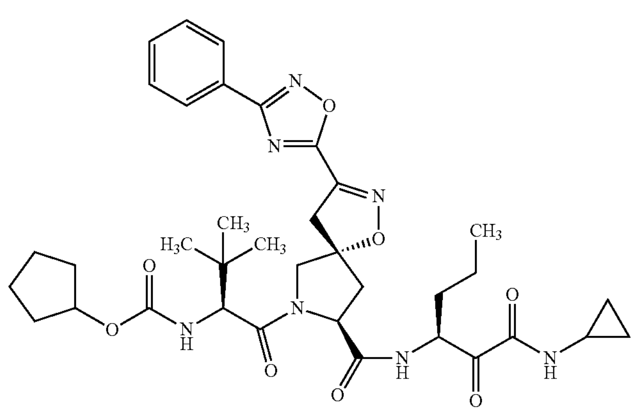 | 693 |

TABLE 1-continued

Exemplary compounds of Formula (I).

| Structure | Compound No. |
|---|---|
| 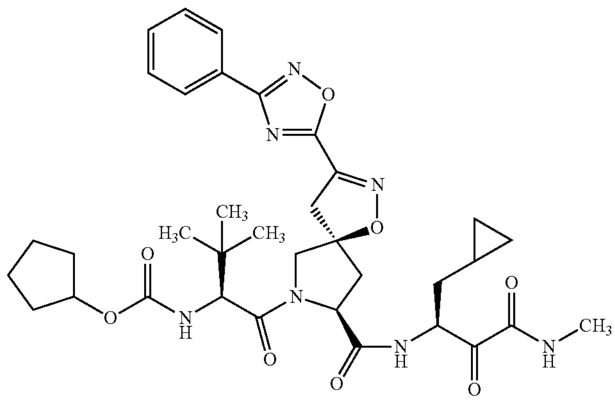 | 694 |
| 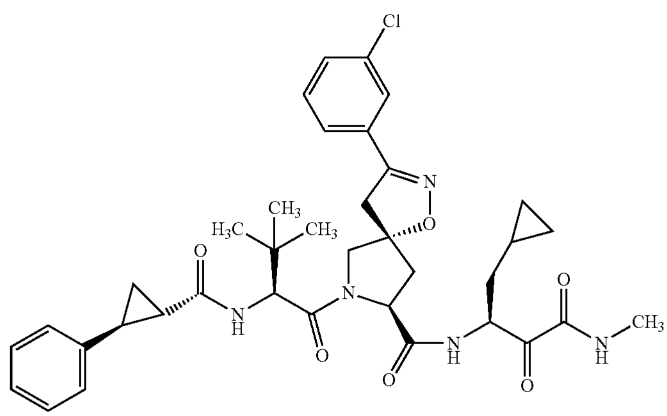 | 695 |
| 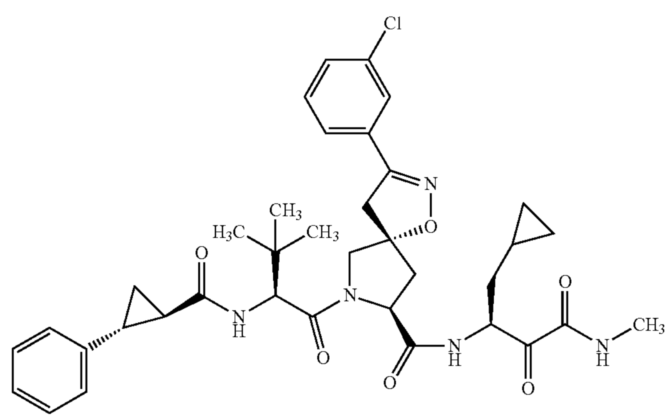 | 696 |

TABLE 1-continued

Exemplary compounds of Formula (I).

| Structure | Compound No. |
|---|---|
| 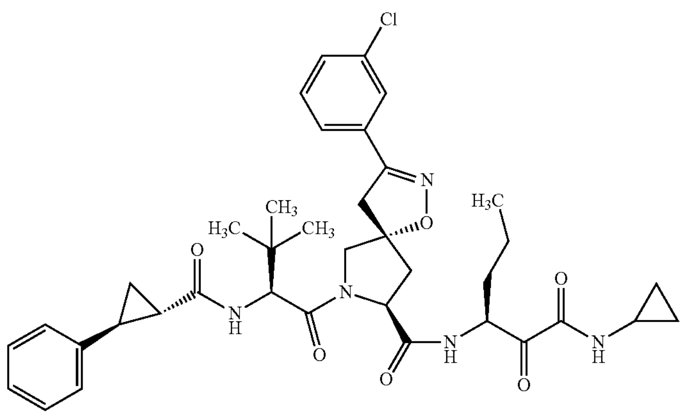 | 697 |
| 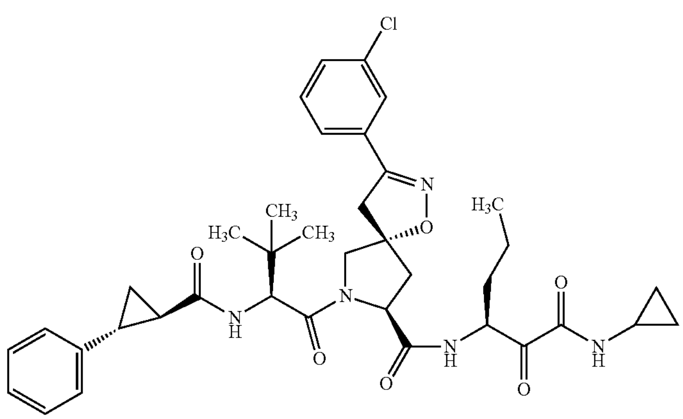 | 698 |
| 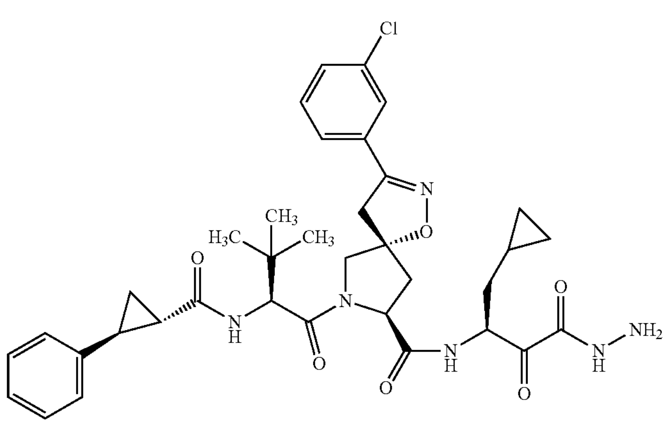 | 699 |

TABLE 1-continued

Exemplary compounds of Formula (I).

| Structure | Compound No. |
|---|---|
| 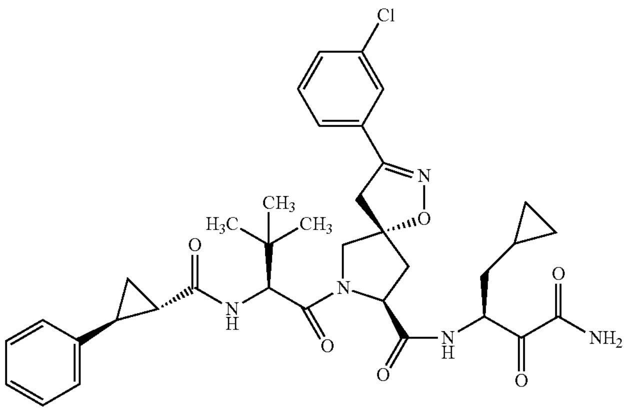 | 700 |
| 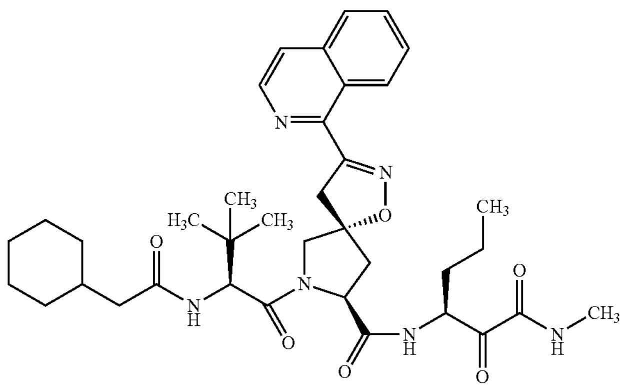 | 701 |
| 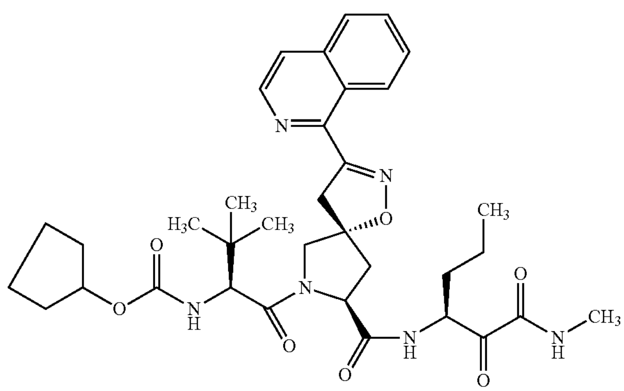 | 702 |
| 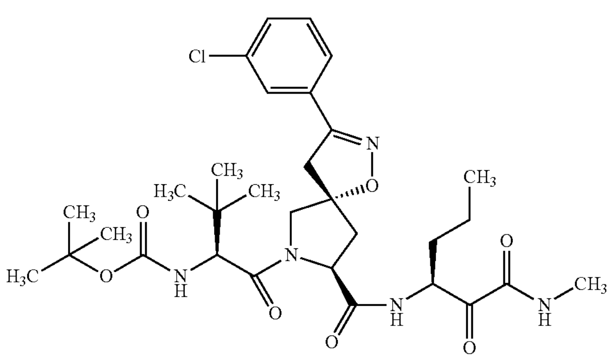 | 703 |

TABLE 1-continued

Exemplary compounds of Formula (I).

| Structure | Compound No. |
|---|---|
| 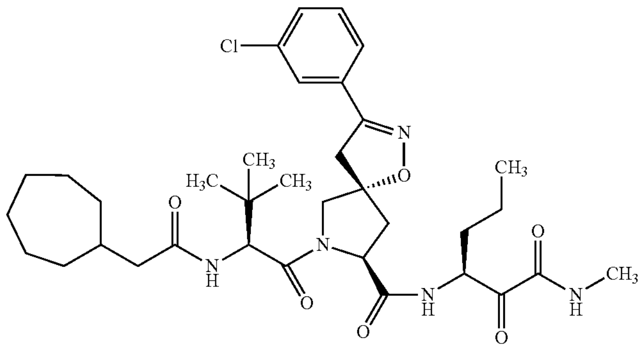 | 704 |
| 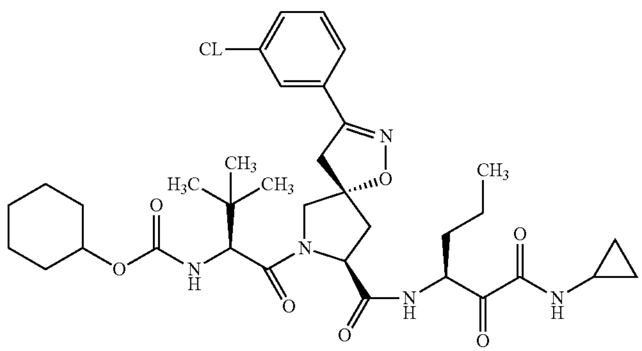 | 705 |
| 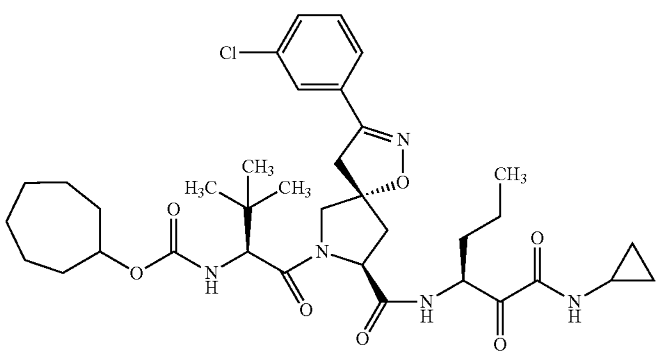 | 706 |
| 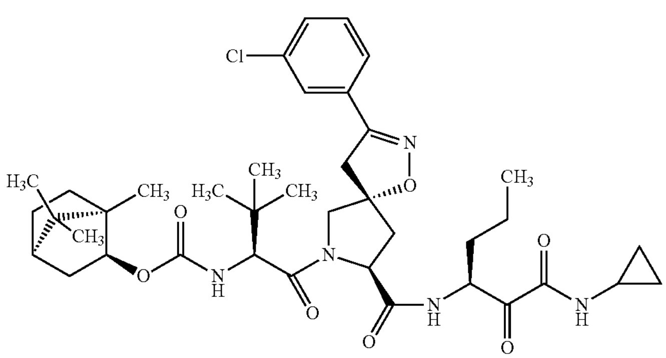 | 707 |

TABLE 1-continued

Exemplary compounds of Formula (I).

| Structure | Compound No. |
|---|---|
| 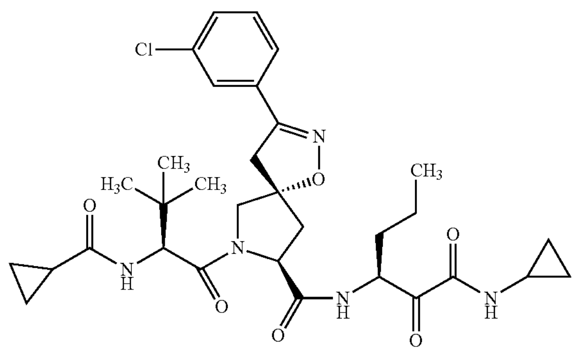 | 708 |
| 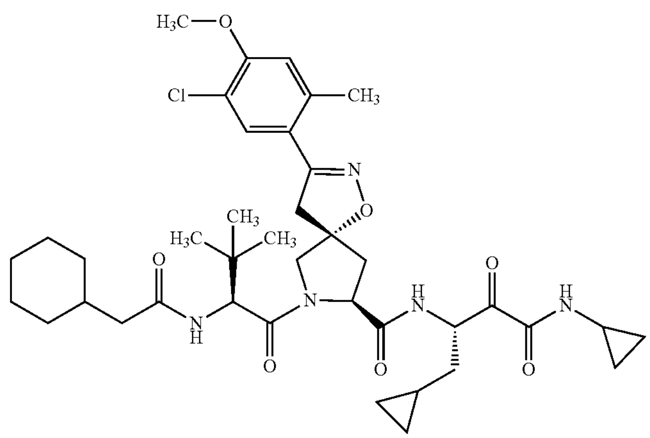 | 709 |
| 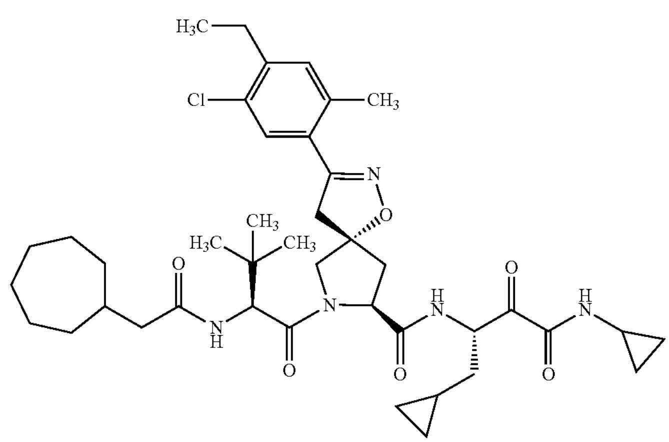 | 710 |

TABLE 1-continued

Exemplary compounds of Formula (I).

| Structure | Compound No. |
|---|---|
| 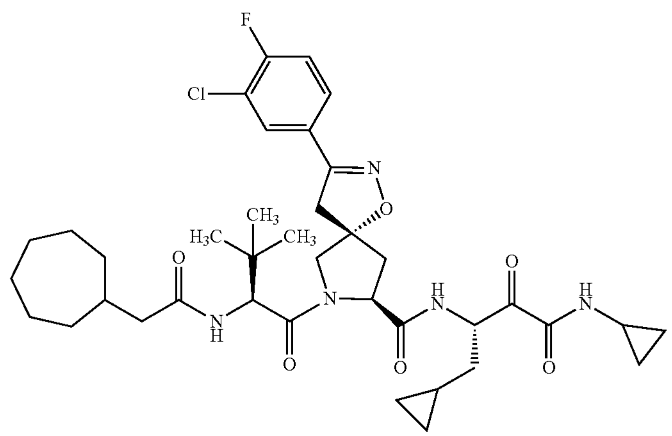 | 711 |
| 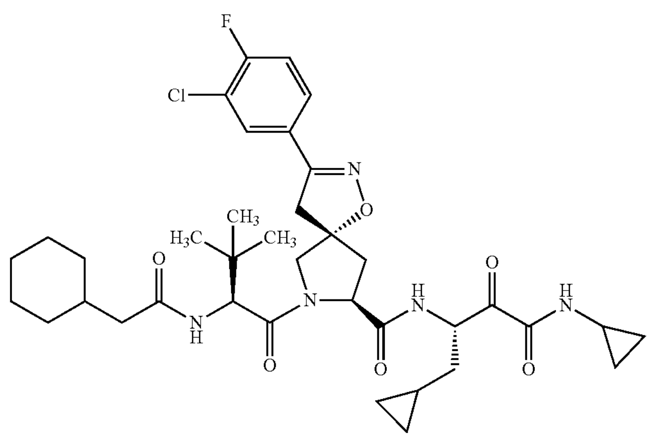 | 712 |
| 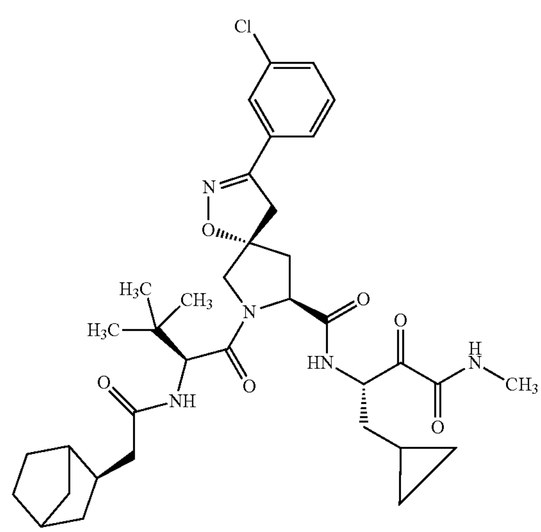 | 713 |

TABLE 1-continued

Exemplary compounds of Formula (I).

| Structure | Compound No. |
|---|---|
| 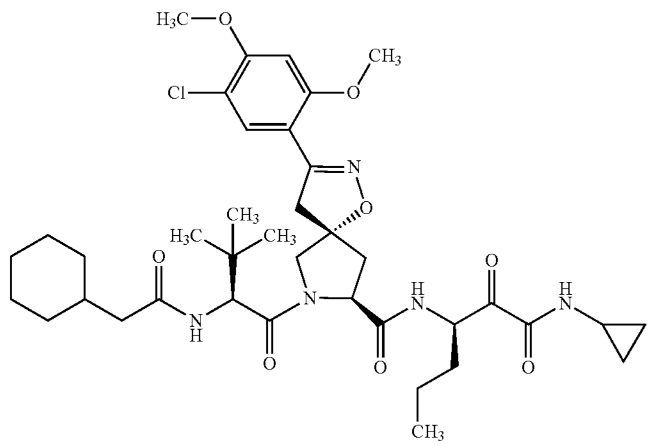 | 714 |
| 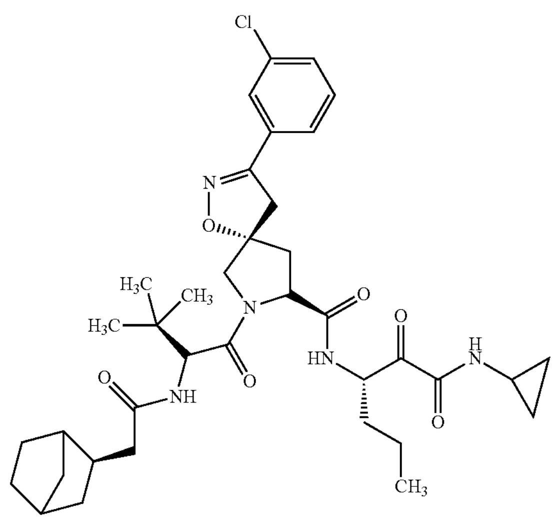 | 715 |
| 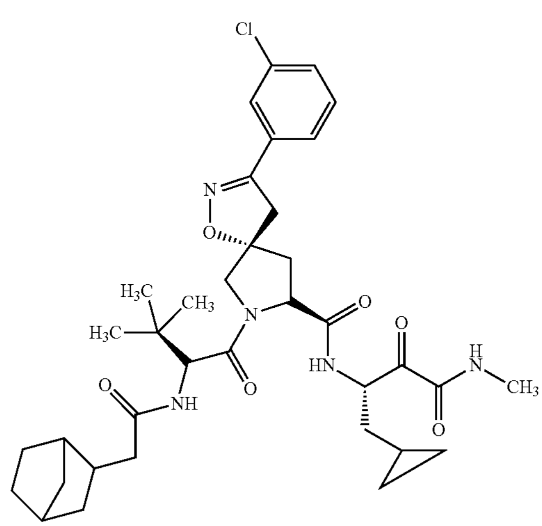 | 716 |

TABLE 1-continued
Exemplary compounds of Formula (I).
| Structure | Compound No. |
|---|---|
| 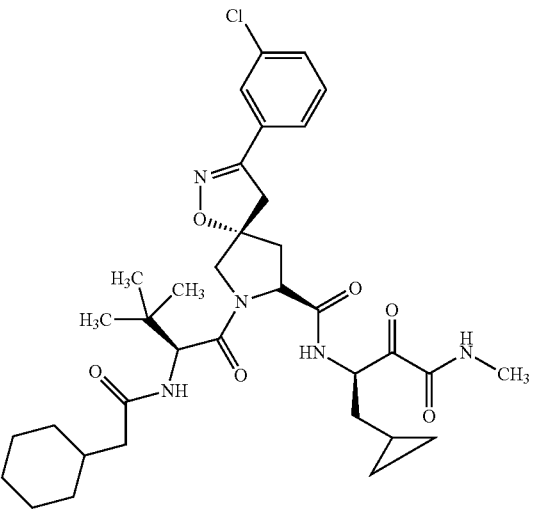 | 717 |
| 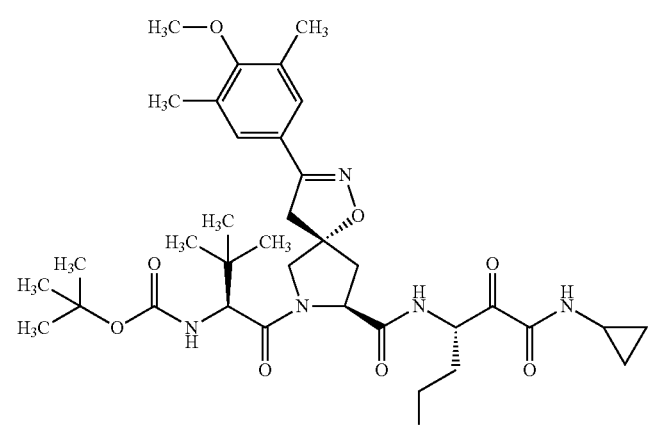 | 718 |
| 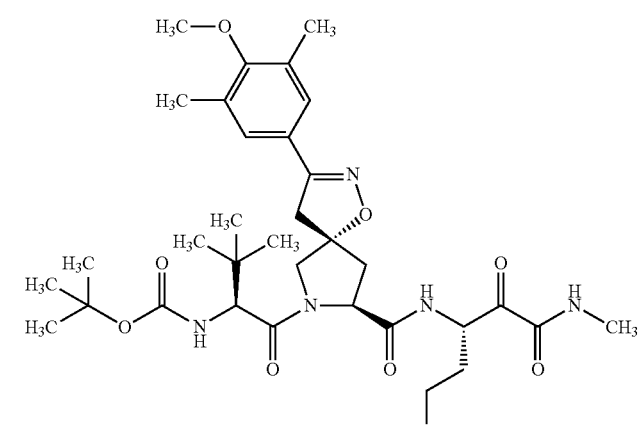 | 719 |

TABLE 1-continued
Exemplary compounds of Formula (I).
| Structure | Compound No. |
|---|---|
| 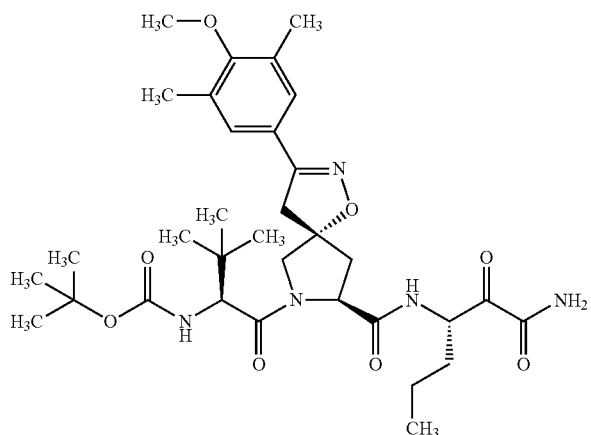 | 720 |
| 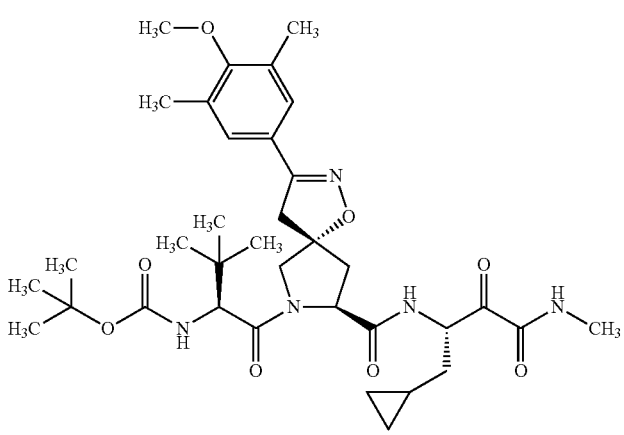 | 721 |
| 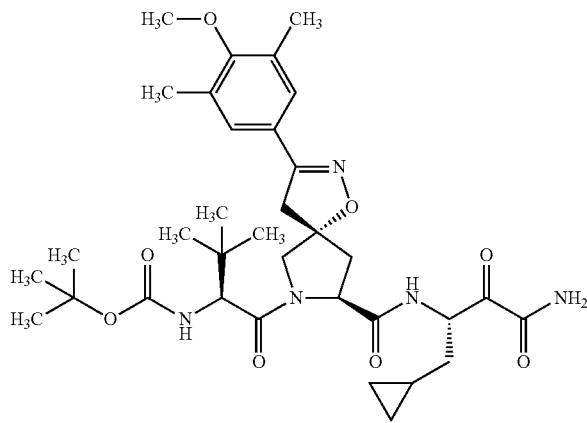 | 722 |

TABLE 1-continued

Exemplary compounds of Formula (I).

| Structure | Compound No. |
|---|---|
| 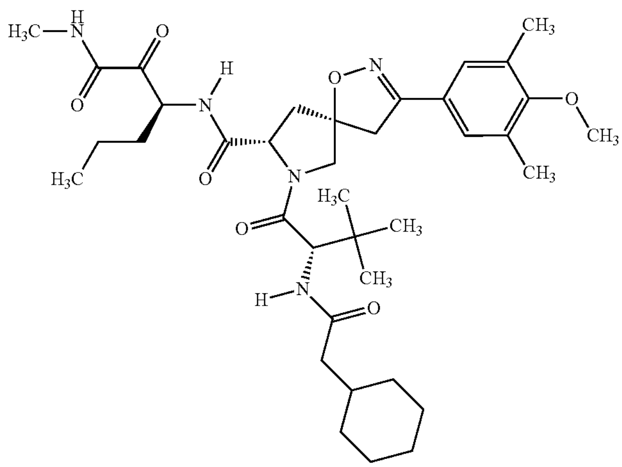 | 723 |
| 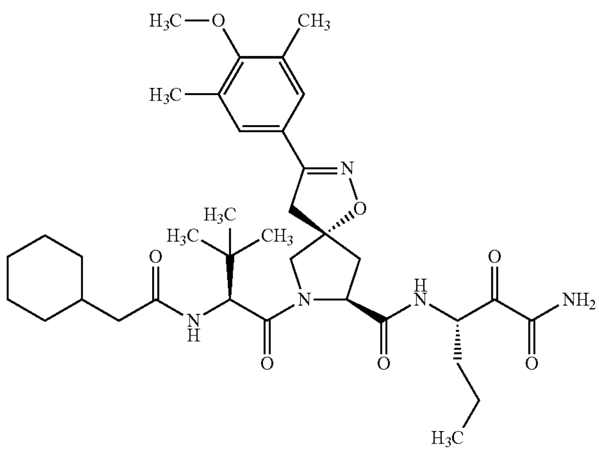 | 724 |
| 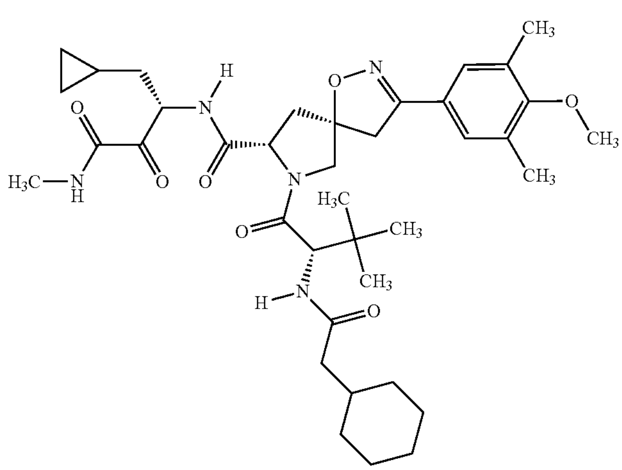 | 725 |

TABLE 1-continued
Exemplary compounds of Formula (I).
| Structure | Compound No. |
|---|---|
| 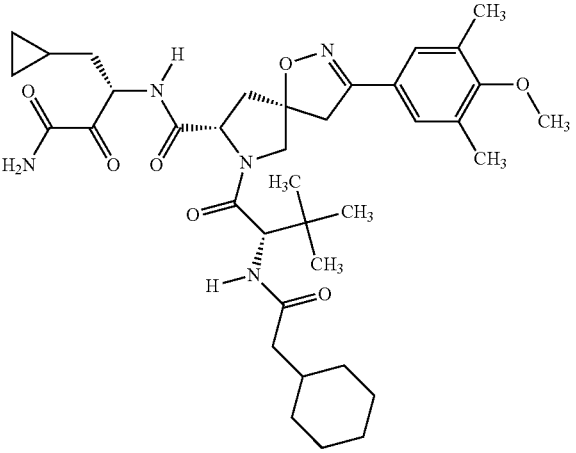 | 726 |
| 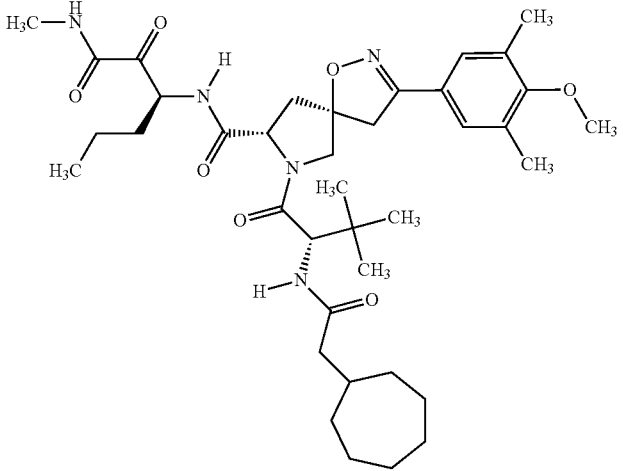 | 727 |
| 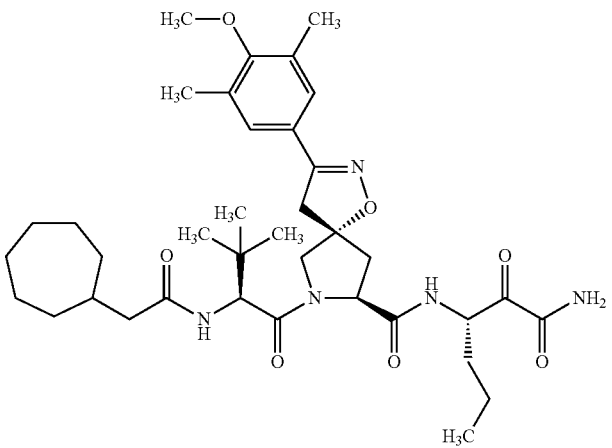 | 728 |

TABLE 1-continued

Exemplary compounds of Formula (I).

| Structure | Compound No. |
|---|---|
| 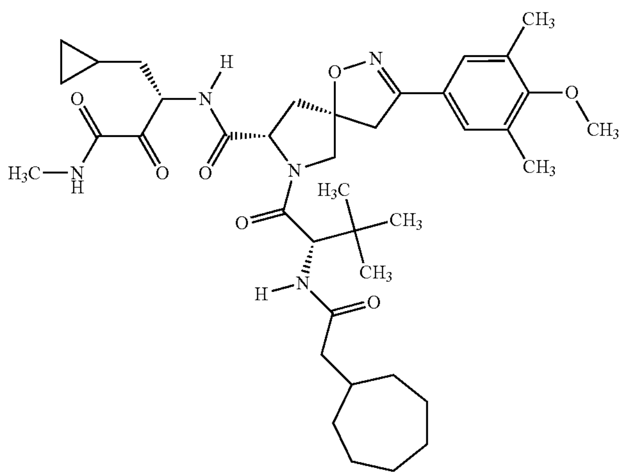 | 729 |
| 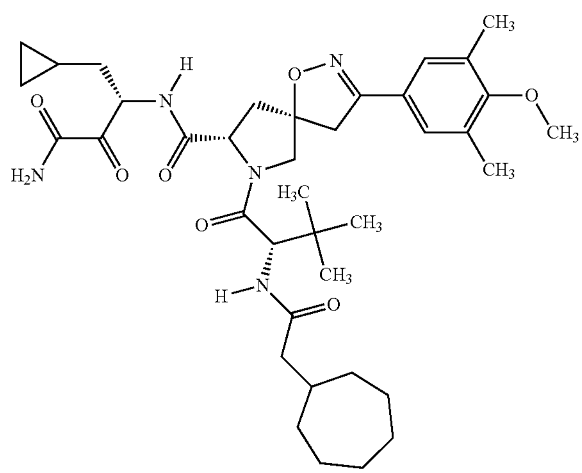 | 730 |
| 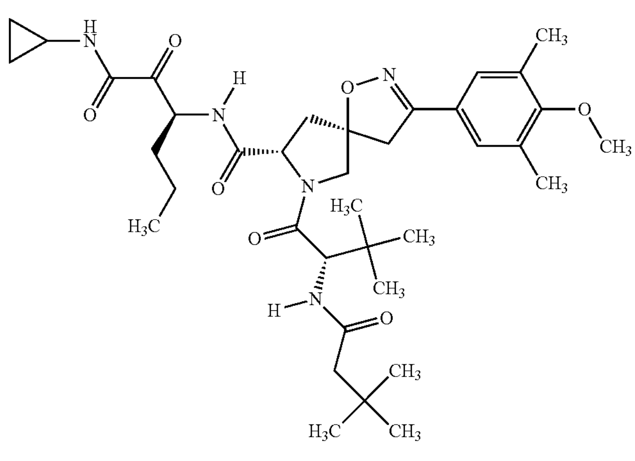 | 731 |

TABLE 1-continued
Exemplary compounds of Formula (I).
| Structure | Compound No. |
|---|---|
| 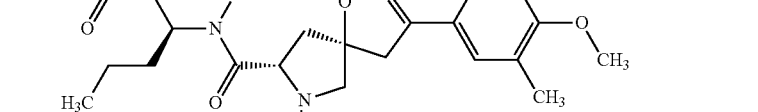 | 732 |
| 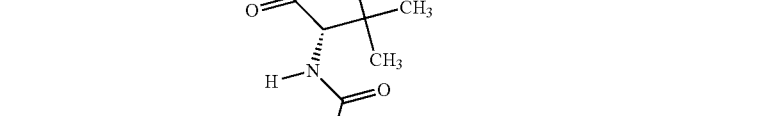 | 733 |
| 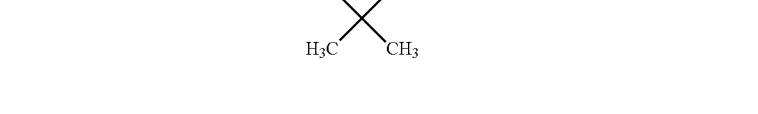 | 734 |

TABLE 1-continued
Exemplary compounds of Formula (I).
| Structure | Compound No. |
|---|---|
| 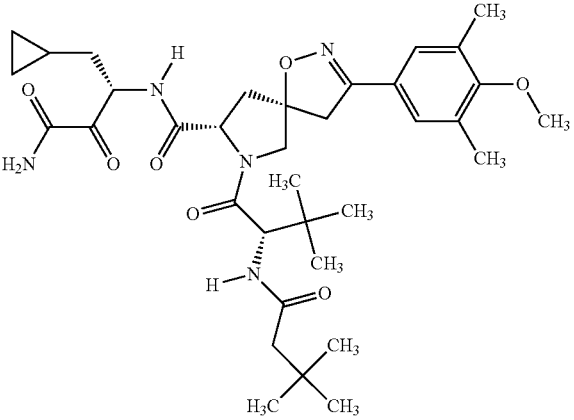 | 735 |
| 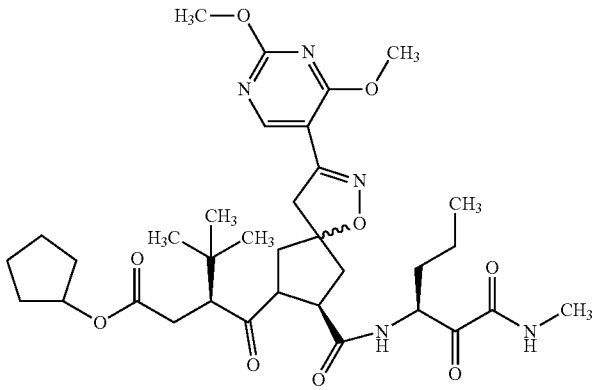 | 736 |
| 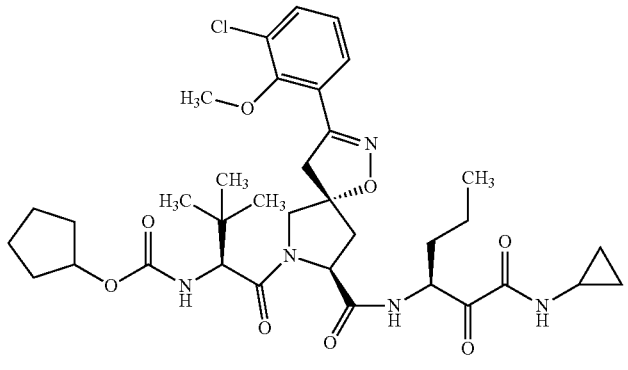 | 737 |
| 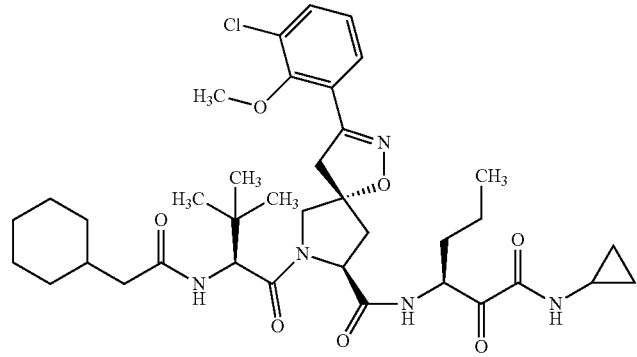 | 738 |

TABLE 1-continued

Exemplary compounds of Formula (I).

| Structure | Compound No. |
|---|---|
| 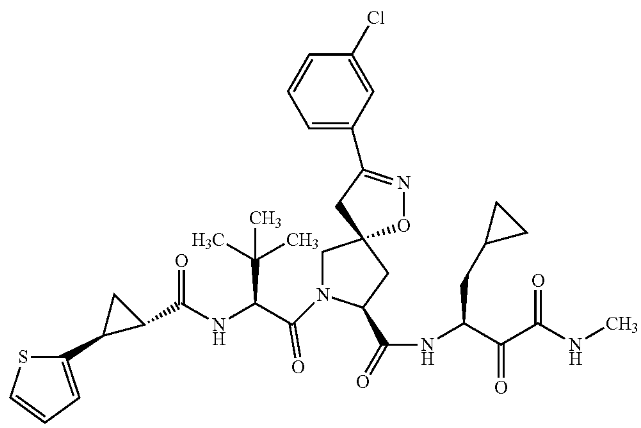 | 739 |
| 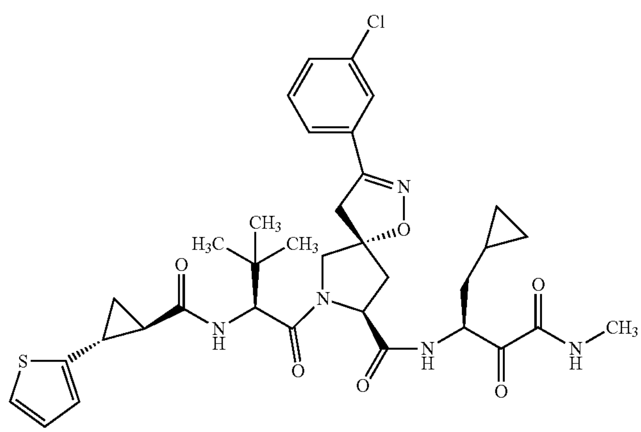 | 740 |
| 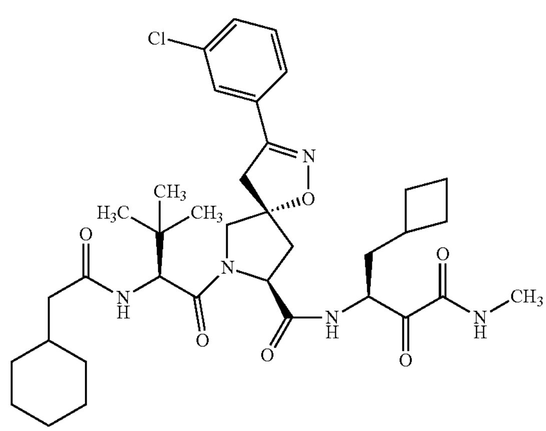 | 741 |

TABLE 1-continued

Exemplary compounds of Formula (I).

| Structure | Compound No. |
|---|---|
| 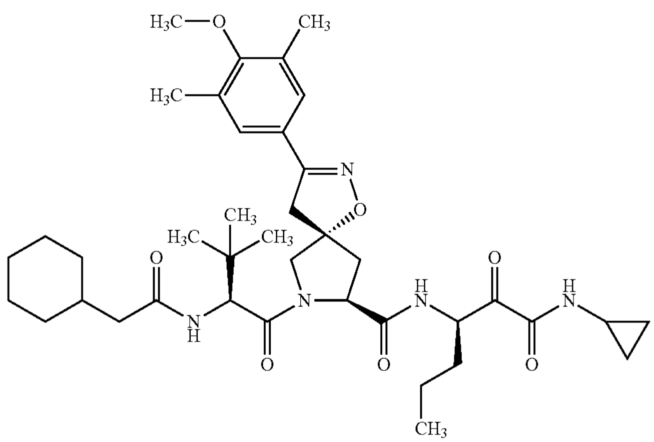 | 742 |
| 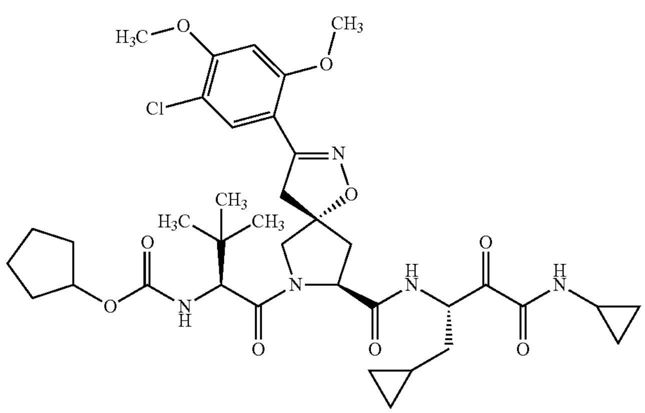 | 743 |
| 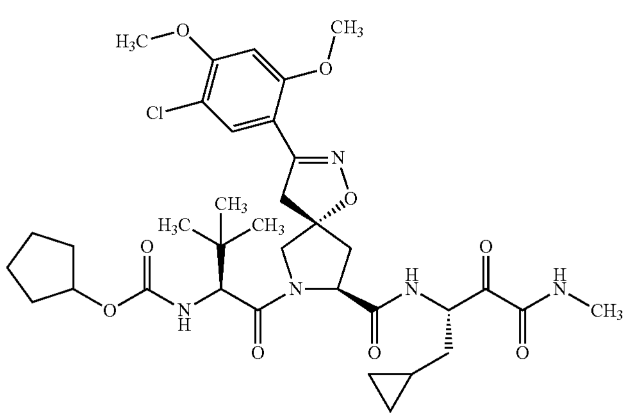 | 744 |

TABLE 1-continued

Exemplary compounds of Formula (I).

| Structure | Compound No. |
|---|---|
| 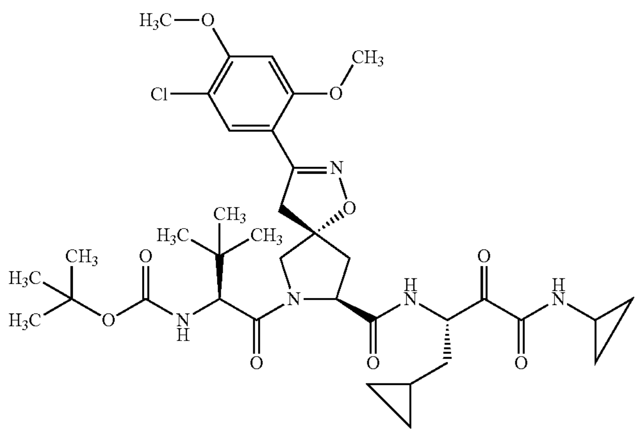 | 745 |
| 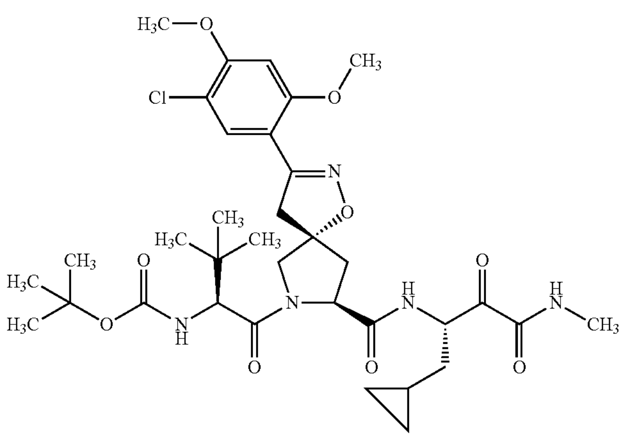 | 746 |
| 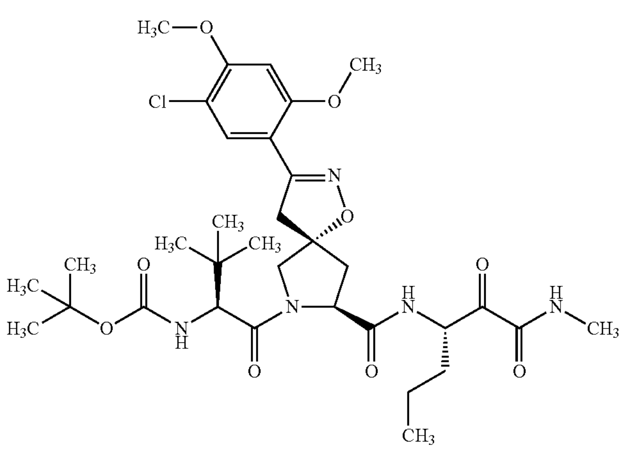 | 747 |

TABLE 1-continued

Exemplary compounds of Formula (I).

| Structure | Compound No. |
|---|---|
| 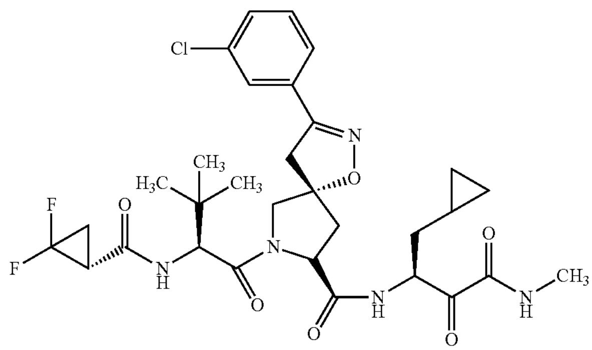 | 748 |
| 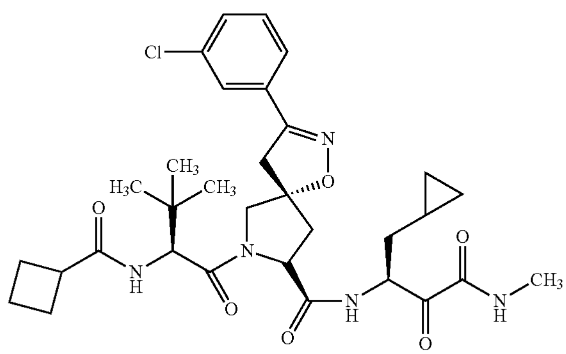 | 749 |
| 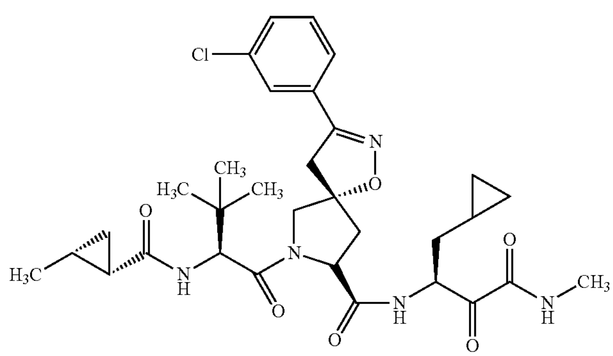 | 750 |
| 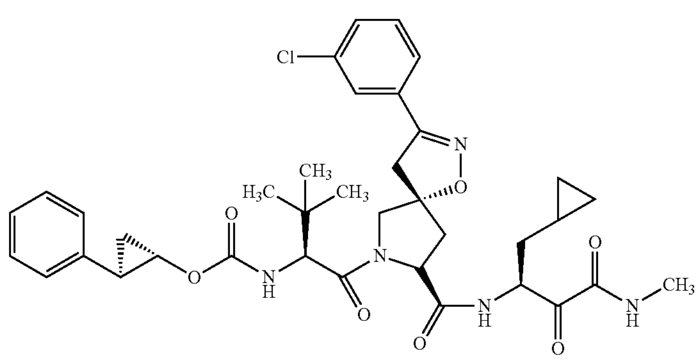 | 751 |

TABLE 1-continued
Exemplary compounds of Formula (I).
| Structure | Compound No. |
|---|---|
| 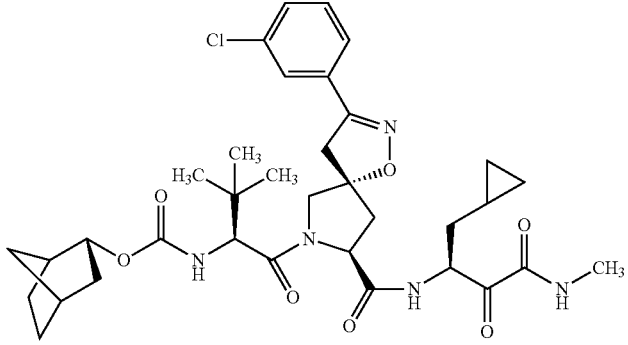 | 752 |
| 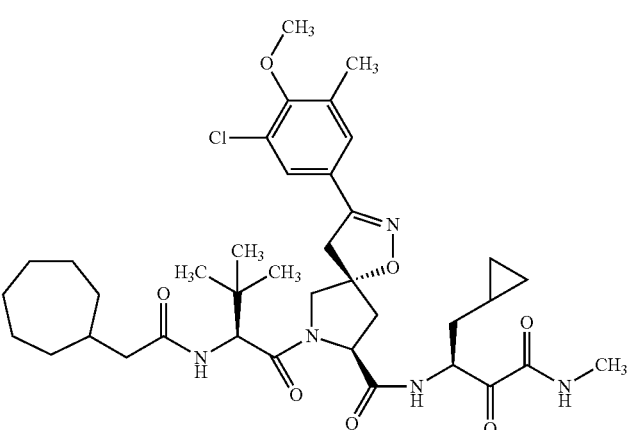 | 753 |
| 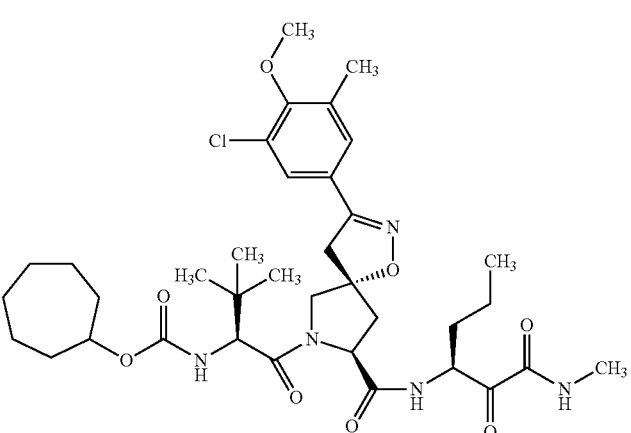 | 754 |

TABLE 1-continued

Exemplary compounds of Formula (I).

| Structure | Compound No. |
|---|---|
| 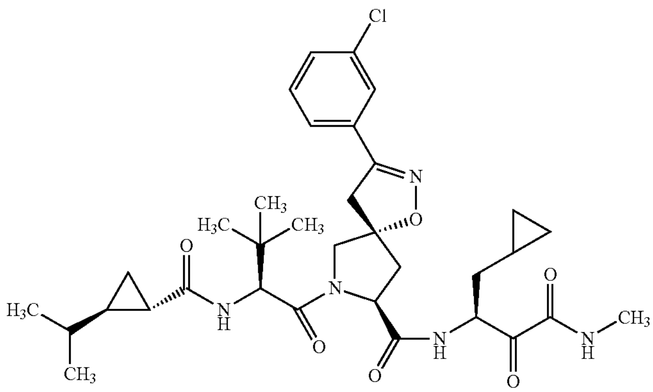 | 755 |
| 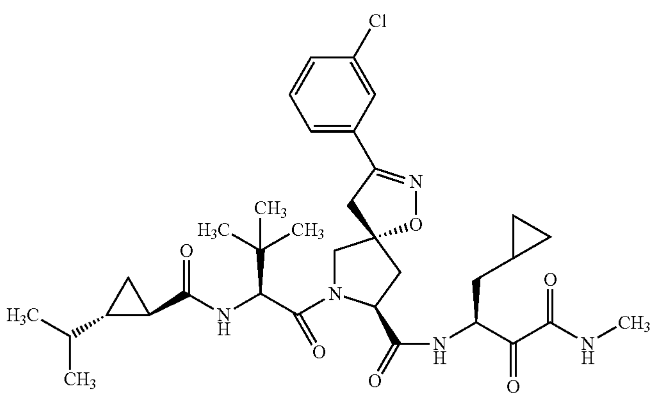 | 756 |
| 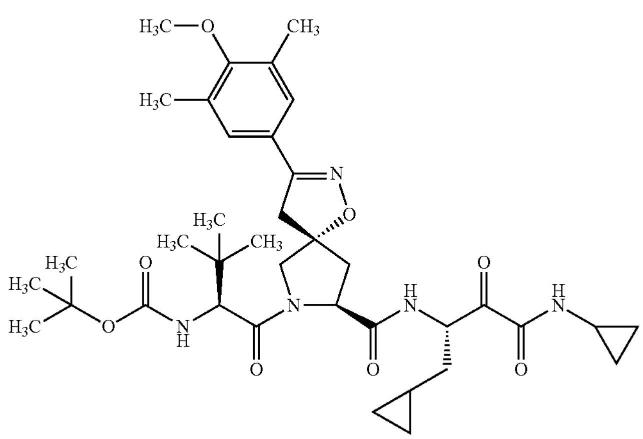 | 757 |

TABLE 1-continued

Exemplary compounds of Formula (I).

| Structure | Compound No. |
|---|---|
| 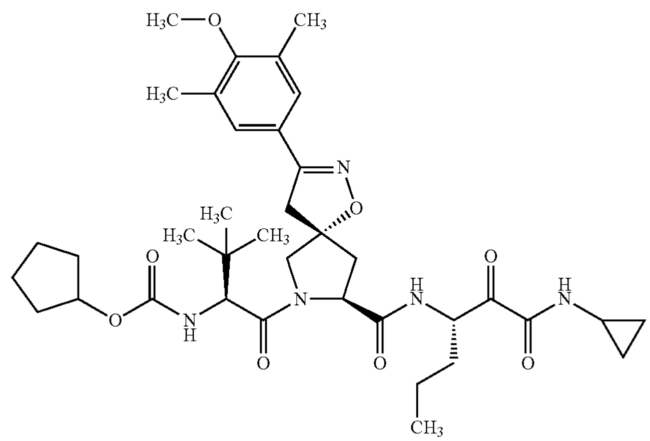 | 758 |
| 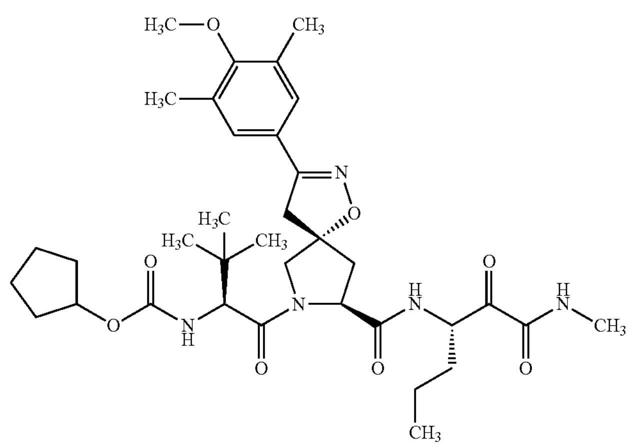 | 759 |
| 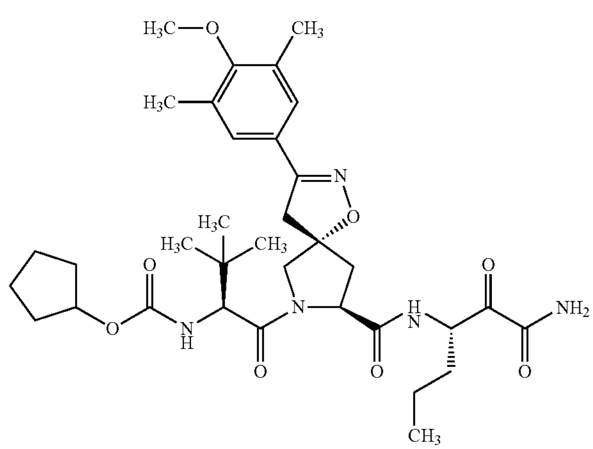 | 760 |

TABLE 1-continued

Exemplary compounds of Formula (I).

| Structure | Compound No. |
|---|---|
| 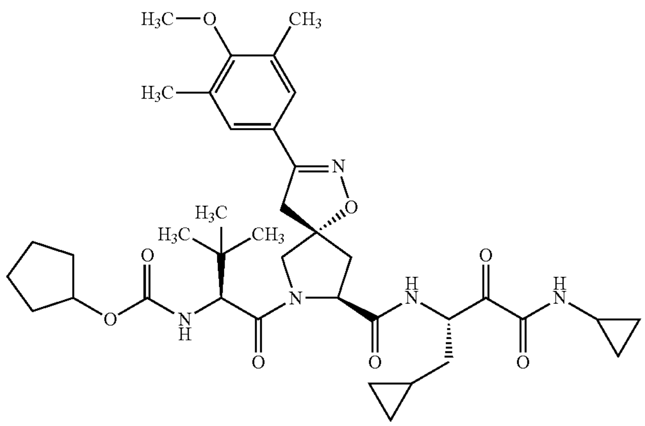 | 761 |
| 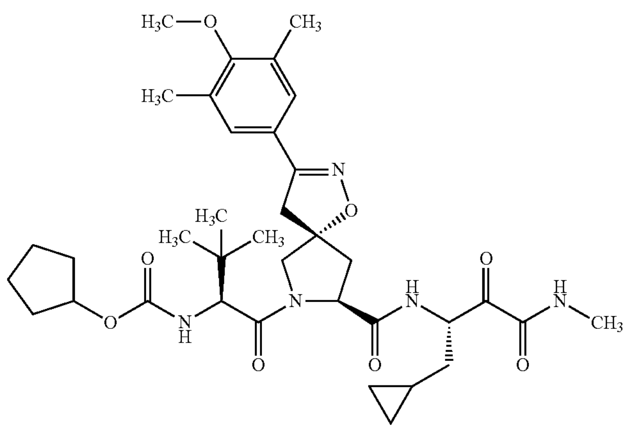 | 762 |
| 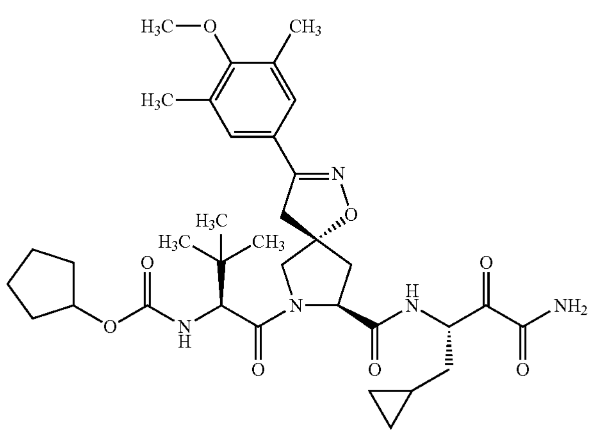 | 763 |

TABLE 1-continued
Exemplary compounds of Formula (I).
| Structure | Compound No. |
|---|---|
| 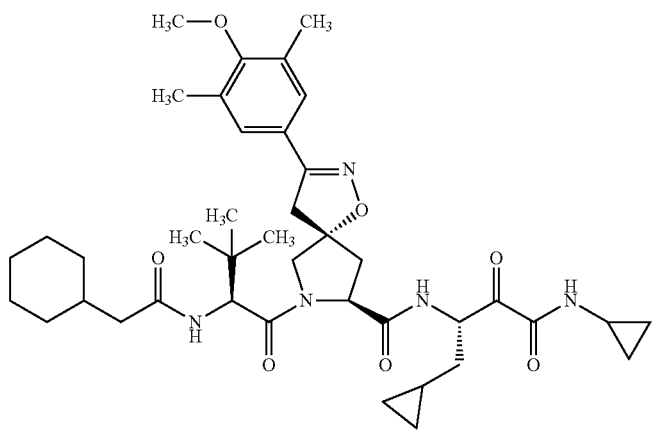 | 764 |
| 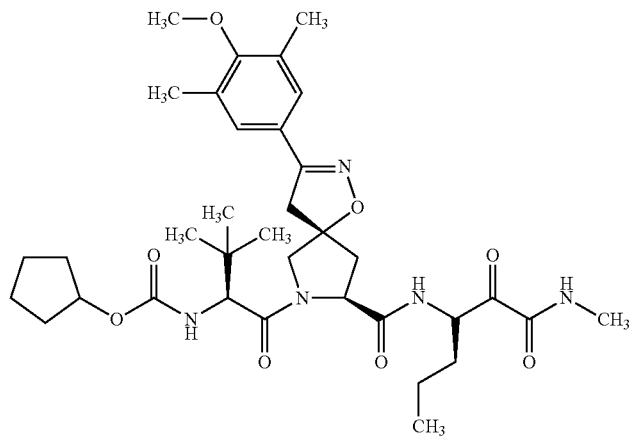 | 765 |
| 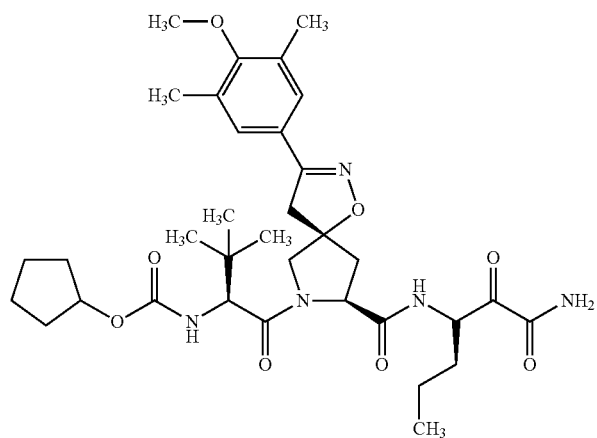 | 766 |

TABLE 1-continued

Exemplary compounds of Formula (I).

| Structure | Compound No. |
|---|---|
| 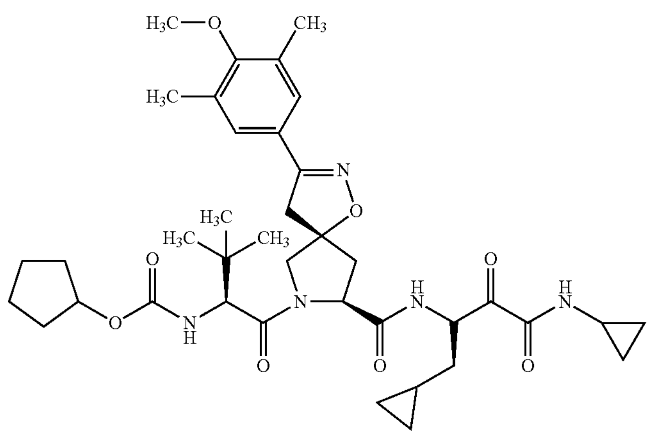 | 767 |
| 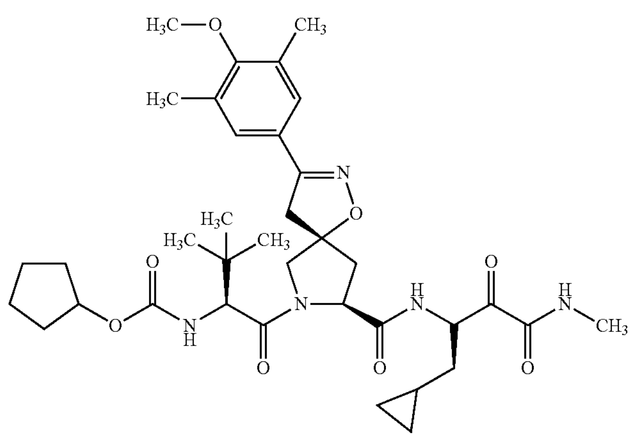 | 768 |
| 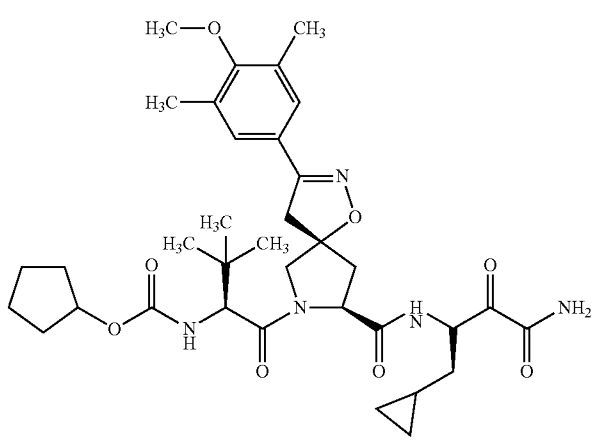 | 769 |

TABLE 1-continued

Exemplary compounds of Formula (I).

| Structure | Compound No. |
|---|---|
| 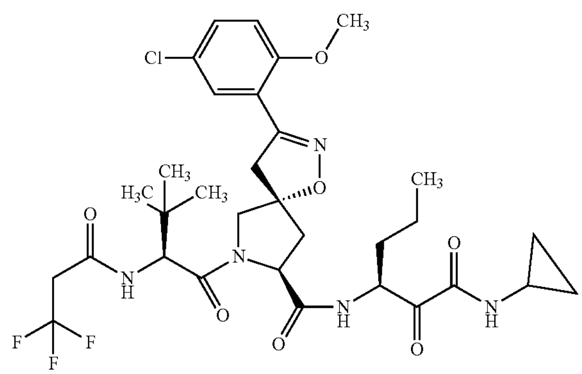 | 770 |
| 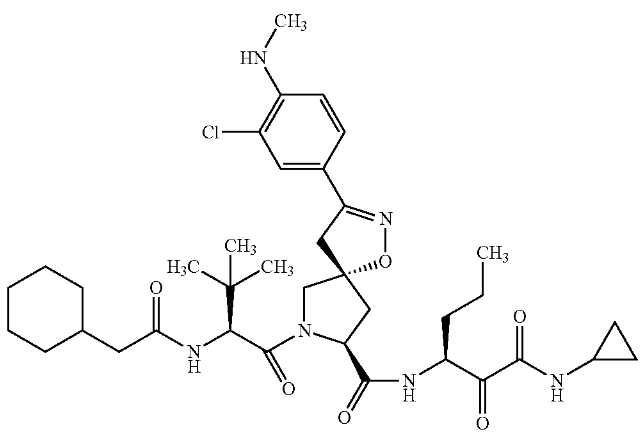 | 771 |
| 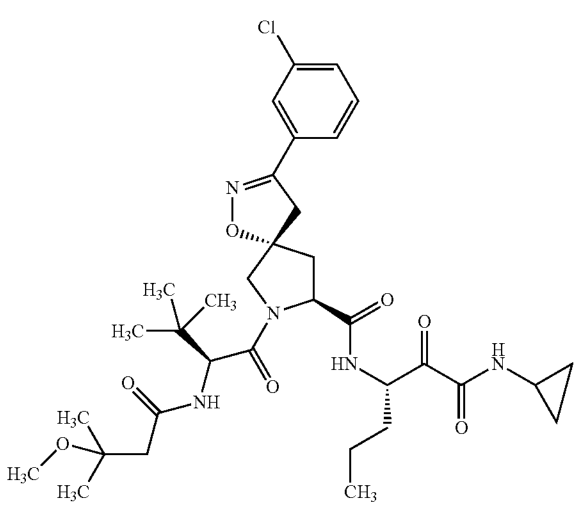 | 772 |

TABLE 1-continued

Exemplary compounds of Formula (I).

| Structure | Compound No. |
|---|---|
| 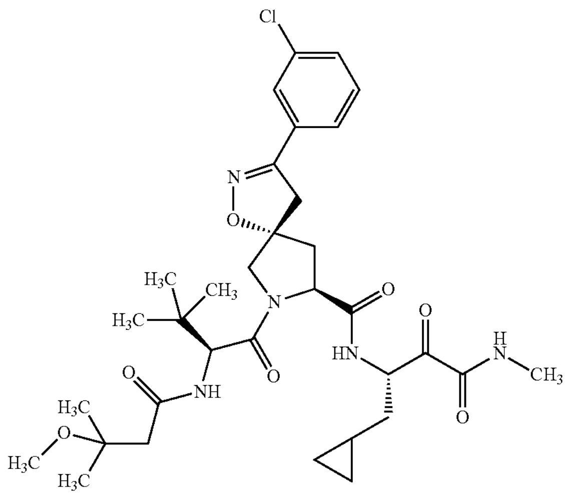 | 773 |
| 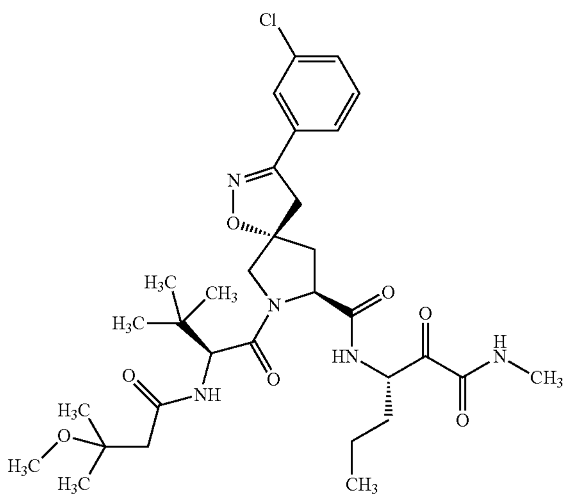 | 774 |
| 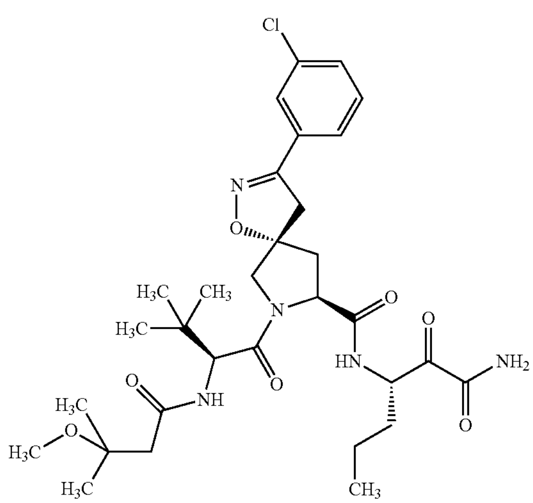 | 775 |

TABLE 1-continued

Exemplary compounds of Formula (I).

| Structure | Compound No. |
|---|---|
| 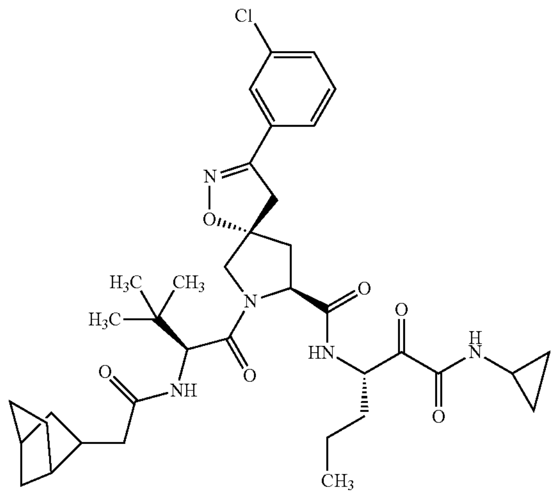 | 776 |
| 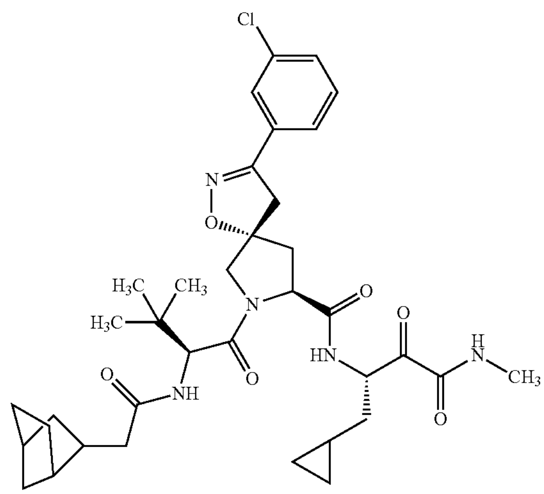 | 777 |
| 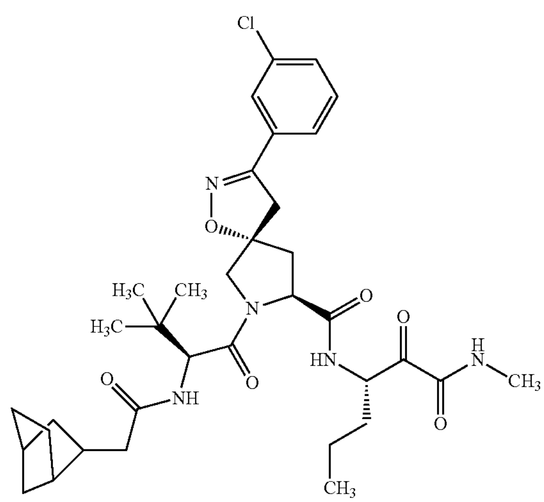 | 778 |

TABLE 1-continued

Exemplary compounds of Formula (I).

| Structure | Compound No. |
|---|---|
| 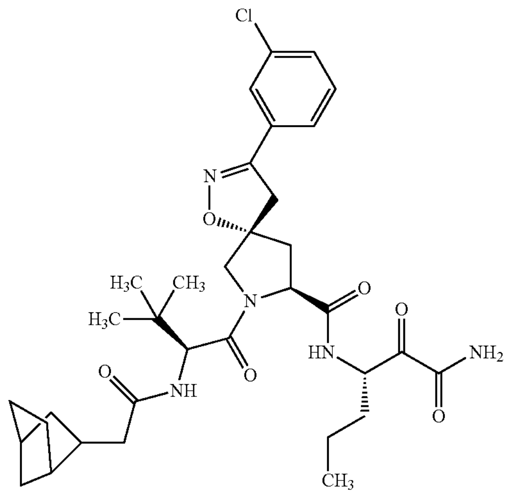 | 779 |
| 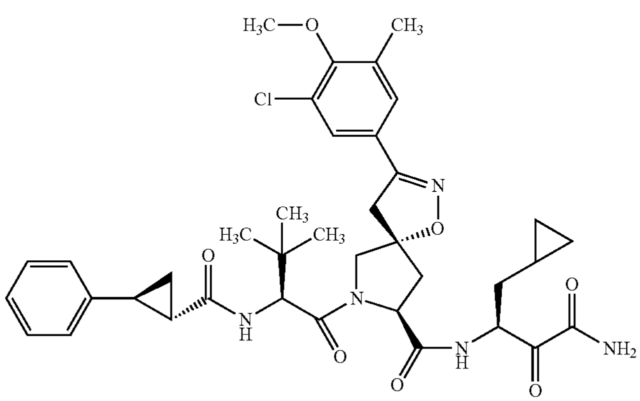 | 780 |
| 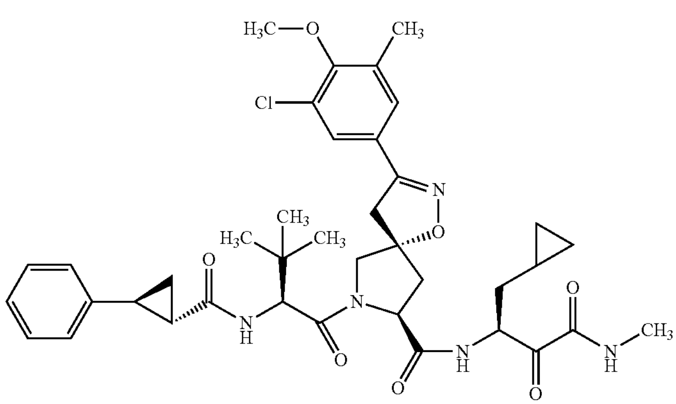 | 781 |

TABLE 1-continued

Exemplary compounds of Formula (I).

| Structure | Compound No. |
|---|---|
| 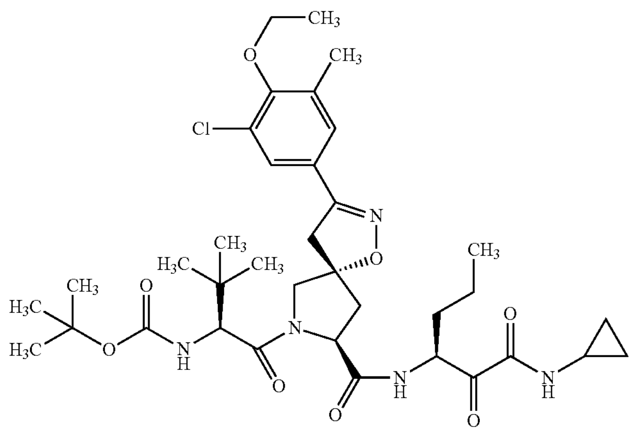 | 782 |
| 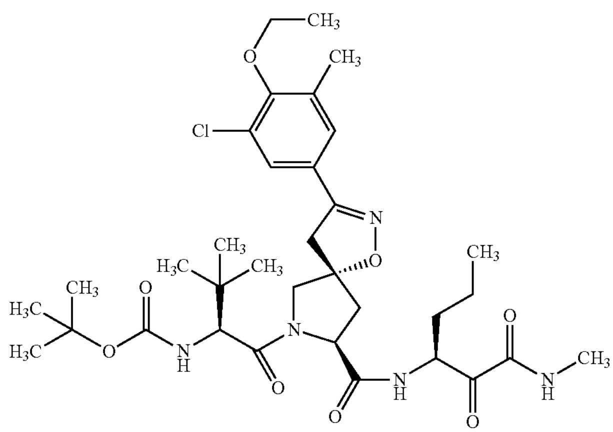 | 783 |
| 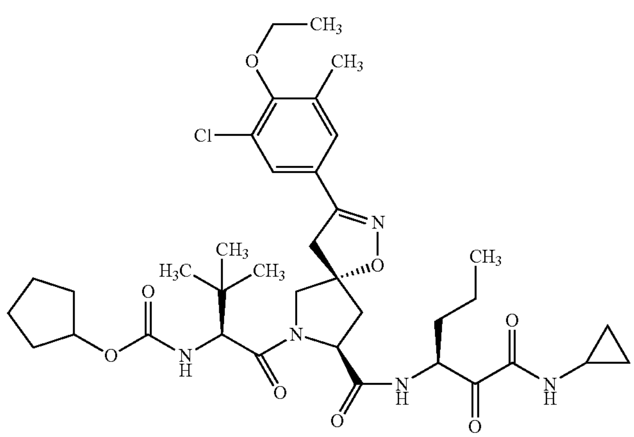 | 784 |

TABLE 1-continued

Exemplary compounds of Formula (I).

| Structure | Compound No. |
|---|---|
| 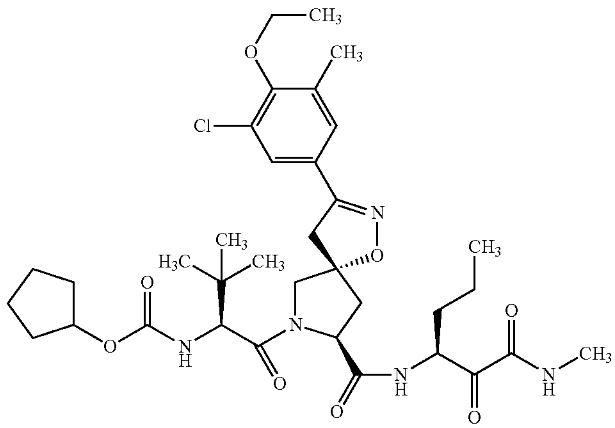 | 785 |
| 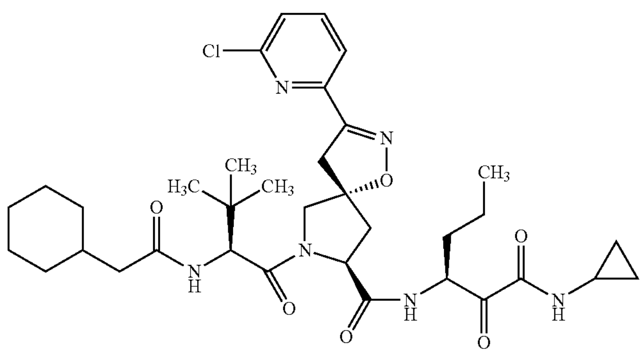 | 786 |
| 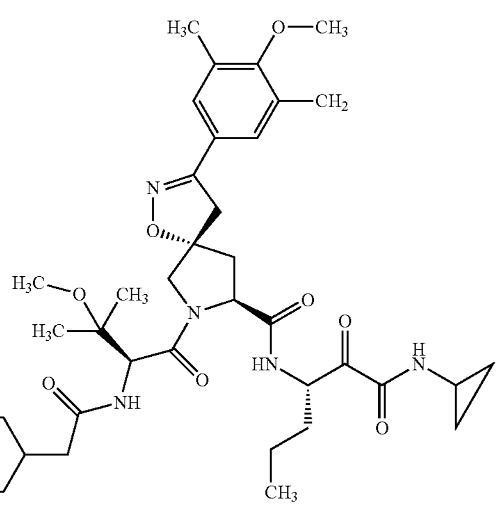 | 787 |

TABLE 1-continued

Exemplary compounds of Formula (I).

| Structure | Compound No. |
|---|---|
| 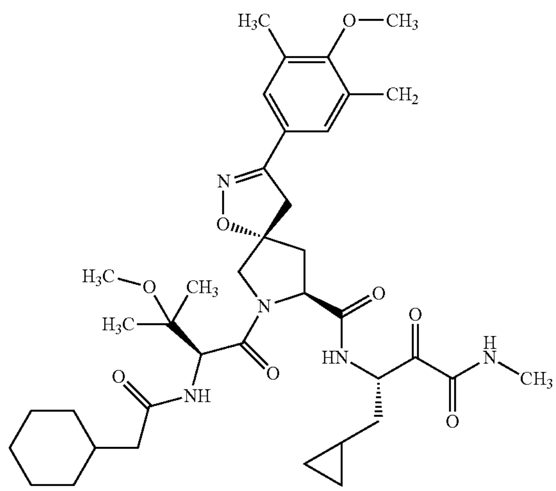 | 788 |
| 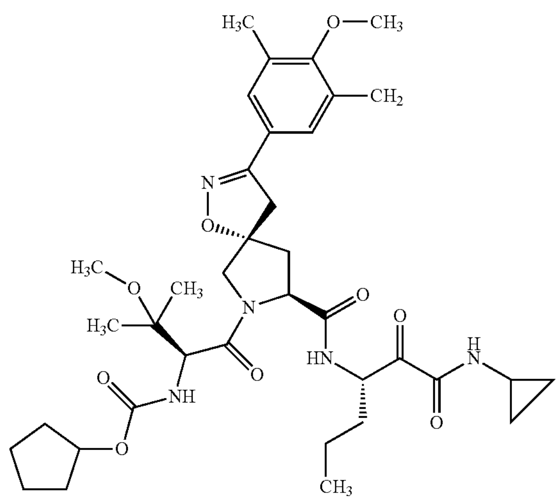 | 789 |
| 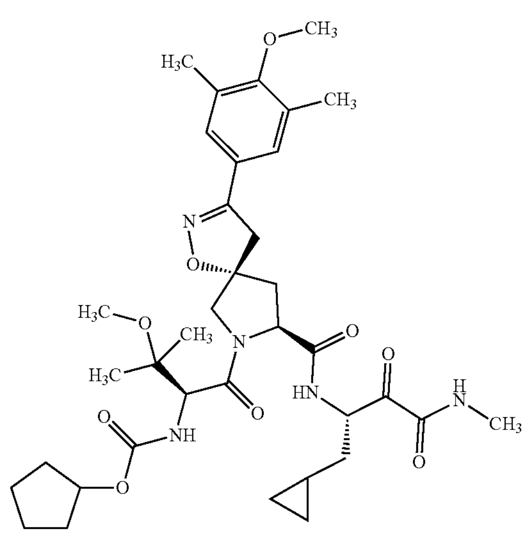 | 790 |

TABLE 1-continued

Exemplary compounds of Formula (I).

| Structure | Compound No. |
|---|---|
| 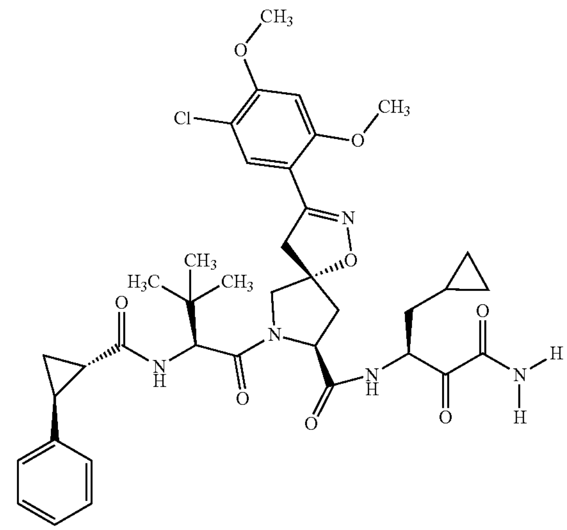 | 791 |
| 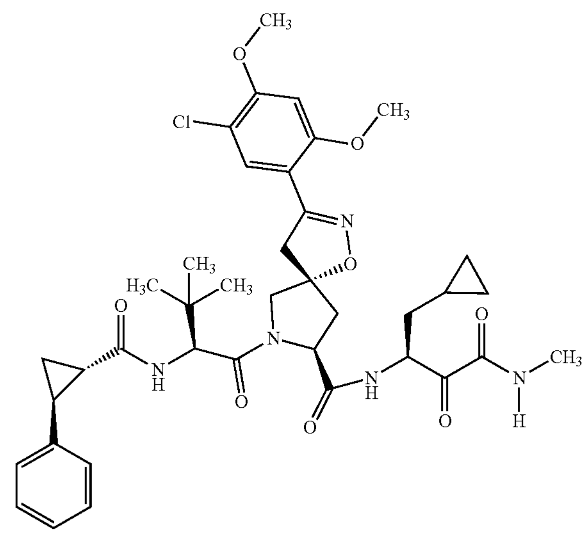 | 792 |
| 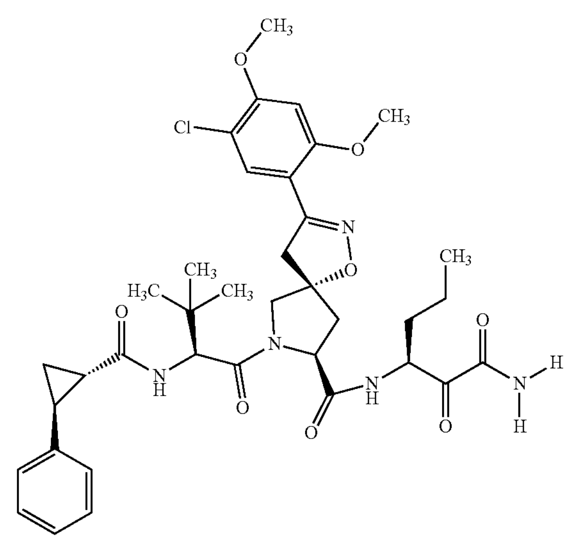 | 793 |

TABLE 1-continued

Exemplary compounds of Formula (I).

| Structure | Compound No. |
|---|---|
| 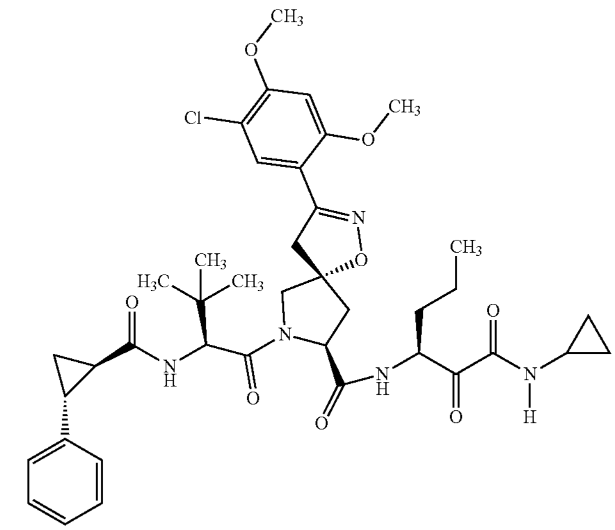 | 794 |
| 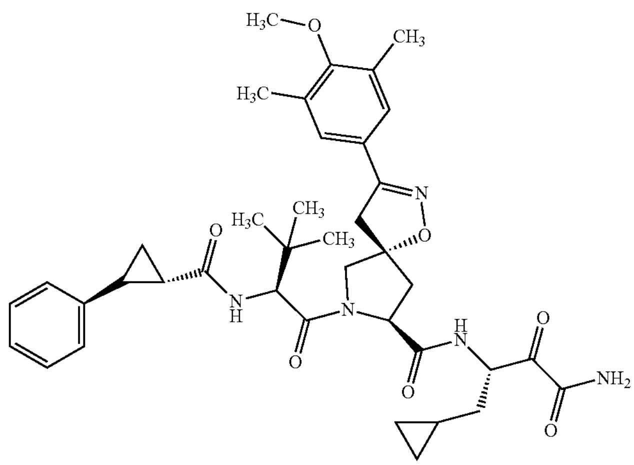 | 795 |
| 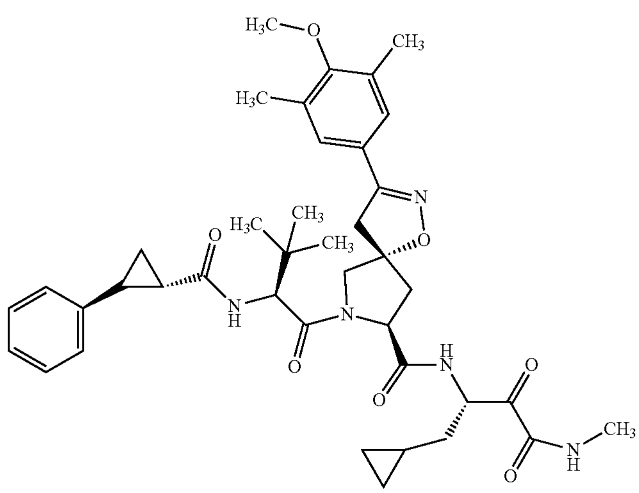 | 796 |

TABLE 1-continued

Exemplary compounds of Formula (I).

| Structure | Compound No. |
|---|---|
| 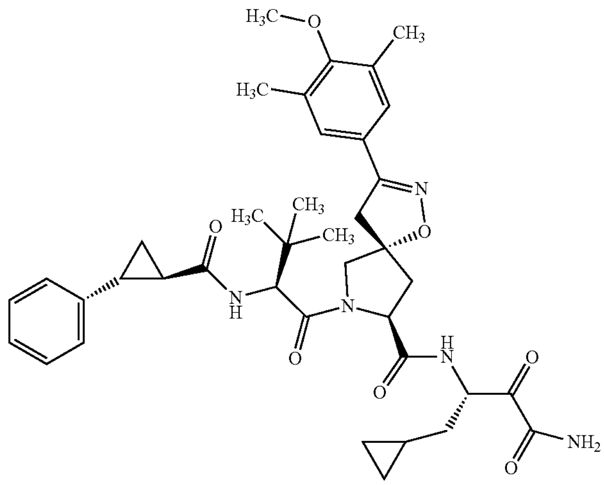 | 797 |
| 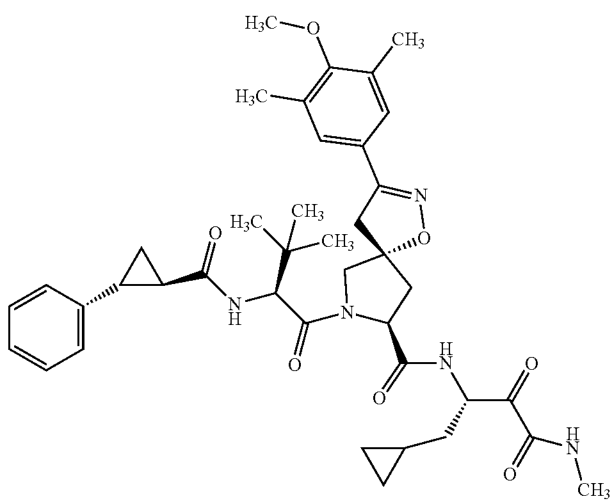 | 798 |
| 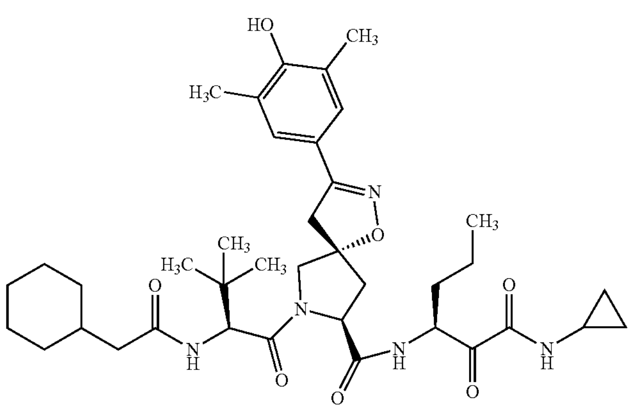 | 799 |

TABLE 1-continued

Exemplary compounds of Formula (I).

| Structure | Compound No. |
|---|---|
| 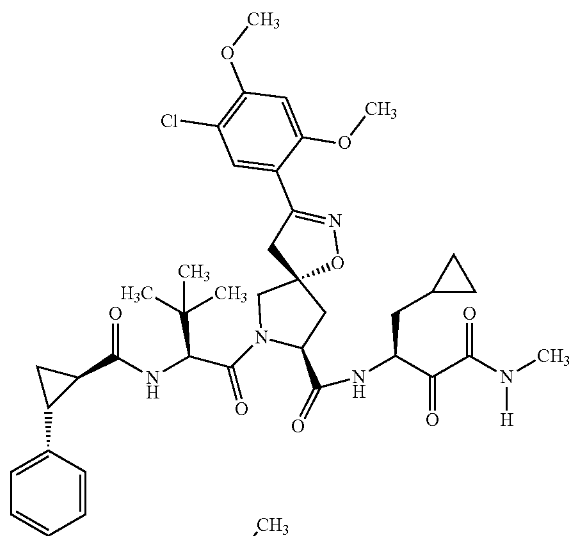 | 800 |
| 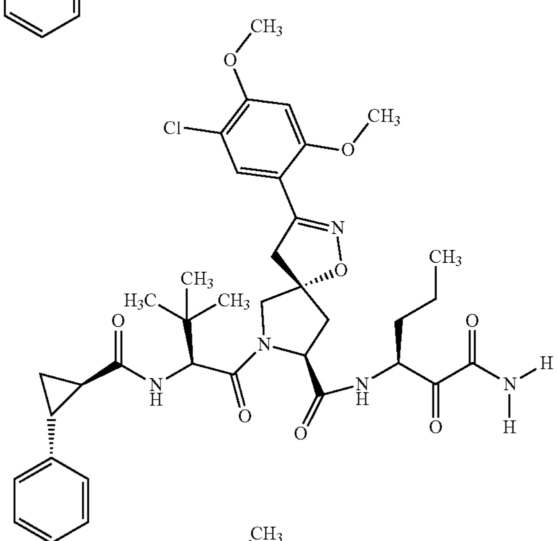 | 801 |
| 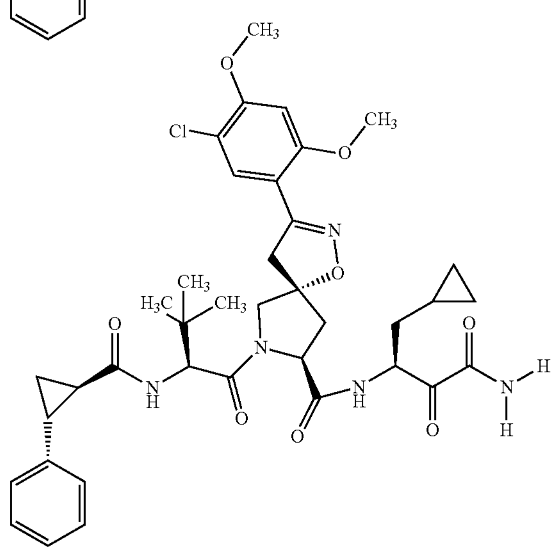 | 802 |

TABLE 1-continued

Exemplary compounds of Formula (I).

| Structure | Compound No. |
|---|---|
| 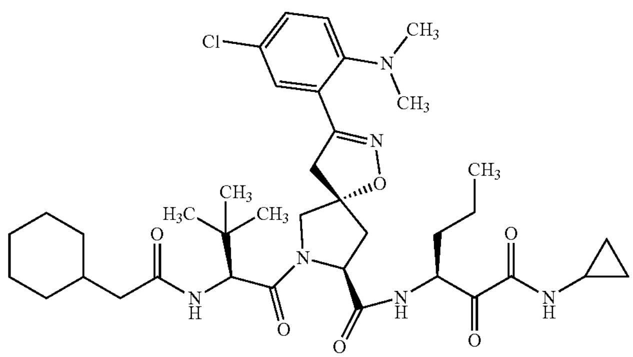 | 803 |
| 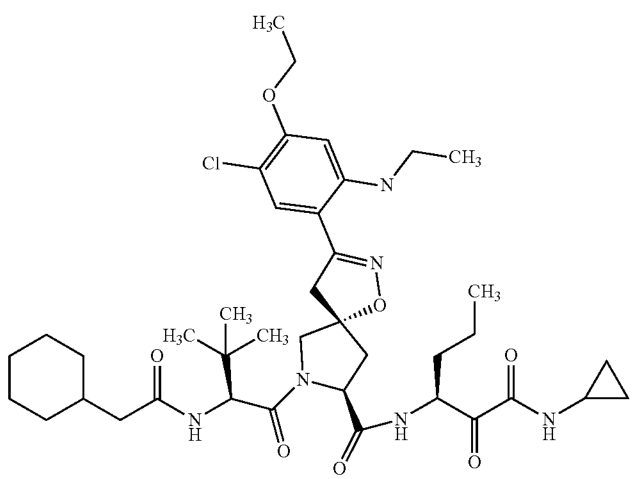 | 804 |
| 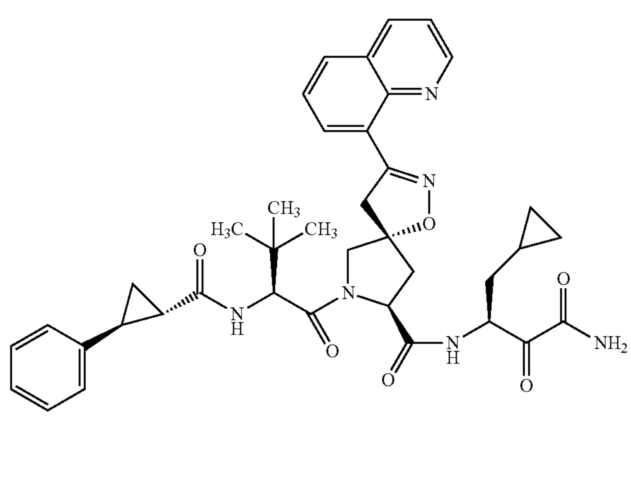 | 805 |

TABLE 1-continued

Exemplary compounds of Formula (I).

| Structure | Compound No. |
|---|---|
| 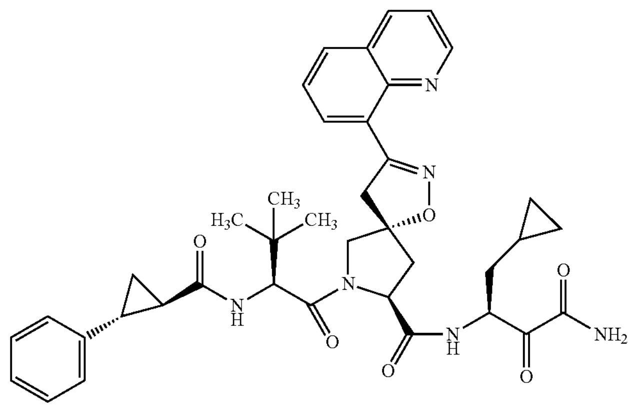 | 806 |
| 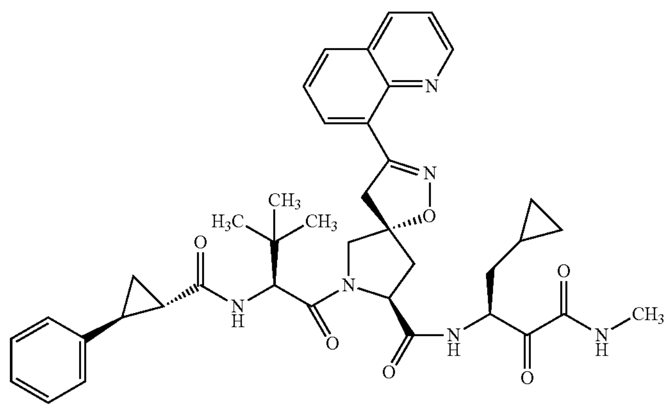 | 807 |
| 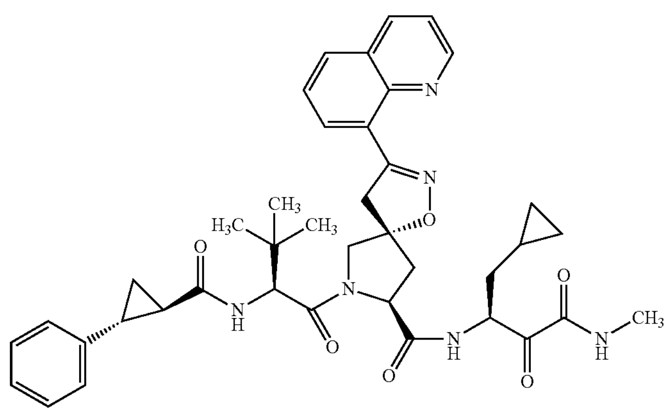 | 808 |

TABLE 1-continued
Exemplary compounds of Formula (I).
| Structure | Compound No. |
|---|---|
| 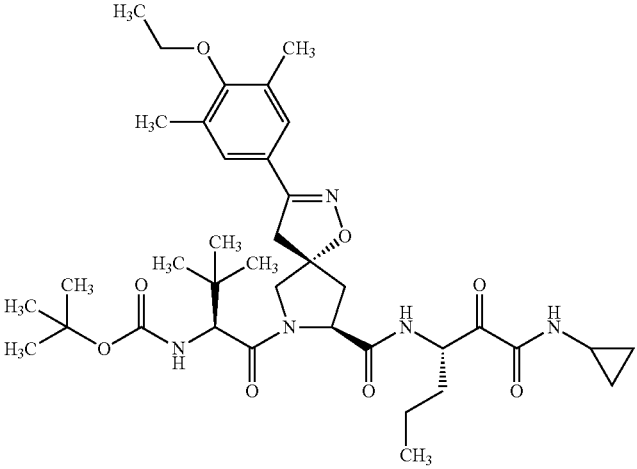 | 809 |
| 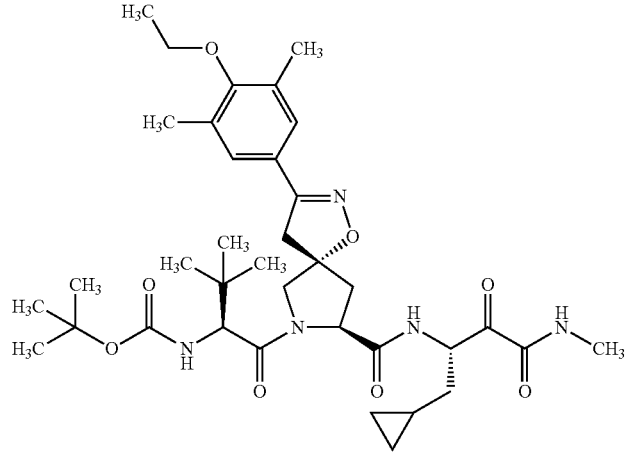 | 810 |
| 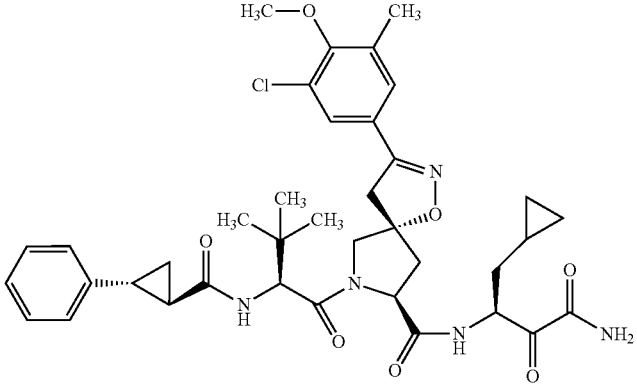 | 811 |

TABLE 1-continued

Exemplary compounds of Formula (I).

| Structure | Compound No. |
|---|---|
| 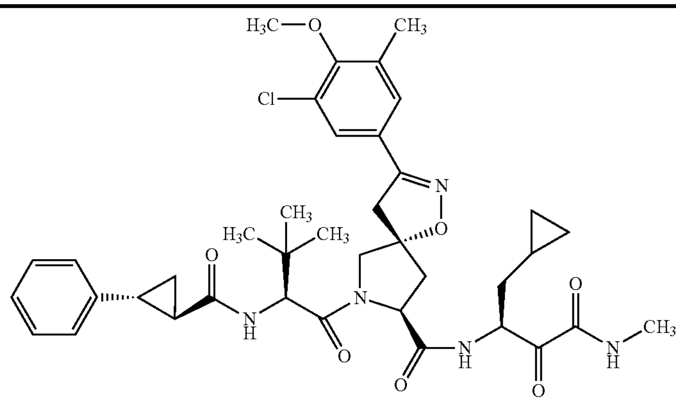 | 812 |
| 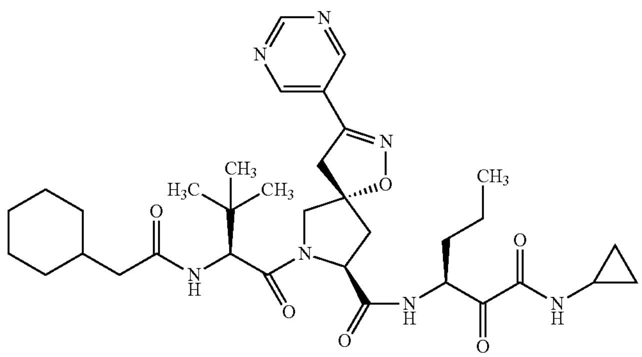 | 813 |
| 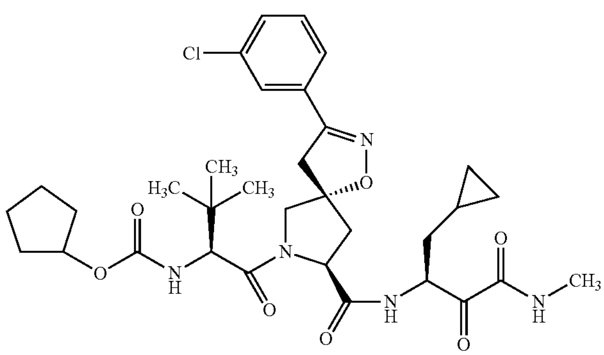 | 814 |
| 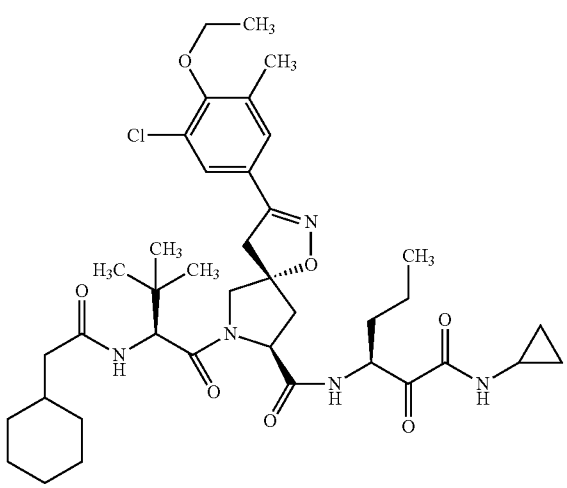 | 815 |

TABLE 1-continued

Exemplary compounds of Formula (I).

| Structure | Compound No. |
|-----------|--------------|
| 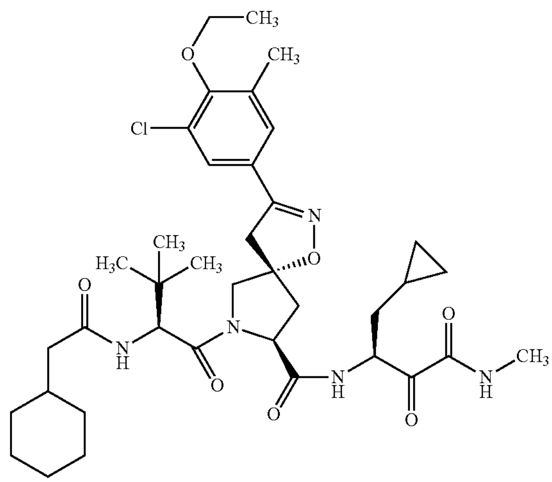          | 816          |
| 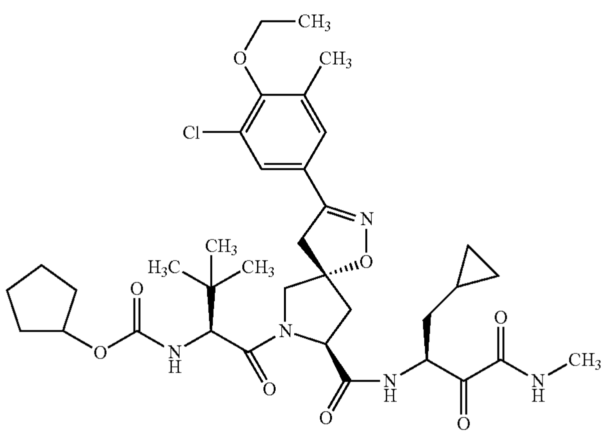          | 817          |
| 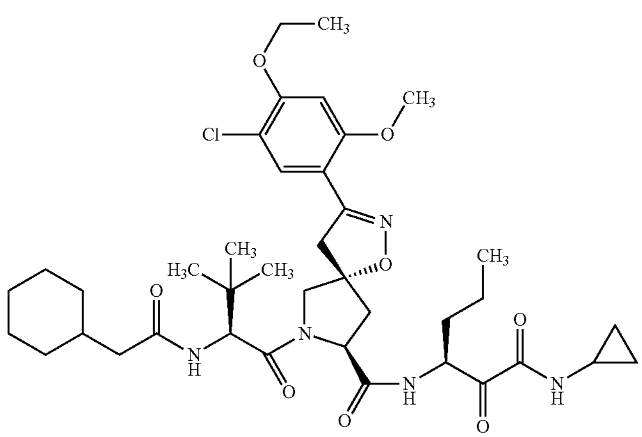          | 818          |

TABLE 1-continued

Exemplary compounds of Formula (I).

| Structure | Compound No. |
|---|---|
| 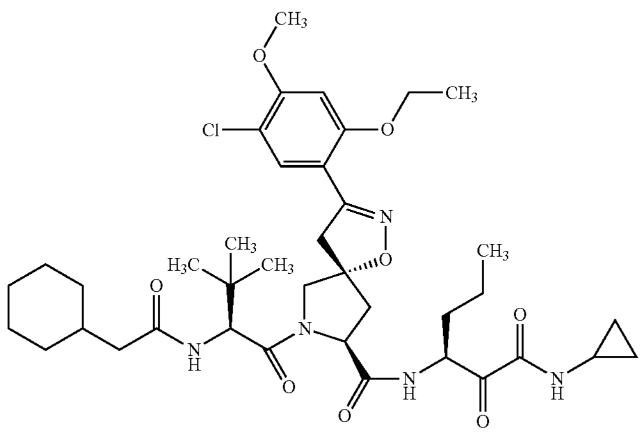 | 819 |
| 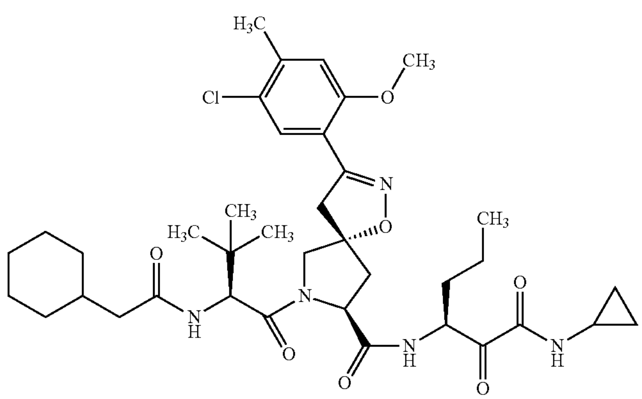 | 820 |
| 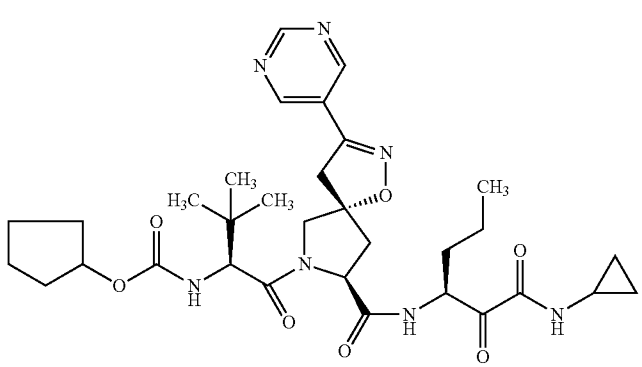 | 821 |

TABLE 1-continued

Exemplary compounds of Formula (I).

| Structure | Compound No. |
|---|---|
| 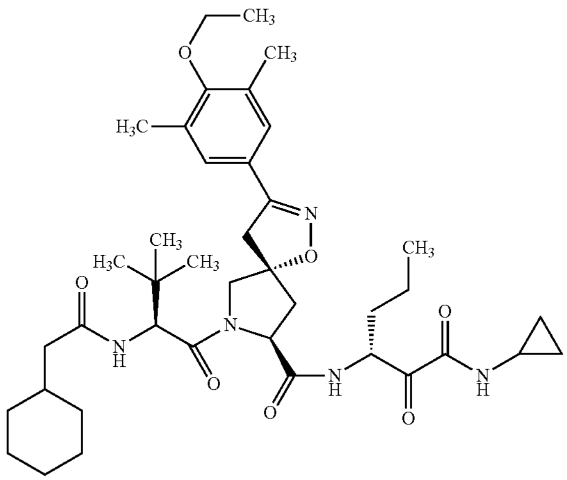 | 822 |
| 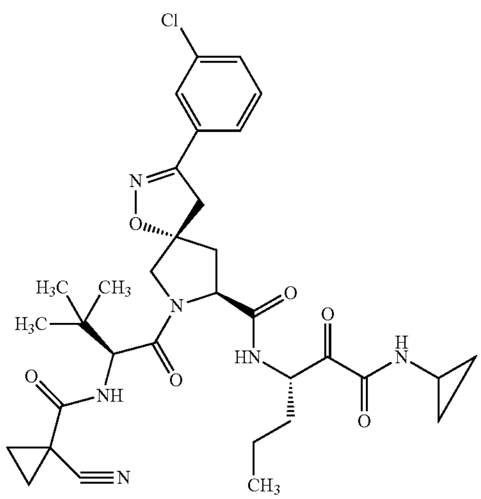 | 823 |
| 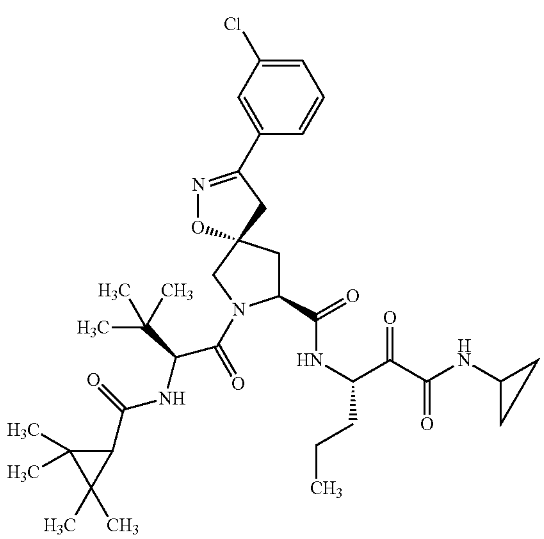 | 824 |

TABLE 1-continued

Exemplary compounds of Formula (I).

| Structure | Compound No. |
|---|---|
| 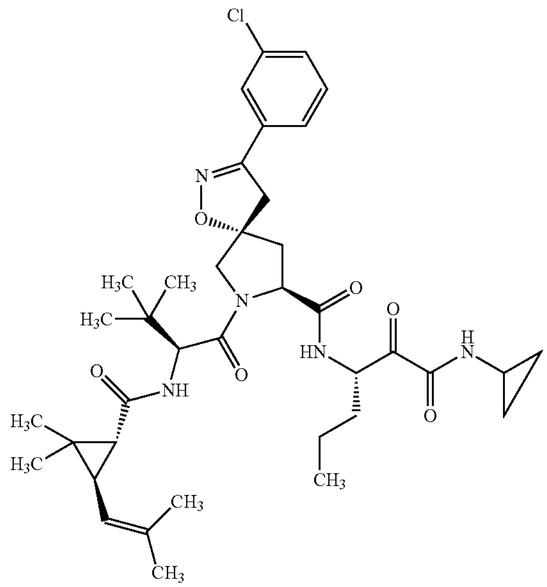 | 825 |
| 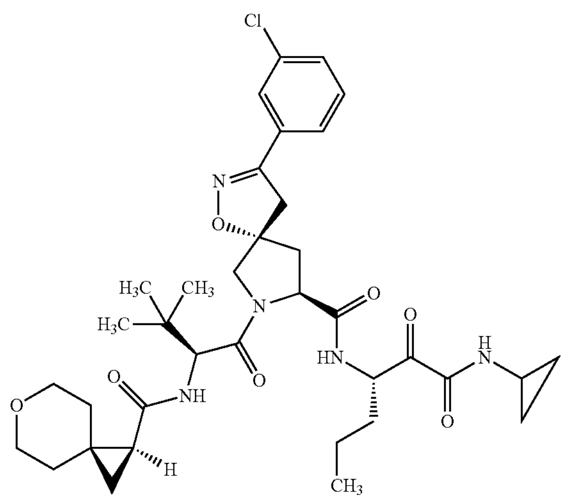 | 826 |
| 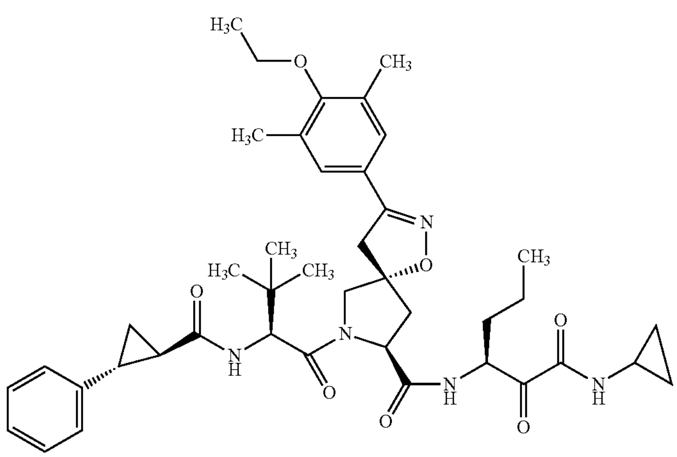 | 827 |

TABLE 1-continued

Exemplary compounds of Formula (I).

| Structure | Compound No. |
|---|---|
| 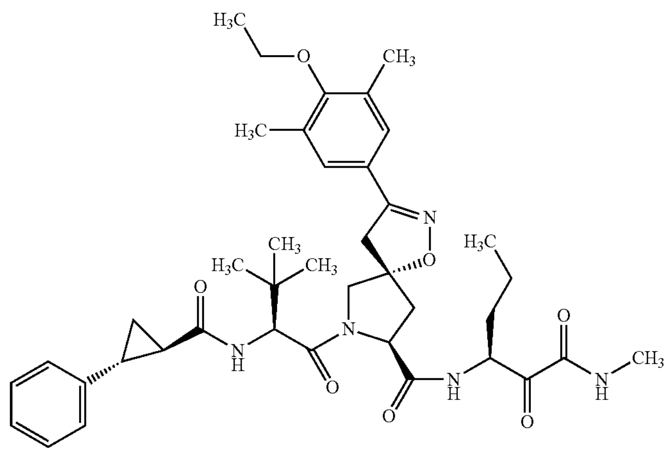 | 828 |
| 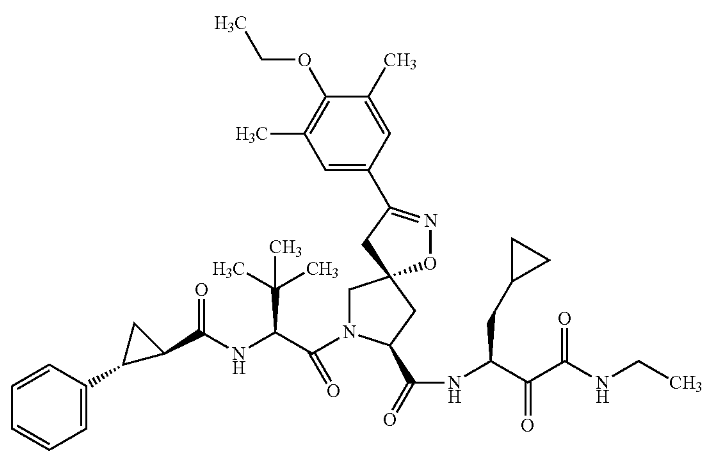 | 829 |
| 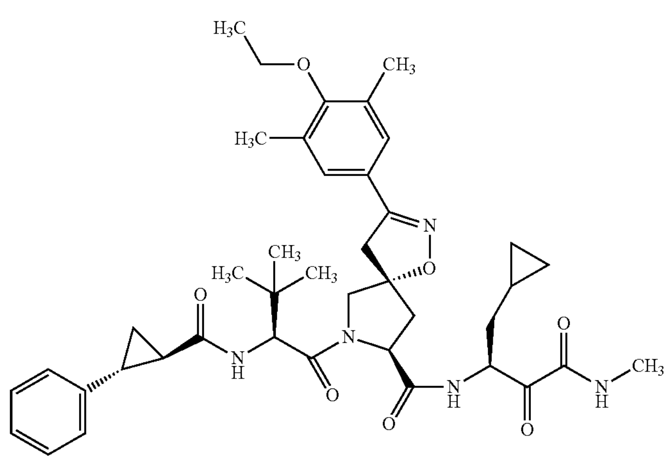 | 830 |

TABLE 1-continued

Exemplary compounds of Formula (I).

| Structure | Compound No. |
|---|---|
| 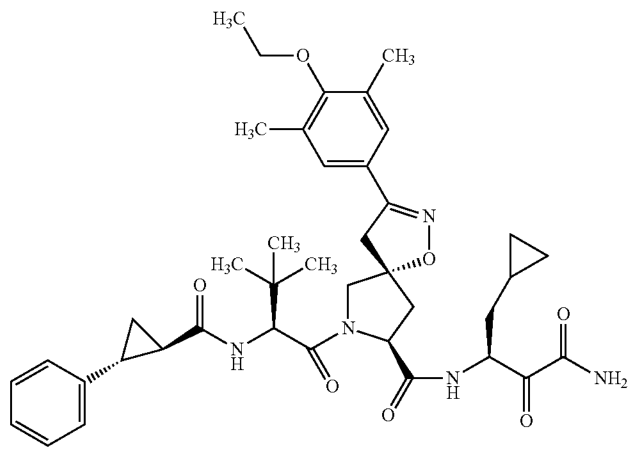 | 831 |
| 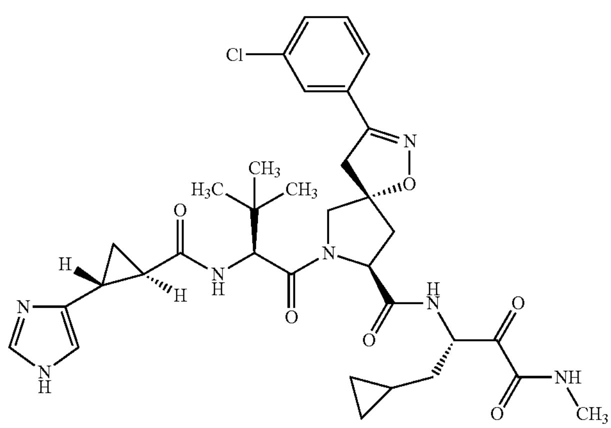 | 832 |
| 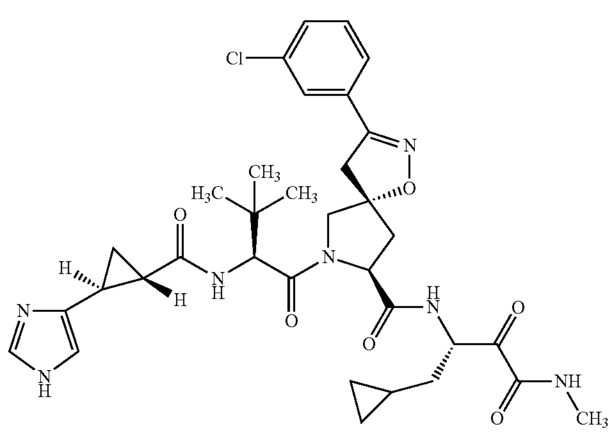 | 833 |

TABLE 1-continued

Exemplary compounds of Formula (I).

| Structure | Compound No. |
|---|---|
| 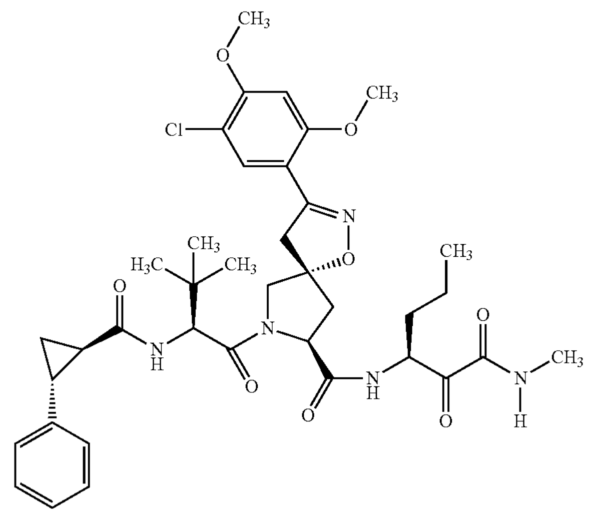 | 834 |
| 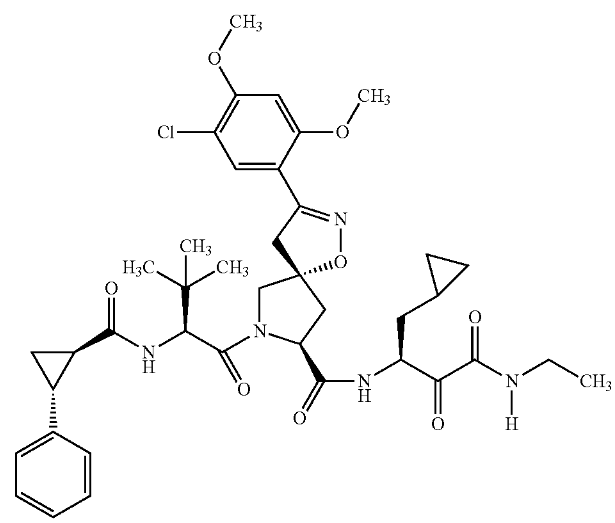 | 835 |
| 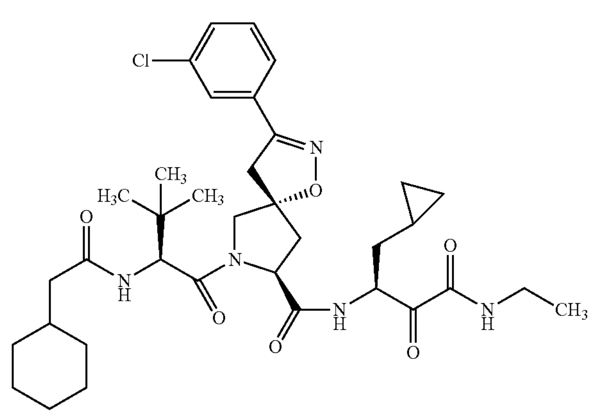 | 836 |

TABLE 1-continued

Exemplary compounds of Formula (I).

| Structure | Compound No. |
|---|---|
| 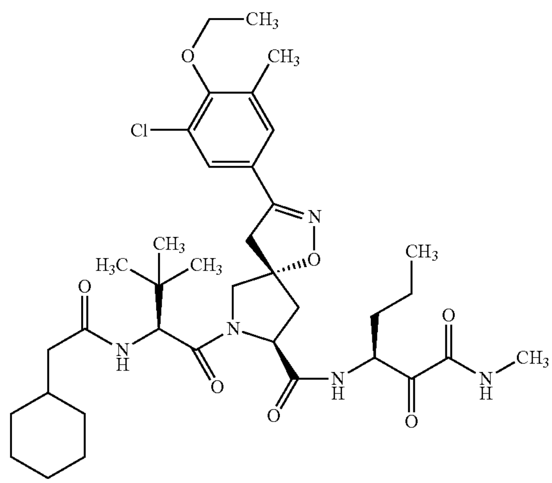 | 837 |
| 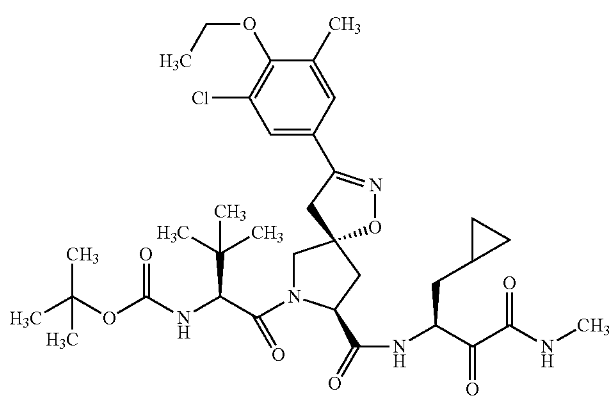 | 838 |
| 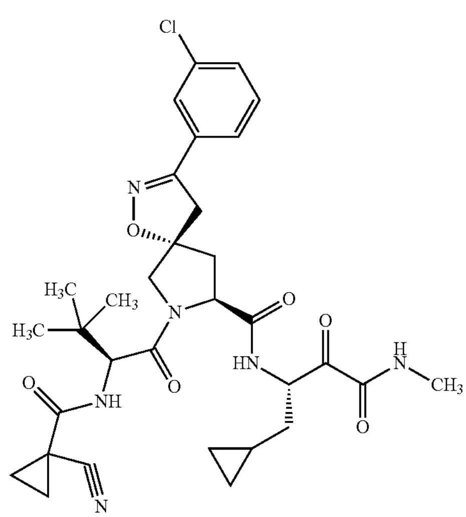 | 839 |

TABLE 1-continued

Exemplary compounds of Formula (I).

| Structure | Compound No. |
|---|---|
| 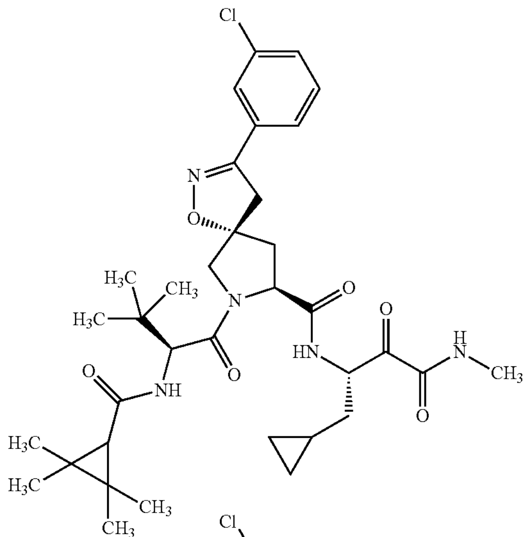 | 840 |
| 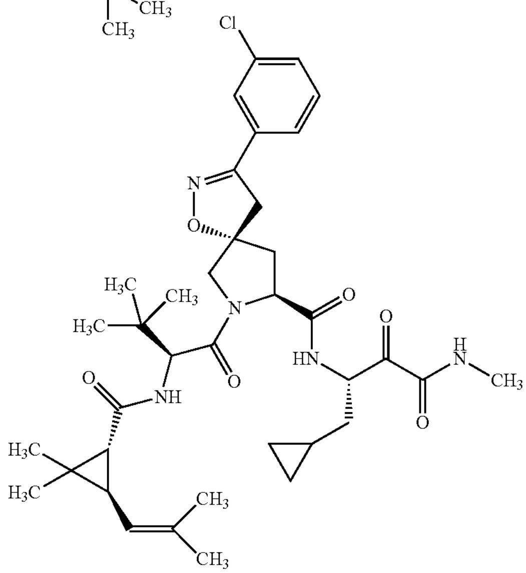 | 841 |
| 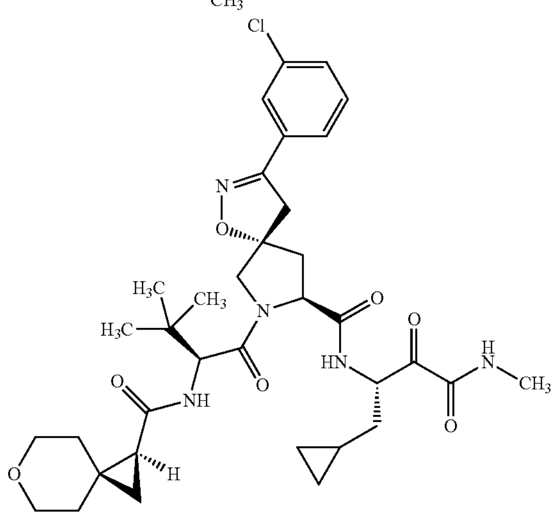 | 842 |

TABLE 1-continued

Exemplary compounds of Formula (I).

| Structure | Compound No. |
|---|---|
| 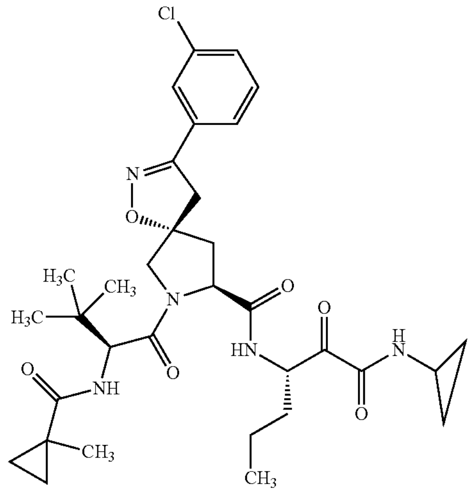 | 843 |
| 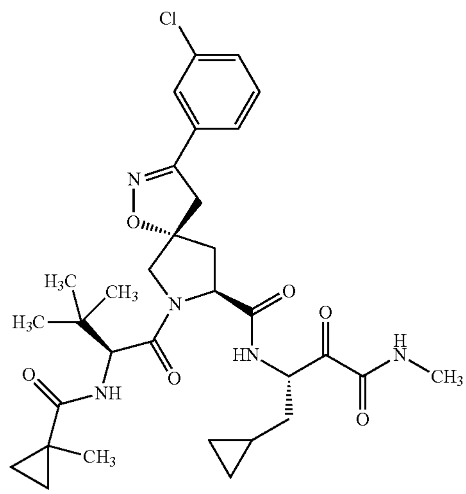 | 844 |
| 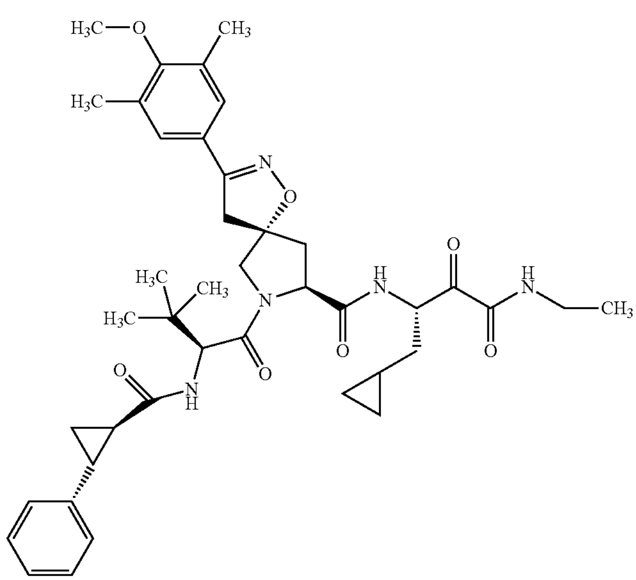 | 845 |

TABLE 1-continued

Exemplary compounds of Formula (I).

| Structure | Compound No. |
|---|---|
| 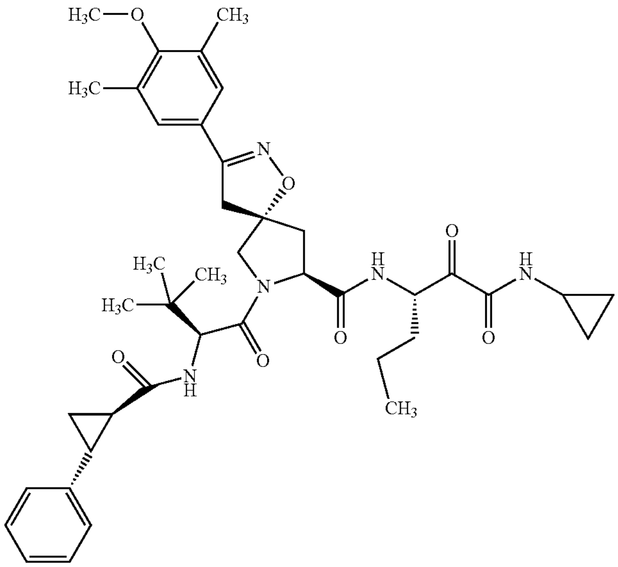 | 846 |
| 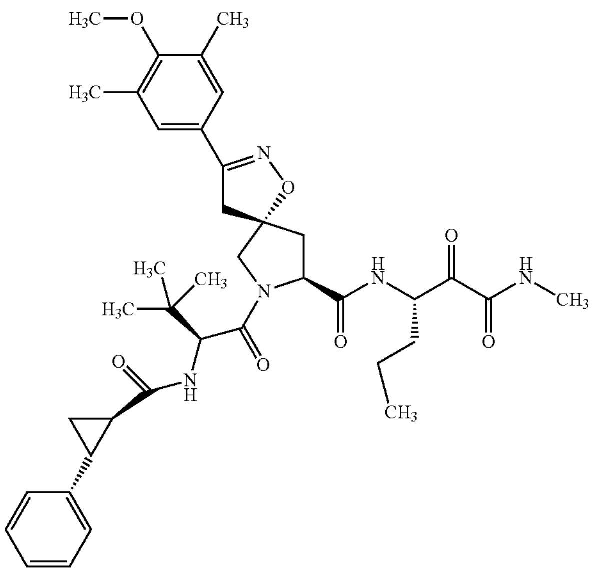 | 847 |
| 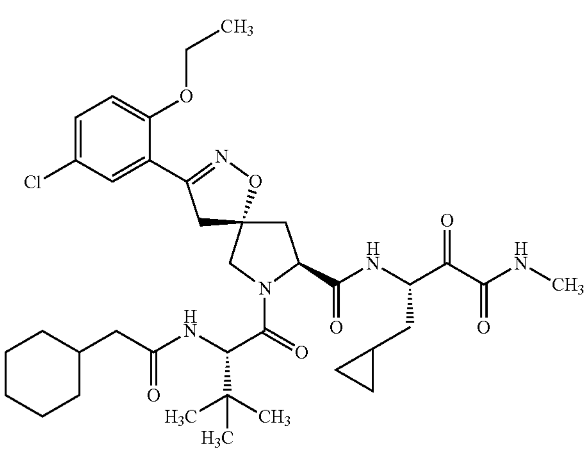 | 848 |

TABLE 1-continued

Exemplary compounds of Formula (I).

| Structure | Compound No. |
|---|---|
| 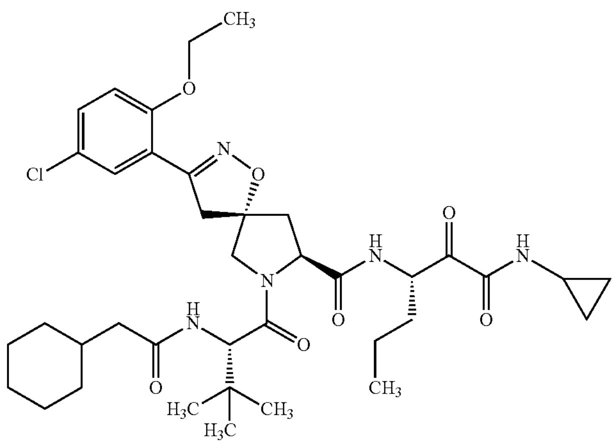 | 849 |
| 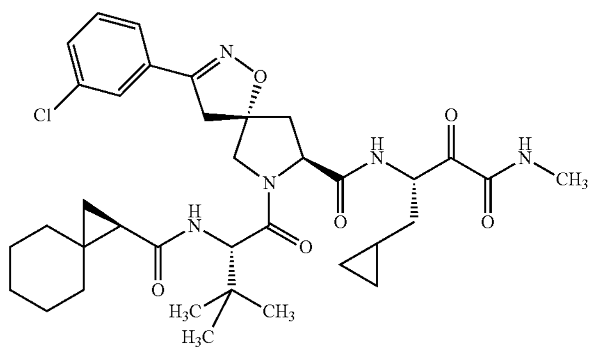 | 850 |
| 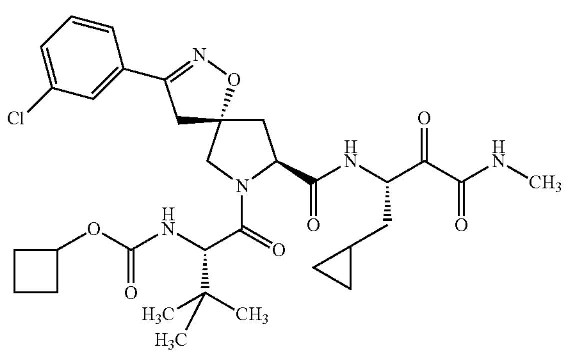 | 851 |
| 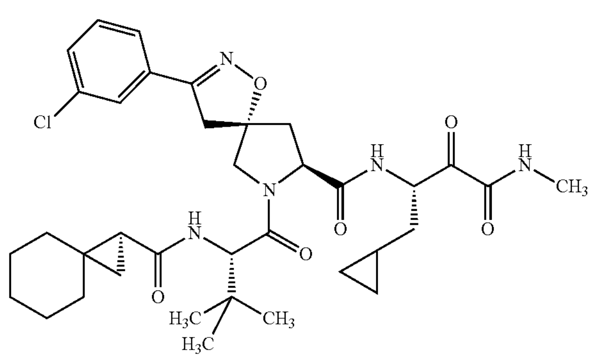 | 852 |

TABLE 1-continued

Exemplary compounds of Formula (I).

| Structure | Compound No. |
|---|---|
| 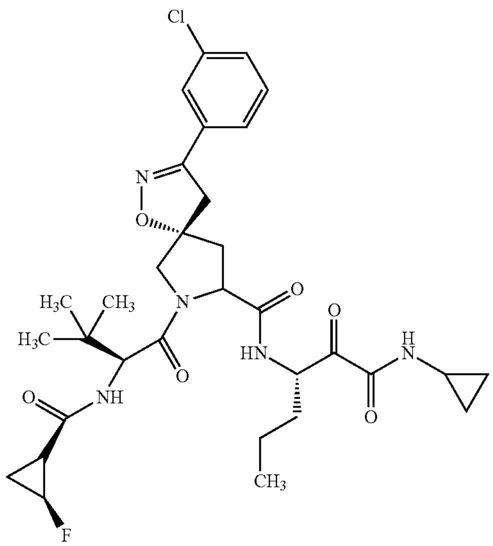 | 853 |
| 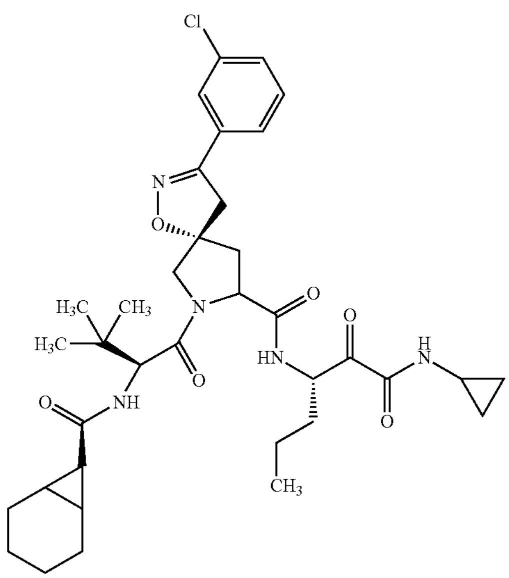 | 854 |
| 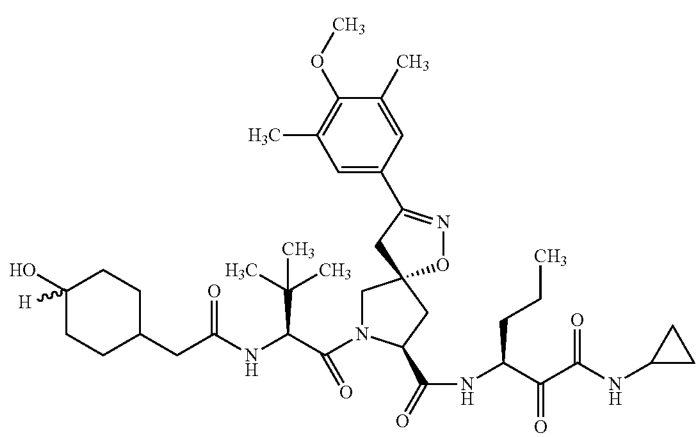 | 855 |

TABLE 1-continued

Exemplary compounds of Formula (I).

| Structure | Compound No. |
|---|---|
| 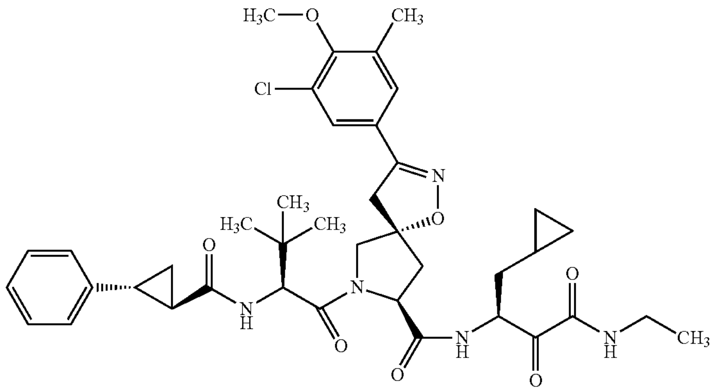 | 856 |
| 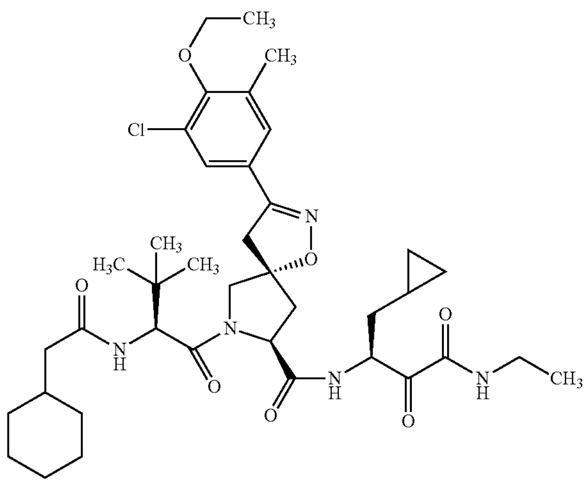 | 857 |
| 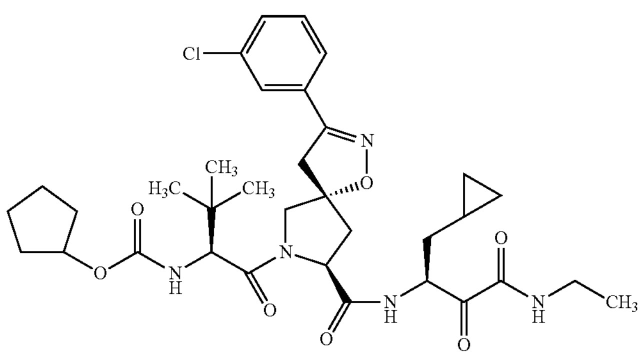 | 858 |
| 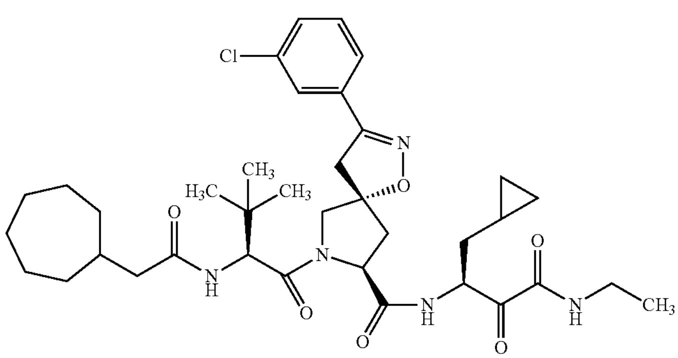 | 859 |

TABLE 1-continued
Exemplary compounds of Formula (I).
| Structure | Compound No. |
|---|---|
| 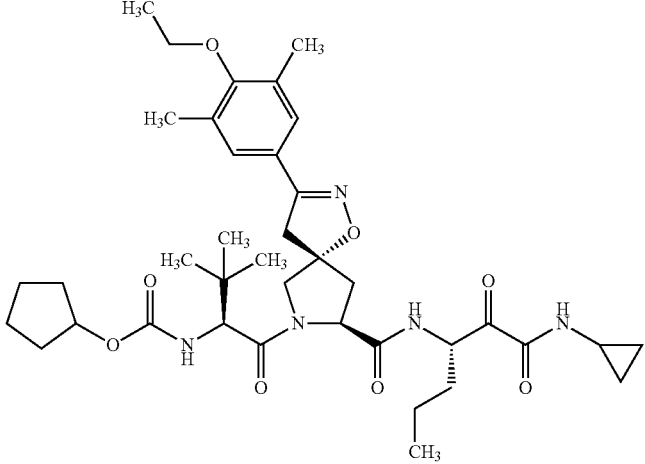 | 860 |
| 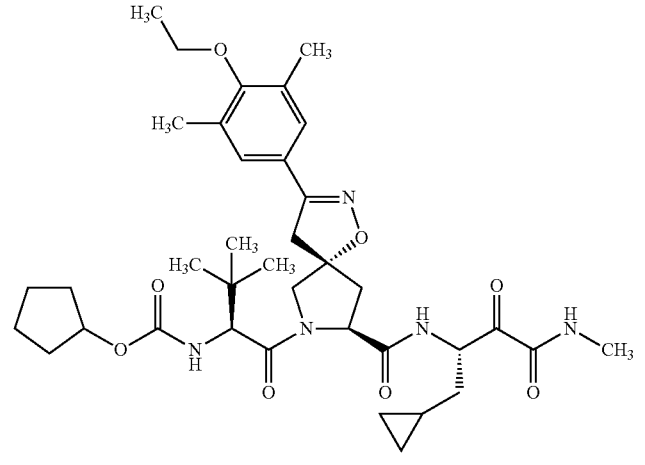 | 861 |
| 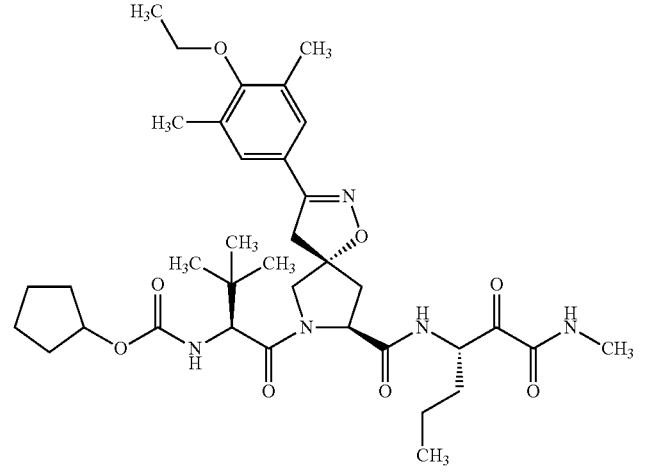 | 862 |

TABLE 1-continued

Exemplary compounds of Formula (I).

| Structure | Compound No. |
|---|---|
| 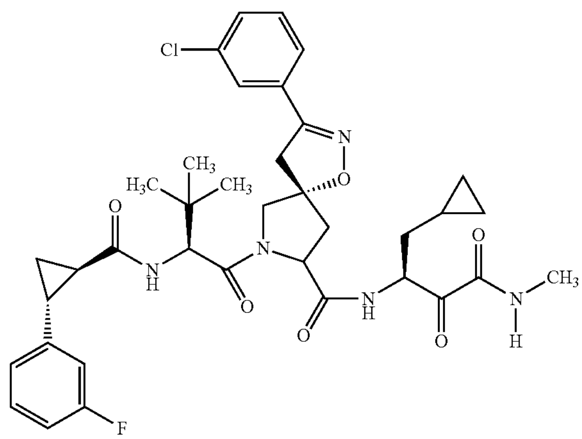 | 863 |
| 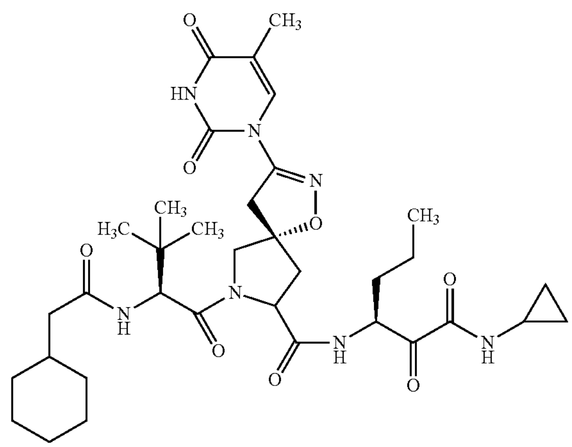 | 864 |
| 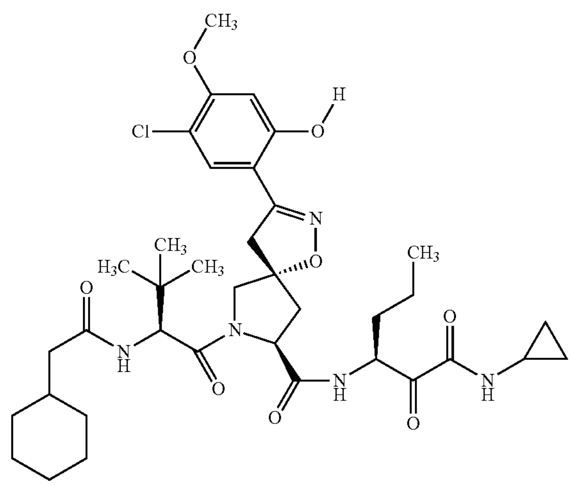 | 865 |

TABLE 1-continued

Exemplary compounds of Formula (I).

| Structure | Compound No. |
|---|---|
| 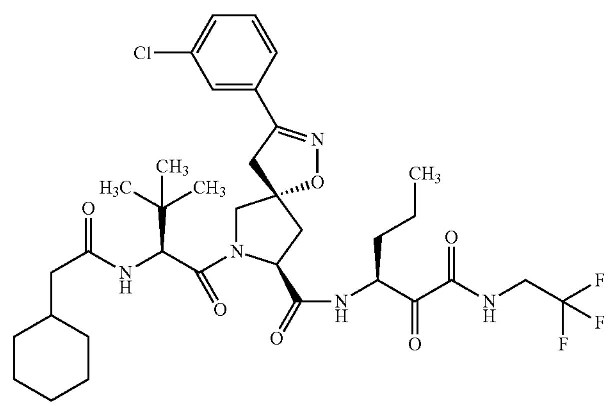 | 866 |
| 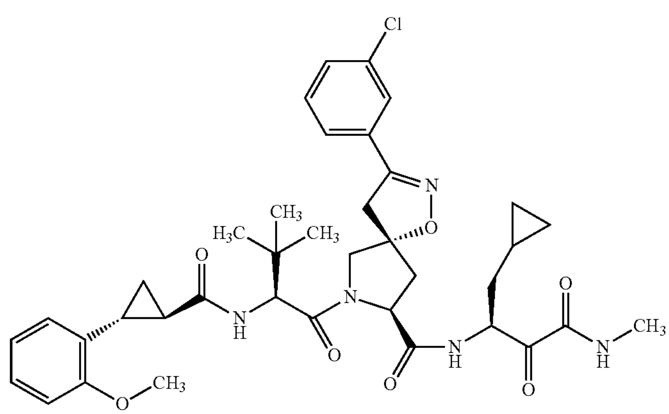 | 867 |
| 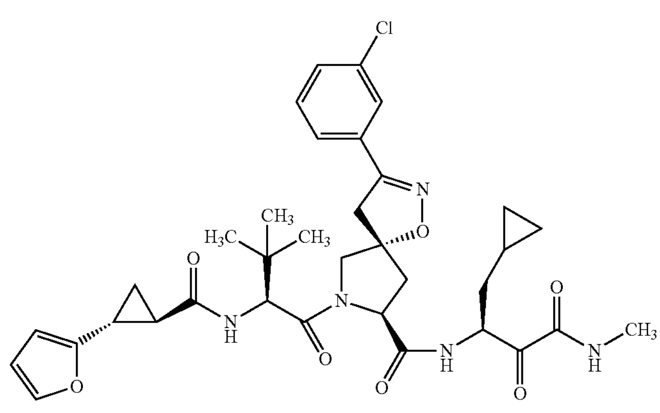 | 868 |

TABLE 1-continued

Exemplary compounds of Formula (I).

| Structure | Compound No. |
|---|---|
| 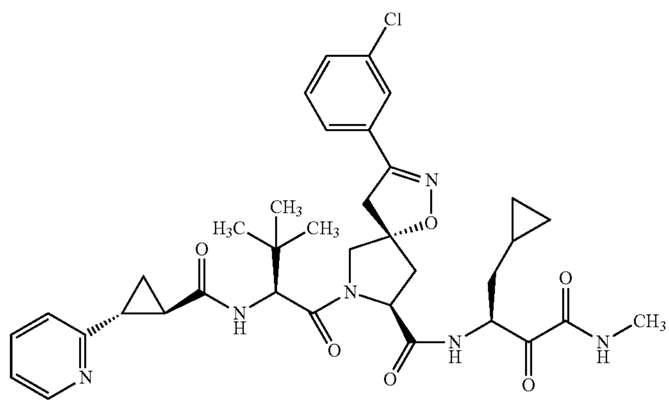 | 869 |
| 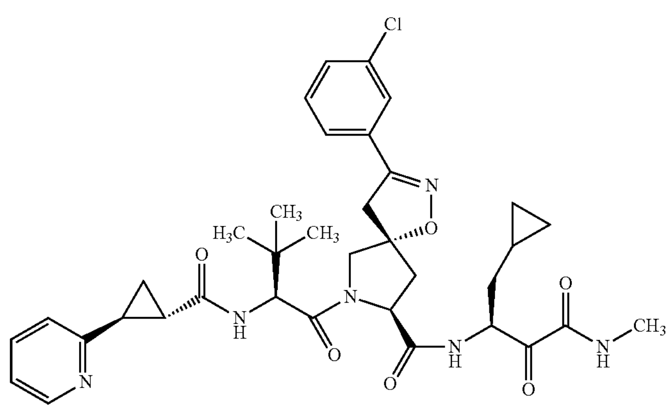 | 870 |
| 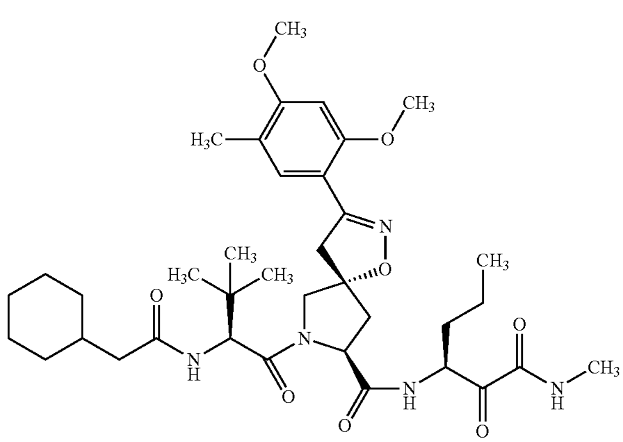 | 871 |

TABLE 1-continued

Exemplary compounds of Formula (I).

| Structure | Compound No. |
|---|---|
| 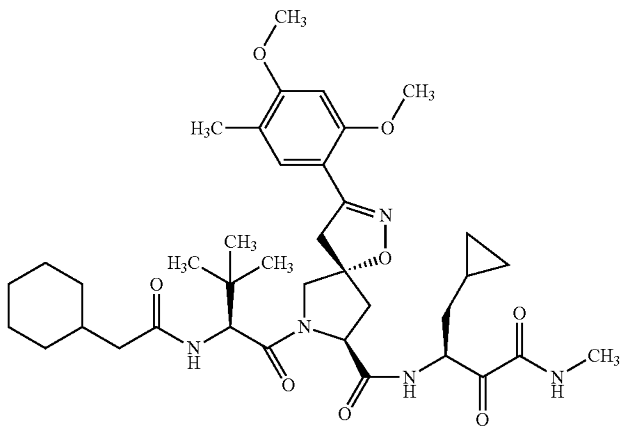 | 872 |
| 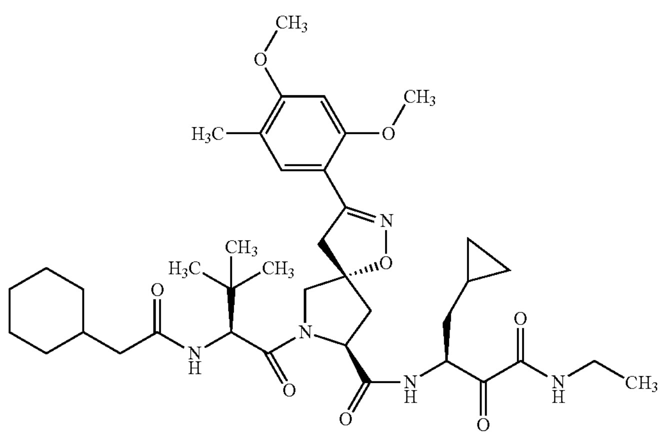 | 873 |
| 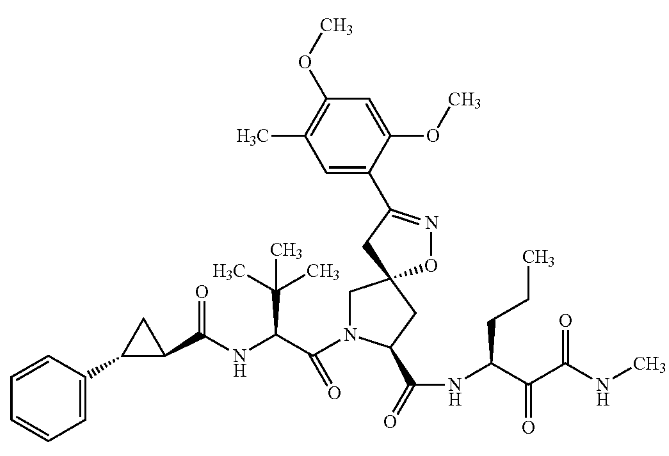 | 874 |

TABLE 1-continued
Exemplary compounds of Formula (I).
| Structure | Compound No. |
| --- | --- |
| 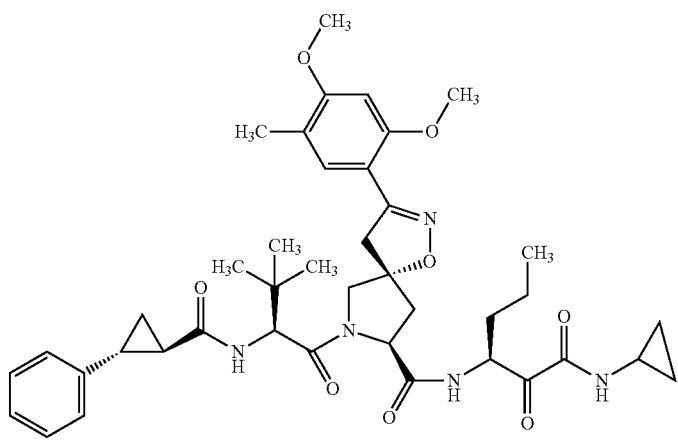 | 875 |
| 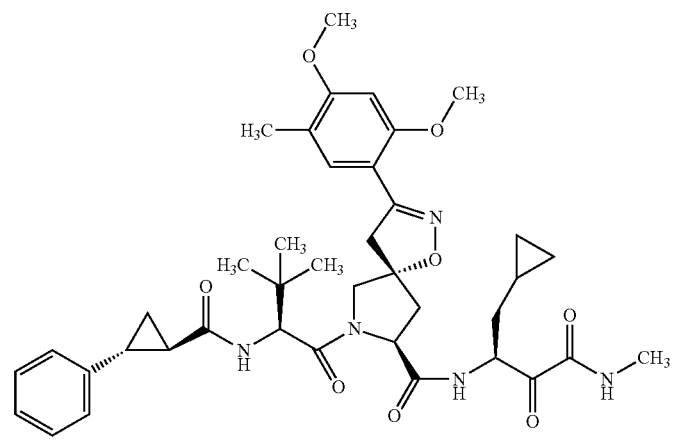 | 876 |
| 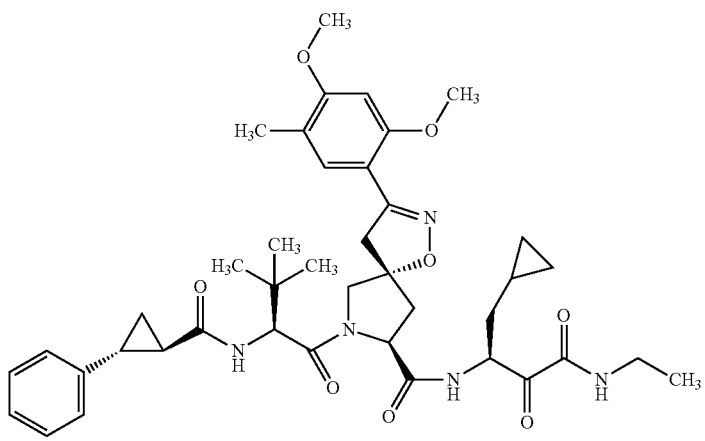 | 877 |

TABLE 1-continued

Exemplary compounds of Formula (I).

| Structure | Compound No. |
|---|---|
| 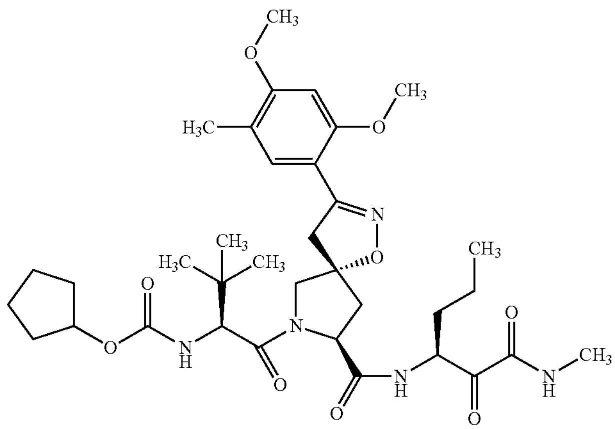 | 878 |
| 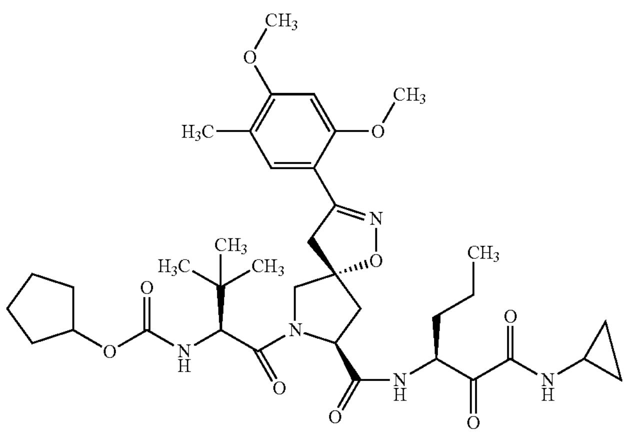 | 879 |
| 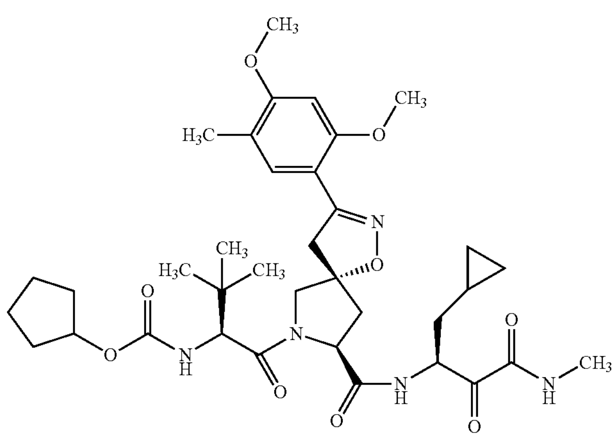 | 880 |

TABLE 1-continued
Exemplary compounds of Formula (I).
| Structure | Compound No. |
|---|---|
| 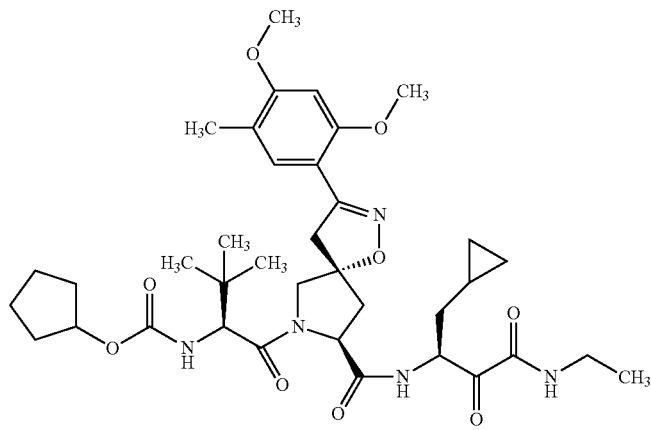 | 881 |
| 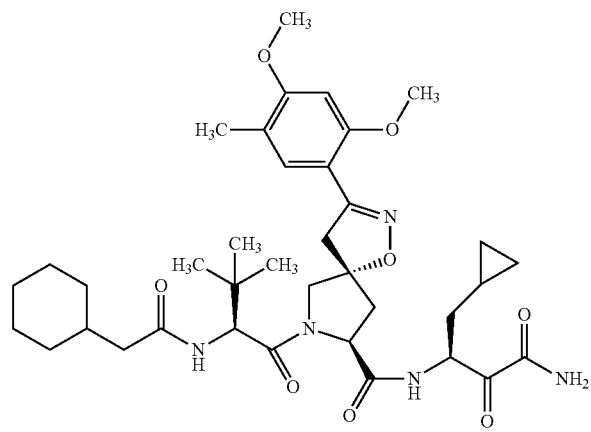 | 882 |
| 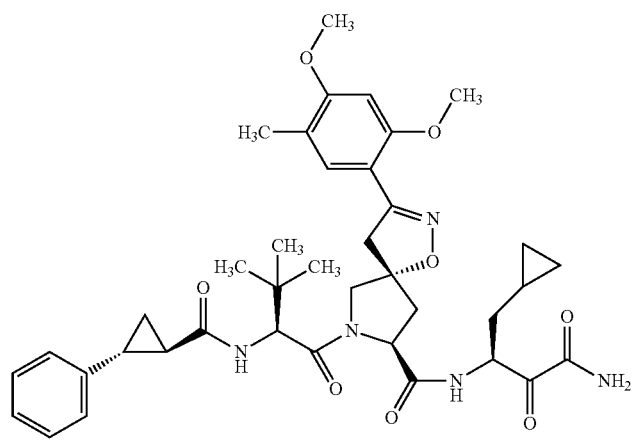 | 883 |

TABLE 1-continued

Exemplary compounds of Formula (I).

| Structure | Compound No. |
|---|---|
| 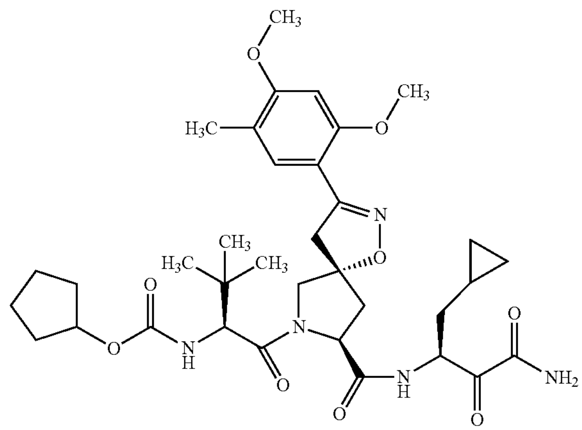 | 884 |
| 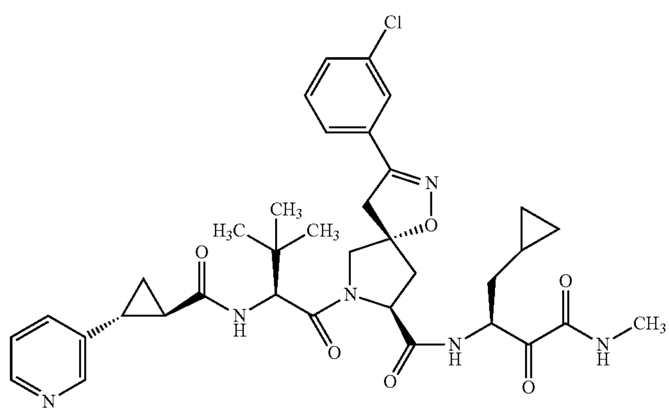 | 885 |
| 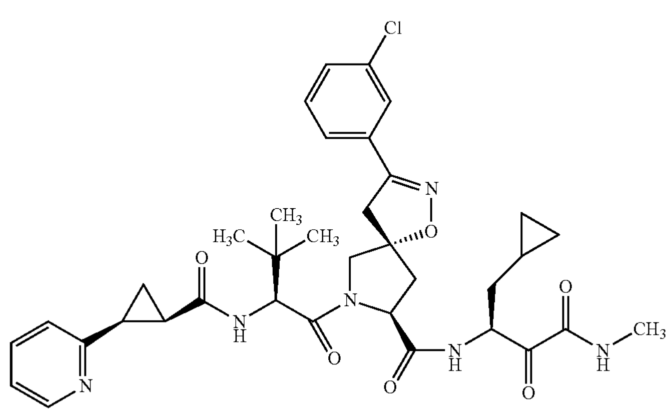 | 886 |

TABLE 1-continued

Exemplary compounds of Formula (I).

| Structure | Compound No. |
|---|---|
| 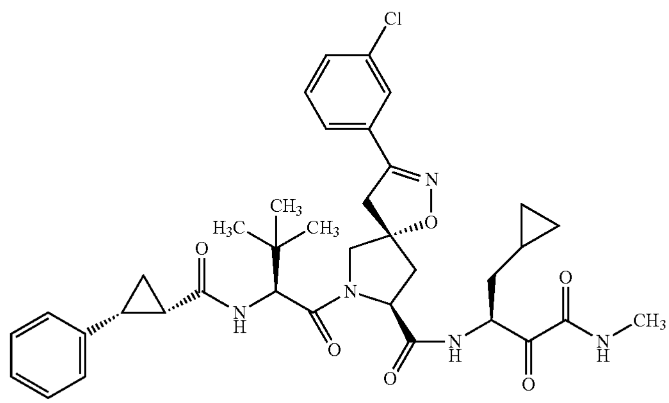 | 887 |
| 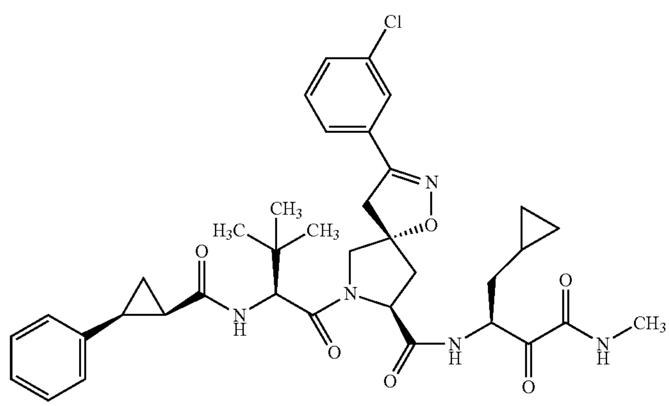 | 888 |
| 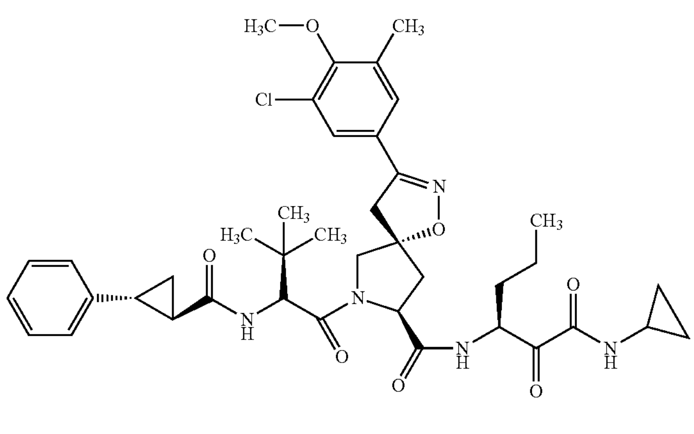 | 889 |

TABLE 1-continued

Exemplary compounds of Formula (I).

| Structure | Compound No. |
|---|---|
| 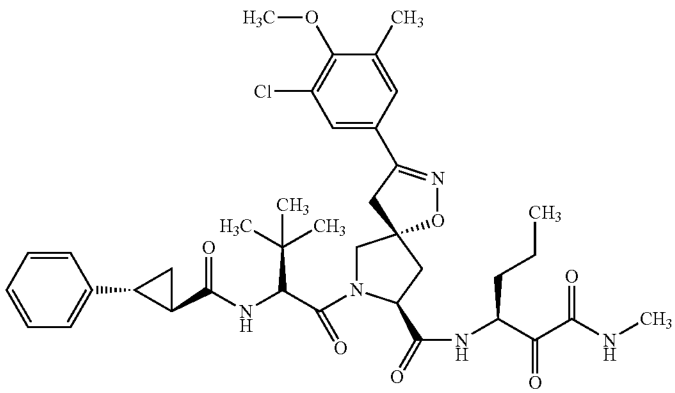 | 890 |
| 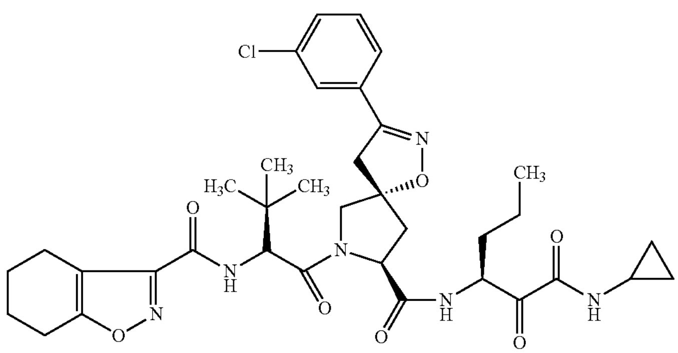 | 891 |
| 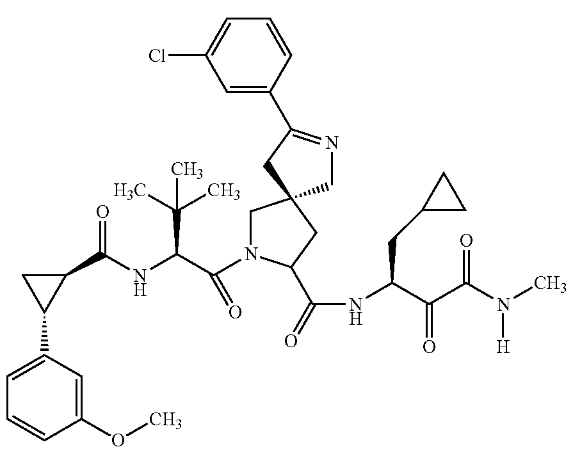 | 892 |

TABLE 1-continued

Exemplary compounds of Formula (I).

| Structure | Compound No. |
|---|---|
| 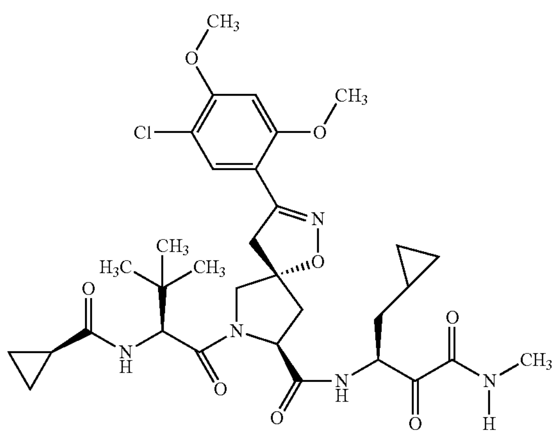 | 893 |
| 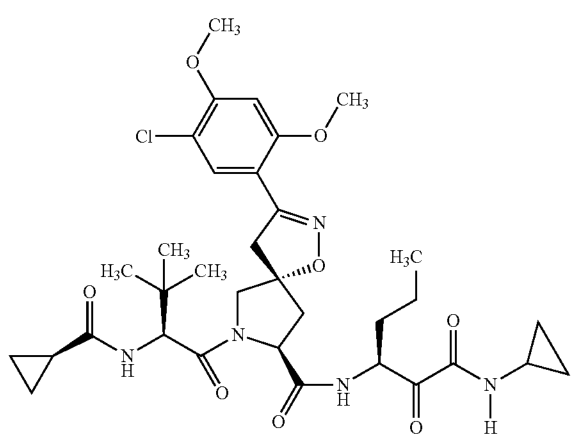 | 894 |
| 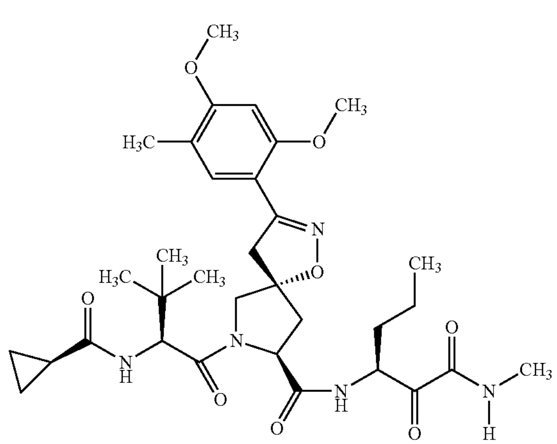 | 895 |

TABLE 1-continued

Exemplary compounds of Formula (I).

| Structure | Compound No. |
|---|---|
| 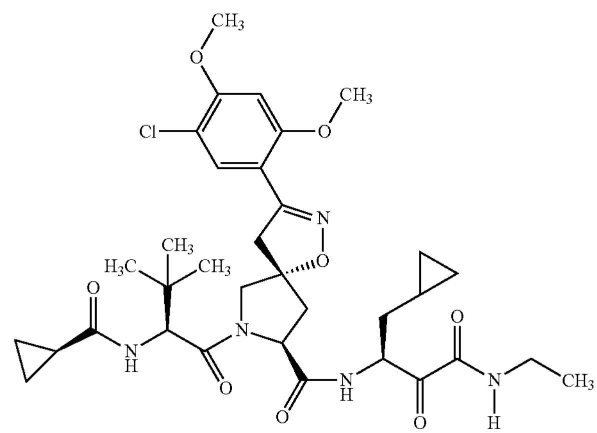 | 896 |
| 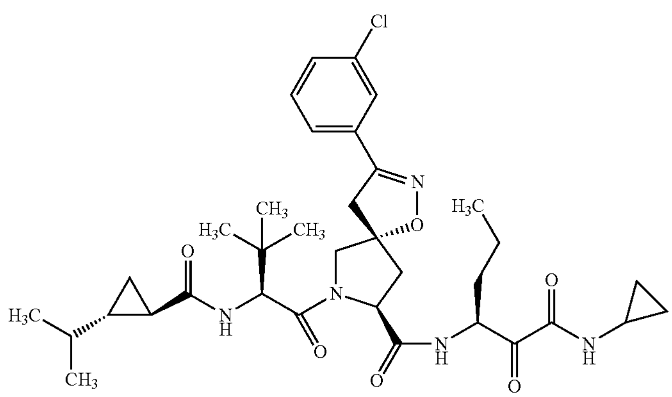 | 897 |
| 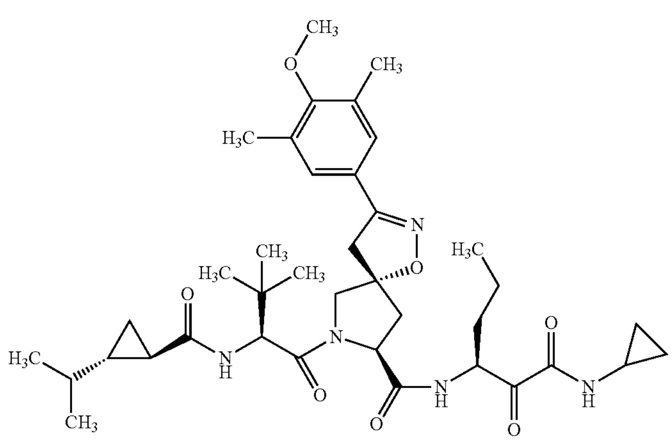 | 898 |

TABLE 1-continued

Exemplary compounds of Formula (I).

| Structure | Compound No. |
|---|---|
| 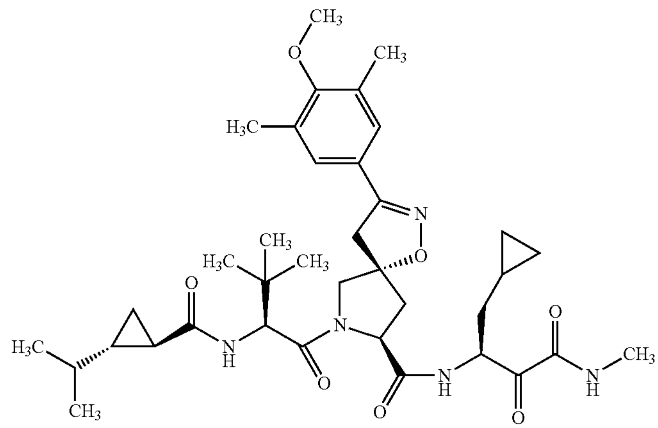 | 899 |
| 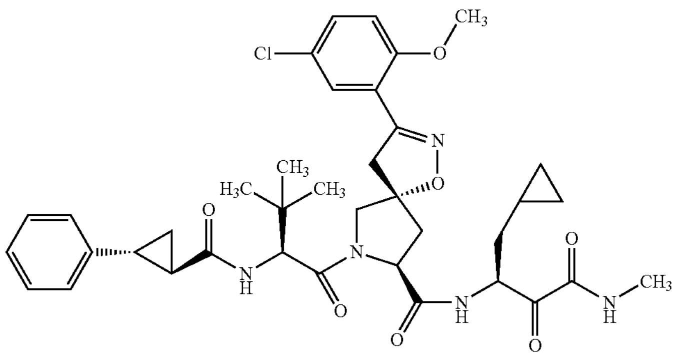 | 900 |
| 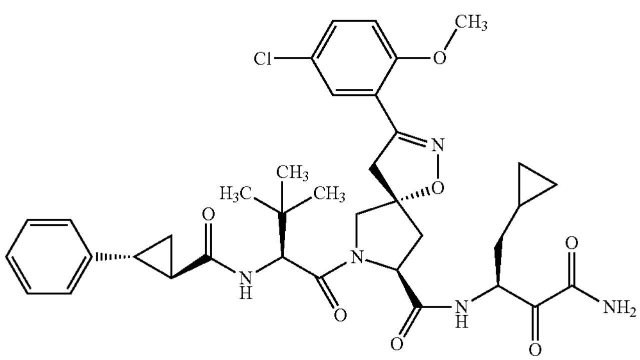 | 901 |
| 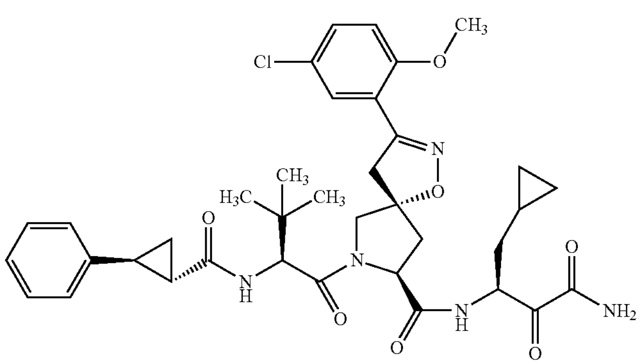 | 902 |

TABLE 1-continued

Exemplary compounds of Formula (I).

| Structure | Compound No. |
|---|---|
| 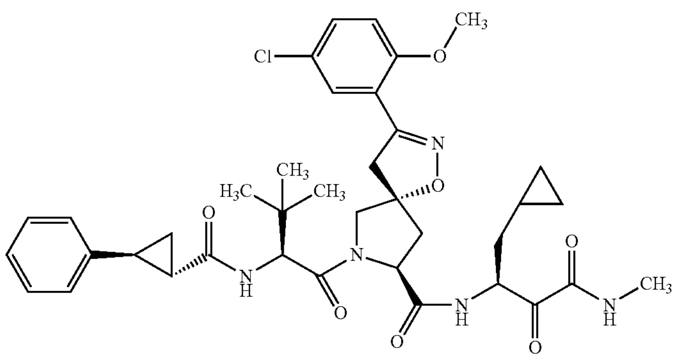 | 903 |
| 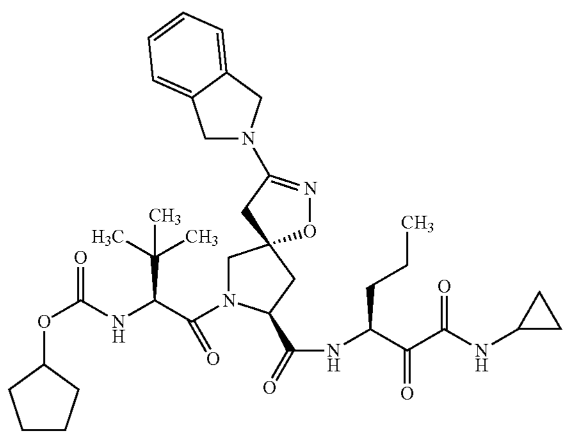 | 904 |
| 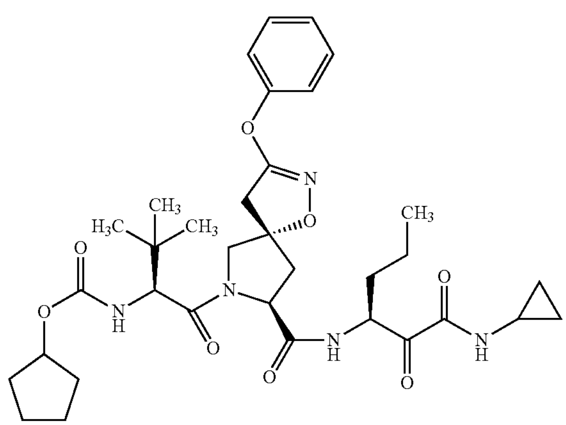 | 905 |

TABLE 1-continued

Exemplary compounds of Formula (I).

| Structure | Compound No. |
|---|---|
| 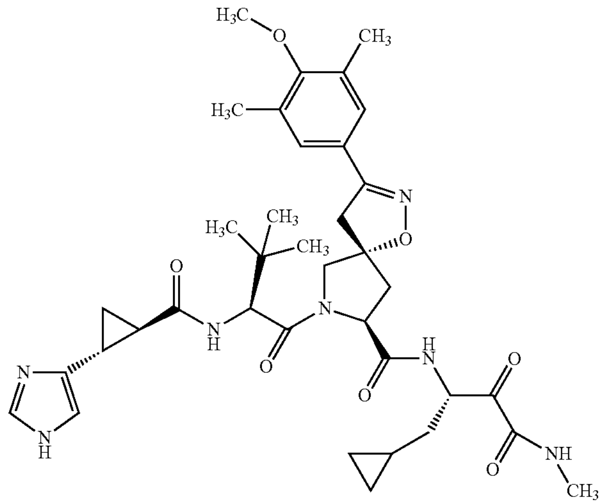 | 906 |
| 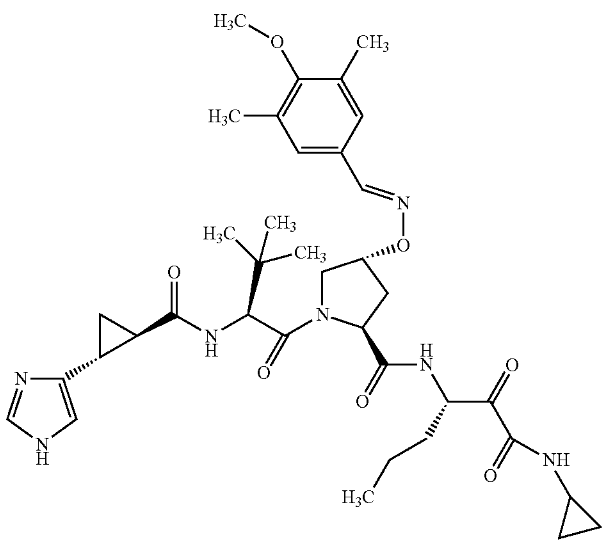 | 907 |
| 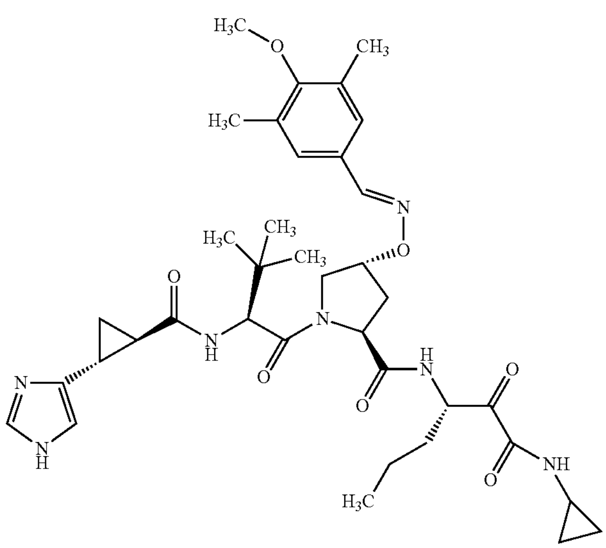 | 908 |

TABLE 1-continued

Exemplary compounds of Formula (I).

| Structure | Compound No. |
|---|---|
| 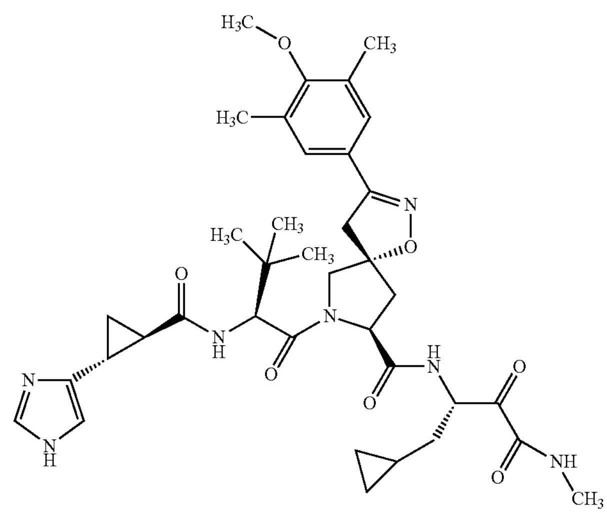 | 909 |
| 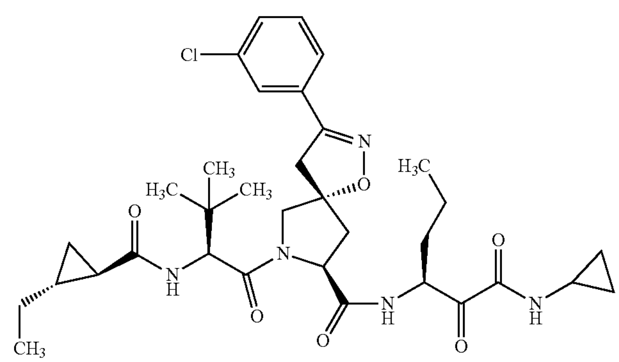 | 910 |
| 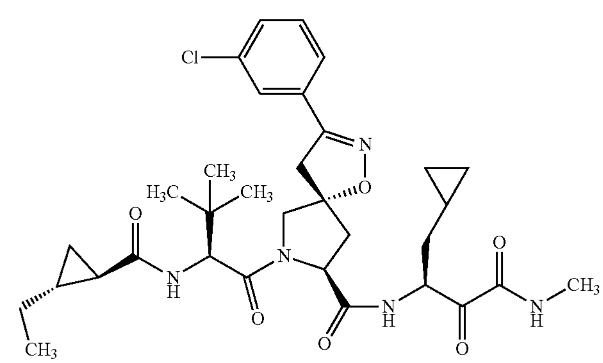 | 911 |

TABLE 1-continued
Exemplary compounds of Formula (I).
| Structure | Compound No. |
|---|---|
| 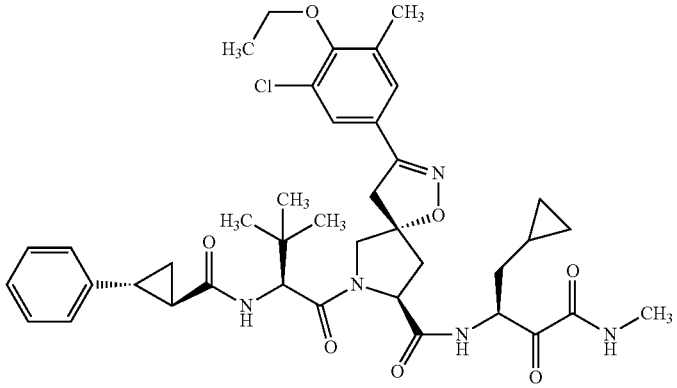 | 912 |
| 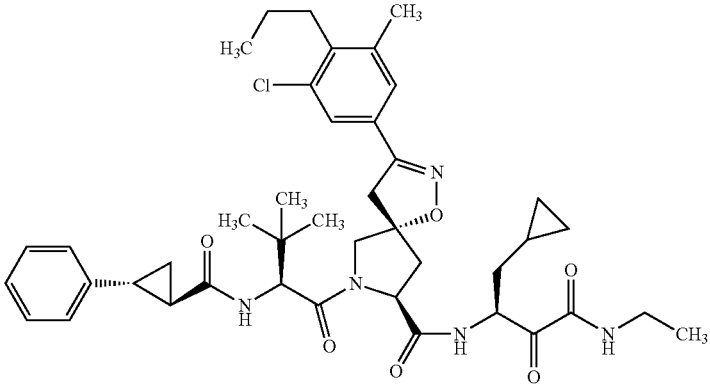 | 913 |
| 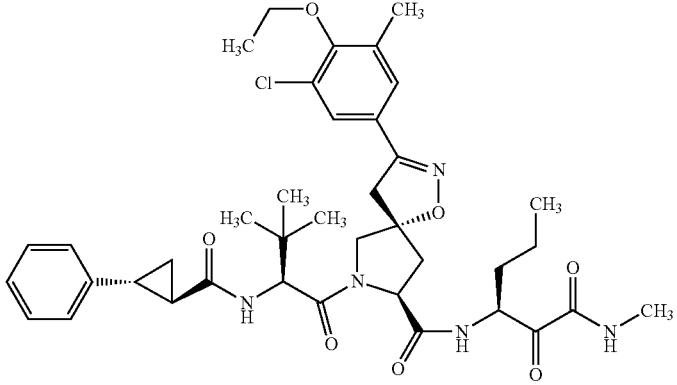 | 914 |
| 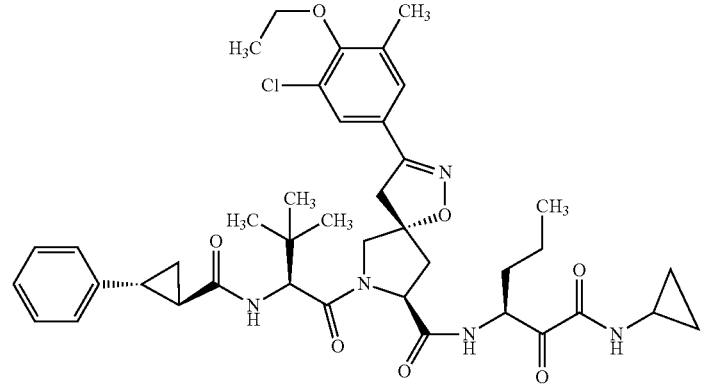 | 915 |

TABLE 1-continued

Exemplary compounds of Formula (I).

| Structure | Compound No. |
|---|---|
| 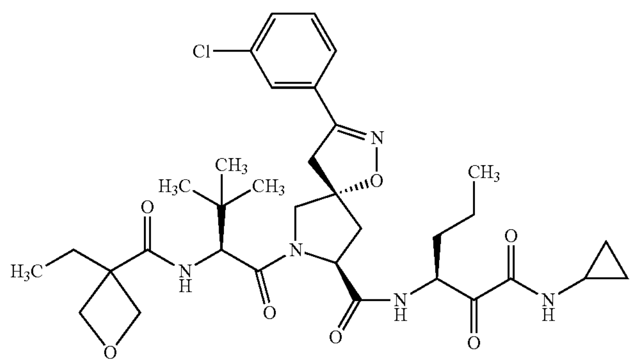 | 916 |
| 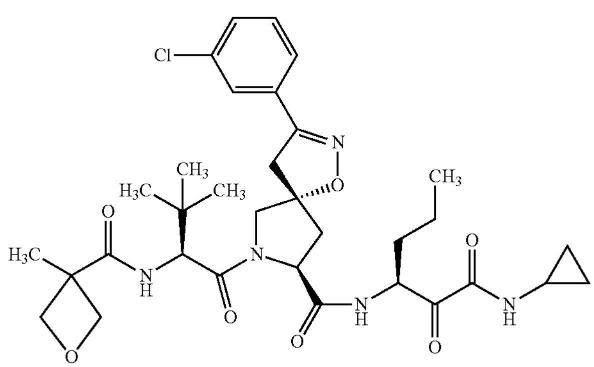 | 917 |
| 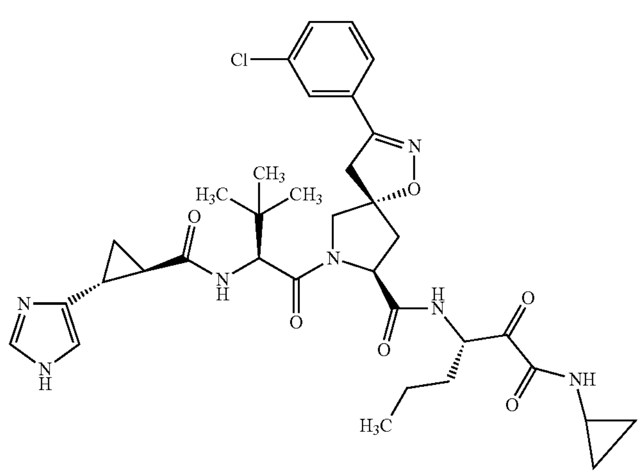 | 918 |

TABLE 1-continued

Exemplary compounds of Formula (I).

| Structure | Compound No. |
|---|---|
| 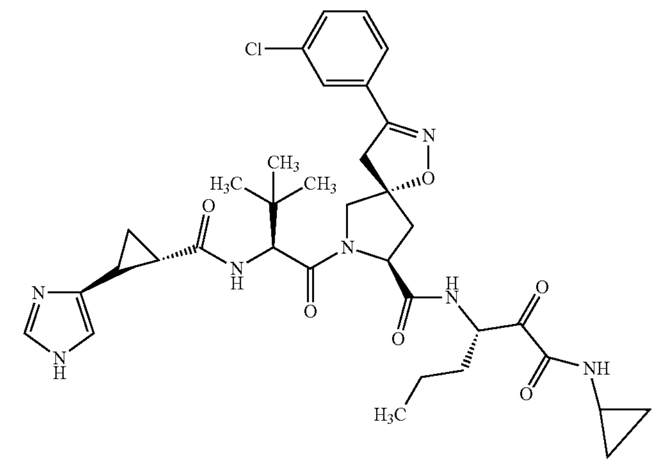 | 919 |
| 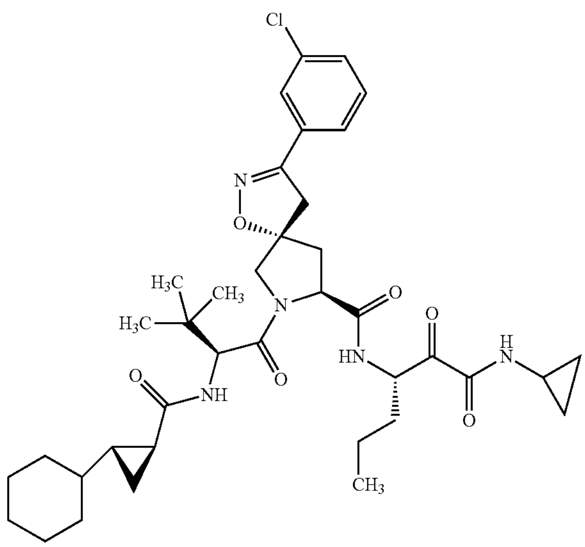 | 920 |
| 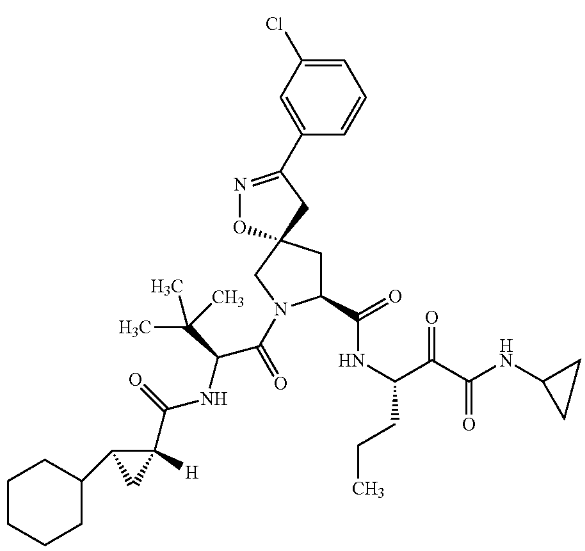 | 921 |

TABLE 1-continued

Exemplary compounds of Formula (I).

| Structure | Compound No. |
|---|---|
| 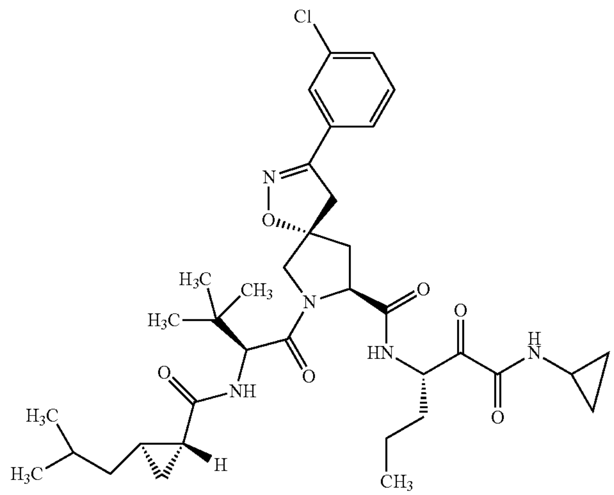 | 922 |
| 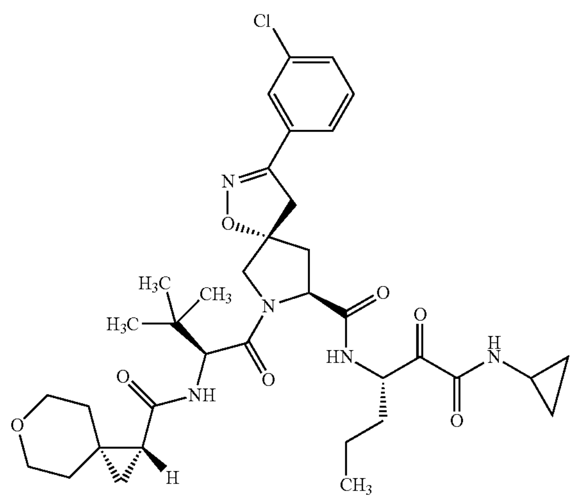 | 923 |
| 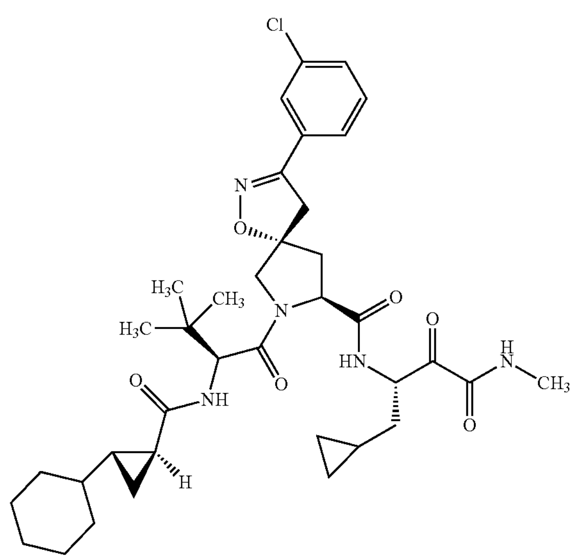 | 924 |

TABLE 1-continued

Exemplary compounds of Formula (I).

| Structure | Compound No. |
|---|---|
| 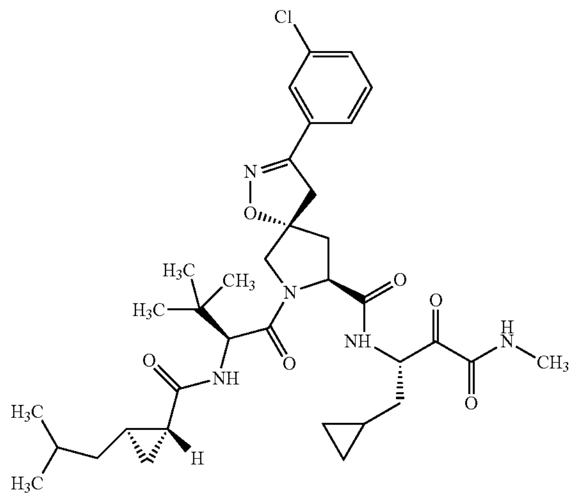 | 925 |
| 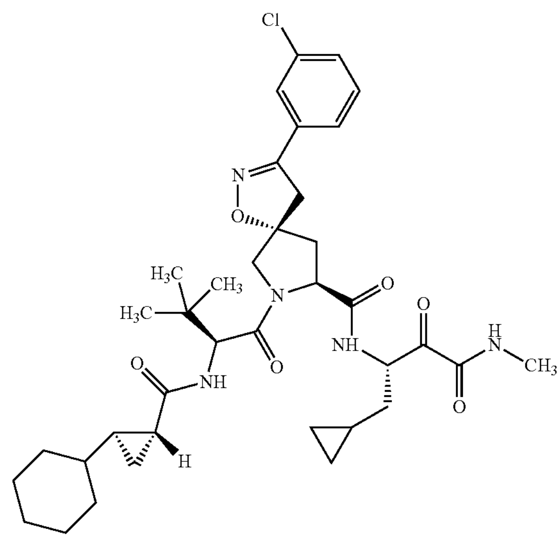 | 926 |
| 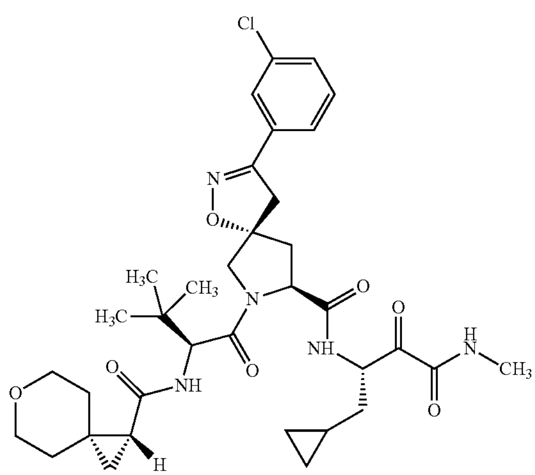 | 927 |

TABLE 1-continued

Exemplary compounds of Formula (I).

| Structure | Compound No. |
|---|---|
| 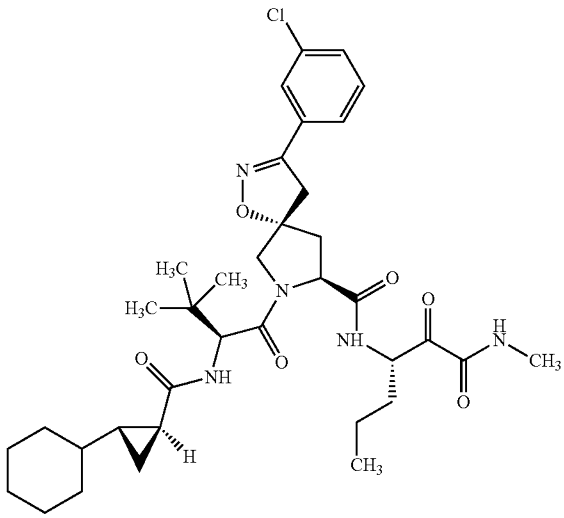 | 928 |
| 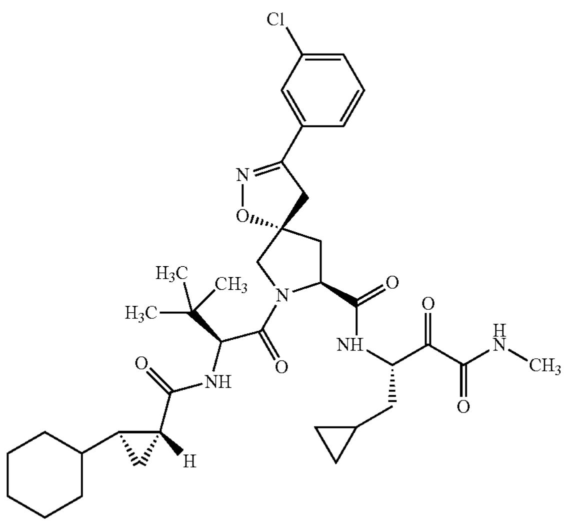 | 929 |
| 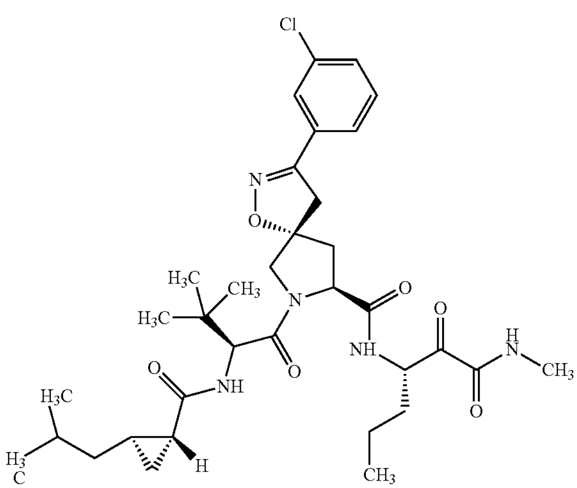 | 930 |

TABLE 1-continued

Exemplary compounds of Formula (I).

| Structure | Compound No. |
|---|---|
| 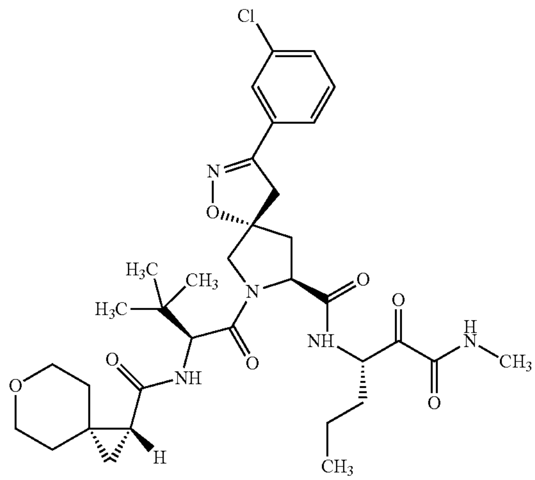 | 931 |
| 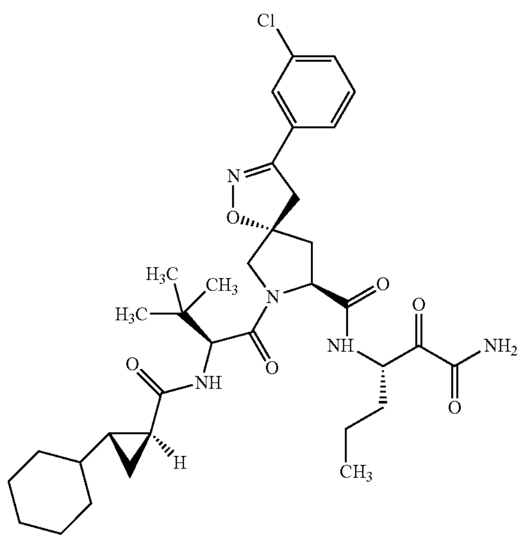 | 932 |
| 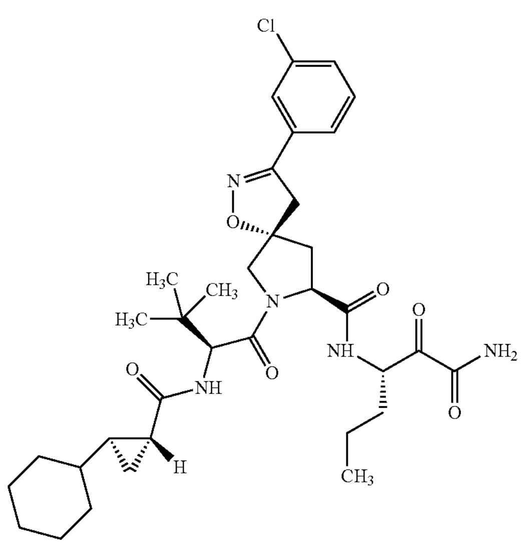 | 933 |

TABLE 1-continued

Exemplary compounds of Formula (I).

| Structure | Compound No. |
|---|---|
| 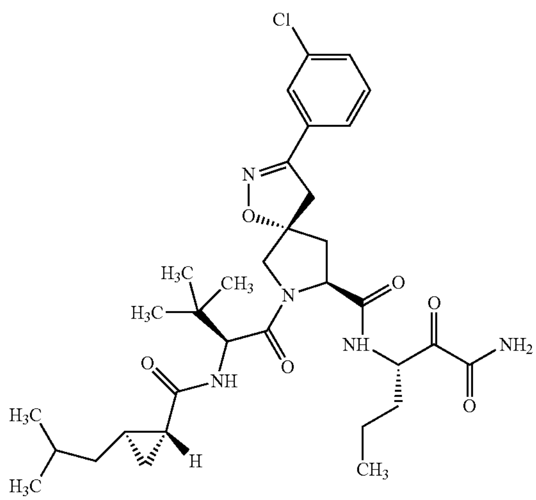 | 934 |
| 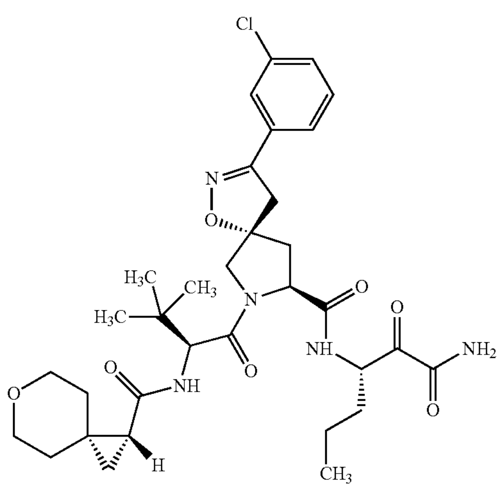 | 935 |
| 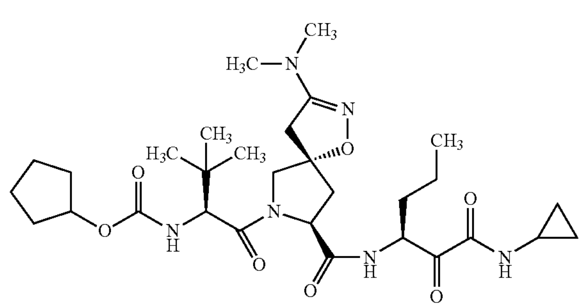 | 936 |

TABLE 1-continued

Exemplary compounds of Formula (I).

| Structure | Compound No. |
|---|---|
| 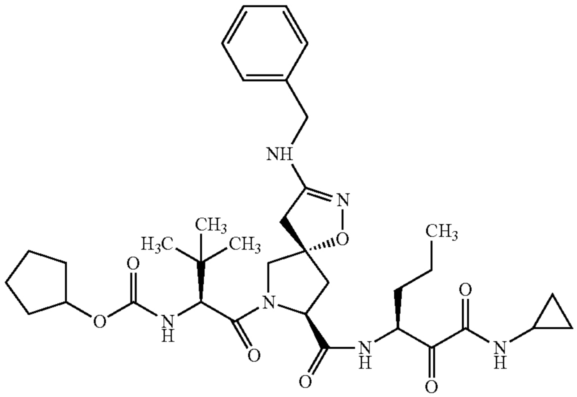 | 937 |
| 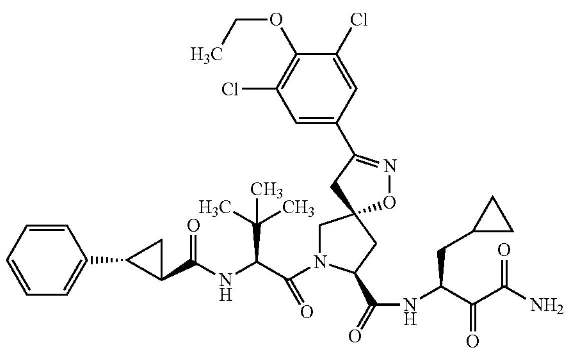 | 938 |
| 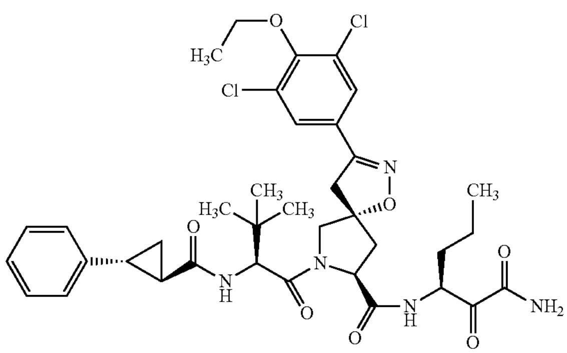 | 939 |
| 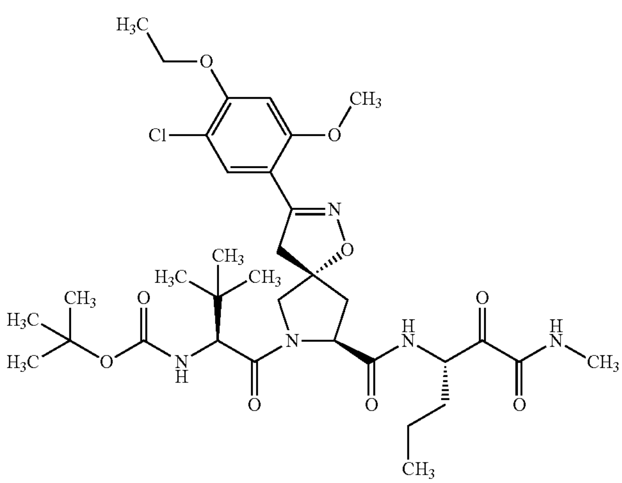 | 940 |

TABLE 1-continued

Exemplary compounds of Formula (I).

| Structure | Compound No. |
|---|---|
| 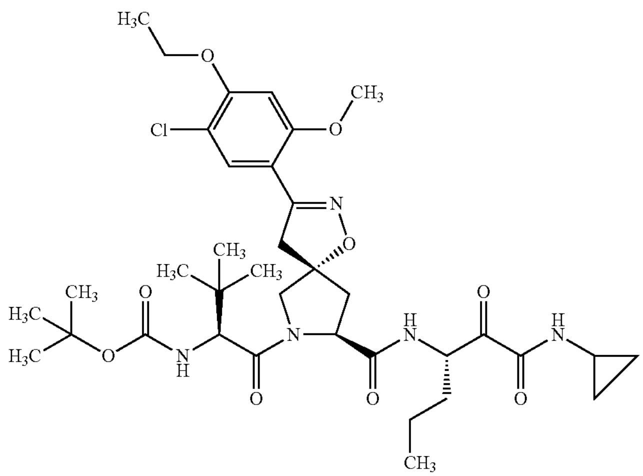 | 941 |
| 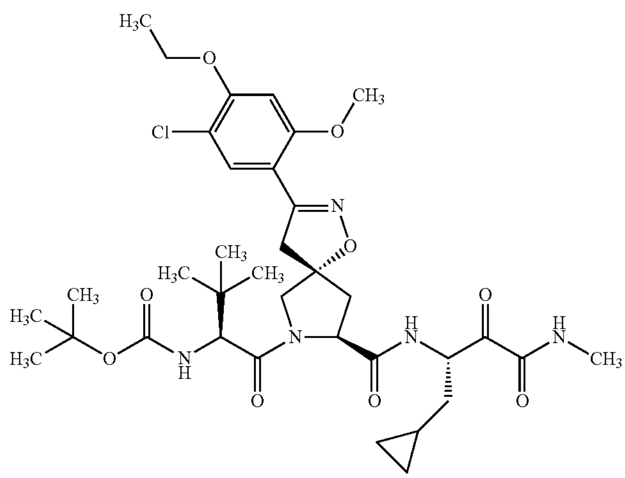 | 942 |
| 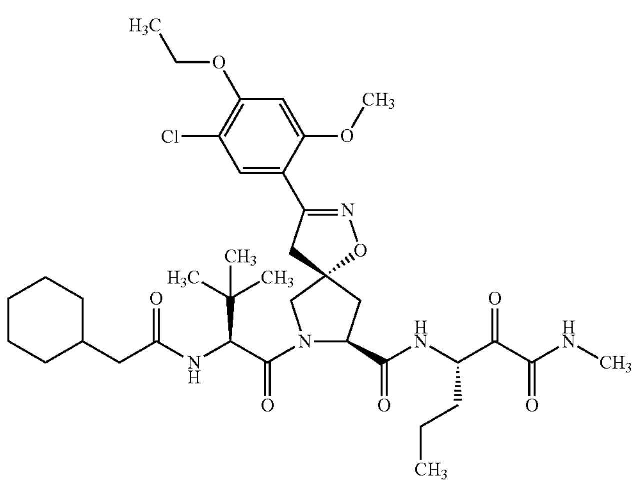 | 943 |

TABLE 1-continued

Exemplary compounds of Formula (I).

| Structure | Compound No. |
|---|---|
| 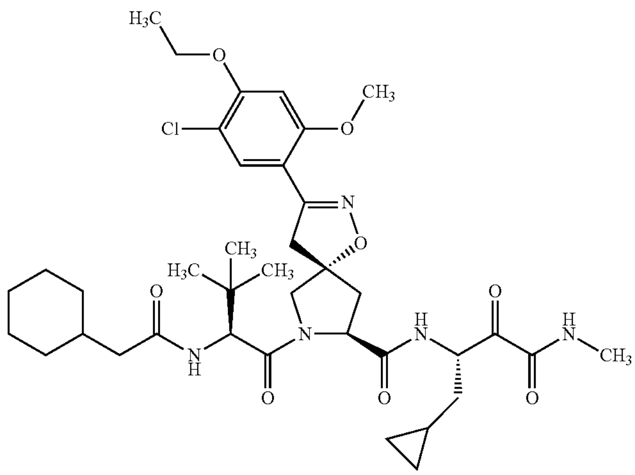 | 944 |
| 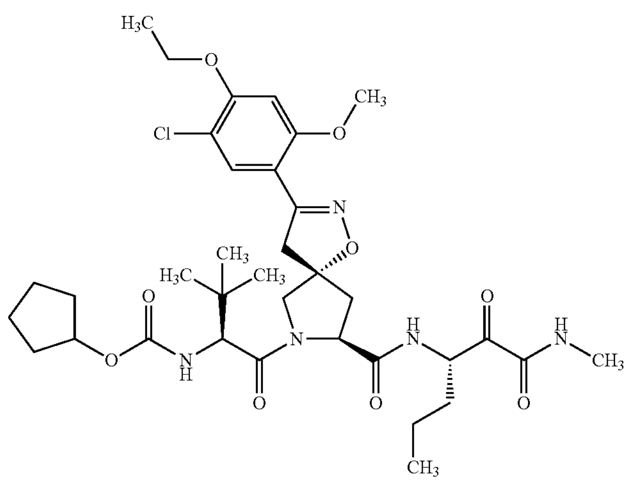 | 945 |
| 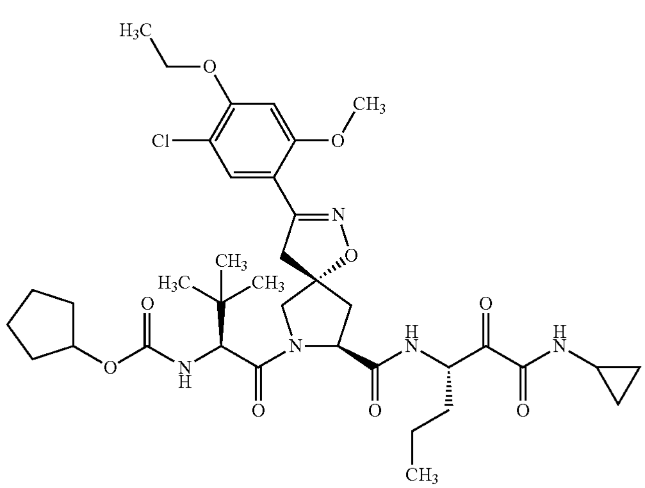 | 946 |

TABLE 1-continued
Exemplary compounds of Formula (I).
| Structure | Compound No. |
|---|---|
| 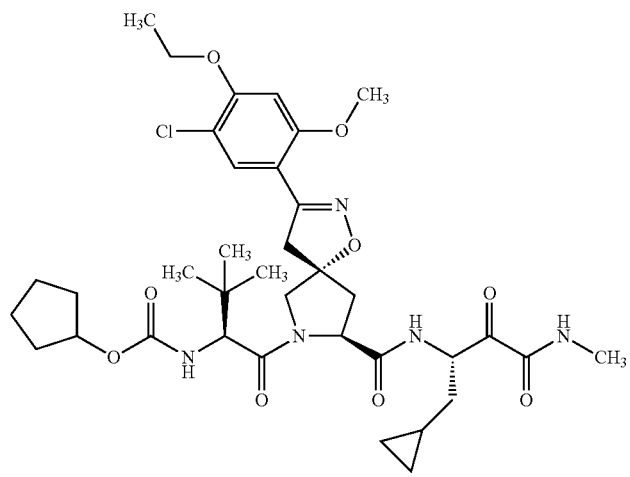 | 947 |
| 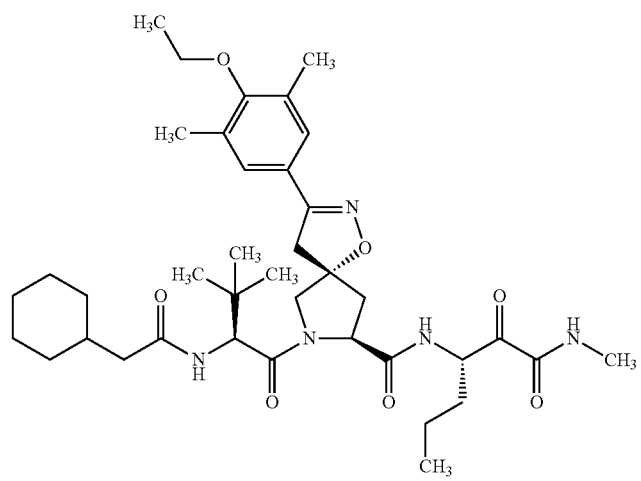 | 948 |
| 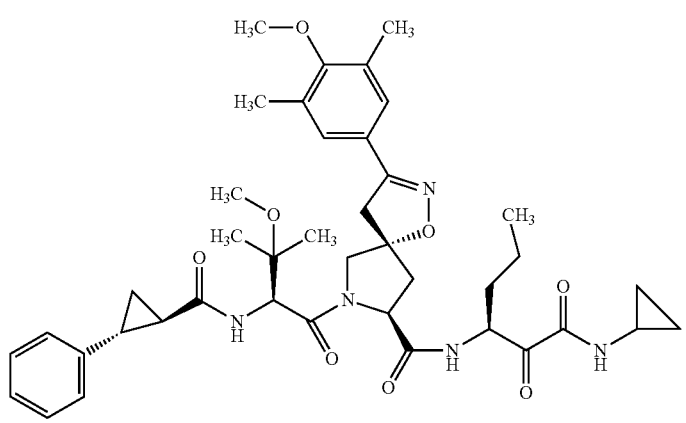 | 949 |

TABLE 1-continued
Exemplary compounds of Formula (I).
| Structure | Compound No. |
|---|---|
| 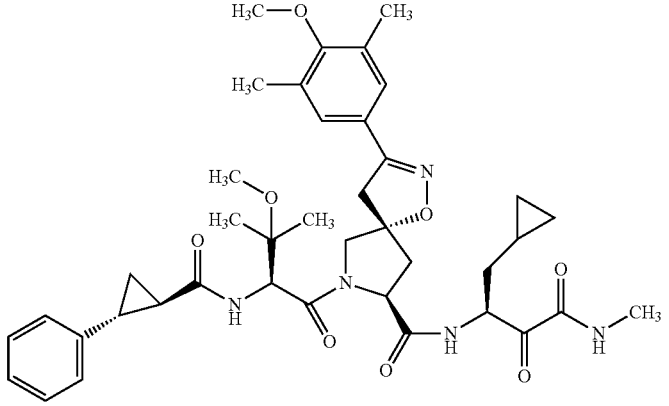 | 950 |
| 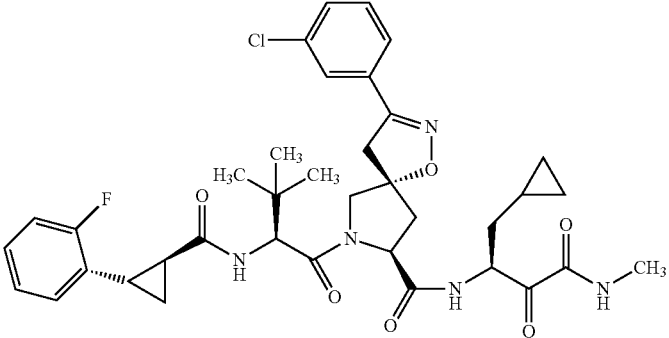 | 951 |
| 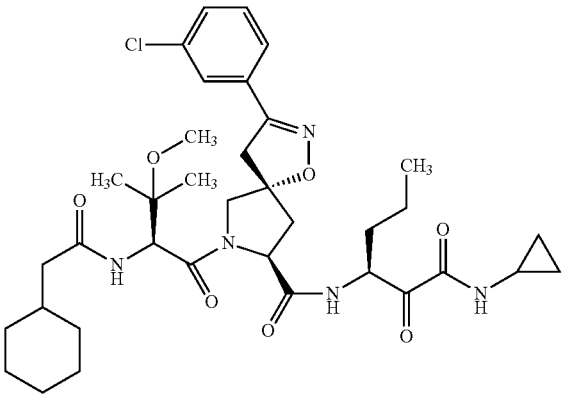 | 952 |
| 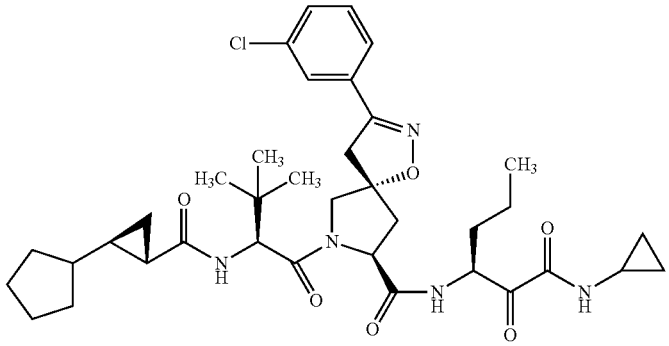 | 953 |

TABLE 1-continued

Exemplary compounds of Formula (I).

| Structure | Compound No. |
|---|---|
| 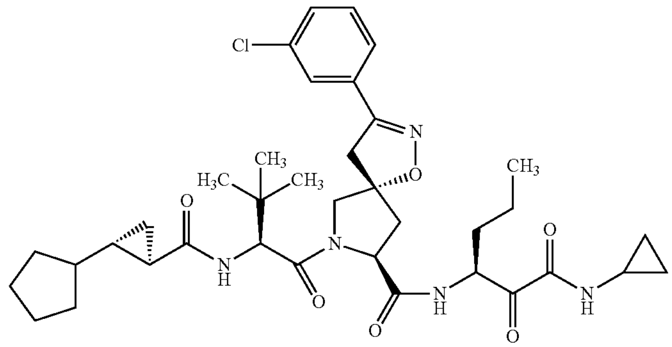 | 954 |
| 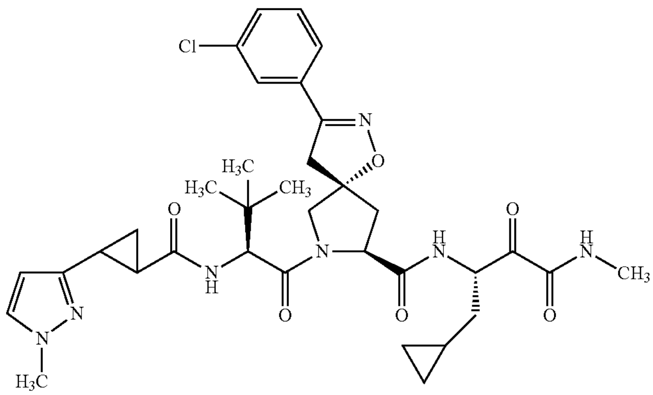 | 955 |
| 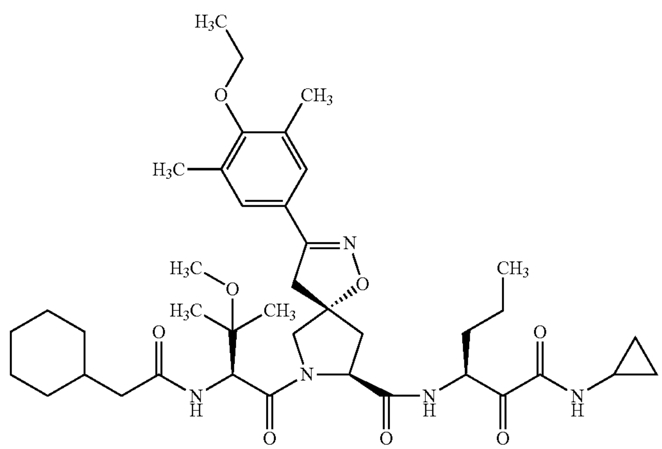 | 956 |
| 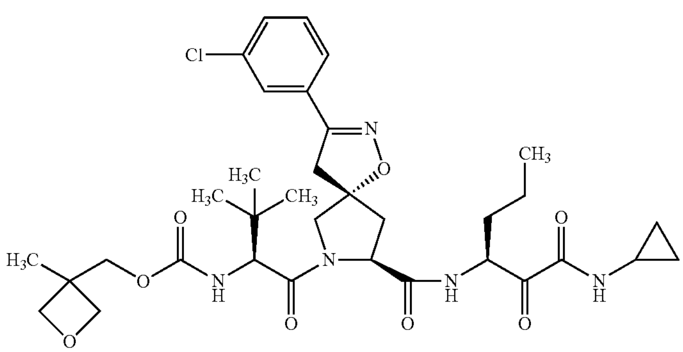 | 957 |

TABLE 1-continued

Exemplary compounds of Formula (I).

| Structure | Compound No. |
|---|---|
| 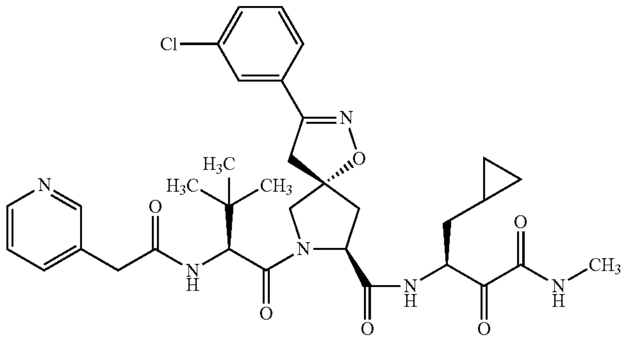 | 958 |
| 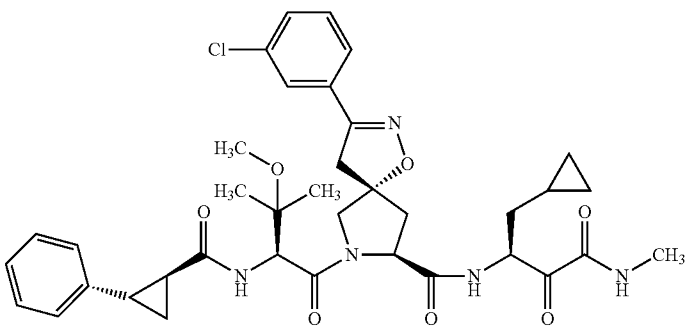 | 959 |
| 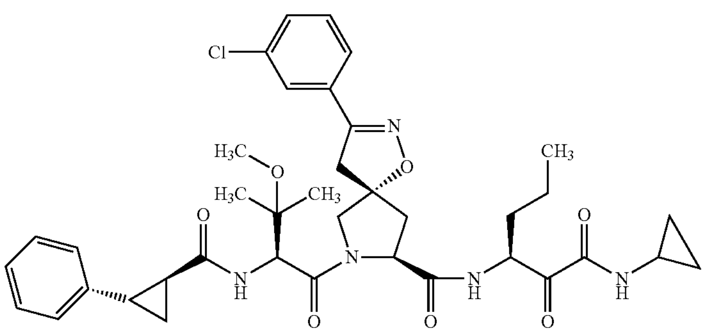 | 960 |
| 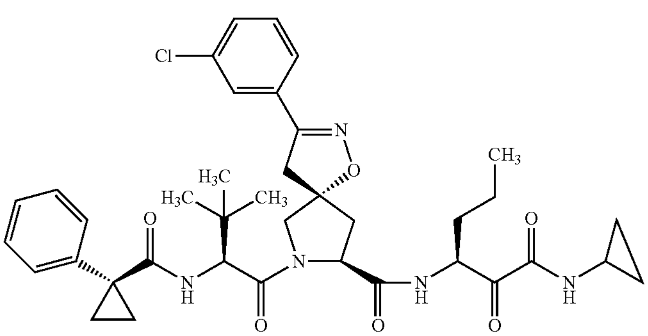 | 961 |

TABLE 1-continued
Exemplary compounds of Formula (I).
| Structure | Compound No. |
|---|---|
| 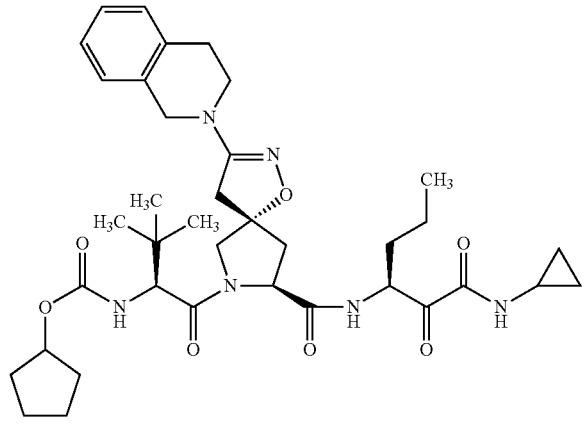 | 962 |
| 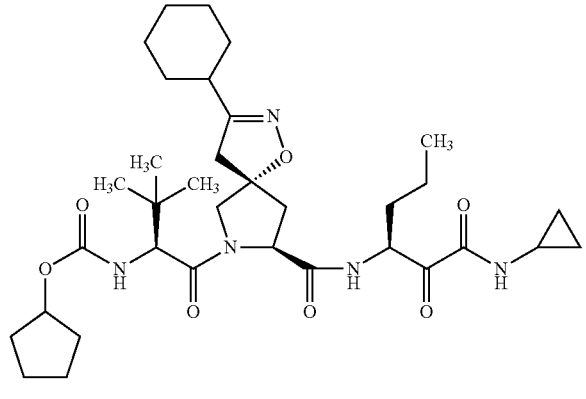 | 963 |
| 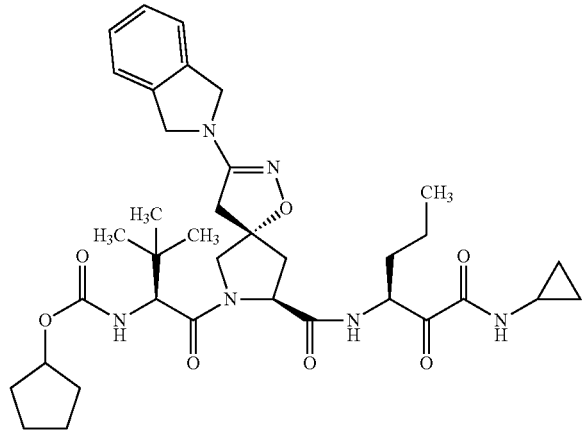 | 964 |

TABLE 1-continued

Exemplary compounds of Formula (I).

| Structure | Compound No. |
|---|---|
| 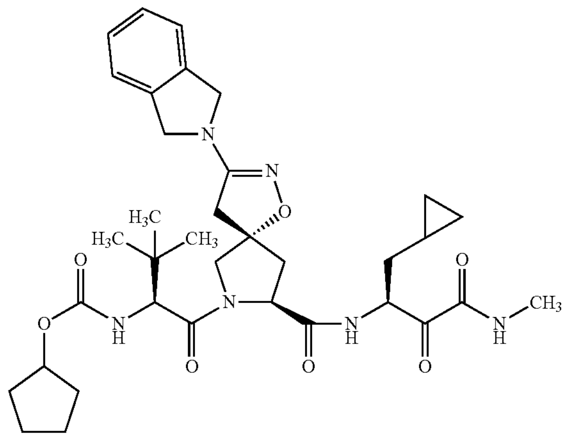 | 965 |
| 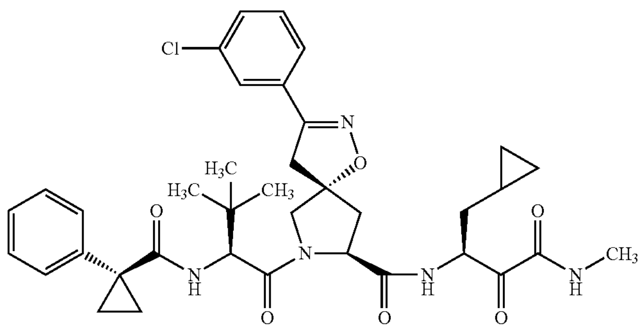 | 966 |
| 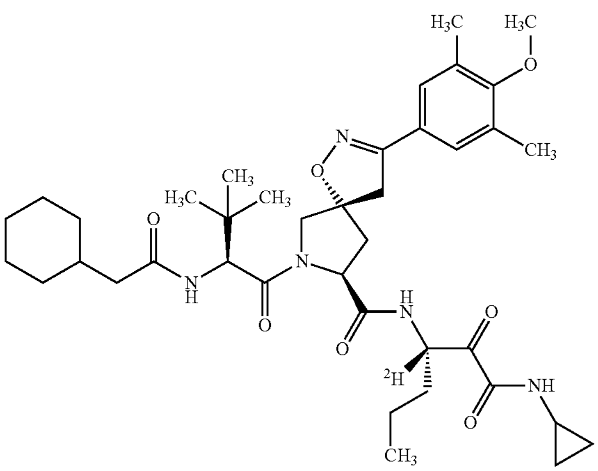 | 967 |
| 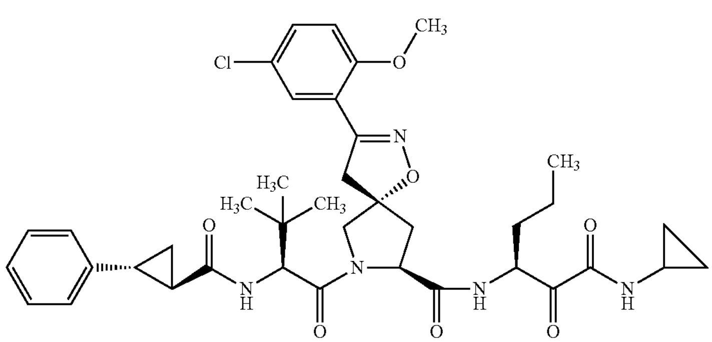 | 968 |

TABLE 1-continued
Exemplary compounds of Formula (I).
| Structure | Compound No. |
|---|---|
| 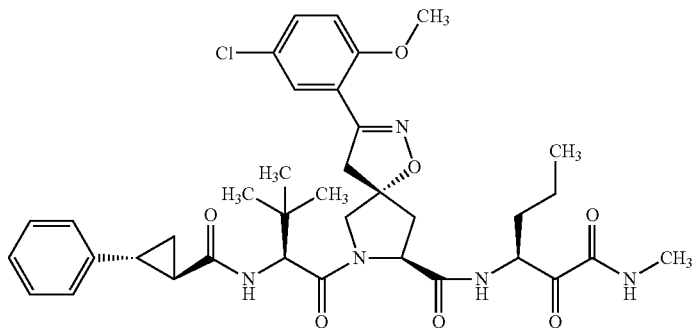 | 969 |
| 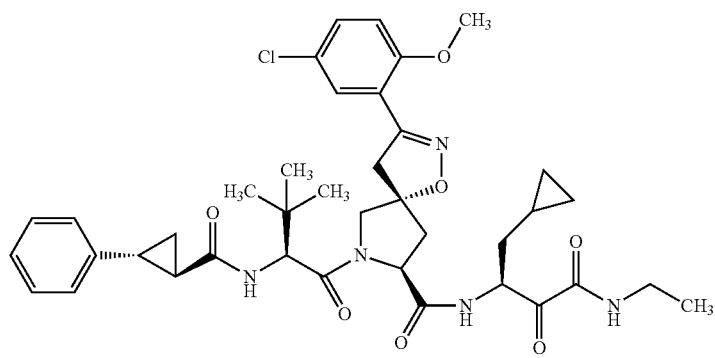 | 970 |
| 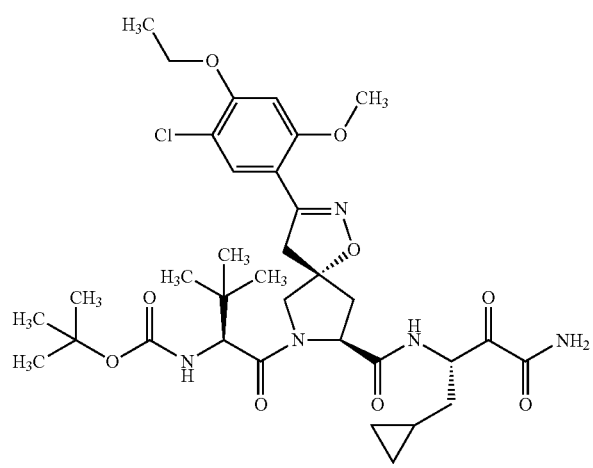 | 971 |

TABLE 1-continued
Exemplary compounds of Formula (I).
| Structure | Compound No. |
|---|---|
| 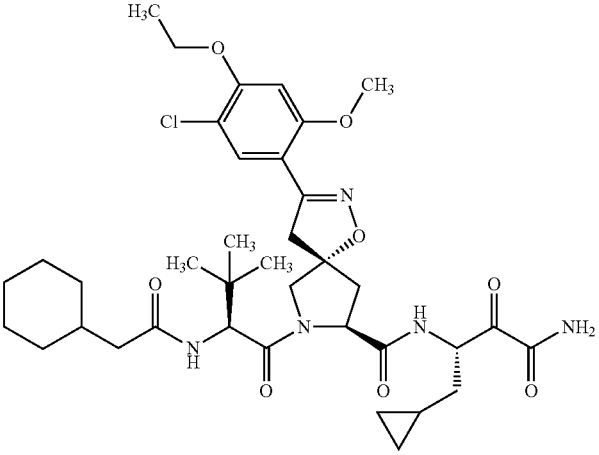 | 972 |
| 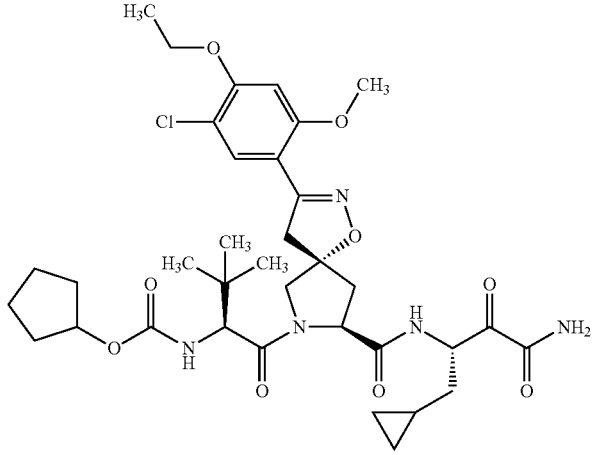 | 973 |
| 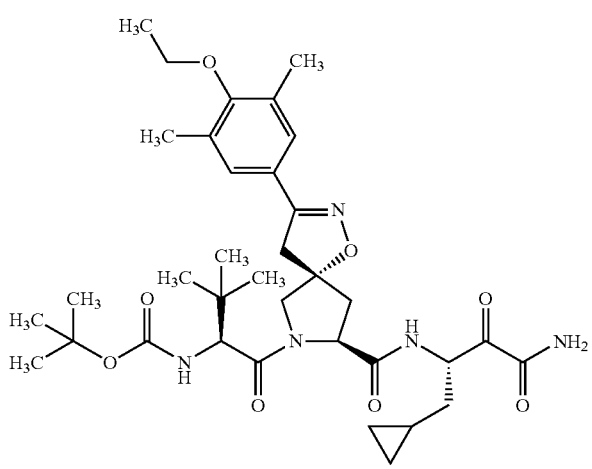 | 974 |

TABLE 1-continued

Exemplary compounds of Formula (I).

| Structure | Compound No. |
|---|---|
| 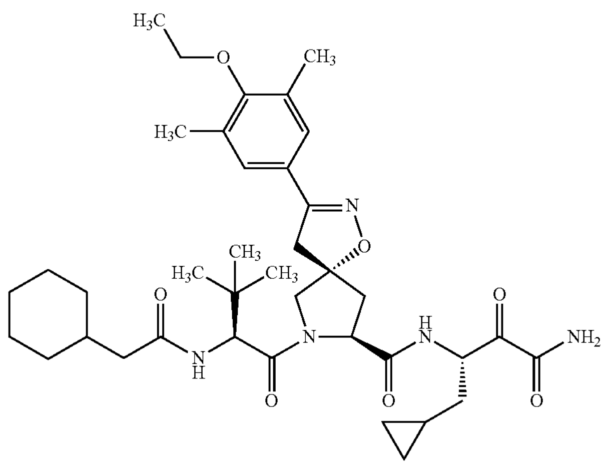 | 975 |
| 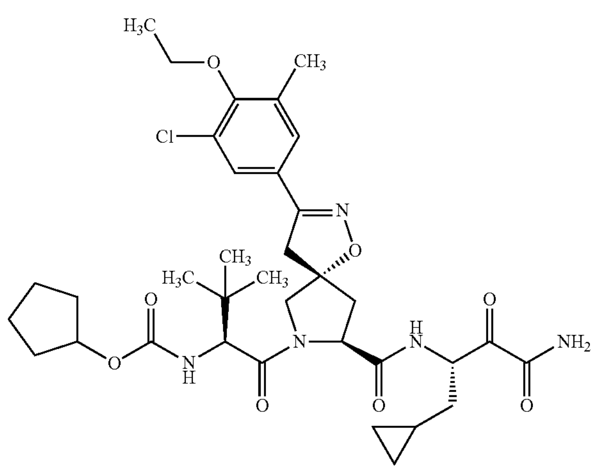 | 976 |
| 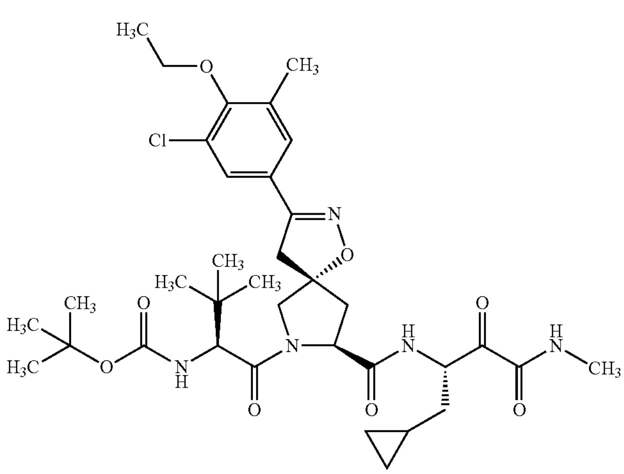 | 977 |

TABLE 1-continued

Exemplary compounds of Formula (I).

| Structure | Compound No. |
|---|---|
| 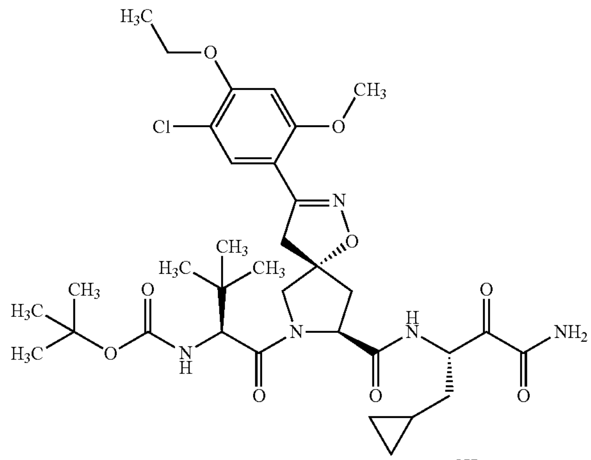 | 978 |
| 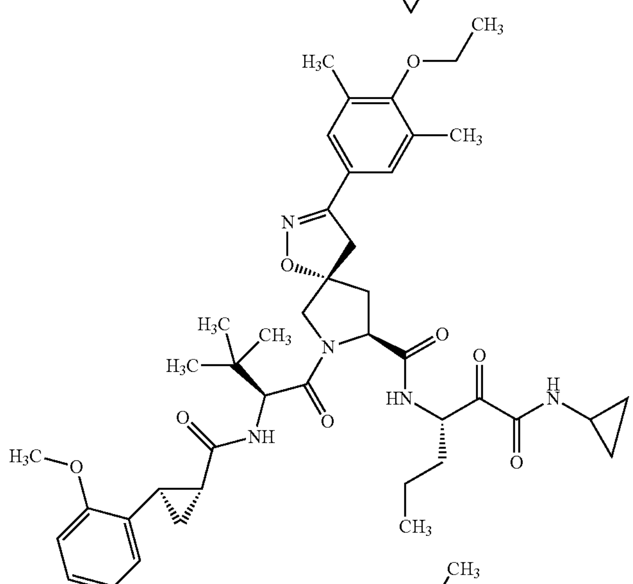 | 979 |
| 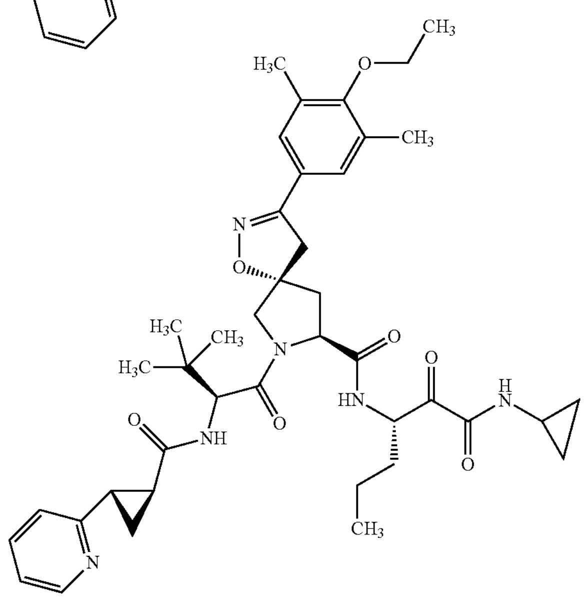 | 980 |

TABLE 1-continued
Exemplary compounds of Formula (I).
| Structure | Compound No. |
|---|---|
| 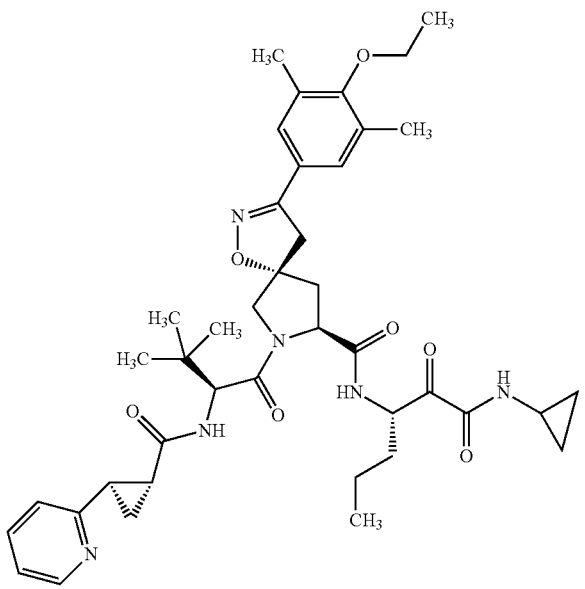 | 981 |
| 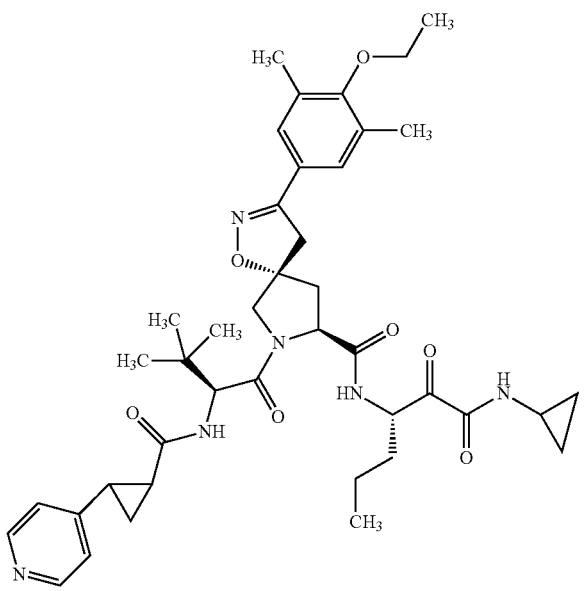 | 982 |

TABLE 1-continued
Exemplary compounds of Formula (I).
| Structure | Compound No. |
|---|---|
| 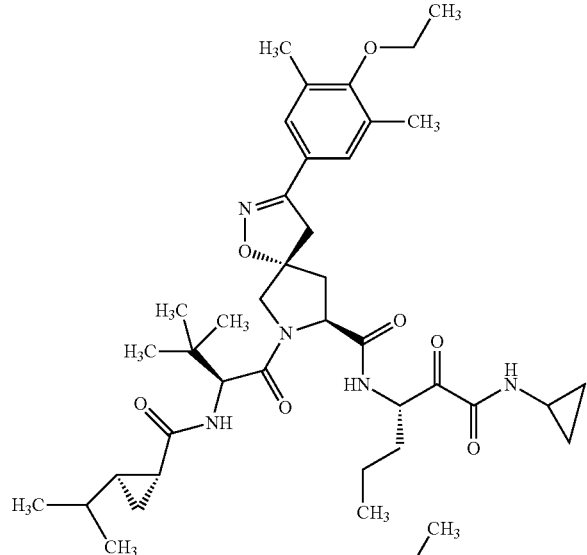 | 983 |
| 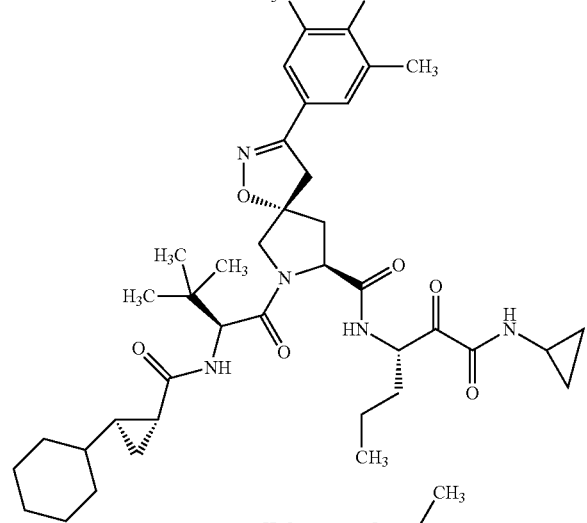 | 984 |
| 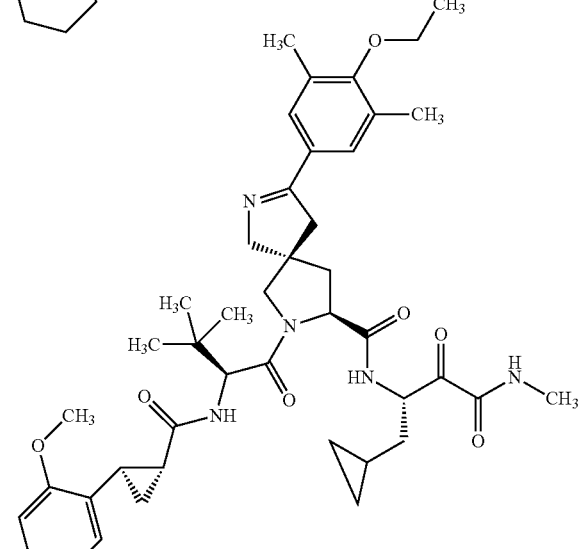 | 985 |

TABLE 1-continued
Exemplary compounds of Formula (I).
| Structure | Compound No. |
|---|---|
| 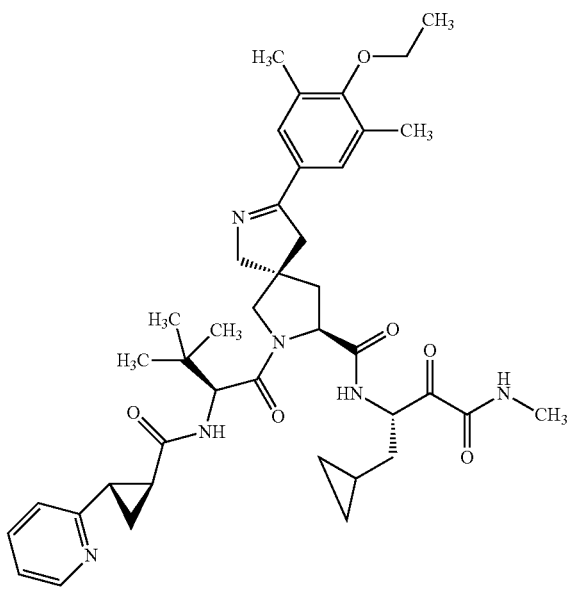 | 986 |
| 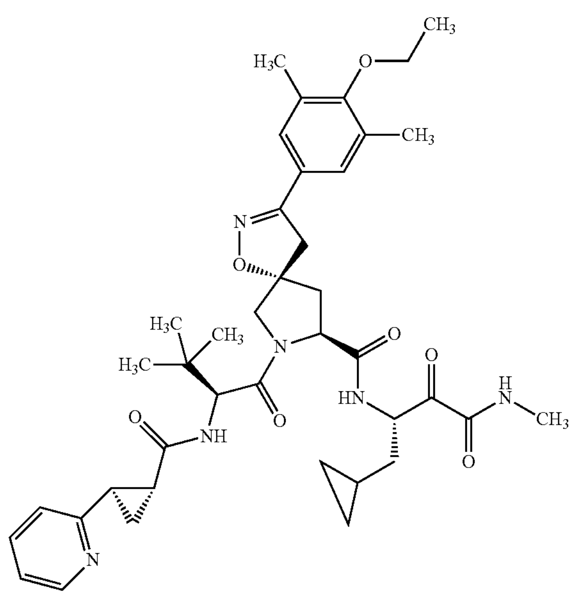 | 987 |

TABLE 1-continued
Exemplary compounds of Formula (I).
| Structure | Compound No. |
|---|---|
| 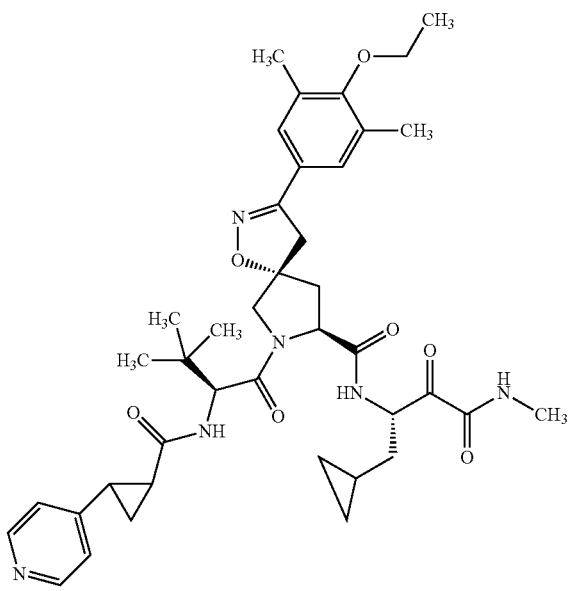 | 988 |
| 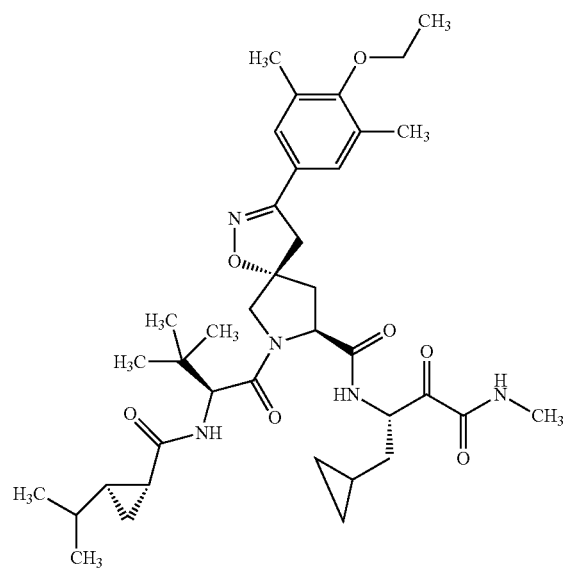 | 989 |

TABLE 1-continued
Exemplary compounds of Formula (I).
| Structure | Compound No. |
|---|---|
| 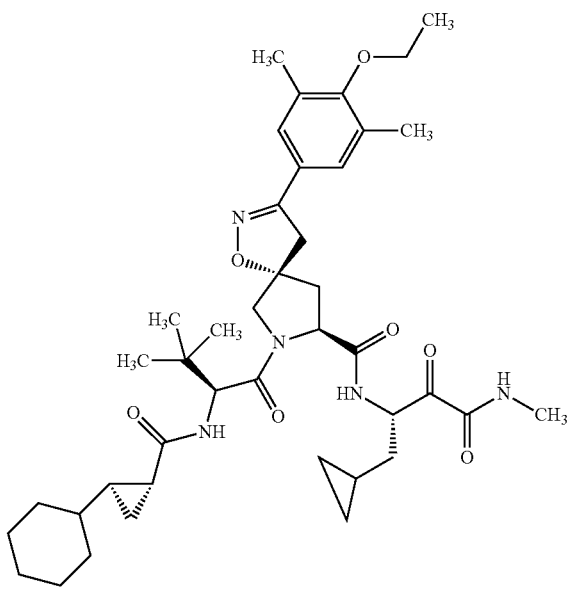 | 990 |
| 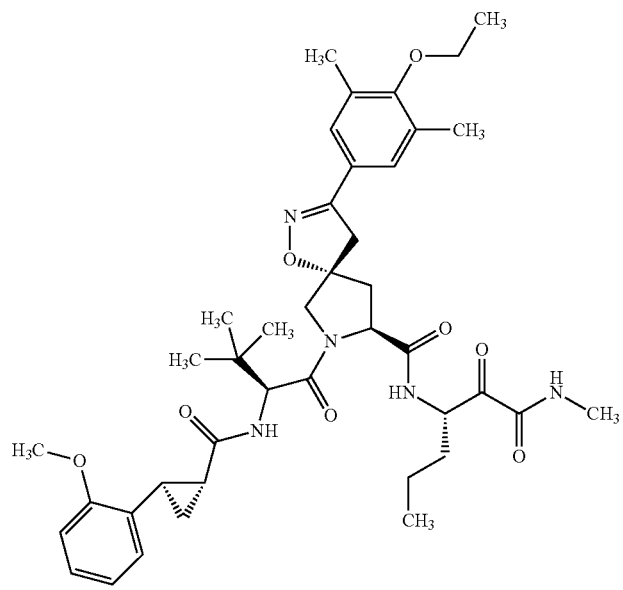 | 991 |

TABLE 1-continued
Exemplary compounds of Formula (I).
| Structure | Compound No. |
|---|---|
| 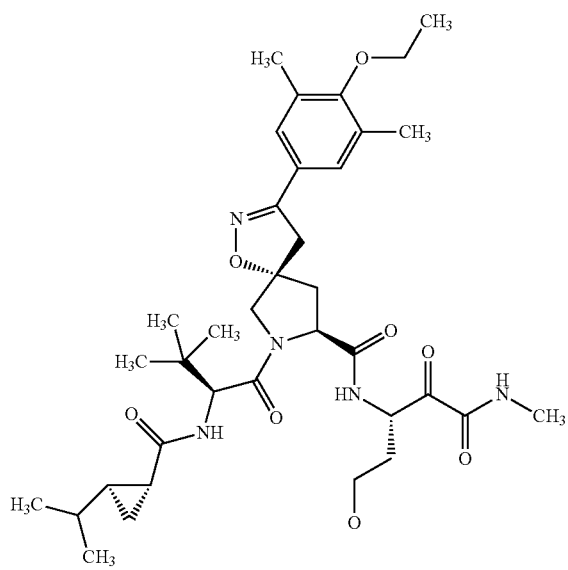 | 992 |
| 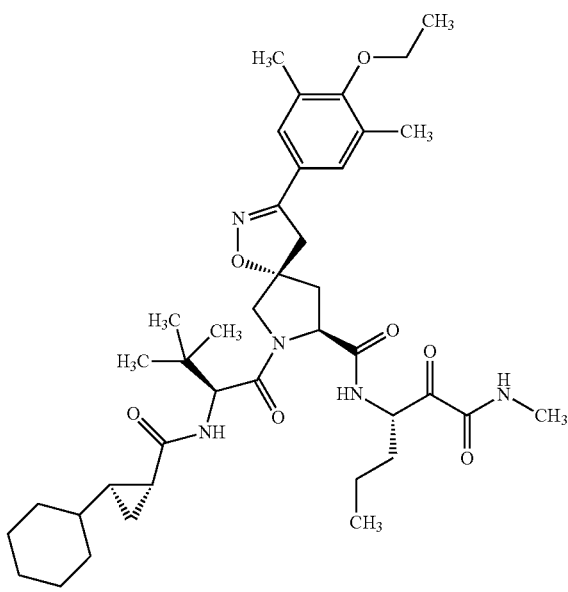 | 993 |

| Structure | Compound No. |
|---|---|
| 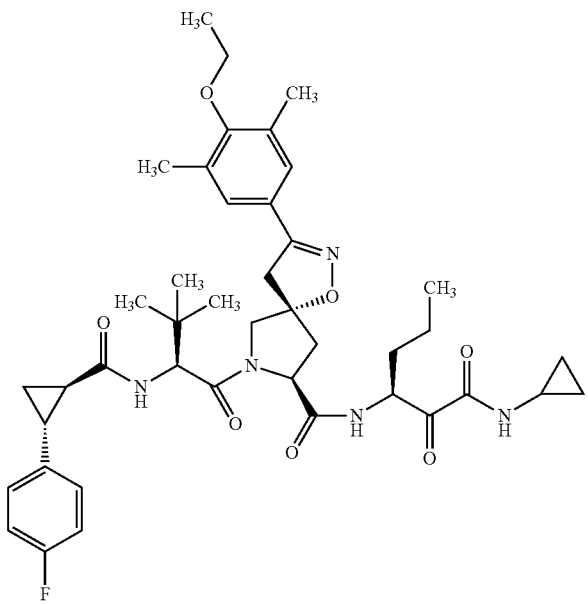 | 994 |
| 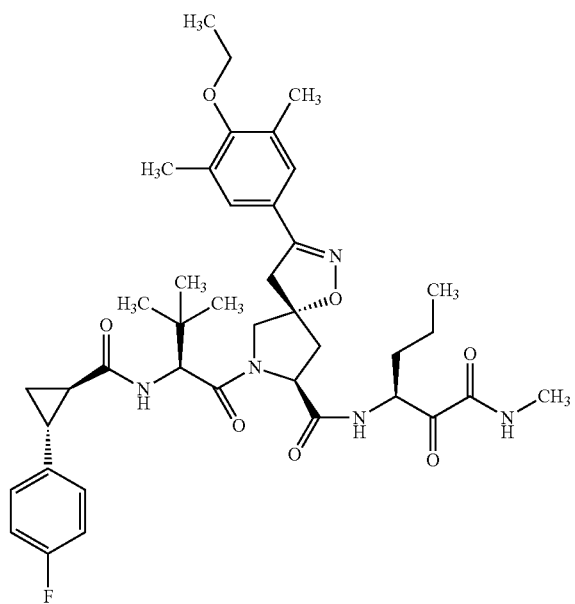 | 995 |

TABLE 1-continued
Exemplary compounds of Formula (I).
| Structure | Compound No. |
|---|---|
| 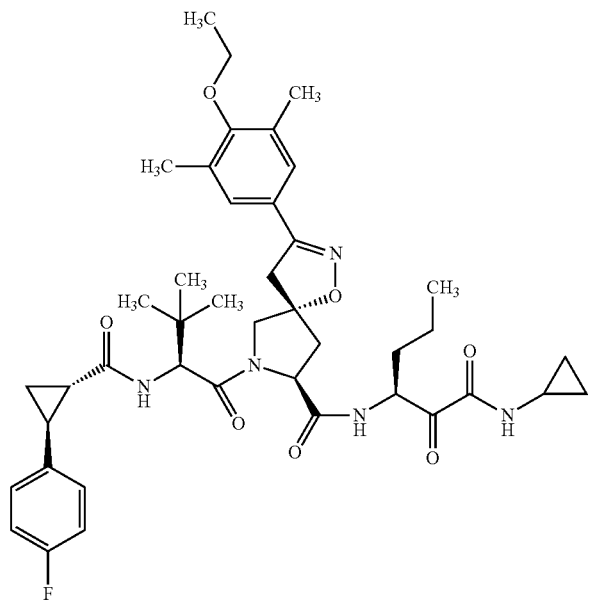 | 996 |
| 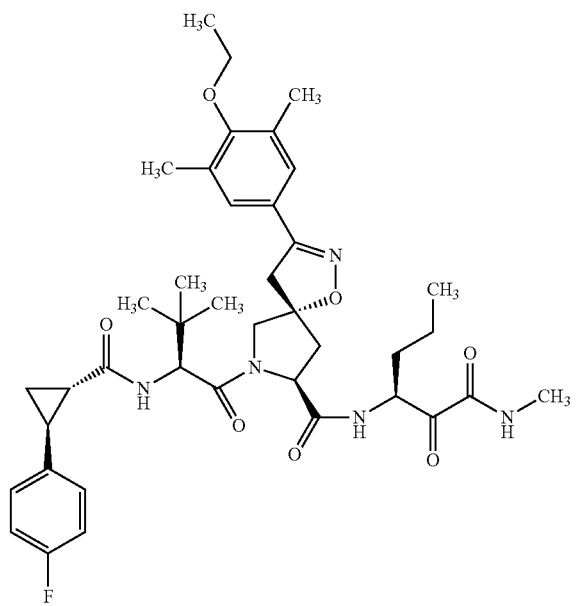 | 997 |

TABLE 1-continued
Exemplary compounds of Formula (I).
| Structure | Compound No. |
|---|---|
| 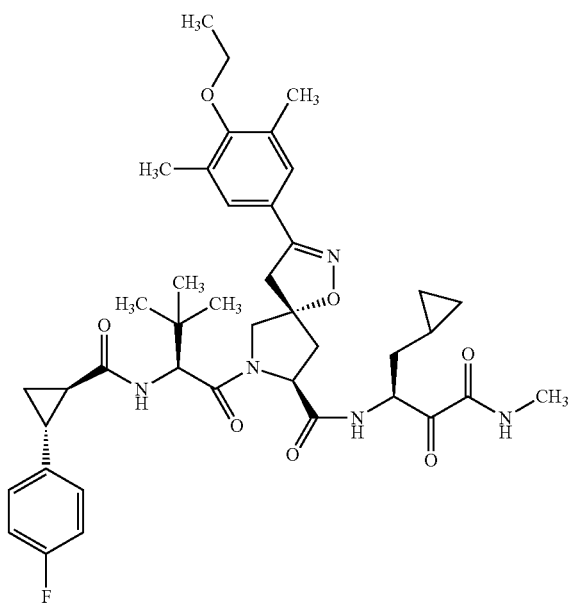 | 998 |
| 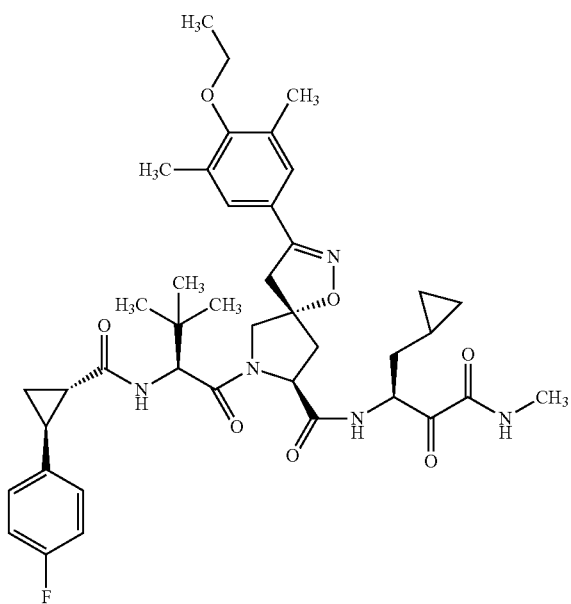 | 999 |

TABLE 1-continued

Exemplary compounds of Formula (I).

| Structure | Compound No. |
|---|---|
| 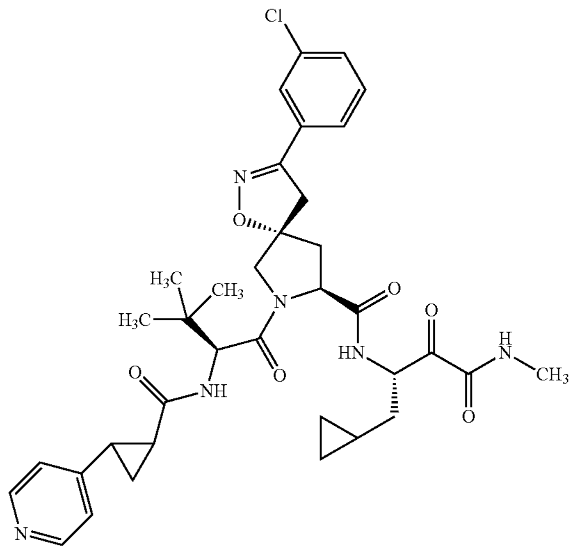 | 1000 |
| 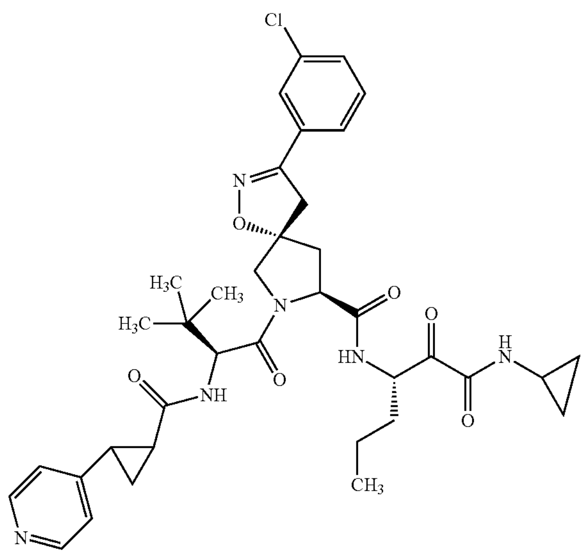 | 1001 |
| 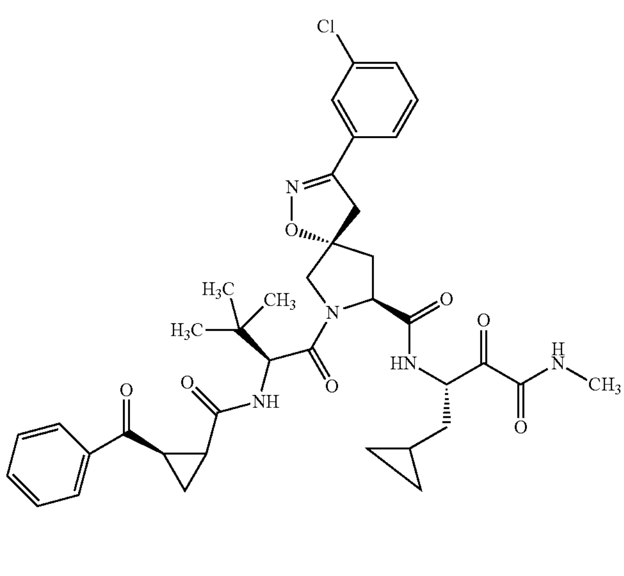 | 1002 |

TABLE 1-continued
Exemplary compounds of Formula (I).
| Structure | Compound No. |
|---|---|
| 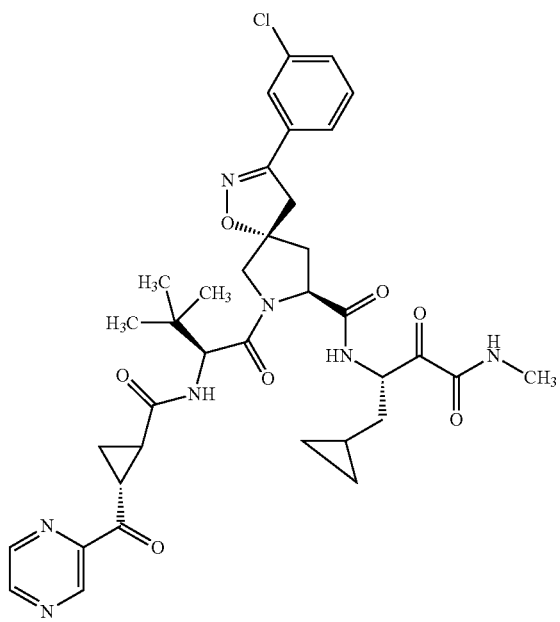 | 1003 |
| 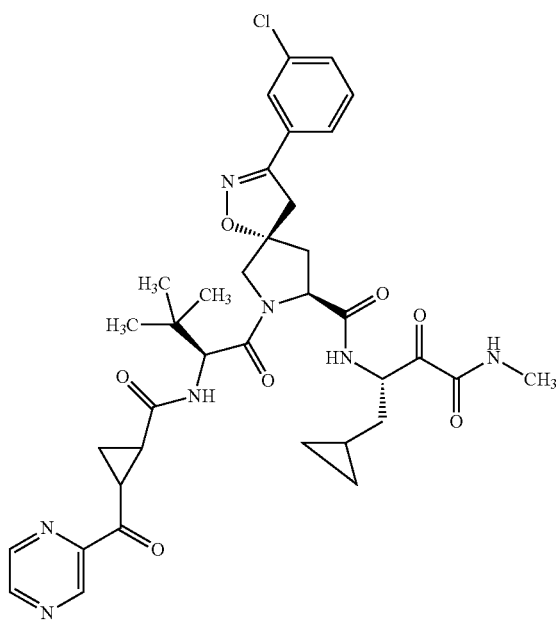 | 1004 |

TABLE 1-continued
Exemplary compounds of Formula (I).
| Structure | Compound No. |
|---|---|
| 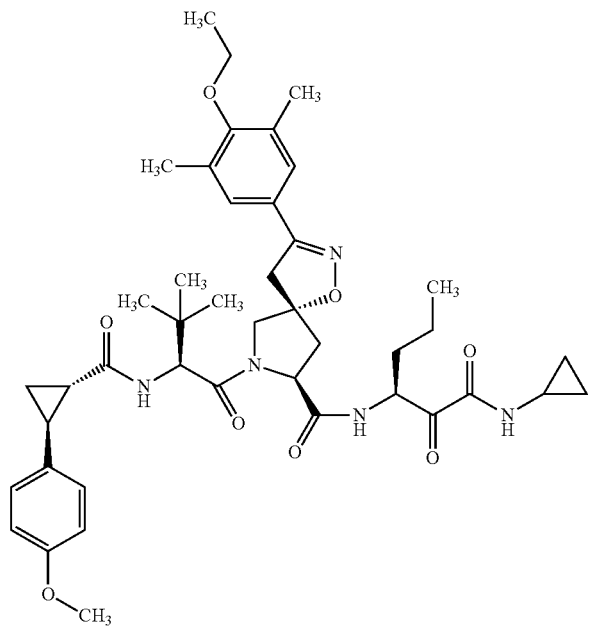 | 1005 |
| 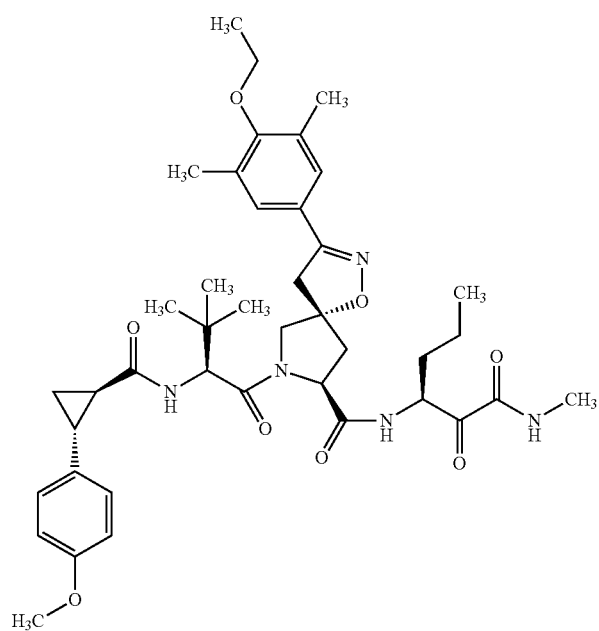 | 1006 |

TABLE 1-continued
Exemplary compounds of Formula (I).
| Structure | Compound No. |
|---|---|
| 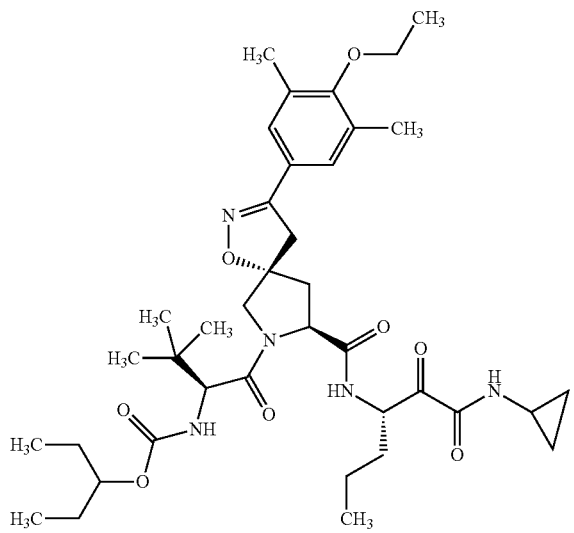 | 1007 |
| 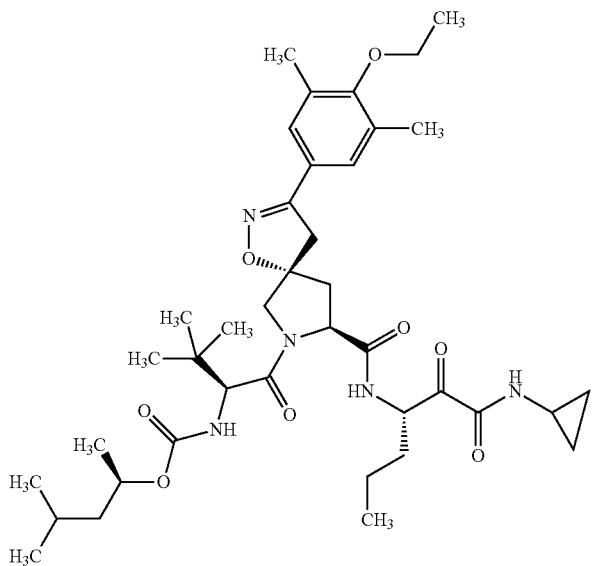 | 1008 |

TABLE 1-continued

Exemplary compounds of Formula (I).

| Structure | Compound No. |
|---|---|
| 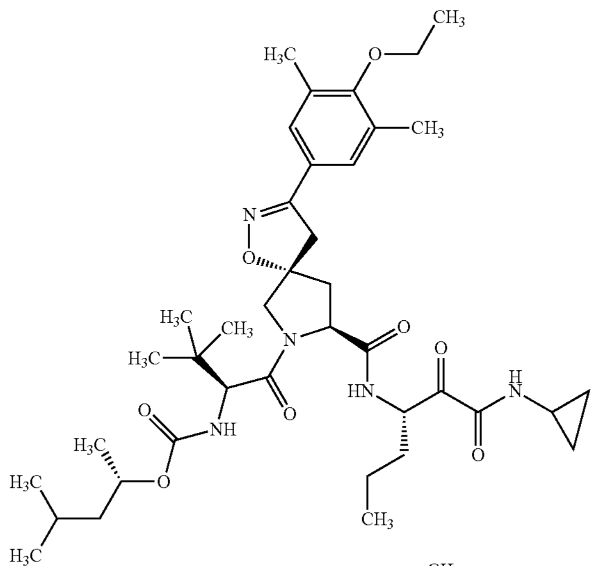 | 1009 |
| 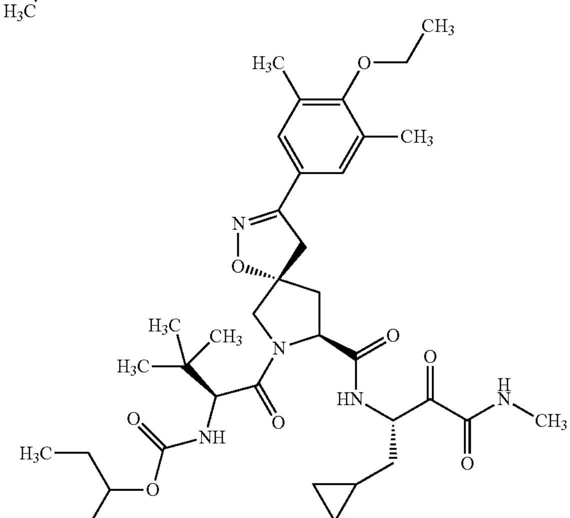 | 1010 |
| 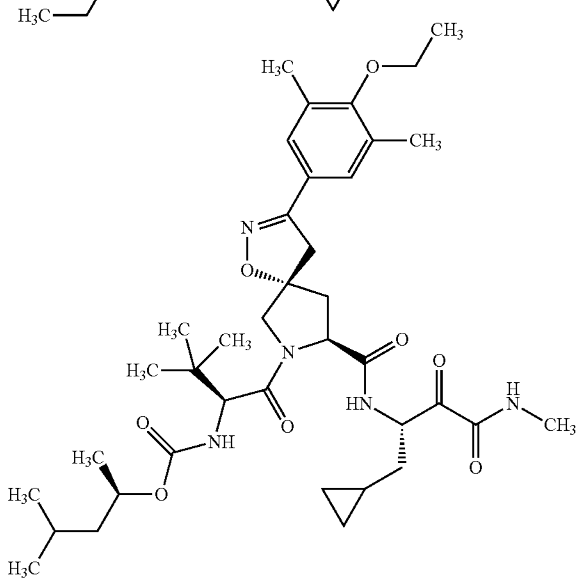 | 1011 |

TABLE 1-continued
Exemplary compounds of Formula (I).
| Structure | Compound No. |
|---|---|
| 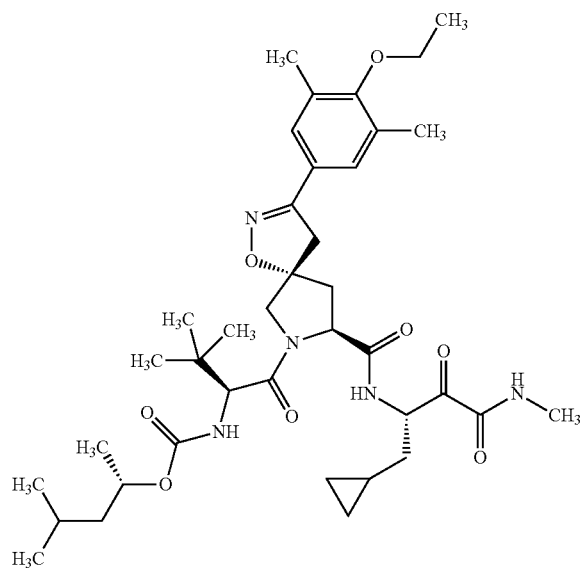 | 1012 |
| 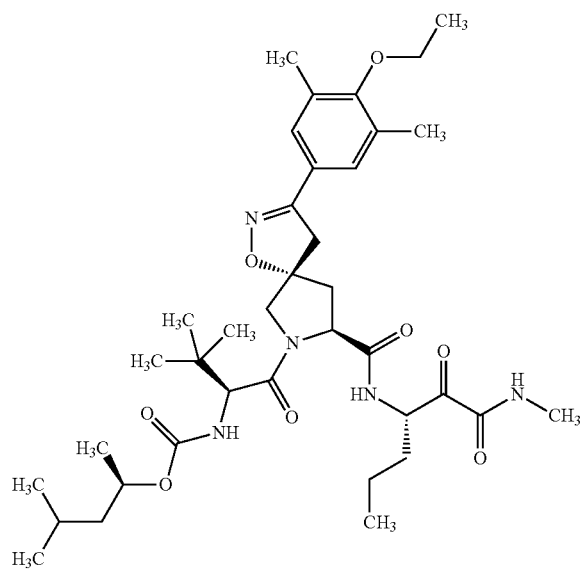 | 1013 |

TABLE 1-continued
Exemplary compounds of Formula (I).
| Structure | Compound No. |
|---|---|
| 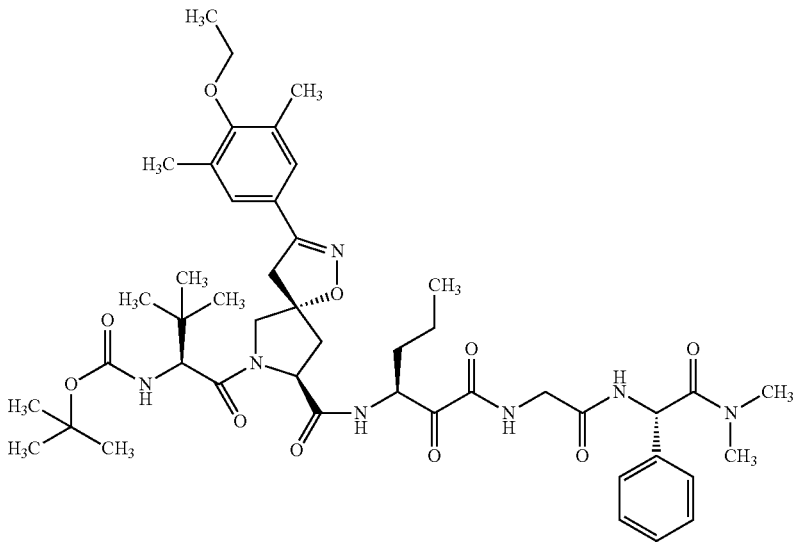 | 1014 |
| 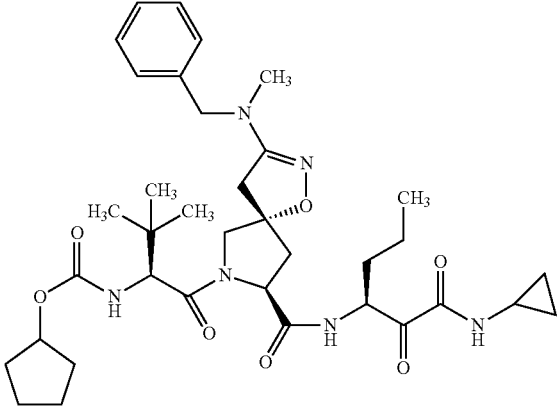 | 1015 |
| 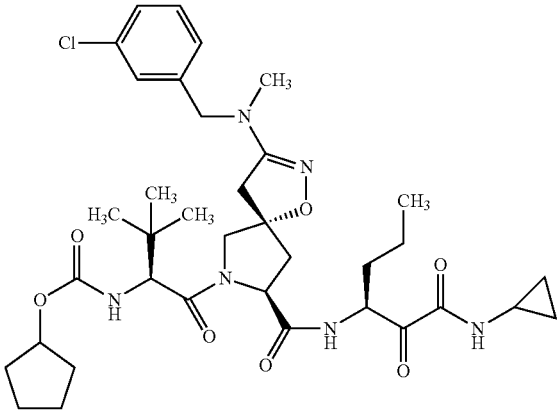 | 1016 |

//734
TABLE 1-continued
Exemplary compounds of Formula (I).
| Structure | Compound No. |
|---|---|
| 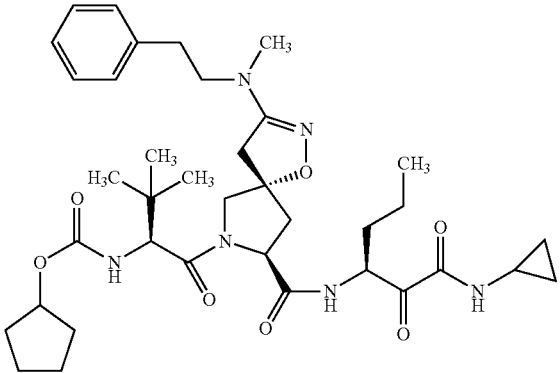 | 1017 |
| 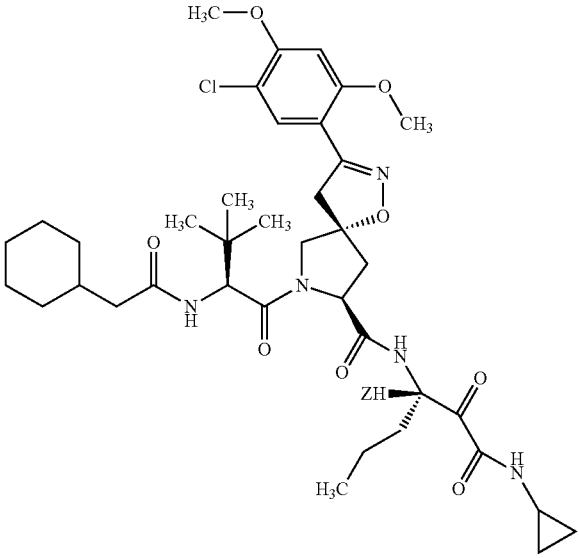 | 1018 |
| 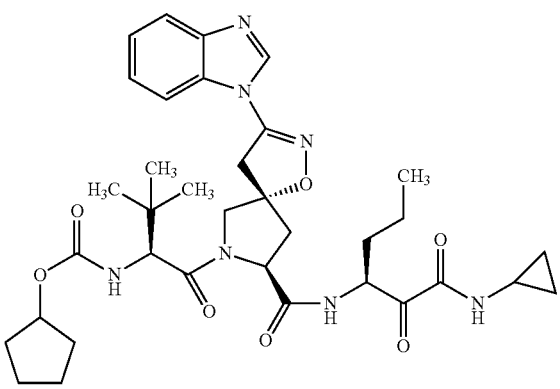 | 1019 |

TABLE 1-continued

Exemplary compounds of Formula (I).

| Structure | Compound No. |
|---|---|
| 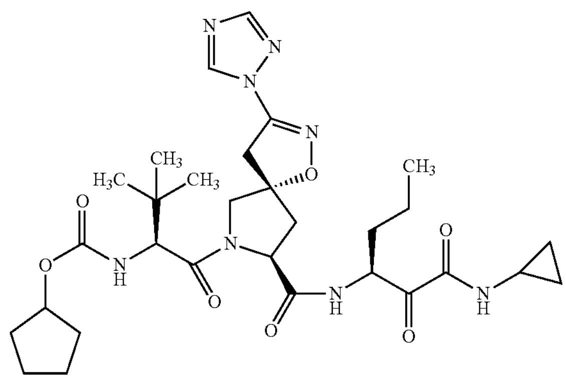 | 1020 |
| 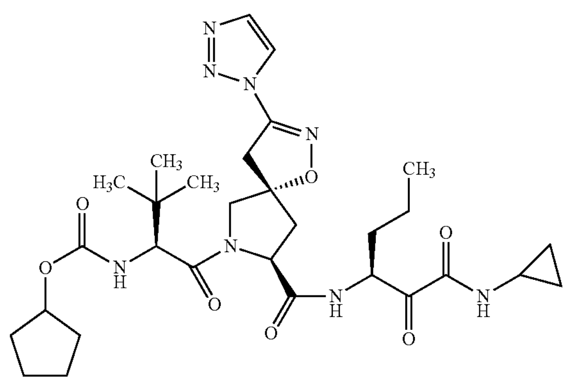 | 1021 |
| 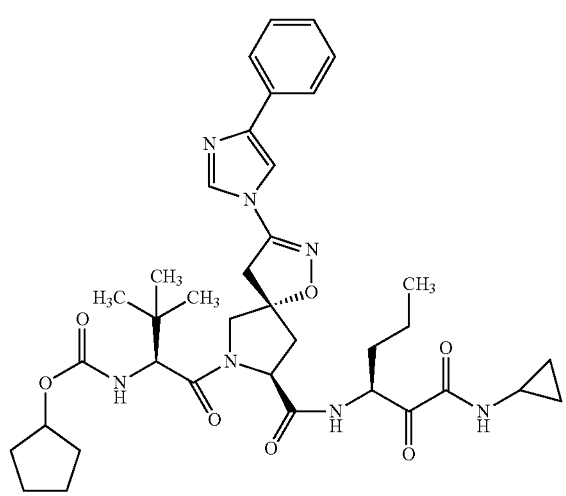 | 1022 |

TABLE 1-continued
Exemplary compounds of Formula (I).
| Structure | Compound No. |
|---|---|
| 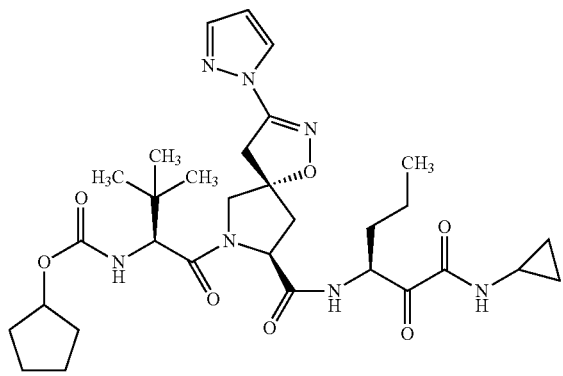 | 1023 |
| 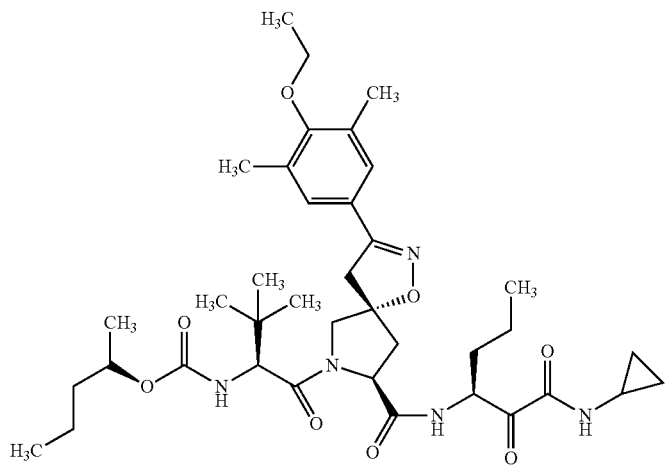 | 1024 |
| 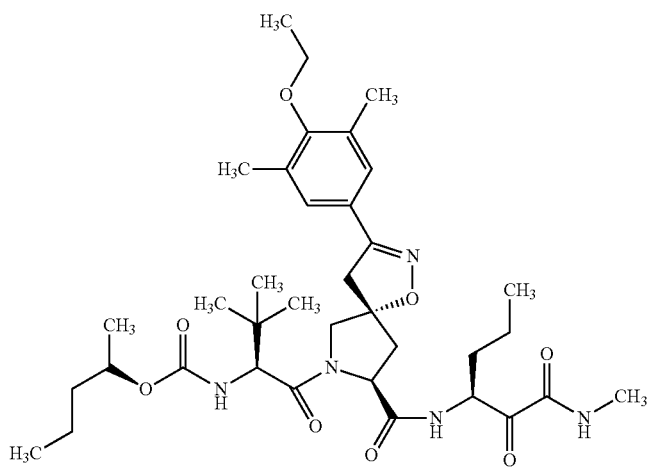 | 1025 |

TABLE 1-continued

Exemplary compounds of Formula (I).

| Structure | Compound No. |
|---|---|
| 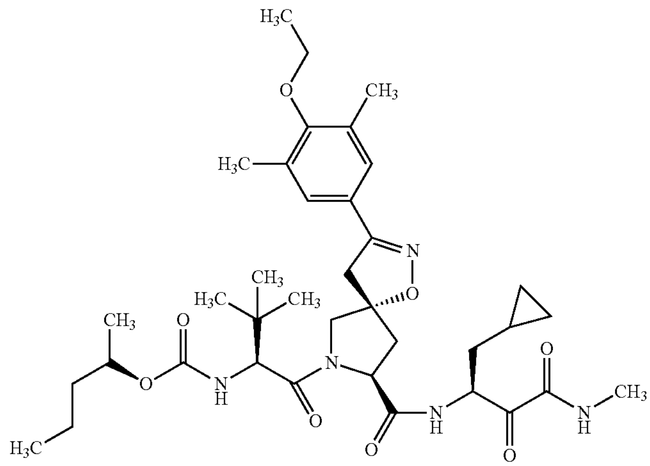 | 1026 |
| 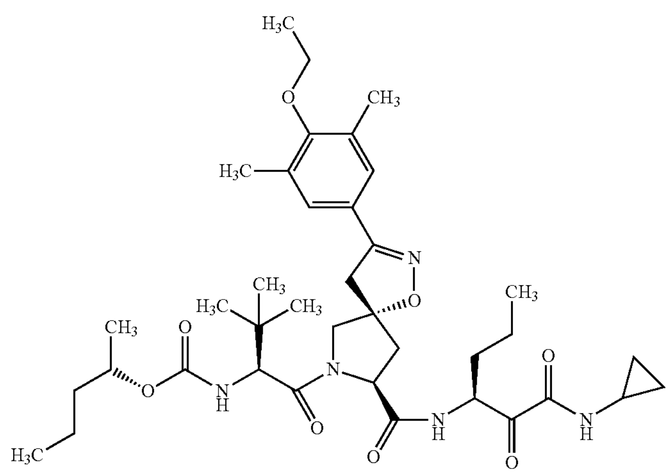 | 1027 |
| 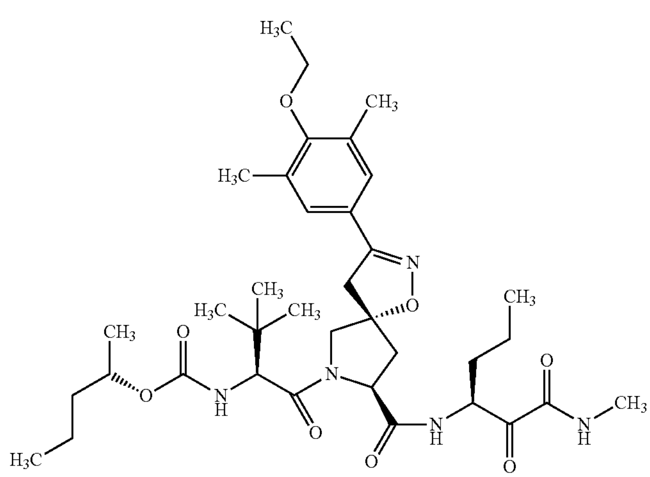 | 1028 |

TABLE 1-continued
Exemplary compounds of Formula (I).
| Structure | Compound No. |
|---|---|
| 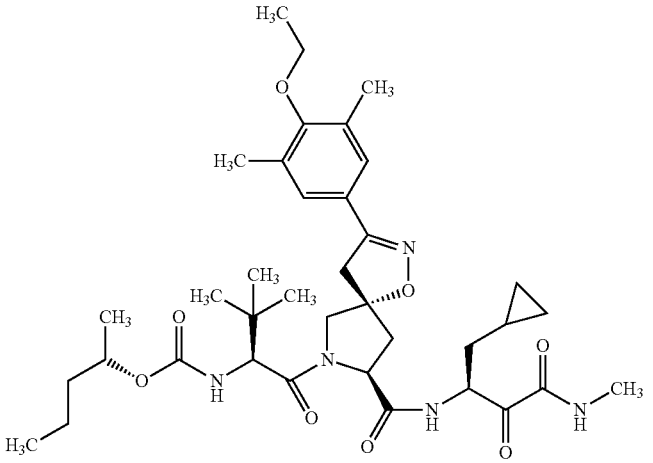 | 1029 |
| 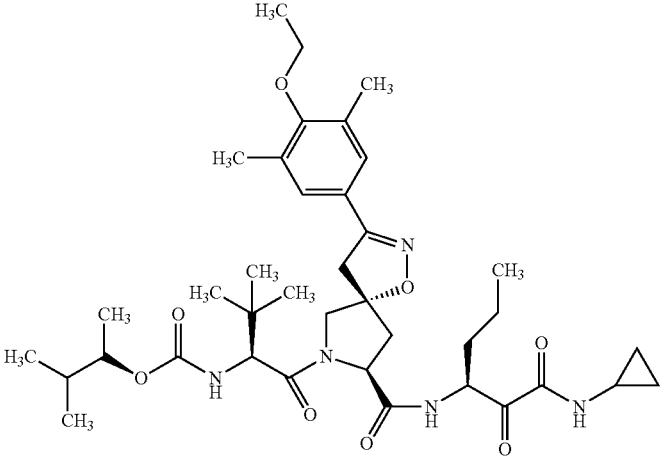 | 1030 |
| 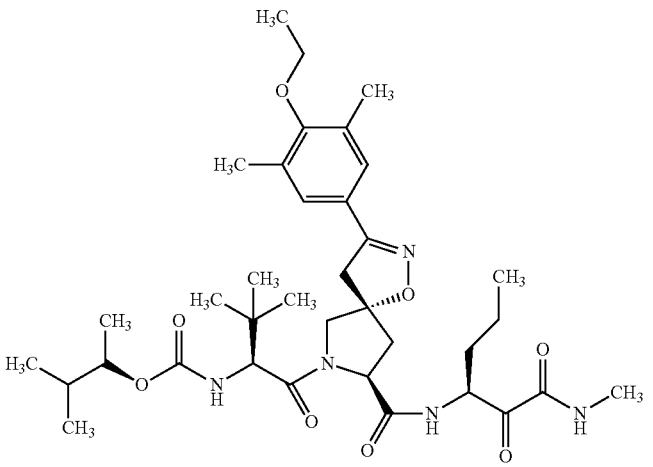 | 1031 |

TABLE 1-continued
Exemplary compounds of Formula (I).
| Structure | Compound No. |
|---|---|
| 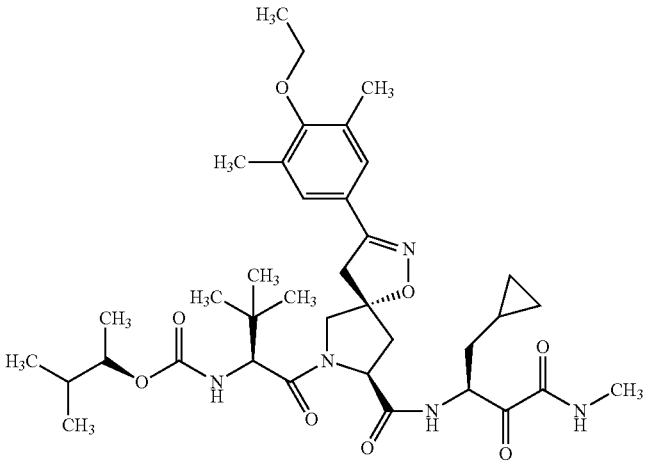 | 1032 |
| 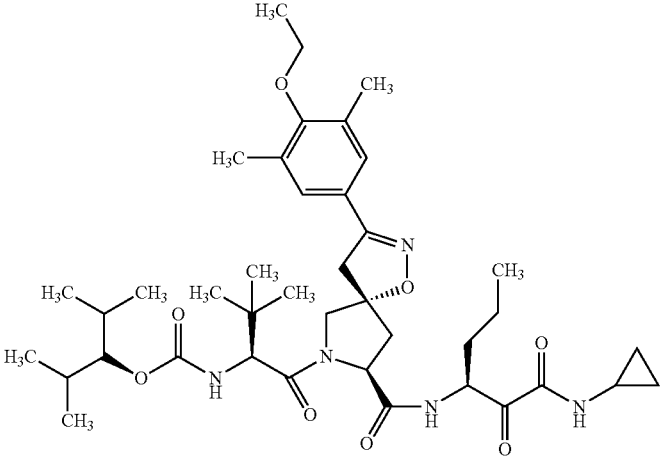 | 1033 |
| 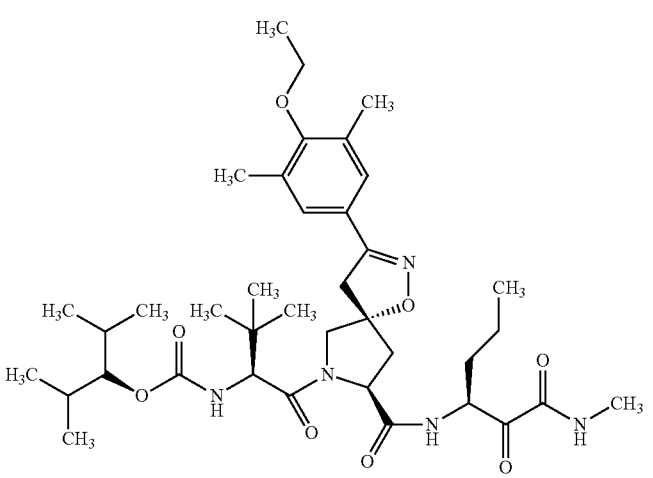 | 1034 |

TABLE 1-continued

Exemplary compounds of Formula (I).

| Structure | Compound No. |
|---|---|
| 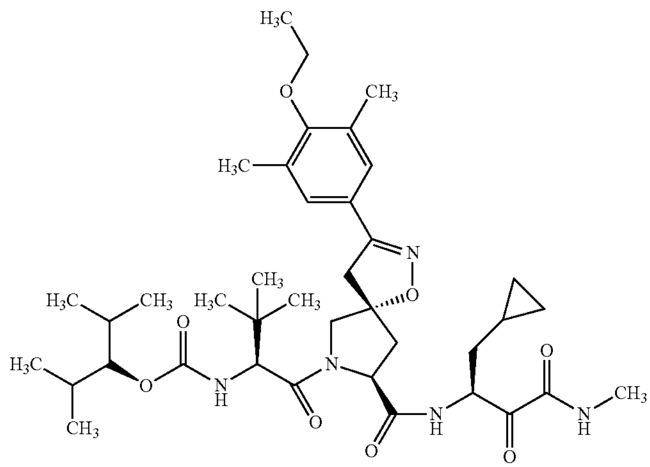 | 1035 |
| 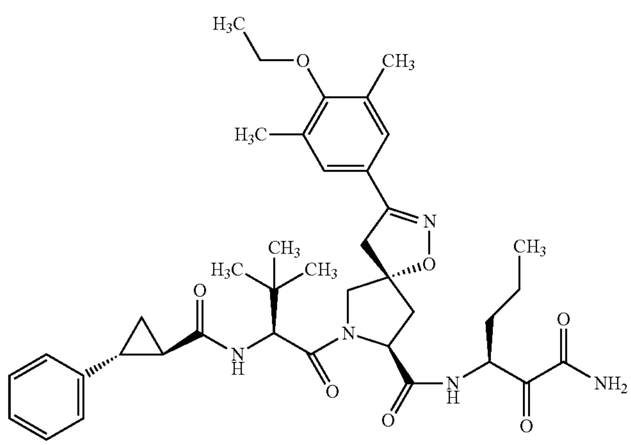 | 1036 |
| 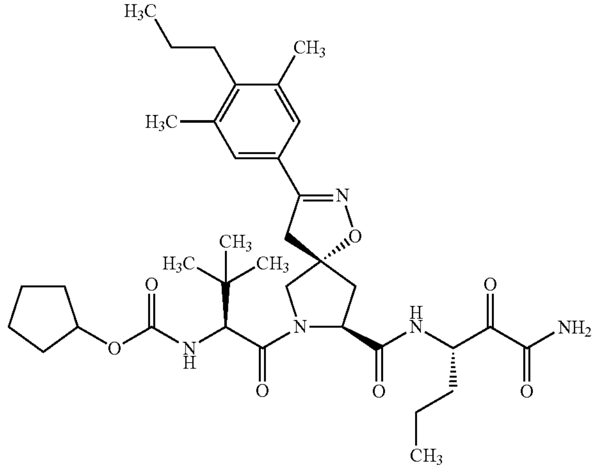 | 1037 |

TABLE 1-continued

Exemplary compounds of Formula (I).

| Structure | Compound No. |
|---|---|
| 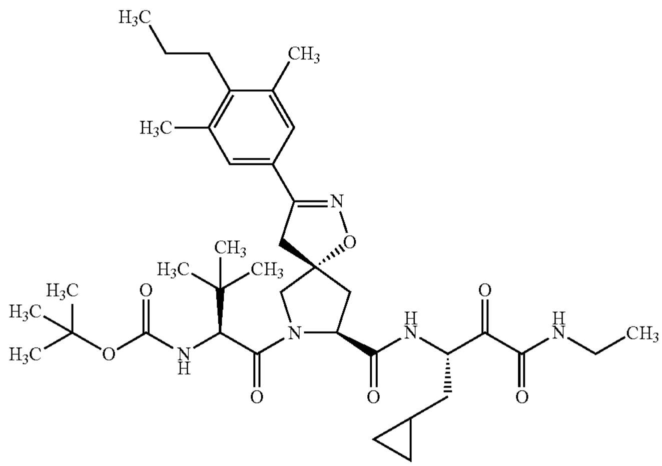 | 1038 |
| 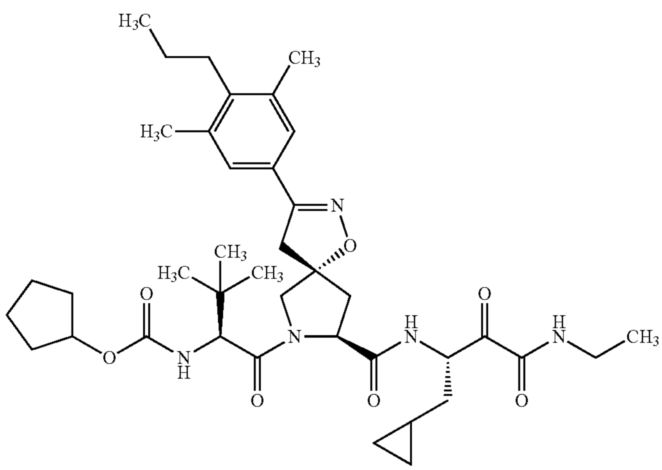 | 1039 |
| 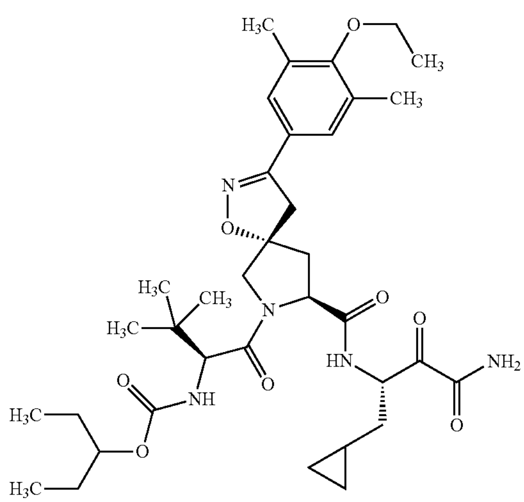 | 1040 |

TABLE 1-continued

Exemplary compounds of Formula (I).

| Structure | Compound No. |
|---|---|
| 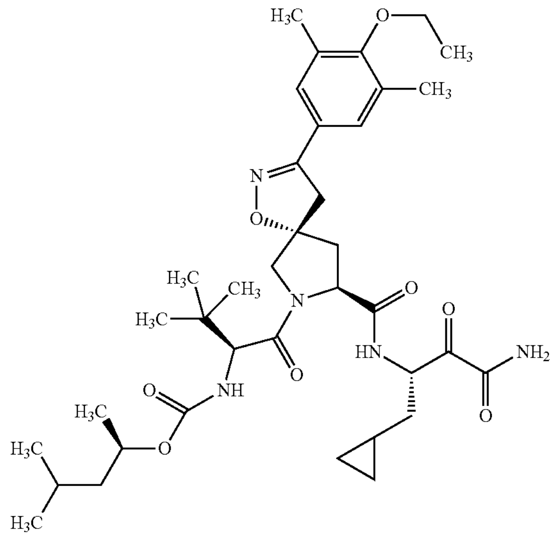 | 1041 |
| 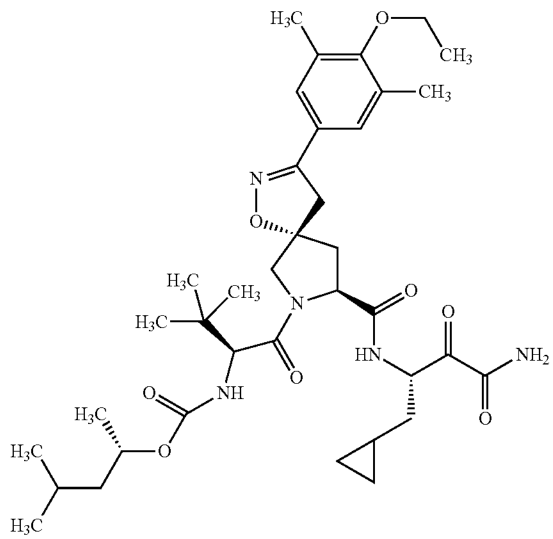 | 1042 |
| 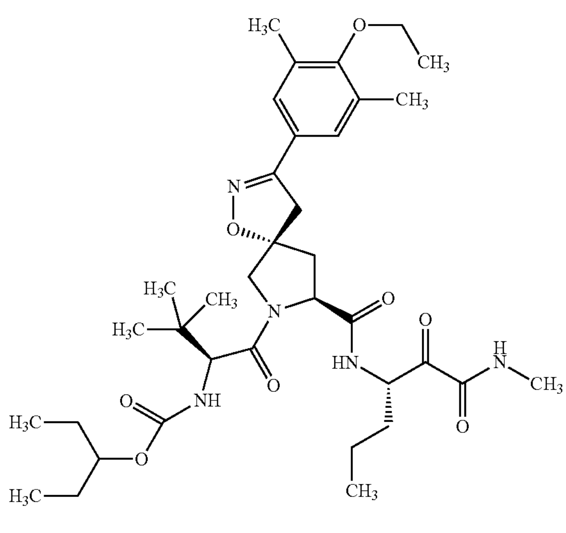 | 1043 |

| Structure | Compound No. |
|---|---|
| 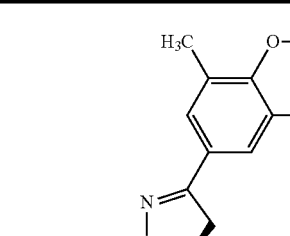 | 1044 |

II. Synthesis of the Compounds

Compounds of Formula I may be readily synthesized from commercially available starting materials using the exemplary synthetic routes provided below. Exemplary synthetic routes to produce compounds of Formula I are provided below in the Preparations, Methods, Examples, and Schemes. For example, the spiroisoxazoline moiety may be prepared by 1,3-dipolar addition between a nitrile oxide and a methylene proline as reported by Kurth, M. J., et al., in J. Org. Chem., 2002, 67, pp. 5673-5677, and as illustrated in Scheme 1 below. The nitrile oxides can be generated from cholooximes or nitroalkanes using known methods.

Scheme I provides a general representation of processes for preparing compounds of Formula (I). Its overall strategy is to construct a compound of formula 1h followed by selective removal of the protecting group PG, in the presence of $PG_2$ to provide the intermediate 1j. The substituent $R_1$ may then be coupled to 1j, which provides intermediates of formula 1k containing $R_1$. In some embodiments, $R_1$ may itself contain a protecting group which may be selectively removed in the presence of $PG_2$, followed by further elaboration. Subsequent to the addition of the $R_1$ moiety, the $PG_2$ group is removed to provide the intermediate 1m. Coupling of 1m with an $R_2$ moiety then provides the peptidomimetic compounds of Formula (I).

Scheme 1

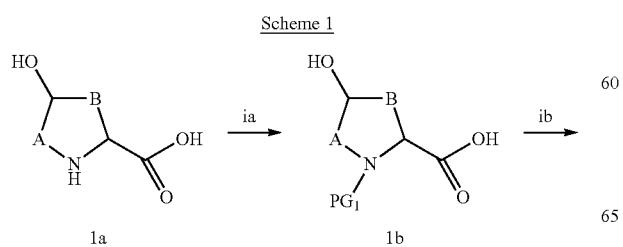

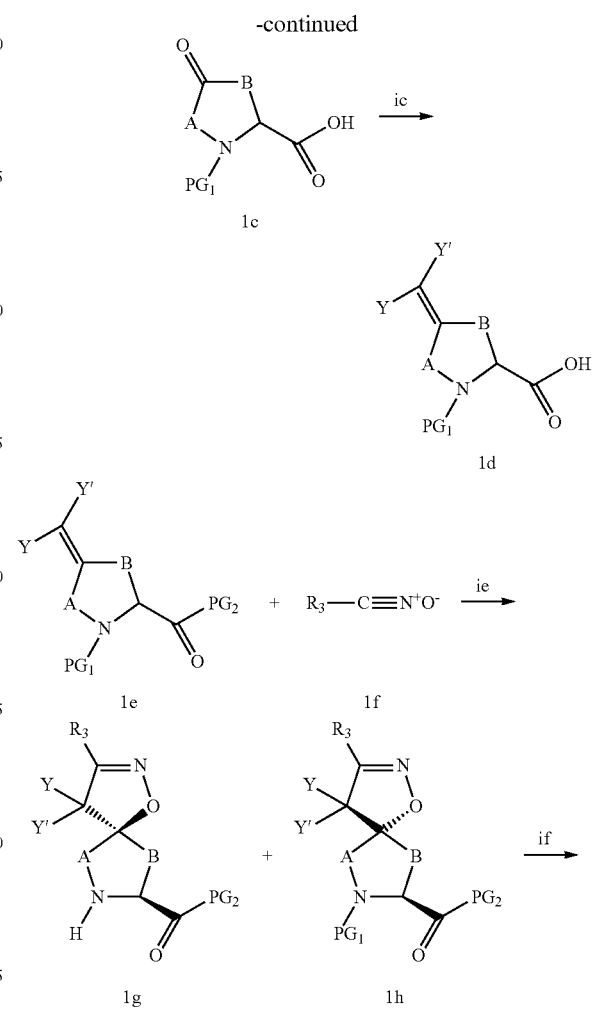

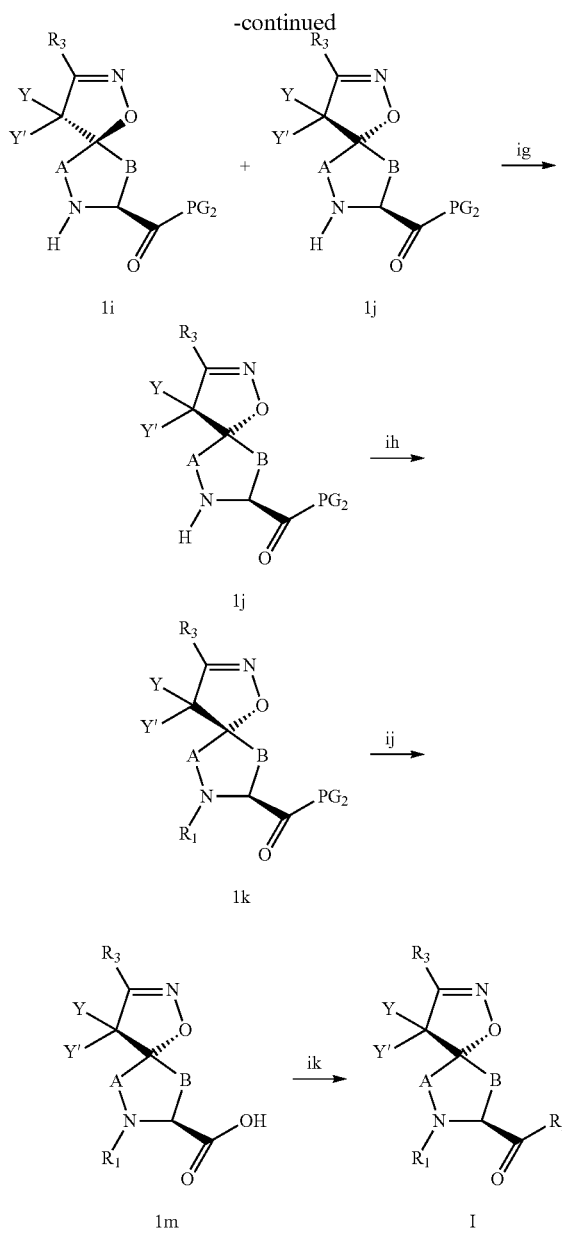

protected (step id) with a suitable protecting group such as, for example, a t-butyl ester under known conditions (ibid) to provide the intermediate 1e.

Reaction of 1e with a nitrile oxide if provides a mixture of the syn and anti isomers of the spiroisoxazolines 1g and 1h. As referred to herein, syn- means that the 2-carboxyl moiety of the proline ring and the oxygen of the isoxazoline ring are on the same side of a plane as described by the proline ring. The term anti- means that the 2-carboxyl moiety of the proline ring and the oxygen of the isoxazoline ring are on the opposite side of a plane as described by the proline ring. Thus, 1g represents a syn- compound of the invention and 1h represents an anti- compound of the invention.

In some embodiments, when $PG_1$ is Boc and $PG_2$ is t-butoxy, selective removal of the protecting group $PG_1$ from 1g and 1h in the presence of the protecting group $PG_2$ may be achieved with a sulfonic acid such as, for example, methane sulfonic acid in a suitable organic solvent at temperatures from about $-40°$ C. to about $40°$ C., from about $-20°$ C. to about $20°$ C. and from about $-5°$ C. to about $5°$ C. Suitable organic solvents include, for example, methylene chloride and tetrahydrofuran.

The isomers 1i and 1j may be separated advantageously by crystallization of a mixture of the corresponding organic acid salts which avoids more complicated methods such as, e.g., chromatography. Suitable organic salts include those of organic carboxylic acids, e.g., acetic acid, optionally substituted benzoic acids, tartaric acid, malonic acid, fumaric acid, oxalic acid, mandelic acid, citric acid, p-toluoyl tartaric acid and maleic acid; organic sulfonic acids, e.g., methane sulfonic acid, optionally substituted benzene sulfonic acids, trifluoromethane sulfonic acid and camphor sulfonic acid.

A single spiroisoxazoline isomer, for example 1j, is coupled with an acid $R_1COOH$ in the presence of a coupling reagent such as, for example, EDCI to provide the intermediate spiroisoxazoline 1k. Selective removal of the protecting group $PG_2$ of 1k to give 1m with minimum racemization or cleavage of the $R_1$ side chain is achieved by a suitable mineral acid in a suitable organic solvent at temperatures from about $-40°$ C. to about $40°$ C., from about $-20°$ C. to about $20°$ C. and from about $-5°$ C. to about $5°$ C. Suitable mineral acids include, for example, concentrated hydrochloric acid or concentrated sulfuric acid. Suitable organic solvents include, for example, methylene chloride and tetrahydrofuran. The spiroisoxazoline 1m is then coupled with an amine moiety $R_2$ to provide the compounds of Formula I.

Referring again to Scheme 1, in one example, the hydroxy proline 1a is protected as the Boc derivative (i.e., step ia) to provide the protected proline 1b, wherein $PG_1$ is t-butyloxycarbonate, using known methods. See, e.g., T. W. Greene and P. G. M. Wuts, Protective Groups in Organic Synthesis, $3^{rd}$ edition, John Wiley and Sons, Inc. (1999). Oxidation of 1b (i.e., step ib) provides the keto-pyrrolidine acid 1c. The oxidation is achieved with a suitable reagent such as, for example, sodium hypochlorite in the presence of TEMPO. Next, in step ic, the keto-pyrrolidine acid 1c is reacted with a Wittig reagent such as, for example, a triphenylphosphonium ylid of the formula $(Ph)_3P=C(Y)(Y')$ and using known conditions, to provide an exomethylene compound of formula 1d. Use of the free acid 1c to provide the corresponding free acid 1d is advantageous as the acid 1d may be expediently purified from neutral or basic by-products by simple extraction of 1d into aqueous basic solution. The acid 1d is subsequently Referring again to Scheme 1, $PG_1(CO)$— can be an amine protecting group, wherein $PG_1$ is, for example, methoxycarbonyl, t-butyloxycarbonyl, 9-flourenylmethyloxycarbonyl, or benzyloxycarbonyl. $PG_2(CO)$— can be an acid or acid protecting group wherein $PG_2$ is, for example, —OH, methoxy, t-butyloxy or benzyloxy.

Each of $PG_1$ and $PG_2$ groups may be incorporated into the core spiroisoxazoline structure either individually or together using known methods and as further described herein. For example, if the desired $R_1$ substituted is a group other than a $PG_1$ group (e.g., a protecting group), the $PG_1$ group may be removed to provide a compound with a free amine group. That amine group and an appropriate moiety may be coupled under known coupling conditions to provide a compound wherein $R_1$ is a moiety of a protease inhibitor. For example, if the $PG_2$ moiety is protected, the protecting group may be removed and an $R_2$ moiety may be incorporated.

Another method for producing compounds of the present invention is illustrated below in Scheme 2.

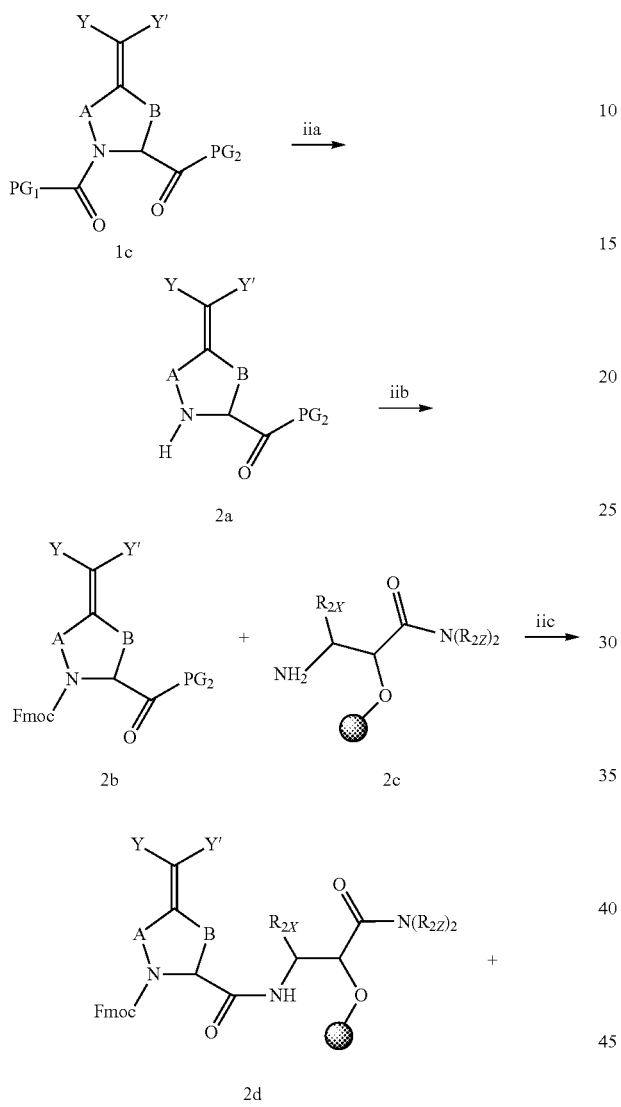

Scheme 2

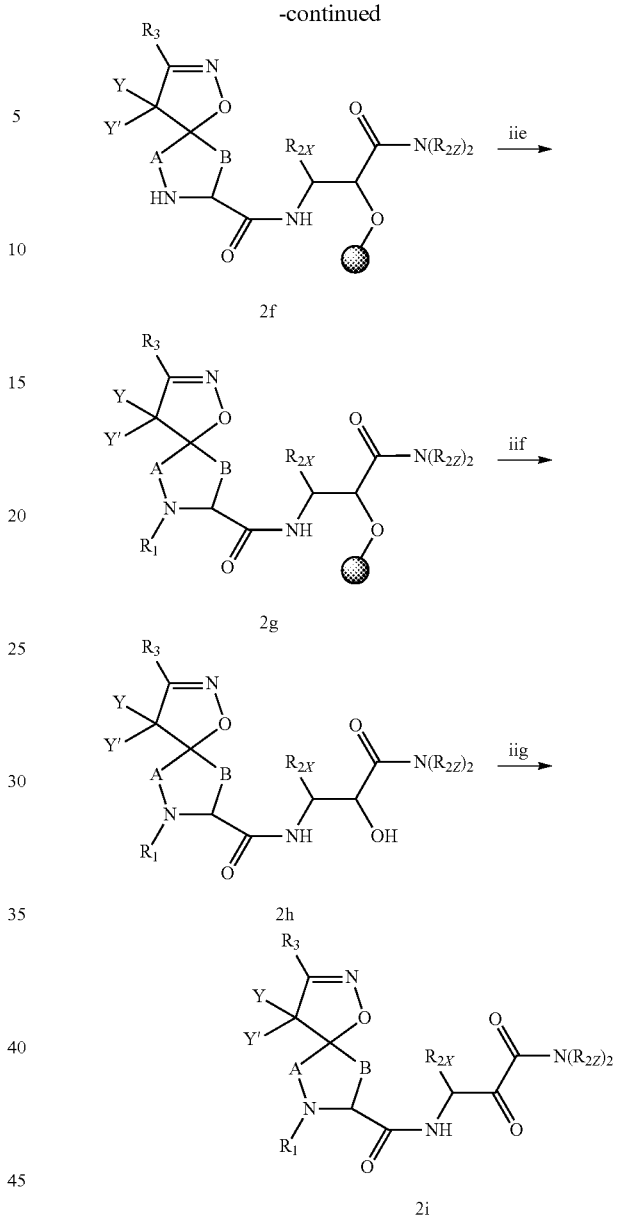

Referring to Scheme 2, the symbol

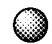

represents a polymeric resin to which reactants are bound by a functionality that allows further modification and subsequent removal of the product from the resin. A suitable resin is a polymer bound dihydropyran (DHP) resin as described by Ellman et. al. in Tetrahedron Letters, 1994, 35, 9333.

In step iia, simultaneous deprotection of both the amine and acid may be achieved by contacting the proline 1e with an acid, for example, trifluoroacetic acid in methylene chloride to give the amino acid 2a. Reaction of 2a, step iib, with an activated Fmoc derivative, for example, N-(9H-Fluoren-9yl-methoxycarbonyloxy)succinimide (Fmoc-OSu), in the presence of a mild inorganic base, such as sodium carbonate, gives the Fmoc derivative 2b.

Preparation of the resin bound peptide 2d may be accomplished by reacting the Fmoc derivative 2b with the DHP resin bound amino-alcohol 2c, step iiic, which reacts with the free acid 2b, in the presence of a coupling reagent such as, for example, O-Benzotriazole-N,N,N',N'-tetramethyl-uronium-hexafluoro-phosphate (HBTU), a racemization suppressant, such as 1-hydroxybenzotriazole (HOBT) and a tertiary amine, such as di-isopropylethyl amine (DIEA).

As in Scheme 1, an $R_3$-substituted nitrile oxide if may undergo a dipolar cycloaddition reaction with the resin bound peptide 2d to provide two isomers, syn- and anti-, of the compound 2e. Next in step iid, the Fmoc protecting group is removed by contacting 2e with a secondary amine such as, for example, piperidine in a polar solvent such as dimethylformamide to give 2f. Formation of the peptide 2g, via step iie, can be achieved through reaction of 2f with a carboxylic acid in the presence of a coupling reagent such as HBTU, a racemization suppressant such as HOBt, and a tertiary amine such as DIEA. Cleavage of the peptide-resin 2g, step iif, to give the alpha-hydroxy-amide 2h, can be achieved by contacting 2g with a strong acid such as, for example, trifluoroacetic acid and water.

In the final step, iig, the alpha-hydroxy-amide 2h is oxidized to 2i using a Dess-Martin periodinane oxidation or a Pfitzner-Moffat oxidation.

Alternatively, compounds of Formula I may be prepared using resin bound reagents as illustrated below in Scheme 3.

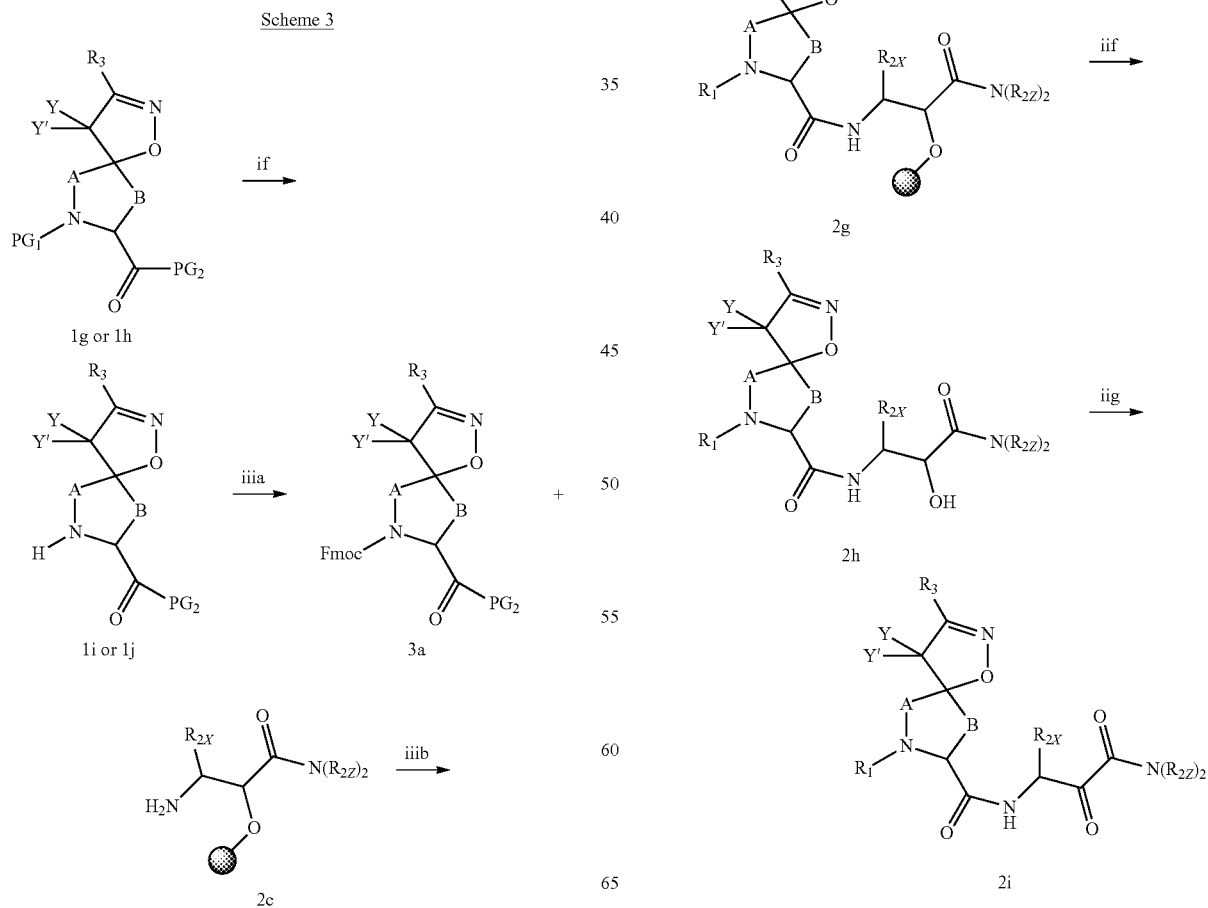

In Scheme 3, the selective removal of the PG, in the presence of PG$_2$ (step it) provides spiroisoxazoline isomer(s) 1i and/or 1j. Reaction of 1i and/or 1j, in step iiia, with an activated Fmoc derivative, e.g., N-(9H-Fluoren-9-ylmethoxycarbonyloxy)succinimide (Fmoc-OSu), in the presence of a mild inorganic base, such as sodium carbonate, provides the Fmoc derivative 3a.

Preparation of the resin bound peptide 2e may be accomplished by reaction of the Fmoc derivative 3a with the DHP resin bound amino-alcohol 2c, via step iiib, which reacts with a free acid 3b, in the presence of a coupling reagent (e.g., O-Benzotriazole-N,N,N',N'-tetramethyl-uronium-hexafluoro-phosphate (HBTU)), a racemization suppressant (e.g., 1-hydroxybenzotriazole (HOBT)), and a tertiary amine (e.g., di-isopropylethyl amine (DIEA)).

In step iid, the Fmoc protecting group is removed by contacting 2e with a secondary amine such as, e.g., piperidine in a polar solvent such as dimethylformamide to give 2f. Formation of the peptide 2g can be achieved, e.g., by reacting 2f with a carboxylic acid in the presence of a coupling reagent (e.g., HBTU), a racemization suppressant (e.g., HOBt) and a tertiary amine (e.g., DIEA). Cleavage of the peptide-resin 2g to give the free peptide 2h can be achieved, e.g., by contacting 2g with a strong acid (e.g., trifluoroacetic acid) and water.

In the final step, iig, the alcohol of 2h can be oxidized to 2i, e.g., with Dess-Martin periodinane or sodium hypochlorite and TEMPO.

Scheme 4 below illustrates a synthetic pathway for compounds of Formula I in which R$_1$ and R$_2$, together with the atoms to which they are attached, form an optionally substituted macrocyclic heterocycloaliphatic.

Scheme 4

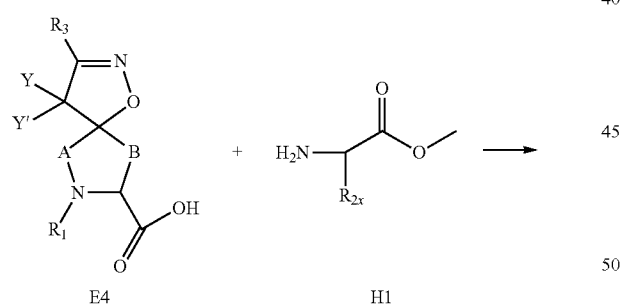

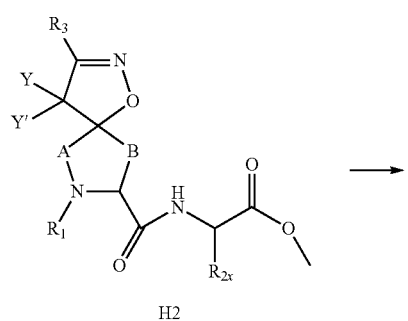

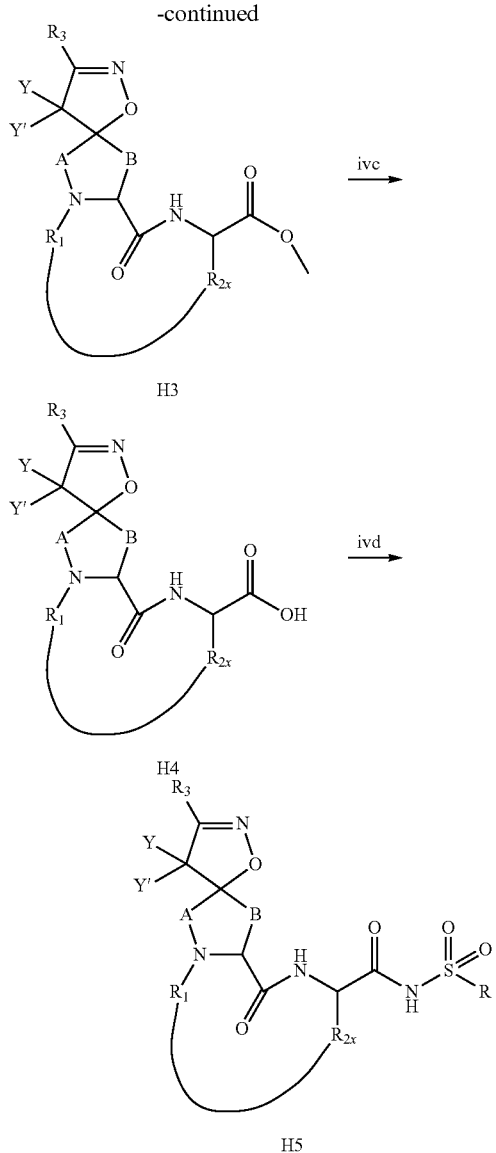

Referring to Scheme 4, the spiroisoxazoline acid E4 reacts with the amino ester H1 in the presence of a coupling reagent to provide the intermediate H2. Macrocyclization of H2 results in compound H3. Hydrolysis of the ester H2 provides acid H4. Reaction of acid H4 with a sulfonamide or sulfamide in the presence of a coupling reagent provides the product H5.

Shown below in Schemes 5, 6, 7, 8, and 9 are examples of total synthesis of compounds of formula (I) according to one of the methods described above.

Scheme 5

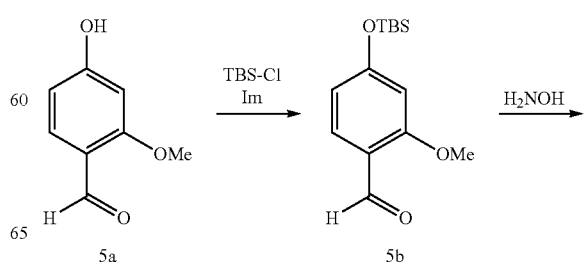

761
-continued
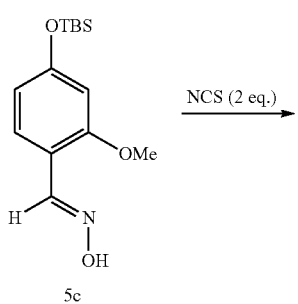
5c
NCS (2 eq.) →
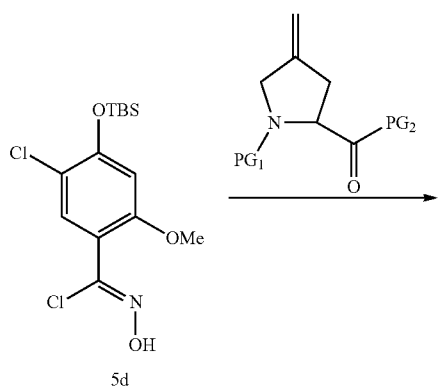
5d
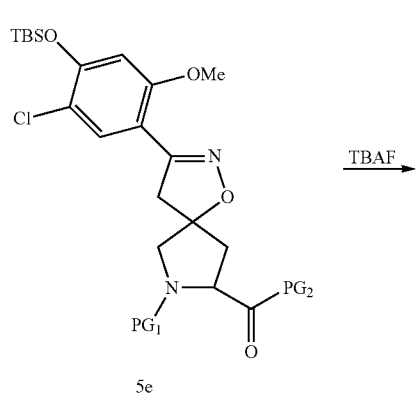
5e
TBAF →
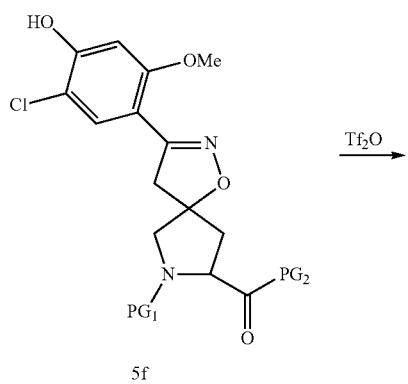
5f
Tf₂O →
762
-continued
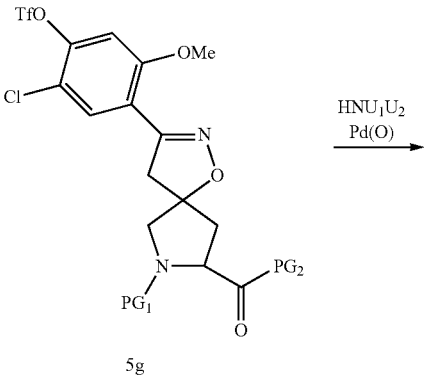
5g
HNU₁U₂
Pd(0) →
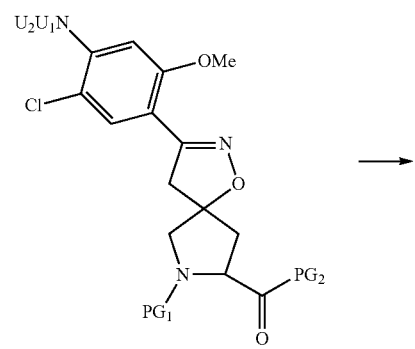
5h
→
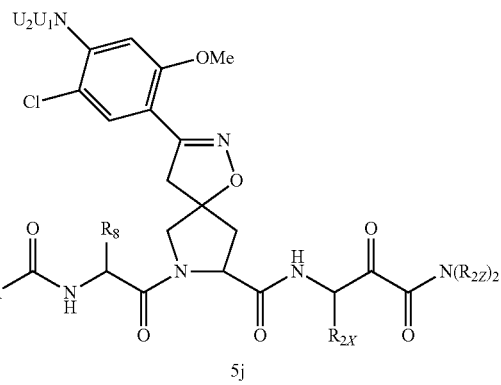
5j
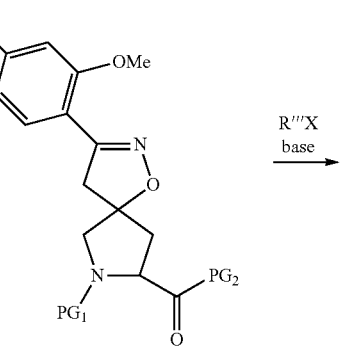
5f
R'''X
base →

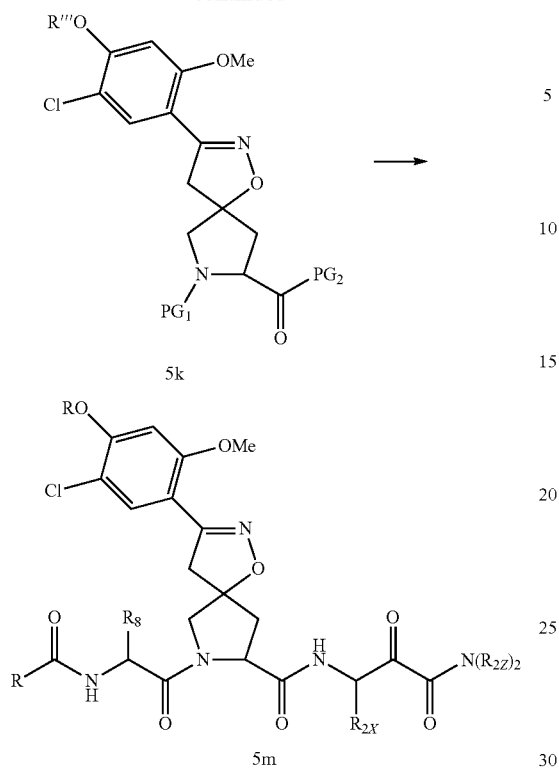

Referring to Scheme 5, the protected t-butyldimethylsilyl-hydroxybenzaldehyde 5b is converted to the hydroxamoyl chloride 5d as previously described. Reaction of 5d with the exomethylene pyrrolidine provides the spiroisoxazoline 5e. Deprotection of 5e to 5f followed by reaction with triflic anhydride provides the triflate 5g. Reaction of 5f with an amine $HNU_1U_2$ provides the intermediate spiroisoxazoline 5h which is converted to compounds of the invention as previously described.

Alternatively, the hydroxy-spiroisoxazoline intermediate 5f may be alkylated to provide the intermediate 5k which may be similarly converted to compounds of the invention.

Scheme 6:

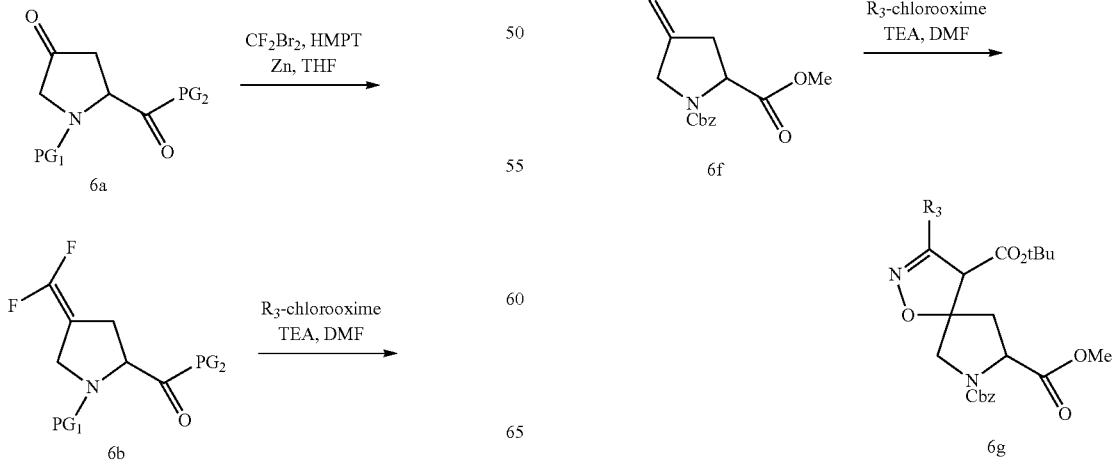

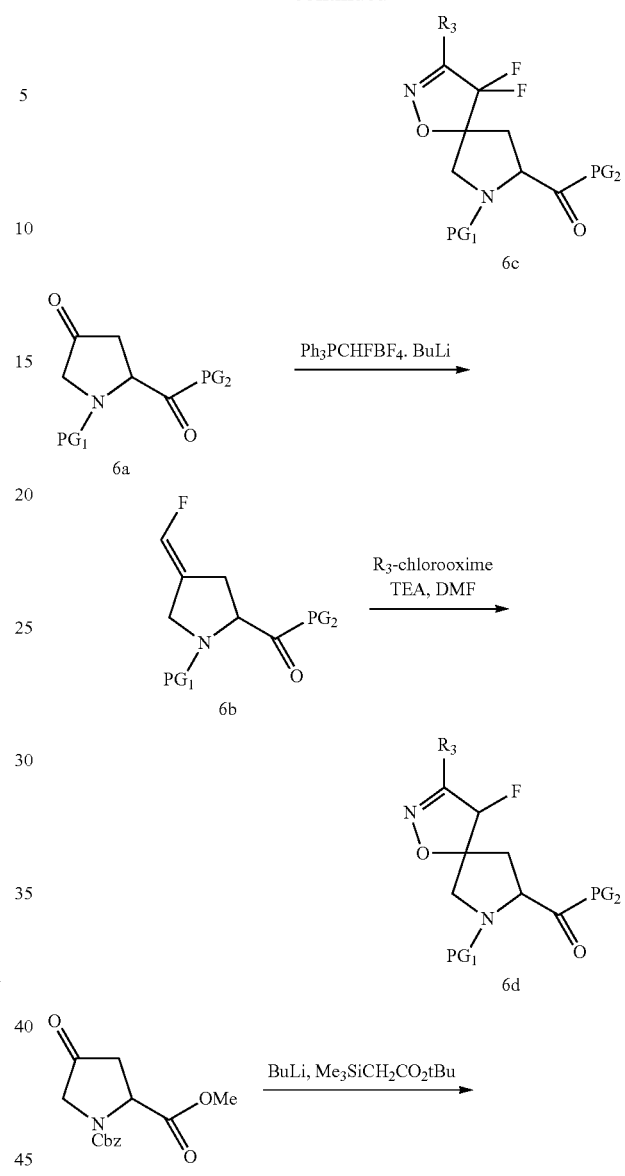

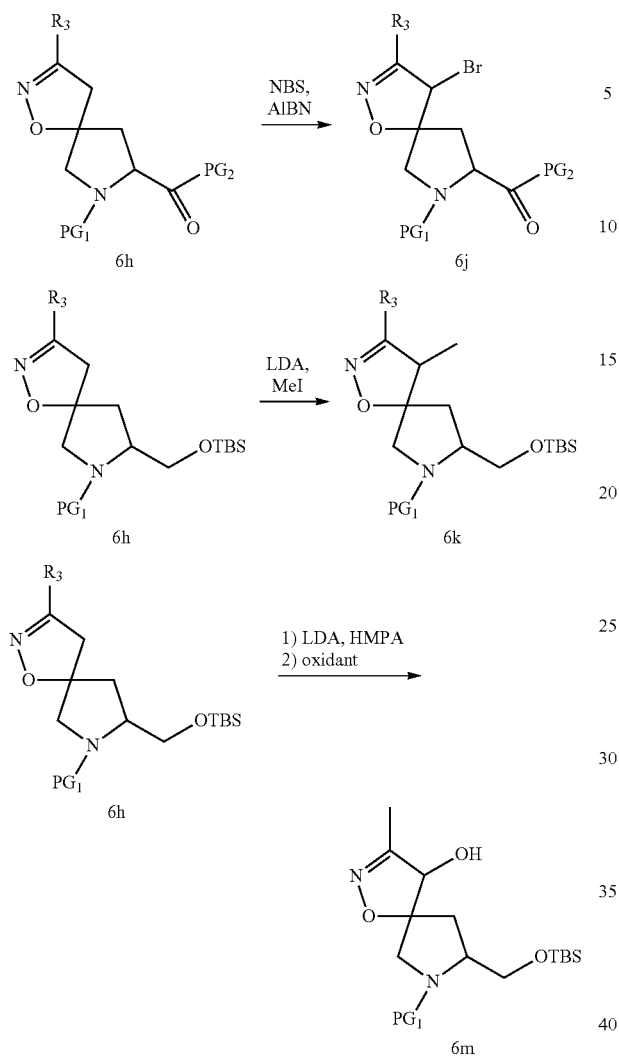
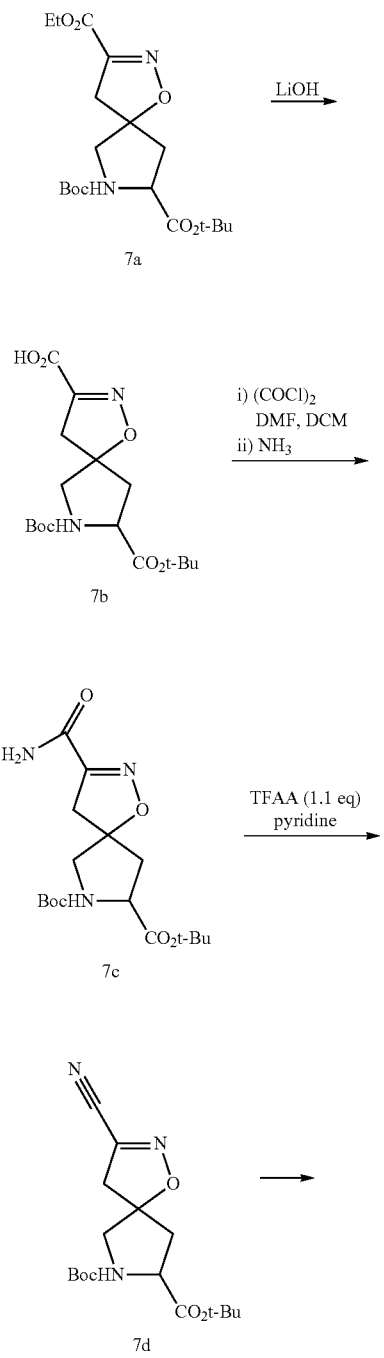

Referring to Scheme 6, reaction of the diprotected pyrrolidinone with difluorodibromomethane in the presence of HMPT and zinc provides the difluoroexomethylene intermediate 6b. Dipolar addition with the nitrile oxide 1f as previously described provides the difluorospiroisoxazoline 6c. In a similar fashion, the intermediates 6b and 6f are prepared from 6a and 6e respectively and converted to the corresponding substituted isooxazolines 6d and 6g.

In other variations, the intermediate 6h may be brominated to give 6j, alkylated to provide 6k or oxidized to provide 6m using the reagents illustrated.

Scheme 7:

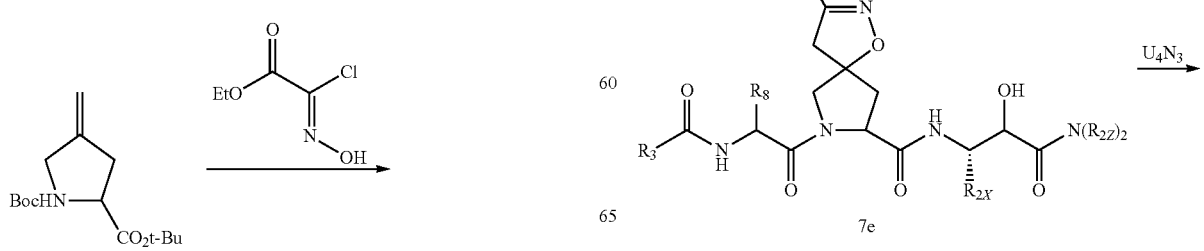

767
-continued

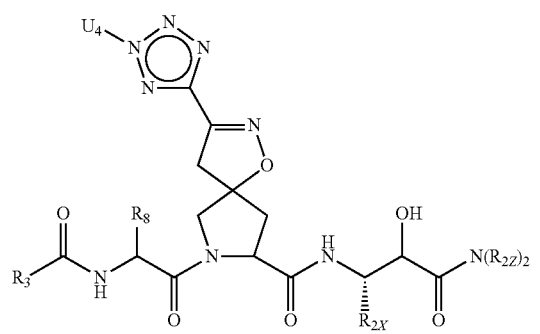

7f

↓ [O]

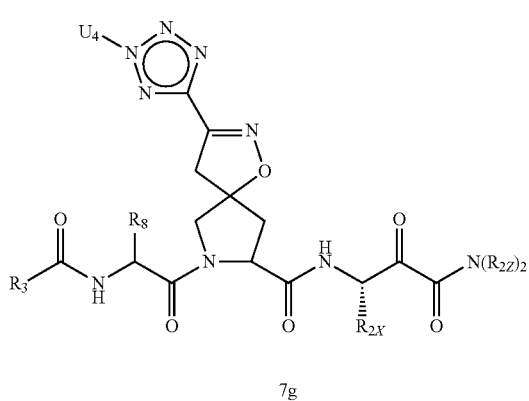

7g

7a →

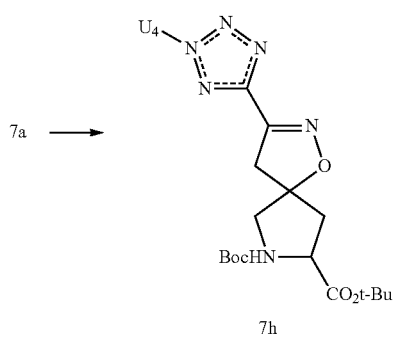

7h

→

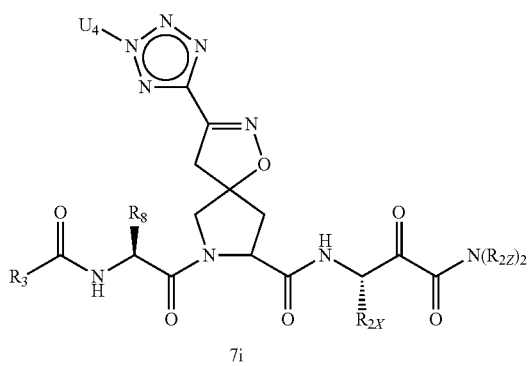

7i

768

Referring to Scheme 7, dipolar addition of the exomethylene pyrrolidine shown with if wherein $R_3$ is —COOEt, leads to the ester 7a. Hydrolysis of the ethyl ester in 7a, conversion to the acid chloride (not shown) and reaction with ammonia provides the amide 7c. Reaction of 7c with trifluoroacetic anhydride provides the nitrile 7d which is converted to the peptidic intermediate 7e by methods previously described. The intermediate 7e reacts with an azide $U_4N_3$ to provide the tetrazole 7f which is oxidized to a compound of the invention 7g. In a variation of this scheme, the ester 7a may be converted to the triazole 7h and subsequently to compounds of the invention 7I.

Scheme 8:

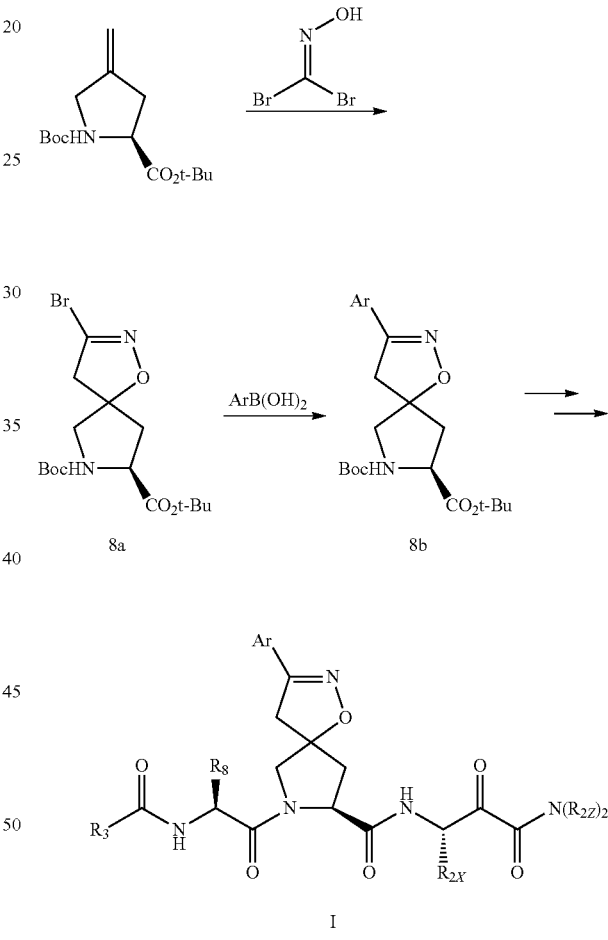

Referring to Scheme 8, dipolar addition as previously described but using hydroxycarbonimidic dibromide provides the bromoisoxazoline 8a. Reaction of 8a with an arylboronic acid in the presence of a palladium catalyst (Suzuki conditions) provides the intermediate 8b which is converted to compounds of the invention by methods previously described. The AR in step 8a and 8b represents aryl or heteroaryl.

Scheme 9:
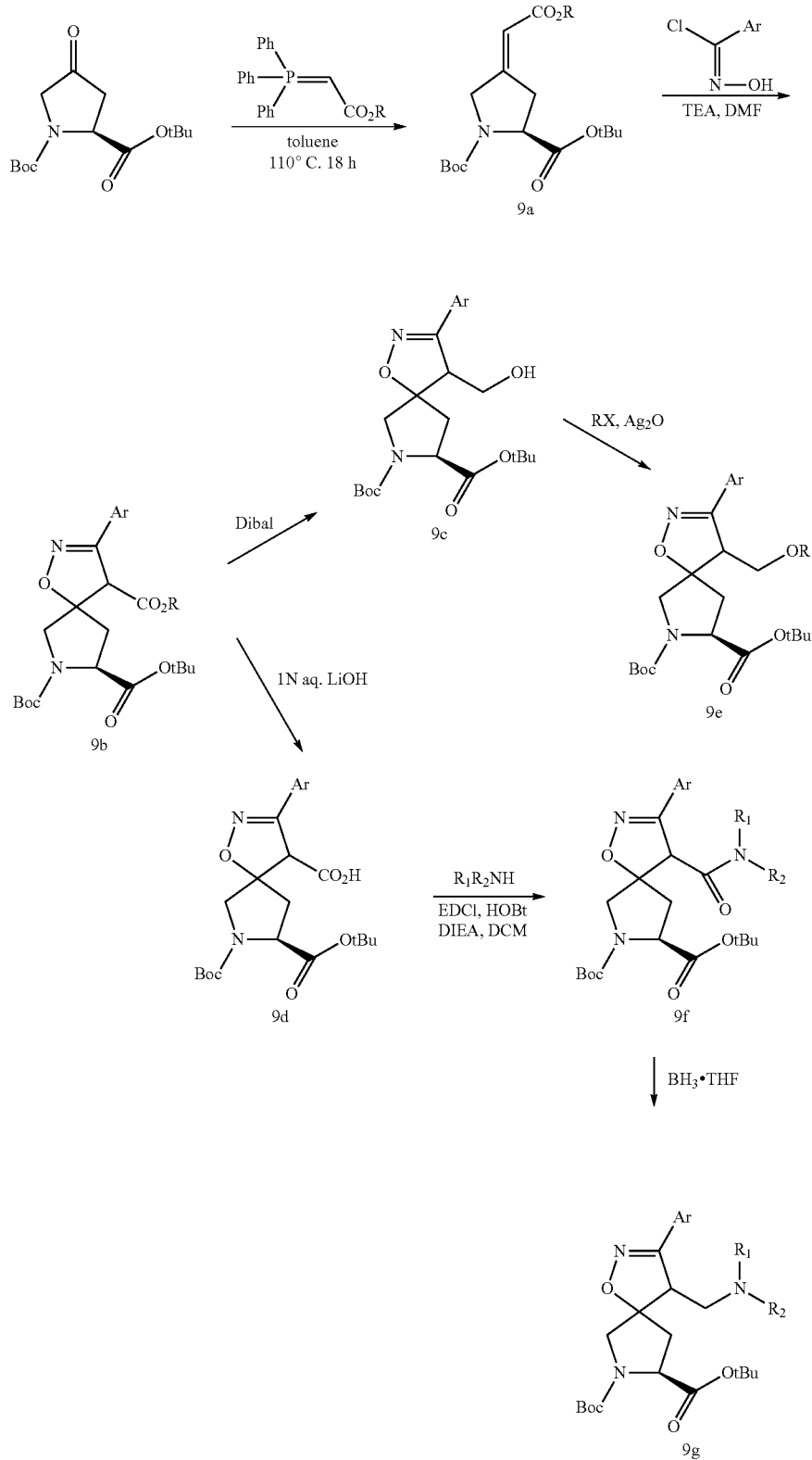

Referring to Scheme 9, the Wittig product 9a undergoes a dipolar addition to provide the spiroisoxazoline 9b. Reduction of 9b with, for example, DIBAL provides the alcohol 9c which may be alkylated to provide the intermediate 9e which subsequently may be converted to compounds of the invention by methods previously described. Hydrolysis of ester 9b with, e.g., LiOH, will provide carboxylic acid 9d which can be converted to compounds of formula I as described herein.

Scheme 10:

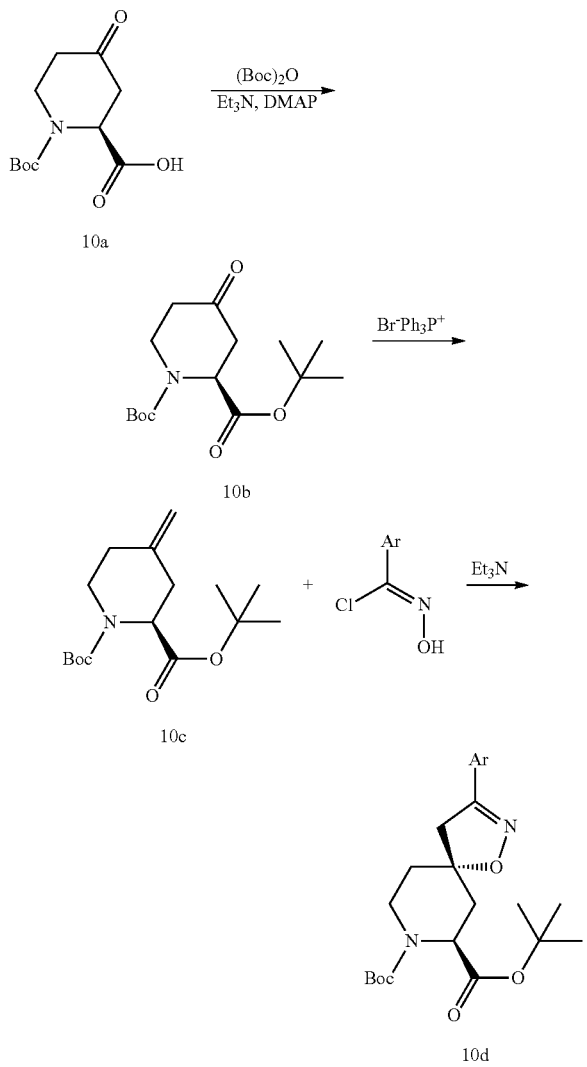

Referring to scheme 10, the diprotected piperidinone 10b undergoes a Wittig type reaction to form the exomethylene compound 10c which undergoes dipolar addition as previously described to provide a 4.5 spiroisoxazoline 10d which may be converted to compounds of the invention as previously described.

III. Formulations, Administrations, and Uses

Another embodiment of this invention provides a pharmaceutical composition comprising a compound of formula (I) or pharmaceutically acceptable salts or mixtures of salts thereof. According to another embodiment, the compound of formula (I) is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2 hydroxy-ethanesulfonate, lactate, maleate, methanesulfonate, 2 naphthalenesulfonate, nicotinate, oxalate, pamoate, pectinate, persulfate, 3 phenyl propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N methyl D glucamine, and salts with amino acids such as arginine, lysine, and so forth.

Also, the basic nitrogen containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

According to another embodiment, the compositions of this invention are formulated for pharmaceutical administration to a mammal. In one embodiment said mammal is a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra articular, intra synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non toxic parenterally acceptable diluent or solvent, for example as a solution in 1,3 butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, dosage levels of between about 0.01 and about 100 mg/kg body weight per day of the protease inhibitor compounds described herein are useful in a monotherapy for the prevention and treatment of antiviral, particularly anti-HCV mediated disease. In another embodiment, dosage levels of between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In one embodiment, such preparations contain from about 20% to about 80% active compound.

When the compositions of this invention comprise a combination of a compound of formula I and one or more additional therapeutic or prophylactic agents, both the compound and the additional agent should be present at dosage levels of between about 10 to 100% of the dosage normally administered in a monotherapy regimen. In another embodiment, the additional agent should be present at dosage levels of between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutical compositions are formulated for oral administration.

In another embodiment, the compositions of this invention additionally comprise another anti-viral agent, preferably an anti-HCV agent. Such anti-viral agents include, but are not limited to, immunomodulatory agents, such as $\alpha$, $\beta$, and $\gamma$-interferons, pegylated derivatized interferon-$\alpha$ compounds, and thymosin; other anti-viral agents, such as ribavirin, amantadine, and telbivudine; other inhibitors of hepatitis proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, and 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., Antimicrobial & Antiviral Chemotherapy, 44, p. 859 (2000) and U.S. Pat. No. 6,541,496.

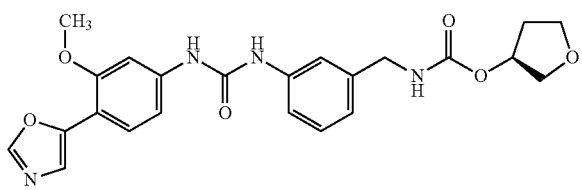

The following definitions are used herein (with trademarks referring to products available as of this application's filing date):

"Peg-Intron" means PEG-INTRON®, peginteferon alfa-2b, available from Schering Corporation, Kenilworth, N.J.;

"Intron" means INTRON-A®, interferon alfa-2b available from Schering Corporation, Kenilworth, N.J.;

"ribavirin" means ribavirin (1-beta-D-ribofuranosyl-1H-1, 2,4-triazole-3-carboxamide, available from ICN Pharmaceuticals, Inc., Costa Mesa, Calif.; described in the Merck Index, entry 8365, Twelfth Edition; also available as REBETROL® from Schering Corporation, Kenilworth, N.J., or as COPEGASUS® from Hoffmann-La Roche, Nutley, N.J.;

"Pagasys" means PEGASYS®, peginterferon alfa-2a available Hoffmann-La Roche, Nutley, N.J.;

"Roferon" mean ROFERON®, recombinant interferon alfa-2a available from Hoffmann-La Roche, Nutley, N.J.;

"Berefor" means BEREFOR®, interferon alfa 2 available from Boehringer Ingelheim Pharmaceutical, Inc., Ridgefield, Conn.;

SUMIFERON®, a purified blend of natural alpha interferons such as Sumiferon available from Sumitomo, Japan;

WELLFERON®, interferon alpha n1 available from Glaxo_Wellcome LTd., Great Britain; and ALFERON®, a mixture of natural alpha interferons made by Interferon Sciences, and available from Purdue Frederick Co., CT.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) INTRON-A® (interferon-alpha 2B, Schering Plough),
(b) PEG-INTRON®,
(c) PEGASYS®,
(d) ROFERON®,
(e) BEREFOR®,
(f) SUMIFERON®,
(g) WELLFERON®,
(h) consensus alpha interferon available from Amgen, Inc., Newbury Park, Calif.,
(i) ALFERON®;
(j) VIRAFERON®;
(k) INFERGEN®;
(l) ALBUFERON™.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, Albuferon™ (albumin-Interferon alpha) available from Human Genome Sciences; PEG-INTRON® (peginterferon alfa-2b, available from Schering Corporation, Kenilworth, N.J.); INTRON-A®, (interferon alfa-2b available from Schering Corporation, Kenilworth, N.J.); ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition); REBETROL® (Schering Corporation, Kenilworth, N.J.), COPEGUS® (Hoffmann-La Roche, Nutley, N.J.); PEGASYS® (peginterferon alfa-2a available Hoffmann-La Roche, Nutley, N.J.); ROFERON® (recombinant interferon alfa-2a available from Hoffmann-La Roche, Nutley, N.J.); BEREFOR® (interferon alfa 2 available from Boehringer Ingelheim Pharmaceutical, Inc., Ridgefield, Conn.); SUMIFERON® (a purified blend of natural alpha interferons such as Sumiferon available from Sumitomo, Japan); WELLFERON® (interferon alpha n1 available from Glaxo Wellcome Ltd., Great Britain); ALFERON® (a mixture of natural alpha interferons made by Interferon Sciences, and available from Purdue Frederick Co., CT); α-interferon; natural alpha interferon 2a; natural alpha interferon 2b; pegylated alpha interferon 2a or 2b; consensus alpha interferon (Amgen, Inc., Newbury Park, Calif.); VIRAFERON®; INFERGEN®; REBETRON® (Schering Plough, Interferon-alpha 2B+Ribavirin); pegylated interferon alpha (Reddy, K. R. et al. "Efficacy and Safety of Pegylated (40-kd) Interferon alpha-2a Compared with Interferon alpha-2a in Noncirrhotic Patients with Chronic Hepatitis C" (Hepatology, 33, pp. 433-438 (2001); consensus interferon (Kao, J. H., et al., "Efficacy of Consensus Interferon in the Treatment of Chronic Hepatitis" J. Gastroenterol. Hepatol. 15, pp. 1418-1423 (2000); lymphoblastoid or "natural" interferon; interferon tau (Clayette, P. et al., "IFN-tau, A New Interferon Type I with Antiretroviral activity" Pathol. Biol. (Paris) 47, pp. 553-559 (1999); interleukin-2 (Davis, G. L. et al., "Future Options for the Management of Hepatitis C." Seminars in Liver Disease, 19, pp. 103-112 (1999); Interleukin-6 (Davis et al. "Future Options for the Management of Hepatitis C." Seminars in Liver Disease, 19, pp. 103-112 (1999); interleukin-12 (Davis, G. L. et al., "Future Options for the Management of Hepatitis C." Seminars in Liver Disease, 19, pp. 103-112 (1999); and compounds that enhance the development of type 1 helper T cell response (Davis et al., "Future Options for the Management of Hepatitis C." Seminars in Liver Disease, 19, pp. 103-112 (1999)). Also included are compounds that stimulate the synthesis of interferon in cells (Tazulakhova, E. B. et al., "Russian Experience in Screening, analysis, and Clinical Application of Novel Interferon Inducers" J. Interferon Cytokine Res., 21 pp. 65-73) including, but are not limited to, double stranded RNA, alone or in combination with tobramycin, and Imiquimod (3M Pharmaceuticals; Sauder, D. N. "Immunomodulatory and Pharmacologic Properties of Imiquimod" J. Am. Acad. Dermatol., 43 pp. S6-11 (2000).

Compounds that stimulate the synthesis of interferon in cells (Tazulakhova, E. B. et al., "Russian Experience in Screening, analysis, and Clinical Application of Novel Interferon Inducers" J. Interferon Cytokine Res., 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" J. Am. Acad. Dermatol., 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

Still other agents include those described in various published U.S. patent applications. These publications provide additional teachings of compounds and methods that could be used in combination with VX-950 in the methods of this invention, particularly for the treatment of hepatitis. It is contemplated that any such methods and compositions may be used in combination with the methods and compositions of the present invention. For brevity, the disclosure the disclosures from those publications is referred to be reference to the publication number but it should be noted that the disclosure of the compounds in particular is specifically incorporated herein by reference. Exemplary such publications include U.S. Patent Publication No. 20040058982; U.S. Patent Publication No. 20050192212; U.S. Patent Publication No. 20050080005; U.S. Patent Publication No. 20050062522; U.S. Patent Publication No. 20050020503; U.S. Patent Publication No. 20040229818; U.S. Patent Publication No. 20040229817; U.S. Patent Publication No. 20040224900; U.S. Patent Publication No. 20040186125; U.S. Patent Publication No. 20040171626; U.S. Patent Publication No. 20040110747; U.S. Patent Publication No. 20040072788; U.S. Patent Publication No. 20040067901; U.S. Patent Publication No. 20030191067; U.S. Patent Publication No. 20030187018; U.S. Patent Publication No. 20030186895; U.S. Patent Publication No. 20030181363; U.S. Patent Publication No. 20020147160; U.S. Patent Publication No. 20040082574; U.S. Patent Publication No. 20050192212; U.S. Patent Publication No. 20050187192; U.S. Patent Publication No. 20050187165; U.S. Patent Publication No. 20050049220; and U.S. Patent Publication No. US2005/0222236.

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, WO 95/07696 and WO 95/09614.

Methods for measuring the ability of a compound to inhibit cytochrome P450 monooxygenase activity are known. See, e.g., U.S. Pat. No. 6,037,157, and Yun, et al. Drug Metabolism & Disposition, vol. 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. In one embodiment, the methods of this invention are used to treat a patient suffering from a HCV infection. Such treatment may completely eradicate the viral infection or reduce the severity thereof. In another embodiment, the patient is a human being.

In an alternate embodiment, the methods of this invention additionally comprise the step of administering to said patient an anti-viral agent preferably an anti-HCV agent. Such antiviral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including but not limited to helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

Pharmaceutical compositions may also be prescribed to the patient in "patient packs" containing the whole course of treatment in a single package, usually a blister pack. Patient packs have an advantage over traditional prescriptions, where a pharmacist divides a patients supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least one compound of formula I (in dosages according to this invention) and an information insert containing directions on the use of the combination of the invention. Any composition, dosage form, therapeutic regimen or other embodiment of this invention may be presented in a pharmaceutical pack. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection (or for use in another method of this invention), comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a dose of at least one compound of formula I (and optionally an additional agent). Typically, such a kit will comprise, e.g. a composition of each compound and optional additional agent(s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

A kit according to this invention could embody any aspect of this invention such as any composition, dosage form, therapeutic regimen, or pharmaceutical pack. The packs and kits according to this invention optionally comprise a plurality of compositions or dosage forms. Accordingly, included within this invention would be packs and kits containing one composition or more than one composition.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as, for example, shunts and stents.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. In one embodiment, the viral serine protease isolated by this method is HCV NS3-NS4A protease.

All references cited within this document are incorporated herein by reference.

IV. Methods and Examples

In order that the invention described herein may be more fully understood, the following methods and examples are provided. It should be understood that these methods and examples are for illustrative purposes only and are not to be construed as limiting this invention in any manner.

A. Preparation of Intermediates for Compounds of Formula I

Set forth below are various methods for preparing intermediates that can be used to synthesize the compound of Formula I.

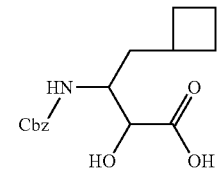

Preparation of 3-(benzyloxycarbonylamino)-4-cyclobutyl-2-hydroxybutanoic acid

A solution of the cyanohydrin prepared according to methods described in WO 04/113294 (1 g, 3.65 mmol) in conc. HCl (12 mL) was heated to reflux for 18 hours. The reaction was concentrated in vacuo to afford the desired amino acid as an HCl salt (1.7 g) which was used in the next step without further purification. A solution of the above HCl salt in THF was treated with DIPEA (2.68 g) and Z—OSu (5.16 g). The reaction mixture was stirred at room temperature for 8 hours. The reaction mixture was diluted with toluene and HCl (12 N, until pH=1). After separation, the organic layer was extracted with sat. NaHCO₃ (50 mL, twice). The aqueous layer was made acidic with HCl (6 N) until pH=1 and extracted with EtOAc (200 mL). The combined organic layer was dried and concentrated in vacuo to afford the title compound (0.6 g). (M+1) 308.

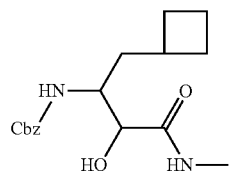

Preparation of benzyl 1-cyclobutyl-3-hydroxy-4-(methylamino)-4-oxobutan-2-ylcarbamate To a solution of 3-(benzyloxycarbonylamino)-4-cyclobutyl-2-hydroxybutanoic acid (250 mg, 0.81 mmol) in DCM (20 mL) was added HOSu (140 mg, 1.22 mmol), EDC (234 mg, 1.22 mmol). After stirring for 1 hour, methylamine in THF (2 N, 0.81 mL) was added to the above mixture. The reaction mixture was stirred for 18 hours and then concentrated in vacuo. The residue was purified by Gilson Prep to afford the title compound (135 mg). ¹H-NMR (CDCl₃): δ 7.54-7.28 (m, 5H), 6.67 (NH, 1H), 5.03 (dd, 2H), 3.68 (m, 1H), 2.73 (m, 3H), 2.26 (m, 1H), 1.97-1.31 (m, 9H). (M+1) 321.

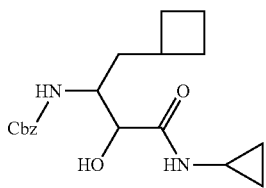

Preparation of benzyl 1-cyclobutyl-4-(cyclopropylamino)-3-hydroxy-4-oxobutan-2-ylcarbamate To a solution of 3-(benzyloxycarbonylamino)-4-cyclobutyl-2-hydroxybutanoic acid (600 mg, 1.95 mmol) in DCM (20 mL) was added HOSu (337 mg, 2.93 mmol), EDC (562 mg, 2.93 mmol). After stirring for 1 hour, cyclopropylamine (223 mg, 3.9 mmol) was added to the above mixture. The product was extracted with EtOAc. The combined organic layer was then washed with HCl (1N), water, NaHCO₃, and brine and then concentrated in vacuo to afford benzyl 1-cyclobutyl-4-(cyclopropylamino)-3-hydroxy-4-oxobutan-2-ylcarbamate (530 mg). (M+1) 347.

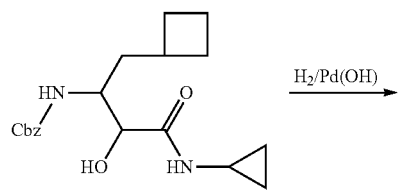

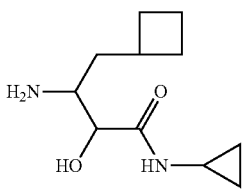

Preparation of 3-amino-4-cyclobutyl-N-cyclopropyl-2-hydroxybutanamide

To a solution of the CBz amide (530 mg, 1.53 mmol) in MeOH (30 mL) was added Pd(OH)₂/C (106 mg). The mixture was stirred under H₂ (1 atm) for 18 hours. After filtration, the filtrate was concentrated in vacuo to afford the title compound (300 mg). ¹H-NMR (CDCl₃): δ 3.29 (m, 1H), 2.74 (m, 1H), 2.37-1.66 (m, 9H), 1.40 (m, 1H), 0.78 (m, 2H), 0.51 (m, 2H). (M+1) 213.

The following compounds were prepared in a similar fashion to preparing 3-amino-4-cyclobutyl-N-cyclopropyl-2-hydroxybutanamide by using the appropriate amine:

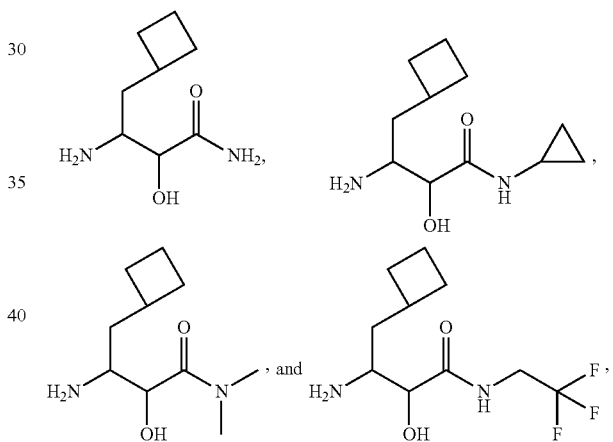

Preparation of 3-amino-N-cyclopropyl-2-hydroxyhept-6-ynamide

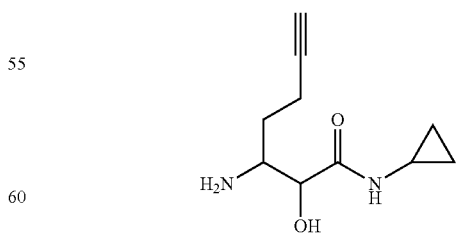

3-Amino-N-cyclopropyl-2-hydroxyhept-6-ynamide was prepared as described by N. Kobayashi, et al. in US 2003/0153788, which is incorporated herein by reference in its entirety. ¹H-NMR (500 MHz, DMSO-d₆): 8.18 (s), 6.34 (s), 4.22 (s), 3.45 (s), 3.17 (s), 2.84 (s), 2.69 (d, J=3.2 Hz), 2.30 (m), 2.24 (m), 1.70 (m), 1.59 (m), 0.62 (d, J=5.0 Hz), 0.53 (s) ppm; FIA m/z 197.01 ES+.

Preparation of Cbz-Protected (3S)-3-amino-4-cyclopropyl-2-hydroxy-N-methylbutanamide

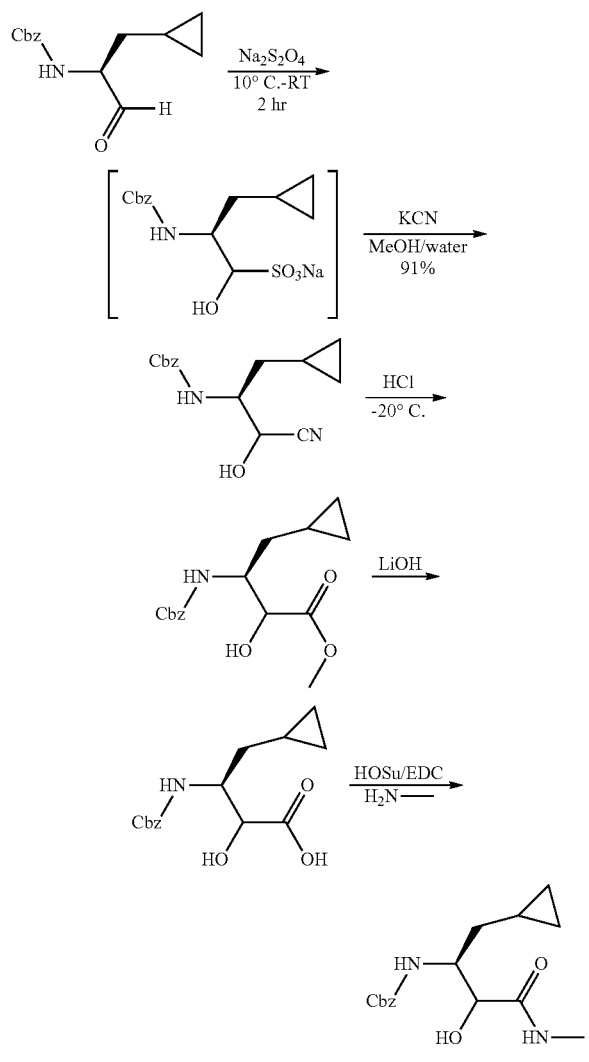

Step 1: Preparation of benzyl (2S)-1-cyano-3-cyclopropyl-1-hydroxypropan-2-ylcarbamate

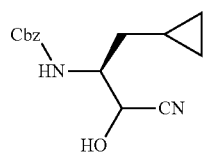

To a solution of the aldehyde (7.9 g, 32 mmol) in MeOH (50 mL) at 10° C. was added Na₂S₂O₄ (6.13 g, 35.2 mmol) and the resulting mixture was warmed to room temperature and stirred for 2 hours then cooled to 10° C. To this reaction mixture, a solution of KCN in water (50 mL) was added. After stirring at room temperature for 18 hours, the mixture was extracted with TBME (100 mL, twice). The combined organic layers were washed with water and brine, dried and concentrated in vacuo to afford the title compound (8 g). (M+1) 275.

Step 2: Preparation of (3S)-methyl 3-(benzyloxycarbonylamino)-4-cyclopropyl-2-hydroxybutanoate

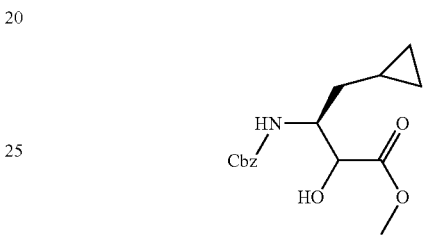

To a solution of the cyanohydrin (1 g, 3.65 mmol) in MeOH (15 mL) at −20° C. was bubbled through a stream of dry HCl gas for 30 minutes. The resulting mixture was stirred at room temperature for 2 hours. The reaction mixture was purged with nitrogen gas for 30 minutes and then concentrated. The residue at 0° C. was quenched with ice water and then stirred at room temperature for 1 hour. The product was extracted with EtOAc. The combined organic layer was washed with NaHCO₃, water, brine and concentrated in vacuo to afford the title compound (0.5 g). ¹H-NMR (CDCl₃) δ: 7.31-7.30 (m, 5H), 5.09 (d, 2H), 4.44-4.14 (m, 2H), 3.78 (d, 3H), 1.58-1.42 (m, 2H), 0.70 (m, 1H), 0.47 (t, 2H), 0.11-0.01 (m, 2H). (M+1) 308.

Step 3: Preparation of (3S)-3-(benzyloxycarbonylamino)-4-cyclopropyl-2-hydroxybutanoic acid

To a solution of the methyl ester of Step 2 (400 mg; 1.3 mmol) in THF (8 mL) and water (6.63 mL) was added LiOH (1 N; 1.37 mL). The reaction mixture was stirred for 30 minutes and then acidified with 1.0 N HCl to pH=3≈4. The mixture was extracted with EtOAc (20 mL, twice). The combined organic layer was washed with water, brine, and then concentrated in vacuo to afford the title compound (370 mg). (M+1) 294.

Step 4: Preparation of benzyl (2S)-1-cyclopropyl-3-hydroxy-4-(methylamino)-4-oxobutan-2-ylcarbamate

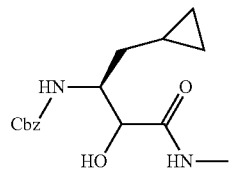

To a solution of (3S)-3-(benzyloxycarbonylamino)-4-cyclopropyl-2-hydroxybutanoic acid (180 mg, 0.26 mmol) in DCM (20 mL) was added HOSu (105 mg, 0.92 mmol), EDC (175 mg, 0.92 mmol). After stirred for 30 minutes, methylamine in THF (2 N, 0.92 mL) was added to above mixture. The reaction mixture was stirred for 18 hours and then concentrated in vacuo. The residue was purified by Gilson Prep to afford title compound (50 mg). $^1$H-NMR (CDCl$_3$): δ 7.53-7.26 (m, 5H), 6.83 (NH, 1H), 5.25 (NH, 1H), 5.05 (m, 2H), 4.25-3.89 (m, 3H), 2.70 (m, 3H), 1.4 (m, 1H), 0.86 (m, 1H), 0.61 (m, 1H), 0.38 (m, 2H), 0.33 (m, 2H). (M+1) 307.

The following compounds can be prepared in the similar manner by using appropriate amines, followed by hydrogenation.

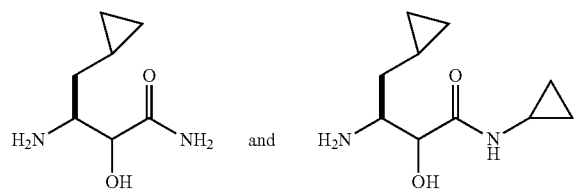

The following compounds can be prepared in the methods described by Perni, R. et al. in WO 01/74768, which is incorporated herein by reference in its entirety.

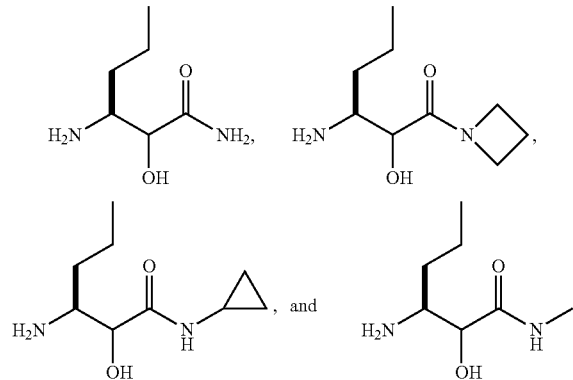

Preparation of (S)-2-(cyclopentyloxycarbonylamino)-3,3-dimethylbutanoic acid

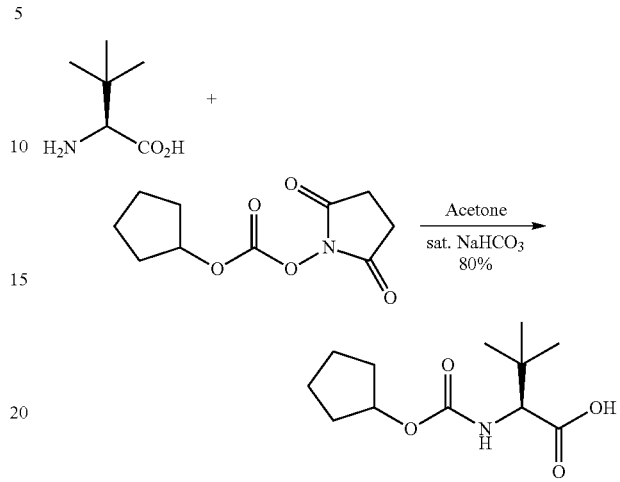

In a 5 L RB flask dissolved t-butyl glycine (74 g, 0.56 mol, 1.02 eq.) in saturated sodium bicarbonate (11 vol). Cyclopentyl 2,5-dioxopyrrolidin-1-yl carbonate (126 g, 0.55 mol, 1 eq.) was dissolved in acetone (5.5 vol) and the solution slowly added via addition funnel at room temperature to the solution of the glycine. The reaction mixture was stirred at room temperature until complete (approximately 4 hours). The acetone was removed under reduced pressure and the remaining aqueous solution was extracted with 30% ethyl acetate in hexanes (thrice, 5.5 vol each). The organic layers were discarded. The pH of the aqueous layer was adjusted to 2 with 2 N HCl and then extracted with ethyl acetate (thrice, 5.5 vol). The combined organic layers were dried (Na$_2$SO$_4$), filtered, and the solvent removed under reduced pressure to provide a clear oil the slowly crystallized. The crude product was crystallized from hexanes/ethyl acetate to provide (S)-2-(cyclopentyloxycarbonylamino)-3,3-dimethylbutanoic acid as a white solid (82 g). The mother liquid was stripped and a second crop of crystals obtained (combined yield 105.54 g).

Preparation of Sulfonyl Compounds

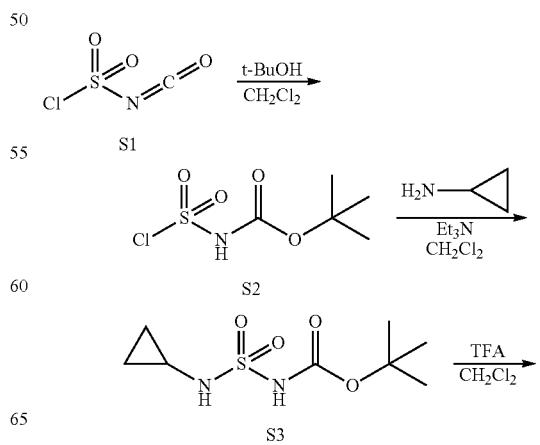

-continued

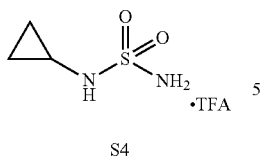

S4

-continued

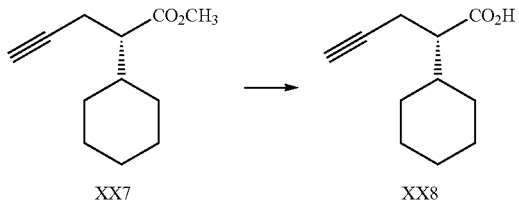

Compounds S1, S2, S3, and S4, shown above, were prepared according to procedures described in WO 2005/095403 and PCT/US2005/010494, hereby incorporated by references by their entireties. Specifically, to a solution of chlorosulfonylisocyanate (10 mL, 115 mmol) in $CH_2Cl_2$ (200 mL) at 0° C. was added t-BuOH (11 mL, 1 eq.). The mixture was stirred for 60 minutes, then added via cannula into a solution of cyclopropylamine (6.6 g) in $CH_2Cl_2$ (200 mL) with triethylamine (30 mL) at 0° C. concurrently with a solution of triethylamine (50 mL) in $CH_2Cl_2$ (100 mL) via addition funnel. Internal temperature was maintained below 8° C. Stirred at room temperature after completion of addition for 4 hours. The reaction was then diluted with $CH_2Cl_2$ and transferred to a separatory funnel, washed with 1 N HCl (twice, 400 mL each), brine (300 mL), dried ($MgSO_4$), filtered and concentrated. The product was recrystallized from ethyl acetate/hexanes to yield 16.8 g (71.3 mmol) of S3. Compound S3 was deprotected with trifluoroacetic acid in $CH_2Cl_2$ to give compound S4.

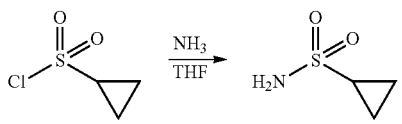

Ammonia gas was bubbled through a gas dispersion tube into THF (40 mL) cooled to 0° C. for 5 minutes. To this solution at 0° C. was added cyclopropylsulfonylchloride (1 gram, 7.1 mmol). The reaction was stirred at room temperature overnight, then filtered through a plug of silica gel, followed by elution with EtOAc to yield 750 mg (6.19 mmol) of cyclopropylsulfonamide. $^1$H-NMR (500 MHz, Methanol-$d_4$): 4.79 (s, 2H), 2.59-2.54 (m, 1H), 1.06-0.96 (m, 4H).

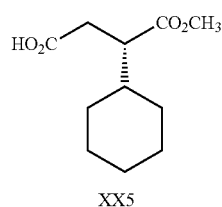

XX5

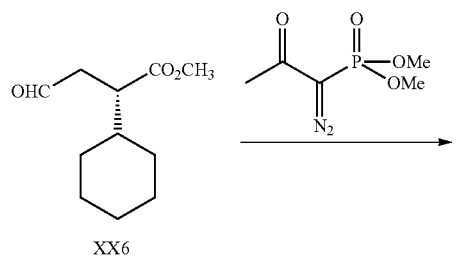

XX6

To a solution of compound XX5 (1.37 g, 6.41 mmol) in THF (30 mL) at 0° C. was added dropwise borane-dimethylsulfide (3.85 mL, 7.8 mmol, 2.0 M in toluene). The reaction mixture was stirred for 1 h with gradual warming to room temperature, quenched with $H_2O$ (20 mL), and extracted with ethyl acetate (thrice, 30 mL each). The combined organics were dried and concentrated under reduced pressure to provide 1.3 g of a colorless oil which was used without further purification. To oxalyl chloride (2.24 mL, 25.6 mmol) in $CH_2Cl_2$ (15 mL, anhydrous) at −78° C. under inert atmosphere was added dropwise a solution of DMSO (2.73 mL, 38.5 mmol) in $CH_2Cl_2$ (8 mL). After stirring for 10 min, a solution of the alcohol (1.3 g, 6.41 mmol) in $CH_2Cl_2$ (6 mL) was added dropwise. After an additional 10 min, triethylamine (7.15 mL, 51.3 mmol) in $CH_2Cl_2$ was added and the reaction was stirred another 30 min with gradual warming to 0° C. The reaction mixture was washed with 1 M HCl (20 mL) followed by brine (20 mL). The organic layer was dried over $MgSO_4$ and concentrated under reduced pressure. The resulting oil was purified via silica gel chromatography to afford 748 mg (over 2 steps) of aldehyde XX6. $^1$H-NMR (500 MHz, $CDCl_3$): 9.75 (s, 1H), 3.67 (s, 3H), 2.91-2.85 (m, 1H), 2.78-2.74 (m, 1H), 2.56-2.52 (m, 1H), 1.74-1.71 (m, 2H), 1.66-1.58 (m, 4H), 1.27-0.95 (m, 5H).

To a solution of compound XX6 (581 mg, 2.9 mmol) and $K_2CO_3$ (811 mg, 5.9 mmol) in MeOH (15 mL) was added dimethyl 1-diazo-2-oxopropylphosphonate (676 mg, 3.5 mmol, Synlett 1996, p. 521). The reaction was stirred 1 h at room temperature, diluted wth $Et_2O$ (20 mL), and washed with saturated $NaHCO_3$ solution (10 mL, aqueous). The organic layer was dried over $MgSO_4$ and concentrated under reduced pressure to give 600 mg of alkyne XX7 which was used without further purification. $^1$H-NMR (500 MHz, $CDCl_3$): 3.69 (s, 3H), 2.48-2.37 (m), 1.95 (s, H), 1.73-1.60 (m), 1.30-0.94 (m).

To a solution of compound XX7 (600 mg, 2.9 mmol) in a solution of $THF/H_2O/MeOH$ (25 mL, 2:1:2) was added LiOH monohydrate (850 mg, 20.3 mmol). The reaction mixture was stirred 2 h at room temperature, acidified using 1 N HCl (25 mL), and extracted with EtOAc (thrice, 15 mL each). The combined organics were dried over $MgSO_4$ and concentrated to yield 533 mg of carboxylic acid XX8, which was used without further purification.

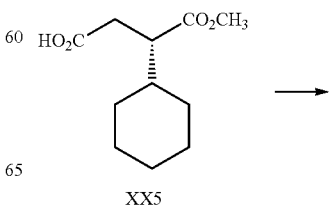

XX5

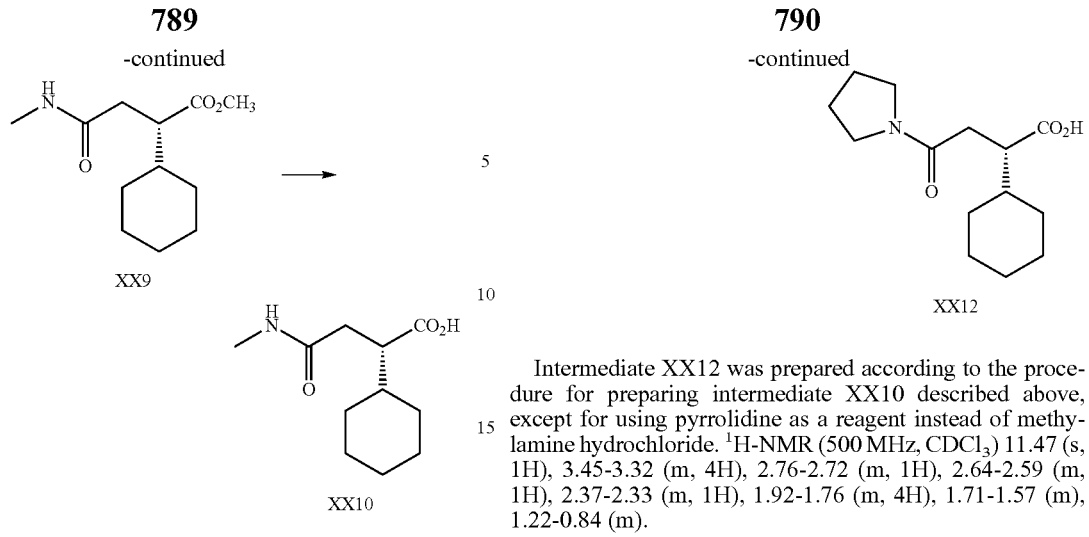

XX9

XX10

To a solution of compound XX5 (100 mg, 0.5 mmol) in $CH_2Cl_2$ (2.5 mL) was added EDC (107 mg, 0.6 mmol), HOBt (76 mg, 0.6 mmol) and triethylamine (195 μL, 1.4 mmol). To the activated acid solution was added methylamine hydrochloride (38 mg, 0.6 mmol) and the reaction was stirred at room temperature for 12 h. The reaction mixture was washed with $H_2O$ (2 mL), 1 N HCl (2 mL) and saturated $NaHCO_3$ solution (2 mL). The organic layer was dried over $MgSO_4$ and concentrated to give 100 mg of amide XX9, which was used without further purification. $^1$H-NMR (500 MHz, $CDCl_3$) 3.61 (s, 3H), 2.75-2.70 (m, 4H), 2.48-2.42 (m, 1H), 2.28-2.24 (m, 1H), 1.66-1.48 (m, 6H), 1.35-0.90 (m, 5H).

To a solution of compound XX9 (100 mg, 0.5 mmol) in a solution of $THF/H_2O/MeOH$ (3 mL, 2:1:2) was added LiOH monohydrate (124 mg, 3 mmol). The reaction mixture was stirred 2 h at room temperature, acidified using 1 N HCl (4 mL), and extracted with EtOAc (3×5 mL). The combined organics were dried over $MgSO_4$ and concentrated to yield 87 mg of carboxylic acid XX10, which was used without further purification. $^1$H-NMR (500 MHz, $CDCl_3$) 11.32 (s, H), 2.75-2.64 (m, H), 2.52-2.46 (m, H), 2.37-2.33 (m, H), 2.25 (td, J=8.7, 2.9 Hz, H), 1.97 (s, H), 1.79 (s, H), 1.74-1.62 (m, H), 1.59-1.49 (m, H), 1.23-1.12 (m, H), 1.08-0.81 (m, H).

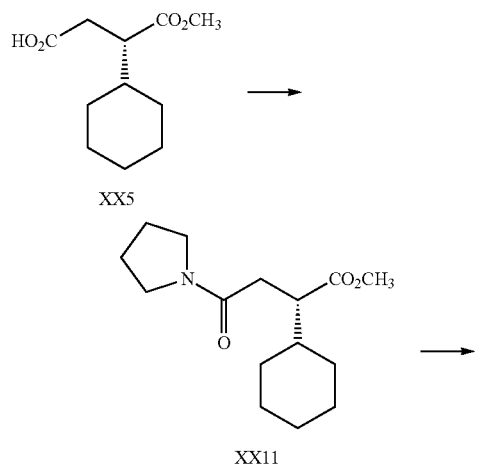

XX5

XX11

XX12

Intermediate XX12 was prepared according to the procedure for preparing intermediate XX10 described above, except for using pyrrolidine as a reagent instead of methylamine hydrochloride. $^1$H-NMR (500 MHz, $CDCl_3$) 11.47 (s, 1H), 3.45-3.32 (m, 4H), 2.76-2.72 (m, 1H), 2.64-2.59 (m, 1H), 2.37-2.33 (m, 1H), 1.92-1.76 (m, 4H), 1.71-1.57 (m), 1.22-0.84 (m).

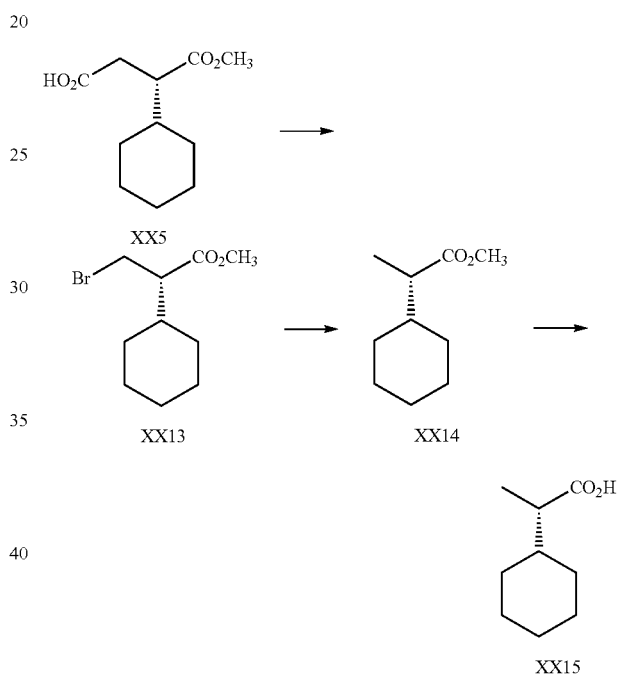

XX13

XX14

XX15

To a solution of compound XX5 (1 g, 4.7 mmol) and HgO yellow (1.01 g, 4.7 mmol) in $CCl_4$ (23 mL) at reflux was added dropwise over 30 min a solution of bromine (264 μL, 5.1 mmol) in $CCl_4$ (5 mL). The reaction was stirred at reflux for 1 h, cooled to room temperature, diluted with $CH_2Cl_2$ (20 mL), washed with 1 N HCl (10 mL), $H_2O$ (10 mL), and brine (10 mL). The organic layer was dried over $MgSO_4$ and concentrated under reduced pressure to yield 1.3 g of compound XX13 as a colorless oil that was used without further purification. $^1$H-NMR (500 MHz, $CDCl_3$): 3.67 (s, 3H), 3.52-3.44 (m, 2H), 2.63-2.58 (m, 1H), 1.70-1.64 (m, 3H), 1.60-1.54 (m, 3H), 1.24-0.92 (m, 5H).

To a solution of compound XX13 (578 mg, 2.3 mmol) in DMSO (12 mL) was added sodium borohydride (177 mg, 4.7 mmol). The reaction mixture was stirred at 90° C. for 1 h, diluted with $H_2O$ (10 mL), and extracted with hexanes (3×15 mL). The combined organics were dried over $MgSO_4$ and concentrated under reduced pressure. Purification via silica gel chromatography, eluting with EtOAc/petroleum ether, afforded 204 mg of compound XX14. $^1$H-NMR (500 MHz, $CDCl_3$): 3.59 (s, 3H), 2.18 (m, 1H), 1.69-1.43 (m, 6H), 1.21-0.83 (m, 8H).

Intermediate XX15 was prepared according to the procedure for preparing intermediate XX10, step b, except for using substrate XX14 instead of XX9.

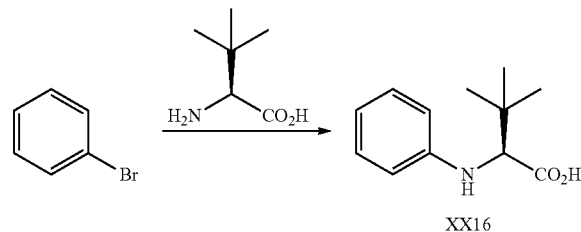

XX16

To a solution of (S)-2-amino-3,3-dimethylbutanoic acid (787 mg, 6.0 mmol), bromobenzene (632 μL, 6.0 mmol), K$_2$CO$_3$ (1.24 g, 9.0 mmol) and CuI (114 mg, 0.6 mmol) was added N,N-dimethylacetamide (7.5 mL). The contents were stirred for 16 h at 90° C. in a sealed pressure vessel. The reaction mixture was diluted with H$_2$O (15 mL), cooled to 0° C., and acidified to pH≈5 using 1 N HCl. The mixture was extracted with EtOAc (3×20 mL), and the combined organics were washed with brine (1×15 mL), dried over MgSO$_4$, and concentrated under reduced pressure. The resulting residue was purified via silica gel chromatography to provide 150 mg of compound XX16. $^1$H-NMR (500 MHz, CDCl$_3$): 7.11-7.09 (m, 2H), 6.69 (t, J=7.3 Hz, 1H), 6.60-6.59 (m, 2H), 3.69 (s, 1H), 1.02 (s, 9H).

XX17

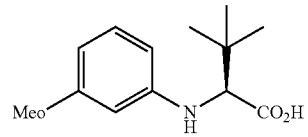

Intermediate XX17 was prepared according to the procedure for preparing XX16, except for using 1-bromo-3-methoxybenzene as a reagent instead of bromobenzene. $^1$H-NMR (500 MHz, CDCl$_3$): 6.98 (t, J=8.1 Hz, 1H), 6.24-6.18 (m, 2H), 6.14 (s, 1H), 3.69 (s, 1H), 3.66 (s, 3H), 1.00 (s, 9H).

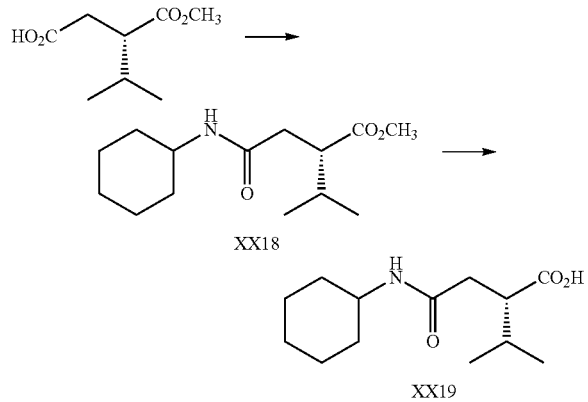

To a solution of (S)-3-(methoxycarbonyl)-4-methylpentanoic acid (200 mg, 1.2 mmol) in CH$_2$Cl$_2$ (6 mL) was added EDC (264 mg, 1.4 mmol), HOBt (186 mg, 1.4 mmol) and triethylamine (481 μL, 3.5 mmol). To the activated acid solution was added cyclohexylamine (158 μL, 1.4 mmol) and the reaction was stirred 4 hours. The reaction mixture was washed with H$_2$O (3 mL), 1 NHCl (3 mL), and saturated NaHCO$_3$ solution (3 mL). The organic layer was dried over MgSO$_4$, and concentrated under reduced pressure to afford 290 mg of compound XX18 which was used without further purification. $^1$H-NMR (500 MHz, CDCl$_3$): 5.78 (d, J=7.5 Hz, 1H), 3.69-3.61 (m, 4H), 2.73-2.69 (m, 1H), 2.45-2.40 (m, 1H), 2.24-2.20 (m, 1H), 1.85 (m, 1H), 1.82-1.76 (m, 2H), 1.63-1.60 (m, 2H), 1.54-1.50 (m, 1H), 1.31-1.22 (m, 2H), 1.12-1.00 (m, 3H), 0.90-0.85 (m, 6H).

Intermediate XX19 was prepared according to the procedure for preparing compound XX10 described above, except for using substrate XX18 as a reagent instead of compound XX9. ES (+) MS: m/e 256 (M+H)$^+$.

XX20

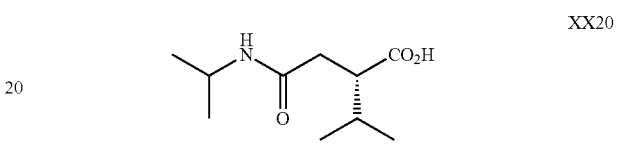

Intermediate XX20 was prepared according to the procedure for preparing compound XX18 or XX19 described above, except for using isopropylamine as a reagent instead of cyclohexylamine. ES (+) MS: m/e 216 (M+H)$^+$.

XX21

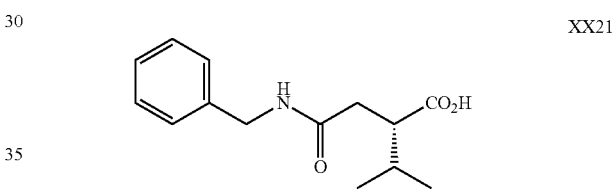

Intermediate XX21 was prepared according to the procedure for preparing XX18 or XX19 described above, except for using benzylamine as a reagent instead of cyclohexylamine. ES (+) MS: m/e 264 (M+H)$^+$.

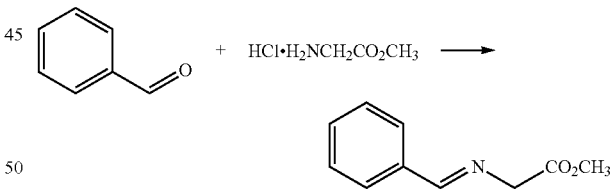

Glycine methyl ester hydrochloride (50.0 g) was suspended in MTBE (300 mL) at RT. To this was added benzaldehyde (40.5 mL) and anhydrous Na$_2$SO$_4$ (33.9 g). The suspension was cooled in an ice-water bath for 20 minutes, then triethylamine (80 mL) was added dropwise over 15 minutes. After 5 minutes, the reaction was removed from the ice-water bath, and stirred at RT for 24 hours. The reaction was quenched with 200 mL ice-water mixture and the organic layer was separated. The aqueous layer was extracted with MTBE (200 mL). The organic layers were combined, washed with a 1:1 mixture of brine and saturated NaHCO$_3$ (aq.), dried (MgSO$_4$), and concentrated to yield 62.83 grams of the N-benzyl imine as a yellow oil. $^1$H-NMR (500 MHz, CDCl$_3$): 8.30 (s, 1H), 7.78-7.77 (m, 2H), 7.45-7.40 (m, 3H), 4.42 (s, 2H), 3.78 (s, 3H).

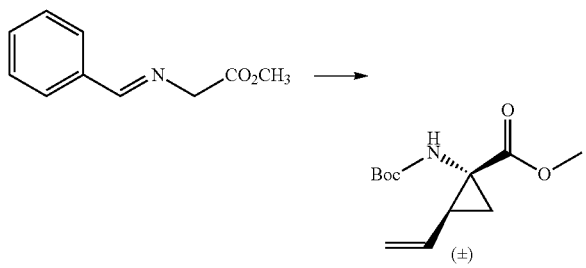

Lithium tert-butoxide (15.13 g) was suspended in dry toluene (200 mL) at room temperature. To this was added dropwise a solution of the N-benzyl imine of glycine methyl ester (16.89 g) and 1,4-dibromo-2-butene (19.28 g) in toluene (100 mL) over 40 minutes. The red solution was stirred for 100 minutes, then quenched with H$_2$O (200 mL). The contents were transferred to a separatory funnel and diluted with MTBE (200 mL). The layers were separated and the aqueous layer was extracted with MTBE. The combined organic layers were stirred with 1 N HCl (aq.) (500 mL) for 3 hours. The layers were separated and the organic layer was extracted with H$_2$O (100 mL). The aqueous layers were combined, NaCl (250 g) and MTBE (700 mL) were added and the pH was brought to ≈13 with 10 N NaOH (aq). The organic layer was separated and the aqueous layer was extracted with MTBE (twice, 300 mL each). The organic layers were combined, dried (MgSO$_4$), and concentrated to a volume of ≈400 mL. To the solution was added di-tert-butyl dicarbonate (25.0 g) and the reaction was stirred for 3 days. Additional di-tert-butyl dicarbonate (5.6 g) was added, followed by heating of the reaction in a 60° C. bath for 1 hour. The reaction was purified by flash silica gel column chromatography with EtOAc/hexane (1:9) as eluent to yield 10.89 g of racemic N-Boc-(1R,2S)/(1S,2R)-1-amino-2-vinylcyclopropane carboxylic acid methyl ester. See, e.g., WO00/09558 and Beaulieu, P. L. et al., J. Org. Chem., 70 (15), 5869-5879, 2005. $^1$H-NMR (500 MHz, CDCl$_3$): 5.78-5.71 (m, 1H), 5.29-5.26 (m, 1H), 5.11 (dd, J=1.2, 10.3 Hz, 1H), 3.71 (s, 3H), 2.14 (q, J=8.8 Hz, 1H), 1.79 (s, 1H), 1.53-1.45 (m, 10H).

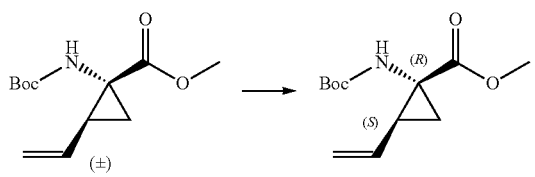

Racemic N-Boc-(1R,2S)/(1S,2R)-1-amino-2-vinylcyclopropane carboxylic acid methyl ester (4.2 g) was dissolved in acetone (80 mL) and then diluted with water (160 mL). The pH was adjusted to 7.8 with 0.2N NaOH (aq). Subtilisin A (product P-5380 from Sigma, St. Louis, Mo., USA) (4.5 g) was added to the solution. Its pH was maintained between 7.4 and 8.7 for 3 days by the dropwise addition of 0.1 N NaOH (aq.). When HPLC analysis (Chiralpak AD from Daicel Chemical Industries, Tokyo, 4.6 mm×250 mm, 0.5 mL/min, 10-85% 2-propanol/hexanes over 10 minutes, monitor 215.4 nm) of the reaction indicated the presence of only the (1R, 2S)-enantiomer (retention time of (1R,2S)=6.2 min, (1S,2R) =5.9 min) the pH was brought to 8.5 with 2 N NaOH (aq). The contents of the reaction were transferred to a separatory funnel and extracted with MTBE (3×400 mL). The extracts were washed with saturated NaHCO$_3$ (aq) solution (3×150 mL), water (2×200 mL), and dried (MgSO$_4$). The solution was filtered, concentrated, diluted with CH$_2$Cl$_2$, dried (MgSO$_4$), filtered, and concentrated to yield 1.95 g of N-Boc-(1R,2S)-1-amino-2-vinylcyclopropane carboxylic acid methyl ester.

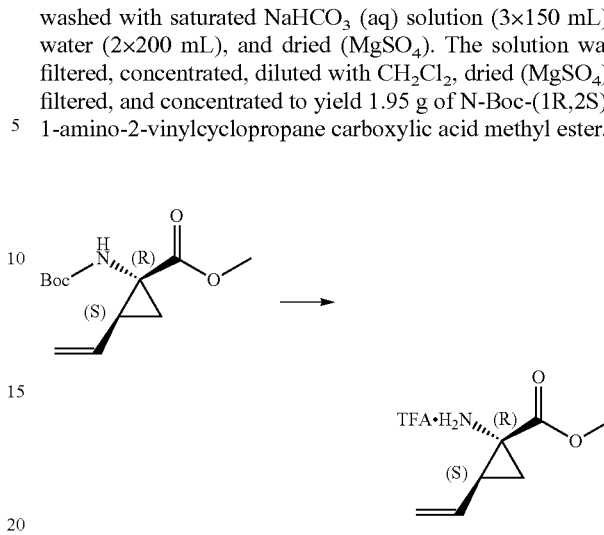

N-Boc-(1R,2S)-1-amino-2-vinylcyclopropane carboxylic acid methyl ester (125 mg, 0.52 mmol) stirred in CH$_2$Cl$_2$/TFA (1:1, 2 mL) at RT for 90 minutes. Solvents removed under vacuum to yield (1R,2S)-1-amino-2-vinylcyclopropane carboxylic acid methyl ester trifluoroacetic acid salt.

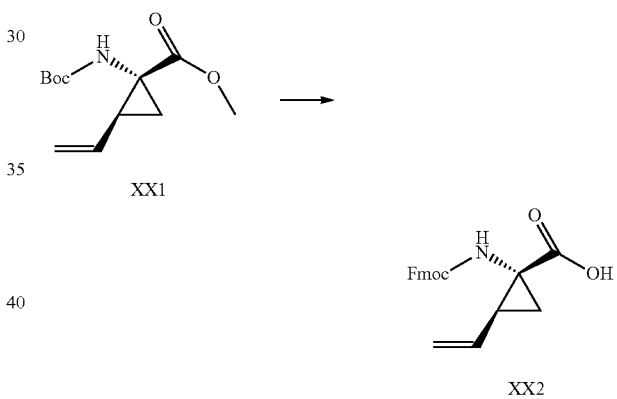

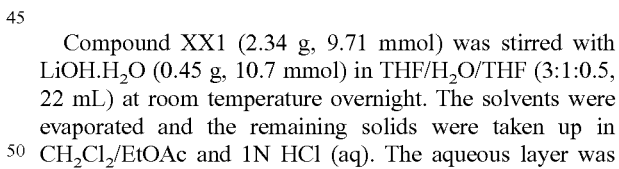

Compound XX1 (2.34 g, 9.71 mmol) was stirred with LiOH.H$_2$O (0.45 g, 10.7 mmol) in THF/H$_2$O/THF (3:1:0.5, 22 mL) at room temperature overnight. The solvents were evaporated and the remaining solids were taken up in CH$_2$Cl$_2$/EtOAc and 1N HCl (aq). The aqueous layer was extracted with CH$_2$Cl$_2$ and the combined organic extracts were dried (MgSO$_4$), filtered, and concentrated. This material was dissolved in CH$_2$Cl$_2$ (10 mL) at room temperature and treated with trifluoroacetic acid (10 mL). HPLC analysis at 70 minutes showed no starting material was present. The solvents were removed in vacuo to yield a viscous light colored oil. This was taken up in additional CH2Cl2 (30 mL) and evaporated on a rotary evaporator to yield a tan solid. This solid was dissolved in saturated NaHCO$_3$ (aq) and acetone (1:1, 50 mL) and treated with Fmoc-Cl (2.65 g, 10.2 mmol). After 4 hours, the contents of the flask were transferred to a separatory funnel with CH$_2$Cl$_2$ and acidified with 2N HCl (aq). The aqueous layer was extracted with CH$_2$Cl$_2$, the combined organic layers were dried (MgSO4) filtered, and concentrated to yield 1.86 g (5.3 mmol) of XX2 as a light yellow solid. (M+1)=350.1

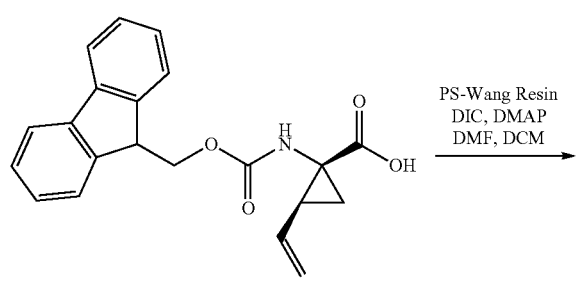

XX3

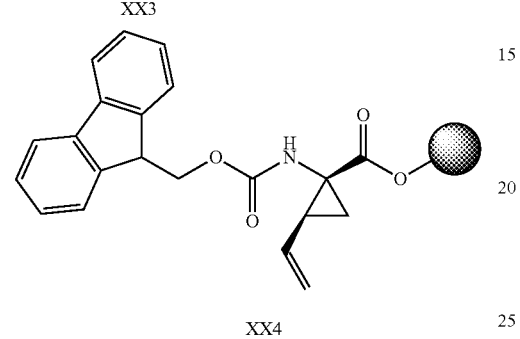

XX4

PS-Wang resin (2.0 g, 1.0 eq.) swelled in DMF (enough to cover). (1R,2S)-1-(((9H-fluoren-9-yl)methoxy)carbonyl)amino)-2-vinylcyclopropanecarboxylic acid (XX3) (922 mg, 1.1 eq.) was stirred in DCM. Diisopropylcarbodiimide (409 uL, 1.1 eq.) was added to the DCM solution and stirred at 4° C. for 2 hours, then added to resin and DMF. Dimethylaminopyridine (29 mg, 0.1 eq.) in DMF was added to resin solution and shaken for 5 hours. Drained and washed with DMF (thrice) and DCM (thrice) to yield Compound XX4.

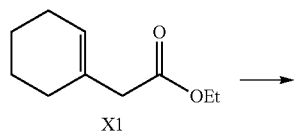

X1

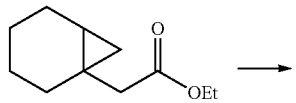

X2

Preparation of 2-(bicyclo[4.1.0]heptan-1-yl)acetic acid X2

Commercially available compound X1 (Aldrich Chemical Co., Milwaukee, Wis., USA) was converted to X2 according to method described by E. J. Kantorowski et al. in J. Org. Chem., 1999, 64, 570-580. $^1$H-NMR (CDCl$_3$, 500 MHz): 9.2 (br s, 1H), 2.23 (m, 2H), 1.92 (m, 1H), 1.76 (m, 2H), 1.58 (m, 1H), 1.34 (m, 1H), 1.18 (m, 4H), 0.85 (m, 1H), 0.52 (dd, 1H), 0.31 (t, 1H) ppm.

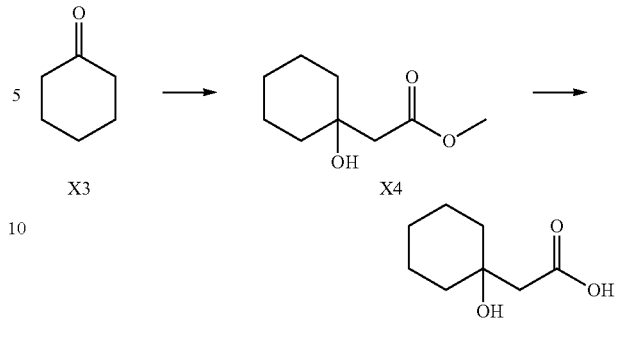

Preparation of 2-(1-hydroxycyclohexyl)acetic acid X5

Compound X4 was prepared using essentially the procedure described in Bull. Chem. Soc. Jpn., 1971, 44, 1090. Specifically, A solution of ethylbromoacetate (8.3 mL) (Aldrich Chemical Co., Milwaukee, Wis., USA) in toluene was added dropwise at 80° C. over 30 min. to a thoroughly stirred mixture of cyclohexanone X3 (4.9 g) and zinc powder (4.9 g) in toluene. The addition was carefully monitored and the temperature was kept at 80° C. After the addition was completed, the mixture was refluxed for 90 min., cooled, decomposed with 1N aqueous HCl, and extracted with Et$_2$O. The organics were washed with water, aq. NaHCO$_3$, dried (MgSO$_4$) and concentrated in vacuo to yield X4 (5.9 g). $^1$H-NMR (CDCl$_3$, 500 MHz) 4.16 (t, 2H), 3.0 (br s, 1H), 2.46 (s, 2H), 1.40-1.69 (m, 10H), 1.27 (t, 3H) ppm; FIA m/z 187.1 ES$^+$.

To a solution of X4 (510 mg) in MeOH was added 1N aqueous NaOH. The reaction mixture was stirred at 60° C. for 1 h, and then concentrated in vacuo. The residue was diluted with water, washed with Et$_2$O and the aqueous layer acidified with 1N aqueous citric acid and extracted with EtOAc. The organics were dried (MgSO$_4$) and concentrated in vacuo to yield after recrystallization compound X5 (220 mg): $^1$H-NMR (CDCl$_3$, 500 MHz) 3.63 (s, 1H), 2.45 (s, 2H), 1.22-1.64 (m, 10H) ppm; FIA m/z 157.2 ES"

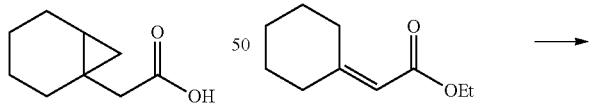

X6

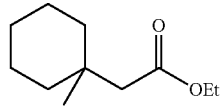

X7

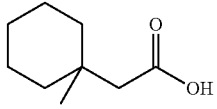

X8

Preparation of 2-(1-methylcyclohexyl)acetic acid (X8)

Commercially available compound X6 (Aldrich Chemical Co., Milwaukee, Wis., USA) was converted to compound X7 according to the method described by N. Asao et al. in Tetrahedron Lett., 2003, 44, 4265. $^1$H-NMR (CDCl$_3$, 500 MHz): 4.12 (q, 2H), 2.22 (s, 2H), 1.30-1.48 (m, 10H), 1.25 (t, 3H), 1.01 (s, 3H) ppm.

To a solution of compound X7 in EtOH was added 1 N aqueous NaOH. The reaction mixture was stirred at 50° C. for 3 hours, and then concentrated in vacuo. The residue was diluted with water, washed with Et$_2$O and the aqueous layer acidified with 1 N aqueous citric acid and extracted with CH$_2$Cl$_2$. The organics were dried (MgSO$_4$) and concentrated in vacuo to yield compound X8. $^1$H-NMR (CDCl$_3$, 500 MHz): 11.7 (s, 1H), 2.26 (s, 2H), 1.32-1.49 (m, 10H), 1.05 (s, 3H) ppm.

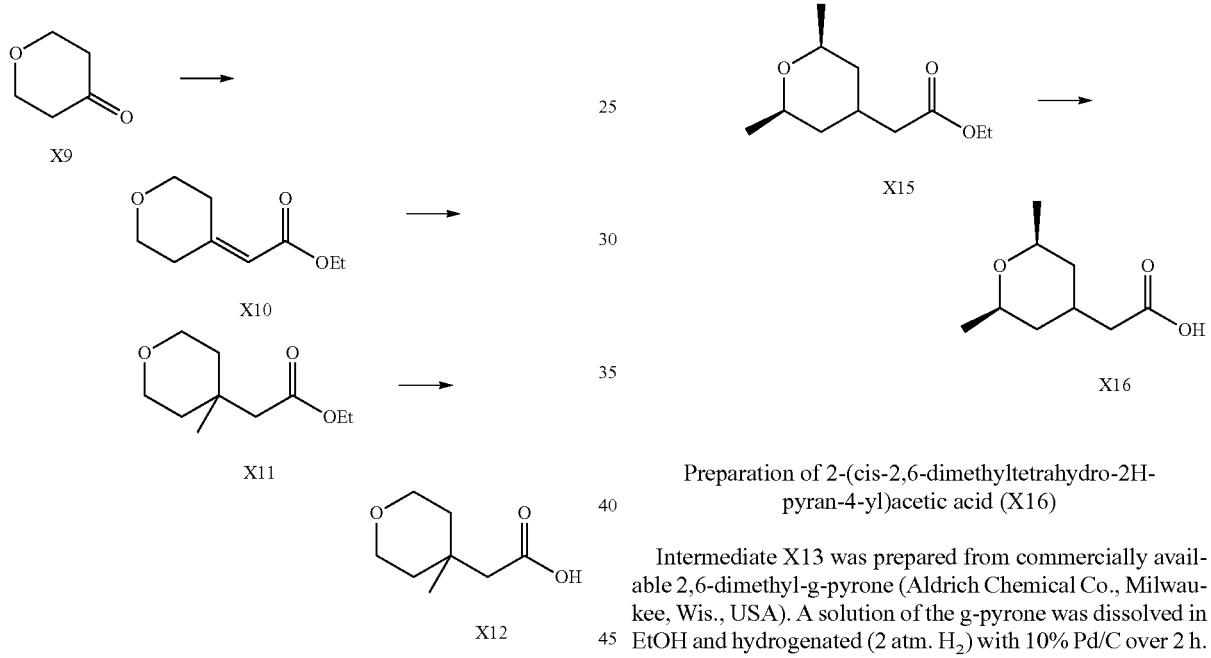

Preparation of 2-(4-methyltetrahydro-2H-pyran-4-yl)acetic acid (X12)

To a solution of dihydro-2H-pyran-4(3H)-one (X9) (3.13 g, from Aldrich) in toluene was added (carbethoxymethylene)-triphenylphosphorane (12.0 g, Aldrich). The solution was stirred at 110° C. for 3 days. The resulting dark solution was concentrated in vacuo and the residue directly purified by column over silica gel to yield compound X10 (4.54 g) as a clear liquid. $^1$H-NMR (CDCl$_3$, 500 MHz): 5.66 (s, 1H), 4.16 (q, 2H), 3.98 (s, 4H), 3.00 (t, 2H), 2.38 (m, 2H), 1.77 (m, 4H), 1.27 (t, 3H) ppm.

Compounds X11 and X12 were obtained in a similar manner as described for compounds X7 and X8. $^1$H-NMR (CDCl$_3$, 500 MHz): 3.64-3.73 (m, 4H), 2.35 (s, 2H), 1.65 (ddd, 2H), 1.50 (ddt, 2H), 1.17 (s, 3H) ppm.

Preparation of 2-(cis-2,6-dimethyltetrahydro-2H-pyran-4-yl)acetic acid (X16)

Intermediate X13 was prepared from commercially available 2,6-dimethyl-g-pyrone (Aldrich Chemical Co., Milwaukee, Wis., USA). A solution of the g-pyrone was dissolved in EtOH and hydrogenated (2 atm. H$_2$) with 10% Pd/C over 2 h. The catalyst was subsequently filtered off and the solution was concentrated in vacuo to yield crude X13 which was purified by column chromatography to yield pure compound X13. $^1$H-NMR (CDCl$_3$, 500 MHz): 3.72 (m, 2H), 2.35 (m, 2H), 2.21 (dd, 2H), 1.32 (d, 6H) ppm.

Compound X14 was then obtained from compound X13 in a similar manner as described for compound X10. $^1$H-NMR (CDCl$_3$, 500 MHz): 5.65 (s, 1H), 4.15 (q, 2H), 3.80 (dt, 1H), 3.49 (m, 2H), 2.17 (dt, 1H), 2.07 (dd, 1H), 1.79 (dt, 1H), 1.28 (m, 9H) ppm. LC-MS m/z 199.126 ES$^+$.

A solution of compound X14 in EtOAc was then hydrogenated (1 atm. H$_2$) with 10% wet Pd/C over 1 hour. The catalyst was subsequently filtered off and the solution was concentrated in vacuo to yield crude compound X15 which was used without further purification for the next step. Compound X16 was then prepared from compound X15 in a similar manner as described for compound X8. $^1$H-NMR (CDCl$_3$, 500 MHz) major diastereomer: 3.50 (m, 2H), 2.27 (d, 2H), 2.07 (m, 1H), 1.71 (m, 2H), 1.19 (d, 6H) 0.92 (m, 2H) ppm; major diastereomer: 3.64 (m, 2H), 2.56 (d, 2H), 2.47 (m, 1H), 1.49 (m, 2H), 1.15 (d, 6H), 0.86 (m, 2H) ppm.

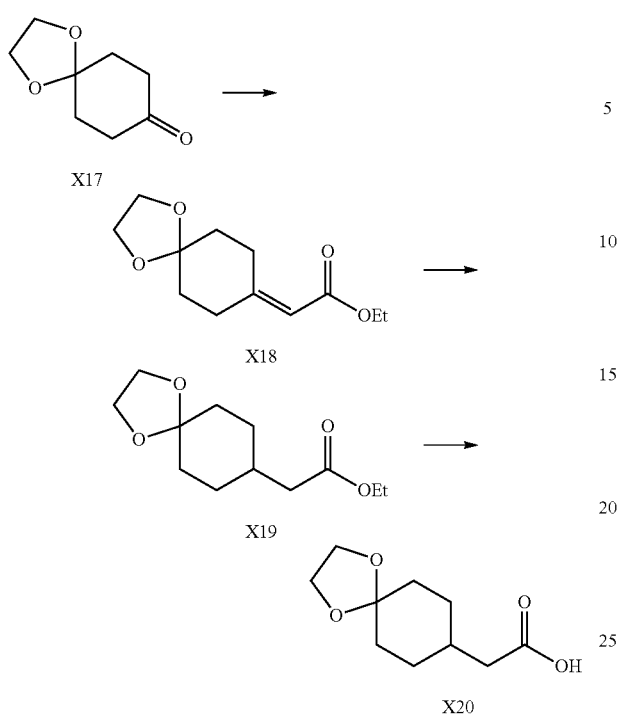

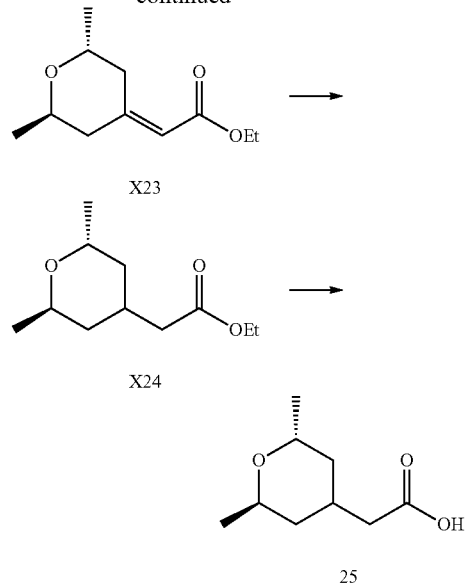

Preparation of 2-(1,4-dioxaspiro[4.5]decan-8-yl)acetic acid X20

Compound X20 was prepared from compound X17 (from Aldrich) according to the procedures described above for preparing compound X16.

Compound X18: $^1$H-NMR (CDCl$_3$, 500 MHz): 5.66 (s, 1H), 4.15 (q, 2H), 3.98 (s, 4H), 3.00 (m, 2H), 2.38 (m, 2H), 1.77 (m, 4H), 1.27 (t, 3H) ppm.

Compound X19: $^1$H-NMR (CDCl$_3$, 500 MHz): 4.12 (q, 2H), 3.93 (s, 4H), (d, 2H), 1.83 (m, 1H), 1.72 (m, 4H), 1.56 (dt, 2H), 1.33 (m, 2H), 1.30 (m, 3H) ppm.

Compound X20: $^1$H-NMR (CDCl$_3$, 500 MHz): 3.93 (s, 4H), 2.28 (d, 2H), 1.73-1.86 (m, 4H), 1.57 (dt, 2H), 1.35 (m, 2H) ppm.

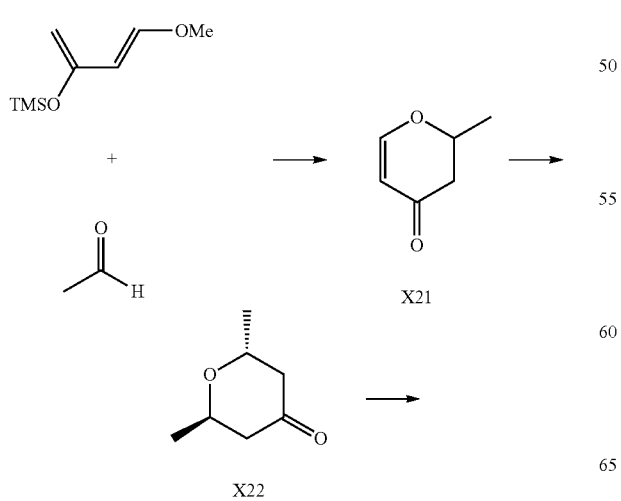

Preparation of 2-(trans-2,6-dimethyltetrahydro-2H-pyran-4-yl)acetic acid 25

Compounds X21 and X22 were prepared according to the method described by S. Danishefsky et al. in J. Org. Chem. 1982, 47, 1597-1598 and D. S. Reddy et al. in J. Org. Chem. 2004, 69, 1716-1719, respectively. Compound X25 was prepared from compound X22 according to the method described above for preparing compound X16.

Compound X23. $^1$H-NMR (CDCl$_3$, 500 MHz): 5.72 (s, 1H), 4.16 (q, 2H), 4.08 (q, 2H), 3.06 (dd, 1H), 2.75 (dd, 1H), 2.39 (dd, 1H), 2.05 (dd, 1H), 1.28 (t, 3H), 1.19 (m, 6H) ppm.

X25: $^1$H-NMR (CDCl$_3$, 500 MHz) 4.24 (m, 1H), 3.78 (m, 1H), 2.25 (m, 3H), 1.71 (m, 1H), 1.53 (m, 1H), 1.46 (m, 1H), 1.29 (d, 3H), 1.13 (d, 3H), 0.90 (m, 1H) ppm.

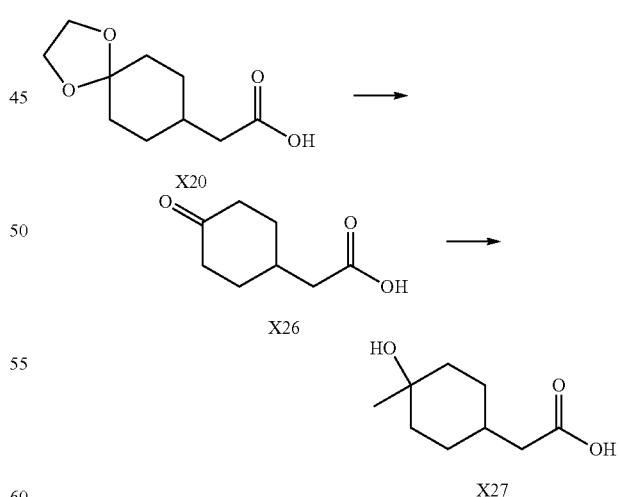

Preparation of 2-(4-hydroxy-4-methylcyclohexyl)acetic acid X27

A solution of compound X20 in dioxane was treated with 4N HCl in dioxane. The reaction solution was stirred at room temperature for 4 hours and concentrated in vacuo to give crude compound X26 which was used without further purification for the next step. To a stirred solution of compound X26 in THF was slowly added MeMgBr (3 N in THF). The resulting mixture was stirred at 40° C. for 3 hours, quenched with 1 N aqueous citric acid and diluted with EtOAc. The phase were separated and the organics were dried (MgSO$_4$), concentrated in vacuo and purified by chromatography over silica gel to give compound X27 as a mixture of two diastereomers: isomer 1: $^1$H-NMR (CDCl$_3$, 500 MHz): 4.50 (br s), 2.27 (m, 2H), 1.75 (m, 1H), 1.65 (m, 4H), 1.39 (m, 4H), 1.22 (s, 3H) ppm; isomer 2: $^1$H-NMR (CDCl$_3$, 500 MHz): 2.12 (m, 2H), 1.69 (m, 3H), 1.56 (m, 2H), 1.39 (m, 2H), 1.12 (s, 3H), 1.05 (m, 2H) ppm.

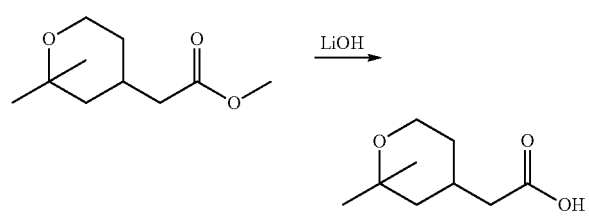

Preparation of 2-(2,2-dimethyltetrahydro-2H-pyran-4-yl)acetic acid

To a solution of the methyl ester (500 mg; 2.69 mmol) in THF (21.5 mL), MeOH (21.5 mL) and water (10.75 mL) was added LiOH (1 N; 10.75 mL). The reaction mixture was stirred for 3 hours. The reaction was acidified with HCl (1 N, pH=5). The product was extracted with EtOAc (twice, 20 mL each). The combined organic layer was then wash with water, brine and concentrated in vacuo to afford 420 mg of 2-(2,2-dimethyltetrahydro-2H-pyran-4-yl)acetic acid. $^1$H-NMR (CDCl$_3$): δ 3.76-3.67 (m, 2H), 2.56-2.19 (m, 3H), 1.63 (m, 2H), 1.26-1.10 (m, 8H). (M+1) 173.

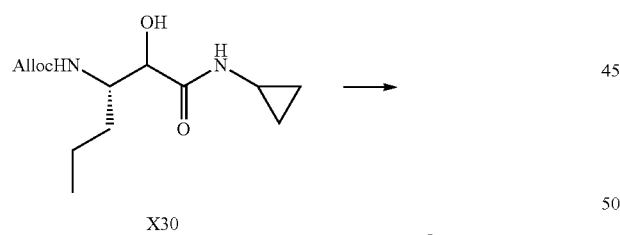

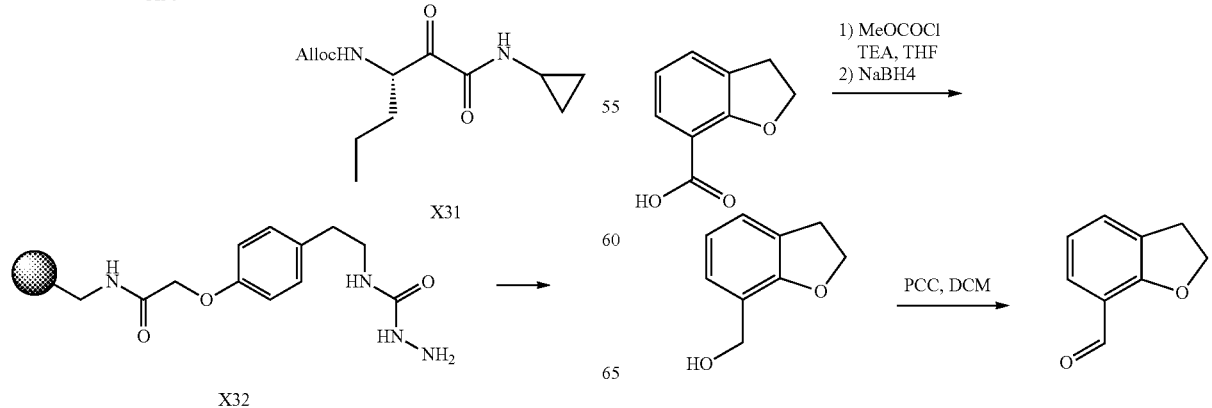

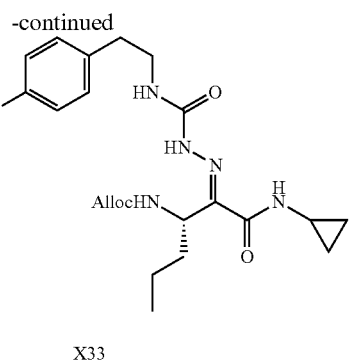

To a solution of compound X30 (64 g, 237 mmol) and EDC (226 g, 1.19 mol) in EtOAc (1.5 L) was added DMSO (400 mL), and the resulting suspension was cooled to 0° C. To this mixture was added a solution of dichloroacetic acid in EtOAc (1:1 v/v, 130 mL) keeping the internal reaction temperature below 25° C. The reaction was warmed to room temperature, stirred for 15 minutes, cooled to 0° C., and quenched with 1 N HCl (1 L). The organic layer was separated, washed with H$_2$O (2×500 mL), dried over MgSO$_4$, and concentrated under reduced pressure. The resulting oil was filtered through a plug of silica eluting with EtOAc/hexanes to afford 48 g of compound X31 as a white solid.

To resin X32 (prepared according to the procedure described in WO 00/23421) (100 g, 0.88 mmol/g) was added a solution of X31 (48 g, 179 mmol) in THF (650 mL), followed by AcOH (30 mL). The mixture was shaken for 16 hours, and the resin was filtered, washed with THF (4 times, 400 mL each) and CH$_2$Cl$_2$ (4 times, 400 mL each) and dried in vacuo. The filtrate and washes were combined and concentrated, and the above procedure was repeated to afford resin X33 with a loading of approximately 0.4 mmol/g.

Preparation of Aldehyde Compounds 5-chloronicotinaldehyde was prepared according to methods described by D. L. Comins et al. in Hetereocycles, 1987, 26 (8), pp. 2159-2164.

Some other aldehydes such as 2-fluoro-5-chlorobenzaldehyde, 2-methoxy-3-methyl benzaldehyde, 2-methoxynicotinaldehyde, 2,3-dihydrobenofuran-7-carbaldehyde can be made from corresponding acid based on following procedure:

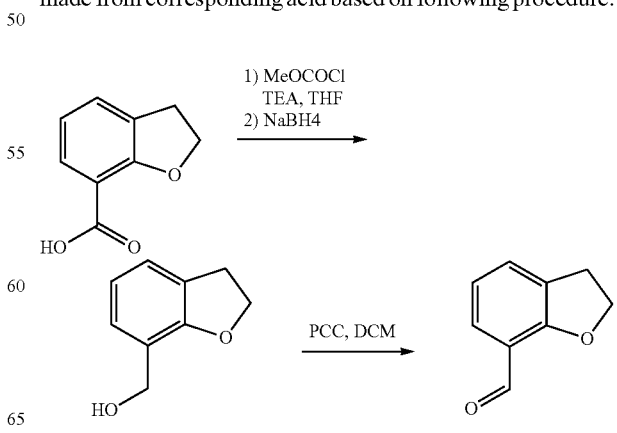

Preparation of 2,3-dihydrobenzofuran-7-carbaldehyde 2,3-Dihydrobenzofuran-7-carboxylic acid (820 mg, 5 mmol) was dissolved in THF (10 mL). To the solution was added TEA (0.7 mL, 5 mmol) and methylchloroformate (0.43 mL, 5 mmol). The solution was stirred for 0.5 hour. The white precipitates were removed by filtration, the filtrate was added to a solution of $NaBH_4$ (437 mg, 12.5 mmol) in $H_2O$ (5 mL). The resulting solution was stirred overnight. The reaction mixture was neutralized with 2 M aqueous HCl solution and then extracted with EtOAc. The organic layer was washed with brine, dried over anhydrous $Na_2SO_4$ and concentrated in vacuo. The crude alcohol was dissolved in DCM. To the solution was added PCC (1.83 g, 7.5 mmol). The mixture was stirred for 2 hours at room temperature and diluted with diethyl ether, then ether layers were decanted. Combined organic layer was filtered though a layer of Celite®. The filtrate was concentrated to give crude product. The crude was purified from column with 10% EtOAc/hexane to afford 450 mg of 2,3-dihydrobenzofuran-7-carbaldehyde as a slightly yellow solid. HPLC 4.3 min.

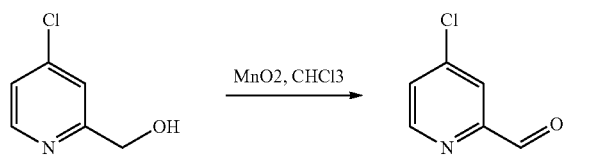

Preparation of 4-chloropicolinaldehyde

A suspension of $MnO_2$ (7.3 g, 84 mmol) and (4-chloro-pyrindin-2-yl)methanol (1 g, 7 mmol) in $CHCl_3$ was heated to refulx for 90 minutes. The mixture was filtered though a layer of Celite® and concentrated in vacuo to afford 520 mg of 4-chloropicolinaldehyde as a white solid. HPLC 1.8 minutes and MS 142 as M=1 peak.

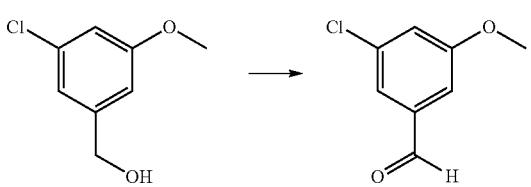

Preparation of 3-chloro-5-methoxybenzaldehyde

A mixture of 3-chloro-5-methoxybenzyl alcohol (5.0 g, 28.9 mmol) and pyridinium chlorochromate (20% on alumina, 40 g, 37.8 mmol) was allowed to stir for 1.25 hr. Diethyl ether (200 ml) was then added followed by filtration of precipitate. The filtrate was concentrated under reduced pressure and the resulting residue was purified via silica gel chromatography using 40% dichloromethane, 60% petroleum ether as eluant, to give 3.8 g of 3-chloro-5-methoxybenzaldehyde. $^1$H-NMR ($CDCl_3$): 3.84 (s, 3H) 7.13 (s, 1H), 7.28 (s, 1H), 7.41 (s, 1H), 9.89 (s, 1H).

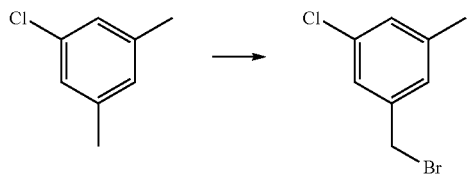

Preparation of 1-(bromomethyl)-3-chloro-5-methylbenzene

To a solution of m-chloroxylene (0.96 g, 6.8 mmol) in carbon tetrachloride at reflux was added N-bromosuccinmide (1.4 g, 7.5 mmol) followed by benzoyl peroxide (1.6 g, 6.8 mmol). The reaction was allowed to stir for 20 minutes and cooled to room temperature, filtered off precipitate and the filtrate was concentrated under reduced pressure and the resulting residue was purified via silica gel chromatography using petroleum ether as eluant to give 0.89 g of 1-(bromomethyl)-3-chloro-5-methylbenzene. NMR ($CDCl_3$): 2.31 (s, 3H) 4.37 (s, 2H) 7.09 (s, 1H) 7.12 (s, 1H) 7.20 (s, 1H).

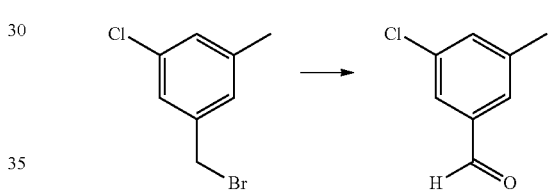

Preparation of 3-chloro-5-methylbenzaldehyde

To a solution of sodium metal (52 mg, 2.3 mmol) in ethanol was added 2-nitropropane (0.23 g, 2.4 mmole) followed by the addition of 3-chloro-5-methybenzylbromide (0.5 g, 2.3 mmol). The reaction was allowed to stir for 3 hours and the precipitate formed was filtered off. The filtrate was concentrated under reduced pressure, redissolved in diethylether and washed with 1N sodium hydroxide (twice), water, and dried over sodium sulfate, filtered and the filtrate was concentrated under reduced pressure. The resulting residue was purified via silica gel chromatography using 10% dichloromethane and 90% petroleum ether, to give 0.15 g of 3-chloro-5-methylbenzaldehyde. $^1$H-NMR ($CDCl_3$): 2.46 (s, 3H) 7.43 (s, 1H) 7.56 (s, 1H) 7.68 (s, 1H), 9.92 (s, 1H).

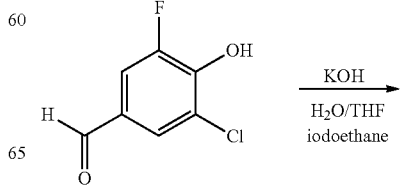

-continued

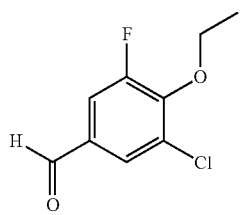

3-Chloro-5-fluoro-4-hydroxybenzaldehyde (1.0 gram, 5.7 mmol) in THF (40 mL) was heated at reflux for 17 hours with KOH (534 mg, 9.5 mmol, 1.7 eq) in water (5 mL) and iodoethane (1 mL, 2.2 eq). The reaction was then transferred to a separatory funnel with water and extracted with methylene chloride (thrice, 150 mL each). The combined organic layers were washed with 10% aqueous HCl (40 mL), dried (MgSO$_4$), and concentrated to a viscous orange liquid to yield 1.13 g of 3-chloro-4-ethoxy-5-fluorobenzaldehyde. $^1$H-NMR (500 MHz, CDCl$_3$): 9.84 (d, J=1.9 Hz, 1H), 7.71 (t, J=1.6 Hz, 1H), 7.53 (dd, J=1.9, 10.7 Hz, 1H), 4.37-4.32 (m, 2H), 1.47-1.40 (m, 3H).

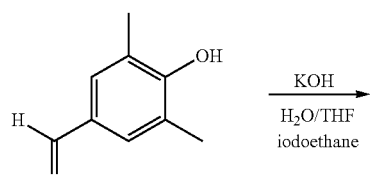

4-Ethoxy-3,5-dimethylbenzaldehyde was prepared in a manner similar to that of 3-chloro-4-ethoxy-5-fluorobenzaldehyde. $^1$H-NMR (300 MHz, CDCl$_3$): 9.89 (s, 1H), 7.56 (s, 2H), 3.91 (q, 7 Hz, 1H), 2.34 (s, 6H), 1.44 (t, J=7 Hz, 6H).

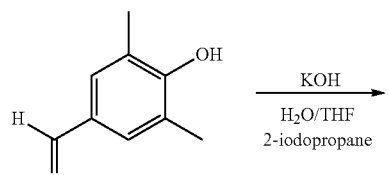

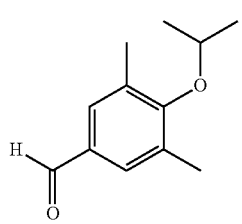

4-Isopropoxy-3,5-dimethylbenzaldehyde was prepared in a manner similar to that of 4-Ethoxy-3,5-dimethylbenzaldehyde. $^1$H-NMR (300 MHz, CDCl$_3$): 9.88 (s, 1H), 7.55 (s, 2H), 4.31 (q, J=6 Hz, 1H), 2.32 (s, 6H), 1.32 (d, J=6 Hz, 6H).

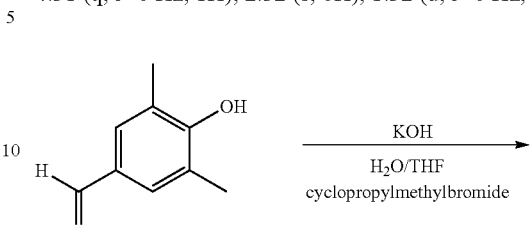

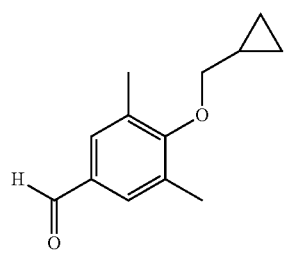

4-(Cyclopropylmethoxy)-3,5-dimethylbenzaldehyde was prepared in a manner similar to that of 4-Ethoxy-3,5-dimethylbenzaldehyde. $^1$H-NMR (300 MHz, CDCl$_3$):

9.87 (s, 1H), 7.55 (s, 2H), 3.69 (d, J=7 Hz, 2H), 2.35 (s, 6H), 1.35-1.23 (m, 1H), 0.67-0.060 (m, 2H), 0.35-0.30 (m, 2H).

Preparation of (S)-1-(tert-butoxycarbonyl)-4-oxopyrrolidine-2-carboxylic acid

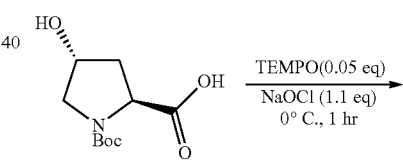

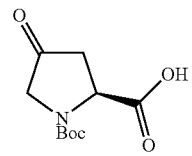

A solution of (2S,4R)-1-(tert-butoxycarbonyl)-4-hydroxy-pyrrolidine-2-carboxylic acid (1.0 eq.) in isopropyl acetate (5 vol) was cooled to 0° C. and TEMPO (0.05 eq.) was added. A solution of bleach (12.5 wt %, 1.2 eq., 2.6 vol) was then slowly added over 1 hour while maintaining the temperature at 0-5° C. The mixture was stirred and monitored by HPLC for completion, then aqueous 10% KHSO$_4$ (2.5 vol) was added, stirred for 10 minutes, and then the phases were separated. The organic phase was washed with aqueous 5% Na$_2$SO$_3$ (2 vol) then brine (1 vol) then dried azeotropically and concentrated to afford the title compound as a solid. The solid was triturated with acetonitrile (1.0 vol) to remove residual color and impurities. $^1$H-NMR (400 MHz, DMSO):

δ 4.54 (m, 1H), 3.82 (m, 1H), 3.67 (m, 1H); 3.15 (m, 1H); ≈2.50 (m, 1H, coincides with DMSO); 1.42 and 1.39 (2 s rotamers, 9H).

Preparation of (S)-1-(tert-butoxycarbonyl)-4-methyl-enepyrrolidine-2-carboxylic acid

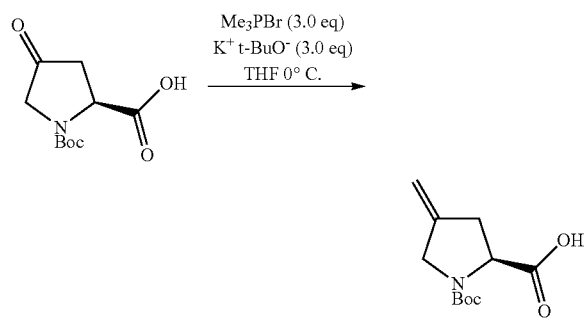

To a suspension of methyltriphenylphosphonium bromide (2.2 eq.) in 2-methyl tetrahydrofuran (3 vol) was added rapidly solid potassium tert-butoxide (2.3 eq.) maintaining the temperature around 0° C. The temperature was kept at +20° C. for 2 hours (a suspension remained) and re-cooled to 0° C. Keeping the temperature below 6° C., (S)-1-(tert-butoxycarbonyl)-4-oxopyrrolidine-2-carboxylic acid (1 eq.) was added over 40 minutes. The reaction was warmed to room temperature and stirred for 16 h and then cooled to 0° C. The reaction was quenched with saturated NaHCO₃ (5 vol) and water (2 vol) and the aqueous layer was separated. The organic layer was extracted with saturated NaHCO₃/water (1.8 vol/1.8 vol) and the combined aqueous layers were filtered through Celite®. The aqueous layer was acidified with 6 N HCl (2.6 vol) at ambient temperature and extracted twice with isopropyl acetate (16 vol, then 8 vol). The organic phase was dried (MgSO₄) and the solvent removed. The crude product was dissolved in isopropyl acetate (10 vol) and extracted with 0.5 M NaOH (10 vol, then 1 vol). The combined aqueous layers were acidified at ambient temperature with 6 N HCl to pH=3, and extracted twice with ethyl acetate (10 vol, then 8 vol). The combined extracts were dried (Na₂SO₄), the solvent removed and the crude product was recrystallized from cyclohexane (5 vol) to afford the title compound. ¹H-NMR (400 MHz, DMSO): δ 12.9, (broad, 1H); 5.00 (m, 2H); 4.24 (dt, J=1.9H, J=7.3 Hz, 1H), 3.91 (m, 2H); 2.98 (m, 1H); 2.50 (m, 1H, coincides with DMSO); 1.41 and 1.36 (2 s rotamers, 9H).

Preparation of (5S,8S)-tert-butyl 3-(3-chlorophenyl)-1-oxa-2,7-diazaspiro[4.4]non-2-ene-8-carboxylate.

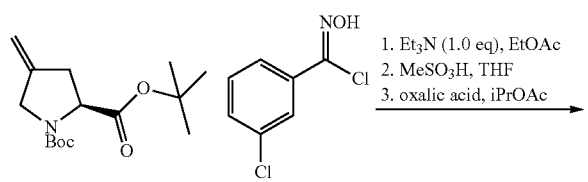

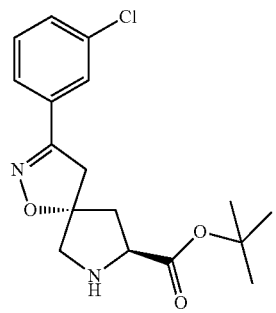

A solution of 3-chloro-N-hydroxybenzimidoyl chloride (175 g, 0.919 moles) in EtOAc (2.1 L) was added to a solution of (S)-di-tert-butyl 4-methylenepyrrolidine-1,2-dicarboxylate (200 g, 0.707 moles) in EtOAc (2.0 L) at room temperature. The mixture was cooled below 10° C. in an ice bath, then triethylamine (128 mL, 0.919 moles) was added slowly. The resultant mixture was stirred overnight then quenched with water (3 L). The phases were separated and the organic phase washed with water (2×1.0 L), dried over MgSO₄, and the solvent removed to afford a mixture of the syn- and anti-spiroisoxazolines as an oil.

The mixture of isomers was dissolved in THF (0.72 L) and cooled to 20° C. Methanesulfonic acid (150 mL) was slowly added maintaining 20 to 30° C. The mixture was stirred at 25° C. and quenched after 7 hours by carefully adding a solution K₂CO₃ (300 g) in water (1 L). The phases were separated and the aqueous phase was extracted with isopropyl acetate (1 L). The organic phases were combined and approximately half of the solvent removed under vacuum. The solution was washed with a 1:1 mixture of saturated brine (250 mL) and water (250 mL). The aqueous phase was extracted with isopropyl acetate (200 mL) and the organic phases combined then dried over K₂CO₃ and filtered to afford a homogeneous solution. The solution volume was made up to 3 L by adding isopropyl acetate and then a solution of oxalic acid (20 g) in isopropyl acetate (400 mL) was slowly added. The solid was isolated by filtration and dried in a vacuum oven. The solid was suspended in isopropyl acetate (1.5 L) and water (1.0 L) then K₂CO₃ was added slowly until the solids fully dissolved. The organic layer was isolated, dried over K₂CO₃, filtered then a solution of oxalic acid (12.5 g) in isopropyl acetate (250 mL) was added slowly. The solid was isolated by filtration and dried in a vacuum oven to give the spiroisoxazolines as a 98:2 anti-:syn- mixture of diastereomers. ¹H-NMR (400 MHz, DMSO-d₆): δ 7.67-7.48 (m, 4H), 4.08 (dd, J=7.9, 8.9 Hz, 1H), 3.55 (s, 2H), 3.27 (d, J=4.0 Hz, 2H), 2.46 (dd, J=7.8, 13.8 Hz, 1H), 2.19 (dd, J=9.1, 13.8 Hz, 1H), 1.46 (d, J=7.5 Hz, 9H).

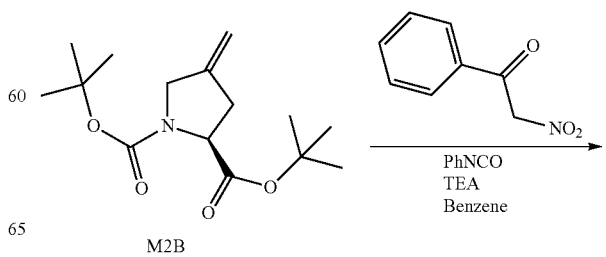

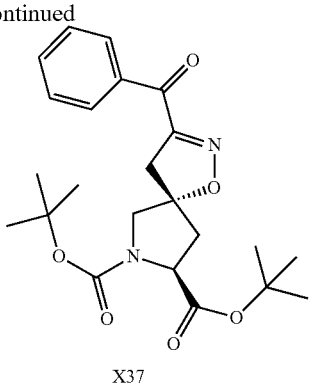

X37

Compound M2B (1.0 g, 1.0 eq) was stirred in 20 mL benzene with benzoylnitromethane (583 mg, 1.0 eq.) and catalytic triethylamine. Phenyl isocyanate (880 uL) was added slowly and stirred for 40 hours. Dark colored precipitate was filtered off and to the filtrate was added 2 mL water and the mixture was stirred for 2 hours. Organics were separated and concentrated, purified by silica gel chromatography (10-90% ethyl acetate/hexanes gradient) to give 350 mg of Compound X37. (M+H=431.2.) $^1$H-NMR (500 MHz, CDCl$_3$): 8.19 (d, 2H), 7.61 (t, 1H), 7.56-7.46 (m, 2H), 4.45-4.36 (m, 1H), 3.99-3.88 (m, 1H), 3.61 (d, 1H), 3.39-3.33 (m, 2H), 2.77 (m, 1H), 2.17-2.12 (m, 1H), 1.49 (s, 9H) 1.46 (s, 9H).

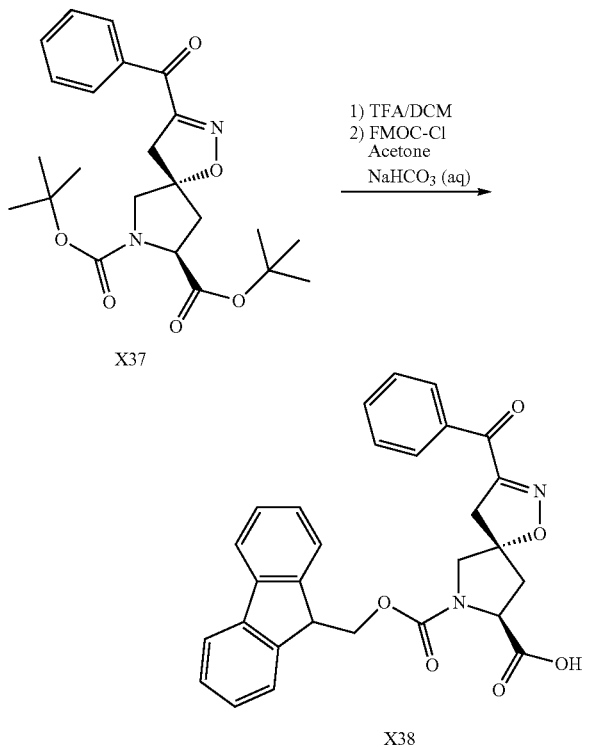

X38

Compound X37 (1.35 g, 1.0 eq.) was stirred in 20 mL 1/1 TFA/DCM for 2 hours. The mixture was concentrated and to it was added 20 mL acetone, 20 mL saturated sodium bicarbonate solution, and FMOC-Cl (1.22 g, 1.5 eq.). The mixture was stirred for 3 hours and diluted with ethyl acetate and a 2 N HCl solution until aqueous became acidic. The mixture was stirred, aqueous extracted with ethyl acetate, combined organics, dried over magnesium sulfate, filtered, and concentrated. The concentrate was purified by silica gel chromatography (100% DCM-10% MeOH/DCM gradient) to give compound X38. (M+H=497.1).

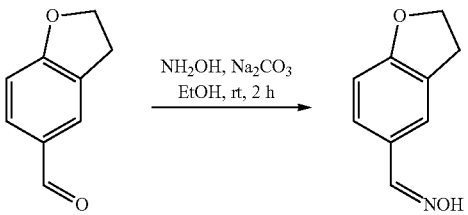

To a solution of 2,3-dihydrobenzofuran 5-carboxaldehyde (1 g, 6.75 mmol) in ethanol (5 mL) was added a 2.4 M of NH$_2$OH (3.3 mL, 8.1 mmol) solution and then 1.2 M of Na$_2$CO$_3$ (3.3 mL, 4.05 mmol). The resulting solution was stirred for 2 hours at room temperature (HPLC showed no starting material left). The reaction mixture was diluted with EtOAc, washed with brine, dried over Na$_2$SO$_4$ and concentrated under vacuum. This afforded 1.0 g of the product as a white solid. ES-MS 164 as M+1 peak.

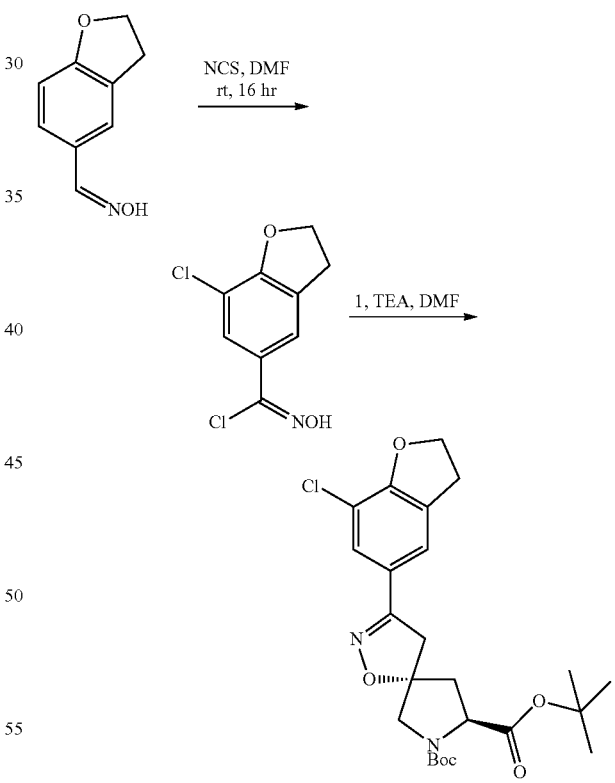

To a solution of aldoxime (426 mg, 2.6 mmol) in DMF (5 mL) was added NCS (697 mg, 5.2 mmol). The resulting mixture was stirred for overnight at room temperature. To the solution was added (S)-di-tert-butyl 4-methylenepyrrolidine-1,2-dicarboxylate, compound 1 (600 mg, 2.1 mmol) and then a solution of TEA (0.37 mL, 2.6 mmol) in DMF (2 mL) was added over 10 minutes. The reaction mixture was stirred for 4 hr at room temperature and then heated to 50-60° C. for 2 hours. The reaction mixture was diluted with EtOAc (20 mL)

and washed with H$_2$O, brine, dried over Na$_2$SO$_4$, concentrated in vacuo. The crude products were purified from flash column chromatography eluted with 30% EtOAc/Hexane, to afford S (500-600 mg) (Rf=0.3) and R isomer (150 mg) (Rf=0.2). ES-MS 479 as M+1 peak.

B. Synthesis of Exemplary Compounds of Formula I

Certain exemplary compounds of Formula I may be prepared by Method 1 as illustrated below.

Method 1:

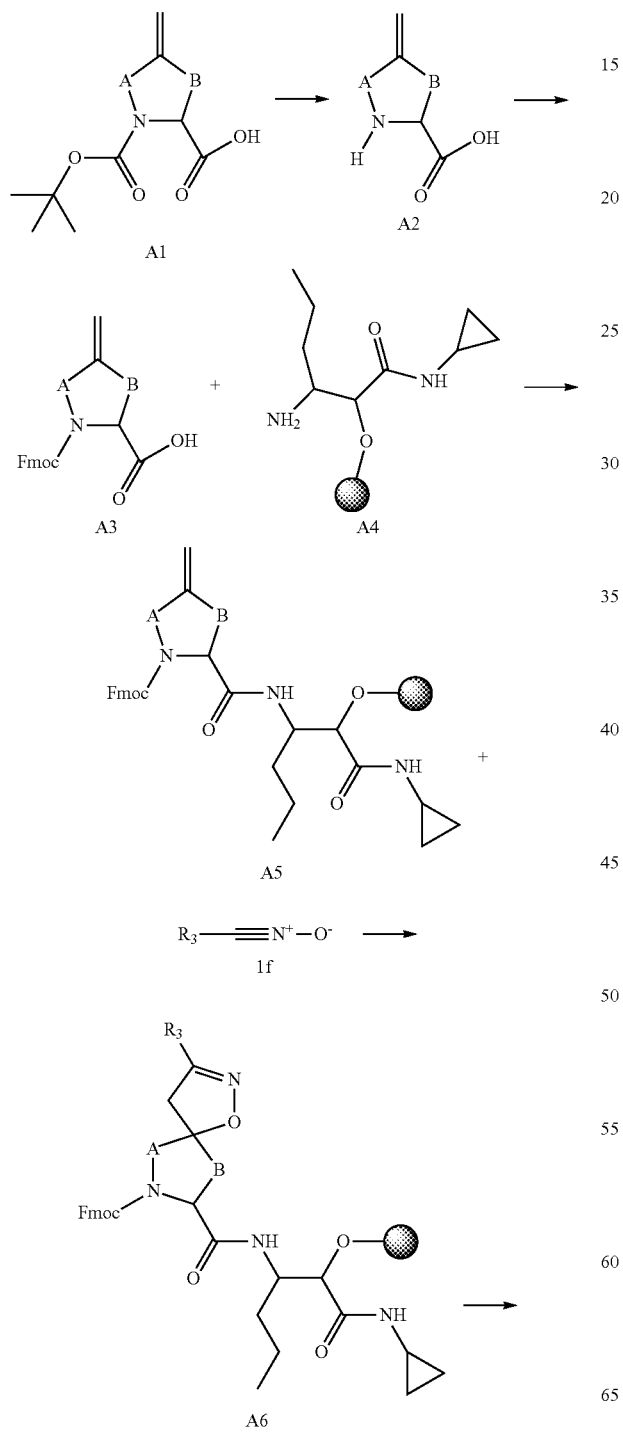

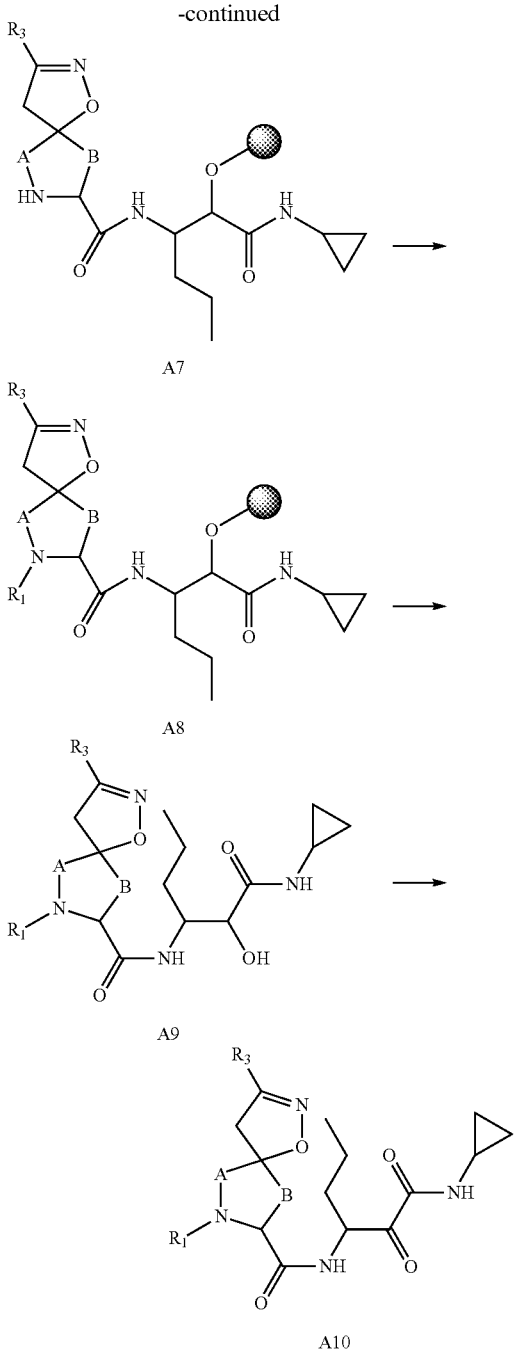

Referring to Method 1, the exomethylene compound A1 is deprotected to A2, which is converted to the corresponding Fmoc derivative A3. Reaction of the resin bound aminoalcohol A4 with A3 in the presence of a coupling reagent provides the resin bound product A5. A dipolar addition reaction of A5 with the nitrile oxide 1f, generated in situ, provides the resin bound spiroisoxazoline A6, which is deprotected to provide the resin bound spiroisoxazoline A7. Reaction of A7 with an R$_1$-carboxylic acid in the presence of a coupling agent provides A8, wherein R$_1$ is R$_4$C(O)—. Cleavage of the spiroisoxazoline from the resin provides the alcohol A9. Oxidation of A9 with an oxidizing reagent such as Dess-Martin periodinane or sodium hypochlorite in the presence of TEMPO provides the final compound A10.

In some instance, $R_4$ may contain an amine functionality. Where $R_4$ contains a protected amine, deprotection of the protected amine to give a free amine, following by a reaction with an activated acid, provides a further elaborated $R_4$. Alternatively, a free amine in $R_4$ may be converted to the corresponding p-nitrophenylcarbamate followed by reactions with an amine or alcohol to provide $R_4$ compounds containing carbamate or urea functionarity.

Preparation of Allyl 1-(cyclopropylamino)-2-(6-(hydroxymethyl)tetrahydro-2H-pyran-2-yloxy)-1-oxohexan-3-ylcarbamate (M1B)

Step 1: Allyl 1-(cyclopropylamino)-2-hydroxy-1-oxohexan-3-ylcarbamate (M1A)

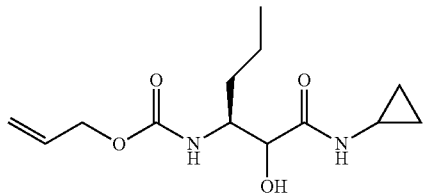

M1A

To a solution of (3S)-3-amino-N-cyclopropyl-2-hydroxyhexanamide (10 g, 53.7 mmol), DIEA (28 mL, 161 mmol, 3 eq.) in methylene chloride (250 mL) was added dropwise at 0° C. to a solution of allylchloroformate (6.8 mL, 64.4 mmol, 1.2 eq.) in DCM (50 mL). The reaction solution was warmed to room temperature and stirred for 4 hours. Water (300 mL) was then slowly added followed by aqueous HCl (1.0 N, 300 mL). The phases were separated and the organics washed with saturated aqueous $NaHCO_3$ (300 mL), brine (300 mL), dried with $MgSO_4$, filtered, and concentrated in vacuo. The resulting off-white solid was recrystallized from 30% hexanes in EtOAc (120 mL) to yield the title compound M1A as a white solid. The mother liquor was concentrated, in vacuo, and recrystallized from 50% hexanes in EtOAc to yield another 4.04 g of M1A. The mother liquor from the second recrystallization was concentrated in vacuo on Celite®, and the resulting Celite® plug was purified by flash chromatography (Isco Companion®, $SiO_2$, DCM to 70% EtOAc in DCM) to give 1.46 g of M1A. The total amount of compound M1A was 13.4 g. (Rf≈0.40 in 1:1 DCM:EtOAc, CAM detection).

Step 2: Allyl 1-(cyclopropylamino)-2-(6-(hydroxymethyl)tetrahydro-2H-pyran-2-yloxy)-1-oxohexan-3-ylcarbamate bound resin (M1B)

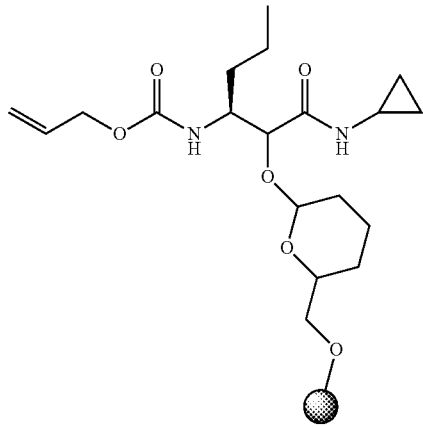

M1B

A 500 mL two neck round bottom flask equipped with an overhead mechanical stirrer and a reflux condenser was charged with M1A (9.08 g, 33.6 mmol, 3 eq.), pyridinium p-toluenesulfonate (5.6 g, 22.4 mmol, 2 eq.), DHP-resin (10.2 g, 11.2 mmol, Novabiochem, Cat# 01-64-0192, loading: 1.1 mmol/g), and dichloroethane (84 mL, [0.4]$_t$). The mixture was gently stirred at 80° C. for 3 days, before being cooled to 50° C. and filtered. The resin was washed with DCM (200 mL) and the combined filtrate were concentrated in vacuo to give the resin M1B, which was additionally washed with DCM (twice), DMF (thrice), DCM-MeOH (thrice in succession), $Et_2O$, and dried under vacuum overnight to yield a light brown resin. The loading of the resin M1B was determined by cleavage of an aliquot (176 mg) of the resin with 90% aq. TFA. Loading: 0.48 mmol/g.

Preparation of (9H-fluoren-9-yl)methyl 2-(1-(cyclopropylamino)-2-hydroxy-1-oxohexan-3-ylcarbamoyl)-4-methylenepyrrolidine-1-carboxylate bound resin (M1E)

Step 1:
3-Amino-N-cyclopropyl-2-hydroxyhexanamide bound resin (M1D)

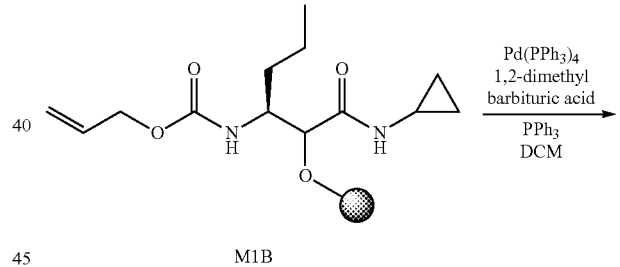

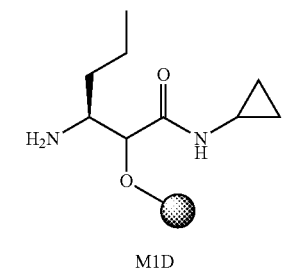

M1D

Allyl 1-(cyclopropylamino)-2-hydroxy-1-oxohexan-3-ylcarbamate bound resin M1B (30 g, 1.0 eq.) was swollen with DCM. 1,3-Dimethylbarbituric acid (24.17 g, 12 eq.) and tetrakis(triphenylphosphine)palladium (1.49 g, 0.1 eq.) were added and the mixture shaken overnight. The mixture was filtered and washed with DMF and DCM to yield the resin M1D.

Step 2: (9H-Fluoren-9-yl)methyl 2-(1-(cyclopropylamino)-2-hydroxy-1-oxohexan-3-ylcarbamoyl)-4-methylenepyrrolidine-1-carboxylate bound resin (M1E)

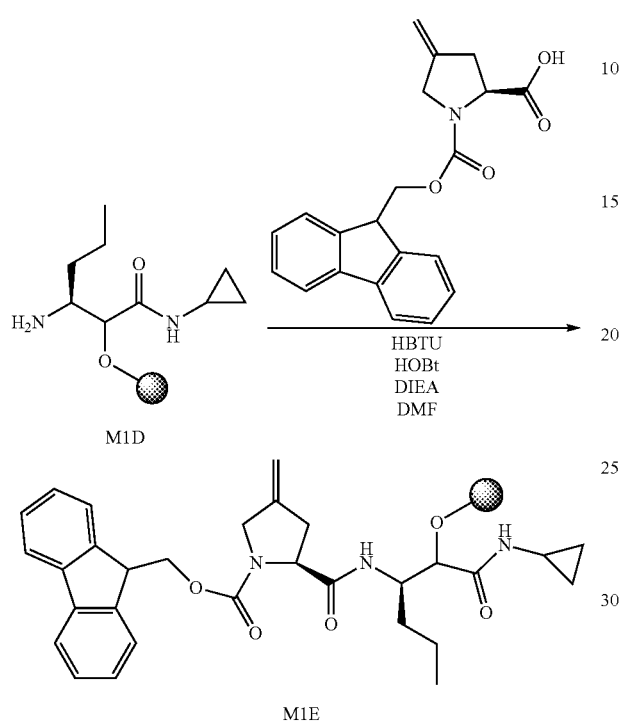

Resin M1D (1.0 g, 1.0 eq.) was stirred in DMF with FMOC-4-exomethyleneproline carboxylic acid (248 mg, 1.1 eq.), HBTU (4.8 mL of 0.5 M DMF solution, 5.0 eq.), HOBt (2.4 mL of 1.0 M DMF solution, 5.0 eq.), DIEA (836 uL, 10.0 eq.) for 3 hours. The resulting mixture was drained and washed with DMF (thrice) and DCM (thrice) to give title compound M1E.

Preparation of Fmoc-Protected Isoxazoline Compound Bound Resin (M1F)

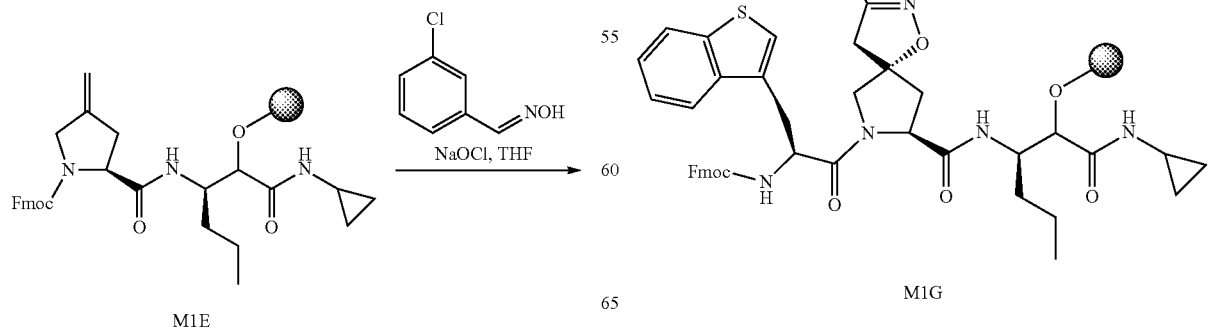

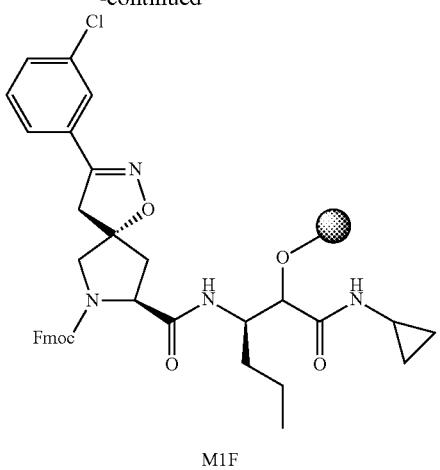

The resin M1E (2 g, 0.94 mmol) in THF was shaken with 3-chlorobenzaldoxime (5 eq.) and bleach (5% NaOCl) (15 eq.) for 18 hours. The resin was then filtered and washed with water, DMF, and DCM to yield the resin compound M1F. An aliquot of the resin was cleaved to provide a sample for LC-mass analysis (M+1=671).

Preparation of Fmoc Protected Isoxazoline Bound Resin Compound (M1G)

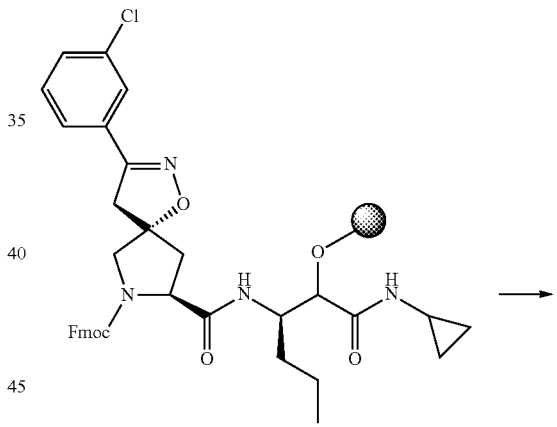

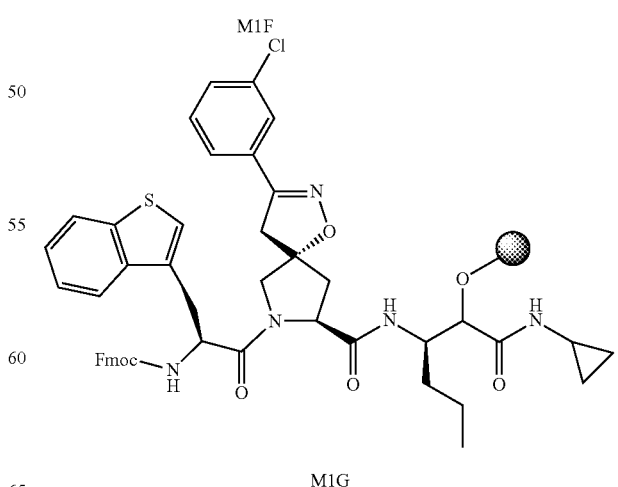

The resin M1F was shaken in 20% piperidine/DMF for 10 minutes, filtered, and washed with DMF and DCM. The THP resin bound spiroisoxazoline proline (0.14 mmol, 0.3 g) was mixed with FMOC-L-3-benzothienyl-ALA (0.56 mmol, 0.25 g), HOBT (0.56 mmol, 0.075 g), N,N-diisopropylethylamine (0.56 mmol, 0.072 g), HBTU (0.56 mmol, 0.21 g) in DMF 2.3 mL and was agitated for 48 hours. The resin was filtered and washed with DMF, dichloromethane, and ether to yield the resin compound M1G.

Preparation of 7-((S)-3-(benzo[b]thiophen-3-yl)-2-(2-cyclohexylacetamido)propanoyl)-3-(3-chlorophenyl)-N-((3R)-1-(cyclopropylamino)-2-hydroxy-1-oxohexan-3-yl)-1-oxa-2,7-diazaspiro[4.4]non-2-ene-8-carboxamide (M1H)

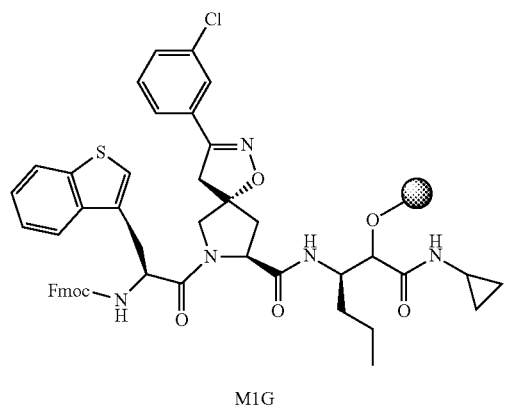

M1G

To the THP-resin bound FMOC protected spiroisoxazoline M1G was added 20% piperidine in DMF (3 mL). The mixture was agitated for 1 hour, filtered, and washed with DMF and dichloromethane. The resin was them mixed with cyclohexylacetic acid (0.56 mmol, 80 mg), HOBT (0.56 mmol, 0.075 g), N,N-diisopropylethylamine (0.56 mmol, 0.072 g), HBTU (0.56 mmol, 0.21 g) in DMF 2.3 mL and was agitated for 48 hr. The resin was filtered and washed with DMF, dichloromethane, and ether. The resin obtained was then mixed with a solution of (50:45:5) trifluoroacetic acid, dichloromethane, and triisopropyl silane (3 mL) and was agitated overnight. The reaction was filtered and washed with dichloromethane. The filtrate was concentrated under vacuum and purified via silica gel chromatography using a gradient of 40% ethyl acetate/60% dichloromethane to 100% ethyl acetate to produce the alcohol M1H.

Example 1

Compound No. 336

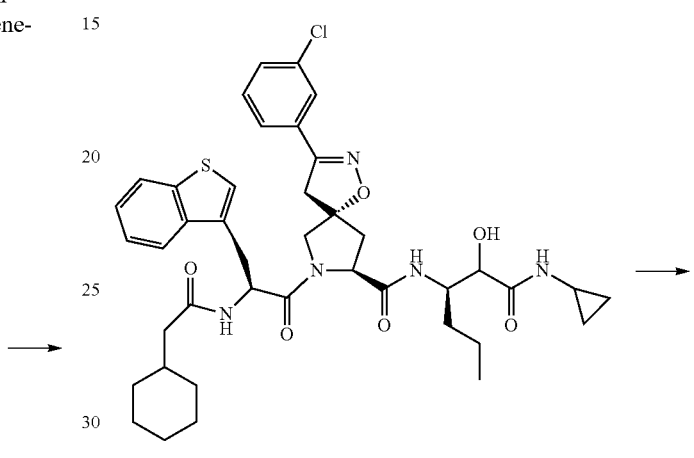

M1H

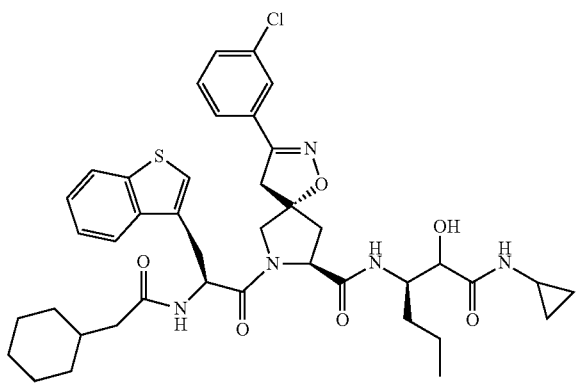

M1H

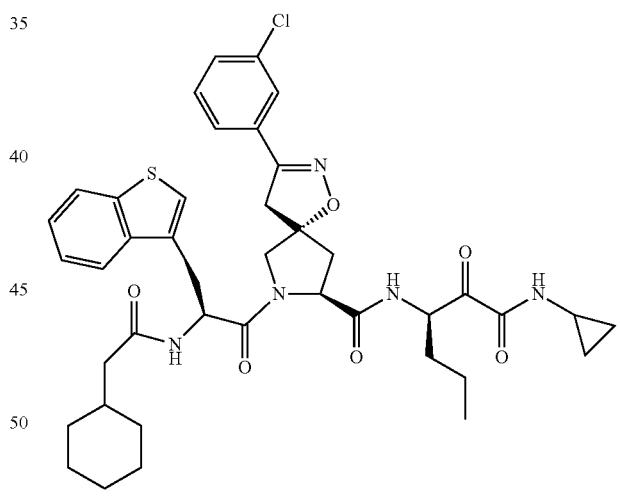

Compound No. 336

To a solution of the hydroxyamide M1H (14 mg, 0.018 mmol) in 0.38 mL of ethyl acetate was added EDC (35 mg, 0.18 mmol) followed by DMSO (0.070 mL). The mixture was cooled in an ice bath and dichloroacetic acid (15 mg, 0.12 mmol) in ethyl acetate (0.15 mL) was added. The reaction was warmed to room temperature and allowed to stir for 15 minutes and then cooled in an ice bath and quenched with 1.0 N HCl (0.21 mL). The solution was partitioned between ethyl acetate and water. The organic phase was washed with water and dried over sodium sulfate and evaporated solvent under vacuum. The resulting residue was purified by chromatography over silica gel using ethyl acetate and hexanes (3:1) as eluant to give Compound No. 336 as a white solid.

Preparation of (9H-fluoren-9-yl)methyl-8-((3S)-1-(cyclopropylamino)-2-hydroxy-1-oxohexan-3-ylcarbamoyl)-3-phenyl-1-oxa-2,7-diazaspiro[4.4]non-2-ene-7-carboxylate (M1N)

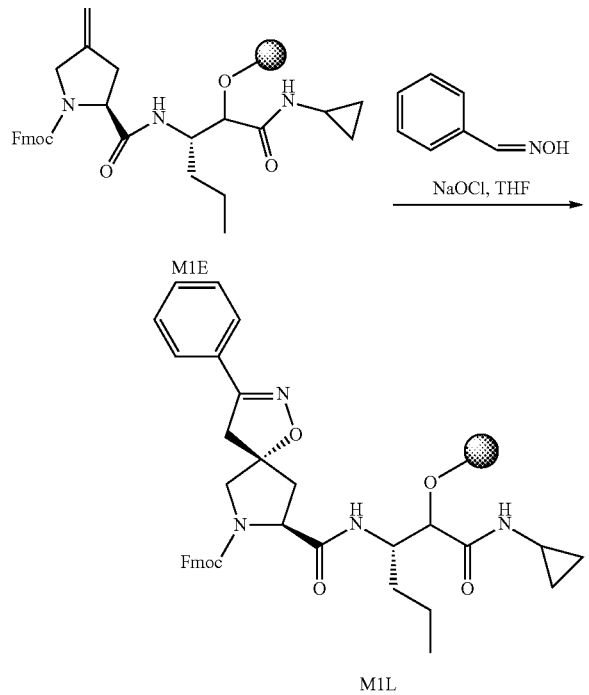

Step 1: Fmoc Protected Phenyl-Substituted Isoxazoline Bound Resin (M1L)

The resin M1E (2 g, 0.94 mmol) in THF was shaken with the oxime (5 eq.) and bleach (5% NaOCl) (15 eq.) for 18 hours. The resin was then filtered and washed with water, DMF, and DCM to give the Fmoc protected phenyl-substituted isoxazoline bound resin M1L. An aliquot of resin was cleaved for LC-mass analysis (M+1=637).

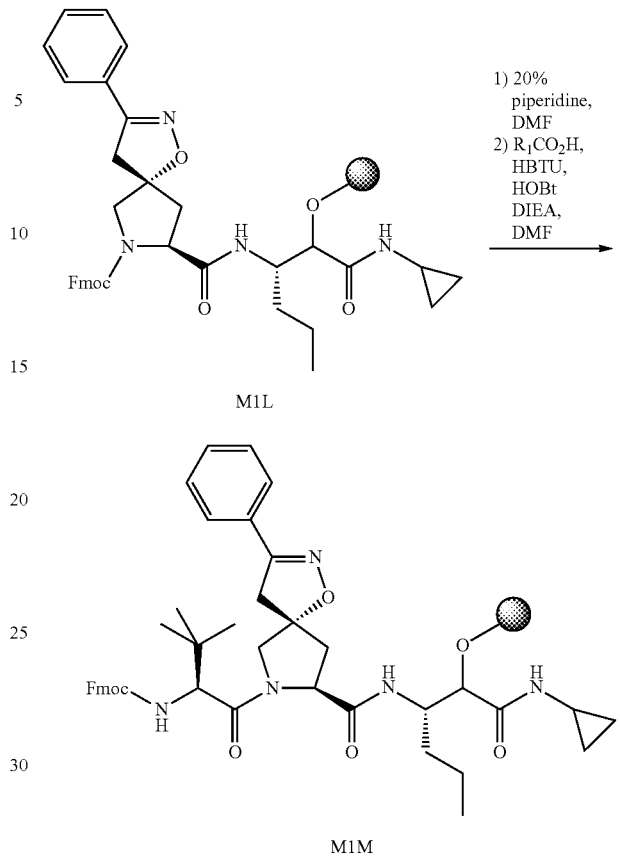

The resin M1L (0.47 mmol) was shaken in 20% piperidine/DMF for 10 minutes, and then filtered and washed with DMF and DCM. The resulting resin was shaken overnight with a solution of Fmoc-tBG-OH (480 mg 3.0 eq.), HOBT (2.82 mL of 0.5 M in DMF, 3.0 eq.), HBTU (2.82 mL of 0.5 M in DMF, 3.0 eq.), and DIEA (0.493 mL, 6.0 eq.). The resin was then filtered and washed with DMF and DCM to give the resin compound M1M, which was used in next reaction without further purification.

Step 2: Compound M1N

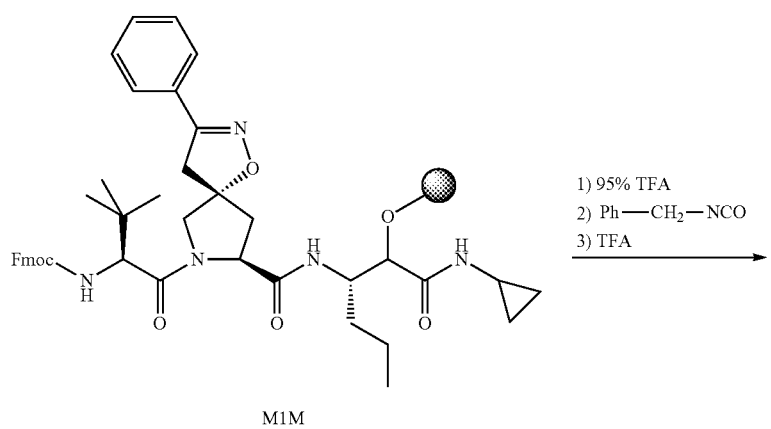

-continued

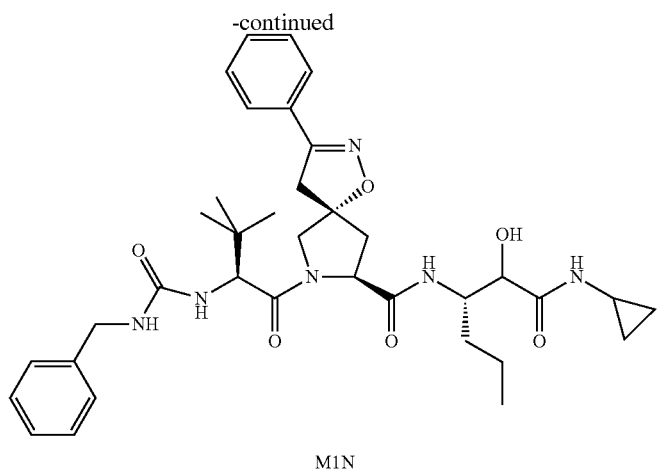

M1N

The resin M1M (0.47 mmol) was shaken in 20% piperidine/DMF for 10 minutes. The resin was filtered, washed with DMF and DCM. The resulting resin (140 mg, 0.065 mmol) was shaken overnight with benzylisocyanate (176 mg 20.0 eq.), then filtered and washed with DMF and DCM. The resin was shaken with 90% TFA in water for 30 min. The resulting solution was concentrated in vacuo to give the compound M1N (0.065 mmol), (M+1) 661, which was used in next reaction without further purification.

Example 2

Compound No. 107

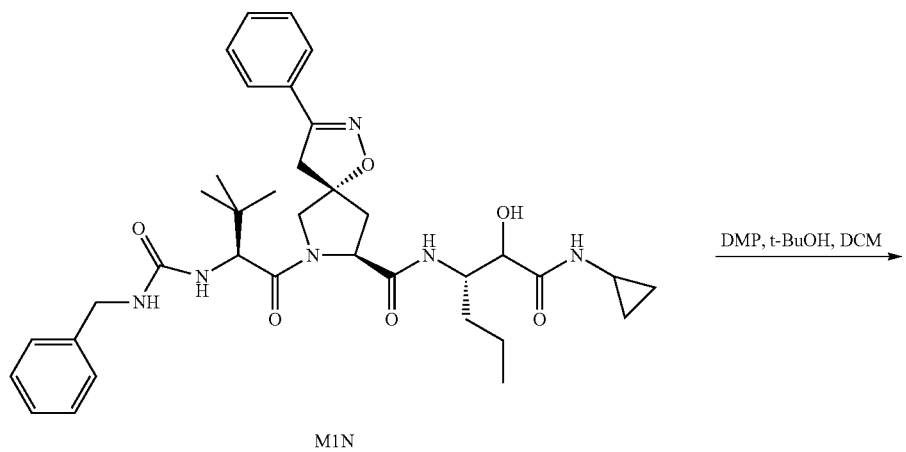

M1N

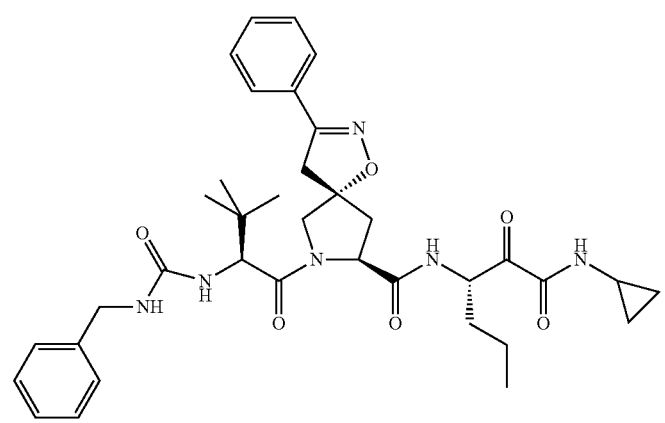

Compound No. 107

823

A solution of amide compound M1N in DCM (3 mL) was stirred with Dess-Martin Periodinane (54 mg, 2 eq.) and t-BuOH (54 uL) for 1 hour, and then sodium thiosulfate was added to the mixture. The product was extracted with EtOAc and the combined organic layer was then washed with water, NaHCO₃, brine and concentrated in vacuo and purified by Gilson Prep HPLC to afford Compound No. 107. (M+1) 659.

Example 3

Compound No. 283

824

HBTU (0.5 mL of 0.5 M in DMF, 3.85 eq.), and DIEA (0.5 mmol, 7.69 eq.). The resin was then filtered and washed with DMF and DCM and was shaken with 90% TFA in water for 30 minutes. The resulting solution was concentrated in vacuo to give the hydroxyl amide compound M1P (0.065 mmol) which was used in the next reaction without further purification. (M+1) 647.

A solution of the hydroxyl amide M1P (0.065 mmol) in DCM (3 mL) was stirred with Dess-Martin Periodinane (41

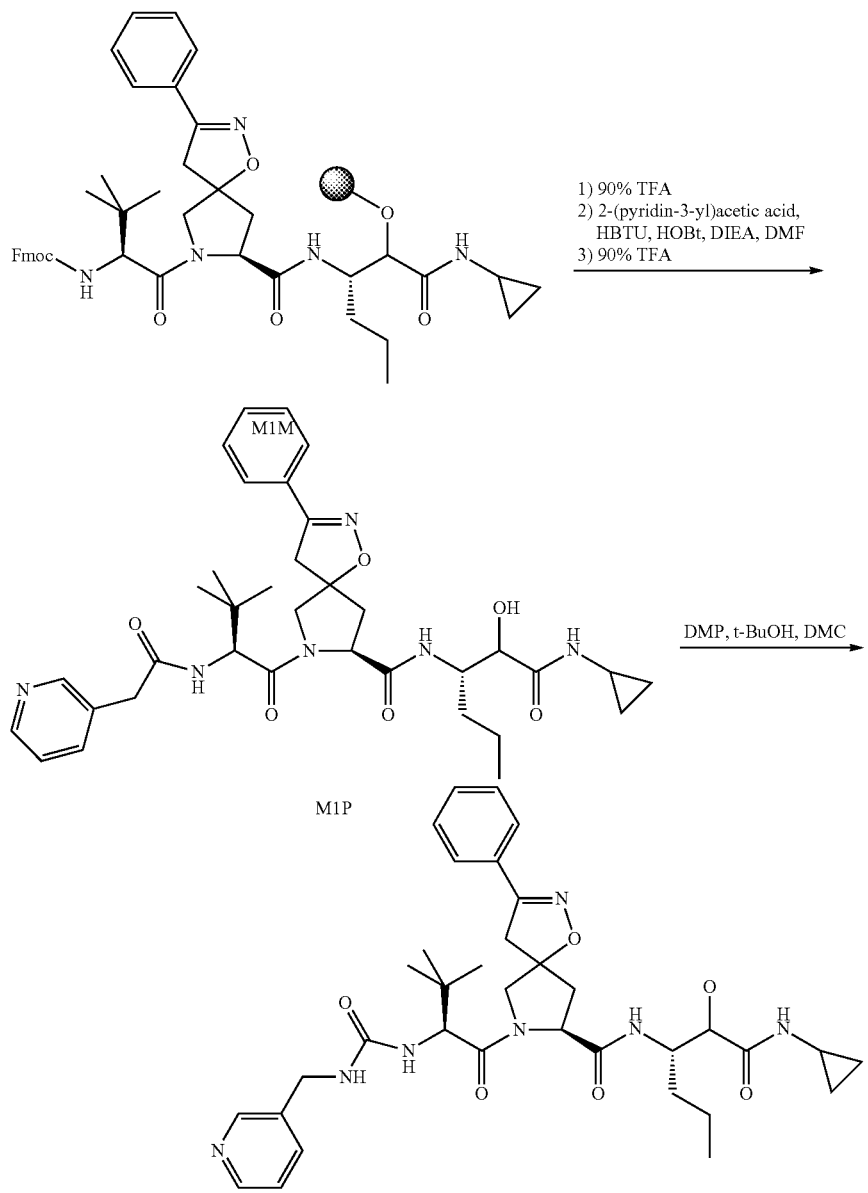

Compound 283

The THP resin M1M (0.065 mmol) was shaken in 20% piperidine/DMF for 10 minutes, and then filtered and washed with DMF and DCM. The resulting resin was shaken overnight with a solution of 2-(pyridin-3-yl)acetic acid (0.25 mmol 3.0 eq.), HOBT (0.5 mL of 0.5 M in DMF, 3.85 eq.), mg, 1.5 eq.) and t-BuOH (41 uL). After stirred for 1 hour, sodium thiosulfate was added to above mixture. The product was extracted with EtOAc. The combined organic layer was then washed with water, NaHCO₃, brine and concentrated in vacuo and purified by Gilson Prep HPLC to afford Compound No. 283 (4 mg). (M+1) 645.

Example 4
Compound No. 61
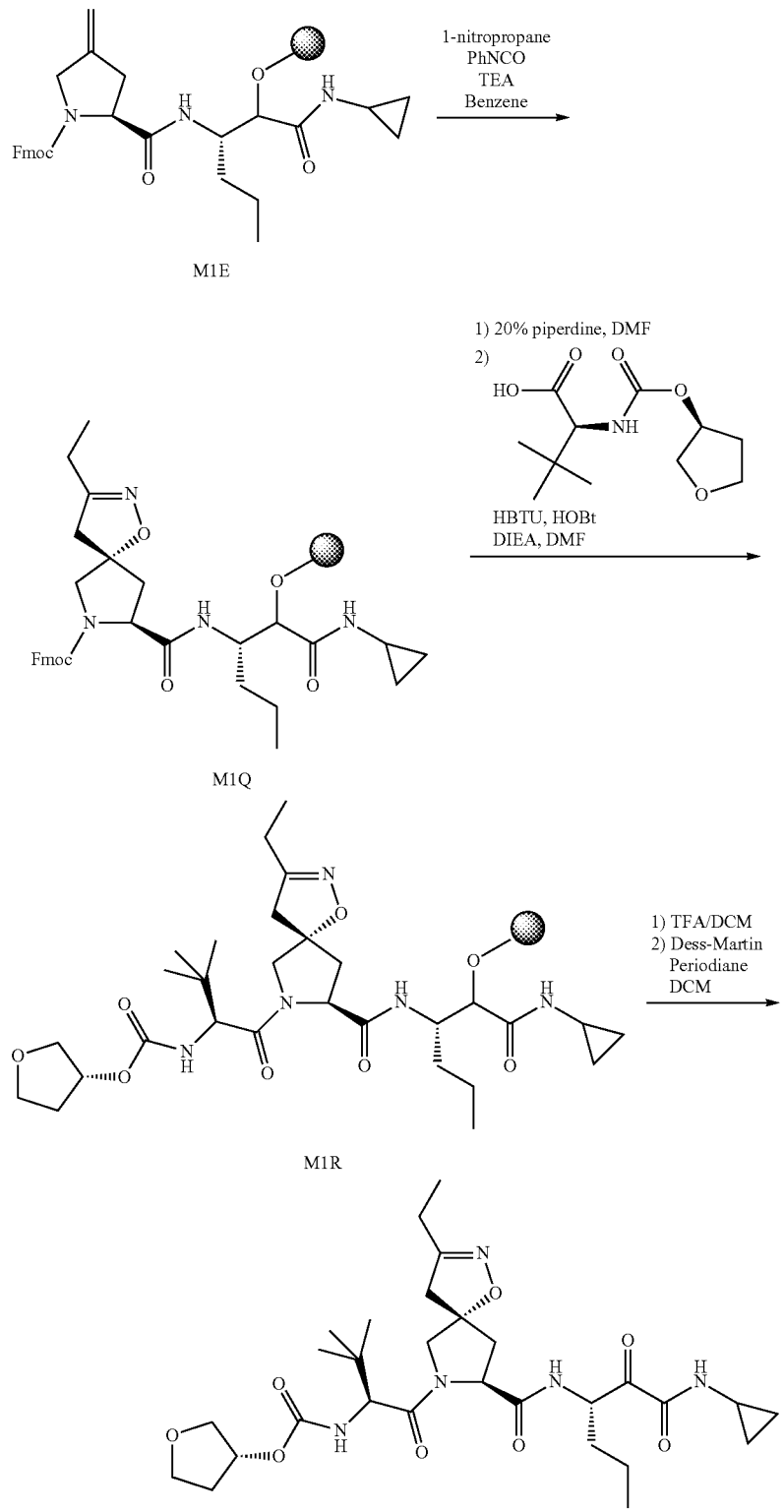

Compound M1E (750 mg, 1.0 eq.) was stirred in benzene with 1-nitropropane (315 uL, 10.0 eq.), and phenylisocyanate (385 uL, 10.0 eq.). Triethylamine (5 uL) was added, and the resulting mixture was shaken overnight, drained, and washed with DMF (thrice) and DCM (thrice). This process was repeated to yield compound M1Q. (M+H=589.0)

Compound M1Q (750 mg, 1.0 eq.) was then shaken in 20% piperidine/DMF for 10 minutes. The resin was filtered and washed with DMF (thrice) followed by DCM (thrice). This process was repeated. The resulting resin was shaken overnight with a solution of (S)-3,3-dimethyl-2-(((S)-tetrahydrofuran-3-yloxy)carbonylamino)butanoic acid (216 mg, 2.5 eq.), HBTU (1.76 mL of 0.5 M in DMF, 3.0 eq.), HOBt (0.88 mL of 1.0 M in DMF, 2.5 eq.), and DIEA (307 uL, 5.0 eq.) in DMF. The resin was then filtered and washed with DMF (thrice) and DCM (thrice) to give compound M1R. (M+H=593.9)

Compound M1R (750 mg, 1.0 eq.) stirred in 1/1 TFA/DCM for 3 hours. The resin was drained and washed with DCM (thrice). All of the organics were concentrated and DCM was added followed by Dess-Martin Periodinane (50 mg, 3.0 eq.). The resulting mixture was stirred for 1 hour, 1 N $Na_2S_2O_3$ was added, and stirred again. A racemic mixture of Compound No. 61 was purified by silica gel chromatography (10-90% ethyl acetate/hexanes gradient) to yield Compound No. 61 as one diastereomer. (M+H=591.8) $^1$H-NMR (500 MHz, $CDCl_3$): 7.12 (d, 1H), 6.91 (d, 1H), 5.48 (d, 1H), 5.34 (td, 1H), 5.24 (s, 1H), 4.69 (t, 1H), 4.28 (d, 1H), 4.13 (s, 2H), 3.93-3.82 (m, 4H), 3.60 (d, 1H), 3.06 (s, 0.5H), 3.03 (s, 0.5H), 2.95 (d, 1H), 2.90 (d, 1H), 2.78 (td, 1H), 2.51-2.47 (m, 1H), 2.44-2.34 (m, 3H), 2.14-2.10 (m, 1H), 1.94-1.88 (m, 1H), 1.63-1.57 (m, 1H), 1.46-1.36 (m, 2H), 1.17 (t, 3H), 0.98 (s, 9H), 0.95-0.83 (m, 5H), 0.59 (dd, 2H)

Example 5

Compound No. 146

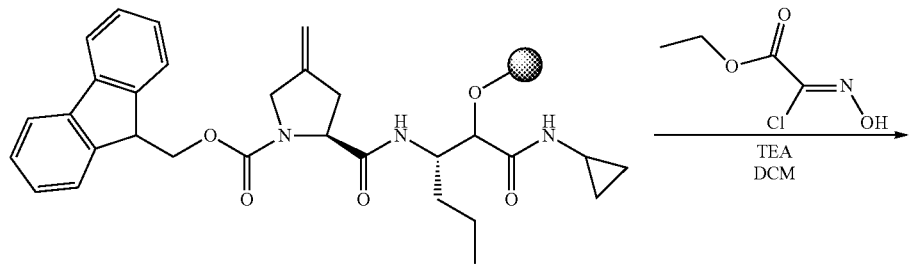

M1E

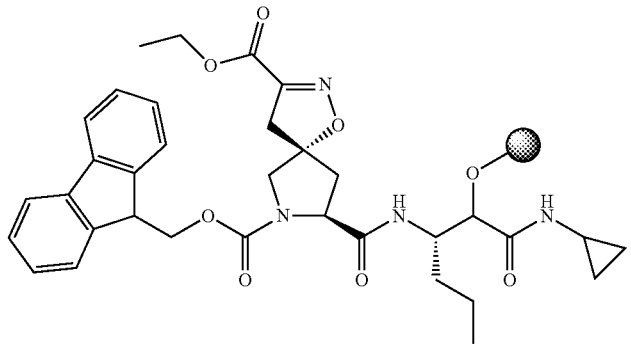

M1S

Compound M1E (50 mg, 1.0 eq.) was stirred in DCM with (Z)-ethyl 2-chloro-2-(hydroxyimino)acetate (7.1 mg, 2.0 eq.). To this mixture was slowly added TEA (6.6 uL, 2.0 eq.) in DCM and the mixture was shaken for 3 hours, then drained and washed with DMF (thrice) and DCM (thrice). This process was repeated to give compound M1S (M+H=632.4).

process was repeated. The resulting resin was shaken overnight with a solution of (S)-3,3-dimethyl-2-(((S)tetrahydrofuran-3-yloxy)carbonylamino)butanoic acid (230 mg 2.0 eq.), HBTU (1.88 mL of 0.5 M in DMF, 2.0 eq.), HOBt (0.94 mL of 1.0 M in DMF, 2.0 eq.), and DIEA (327 uL, 4.0 eq.) in

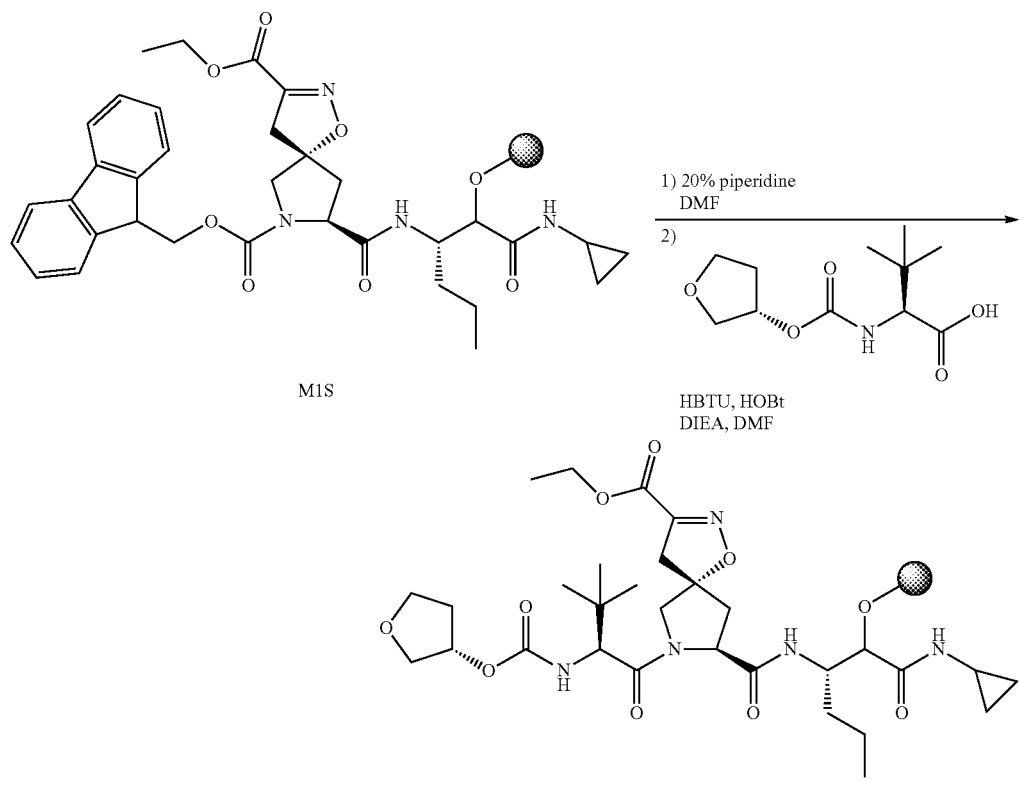

Compound M1S (1.0 g, 1.0 eq.) was shaken in 20% piperidine/DMF for 10 minutes. The resin was filtered and washed with DMF (thrice) followed by DCM (thrice). This 2 mL DMF. The resin was then filtered and washed with DMF (thrice) and DCM (thrice) to give compound M1T (M+H=638.0).

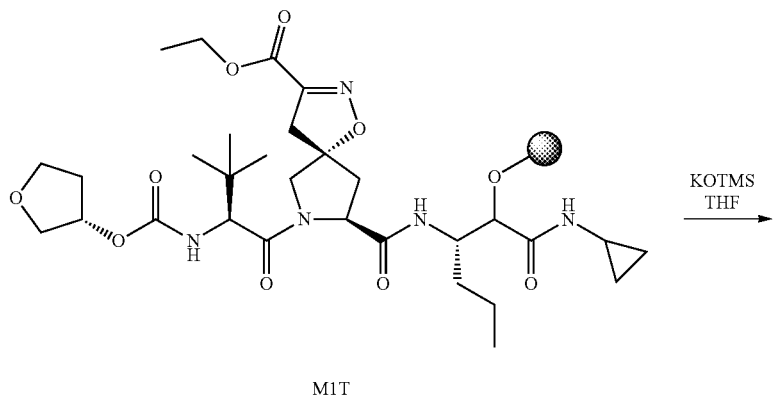

-continued

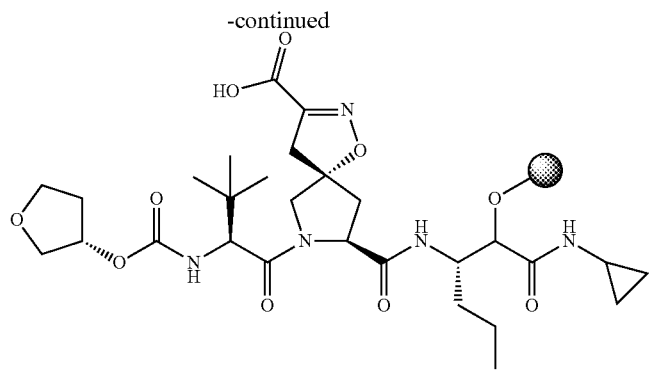

M1U

Compound M1T (750 mg, 1.0 eq.) was shaken in THF with KOTMS (133 mg, 3.0 eq.) for 3 hours. The mixture was then drained and washed with THF/water (1/1), THF, DMF, and DCM (thrice each) to give compound M1U. (M+H=609.5).

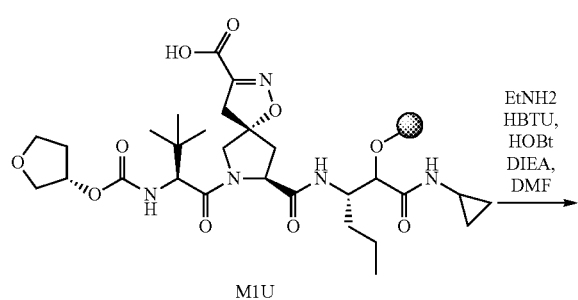

M1U

→ EtNH2, HBTU, HOBt, DIEA, DMF

-continued

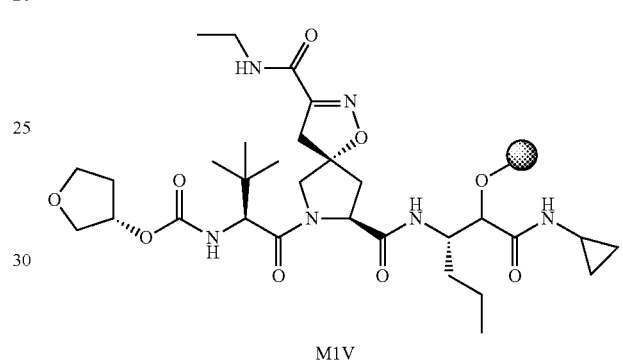

M1V

Compound M1U (250 mg, 1.0 eq.) was shaken overnight with a solution of ethylamine (22 mg 3.0 eq.), HBTU (0.54 mL of 0.5 M in DMF, 3.0 eq.), HOBt (0.27 mL of 1.0 M in DMF, 3.0 eq.), and DIEA (47 uL, 3.0 eq.) in DMF. The resin was then filtered and washed with DMF (thrice) and DCM (thrice) to give compound M1V. (M+H=637.2).

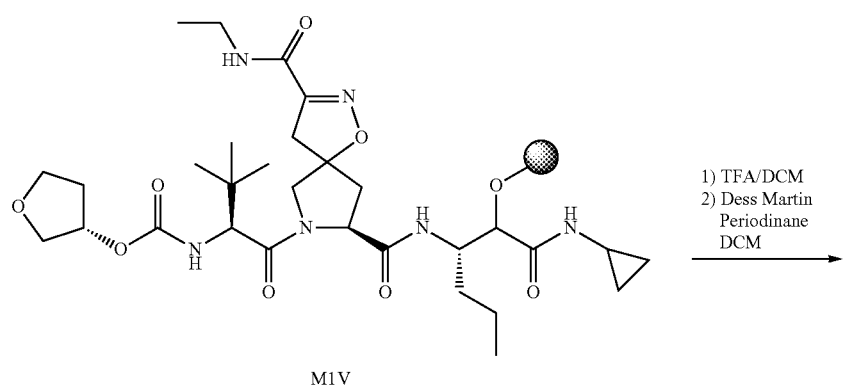

M1V

→ 1) TFA/DCM
2) Dess Martin Periodinane DCM

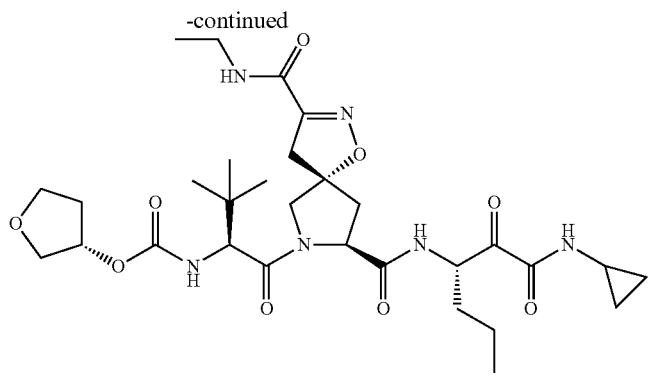

Compound No. 146

Compound M1V (0.4 g, 1.0 eq.) was stirred in 1/1 TFA/DCM for 2 hours and then drained and washed with DCM (thrice). The organic phases were combined and dried, and to it was added DCM followed by Dess-Martin Periodinane (97 mg, 3.0 eq.). The solution was stirred for 1 hour and to it was added 1 N $Na_2S_2O_3$ and the mixture was further stirred. The solution was purified by silica gel chromatography (10-90% ethyl acetate/hexanes gradient) to yield 6.1 mg of Compound No. 146. (M+H=635.0) $^1$H-NMR (CDCl$_3$): 5.5-5.2 (m, 2H), 5.1-5.0 (m, 1H), 4.9-4.7 (m, 2H), 4.5-4.2 (m, 3H), 4.1 (m, 1H), 3.9-3.7 (m, 3H), 3.6-3.5 (m, 2H), 3.5-3.2 (m, 2H), 2.8-2.4 (m, 2H), 2.1 (m, 1H), 2.0-1.8 (m, 3H), 1.8-1.5 (m, 3H), 1.5-1.3 (m, 3H), 1.3-1.2 (m, 2H), 1.0 (s, 9H), 0.9 (t, 3H), 0.8 (m, 2H), 0.6 (m, 2H).

The following compounds of Formula I were also produced according to Method 1 and the preparations described thereunder.

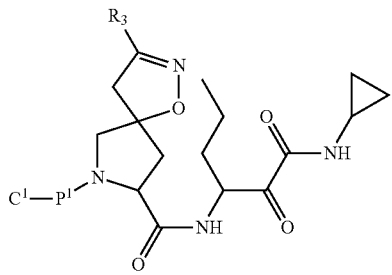

TABLE 2

Additional compounds of formula I produced by method 1.

| Compound No. | Starting Material for P$^1$ | Starting Material for C$^1$ | Starting Material for R$_3$ |
|---|---|---|---|
| 7 | N-FMOC-L-tert-butylglycine | 3-(4-fluorophenyl)-propanoic acid | 3-chloro-benzenecarb aldehyde oxime |
| 12 | N-FMOC-L-tert-butylglycine | Acetic acid | 3-chloro-benzenecarb aldehyde oxime |
| 14 | N-FMOC-L-tert-butylglycine | cyclopentyl-methanol | 3-chloro-benzenecarb aldehyde oxime |
| 24 | N-((S)-tetrahydrofuran-3-yloxy)carbonyl)-L-tert-butylglycine | N/A | 3-Fluoro-benzenecarb aldehyde oxime |
| 27 | N-FMOC-L-tert-butylglycine | cyclobutyl-methanol | 3-chloro-benzenecarb aldehyde oxime |
| 29 | N-FMOC-L-tert-butylglycine | 2-(1-methylcyclo-hexyl)acetic acid | 3-chloro-benzenecarb aldehyde oxime |
| 30 | N-FMOC-L-tert-butylglycine | (S)-5-oxo-1-(thiophen-2-ylmethyl)pyrrolidine-2-carboxylic acid | 3-chloro-benzenecarb aldehyde oxime |
| 33 | N-FMOC-L-tert-butylglycine | cyclohexyl isocyanate | 3-chloro-benzenecarb aldehyde oxime |
| 34 | N-FMOC-L-tert-butylglycine | 5-hydroxy-pentan-2-one | 3-chloro-benzenecarb aldehyde oxime |
| 37 | N-FMOC-L-tert-butylglycine | 2-(tetrahydro-2H-pyran-4-yl)acetic acid | 3-chloro-benzenecarb aldehyde oxime |
| 39 | N-FMOC-L-tert-butylglycine | 2-chlorobenzyl chloroformate | 3-chloro-benzenecarb aldehyde oxime |
| 44 | N-FMOC-L-tert-butylglycine | 4-oxo-pentanoic acid | 3-chloro-benzenecarb aldehyde oxime |
| 53 | N/A | 2-(1-(2,6-di-chlorobenzyl)-piperidin-4-yl)acetic acid | Benzald-oxime |
| 61 | N-((S)-tetrahydrofuran-3-yloxy)carbonyl)-L-tert-butylglycine | N/A | Nitro-propane |
| 71 | N-FMOC-L-tert-butylglycine | (R)-2,3-dihydrobenzo-[b][1,4]dioxine-2-carboxylic acid | 3-chloro-benzenecarb aldehyde oxime |

TABLE 2-continued

Additional compounds of formula I produced by method 1.

| Compound No. | Starting Material for $P^1$ | Starting Material for $C^1$ | Starting Material for $R_3$ |
|---|---|---|---|
| 72 | N-FMOC-L-tert-butylglycine | 2-cyclopentyl-acetic acid | 3-chloro-benzenecarbaldehyde oxime |
| 75 | N-FMOC-L-tert-butylglycine | 2-(2,4-dimethyl-thiazol-5-yl)acetic acid | 3-chloro-benzenecarbaldehyde oxime |
| 76 | N-FMOC-L-tert-butylglycine | Cyclopropyl isocyanate | 3-chloro-benzenecarbaldehyde oxime |
| 85 | N-FMOC-L-tert-butylglycine | 2-Fluoroethyl chloroformate | 3-chloro-benzenecarbaldehyde oxime |
| 92 | N-FMOC-L-tert-butylglycine | 2-(tetrahydro-2H-pyran-4-yl)acetic acid | 3-chloro-benzenecarbaldehyde oxime |
| 93 | N-FMOC-L-tert-butylglycine | cyclohexane-carboxylic acid | 3-chloro-benzenecarbaldehyde oxime |
| 94 | N-FMOC-L-tert-butylglycine | 2-amino-acetamide | 3-chloro-benzenecarbaldehyde oxime |
| 102 | N-FMOC-L-tert-butylglycine | 2-(3-fluoro-4-methylphenyl)-acetic acid | 3-chloro-benzenecarbaldehyde oxime |
| 107 | N-FMOC-L-tert-butylglycine | Benzyl isocyanate | Benzaldoxime |
| 108 | N-FMOC-L-tert-butylglycine | cis-4-methoxy-cyclohexane-carboxylic acid | 3-chloro-benzenecarbaldehyde oxime |
| 110 | N-FMOC-L-tert-butylglycine | Benzyl chloroformate | 3-Chloro-4,6-dimethoxy-benzaldoxime |
| 112 | N-FMOC-L-tert-butylglycine | 2-(tetrahydro-2H-pyran-4-yl)acetic acid | 2-nitro-1-phenyl ethanone |
| 118 | N-FMOC-L-tert-butylglycine | 2-(4-fluoro-phenyl)ethanol | 3-Chloro-benzene carbaldehyde oxime |
| 119 | N-FMOC-L-tert-butylglycine | tert-Butyl isocyanate | 2-nitro-1-phenyl ethanone |
| 122 | N-FMOC-L-tert-butylglycine | 3-Fluorobenzyl isocyanate | 3-Chloro-benzene carbaldehyde oxime |
| 123 | N-FMOC-L-tert-butylglycine | Ethyl isocyanate | 3-Chloro-benzene carbaldehyde oxime |
| 124 | N-FMOC-O-Methyl-L-Threonine | 2-cyclohexyl-acetic acid | 3-Chloro-benzene carbaldehyde oxime |
| 125 | (2R,3S)-N-FMOC-2-Amino-3-phenyl-butyric acid | 2-cyclohexyl-acetic acid | 3-chloro-benzenecarbaldehyde oxime |
| 128 | N-FMOC-L-tert-butylglycine | 4-(1H-pyrrole-2,5-dione)phenyl isocyanate | 3-chloro-benzenecarbaldehyde oxime |
| 135 | N-FMOC-L-tert-butylglycine | 1-isopropyl-4-oxo-1,4-dihydroquinoline-3-carboxylic acid | 3-chloro-benzenecarbaldehyde oxime |
| 139 | N-FMOC-L-tert-butylglycine | (R)-2-hydroxy-2-phenylpropanoic acid | 3-chloro-benzenecarbaldehyde oxime |
| 146 | N-((S)-tetrahydrofuran-3-yloxy)carbonyl)-L-tert-butylglycine | N/A | 2-Chloro-2-hydroximino-acetic aicd ethyl ester (chlorooxime) |
| 152 | N-FMOC-L-tert-butylglycine | (tetrahydro-furan-3-yl)methanol | 3-chloro-benzenecarbaldehyde oxime |
| 154 | N-Alloc-L-tert-butylglycine | N/A | 4-Fluoro-benzenecarbaldehyde oxime |
| 155 | N-FMOC-L-tert-butylglycine | 2-(5-fluoro-2-methylphenyl)-acetic acid | 3-chloro-benzenecarbaldehyde oxime |
| 156 | N-FMOC-L-tert-butylglycine | Isobutylamine | 3-chloro-benzenecarbaldehyde oxime |
| 159 | N-FMOC-L-tert-butylglycine | 2-(thiophen-3-yl)ethanol | 3-chloro-benzenecarbaldehyde oxime |
| 160 | N-CBZ-L-tert-butylglycine | N/A | 4-Fluoro benzene carbaldehyde oxime |
| 161 | N-FMOC-L-tert-butylglycine | 5-acetamido-2-acetylthiophene-3-carboxylic acid | 3-chloro-benzenecarbaldehyde oxime |
| 164 | N-CBZ-L-tert-butylglycine | N/A | 2-Chloro-benzenecarbaldehyde oxime |
| 167 | N-FMOC-L-tert-butylglycine | (2-methylpyridin-3-yl)methanol | 3-chloro-benzenecarbaldehyde oxime |
| 173 | N-FMOC-L-tert-butylglycine | 2,2-difluoro-ethylamine | 3-chloro-benzenecarbaldehyde oxime |
| 174 | N-FMOC-L-tert-butylglycine | m-tolylmethanol | 3-chloro-benzenecarbaldehyde oxime |
| 180 | N-FMOC-L-tert-butylglycine | Acetic acid | Nitroethane |
| 183 | N-CBZ-L-tert-butylglycine | N/A | 3-Fluoro-benzenecarbaldehyde oxime |
| 185 | N-FMOC-L-3-Thienyl-Alanine | 2-cyclohexylacetic acid | 3-chloro-benzenecarbaldehyde oxime |
| 193 | N-FMOC-L-tert-butylglycine | Isopropyl chloroformate | 3-chloro-benzenecarbaldehyde oxime |
| 199 | N-CBZ-L-tert-butylglycine | N/A | 9-Anthraldehyde oxime |

TABLE 2-continued

Additional compounds of formula I produced by method 1.

| Compound No. | Starting Material for P¹ | Starting Material for C¹ | Starting Material for R₃ |
|---|---|---|---|
| 201 | N-FMOC-L-tert-butylglycine | (3-methoxyphenyl)methanol | 3-chlorobenzenecarbaldehyde oxime |
| 203 | N-FMOC-L-tert-butylglycine | (3,5-difluorophenyl)methanol | 3-chlorobenzenecarbaldehyde oxime |
| 205 | N-FMOC-L-tert-butylglycine | Benzyl isocyanate | 3-chlorobenzenecarbaldehyde oxime |
| 207 | N-FMOC-L-Glycine | Ethyl chloroformate | 3-chlorobenzenecarbaldehyde oxime |
| 208 | N-CBZ-L-tert-butylglycine | N/A | 2-Naphthaldehyde oxime |
| 209 | N-FMOC-L-tert-butylglycine | (3-fluorophenyl)methanol | 3-chlorobenzenecarbaldehyde oxime |
| 210 | N-FMOC-L-tert-butylglycine | 2-chlorobenzyl chloroformate | 3-Chloro-4,6-dimethoxybenzaldoxime |
| 213 | N-FMOC-4-Methoxy-L-Phenylalanine | 2-cyclohexylacetic acid | 3-chlorobenzenecarbaldehyde oxime |
| 216 | N-FMOC-L-tert-butylglycine | 5-oxo-1-(thiophen-2-ylmethyl)-pyrrolidine-3-carboxylic acid | 3-chlorobenzenecarbaldehyde oxime |
| 235 | N-CBZ-L-tert-butylglycine | N/A | nitrobutane |
| 237 | N-FMOC-L-tert-butylglycine | 3-(2-methyl-1H-imidazol-1-yl)propanoic acid | 3-chlorobenzenecarbaldehyde oxime |
| 241 | N-FMOC-L-tert-butylglycine | (S)-1-isopropyl-5-oxopyrrolidine-2-carboxylic acid | 3-chlorobenzenecarbaldehyde oxime |
| 242 | N-FMOC-L-tert-butylglycine | N-FMOC-L-cyclohexylglycine followed by 2-pyrazine carboxylic acid | Piperonal oxime |
| 243 | N-((S)-tetrahydrofuran-3-yloxy)carbonyl)-L-tert-butylglycine | N/A | nitrobutane |
| 249 | N-FMOC-L-tert-butylglycine | cyclohexanemethyl isocyanate | Benzaldoxime |
| 254 | N-FMOC-L-tert-butylglycine | 1-(thiophen-2-yl)propan-2-ol | 3-chlorobenzenecarbaldehyde oxime |
| 259 | N-FMOC-L-tert-butylglycine | 3,4,5-trimethoxybenzyl isocyanate | 3-chlorobenzenecarbaldehyde oxime |
| 260 | N-FMOC-L-tert-butylglycine | 2-methoxyethyl chloroformate | 3-chlorobenzenecarbaldehyde oxime |
| 261 | N-FMOC-L-tert-butylglycine | benzyl 4-isocyanatopiperidine-1-carboxylate | 3-chlorobenzenecarbaldehyde oxime |
| 262 | N/A | 4-nitrophenyl choroformate | 3-chlorobenzenecarbaldehyde oxime |
| 276 | 2-((3S,4aS,8aS)-3-(tert-butylcarbamoyl)octahydroisoquinolin-2(1H)-yl)acetic acid | N/A | 3-chlorobenzenecarbaldehyde oxime |
| 278 | N-FMOC-L-tert-butylglycine | benzyl chloroformate | 2-(4-Methoxyphenoxy)benzenecarbaldehyde oxime |
| 283 | N-FMOC-L-tert-butylglycine | 2-(pyridin-3-yl)acetic acid | Benzaldoxime |
| 287 | N-FMOC-L-tert-butylglycine | 2-(3-methoxyphenyl)acetic acid | 3-chlorobenzenecarbaldehyde oxime |
| 288 | N-FMOC-L-tert-butylglycine | 1-Naphthyl isocyanate | Benzaldoxime |
| 289 | N-FMOC-2-Trifluoromethyl-L-Phenylalanine | 2-cyclohexylacetic acid | 3-chlorobenzenecarbaldehyde oxime |
| 291 | N-FMOC-L-tert-butylglycine | spiro[indene-1,4'-piperidin]-3(2H)-one | 3-chlorobenzenecarbaldehyde oxime |
| 294 | N-FMOC-L-tert-butylglycine | 2-cyclohexylacetic acid | 3-chlorobenzenecarbaldehyde oxime |
| 308 | N-FMOC-L-tert-butylglycine | (tetrahydro-2H-pyran-2-yl)methanol | 3-chlorobenzenecarbaldehyde oxime |
| 311 | N-FMOC-L-tert-butylglycine | 2-(pyrrolidine-1-carbonyl)cyclohexanecarboxylic acid | 3-chlorobenzenecarbaldehyde oxime |
| 313 | N/A | benzyl isocyanate | 3-Chloro-4,6-dimethoxybenzaldoxime |
| 317 | N-FMOC-L-tert-butylglycine | 2-(1-oxoisoindolin-2-yl)propanoic acid | 3-chlorobenzenecarbaldehyde oxime |
| 324 | N-FMOC-L-tert-butylglycine | (R)-3-(1-cyanoethyl) benzoic acid | 3-chlorobenzenecarbaldehyde oxime |
| 329 | N-FMOC-L-tert-butylglycine | cyclohexylacetic acid | Nitropropane |
| 331 | N-FMOC-L-tert-butylglycine | acetic acid | 4-Fluorobenzene carbaldehyde oxime |
| 333 | N-FMOC-L-tert-butylglycine | (S)-1-methylbenzylamine | 3-Chlorobenzene carbaldehyde oxime |
| 334 | N-FMOC-L-tert-butylglycine | (S)-2-methyl-3-phenylpropanoic acid | 3-chlorobenzenecarbaldehyde oxime |
| 336 | N-FMOC-L-3-Benzothienyl-Alanine | 2-cyclohexylacetic acid | 3-chlorobenzenecarbaldehyde oxime |

TABLE 2-continued

Additional compounds of formula I produced by method 1.

| Compound No. | Starting Material for P¹ | Starting Material for C¹ | Starting Material for R₃ |
|---|---|---|---|
| 338 | N-FMOC-2-Fluoro-L-Phenylalanine | 2-cyclohexyl-acetic acid | 3-chloro-benzenecarb aldehyde oxime |
| 340 | N-CBZ-L-tert-butylglycine | N/A | 4-Phenyl-benzenecarb aldehyde oxime |
| 341 | N-((S)-tetrahydrofuran-3-yloxy)carbonyl)-L-tert-butylglycine | N/A | 2-chloro-2-hydroximino-acetic acid ethyl ester (chlorooxime) followed by ester hydrolysis and coupling of ethylamine |
| 342 | N/A | pyridine 3-methanol | 3-chloro-benzenecarb aldehyde oxime |
| 345 | N-(5-methyl-3-nitroprydinyl)-L-tert-butylglycine | N/A | 3-chloro-benzenecarb aldehyde oxime |
| 349 | N-FMOC-L-tert-butylglycine | 2-(4-fluoro-phenyl)ethanol | 3-chloro-benzenecarb aldehyde oxime |
| 352 | N-((S)-tetrahydrofuran-3-yloxy)carbonyl)-L-tert-butylglycine | N/A | Pyridine-4-aldoxime |
| 357 | N-FMOC-L-tert-butylglycine | pyridin-4-ylmethanol | 3-chloro-benzenecarb aldehyde oxime |
| 358 | N-((S)-tetrahydrofuran-3-yloxy)carbonyl)-L-tert-butylglycine | N/A | 4-Trifluoro-methoxyb enzenecar-baldehyde oxime |
| 365 | N-CBZ-L-tert-butylglycine | N/A | 4-Trifluoro-methoxyb enzenecar-baldehyde oxime |
| 367 | N/A | 3,4,5-trimeth-oxybenzyl isocyanate | Benzald-oxime |
| 373 | N-FMOC-L-tert-butylglycine | 3-(pyridin-2-yl)propan-1-ol | 3-chloro-benzenecarb aldehyde oxime |
| 374 | N-FMOC-L-tert-butylglycine | tetrahydro-2H-pyran-4-ol | 3-chloro-benzenecarb aldehyde oxime |
| 377 | N-FMOC-L-tert-butylglycine | (S)-1-(3-chloro-benzyl)-5-oxopyrrolidine-2-carboxylic acid | 3-chloro-benzenecarb aldehyde oxime |
| 378 | N-FMOC-L-tert-butylglycine | pyridin-2-ylmethanol | 3-chloro-benzenecarb aldehyde oxime |
| 379 | N-FMOC-L-tert-butylglycine | isopropyl isocyanate | 3-chloro-benzenecarb aldehyde oxime |
| 381 | N-FMOC-L-tert-butylglycine | 4-oxo-3,4-dihydro-phthalazine-1-carboxylic acid | 3-chloro-benzenecarb aldehyde oxime |
| 383 | N-CBZ-L-tert-butylglycine | N/A | Nitro-propane |
| 387 | N-FMOC-L-tert-butylglycine | (3R,3aS,6aR)-hexahydrofuro[2,3-b]furan-3-ol | 3-chloro-benzenecarb aldehyde oxime |
| 389 | N-FMOC-L-tert-butylglycine | 3-(pyridin-3-yl)propan-1-ol | 3-chloro-benzenecarb aldehyde oxime |
| 390 | N-FMOC-L-tert-butylglycine | cyclohexyl-acetic acid | 2-nitro-1-phenyl ethanone |
| 398 | N-((S)-tetrahydrofuran-3-yloxy)carbonyl)-L-tert-butylglycine | N/A | 4-Fluoro-benzenecarb aldehyde oxime |
| 400 | N-FMOC-L-tert-butylglycine | N-FMOC-L-cyclohexylglycine followed by 2-pyrazine carboxylic acid | Nitrobutane |
| 402 | N-FMOC-L-tert-butylglycine | 2-(5-oxo-2-(thiophen-2-yl)cyclopent-1-enyl)acetic acid | 3-chloro-benzenecarb aldehyde oxime |
| 407 | N-FMOC-L-tert-butylglycine | ethyl chloroformate | 3-chloro-benzenecarb aldehyde oxime |
| 417 | N-FMOC-L-tert-butylglycine | N-FMOC-L-tert-butylglycine followed by 2-pyrazine carboxylic acid | 4-Fluoro-benzenecarb aldehyde oxime |
| 427 | N-FMOC-L-Phenylalanine | ethyl chloroformate | 3-chloro-benzenecarb aldehyde oxime |
| 431 | N-FMOC-L-tert-butylglycine | 2-o-tolyl-acetic acid | 3-chloro-benzenecarb aldehyde oxime |
| 432 | N-FMOC-L-tert-butylglycine | N-methyl ethylamine | 3-chloro-benzenecarb aldehyde oxime |
| 437 | N-FMOC-S-tert-Butyl-L-Cysteine | 2-cyclohexyl-acetic acid | 3-chloro-benzenecarb aldehyde oxime |
| 450 | N-FMOC-L-tert-butylglycine | N-FMOC-L-tert-butylglycine followed by 2-pyrazine carboxylic acid | Piperonal oxime |
| 454 | N-FMOC-L-tert-butylglycine | 2-(quinolin-8-ylthio)acetic acid | 3-chloro-benzenecarb aldehyde oxime |
| 459 | N-FMOC-L-Norleucine | 2-cyclohexyl-acetic acid | 3-chloro-benzenecarb aldehyde oxime |
| 462 | N-FMOC-L-tert-butylglycine | cyclohexyl-acetic acid | Piperonal oxime |

TABLE 2-continued

Additional compounds of formula I produced by method 1.

| Compound No. | Starting Material for P¹ | Starting Material for C¹ | Starting Material for R₃ |
|---|---|---|---|
| 463 | N-FMOC-L-tert-butylglycine | 2-phenylethanol | 3-chlorobenzenecarbaldehyde oxime |
| 465 | N-(Cyclopentylformoyl)-L-tert-butylglycine | N/A | 4-Fluorobenzenecarbaldehyde oxime |
| 467 | N-FMOC-L-tert-butylglycine | 2-(bicyclo[2.2.1]heptan-2-yl)acetic acid | 3-chlorobenzenecarbaldehyde oxime |
| 471 | N-FMOC-L-tert-butylglycine | p-tolylmethanol | 3-chlorobenzenecarbaldehyde oxime |
| 474 | N-FMOC-L-tert-butylglycine | 2-methyl-3-(3-methyl-1H-pyrazol-1-yl)propanoic acid | 3-chlorobenzenecarbaldehyde oxime |
| 477 | N-FMOC-L-tert-butylglycine | (S)-1-methoxy-3,3-dimethyl-butan-2-amine | 3-chlorobenzenecarbaldehyde oxime |
| 484 | N-FMOC-L-tert-butylglycine | Succinic Anhydride | 3-chlorobenzenecarbaldehyde oxime |
| 487 | N-FMOC-L-tert-butylglycine | 2-(6-methoxy-3-oxo-2,3-dihydro-1H-inden-1-yl)acetic acid | 3-chlorobenzenecarbaldehyde oxime |
| 487 | N-FMOC-L-tert-butylglycine | 2-(3-oxo-2,3-dihydro-1H-inden-1-yl)acetic acid | 3-chlorobenzenecarbaldehyde oxime |
| 492 | N-FMOC-L-tert-butylglycine | tert-Butyl isocyanate | 3-chlorobenzenecarbaldehyde oxime |
| 497 | N-FMOC-L-tert-butylglycine | pyridin-3-ylmethylamine | 3-chlorobenzenecarbaldehyde oxime |
| 503 | N-FMOC-L-tert-butylglycine | trans-4-methoxycyclohexanecarboxylic acid | 3-chlorobenzenecarbaldehyde oxime |
| 504 | N-FMOC-L-tert-butylglycine | 3-(pyridin-3-yl)propanoic acid | 3-chlorobenzenecarbaldehyde oxime |
| 505 | N-FMOC-L-tert-butylglycine | 3-(2,5-dioxoimidazolidin-4-yl)propanoic acid | 3-chlorobenzenecarbaldehyde oxime |
| 512 | N-FMOC-L-tert-butylglycine | (2-fluorophenyl)methanol | 3-chlorobenzenecarbaldehyde oxime |
| 515 | N-FMOC-L-tert-butylglycine | tetrahydro-2H-pyran-3-ol | 3-chlorobenzenecarbaldehyde oxime |
| 517 | N-FMOC-L-tert-butylglycine | N/A | Nitroethane |
| 518 | N-FMOC-L-tert-butylglycine | (S)-1-(3-methylbenzyl)-5-oxopyrrolidine-2-carboxylic acid | 3-chlorobenzenecarbaldehyde oxime |
| 520 | N-FMOC-L-tert-butylglycine | benzyl chloroformate | Benzaldoxime |
| 523 | N-FMOC-L-tert-butylglycine | tetrahydro-2H-pyran-4-carboxylic acid | 3-chlorobenzenecarbaldehyde oxime |
| 526 | N-FMOC-L-tert-butylglycine | benzyl chloroformate | 3-chlorobenzenecarbaldehyde oxime |
| 528 | N-FMOC-L-tert-butylglycine | 3-(1H-indazol-1-yl)propanoic acid | 3-chlorobenzenecarbaldehyde oxime |
| 532 | N-FMOC-L-tert-butylglycine | 3-methylbutanoic acid | 3-chlorobenzenecarbaldehyde oxime |
| 533 | N/A | N/A | 4-Fluorobenzenecarbaldehyde oxime |
| 538 | N-FMOC-L-tert-butylglycine | 2-cyano-2-methyl-3-phenylpropanoic acid | 3-chlorobenzenecarbaldehyde oxime |
| 544 | N-FMOC-L-tert-butylglycine | 3-(1H-benzo[d]imidazol-1-yl)-2-methylpropanoic acid | 3-chlorobenzenecarbaldehyde oxime |
| 547 | N-FMOC-L-tert-butylglycine | N-FMOC-L-cyclohexylglycine followed by 2-pyrazine carboxylic acid | Nitropropane |
| 553 | N-FMOC-L-tert-butylglycine | 2-(2,6-dioxo-1,2,3,6-tetrahydropyrimidin-4-yl)acetic acid | 3-chlorobenzenecarbaldehyde oxime |
| 557 | N-FMOC-L-tert-butylglycine | (1R,6S)-6-(methoxycarbonyl)-cyclohex-3-enecarboxylic acid | 3-chlorobenzenecarbaldehyde oxime |
| 558 | N-FMOC-L-tert-butylglycine | phenyl isocyanate | 3-chlorobenzenecarbaldehyde oxime |
| 559 | N-FMOC-L-tert-butylglycine | tert-Butyl isocyanate | Nitropropane |
| 561 | N-FMOC-L-tert-butylglycine | (2,5-difluorophenyl)methanol | 3-chlorobenzenecarbaldehyde oxime |
| 563 | N-FMOC-L-tert-butylglycine | Pyridine 3-methanol | 3-chlorobenzenecarbaldehyde oxime |
| 566 | N-FMOC-L-tert-butylglycine | 2-(tetrahydro-2H-pyran-4-yl)acetic acid | Nitropropane |
| 576 | N-FMOC-L-tert-butylglycine | 3-pyridyl isocyanate | 3-chlorobenzenecarbaldehyde oxime |
| 580 | N-FMOC-L-tert-butylglycine | ethyl isocyanate | Benzaldoxime |
| 582 | N-FMOC-L-tert-butylglycine | 2-(thiophen-2-yl)ethanol | 3-chlorobenzenecarbaldehyde oxime |
| 583 | N-FMOC-L-tert-butylglycine | benzyl isocyanate | 3-chlorobenzenecarbaldehyde oxime |

All starting materials for $R_3$ listed in Table 2 and all other tables herein were either commercially available (nitro or oxime) or readily prepared from corresponding aldehyde precursors.

Additionally, Compound Nos. 20, 22, 53, 81, 103, 116, 166, 187, 189, 194, 197, 200, 220, 223, 226, 245, 252, 271, 204, 307, 319, 339, 354, 360, 361, 371, 392, 393, 435, 449, 506, 514, 531, and 585 were also produced by using Method 1.

Certain other compounds of the invention may be prepared as illustrated by Method 2.

Method 2:

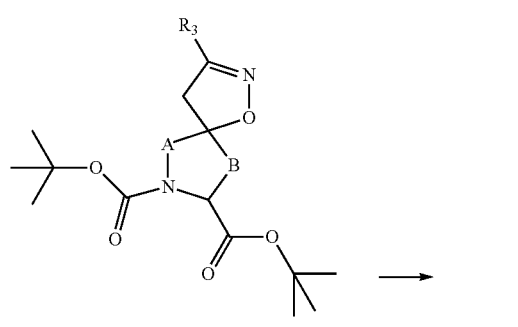

B1

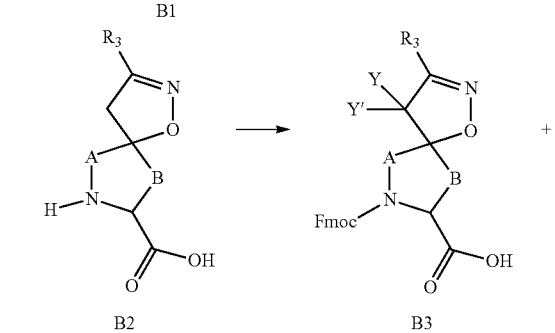

B2        B3

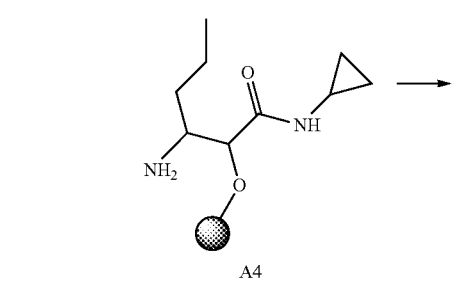

A4

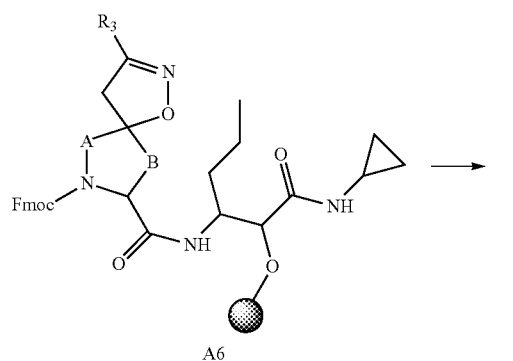

A6

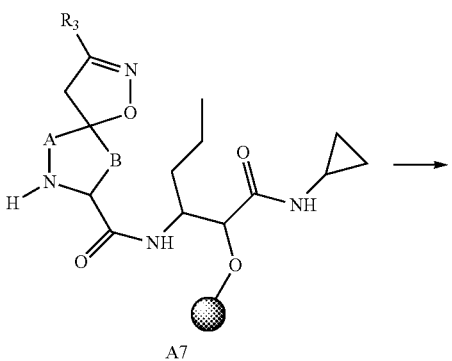

A7

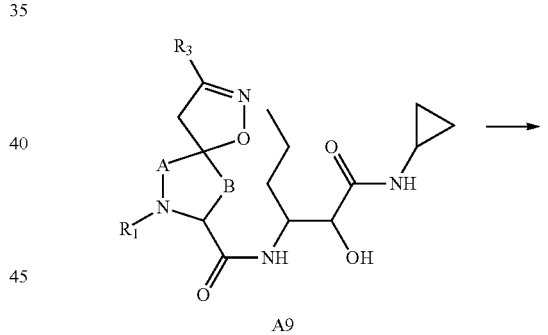

A8

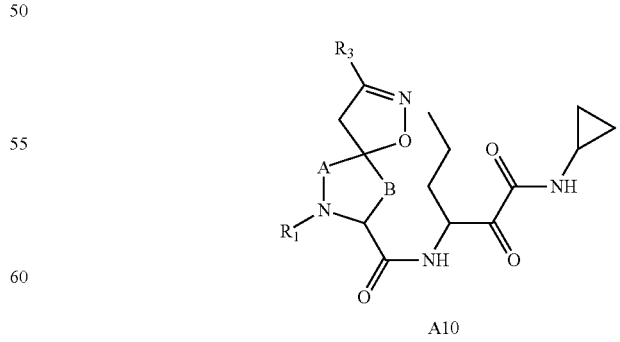

A9

A10

Referring to Method 2, the protected spiroisoxazoline B1 is deprotected to B2 which in turn is converted to the Fmoc derivative B3. Reaction of B3 with the resin bound aminoal-

Example 6

Compound No. 281

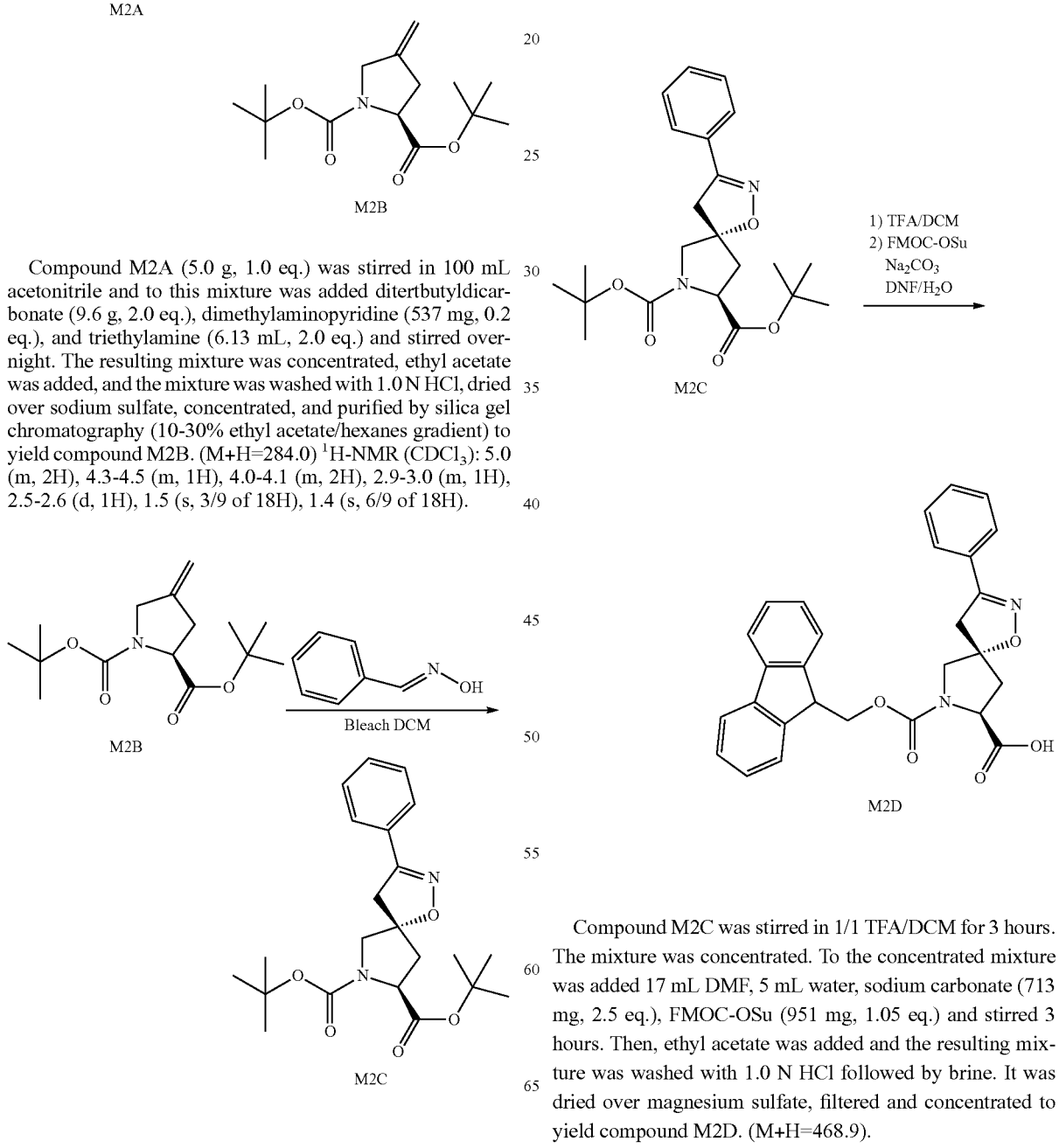

Compound M2A (5.0 g, 1.0 eq.) was stirred in 100 mL acetonitrile and to this mixture was added ditertbutyldicarbonate (9.6 g, 2.0 eq.), dimethylaminopyridine (537 mg, 0.2 eq.), and triethylamine (6.13 mL, 2.0 eq.) and stirred overnight. The resulting mixture was concentrated, ethyl acetate was added, and the mixture was washed with 1.0 N HCl, dried over sodium sulfate, concentrated, and purified by silica gel chromatography (10-30% ethyl acetate/hexanes gradient) to yield compound M2B. (M+H=284.0) $^1$H-NMR (CDCl$_3$): 5.0 (m, 2H), 4.3-4.5 (m, 1H), 4.0-4.1 (m, 2H), 2.9-3.0 (m, 1H), 2.5-2.6 (d, 1H), 1.5 (s, 3/9 of 18H), 1.4 (s, 6/9 of 18H).

Compound M2B (2.0 g, 1.0 eq.) stirred in 35 mL DCM with benzaldoxime (2.67 g, 2.0 eq.). The solution was cooled on an ice bath and to this bleach (5% NaOCl) (34.9 mL) was slowly added. The mixture was then warmed to room temperature and stirred for 2 hours. The aqueous layer was separated and extracted with DCM twice. The organics were combined and dried over magnesium sulfate, filtered and concentrated. Purified via silica gel chromatography (5-30% ethyl acetate/hexanes gradient) yielded compound M2C. (M+H=403.1)$^1$H-NMR (500 MHz, CDCl$_3$): 7.64-7.63 (m, 2H), 7.41-7.40 (m, 3H), 4.43-4.37 (t, 1H), 3.94-3.85 (dd, 1H), 3.62 (t, 1H), 3.44-3.38 (m, 1H), 3.29-3.24 (m, 1H), 2.74 (m, 1H), 2.14-2.10 (m, 1H), 1.49 (s, 9H), 1.46 (s, 9H).

Compound M2C was stirred in 1/1 TFA/DCM for 3 hours. The mixture was concentrated. To the concentrated mixture was added 17 mL DMF, 5 mL water, sodium carbonate (713 mg, 2.5 eq.), FMOC-OSu (951 mg, 1.05 eq.) and stirred 3 hours. Then, ethyl acetate was added and the resulting mixture was washed with 1.0 N HCl followed by brine. It was dried over magnesium sulfate, filtered and concentrated to yield compound M2D. (M+H=468.9).

847
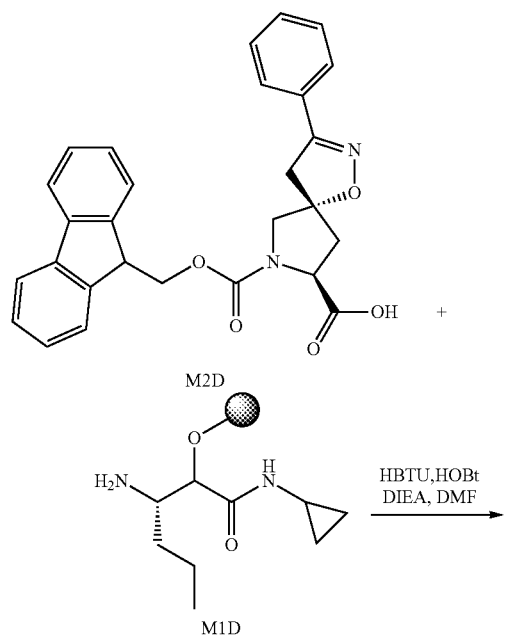
M2D
M1D
848
-continued
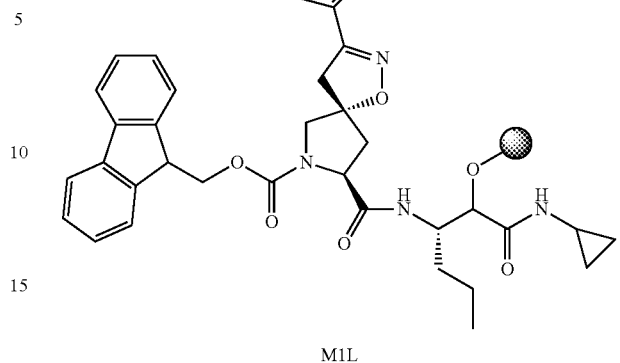
M1L
Compound M2D (1.26 g, 2.0 eq.) was stirred in DMF with M1D (2.5 g, 1.0 eq.), HBTU (12 mL of 0.5 M in DMF, 5.0 eq.), HOBt (6 mL of 1.0 M in DMF, 5.0 eq.), and Hünig's base (2.09 mL, 10.0 eq.) overnight. The mixture was drained and washed with DMF (thrice) and DCM (thrice) to yield compound M1L. (M+H=637.0).
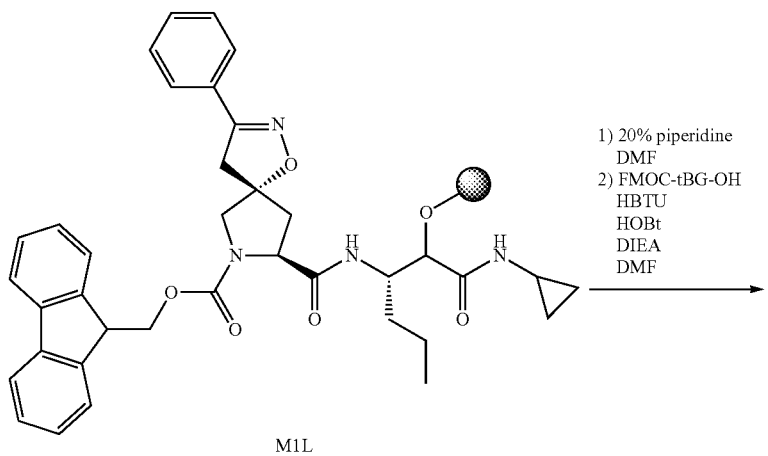
M1L
1) 20% piperidine
   DMF
2) FMOC-tBG-OH
   HBTU
   HOBt
   DIEA
   DMF
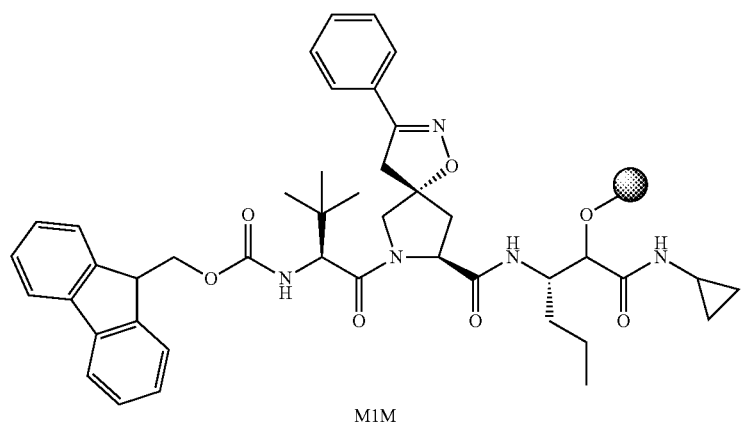
M1M Compound M1L (0.4 g, 1.0 eq.) was shaken in 20% piperidine/DMF for 10 minutes before being filtered and washed with DMF (thrice) followed by DCM (thrice). This process was repeated. The resulting resin was shaken overnight with a solution of FMOC-tert-butylglycine (200 mg 3.0 eq.), HBTU (1.15 mL of 0.5 M in DMF, 3.0 eq.), HOBt (0.58 mL of 1.0 M in DMF, 3.0 eq.), and DIEA (167 uL, 5.0 eq.) in 2 mL DMF. The resin was then filtered and washed with DMF (thrice) and DCM (thrice) to give compound M1M. (M+H=750.1).

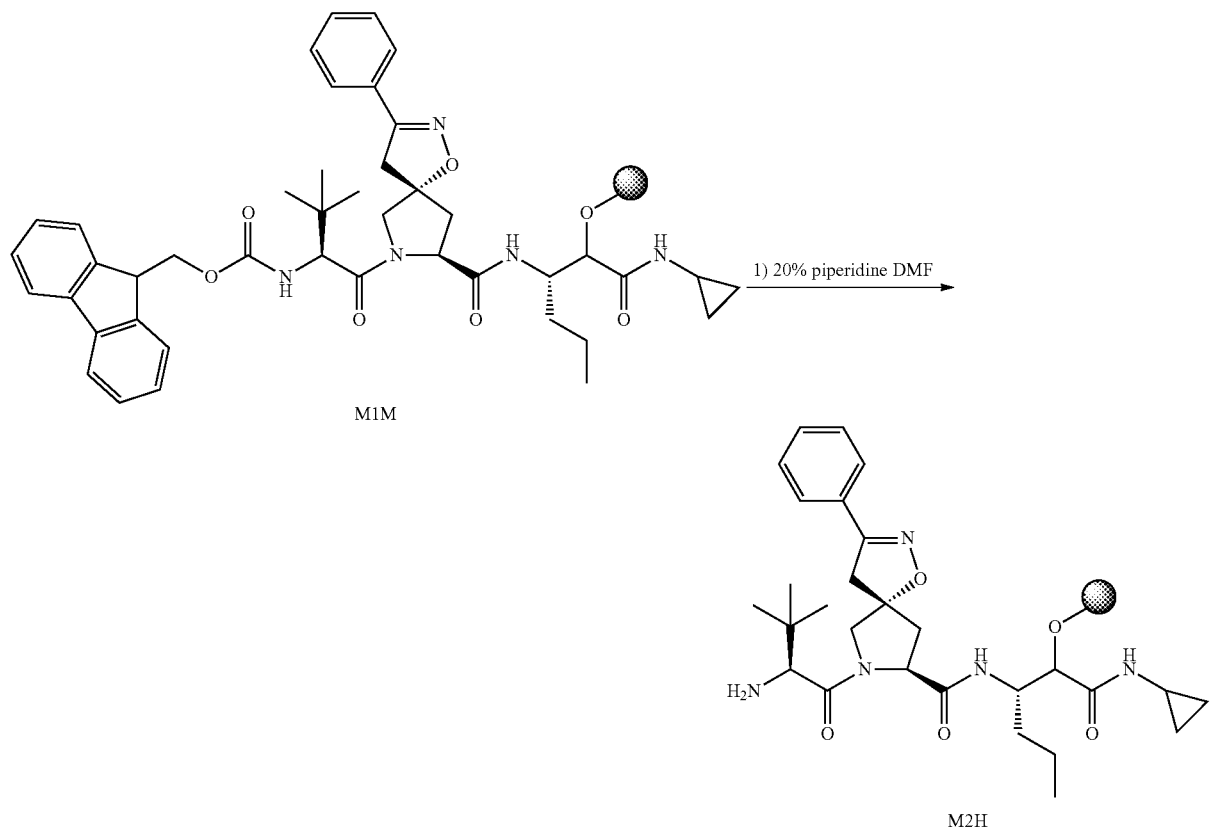

Compound M1M (0.4 g, 1.0 eq.) was shaken in 20% piperidine/DMF for 10 minutes and the resin was filtered and washed with DMF (thrice) followed by DCM (thrice). This process was repeated to give Compound M2H.

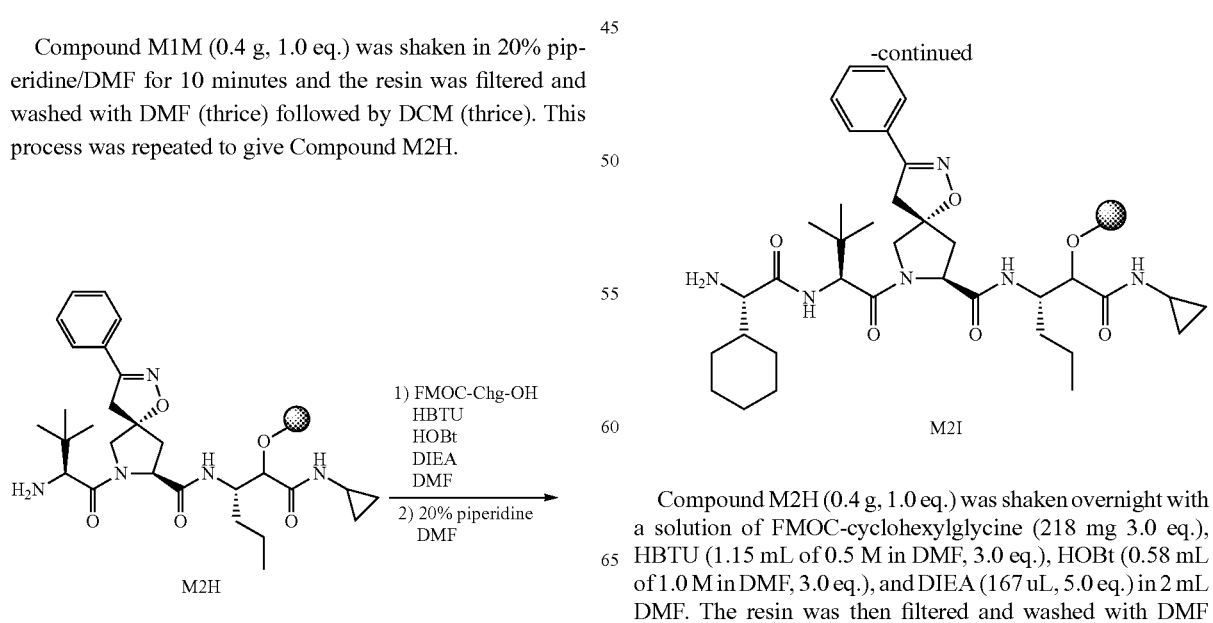

Compound M2H (0.4 g, 1.0 eq.) was shaken overnight with a solution of FMOC-cyclohexylglycine (218 mg 3.0 eq.), HBTU (1.15 mL of 0.5 M in DMF, 3.0 eq.), HOBt (0.58 mL of 1.0 M in DMF, 3.0 eq.), and DIEA (167 uL, 5.0 eq.) in 2 mL DMF. The resin was then filtered and washed with DMF (thrice) and DCM (thrice). The resin was then treated with 20% piperidine/DMF for 10 minutes. The resin was filtered and washed with DMF (thrice) followed by DCM (thrice). This process was repeated to give Compound M2I.

Compound M2I (0.4 g, 1.0 eq.) was shaken overnight with a solution of pyrazine carboxylic acid (71 mg, 3.0 eq.), HBTU (1.15 mL of 0.5 M in DMF, 3.0 eq.), HOBt (0.58 mL of 1.0 M in DMF, 3.0 eq.), and DIEA (167 uL, 5.0 eq.) in 2 mL DMF.

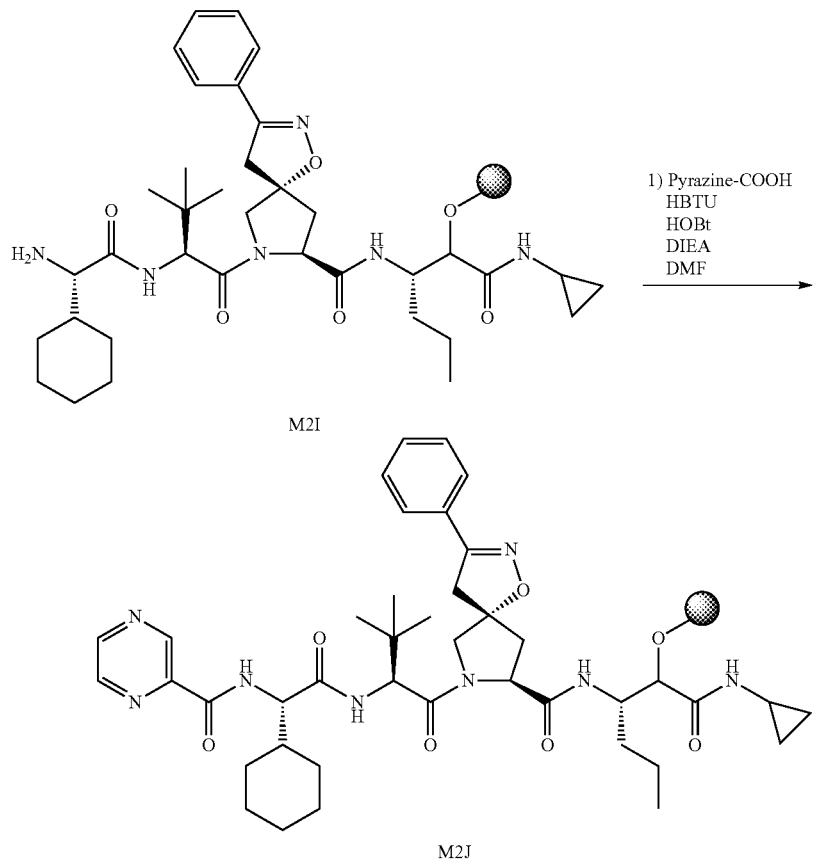

40

The resin was then filtered and washed with DMF (thrice) and (thrice) to give compound M2J. (M+H=772.9).

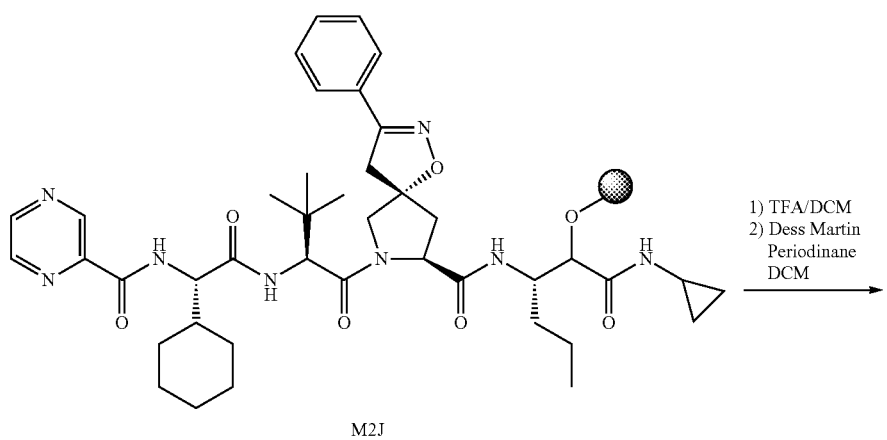

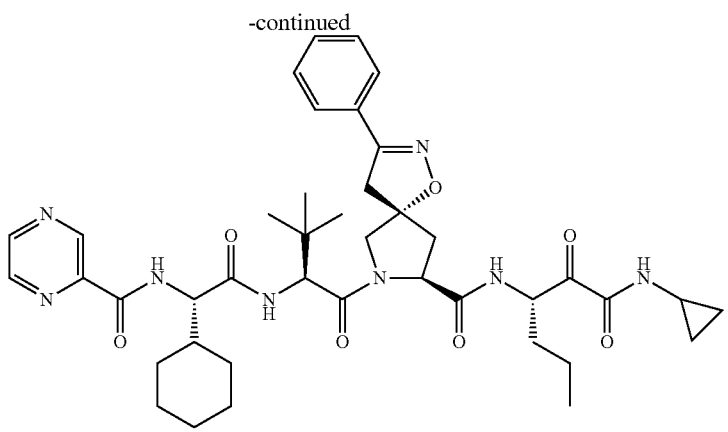

Compound No. 281

Compound M2J (0.4 g, 1.0 eq.) was stirred in 1/1 TFA/DCM for 2 hours. The resin was drained and washed with DCM (thrice). The result was concentrated all organics and added DCM followed by Dess Martin Periodinane (97 mg, 3.0 eq.). Stirred for 1 hour and added 1N $Na_2S_2O_3$ and stirred. The solution was purified by silica gel chromatography (10-90% ethyl acetate/hexanes gradient) to yield 42 mg of Compound No. 281. (M+H=771.0). $^1$H-NMR (500 MHz, $CDCl_3$): 9.38 (d, 1H), 8.75 (d, 1H), 8.56 (t, 1H), 8.31 (d, 1H), 7.64-7.62 (m, 2H), 7.42-7.38 (m, 3H), 7.33 (d, 1H), 7.15 (s, 1H), 6.89 (d, 1H), 5.45-5.41 (m, 1H), 4.85 (t, 1H), 4.69 (d, 1H), 4.57-4.54 (m, 1H), 4.26 (d, 1H), 3.76 (d, 1H), 3.46-3.35 (m, 2H), 2.82 (td, 1H), 2.56 (d, 2H), 1.96-1.87 (m, 2H), 1.76 (m, 4H), 1.65-1.59 (m, 2H), 1.48-1.42 (m, 2H), 1.24 (m, 2H), 1.09 (m, 2H), 0.97 (s, 9H), 0.93 (t, 2H), 0.88-0.84 (m, 2H), 0.65 (t, 2H).

Listed below in Table 3 are additional compounds of Formula I prepared by Method 2.

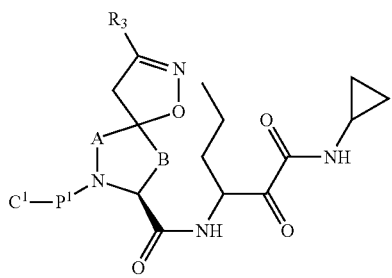

TABLE 3

Additional compounds of formula I produced by method 2.

| Compound No. | Starting Material for $P^1$ | Starting Material for $C^1$ | Starting Material for $R_3$ |
|---|---|---|---|
| 40 | N-((S)-tetrahydrofuran-3-yloxy)carbonyl)-L-tert-butylglycine | N/A | 2,6-Dichloro-benzaldoxime |
| 51 | N/A | 1H-pyrrole-2-carboxylic acid | Piperonal oxime |
| 80 | N/A | 1H-pyrrole-2-carboxylic acid | Benzaldoxime |
| 101 | N-FMOC-L-tert-butylglycine | 1-Naphthylsulfonyl chloride | Benzaldoxime |

TABLE 3-continued

Additional compounds of formula I produced by method 2.

| Compound No. | Starting Material for $P^1$ | Starting Material for $C^1$ | Starting Material for $R_3$ |
|---|---|---|---|
| 147 | N-FMOC-L-tert-butylglycine | N-FMOC-L-cyclohexylglycine followed by 2-pyrazine carboxylic acid | 2,6-Dichloro-benzaldoxime |
| 151 | N-Alloc-L-tert-butylglycine | N/A | Benzaldoxime |
| 202 | N-((S)-tetrahydrofuran-3-yloxy)carbonyl)-L-tert-butylglycine | N/A | Benzaldoxime |
| 228 | N-FMOC-L-tert-butylglycine | Acetic acid | Benzaldoxime |
| 281 | N-FMOC-L-tert-butylglycine | N-FMOC-L-cyclohexylglycine followed by 2-pyrazine carboxylic acid | Benzaldoxime |
| 325 | N-FMOC-L-tert-butylglycine | Acetic acid | Piperonal oxime |
| 327 | N-Alloc-L-tert-butylglycine | N/A | Piperonal oxime |
| 343 | N-((S)-tetrahydrofuran-3-yloxy)carbonyl)-L-tert-butylglycine | N/A | Piperonal oxime |
| 428 | N-FMOC-L-tert-butylglycine | N-FMOC-L-cyclohexylglycine followed by 2-pyrazine carboxylic acid | Benzaldoxime |
| 464 | N/A | 1H-pyrrole-2-carboxylic acid | Piperonal oxime |
| 491 | N-((S)-tetrahydrofuran-3-yloxy)carbonyl)-L-tert-butylglycine | N/A | Benzaldoxime |
| 527 | N-((S)-tetrahydrofuran-3-yloxy)carbonyl)-L-tert-butylglycine | N/A | Piperonal oxime |
| 536 | N-FMOC-L-tert-butylglycine | 1-Naphthylsulfonyl chloride | Piperonal oxime |
| 570 | N-FMOC-L-tert-butylglycine | Acetic acid | Piperonal oxime |
| 578 | N-FMOC-L-tert-butylglycine | Acetic acid | Benzaldoxime |
| 584 | N/A | 1H-pyrrole-2-carboxylic acid | Benzaldoxime |

Certain other compounds of Formula I may be prepared as illustrated by Method 3.

Method 3:

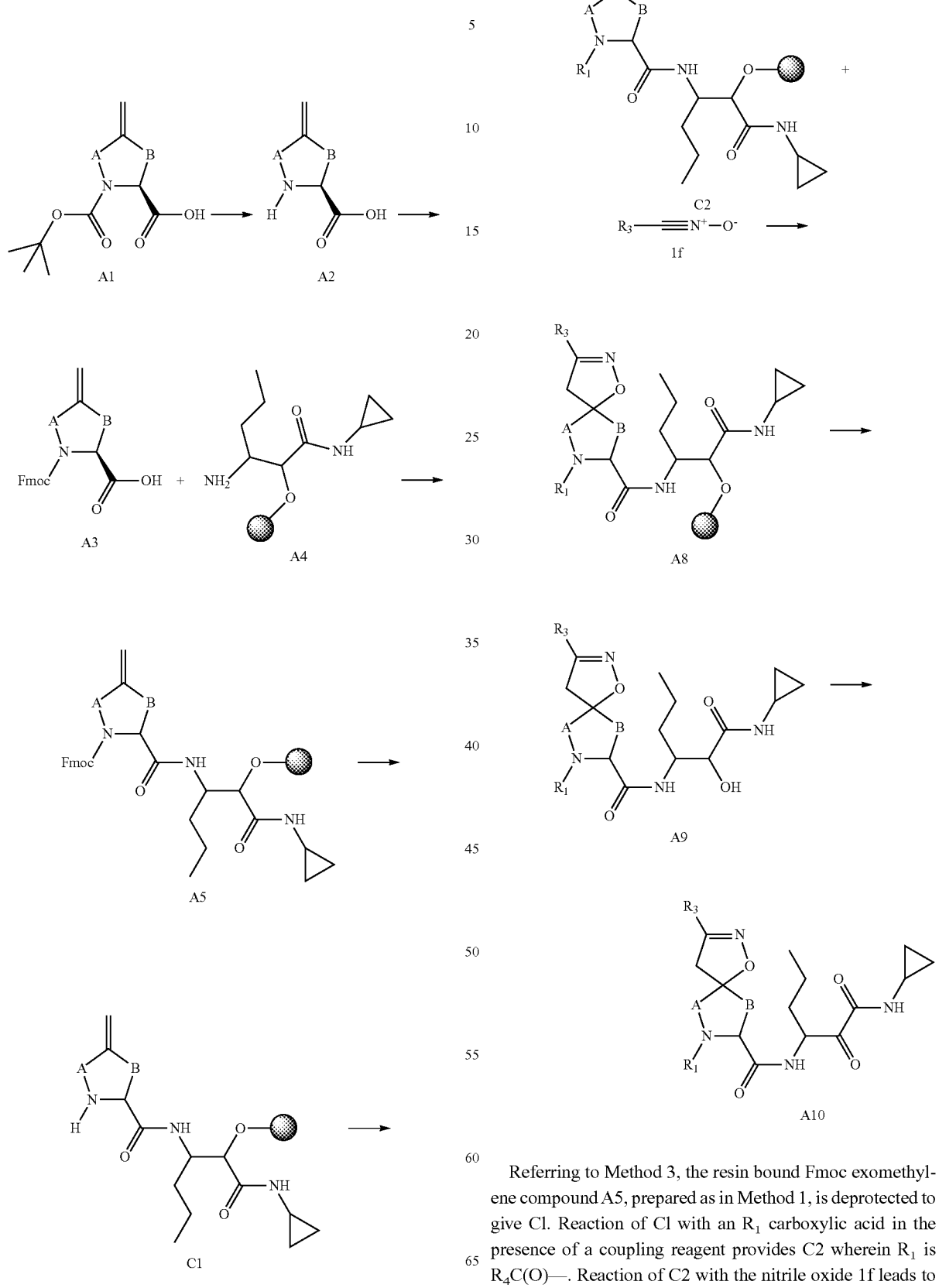

Referring to Method 3, the resin bound Fmoc exomethylene compound A5, prepared as in Method 1, is deprotected to give C1. Reaction of C1 with an $R_1$ carboxylic acid in the presence of a coupling reagent provides C2 wherein $R_1$ is $R_4C(O)$—. Reaction of C2 with the nitrile oxide 1f leads to A8 which is converted to A10 as illustrated in Method 1.

Example 7

Compound No. 239

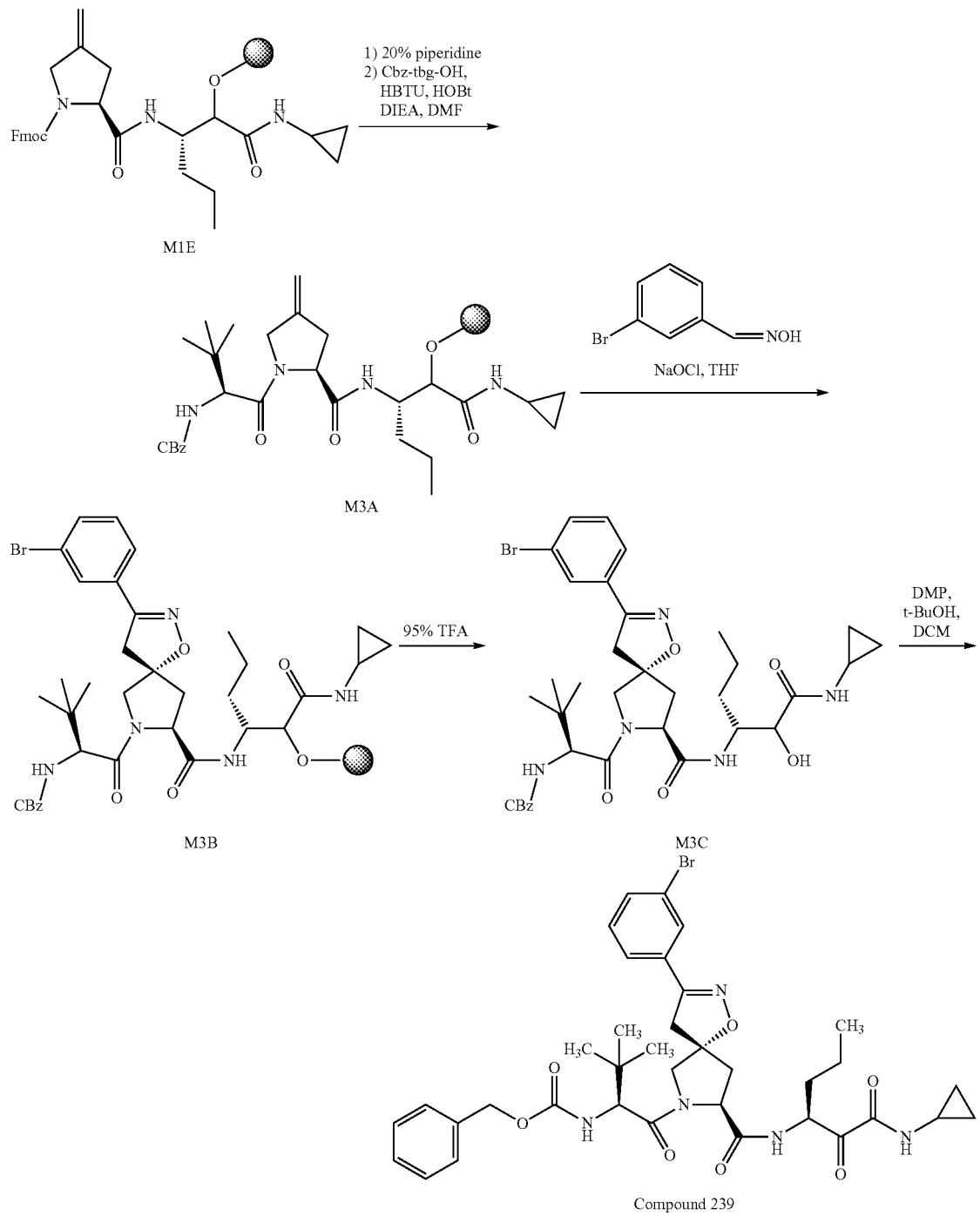

The resin M1E (0.47 mmol) was shaken in 20% piperidine/DMF for 10 minutes and then filtered and washed with DMF and DCM. The resulting resin was shaken again overnight with a solution of Cbz-tBG-OH (374 mg, 3.0 eq.), HOBT (2.82 mL of 0.5 M in DMF, 3.0 eq.), HBTU (2.82 of 0.5 M in DMF, 3.0 eq.), and DIEA (0.493 mL, 6.0 eq.). The resin was then filtered and washed with DMF and DCM to give the resin compound M3A (0.47 g), which was used in next reaction without further purification.

The Cbz resin M3A (0.0611 mmol) in THF was shaken with 3-bromo-phenyl oxime (10 eq.) and bleach (5% NaOH) (20 eq.) for 12 hours. The resin was then filtered and washed with water, DMF, DCM to give the resin M3B.

The resin M3B was shaken with 95% TFA in water for 30 minutes and the resulting solution was concentrated in vacuo to give the compound M3C (0.031 mmol), (M+1) 740, which was used in next reaction without further purification.

A solution of the compound M3C (0.031 mmol) in DCM (3 mL) was stirred with Dess-Martin Periodinane (26 mg, 2 eq.) and t-BuOH (26 uL). After stirring for 1 hour, sodium thiosulfate was added to above mixture. The product was extracted with EtOAc and the combined organic layer was then washed with water, $NaHCO_3$, brine and concentrated in vacuo and purified by Gilson Prep HPLC to afford Compound No. 239. (M+1) 738.

Example 8

Compound No. 535

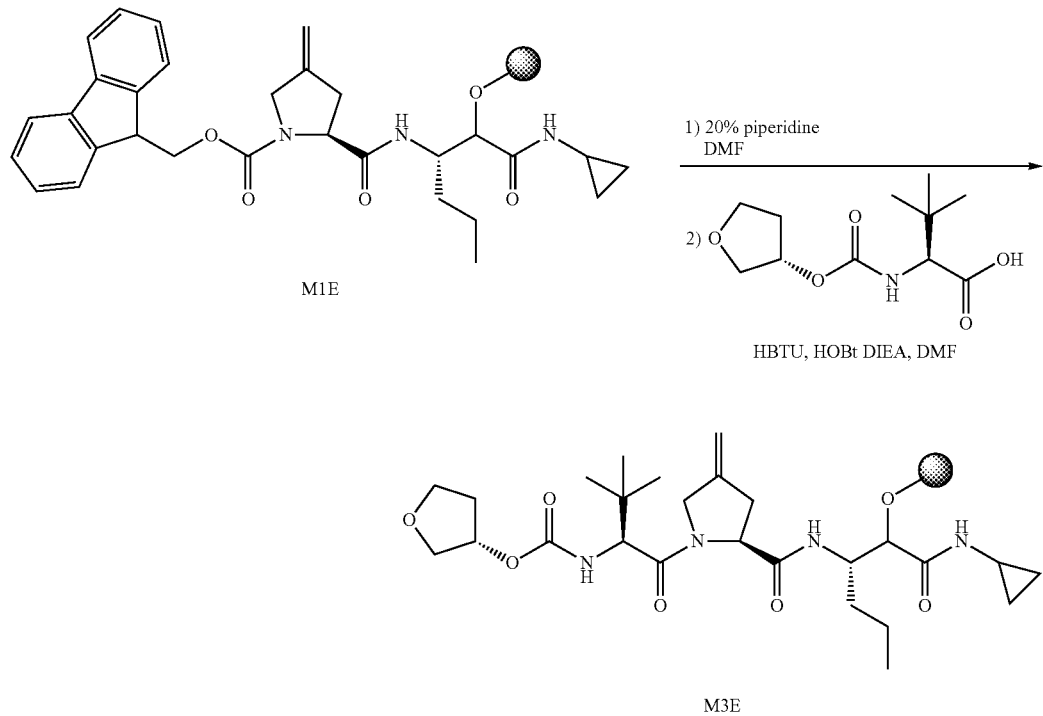

Compound M1E (10.0 g, 1.0 eq.) was shaken in 20% piperidine/DMF for 10 minutes. The resin was filtered and washed with DMF (thrice) followed by DCM (thrice). This process was repeated. The resulting resin was shaken overnight with a solution of (S)-2,3-dimethyl-2-(((S)-tetrahydrofuran-3-yloxy)carbonylamino)butanoic acid (3.46 g, 3.0 eq.), HBTU (28.2 mL of 0.5 M in DMF, 3.0 eq.), HOBt (14.1 mL of 1.0M in DMF, 3.0 eq.), and DIEA (4.91 mL, 6.0 eq.) in DMF. The resin was then filtered and washed with DMF (thrice) and DCM (thrice) to give compound M3E. (M+H=523.1)

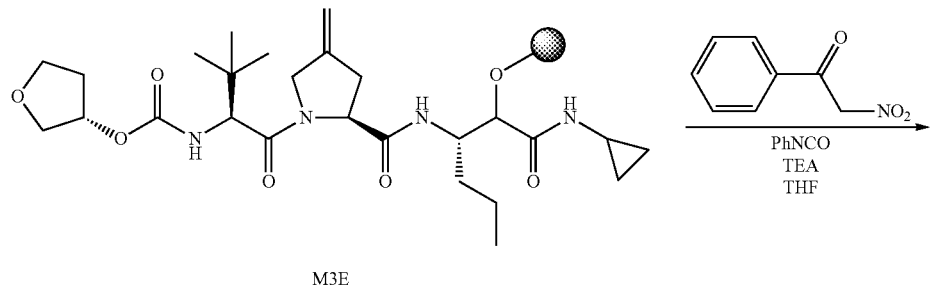

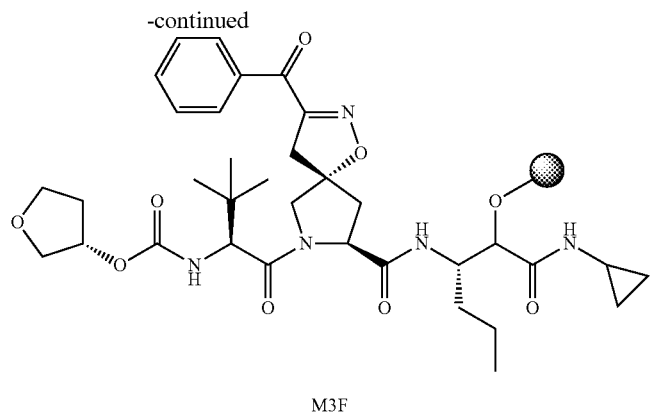

M3F

Compound M3E (300 mg, 1.0 eq.) was stirred in THF and 2-nitro-1-phenylethanone (272 mg, 10.0 eq.) was added to the mixture followed by phenyl isocyanate (179 uL, 10.0 eq.) and catalytic TEA (10 uL). The resulting mixture was shaken overnight, drained, and washed with DMF, THF, and DCM (thrice each) to give compound M3F (M+H=669.8).

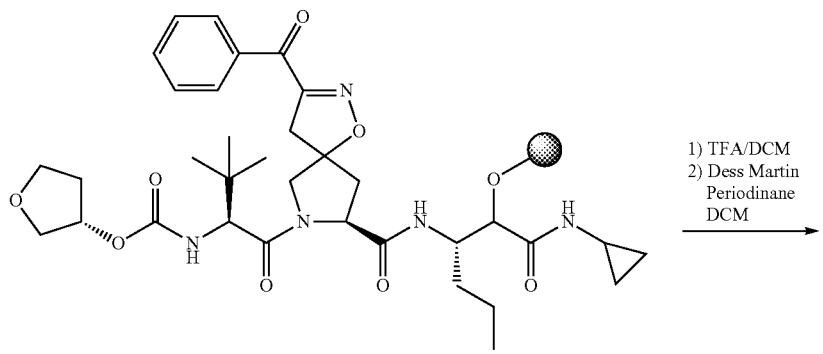

M3F

1) TFA/DCM
2) Dess Martin Periodinane DCM

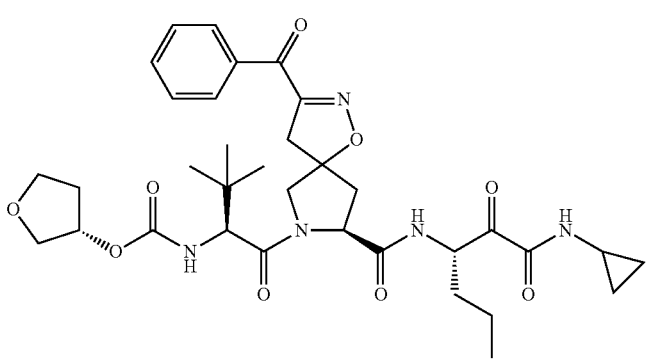

Compound No. 535

Compound M3F (0.4 g, 1.0 eq.) was stirred in 1/1 TFA/DCM for 2 hours. The resin was drained and washed with DCM (thrice), all organics were concentrated, and DCM was added followed by Dess-Martin Periodinane (97 mg, 3.0 eq.). The resulting mixture was stirred for 1 hour, 1 N $Na_2S_2O_3$ was added and again, stirred. The reaction mixture was purified via silica gel chromatography (10-90% ethyl acetate/hexanes gradient) to yield Compound No. 535. M+H=668.1. $^1$H-NMR (500 MHz, $CDCl_3$): 8.19 (d, 2H), 7.61 (t, 1H), 7.47 (t, 2H), 7.19 (d, 1H), 6.93 (d, 1H), 5.52 (d, 1H), 5.37-5.33 (m, 1H, 5.24 (s, 1H), 4.78 (t, 1H), 4.32-4.29 (m, 2H), 3.93-3.79 (m, 4H), 3.70 (d, 1H), 3.48-3.36 (m, 2H), 2.79 (td, 1H), 2.68-2.63 (m, 1H), 2.55-2.50 (m, 1H), 2.12-2.04 (m, 1H), 1.96-1.89 (m, 1H), 1.66-1.59 (m, 1H), 1.47-1.37 (m, 2H), 1.00 (s, 9H), 0.94-0.81 (m, 6H), 0.63-0.57 (m, 2H).

Listed below in Table 4 are additional compounds of Formula I prepared by Method 3.

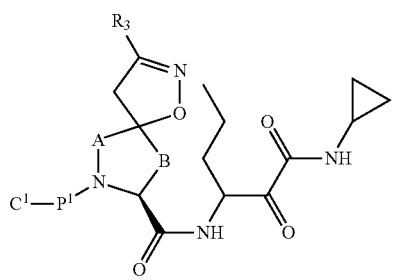

TABLE 4

Additional compounds of formula I produced by method 3.

| Compound No. | Starting Material for P¹ | Starting Material for C¹ | Starting Material for R₃ |
|---|---|---|---|
| 4 | N-((S)-tetrahydrofuran-3-yloxy)carbonyl)-L-tert-butylglycine | N/A | 3-Chloro-5-fluorobenzaldoxime |
| 8 | N-((S)-tetrahydrofuran-3-yloxy)carbonyl)-L-tert-butylglycine | N/A | 3-(Cyclopentyloxy)-4-methoxybenzaldehyde |
| 9 | N-((S)-tetrahydrofuran-3-yloxy)carbonyl)-L-tert-butylglycine | N/A | 3,5-Di(trifluoromethyl)benzaldoxime |
| 11 | N/A | (S)-2,5-dioxopyrrolidin-1-yl tetrahydrofuran-3-yl carbonate | 3-fluoro-4-methylbenzaldoxime |
| 15 | N-((S)-tetrahydrofuran-3-yloxy)carbonyl)-L-tert-butylglycine | N/A | 3-Chloro-4-methoxybenzaldoxime |
| 16 | N-FMOC-L-tert-butylglycine | 2-(tetrahydro-2H-pyran-4-yl)acetic acid | 4-Methoxybenzaldoxime |
| 25 | N-((S)-tetrahydrofuran-3-yloxy)carbonyl)-L-tert-butylglycine | N/A | 3,5-Difluorobenzaldoxime |
| 32 | N-((S)-tetrahydrofuran-3-yloxy)carbonyl)-L-tert-butylglycine | N/A | 3,4-Dichlorobenzaldoxime |
| 36 | N-((S)-tetrahydrofuran-3-yloxy)carbonyl)-L-tert-butylglycine | N/A | 3,4-Dimethylbenzaldoxime |
| 47 | N/A | (S)-2,5-dioxopyrrolidin-1-yl tetrahydrofuran-3-yl carbonate | 4-Ethylbenzaldoxime |
| 52 | N-((S)-tetrahydrofuran-3-yloxy)carbonyl)-L-tert-butylglycine | N/A | 4-Trifluoromethylbenzaldoxime |
| 55 | N-FMOC-L-tert-butylglycine | 2-cyclohexylacetic acid | 4-Chlorobenzaldoxime |
| 56 | N-FMOC-L-tert-butylglycine | 2-cyclohexylacetic acid | 3,5-Dichlorobenzaldoxime |
| 64 | N-((S)-tetrahydrofuran-3-yloxy)carbonyl)-L-tert-butylglycine | N/A | 4-Trifluoromethylbenzaldoxime |
| 66 | N-FMOC-L-tert-butylglycine | 2-cyclohexylacetic acid | 3-Chloro-4-fluorobenzaldoxime |
| 70 | N-((S)-tetrahydrofuran-3-yloxy)carbonyl)-L-tert-butylglycine | N/A | Cyclopentanecarboxaldehyde |
| 78 | N-FMOC-L-tert-butylglycine | 2-(tetrahydro-2H-pyran-4-yl)acetic acid | 3,4-Dichlorobenzaldoxime |
| 82 | N-FMOC-L-tert-butylglycine | 2-(tetrahydro-2H-pyran-4-yl)acetic acid | Piperonal oxime |
| 83 | N-((S)-tetrahydrofuran-3-yloxy)carbonyl)-L-tert-butylglycine | N/A | 3-Chlorobenzaldoxime |
| 95 | N-FMOC-L-tert-butylglycine | 2-cyclohexylacetic acid | 3-Chloro-5-fluorobenzaldoxime |
| 106 | N-((S)-tetrahydrofuran-3-yloxy)carbonyl)-L-tert-butylglycine | N/A | 3,5-Difluorobenzaldoxime |
| 109 | N-((S)-tetrahydrofuran-3-yloxy)carbonyl)-L-tert-butylglycine | N/A | 3-Methyl-4-chlorobenzaldoxime |
| 142 | N-((S)-tetrahydrofuran-3-yloxy)carbonyl)-L-tert-butylglycine | N/A | Cyclohexanecarboxaldehyde |
| 149 | N-((S)-tetrahydrofuran-3-yloxy)carbonyl)-L-tert-butylglycine | N/A | 3-Trifluoromethylbenzaldoxime |
| 150 | N-((S)-tetrahydrofuran-3-yloxy)carbonyl)-L-tert-butylglycine | N/A | 2,2-Dimethylchromane-6-carbaldehyde |
| 171 | N-FMOC-L-tert-butylglycine | 2-(tetrahydro-2H-pyran-4-yl)acetic acid | 3-Cyanobenzaldoxime |
| 177 | N-FMOC-L-tert-butylglycine | 2-(tetrahydro-2H-pyran-4-yl)acetic acid | 4-Cyanobenzaldoxime |
| 191 | N-((S)-tetrahydrofuran-3-yloxy)carbonyl)-L-tert-butylglycine | N/A | 3,5-Dimethyl-4-methoxybenzaldoxime |
| 196 | N-((S)-tetrahydrofuran-3-yloxy)carbonyl)-L-tert-butylglycine | N/A | 3,4-Dimethoxybenzaldoxime |
| 198 | N/A | (S)-2,5-dioxopyrrolidin-1-yl tetrahydrofuran-3-yl carbonate | 3,5-Dimethyl-4-methoxybenzaldoxime |
| 215 | N-((S)-tetrahydrofuran-3-yloxy)carbonyl)-L-tert-butylglycine | N/A | 3,4,5-Trifluorobenzaldoxime |
| 222 | N/A | (S)-2,5-dioxopyrrolidin-1-yl tetrahydrofuran-3-yl carbonate | 2,2-Difluoro-1,3-benzodioxole-5-carboxaldehyde |
| 224 | N-((S)-tetrahydrofuran-3-yloxy)carbonyl)-L-tert-butylglycine | N/A | 3,5-Dimethyl-4-methoxybenzaldoxime |
| 229 | N-((S)-tetrahydrofuran-3-yloxy)carbonyl)-L-tert-butylglycine | N/A | Methyl 4-nitrobutyrate |
| 234 | N-FMOC-L-tert-butylglycine | 2-(tetrahydro-2H-pyran-4-yl)acetic acid | 3-Chloro-5-fluorobenzaldoxime |
| 236 | N-((S)-tetrahydrofuran-3-yloxy)carbonyl)-L-tert-butylglycine | N/A | 3-Chloro-4-methoxybenzaldoxime |
| 239 | N-CBZ-L-tert-butylglycine | N/A | 3-Bromobenzaldoxime |

TABLE 4-continued

Additional compounds of formula I produced by method 3.

| Compound No. | Starting Material for P$^1$ | Starting Material for C$^1$ | Starting Material for R$_3$ |
|---|---|---|---|
| 240 | N/A | (S)-tetrahydrofuran-3-yl-carbonate | 4-Trifluoromethyl-benzaldoxime |
| 244 | N-((S)-tetrahydrofuran-3-yloxy)carbonyl)-L-tert-butylglycine | N/A | 3-Trifluoro-methoxy-benzaldoxime |
| 251 | N-((S)-tetrahydrofuran-3-yloxy)carbonyl)-L-tert-butylglycine | N/A | Phenylnitroethane |
| 257 | N-((S)-tetrahydrofuran-3-yloxy)carbonyl)-L-tert-butylglycine | N/A | 3-Phenylbenzaldoxime |
| 258 | N-((S)-tetrahydrofuran-3-yloxy)carbonyl)-L-tert-butylglycine | N/A | 3-fluoro-5-trifluoromethyl-benzaldoxime |
| 270 | N-FMOC-L-tert-butylglycine | 2-(tetrahydro-2H-pyran-4-yl)acetic acid | 3-Chloro-4-fluoro-benzaldoxime |
| 274 | N/A | (S)-tetrahydrofuran-3-yl-carbonate | 3,5-Dichloro-benzaldoxime |
| 279 | N-FMOC-L-tert-butylglycine | 2-(tetrahydro-2H-pyran-4-yl)acetic acid | 3-Chloro-4-methoxy-benzaldoxime |
| 285 | N-FMOC-L-tert-butylglycine | 2-(tetrahydro-2H-pyran-4-yl)acetic acid | 3,5-Dichloro-benzaldoxime |
| 299 | N-FMOC-L-tert-butylglycine | 2-(tetrahydro-2H-pyran-4-yl)acetic acid | 4-Chlorobenzaldoxime |
| 301 | N-((S)-tetrahydrofuran-3-yloxy)carbonyl)-L-tert-butylglycine | N/A | 3-Chloro-4-fluoro-benzaldoxime |
| 306 | N-((S)-tetrahydrofuran-3-yloxy)carbonyl)-L-tert-butylglycine | N/A | 3,5-Dichloro-benzaldoxime |
| 314 | N-((S)-tetrahydrofuran-3-yloxy)carbonyl)-L-tert-butylglycine | N/A | Methyl 4-formyl-benzoate |
| 316 | N-((S)-tetrahydrofuran-3-yloxy)carbonyl)-L-tert-butylglycine | N/A | 2,2-Difluoro-1,3-benzodioxole-5-carboxaldehyde |
| 318 | N-((S)-tetrahydrofuran-3-yloxy)carbonyl)-L-tert-butylglycine | N/A | 4-Chlorobenzaldoxime |
| 322 | N-((S)-tetrahydrofuran-3-yloxy)carbonyl)-L-tert-butylglycine | N/A | 3-Chloro-5-fluoro-benzaldoxime |
| 323 | N-FMOC-L-tert-butylglycine | 2-cyclohexylacetic acid | 3,4-Dichloro-benzaldoxime |
| 330 | N-((S)-tetrahydrofuran-3-yloxy)carbonyl)-L-tert-butylglycine | N/A | 3,5-Di(trifluoromethyl)-benzaldoxime |
| 348 | N/A | (S)-tetrahydrofuran-3-yl-carbonate | 3-fluoro-5-trifluoromethyl-benzaldoxime |
| 353 | N-((S)-tetrahydrofuran-3-yloxy)carbonyl)-L-tert-butylglycine | N/A | Methyl 3-formyl-benzoate |
| 362 | N-FMOC-L-tert-butylglycine | 2-cyclohexylacetic acid | 3,5-Dimethyl-4-methoxybenzaldoxime |
| 363 | N-((S)-tetrahydrofuran-3-yloxy)carbonyl)-L-tert-butylglycine | N/A | 2,2-Difluoro-1,3-benzodioxole-5-carboxaldehyde |
| 364 | N-((S)-tetrahydrofuran-3-yloxy)carbonyl)-L-tert-butylglycine | N/A | 4-Chloro phenylglyoxylohydroxamyl chloride |
| 385 | N-((S)-tetrahydrofuran-3-yloxy)carbonyl)-L-tert-butylglycine | N/A | 4-Methylbenzaldoxime |
| 391 | N-((S)-tetrahydrofuran-3-yloxy)carbonyl)-L-tert-butylglycine | N/A | 3,5-Dichloro-benzaldoxime |
| 403 | N-((S)-tetrahydrofuran-3-yloxy)carbonyl)-L-tert-butylglycine | N/A | 2-Chloro-6-fluoro-benzaldoxime |
| 405 | N/A | (S)-tetrahydrofuran-3-yl-carbonate | 4-Isopropyl-benzaldoxime |
| 413 | N/A | (S)-tetrahydrofuran-3-yl-carbonate | 3-Methyl-4-fluoro-benzaldoxime |
| 414 | N/A | (S)-tetrahydrofuran-3-yl-carbonate | 3,4,5-Trifluoro-benzaldoxime |
| 423 | N-((S)-tetrahydrofuran-3-yloxy)carbonyl)-L-tert-butylglycine | N/A | 3-fluoro-4-methyl-benzaldoxime |
| 425 | N-((S)-tetrahydrofuran-3-yloxy)carbonyl)-L-tert-butylglycine | N/A | 3-(4-Pyridyl)benzaldehyde |
| 434 | N-CBZ-L-tert-butylglycine | N/A | 2,3-Dimethoxy-benzaldoxime |
| 436 | N-FMOC-L-tert-butylglycine | 2-cyclohexylacetic acid | 3-Methyl-4-chloro-benzaldoxime |
| 444 | N-((S)-tetrahydrofuran-3-yloxy)carbonyl)-L-tert-butylglycine | N/A | 3-Methylbenzaldoxime |
| 448 | N-((S)-tetrahydrofuran-3-yloxy)carbonyl)-L-tert-butylglycine | N/A | 3-(4-chlorophenyl(-2,1-benzisoxazole-5-carbaldehyde oxime |
| 451 | N/A | (S)-tetrahydrofuran-3-yl-carbonate | 3-Trifluoromethyl-4-fluoro-benzaldoxime |
| 455 | N-((S)-tetrahydrofuran-3-yloxy)carbonyl)-L-tert-butylglycine | N/A | 3,4,5-Trifluoro-benzaldoxime |
| 456 | N-((S)-tetrahydrofuran-3-yloxy)carbonyl)-L-tert-butylglycine | N/A | 1,4-benzodioxan-6-carboxaldehyde |
| 472 | N-((S)-tetrahydrofuran-3-yloxy)carbonyl)-L-tert-butylglycine | N/A | 2-Furanaldoxime |
| 480 | N-((S)-tetrahydrofuran-3-yloxy)carbonyl)-L-tert-butylglycine | N/A | Methyl 3-formyl-benzoate |
| 481 | N-((S)-tetrahydrofuran-3-yloxy)carbonyl)-L-tert-butylglycine | N/A | 3-(Carboxy)benzaldoxime |

TABLE 4-continued

Additional compounds of formula I produced by method 3.

| Compound No. | Starting Material for P¹ | Starting Material for C¹ | Starting Material for R₃ |
|---|---|---|---|
| 482 | N-((S)-tetrahydrofuran-3-yloxy)carbonyl)-L-tert-butylglycine | N/A | 2-Chloro-6-fluoro-benzaldoxime |
| 486 | N-FMOC-L-tert-butylglycine | 2-cyclohexylacetic acid | 3-Chloro-4-methoxy-benzaldoxime |
| 490 | N-FMOC-L-tert-butylglycine | 2-(tetrahydro-2H-pyran-4-yl)acetic acid | 3-Methyl-4-chloro-benzaldoxime |
| 498 | N-((S)-tetrahydrofuran-3-yloxy)carbonyl)-L-tert-butylglycine | N/A | 3-fluoro-5-trifluoromethyl-benzaldoxime |
| 509 | N-((S)-tetrahydrofuran-3-yloxy)carbonyl)-L-tert-butylglycine | N/A | 3-Trifluoromethyl-benzaldoxime |
| 511 | N-((S)-tetrahydrofuran-3-yloxy)carbonyl)-L-tert-butylglycine | N/A | 4-Nitro-benzaldoxime |
| 519 | N-((S)-tetrahydrofuran-3-yloxy)carbonyl)-L-tert-butylglycine | N/A | 3,5-Dimethyl-benzaldoxime |
| 524 | N/A | (S)-tetrahydrofuran-3-yl-carbonate | 4-Trifluoro-methoxy-benzaldoxime |
| 525 | N-FMOC-L-tert-butylglycine | 2-(tetrahydro-2H-pyran-4-yl)acetic acid | 3-Methoxy-benzaldoxime |
| 530 | N-((S)-tetrahydrofuran-3-yloxy)carbonyl)-L-tert-butylglycine | N/A | 4-Hydroxy-benzaldoxime |
| 535 | N-((S)-tetrahydrofuran-3-yloxy)carbonyl)-L-tert-butylglycine | N/A | 2-nitro-l-phenyl-ethanone |
| 539 | N-FMOC-L-tert-butylglycine | 2-(tetrahydro-2H-pyran-4-yl)acetic acid | 3-Methyl-4-fluoro-benzaldoxime |
| 543 | N-((S)-tetrahydrofuran-3-yloxy)carbonyl)-L-tert-butylglycine | N/A | 4-(Carboxy)ben-zaldoxime |
| 545 | N-((S)-tetrahydrofuran-3-yloxy)carbonyl)-L-tert-butylglycine | N/A | 3-Trifluoromethyl-4-fluoro-benzaldoxime |
| 548 | N-FMOC-L-tert-butylglycine | 2-cyclohexylacetic acid | 3-Chloro-4-fluorobenzald-oxime |
| 550 | N-((S)-tetrahydrofuran-3-yloxy)carbonyl)-L-tert-butylglycine | N/A | 3-fluoro-4-methyl-benzaldoxime |
| 551 | N-((S)-tetrahydrofuran-3-yloxy)carbonyl)-L-tert-butylglycine | N/A | Methyl 4-formyl-benzoate |
| 555 | N-((S)-tetrahydrofuran-3-yloxy)carbonyl)-L-tert-butylglycine | N/A | 3-Methyl-4-fluoro-benzaldoxime |
| 560 | N-((S)-tetrahydrofuran-3-yloxy)carbonyl)-L-tert-butylglycine | N/A | 3-Trifluoromethyl-benzaldoxime |
| 572 | N-FMOC-L-tert-butylglycine | 2-(tetrahydro-2H-pyran-4-yl)acetic acid | 3,5-Dimethyl-4-methoxybenzald-oxime |

Certain other compounds of Formula I may be prepared as illustrated by Method 4.

Method 4:

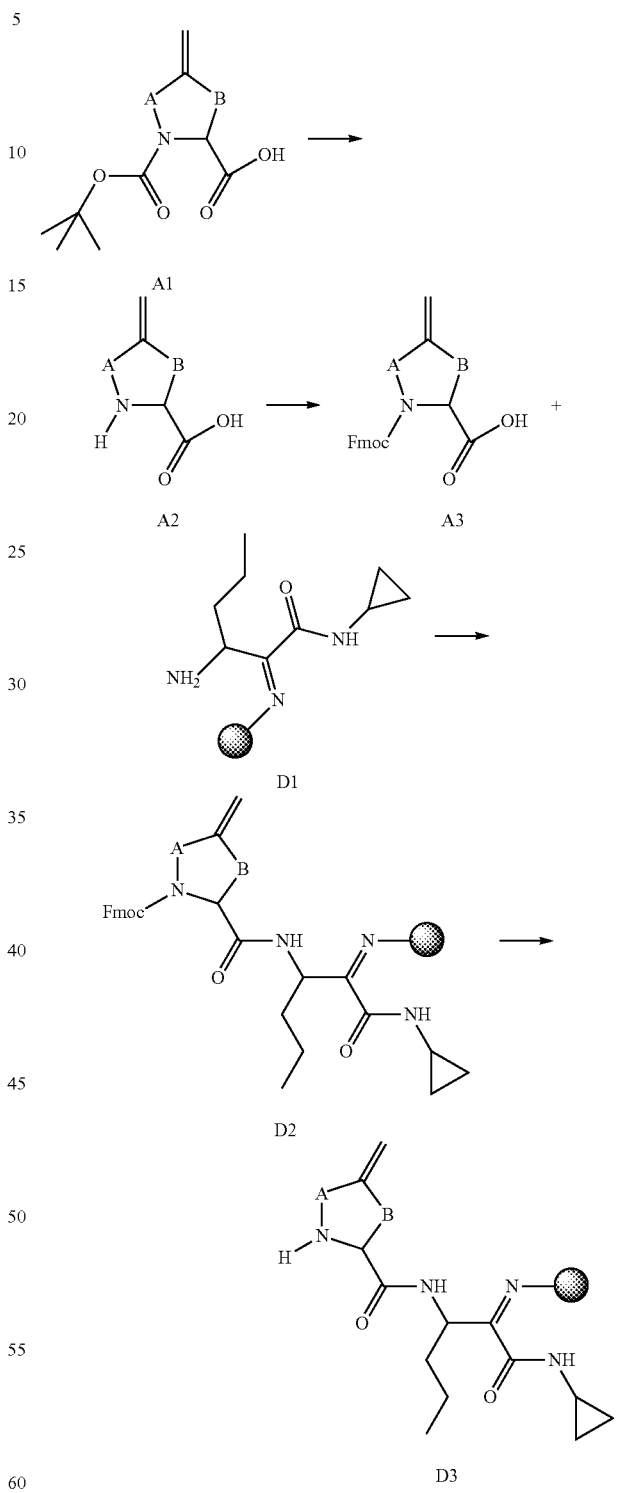

Referring to Method 4, the Fmoc derivative A3 is prepared as described in Method 1. Reaction of A3 with the resin bound imino amide D1 in the presence of a coupling reagent provides the compound bound resin D2. The resin bound imino amide D1 may be prepared from the diketo compound X31 by reaction with an amino resin such as, for example, a derivatized aminomethylated polystyrene, e.g., X32. Deprotection of D2 provides D3 which reacts with an $R_1$ carboxylic acid in the presence of a coupling reagent to provide D4 wherein $R_1$ is $R_4C(O)$—. Reaction of D4 with the nitrile oxide if provides D5 which on hydrolysis from the resin provides A10.

Example 9

Compound No. 303

DMF (10 times), DCM (4 times) and dried to afford resin M4B.

To the resin M4B (20 g, 8 mmol) was added 20% piperidine in DMF (100 mL), shaken for 1 hour, and then washed with DMF (10 times), DCM (4 times). To the resin was added a mixture of Fmoc-tert-butylglycine (5.6 g, 16 mmol), HBTU (6.1 g, 16 mmol), HOBt (2.2 g, 16 mmol) and $(iPr)_2NEt$ (2.9 mL, 16 mmol) in DMF (100 mL). The suspension was shaken

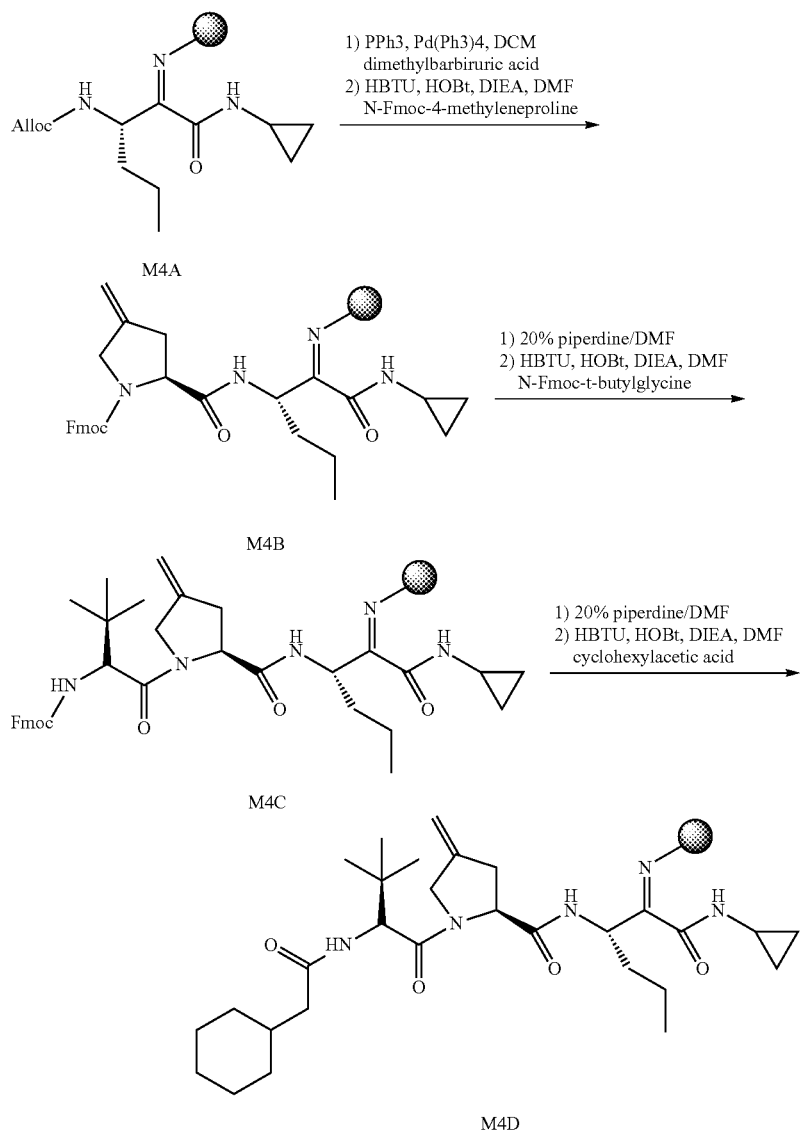

To a suspension of resin M4A, which has the same structure as X33, (20 g, 0.4 mmol/g, 8 mmol) in DCM (100 mL) was added $PPh_3$ (21 g, 80 mmol), dimethyl barbituric acid (12.5 g, 80 mmol) and $Pd(PPh_3)_4$ (920 mg, 0.8 mmol). The suspension was shaken overnight, drained, washed with DMF (10 times) and DCM (4 times). N-Fmoc-4-methyleneproline (3.0 g, 8.8 mmol), HBTU (3.3 g, 8.8 mmol) and HOBt (1.1 g, 8.8 mmol) and DIEA (1.6 mL, 8.8 mmol) were dissolved in DMF (100 mL). The solution was added to the resin and shaken overnight. The resin was then drained, washed with overnight, drained, washes with DMF (10 times), DCM (4 times) and dried to afford the resin M4C.

To the resin M4C (20 g, 8 mmol) was added 20% piperidine in DMF (100 mL), shaken for 1 hour, and then washed with DMF (10 times), DCM (4 times). To the resin was added a mixture of cyclohexylacetic acid (1.42 g, 10 mmol), HBTU (3.8 g, 10 mmol), HOBt (1.35 g, 10 mmol) and $(iPr)_2NEt$ (1.8 mL, 10 mmol) in DMF (100 mL). The suspension was shaken overnight, drained, washes with DMF (10 times), DCM (4 times) and dried to afford the resin M4D.

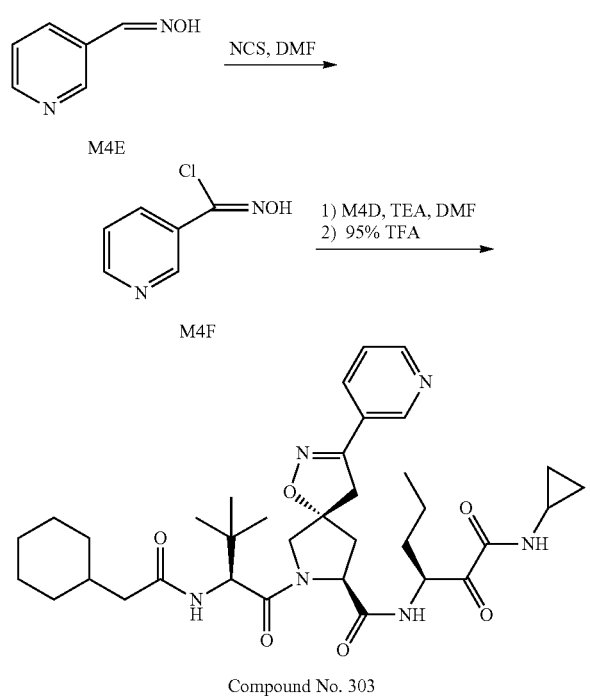

Compound No. 303

A solution of 3-pyridinealdoxime (M4E) (122 mg, 1 mmol) in DMF (3 mL) was added NCS (134 mg, 1 mmol). The mixture was heated to 50-60° C. for 30 minutes. After cooling down to room temperature, the 3-pyridinechloroxime (M4F) solution was added to a resin M4D (300 mg, 0.12 mmol). To the mixture was added TEA (0.14 mL, 1 mmol) and the reaction mixture was heated to 50-60° C. for 4 hours. The reaction mixture was drained and washed with DMF (6 times) and DCM (6 times). The resin was treated with 95% TFA for 5 hours. The mixture was drained, and washed with DCM. The filtrate was concentrated in vacuo, purified from column 50-100% EtOAc/Hex to afford 7 mg colorless solid as product Compound No. 303. HPLC 5.7-6.4 minutes; MS 651.5 and LC-MS 3.9 minutes.

Listed below in Table 5 are additional compounds produced by Method 4.

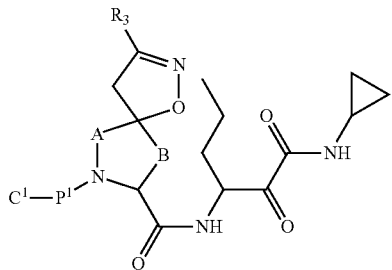

TABLE 5

Additional compounds of formula I produced by method 4.

| Compound No. | Starting Material for P¹ | Starting Material for C¹ | Starting Material for R₃ |
|---|---|---|---|
| 41 | N-FMOC-L-tert-butylglycine | 2-Cyclohexylacetic acid | 5-Bromoprydine-3-carbaldehyde |
| 179 | N-FMOC-L-tert-butylglycine | 2-Cyclohexylacetic acid | 5-Bromo-2-Furaldehyde |

TABLE 5-continued

Additional compounds of formula I produced by method 4.

| Compound No. | Starting Material for P¹ | Starting Material for C¹ | Starting Material for R₃ |
|---|---|---|---|
| 230 | N-FMOC-L-tert-butylglycine | 2-Cyclohexylacetic acid | 2-methylbenzofuran-3-carbaldehyde |
| 303 | N-FMOC-L-tert-butylglycine | 2-Cyclohexylacetic acid | 3-Pyridine-carboxaldehyde |
| 495 | N-FMOC-L-tert-butylglycine | 2-Cyclohexylacetic acid | 4-Chloro-1-methyl-1H-pyrazole-3-carbaldehyde |
| 552 | N-FMOC-L-tert-butylglycine | 2-Cyclohexylacetic acid | 2,3-Dihydrobenzo[b]-furan-5-carboxaldehyde |

Certain other compounds of the invention may be prepared as illustrated in Methods 5A and 5B.

Method 5A:

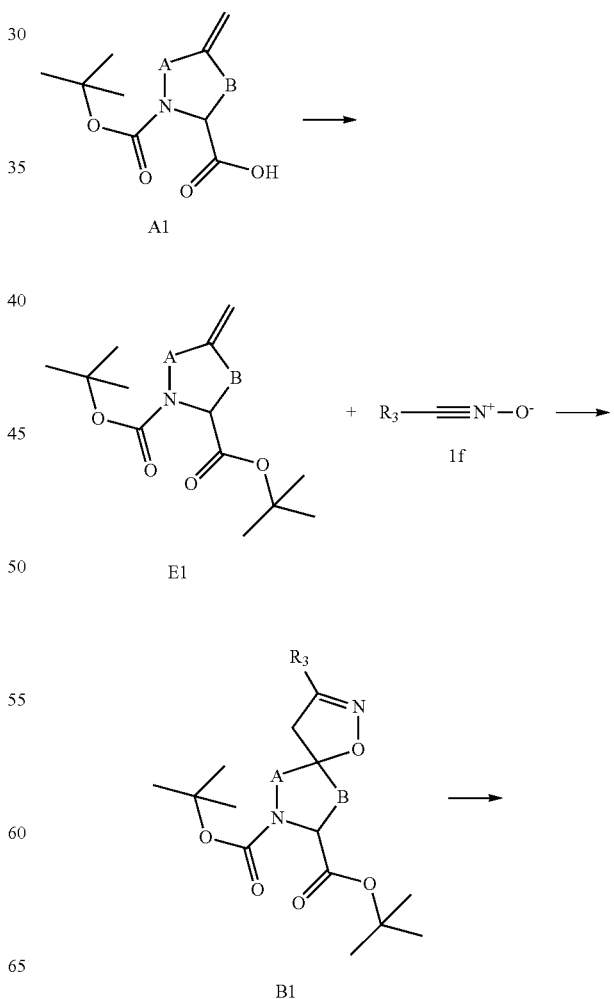

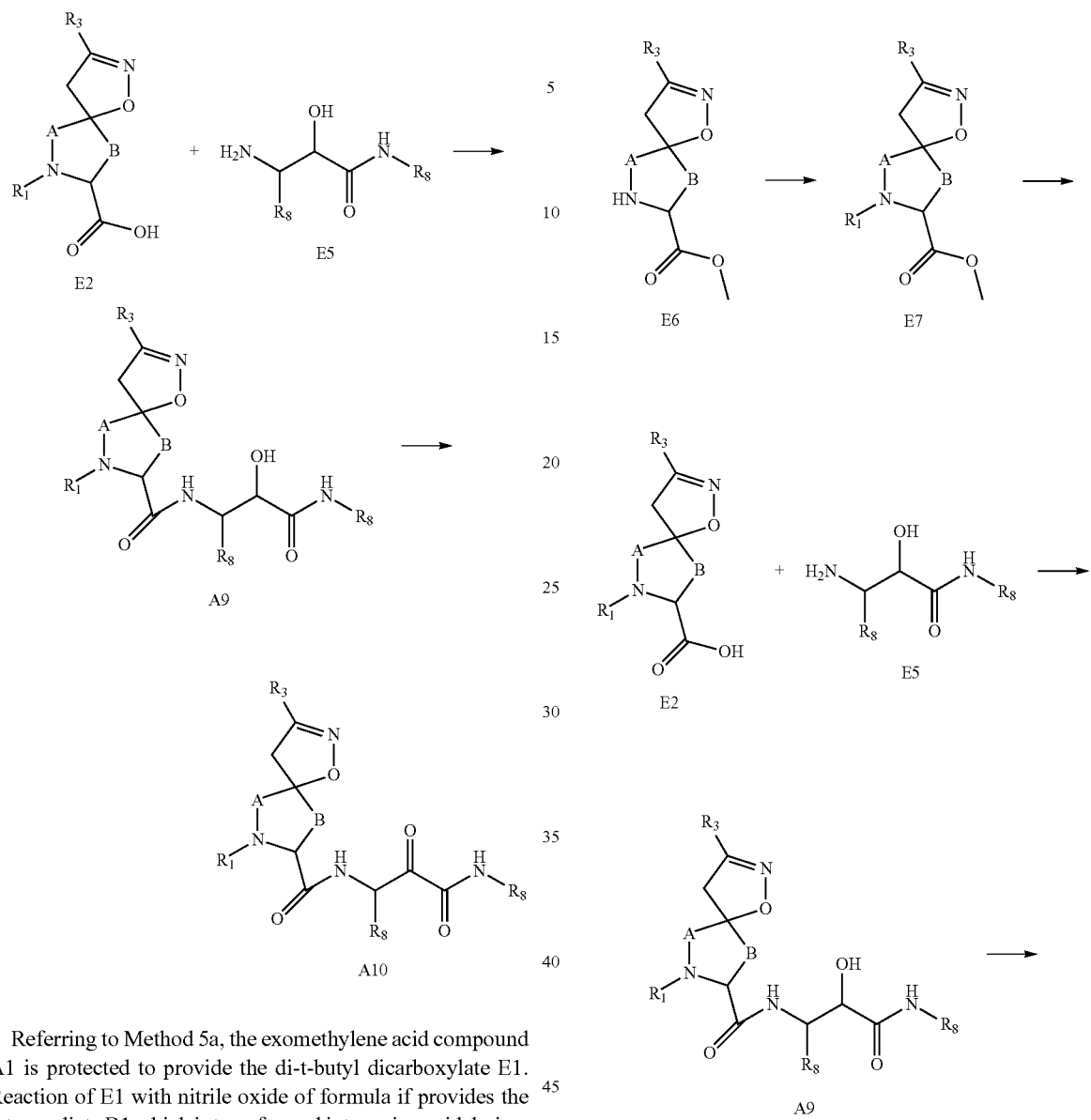

Referring to Method 5a, the exomethylene acid compound A1 is protected to provide the di-t-butyl dicarboxylate E1. Reaction of E1 with nitrile oxide of formula if provides the intermediate B1 which is transformed into amino acid derivative E2. Reaction of E2 with an aminoalcohol E5 provides A9. Compound A9 is converted to A10 as described in Method 1.

Method 5B:

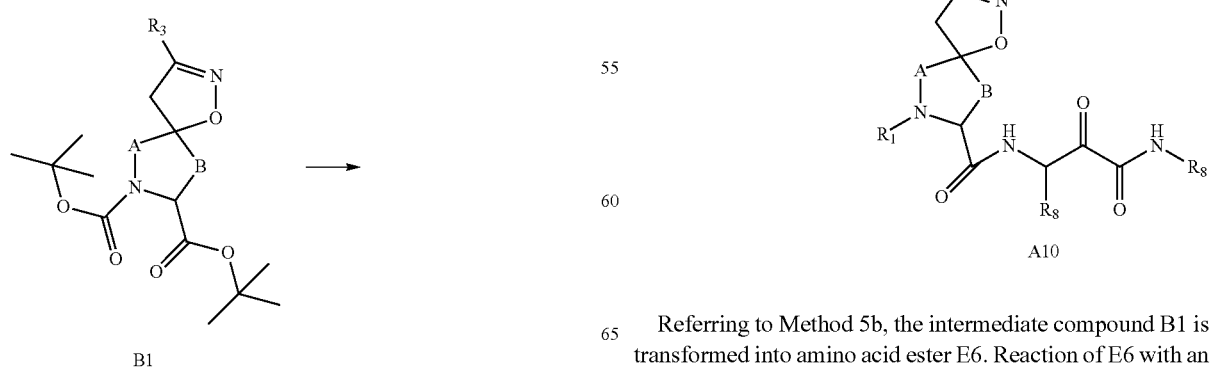

Referring to Method 5b, the intermediate compound B1 is transformed into amino acid ester E6. Reaction of E6 with an $R_1$ carboxylic acid in the presence of a coupling reagent provides E7 wherein $R_1$ is $R_4C(O)$—. E7 is deprotected to provide E2 which is converted to A10 as described in Method 1.

Example 10

Compound No. 422

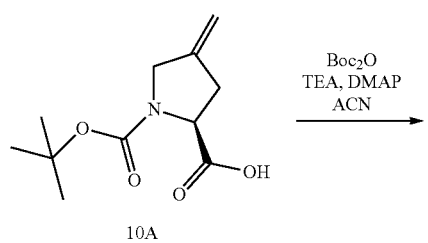

10A

Compound 10A (5.0 g, 1.0 eq.) was stirred in 100 mL acetonitrile and to the solution were added ditertbutyldicarbonate (9.6 g, 2 eq.), dimethylaminopyridine (537 mg, 0.2 eq.), and triethylamine (6.13 mL, 2.0 eq.). The mixture was stirred overnight, concentrated, added ethyl acetate, washed with 1.0N HCl, dried over sodium sulfate, concentrated, and purified with silica gel chromatography (10-30% ethyl acetate/hexanes gradient) to give compound M2B. (M+H=284.0). $^1$H-NMR (CDCl$_3$): 5.0 (m, 2H), 4.3-4.5 (m, 1H), 4.0-4.1 (m, 2H), 2.9-3.0 (m, 1H), 2.5-2.6 (d, 1H), 1.5 (s, 3/9 of 18H), 1.4 (s, 6/9 of 18H).

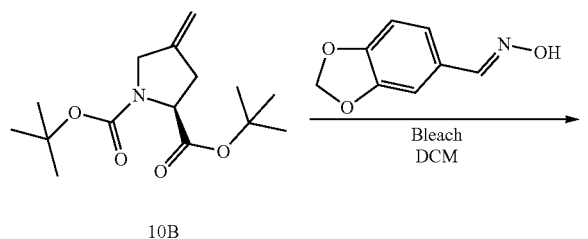

10B

10C

Compound 10B (10.0 g, 1.0 eq.) was stirred in 175 mL DCM with piperonaloxime (11.5 g, 2.0 eq.). The solution was cooled on an ice bath and to it added bleach (175 mL) slowly. The mixture was then warmed to room temperature, stirred for 2 hours, separated and its aqueous layer extracted with DCM twice. Organics were combined and dried over magnesium sulfate, filtered and concentrated. The residue was purified and separated diastereomers by silica gel chromatography (5-30% ethyl acetate/hexanes gradient) to yield 4.1 g of Compound 10C. (M+H=446.9.) $^1$H-NMR (CDCl$_3$): 7.25 (m, 1H), 7.0 (d, 1H), 6.8 (d, 1H), 6.0 (s, 2H), 4.6-4.4 (m, 1H), 4.0-3.8 (m, 1H), 3.7-3.6 (m, 1H) 3.4-3.3 (m, 1H), 3.3-3.2 (m, 1H), 2.8-2.7 (m, 1H), 2.3-2.2 (m, 1H), 1.5 (s, 9H), 1.4 (s, 9H).

Alternatively, compound 10B was prepared by the following procedures:

Preparation: (S)-di-tert-butyl 4-methylenepyrrolidine-1,2-dicarboxylate

Procedure 1

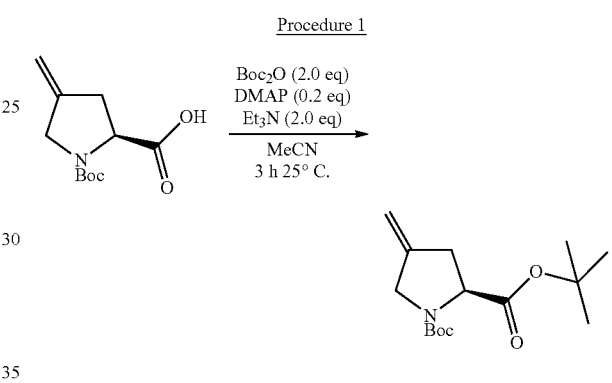

Triethylamine (2 eq.) was added to a solution of (S)-1-(tert-butoxycarbonyl)-4-methylenepyrrolidine-2-carboxylic acid (1.0 eq.), di-tert-butyldicarbonate (2.0 eq.), and DMAP (0.2 eq.) in acetonitrile (10 vol) at ambient temperature. The reaction mixture was stirred for 16 h, then diluted with isopropyl acetate (25 vol). A wash with water (20 vol., twice) was followed by a filtration over Na$_2$SO$_4$ and solvent removal. The crude product was purified by filtration through a pad of silica gel (37 vol silica, first flush with heptane (80 vol), second flush with 10% ethyl acetate in heptane (30 vol)). Removal of solvent from the second flush gave compound 10B.

Procedure 2

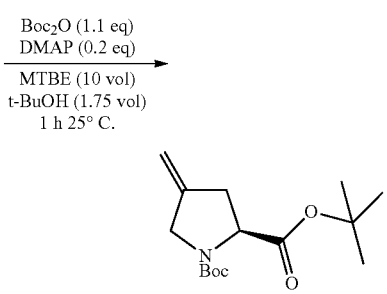

A solution of di-tert-butyl dicarbonate (1.1 eq.) in MTBE (2 vol.) was added to a mixture of (S)-1-(tert-butoxycarbonyl)-4-methylenepyrrolidine-2-carboxylic acid (1.0 eq.) and DMAP (0.2 eq.) in MTBE (8 vol) and t-butanol (1.75 vol.). The mixture was stirred for 1 hour, at which point gas evolution ceased. The mixture was washed with 1 N HCl (3 vol.), then saturated aqueous NaHCO₃ (3 vol.) and then brine (3 vol.). The solvent is then removed to afford compound 10B.

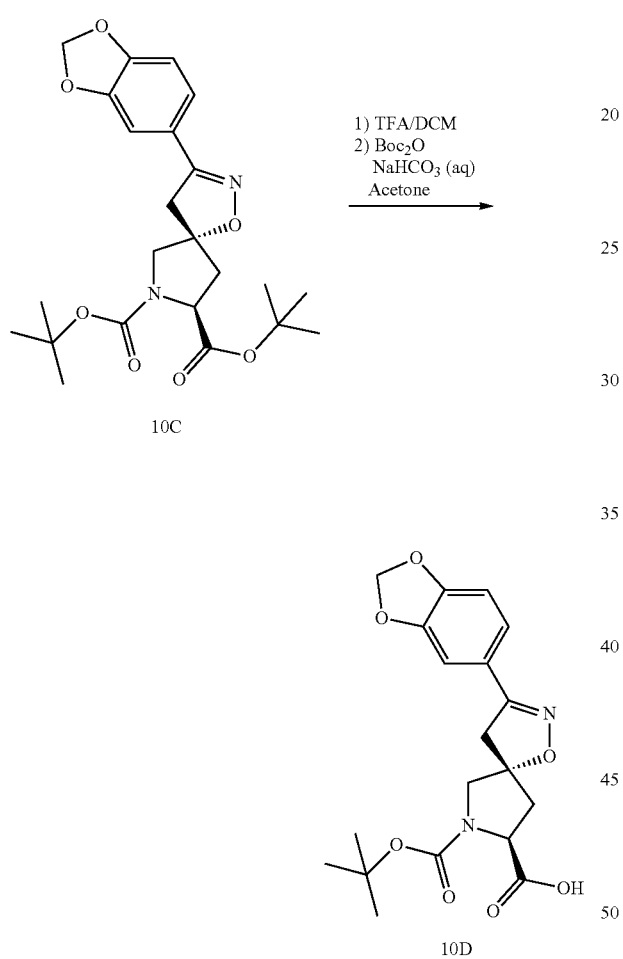

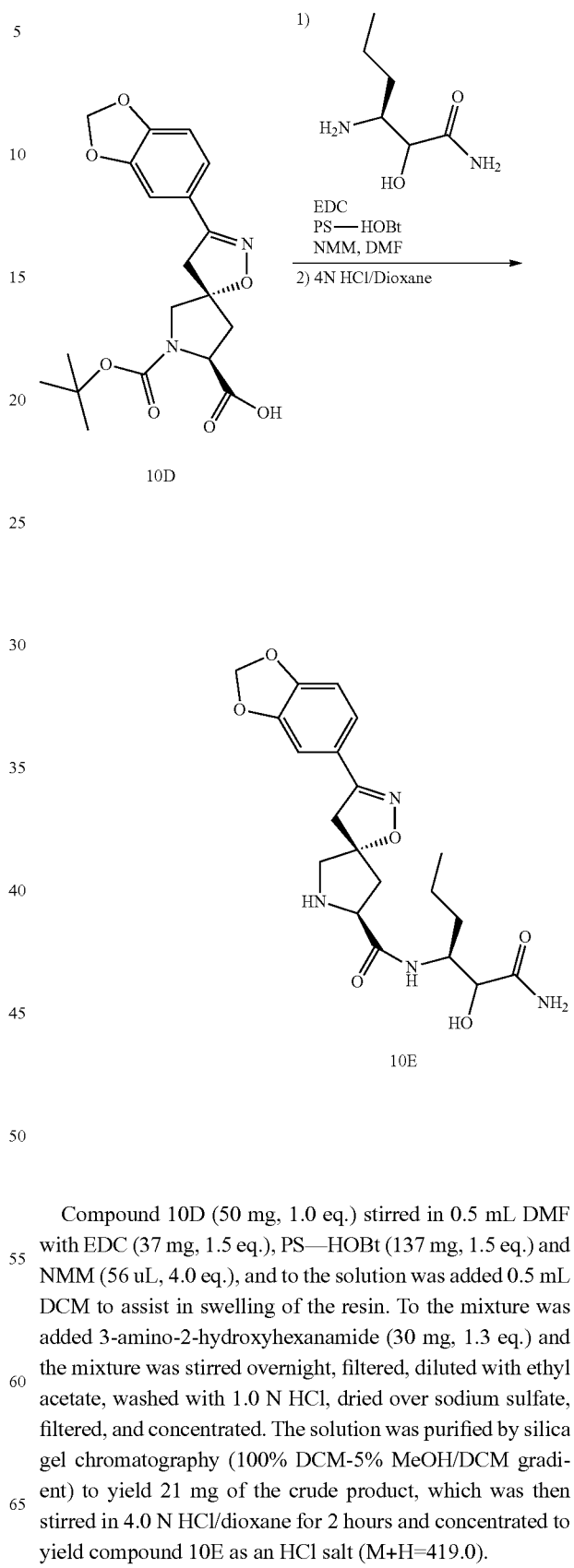

Compound 10C (4.0 g, 1.0 eq.) was stirred in 1/1 TFA/DCM for 3 hours and the solution was concentrated. To the concentrate was added 100 mL acetone, 100 mL saturated sodium bicarbonate solution, and ditertbutyldicarbonate and the resulting solution was stirred overnight and then acidified with 1.0 N HCl solution and extracted with ethyl acetate (thrice). The organics were washed with brine solution and dried over magnesium sulfate, filtered and concentrated to yield 4.0 g of Compound 10D (M+H=391.1).

Compound 10D (50 mg, 1.0 eq.) stirred in 0.5 mL DMF with EDC (37 mg, 1.5 eq.), PS—HOBt (137 mg, 1.5 eq.) and NMM (56 uL, 4.0 eq.), and to the solution was added 0.5 mL DCM to assist in swelling of the resin. To the mixture was added 3-amino-2-hydroxyhexanamide (30 mg, 1.3 eq.) and the mixture was stirred overnight, filtered, diluted with ethyl acetate, washed with 1.0 N HCl, dried over sodium sulfate, filtered, and concentrated. The solution was purified by silica gel chromatography (100% DCM-5% MeOH/DCM gradient) to yield 21 mg of the crude product, which was then stirred in 4.0 N HCl/dioxane for 2 hours and concentrated to yield compound 10E as an HCl salt (M+H=419.0).

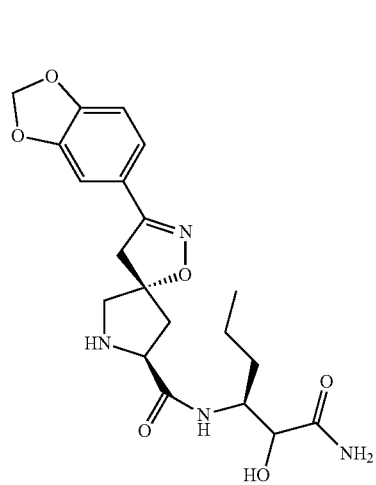

10E

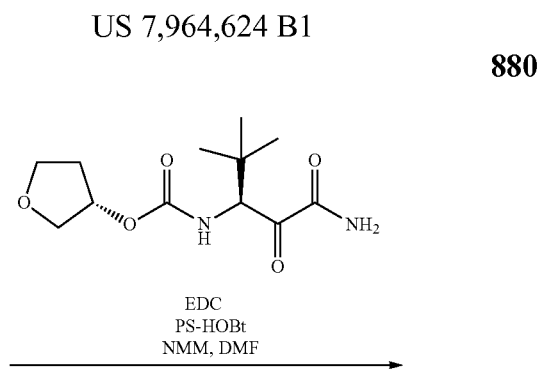

EDC
PS-HOBt
NMM, DMF

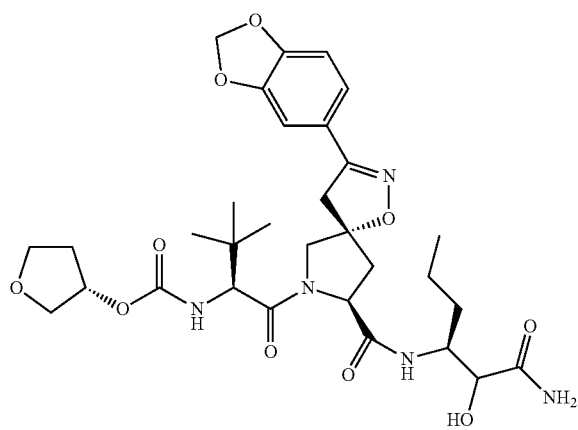

10F

Compound 10E (21 mg, 1.0 eq.) was stirred in DMF with NMM (13 uL, 1.4 eq.) and to the solution was added a solution of (S)-3,3-dimethyl-2-(((S)-tetrahydrofuran-3-yloxy)carbonylamino)butanoic acid (14 mg, 1.4 eq.), EDC (11 mg, 1.4 eq.), and PS—HOBt (40 mg, 1.4 eq.) in DMF, with enough DCM to swell the resin. The mixture was stirred overnight, filtered, washed with 1.0 N HCl, dried over sodium sulfate, filtered and then concentrated to give compound 10F, which was used without further purification. (M+H=646.4)

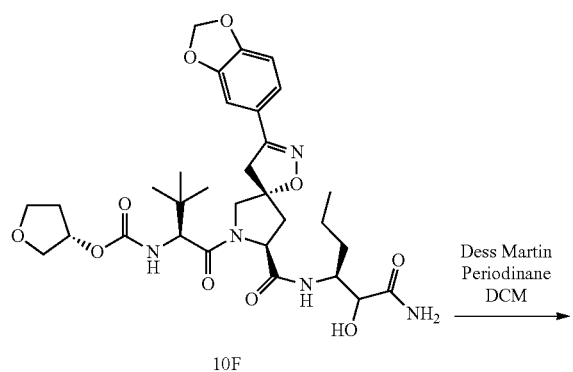

10F

Dess Martin Periodinane
DCM

-continued

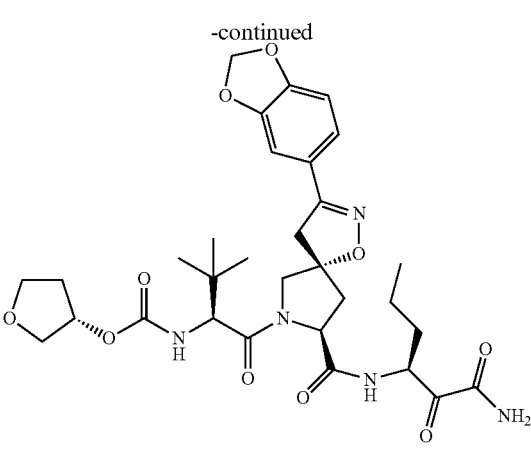

Compound No. 422

Compound 10F was stirred in DCM and to the solution was added Dess-Martin Periodinane (≈3.0 eq.). The solution was stirred for 1 hour, added to it 1.0 N $Na_2S_2O_3$, and stirred. The mixture was purified by silica gel chromatography (10-90% ethyl acetate/hexanes gradient) to yield 9 mg of Compound No. 422 (M+H=644.3). $^1$H-NMR (CDCl$_3$): 7.3 (m, 1H), 7.15 (m, 1H), 6.95 (m, 1H), 6.8 (m, 1H), 6.75 (m, 1H), 6.0 (s, 2H), 5.5-5.4 (m, 2H), 5.4-5.3 (m, 2H), 4.8-4.7 (m, 1H), 4.3 (m, 1H), 4.2 (m, 1H), 4.0-3.8 (m, 3H), 3.7 (m, 1H), 3.4-3.2 (m, 2H), 2.6 (m, 1H), 2.5 (m, 1H), 2.2-2.1 (m, 1H), 2.1-2.0 (m, 1H), 1.9 (m, 1H), 1.6 (m, 1H), 1.5-1.4 (m, 2H), 1.0-0.9 (m, 13H).

Example 11

Compound No. 562

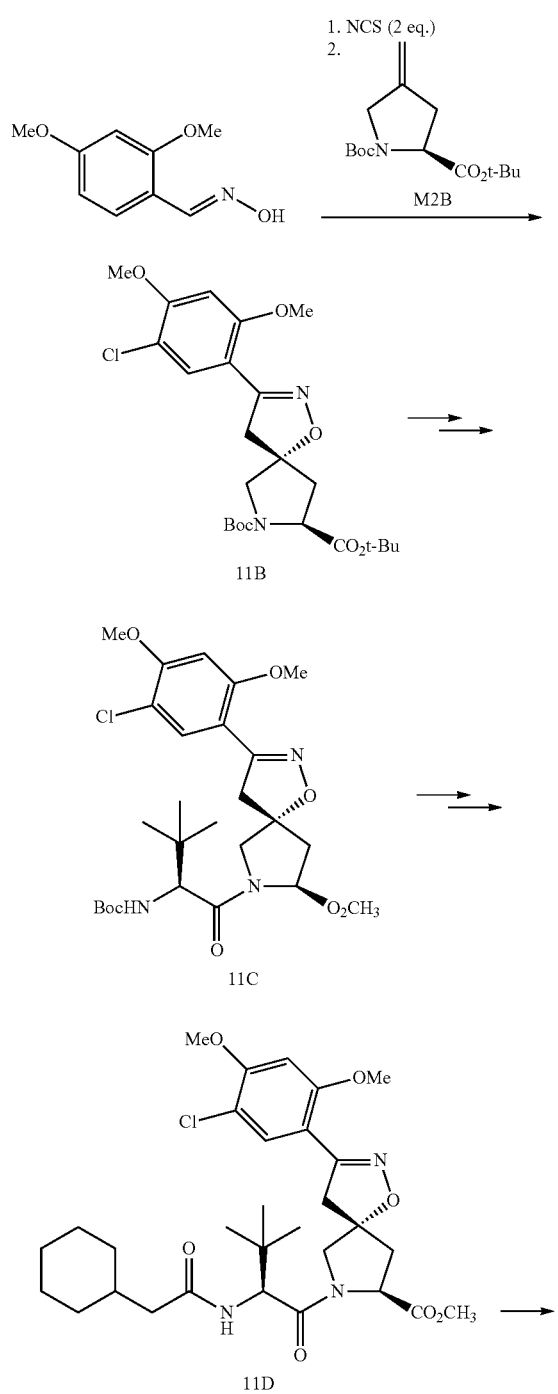

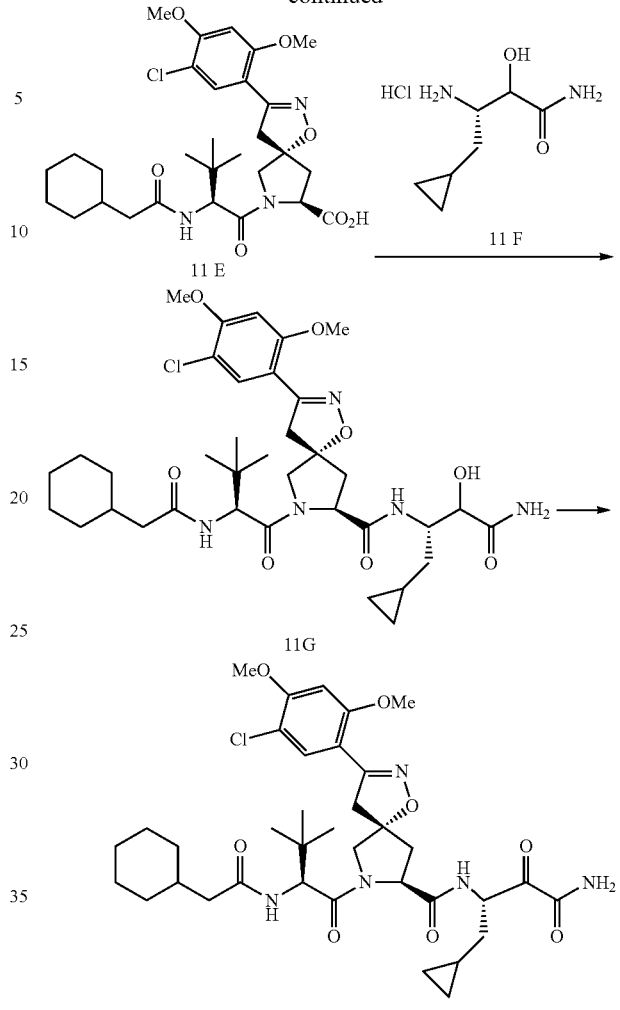

To 2,4-dimethoxybenzaldoxime (4.5 g, 24.8 mmol) in DMF (135 mL) was added dropwise over 2 h at room temperature a solution of N-chlorosuccinimide (6.6 g, 49.7 mmol) in DMF (135 mL). The reaction was stirred 14 hours and compound M2B (5.2 g, 18.4 mmol) was added followed by dropwise addition over 1 h of a solution of triethylamine in DMF (2.6 mL, 18.4 mmol, in 15 mL). After stirring for 3 h, the reaction mixture was washed with $H_2O$ and dried over $MgSO_4$. The resulting residue was purified via silica gel chromatography to afford 5.8 g of compound 11B as a tan solid. ES (+) MS: m/e 497 (M+H)$^+$.

To compound 11B (5.5 g, 11.1 mmol) in $CH_2Cl_2$ (30 mL) was added trifluoroacetic acid (30 mL). The reaction mixture was stirred for 90 minutes at room temperature and concentrated under reduced pressure to provide a tan solid, which was dissolved in MeOH (60 mL) and heated to reflux. Concentrated sulfuric acid (≈5 mL) was added dropwise and the reaction was refluxed for 3 hours, after which the solvent was removed under reduced pressure. The resulting residue was dissolved in $CH_2Cl_2$ (75 mL) and carefully treated with a saturated $NaHCO_3$ solution until pH 9. The organic layer was dried over $MgSO_4$ and concentrated to provide the intermediate amino ester. To N-Boc-tert-butylglycine (3.1 g, 13.6 mmol) in $CH_2Cl_2$ (60 mL) was added EDC (2.6 g, 13.6 mmol), HOBt (1.8 g, 13.6 mmol) and triethylamine (5.5 mL, 39.5 mmol). After stirring 5 minutes, the above amino ester was added and the reaction was stirred at room temperature 14 hours. The reaction mixture was washed with $H_2O$, 1 N HCl, and saturated $NaHCO_3$ solution. The organic layer was dried over $MgSO_4$ and concentrated in vacuo to provide 5.6 g of compound 11C (over 3 steps) as a brown solid which was used without further purification. ES (+) MS: m/e 568 $(M+H)^+$.

To compound 11C (600 mg, 1.1 mmol) in $CH_2Cl_2$ (3 mL) was added trifluoroacetic acid (3 mL). The reaction was stirred for 1 hour and concentrated under reduced pressure to give the desired amine product as the TFA salt. To cyclohexylacetic acid (181 mg, 1.3 mmol) in $CH_2Cl_2$ (6 mL) was added EDC (243 mg, 1.3 mmol), HOBt (171 mg, 1.3 mmol) and triethylamine (516 µL, 3.7 mmol). After stirring for 5 minutes, the above amine was added and the reaction was stirred at room temperature 14 hours. The reaction mixture was washed with $H_2O$, 1 N HCl, and saturated $NaHCO_3$ solution. The organic layer was dried over $MgSO_4$ and concentrated in vacuo, and the resulting residue was purified via silica gel chromatography to provide 460 mg of compound 11D (over 2 steps) as an off-white solid. ES (+) MS: m/e 592 $(M+H)^+$.

To compound 11D (460 mg, 0.8 mmol) in a solution of $THF/H_2O$ (5 mL, 3:1 v/v) was added LiOH monohydrate (82 mg, 1.9 mmol). The reaction mixture was stirred at room temperature 14 hours, acidified using 1 N HCl, and extracted with EtOAc. The organic layer was dried over $MgSO_4$ and concentrated under reduced pressure to provide 405 mg of compound 11E, which was used without further purification. ES (+) MS: m/e 578 $(M+H)^+$.

To compound 11E (80 mg, 0.14 mmol) in $CH_2Cl_2$ (1 mL) was added EDC (38 mg, 0.2 mmol), HOBt (27 mg, 0.2 mmol) and triethylamine (68 µL, 0.5 mmol). After stirring for 5 minutes, compound 11F was added and the reaction was stirred at room temperature 14 hours. The reaction mixture was washed with $H_2O$, 1 N HCl, and saturated $NaHCO_3$ solution. The organic layer was dried over $MgSO_4$ and concentrated in vacuo to provide 95 mg of compound 11G as a brown solid which was used without further purification. ES (+) MS: m/e 718 $(M+H)^+$.

To compound 11G (95 mg, 0.14 mmol) in $CH_2Cl_2$ (1 mL) was added Dess-Martin periodinane (71 mg, 0.17 mmol). After stirring for 30 minutes, the reaction was quenched with 1 N $Na_2S_2O_3$. The organic layer was purified via silica gel chromatography to give Compound No. 562, i.e., compound 11H shown above, as a white solid. ES (+) MS: m/e 716 $(M+H)^+$.

Example 12

Compound No. 362

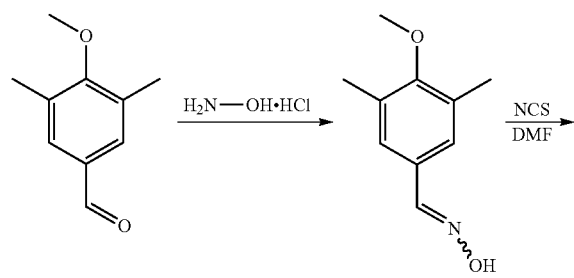

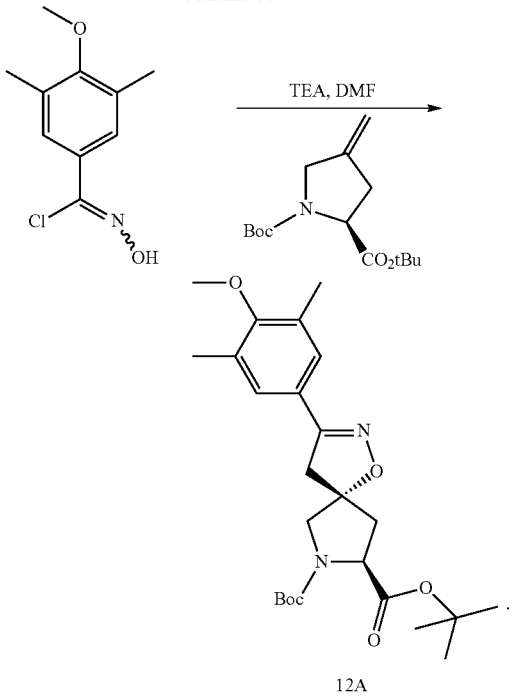

12A

4-Methoxy-3,5-dimethylbenzaldehyde (1.86 g, 11.3 mmol) was dissolved in ethanol (30 mL) and stirred with hydroxylamine hydrochloride (2.4 M aq. solution, 5.65 mL, 1.2 eq.) and $Na_2CO_3$ (1.2 M solution, 5.65 mL, 0.6 eq.) at room temperature for 2.5 hours. The mixture was then heated to 60° C. and additional hydroxylamine hydrochloride and $Na_2CO_3$ was added. The mixture was again stirred overnight at 60° C., transferred to a separatory funnel, diluted with EtOAc. The organic layer was separated, washed with brine, dried over $MgSO_4$, filtered and concentrated. The product was purified by ISCO chromatography with EtOAc/hexanes eluent to yield 1.55 g (8.56 mmol) of 4-methoxy-3,5-dimethylbenzaldehyde oxime as a white solid. M+1=180.0.

To a solution 4-methoxy-3,5-dimethylbenzaldehyde oxime (1.34 g, 7.48 mmol) in DMF (10 mL) was added N-chlorosuccinimide (1.76 g, 13.2 mmol). This solution was stirred until starting material was consumed as indicated by HPLC. To the solution was then added a solution of (S)-di-tert-butyl 4-methylenepyrrolidine-1,2-dicarboxylate (2.1 g, 1.0 eq.) in DMF (5 mL). To the solution was added triethylamine (1.2 eq.) dropwise, and the reaction mixture was stirred for 2 hours. The reaction was then diluted with EtOAc and the organic phase was washed with water, brine, dried ($MgSO_4$), filtered and concentrated. The product was purified over silica gel on an ISCO Combiflash using EtOAc/hexanes as the eluent to yield 912 mg (1.98 mmol) of compound 12A. M+1=461.4. $^1$H-NMR (500 MHz, $CDCl_3$): 7.30 (s, 2H), 4.40-4.32 (m, 1H), 3.98-3.79 (m, 1H); 3.74 (s, 3H), 3.64-3.58 (m, 1H), 3.40-3.34 (m, 1H), 3.24-3.19 (m, 1H), 2.72 (dd, J=8.7, 12.9 Hz, 1H), 2.29 (s, 6H), 2.11-2.07 (m, 1H), 1.54-1.45 (m, 18H).

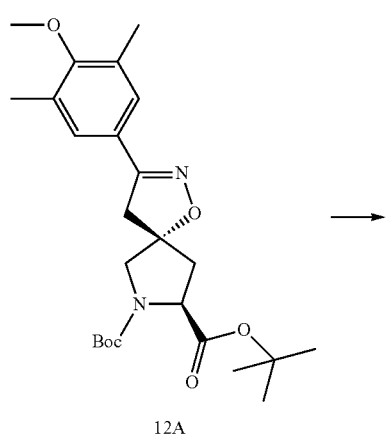

12A

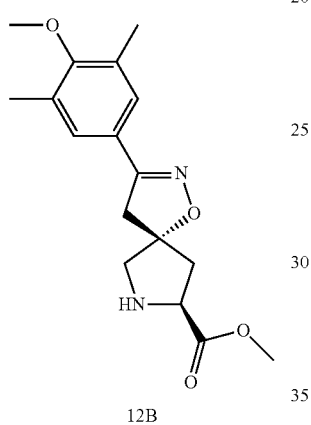

12B

Compound 12A (910 mg, 1.98 mmol) was stirred in CH$_2$Cl$_2$/trifluoroacetic acid (1:1, 20 mL) until HPLC indicated complete deprotection of starting material. The intermediate amino acid was concentrated and then dissolved in methanol (30 mL) and heated to reflux with concentrated H$_2$SO$_4$ until the starting material was consumed as indicated by HPLC. Concentrated material in vacuo, then dissolved in EtOAc and washed with NaHCO$_3$, brine, dried over MgSO$_4$ and concentrated to give compound 12B. M+1=319.0

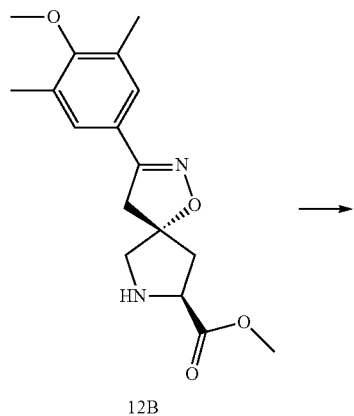

12B

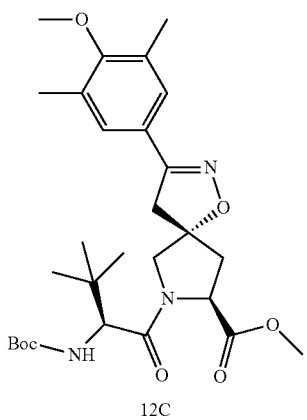

12C

Compound 12B (727 mg, 2.28 mmol) was dissolved in DMF (3 mL) with Boc-t-butylglycine (686 mg, 3.0 mmol), EDC.HCl (659 mg, 3.43 mmol), HOBt (460 mg, 3.4 mmol), and DIEA (1.2 mL, 6.89 mmol) and stirred at room temperature overnight. The reaction was then transferred to a separatory funnel and diluted with EtOAc. The organic layer was washed with 1 N HCl (twice, 20 mL each), sat. aq. NaHCO$_3$ (25 mL), water (10 mL), brine (10 mL), dried over MgSO$_4$ and concentrated. The crude product 12C was purified over silica gel on an ISCO Combiflash with EtOAc/Hexanes as eluent to yield 231 mg (0.435 mmol) of compound 12C as a clear colorless oil. LCMS (M+1)=532.45

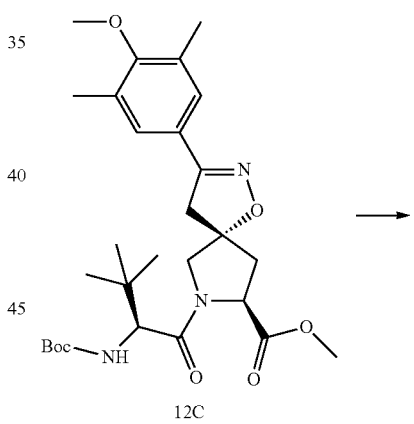

12C

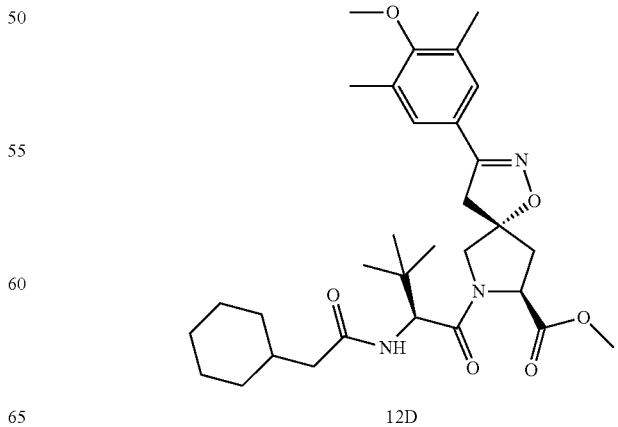

12D

Compound 12C (231 mg, 0.435 mmol) was stirred in 4N HCl in dioxane (15 mL) for 90 minutes at which point TLC analysis indicated no starting material was present in the reaction mixture. The HCl and dioxane were evaporated to yield an off-white foam. A portion of this intermediate (0.35 mmol), EDC.HCl (96 mg, 0.50 mmol.), HOBt (72 mg, 0.53 mmol), and cyclohexaneacetic acid (78 mg, 0.55 mmol) were stirred in DMF (3.5 mL). To this was added DIEA (0.18 mL, 1.0 mmol) and the reaction was stirred overnight. The reaction was then diluted with EtOAc and transferred to a separatory funnel where the layers were separated and the organic phase was washed with 1.0 N HCl, saturated aq. NaHCO$_3$, brine, dried over MgSO$_4$ and concentrated. The product was purified over silica gel on an ISCO Combiflash with EtOAc/hexane as eluent to yield 219 mg (0.394 mmol) of compound 12D as a clear oil. M+1=556.4

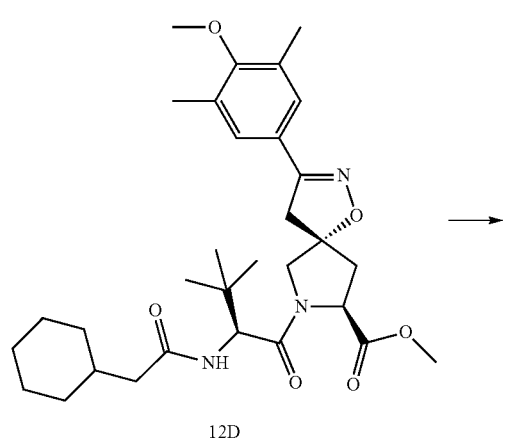

12D

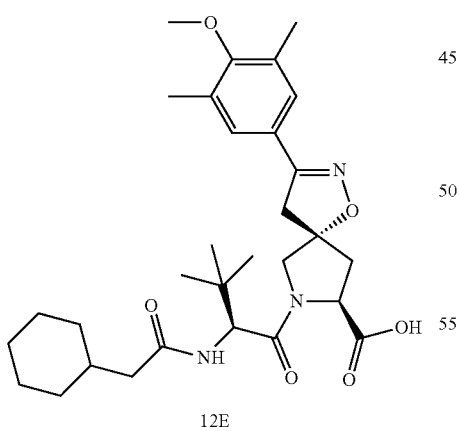

12E

Compound 12D (219 mg, 0.394 mmol) in THF/H$_2$O/MeOH (4:1:1, 6 mL) was stirred with LiOH.H$_2$O (1.5 eq.) at room temperature overnight. The reaction was then acidified with 1.0 N HCl and extracted with CH$_2$Cl$_2$. The organic layer was washed with brine, dried over MgSO$_4$ and concentrated to yield 207 mg (0.382 mmol) of compound 12E. M+1=548.4

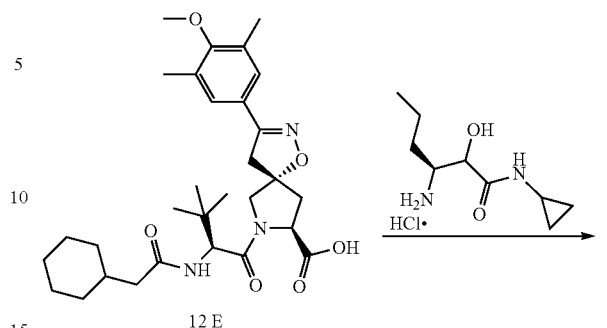

12E

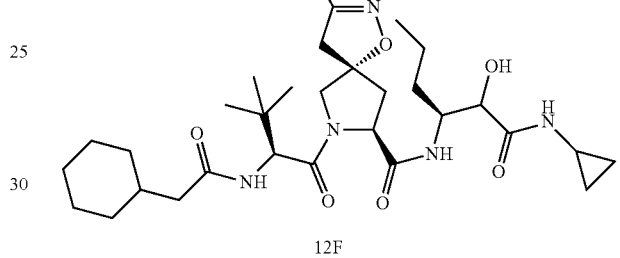

12F

Compound 12E (207 mg, 0.382 mmol) was stirred with HOBt (107 mg, 0.792 mmol), EDC.HCl (144 mg, 0.764 mmol), and hydroxyamine hydrochloride (168 mg, 0.75 mmol) in DMF (2.0 mL) at room temperature and treated with DIEA (0.400 mL, 2.3 mmol). The reaction was stirred overnight, diluted with EtOAc, washed with 1N HCl, saturated NaHCO$_3$, and the combined aqueous layers were back extracted with EtOAc. The organic layers were combined, dried over MgSO$_4$, concentrated and purified over silica gel on an ISCO combiflash with EtOAc/Hexanes as eluent to yield 227 mg (0.320 mmol) of compound 12F as a white solid. (M+TFA) M−1=822.6.

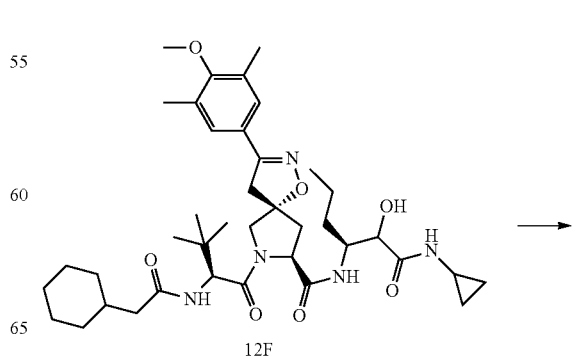

12F

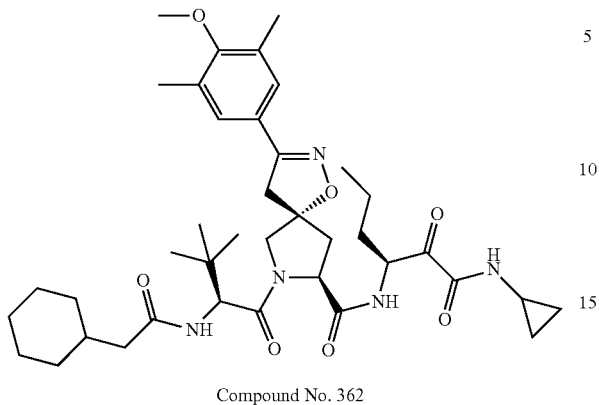

Compound No. 362

Compound 12F (227 mg, 0.320 mmol) was dissolved at room temperature in CH$_2$Cl$_2$ (4 mL) and treated with Dess-Martin periodinane (142 mg, 1.0 eq.). After 15 minutes, TLC showed the reaction to be complete, and the reaction solution was quenched by the addition of water and stirred vigorously. Additional CH$_2$Cl$_2$ was added, the organic layer was separated and purified over silical gel on an ISCO combiflash with EtOAc/Hexanes as eluent to yield 159 mg (0.225 mmol) of Compound No. 362. FIA MS (M+1)=708.42. $^1$H-NMR (500 MHz, CDCl$_3$): 7.30 (s, 2H), 7.17 (d, 1H), 6.93 (d, 1H), 6.15 (d, 1H), 5.39-5.33 (m, 1H), 4.72 (t, 1H), 4.66 (d, 1H), 4.25 (d, 1H), 3.74 (s, 3H), 3.74-3.69 (m, 1H), 3.42 (d, 1H), 3.30 (d, 1H), 2.81-2.75 (m, 1H), 2.58-2.46 (m, 2H), 2.29 (s, 6H), 2.16-2.10 (m, 1H), 2.08-2.00 (m, 1H), 1.97-1.88 (m, 1H), 1.85-1.57 (m, 8H), 1.51-1.35 (m, 2H), 1.33-1.22 (m, 2H), 1.20-1.07 (m, 1H), 1.02-0.96 (m, 10H), 0.92 (t, 3H), 0.88-0.80 (m, 2H), 0.66-0.56 (m, 2H).

Example 13

Compound No. 247

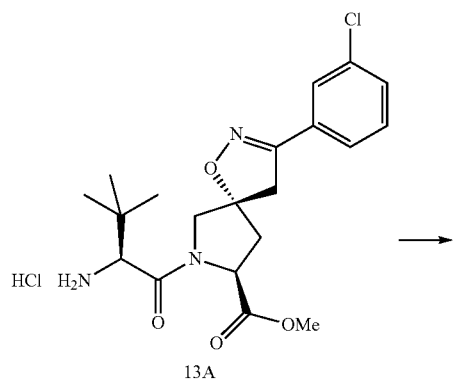

13A

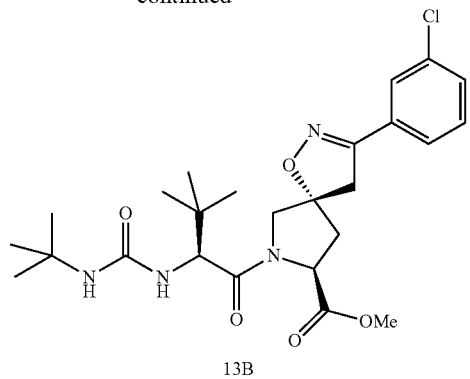

13B

To a solution of compound 13A (222 mg, 0.5 mmol) was added TEA (0.14 mL) and t-butylisocyanate (0.6 mmol). The resulting solution was stirred overnight and then diluted with EtOAc (20 mL), washed with water (10 mL), dried over Na$_2$SO$_4$ and concentrated in vacuo. The crude product was purified chromatography on silica gel to afford compound 13B as a white solid (190 mg). HPLC 8.48 min; LC-MS m/z 507.2 ES$^+$.

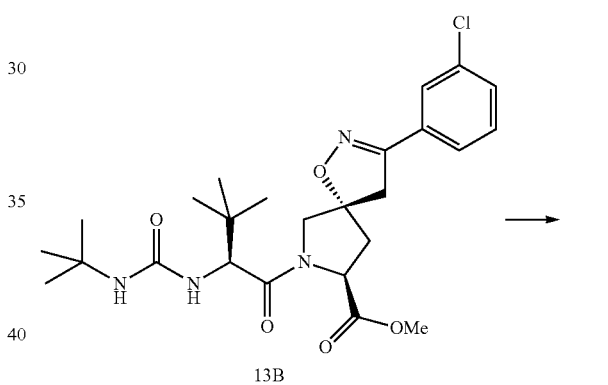

13B

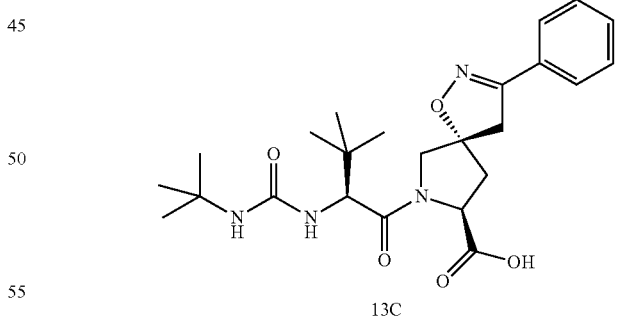

13C

Compound 13B was dissolved in THF and the solution was treated with 1.0 N aqueous LiOH and water. The reaction mixture was stirred for 1 hour, and concentrated in vacuo. The residue was then diluted with water, washed with Et$_2$O and acidified with 1 N aqueous HCl. The resulting mixture was extracted twice with CH$_2$Cl$_2$ and the combined organics were dried over MgSO$_4$, filtered and concentrated in vacuo to give crude compound 13C which was used without further purification for the next step. LC-MS m/z 493.22 ES$^+$, 491.21 ES$^-$.

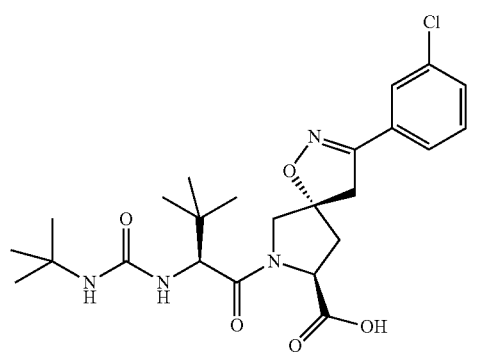

13C

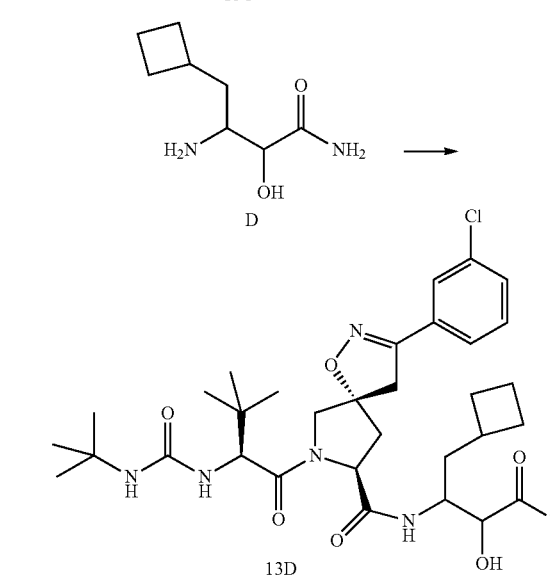

D

13D

A solution of compound 13C (20.6 mg) in CH$_2$Cl$_2$ (800 µL) was treated with 1-(3-dimethylaminopropyl)-3-ethylcarbodiimide hydrochloride (10 mg) and hydroxybenzotriazole (7 mg) for 1 hour. Diisopropylamine (16 µL) and 3-amino-4-cyclobutyl-2-hydroxybutanamide D (10.5 mg) were then added in one portion and the resulting reaction solution was stirred at room temperature for another 16 hours. The mixture was then washed with 1N aqueous HCl, 1:1 solution of 1N aqueous K$_2$CO$_3$:1N aqueous NaHCO$_3$, and brine in succession. The organics were then dried (MgSO$_4$), concentrated in vacuo and purified by chromatography over silica (0% to 4% MeOH in CH$_2$Cl$_2$) to yield compound 130 (11.6 mg). LC-MS m/z 647.25 ES$^+$.

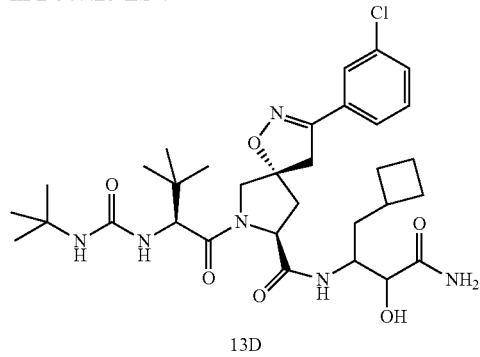

13D

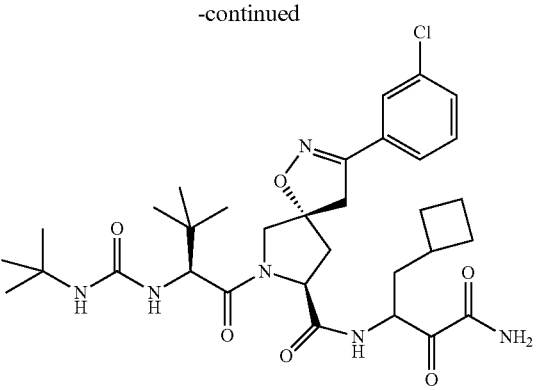

Compound No. 247

A solution of compound 13D (11.6 mg) in CH$_2$Cl$_2$ (1 mL) was charged with Dess-Martin periodinane (8.4 mg) and the reaction mixture was stirred at room temperature for 2 hours. The resulting white mixture was then washed with 1.0 N aqueous Na$_2$S$_2$O$_3$, the phase were separated and the organics were the dried over MgSO$_4$, concentrated in vacuo and purified by chromatography over silica (30% to 65% EtOAc in hexanes) to yield 6.7 mg of Compound No. 247 as a white solid: $^1$H-NMR (500 MHz, CDCl$_3$): 7.61 (s), 7.52 (d, J=6.1 Hz), 7.39 (d, J=7.8 Hz), 7.34 (t, J=7.8 Hz), 6.87 (s), 6.77 (s), 5.89 (s), 5.67 (s), 5.23-5.19 (m), 4.83-4.79 (m), 4.47 (s), 4.38 (d, J=11.0 Hz), 3.72 (dd, J=3.1, 11.2 Hz), 3.45 (m), 3.30 (d), 2.64 (m), 2.56 (m), 2.44-2.36 (m), 2.08-1.98 (m), 1.86-1.68 (m), 1.64-1.58 (m), 1.33-1.22 (m), 1.05-1.00 (m, H), 0.95-0.92 (m, H) ppm. LC-MS m/z 647.25 ES$^+$.

Example 14

Compound No. 57

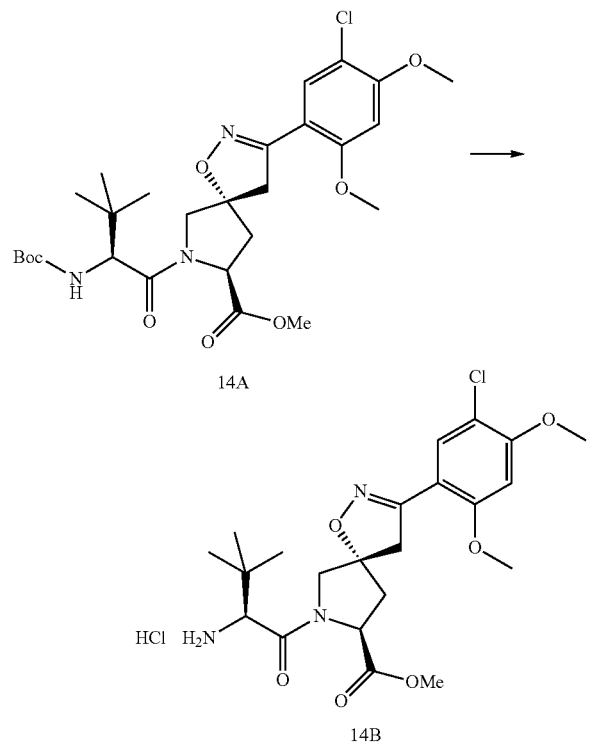

14A

14B

A solution of compound 14A (512 mg) in dioxane was treated with 4 N HCl in dioxane. The reaction solution was stirred at room temperature for 45 minutes and concentrated in vacuo. The resulting residue was dissolved in a small amount of $CH_2Cl_2$ and crystallized from $Et_2O$/Hexanes to give compound 14B as a white solid (362 mg). LC-MS m/z 468.24 ES$^+$.

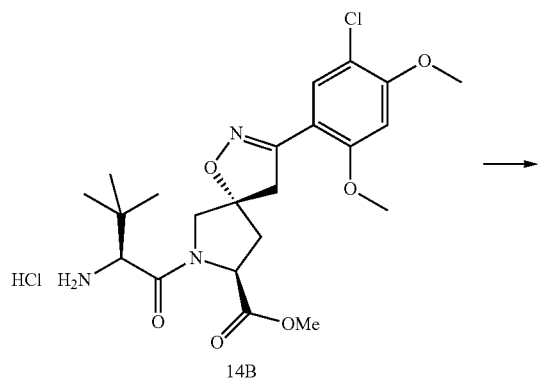

14B

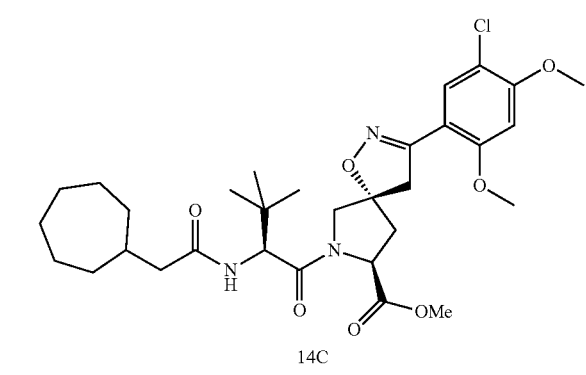

14C

A solution of cycloheptane acetic acid (83 mg, Aldrich Chemical Co., Milwaukee, Wis.) in $CH_2Cl_2$ (4 mL) was treated with 1-(3-dimethylaminopropyl)-3-ethylcarbodiimide hydrochloride (103 mg) and hydroxybenzotriazole (72 mg) for 1 hour. Diisopropylamine (160 µL) and intermediate 14B (179 mg) were then added in one portion and the resulting reaction solution was stirred at room temperature for another 2 hours. The mixture was then washed with 1 N aqueous HCl, 1:1 solution of 1 N aqueous $K_2CO_3$:1 N aqueous $NaHCO_3$, and brine in succession. The organics were the dried ($MgSO_4$), concentrated in vacuo and purified by chromatography over silica (15% to 60% EtOAc in hexanes) to yield compound 14C (188 mg). LC-MS m/z 606.25 ES$^+$.

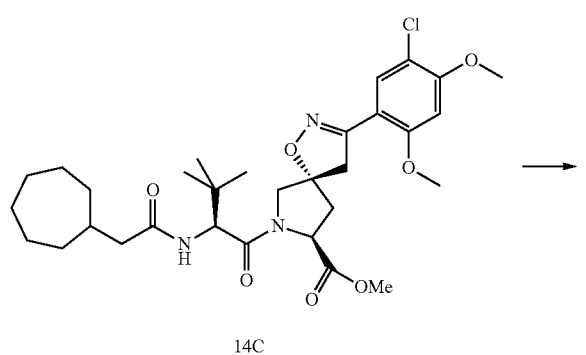

14C

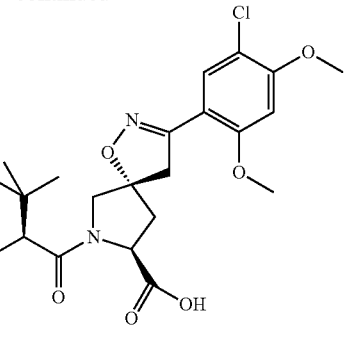

14D

Compound 14C (186 mg) was dissolved in THF (3 mL) and the solution was treated with 1 N aqueous LiOH (620 µL) and water (1 mL). The reaction mixture was stirred for 45 minutes at room temperature, and concentrated in vacuo. The residue was then diluted with water, washed with $Et_2O$ and acidified with 1 N aqueous HCl. The resulting mixture was extracted twice with EtOAc and the combined organics were dried over $MgSO_4$, filtered and concentrated in vacuo to give crude compound 14D which was used without further purification for the next step. LC-MS m/z 592.25 ES$^+$, 590.35 ES$^-$.

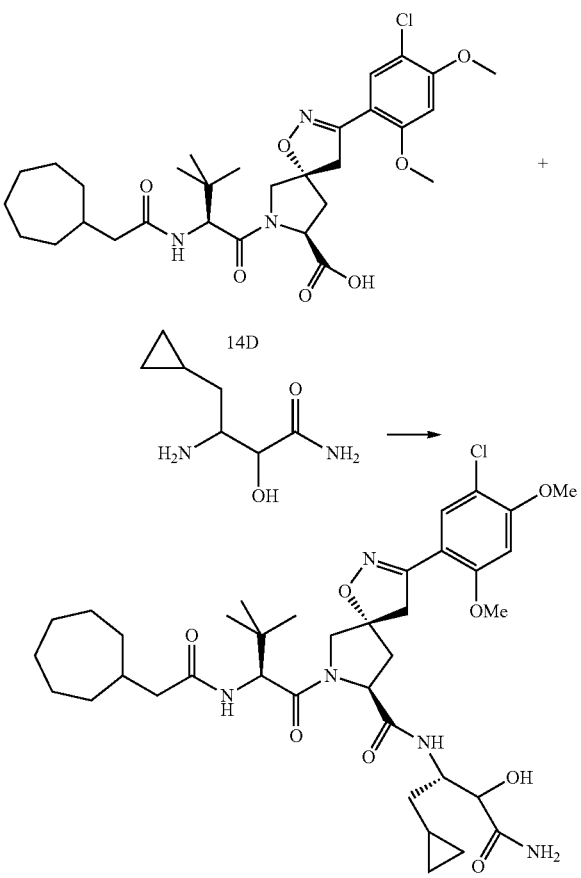

14D

14F

A solution of compound 14D (89 mg) in $CH_2Cl_2$ (1 mL)/DMF (1 mL) was treated with 1-(3-dimethylaminopropyl)-

3-ethylcarbodiimide hydrochloride (44 mg) and hydroxybenzotriazole (31 mg) for 1 hour. Diisopropylamine (70 µL) and (3S)-3-amino-4-cyclopropyl-2-hydroxybutanamide (35 mg) were then added in one portion and the resulting reaction solution was stirred at room temperature for another 16 hours. The mixture was then washed with 1 N HCl, 1:1 solution of 1N aqueous $K_2CO_3$:1N aqueous $NaHCO_3$, and brine in succession. The organics were the dried over $MgSO_4$, concentrated in vacuo and purified by chromatography over silica (0% to 5% MeOH in $CH_2Cl_2$) to yield 96 mg of compound 14F. LC-MS m/z 732.21 ES+.

A solution of compound 14F (96 mg) in $CH_2Cl_2$ (1.5 mL) was charged with Dess-Martin periodinane (83 mg) and the reaction mixture was stirred at room temperature for 2 hours. The resulting white mixture was then washed with 1 N aqueous $Na_2S_2O_3$, the phase were separated and the organics were the dried over $MgSO_4$, concentrated in vacuo and purified by chromatography over silica (10% to 95% EtOAc in hexanes) to yield Compound No. 57 (44 mg) as a white solid. $^1$H-NMR (500 MHz, $CDCl_3$): 7.76 (s), 6.75 (br s), 6.48 (s), 6.07 (d), 5.40 (m), 4.67 (m), 4.22 (d), 3.95 (s), 3.87 (s), 3.75 (d), 3.43 (m), 2.51 (m), 2.10 (m), 1.30-1.87 (m), 1.12-1.28 (m), 0.97 (m), 0.79 (m), 0.15 (m), 0.03 (m) ppm. LC-MS m/z 730.35 ES+, 728.35 ES−.

Example 15

Compound No. 600

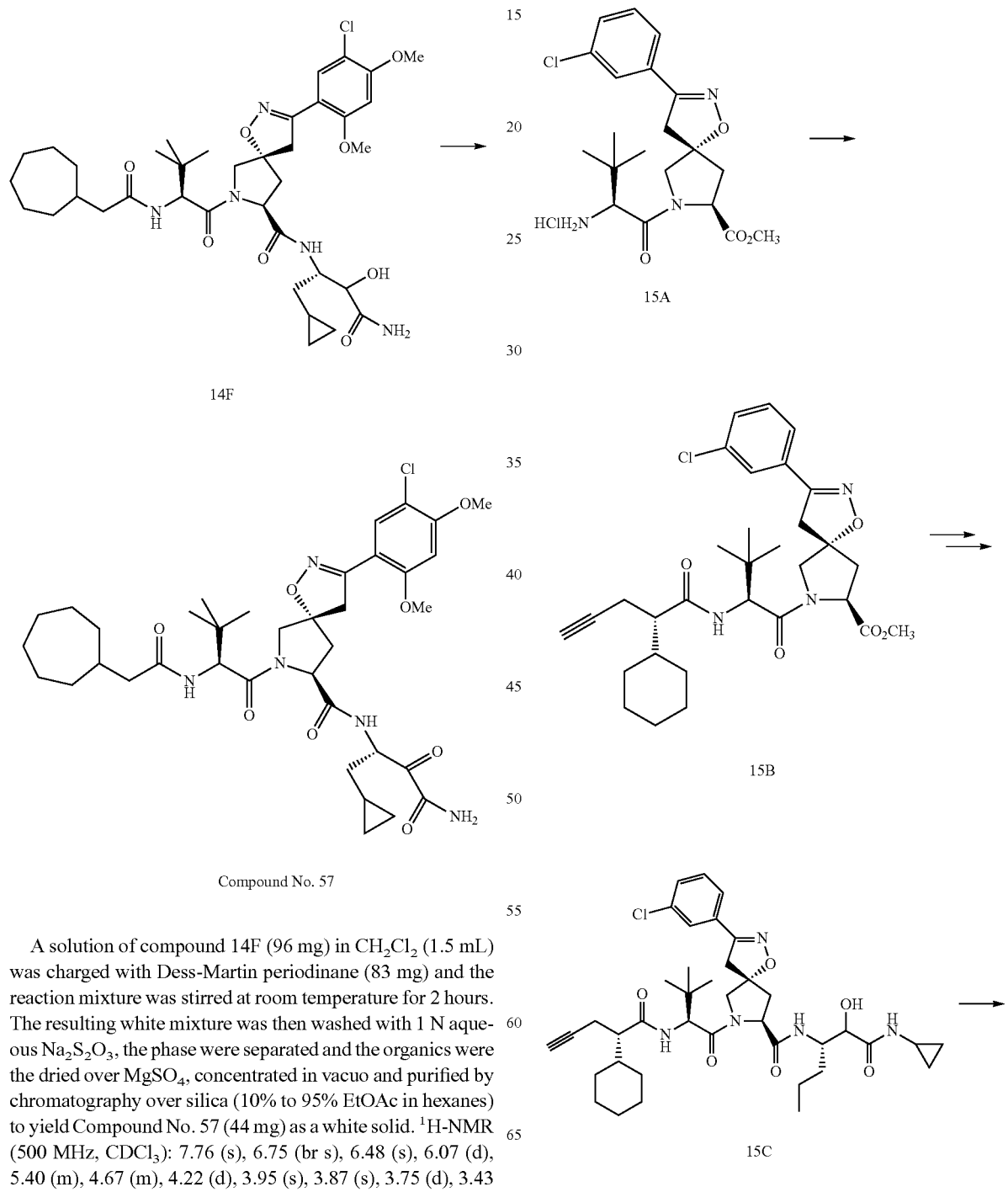

897

-continued

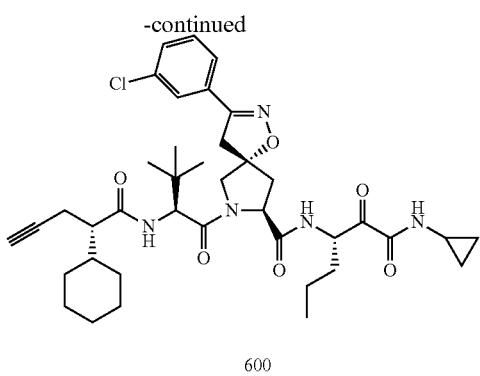

600

Compound 600 has the same structure as compound 266 in Table 1.

To a solution of (R)-2-cyclohexylbut-3-ynoic acid (430 mg, 2.4 mmol) in CH$_2$Cl$_2$ (10 mL) was added EDC (458 mg, 2.4 mmol), HOBt (324 mg, 2.4 mmol) and triethylamine (836 µL, 6.0 mmol). After stirring for 5 minutes, compound 15A (800 mg, 2.0 mmol) was added and the reaction was stirred 16 hours. The mixture was washed with H$_2$O, 1 N HCl, and saturated NaHCO$_3$ solution. The organic layer was dried over MgSO$_4$ and concentrated under reduced pressure to provide 1.23 g crude compound 15B, which was purified by silica gel chromatography. ES (+) MS: m/e 570 (M+H)$^+$.

To a solution of compound 15B (220 mg, 0.4 mmol) in THF/H$_2$O (2 mL, 3:1 v/v) was added LiOH monohydrate (115 mg, 3 mmol). The mixture was stirred for 2 hours, acidified using 1 N HCl (6 mL) and extracted with EtOAc (thrice, 10 mL). The combined organics were dried over MgSO$_4$ and concentrated to afford a colorless oil which was used without further purification. The oil was dissolved in CH$_2$Cl$_2$ (2 mL), then EDC (90 mg, 0.5 mmol), HOBt (63 mg, 0.5 mmol) and triethylamine (163 µL, 1.2 mmol) were added. After stirring for 5 minutes, (3S)-3-amino-N-cyclopropyl-2-hydroxyhexanamide (87 mg, 0.5 mmol) was added. The reaction was stirred 12 hours, washed with H$_2$O, 1 N HCl, and saturated NaHCO$_3$ solution. The organic layer was dried over MgSO$_4$ and concentrated under reduced pressure to provide 215 mg of compound 15C as a colorless oil, which was used without further purification. ES (+) MS: m/e 724 (M+H)$^+$.

To a solution of compound 15C (53 mg, 0.07 mmol) in CH$_2$Cl$_2$ (0.5 mL) was added Dess-Martin periodinane (41 mg, 0.1 mmol). The mixture was stirred for 30 minutes, quenched with 1 Na$_2$S$_2$O$_3$, and separated. The organic layer was purified by silica gel chromatography to provide 20 mg of Compound No. 600. $^1$H-NMR (500 MHz, CDCl$_3$): 7.53 (d, J=1.6 Hz, 1H), 7.43 (d, J=7.6 Hz, 1H), 7.31-7.25 (m, 2H), 6.83 (d, J=3.3 Hz, 1H), 6.24-6.21 (m, 1H), 5.30-5.26 (m, 1H), 4.70-4.58 (m, 2H), 4.23-4.21 (m, 1H), 3.64 (dd, 1H), 3.36-3.20 (m, 2H), 2.70-2.68 (m, 1H), 2.57-2.35 (m), 2.04-1.82 (m), 1.72-1.30 (m, 10H), 1.18-0.75 (m), 0.55-0.40 (m).

Example 16

Compound No. 602

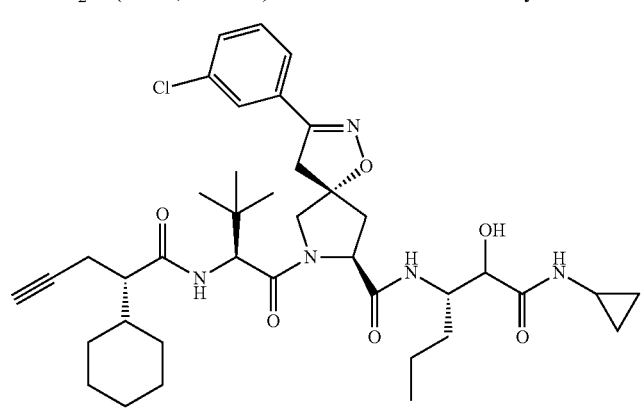

15C

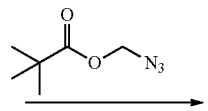

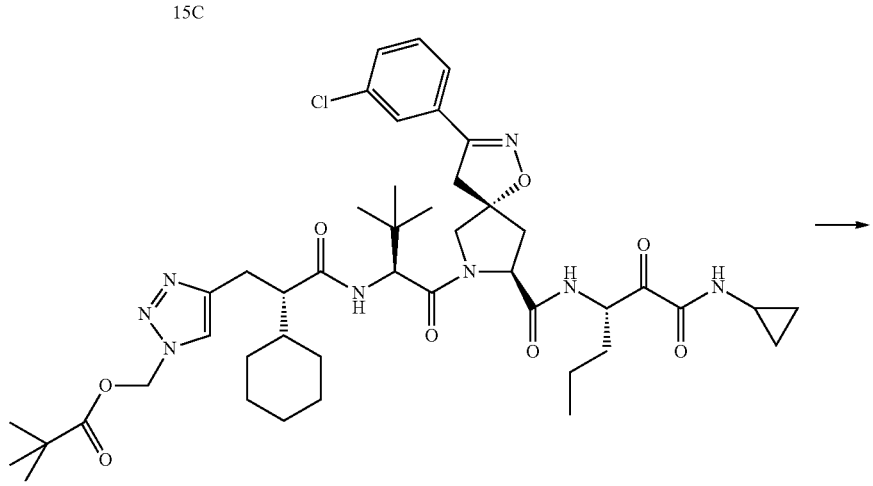

16B

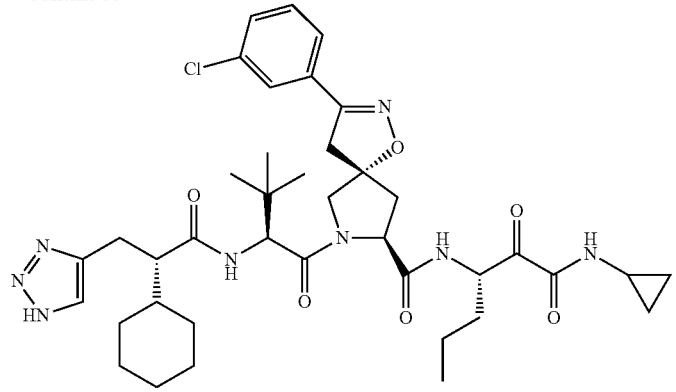

602

Compound 602 has the same structure as compound 212 in Table 1.

To a solution of compound 15C prepared above (20 mg, 0.03 mmol) and azidomethyl pivalate (4 mg, 0.03 mmol, prepared according to Syn. Lett., 2005, 18, pp. 2847-2850) in tert-butanol/H$_2$O (1204, 1:1 v/v) was added an aqueous solution of sodium ascorbate (10 μL, 0.01 mmol, 1.0 M) followed by an aqueous solution of copper(II) sulfate pentahydrate (5 μL, 0.001 mmol, 0.3 M). The reaction mixture was stirred 12 hours at room temperature, diluted with H$_2$O, and extracted with EtOAc. The combined organics were washed with 5% ammonium hydroxide followed by brine, and were dried over MgSO$_4$ and concentrated under reduced pressure to provide 25 mg of crude compound 16B, which was used without further purification. ES (+) MS: m/e 881 (M+H)$^+$.

To a solution of compound 16B in MeOH (120 μL) was added aqueous NaOH (120 μL, 1 M). The reaction was stirred at room temperature for 2 hours, then treated with 1 M HCl (120 μL) followed by H$_2$O (120 μL). The mixture was extracted with CH$_2$Cl$_2$ (thrice, 200 μL each). The combined extracts were washed with brine and concentrated to a volume of approximately 100 μL. To this solution was added Dess-Martin periodinane (17 mg, 0.04 mmol) and the reaction was stirred 30 minutes. The mixture was quenched with 1 M Na$_2$S$_2$O$_3$ (150 μL), and the organic layer was separated and purified via silica gel chromatography to afford 3 mg of Compound No. 602. ES (+) MS: m/e 765 (M+H)$^+$.

Listed below in Table 6 are additional compounds of Formula I prepared by Methods 5a and 5b.

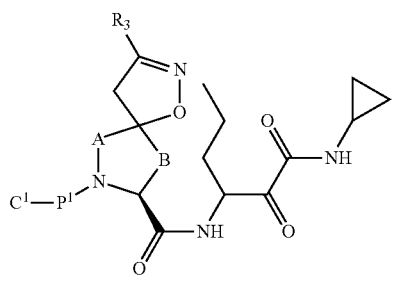

TABLE 6

Additional compounds of formula I produced by methods 5a and 5b.

| Compound No. | Starting Material for P$^1$ | Starting Material for C$^1$ | Starting Material for R$_3$ |
|---|---|---|---|
| 5 | N-BOC-L-tert-butylglycine | 2-(4-hydroxy-4-methylcyclohexyl)-acetic acid | 3-Chloro-benzaldoxime |
| 10 | (S)-4-(benzyl-amino)-2-isopropyl-4-oxobutanoic acid | N/A | 3-chloro-benzaldoxime |
| 13 | N-BOC-L-tert-butylglycine | 2-Norbornaneacetic acid | 3-chloro-benzaldoxime |
| 19 | N-BOC-L-tert-butylglycine | 2-(bicyclo[4.1.0]-heptan-1-yl)acetic acid | 3-chloro-benzaldoxime |
| 21 | (S)-4-(cyclohexyl-amino)-2-isopropyl-4-oxobutanoic acid | N/A | 3-chloro-benzaldoxime |
| 23 | N-BOC-L-tert-butylglycine | 2-Cyclohexylacetic acid | 3-Chloro-benzaldoxime |
| 26 | N-BOC-L-tert-butylglycine | N-Benzoyl-L-Proline | 3-Chloro-benzaldoxime |
| 27 | N-BOC-L-tert-butylglycine | Cyclobutaneacetic acid | 3-Chloro-benzaldoxime |
| 43 | N-BOC-L-tert-butylglycine | 2-Cyclohexylacetic acid | 2,4-Dimethoxy-5-chloro-benzaldoxime |
| 48 | N-BOC-L-tert-butylglycine | 2-Norbornaneacetic acid | 2,4-Dimethoxy-5-chloro-benzaldoxime |
| 50 | N-BOC-L-tert-butylglycine | 2-Cyclohexylacetic acid | 3-Chloro-benzaldoxime |
| 59 | N-BOC-L-tert-butylglycine | 2-cycloheptylacetic acid | 2,4-Dimethoxy-5-chloro-benzaldoxime |
| 63 | N-BOC-L-tert-butylglycine | 2-Cyclohexylacetic acid | 3-Chloro-benzaldoxime |
| 67 | N-BOC-L-tert-butylglycine | 2-(tetrahydro-2H-pyran-4-yl)acetic acid | 3-Chloro-5-fluoro-4-ethoxy-benzaldoxime |
| 86 | N-BOC-L-tert-butylglycine | Isopropyl isocyanate | Piperonal oxime |
| 90 | N-BOC-L-tert-butylglycine | N/A | 3-Chloro-benzaldoxime |
| 104 | N-BOC-L-tert-butylglycine | Tert-butylacetic acid | 2,4-Dimethoxy-5-chloro-benzaldoxime |
| 105 | N-BOC-L-tert-butylglycine | N/A | 3-Chloro-benzaldoxime |

TABLE 6-continued

Additional compounds of formula I produced by methods 5a and 5b.

| Compound No. | Starting Material for P¹ | Starting Material for C¹ | Starting Material for R₃ |
|---|---|---|---|
| 117 | N-BOC-L-tert-butylglycine | 4-methyltetrahydro-2H-pyran-4-carboxylic acid | 3-Chloro-benzaldoxime |
| 121 | N-BOC-L-tert-butylglycine | 2-(2,2-dimethyltetrahydro-2H-pyran-4-yl)acetic acid | 3-Chloro-benzaldoxime |
| 126 | N-BOC-L-tert-butylglycine | 2-Cyclohexylacetic acid | 3-Chloro-5-fluoro-4-ethoxy-benzaldoxime |
| 129 | N-BOC-L-tert-butylglycine | 2-cycloheptylacetic acid | 2,4-Dimethoxy-5-chloro-benzaldoxime |
| 131 | N-BOC-L-tert-butylglycine | N/A | 2,4-Dimethoxy-5-chloro-benzaldoxime |
| 136 | N-BOC-L-tert-butylglycine | 2-Cyclohexylacetic acid | 3-Chloro-5-fluoro-4-ethoxy-benzaldoxime |
| 145 | N-BOC-L-tert-butylglycine | 2-(tetrahydro-2H-pyran4-yl)acetic acid | Piperonal oxime |
| 153 | N-BOC-L-tert-butylglycine | 2-((2R,5R)-2,5-dimethyltetrahydro-2H-pyran-4-yl)acetic acid | 3-Chloro-benzaldoxime |
| 168 | N-BOC-L-tert-butylglycine | 2-Cyclohexylacetic acid | Thiophene-3-carboxaldehyde |
| 172 | N-Phenyl-L-tert-butylglycine | N/A | 3-chloro-benzaldoxime |
| 178 | N-BOC-L-tert-butylglycine | 2-(tetrahydro-2H-pyran-4-yl)acetic acid | 3-Chloro-5-fluoro-4-ethoxy-benzaldoxime |
| 184 | N-BOC-L-tert-butylglycine | 4-methyltetrahydro-2H-pyran-4-carboxylic acid | 3-Chloro-benzaldoxime |
| 188 | N-BOC-L-tert-butylglycine | 2-Cyclohexylacetic acid | 3-Chloro-benzaldoxime |
| 192 | N-BOC-L-tert-butylglycine | cyclopentyl 2,5-dioxopyrrolidin-1-yl carbonate | 2,4-Dimethoxy-5-chloro-benzaldoxime |
| 195 | N-BOC-L-tert-butylglycine | 2-cyclohexylacetic acid | 3-chloro-4-methoxy-5-methyl-benzaldoxime |
| 211 | 2-(tert-butoxycarbonyl-amino)-2-(1-methoxycyclopropyl)-acetic acid | 2-cyclohexylacetic acid | 3-chloro-benzaldoxime |
| 212 | N-BOC-L-tert-butylglycine | (S)-2-cyclohexyl-3-(1H-1,2,3-triazol-4-yl)propanoic acid | 3-chloro-benzaldoxime |
| 214 | N-(3-methoxy-phenyl)-L-tert-butylglycine | N/A | 3-chloro-benzaldoxime |
| 217 | N-BOC-L-tert-butylglycine | 2-Cyclohexylacetic acid | 3-Chloro-benzaldoxime |
| 219 | N-BOC-L-tert-butylglycine | 2-cycloheptylacetic acid | 3-Chloro-benzaldoxime |
| 225 | N-BOC-L-tert-butylglycine | cyclopentyl 2,5-dioxopyrrolidin-l-yl carbonate | 3-Chloro-benzaldoxime |
| 231 | N-BOC-L-tert-butylglycine | 2-Cyclohexylacetic acid | 3-Chloro-benzaldoxime |
| 233 | N-BOC-L-tert-butylglycine | 2-(1-hydroxycyclohexyl)-acetic acid | 3-Chloro-benzaldoxime |
| 247 | N-BOC-L-tert-butylglycine | tert-Butyl isocyanate | 3-Chloro-benzaldoxime |
| 256 | N-BOC-L-tert-butylglycine | 2-cyclohexylacetic acid | 5-Ethyl-2-furaldoxime |
| 263 | N-BOC-L-tert-butylglycine | 2-Cyclohexylacetic acid | 3-Chloro-5-fluoro-4-ethoxy-benzaldoxime |
| 264 | N-BOC-L-tert-butylglycine | N/A | 2,4-Dimethoxy-5-chloro-benzaldoxime |
| 266 | N-BOC-L-tert-butylglycine | (S)-2-cyclohexylpent-4-ynoic acid | 3-chloro-benzaldoxime |
| 268 | N-BOC-L-tert-butylglycine | 2-Cyclohexylacetic acid | 3-Chloro-benzaldoxime |
| 273 | N-BOC-L-tert-butylglycine | 2-Cyclohexylacetic acid | 3-Chloro-benzaldoxime |
| 280 | (S)-2-isopropyl-4-(isopropyl amino)-4-oxobutanoic acid | N/A | 3-chloro-benzaldoxime |
| 282 | N-BOC-L-tert-butylglycine | 2-(tetrahydro-2H-pyran-4-yl)acetic acid | 2,4-Dimethoxy-5-Chloro-benzaldoxime |
| 284 | N-BOC-L-tert-butylglycine | (S)-2-cyclohexylpropanoic acid | 3-chloro-benzaldoxime |
| 286 | N-BOC-L-tert-butylglycine | 2-(4-methyltetrahydro-2H-pyran-4-yl)acetic acid | 2,4-Dimethoxy-5-chloro-benzaldoxime |
| 290 | N-CBZ-L-tert-butylglycine | N/A | Piperonal oxime |
| 294 | N-BOC-L-tert-butylglycine | 2-cyclohexylacetic acid | 3-chloro-benzaldoxime |
| 295 | N-((S)-tetra-hydrofuran-3-yloxy)carbonyl)-L-tert-butylglycine | N/A | Piperonal oxime |
| 297 | N-BOC-L-tert-butylglycine | Tert-butylacetic acid | 2,4-Dimethoxy-5-chloro-benzaldoxime |
| 307 | N-BOC-L-tert-butylglycine | 2-Cyclohexylacetic acid | 2,4-Dimethoxy-5-chloro-benzaldoxime |
| 310 | N-BOC-L-tert-butylglycine | 2-(tetrahydro-2H-pyran-4-yl)acetic acid | 3,5-Dimethyl-4-methoxybenzaldehyde |
| 326 | N-BOC-L-tert-butylglycine | 2-(tetrahydro-2H-pyran-4-yl)acetic acid | 2,4-Dimethoxy-5-Chloro benzaldoxime |
| 335 | N-CBZ-L-tert-butylglycine | N/A | 2,4-Dimethoxy-benzaldoxime |
| 337 | N-BOC-L-tert-butylglycine | cyclopentyl 2,5-dioxopyrrolidin-l-yl carbonate | 3-Chloro-benzaldoxime |
| 344 | N-BOC-L-tert-butylglycine | N-FMOC-L-cyclohexylglycine followed by 2-pyrazine carboxylic acid | 3-Chloro-benzaldoxime |
| 346 | N-BOC-L-tert-butylglycine | 2-Norbornaneacetic acid | 3-Chloro-benzaldoxime |
| 351 | N/A | Tert-butylacetic acid | 3-chloro-benzaldoxime |
| 356 | N-BOC-L-tert-butylglycine | 2-(4-methyltetrahydro-2H-pyran-4-yl)acetic acid | 2,4-Dimethoxy-5-chloro-benzaldoxime |
| 362 | N-BOC-L-tert-butylglycine | 2-Cyclohexylacetic acid | 3,5-Dimethyl-4-methoxy-benzalehyde |
| 369 | N-BOC-L-tert-butylglycine | cyclopentyl 2,5-dioxopyrrolidin-l-yl carbonate | 3-Chloro-benzaldoxime |
| 375 | N-BOC-L-tert-butylglycine | 2-(tetrahydro-2H-pyran-4-yl)acetic acid | Piperonal oxime |
| 382 | N-BOC-L-tert-butylglycine | isopropylisocyanate | Piperonal oxime |
| 388 | N-BOC-L-tert-butylglycine | Cyclohexylacetic acid | 3-Chloro-benzaldoxime |

TABLE 6-continued

Additional compounds of formula I produced by methods 5a and 5b.

| Compound No. | Starting Material for P¹ | Starting Material for C¹ | Starting Material for $R_3$ |
|---|---|---|---|
| 411 | N-BOC-L-tert-butylglycine | 2-(tetrahydro-2H-pyran-4-yl)acetic acid | 3-Chloro-5-fluoro-4-ethoxy-benzaldoxime |
| 415 | N-CBZ-L-tert-butylglycine | N/A | Piperonal oxime |
| 418 | N-BOC-L-tert-butylglycine | 2-((2S,5R)-2,5-dimethyltetrahydro-2H-pyran-4-yl)acetic acid | 3-Chloro-benzaldoxime |
| 419 | N-BOC-L-tert-butylglycine | 2-(2,2-dimethyltetrahydro-2H-pyran-4-yl)acetic acid | 3-Chloro-benzaldoxime |
| 440 | N-BOC-L-tert-butylglycine | cyclopentyl 2,5-dioxopyrrolidin-1-yl carbonate | 2,4-Dimethoxy-5-chloro-benzaldoxime |
| 442 | N-BOC-L-tert-butylglycine | 2-((2S,5R)-2,5-dimethyltetrahydro-2H-pyran-4-yl)acetic acid | 3-Chloro-benzaldoxime |
| 445 | N-BOC-L-tert-butylglycine | 2-(1,4-dioxaspiro[4.5]decan-8-yl)acetic acid | 3-Chloro-benzaldoxime |
| 446 | N-BOC-L-tert-butylglycine | 2-Norbornaneacetic acid | 2,4-Dimethoxy-5-chloro-benzaldoxime |
| 453 | N-BOC-L-tert-butylglycine | 2-Cyclohexylacetic acid | 3-Chloro-benzaldoxime |
| 468 | N-BOC-L-tert-butylglycine | 2-((2R,5R)-2,5-dimethyltetrahydro-2H-pyran-4-yl)acetic acid | 3-Chloro-benzaldoxime |
| 473 | N-BOC-L-tert-butylglycine | Tert-butylacetic acid | 2,4-Dimethoxy-5-chloro-benzaldoxime |
| 485 | N-BOC-L-tert-butylglycine | trans-2-phenyl-1-cyclopropane-carboxylic acid | 3-Chloro-benzaldoxime |
| 502 | N-BOC-L-tert-butylglycine | N-FMOC-L-cyclohexylglycine followed by 2-pyrazine carboxylic acid | 3-Chloro-benzaldoxime |
| 510 | N-BOC-L-tert-butylglycine | 2-(tetrahydro-2H-pyran-4-yl)acetic acid | 2,4-Dimethoxy-5-Chloro-benzaldoxime |
| 516 | N-((S)-tetrahydro-furan-3-yloxy)-carbonyl)-L-tert-butylglycine | N/A | 2,4-Dimethoxy-benzaldoxime |
| 522 | N-BOC-L-tert-butylglycine | 2-Cyclohexylacetic acid | 3-Chloro-benzaldoxime |
| 529 | N-BOC-L-tert-butylglycine | 2-(4-methyltetra-hydro-2H-pyran-4-yl)acetic acid | 2,4-Dimethoxy-5-chloro-benzaldoxime |
| 541 | N-BOC-L-tert-butylglycine | 2-(4-methyltetra-hydro-2H-pyran-4-yl)acetic acid | 3-chloro-benzaldoxime |
| 542 | N-BOC-L-tert-butylglycine | tert-Butyl isocyanate | 3-chloro-benzaldoxime |
| 549 | N-BOC-L-tert-butylglycine | (S)-2-cyclohexyl-4-oxo-4-(pyrrolidin-1-yl)butanoic acid | 3-chloro-benzaldoxime |
| 554 | N-BOC-L-tert-butylglycine | 2-(tetrahydro-2H-pyran-4-yl)acetic acid | 5-Ethyl-2-furaldoxime |
| 562 | N-BOC-L-tert-butylglycine | 2-Cyclohexylacetic acid | 2,4-Dimethoxy-5-chloro-benzaldoxime |
| 569 | N-BOC-L-tert-butylglycine | (S)-2-cyclohexyl-4-(methylamino)-4-oxobutanoic acid | 3-chloro-benzaldoxime |
| 575 | N-BOC-L-tert-butylglycine | 2-(4-hydroxy-4-methylcyclohexyl)acetic acid | 3-chloro-benzaldoxime |
| 577 | N-BOC-L-tert-butylglycine | 2-Cyclohexylacetic acid | 2,4-Dimethoxy-5-chloro-benzaldoxime |
| 581 | N-BOC-L-tert-butylglycine | N/A | 2,4-Dimethoxy-5-chloro-benzaldoxime |
| 589 | N-BOC-L-tert-butylglycine | 2-Cyclohexylacetic acid | 5-Chloro-8-quinoline-carbaldoxime |
| 590 | N-BOC-L-tert-butylglycine | 2-Cyclohexylacetic acid | 2-Methoxy-3-methyl-benzaldoxime |

Certain other compounds of Formula I may be prepared by Method 6 as illustrated below.

Method 6:

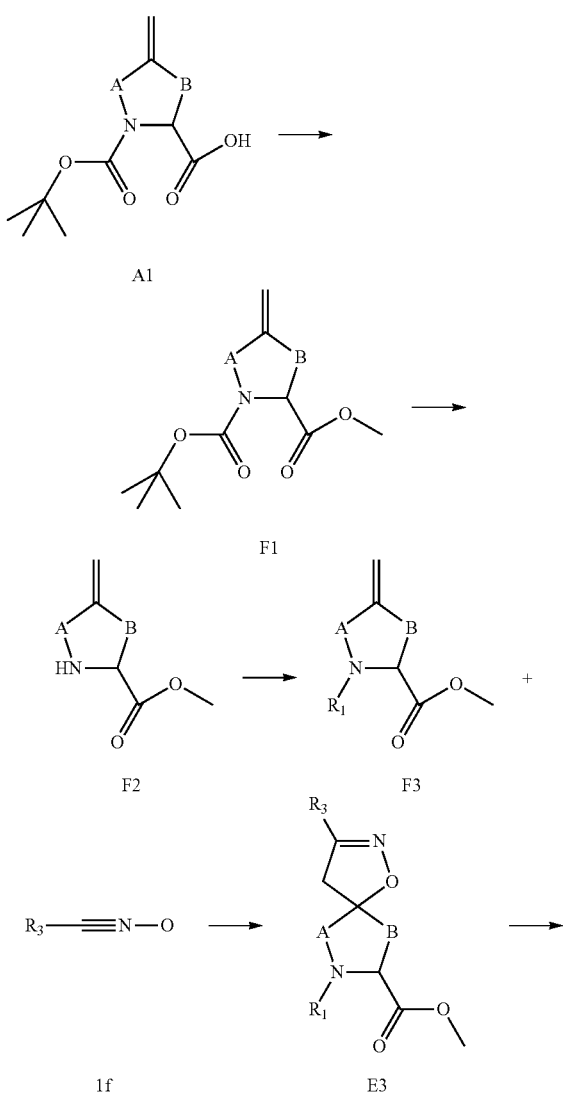

-continued

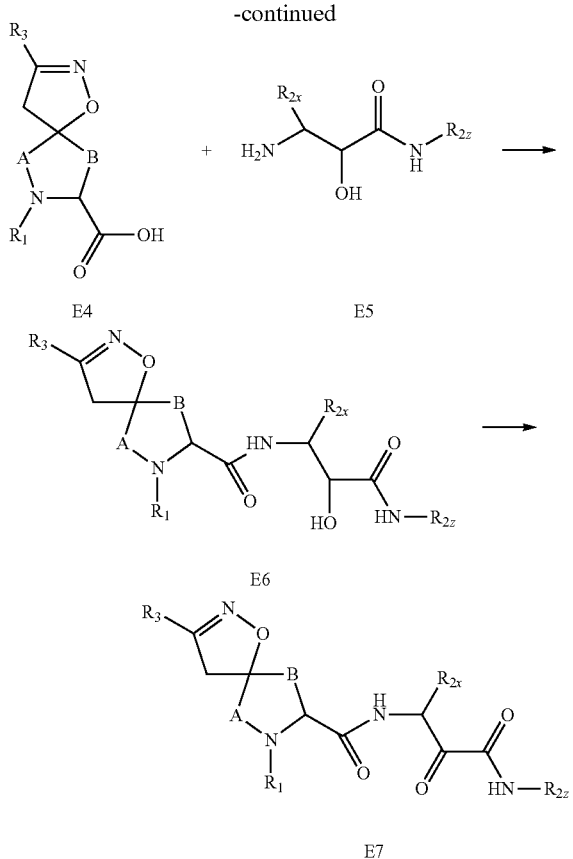

E4

E5

E6

E7

Referring to Method 6, the intermediate A1 is converted to the Boc-methyl ester F1. Removal of the Boc group from F1 provides the amine-ester F2 which is reacted with an $R_1$ carboxylic acid in the presence of a coupling reagent to provide F3 wherein $R_1$ is $R_4C(O)$—. F3 reacts with a nitrile oxide if to provide the spiroisoxazoline acid E4 after hydrolysis of the corresponding methyl ester E3. Conversion of E4 to E7 is achieved as described in Method 5a.

Example 17

Compound No. 267

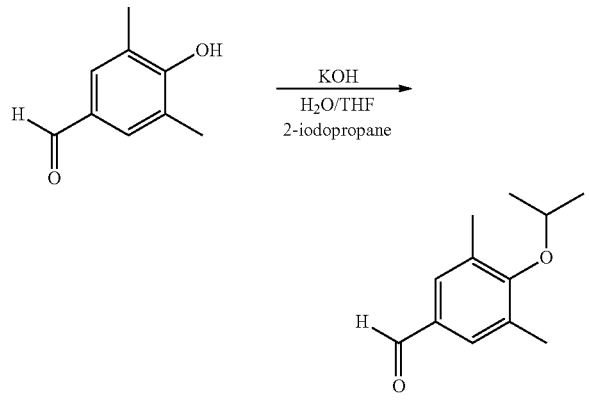

4-Hydroxy-3,5-dimethylbenzaldehyde (2.5 g, 16.6 mmol) in THF (100 mL) was treated with KOH (1.5 eq. of 1 N aq. solution, 25 mL) and 2-iodopropane (2.0 eq.) and heated at reflux for 5 days. The reaction was then cooled, transferred to a separatory funnel, diluted with MTBE, washed with $H_2O$, 1 N NaOH (twice), 0.5 N HCl (aq.), brine, dried over $MgSO_4$ and concentrated. The product was purified over silica gel on an ISCO combiflash to yield 1.99 g (10.34 mmol) 4-isopropoxy-3,5-dimethylbenzaldehyde as a colorless liquid. $H^1$ NMR (300 MHz, $CDCl_3$) 9.89 (s, 1H), 7.55 (s, 2H), 4.41-4.26 (m, 1H), 2.32 (s, 6H), 1.32 (d, J=6 Hz, 6H).

4-(Isopropoxy)-3,5-dimethylbenzaldehyde (1.98 g, 10.3 mmol) in EtOH (60 mL) was heated to 60° C. with hydroxylamine hydrochloride (2.4 M aq. solution, 5.2 mL, 1.2 eq.) and $Na_2CO_3$ (1.2 M solution, 5.2 mL, 0.6 eq.) at room temperature for 2 hours. The reaction was transferred to a separatory funnel, diluted with EtOAc; the organic layer was separated, washed with brine, dried ($MgSO_4$), filtered and concentrated to yield 710 mg (3.24 mmol) of 4-(isopropoxy)-3,5-dimethylbenzaldehyde oxime as a light yellow oil. $^1$H-NMR (500 MHz, $CDCl_3$): 8.10 (s, 1H), 7.23 (s, 2H), 4.29-4.18 (m, 1H), 2.29 (s, 6H), 1.29 (d, 6H).

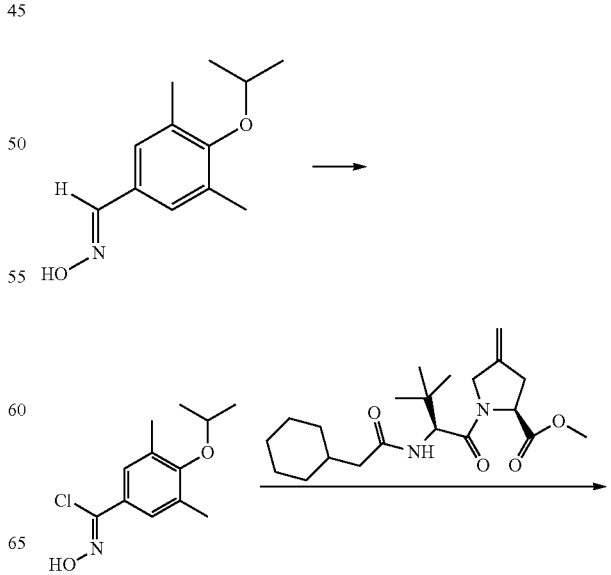

-continued

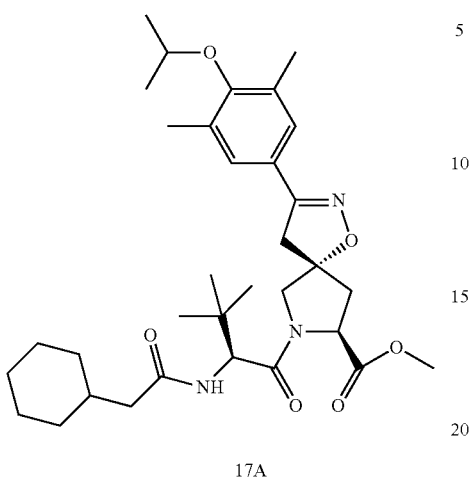

17A 4-(Isopropoxy)-3,5-dimethylbenzaldehyde oxime (166 mg, 0.801 mmol) in DMF (3 mL) at room temperature was stirred overnight with NCS (130 mg, 0.974 mmol). To this reaction was added the methyl ester (257 mg, 0.679 mmol) in DMF (1.5 mL) and triethylamine (1.2 eq.). This was stirred overnight at room temperature. The reaction was then diluted with EtOAc/Hexanes (4:1) and washed with 1N HCl (aq.). The layers were separated and the aqueous layer was back extracted with EtOAc/Hexanes (4:1). The organic layers were combined, washed with brine, dried (MgSO$_4$), and concentrated. The compound was purified over silica gel on an ISCO Combiflash with EtOAc/Hexanes as eluent to yield 173 mg (0.296 mmol) of compound 17A as a white solid. LCMS (M+1)=584.3

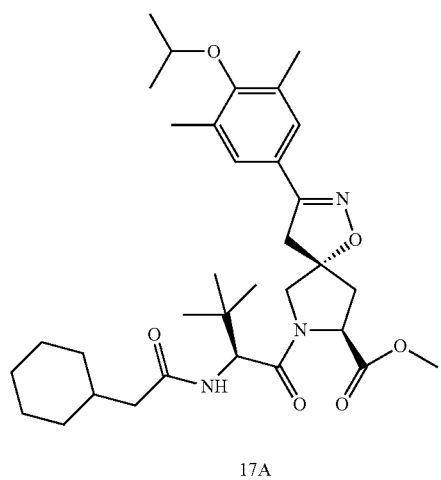

17A

-continued

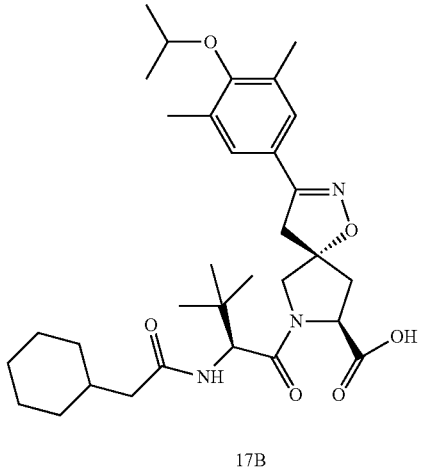

17B

The compound 17A (173 mg, 0.30 mmol) was stirred with LiOH.H$_2$O (1.1 eq.) in THF/MeOH/H$_2$O (4:1:1, 3 mL) at RT overnight. The reaction was diluted with EtOAc, acidified with 1N HCl (aq) and the layers were separated. The aqueous layer was back extracted with EtOAc, the organic layers combined, washed with brine, dried (MgSO$_4$) and concentrated to yield 171 mg (0.30 mmol) of compound 17B as a white solid. FIA MS (M+1)=570.3.

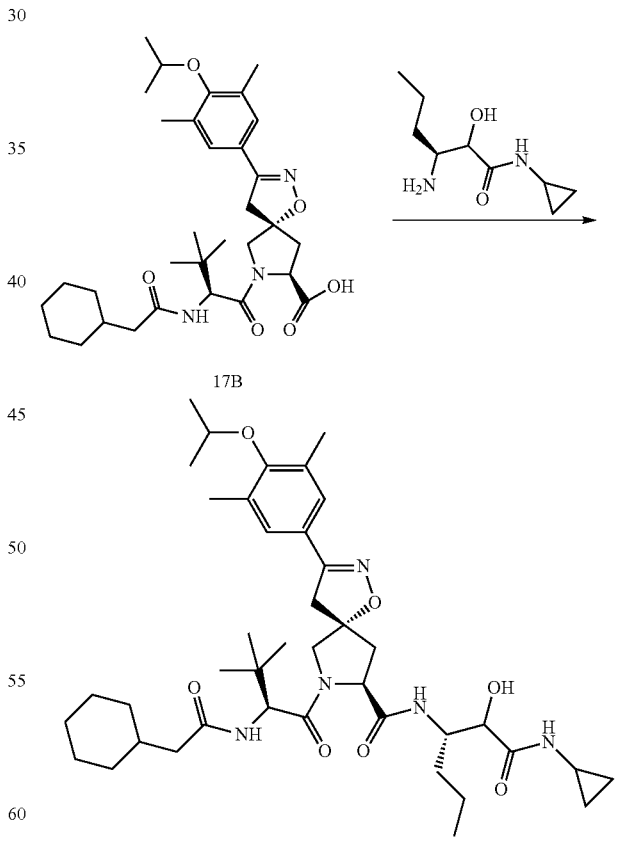

17C

Carboxylic acid 17B (83 mg, 0.146 mmol), EDC.HCl (37 mg, 1.3 eq.), HOBt (26 mg, 1.3 eq.), (3S)-3-amino-N-cyclopropyl-2-hydroxyhexanamide hydrochloride (64 mg, 2.0 eq.), and DIEA (0.100 mL, 4.0 eq.) were stirred in DMF (0.9 mL) at room temperature overnight. The reaction mixture was then diluted with EtOAc and washed with 1 N HCl (aq) (twice). The aqueous layer was separated and back extracted with EtOAc. The organic layers were combined, washed with brine, dried (MgSO$_4$), and concentrated. The product was purified over silica gel on an ISCO combiflash to yield 85 mg (0.115 mmol) of compound 17C. LCMS (M+1)=738.3

(d, 1H), 2.86-2.74 (m, 1H), 2.63-2.42 (m, 2H), 2.29 (s, 6H), 2.19-1.85 (m, 3H), 1.84-0.82 (m, 34H), 0.65-0.58 (m, 2H).

Example 18

Compound No. 556

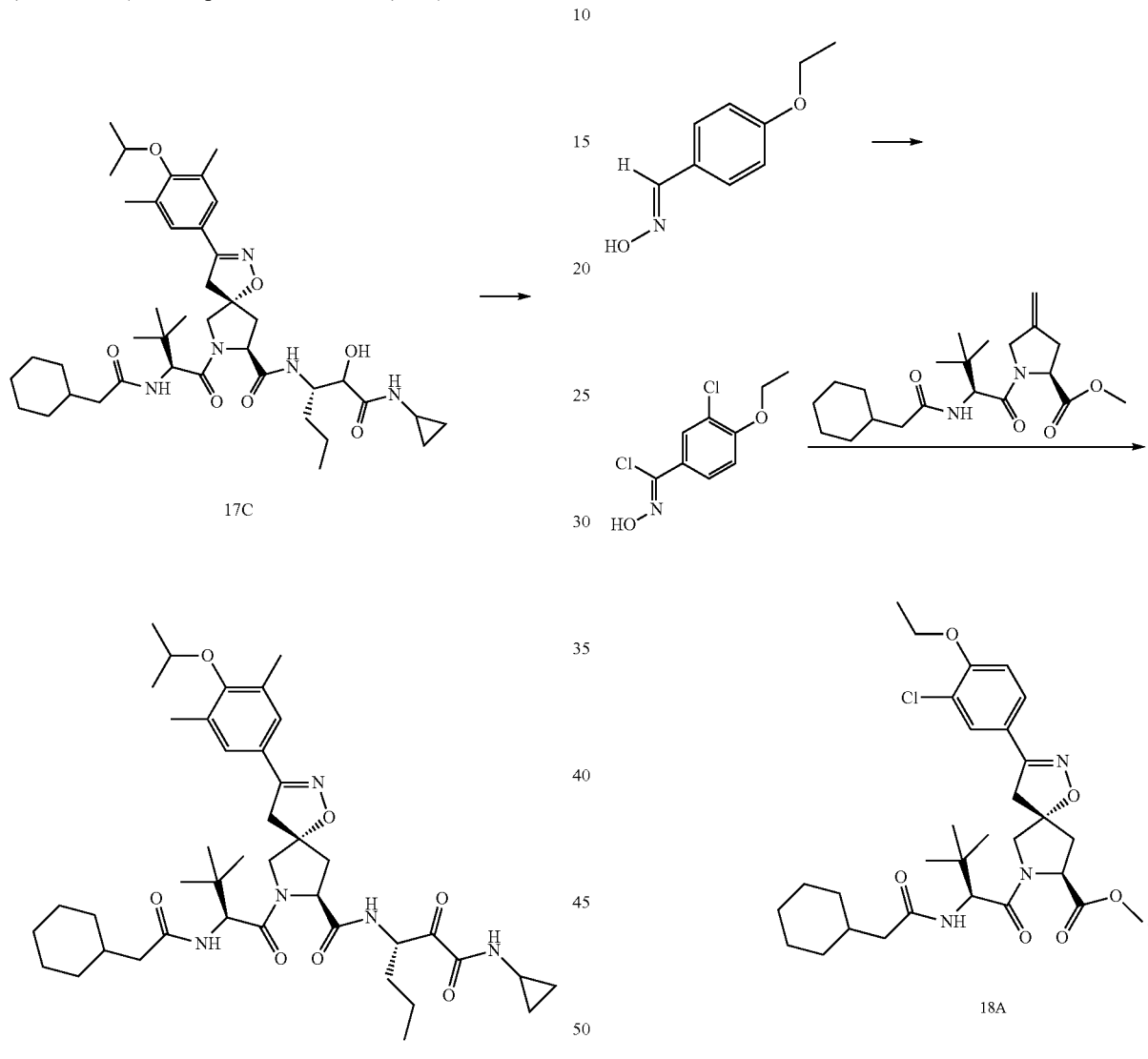

17C

Compound No. 267

18A

Compound 17C (85 mg, 0.115 mmol) in CH$_2$Cl$_2$ (1.0 mL) was treated with Dess-Martin periodinane (54 mg, 1.1 eq.) for 30 minutes. The reaction was quenched with equal volumes (≈1 mL) of saturated aqueous NaHCO$_3$ and 1 N Na$_2$S$_2$O$_3$ (aq). The organic layer was separated and purified directly over silica gel on an ISCO combiflash to yield 77 mg (0.105 mmol) of Compound No. 267. FIA MS (M+1)=736.2. $^1$H-NMR (300 MHz, CDCl$_3$): 7.33-7.26 (m, 2H), 7.12 (d, 1H), 6.91 (d, 1H), 6.12 (d, 1H), 5.45-5.32 (m, 1H), 4.78-4.63 (m, 2H), 4.29-4.17 (m, 2H), 3.71 (d, 1H), 3.43 (d, 1H), 3.30

4-Ethoxybenzaldehyde oxime (204 mg, 1.24 mmol), was dissolved in DMF (to 0.2 M) and treated with NCS (1 eq.). The reaction was stirred until starting material was consumed. One half of the reaction volume was removed and treated with additional NCS (1.5 eq.) and stirred overnight. To this solution was then added the methyl ester (200 mg, 0.85 eq.) in DMF (0.3 mL) and triethylamine (0.10 mL, 1.1 eq.). The reaction was stirred overnight at room temperature, then diluted with EtOAc, washed with 1 N HCl (aq.), and washed with brine. The aqueous layer was back extracted with EtOAc and the combined organic layers were washed with brine, dried (MgSO$_4$), and concentrated to a dark oil. The product was purified over silica gel on an ISCO combiflash to yield 97 mg (0.168 mmol) of compound 18A. LCMS (M+1)=576.3

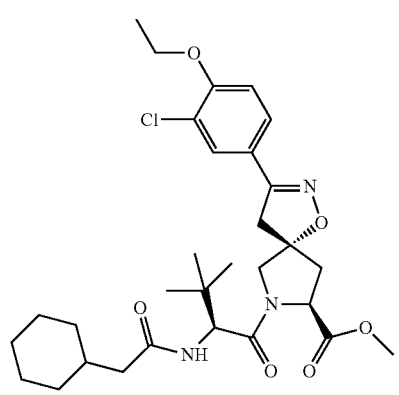

18A

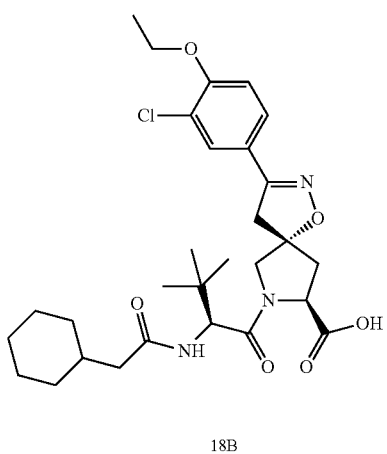

18B

Compound 18A (97 mg, 0.168 mmol) was dissolved in THF/MeOH/H2O (8:1:1, 5 mL) and treated with LiOH.H2O (1.1 eq.) at room temperature overnight. The reaction was concentrated, diluted in EtOAc and methanol and washed with 1N HCl (aq). The aqueous layer was separated and extracted with EtOAc. The combined organic layers were washed with brine, dried over MgSO₄ and concentrated to yield 76 mg (0.135 mmol) of compound 18B. FIA MS (M−1)=560.4

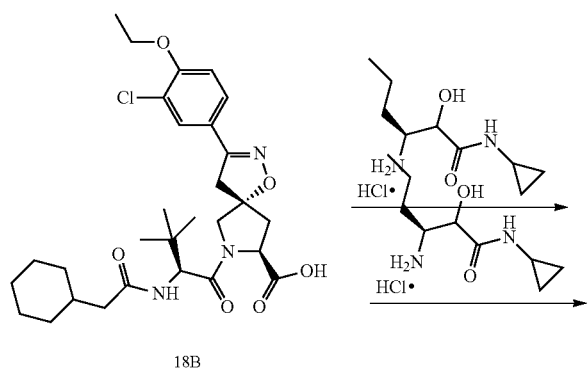

18B

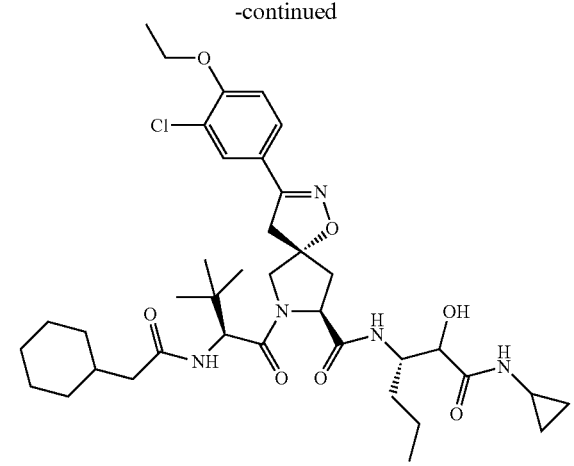

18C

Compound 18B (35 mg, 0.062 mmol), EDC.HCl (15 mg, 1.3 eq.), HOBt (12 mg, 1.3 eq.), an amino alcohol hydrochloride (55 mg, 2.0 eq.), and DIEA (0.044 mL, 4.0 eq.) were stirred in DMF (0.7 mL) at room temperature overnight. The reaction was then diluted with EtOAc and washed with 1 N HCl (aq) (twice). The aqueous layer was separated and back extracted with EtOAc. The organic layers were combined, washed with brine, dried (MgSO₄), anc concentrated. The product was purified over, silica gel on an ISCO combiflash to yield 28 mg (0.038 mmol) of compound 18C. LCMS (M+1)=730.2

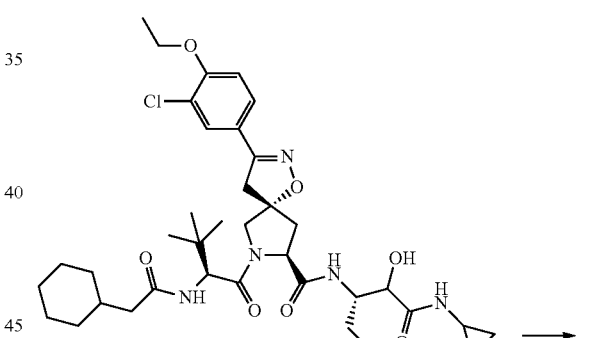

18C

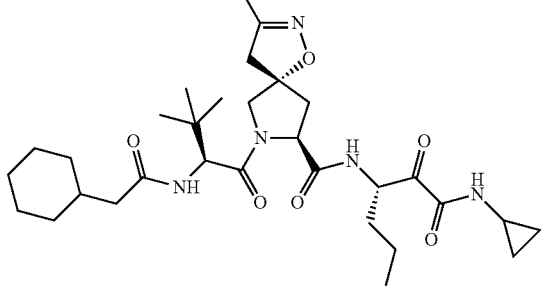

Compound No. 556

Compound 18C (28 mg, 0.038 mmol) in $CH_2Cl_2$ (0.7 mL) was treated with Dess-Martin periodinane (18 mg, 1.1 eq.) for 30 minutes. The reaction was quenched with equal volumes (≈1 mL) of saturated aqueous $NaHCO_3$ and 1N $Na_2S_2O_3$ (aq.). The organic layer was separated and purified directly over silica gel on an ISCO Optix 10× to yield 24 mg (0.033 mmol) of Compound No. 556. FIA MS (M+1)=728.2. $^1$H-NMR (300 MHz, $CDCl_3$): 7.65 (d, 1H), 7.48 (dd, 1H), 7.11 (d, 1H), 6.95-6.88 (m, 2H), 6.08 (d, 1H), 5.40-5.31 (m, 2H), 4.78-4.63 (m, 2H), 4.26 (d, 1H), 4.20-4.11 (m, 2H), 3.71 (d, 1H), 3.42 (d, 1H), 3.27 (d, 1H), 2.84-2.73 (m, 1H), 2.63-2.46 (m, 2H), 2.20-1.86 (m, 3H), 1.62-0.85 (m, 30H), 0.66-0.58 (m, 2H)

Listed below in Table 7 are additional compounds of Formula I prepared by Method 6.

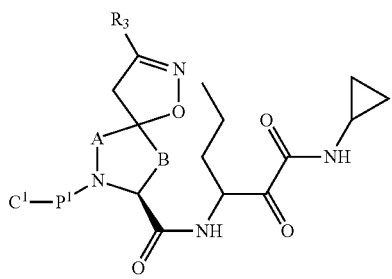

TABLE 7

Additional compounds of formula I prepared by method 6.

| Compound No. | Starting Material for $P^1$ | Starting Material for $C^1$ | Starting Material for $R_3$ |
|---|---|---|---|
| 18 | N-BOC-L-tert-butylglycine | 2-Cyclohexylacetic acid | 7-Chloro-2,3-dihydrobenzo[b]furan-5-carboxaldoxime |
| 19 | N-BOC-L-tert-butylglycine | 2-Cyclohexylacetic acid | 3-Chloro-4-methyl-benzaldoxime |
| 28 | N-BOC-L-tert-butylglycine | 2-Cyclohexylacetic acid | 2-Cyano-benzaldoxime |
| 31 | N-BOC-L-tert-butylglycine | 2-cyclohexylacetic acid | 8-Quinoline-carbaldoxime |
| 38 | N-BOC-L-tert-butylglycine | 2-Cyclohexylacetic acid | 2,5-Dichloro-3-methoxy-benzaldoxime |
| 42 | N-BOC-L-tert-butylglycine | 2-Cyclohexylacetic acid | 8-Quinoline-carboxaldoxime |
| 62 | N-BOC-L-tert-butylglycine | 2-Cyclohexylacetic acid | 5-chloro-3-Thiophene-carboxaldoxime |
| 68 | N-BOC-L-tert-butylglycine | 2-cyclohexylacetic acid | 8-Quinoline-carbaldoxime |
| 74 | N-BOC-L-tert-butylglycine | 2-Cyclohexylacetic acid | 8-chloro-2,2-dimethylchromane-6-carbaldoxime |
| 89 | N-BOC-L-tert-butylglycine | 2-Cyclohexylacetic acid | 3-nitro-benzaldoxime |
| 97 | N-BOC-L-tert-butylglycine | 2-cyclohexylacetic acid | 3-Chloro-4-isopropoxy-benzaldoxime |
| 111 | N-BOC-L-tert-butylglycine | 2-Cyclohexylacetic acid | 3-Chloro-4-methoxy-5-methyl-benzaldoxime |
| 114 | N-BOC-L-tert-butylglycine | 2-Cyclohexylacetic acid | 3-Chloro-4-methoxy-5-methyl-benzaldoxime |
| 132 | N-BOC-L-tert-butylglycine | 2-Cyclohexylacetic acid | 5-Chloro-nicotinaldoxime |
| 134 | N-BOC-L-tert-butylglycine | 2-Cyclohexylacetic acid | 5-Chloro-2,3-dihydro-benzo[b]furan-7-carboxaldoxime |
| 158 | N-BOC-L-tert-butylglycine | 2-Cyclohexylacetic acid | 3-Chloro-6-methoxy benzaldoxime |
| 165 | N-BOC-L-tert-butylglycine | 2-Cyclohexylacetic acid | 5-Chloro-2-methoxy-nicotinaldoxime |
| 168 | N-BOC-L-tert-butylglycine | 2-Cyclohexylacetic acid | 3-Thiophene-carboxaldoxime |
| 169 | N-BOC-L-tert-butylglycine | 2-Cyclohexylacetic acid | 3-Chloro-2-fluoro-benzaldoxime |
| 170 | N-BOC-L-tert-butylglycine | 2-Cyclohexylacetic acid | 5-Chloro-2,2-dimethyl-2,3-dihydrobenzo[b]furan-7-carboxaldoxime |
| 250 | N-BOC-L-tert-butylglycine | 2-Cyclohexylacetic acid | 3-Chloro-5-methoxybenzaldoxime |
| 267 | N-BOC-L-tert-butylglycine | 2-cyclohexylacetic acid | 4-Isopropoxy-3,5-dimethyl-benzaldoxime |
| 292 | N-BOC-L-tert-butylglycine | 2-Cyclohexylacetic acid | 5-Chloro-nicotinaldoxime |
| 305 | N-BOC-L-tert-butylglycine | 2-Cyclohexylacetic acid | 6-Fluoro-1,3-benzodioxene-8-carbaldoxime |
| 312 | N-BOC-L-tert-butylglycine | 2-Cyclohexylacetic acid | 5-Chloro-6-methoxynicotinaldoxime |
| 315 | N-BOC-L-tert-butylglycine | 2-Cyclohexylacetic acid | 5-Chloro-4-Methyl-3,4-dihydro-2H-1,4-benzoxazine-7-carbaldoxime |
| 321 | N-BOC-L-tert-butylglycine | 2-Cyclohexylacetic acid | 5-Chloro-2,3-dimethoxy-benzaldoxime |
| 366 | N-BOC-L-tert-butylglycine | 2-Cyclohexylacetic acid | 5-Chloro-4-methoxy-2-methyl-benzaldoxime |
| 370 | N-BOC-L-tert-butylglycine | 2-Cyclohexylacetic acid | 5-Chloro-piperonal oxime |
| 396 | N-BOC-L-tert-butylglycine | 2-Cyclohexylacetic acid | 3-Chloro-5-methyl-benzaldoxime |
| 406 | N-BOC-L-tert-butylglycine | 2-cyclohexylacetic acid | 4-Cyclopropyl methoxy-3,5-dimethyl-benzaldoxime |
| 430 | N-BOC-L-tert-butylglycine | 2-Cyclohexylacetic acid | 8-Chloro-1-methyl-1,2,3,4-tetrahydro-quinoline-6-carbaldoxime |
| 469 | N-BOC-L-tert-butylglycine | 2-Cyclohexylacetic acid | 2-Methoxy-nicotinaldoxime |
| 478 | N-BOC-L-tert-butylglycine | 2-Cyclohexylacetic acid | 5-Chloro-2-thiophene-carboxaldoxime |
| 494 | N-BOC-L-tert-butylglycine | 2-Cyclohexylacetic acid | 3-Chloro-4,5-dimethoxy-benzaldoxime |
| 499 | N-BOC-L-tert-butylglycine | 2-Cyclohexylacetic acid | 7-Chloro-2,3-dihydro-benzo[b]furan-5-carboxaldoxime |
| 500 | N-BOC-L-tert-butylglycine | 2-Cyclohexylacetic acid | 4-Methoxy-3-methyl-benzaldoxime |
| 513 | N-BOC-L-tert-butylglycine | 2-cyclohexylacetic acid | 4-Ethoxy-3,5-dimethyl-benzaldoxime |
| 556 | N-BOC-L-tert-butylglycine | 2-cyclohexylacetic acid | 3-Chloro-4-ethoxy-benzaldoxime |

TABLE 7-continued

Additional compounds of formula I prepared by method 6.

| Compound No. | Starting Material for P¹ | Starting Material for C¹ | Starting Material for R₃ |
|---|---|---|---|
| 591 | N-BOC-L-tert-butylglycine | 2-Cyclohexylacetic acid | 2-Pyridine carboxaldoxime |
| 592 | N-BOC-L-tert-butylglycine | 2-Cyclohexylacetic acid | 2-Pyridine carboxaldoxime |
| 593 | N-BOC-L-tert-butylglycine | 2-Cyclohexylacetic acid | 4-Chloro-2-pyridine-carboxaldoxime |
| 594 | N-BOC-L-tert-butylglycine | 2-Cyclohexylacetic acid | 3-Chloro-6-fluoro-benzaldoxime |

Certain other compounds of the invention may be prepared by Method 7 as illustrated below.

Method 7:

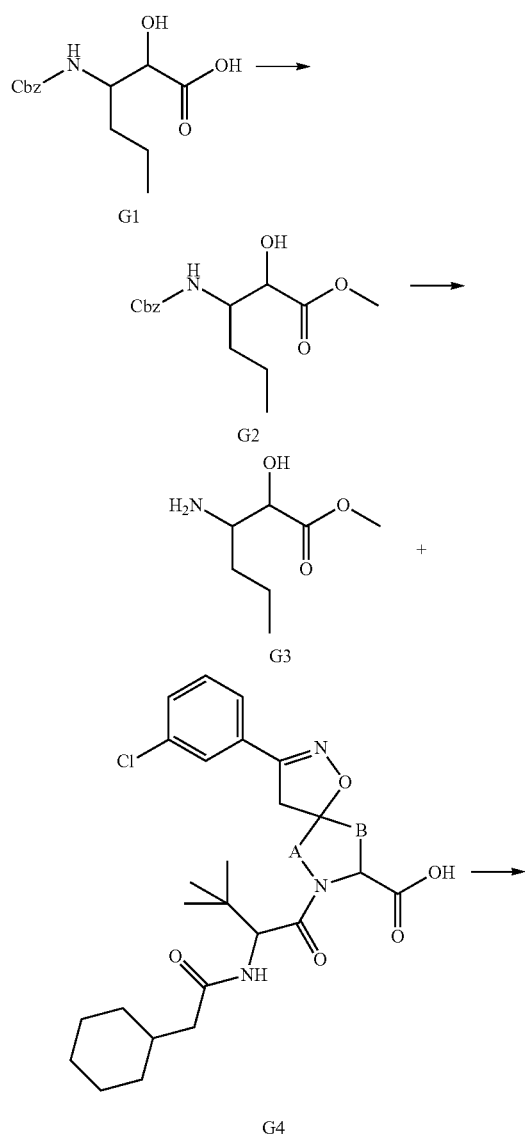

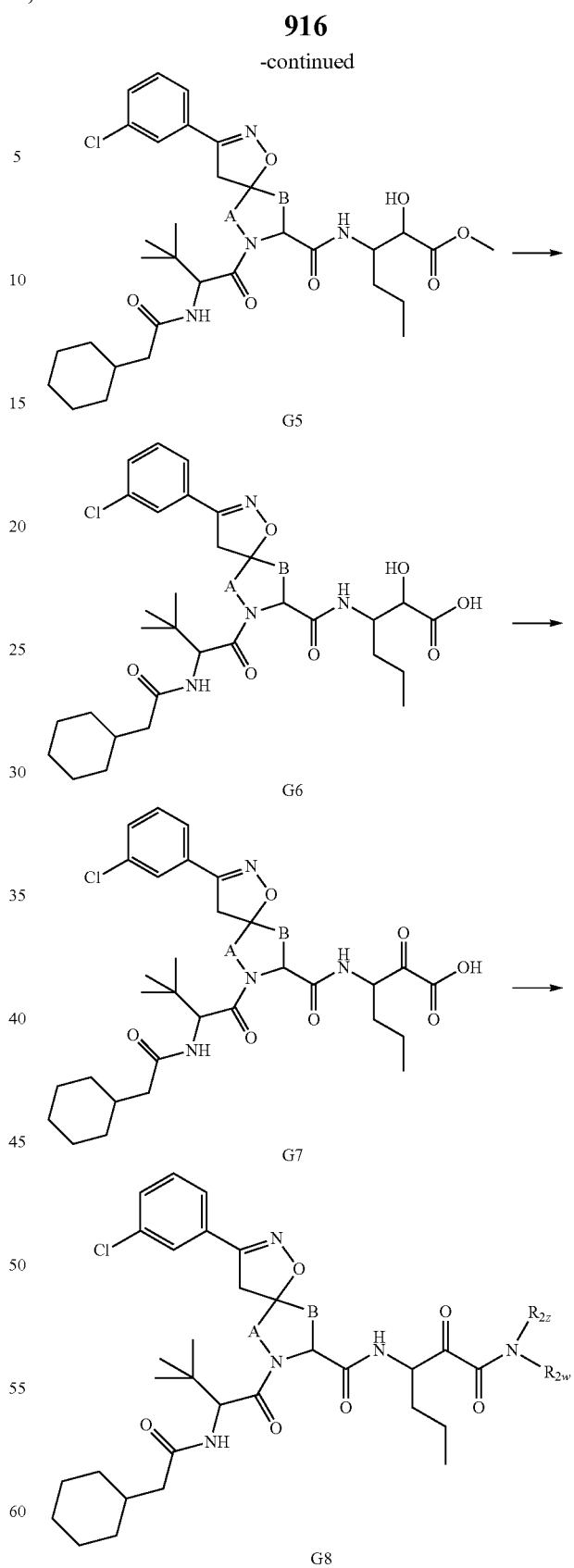

Referring to Method 7, the Cbz hydroxy acid G1 is converted to the methyl ester G2 and deprotected to provide the amino-ester G3. Reaction of G3 with the spiroisoxazoline acid G4 in the presence of a coupling reagent provides the intermediate G5. Hydrolysis of the methyl ester of G5 provides the hydroxy acid G6 which is oxidized with, for example, Dess-Martin periodinane to provide the ketoacid G7. Reaction of G7 with an amine $R_{13}R_{10}NH$ in the presence of a coupling reagent provides the final product G8.

Example 19

Compound No. 275

Step 1: Preparation of Compound Q

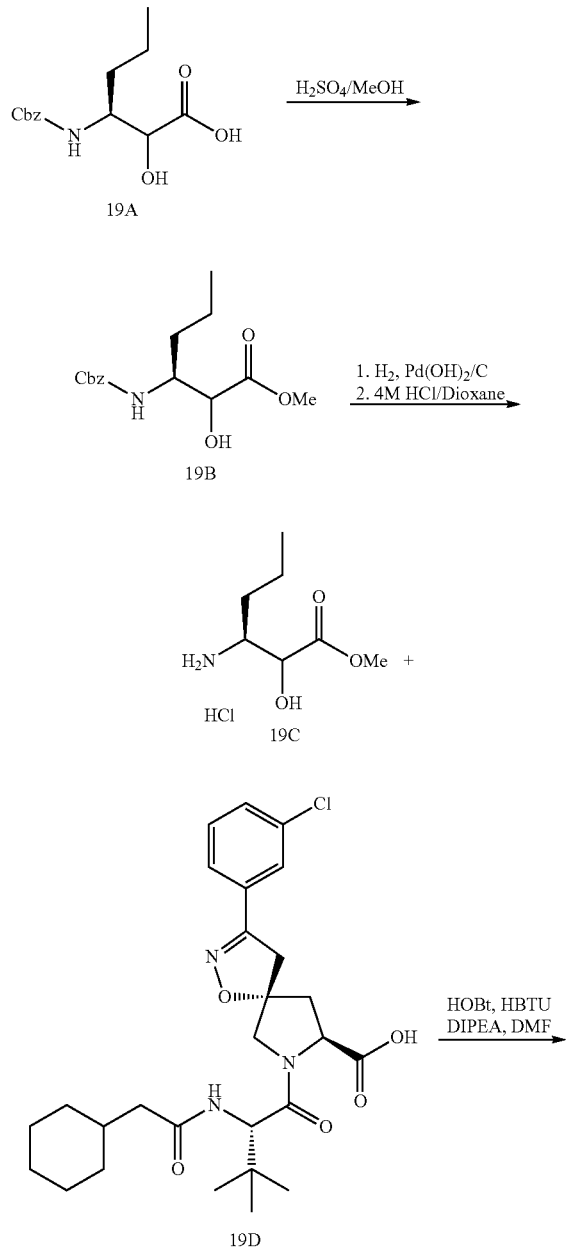

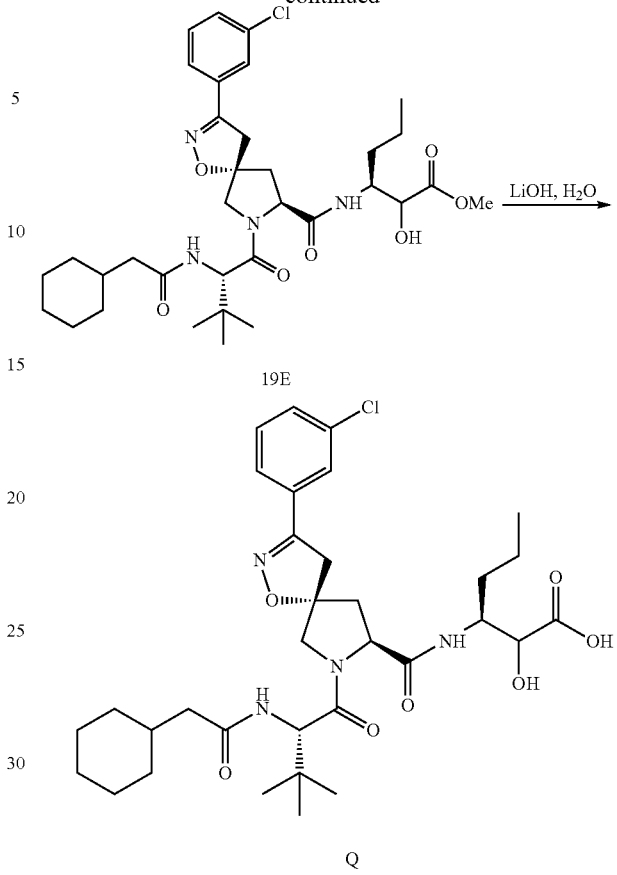

1.00 g of acid 19A was dissolved in 14 mL of methanol and heated to reflux. Two drops of concentrated $H_2SO_4$ was added and the reaction refluxed overnight. The mixture was cooled to room temperature, and neutralized with 50 mL of $NaHCO_3$ (sat. aq.). The reaction mixture was extracted three times with 50 mL of ethyl acetate. The combined organic extracts were dried over magnesium sulfate and evaporated to yield 1.01 g of compound 19B as a white powder. Major diastereomer $^1$H-NMR (300 MHz, $CDCl_3$) δ: 7.40-7.31 (m, 5H), 5.12 (s, 2H), 4.99 (d, 1H, J=8.7 Hz), 4.35 (s, 1H), 4.15-4.02 (m, 1H), 3.81 (s, 3H), 3.05 (br s, 1H), 1.67-1.17 (m, 4H), 0.91 (t, 3H, J=6.8 Hz). Minor diastereomer $^1$H-NMR (300 MHz, $CDCl_3$) δ: 7.40-7.31 (m, 5H), 5.07 (s, 2H), 4.90 (d, 1H, J=9.8 Hz), 4.19 (s, 1H), 4.15-4.02 (m, 1H), 3.76 (s, 3H), 3.03 (br s, 1H), 1.67-1.17 (m, 4H), 0.96 (t, 3H, J=7.1 Hz).

1.00 g of CBz-protected methyl ester 19B was dissolved in 11 mL of methanol. 150 mg of $Pd(OH)_2$ (20 wt % on carbon) was added, and the mixture flushed with 1 atm of hydrogen gas and stirred at room temperature for 3 hours. The methanolic solution was filtered through a Celite® plug and the filter pad rinsed with additional methanol. Upon evaporation, a light yellow oil was collected and redissolved in 5 mL of DCM and treated with 1.5 mL of 4 M HCl solution in dioxane. Upon stirring for 1 minute, the reaction was evaporated. 0.65 g of compound 19C was collected as a white powder, and characterized by LCMS (M+1=162.0).

0.80 g of the spiroisoxazoline acid of compound 19D was stirred with 0.33 g of HOBt, 0.81 g of HBTU, and 15 mL of DMF. To the stirring solution was added 807 μL of DIPEA, and stirred for 10 minutes. 0.33 g of the hydrochloride salt 19C was added. The reaction was stirred at room temperature for 3 hours. To the reaction mixture was added 200 mL of EtOAc, and the mixture washed twice with 100 mL of NaHCO₃ (sat. aq.), then 100 mL of brine. The organic phase was dried over MgSO₄ and evaporated. The crude reaction mixture was purified by elution through silica gel column (40 g column, gradient elution, 40-55% EtOAc:Hexanes) to give 1.02 g of compound 19E as a white powder, which was identified by LCMS (M+1=661.3).

1.04 g of methyl ester 19E was stirred in 6 mL of THF and to this solution was added 3 mL of 1 M LiOH (aq). The reaction was stirred at room temperature for 2 hours where it was determined by HPLC to be complete. The reaction was treated with 6 mL of 1 M HCl, and extracted three times with 15 mL of ethyl acetate. The combined extracts were evaporated to give 1.00 g of compound Q as a beige solid which was carried on to the next step.

Step 2: Preparation of Compound R

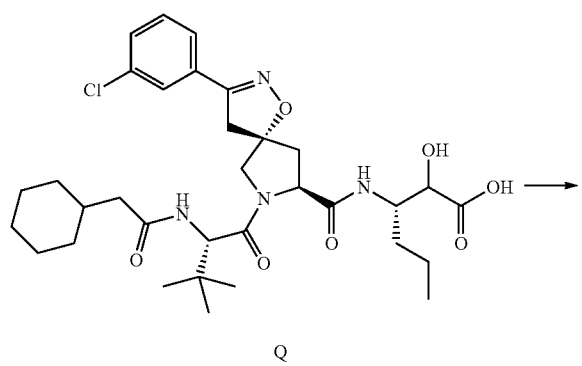

Q

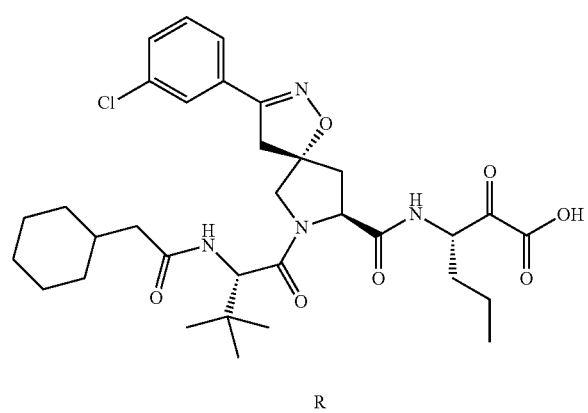

R

To a solution of compound Q (0.300 g, 0.46 mmol) in CH₂Cl₂ (15 mL) was added 5.58 mL of a 0.16 M solution of Dess Martin periodinane in CH₂Cl₂ dropwise. After it was stirred for 4 hours at room temperature, 10 mL of 1M Na₂S₂O₃ solution was added and the reaction mixture was stirred for 30 minutes at ambient temperature. The organic layer was separated, washed with water, dried over Na₂SO₄, filtered and concentrated. The crude mixture was redissolved in CH₂Cl₂ and precipitated with Hexanes and filtered to give 230 mg of compound R. LC/MS: m/z 645.7 $(M+H)^+$ at 1.99 minutes (10-99% CH₃CN (0.035% TFA)/H₂O (0.05% TFA))

Step 3: Preparation of Compound No. 275

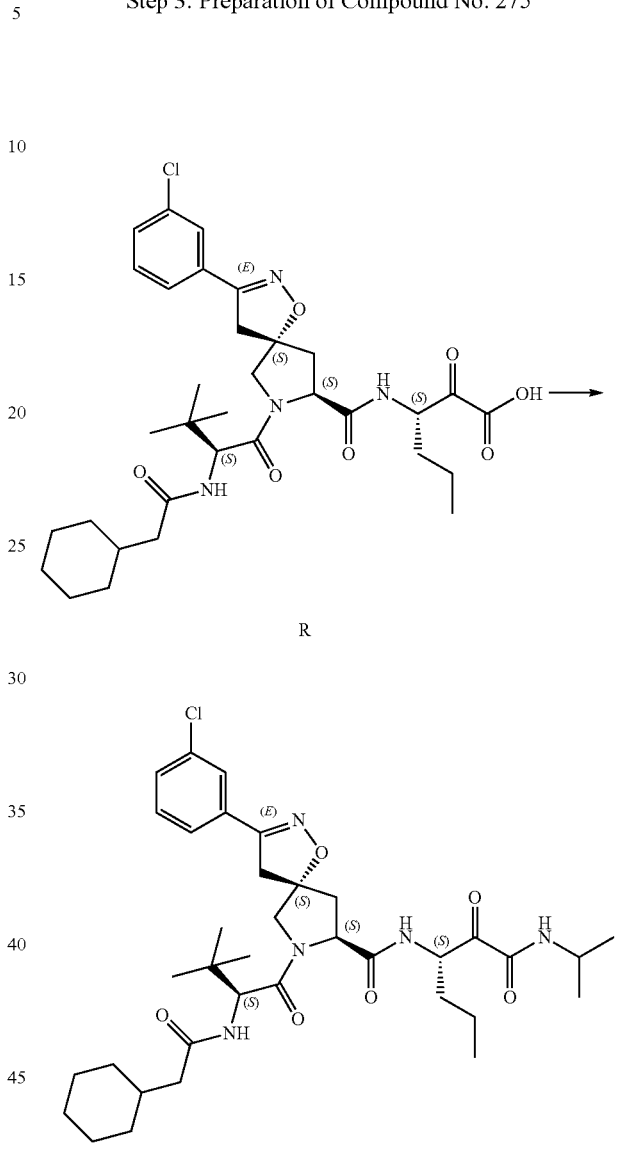

R

Compound No. 275

To a suspension of compound R (20 mg, 0.0.031 mmol) in anhydrous acetonitrile was added pyridine (10 μL, 0.124 mmol), 2-chloro-1-methyl-pyridinium iodide (15.3 mg, 0.06 mmol), HOBt (6.8 mg, 0.05 mmol), followed by the addition of a 504 solution of isopropylamine (3.7 mg, 0.062 mmol) in anhydrous acetonitrile. The reaction was allowed to stir at room temperature and complete after two hours. The reaction mixture was quenched with 1 mL of saturated aqueous sodium bicarbonate solution, the layers were separated and aqueous layer was extracted three times with CH₂Cl₂. The combined organics were dried over Na₂SO₄, filtered and concentrated under reduced pressure. The residue was dissolved in 1.5 mL CH₂Cl₂ and purified by normal phase HPLC (10-

99% EtOAc/Hexanes) to yield Compound No. 275. LC/MS: m/z 686.7 (M+H)+ at 2.01 minutes (10-99% CH3CN (0.035% TFA)/H2O (0.05% TFA))

Example 20

Compound No. 181

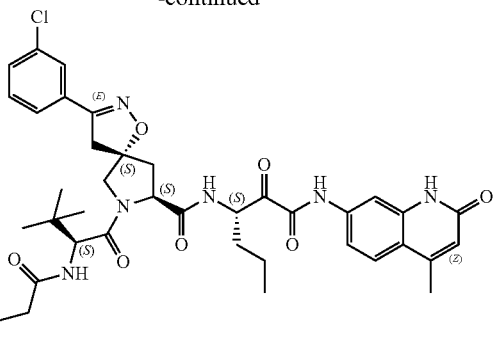

Compound No. 181

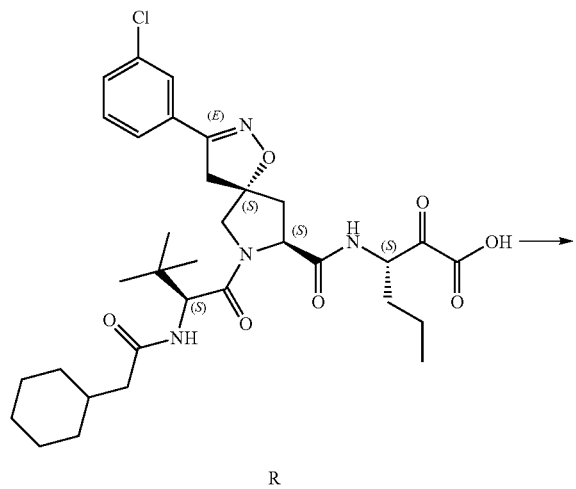

R

To a suspension of R (20 mg, 0.031 mmol) in anhydrous 1,4-dioxane was added pyridine (7.6 μL, 0.093 mmol), then pentafluorophenyl trifluoroacetate (8.8 μL, 0.05 mmol) and allowed to stir for 1.5 hours at room temperature, upon which 7-amino-4-methyl-1H-quinolin-2-one (14 mg, 0.08 mmol) was added. The reaction was allowed to stir at room temperature and complete after one hour. The reaction mixture was quenched with 1 mL of saturated aqueous sodium bicarbonate solution, the layers were separated and aqueous layer was extracted three times with CH2Cl2. The combined organics were dried over Na2SO4, filtered and concentrated under reduced pressure. The residue was dissolved in 1.5 mL CH2Cl2 and purified by normal phase HPLC (10-99% EtOAc/Hexanes) to yield Compound No. 181. LC/MS: m/z 801.7 (M+H)+ at 2.06 minutes (10-99% CH3CN (0.035% TFA)/H2O (0.05% TFA)).

Example 21

Compound No. 605

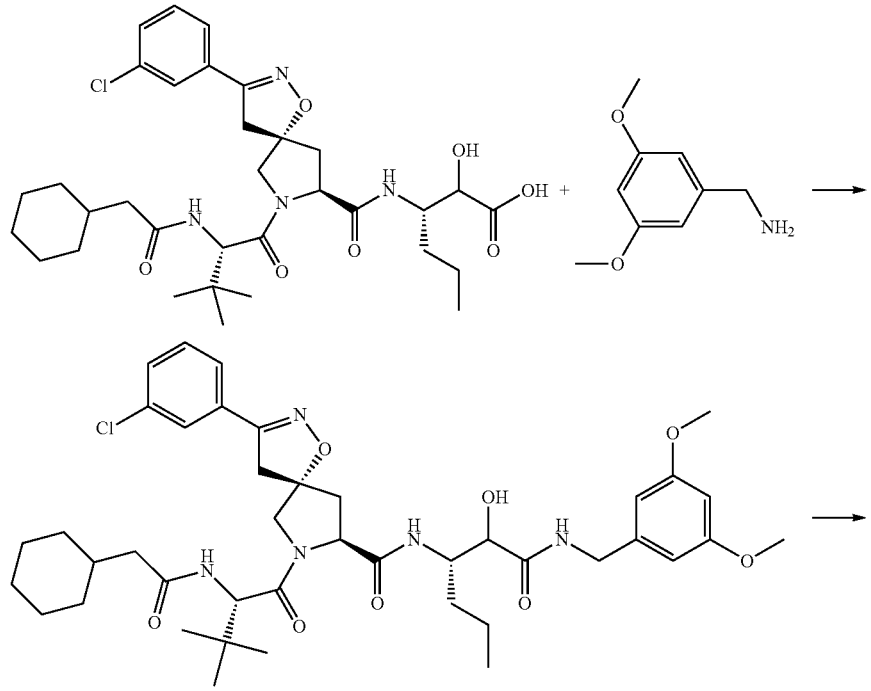

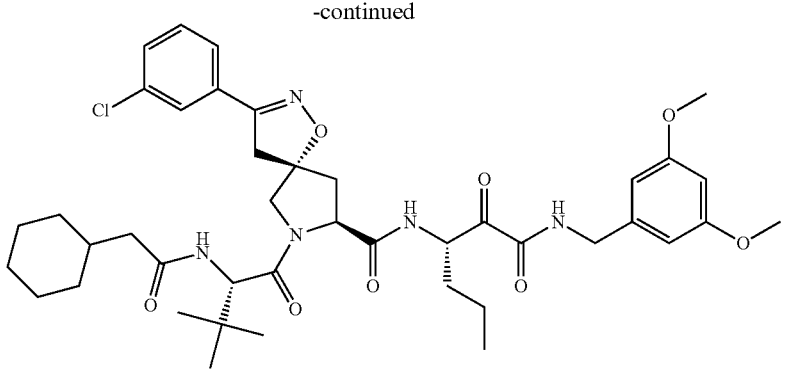

Compound No. 605

A mixture of (3S)-3-(5S,8S)-3-(3-chlorophenyl)-7-((S)-2-(2-cyclohexylacetamido)-3,3-dimethylbutanoyl)-1-oxa-2,7-diazaspiro[4.4]non-2-enecarboxamido)-2-hydroxyhexanoic acid (0.02 g, 0.03 mmol), (3,5-dimethoxyphenyl)methanamine (5.68 mg, 0.033 mmol), HOBt (6.8 mg, 0.05 mmol), DIPEA (22 μL, 0.124 mmol) and $CH_2Cl_2$ (70 μL) was stirred at room temperature for 10 minutes. To the mixture was then added a solution of Mukaiyama's reagent (2-chloro-1-[4-(1H,1H,2H,2H-perfluoro-9-methyldecyl)benzyl]pyridinium hexafluorophosphate) in 200 μL of acetonitrile and the reaction was stirred at room temperature. After 5 hours, 1.34 mL of 0.3 M Dess-Martin Periodinane in $CH_2Cl_2$ was added and the mixture stirred. After 2 hours, the oxidant was quenched with 1.0 mL of saturated $NaHCO_3$, 1 mL of 1N $Na_2S_2O_3$ and stirred vigorously. The organic layer was separated, dried over $Na_2SO_4$, filtered and concentrated. The residue was dissolved in 1.5 mL $CH_2Cl_2$ and purified by normal phase HPLC (10%-99% Ethyl acetate/Hexanes) to yield Compound No. 605, (5S,8S)-3-(3-chlorophenyl)-7-(S)-2-(2-cyclohexylacetamido)-3,3-dimethylbutanoyl)-N-((S)-1-(3,5-dimethoxybenzylamino)-1,2-dioxohexan-3-yl)-1-oxa-2,7-diazaspiro[4.4]non-2-ene-8-carboxamide. LC/MS: m/z 794.7 $(M+H)^+$ at 4.11 minutes (10%-99% $CH_3CN$ (0.035% TFA)/$H_2O$ (0.05% TPA)).

Listed below in Table 8 are reagents used to prepare additional compounds of Formula I by Method 7.

TABLE 8

Reagents used to prepare additional compounds of formula I by method 7.

| Compound No. | $R_{2z}R_{2w}NH$ |
|---|---|
| 2 | tert-butylamine |
| 6 | 2-aminoindane |
| 17 | benzo[d]thiazol-2-amine |
| 49 | 3-((tetrahydrofuran-3-yl)methoxy)azetidine |
| 58 | (R)-(+)-1-(3-methoxyphenyl)ethylamine |
| 69 | 6-Methoxytryptamine |
| 73 | 4-1H-pyrazol-1-yl-benzylamine |
| 77 | benzylamine |
| 79 | azetidine |
| 84 | 2,5-dimethoxyaniline |
| 91 | (4-(4-methoxyphenyl)tetrahydro-2H-pyran-4-yOmethanamine |
| 96 | 3-cyano-4-methylaniline |

TABLE 8-continued

Reagents used to prepare additional compounds of formula I by method 7.

| Compound No. | $R_{2z}R_{2w}NH$ |
|---|---|
| 99 | cyclohexylamine |
| 113 | N,N-Diethylamine |
| 120 | Phenyl-2-pyridinemethylamine |
| 127 | 3',5'-dimethoxybenzylamine |
| 133 | 3-Ethoxyazetidine |
| 138 | 1-(3-(2-aminopropyl)-1H-indol-5-yl)ethanone |
| 140 | Ethylamine |
| 141 | 2,3-dihydro-1,4-benzodioxin-2-ylmethylamine |
| 143 | Isobutylamine |
| 148 | N-(3-aminophenyl)methanesulfonamide |
| 176 | (2-Phenyl-1,3-thiazol-4-yl)metylamine |
| 181 | 7-amino-4-methylquinolin-2(1H)-one |
| 182 | N-Methylethylamine |
| 186 | (3R)-(+)-3-acetamidopyrrolidine |
| 206 | beta-alanine-4-methoxy-betanaphthylamide |
| 221 | N-ethyl-3,4-methylenedioxyamphetamine |
| 238 | (R)-3-((tetrahydrofuran-2-yl)methoxy)azetidine |
| 253 | Dimethylamine |
| 255 | (S)-(−)-1-(3-methoxyphenyl)ethylamine |
| 265 | cyclopropylmethylamine |
| 275 | Isopropylamine |
| 277 | (S)-(+)-tetrahydrofurfurylamine |
| 293 | 3-aminoisoxazole |
| 296 | (S)-alpha-methylbenzylamine |
| 298 | 3-Pyrazol-1-yl-benzylamine |
| 300 | 1-(Ethyl)propylamine |
| 302 | 5-Methoxytryptamine |
| 347 | (R)-(−)-2-(methoxymethyl)pyrrolidine |
| 350 | N-Methyl-N-propylamine |
| 355 | 3-Aminobenzamide |
| 368 | 3-(tetrahydrofuran-3-yloxy)azetidine |
| 372 | Cyclopentylamine |
| 399 | 1-Aminocyclopropane-1-carboxylic acid methyl ester |
| 401 | Cyclobutylamine |
| 404 | 2-Methoxyethylamine |
| 408 | 3-(Aminoethyl)pyridine |

TABLE 8-continued

Reagents used to prepare additional compounds of formula I by method 7.

| Compound No. | $R_{2z}R_{2w}NH$ |
|---|---|
| 410 | Morpholine |
| 426 | 3-Hydroxy-3-methylazetidine |
| 429 | 1-Phenylcyclopropylamine |
| 433 | [3-(4-chlorophenyl0-5-isoxazolyl}methanamine |
| 441 | Furfurylamine |
| 447 | 2-(3-Pyridyl)ethylamine |
| 452 | (R)-2-Butylamine |
| 458 | 3-(2-aminoethyl)indolin-2-one |
| 461 | 4-(Aminomethyl)pyridine |
| 479 | 2-Fluoroethylamine |
| 488 | 2-methoxyphenoxyethylamine |
| 493 | Methylamine |
| 496 | Pyrrolidine |
| 507 | (S)-2-Amino-1,1-dihenyl-1-propanol |
| 508 | (S)-(+)-2-(methoxymethyl)pyrrolidine |
| 521 | 3,3-difluoro-azetidine |
| 537 | Propylamine |
| 540 | 2-(3-methoxyphenyl)ethylamine |
| 546 | (R)-alpha-methylbenzylamine |
| 565 | 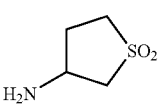 |
| 567 | 2-aminomethyl benzimidazole |
| 568 | Pipecoline |
| 573 | 3,4-Difluoroaniline |
| 588 | 3-cyanoaniline |

Preparation of Non-Commercial Azetidines Listed in Table 8

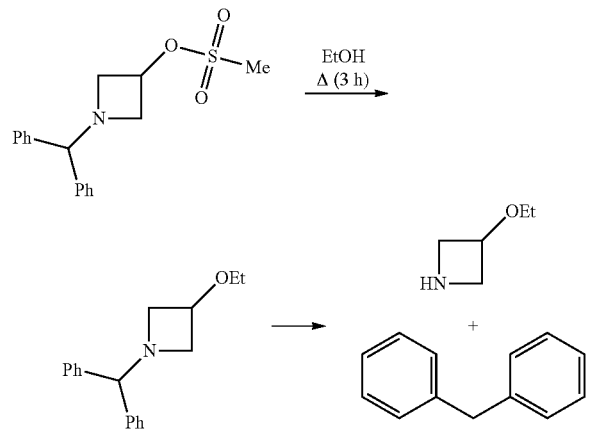

N-Benzyhydryl-3-methanesulfonylazetidine (104 mg) was combined with ethanol (1.0 mL) and heated in a sealed vial at 95° C. overnight. The reaction was monitored by TLC (30% EtOAc:Hexane). Workup was conducted by adding 1 mL of saturated potassium carbonate solution, and extracting twice with 0.5 mL of ethyl acetate. The combined organic extracts were purified on silica (4 g column, gradient elution, 0-30% EtOAc:hexane). Yielded 49 mg of N-benzhydryl-3-ethoxyazetidine as a clear colorless oil. LCMS (M+1=268.2).

N-Benzhydryl-3-ethoxyazetidine (49 mg) was dissolved in 1 mL of methanol. 22 mg of 10% Pd/C (Degussa-type) was added, and the reaction was carried out under a hydrogen atmosphere. The reaction was stirred at room temperature for 64 h. The mixture was filtered through the Celite®, washed thoroughly with methanol, and evaporated to give a yellow oil (30 mg). The oil consists of a mixture of diphenylmethane and the free azetidine. The crude oil mixture was carried onto subsequent transformations and used in excess.

The following azetidines were prepared in a similar fashion as above, by using the corresponding alcohols.

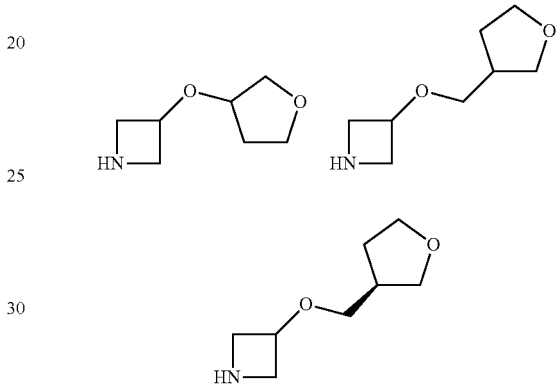

The azetidine

was prepared in the method described by Frigola, J. et al. in J. Med. Chem., 36 (1993), 801-810.

Certain other compounds of Formula I may be prepared by Method 8 as illustrated below.

Method 8:

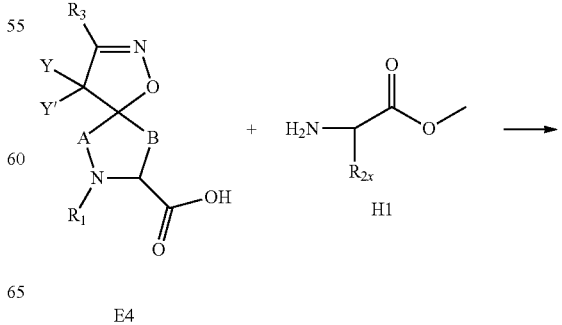

E4

-continued

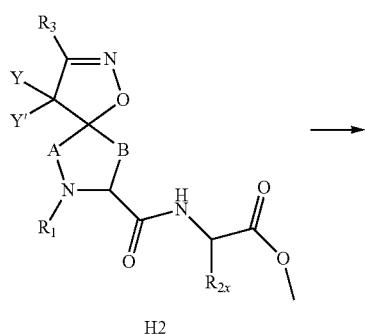

H2

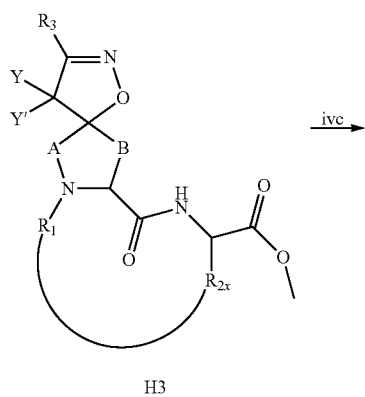

H3

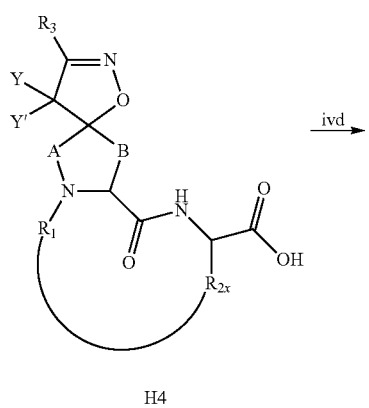

H4

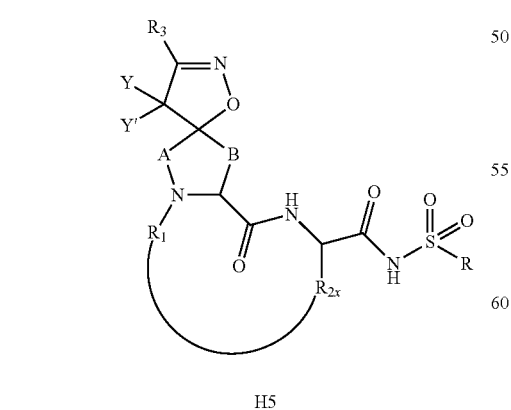

H5

Referring to Method 8, the spiroisoxazoline acid E4 reacts with the amino ester H1 in the presence of a coupling reagent to provide the intermediate H2. Macrocyclization of H2 results in compound H3. Hydrolysis of the ester H2 provides acid H4. Reaction of acid H4 with a sulfonamide or sulfamide in the presence of a coupling reagent provides the product H5.

Example 22

Compound No. 409

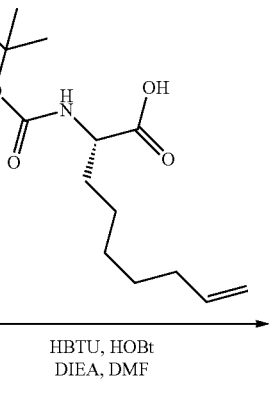

22A

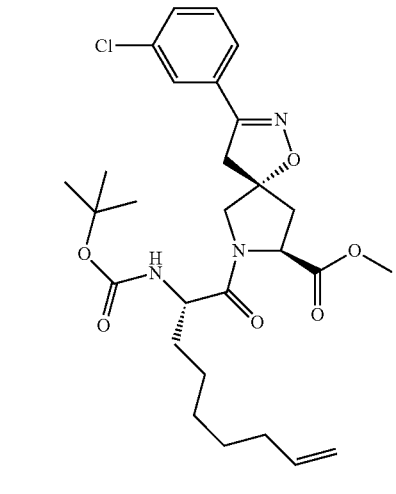

22B (S)-2-(tert-butoxycarbonylamino)non-8-enoic acid, purchased from RSp Amino Acid located in Massachusetts, (179 mg, 1.0 eq.) was stirred in DMF with HBTU (376 mg, 1.5 eq.), HOBt (94 mg, 1.05 eq.), and DIEA (345 uL, 3.0 eq.) for 15 minutes. Added compound 22A (194 mg, 1.0 eq.) and stirred overnight. To the solution was added ethyl acetate. The solution was washed with 1 N HCl (thrice) followed by brine, dried over sodium sulfate, filtered, concentrated and purified by silica chromatography (10-30% ethyl acetate/hexanes gradient) to yield compound 22B (253 mg). (M+H=548.2).

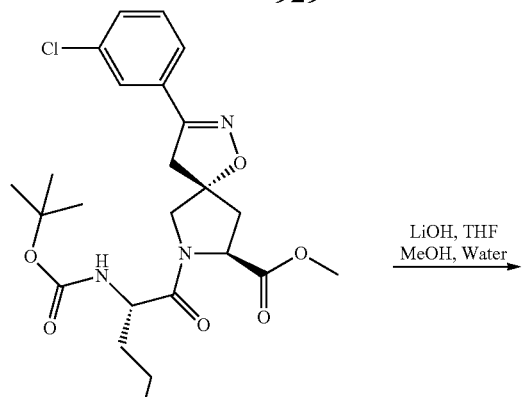

22B

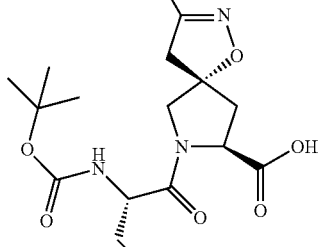

22C

Compound 22B (253 mg, 1.0 eq.) was stirred in THF (1 mL) and methanol (0.5 mL). To the solution was added lithium hydroxide (97 mg, 5.0 eq.) in water (0.5 mL) and stirred for 2 more hours. The mixture was diluted with ethyl acetate, washed with 1 N HCl, then brine, and the solution was dried over MgSO₄, filtered and concentrated to yield compound 22C (235 mg) as a pure white solid (M+H=534.2).

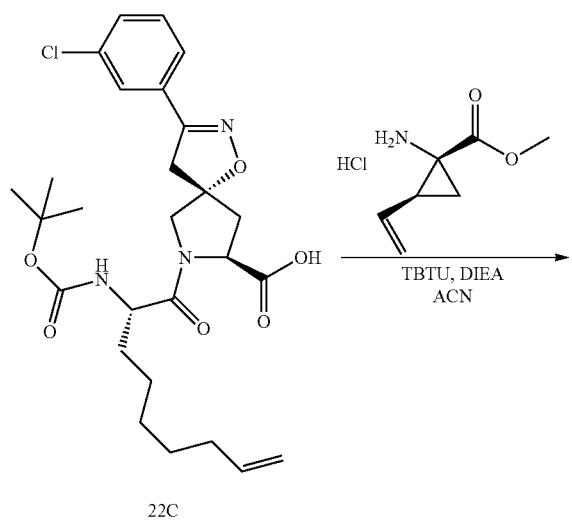

22C

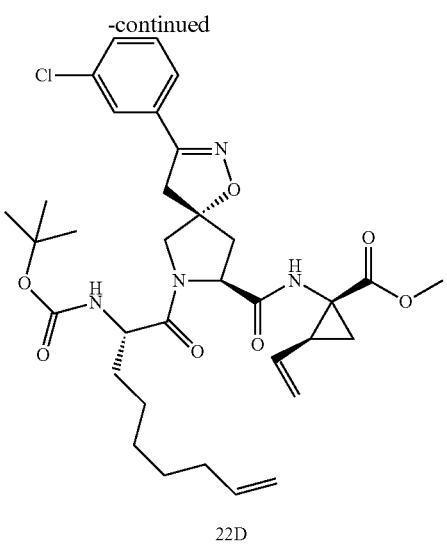

22D

Compound 22C (247 mg, 1.0 eq.) stirred in 1 mL acetonitrile. To the solution was added TBTU (297 mg, 2.0 eq.), DIEA (241 uL, 3.0 eq.), then (1R,2S)-methyl-1-amino-2-vinylcyclopropanecarboxylate (86 mg, 1.2 eq.) and stirred overnight. The solution was diluted with ethyl acetate and washed with 1 N HCl then brine, dried over sodium sulfate, filtered, concentrated and purified by silica chromatography (10-70% ethyl acetate/hexanes gradient) to yield compound 22D (230 mg). (M+H=657.2).

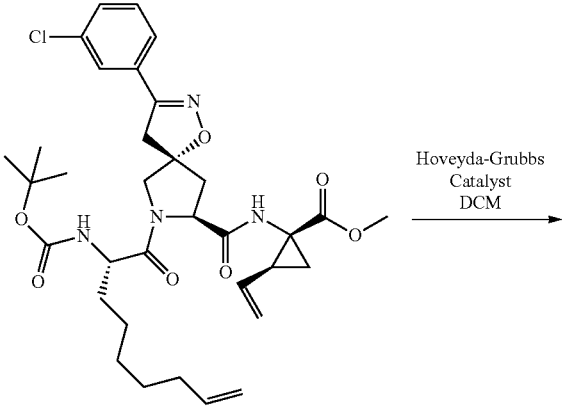

22D

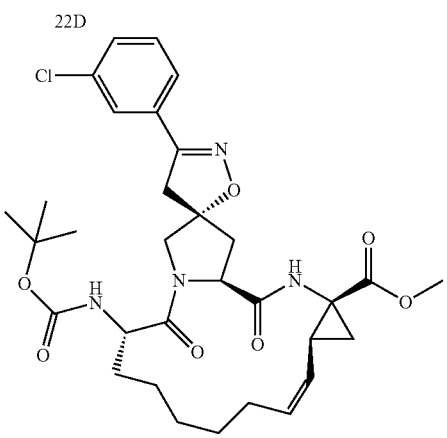

22E

Compound 22D (230 mg, 1.0 eq.) was stirred in 70 mL CH$_2$Cl$_2$ with Hoveyda-Grubbs catalyst (22 mg, 0.1 eq.) at reflux for 1 hour, and the solution cooled to room temperature and purified by silica chromatography (10-70% ethyl acetate/hexanes) to yield compound 22E (172 mg)

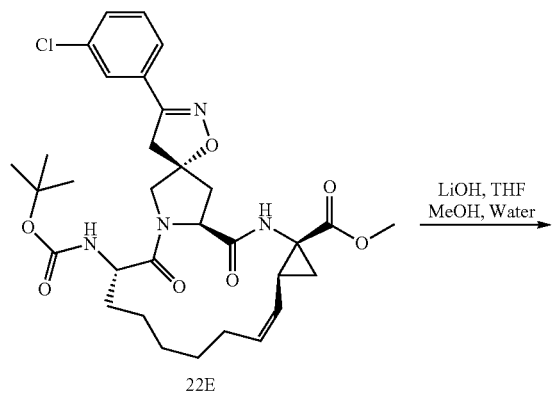

22E

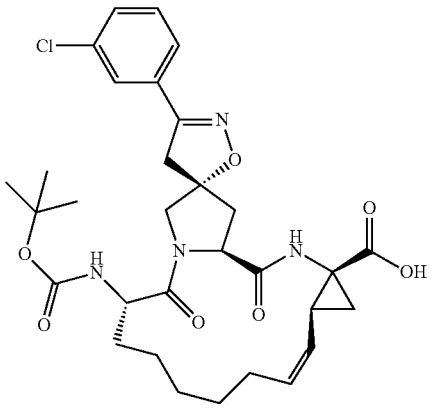

Compound 137

Compound 22E (172 mg, 1.0 eq.) was stirred in THF (1 mL) and methanol (0.5 mL). To the solution was added LiOH (46 mg, 4.0 eq.) in 0.5 mL water and solution stirred for 2 more hours. To the solution again was added ethyl acetate and washed with 1N HCl and brine, dried over magnesium sulfate, filtered, and concentrated to yield compound 22F (155 mg) as a pure white solid (M+H=617.1).

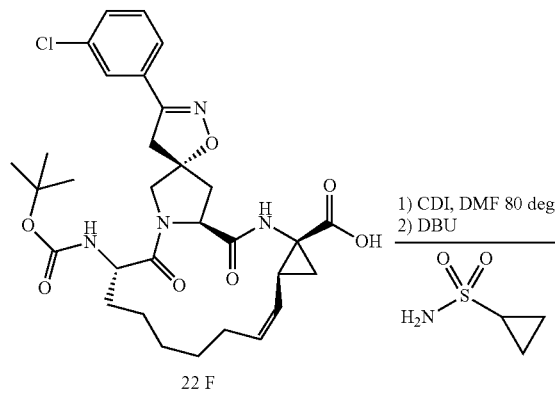

22 F

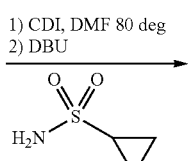

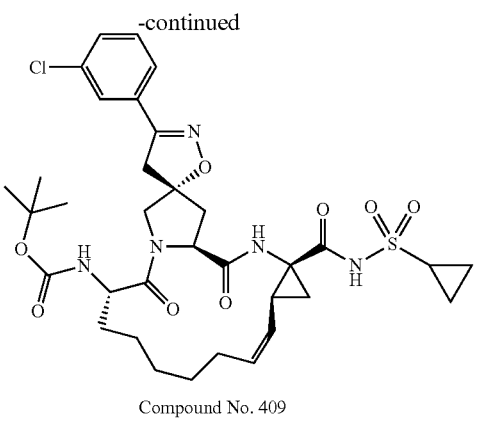

Compound No. 409

Compound 22F (155 mg, 1.0 eq.) stirred in 1 mL DMF with carbonyldiimidazole (49 mg, 1.2 eq.) at 80° C. for 15 minutes. To the solution was added cyclopropanesulfonamide (49 mg, 1.6 eq.) followed by DBU (36 uL, 1.0 eq.) and stirred for another 10 minutes at 80° C. Then to the solution was added ethyl acetate and solution washed with 1 N HCl and brine, dried over MgSO$_4$, filtered, and concentrated. The product was purified by silica chromatography (100% DCM to 5% methanol/DCM gradient) to give Compound No. 409 (64 mg, 35%). (M+H=718.1.)

Listed below in Table 9 are additional compounds of Formula I prepared by Method 8.

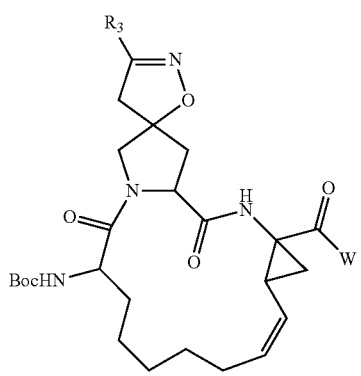

TABLE 9

Additional compounds of formula I prepared by method 8.

| Compound No. | Starting Material for W | Starting Material for R3 |
|---|---|---|
| 1 | OH | 7-Chloro-2,3-dihydrobenzo[b]furan-5-carboxaldoxime |
| 137 | OH | 3-Chlorobenzaldoxime |
| 163 | Cyclopropane sulfonamide | Phenylglyoxylohydroxamyl chloride |
| 232 | Cyclopropane sulfonamide | 3-Chlorobenzaldoxime |
| 320 | OH | Phenylglyoxylohydroxamyl chloride |
| 386 | Cyclopropane sulfonamide | 7-Chloro-2,3-dihydrobenzo[b]furan-5-carboxaldoxime |
| 409 | Cyclopropane sulfonamide | 3-Chlorobenzaldoxime |
| 470 | OH | 3-Chlorobenzaldoxime |

Certain other compounds of Formula I may be prepared in Method 9 as illustrated below.

Method 9:

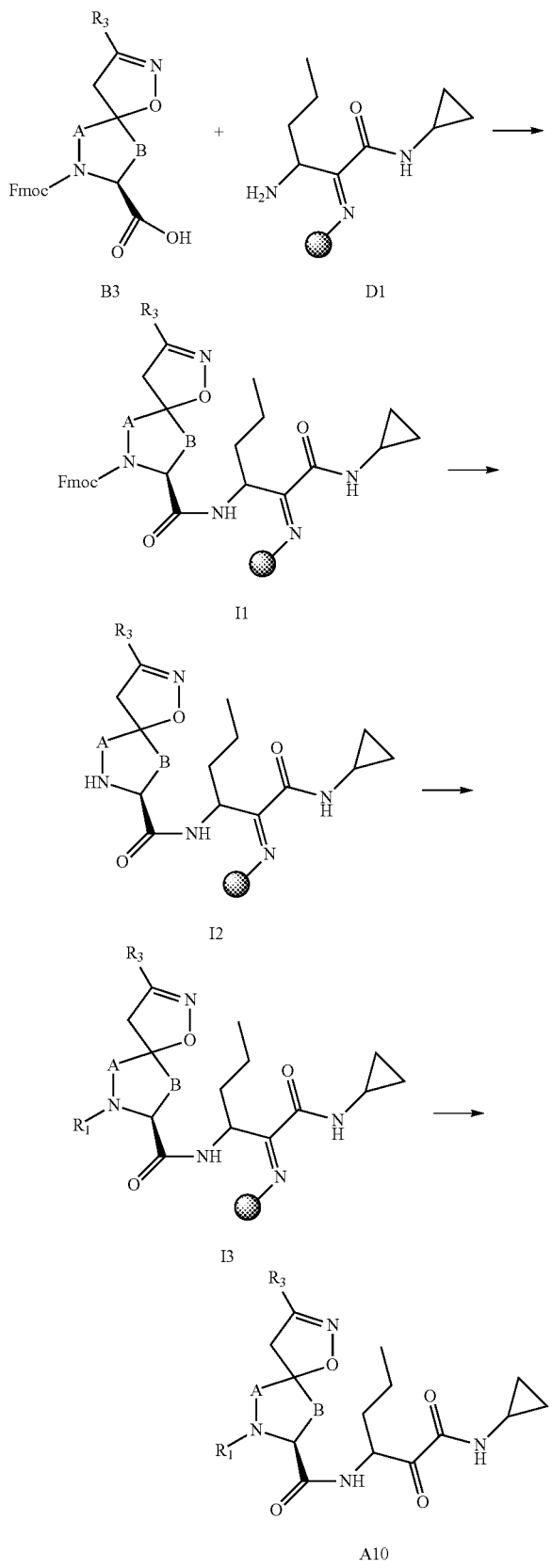

Referring to Method 9, the protected spiroisoxazoline B3 (prepared by Method 2) reacts with the resin bound iminoamine D1 to provide the intermediate I1. Deprotection of I1 provides the amine I2 which reacts with an $R_1$ carboxylic acid in the presence of a coupling reagent to provide I3 wherein $R_1$ is $R_4C(O)$—. Hydrolysis of I3 provides the final compound A10.

A person skilled in the art can use the examples and methods described herein, along with known synthetic methodologies, to synthesize compounds of Formula I according to Method 9 illustrated above.

Listed below in Table 10 are additional compounds of Formula I prepared by Method 9.

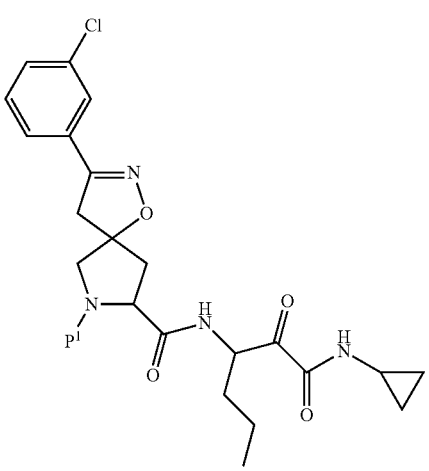

TABLE 10

Additional compounds of formula I prepared by method 9.

| Compound No. | $P^1$ |
|---|---|
| 46 | 5-Bromoindole-2-carboxylic acid |
| 54 | Acetyl-D-ethionine |
| 60 | 2-(R)-[[(4-Methylphenyl)Sulfonyl]amino]-2-phenylacetic acid |
| 65 | 2-oxo-1-phenylpyrrolidine-3-carboxylic acid |
| 88 | Acetyl-D-Methyltyrosine-OH |
| 98 | N-Acetyl-L-leucine |
| 100 | 2-[[(4-Fluorophenyl)Sulfonyl]amino]-3-methylbutanoic acid |
| 157 | 5,6-dimethoxyindole-2-carboxylic acid |
| 218 | Pyr-Val-OH |
| 227 | 1-carbamoylcyclopropanecarboxylic acid |
| 246 | 5-(2,4-dimethylphenylamino)-5-oxopentanoic acid |
| 248 | 4-Chloro-2-(6-methoxypyridin-3-ylamino)benzoic acid |
| 309 | 3-[[(4-acetamidophenyl)sulfonyl]amino]-3-propanoic acid |
| 328 | 3-(3,4-dihydroisoquinolin-2(1H)-ylsulfonyl)benzoic acid |
| 332 | (S)-2-acetamido-3-(4-isopropoxyphenyl)propanoic acid |
| 376 | 3-(2-oxobenzo[d]oxazol-3(2H)-yl)propanoic acid |
| 380 | 4-trifluoromethoxyphenylacetic acid |
| 395 | 2-[[(4-Methoxyphenyl)Sulfonyl]amino]-3-methylbutanoic acid |
| 397 | 2-((S)-2-oxo-4-phenyloxazolidin-3-yl)acetic acid |
| 412 | Acetyl-D-tyrosine-OH |
| 416 | 2-(R)-[[(4-Chlorophenyl)Sulfonyl]amino]-3-methylpentanoic acid |
| 420 | 3-(2-diethylamino)-2-oxoethyl)1H-indole-2-carboxylic acidi |
| 421 | trans-2-Phenyl-1-cyclopropanecarboxylic acid |
| 466 | 2-[[(4-Fluorophenyl)Sulfonyl]amino]-2-phenylacetic acid |
| 476 | 2-(S)-[[(4-Methylphenyl)Sulfonyl]amino]-2-phenylacetic acid |
| 483 | 3-(N-Phenylphenylsulfonamido)propanoic acid |

TABLE 10-continued

Additional compounds of formula I prepared by method 9.

| Compound No. | P¹ |
|---|---|
| 489 | 2-(R)-[[(4-Methoxyphenyl)Sulfonyl]amino]-3-methyl-butanoic acid |
| 501 | 2-+(Phenyl Sulfonyl)amino]-2-phenylacetic acid |
| 534 | 2-(R)-[[(4-Methoxyphenyl)Sulfonyl]amino]-3-methyl-pentanoic acid |
| 574 | 2-(1-oxoisoindolin-2-yl)propanoic acid |
| 586 | 6-(2,5-dimethoxyphenyl)-2-oxo-1,2,3,6-tetrahydro-pyrimidine-4-carboxylic acid |
| 587 | 2-(R)-[[(4-Methoxyphenyl)Sulfonyl]amino]-4-methyl-pentanoic acid |

Certain other compounds of Formula I may be prepared in Method 10 as illustrated below.

Method 10:

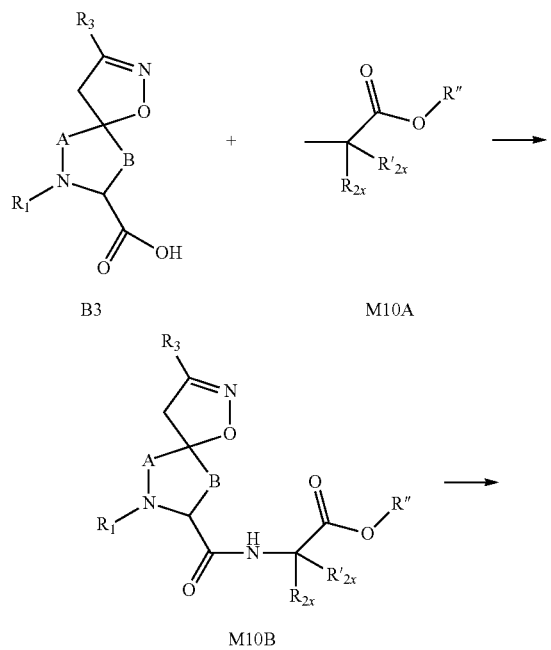

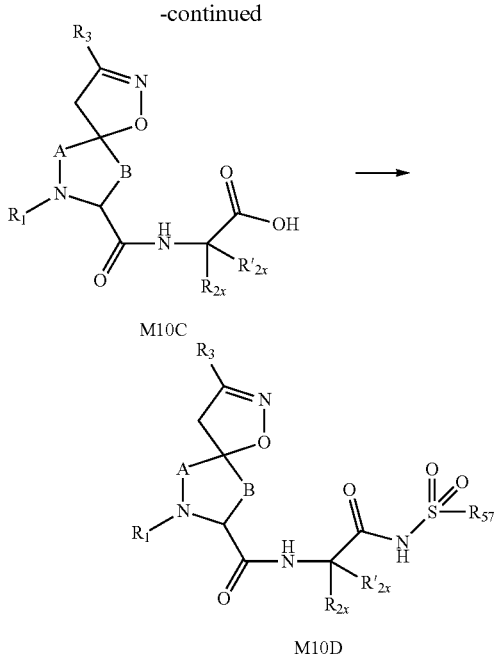

Referring to Method 10, the protected spiroisoxazoline B3 (e.g., $R_1$ is Fmoc) reacts with M10A (R″, e.g., can be methyl or immobilized on PS-Wang resin) to provide intermediate M10B. Hydrolysis of M10B yields the carboxylic acid M10C, which is subsequently coupled with the appropriate sulfonamide to afford the final compound M10D. M10C can also be a final compound of formula I.

Similarly, a person skilled in the art can use the examples and methods described herein, along with known synthetic methodologies, to synthesize compounds of Formula I according to Method 10 illustrated above.

Listed below in Table 11 are additional compounds of Formula I prepared by Method 10.

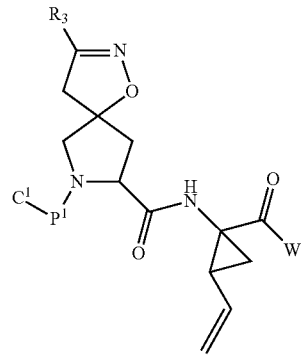

TABLE 11

Additional compounds of formula I prepared by method 10.

| Compound No. | W Starting Material | P1 Starting Material | C1 Starting Material | R3 Starting Material |
|---|---|---|---|---|
| 35 | Cyclopropane sulfonamide | N-Boc-L-tert-butylglycine | NA | 3-Chlorobenzaldoxime |
| 45 | Cyclopropane sulfonamide | N-((S)-tetrahydrofuran-3-yloxy)carbonyl)-L- | NA | 3-Chlorobenzaldoxime |

TABLE 11-continued

Additional compounds of formula I prepared by method 10.

| Compound No. | W Starting Material | P1 Starting Material | C1 Starting Material | R3 Starting Material |
|---|---|---|---|---|
| 57 | Cyclopropane sulfonamide | tert-butylglycine N-Boc-L-tert-butylglycine | NA | 7-Chloro-2,3-dihydrobenzo[b]furan-5-carboxaldoxime |
| 115 | ![cyclopropane sulfamide structure] | N-Boc-L-tert-butylglycine | 2-cyclohexylacetic acid | 3-Chlorobenzaldoxime |
| 130 | Cyclopropanesulfonamide | N-Alloc-L-tert-butylglycine | NA | 3-Chlorobenzaldoxime |
| 144 | OH | N-Boc-L-tert-butylglycine | 2-cyclohexylacetic acid | 3-Chlorobenzaldoxime |
| 162 | Cyclopropane sulfonamide | N-Boc-L-tert-butylglycine | cyclohexylacetic acid | 3-Chlorobenzaldoxime |
| 190 | Cyclopropane sulfonamide | N-Boc-L-tert-butylglycine | cyclopentyl 2,5-dioxopyrrolidin-1-yl carbonate | 3-Chlorobenzaldoxime |
| 269 | OH | N-((S)-tetrahydrofuran-3-yloxy)carbonyl)-L-tert-butylglycine | NA | 3-Chlorobenzaldoxime |
| 272 | OH | N-Boc-L-tert-butylglycine | cyclopentyl 2,5-dioxopyrrolidin-1-yl carbonate | Nitropropane |
| 359 | Cyclopropane sulfonamide | N-Boc-L-tert-butylglycine | 2-(tetrahydro-2H-pyran-4-yl)acetic acid | 3-Chlorobenzaldoxime |
| 384 | OH | N-Boc-L-tert-butylglycine | 2-(tetrahydro-2H-pyran-4-yl)acetic acid | 3-Chlorobenzaldoxime |
| 438 | Cyclopropane sulfonamide | N-Boc-L-tert-butylglycine | cyclopentyl 2,5-dioxopyrrolidin-1-yl carbonate | Nitropropane |
| 439 | OH | N-Boc-L-tert-butylglycine | NA | 3-Chlorobenzaldoxime |
| 443 | OH | N-Boc-L-tert-butylglycine | cyclopentyl 2,5-dioxopyrrolidin-1-yl carbonate | 3-Chlorobenzaldoxime |
| 457 | OH | N-Boc-L-tert-butylglycine | tert-Butylisocyanate | 3-Chlorobenzaldoxime |
| 460 | OH | N-Alloc-L-tert-butylglycine | NA | 3-Chlorobenzaldoxime |

Additional compounds of the invention may be prepared as illustrated in the scheme Method 11.

Method 11:

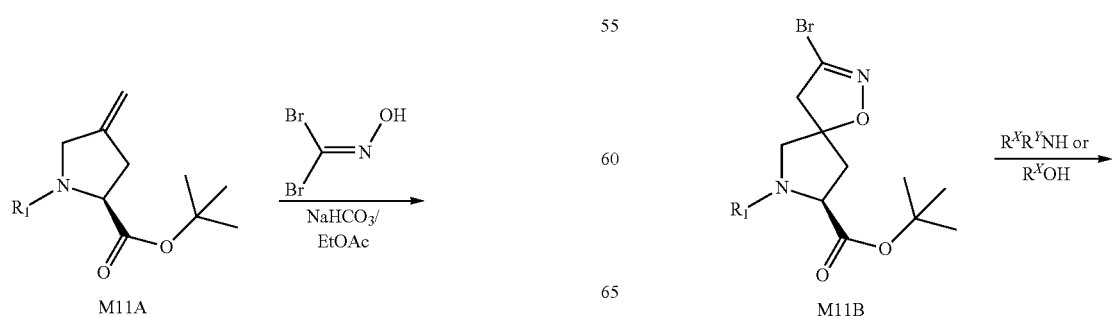

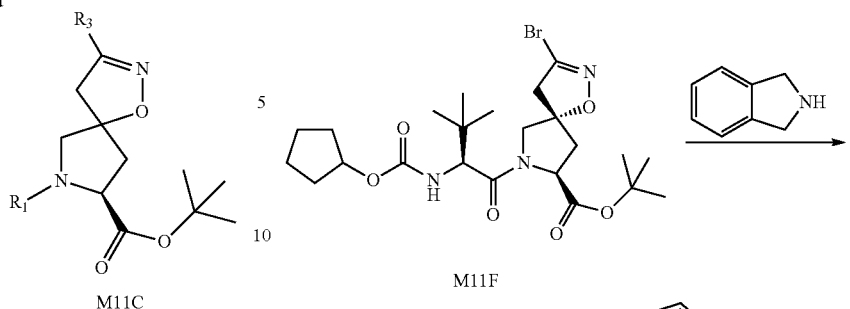

M11C

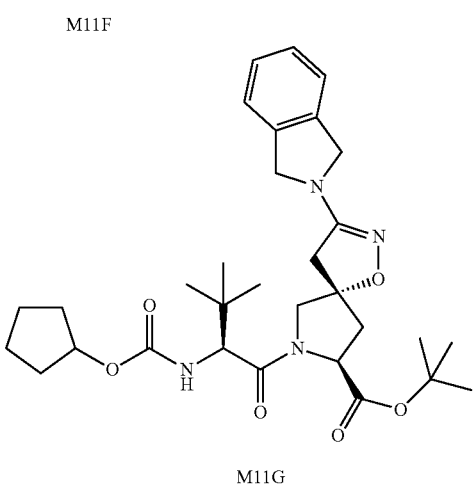

M11F

Referring to Method 11, reaction of the methylene compound M11A with 1,1-dibromoformaldoxime in the presence of a mild base such as, for example, sodium bicarbonate provides the bromospiroisoxazoline M11B. Reaction of M11B with an amine $R^xR^yNH$ or an arylalcohol $R^xOH$ provides the intermediate M11C wherein $R_3$ is an optionally substituted amino or optionally substituted aryloxy. Deprotection of M11C to provide the corresponding acid followed by reaction with an appropriate amino compound according to procedures previously described provides compounds of the invention.

Example 23

Preparation of Intermediates for Compounds Wherein $R_3$ is Amino or Aryloxy

Step 1:

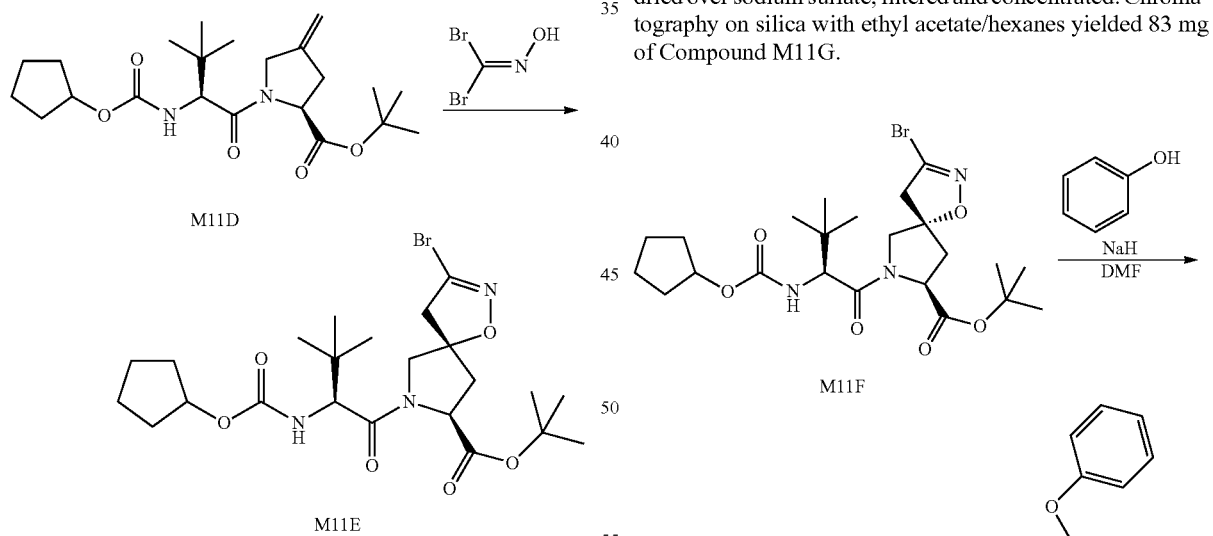

M11D

M11E

Compound M11D (6.96 g, 1.0 eq) was stirred in 85 mL ethyl acetate. Sodium bicarbonate (6.30 g 4.4 eq) was added followed by dibromoformaldoxime (4.11 g, 1.2 eq) and the mixture stirred overnight at room temperature. Water (85 mL) was added and the mixture stirred until clear. The phases were separated, the aqueous phase extracted with ethyl acetate and the combined organic phases were dried over sodium sulfate, filtered, and concentrated. Chromatography on silica column with ethyl acetate/hexanes gradient yielded 5.55 grams of Compound M11E and 0.93 grams of its diastereomer (6:1 ratio).

M11G

Compound M11F (100 mg, 1.0 eq) was stirred in 270 uL of isoindoline at 95° C. overnight. The mixture was diluted with ethyl acetate and washed with 1N HCl. The organic phase was dried over sodium sulfate, filtered and concentrated. Chromatography on silica with ethyl acetate/hexanes yielded 83 mg of Compound M11G.

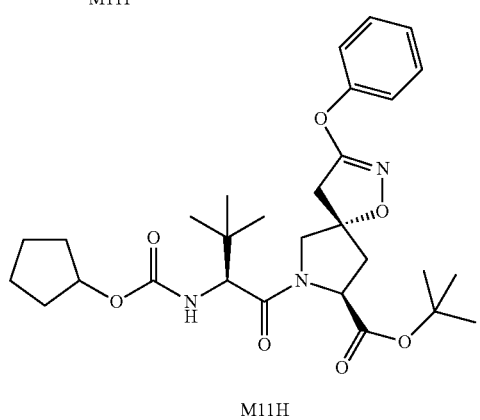

M11F

M11H

Phenol (20 mg, 1.1 eq) stirred in 350 uL DMF. Sodium hydride (8.3 mg, 1.1 eq, 60%) was added and the mixture stirred for 5 minutes. Compound M11F was added and the mixture stirred at 90° C. overnight. The mixture was partitioned between 1N HCl and ethyl acetate, and the organic phase dried over sodium sulfate, filtered and concentrated to give 70 mg Compound M11H.

Additional Examples

Example 23

Compound No. 610

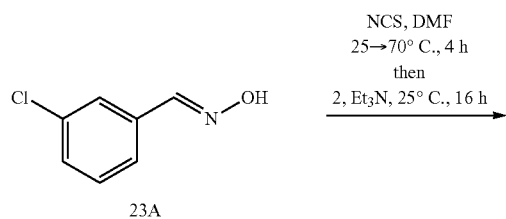

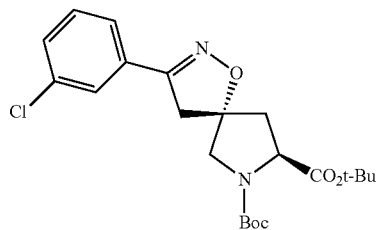

Oxime 23A (6.29 g, 40.4 mmol) was dissolved in DMF (63 mL) and N-chlorosuccinimide (5.39 g, 40.4 mmol) was added portionwise to the stirring solution. Stirring continued for 3 hours at room temperature when conversion was determined to be 56% (by HPLC). The reaction was pushed to completion by gentle heating at 70° C. for 45 minutes. 4-Methyleneproline derivative (8.81 g, 31.1 mmol) was added and rinsed into the solution using DMF (5 mL). Triethylamine (5.7 mL) was carefully added dropwise over 30 minutes. The reaction was then stirred at room temperature for 16 hours overnight. An aliquot was analyzed by HPLC and it was determined to contain a 4:1 ratio of cycloaddition diasteromers. Ethyl acetate (200 mL) was added and the organic phase was washed with water (thrice, 200 mL each) and brine (200 mL). The organic phase was then dried over magnesium sulfate and evaporated. The crude oil was divided into two portions and each was purified using an ISCO combiflash equipped with a 330 g silica column (10-20% EtOAc: pet. ether, 72 minutes). The desired product was the major isomer which eluted from the column ahead of the minor isomer and 9.42 g of 23B was obtained as an orange oil. The minor isomer was also isolated, subjected to a recrystallization from EtOAc:hexane, and obtained as an off-white crystalline powder (1.53 g).

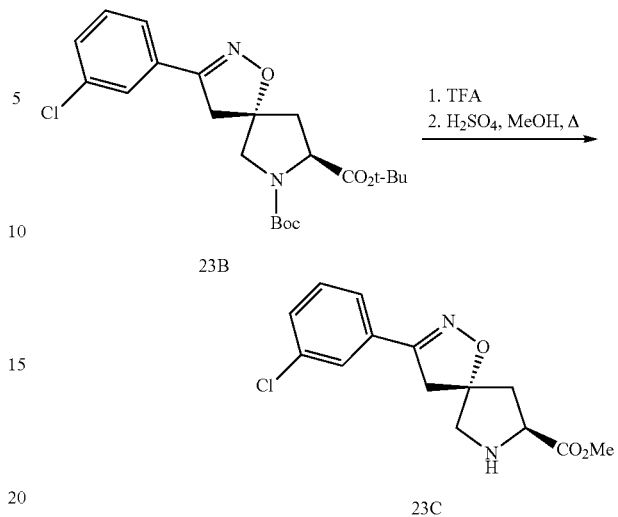

Compound 23B (9.42 g) was stirred in trifluoroacetic acid (12 mL) for 2 hours. The solvent was evaporated and replaced with methanol (50 mL). The solution was heated to reflux and $H_2SO_4$ (3.0 mL) was added dropwise. The reaction was refluxed for a total of 6 hours when by HPLC, conversion to the methylester was determined to be greater than 95%. The reaction was cooled and evaporated to remove the excess methanol. The resulting oil was redissolved in $CH_2Cl_2$ (200 mL) and neutralized with saturated sodium bicarbonate (200 mL). The organic phase was collected, and the aqueous phase was extracted with $CH_2Cl_2$ (twice, 100 mL each). The organic extracts were combined, evaporated over magnesium sulfate, and evaporated to give 5.09 g of compound 23C as an oil that was immediately carried onto the next step.

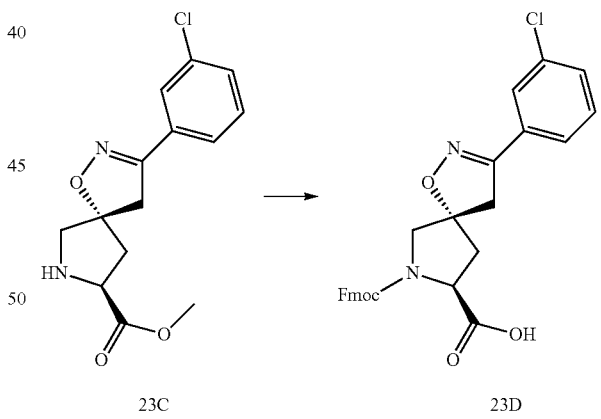

The amino ester 23C (1.25 g, 4.24 mmol) was treated with $LiOH.H_2O$ (186 mg, 4.4 mmol) in $THF/H_2O$ (3:1, 10 mL) for 45 minutes. The solvents were removed in vacuo to obtain a solid. This solid was slurried in acetone (20 mL) and saturated $NaHCO_3$ (aq) (20 mL) at room temperature. Fmoc-Cl (1.12 g, 4.33 mmol) was added and the reaction was monitored by HPLC. After 20 minutes, the contents of the reaction flask were transferred to a separatory funnel with $CH_2Cl_2$ and acidified with 2 N HCl (aq.). The aqueous phase was extracted with $CH_2Cl_2$ (twice, 100 mL each). The resulting emulsion was filtered, and the organic layers were combined, dried over $MgSO_4$, and concentrated to give compound 23D.

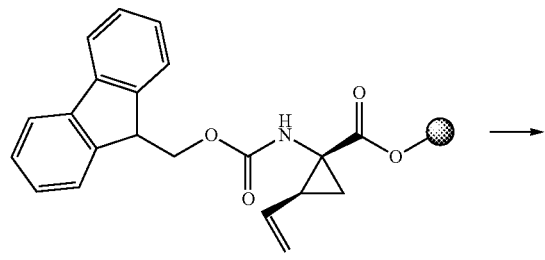

XX4

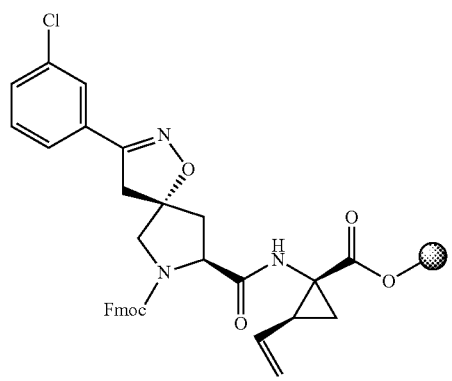

23F

Compound XX4 was shaken in a solution of 20% piperidine in DMF (20 mL) for 60 minutes. The resin was washed with DMF (thrice), CH$_2$Cl$_2$ (thrice) and repeated. The resulting resin was then shaken with compound 23D (437 mg, 0.87 mmol), HATU (392 mg, 1.03 mmol), and DIEA (0.300 mL, 1.72 mmol) in DMF (10 mL) overnight. The result compound bound resin 23F was then washed with DMF (thrice), CH$_2$Cl$_2$ (thrice) and repeated. (M+1)=612.26.

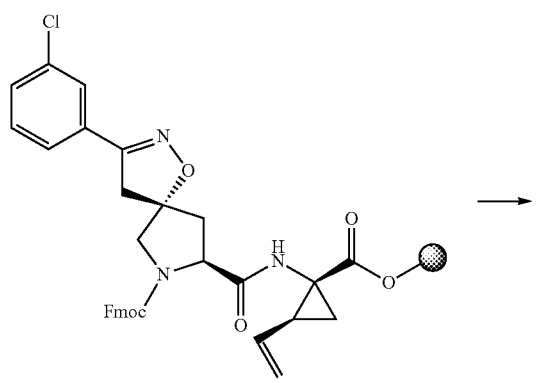

23F

-continued

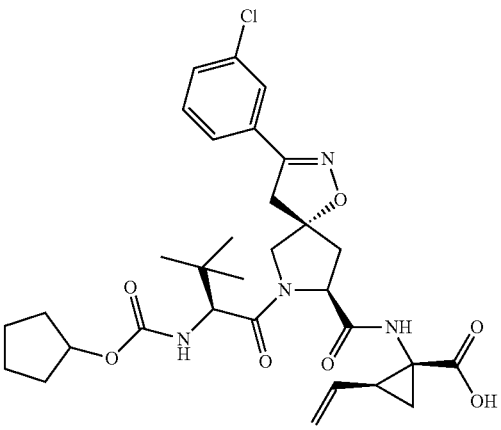

Compound 443

The compound bound resin 23F was shaken in 20% piperidine in DMF (8 mL) for 2 hours. The resin was then washed with DMF (thrice), CH$_2$Cl$_2$ (thrice) and repeated. (M+1)=390.1. This resin was then shaken overnight in DMF with (S)-2-(cyclopentyloxycarbonylamino)-3,3-dimethylbutanoic acid (3 eq.), HOBT (3 eq.), HBTU (3 eq.), and DIEA (6 eq.). The resin was washed with DMF (thrice) and CH$_2$Cl$_2$ (thrice) and repeated, then shaken for 100 minutes in TFA (5 mL). The resulting resin was filtered and the filtrate concentrated and purified by reverse phase chromatography to yield 9.4 mg of Compound 443 as a white solid. (M+1)=615.6, $^1$H-NMR (500 MHz, DMSO-d$_6$): 8.63 (s, 1H), 7.67 (s, 1H), 7.63 (d, J=6.7 Hz, 1H), 7.55-7.49 (m, 2H), 6.90 (d, J=8.4 Hz, 1H), 5.77-5.69 (m, 1H), 5.20-5.17 (m, 1H), 5.06 (d, J=10.5 Hz, 1H), 4.93 (brs, 1H), 4.35 (t, J=7.7 Hz, 1H), 4.11 (d, J=8.8 Hz, 1H), 4.06 (d, J=10.9 Hz, 1H), 3.80 (d, J=11.6 Hz, 1H), 3.62-3.50 (m, 2H), 2.63-2.31 (m, 2H), 2.18-2.13 (m, 1H), 2.07-2.01 (m, 1H), 1.87-1.51 (m, 9H), 1.29-1.28 (m, 1H), 0.95-0.91 (brs, 9H).

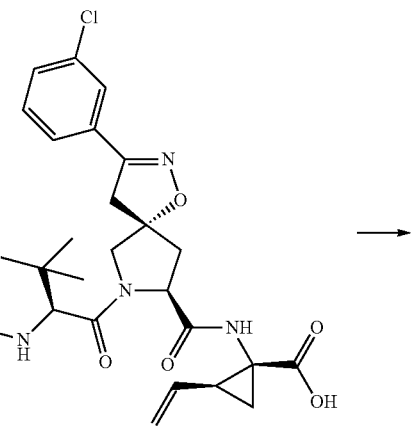

23G

Compound No. 190

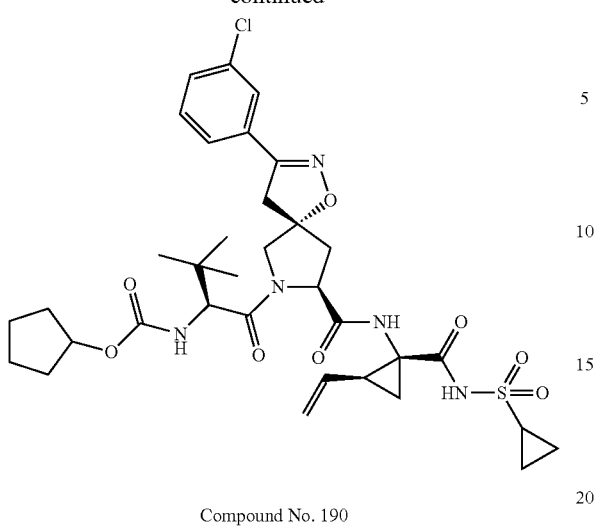

Compound 23G (6.6 mg, 0.011 mmol) was stirred in DMF (0.5 mL) with CDI (2.8 mg, 0.017 mmol) for 1 hour at 80° C. Cyclopropyl sulfonamide (3.8 mg, 0.031 mmol) and DBU (0.01 mL) were added, the heat was removed and the reaction was stirred overnight at room temperature. The reaction was purified by reverse phase chromatography to yield 2.8 mg of Compound No. 190 (0.0039 mmol). (M+1)=718.1. $^1$H-NMR (500 MHz, methanol-$d_4$): 9.26 (s, 0.4H), 9.02 (s, 0.6H), 7.72 (d, J=1.7 Hz, 1H), 7.61 (dd, J=1.3, 7.3 Hz, 1H), 7.47-7.41 (m, 2H), 5.81-5.73 (m, 1H), 5.33-5.30 (m, 1H), 5.14-5.10 (m, 1H), 5.03 (brs, 1H), 4.45-4.41 (m, 1H), 4.31-4.25 (m, 2H), 3.94 (d, J=11.0 Hz, 1H), 3.62-3.53 (m, 2H), 2.99-2.92 (m, 1H), 2.55-2.49 (m, 1H), 2.29-2.23 (m, 2H), 1.89-1.53 (m, 10H), 1.44-1.40 (m, 1H), 1.32-1.24 (m, 1H), 1.19-1.02 (m, 2H), 0.90 (s, 9H).

Example 24

Compound No. 618

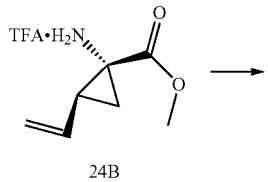

24B

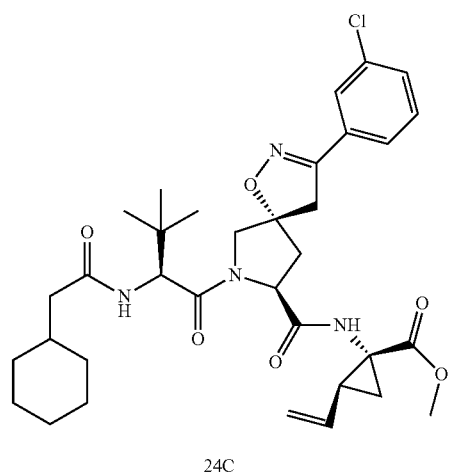

24C

Carboxylic acid 24A (69 mg, 0.13 mmol), HATU (50 mg, 0.13 mmol), compound 24B (0.13 mmol), and DIEA (0.045 mL, 0.26 mmol) were stirred in acetonitrile (1.5 mL) for 2 hours. The reaction was then diluted in EtOAc, washed with saturated NaHCO$_3$ (aq), brine, dried (MgSO$_4$), and concentrated. Purification on silica gel yielded 76 mg (0.12 mmol) of compound 24C. LCMS (M+1)=614.4.

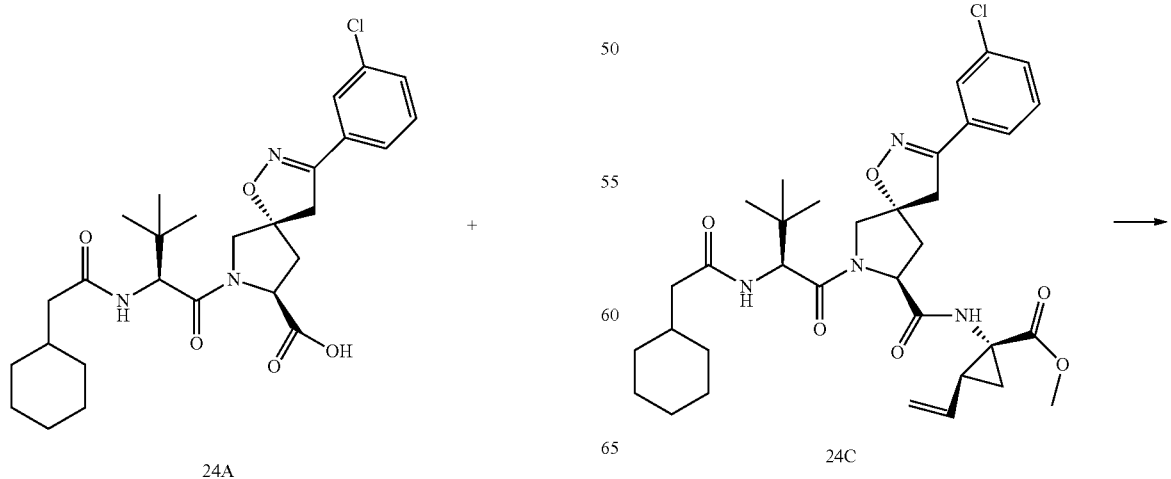

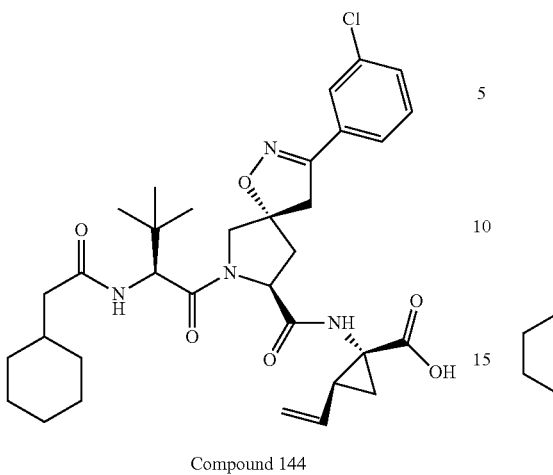

Compound 144

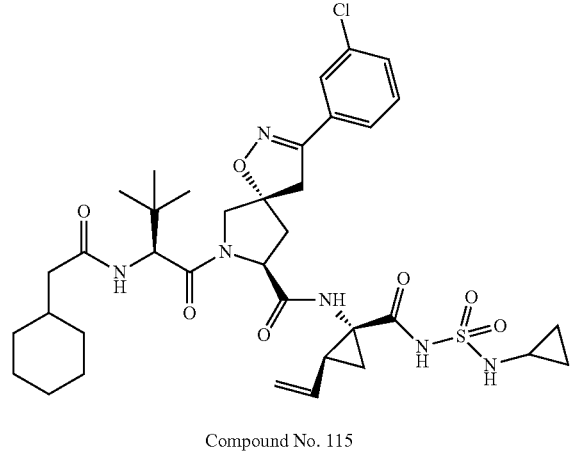

Compound No. 115

The methyl ester 24C (76 mg, 0.12 mmol) dissolved in THF/H$_2$O (5:1, 2 mL) and stirred overnight with LiOH.H$_2$O (1.5 eq.). Acidified reaction with 1N HCl (aq) and concentrated. Residue was dissolved in CH$_2$Cl$_2$/MeOH (93:7) and eluted through a plug of silica gel to yield 75 mg (0.11 mmol) of Compound No. 144. LCMS (M+1=627.4). $^1$H-NMR (500 MHz, Methanol-d$_4$): 7.84 (d, J=9.1 Hz, 0.5H), 7.71 (s, 1H), 7.60 (d, J=7.2 Hz, 1H), 7.45-7.40 (m, 2H), 5.90-5.83 (m, 1H), 5.23 (d, J=1.4 Hz, 1H), 5.07 (d, J=10.3 Hz, 1H), 4.60 (m, 1H), 4.52-4.49 (m, 1H), 4.27 (m, 1H), 3.90 (m, 1H), 3.59-3.48 (m, 2H), 2.58 (dd, J=8.0, 12.6 Hz, 1H), 2.37-2.32 (m, 1H), 2.21-2.12 (m, 4H), 1.76-1.61 (m, 6H), 1.45-1.42 (m, 1H), 1.32-1.14 (m, 4H), 1.05-0.95 (m, 9H), 0.91 (m, 3H).

The carboxylic acid 22D (18.5 mg, 0.029 mmol) stirred with CDI (6.0 mg) in DMF (1.5 mL) at 80° C. for 10 minutes. The reaction was cooled to room temperature and compound 24E in DMF (0.15 mL) with DBU (4 eq.) was added and the reaction was heated in an 80° C. bath for 20 minutes. The reaction was purified directly by reverse phase chromatography to yield 7.6 mg of Compound No. 115. LCMS (M+1=745.2), $^1$H-NMR (500 MHz, methanol-d$_4$): 9.30 (s, 0.5H), 8.02 (m, 0.5H), 7.71 (m, 1H), 7.60 (dt, J=7.2, 1.3 Hz, 1H), 7.46-7.41 (m, 2H), 5.86-5.79 (m, 1H), 5.35-5.28 (m, 1H), 5.12-5.10 (m, 1H), 4.65 (m, 1H), 4.42 (dd, J=6.9, 10.6 Hz, 1H), 4.28 (d, J=11.3 Hz, 1H), 3.95 (d, J=11.4 Hz, 1H), 3.62-3.47 (m, 2H), 2.51-2.47 (m, 1H), 2.35-2.31 (m, 1H), 2.25-2.12 (m, 4H), 1.89 (dd, J=5.4, 8.1 Hz, 1H), 1.80-1.64 (m, 6H), 1.45-1.39 (m, 1H), 1.33-1.15 (m, 3H), 1.04-0.97 (m, 11H), 0.73-0.57 (m, 4H).

Listed below in Table 12 are some physical data of exemplary compounds of Formula I.

LC/MS data were acquired using the following:
Mass spectrometers: PESciex API-150-EX or Waters/Micromass ZQ or Waters/Micromass Quattro II, or Waters/Micromass ZMD; Pumps: Shimadzu LC-8A or Agilent 1100; Autosamplers: Gilson 215 or Gilson 819.

The following methods were used: 3.0 mL/min flow rate, 10-99% CH$_3$CN (0.035% TFA)/H2O (0.05% TFA) gradient, Phenomenex Luna 5m C18 column (50×4.60 mm); 1.5 mL/min flow rate, 10-90% CH$_3$CN (0.2% Formic acid)/H2O (0.2% Formic Acid) in 3 minutes, YMC-Pack Pro-C18 column (50×4.6 mm); 1.0 mL/min flow rate, 10-90% CH$_3$CN (0.2% Formic acid)/H$_2$O (0.2% Formic Acid) in 5 minutes, YMC-Pro-C18 column (50×2.0 mm); 1.5 mL/min flow rate, 10-90% CH$_3$CN (0.1% TFA))/H2O (0.1TFA) in 3 minutes, YMC-Pack Pro-C18 column (50×4.60 mm).

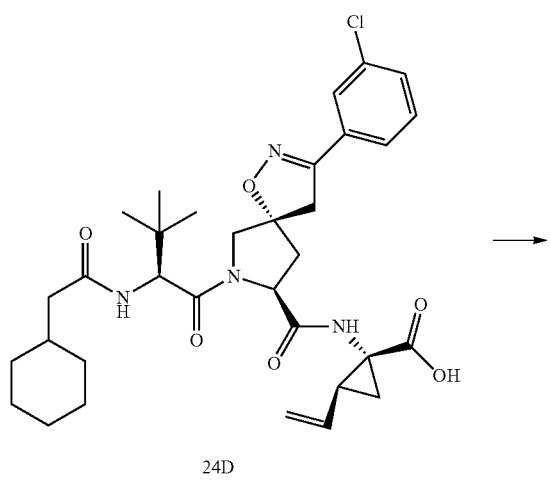

24D

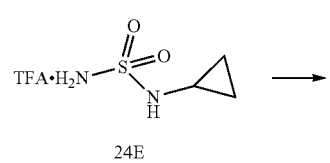

24E

TABLE 12

Physical data for exemplary compounds of Formula I.

| Compound No. | LCMS (M + 1) | LCMS RT | FIA-MS (M − 1) | FIA-MS (M + 1) | NMR |
|---|---|---|---|---|---|
| 1 | | | 754.4 | 756.1 | |
| 2 | 700.2 | 3.99 | | | |
| 3 | 698.8 | 3.84 | | | |
| 4 | | | 763 | 765 | |
| 5 | 686.3 | 2.8 | | | |
| 6 | 760.9 | 2.4 | | | |
| 7 | 710.2 | 3.35 | | | |

TABLE 12-continued

Physical data for exemplary compounds of Formula I.

| Compound No. | LCMS (M + 1) | LCMS RT | FIA-MS (M − 1) | FIA-MS (M + 1) | NMR |
|---|---|---|---|---|---|
| 8 | | | | 707.9 | |
| 9 | | | 638 | 640 | |
| 10 | | | 724 | 726.1 | |
| 11 | | | 662.4 | 664.3 | |
| 12 | 602 | 2.94 | | | |
| 13 | 668.2 | 3.6 | | | |
| 14 | | | | 580.9 | |
| 15 | | | 725.1 | 726.1 | |
| 16 | | | | 691.8 | |
| 17 | 791.8 | 2.29 | | | |
| 18 | 752.4 | 3.74 | | | |
| 19 | 696.3 | 3.7 | | | H-NMR (500 MHz, CDCl3) 7.61 (d, J = 1.7 Hz, H), 7.51(d, J = 7.7 Hz, H), 7.38(d, J = 8.2 Hz, H), 7.33(t, J = 7.8 Hz, H), 7.26(s, CDCl3), 7.16 (t, J = 6.5 Hz, H), 6.91 (d, J = 3.3 Hz, H), 6.55-6.50(m, H), 5.35 (dd, J = 4.1, 8.5 Hz, H), 4.77-4.74 (m, H), 4.66(d, J = 9.4 Hz,H), 4.29(d, J = 11.1 Hz,H), 3.71(d, J = 11.2 Hz, H), 3.47 (d, 1H), 3.29 (d, 1H), 2.78 (td, J = 7.3, 3.7 Hz, H), 2.63-2.59 (m, H), 2.52-2.49 (m, H), 2.07-2.30 (m, 2H), 1.98-1.92 (m, H), 1.77-1.61 (m, H), 1.47-1.40 (m, H), 1.35-1.25 (m, H), 1.21 (dd, J = 6.6, 12.5 Hz, H), 1.01 (s, 9H), 0.98-0.83(m, H), 0.61-0.51 (m, H), 0.39 (t, J = 4.8 Hz, H) ppm |
| 20 | 672 | 3.24 | | | |
| 21 | | | 697.9 | 699.8 | |
| 22 | 713 | 3.9 | | | CDCl3; 7.77 (d, 2H),7.58 (m, 4H), 7.41 (t, 2H), 7.32 (3H) |
| 23 | 710 | 4.5 | | | |
| 24 | | | 630.3 | 632.2 | |
| 25 | | | 684.6 | 686.5 | |
| 26 | 761.4 | 3.23 | | | |
| 27 | 672.4 | 3.7 | | | |
| 28 | 675.3 | 3.44 | | | |
| 29 | 698.3 | 613.8 | | | |
| 30 | 767.6 | 3.15 | | | |
| 31 | 701.3 | 2.74 | | | |
| 32 | | | 730.3 | 732.1 | |
| 33 | 685 | 3.5 | | | |
| 34 | | | | 559 | |
| 35 | 706.1 | 3.66 | | | |
| 36 | | | 675.5 | 677.3 | |
| 37 | 712 | 3.19 | | | |
| 38 | 748.1 | 3.86 | | | |
| 39 | 728 | 3.82 | | | |
| 40 | | | 655.3 | 657.2 | |
| 41 | 729 | 3.4 | | | |
| 42 | 701.3 | 2.75 | | | |
| 43 | | | 654.1 | 656.1 | |
| 44 | 658 | 3 | | | |
| 45 | 720.2 | 3.29 | | | |
| 46 | 670 | 3.78 | | | |
| 47 | | | 734.2 | 736.1 | |
| 48 | 728.2 | 3.47 | | | |
| 49 | 784.2 | 3.71 | | | |
| 50 | 696.6 | 3.76 | | | |
| 51 | | | 548.1 | 550 | |
| 52 | | | | 704 | |
| 53 | 696 | 2.04 | | | |
| 54 | 634 | 3.24 | | | |
| 55 | | | 642.3 | 644.2 | |
| 56 | | | 600.6 | 602.4 | |
| 57 | | | | 755 | |
| 58 | 778.9 | 2.38 | | | |
| 59 | 730.2 | 3.58 | | | |
| 60 | 734.4 | 3.67 | | | |
| 61 | 591.8 | 2.6 | | | |
| 62 | 690.2 | 3.64 | | | |
| 63 | 698 | 3.83 | | | |
| 64 | | | | 595 | |
| 65 | 634.4 | 1.8 | | | |
| 66 | | | 734.4 | 736.2 | |
| 67 | | | 720.4 | 722.2 | |
| 68 | 675.2 | 2.6 | | | |
| 69 | 817.7 | 3.97 | | | |
| 70 | | | 712.4 | 714.3 | |
| 71 | 722.1 | 3.59 | | | |
| 72 | 670 | 3.53 | | | |
| 73 | 800.7 | 3.97 | | | |
| 74 | | | 682 | 684 | |
| 75 | 713.1 | 2.8 | | | |
| 76 | 643 | 3.09 | | | |
| 77 | 734.2 | 3.92 | | | |
| 78 | | | | | |
| 79 | 684.2 | 3.7 | | | |
| 80 | | | 553.1 | 555 | |
| 81 | 687 | 2.1 | | | |
| 82 | | | 611 | 612.6 | |
| 83 | | | 772.1 | 774 | |
| 84 | 780.9 | 4.39 | | | |
| 85 | 650 | 3.26 | | | |
| 86 | | | 676.5 | 678.3 | |
| 87 | 712 | 3.2 | | | |
| 88 | 666 | 3.31 | | | |
| 89 | 695.2 | 3.53 | | | |
| 90 | | | 758 | 759.9 | |
| 91 | 848.7 | 2.3 | | | |
| 92 | 686 | 3.05 | | | |
| 93 | 670.4 | 3.56 | | | |
| 94 | 660 | 2.69 | | | |
| 95 | | | 583.9 | 585.7 | |
| 96 | 759.3 | 4.02 | | | |
| 97 | | | 670.1 | 672.1 | |
| 98 | 602.6 | 1.63 | | | |
| 99 | 726.7 | 2.4 | | | |
| 100 | 704 | 3.64 | | | |
| 101 | | | 666.1 | 668.3 | |
| 102 | 710.2 | 3.6 | | | |
| 103 | 657 | 3.2 | | | |
| 104 | 690 | 3.24 | | | |
| 105 | | | 682.1 | 684.2 | |
| 106 | | | 690.1 | 691.9 | |
| 107 | 659 | 3.22 | | | |

TABLE 12-continued

Physical data for exemplary compounds of Formula I.

| Compound No. | LCMS (M + 1) | LCMS RT | FIA-MS (M − 1) | FIA-MS (M + 1) | NMR |
|---|---|---|---|---|---|
| 108 | 700 | 3.32 | | | |
| 109 | | | 706.4 | 708.4 | |
| 110 | 754 | 3.6 | | | |
| 111 | | | 652.1 | 654 | |
| 112 | | | | 684 | |
| 113 | 700.7 | 2.3 | | | |
| 114 | | | 712.4 | 714.3 | |
| 115 | 745.2 | 3.73 | | | |
| 116 | | | 716.3 | 718 | |
| 117 | | | | 653 | |
| 118 | 726.4 | 3.6 | | | |
| 119 | | | | 691.8 | |
| 120 | 811.5 | 3.95 | | | |
| 121 | 714 | 3.27 | | | |
| 122 | 711 | 3.42 | | | |
| 123 | 631 | 3.09 | | | |
| 124 | 686.2 | 3.4 | | | |
| 125 | 732.2 | 3.7 | | | |
| 126 | | | 680.55 | 682.4 | |
| 127 | 794.7 | 4.11 | | | |
| 128 | 774 | 3.28 | | | |
| 129 | 758.2 | 3.78 | | | |
| 130 | 690.2 | 3.48 | | | |
| 131 | 720 | 3.53 | | | |
| 132 | 711.4 | 3.5 | | | |
| 133 | 728.6 | 3.8 | | | |
| 134 | 726.2 | 3.7 | | | |
| 135 | 773.1 | 3.5 | | | |
| 136 | | | 666 | 668.1 | |
| 137 | | | 708.2 | 710.1 | |
| 138 | 843.9 | 2.2 | | | |
| 139 | 708 | 3.35 | | | |
| 140 | 672.7 | 2.13 | | | |
| 141 | 792.7 | 4.13 | | | |
| 142 | | | 676.2 | 677.9 | |
| 143 | 700.7 | 2.32 | | | |
| 144 | 627.4 | 3.43 | | | |
| 145 | | | | 707.8 | |
| 146 | 635 | 2.47 | | | |
| 147 | | | 690 | 691.9 | |
| 148 | 813.9 | 2.15 | | | |
| 149 | | | | 606.8 | |
| 150 | | | 713.5 | 715.2 | |
| 151 | | | 706 | 707.8 | |
| 152 | 688.4 | 3.2 | | | |
| 153 | 714.3 | 3.2 | | | |
| 154 | | | 700.1 | 701.9 | |
| 155 | 709.6 | 3.59 | | | |
| 156 | 658 | 3.35 | | | |
| 157 | 650 | 3.32 | | | |
| 158 | 714.3 | 3.72 | | | |
| 159 | | | 688.3 | 690.3 | |
| 160 | | | 613.5 | 615.4 | |
| 161 | 769.1 | 3.5 | | | |
| 162 | 730.2 | 3.7 | | | |
| 163 | | | | 708 | |
| 164 | | | 630.1 | 632.1 | |
| 165 | 715.2 | 3.73 | | | |
| 166 | 710 | 3.46 | | | |
| 167 | 709.4 | 2.2 | | | |
| 168 | 656.3 | 3.46 | | | |
| 169 | 702.2 | 3.71 | | | |
| 170 | 754.2 | 3.96 | | | |
| 171 | | | | 613.1 | |
| 172 | | | | 717.1 | |
| 173 | 667 | 3.17 | | | |
| 174 | | | 642.3 | 644.3 | |
| 175 | 701.2 | 2.76 | | | |
| 176 | 817.7 | 4.1 | | | |
| 177 | | | 787 | 789 | |
| 178 | | | 576.1 | 578.1 | |
| 179 | 718.2 | 3.55 | | | |
| 180 | | | 770.1 | 772.1 | |
| 181 | 801.7 | 2.06 | | | |
| 182 | 686.7 | 2.19 | | | |
| 183 | | | 714 | 715.9 | |
| 184 | 672.2 | 2.96 | | | |
| 185 | 724.2 | 3.6 | | | |
| 186 | 755.3 | 3.41 | | | |
| 187 | 708 | 3.53 | | | |
| 188 | 698 | 3.76 | | | |
| 189 | 722 | 3.5 | | | |
| 190 | 718.1 | 3.68 | | | |
| 191 | | | 710.4 | 712.4 | |
| 192 | | | 683.3 | 685.3 | |
| 193 | 646 | 3.44 | 702 | 703.7 | |
| 194 | | | 672.1 | 674 | |
| 195 | 700.2 | 3.59 | | | |
| 196 | | | 672.1 | 674 | |
| 197 | 722 | 3.39 | | | |
| 198 | | | 723.8 | 725.7 | |
| 199 | | | 766.2 | 768.2 | |
| 200 | | | 746.2 | 748.1 | |
| 201 | | | 567.1 | 568.8 | |
| 202 | | | 638 | 640 | |
| 203 | 730.3 | 3.7 | | | |
| 204 | 734.2 | 3.85 | | | |
| 205 | 637 | 3.35 | | | |
| 206 | 871.9 | 3.96 | | | |
| 207 | 576 | 2.87 | | | |
| 208 | | | 718.2 | 719.95 | |
| 209 | | | 716.3 | 718.1 | |
| 210 | 675 | 3.5 | | | |
| 211 | 698.2 | 3.47 | | | |
| 212 | | | 692.6 | 694.5 | |
| 213 | 748.2 | 3.6 | | | |
| 214 | | | 769.3 | 770.9 | |
| 215 | | | 733.3 | 735.3 | |
| 216 | 767.1 | 3.1 | | | |
| 217 | 670 | 3.6 | | | |
| 218 | 657 | 3 | | | |
| 219 | 670.2 | 3.65 | | | |
| 220 | | | 504.1 | 506 | |
| 221 | 792.9 | 4.1 | | | |
| 222 | | | 593 | 594.9 | |
| 223 | 678 | 3.42 | | | |
| 224 | | | 707.9 | 710.1 | |
| 225 | | | | 795 | |
| 226 | 698 | 3.89 | | | |
| 227 | 558.5 | 2.91 | | | |
| 228 | | | | 670 | |
| 229 | 649.7 | 2.55 | | | |
| 230 | 704.3 | 3.7 | | | |
| 231 | 684 | 3.73 | | | |
| 232 | 718.1 | 3.82 | | | |
| 233 | 700.34 | 3.3 | | | 1H-NMR (500MHz, CDCl3): 7.61 (t, J = 1.6 Hz, 1H), 7.53 (dd, J = 1.2, 7.6 Hz, 1H), 7.39 (dd, J = 1.7, 6.9 Hz, 1H), 7.34 (t, J = 7.8 Hz, 1H), 7.26 (s, CDCl3), 7.16 (d, J = 7.3 Hz, 1H), 6.91 (d, J = 3.4 Hz, 1H), 6.62 (d, J = 9.2 Hz, 1H), 5.35 (d, J = 4.1 Hz, 1H), 4.76 (t, J = 7.8 Hz, 1H), 4.64 (d, J = 9.3 Hz, 1H), 4.29 (d, J = 10.8 |

TABLE 12-continued

Physical data for exemplary compounds of Formula I.

| Compound No. | LCMS (M + 1) | LCMS RT | FIA-MS (M − 1) | FIA-MS (M + 1) | NMR |
|---|---|---|---|---|---|
| | | | | | Hz, 1H), 3.71 (d, J = 11.2 Hz, 1H), 3.29-3.49 (dd, J = 2H), 2.78 (m, 1H), 2.63-2.59 (m, 1H), 2.53-2.51 (m, 1H), 2.37 (d, J = 2.2 Hz, H), 1.90-1.96 (m, 1H), 1.68-1.60 (m, H), 1.47-1.40 (m, H), 1.21-1.32 (m), 0.99 (s, 9H), 0.95-0.83 (m, H), 0.60 (dd, J = 3.4, 9.5 Hz, H) ppm |
| 234 | | | 722 | 724 | |
| 235 | 626.1 | 3.34 | | | |
| 236 | | | 716.1 | 718.2 | |
| 237 | 696.2 | 2.04 | | | |
| 238 | 784.2 | 3.77 | | | |
| 239 | 738 | 3.8 | | | |
| 240 | | | 668.2 | 670.2 | |
| 241 | 713.4 | 2.94 | | | |
| 242 | | | 667.4 | 669.4 | |
| 243 | 605.9 | 2.77 | | | |
| 244 | | | | 653.2 | |
| 245 | 682 | 3.58 | | | |
| 246 | 664.7 | 3.39 | | | |
| 247 | 645.3 | 3.3 | | | |
| 248 | 707.4 | 3.7 | | | |
| 249 | 665 | 3.49 | | | |
| 250 | 714.2 | 3.8 | | | |
| 251 | | | 613.4 | 615.2 | |
| 252 | 682 | 3.7 | | | |
| 253 | 672.3 | 3.72 | | | |
| 254 | 728.4 | 3.6 | | | |
| 255 | 778.9 | 2.37 | | | |
| 256 | 668.5 | 3.6 | | | |
| 257 | | | 626 | 628 | |
| 258 | | | 566.3 | 568.1 | |
| 259 | 783 | 3.24 | | | |
| 260 | 662 | 3.16 | | | |
| 261 | 821 | 3.21 | | | |
| 262 | 612 | 3.4 | | | |
| 263 | | | 608.9 | 611 | |
| 264 | 692 | 3.31 | | | |
| 265 | 698.3 | 3.87 | | | |
| 266 | | | 704.3 | 706.2 | |
| 267 | | | 575.6 | 577.4 | |
| 268 | 752 | 3.87 | | | |
| 269 | 617.6 | 2.71 | | | |
| 270 | | | | 720 | |
| 271 | 704 | 3.61 | | | |
| 272 | | | 696 | 698.1 | |
| 273 | 644 | 3.46 | | | |
| 274 | | | 714.1 | 716.2 | |
| 275 | 686.7 | 2.21 | | | |
| 276 | | | 716.1 | 717.8 | |
| 277 | 728.3 | 3.75 | | | |
| 278 | 782 | 3.9 | | | |
| 279 | | | 670.3 | 672.2 | |
| 280 | | | 638.2 | 640 | |
| 281 | | | 684.5 | 686.4 | |
| 282 | 772.2 | 3.19 | | | |
| 283 | 645 | 2.02 | | | |
| 284 | 698 | 3.8 | | | |
| 285 | | | 695.7 | 697.6 | |
| 286 | 760 | 3.13 | | | |
| 287 | 708 | 3.4 | | | |
| 288 | 695 | 3.46 | | | |
| 289 | 786.2 | 3.7 | | | |
| 290 | | | 695.7 | 697.6 | |
| 291 | 787 | 3.02 | | | |
| 292 | 685.4 | 3.36 | | | |
| 293 | 711.1 | 3.7 | | | |
| 294 | 684 | 3.76 | | | |
| 295 | | | 654.5 | 656.5 | |
| 296 | 748.7 | 2.37 | | | |
| 297 | 718 | 3.48 | | | |
| 298 | 800.6 | 2.3 | | | |
| 299 | | | 706.6 | 708.3 | |
| 300 | 714.7 | 2.36 | | | |
| 301 | | | 692.1 | 694.1 | |
| 302 | 817.9 | 3.96 | | | |
| 303 | 651.5 | 2.9 | | | |
| 304 | 727 | 2.87 | | | |
| 305 | 726.2 | 3.52 | | | |
| 306 | | | 757.5 | 759.5 | |
| 307 | 744 | 3.57 | | | |
| 308 | 702.5 | 3.4 | | | |
| 309 | 715.3 | 3.59 | | | |
| 310 | | | 683 | 685 | |
| 311 | 767.2 | 3.4 | | | |
| 312 | | | 789.1 | 791 | |
| 313 | 640 | 3.1 | | | |
| 314 | | | 718 | 720 | |
| 315 | 755.3 | 3.67 | | | |
| 316 | | | 813 | 815 | |
| 317 | 747.2 | 3.35 | | | |
| 318 | | | 644.1 | 645.9 | |
| 319 | 658 | 3.57 | | | |
| 320 | | | 775.3 | 777.1 | |
| 321 | 744.3 | 3.75 | | | |
| 322 | | | | 666 | |
| 323 | | | | 746.3 | |
| 324 | 716.9 | 3.5 | | | |
| 325 | | | | 676.5 | |
| 326 | | | 654.1 | 655.9 | |
| 327 | | | 686.5 | 688.4 | |
| 328 | 746.7 | 3.65 | | | |
| 329 | | | 613.4 | 615.2 | |
| 330 | | | | 678 | |
| 331 | | | 726.5 | 728.3 | |
| 332 | 694.5 | 1.82 | | | |
| 333 | 707 | 3.43 | | | |
| 334 | 705.8 | 3.66 | | | |
| 335 | 720 | 3.5 | | | |
| 336 | 774.2 | 3.8 | | | |
| 337 | | | 680.6 | 682.6 | |
| 338 | 736.2 | 3.6 | | | |
| 339 | 757 | 3.24 | | | |
| 340 | | | 682 | 684 | |
| 341 | 697.1 | 2.86 | | | |
| 342 | 626 | 2.3 | | | |
| 343 | | | | 559 | |
| 344 | | | | 684.2 | |
| 345 | 696 | 3.98 | | | |
| 346 | 710.2 | 3.52 | | | |
| 347 | 742.7 | 2.28 | | | |
| 348 | | | 531.6 | 533.3 | |
| 349 | 730.4 | 3.5 | | | |
| 350 | 700.3 | 3.94 | | | |
| 351 | | | 634.5 | 636.3 | |
| 352 | | | 675.6 | 677.3 | |
| 353 | | | | 691.9 | |
| 354 | | | 700.6 | 702.5 | |
| 355 | 762.2 | 3.91 | | | |
| 356 | 760 | 3.11 | | | |
| 357 | 695 | 2.24 | | | |
| 358 | | | 686.1 | 687.9 | |
| 359 | 732.4 | 3.12 | | | |
| 360 | 698 | 3.87 | | | |
| 361 | 698 | 3.83 | | | |
| 362 | | | 652 | 654 | |

TABLE 12-continued

Physical data for exemplary compounds of Formula I.

| Compound No. | LCMS (M + 1) | LCMS RT | FIA-MS (M − 1) | FIA-MS (M + 1) | NMR |
|---|---|---|---|---|---|
| 363 | | | 722 | 724.1 | |
| 364 | 701.9 | 3.21 | | | |
| 365 | | | | 676.1 | |
| 366 | 728.1 | 3.6 | | | |
| 367 | 636 | 2.8 | | | |
| 368 | 770.2 | 3.64 | | | |
| 369 | | | −721.1 | −723.2 | |
| 370 | 728.3 | 3.62 | | | |
| 371 | 695 | 3.7 | | | |
| 372 | 712.3 | 3.98 | | | |
| 373 | 723.4 | 2.3 | | | |
| 374 | 688.4 | 3.2 | | | |
| 375 | | | 656 | 658 | |
| 376 | 636.3 | 3.36 | | | |
| 377 | 795.4 | 3.29 | | | |
| 378 | | | 761.1 | 763 | |
| 379 | 645 | 3.16 | | | |
| 380 | 649.5 | 1.97 | | | |
| 381 | 731.4 | 3.3 | | | |
| 382 | | | 758.3 | 760.1 | |
| 383 | 612.1 | 3.2 | | | |
| 384 | 629.4 | 2.78 | | | |
| 385 | | | 504.1 | 506 | |
| 386 | | | 504.1 | 506 | |
| 387 | 716 | 3.13 | | | |
| 388 | 656 | 3.42 | | | |
| 389 | 723.4 | 2.3 | | | |
| 390 | | | 696.1 | 698 | |
| 391 | | | 583 | 584.8 | |
| 392 | 660 | 3.05 | | | |
| 393 | 696 | 4.05 | | | |
| 394 | 703.3 | 513.3 | | | |
| 395 | 730 | 3.55 | | | |
| 396 | 698.25 | 3.89 | | | |
| 397 | 650.5 | 1.73 | | | |
| 398 | | | 696.1 | 698. | |
| 399 | 742.7 | 2.16 | | | |
| 400 | | | 583 | 584.8 | |
| 401 | 698.3 | 3.9 | | | |
| 402 | 764.1 | 3.4 | | | |
| 403 | | | 716.9 | 719 | |
| 404 | 702.5 | 2.07 | | | |
| 405 | | | | | |
| 406 | | | 670.1 | 672.2 | |
| 407 | 632 | 3.35 | | | |
| 408 | 735.7 | 3.14 | | | |
| 409 | | | | | |
| 410 | 714.5 | 2.12 | | | |
| 411 | | | 566.10 | 568 | |
| 412 | 652 | 3 | | | |
| 413 | | | 717.9 | 719.8 | |
| 414 | | | 769.1 | 771 | |
| 415 | | | 639.5 | 641.5 | |
| 416 | 734.5 | 3.83 | | | |
| 417 | | | | 653.3 | |
| 418 | 686.3 | 3.1 | | | |
| 419 | 714 | 3.26 | | | |
| 420 | 704 | 3.56 | | | |
| 421 | 591.6 | 1.87 | | | |
| 422 | | | 693.4 | 695.4 | |
| 423 | | | 714.2 | 716.1 | |
| 424 | 706 | 3.31 | | | |
| 425 | | | 691.8 | 693.8 | |
| 426 | 714.2 | 3.48 | | | |
| 427 | 666 | 3.38 | | | |
| 428 | | | 702.1 | 704 | |
| 429 | 760.9 | 2.38 | | | |
| 430 | 753.2 | 3.86 | | | |
| 431 | 691.9 | 3.3 | | | |
| 432 | 645 | 3.05 | | | |
| 433 | 835.7 | 4.16 | | | |
| 434 | 720 | 3.5 | | | |
| 435 | 744 | 3.56 | | | |
| 436 | | | 774 | 776.2 | |
| 437 | 730.2 | 3.7 | | | |
| 438 | | | 548.2 | 549.9 | |
| 439 | 603.4 | 3.34 | | | |
| 440 | | | 602.6 | 604.4 | |
| 441 | 724.9 | 2.22 | | | |
| 442 | | | 712.6 | 714.5 | |
| 443 | 615.6 | 3.25 | | | |
| 444 | | | 676.2 | 678.2 | |
| 445 | 742.35 | 3.2 | | | |
| 446 | 756.2 | 3.68 | | | |
| 447 | 749.7 | 1.78 | | | |
| 448 | | | 608.1 | 610 | |
| 449 | 756 | 351 | | | |
| 450 | | | 698.3 | 700.2 | |
| 451 | | | | 630 | |
| 452 | 700.3 | 3.94 | | | |
| 453 | 694.3 | 3.64 | | | |
| 454 | 761.1 | 3.3 | | | |
| 455 | | | | 724.4 | |
| 456 | | | 710.5 | 712.2 | |
| 457 | 602.4 | 3.12 | | | |
| 458 | 803.7 | 3.97 | | | |
| 459 | 684.2 | 3.6 | | | |
| 460 | 587.5 | 3.01 | | | |
| 461 | 735.7 | 1.8 | | | |
| 462 | | | 610.1 | 611.9 | |
| 463 | 708.4 | 3.7 | | | |
| 464 | | | 706.1 | 708.2 | |
| 465 | | | 740.4 | 742.2 | |
| 466 | 738.6 | 3.63 | | | |
| 467 | 696.345 | 3.7 | | | |
| 468 | 686.2 | 2.98 | | | |
| 469 | 681.3 | 3.39 | | | |
| 470 | | | 610.1 | 612.05 | |
| 471 | 708.2 | 3.5 | | | |
| 472 | | | 837 | 839.1 | |
| 473 | | | 706 | 708.1 | |
| 474 | 710.2 | 3.2 | | | |
| 475 | 714 | 3.3 | | | |
| 476 | 734.4 | 3.67 | | | |
| 477 | 717.37 | 3.3 | | | |
| 478 | 690.2 | 3.73 | | | |
| 479 | 690.2 | 3.66 | | | |
| 480 | | | 672 | 673.9 | |
| 481 | | | 718 | 720 | |
| 482 | | | 698.2 | 700.1 | |
| 483 | 734.6 | 1.87 | | | |
| 484 | 660 | 1.44 | | | |
| 485 | 676 | 3.38 | | | |
| 486 | | | 803.6 | 805.4 | |
| 487 | 762 | 3.26 | | | |
| 488 | 794.7 | 4.07 | | | |
| 489 | 716.5 | 3.59 | | | |
| 490 | | | 709.4 | 711.4 | |
| 491 | | | | 754 | |
| 492 | 659 | 3.39 | 734.4 | 736.2 | |
| 493 | 658.3 | 3.61 | | | |
| 494 | 744.2 | 3.71 | | | |
| 495 | 688.2 | 3.3 | | | |
| 496 | 698.3 | 3.83 | | | |
| 497 | 694 | 2.16 | | | |
| 498 | | | 670.3 | 672.2 | |
| 499 | 726.2 | 3.65 | | | |
| 500 | 694.3 | 3.64 | | | |
| 501 | 720.5 | 3.62 | | | |
| 502 | | | 724.1 | 725.9 | |
| 503 | 700 | 3.36 | | | |
| 504 | 692.8 | 2.13 | | | |
| 505 | 713.8 | 2.73 | | | |
| 506 | 718 | 1.87 | | | |
| 507 | 854.7 | 4.15 | | | |
| 508 | 686.7 | 2.21 | | | |
| 509 | | | | 724.3 | |
| 510 | 756.2 | 2.95 | | | |

TABLE 12-continued

Physical data for exemplary compounds of Formula I.

| Compound No. | LCMS (M + 1) | LCMS RT | FIA-MS (M − 1) | FIA-MS (M + 1) | NMR |
|---|---|---|---|---|---|
| 511 | | | 680.5 | 682.54 | |
| 512 | | | 746.4 | 748.3 | |
| 513 | | | 726.4 | 728.2 | |
| 514 | 635 | 3.68 | | | |
| 515 | 688.4 | 3.2 | | | |
| 516 | 700 | 2.98 | | | |
| 517 | | | 744.1 | 746.1 | |
| 518 | 775.2 | 3.3 | | | |
| 519 | | | | 636 | |
| 520 | 660 | 3.5 | | | |
| 521 | 720.1 | 3.84 | | | |
| 522 | 670 | 3.59 | | | |
| 523 | 672 | 3.1 | | | |
| 524 | | | | | |
| 525 | | | 735.2 | 737 | |
| 526 | 694 | 3.64 | | | |
| 527 | | | 746.1 | 748.1 | |
| 528 | 731.9 | 3.38 | | | |
| 529 | 732 | 2.89 | | | |
| 530 | | | | 722 | |
| 531 | 650 | 3.46 | | | |
| 532 | 644 | 3.39 | | | |
| 533 | | | 694 | 696 | |
| 534 | 730.5 | 3.67 | | | |
| 535 | 668.2 | 3 | | | |
| 536 | | | 705.8 | 707.9 | |
| 537 | 742.7 | 2.25 | | | |
| 538 | 731.2 | 3.7 | | | |
| 539 | | | 743.2 | 744.2 | |
| 540 | 778.9 | 4.15 | | | |
| 541 | 700.34 | 3.2 | | | |
| 542 | 685.34 | 3.5 | | | |
| 543 | | | 695.7 | 697.7 | |
| 544 | 746.2 | 2.3 | | | |
| 545 | | | 696.1 | 697.9 | |
| 546 | 748.7 | 2.38 | | | |
| 547 | | | 726.4 | 728.25 | |
| 548 | | | 682 | 684 | |
| 549 | | | 696 | 697.9 | |
| 550 | | | 653.3 | 654 | |
| 551 | | | | 609.3 | |
| 552 | 692.3 | 3.51 | | | |
| 553 | 712.2 | 2.6 | | | |
| 554 | 670.5 | 2.9 | | | |
| 555 | | | | | |
| 556 | | | | | |
| 557 | 725.8 | 3.4 | | | |
| 558 | 679 | 3.46 | | | |
| 559 | | | 702 | 704 | |
| 560 | | | 696.2 | 698 | |
| 561 | 730.4 | 3.7 | | | |
| 562 | 716 | 3.41 | | | |
| 563 | 695 | 2.46 | | | |
| 564 | | | | 707.9 | |
| 565 | 762.2 | 3.55 | | | |
| 566 | | | 628 | 630 | |
| 567 | 774.7 | 3.19 | | | |
| 568 | 712.7 | 2.3 | | | |
| 569 | | | | 671.9 | |
| 570 | | | 656.1 | 658.2 | |
| 571 | 730.2 | 3.4 | | | |
| 572 | | | 639.1 | 641.2 | |
| 573 | | | | 694.1 | |
| 574 | 634.5 | 1.7 | | | |
| 575 | 714.4 | 3.1 | | | |
| 576 | 680 | 2.2 | | | |
| 577 | 718 | 3.51 | | | |
| 578 | | | 680.5 | 682.4 | |
| 579 | 698 | 3.72 | | | |
| 580 | 597 | 2.87 | | | |
| 581 | 720 | 3.51 | | | |
| 582 | 714.4 | 3.6 | | | |
| 583 | 693 | 3.35 | | | |
| 584 | | | | 744 | |
| 585 | 762 | 3.68 | | | |
| 586 | 707 | 3.2 | | | |
| 587 | 730.5 | 3.68 | | | |
| 588 | 745.7 | 4.09 | | | |
| 589 | 735.20 | 3.70 | | | |
| 590 | 694.30 | 3.65 | | | |
| 591 | 651.30 | 3.26 | | | |
| 592 | 651.30 | 3.24 | | | |
| 593 | 685.20 | 3.53 | | | |
| 594 | 700.20 | 3.72 | | | |

Additional compounds, some of their physical data and method of synthesis are provided in Table 13.

TABLE 13

| Cmpd No. | LC/MASS PLUS | FIA MS+ | Syn. Method |
|---|---|---|---|
| 595 | 715.23 | | 5B |
| 596 | 689.24 | | 5B |
| 597 | 727.20 | | 6 |
| 598 | 775.10 | | 6 |
| 599 | 685.20 | | 6 |
| 600 | | 729.16 | |
| 601 | 729.10 | | 6 |
| 602 | 687.20 | | 5B |
| 603 | 673.17 | | 5B |
| 604 | 703.00 | | 5B |
| 605 | 716.00 | | 5B |
| 606 | 742.00 | | 5B |
| 607 | 676.00 | | 5B |
| 608 | 702.00 | | 5B |
| 609 | 676.00 | | 5B |
| 610 | 690.00 | | 5B |
| 611 | 716.00 | | 5B |
| 612 | 650.00 | | 5B |
| 613 | 676.00 | | 5B |
| 614 | 724.20 | | 6 |
| 615 | 708.20 | | 6 |
| 616 | | 744.1 | 5B |
| 617 | | 684.1 | 5B |
| 618 | 704.70 | | 5B |
| 619 | 677.60 | | 5B |
| 620 | | 688 | 5B |
| 621 | | 662 | 5B |
| 622 | | 702 | 5B |
| 623 | | 676 | 5B |
| 624 | | 662 | 5B |
| 625 | | 636 | 5B |
| 626 | | 664 | 5B |
| 627 | | 638 | 5B |
| 628 | | 704 | 5B |
| 629 | | 678 | 5B |
| 630 | | 678 | 5B |
| 631 | | 652 | 5B |
| 632 | 688.20 | | 5B |
| 633 | 686.10 | | 5B |
| 634 | 702.20 | | 5B |
| 635 | 700.10 | | 5B |
| 636 | 674.10 | | 5B |
| 637 | 688.20 | | 5B |
| 638 | 735.10 | | 6 |
| 639 | 723.10 | | 6 |
| 640 | 688.20 | | 5B |
| 641 | 702.20 | | 5B |
| 642 | 714.20 | | 5B |
| 643 | 728.10 | | 6 |
| 644 | 651.21 | | 5B |
| 645 | 704.00 | | 5B |
| 646 | 678.00 | | 5B |
| 647 | 663.70 | | 5B |

TABLE 13-continued

| | | | |
|---|---|---|---|
| 648 | 689.70 | | 5B |
| 649 | 728.70 | | 5B |
| 650 | | 690 | 5B |
| 651 | | 676 | 5B |
| 652 | | 690 | 5B |
| 653 | | 664 | 5B |
| 654 | | 650 | 5B |
| 655 | 732.70 | | 5B |
| 656 | 718.70 | | 5B |
| 657 | 730.60 | | 5B |
| 658 | 700.10 | | 5B |
| 659 | 701.00 | | 6 |
| 660 | 689.00 | | 6 |
| 661 | | 714 | 5B |
| 662 | | 728 | 5B |
| 663 | | 688 | 5B |
| 664 | | 702 | 5B |
| 665 | | 716 | 5B |
| 666 | 673.10 | | 6 |
| 667 | 701.19 | | 5B |
| 668 | 684.12 | | 5B |
| 669 | | 708.2 | 6 |
| 670 | 687.70 | | 5B |
| 671 | 665.20 | | 6 |
| 672 | 742.00 | | 6 |
| 673 | 716.00 | | 6 |
| 674 | 728.00 | | 6 |
| 675 | 742.00 | | 6 |
| 676 | 728.00 | | 6 |
| 677 | 700.40 | | 6 |
| 678 | 700.40 | | 6 |
| 679 | 688.10 | | 5B |
| 680 | 662.10 | | 5B |
| 681 | 648.20 | | 5B |
| 682 | 690.10 | | 5B |
| 683 | 664.10 | | 5B |
| 684 | 650.10 | | 5B |
| 685 | 702.10 | | 5B |
| 686 | 676.10 | | 5B |
| 687 | 662.10 | | 5B |
| 688 | 674.10 | | 5B |
| 689 | 704.00 | | 6 |
| 690 | 690.00 | | 6 |
| 691 | | 692.1 | 5A |
| 692 | | 706.1 | 5A |
| 693 | | 692.1 | 5A |
| 690 | 690.00 | | 6 |
| 692 | | 706.1 | 5A |
| 693 | | 692.1 | 5A |
| 694 | 690.04 Lot 2: 690.10 | | 5B |
| 695 | 690.04; Lot 2: 690.10 | | 5B |
| 696 | 704.62 | | 5B |
| 697 | 704.04 | | 5B |
| 698 | 676.06 | | 5B |
| 699 | 676.07 | | 5B |
| 700 | 675.00 | | 6 |
| 701 | 663.00 | | 6 |
| 702 | 634.00 | | 5B |
| 703 | 672.00 | | 5B |
| 704 | 686.10 | | 5B |
| 705 | 700.10 | | 5B |
| 706 | | 740.1 | 5B |
| 707 | 628.10 | | 5B |
| 708 | | 740 | 5B |
| 709 | | 754 | 5B |
| 710 | | 728 | 5B |
| 711 | | 714 | 5B |
| 712 | | 682.2 | 5B |
| 713 | | 744 | 5B |
| 714 | 696.10 | | 5B |
| 715 | | 682.2 | 5B |
| 716 | | 670.1 | 5B |
| 717 | 684.60 | | 5B |
| 718 | 658.80 | | 5B |
| 719 | 644.60 | | 5B |
| 720 | 670.60 | | 5B |
| 721 | 656.60 | | 5B |
| 722 | 682.60 | | 5B |
| 723 | 668.70 | | 5B |
| 724 | 694.70 | | 5B |
| 725 | 680.70 | | 5B |
| 726 | 696.70 | | 5B |
| 727 | 682.70 | | 5B |
| 728 | 708.70 | | 5B |
| 729 | 694.80 | | 5B |
| 730 | 682.70 | | 5B |
| 731 | 656.60 | | 5B |
| 732 | 642.70 | | 5B |
| 733 | 668.70 | | 5B |
| 734 | 654.70 | | 5B |
| 735 | 674.80 | | 6 |
| 736 | 702.10 | | 6 |
| 737 | 714.10 | | 6 |
| 738 | 696.00 | | 5B |
| 739 | 696.00 | | 5B |
| 740 | | 684.6 | 5A |
| 741 | | 708 | 5B |
| 742 | 744.60 | | 5B |
| 743 | 718.70 | | 5B |
| 744 | 732.70 | | 5B |
| 745 | 706.60 | | 5B |
| 746 | 694.50 | | 5B |
| 747 | 650.10 | | 5B |
| 748 | 628.10 | | 5B |
| 749 | 628.10 | | 5B |
| 750 | 706.00 | | 5B |
| 751 | 684.10 | | 5B |
| 752 | 727.00 | | 5B |
| 753 | 716.00 | | 5B |
| 754 | 656.10 | | 5B |
| 755 | 656.10 | | 5B |
| 756 | 697.00 | | 5B |
| 757 | 697.00 | | 5B |
| 758 | 670.90 | | 5B |
| 759 | 656.90 | | 5B |
| 760 | 709.00 | | 5B |
| 761 | 682.90 | | 5B |
| 762 | 668.90 | | 5B |
| 763 | 721.00 | | 5B |
| 764 | 671.00 | | 5B |
| 765 | 656.90 | | 5B |
| 766 | 709.00 | | 5B |
| 767 | 682.90 | | 5B |
| 768 | 668.90 | | 5B |
| 769 | 700.00 | | 5B |
| 770 | 713.00 | | 6 |
| 771 | 674.00 | | 5B |
| 772 | 660.10 | | 5B |
| 773 | 648.10 | | 5B |
| 774 | 634.10 | | 5B |
| 775 | 696.10 | | 5B |
| 776 | 682.10 | | 5B |
| 777 | 670.10 | | 5B |
| 778 | 656.10 | | 5B |
| 779 | 720.00 | | 5B |
| 780 | 734.00 | | 5B |
| 781 | | 718.1 | 6 |
| 782 | | 692.1 | 6 |
| 783 | | 730.2 | 6 |
| 784 | | 704 | 6 |
| 785 | 685.80 | | 6 |
| 786 | 724.60 | | 5B |
| 787 | 710.41 | | 5B |
| 788 | 712.60 | | 5B |
| 789 | 698.60 | | 5B |
| 790 | 736.50 | | 5B |
| 791 | 750.60 | | 5B |
| 792 | 724.50 | | 5B |
| 793 | 764.60 | | 5B |
| 794 | 700.50 | | 5B |
| 795 | 714.50 | | 5B |
| 796 | 700.50 | | 5B |
| 797 | 714.50 | | 5B |
| 798 | 694.64 | | 6 |
| 799 | 750.50 | | 5B |
| 800 | 724.50 | | 5B |

TABLE 13-continued

| | | | | |
|---|---|---|---|---|
| 801 | 736.30 | | | 5B |
| 802 | 727.80 | | | 6 |
| 803 | 772.00 | | | 6 |
| 804 | 693.60 | | | 5B |
| 805 | 693.60 | | | 5B |
| 806 | 707.70 | | | 5B |
| 807 | 707.60 | | | 5B |
| 808 | | 698 | | 5B |
| 809 | | 684 | | 5B |
| 810 | 720.00 | | | 5B |
| 811 | 734.00 | | | 5B |
| 812 | 652.90 | | | 6 |
| 813 | 658.00 | | | 5B |
| 814 | 742.00 | | | 5B |
| 815 | 728.00 | | | 5B |
| 816 | 716.00 | | | 5B |
| 817 | 758.60 | | | 6 |
| 818 | 758.50 | | | 6 |
| 819 | 728.60 | | | 6 |
| 820 | 640.80 | | | 6 |
| 821 | | | 722.7 | 5B |
| 822 | | | 653.4 | 5B |
| 823 | | | 684.6 | 5B |
| 824 | | | 710.6 | 5B |
| 825 | | | 698.5 | 5B |
| 826 | 742.60 | | | 5B |
| 827 | 716.50 | | | 5B |
| 828 | 742.60 | | | 5B |
| 829 | 728.60 | | | 5B |
| 830 | 714.50 | | | 5B |
| 831 | 680.60 | | | 5B |
| 832 | 680.50 | | | 5B |
| 833 | 738.50 | | | 5B |
| 834 | 764.33 | | | 5B |
| 835 | 684.00 | | | 5B |
| 836 | 716.00 | | | 5B |
| 837 | 704.00 | | | 5B |
| 838 | 639.30 | | | 5B |
| 839 | 670.50 | | | 5B |
| 840 | 696.60 | | | 5B |
| 841 | 684.50 | | | 5B |
| 842 | 642.30 | | | 5B |
| 843 | 628.30 | | | 5B |
| 844 | 728.6 | | | 5B |
| 845 | 728.70 | | | 5B |
| 846 | 702.60 | | | 5B |
| 847 | 714.30 | | | 6 |
| 848 | 728.30 | | | 6 |
| 849 | 682.30 | | | 5B |
| 850 | 644.30 | | | 5B |
| 851 | 682.30 | | | 5B |
| 852 | 646.30 | | | 5B |
| 853 | 682.30 | | | 5B |
| 854 | 724.30 | | | 5B |
| 855 | 748.00 | | | 5B |
| 856 | 742.00 | | | 5B |
| 857 | 672.00 | | | 5B |
| 858 | 698.00 | | | 5B |
| 859 | | 710 | | 5B |
| 860 | | 696 | | 5B |
| 861 | | 684 | | 5B |
| 862 | 708.50 | | | 5B |
| 863 | | 698.3 | | 11 |
| 864 | 731.38 | | | 6 |
| 865 | 726.30 | | | 5B |
| 866 | 720.50 | | | 5B |
| 867 | 680.60 | | | 5B |
| 868 | 691.20 | | | 5B |
| 869 | 691.20 | | | 5B |
| 870 | 698.60 | | | 5B |
| 871 | 710.60 | | | 5B |
| 872 | 724.70 | | | 5B |
| 873 | 718.50 | | | 5B |
| 874 | 744.50 | | | 5B |
| 875 | 730.40 | | | 5B |
| 876 | 744.50 | | | 5B |
| 877 | 686.50 | | | 5B |
| 878 | 712.50 | | | 5B |
| 879 | 698.50 | | | 5B |
| 880 | 712.50 | | | 5B |
| 881 | 696.50 | | | 5B |
| 882 | 716.40 | | | 5B |
| 883 | 684.50 | | | 5B |
| 884 | 691.20 | | | 5B |
| 885 | 691.20 | | | 5B |
| 886 | 690.20 | | | 5B |
| 887 | 690.10 | | | 5B |
| 888 | 748.00 | | | 5B |
| 889 | 722.00 | | | 5B |
| 890 | 709.10 | | | 5B |
| 891 | 720.40 | | | 5B |
| 892 | 674.20 | | | 5B |
| 893 | 688.30 | | | 5B |
| 894 | 662.10 | | | 5B |
| 895 | 687.70 | | | 5B |
| 896 | 670.30 | | | 5B |
| 897 | 694.20 | | | 5B |
| 898 | 680.50 | | | 5B |
| 899 | 720.10 | | | 5B |
| 900 | 706.10 | | | 5B |
| 901 | 706.20 | | | 5B |
| 902 | 720.10 | | | 5B |
| 903 | | | 679.3 | 11 |
| 904 | 654.20 | | | 11 |
| 905 | 704.50 | | | 5B |
| 906 | 718.60 | | | 5B |
| 907 | 718.60 | | | 5B |
| 908 | 704.60 | | | 5B |
| 909 | 656.20 | | | 5B |
| 910 | 642.20 | | | 5B |
| 911 | 748.00 | | | 5B |
| 912 | 762.00 | | | 5B |
| 913 | 736.00 | | | 5B |
| 914 | 761.00 | | | 5B |
| 915 | 672.20 | | | 5B |
| 916 | 658.50 | | | 5B |
| 917 | 694.50 | | | 5B |
| 918 | 694.50 | | | 5B |
| 919 | | | 710.2 | 5B |
| 920 | | | 710.3 | 5B |
| 921 | | | 684.2 | 5B |
| 922 | | | 698.2 | 5B |
| 923 | | | 696.2 | 5B |
| 924 | | | 670.3 | 5B |
| 925 | | | 696.2 | 5B |
| 926 | | | 684.2 | 5B |
| 927 | | | 684.2 | 5B |
| 928 | | | 684.2 | 5B |
| 929 | | | 658.4 | 5B |
| 930 | | | 672.2 | 5B |
| 931 | | | 670.4 | 5B |
| 932 | | | 670.2 | 5B |
| 933 | | | 644.3 | 5B |
| 934 | | | 658.5 | 5B |
| 935 | | | 605.3 | 11 |
| 936 | | | 667.3 | 11 |
| 937 | 734.00 | | | 5B |
| 938 | 722.00 | | | 5B |
| 939 | | | 708 | 5B |
| 940 | | | 734 | 5B |
| 941 | | | 720 | 5B |
| 942 | | | 732 | 5B |
| 943 | | | 744 | 5B |
| 944 | | | 720 | 5B |
| 945 | | | 746 | 5B |
| 946 | | | 732 | 5B |
| 947 | | | 696 | 5B |
| 948 | 744.60 | | | 5B |
| 949 | 730.60 | | | 5B |
| 950 | 708.20 | | | 5B |
| 951 | 700.60 | | | 5B |
| 952 | 696.20 | | | 5B |
| 953 | 696.20 | | | 5B |
| 954 | 694.10 | | | 5B |
| 955 | 738.67 | | | 5B |

TABLE 13-continued

| Example No. | FIA MASS MINUS | FIA MASS PLUS | LC MASS MINUS | LC MASS PLUS | Syn. Method |
|---|---|---|---|---|---|
| 957 | | | 686.41 | 688.06 | 5B |
| 958 | 663.50 | 665.10 | | 665.10 | 5B |
| 959 | | | | 706.60 | 5B |
| 960 | | | | 720.60 | 5B |
| 961 | | | | 704.00 | 5B |
| 962 | | | 691.70 | 693.30 | 11 |
| 963 | | | | 645.30 | 11 |
| 964 | | | | 679.20 | 11 |
| 965 | | | | 665.20 | 11 |
| 966 | | | | 690.00 | 5B |
| 967 | | | | 709.60 | 5B |
| 968 | | | | 734.10 | 5B |
| 969 | | | | 708.10 | 5B |
| 970 | | | | 734.00 | 5B |
| 971 | | 706.00 | | | 5B |
| 972 | | 730.00 | | | 5B |
| 973 | | 718.00 | | | 5B |
| 974 | | 670.00 | | | 5B |
| 975 | | 694.00 | | | 5B |
| 976 | | 682.00 | | | 5B |
| 977 | | | | 672.00 | 5B |
| 978 | | | | 658.00 | 5B |
| 979 | 770.70 | 772.10 | | | 5B |
| 980 | 741.70 | 743.20 | | | 5B |
| 981 | | 743.10 | | | 5B |
| 982 | 741.60 | 743.20 | | | 5B |
| 983 | 706.60 | 708.20 | | | 5B |
| 984 | 746.50 | 748.20 | | | 5B |
| 985 | 756.60 | 758.20 | | | 5B |
| 986 | 727.60 | 729.10 | | | 5B |
| 987 | 727.50 | 729.20 | | | 5B |
| 988 | 727.60 | 729.10 | | | 5B |
| 989 | 692.50 | 694.20 | | | 5B |
| 990 | 732.60 | 734.30 | | | 5B |
| 991 | 744.50 | 746.10 | | | 5B |
| 992 | 680.60 | 682.30 | | | 5B |
| 993 | 720.60 | 722.30 | | | 5B |
| 994 | | | 759.80; 759.60 | 760.20 | 5B |
| 995 | | | | 734.20 | 5B |
| 996 | | | | 760.20 | 5B |
| 997 | | | | 734.20 | 5B |
| 998 | | | | 746.20 | 5B |
| 999 | | | 744.50 | 746.10 | 5B |
| 1000 | 689.50 | 691.10 | | 691.10 | 5B |
| 1001 | 703.60 | 705.10 | | 705.10 | 5B |
| 1002 | 716.40 | 718.30 | | 718.30 | 5B |
| 1003 | 718.60 | 720.00 | | 720.00 | 5B |
| 1004 | 718.60 | 720:00 | | 720.00 | 5B |
| 1005 | | | | 772.10 | 5B |
| 1006 | | | 744.80 | 746.00 | 5B |
| 1007 | 710.70 | 712.30 | | | 5B |
| 1008 | 724.60 | 726.20 | | | 5B |
| 1009 | 724.70 | 726.20 | | | 5B |
| 1010 | 696.50 | 698.20 | | | 5B |
| 1011 | 710.60 | 712.20 | | | 5B |
| 1012 | 710.60 | 712.20 | | | 5B |
| 1013 | 698.70 | 700.20 | | | 5B |
| 1014 | | 876.30 | | | 5B |
| 1015 | 679.70 | 681.20 | | | 11 |
| 1016 | 713.50 | 715.10 | | | 11 |
| 1017 | 693.60 | 695.10 | | | 11 |
| 1018 | | | 743.60 | 745.70 | 5B |
| 1019 | | | 676.60 | 678.00 | 11 |
| 1020 | 627.70 | 629.20 | | | 11 |
| 1021 | | | | 629.20 | 11 |
| 1022 | 702.60 | 704.20 | | | 11 |
| 1023 | 626.60 | 628.30 | | | 11 |
| 1024 | | | | 712.30 | 5B |
| 1025 | | | | 686.20 | 5B |
| 1026 | | | | 698.40 | 5B |
| 1027 | | | | 712.20 | 5B |
| 1028 | | | | 686.30 | 5B |
| 1029 | | | | 698.30 | 5B |
| 1030 | | | | 712.20 | 5B |
| 1031 | | | | 686.20 | 5B |
| 1032 | | | | 698.30 | 5B |
| 1033 | | | | 740.00 | 5B |
| 1034 | | | | 714.30 | 5B |
| 1035 | | | | 726.30 | 5B |
| 1036 | | | | 702.00 | 5B |
| 1037 | | | | 670.00 | 5B |
| 1038 | | | | 698.00 | 5B |
| 1039 | | | | 710.00 | 5B |
| 1040 | | | | 684.20 | 5B |
| 1041 | 696.70 | 698.20 | | | 5B |
| 1042 | 696.60 | 698.20 | | | 5B |
| 1043 | 684.70 | 686.20 | | | 5B |
| 1044 | 698.70 | 700.20 | | | 5B |

V. Assays for Detecting and Measuring Inhibition Properties of Compounds

A. HCV Enzyme Assays

1. Construction and Expression of the HCV NS3 Serine Protease Domain

A DNA fragment encoding residues $Ala^1$-$Ser^{181}$ of the HCV NS3 protease (GenBank CAB46913) was obtained by PCR from the HCV Con1 replicon plasmid, $I_{377}$neo/NS3-3'/wt (re-named as pBR322-HCV-Neo in this study) [V. Lohmann et al., Science, 285, pp. 110-113 (1999)] and inserted into pBEV11 (S. Chamber, et al., personal communication) for expression of the HCV proteins with a C-terminal hexa-histidine tag in E. coli. All constructs were confirmed by sequencing.

The expression constructs for the HCV NS3 serine protease domain was transformed into BL21/DE3 pLysS E. coli cells (Stratagene). Freshly transformed cells were grown at 37° C. in a BHI medium (Difco Laboratories) pplemented with 100 µg/mL carbenicillin and 35 µg/mL chloramphenicol to an optical density of 0.75 at 600 nm. Induction with 1 mM IPTG was performed for four hours at 24° C. The cell paste was harvested by centrifugation and flash frozen at −80° C. prior to protein purification. All purification steps were performed at 4° C. Next, 100 g of cell paste was lysed in 1.5 L of buffer A (50 mM HEPES (pH 8.0), 300 mM NaCl, 0.1% n-octyl-β-D-glucopyranoside, 5 mM β-mercaptoethanol, 10% (v/v) glycerol) and stirred for 30 minutes. The lysate was homogenized using a Microfluidizer (Microfluidics, Newton, Mass.), followed by ultra-centrifugation at 54,000×g for 45 minutes. Imidazole was added to the supernatant to a final concentration of 5 mM along with 2 mL of Ni-NTA resin pre-equilibrated with buffer A containing 5 mM imidazole. The mixture was rocked for three hours and washed with 20 column volumes of buffer A plus 5 mM imidazole. The HCV NS3 protein was eluted in buffer A containing 300 mM imidazole. The eluate was concentrated and loaded onto a Hi-Load 16/60 Superdex 200 column, pre-equilibrated with buffer A. The appropriate fractions of the purified HCV protein were pooled and stored at −80° C.

2. HCV NS3 Protease Domain Peptide Cleavage Assay

This assay is a modification of that described by Landro, et al. (Landro J A, Raybuck S A, Luong Y C, O'Malley E T, Harbeson S L, Morgenstern K A, Rao G and Livingston D L. Biochemistry 1997, 36, 9340-9348), and uses a peptide substrate (NS5AB), based on the NS5A/NS5B cleavage site for genotype 1a HCV. The substrate stock solution (25 mM) was prepared in DMSO containing 0.2 M DTT and stored at −20° C. A synthetic peptide cofactor (KK4A) was used as a substitute for the central core region of NS4A. Peptide sequences are shown in the table below. The reaction was performed in a 96-well microtiter plate format using 25 ηM to 50 ηM HCV NS3 protease domain in buffer containing 50 mM HEPES pH 7.8, 100 mM NaCl, 20% glycerol, 5 mM DTT and 25 μM KK4A. The final DMSO concentration was no greater than 2% v/v. Reactions were quenched by addition of trifluoroacetic acid (TFA) to yield a final concentration of 2.5%.

Peptide Sequences Used with HCV NS3 Protease Domain

| Peptide | Sequence |
|---------|----------|
| NS5AB | NH$_2$-EDVV-(alpha)Abu-CSMSY-COOH [SEQ ID NO:2] |
| KK4A | NH$_2$-KKGSVVIVGRIVLSGK-COOH [SEQ ID NO:3] |

The SMSY product was separated from substrate and KK4A using a microbore separation method. The instrument used was a Agilent 1100 with a G1322A degasser, either a G1312A binary pump or a G1311A quaternary pump, a G1313A autosampler, a G1316A column thermostated chamber and a G1315A diode array detector. The column was a Phenomenex Jupiter, 5 μm C18, 300 Å, 150×2 mm, P/O 00F-4053-B0, with a flow-rate of 0.2 mL/min. The column thermostat was at 40° C. Mobile phases were HPLC grade H$_2$O/0.1% TFA (solvent A) and HPLC grade CH$_3$CN/0.1% TFA (solvent B). The SMSY product peak was quantitated using the data collected at 210 ηM.

3. Construction and Expression of NS3•4A Protease

Using standard recombinant DNA techniques, a cDNA fragment encoding the sequence for NS3 and NS4A, residues Ala$_{1027}$ to Cys$_{1711}$ from the HCV sub-type strain 1a, containing an N-terminal hexa-histidine sequence, was cloned into the baculoviral transfer vector pVL1392 (Webb N R and Summers M D (1990) Expression of proteins using recombinant baculoviruses, Techniques 2:173-188). Recombinant baculovirus containing NS3•4A was produced by co-transfection of pVL1392-His-NS3•4A with linearized Autographa californica nuclear polyhedrosis virus (AcMNPV) DNA into Spodoptera frugoperda (SD) insect cells. The transfected insect cells containing recombinant baculovirus clones were subsequently isolated by plaque purification. High-titer clonal baculovirus was routinely used to infect SD insect cells for protein production. In production, Sf9 cells were grown at 27° C. until they reached a density of 2.0×10$^6$ cells/ml. At this point, the insect cells were infected with virus. After 72 hours or when the cell viability was between 70-80% the culture was harvested and the cells were ready for purification.

4. Purification of NS3•4A Protein

The NS3•4A protein (SEQ ID NO:1) was purified as follows. Cell paste was thawed in at least five volumes of Lysis Buffer (50 mM Na$_2$HPO$_4$ pH 8.0, 10% Glycerol, 300 mM NaCl, 5 mM β-mercaptoethanol, 0.2 mM PMSF, 2.5 μg/ml Leupeptin, 1.0 μg/mlE64, 2.0 μg/ml Pepstatin) per gram of cell paste. The cell paste was then homogenized on ice using a Dounce homogenizer. The cells were next mechanically disrupted by passing once through a microfluidizer (Microfluidics Corporation, Newton, Mass.), and the cell lysate was collected on ice. The cell lysates was centrifuged at 100,000×g for 30 minutes at 4° C. and the supernatants were decanted. Optionally, the pellets were resuspended in wash buffer (Lysis Buffer+0.1% β-octyl glucopyranoside), homogenized using a Dounce homogenizer and centrifuged at 100,000×g for 30 minutes at 4° C. Insoluble NS3° 4A was extracted from the pellets by resuspending in Extraction Buffer (Lysis Buffer+0.5% lauryl maltoside) using 2.5 ml/g cell paste. The mixture was homogenized using a Dounce homogenizer and mixed at 4° C. for three hours or more. The mixture was centrifuged at 100,000×g for 30 minutes at 4° C. The supernatants were decanted and pooled.

The NS3•4A protein was further purified using Nickel-NTA metal affinity chromatography. Imidazole from a 2 M stock, pH 8.0, solution was added to the pooled supernatants so that the final concentration of imidazole was 10 mM. The supernatants were incubated batchwise overnight at 4° C. with Nickel-NTA affinity resin that had been pre-equilibrated with Lysis Buffer+10 mM imidazole. 1 ml of resin per 5 μg of expected NS3-4A was used. The resin was next settled by gravity or by centrifugation at 500×g for five minutes. The resin was next poured into a gravity flow column and washed with 10 or more column volumes of Nickel Wash Buffer (Lysis Buffer+0.1% lauryl maltoside+10 mM imidazole). The column was next eluted with three to four column volumes of Nickel Elution Buffer (Nickel Wash Buffer+300 mM imidazole). The elution fractions were collected on ice and evaluated using SDS-PAGE. To prevent NS3-4A proteolysis, 100 μM DFP protease inhibitor was added to gel samples before adding SDS sample buffer and boiling. The peak fractions were pooled and protein concentration was determined by measuring absorbance at 280 ηm and by dividing by the extinction coefficient (e), which for NS3•4A is 1.01.

The NS3•4A was purified further using gel filtration chromatography. A Superdex 200 26/60 column was equilibrated with Superdex Buffer (20 mM HEPES pH 8.0, 10% glycerol, 300 mM NaCl, 10 mM β-mercaptoethanol, 0.05% lauryl maltoside) at a rate of 3 ml/min. The nickel purified NS3•4A was concentrated in a Centriprep 30 to greater than 2 mg/ml, if necessary, and was filtered through a 0.2 μm syringe filter and up to 10 ml was loaded onto the Superdex 200 column. After 0.3 column volumes passed through, 4-5 ml fractions were collected. Fractions were evaluated by SDS-PAGE. NS3•4A protein elutes in two peaks. Peak 1 contains aggregated NS3•4A and peak 2 contains active protein. The fractions of peak 2 were pooled, aliquoted and frozen at −70° C.

Analysis of NS3•4A protein.

| ANALYSIS | ENTIRE PROTEIN |
|----------|----------------|
| Length | 695 amino acids |
| Molecular Weight | 74,347.78 |
| 1 microgram | 13.450 picot moles |
| Molar Extinction Coefficient | 73430 |
| 1 A280 corresponds to | 1.01 mg/ml |
| Isoelectric Point | 6.50 |
| Charge at pH 7 | −3.58 |

5. HCV NS3 Peptide Cleavage Assay

This assay follows the cleavage of a peptide substrate by full-length hepatitis C viral protein NS3•4A. One of three peptide substrates based on the NS5A/NS5B cleavage site for genotype 1a HCV is used to measure enzyme activity. All substrate stock solutions (25 mM) were prepared in DMSO containing 0.2M DTT and stored at −20° C. A synthetic peptide cofactor (NS4A Peptide) was used to supplement NS4A. Peptide sequences are shown below. The hydrolysis reaction was performed in a 96-well microtiter plate format using 100 ηM to 125 ηM HCV NS3•4A in buffer containing 50 mM HEPES pH 7.8, 100 mM NaCl, 20% glycerol, 5 mM DTT and 25 μM NS4A Peptide. The final DMSO concentration was no greater than 2% v/v. Reactions using NS5AB or NS5AB-EDANS as substrate were quenched by the addition of 10% trifluoroacetic acid (TFA) to yield a final TFA concentration of 2.5%. Reactions using FITC-NS5AB-1 as substrate were quenched by the addition of 0.4M formic acid to yield a final concentration of 0.08M acid.

Enzymatic activity was assessed by separation of substrate and products by reverse phase HPLC. The instrument used was a Agilent 1100 with a G1322A degasser, either a G1312A binary pump or a G1311A quaternary pump, a G1313A autosampler, a G1316A column thermostated chamber, a G1321A fluorescence detector and a G1315A diode array detector. The column thermostat was at 40° C. For substrate NS5AB the column was a Phenomenex Jupiter, 5 µm C18, 300 Å, 150×2 mm, P/O 00F-4053-B0, with a flow-rate of 0.2 mL/min using HPLC grade $H_2O$/0.1% TFA (solvent A) and HPLC grade $CH_3CN$/0.1% TFA (solvent B) as mobile phases. The C-terminal product peak ($NH_2$-SMSY-COOH) was quantitated using the absorbance data collected at 210 ηm. For substrate NS5AB-EDANS the column was a Phenomenex Aqua, 5 µm C18, 125 Å, 50×4.6 mm, P/O 00B-4299-E0, with a flow-rate of 1.0 mL/min using HPLC grade $H_2O$/0.1% TFA (solvent A) and HPLC grade $CH_3CN$/0.1% TFA (solvent B) as mobile phases. The C-terminal product peak ($NH_2$-SMSYT-Asp(EDANS)-KKK-COOH) was quantitated using the fluorescence data collected at 350 ηm excitation/490 ηm emission. For substrate FITC-NS5AB-1 the column was a Phenomenex Prodigy, 5 µm ODS(2), 125 Å, 50×4.6 mm, P/O 00B-3300-E0, with a flow-rate of 1.0 mL/min using 10 mM sodium phosphate pH 7.0 in HPLC grade $H_2O$ (solvent A) and 65% HPLC Grade $CH_3CN$/35% 10 mM sodium phosphate pH 7.0 in HPLC grade H2O (solvent B) as mobile phases. The N-terminal product peak (FITC-Ahx-EDVV-(alpha)Abu-C—COOH) was quantitated using the fluorescence data collected at 440 nm excitation/520 nm emission. Alternatively, the ratio of N-terminal product to unreacted FITC-NS5AB-1 substrate was determined using a Caliper LabChip 3000 with detection at 488 nm excitation/530 nm emission, using a chip buffer of 100 mM Tris pH 7.0, 10 mM EDTA, 0.01% (v/v) Brij-35, and 0.1% (v/v) CR-3.

Peptide sequences used with HCV NS3.

| Peptide | Sequence |
| --- | --- |
| NS4A Peptide | $NH_2$-KKGSVVIVGRIVLSGKPAIIPKK-COOH [SEQ ID NO:4] |
| NS5AB | $NH_2$-EDVV-(alpha)Abu-CSMSY-COOH [SEQ ID NO:2] |
| NS5AB-EDANS | $NH_2$-EDVV-(alpha)Abu- CSMSYT- Asp(EDANS)-KKK-COOH [SEQ ID NO:5] |
| FITC-NS5AB-1 | FITC-Ahx-EDVV-(alpha)Abu-CSMSYTKK-$NH_2$ [SEQ ID NO:6] |

6. Determination of Km and Vmax

To determine the kinetic parameters Km and Vmax, the HCV NS3 protease domain or HCV NS3•4A was reacted with peptide substrate under the assay conditions described above. Peptide substrate concentration was varied between 3 µM and 200 µM, with less than 20 percent conversion at all substrate concentrations. The ratio of the product peak area (as determined by reverse phase HPLC) to the reaction time yielded a rate of enzyme catalyzed hydrolysis. These rate vs. substrate concentration data points were fit to the Michaelis-Menten equation using non-linear regression. The value of $k_{cat}$ was determined from Vmax using the nominal protease concentration and a fully cleaved substrate peptide as an instrument calibration standard.

Kinetic parameters for peptide substrates with HCV NS3 or NS3 protease domain.

| Enzyme | Substrate | Km (µM) | kcat/Km ($M^{-1}sec^{-1}$) |
| --- | --- | --- | --- |
| NS3 Protease Domain | NS5AB | 25 | $3.0 \times 10^4$ |
| NS3•4A | NS5AB | 30 | $7.9 \times 10^3$ |
| NS3•4A | NS5AB-EDANS | 56 | $1.4 \times 10^3$ |
| NS3•4A | FITC-NS5AB-1 | 15 | $1.2 \times 10^3$ |

7. Determination of Compound Potency

To evaluate apparent Ki values, all components except the test compound and substrate were pre-incubated for 5-10 minutes at room temperature. Then, test compound, dissolved in DMSO, was added to the mixture and incubated for either 15 minutes or 60 minutes at 30° C. Neat DMSO was included as a no inhibitor control. The cleavage reaction was initiated by the addition of peptide substrate at a concentration either equal to Km or equal to one-half times Km, and allowed to proceed at 30° C. for 20 minutes. At the end of the reaction the mixture was quenched, and the extent of reaction was determined as described above. Eleven concentrations of compound were used to titrate enzyme activity for inhibition. Activity vs. inhibitor concentration data points were fit to the Morrison equation describing competitive tight-binding enzyme inhibition using non-linear regression (Sculley M J and Morrison J F. *Biochim. Biophys. Acta*, 1986, 874, 44-53).

The tested compounds of formula I generally exhibited Ki values from about 0.008 to about 20 µM. In some embodiments, the compounds of formula I exhibited Ki values from about 0.008 to about 0.100 µM. In some other embodiments, the compounds of formula I exhibited Ki values from about 0.100 to about 0.500 µM. In still some other embodiments, the compounds of formula I exhibited Ki values from 0.500 to about 5.000 µM.

Examples of activities of the compounds of formulae (I, Ia, and Ib) on inhibiting serine protease receptors are shown below in Table 13. For compound activities for serine protease measured using the HCV Enzyme Assays, serine protease activity is illustrated with "+++" if activity was measured to be less than 0.1 µM, "++" if activity was measured to be from 0.1 µM to 0.5 µM, "+" if activity was measured to be greater than 0.5 µM, and "–" if no data was available. It should be noted that 0% efficacy is the minimum response obtained with the DMSO only control. The Enzyme Assay 1 refers to the HCV NS3 Protease Domain Peptide Cleavage Assay and Enzyme Assay 2 refers to the HCV NS3 Peptide Cleavage Assay.

TABLE 13

HCV Enzymatic Assay Activities and efficacies of exemplary compounds in accordance to Formulae I.

| Compound No. | Enzyme Assay 1 | Enzyme Assay 2 |
| --- | --- | --- |
| 1 | – | – |
| 2 | – | – |
| 3 | ++ | +++ |
| 4 | ++ | |
| 5 | +++ | +++ |
| 6 | + | + |
| 7 | + | – |
| 8 | + | – |
| 9 | + | – |
| 10 | + | + |
| 11 | + | – |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 12 | ++ | +++ |
| 13 | +++ | +++ |
| 14 | + | − |
| 15 | ++ | − |
| 16 | + | − |
| 17 | + | ++ |
| 18 | +++ | +++ |
| 19 | ++ | +++ |
| 20 | + | − |
| 21 | + | + |
| 22 | − | − |
| 23 | +++ | ++ |
| 24 | ++ | − |
| 25 | + | − |
| 26 | ++ | +++ |
| 27 | ++ | − |
| 28 | + | ++ |
| 29 | ++ | ++ |
| 30 | ++ | +++ |
| 31 | − | ++ |
| 32 | ++ | − |
| 33 | +++ | − |
| 34 | + | − |
| 35 | − | − |
| 36 | ++ | − |
| 37 | + | − |
| 38 | − | ++ |
| 39 | ++ | − |
| 40 | + | − |
| 41 | +++ | − |
| 42 | ++ | +++ |
| 43 | ++ | +++ |
| 44 | ++ | − |
| 45 | + | ++ |
| 46 | + | + |
| 47 | + | − |
| 48 | − | − |
| 49 | − | +++ |
| 50 | − | +++ |
| 51 | + | − |
| 52 | ++ | − |
| 53 | + | − |
| 54 | + | ++ |
| 55 | ++ | − |
| 56 | ++ | − |
| 57 | − | − |
| 58 | + | + |
| 59 | − | +++ |
| 60 | ++ | ++ |
| 61 | + | − |
| 62 | ++ | ++ |
| 63 | + | + |
| 64 | + | − |
| 65 | + | + |
| 66 | ++ | − |
| 67 | +++ | +++ |
| 68 | − | +++ |
| 69 | + | ++ |
| 70 | + | − |
| 71 | + | − |
| 72 | ++ | − |
| 73 | + | ++ |
| 74 | ++ | +++ |
| 75 | ++ | − |
| 76 | ++ | − |
| 77 | ++ | +++ |
| 78 | ++ | − |
| 79 | ++ | +++ |
| 80 | + | − |
| 81 | + | − |
| 82 | ++ | − |
| 83 | ++ | − |
| 84 | + | + |
| 85 | ++ | − |
| 86 | ++ | − |
| 87 | ++ | ++ |
| 88 | + | ++ |
| 89 | − | ++ |
| 90 | − | +++ |
| 91 | + | + |
| 92 | ++ | − |
| 93 | ++ | +++ |
| 94 | +++ | − |
| 95 | ++ | − |
| 96 | + | ++ |
| 97 | − | +++ |
| 98 | + | ++ |
| 99 | + | + |
| 100 | + | + |
| 101 | + | − |
| 102 | ++ | − |
| 103 | ++ | − |
| 104 | − | +++ |
| 105 | − | +++ |
| 106 | + | − |
| 107 | ++ | − |
| 108 | ++ | − |
| 109 | +++ | − |
| 110 | ++ | − |
| 111 | ++ | ++ |
| 112 | ++ | +++ |
| 113 | + | + |
| 114 | +++ | +++ |
| 115 | + | ++ |
| 116 | + | − |
| 117 | − | ++ |
| 118 | + | − |
| 119 | ++ | ++ |
| 120 | + | + |
| 121 | ++ | +++ |
| 122 | ++ | − |
| 123 | +++ | − |
| 124 | + | ++ |
| 125 | ++ | ++ |
| 126 | ++ | ++ |
| 127 | ++ | ++ |
| 128 | ++ | − |
| 129 | − | +++ |
| 130 | ++ | +++ |
| 131 | − | +++ |
| 132 | ++ | ++ |
| 133 | ++ | ++ |
| 134 | ++ | +++ |
| 135 | + | − |
| 136 | ++ | ++ |
| 137 | − | − |
| 138 | + | + |
| 139 | + | − |
| 140 | ++ | +−− |
| 141 | + | ++ |
| 142 | + | − |
| 143 | ++ | ++ |
| 144 | + | − |
| 145 | ++ | − |
| 146 | + | − |
| 147 | +++ | − |
| 148 | + | + |
| 149 | + | − |
| 150 | ++ | − |
| 151 | ++ | − |
| 152 | ++ | − |
| 153 | ++ | ++ |
| 154 | ++ | − |
| 155 | + | − |
| 156 | +++ | − |
| 157 | + | − |
| 158 | +++ | +++ |
| 159 | ++ | − |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 160 | + | − |
| 161 | + | − |
| 162 | ++ | +++ |
| 163 | +++ | +++ |
| 164 | + | − |
| 165 | ++ | +++ |
| 166 | ++ | − |
| 167 | ++ | − |
| 168 | ++ | ++ |
| 169 | − | ++ |
| 170 | − | +++ |
| 171 | + | + |
| 172 | + | ++ |
| 173 | +++ | − |
| 174 | ++ | − |
| 175 | − | − |
| 176 | ++ | ++ |
| 177 | + | ++ |
| 178 | ++ | ++ |
| 179 | ++ | − |
| 180 | + | − |
| 181 | + | + |
| 182 | + | + |
| 183 | ++ | − |
| 184 | − | +++ |
| 185 | + | ++ |
| 186 | + | + |
| 187 | + | − |
| 188 | + | + |
| 189 | + | − |
| 190 | ++ | +++ |
| 191 | +. | − |
| 192 | − | − |
| 193 | ++ | − |
| 194 | + | − |
| 195 | − | +++ |
| 196 | ++ | − |
| 197 | ++ | − |
| 198 | + | − |
| 199 | + | − |
| 200 | + | − |
| 201 | ++ | − |
| 202 | + | − |
| 203 | ++ | − |
| 204 | ++ | ++ |
| 205 | + | − |
| 206 | ++ | ++ |
| 207 | + | − |
| 208 | ++ | − |
| 209 | ++ | − |
| 210 | + | − |
| 211 | − | +++ |
| 212 | ++ | +++ |
| 213 | + | + |
| 214 | + | − |
| 215 | ++ | − |
| 216 | + | − |
| 217 | +++ | − |
| 218 | + | + |
| 219 | − | +++ |
| 220 | + | − |
| 221 | ++ | ++ |
| 222 | + | − |
| 223 | ++ | − |
| 224 | ++ | − |
| 225 | − | +++ |
| 226 | ++ | − |
| 227 | + | + |
| 228 | + | − |
| 229 | + | − |
| 230 | ++ | − |
| 231 | ++ | − |
| 232 | − | − |
| 233 | ++ | +++ |
| 234 | ++ | − |
| 235 | + | − |
| 236 | + | − |
| 237 | ++ | − |
| 238 | − | + |
| 239 | ++ | − |
| 240 | + | − |
| 241 | + | ++ |
| 242 | +++ | − |
| 243 | + | − |
| 244 | ++ | − |
| 245 | ++ | − |
| 246 | + | + |
| 247 | +++ | − |
| 248 | + | + |
| 249 | ++ | − |
| 250 | − | +++ |
| 251 | + | − |
| 252 | ++ | +++ |
| 253 | + | + |
| 254 | ++ | − |
| 255 | ++ | ++ |
| 256 | ++ | − |
| 257 | ++ | − |
| 258 | + | − |
| 259 | ++ | − |
| 260 | ++ | − |
| 261 | ++ | − |
| 262 | + | − |
| 263 | ++ | +++ |
| 264 | − | +++ |
| 265 | + | ++ |
| 266 | ++ | ++ |
| 267 | − | − |
| 268 | ++ | + |
| 269 | + | + |
| 270 | ++ | − |
| 271 | ++ | +++ |
| 272 | + | + |
| 273 | ++ | − |
| 274 | − | − |
| 275 | ++ | ++ |
| 276 | + | − |
| 277 | + | ++ |
| 278 | + | − |
| 279 | ++ | − |
| 280 | + | + |
| 281 | +++ | − |
| 282 | + | ++ |
| 283 | + | − |
| 284 | ++ | ++ |
| 285 | ++ | − |
| 286 | − | +++ |
| 287 | ++ | − |
| 288 | ++ | − |
| 289 | + | ++ |
| 290 | ++ | − |
| 291 | + | − |
| 292 | ++ | +++ |
| 293 | + | + |
| 294 | ++ | − |
| 295 | ++ | − |
| 296 | + | + |
| 297 | − | +++ |
| 298 | ++ | ++ |
| 299 | + | − |
| 300 | ++ | ++ |
| 301 | ++ | − |
| 302 | ++ | ++ |
| 303 | + | − |
| 304 | ++ | +++ |
| 305 | − | ++ |
| 306 | − | |
| 307 | ++ | +++ |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 308 | ++ | − |
| 309 | + | + |
| 310 | + | + |
| 311 | + | − |
| 312 | +++ | +++ |
| 313 | + | − |
| 314 | ++ | − |
| 315 | +++ | +++ |
| 316 | ++ | − |
| 317 | + | − |
| 318 | ++ | − |
| 319 | ++ | − |
| 320 | + | + |
| 321 | ++ | +++ |
| 322 | + | − |
| 323 | ++ | − |
| 324 | + | − |
| 325 | + | − |
| 326 | ++ | ++ |
| 327 | + | − |
| 328 | + | + |
| 329 | + | + |
| 330 | ++ | − |
| 331 | + | − |
| 332 | + | ++ |
| 333 | ++ | − |
| 334 | + | − |
| 335 | + | − |
| 336 | + | + |
| 337 | − | +++ |
| 338 | + | ++ |
| 339 | ++ | +++ |
| 340 | ++ | − |
| 341 | + | − |
| 342 | + | − |
| 343 | + | − |
| 344 | − | − |
| 345 | + | − |
| 346 | − | +++ |
| 347 | + | + |
| 348 | + | − |
| 349 | ++ | − |
| 350 | + | + |
| 351 | + | + |
| 352 | + | − |
| 353 | + | − |
| 354 | + | − |
| 355 | + | − |
| 356 | − | +++ |
| 357 | ++ | − |
| 358 | ++ | − |
| 359 | ++ | +−− |
| 360 | + | − |
| 361 | ++ | +++ |
| 362 | ++ | +++ |
| 363 | + | − |
| 364 | + | − |
| 365 | ++ | − |
| 366 | ++ | +++ |
| 367 | + | − |
| 368 | − | ++ |
| 369 | − | +++ |
| 370 | ++ | +++ |
| 371 | ++ | − |
| 372 | ++ | ++ |
| 373 | ++ | − |
| 374 | ++ | − |
| 375 | + | − |
| 376 | + | + |
| 377 | ++ | +++ |
| 378 | ++ | − |
| 379 | +++ | − |
| 380 | − | + |
| 381 | ++ | − |
| 382 | +++ | − |
| 383 | + | − |
| 384 | + | + |
| 385 | + | − |
| 386 | − | − |
| 387 | ++ | − |
| 388 | +++ | +++ |
| 389 | + | − |
| 390 | ++ | +++ |
| 391 | ++ | − |
| 392 | ++ | − |
| 393 | ++ | − |
| 394 | +++ | − |
| 395 | + | + |
| 396 | − | +++ |
| 397 | + | + |
| 398 | + | − |
| 399 | + | + |
| 400 | +++ | − |
| 401 | ++ | ++ |
| 402 | ++ | − |
| 403 | + | − |
| 404 | + | ++ |
| 405 | + | − |
| 406 | − | +++ |
| 407 | ++ | − |
| 408 | + | ++ |
| 409 | − | − |
| 410 | + | + |
| 411 | ++ | +++ |
| 412 | ++ | ++ |
| 413 | + | − |
| 414 | + | − |
| 415 | ++ | − |
| 416 | + | ++ |
| 417 | +++ | − |
| 418 | ++ | +++ |
| 419 | ++ | ++ |
| 420 | + | + |
| 421 | + | |
| 422 | ++ | − |
| 423 | + | − |
| 424 | ++ | − |
| 425 | + | − |
| 426 | + | ++ |
| 427 | + | − |
| 428 | ++ | − |
| 429 | + | + |
| 430 | ++ | +++ |
| 431 | ++ | − |
| 432 | + | − |
| 433 | + | + |
| 434 | ++ | − |
| 435 | ++ | − |
| 436 | ++ | − |
| 437 | + | + |
| 438 | + | ++ |
| 439 | + | + |
| 440 | − | − |
| 441 | + | ++ |
| 442 | ++ | +++ |
| 443 | + | + |
| 444 | ++ | − |
| 445 | ++ | +++ |
| 446 | − | +++ |
| 447 | + | ++ |
| 448 | ++ | − |
| 449 | ++ | − |
| 450 | +++ | − |
| 451 | + | − |
| 452 | + | ++ |
| 453 | ++ | − |
| 454 | ++ | − |
| 455 | + | − |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 456 | ++ | − |
| 457 | + | + |
| 458 | + | + |
| 459 | + | ++ |
| 460 | + | + |
| 461 | + | ++ |
| 462 | ++ | − |
| 463 | + | − |
| 464 | + | − |
| 465 | ++ | − |
| 466 | + | + |
| 467 | ++ | +++ |
| 468 | − | +++ |
| 469 | + | ++ |
| 470 | − | − |
| 471 | ++ | − |
| 472 | + | − |
| 473 | − | − |
| 474 | + | − |
| 475 | ++ | − |
| 476 | ++ | ++ |
| 477 | +++ | − |
| 478 | ++ | − |
| 479 | − | − |
| 480 | + | − |
| 481 | + | − |
| 482 | + | − |
| 483 | + | + |
| 484 | ++ | − |
| 485 | − | +++ |
| 486 | ++ | − |
| 487 | ++ | − |
| 488 | + | ++ |
| 489 | + | ++ |
| 490 | ++ | − |
| 491 | + | − |
| 492 | +++ | − |
| 493 | ++ | +++ |
| 494 | +++ | − |
| 495 | + | − |
| 496 | + | + |
| 497 | ++ | − |
| 498 | ++ | − |
| 499 | +++ | +++ |
| 500 | ++ | +++ |
| 501 | + | + |
| 502 | − | − |
| 503 | ++ | − |
| 504 | ++ | − |
| 505 | ++ | − |
| 506 | + | − |
| 507 | + | + |
| 508 | ++ | ++ |
| 509 | + | − |
| 510 | ++ | +++ |
| 511 | ++ | − |
| 512 | ++ | − |
| 513 | − | +++ |
| 514 | + | − |
| 515 | ++ | − |
| 516 | + | − |
| 517 | + | − |
| 518 | +++ | − |
| 519 | ++ | − |
| 520 | + | − |
| 521 | ++ | +++ |
| 522 | − | +++ |
| 523 | ++ | − |
| 524 | + | − |
| 525 | + | − |
| 526 | ++ | − |
| 527 | ++ | − |
| 528 | ++ | − |
| 529 | − | +++ |
| 530 | + | − |
| 531 | ++ | ++ |
| 532 | + | − |
| 533 | + | − |
| 534 | + | + |
| 535 | ++ | − |
| 536 | + | − |
| 537 | + | + |
| 538 | + | − |
| 539 | ++ | − |
| 540 | ++ | ++ |
| 541 | ++ | +++ |
| 542 | +++ | − |
| 543 | + | − |
| 544 | ++ | − |
| 545 | ++ | − |
| 546 | ++ | ++ |
| 547 | +++ | − |
| 548 | ++ | − |
| 549 | +++ | − |
| 550 | ++ | − |
| 551 | ++ | − |
| 552 | ++ | − |
| 553 | ++ | − |
| 554 | + | − |
| 555 | ++ | − |
| 556 | − | +++ |
| 557 | ++ | − |
| 558 | ++ | − |
| 559 | + | + |
| 560 | ++ | − |
| 561 | ++ | − |
| 562 | − | +++ |
| 563 | ++ | − |
| 564 | + | − |
| 565 | + | + |
| 566 | + | + |
| 567 | + | ++ |
| 568 | + | + |
| 569 | +++ | − |
| 570 | ++ | − |
| 571 | ++ | − |
| 572 | ++ | − |
| 573 | + | + |
| 574 | + | + |
| 575 | +++ | +++ |
| 576 | ++ | − |
| 577 | − | +++ |
| 578 | − | |
| 579 | ++ | − |
| 580 | ++ | − |
| 581 | − | +++ |
| 582 | ++ | − |
| 583 | ++ | − |
| 584 | + | − |
| 585 | ++ | − |
| 586 | + | + |
| 587 | + | ++ |
| 588 | + | + |
| 589 | − | − |
| 590 | − | − |
| 591 | − | − |
| 592 | − | − |
| 593 | − | − |
| 594 | − | − |
| 595 | | +++ |
| 596 | | ++ |
| 597 | | ++ |
| 598 | | ++ |
| 599 | | ++ |
| 600 | | ++ |
| 601 | | +++ |
| 602 | | +++ |
| 603 | | +++ |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 604 | | ++ |
| 605 | | ++ |
| 606 | | ++ |
| 607 | | ++ |
| 608 | | ++ |
| 609 | | +++ |
| 610 | | +++ |
| 611 | | +++ |
| 612 | | +++ |
| 613 | | +++ |
| 614 | | +++ |
| 615 | | ++ |
| 616 | | +++ |
| 617 | | ++ |
| 618 | | +++ |
| 619 | | +++ |
| 620 | | +++ |
| 621 | | +++ |
| 622 | | ++ |
| 623 | | +++ |
| 624 | | ++ |
| 625 | | +++ |
| 626 | | +++ |
| 627 | | +++ |
| 628 | | ++ |
| 629 | | +++ |
| 630 | | ++ |
| 631 | | +++ |
| 632 | | +++ |
| 633 | | +++ |
| 634 | | +++ |
| 635 | | +++ |
| 636 | | +++ |
| 637 | | +++ |
| 638 | | +++ |
| 639 | | +++ |
| 640 | | +++ |
| 641 | | +++ |
| 642 | | +++ |
| 643 | | +++ |
| 644 | | ++ |
| 645 | | +++ |
| 646 | | +++ |
| 647 | | ++ |
| 648 | | ++ |
| 649 | | ++ |
| 650 | | ++ |
| 651 | | ++ |
| 652 | | +++ |
| 653 | | ++ |
| 654 | | +++ |
| 655 | | ++ |
| 656 | | ++ |
| 657 | | +++ |
| 658 | | ++ |
| 659 | | − |
| 660 | | +++ |
| 661 | | +++ |
| 662 | | ++ |
| 663 | | ++ |
| 664 | | +++ |
| 665 | | +++ |
| 666 | | +++ |
| 667 | | +++ |
| 668 | | +++ |
| 669 | | +++ |
| 670 | | +++ |
| 671 | | ++ |
| 672 | | ++ |
| 673 | | +++ |
| 674 | | +++ |
| 675 | | +++ |
| 676 | | +++ |
| 677 | | +++ |
| 678 | | ++ |
| 679 | | + |
| 680 | | +++ |
| 681 | | ++ |
| 682 | | +++ |
| 683 | | +++ |
| 684 | | +++ |
| 685 | | +++ |
| 686 | | +++ |
| 687 | | +++ |
| 688 | | +++ |
| 689 | | +++ |
| 690 | | ++ |
| 691 | | ++ |
| 692 | | ++ |
| 693 | | ++ |
| 694 | | ++ |
| 695 | | +++ |
| 696 | | +++ |
| 697 | | +++ |
| 698 | | +++ |
| 699 | | +++ |
| 700 | | +++ |
| 701 | | ++ |
| 702 | | ++ |
| 703 | | +++ |
| 704 | | +++ |
| 705 | | +++ |
| 706 | | +++ |
| 707 | | ++ |
| 708 | | +++ |
| 709 | | ++ |
| 710 | | ++ |
| 711 | | +++ |
| 712 | | +++ |
| 713 | | +++ |
| 714 | | − |
| 715 | | +++ |
| 716 | | +++ |
| 717 | | + |
| 718 | | +++ |
| 719 | | +++ |
| 720 | | +++ |
| 721 | | +++ |
| 722 | | +++ |
| 723 | | +++ |
| 724 | | +++ |
| 725 | | +++ |
| 726 | | +++ |
| 727 | | +++ |
| 728 | | +++ |
| 729 | | +++ |
| 730 | | +++ |
| 731 | | +++ |
| 732 | | ++ |
| 733 | | +++ |
| 734 | | +++ |
| 735 | | +++ |
| 736 | | ++ |
| 737 | | ++ |
| 738 | | ++ |
| 739 | | +++ |
| 740 | | +++ |
| 741 | | +++ |
| 742 | | ++ |
| 743 | | +++ |
| 744 | | +++ |
| 745 | | +++ |
| 746 | | +++ |
| 747 | | +++ |
| 748 | | +++ |
| 749 | | +++ |
| 750 | | +++ |
| 751 | | ++ |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 752 | | +++ |
| 753 | | +++ |
| 754 | | +++ |
| 755 | | +++ |
| 756 | | +++ |
| 757 | | +++ |
| 758 | | +++ |
| 759 | | +++ |
| 760 | | +++ |
| 761 | | +++ |
| 762 | | +++ |
| 763 | | +++ |
| 764 | | ++ |
| 765 | | + |
| 766 | | ++ |
| 767 | | ++ |
| 768 | | ++ |
| 769 | | ++ |
| 770 | | +++ |
| 771 | | +++ |
| 772 | | +++ |
| 773 | | ++ |
| 774 | | ++ |
| 775 | | +++ |
| 776 | | +++ |
| 777 | | +++ |
| 778 | | +++ |
| 779 | | +++ |
| 780 | | +++ |
| 781 | | +++ |
| 782 | | +++ |
| 783 | | +++ |
| 784 | | ++ |
| 785 | | +++ |
| 786 | | ++ |
| 787 | | +++ |
| 788 | | +++ |
| 789 | | +++ |
| 790 | | +++ |
| 791 | | +++ |
| 792 | | +++ |
| 793 | | +++ |
| 794 | | +++ |
| 795 | | +++ |
| 796 | | +++ |
| 797 | | +++ |
| 798 | | +++ |
| 799 | | +++ |
| 800 | | +++ |
| 801 | | +++ |
| 802 | | +++ |
| 803 | | ++ |
| 804 | | ++ |
| 805 | | +++ |
| 806 | | +++ |
| 807 | | ++ |
| 808 | | +++ |
| 809 | | +++ |
| 810 | | +++ |
| 811 | | +++ |
| 812 | | +++ |
| 813 | | + |
| 814 | | +++ |
| 815 | | +++ |
| 816 | | +++ |
| 817 | | +++ |
| 818 | | +++ |
| 819 | | +++ |
| 820 | | +++ |
| 821 | | + |
| 822 | | ++ |
| 823 | | +++ |
| 824 | | +++ |
| 825 | | ++ |
| 826 | | +++ |
| 827 | | +++ |
| 828 | | +++ |
| 829 | | +++ |
| 830 | | +++ |
| 831 | | +++ |
| 832 | | ++ |
| 833 | | +++ |
| 834 | | +++ |
| 835 | | +++ |
| 836 | | +++ |
| 837 | | ++ |
| 838 | | +++ |
| 839 | | ++ |
| 840 | | ++ |
| 841 | | ++ |
| 842 | | +++ |
| 843 | | ++ |
| 844 | | ++ |
| 845 | | +++ |
| 846 | | +++ |
| 847 | | +++ |
| 848 | | +++ |
| 849 | | +++ |
| 850 | | +++ |
| 851 | | +++ |
| 852 | | +++ |
| 853 | | +++ |
| 854 | | +++ |
| 855 | | +++ |
| 856 | | +++ |
| 857 | | +++ |
| 858 | | +++ |
| 859 | | +++ |
| 860 | | +++ |
| 861 | | +++ |
| 862 | | ++ |
| 863 | | +++ |
| 864 | | ++ |
| 865 | | +++ |
| 866 | | ++ |
| 867 | | +++ |
| 868 | | +++ |
| 869 | | +++ |
| 870 | | ++ |
| 871 | | +++ |
| 872 | | +++ |
| 873 | | +++ |
| 874 | | +++ |
| 875 | | +++ |
| 876 | | +++ |
| 877 | | +++ |
| 878 | | +++ |
| 879 | | +++ |
| 880 | | +++ |
| 881 | | +++ |
| 882 | | +++ |
| 883 | | +++ |
| 884 | | +++ |
| 885 | | ++ |
| 886 | | +++ |
| 887 | | ++ |
| 888 | | +++ |
| 889 | | +++ |
| 890 | | +++ |
| 891 | | +++ |
| 892 | | +++ |
| 893 | | +++ |
| 894 | | +++ |
| 895 | | +++ |
| 896 | | +++ |
| 897 | | +++ |
| 898 | | +++ |
| 899 | | +++ |

TABLE 13-continued

HCV Enzymatic Assay Activities and efficacies of exemplary compounds in accordance to Formulae I.

| Compound No. | Enzyme Assay 1 | Enzyme Assay 2 |
|---|---|---|
| 900 | | +++ |
| 901 | | +++ |
| 902 | | +++ |
| 903 | | +++ |
| 904 | | +++ |
| 905 | | ++ |
| 906 | | ++ |
| 907 | | ++ |
| 908 | | +++ |
| 909 | | +++ |
| 910 | | +++ |
| 911 | | +++ |
| 912 | | +++ |
| 913 | | +++ |
| 914 | | +++ |
| 915 | | +++ |
| 916 | | ++ |
| 917 | | ++ |
| 918 | | ++ |
| 919 | | +++ |
| 920 | | ++ |
| 921 | | +++ |
| 922 | | +++ |
| 923 | | +++ |
| 924 | | ++ |
| 925 | | +++ |
| 926 | | +++ |
| 927 | | +++ |
| 928 | | ++ |
| 929 | | +++ |
| 930 | | +++ |
| 931 | | ++ |
| 932 | | +++ |
| 933 | | +++ |
| 934 | | +++ |
| 935 | | +++ |
| 936 | | + |
| 937 | | +++ |
| 938 | | +++ |
| 939 | | +++ |
| 940 | | ++ |
| 941 | | +++ |
| 942 | | +++ |
| 943 | | +++ |
| 944 | | +++ |
| 945 | | +++ |
| 946 | | +++ |
| 947 | | +++ |
| 948 | | +++ |
| 949 | | +++ |
| 950 | | +++ |
| 951 | | +++ |
| 952 | | +++ |
| 953 | | +++ |
| 954 | | +++ |
| 955 | | +++ |
| 956 | | +++ |
| 957 | | ++ |
| 958 | | +++ |
| 959 | | +++ |
| 960 | | +++ |
| 961 | | + |
| 962 | | ++ |
| 963 | | ++ |
| 964 | | ++ |
| 965 | | ++ |
| 966 | | + |
| 967 | | +++ |
| 968 | | +++ |
| 969 | | +++ |
| 970 | | +++ |
| 971 | | +++ |
| 972 | | +++ |
| 973 | | +-- |
| 974 | | +++ |
| 975 | | +++ |
| 976 | | +++ |
| 977 | | +++ |
| 978 | | +++ |
| 979 | | − |
| 980 | | ++ |
| 981 | | +++ |
| 982 | | ++ |
| 983 | | +++ |
| 984 | | +++ |
| 985 | | +++ |
| 986 | | ++ |
| 987 | | − |
| 988 | | − |
| 989 | | − |
| 990 | | − |
| 991 | | +++ |
| 992 | | +++ |
| 993 | | +++ |
| 994 | | +++ |
| 995 | | +++ |
| 996 | | +++ |
| 997 | | +++ |
| 998 | | − |
| 999 | | − |
| 1000 | | − |
| 1001 | | − |
| 1002 | | − |
| 1003 | | − |
| 1004 | | − |
| 1005 | | − |
| 1006 | | − |
| 1007 | | − |
| 1008 | | − |
| 1009 | | − |
| 1010 | | − |
| 1011 | | − |
| 1012 | | − |
| 1013 | | − |
| 1014 | | − |
| 1015 | | − |
| 1016 | | − |
| 1017 | | − |
| 1018 | | − |
| 1019 | | − |
| 1020 | | − |
| 1021 | | − |
| 1022 | | − |
| 1023 | | − |
| 1024 | | − |
| 1025 | | − |
| 1026 | | − |
| 1027 | | − |
| 1028 | | − |
| 1029 | | − |
| 1030 | | − |
| 1031 | | − |
| 1032 | | − |
| 1033 | | − |
| 1034 | | − |
| 1035 | | − |
| 1036 | | − |
| 1037 | | − |
| 1038 | | − |
| 1039 | | − |
| 1040 | | − |
| 1041 | | − |
| 1042 | | − |
| 1043 | | − |
| 1044 | | − |

B. HCV Cell Assays uh-7 cells were propagated in Dulbecco's modified Eagle's medium (DMEM, JRH Biosciences, Lenexa, Kans.) supplemented with 10% heat-inactivated FBS (fetal bovine serum), 2 mM L-glutamine, and nonessential amino acids (JRH). The cells were transfected with an in vitro transcribed HCV replicon RNA identical to replicon 1377neo/NS3-37 wt as described by Lohmann et al. (1999). Stable cell clones were selected and maintained in the presence of 250 µg/mL G418 (Invitrogen, Carlsbad, Calif.). One of the clones, 24-2, was used in the subsequent HCV replicon assays. The replicon cells were propagated in DMEM supplemented with 10% FBS, 2 mM L-glutamine, nonessential amino acids, and 250 µg/mL G418. The cells were split twice per week in fresh media upon reaching confluence. There are approximately 200-300 copies of HCV RNA per replicon cell.

HCV replicon RNA from cells was measured using the Quantigene Discover XL kit (Panomics Inc., Fremont Calif.) as per the manufacturer's instructions. Briefly, compound-treated replicon cells were lysed and immobilized on to capture plates using HCV specific oligonucleotides over night and the relative amounts of captured RNA was measured using oligonucleotide probe sets as per the manufacturer's instructions.

1. 2-Day HCV Replicon $IC_{50}$ Assay

On the day prior to the assay, 104 replicon cells were plated per well of a 96-well plate and allowed to attach and grow overnight in DMEM (Invitrogen, Carlsbad, Calif.) supplemented with 10% heat-inactivated FBS (JRH Biosciences, Lenexa, Kans.), 2 mM L-glutamine (Invitrogen), nonessential amino acids (Invitrogen) and 250 µg/ml G418 (Invitrogen). Compounds were serially diluted in DMEM plus 2% FBS and 0.5% DMSO (Sigma Chemical Co., St. Louis, Mo.) without G418. HCV replicon RNA from cells was measured using the Quantigene Discover XL kit (Panomics Inc., Fremont Calif.) as per the manufacturer's instructions. Briefly, compound-treated replicon cells were lysed and immobilized on to capture plates using HCV specific oligonucleotides overnight and the relative amounts of captured RNA was measured using oligonucleotide probe sets as per the manufacturer's instructions. Unless indicated otherwise, each data point represents the average of three replicates. The $IC_{50}$ is the concentration of the compound at which the HCV replicon RNA level in cells is reduced by 50% as compared to the untreated replicon cell controls. To monitor the effect of compounds on cell proliferation or cell viability, replicon cells were treated with serially diluted compounds for 48 h, after which cell viability was determined using a CellTiter Glo assay (Promega, Madison, Wis.). Each $CC_{50}$ is derived from three replicates and is the concentration of the compound at which the number of viable cells is reduced by 50% as compared to untreated cell controls. The $IC_{50}$ and $CC_{so}$ was determined using 4 parameter curve fitting in the SoftMax Pro program (Molecular Devices, Sunnyvale, Calif.).

2. 5-Day HCV Replicon $IC_{99}$ Assay

On the day prior to the assay, HCV replicon cells were plated at a low density of 2500 cells per well in a 96-well plate so the cells would not reach confluence during 5 days in culture. Compounds were serially diluted in DMEM containing 10% FBS and 0.5% DMSO in the absence of G418. Fresh media and compounds were added to the cells on day 1 and day 3. After the cells were treated with antiviral compounds for 5 days, HCV replicon RNA from cells was measured using the Quantigene Discover XL kit (Panomics Inc., Fremont Calif.) as per the manufacturer's instructions. Briefly, compound-treated replicon cells were lysed and immobilized onto to capture plates using HCV specific oligonucleotides overnight and the relative amounts of captured replicon RNA was measured using oligonucleotide probe sets (Panomics) as per manufacturer's instructions. Each data point represents the average of two replicates. The $IC_{99}$ is the concentration of the compound at which the HCV replicon RNA level in cells is reduced by 2 logs as compared to the untreated cell controls. To monitor the effect of compounds on cell proliferation or cell viability, replicon cells were treated with serially diluted compounds for 5 days, after which cell viability was determined using a CellTiter Glo assay (Promega, Madison, Wis.). Each $CC_{50}$ is derived from two replicates and is the concentration of the compound at which the number of viable cells is reduced by 50% as compared to untreated cell controls. The $IC_{99}$ and $CC_{50}$ were determined by 4 parameter curve fitting method using the Prism software (GraphPad Software Inc., San Diego, Calif.) and Excel program (Microsoft Corporation, Redmond, Wash.).

Using the assays above, compounds of the present invention are determined to be useful serine protease inhibitors.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula (I),

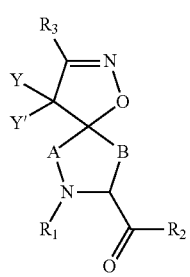

(I)

or a pharmaceutically acceptable salt thereof, wherein:
each A is —CH$_2$—;
each B is —CH$_2$—;
each R$_1$ is

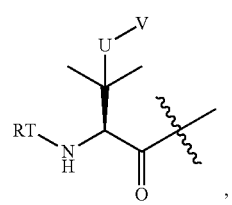

wherein:
U is a bond or —O—;
V is an alkyl;
T is —C(O)—; and
R is an aliphatic, cycloaliphatic, heterocycloaliphatic, aryl, heteroaryl, alkoxy, or cycloalkoxy, and is optionally substituted with 1 to 3 substituents each independently selected from the group consisting of halo, hydroxy, cyano, amino, nitro, aliphatic, haloaliphatic, (aliphatic)oxy, (halo(aliphatic))oxy, (aliphatic(oxy(aryl)))oxy, aryl, heteroaryl, haloaryl, cycloaliphatic, or heterocycloaliphatic;

each $R_2$ is $-Z^B R_5$, wherein each $Z^B$ is independently a bond or an optionally substituted aliphatic wherein up to four carbon units of $Z^B$ are optionally and independently replaced by $-C(O)-$, $-C(S)-$, $-C(O)NR^B-$, $-C(O)NR^B NR^B-$, $-C(O)O-$, $-C(O)C(O)NR^B-$, $-NR^B C(O)O-$, $-NR^B C(O)NR^B-$, $-NR^B-NR^B-$, $-S-$, $-SO-$, $-SO_2-$, $-NR^B-$, $-SO_2 NR^B-$, or $-NR^B SO_2 NR^B-$, provided that $-SO-$, $-SO_2-$, or $-SO_2 NR^B-$ is not directly bound to the carbonyl in formula (I);

each $R_5$ is independently $R^B$, halo, $-OH$, $-CN$, $-NO_2$, $-NH_2$, alkoxy, or haloalkoxy;

each $R^B$ is independently hydrogen, an optionally substituted aliphatic, an optionally substituted cycloaliphatic, an optionally substituted aryl; or an optionally substituted heteroaryl;

or, $R_1$ and $R_2$, together with the atoms to which they are attached, form an optionally substituted heterocycloaliphatic ring;

each $R_3$ is an optionally substituted aliphatic, amino, sulfonyl, sulfanyl, sulfinyl, sulfonamide, sulfamide, sulfo, $-O-R_{3A}$, an optionally substituted cycloaliphatic, an optionally substituted heterocycloaliphatic, an optionally substituted aryl, or an optionally substituted heteroaryl;

each $R_{3A}$ is independently an optionally substituted aliphatic, an optionally substituted cycloaliphatic, an optionally substituted heterocycloaliphatic, an optionally substituted aryl, or an optionally substituted heteroaryl; and each of Y and Y' is H.

2. The compound of claim 1, wherein $R_3$ is an optionally substituted aryl.

3. The compound of claim 2, wherein $R_3$ is a monocyclic, bicyclic, or tricyclic aryl, and is optionally substituted with 1 to 3 substituents each independently selected from the group consisting of halo, hydroxy, cyano, amino, nitro, aliphatic, haloaliphatic, (aliphatic)oxy, (halo(aliphatic))oxy, (aliphatic(oxy(aryl)))oxy, aryl, heteroaryl, haloaryl, cycloaliphatic, or heterocycloaliphatic.

4. The compound of claim 3, wherein $R_3$ is

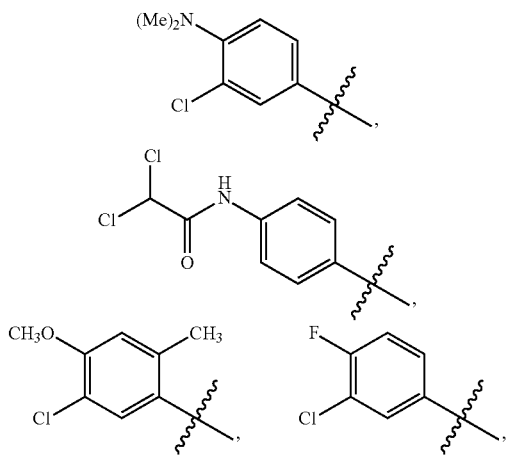

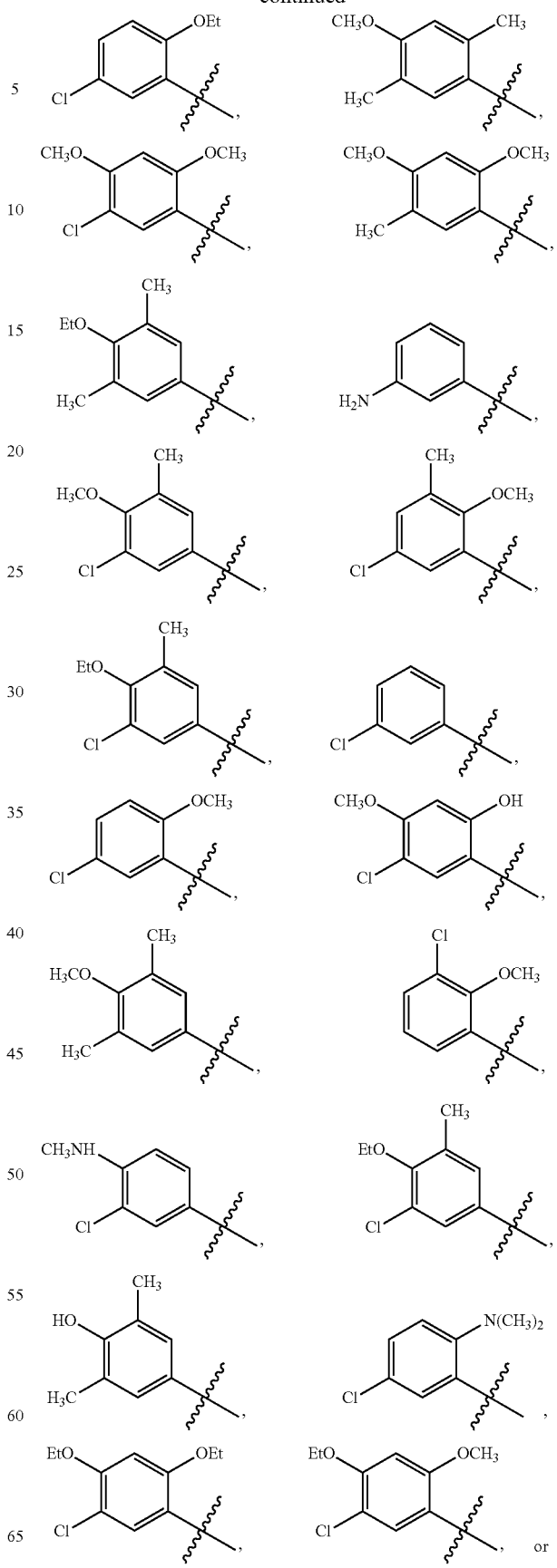

-continued

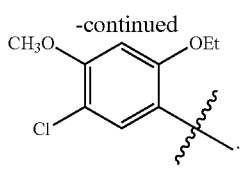

5. The compound of claim 1, wherein $R_3$ is a monocyclic, bicyclic, or tricyclic heteroaryl, and is optionally substituted with 1 to 3 substituents each independently selected from the group consisting of halo, hydroxy, cyano, amino, nitro, aliphatic, haloaliphatic, (aliphatic)oxy, (halo(aliphatic))oxy, (aliphatic(oxy(aryl)))oxy, aryl, heteroaryl, haloaryl, cycloaliphatic, or heterocycloaliphatic.

6. The compound according to claim 5, wherein $R_3$ is

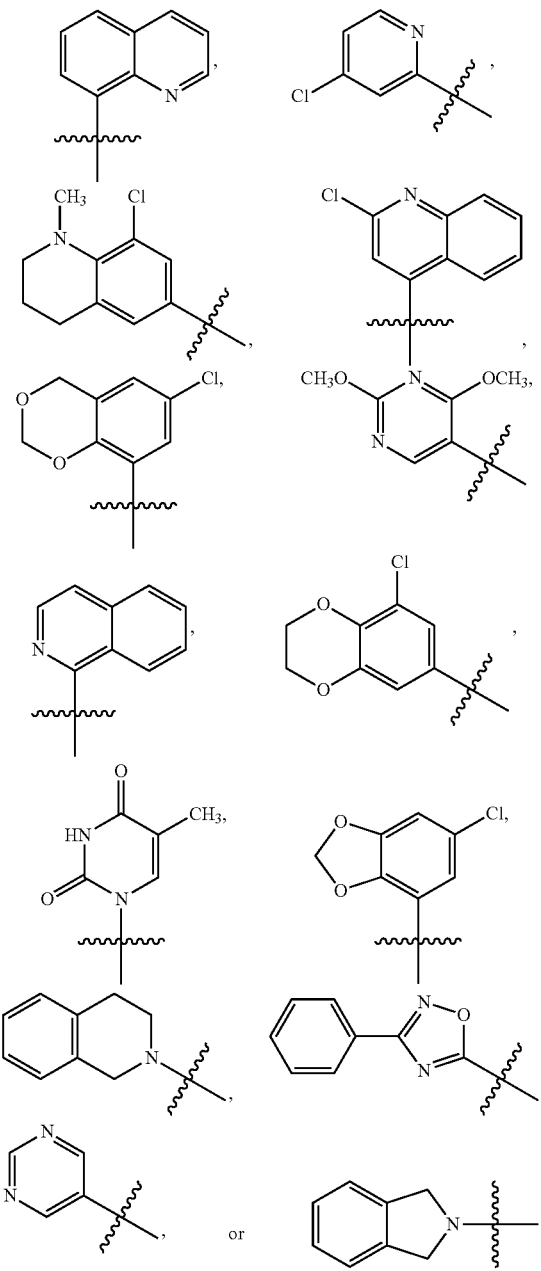

7. The compound of claim 1, wherein $R_3$ is an optionally substituted amino, an optionally substituted heterocycloaliphatic, or an optionally substituted aryloxy.

8. The compound according to claim 7, wherein $R_3$ is

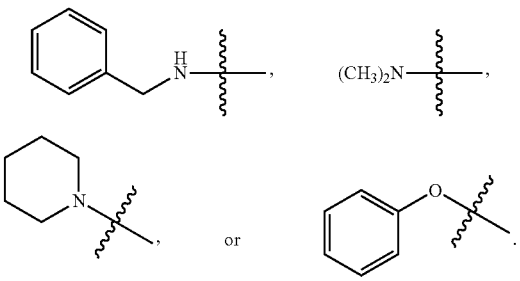

9. The compound of claim 1, wherein $R_1$ is

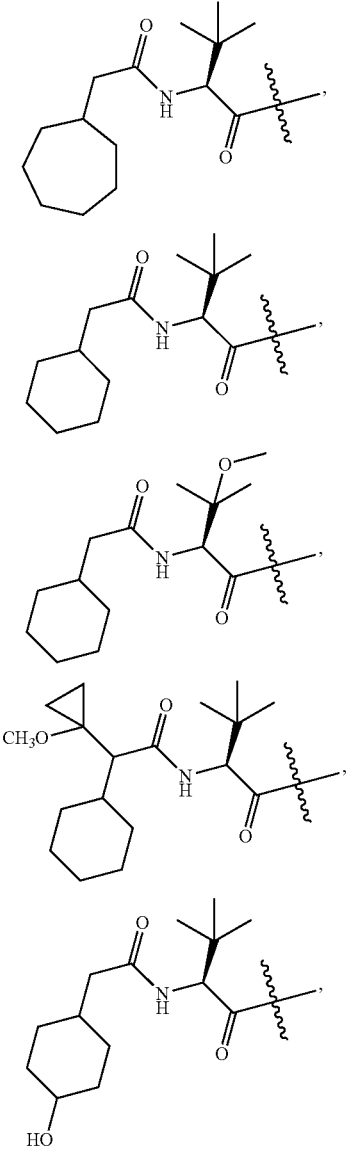

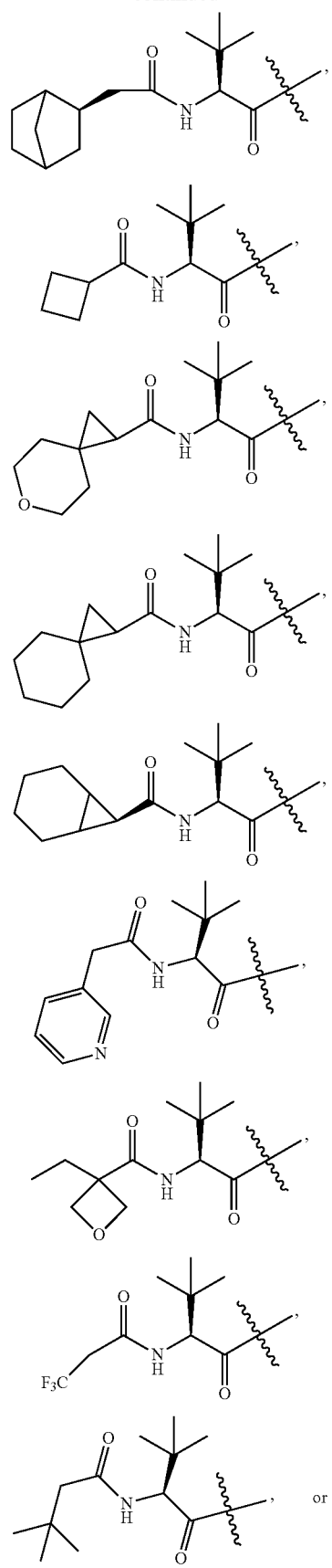
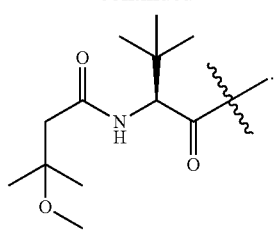
10. The compound of claim 1, wherein $R_1$ is
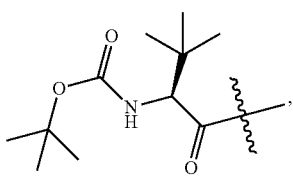
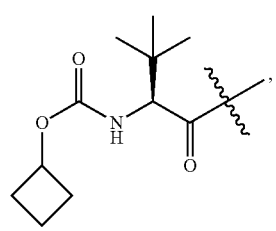
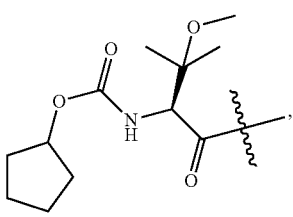
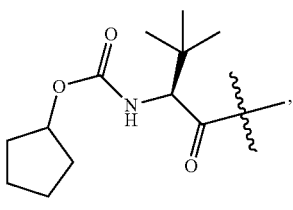
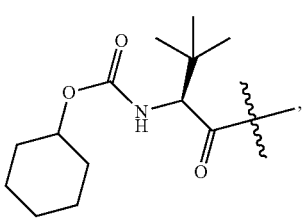
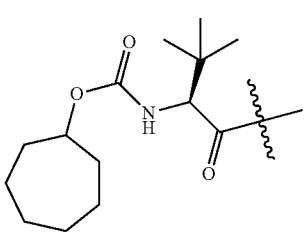

997
-continued
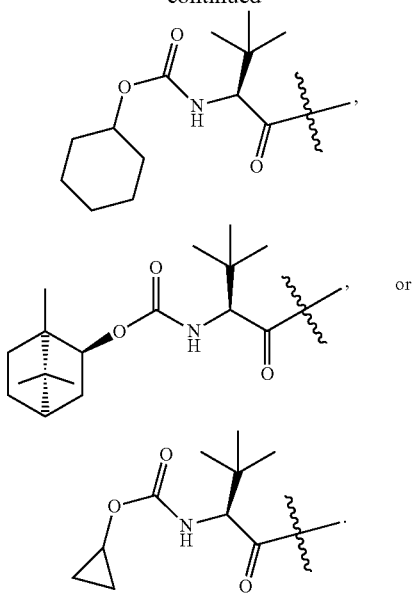
11. The compound of claim 1, wherein $R_1$ is
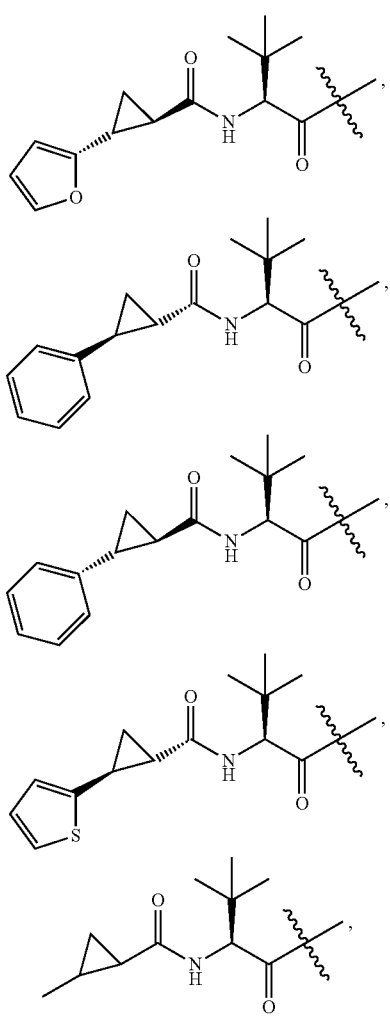
998
-continued
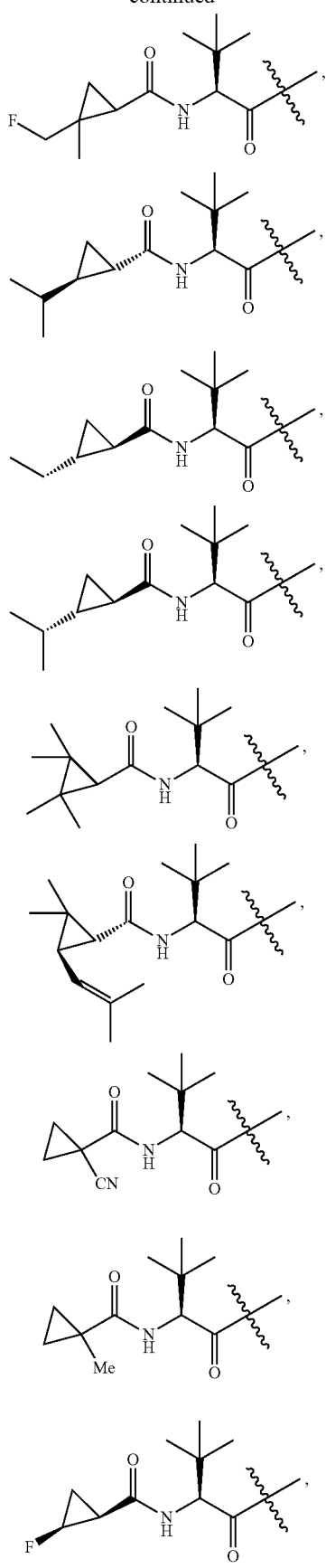

999
-continued
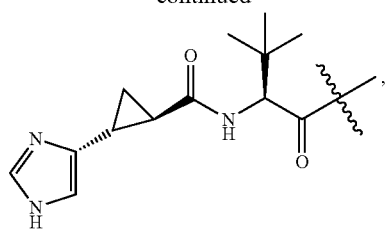
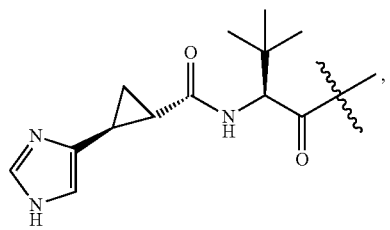
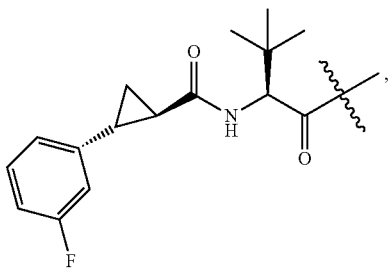
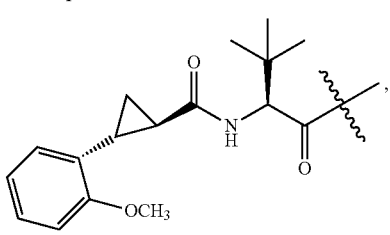
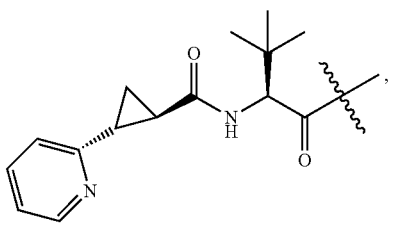
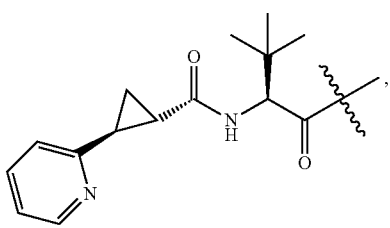
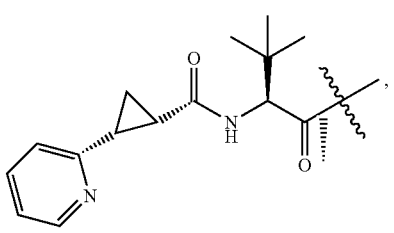
1000
-continued
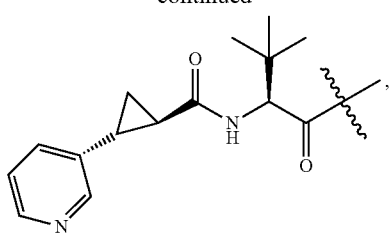
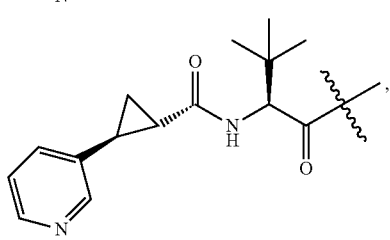
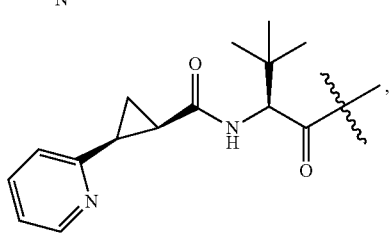
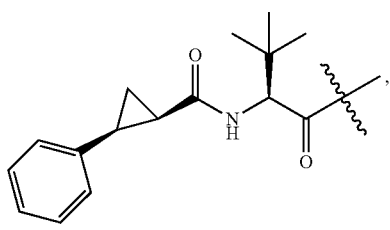
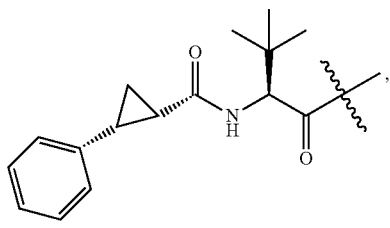
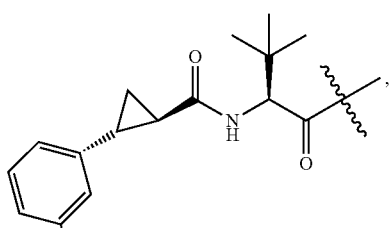
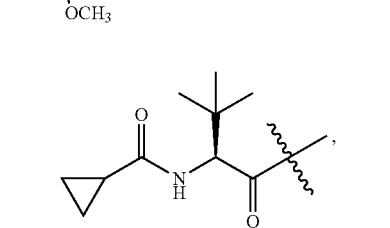

1001
-continued
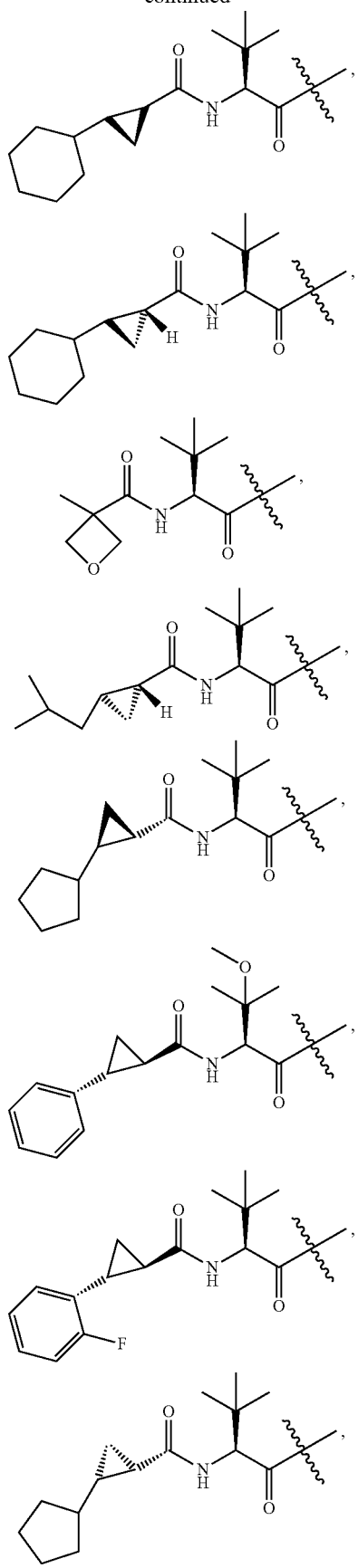
1002
-continued
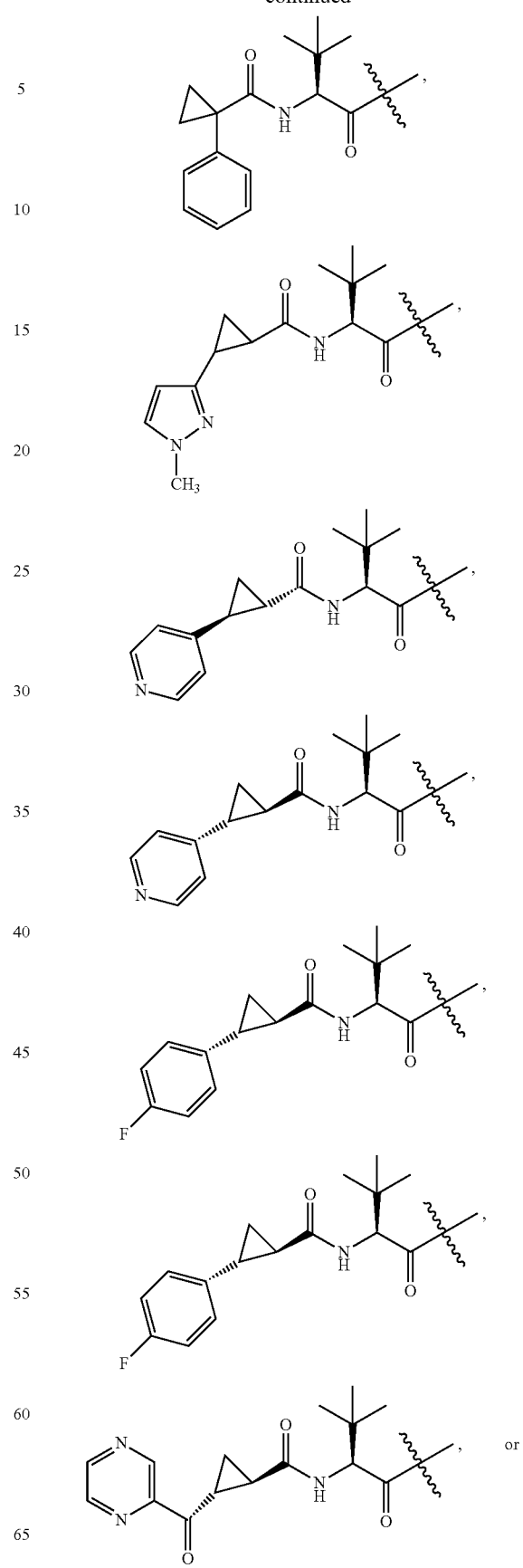

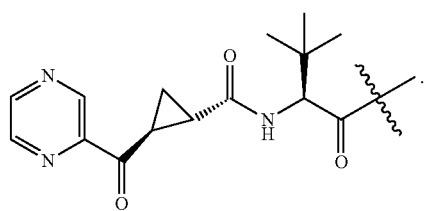

12. The compound of claim 1, wherein R₁ is

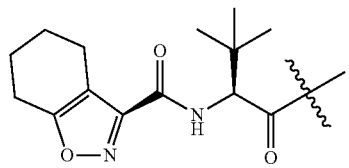

13. The compound of claim 1, wherein R₂ is a (cycloaliphatic(carbonyl(carbonyl(aliphatic))))amino, (amino(carbonyl(carbonyl(aliphatic))))amino, (alkylamino(carbonyl(carbonyl(aliphatic))))amino, (aliphatic(carbonyl(carbonyl(aliphatic))))amino, or (aryl(amino(carbonyl(carbonyl(aliphatic)))))amino, each of which is optionally substituted.

14. The compound of claim 13, wherein R₂ is selected from the group consisting of

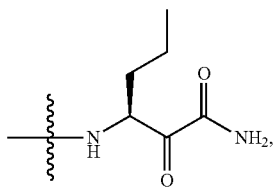

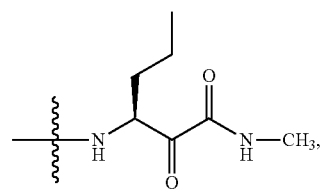

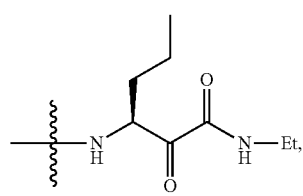

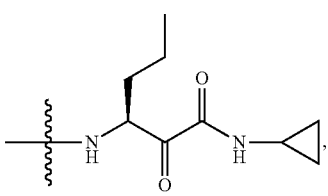

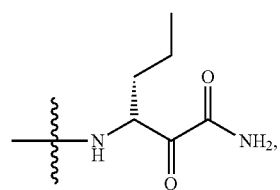

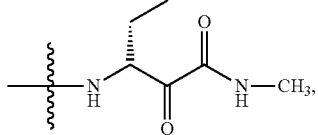

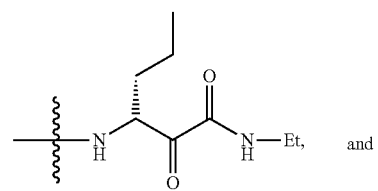 and

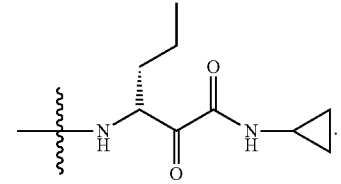

15. The compound of claim 13, wherein R₂ is selected from the group consisting of

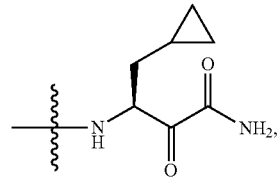

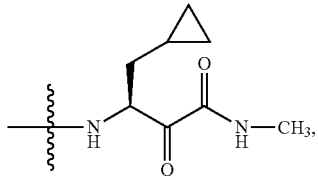

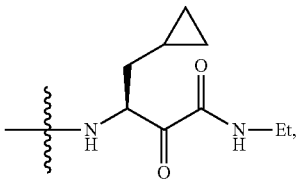

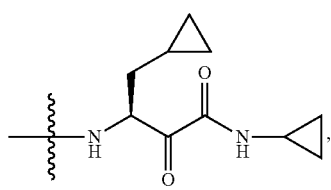

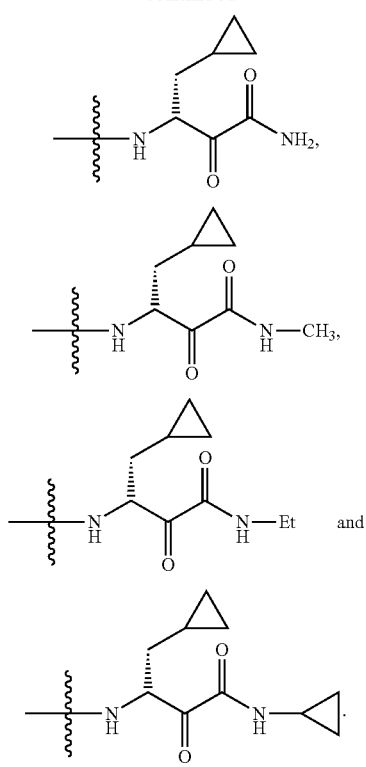

16. The compound of claim 13, wherein $R_2$ is selected from the group consisting of

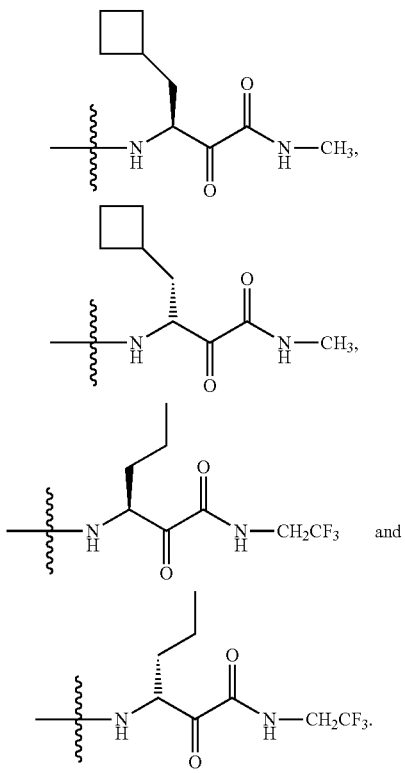

17. The compound of claim 1, wherein $R_2$ is

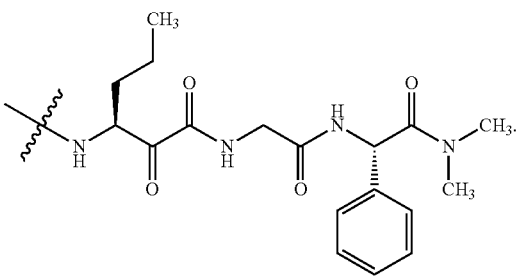

18. The compound of claim 1, wherein $R_1$ and $R_2$, together with the atoms to which they are attached, form an optionally substituted 6-membered heterocycloaliphatic ring.

19. A compound of formula (II), wherein

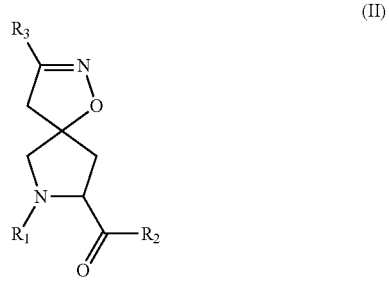

(II)

each $R_1$ is a (cycloalkyl(alkyl)carbonyl))amino)(alkyl)carbonyl;

each $R_2$ is a (cycloalkylamino(carbonyl))(carbonyl)alkyl)) amino or (alkylamino(carbonyl))(carbonyl)alkyl)) amino; and each $R_3$ is an optionally substituted aryl.

20. The compound of claim 19, wherein $R_3$ is phenyl substituted with 1 to 3 substituents each independently selected from the group consisting of $C_{1-4}$ alkoxy, $C_{1-4}$ alkyl, and halo.

21. A compound of formula (II), wherein

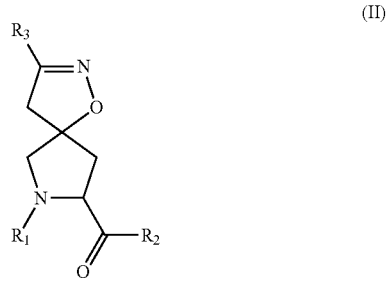

(II)

each $R_1$ is a (cycloalkyl(alkyl)carbonyl))amino)(alkyl)carbonyl;

each $R_2$ is a (cycloalkylamino(carbonyl))(carbonyl)alkyl)) amino or (alkylamino(carbonyl))(carbonyl)alkyl)) amino; and each $R_3$ is a heteroaryl optionally substituted with 1 to 3 substituents each independently selected from the group consisting of $C_{1-4}$ alkoxy, $C_{1-4}$ alkyl, and halo.

22. A compound of formula (II), wherein

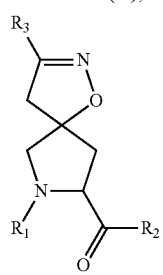

(II)

each $R_1$ is a (cycloalkyl(alkyl)carbonyl))amino)(alkyl)carbonyl;

each $R_2$ is a (cycloalkylamino(carbonyl))(carbonyl)alkyl))amino or (alkylamino(carbonyl))(carbonyl)alkyl))amino; and each $R_3$ is an optionally substituted amino, optionally substituted heterocycloaliphatic, or an optionally substituted aryloxy.

23. A compound selected from the group consisting of:

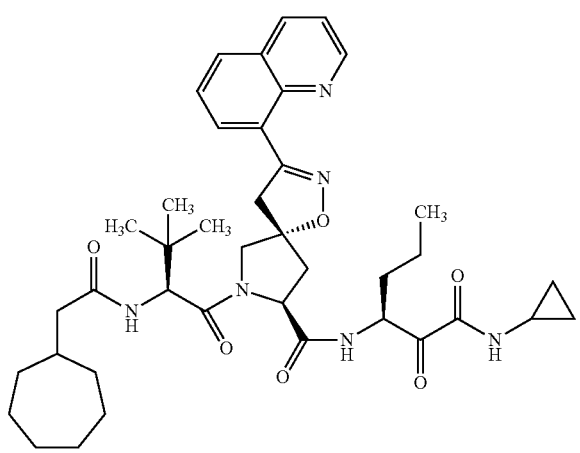

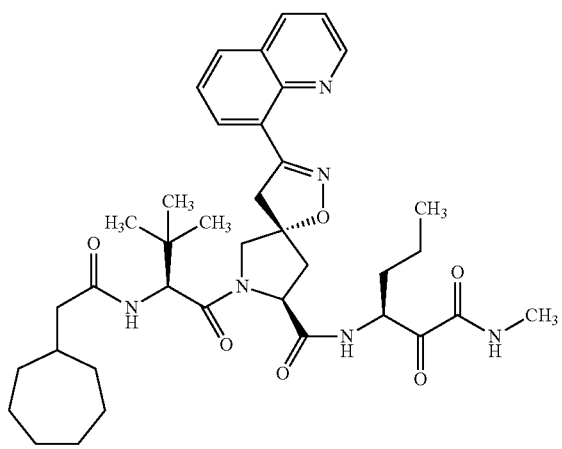

597
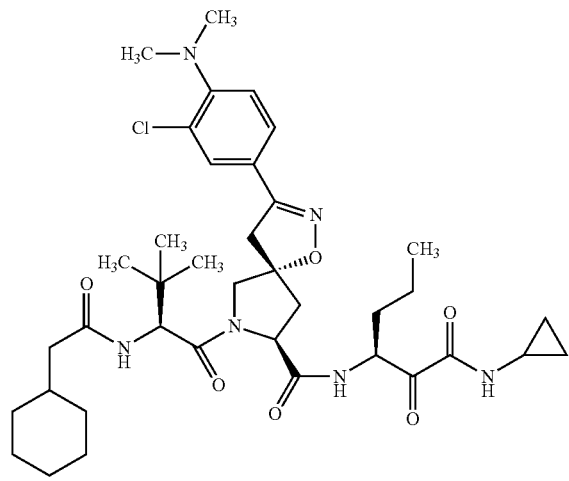
598
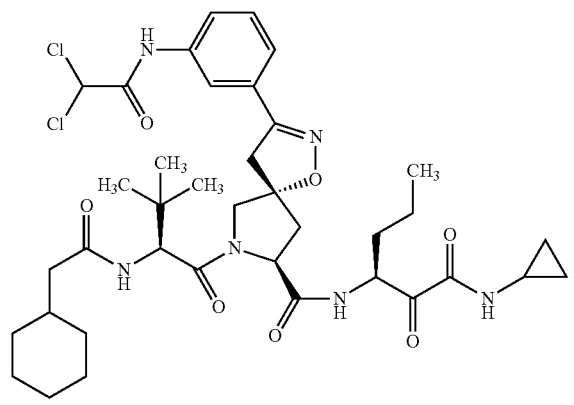
599
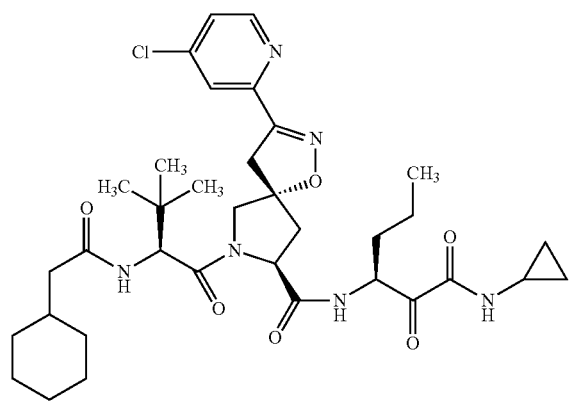

600
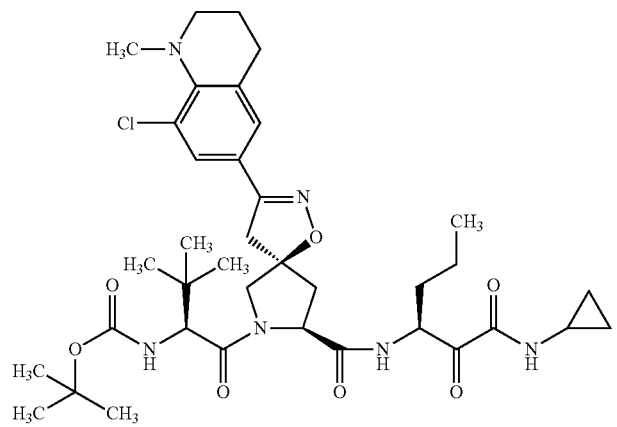
601
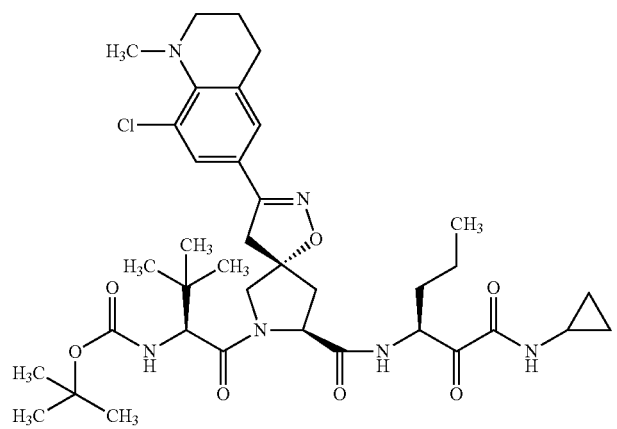
602
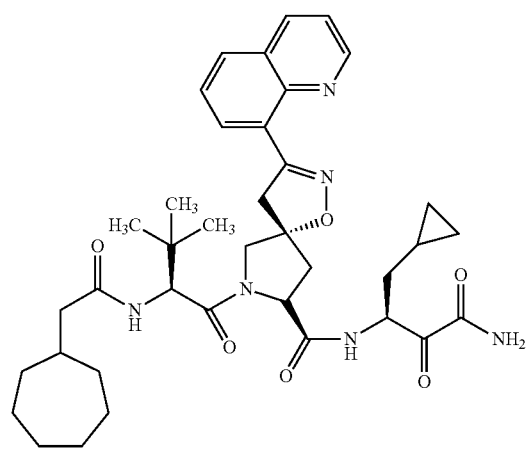

603
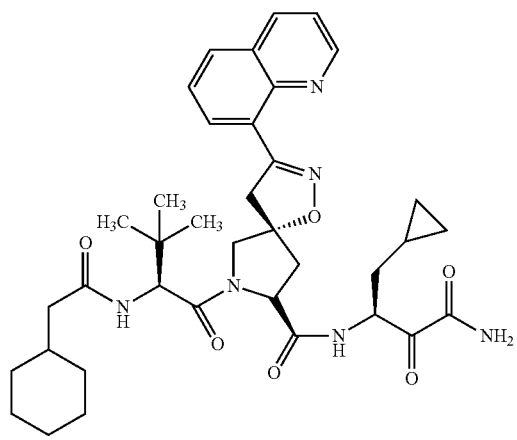
604
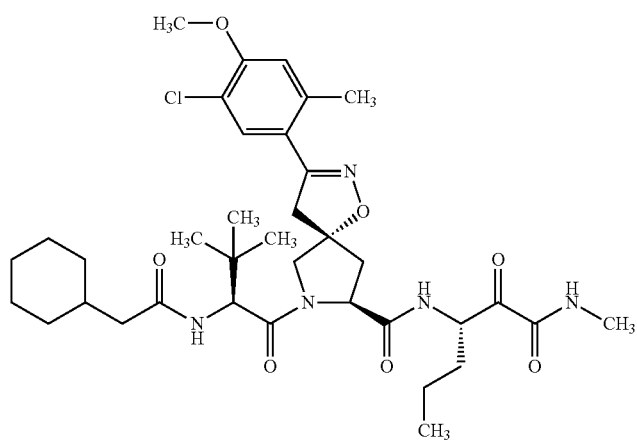
605
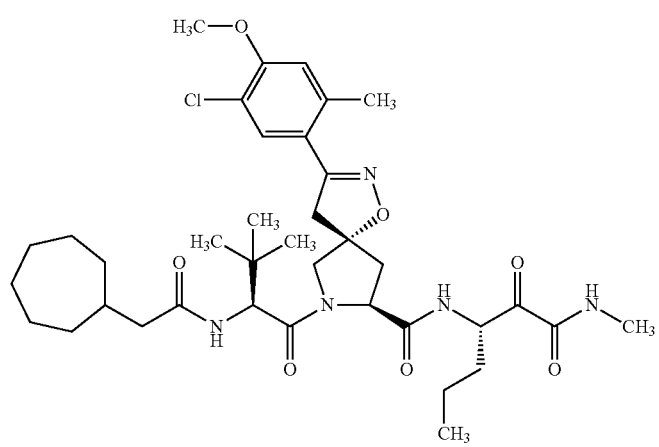

606
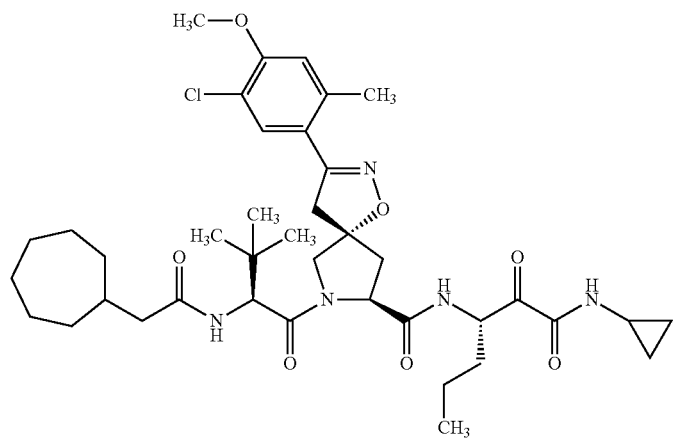
607
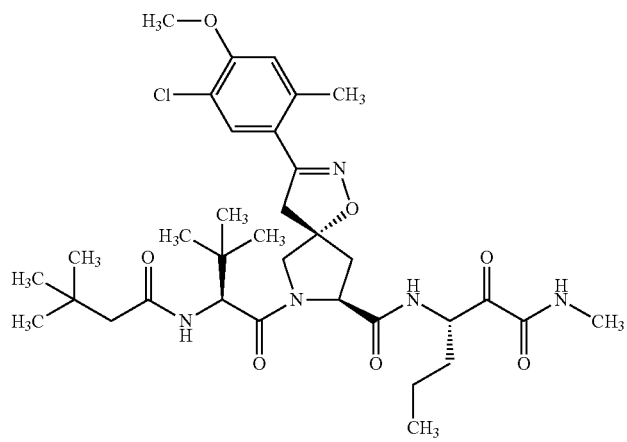
608
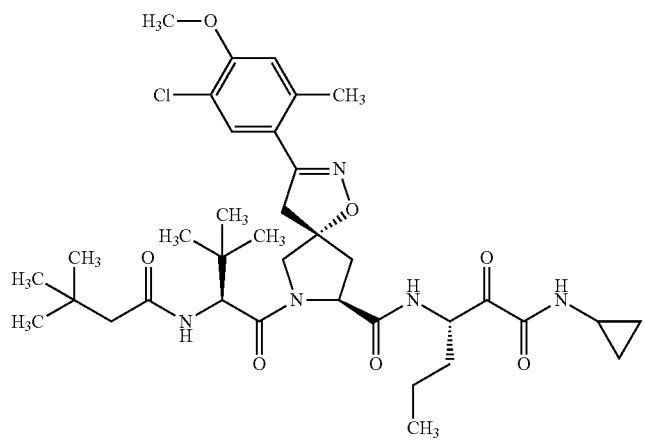

609
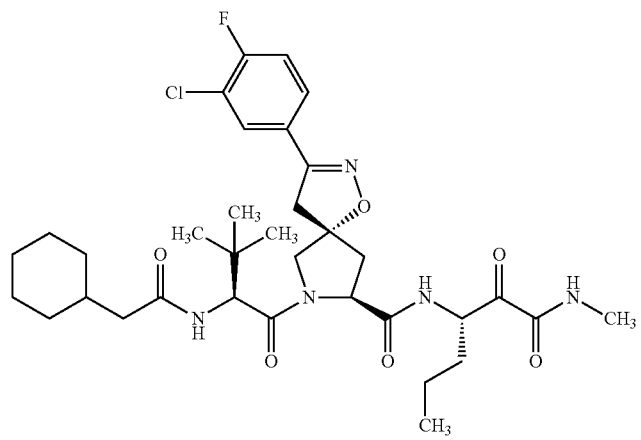
610
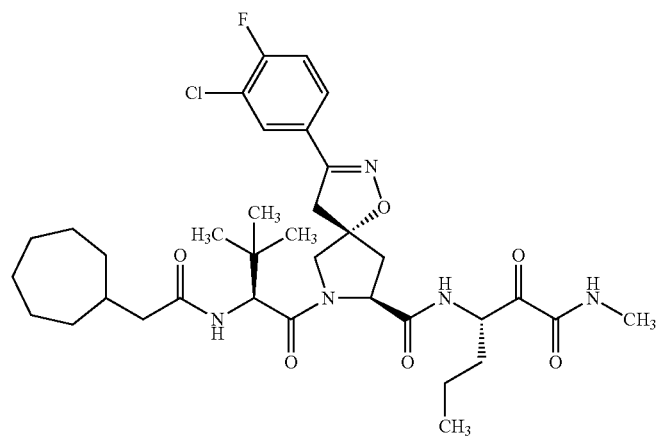
611
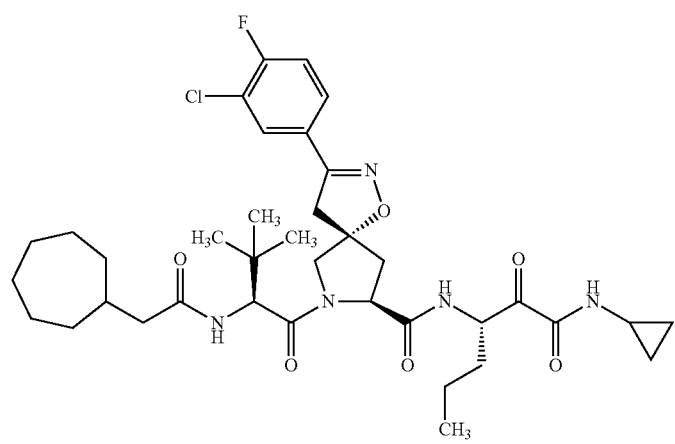

-continued
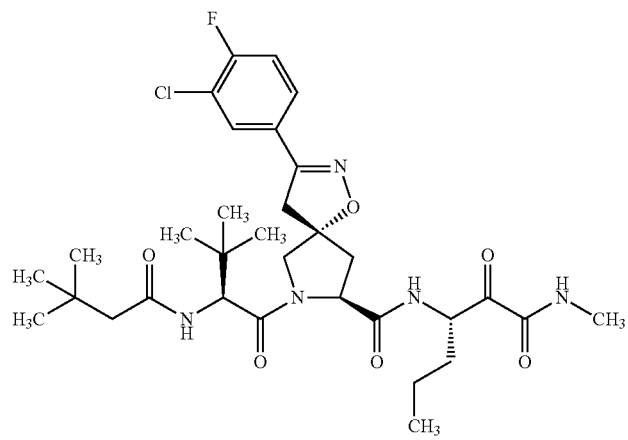
612
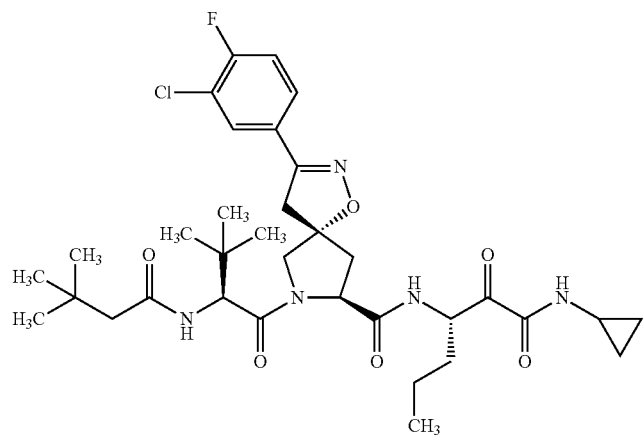
613
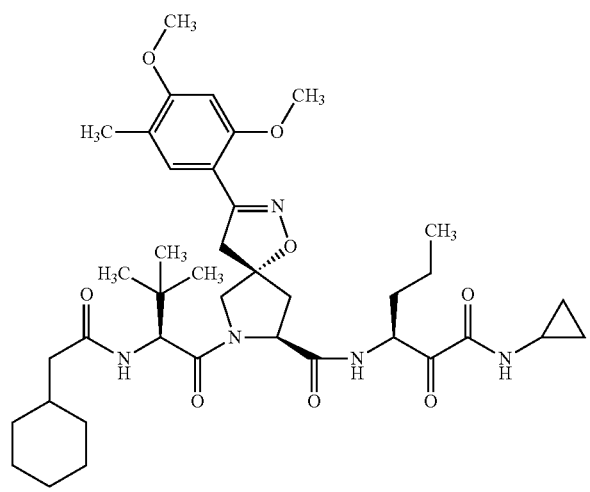
614

-continued
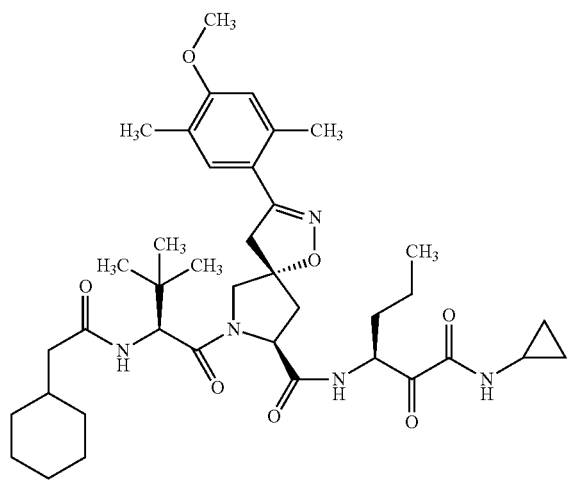
615
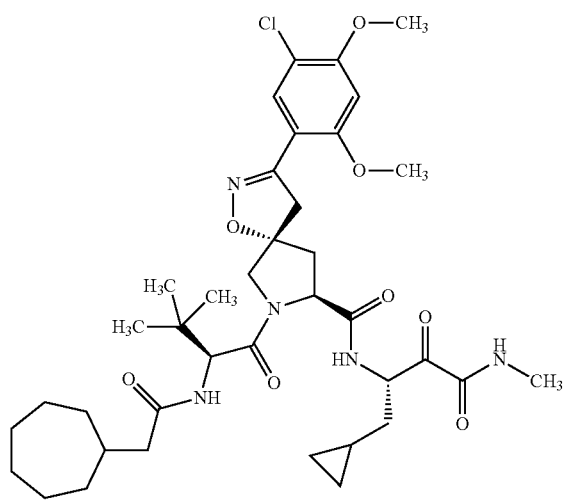
616
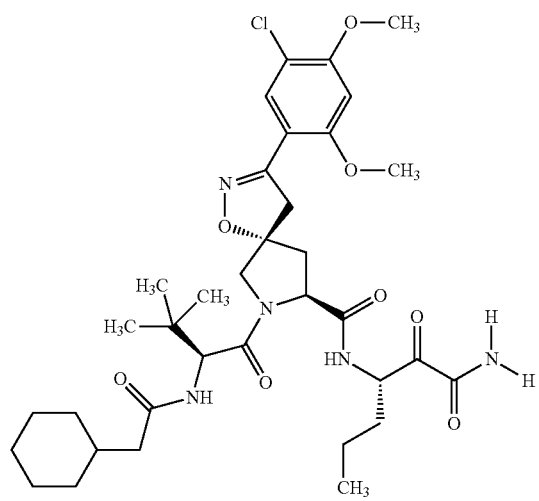
618

619
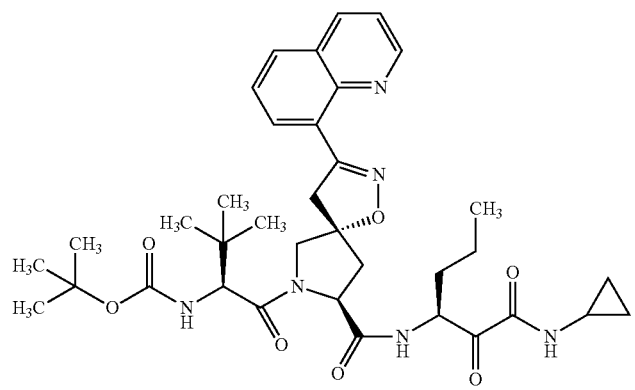
620
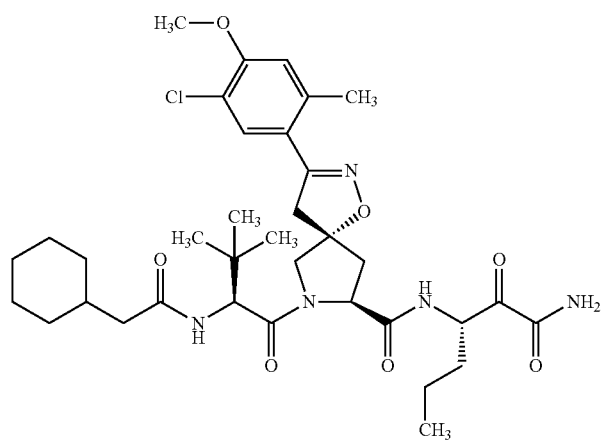
621
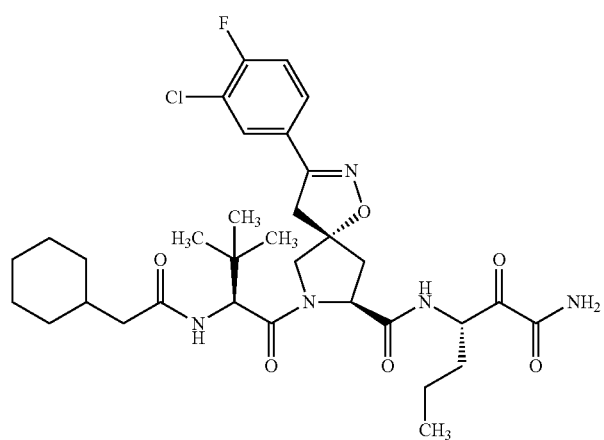

622
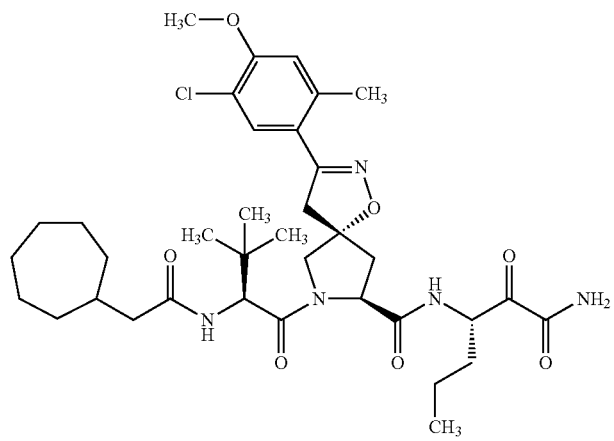
623
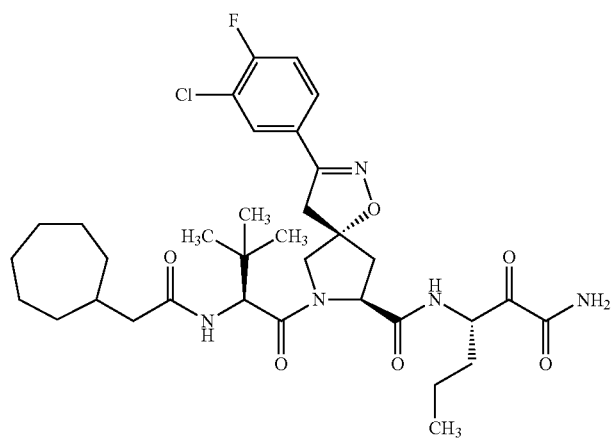
624
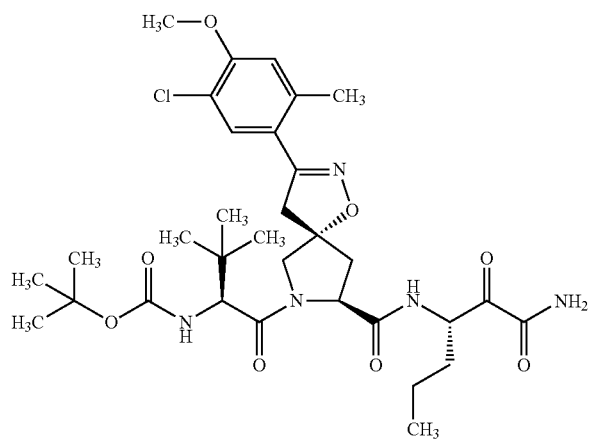

625
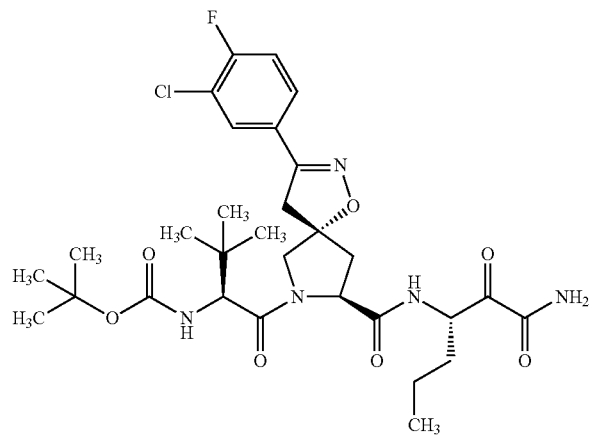
626
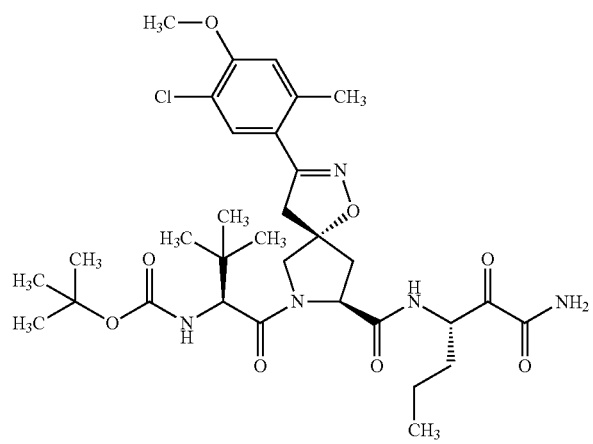
627
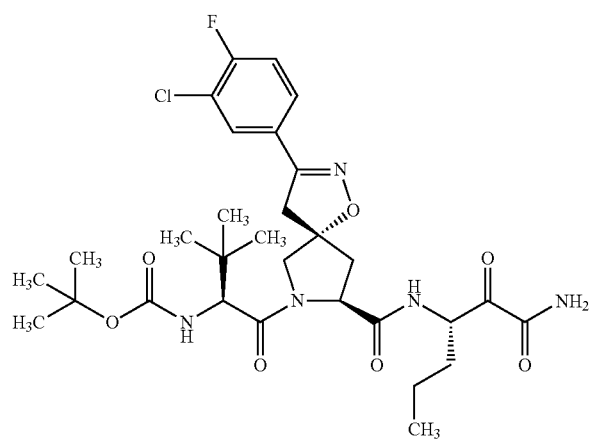

628
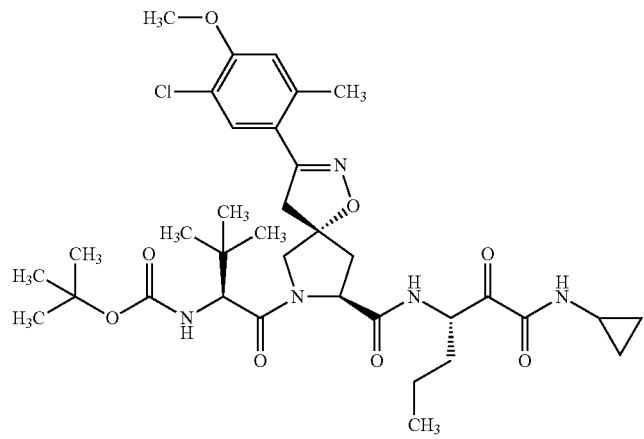
629
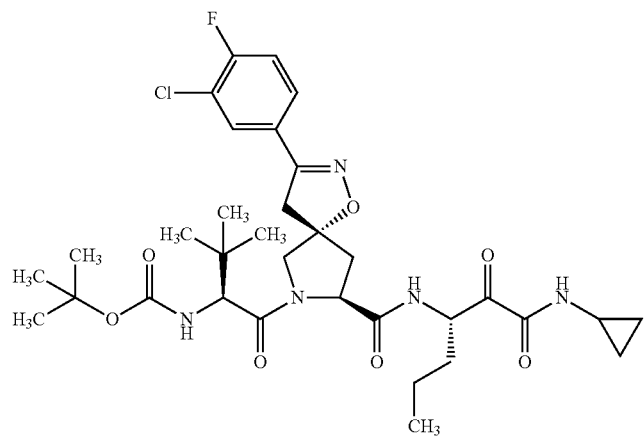
630
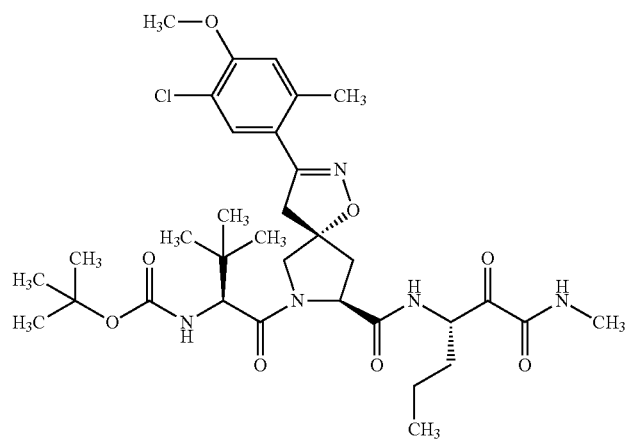

-continued
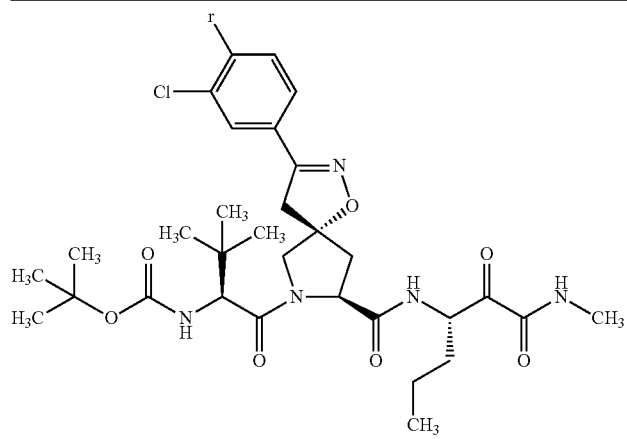
631
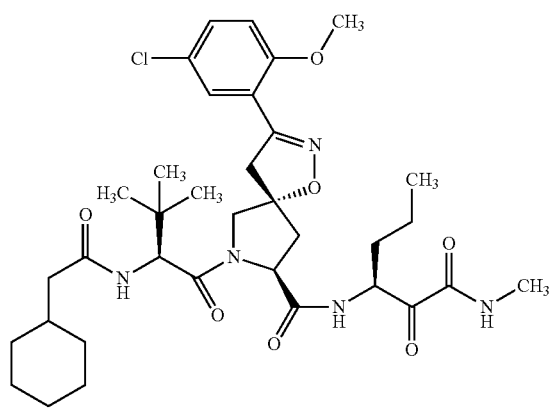
632
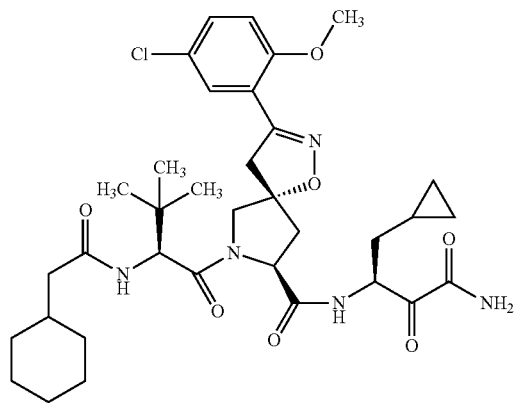
633
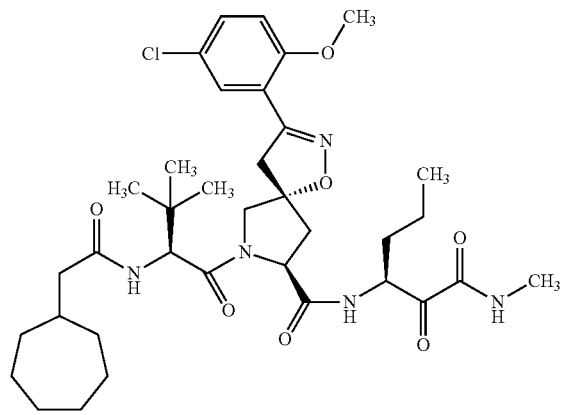
634

635
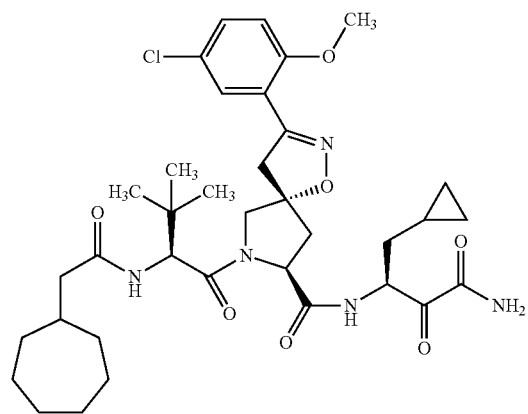
636
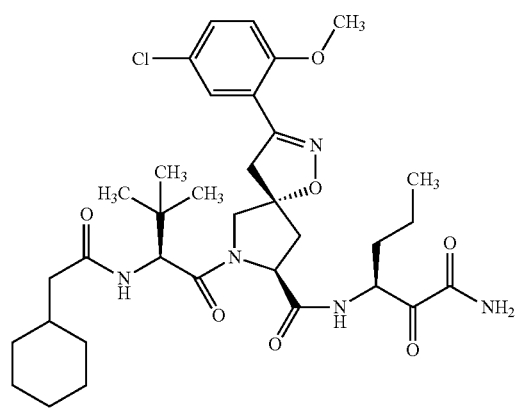
637
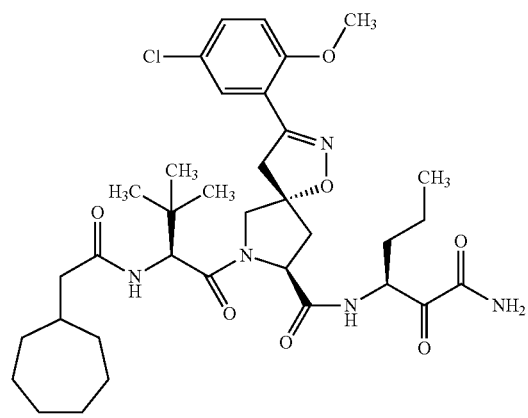

-continued
638
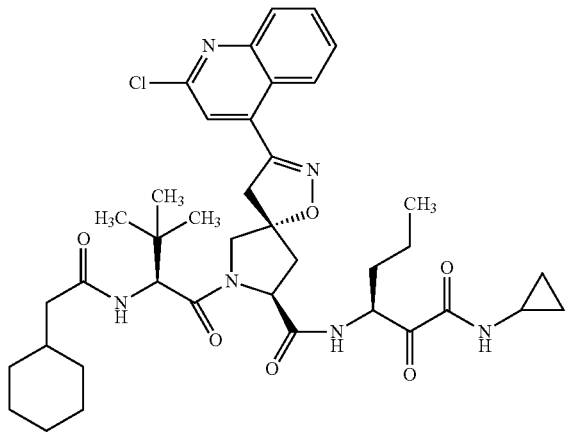
639
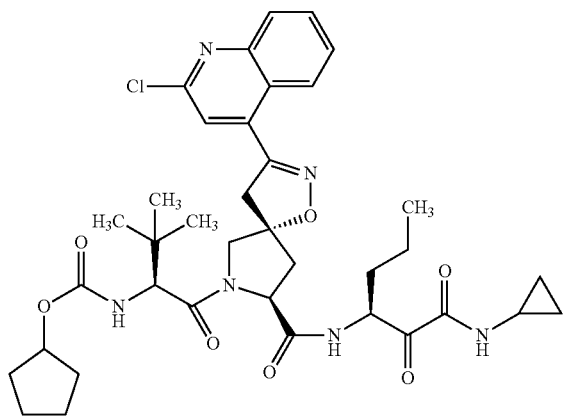
640
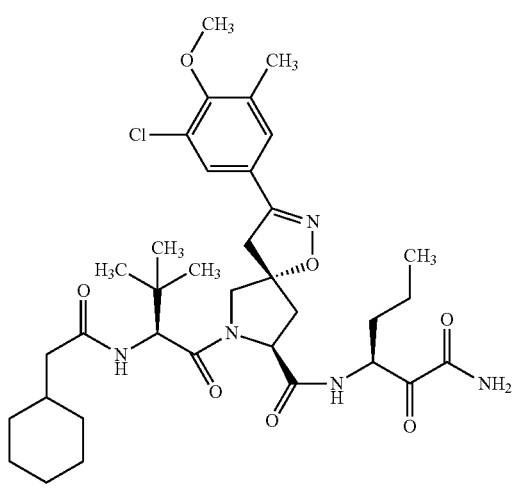

641
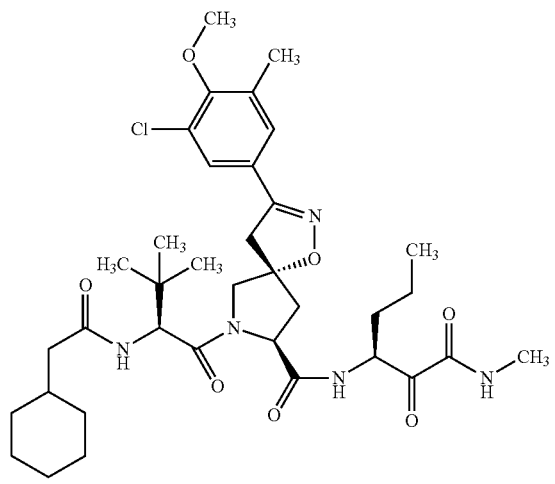
642
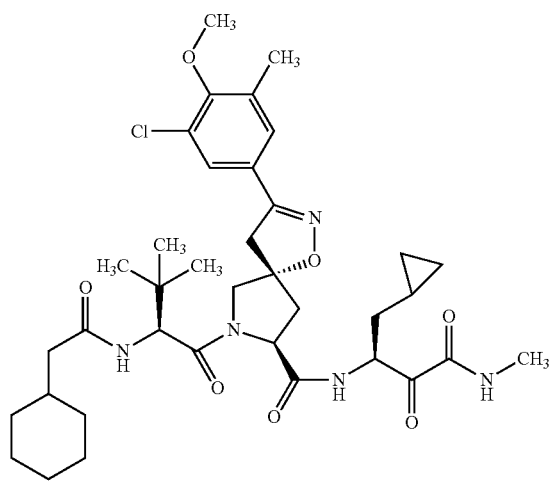
643
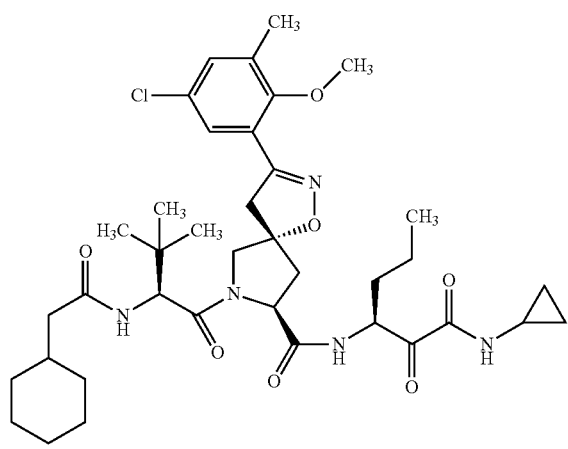

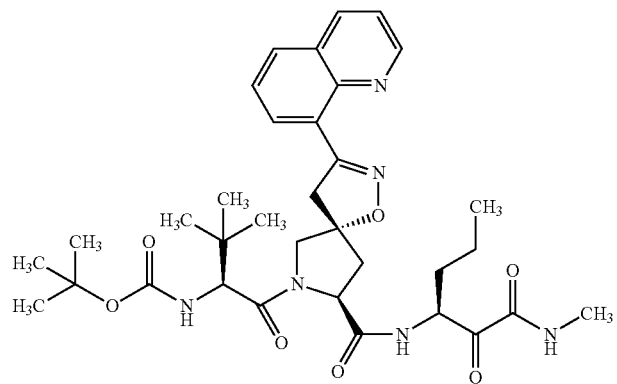
644
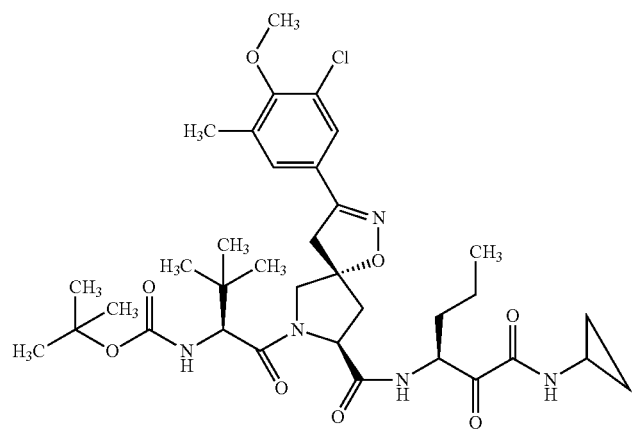
645
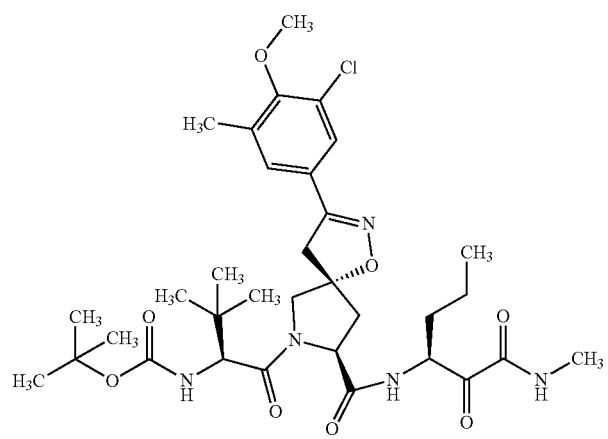
646
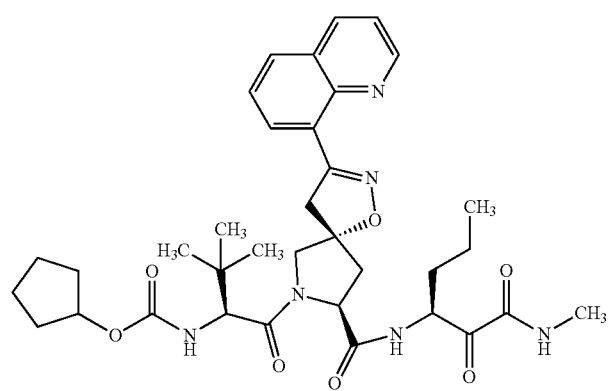
647

648
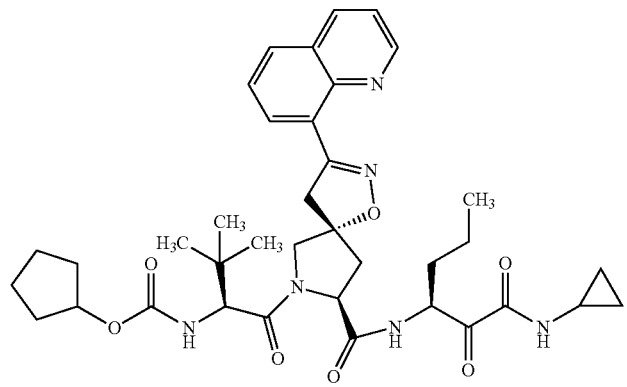
649
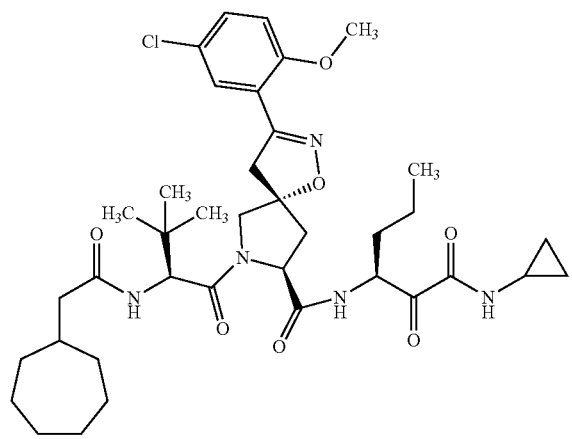
650
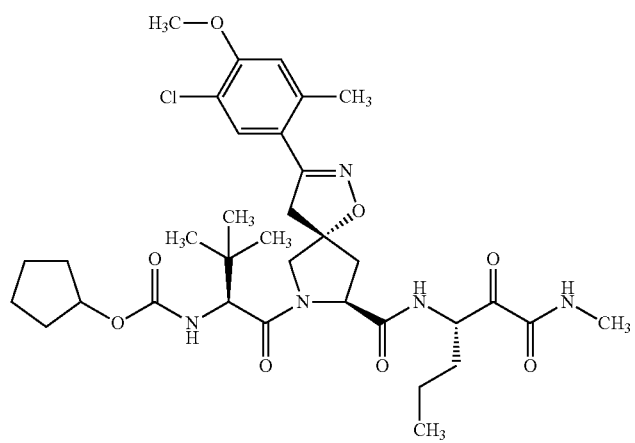

651
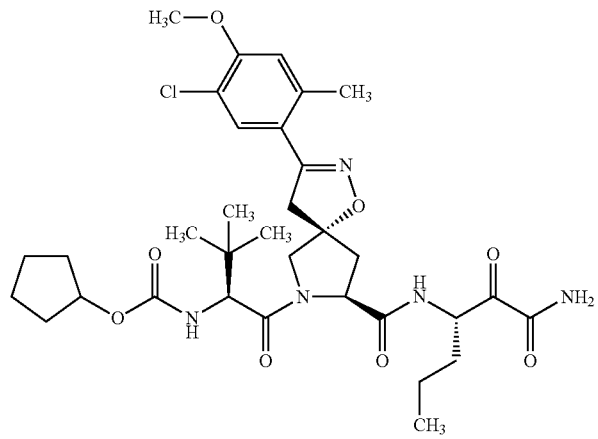
652
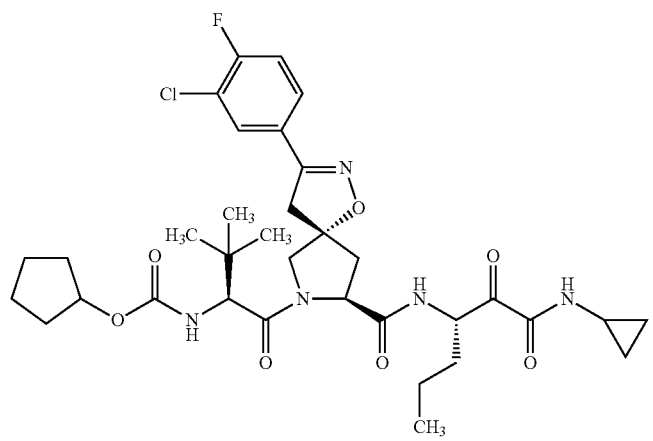
653
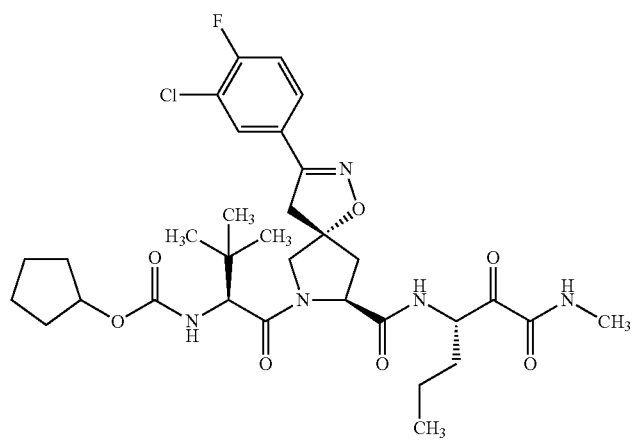

654
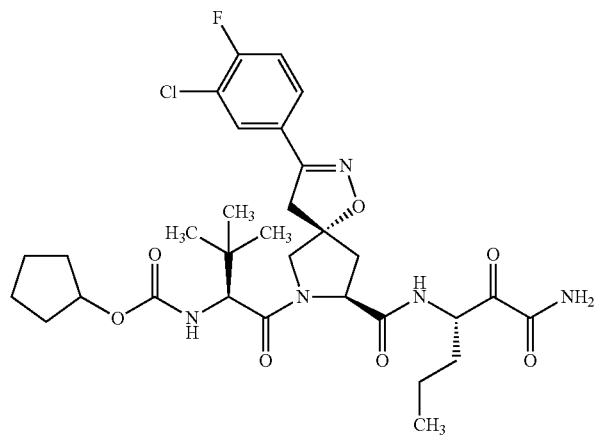
655
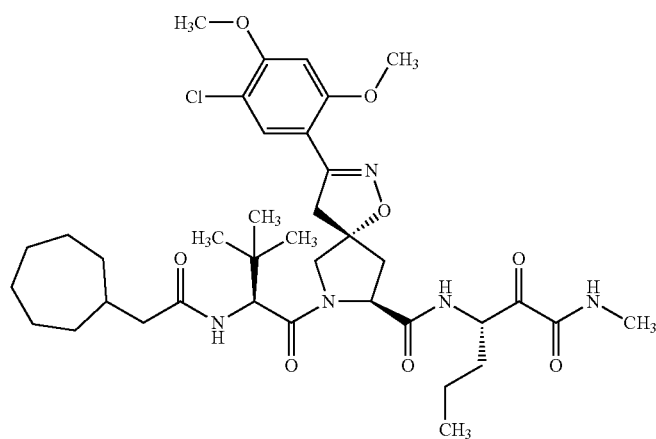
656
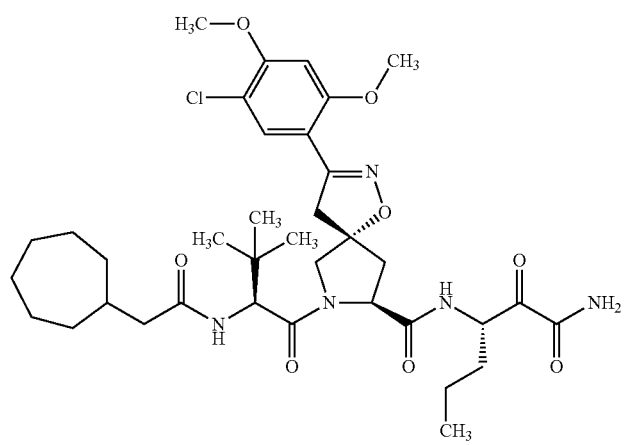

657
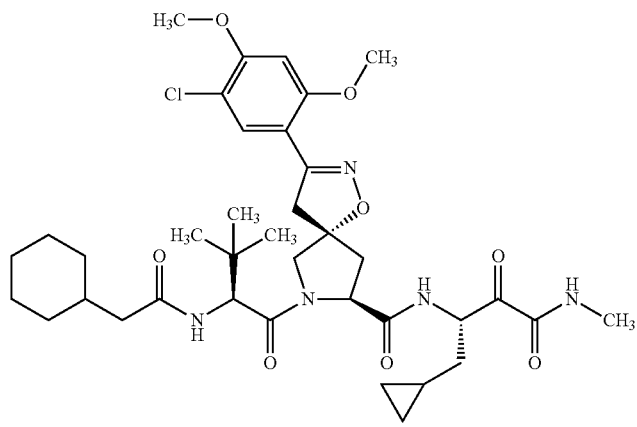
658
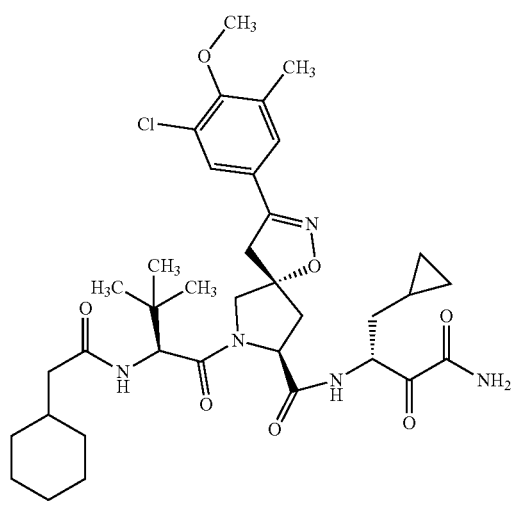
659
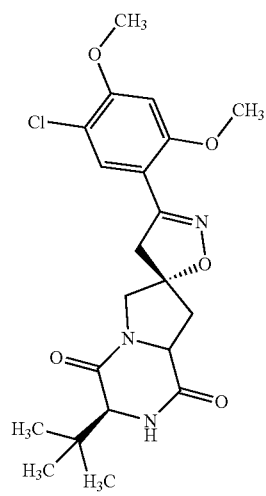

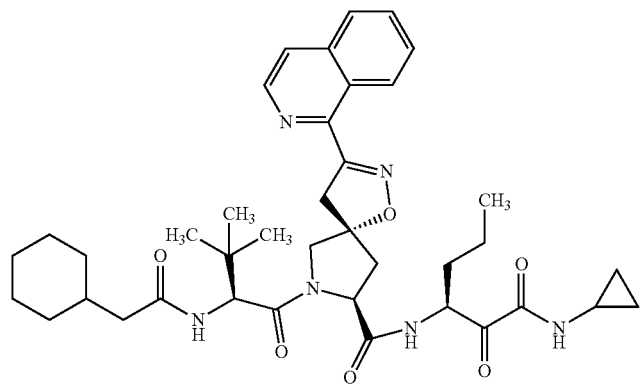
660
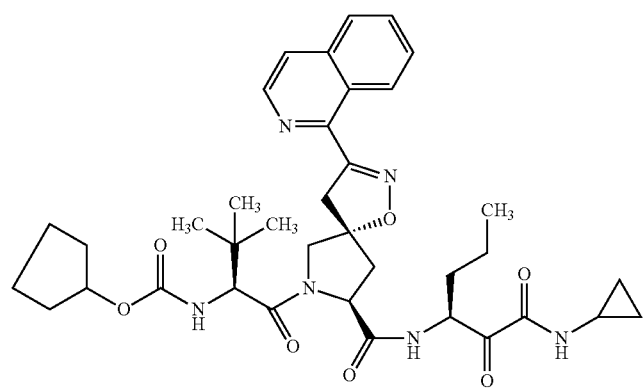
661
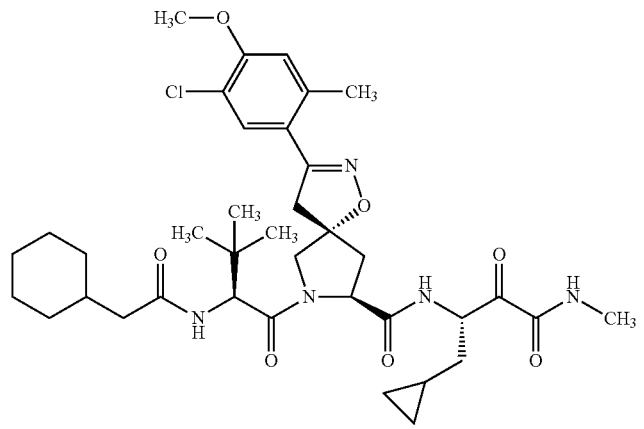
662
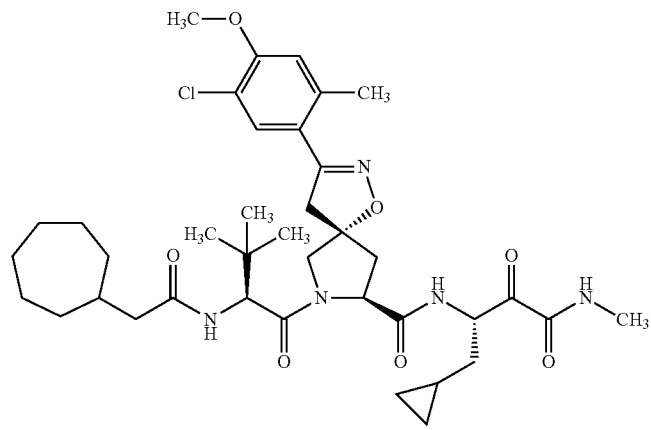
663

664
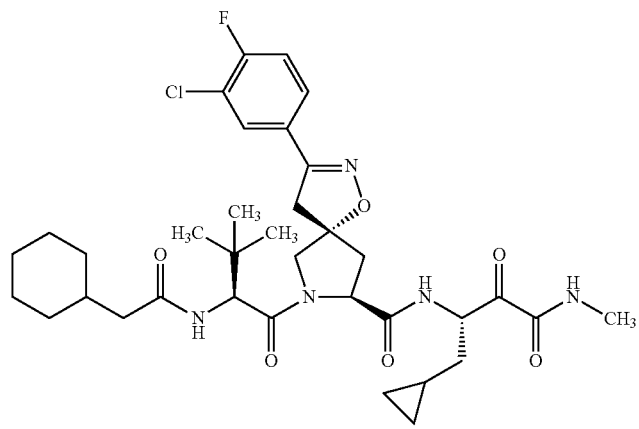
665
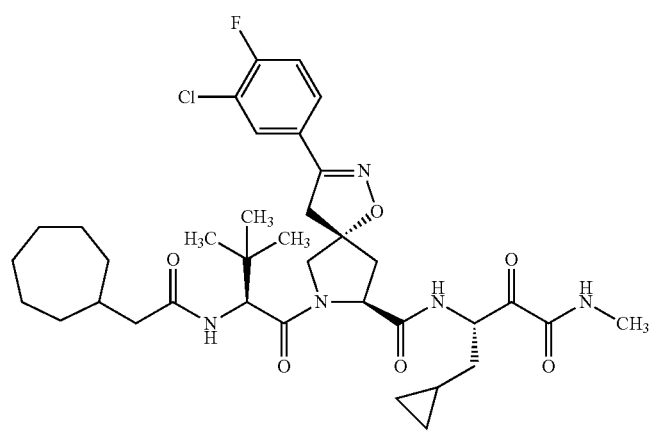
666
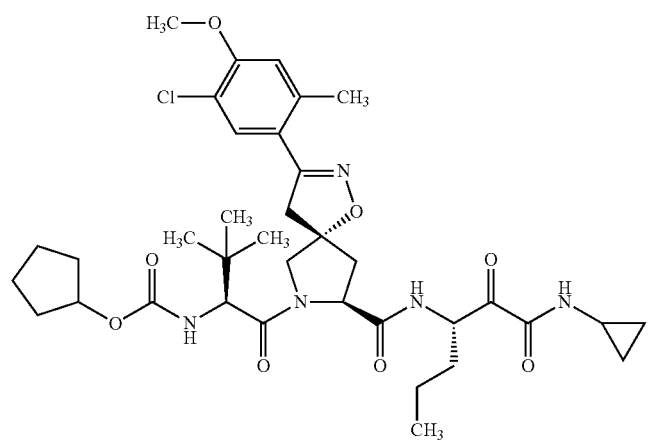

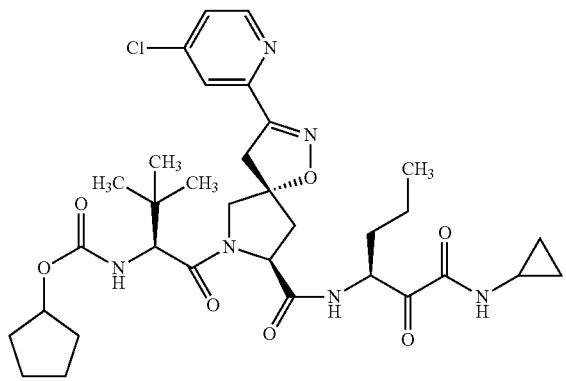
667
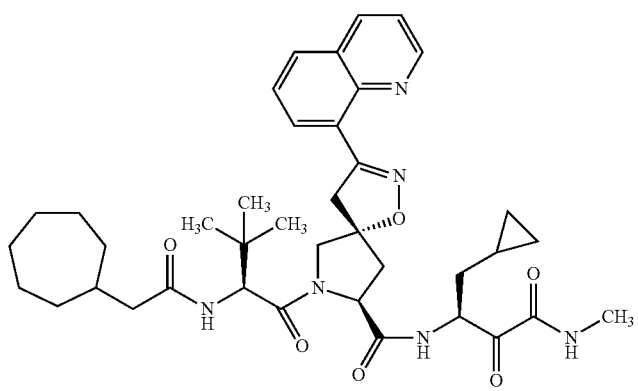
668
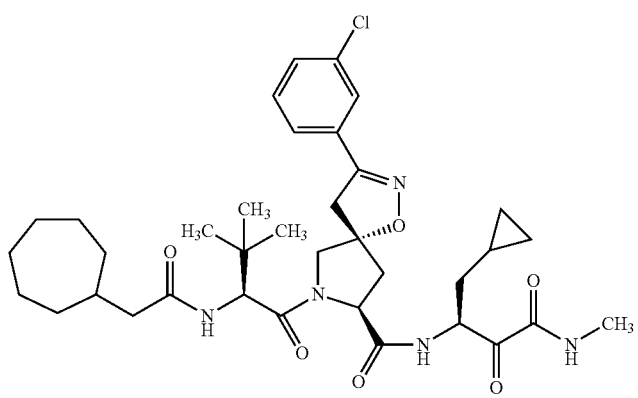
669
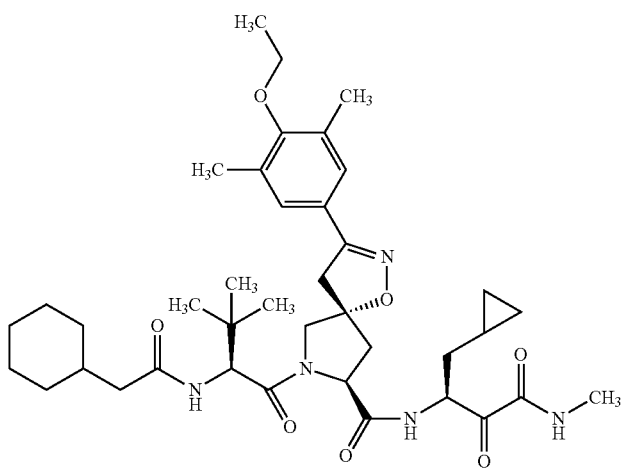
670

671
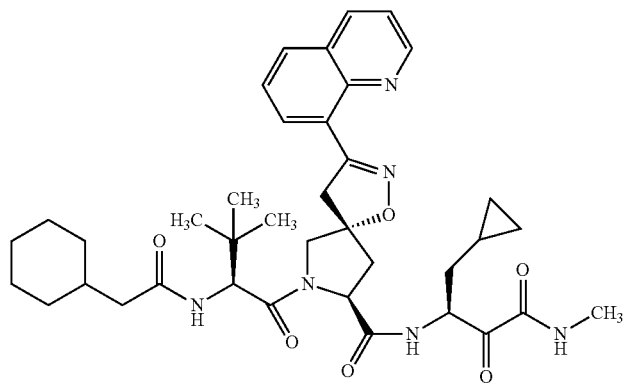
672
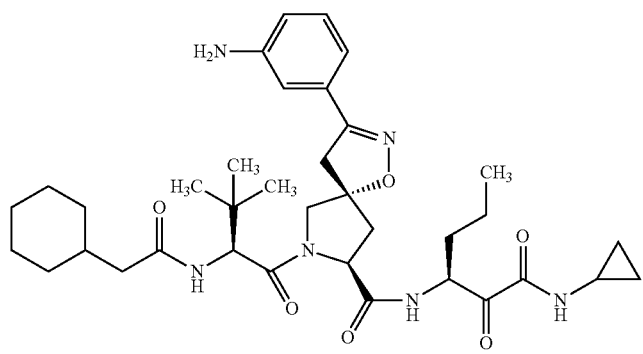
673
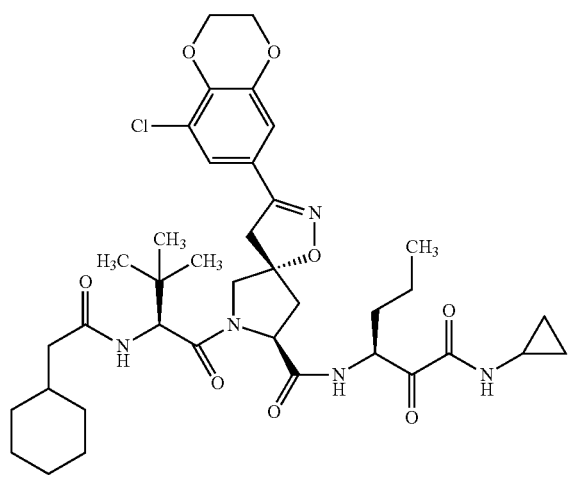

674
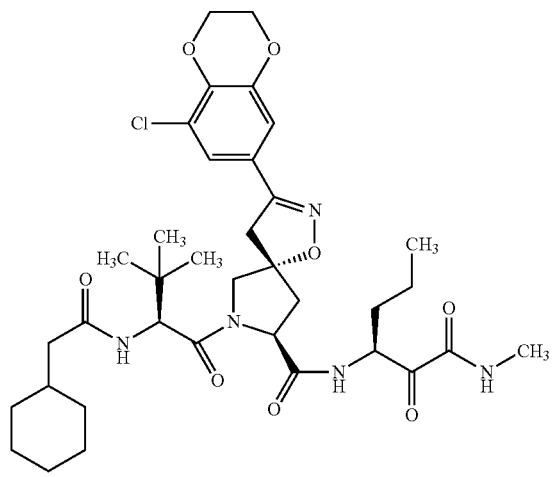
675
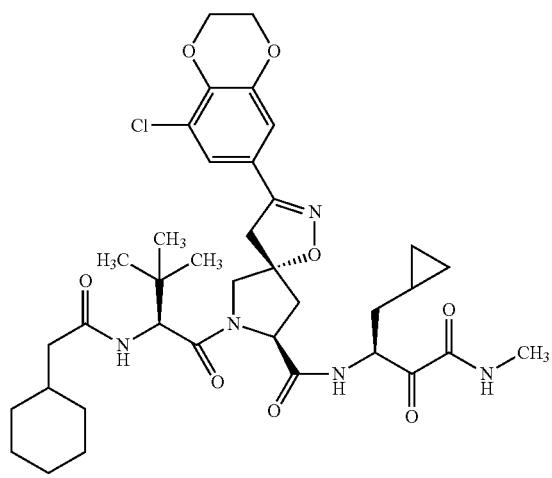
676
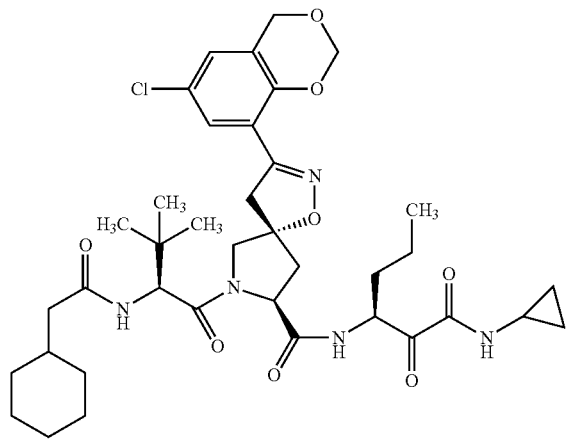

-continued
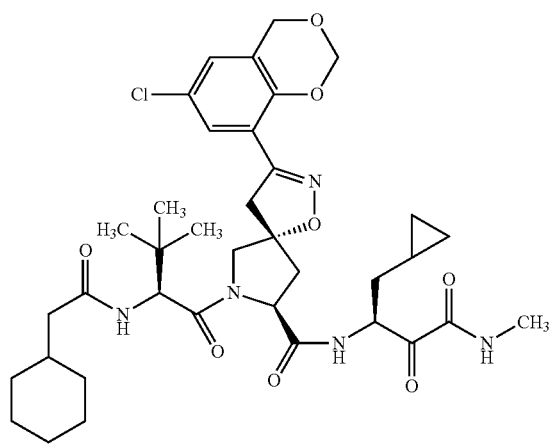
677
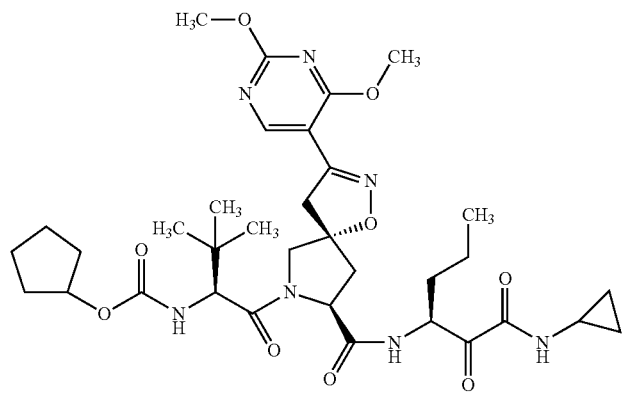
678
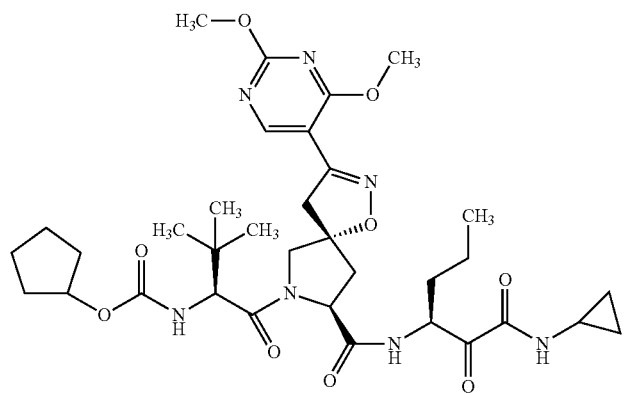
679
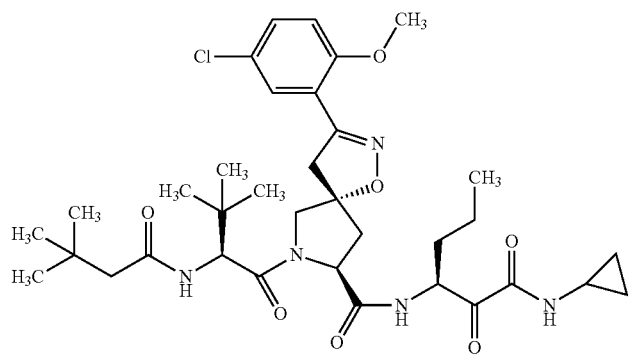
680

-continued
681
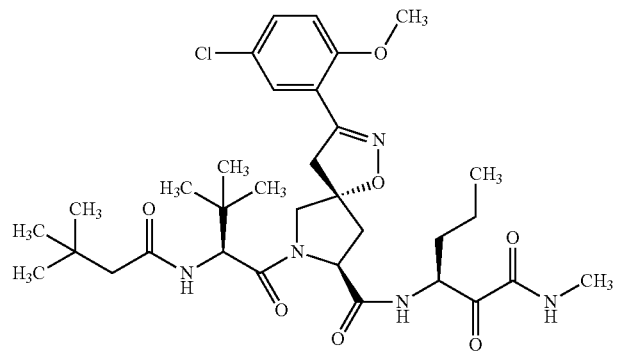
682
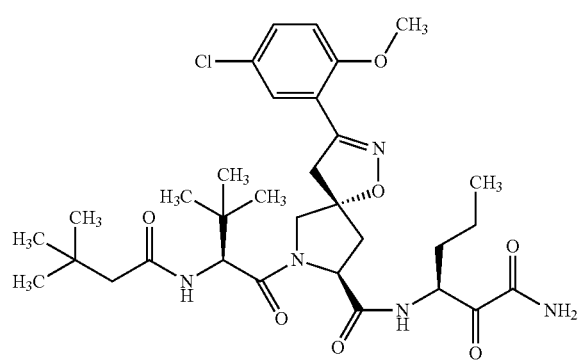
683
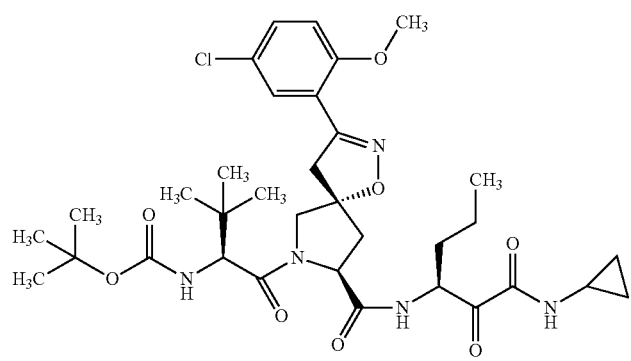
684
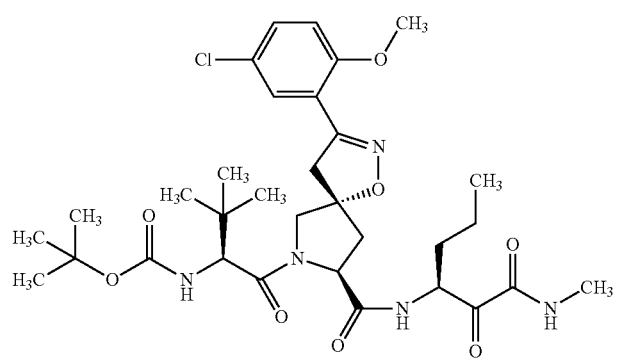

685
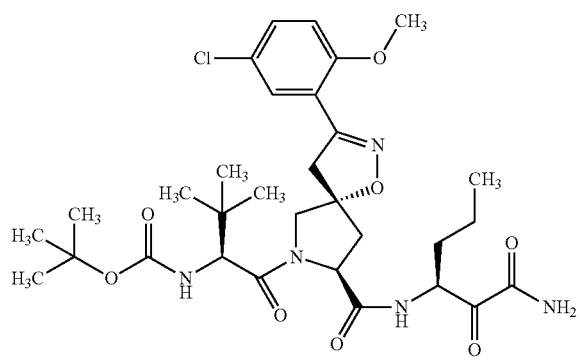
686
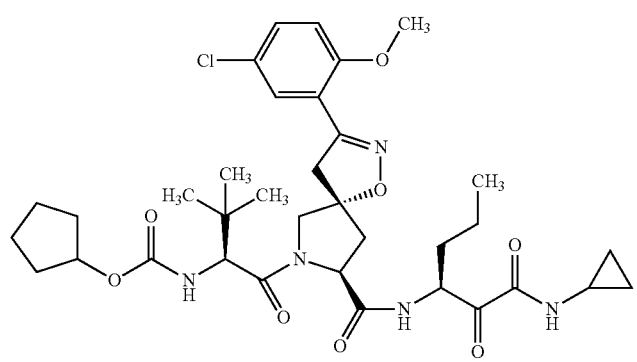
687
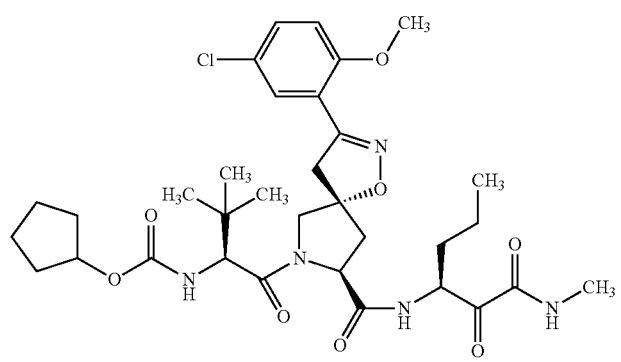
688
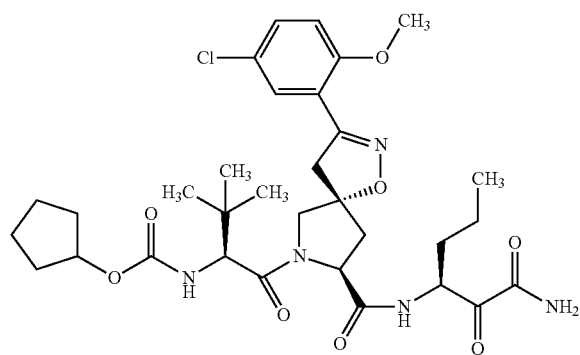

-continued
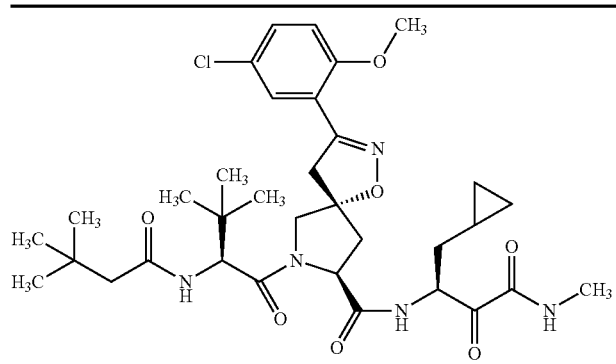
689
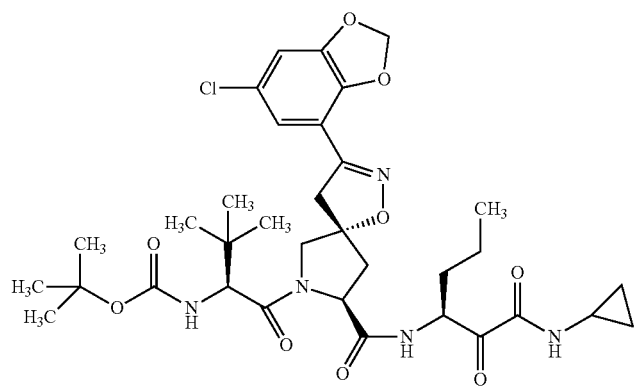
690
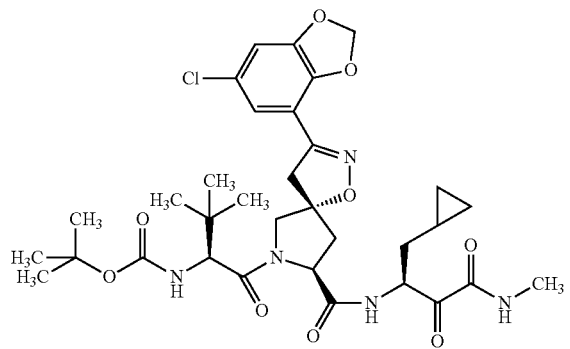
691
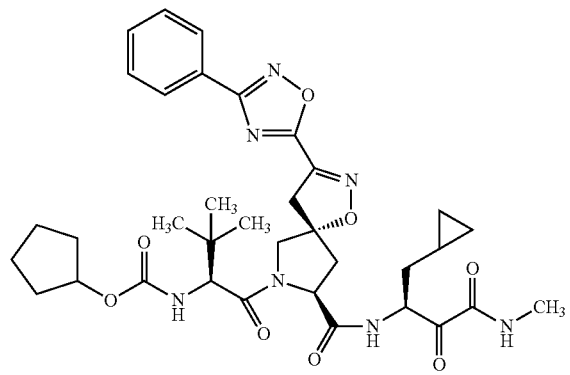
692

-continued
693
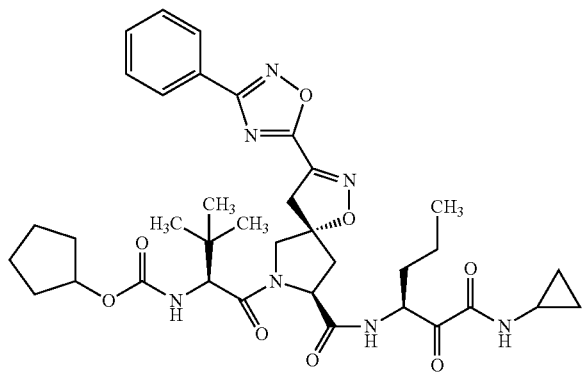
694
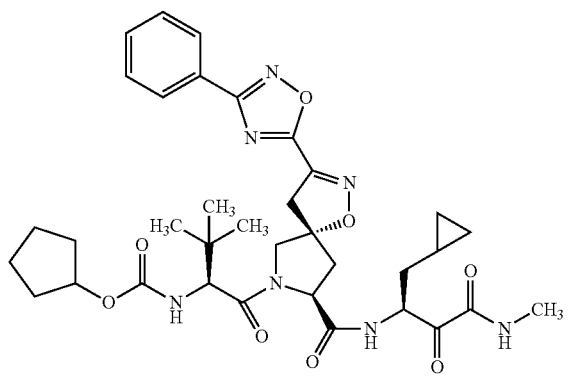
695
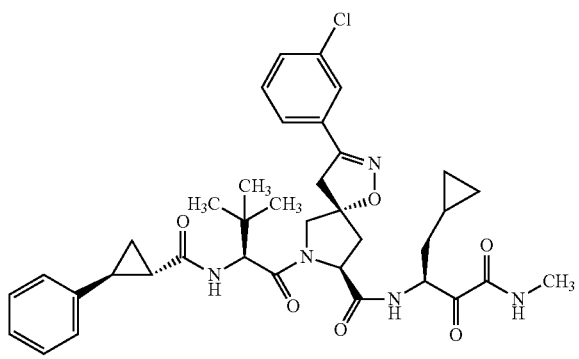
696
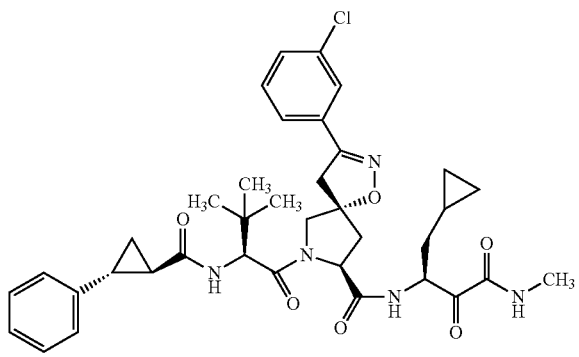

697
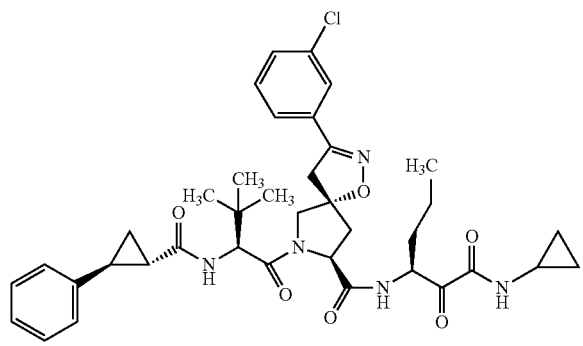
698
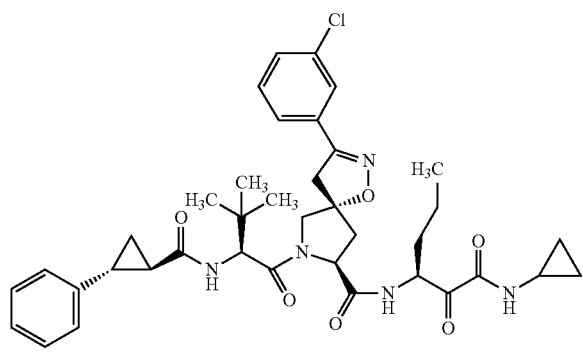
699
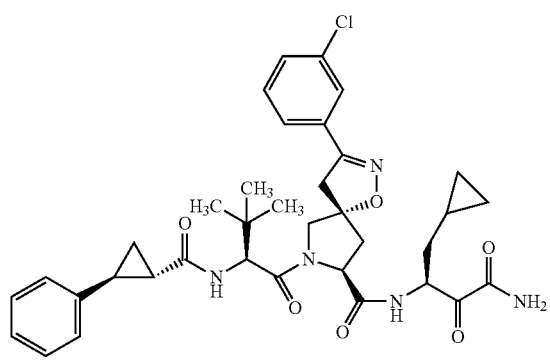
700
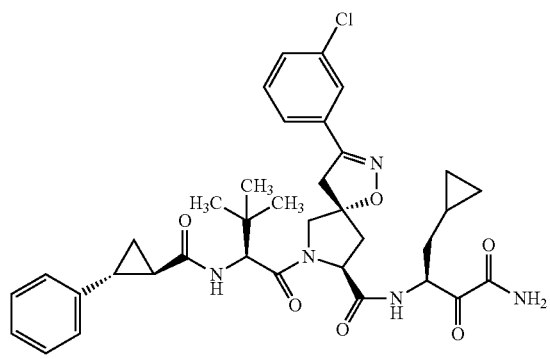

-continued
701
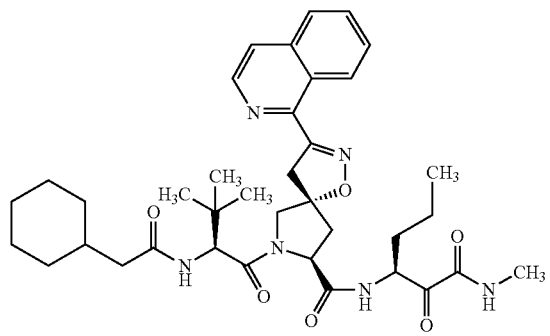
702
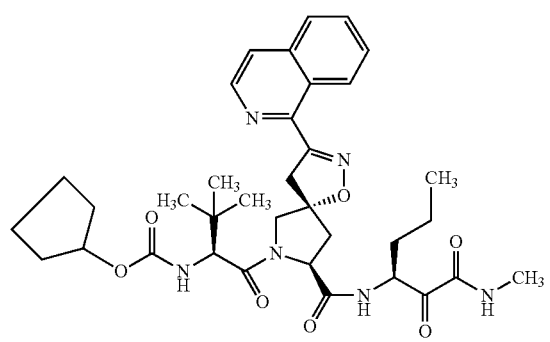
703
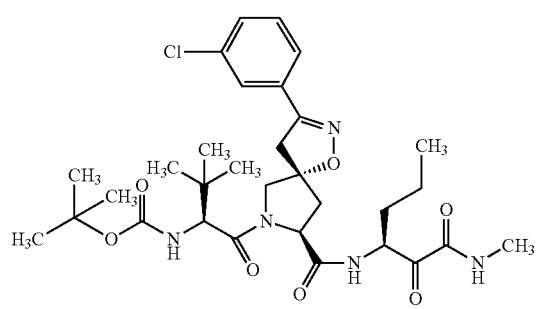
704
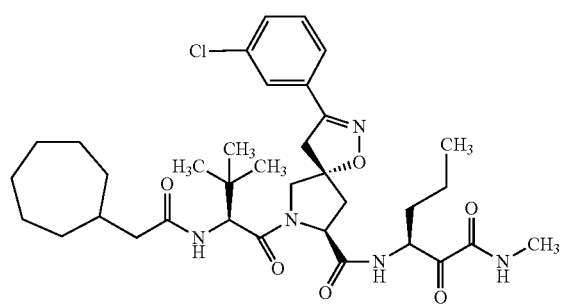
705
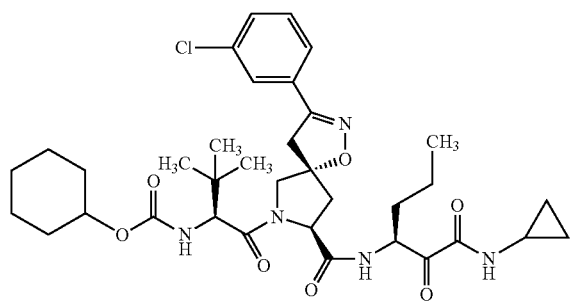

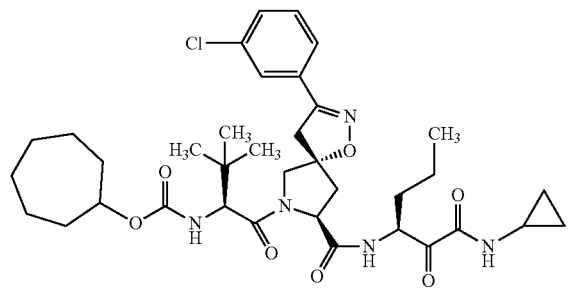
706
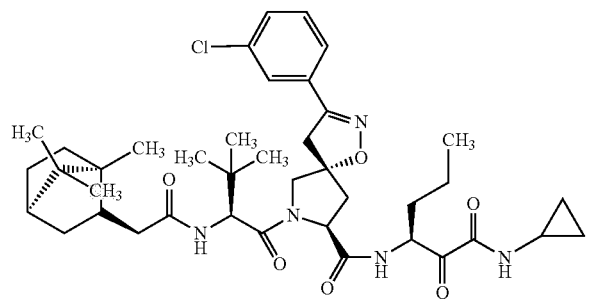
707
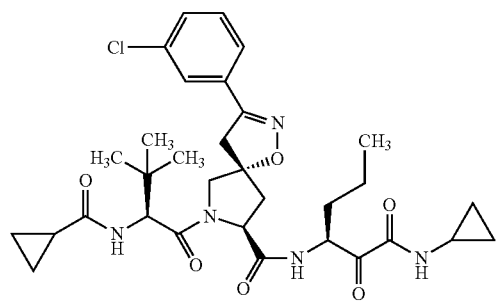
708
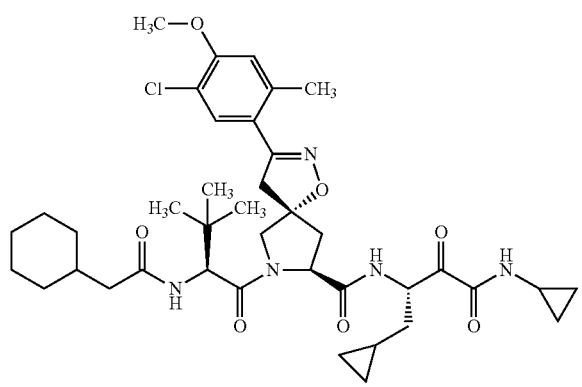
709
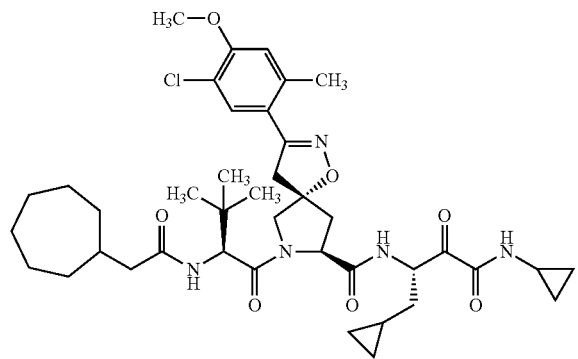
710

711
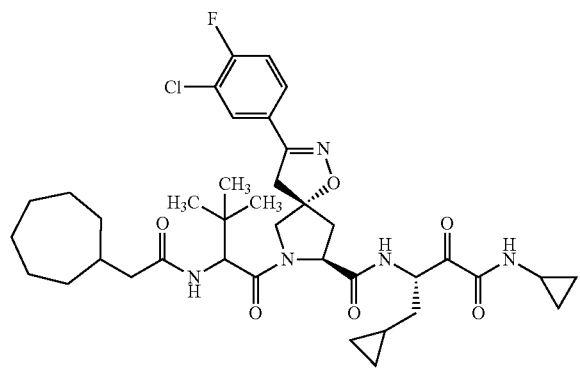
712
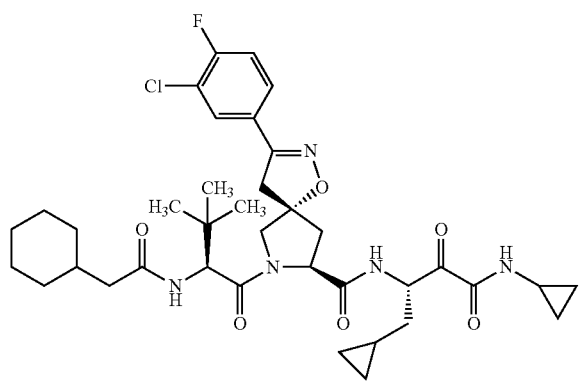
713
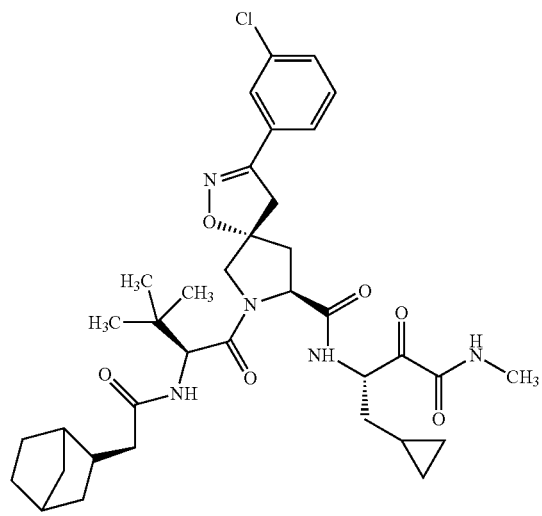

714
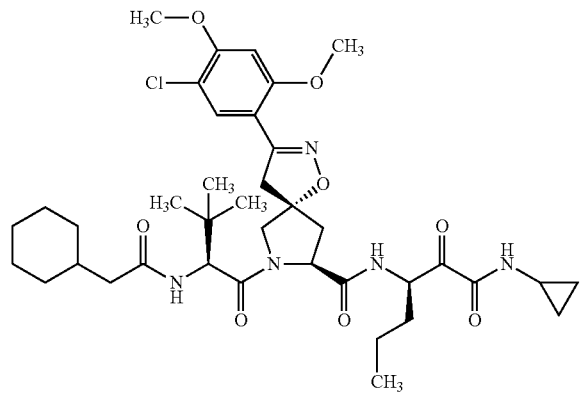
715
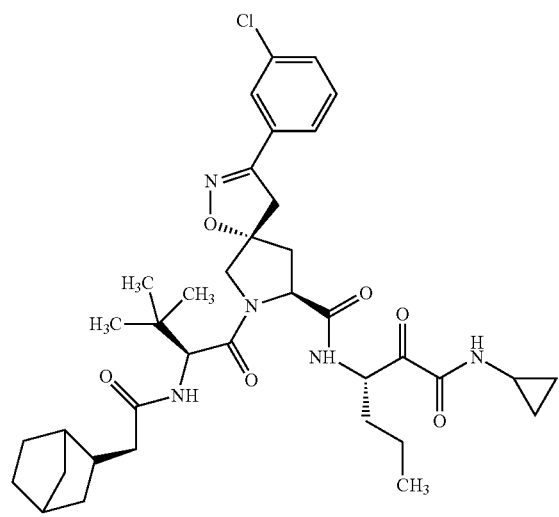
716
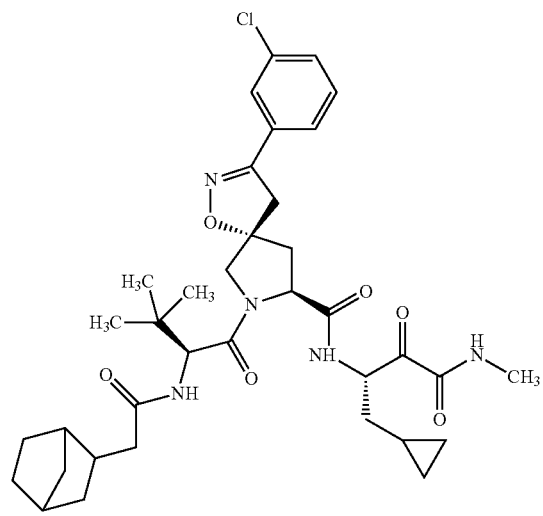

717
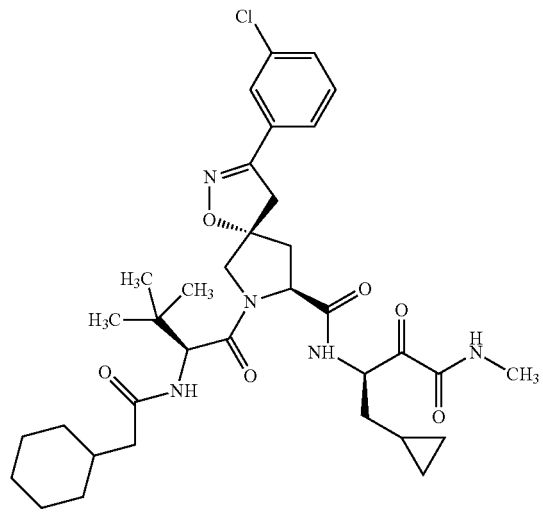
718
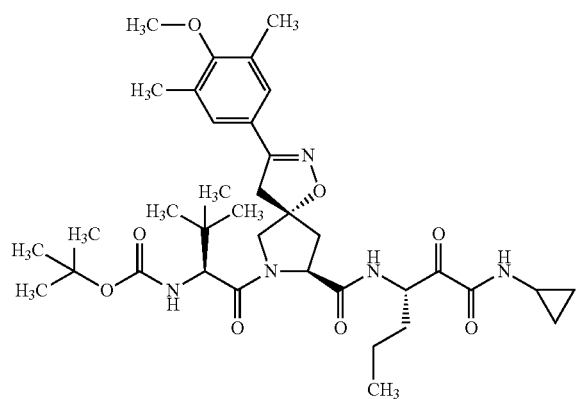
719
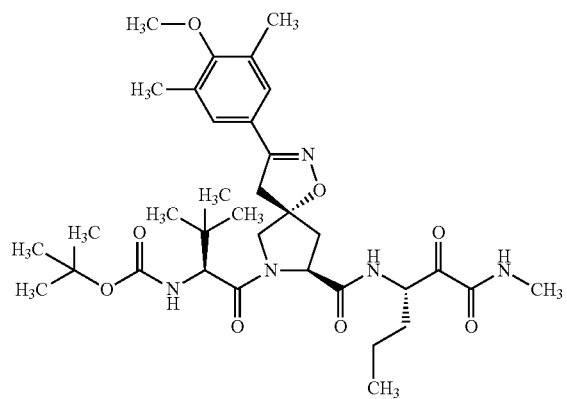

720
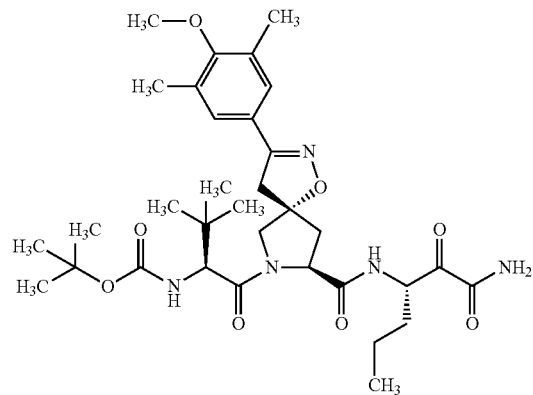
721
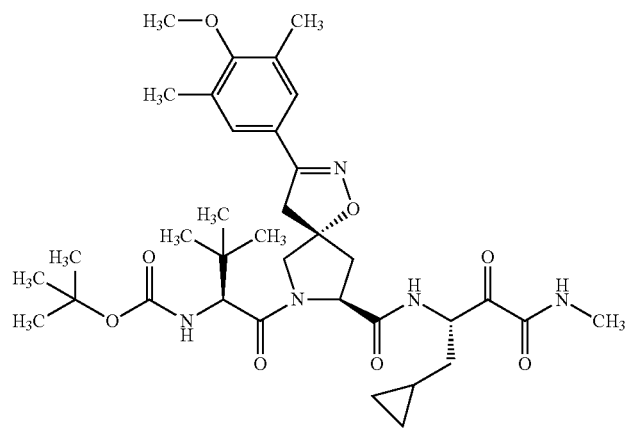
722
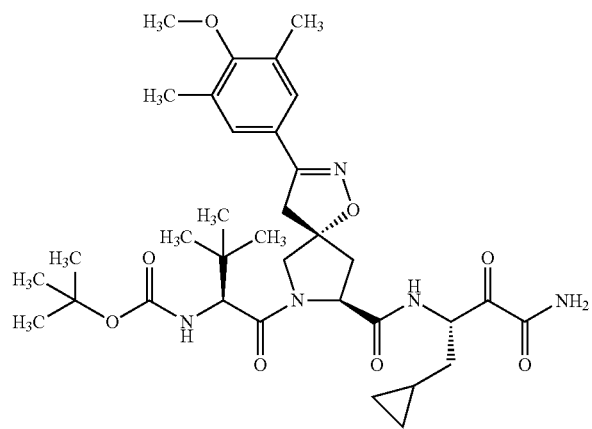

723
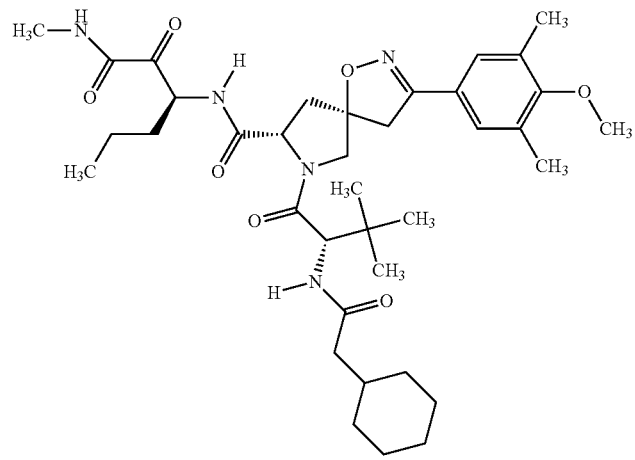
724
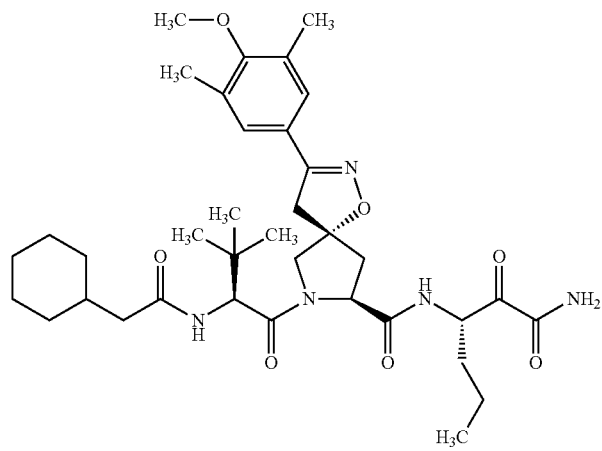
725
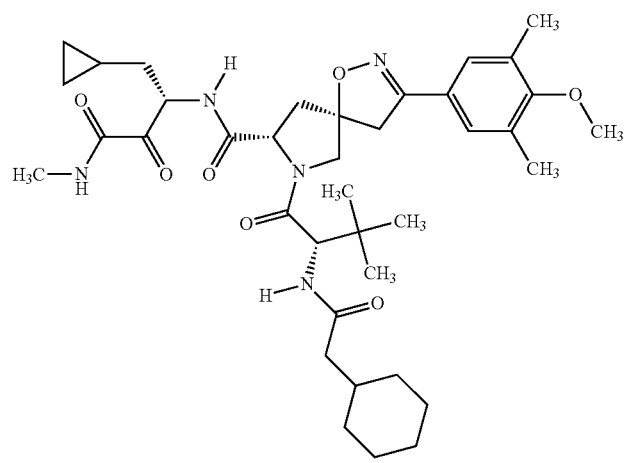

726
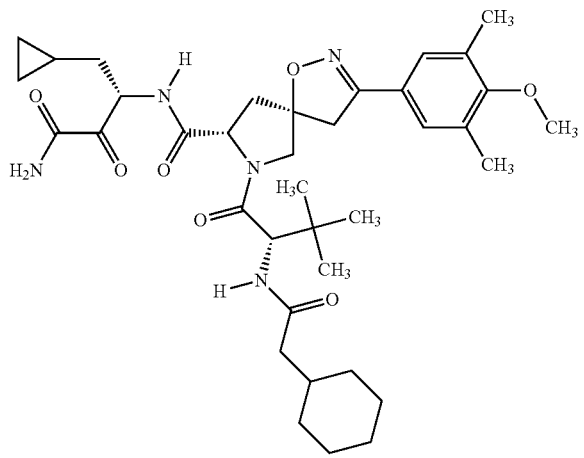
727
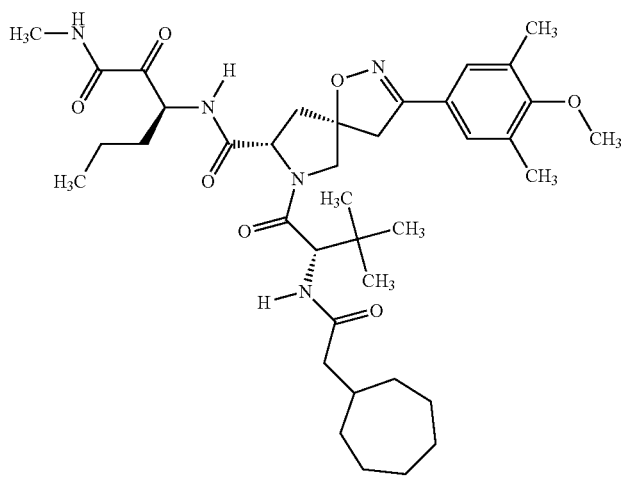
728
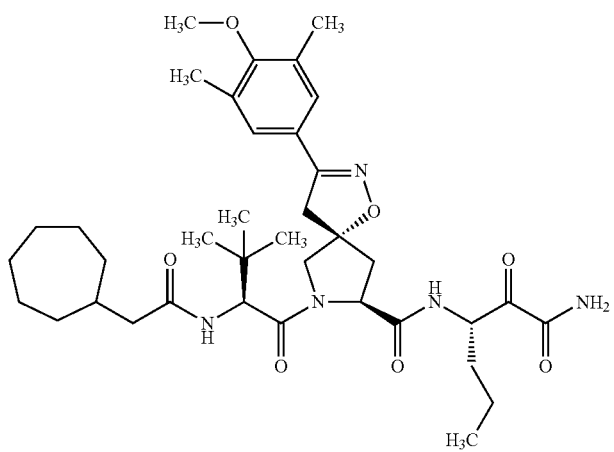

729
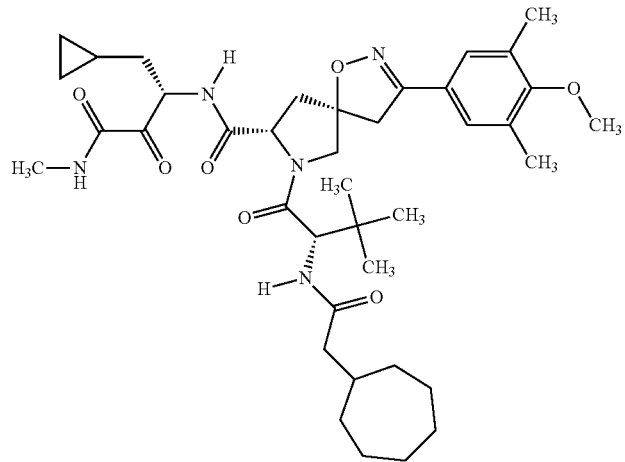
730
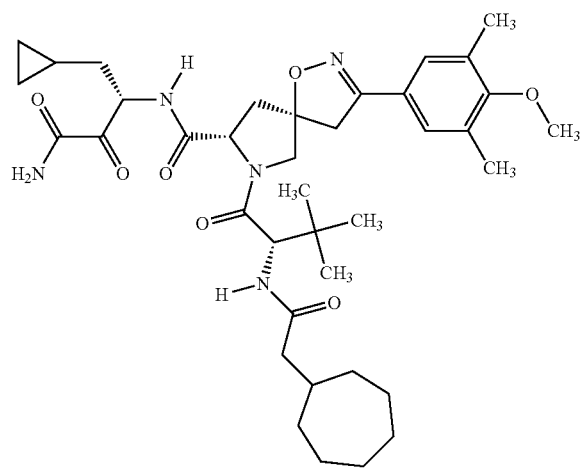
731
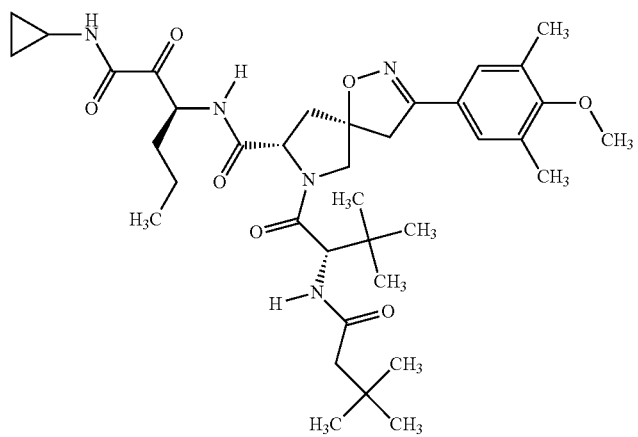

732
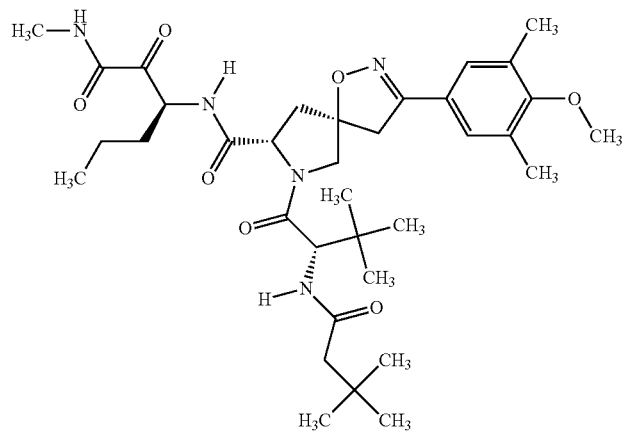
733
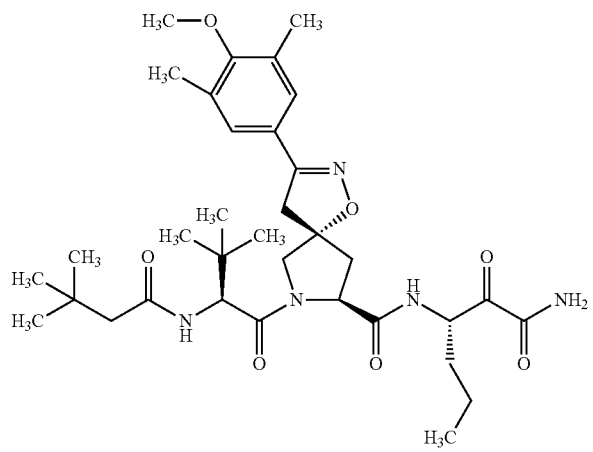
734
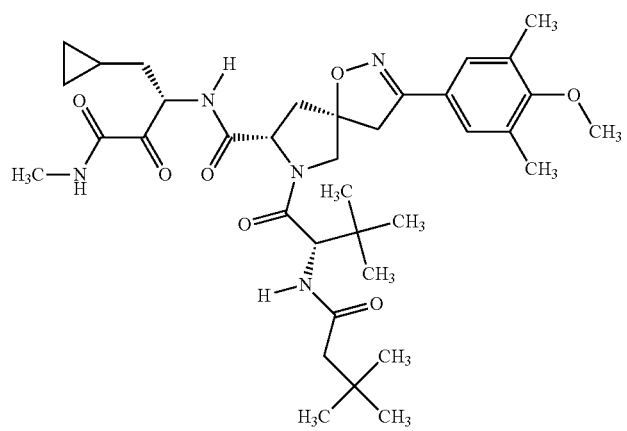

735
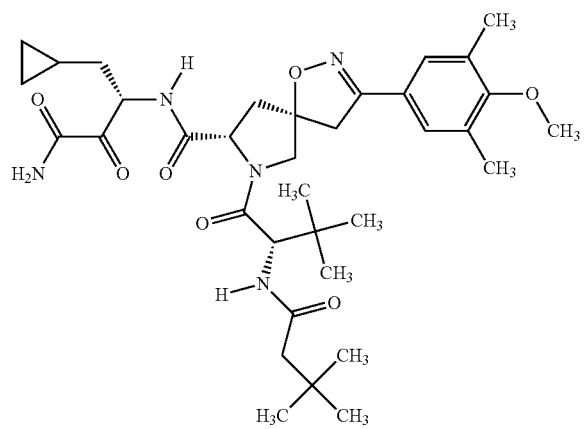
736
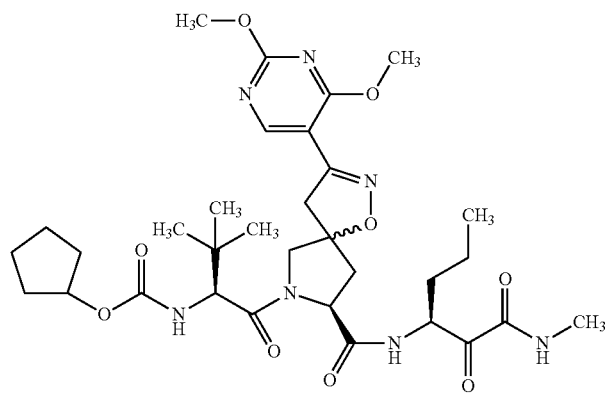
737
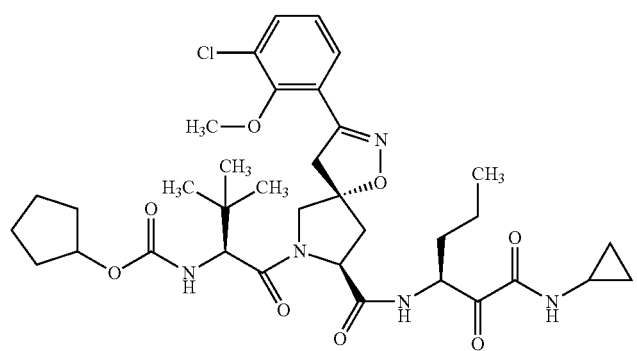
738
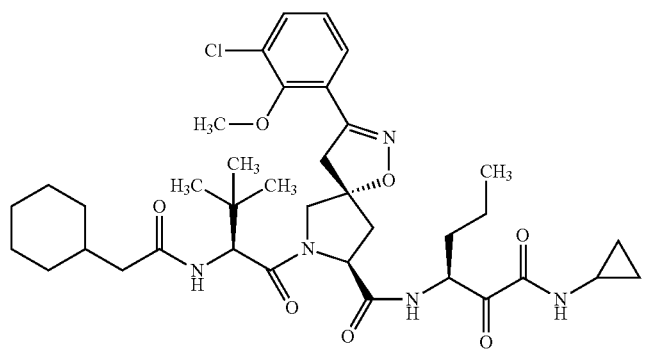

-continued
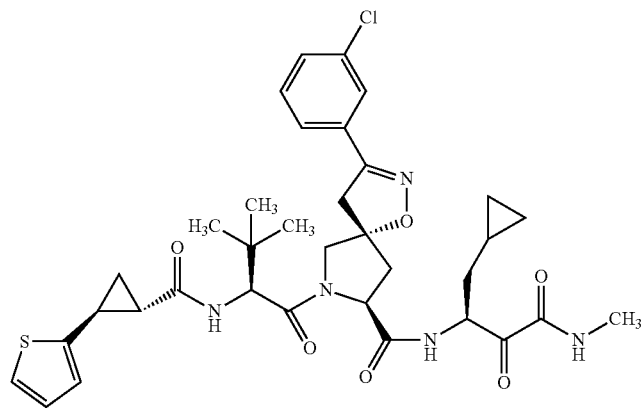
739
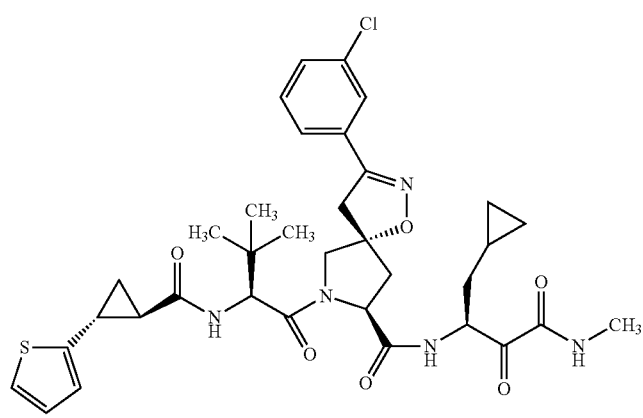
740
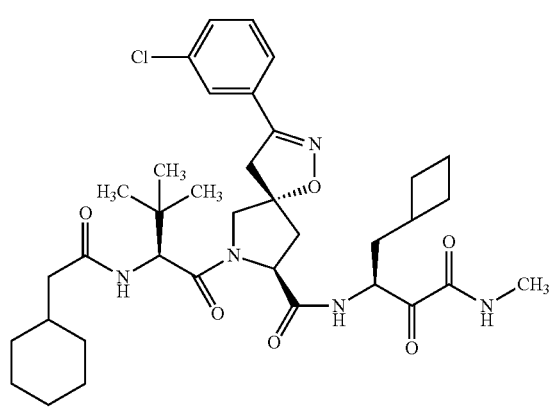
741
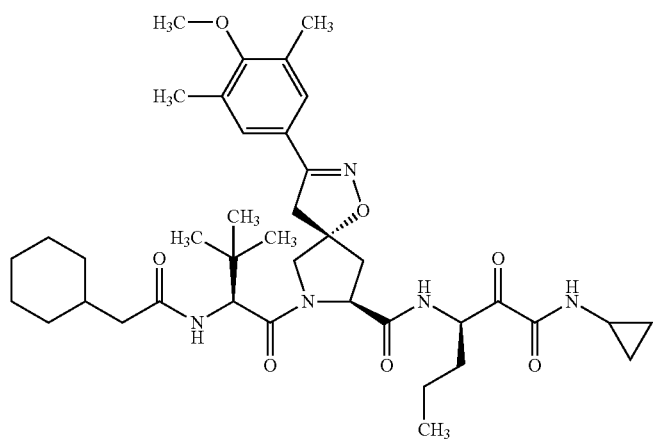
742

743
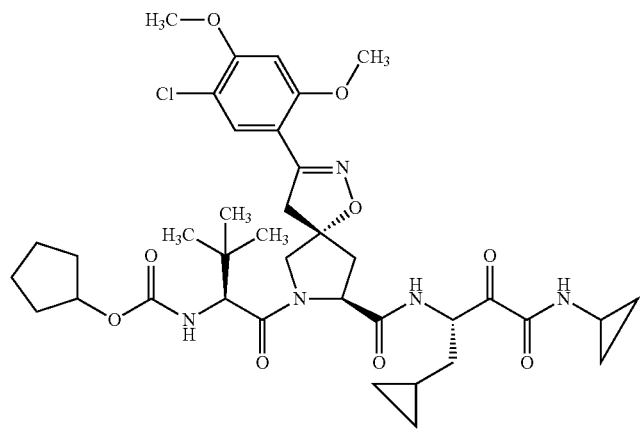
744
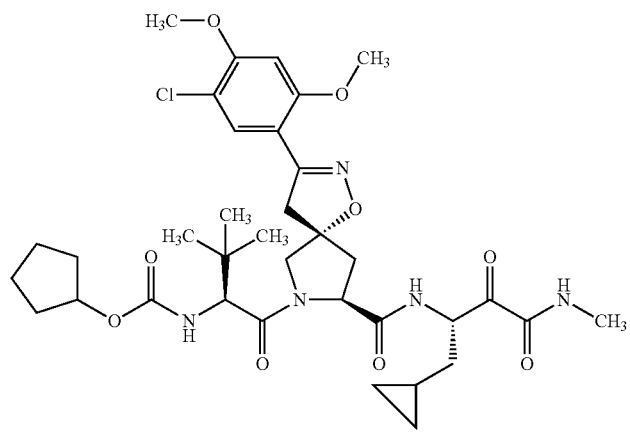
745
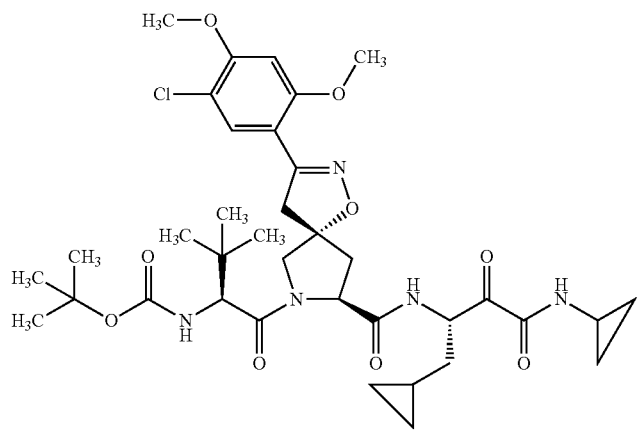

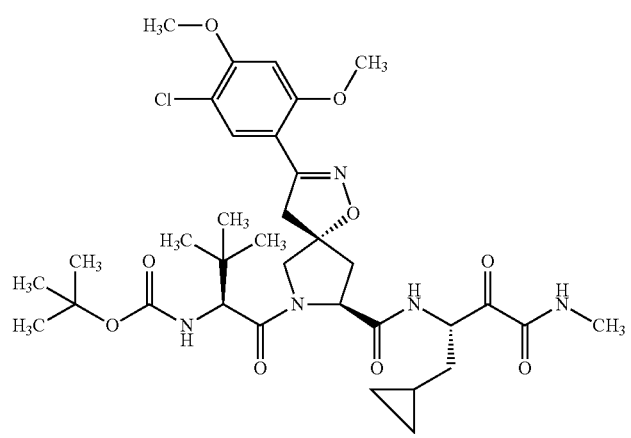
746
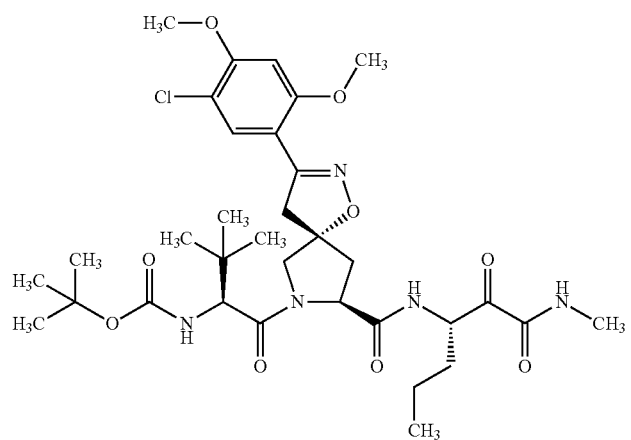
747
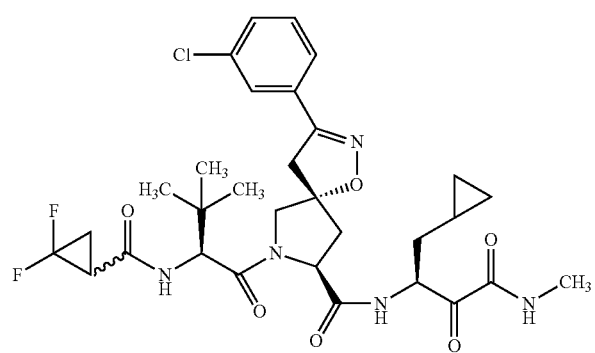
748
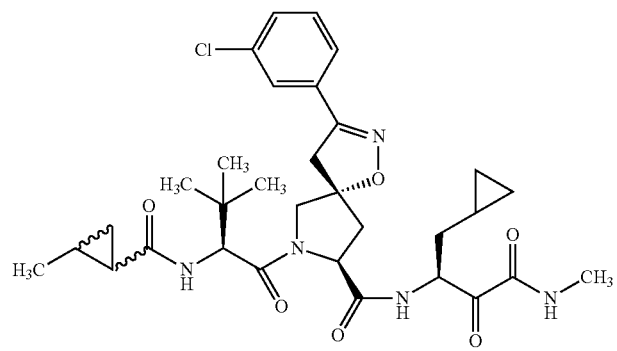
750

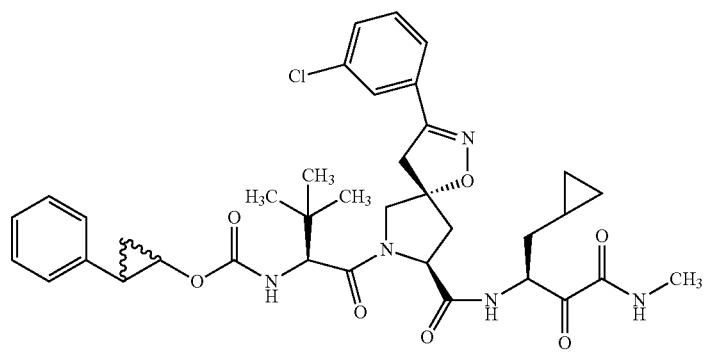
751
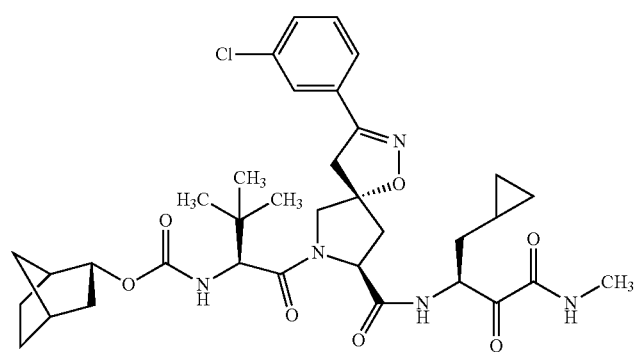
752
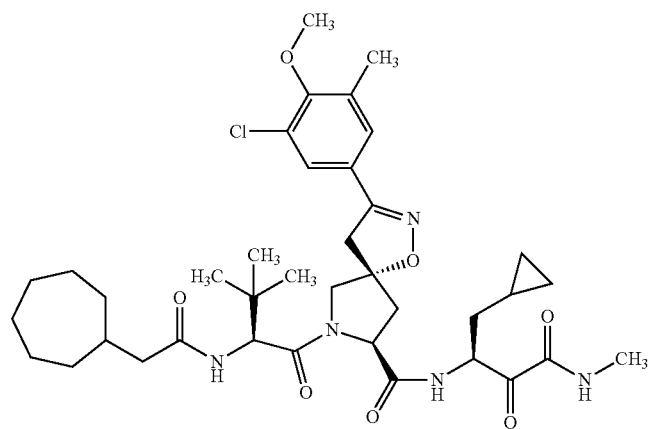
753
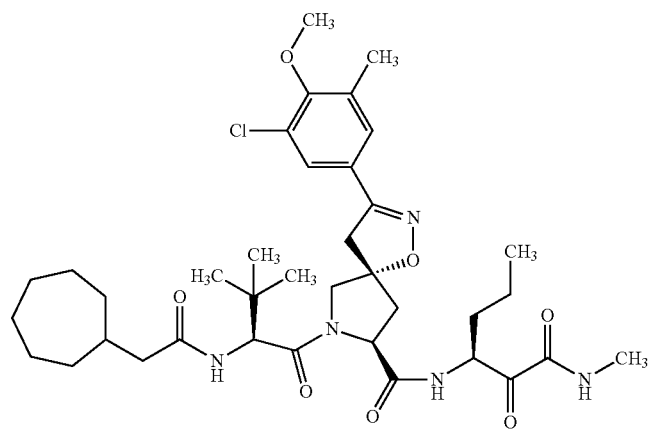
754

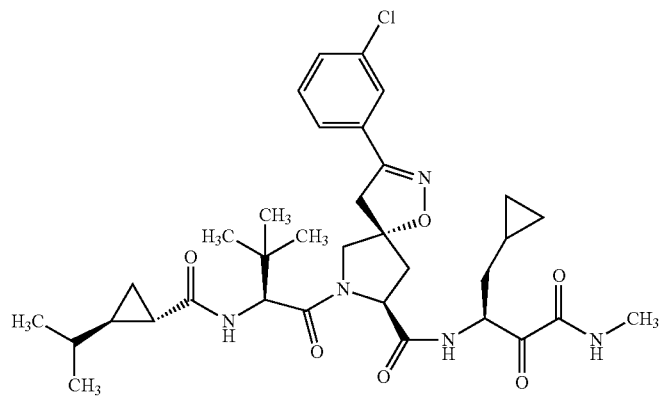
755
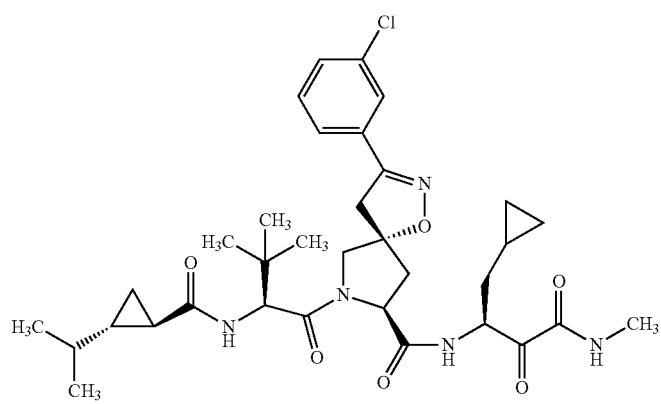
756
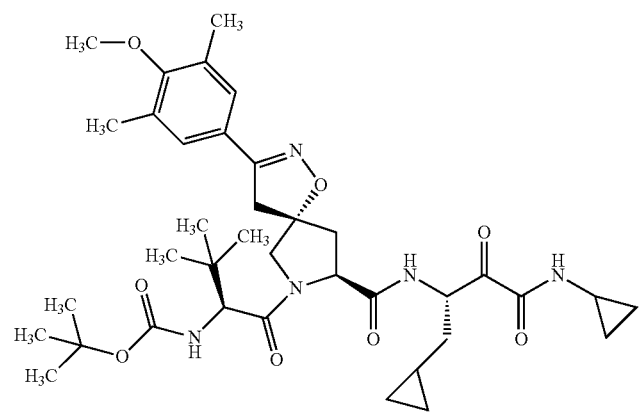
757
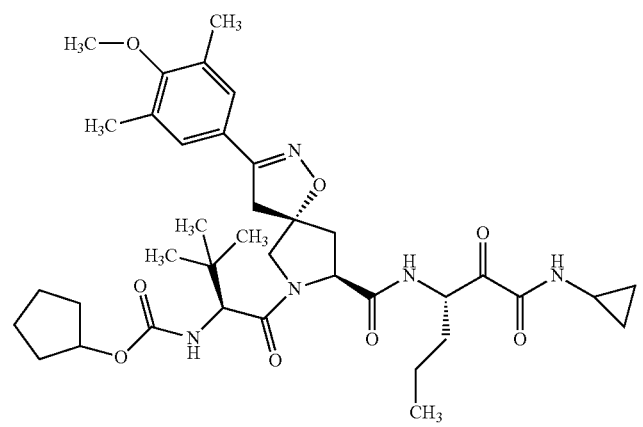
758

759
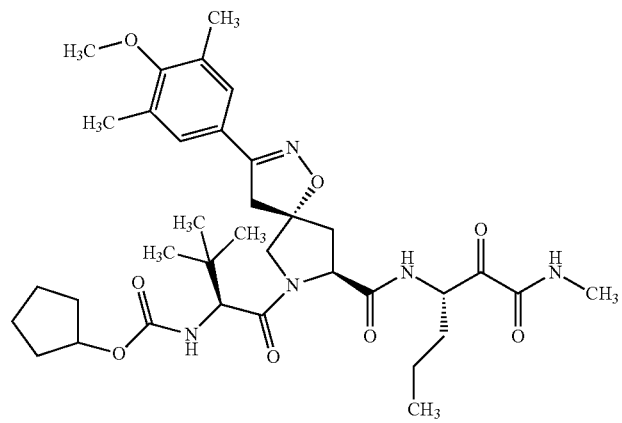
760
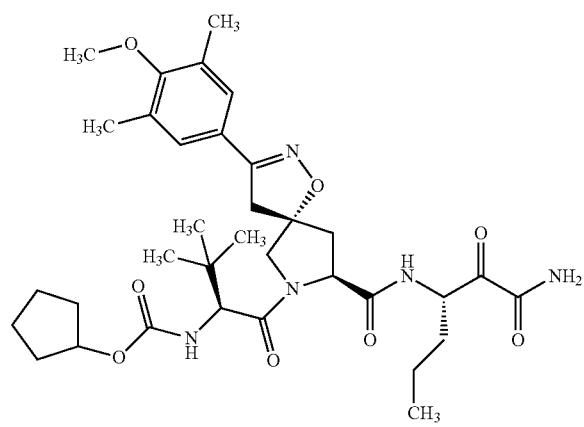
761
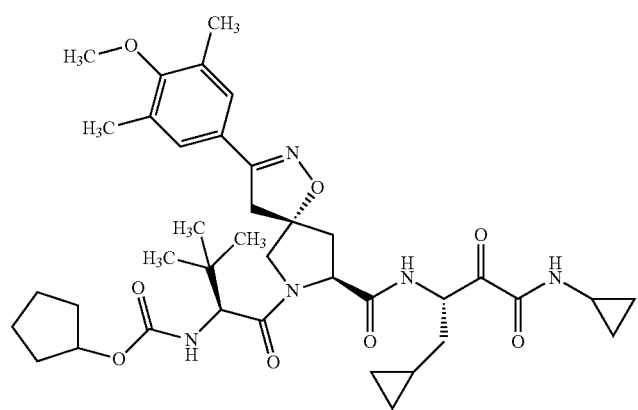

-continued
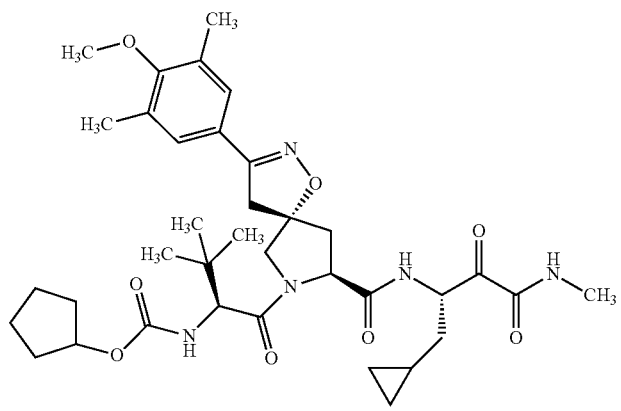
762
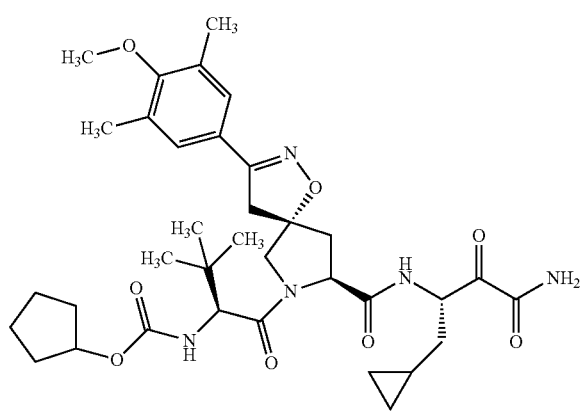
763
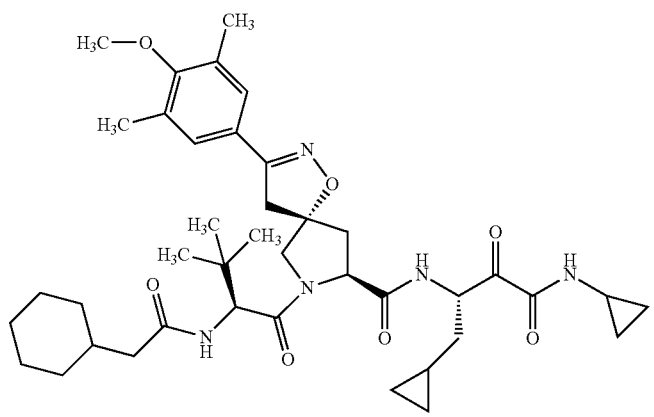
764
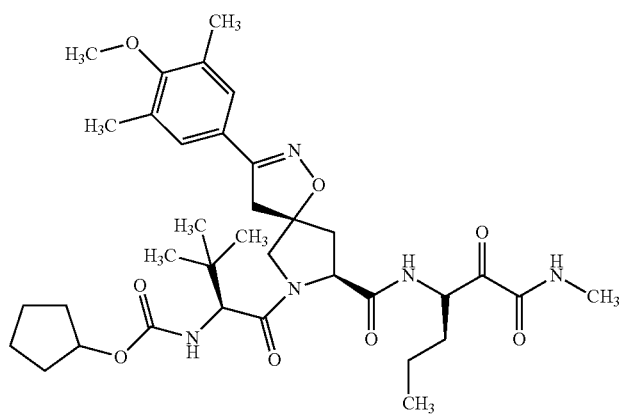
765

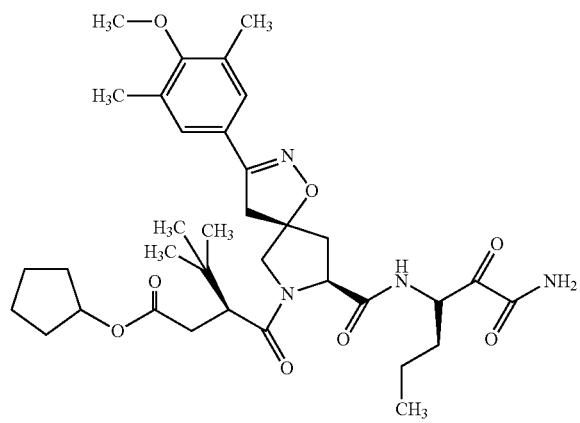
766
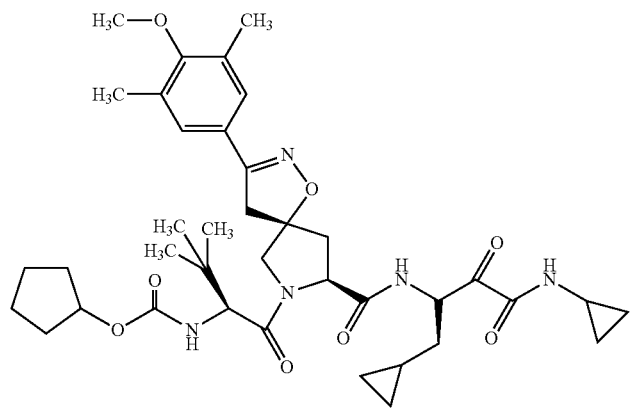
767
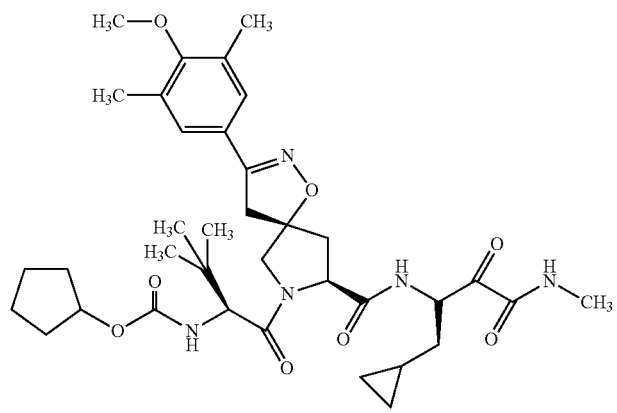
768
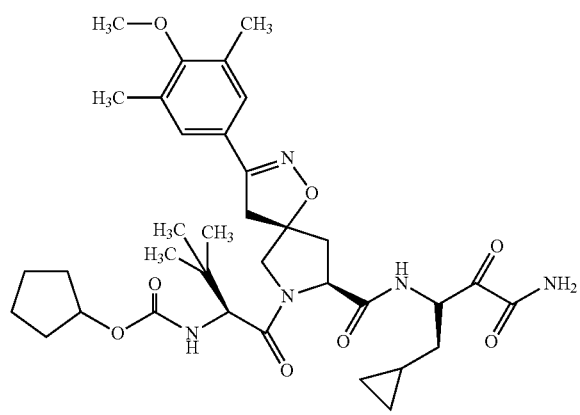
769

770
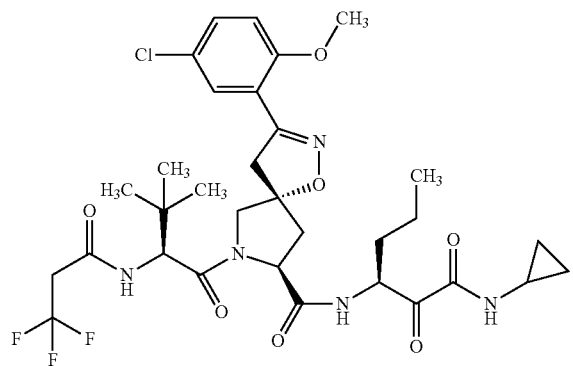
771
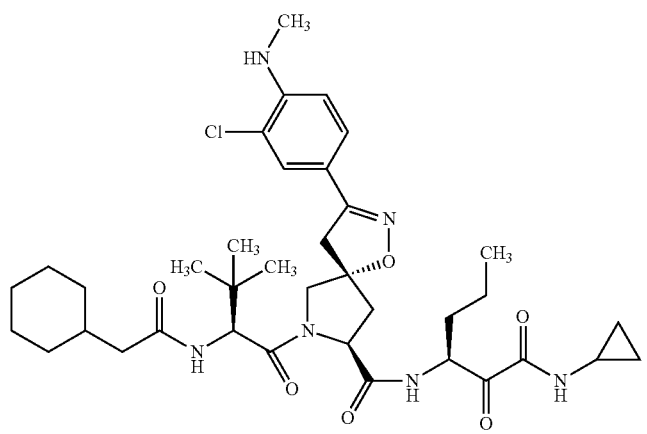
772
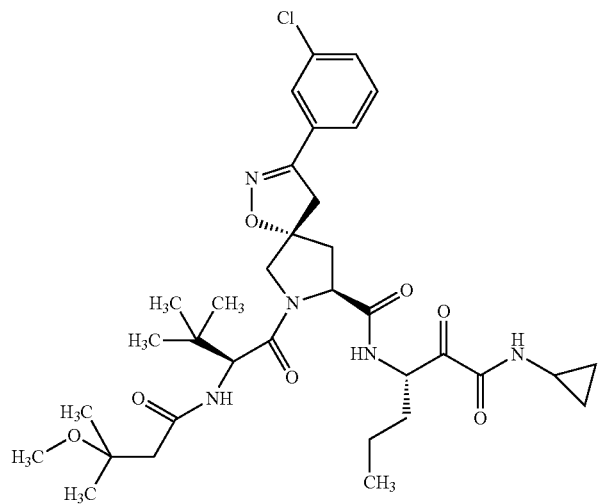

-continued
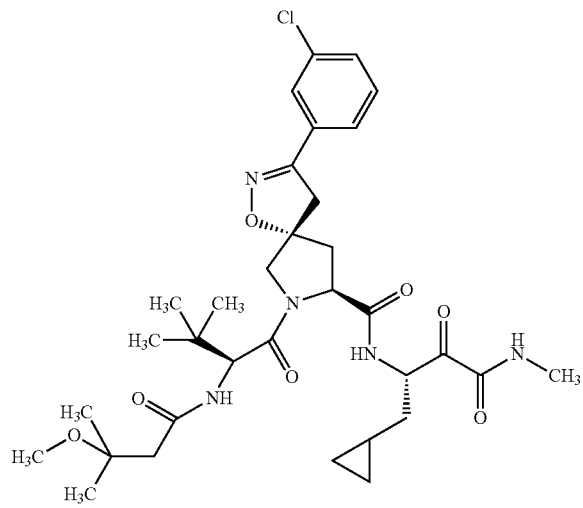
773
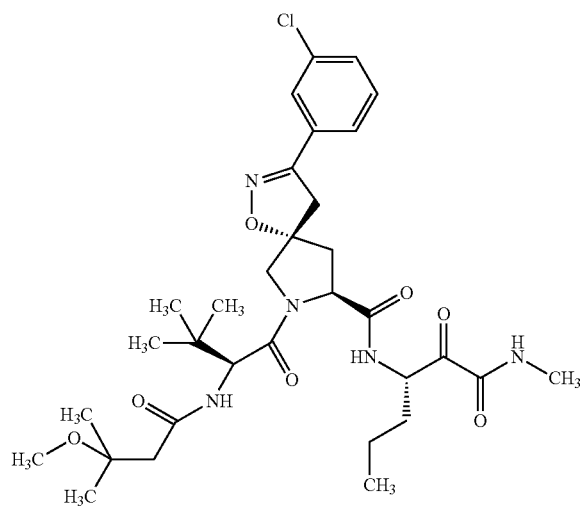
774
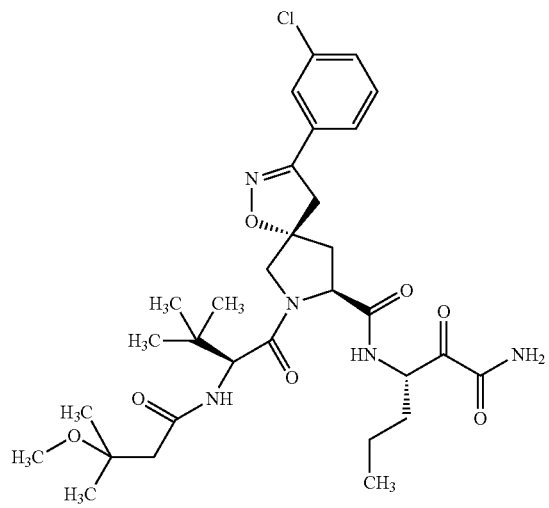
775

-continued
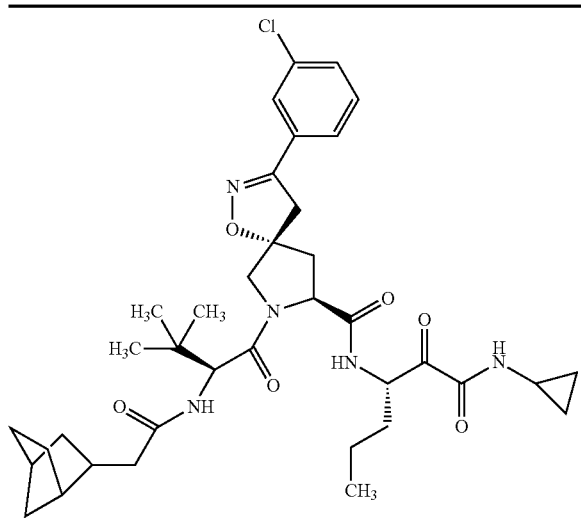
776
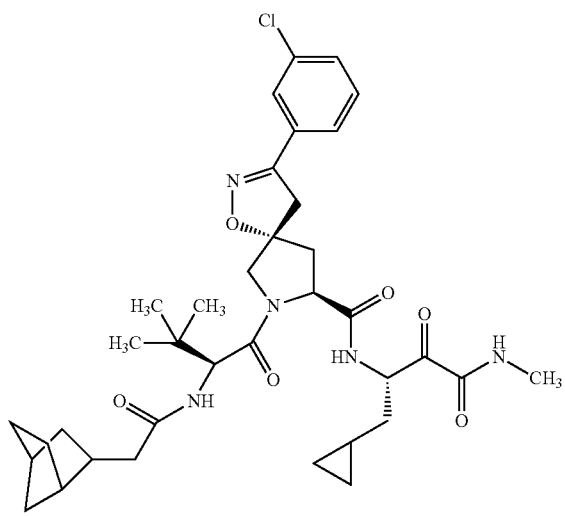
777
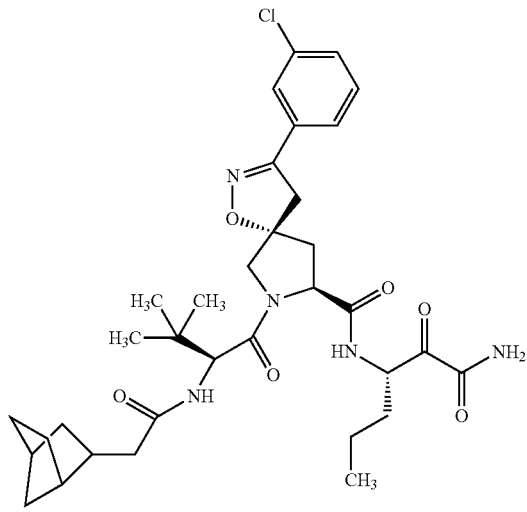
778

-continued
779
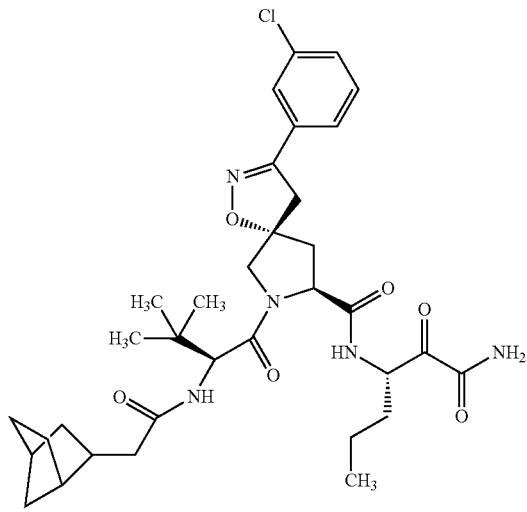
780
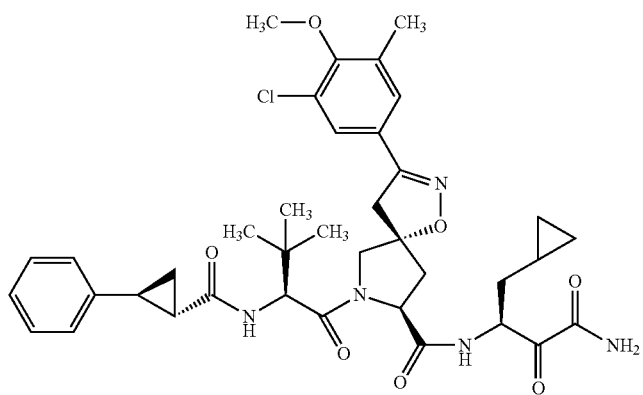
781
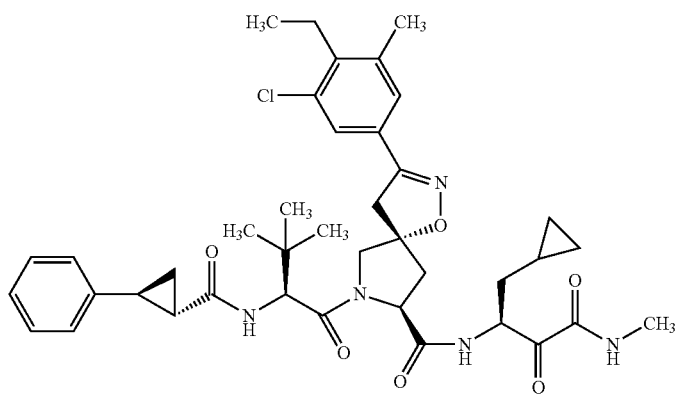

782
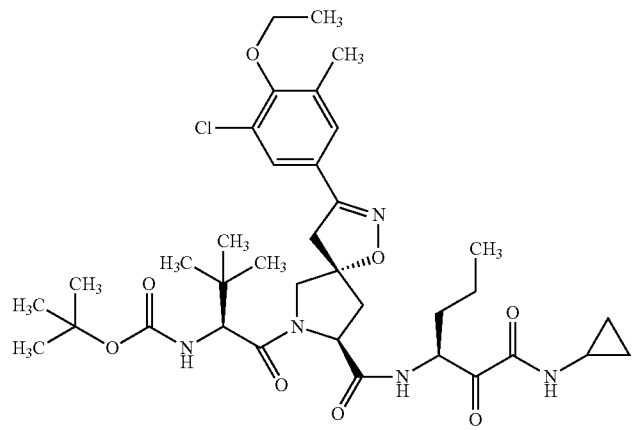
783
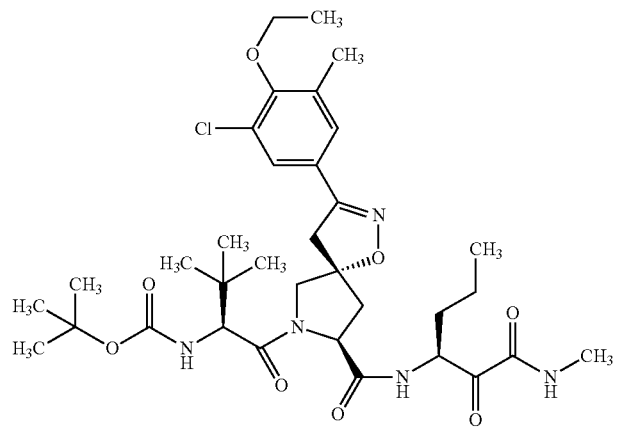
784
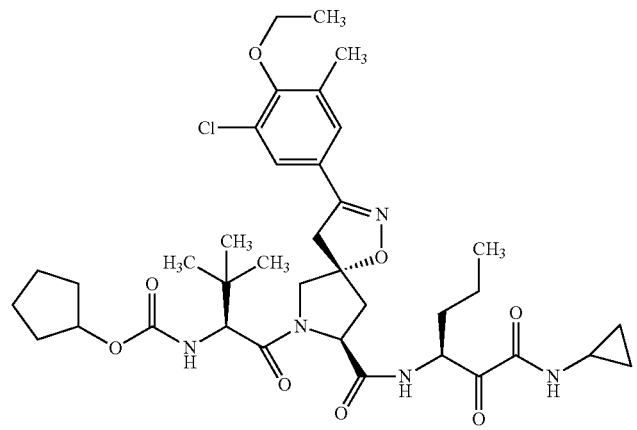

785
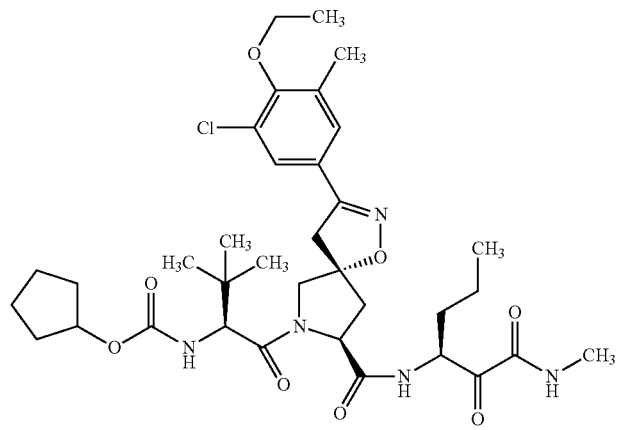
786
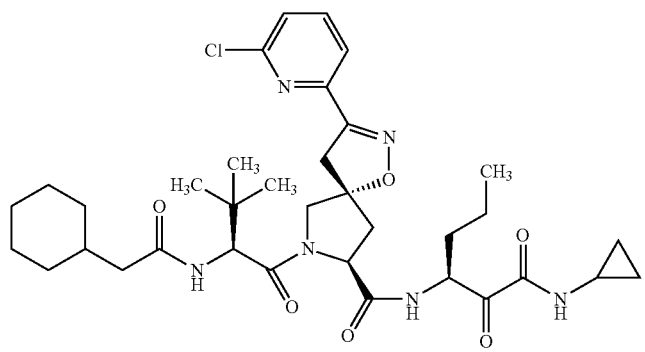
787
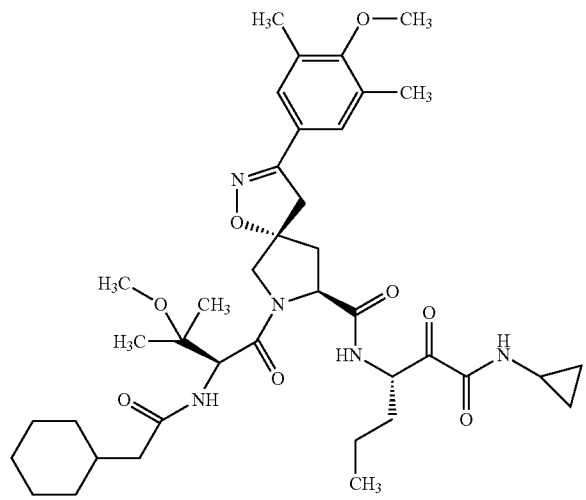

788
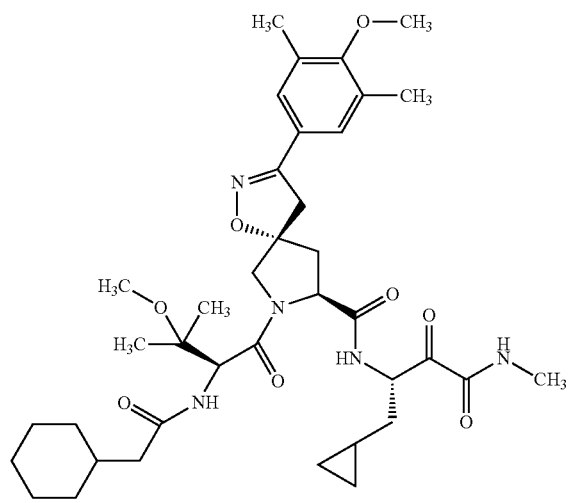
789
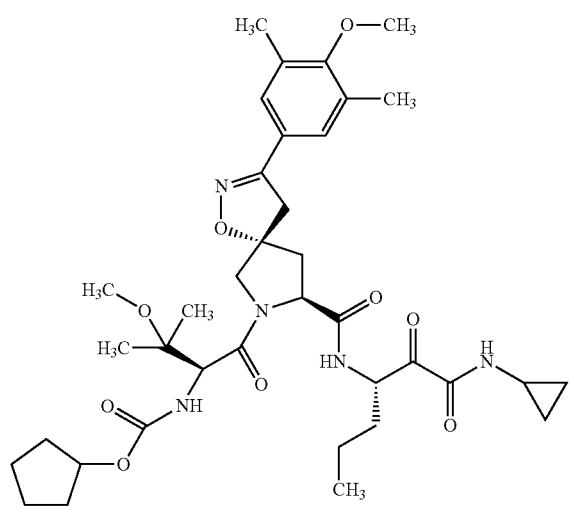
790
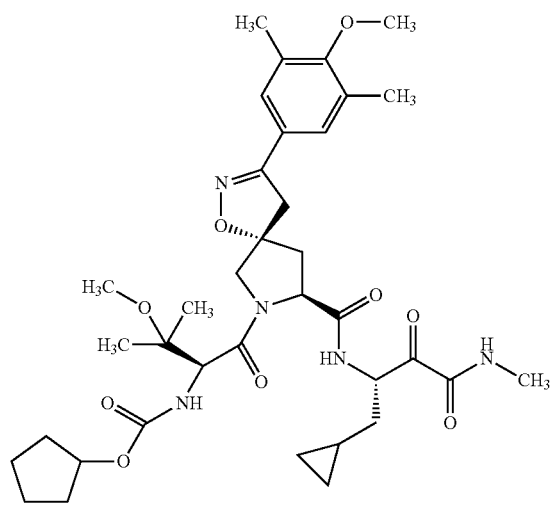

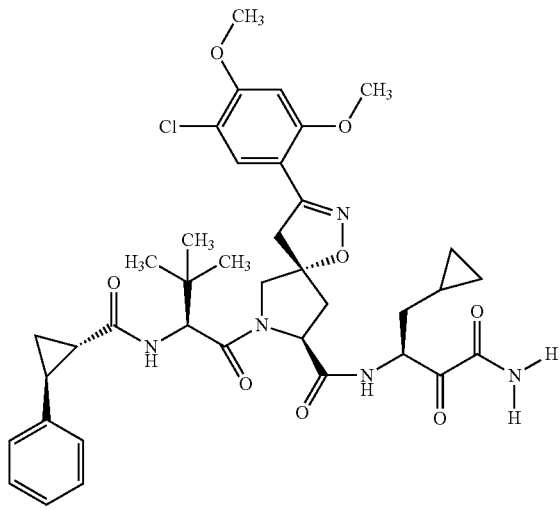
791
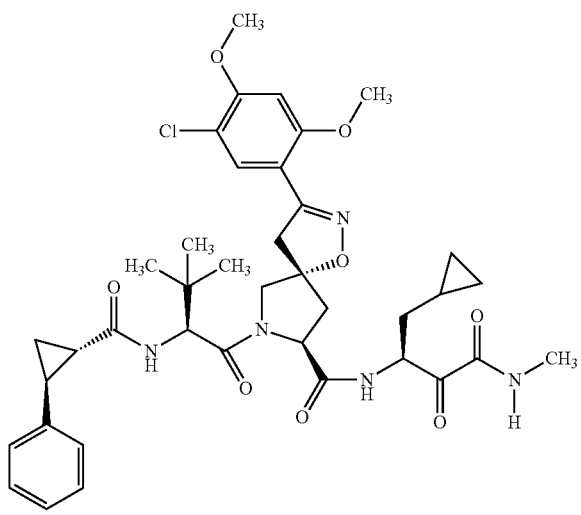
792
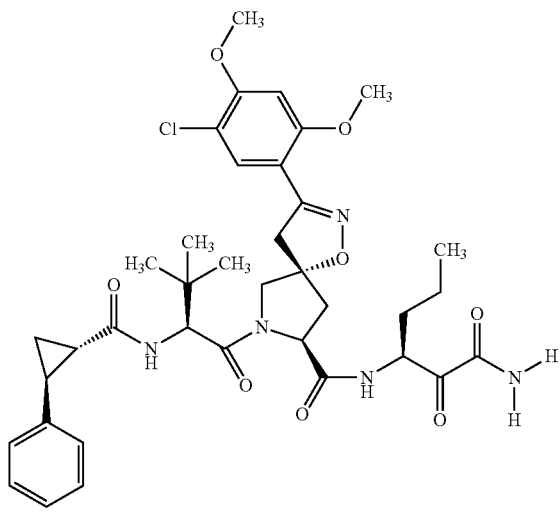
793

794
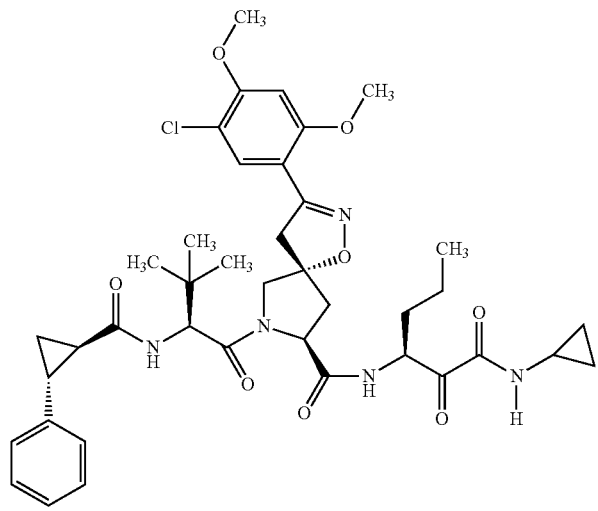
795
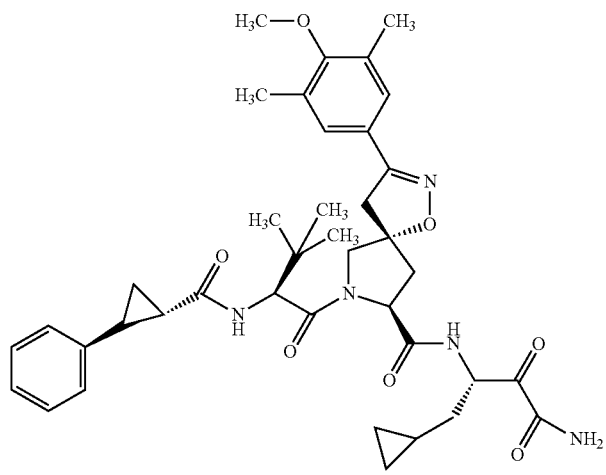
796
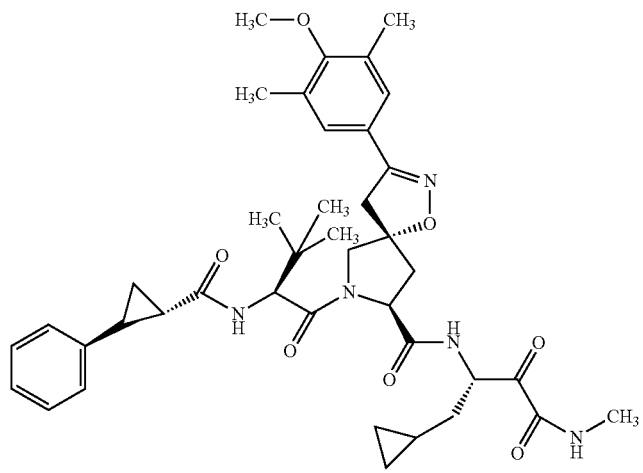

797
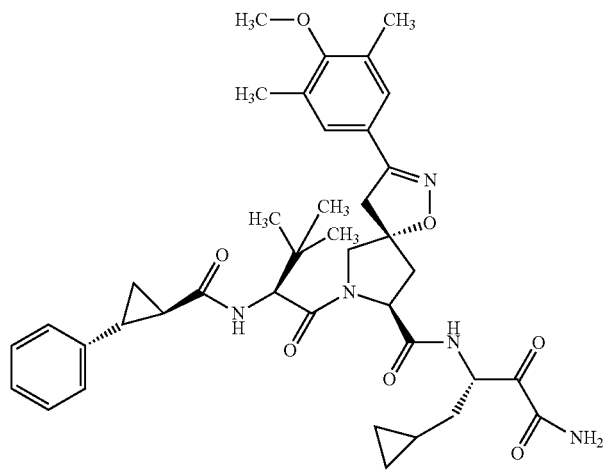
798
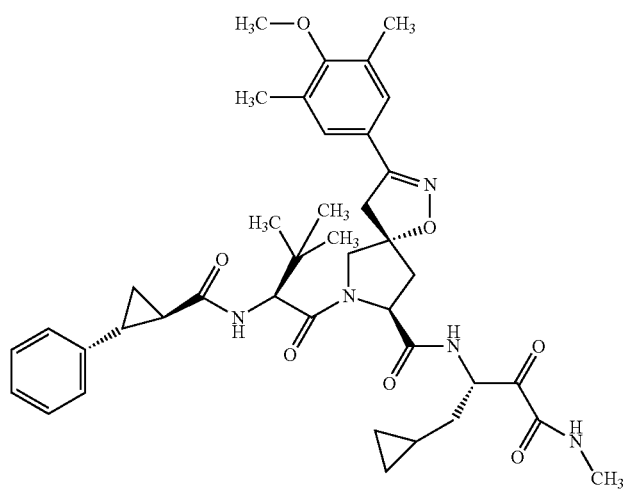
799
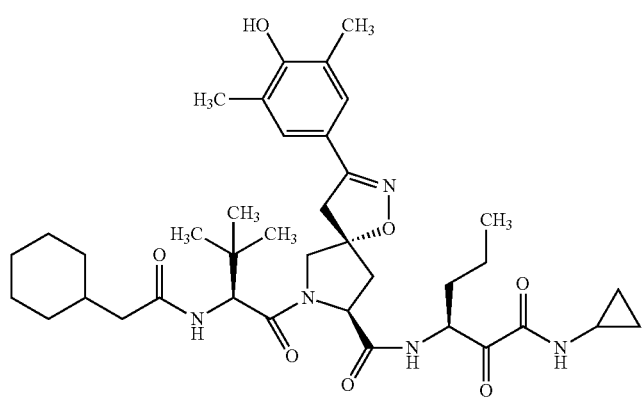

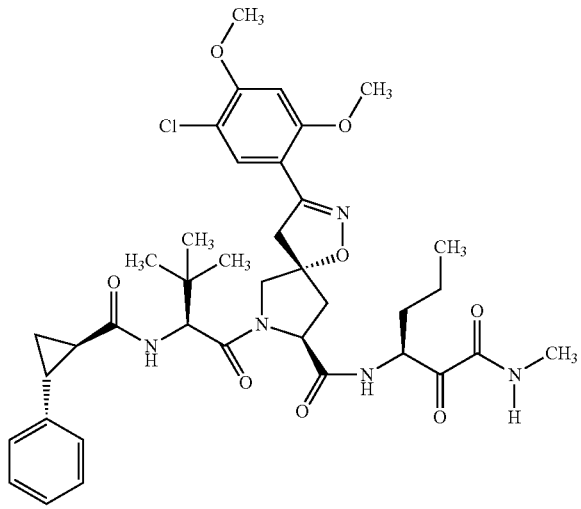
800
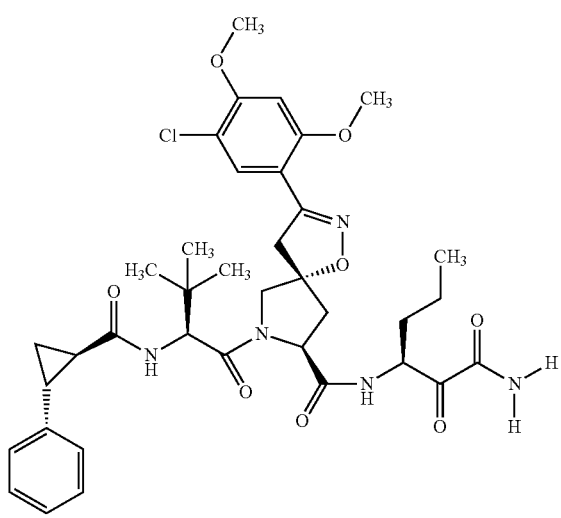
801
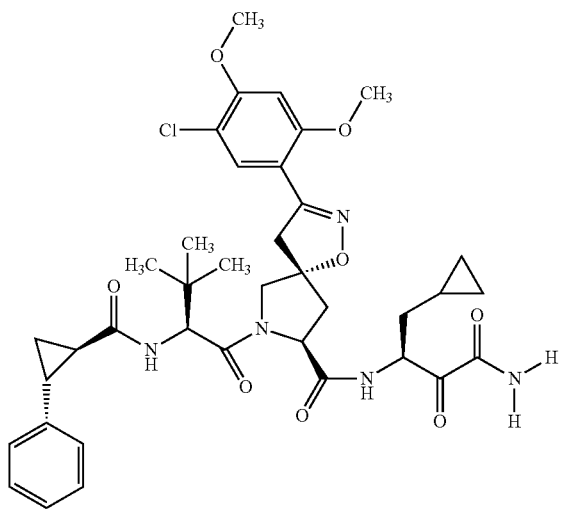
802

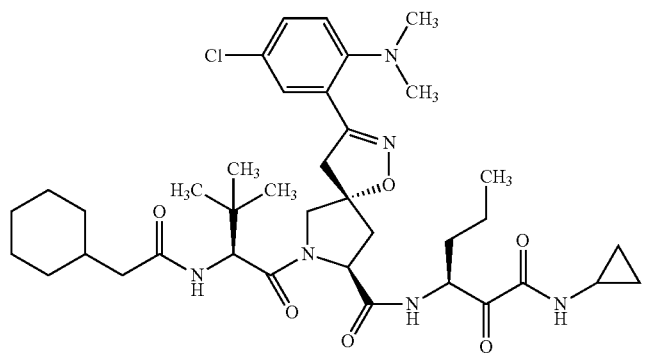
803
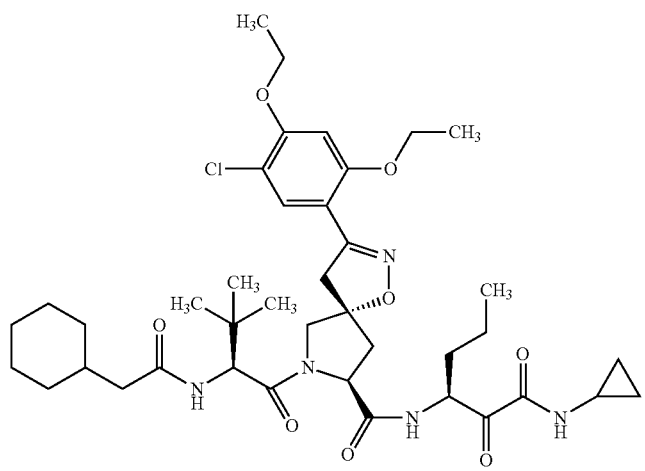
804
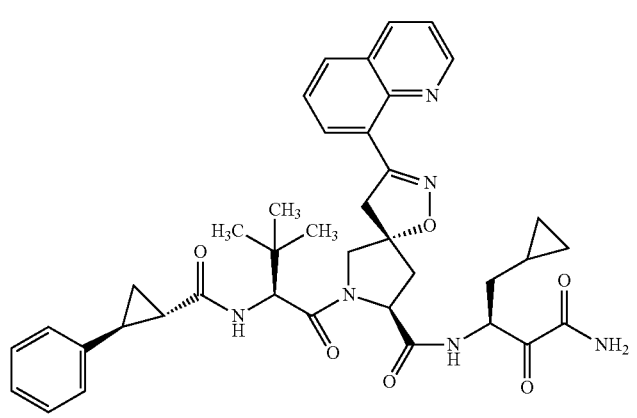
805
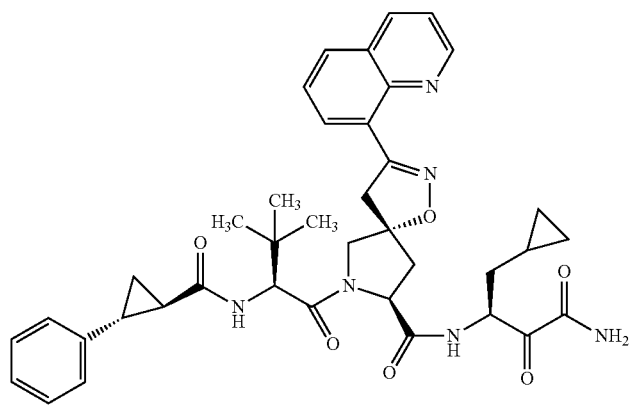
806

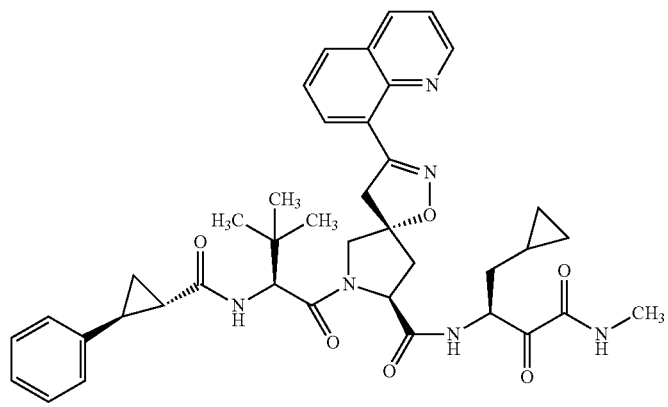
807
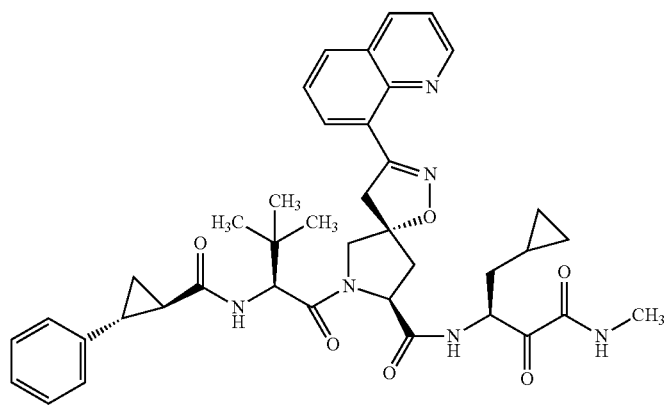
808
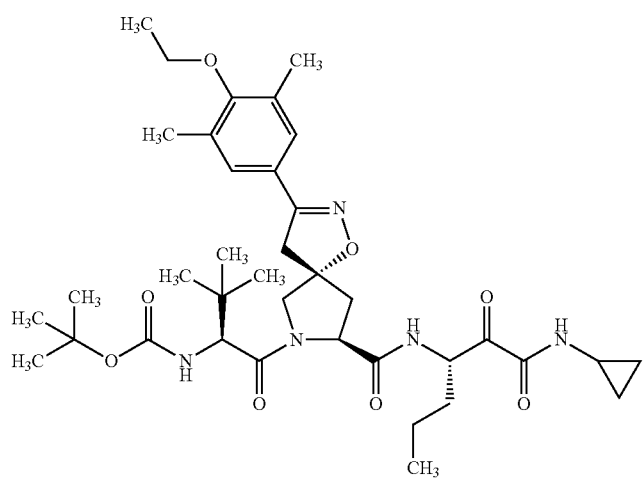
809

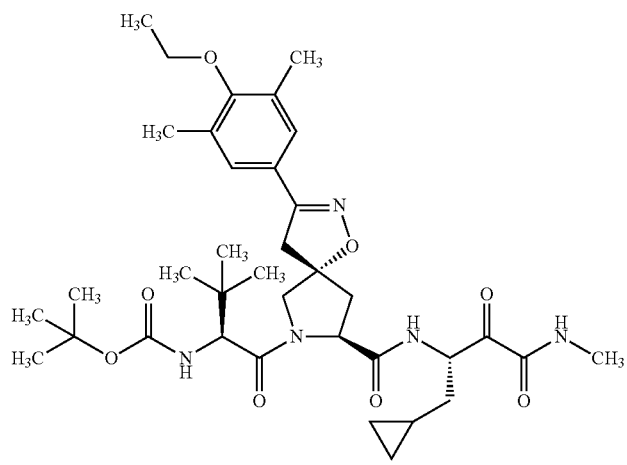
810
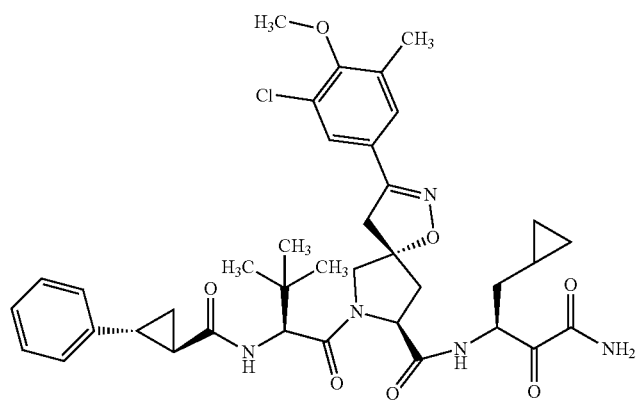
811
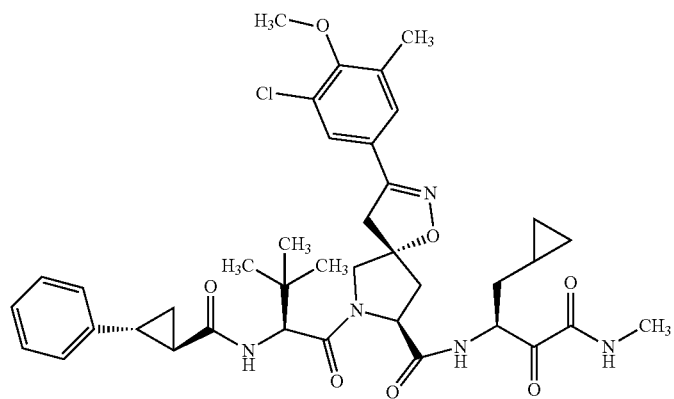
812
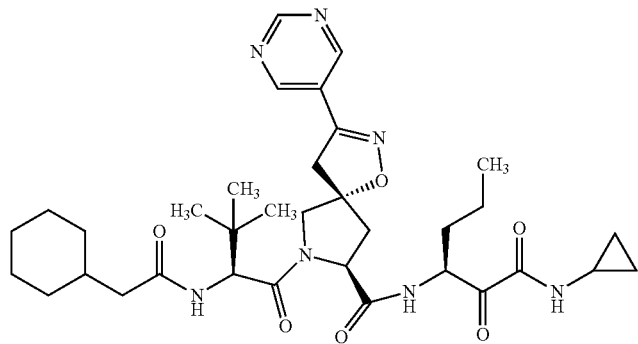
813

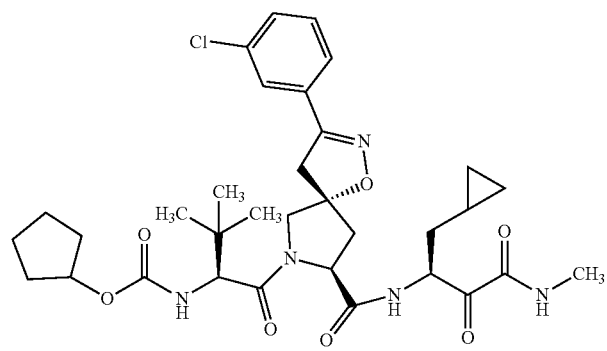
814
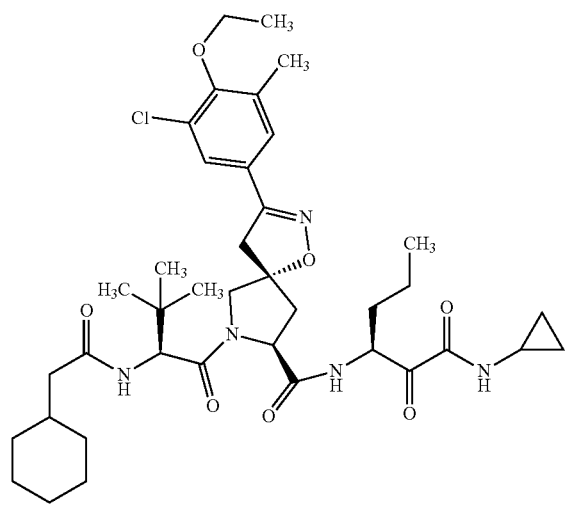
815
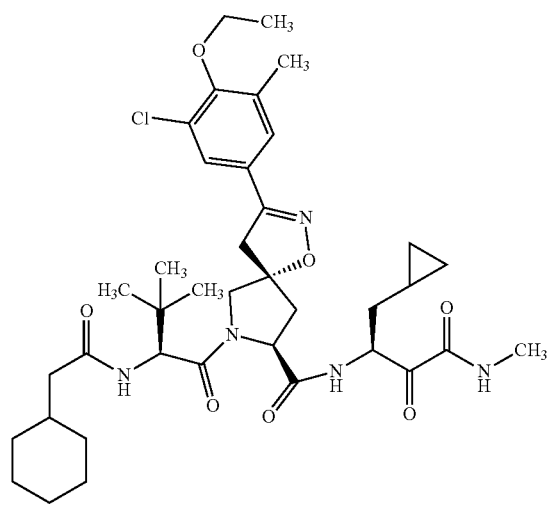
816

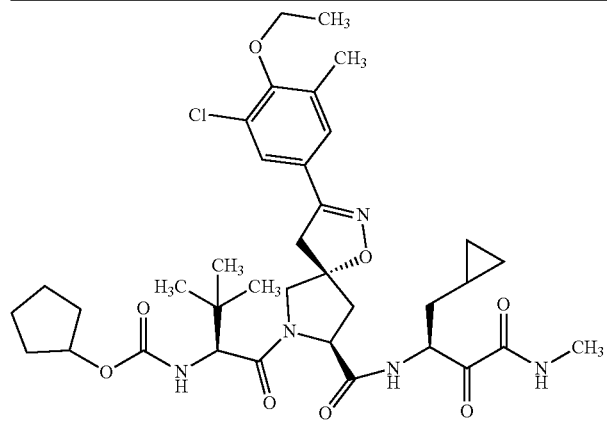
817
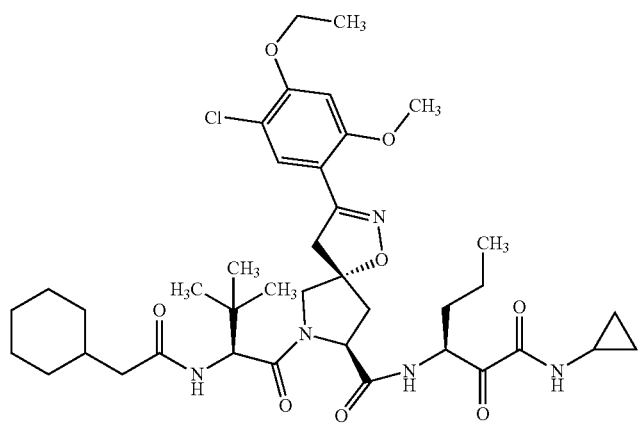
818
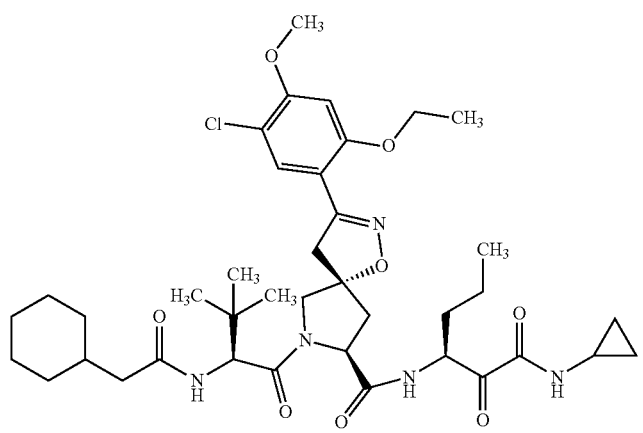
819
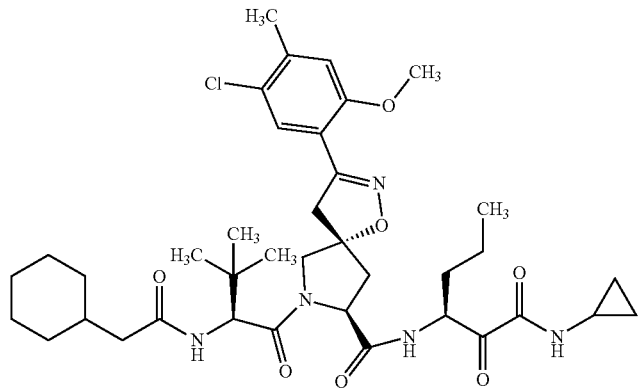
820

821
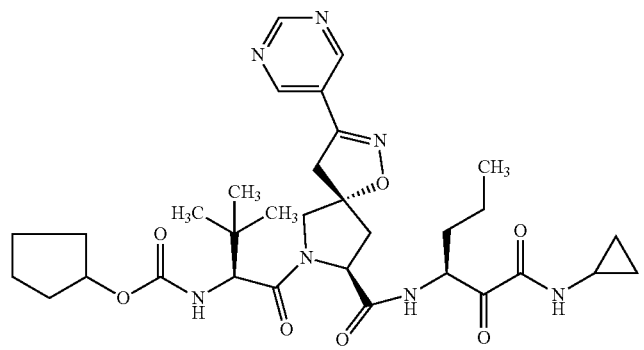
822
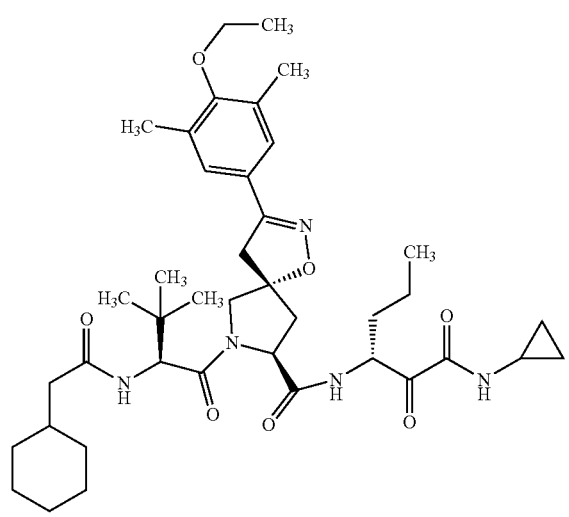
823
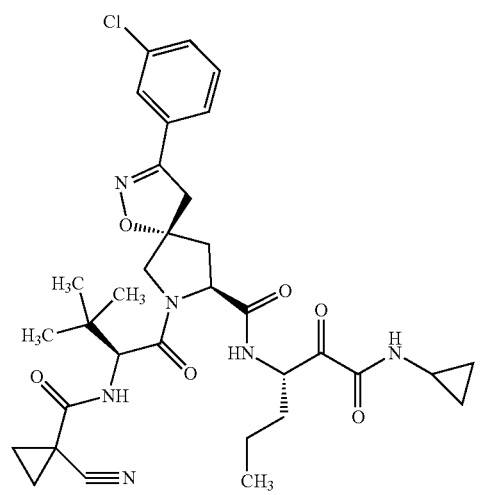

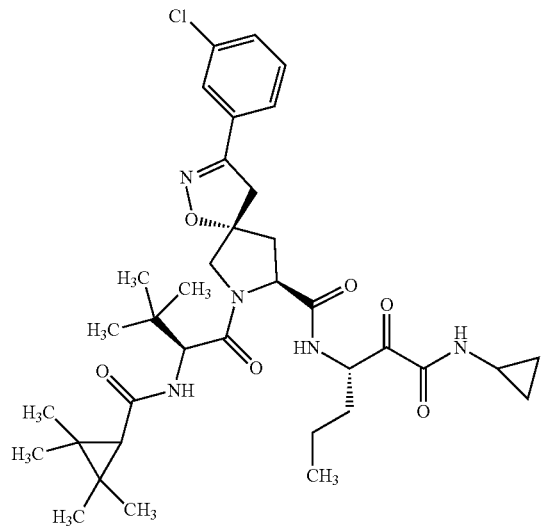
824
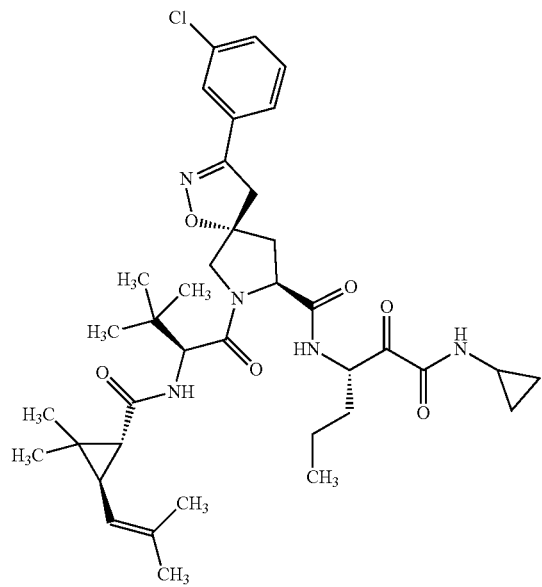
825
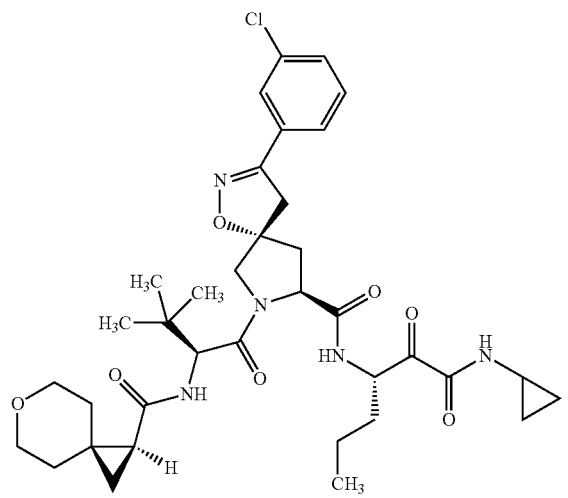
826

827
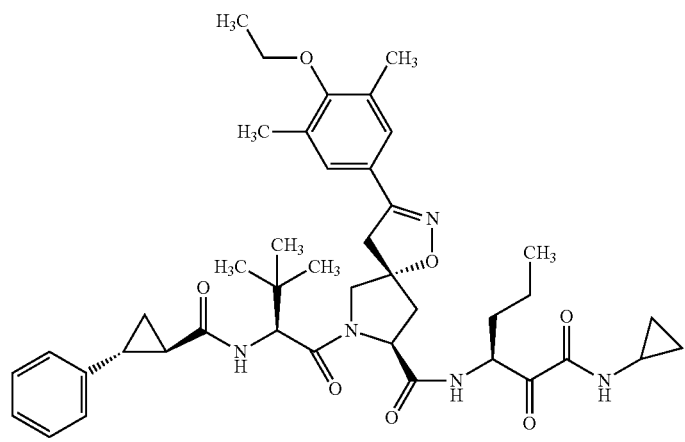
828
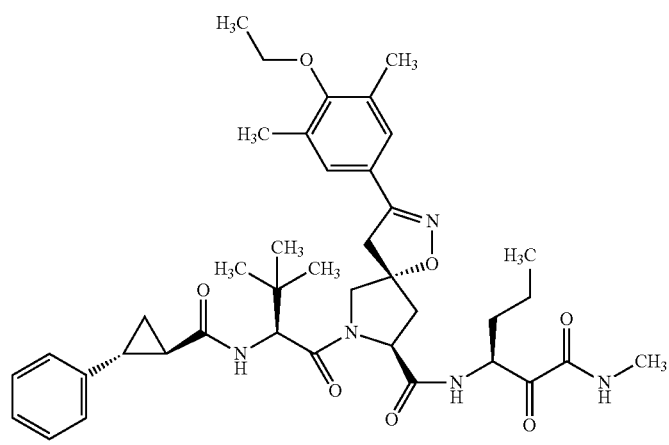
829
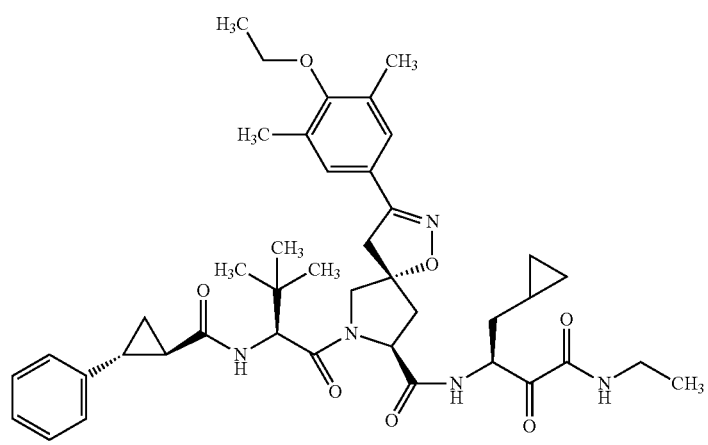

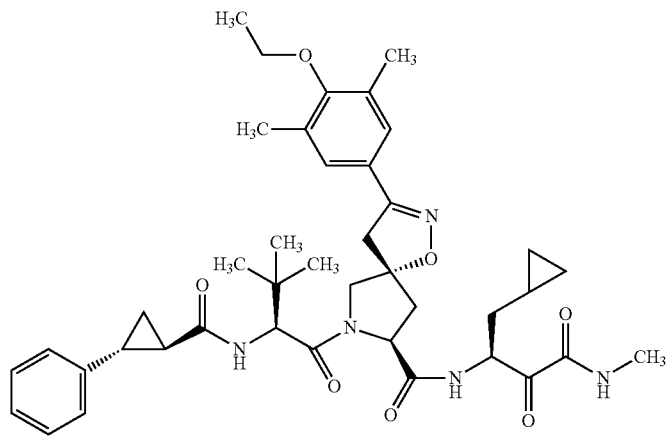
830
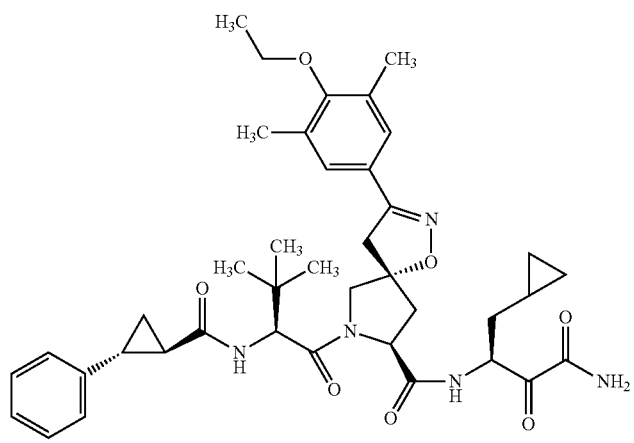
831
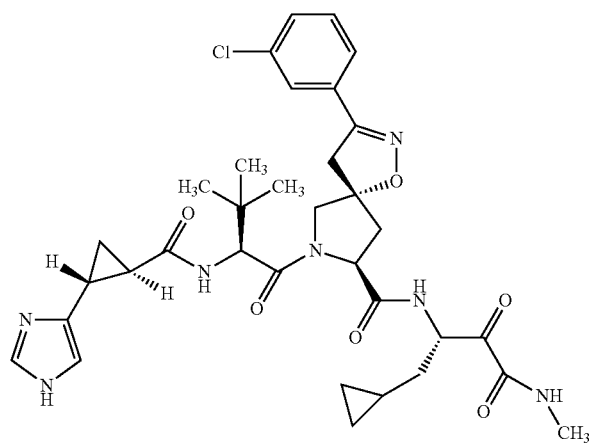
832

833
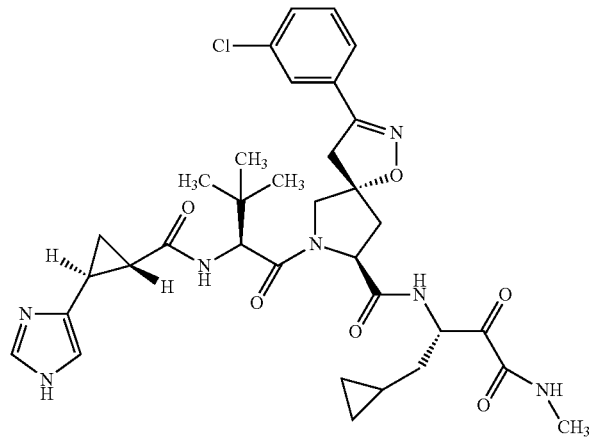
834
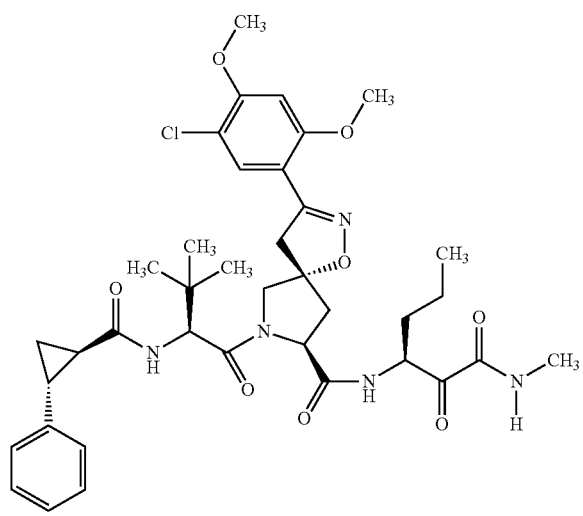
835
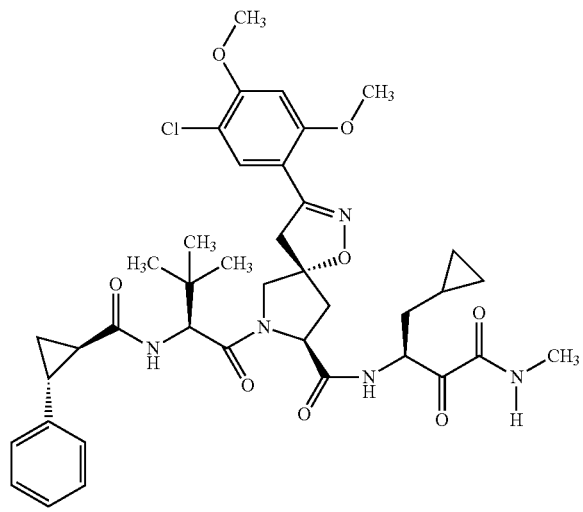

836
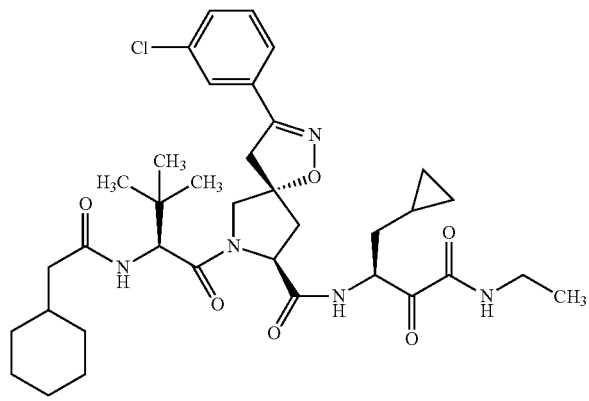
837
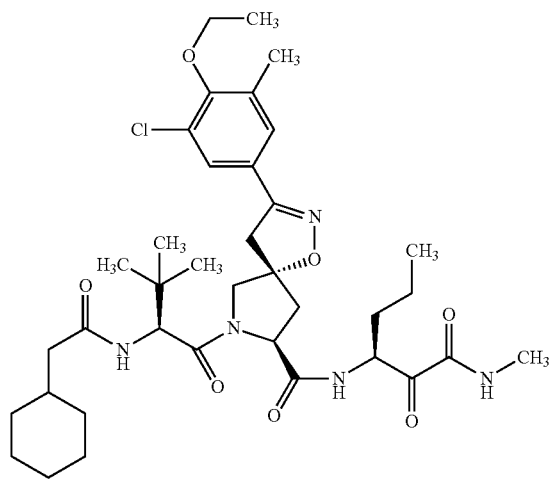
838
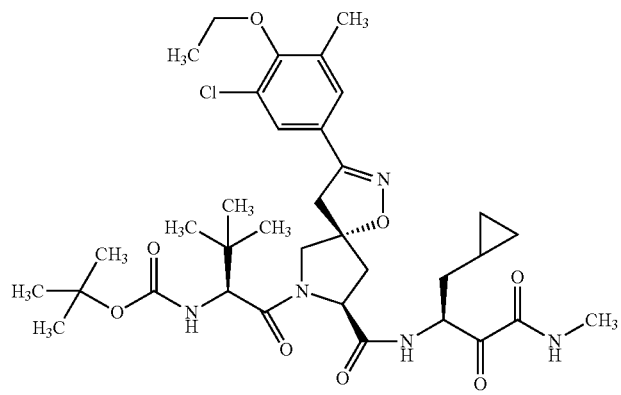

839
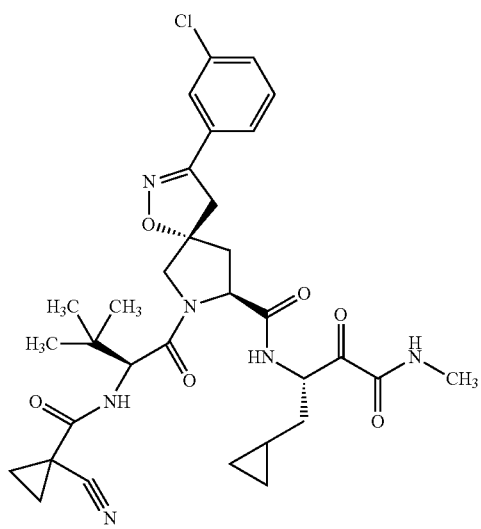
840
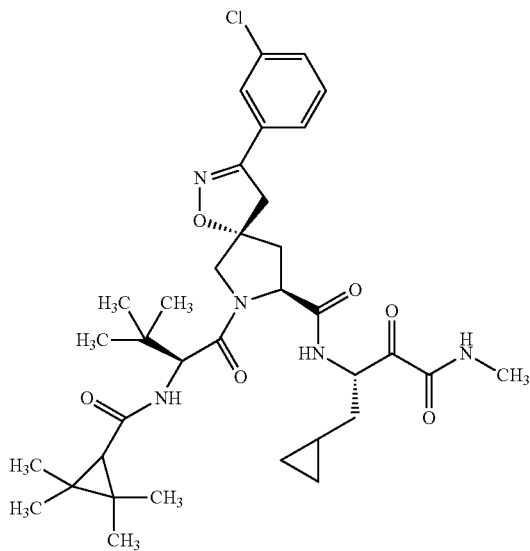
841
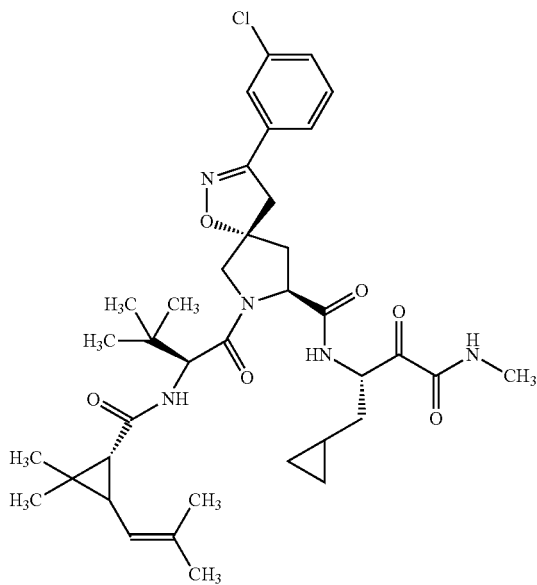

842
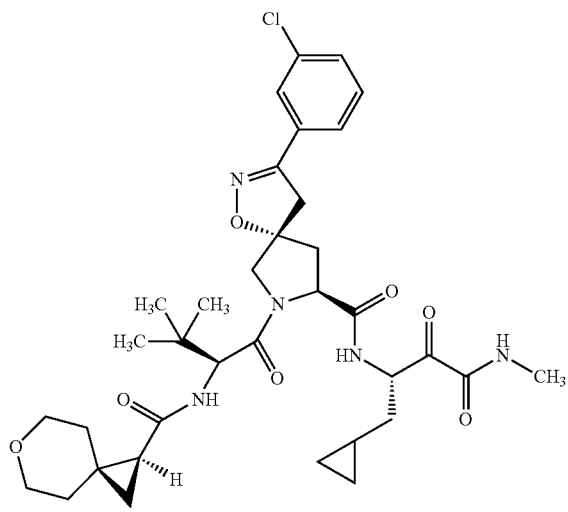
843
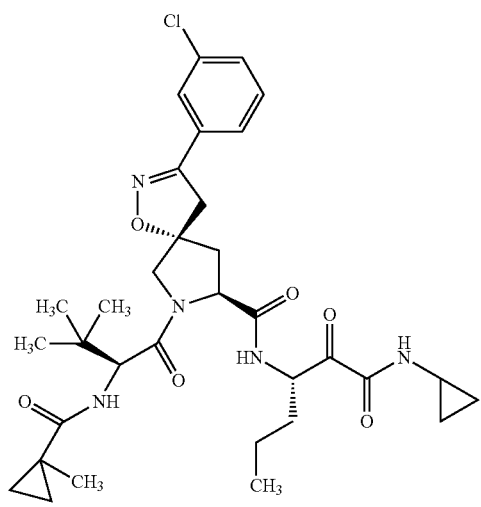
844
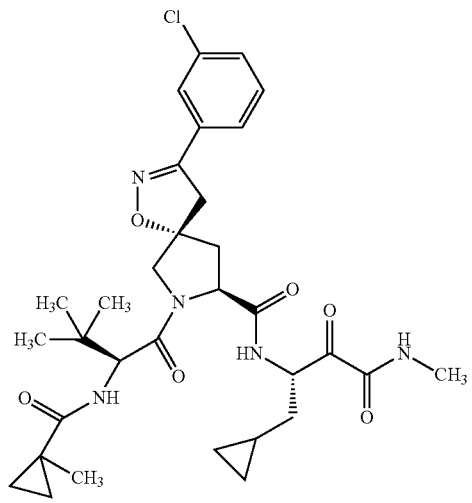

845
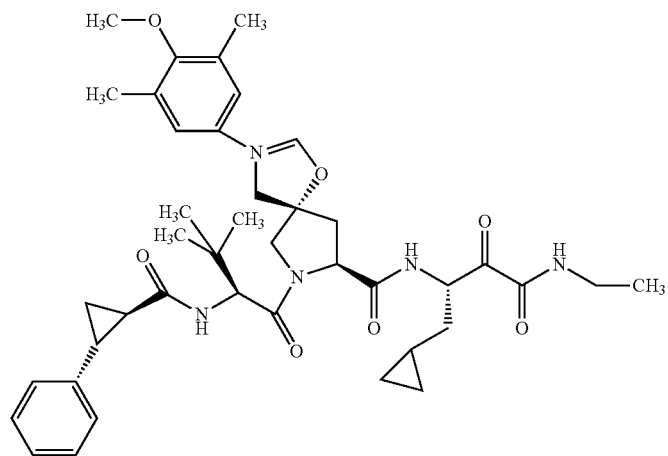
846
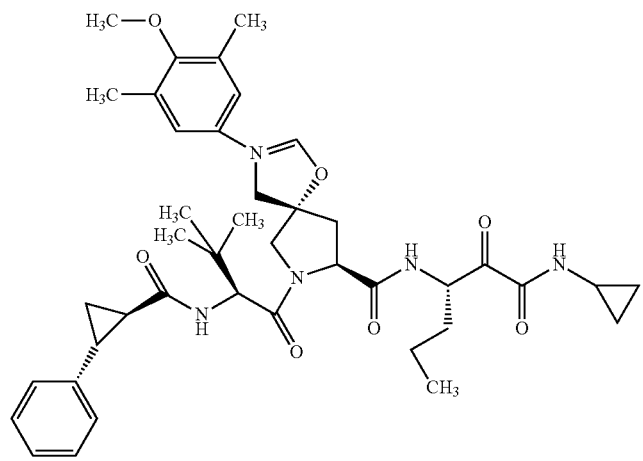
847
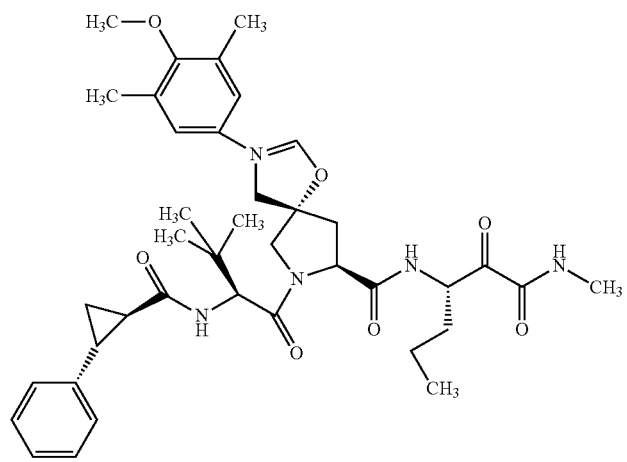

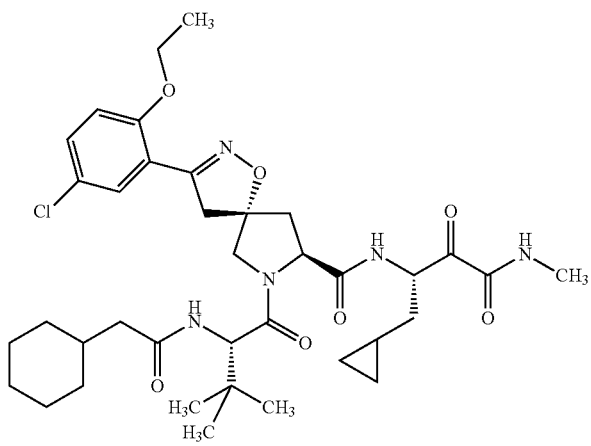
848
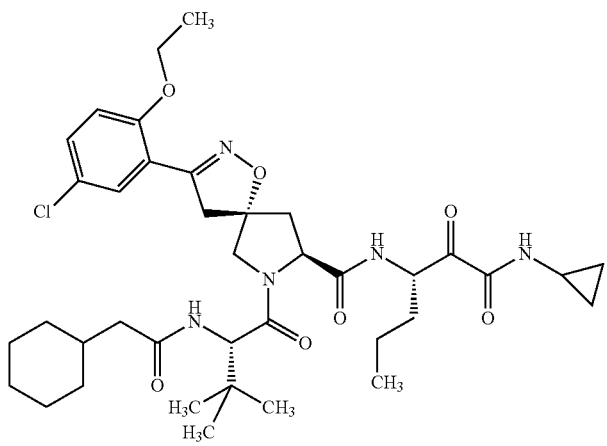
849
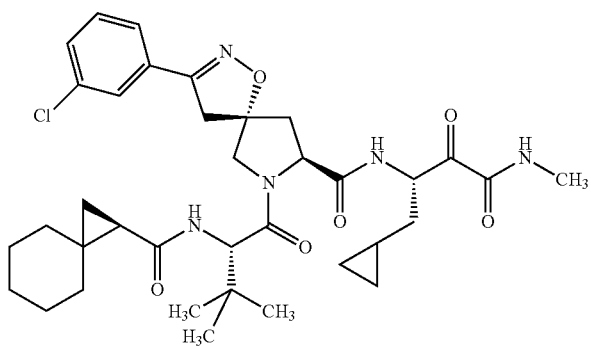
850
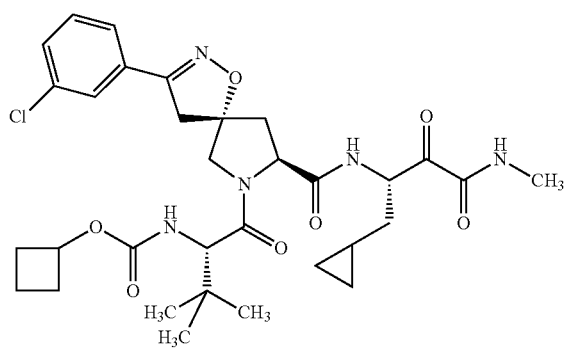
851

852
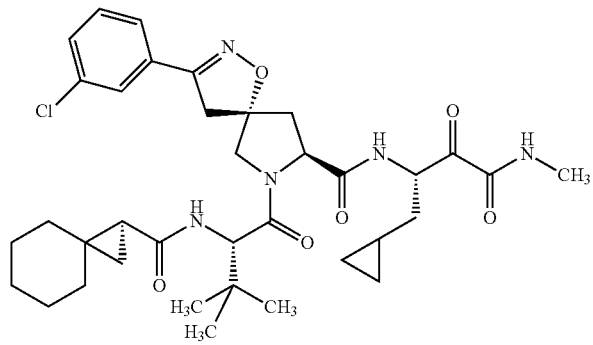
853
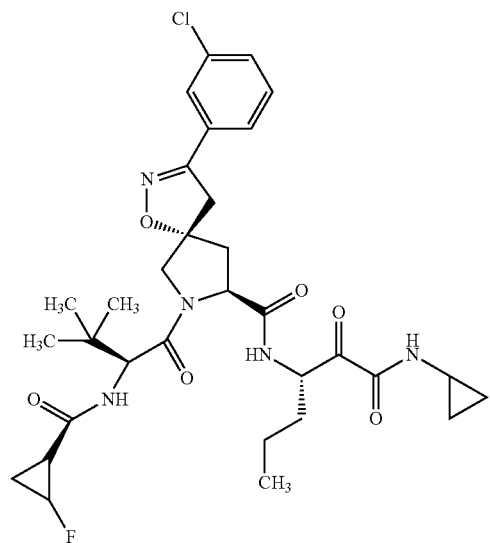
854
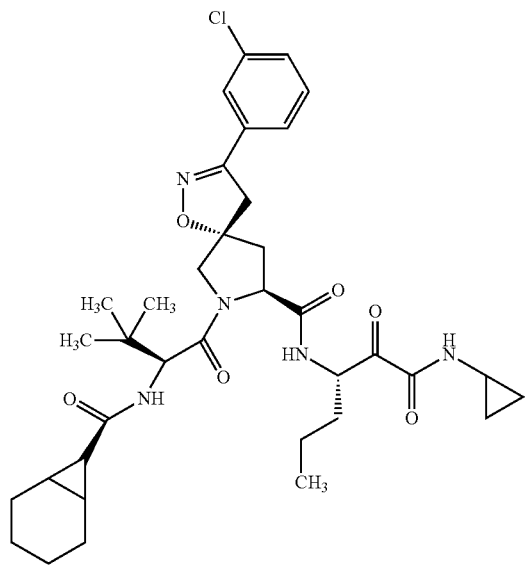

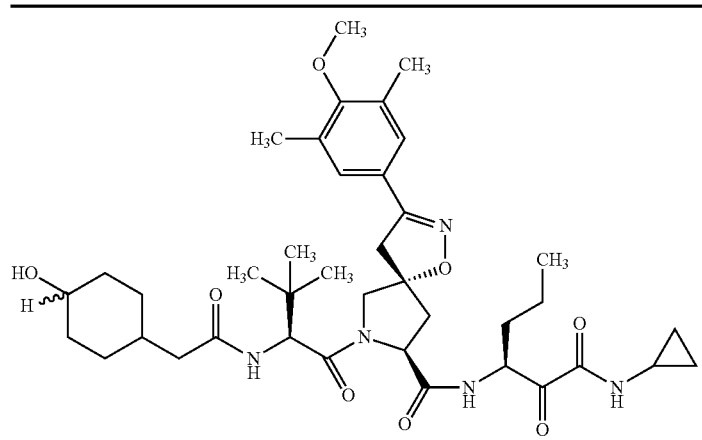
855
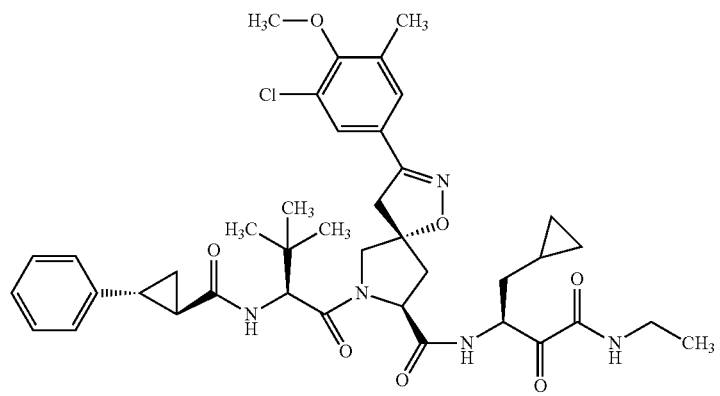
856
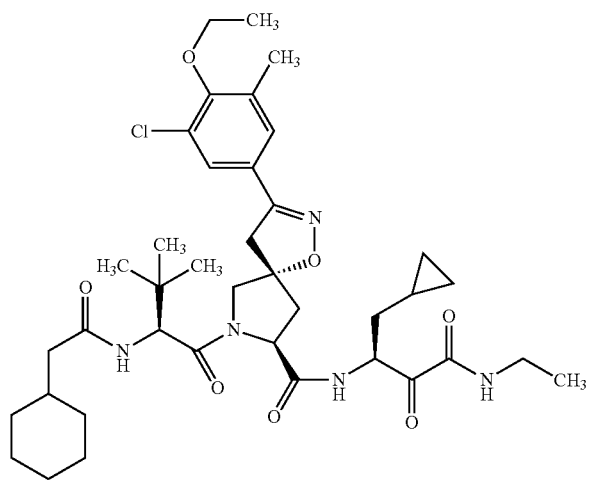
857
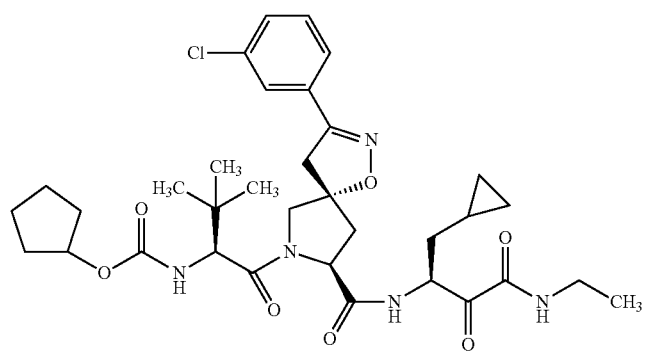
858

859
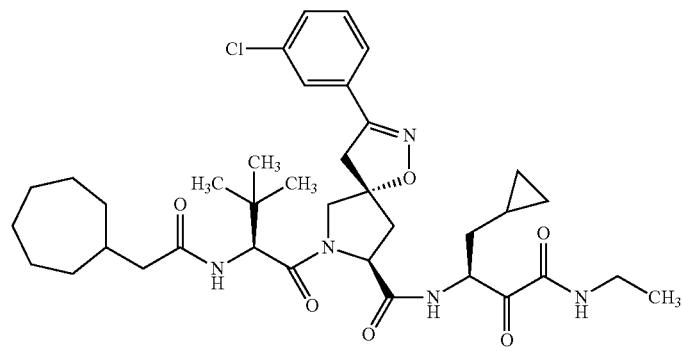
860
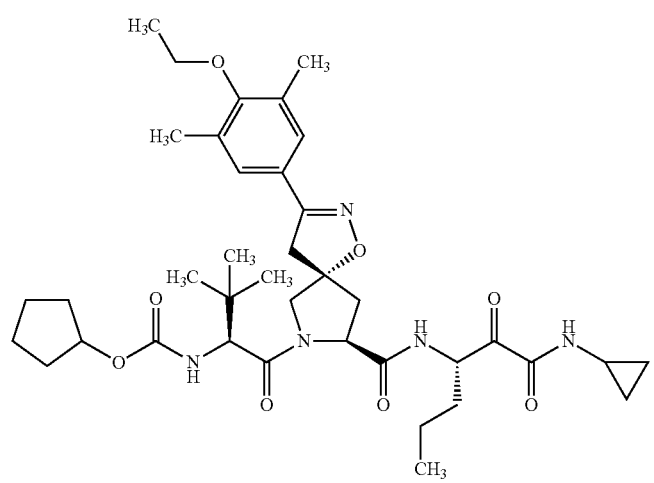
861
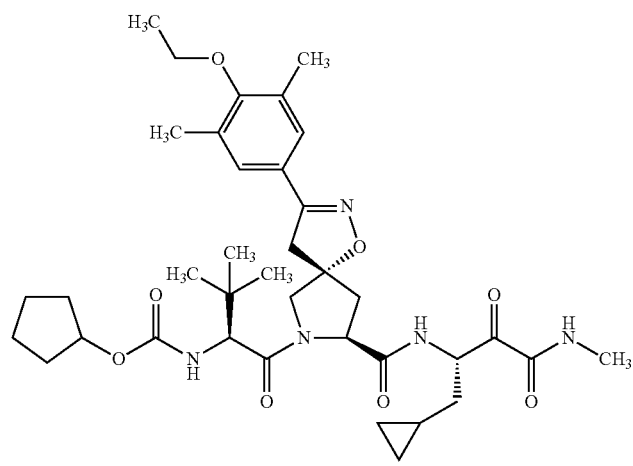

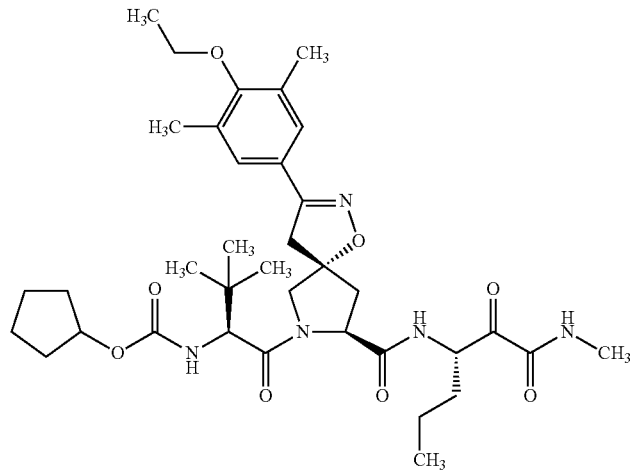
862
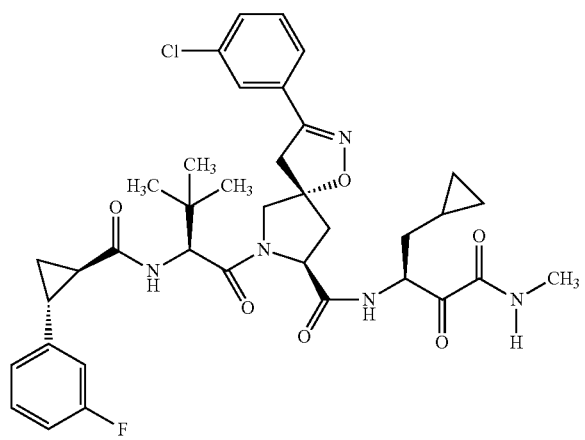
863
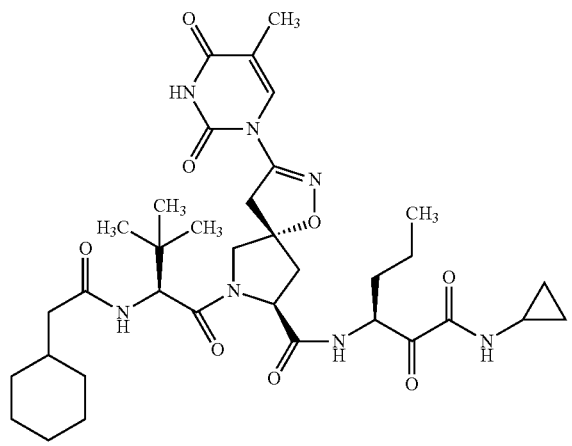
864

865
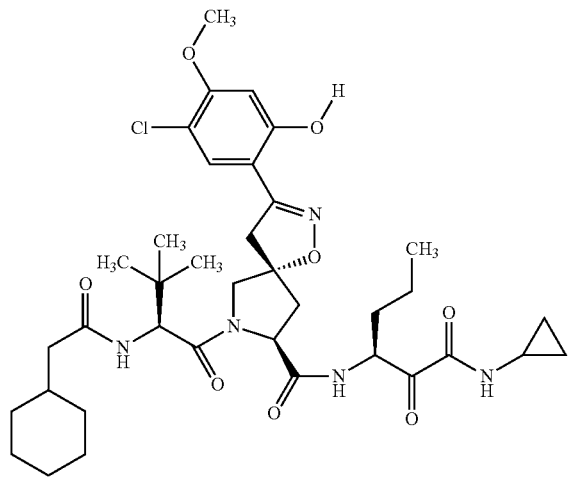
866
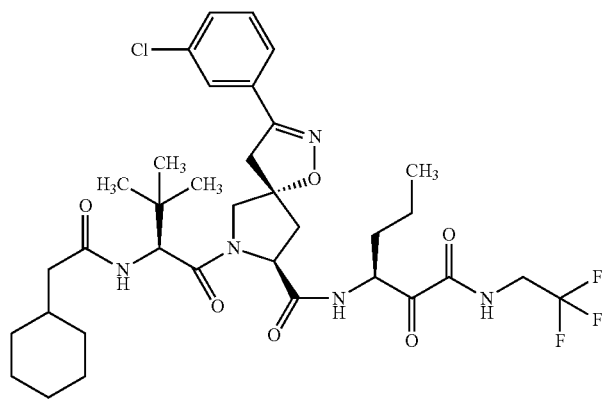
867
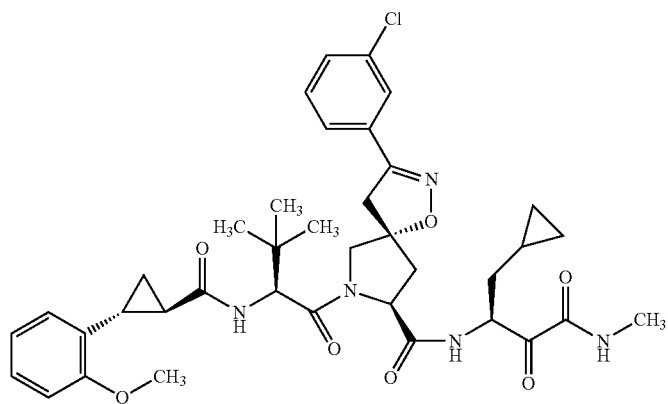

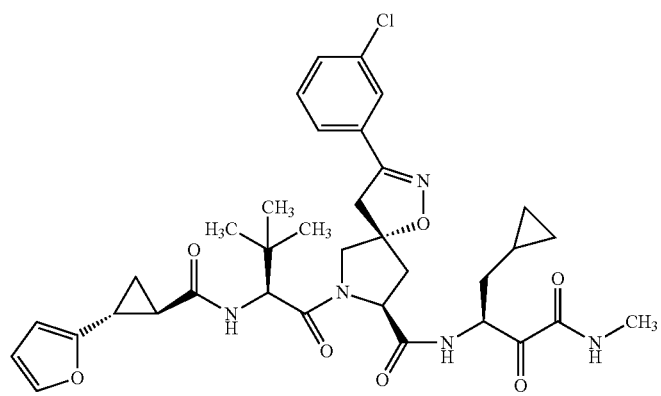
868
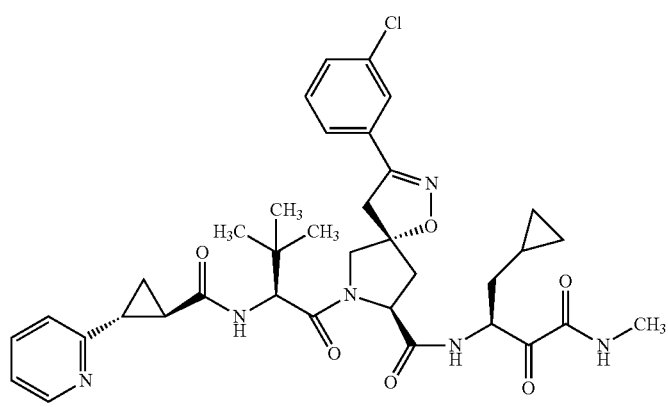
869
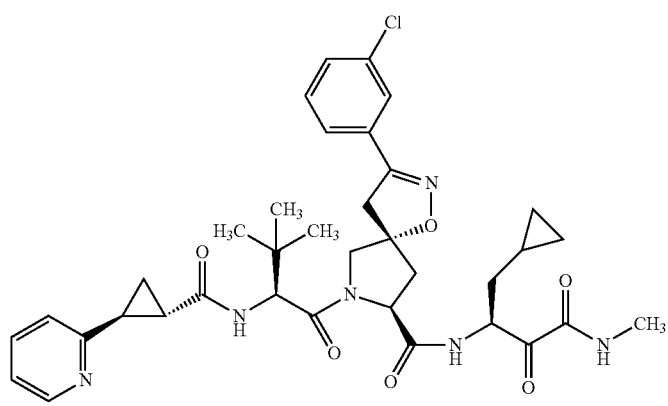
870
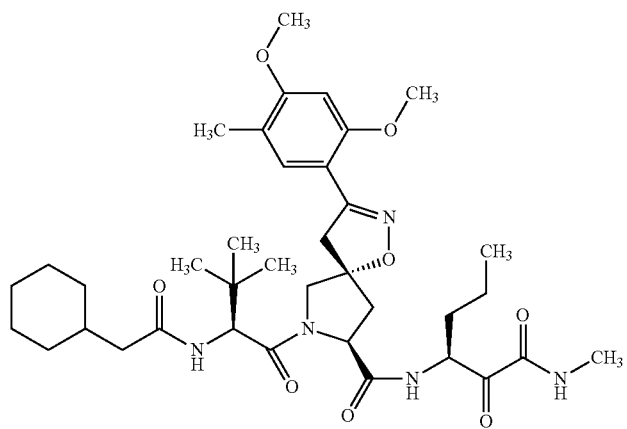
871

872
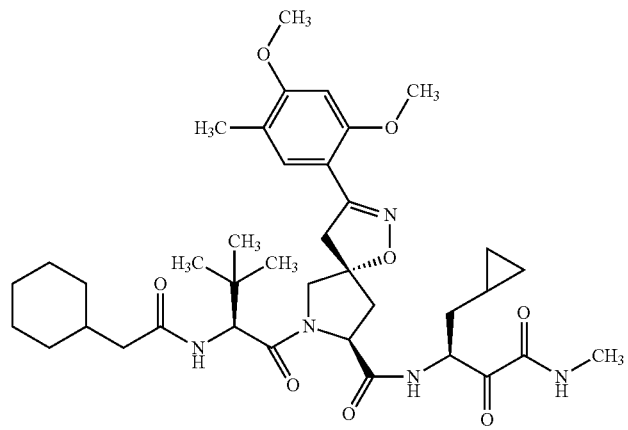
873
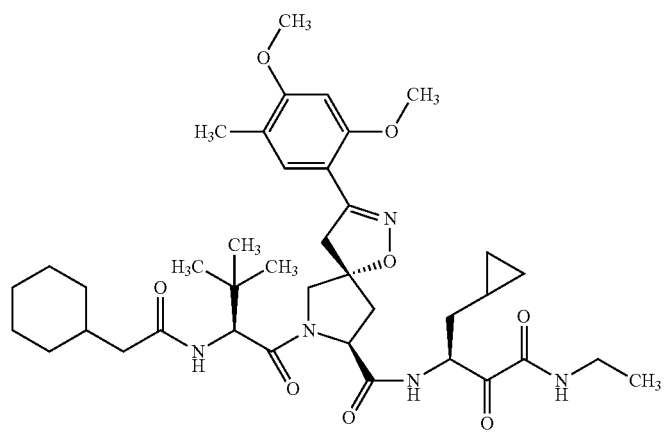
874
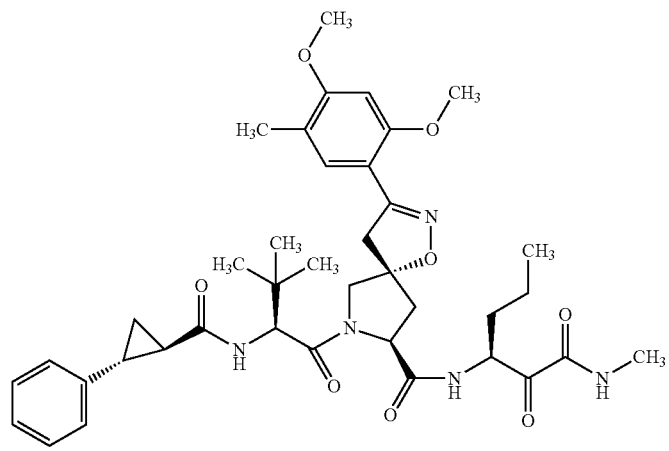

875
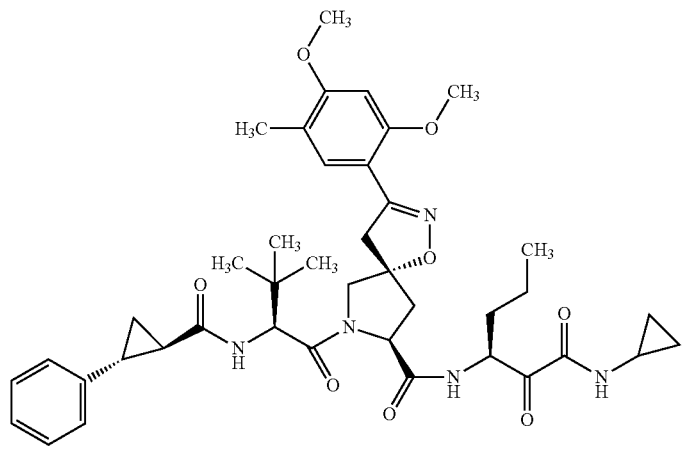
876
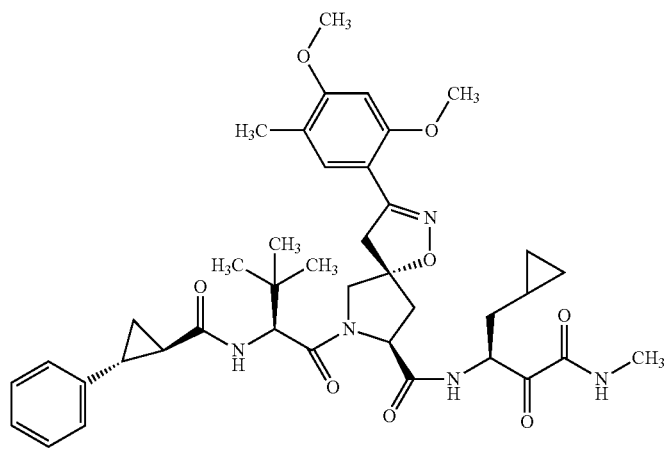
877
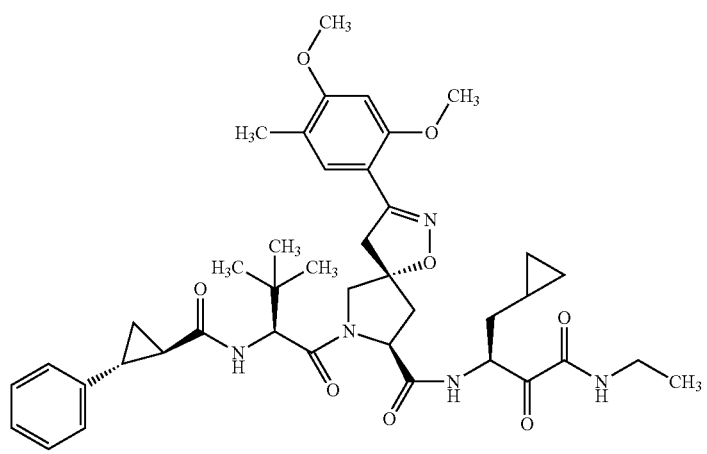

878
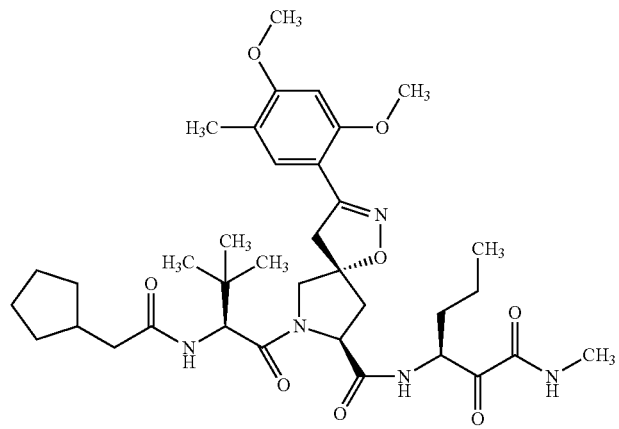
879
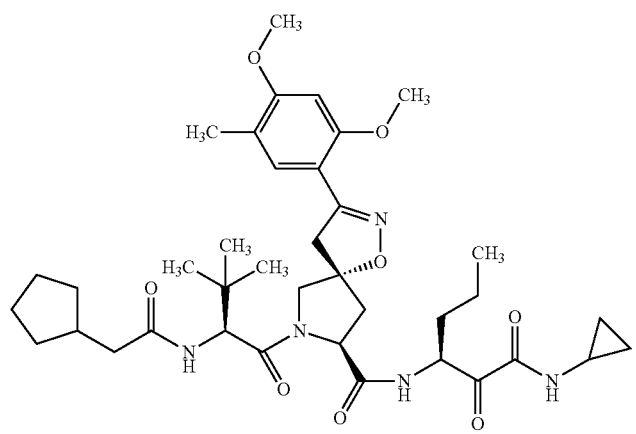
880
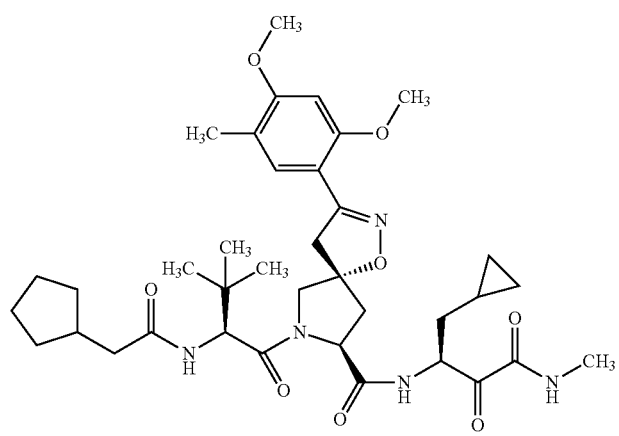

-continued
881
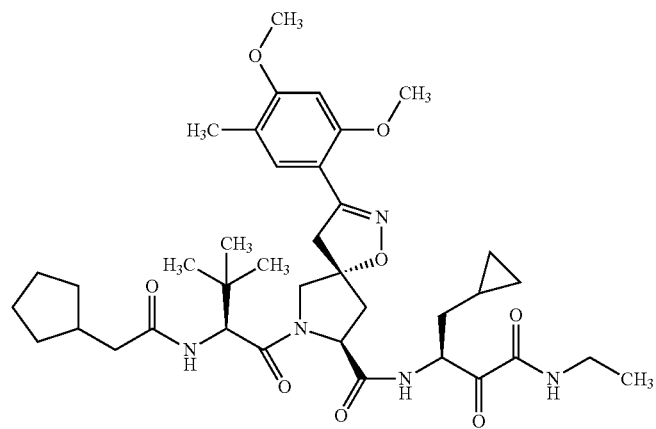
882
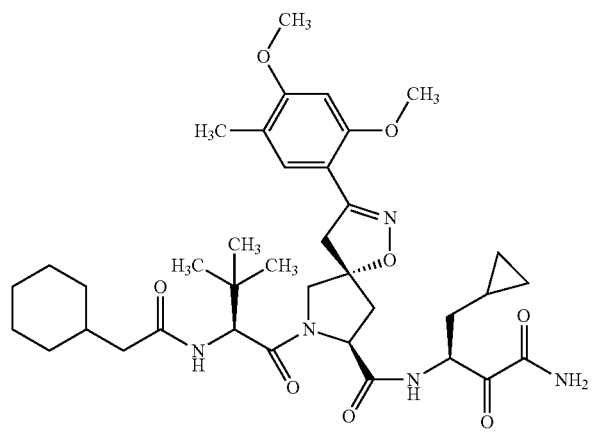
883
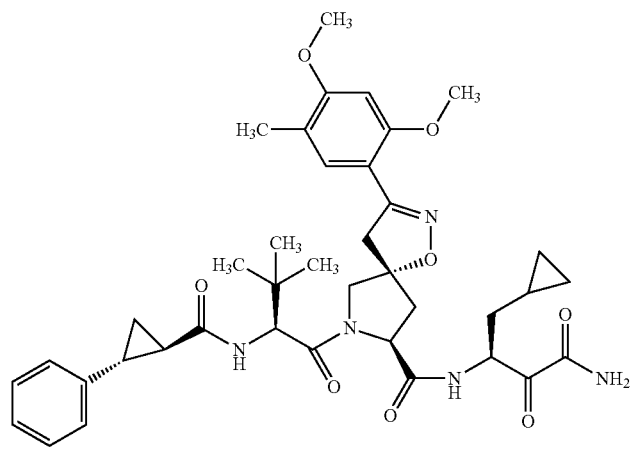

884
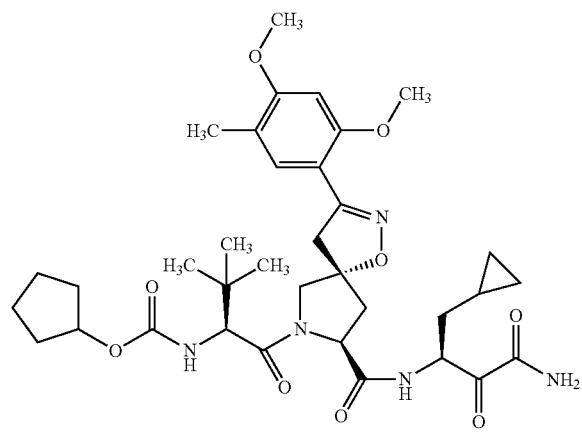
885
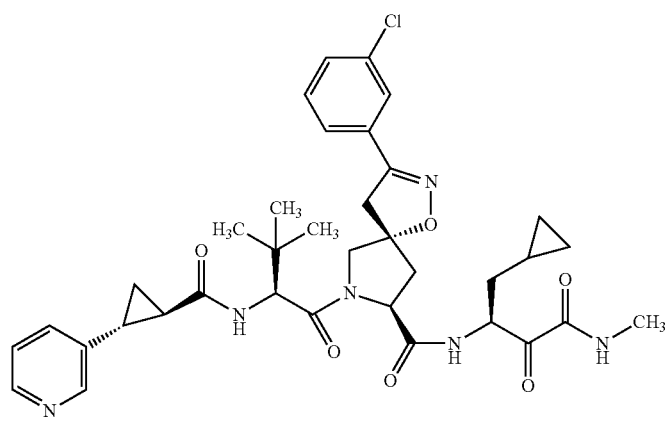
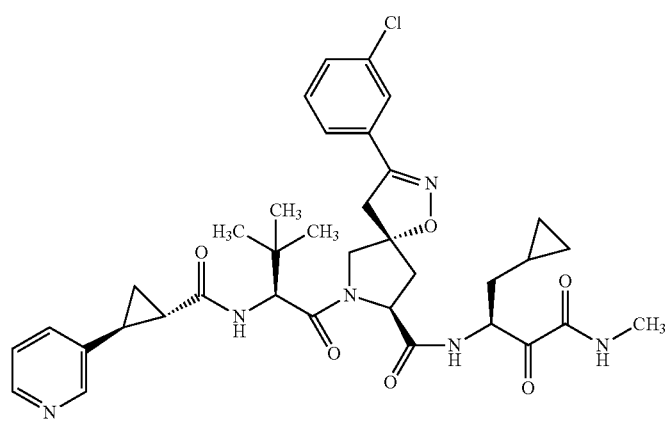

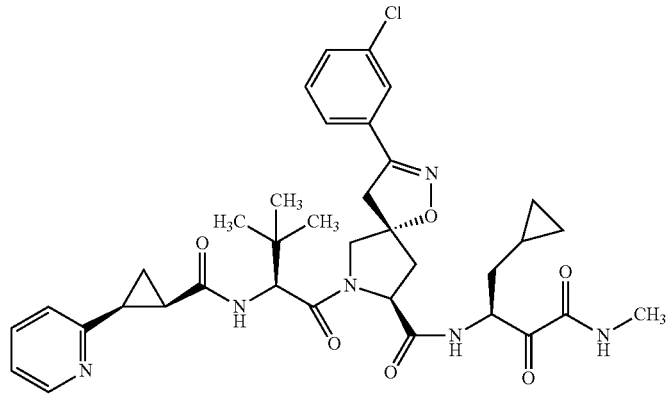
886
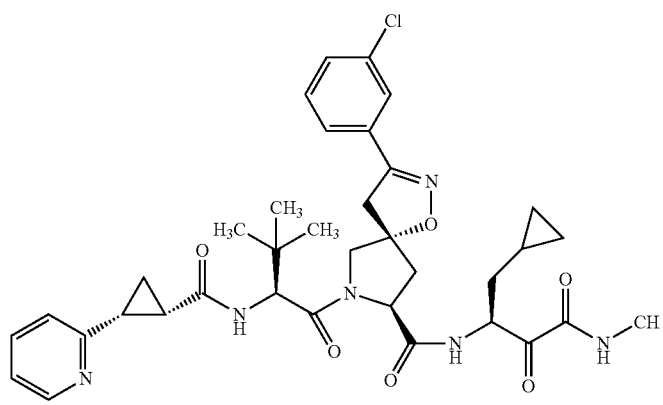
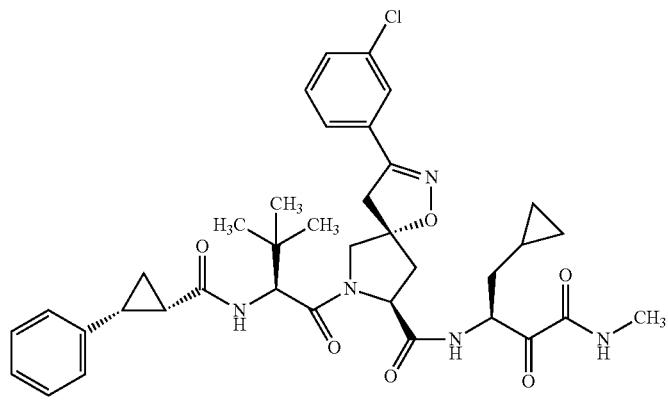
887
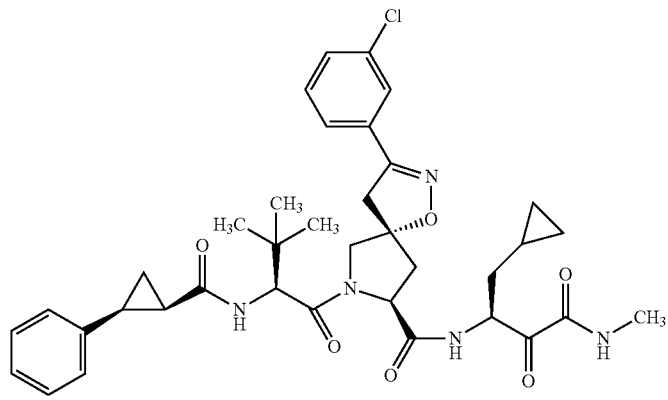
888

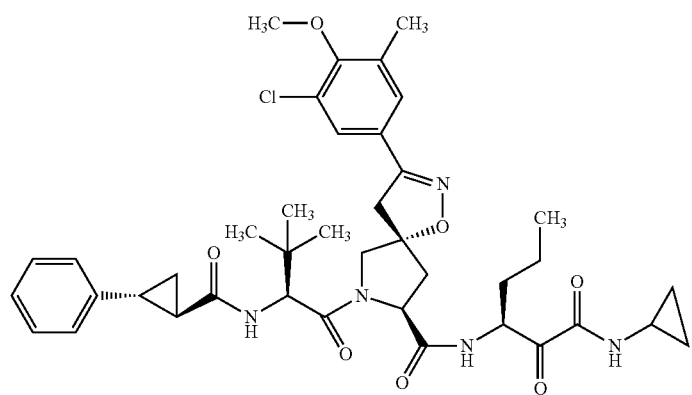
889
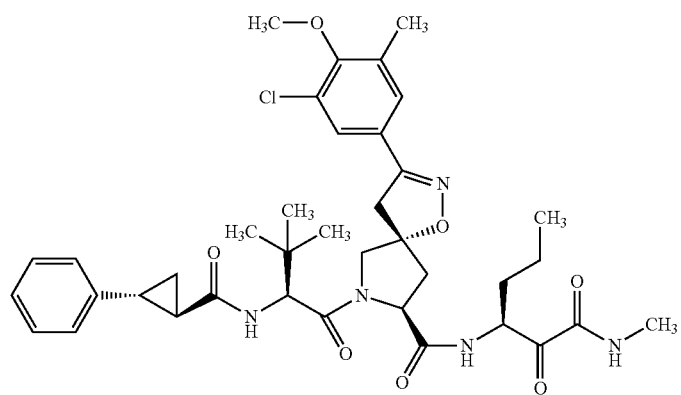
890
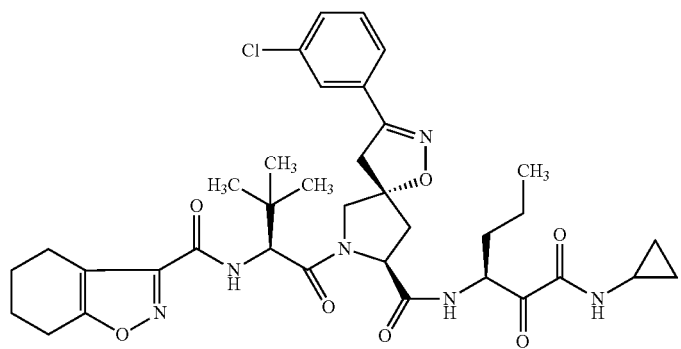
891
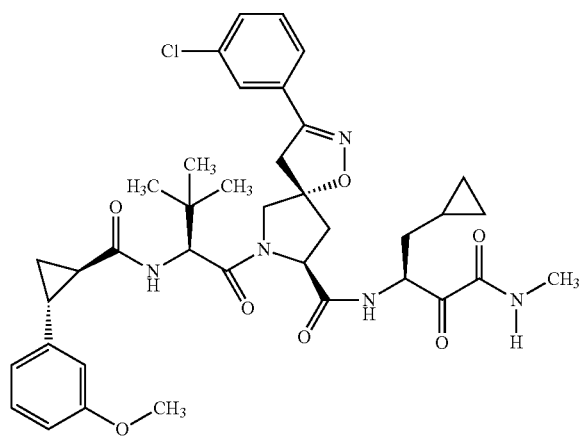
892

893
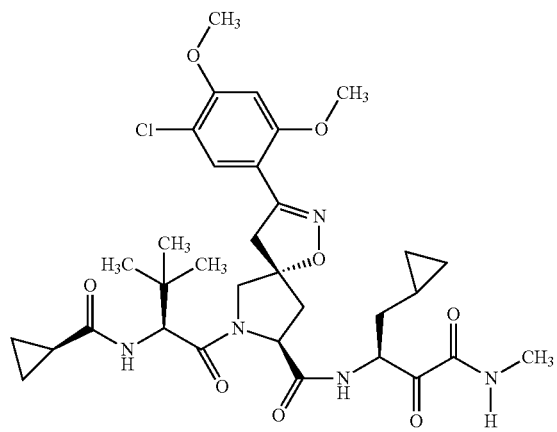
894
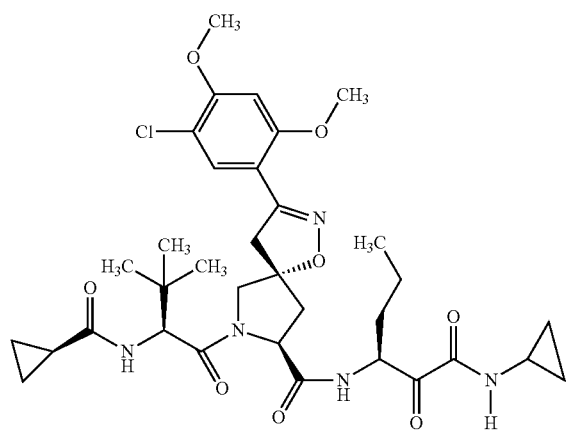
895
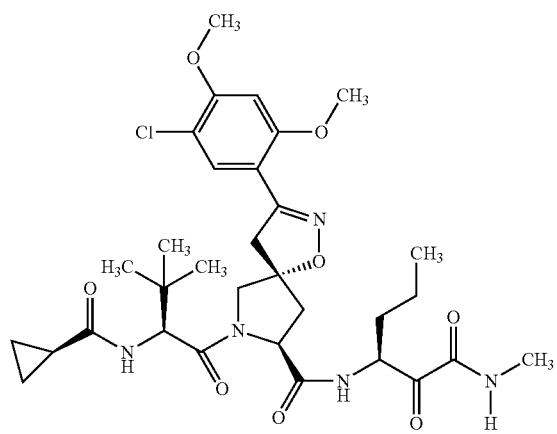

896
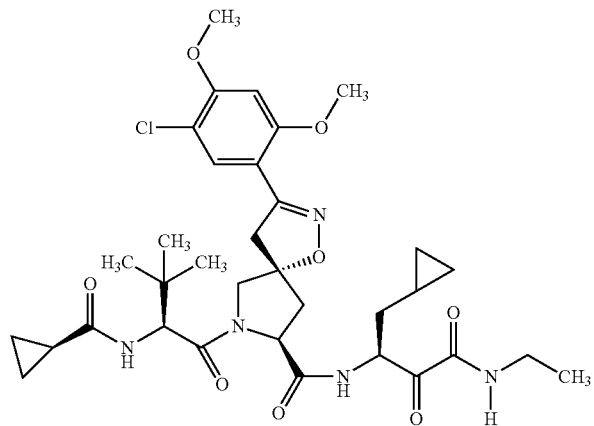
897
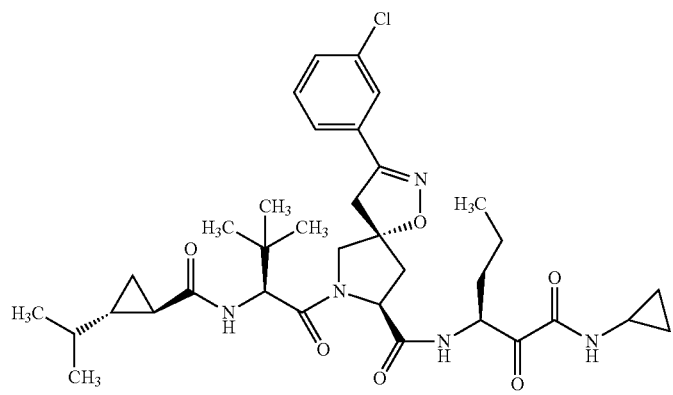
898
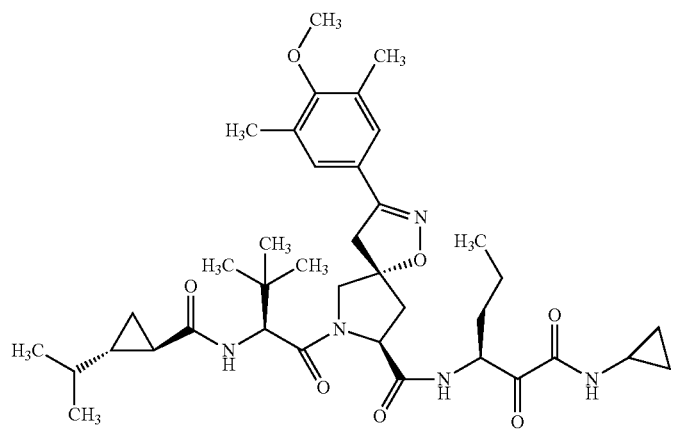

-continued
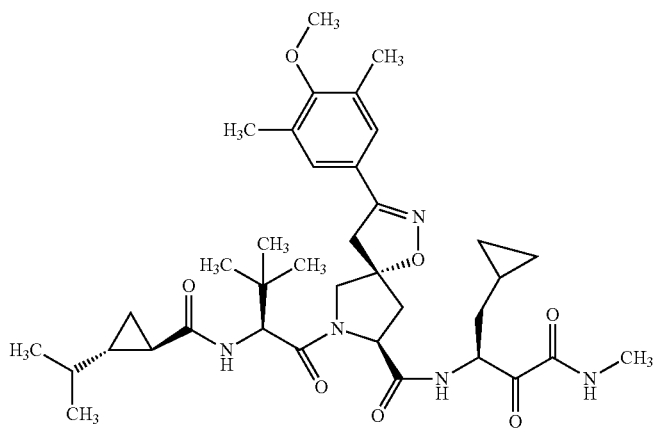
899
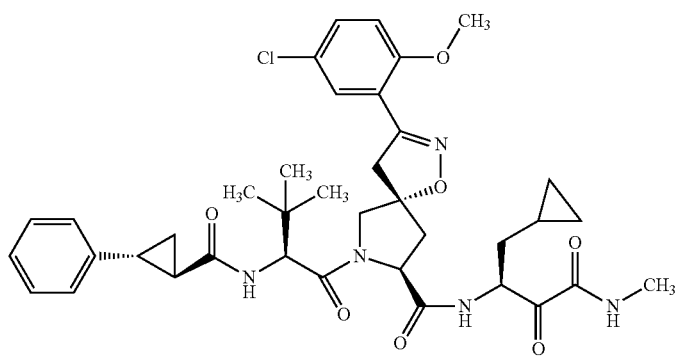
900
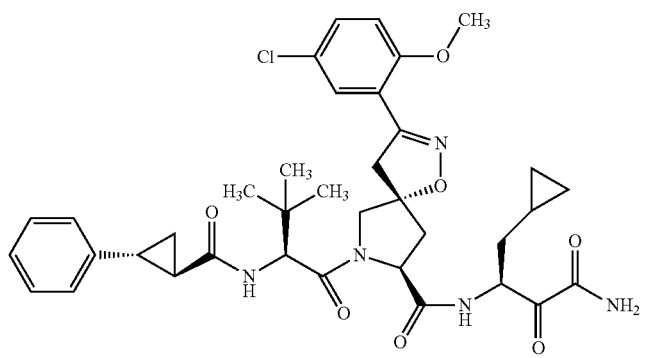
901
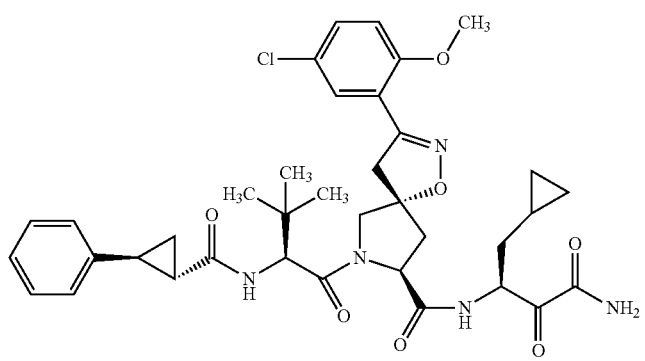
902

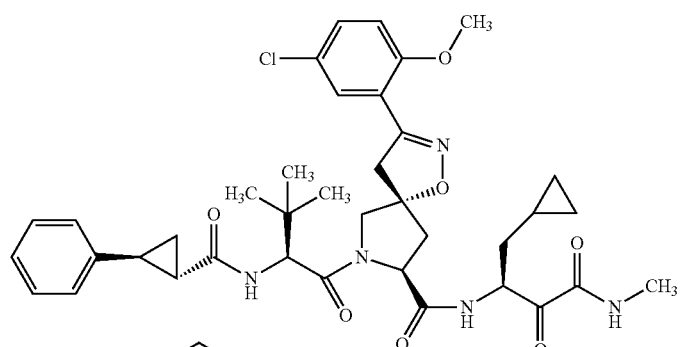
903
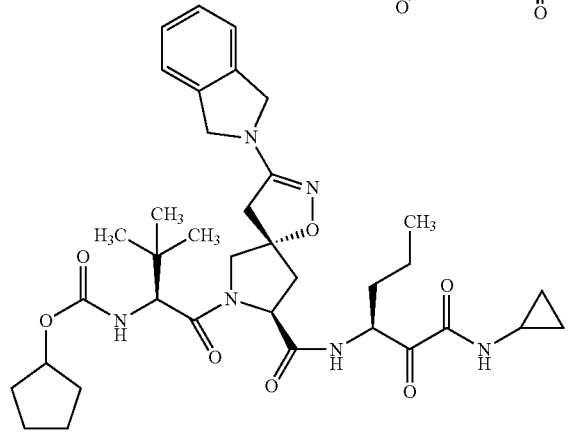
904
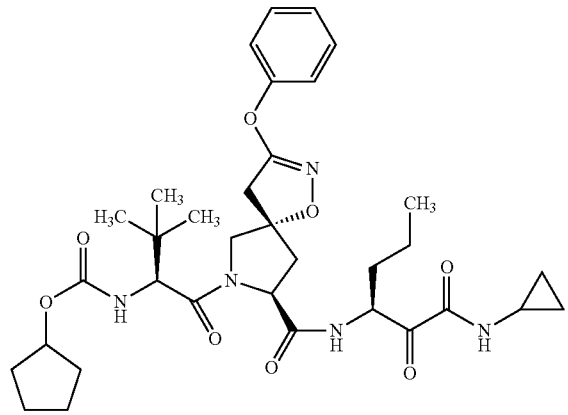
905
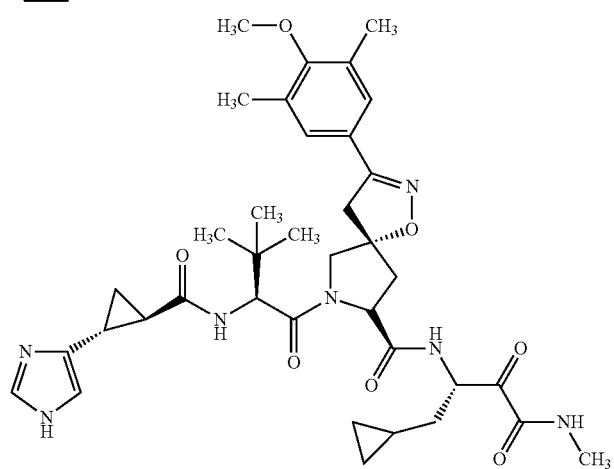
906

907
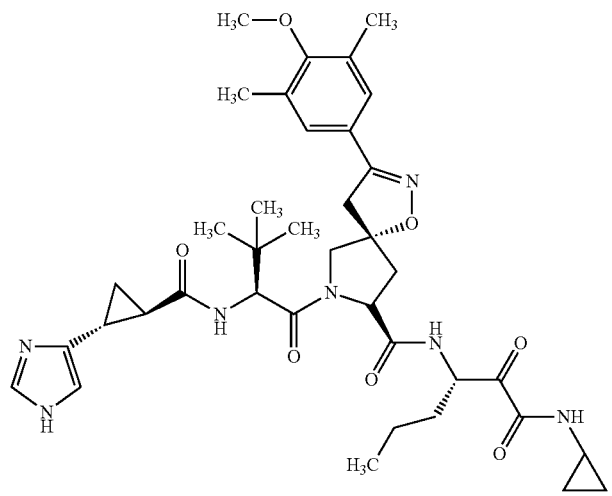
908
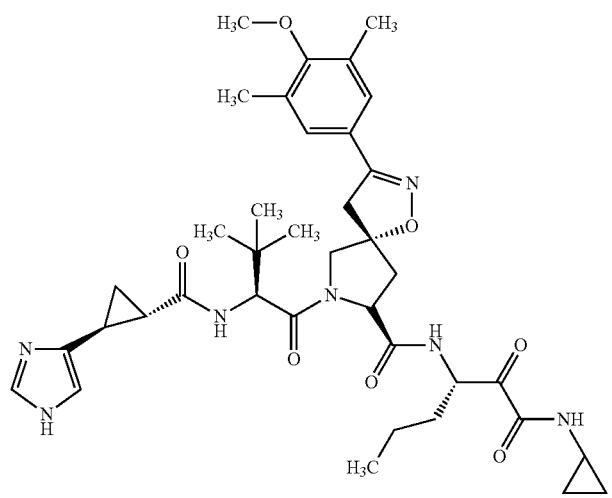
909
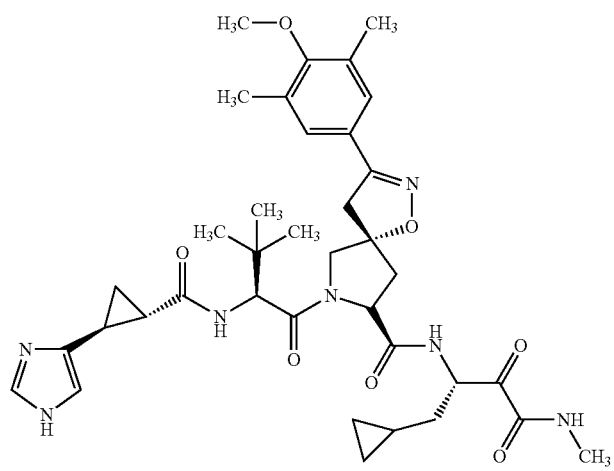

910
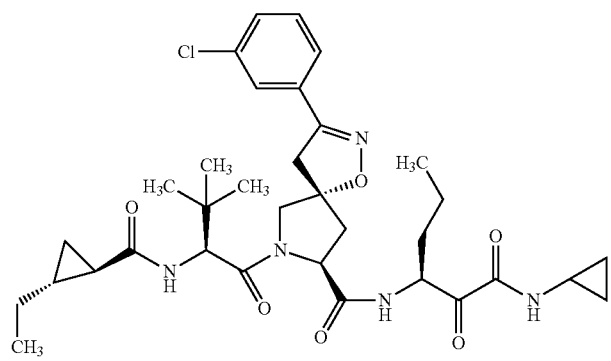
911
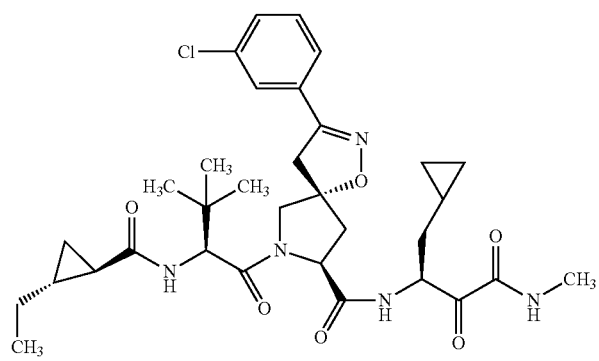
912
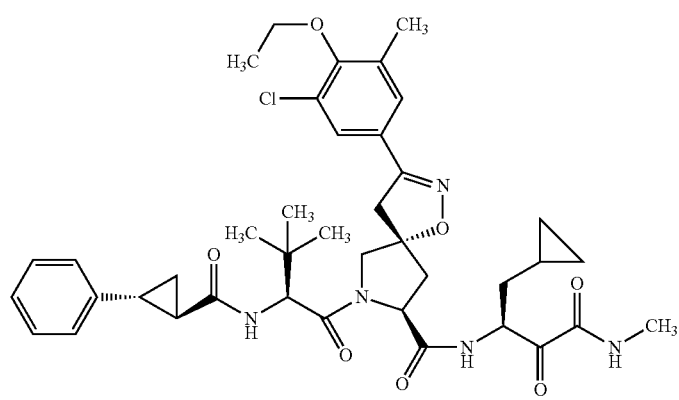
913
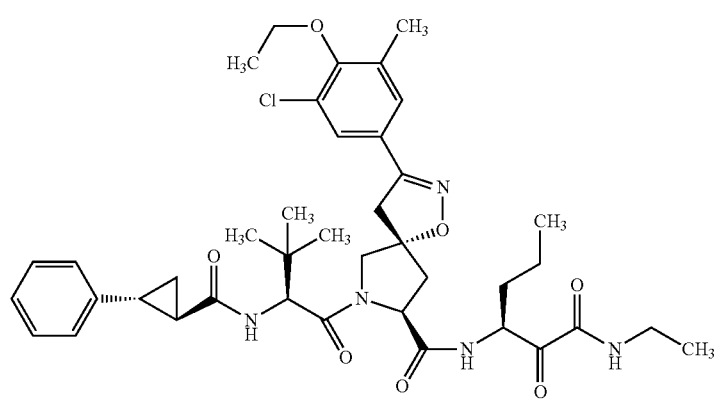

-continued
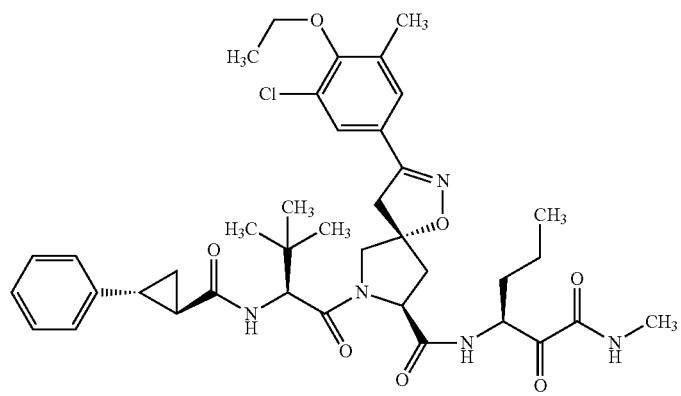
914
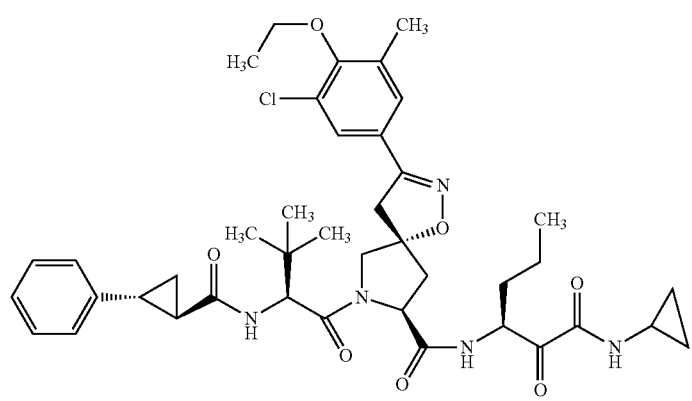
915
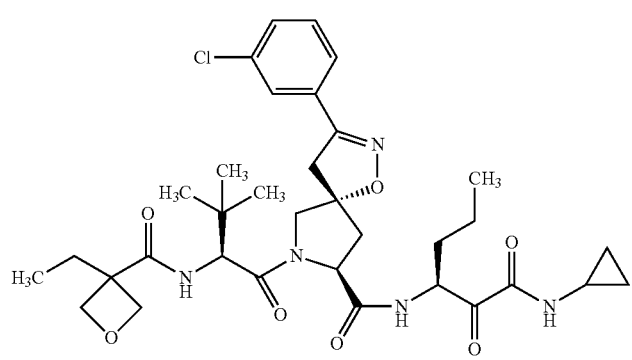
916
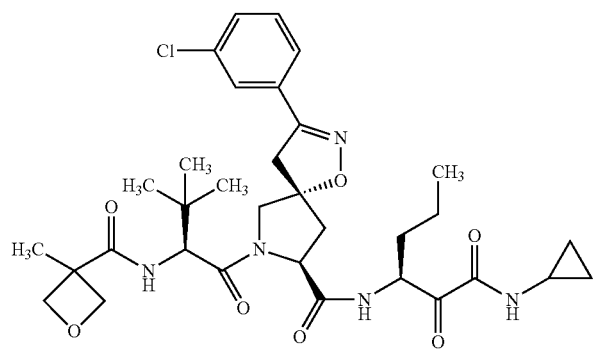
917

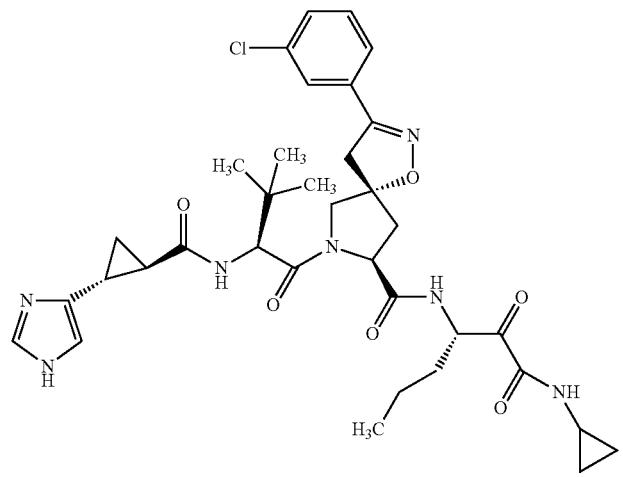
918
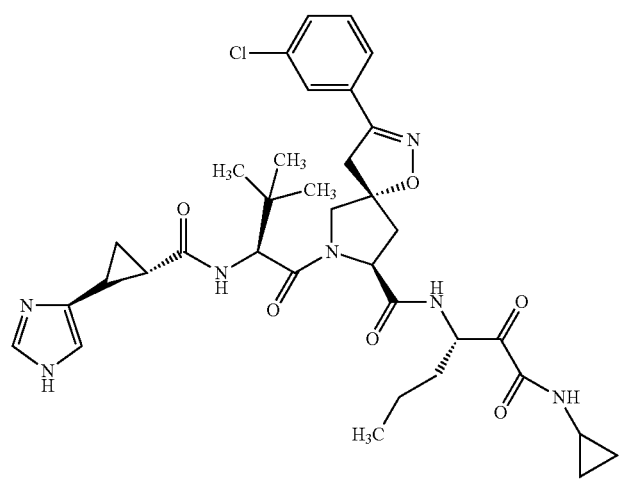
919
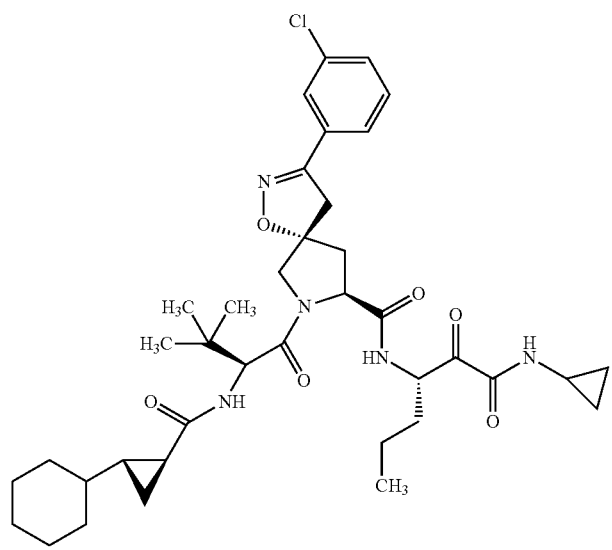
920

921
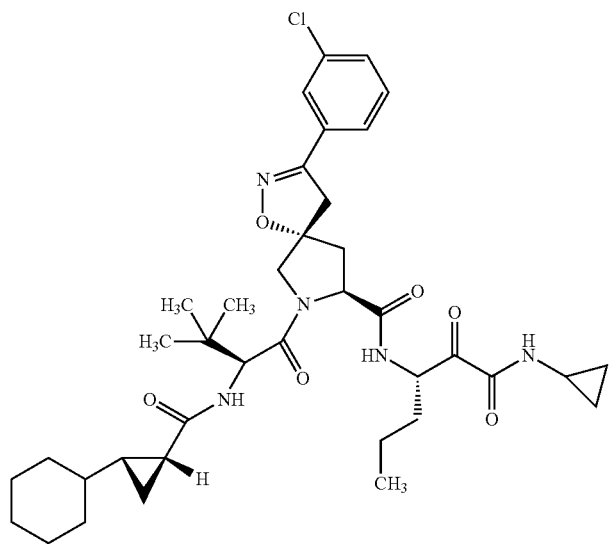
922
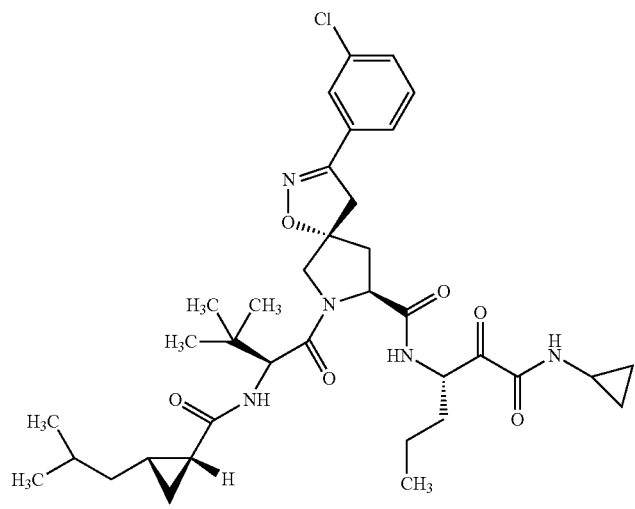
923
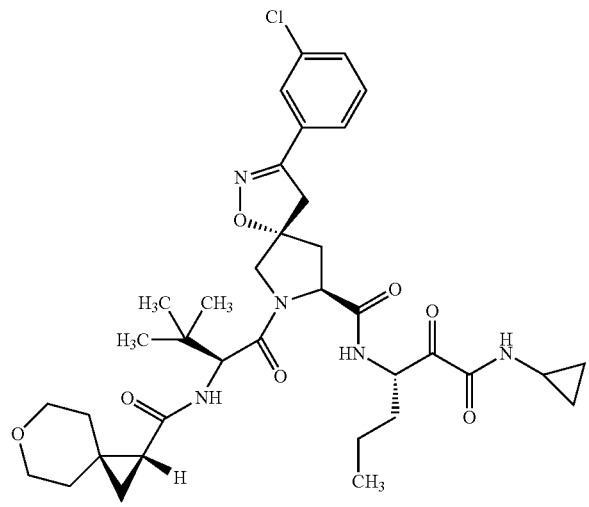

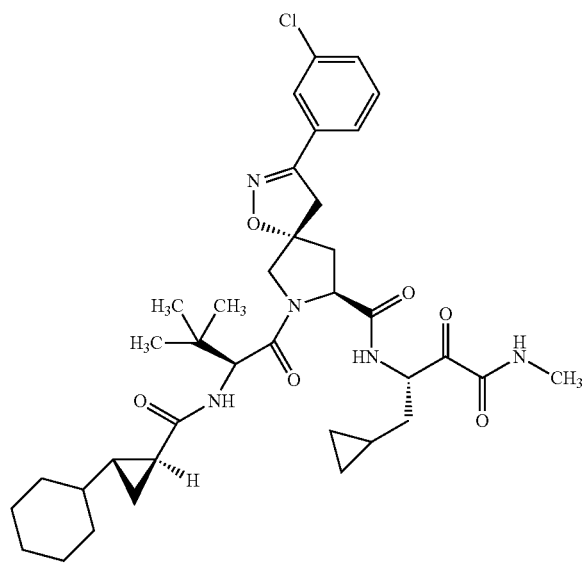
924
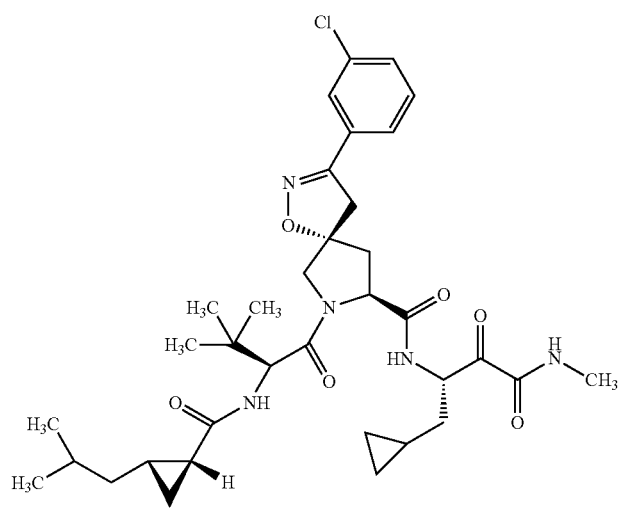
925
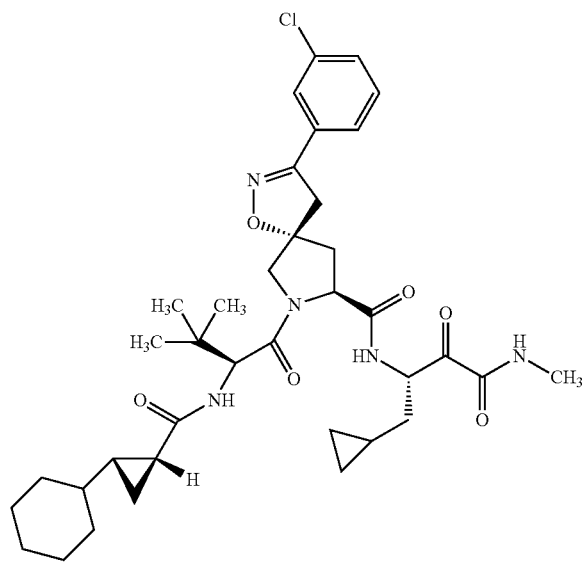
926

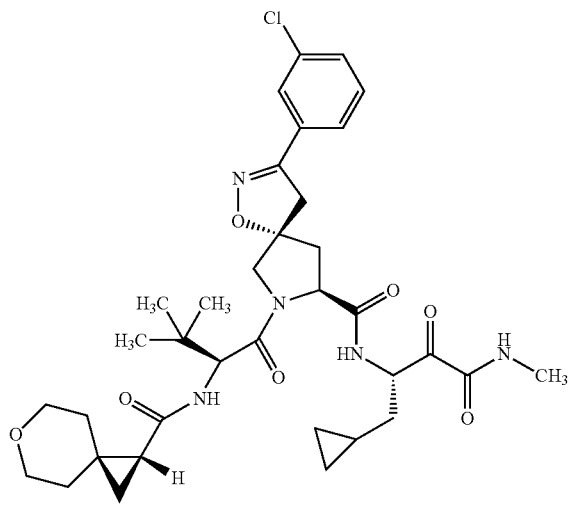
927
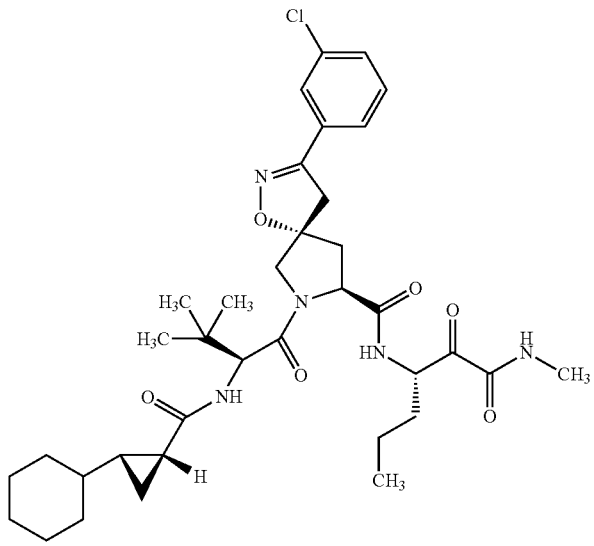
928
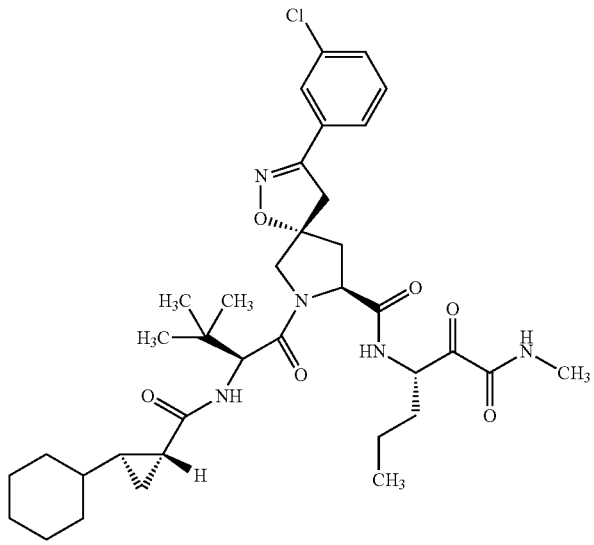
929

930
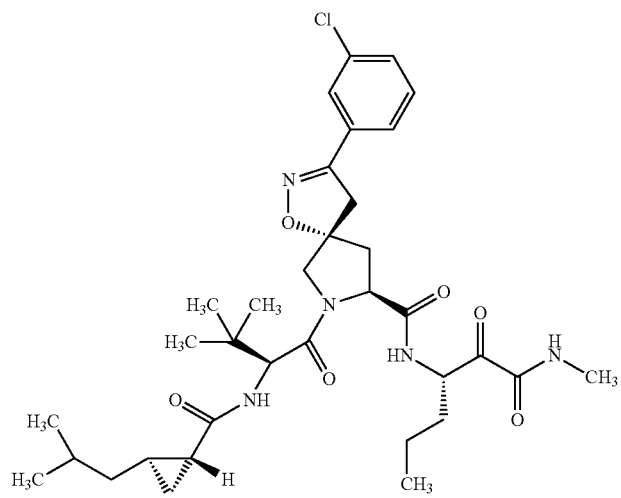
931
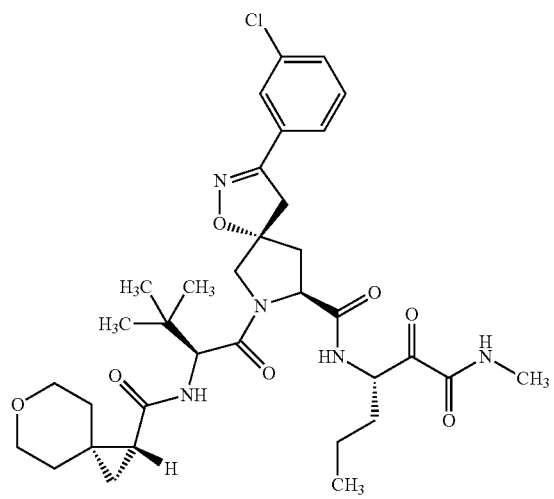
932
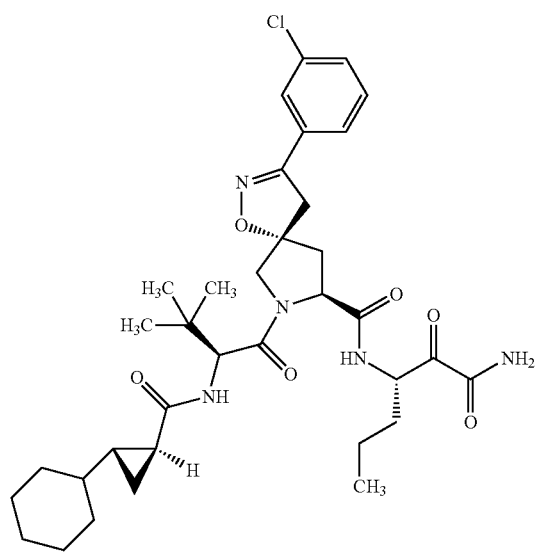

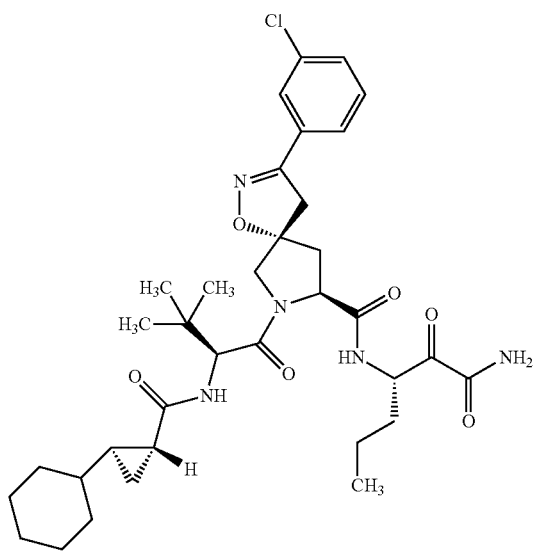
933
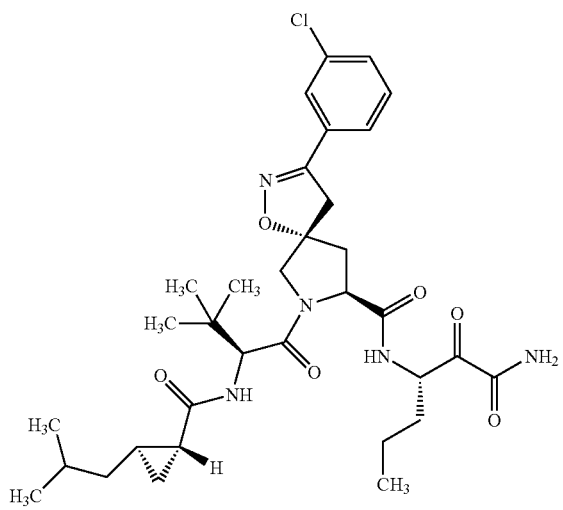
934
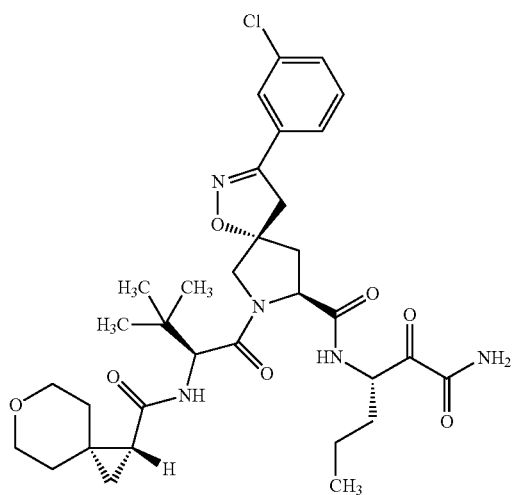
935

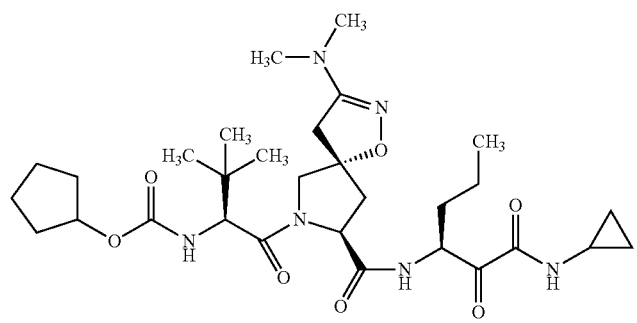
936
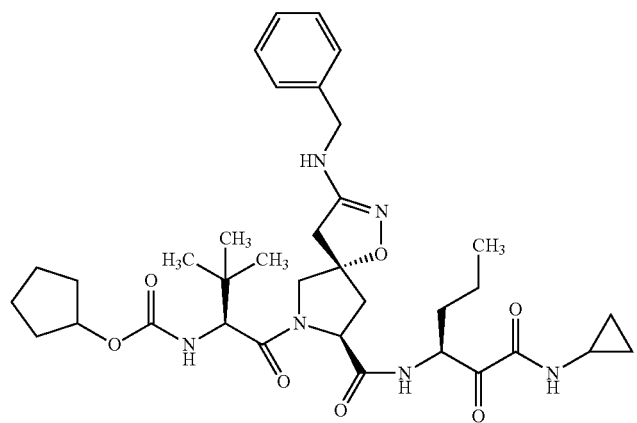
937
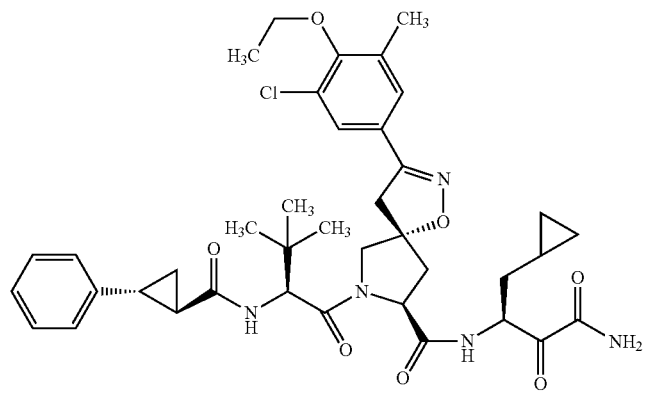
938
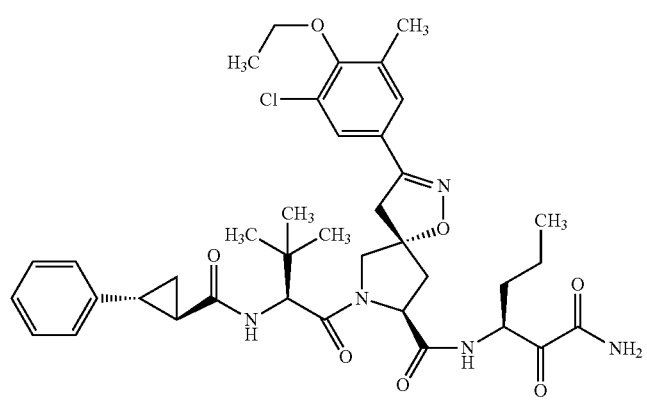
939

940
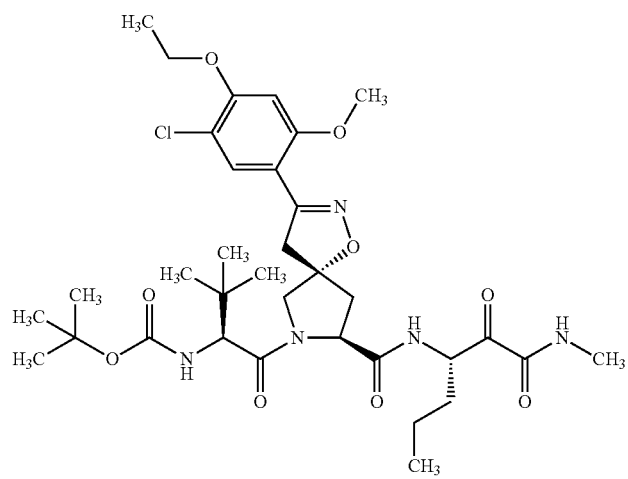
941
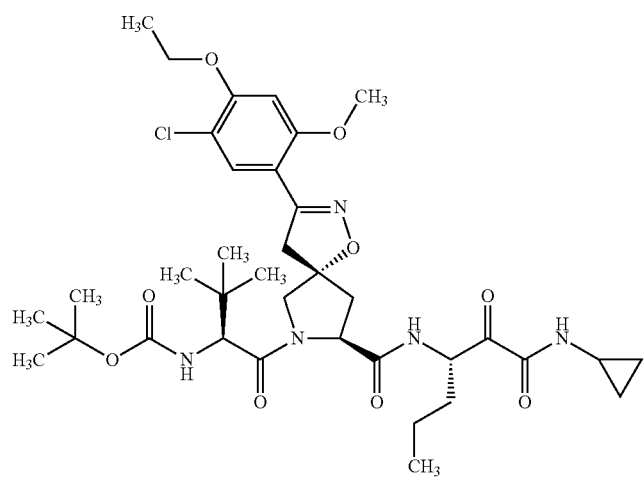
942
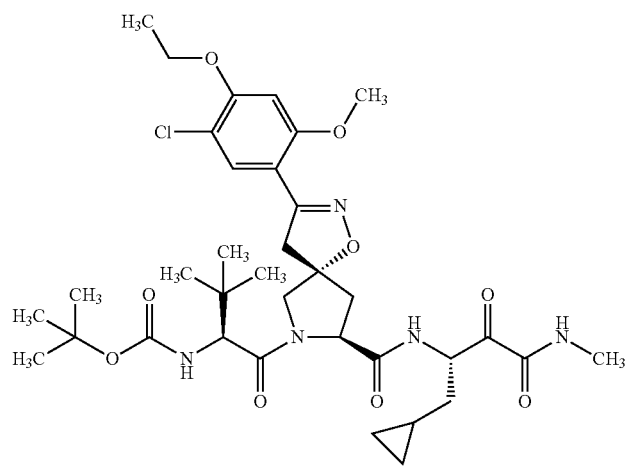

944
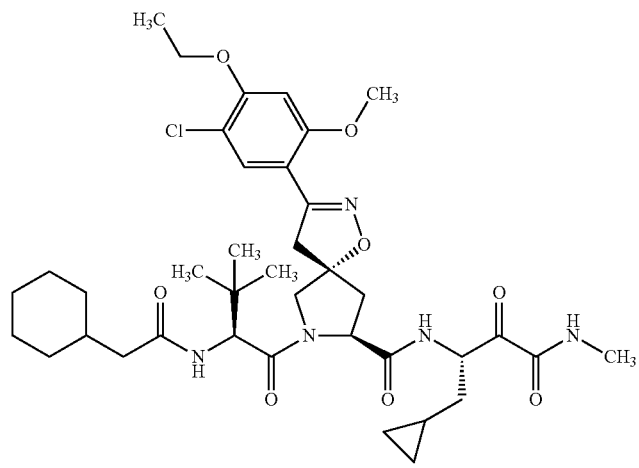
945
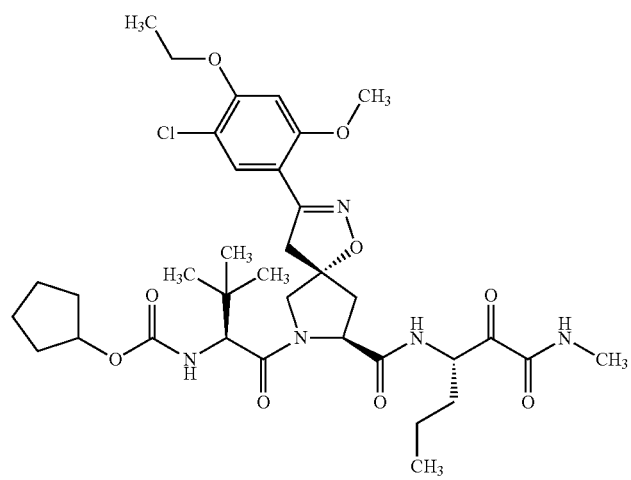
946
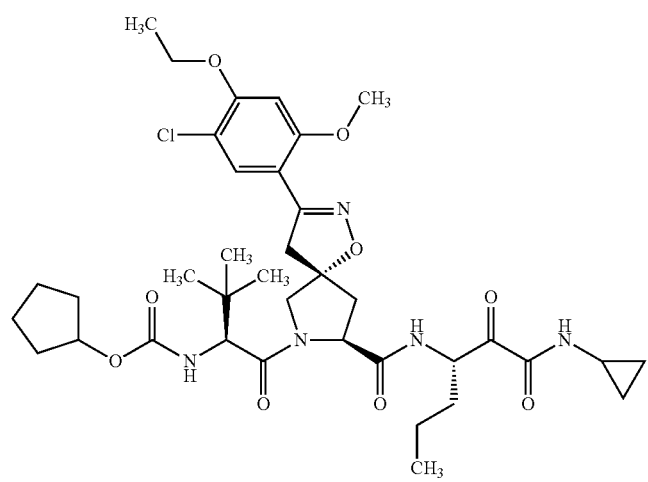

947
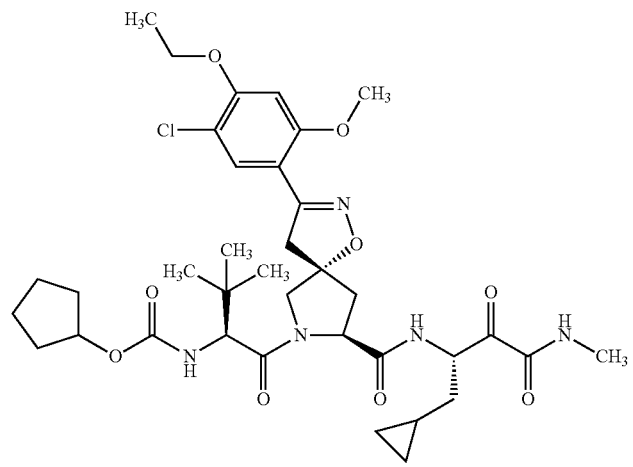
948
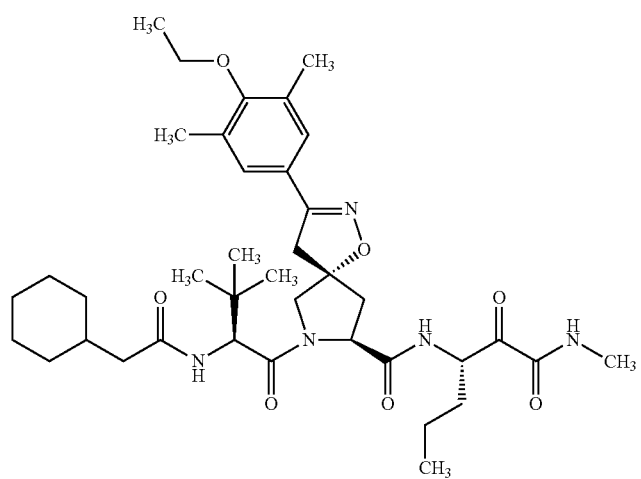
949
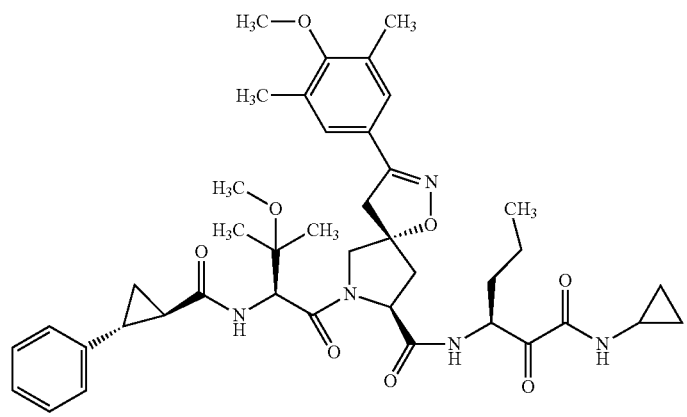

950
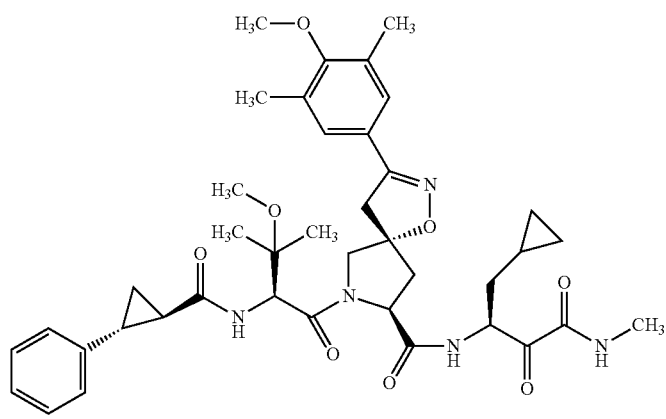
951
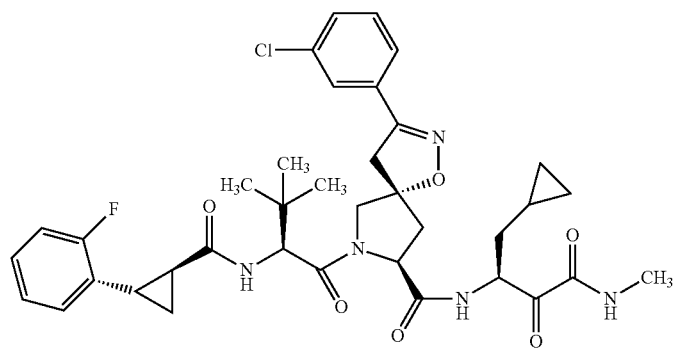
952
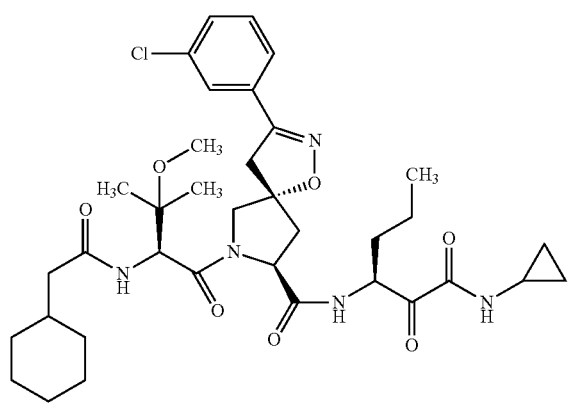
953
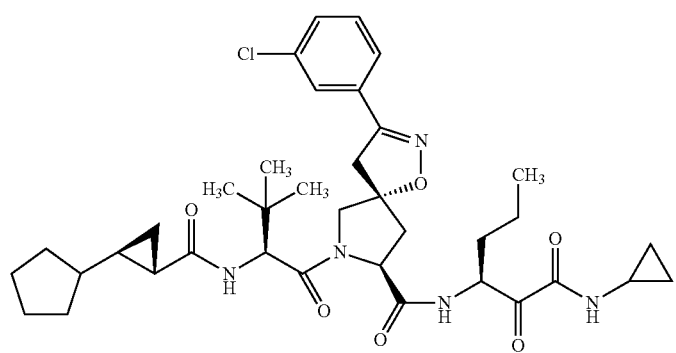

-continued
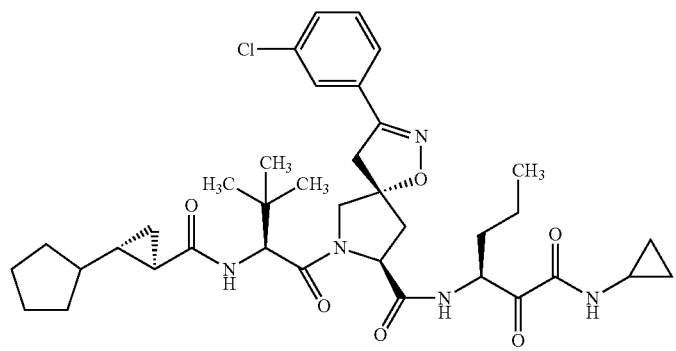
954
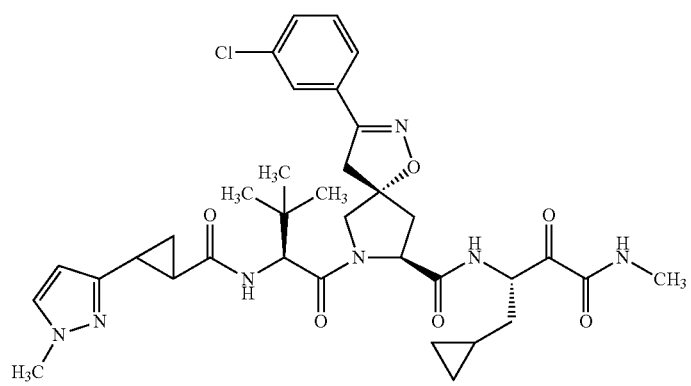
955
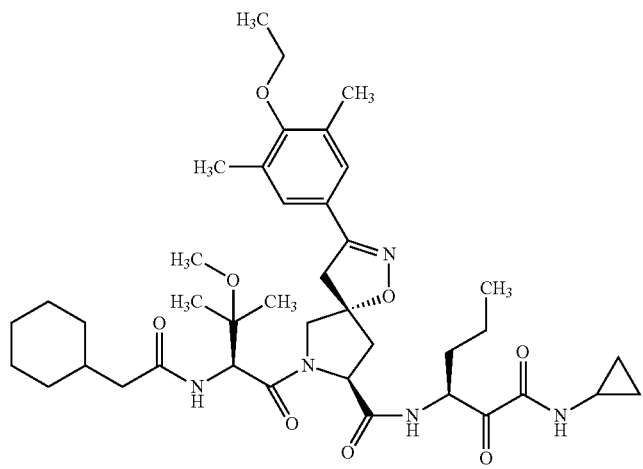
956
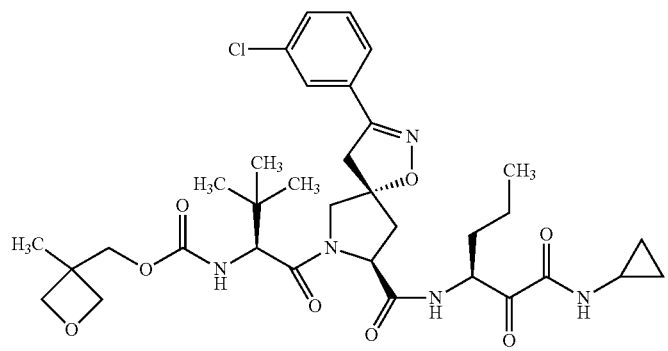
957

958
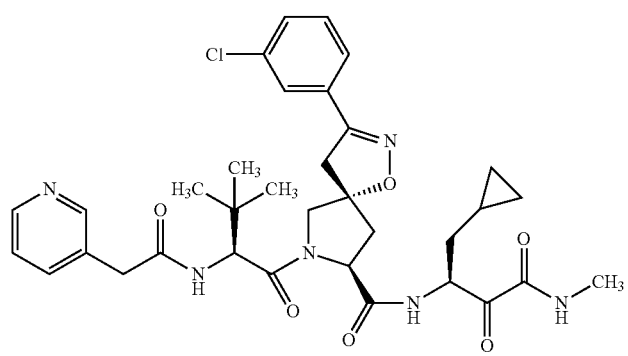
959
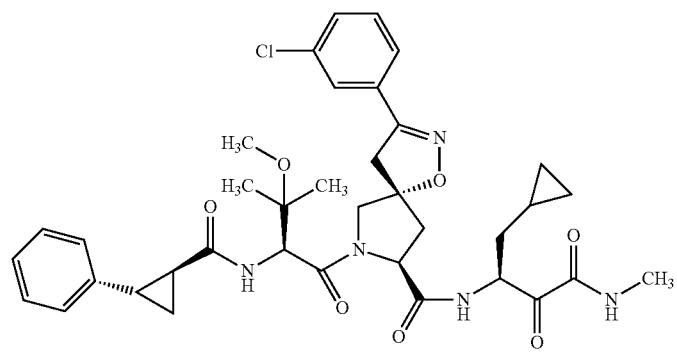
960
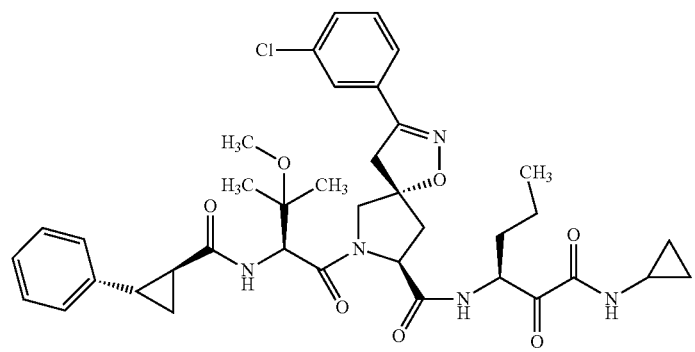
961
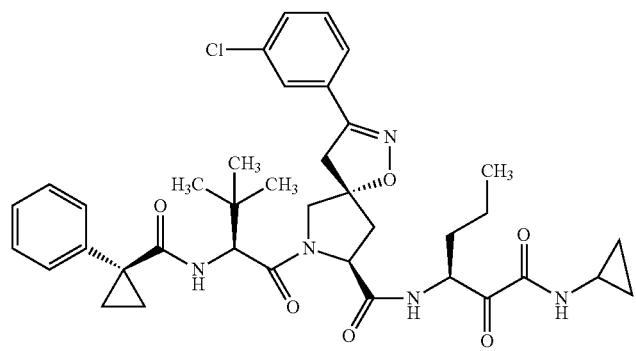

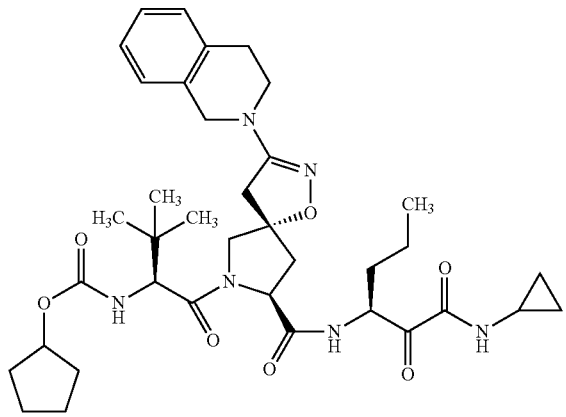
962
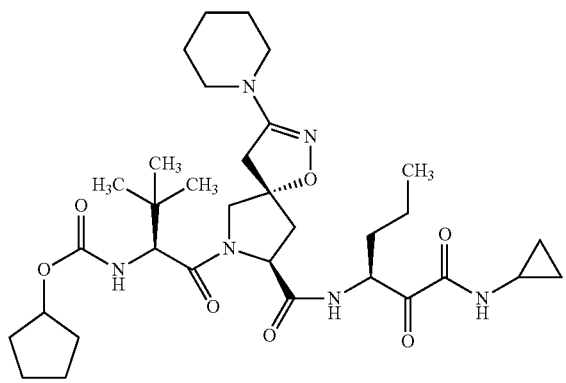
963
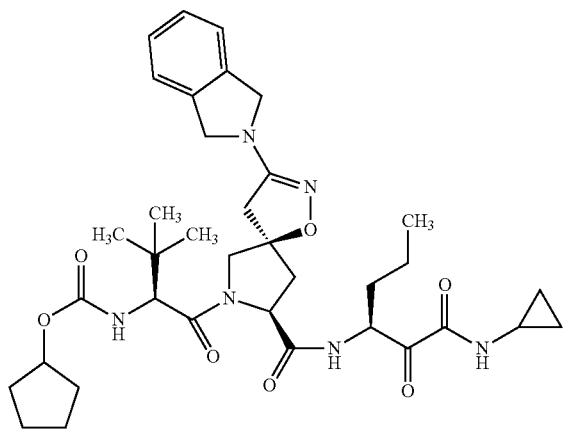
964
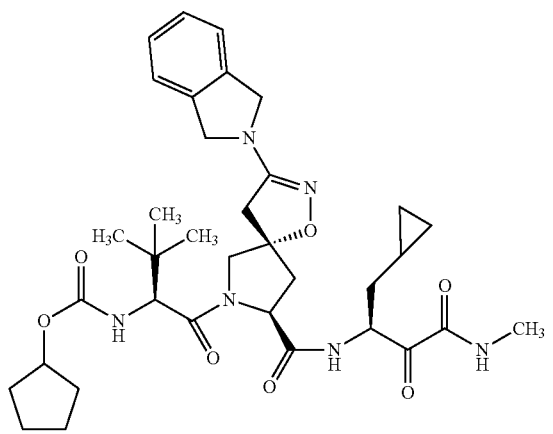
965

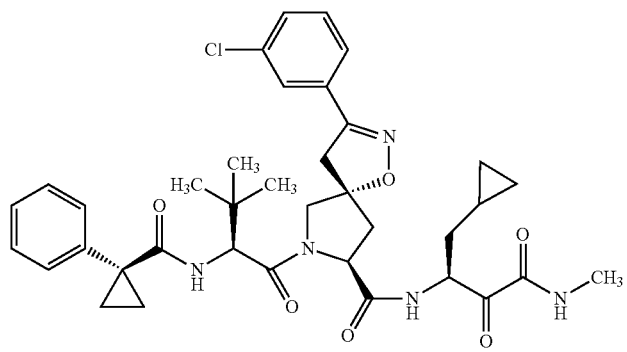
966
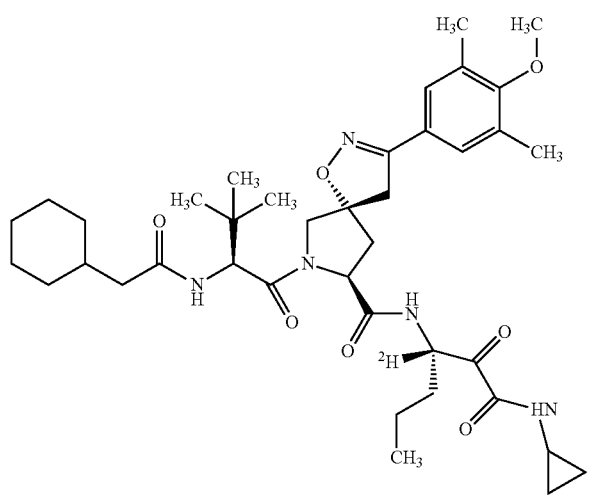
967
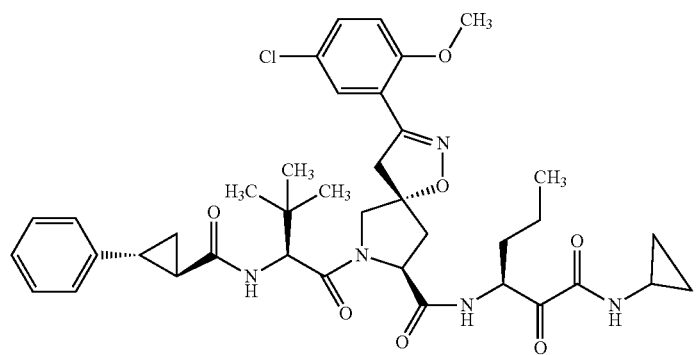
968
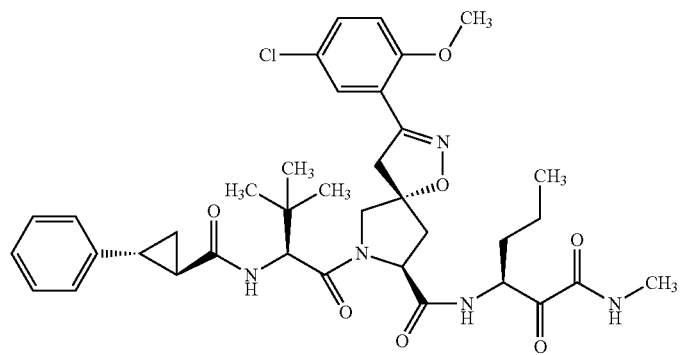
969

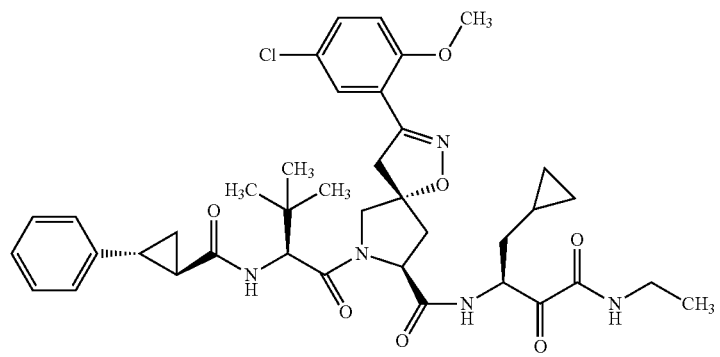
970
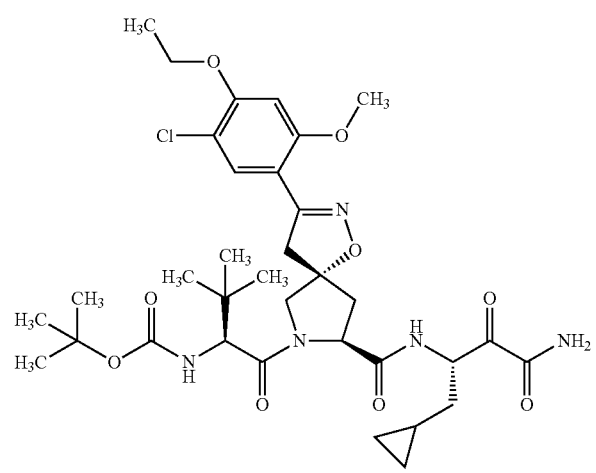
971
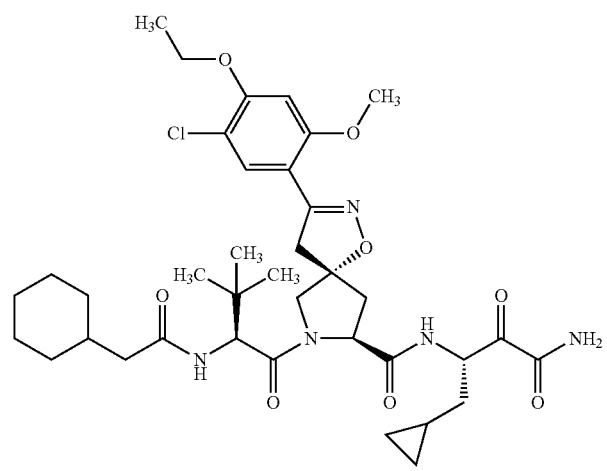
972

973
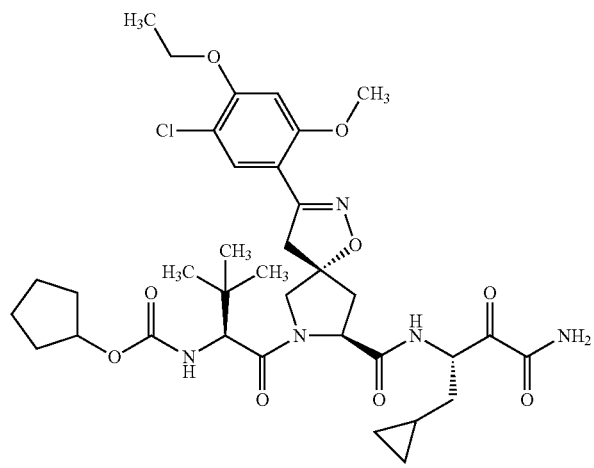
974
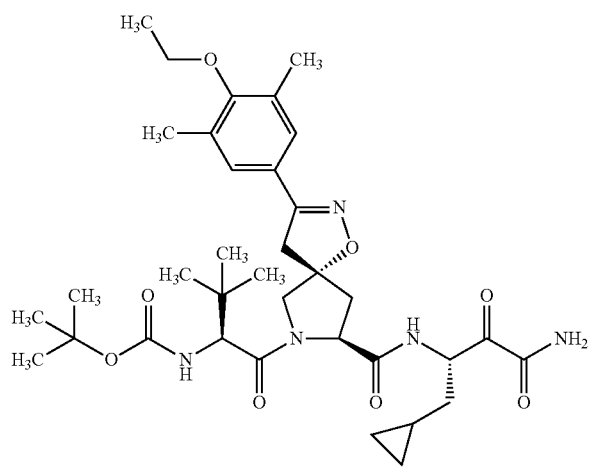
975
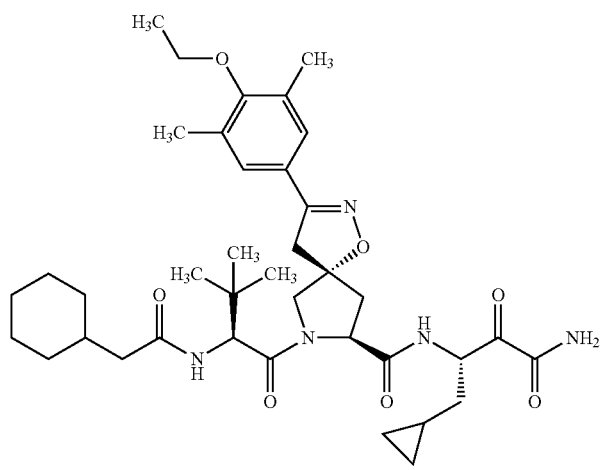

-continued
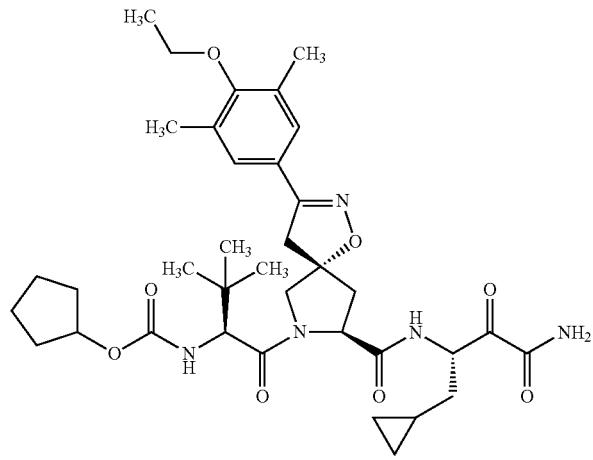
976
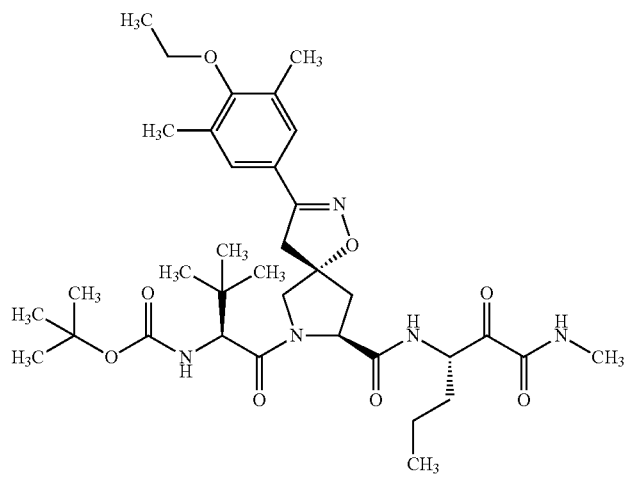
977
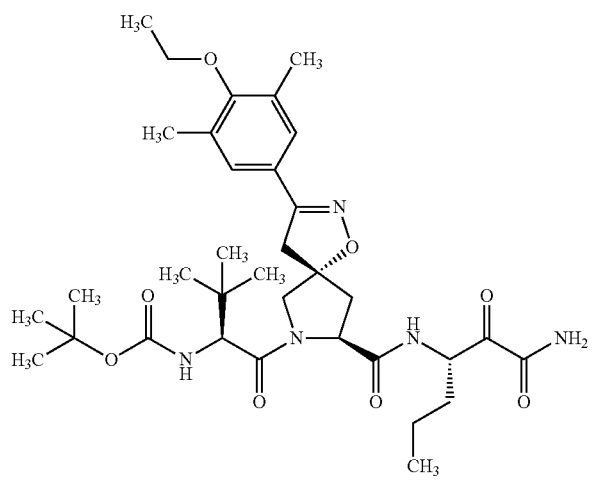
978

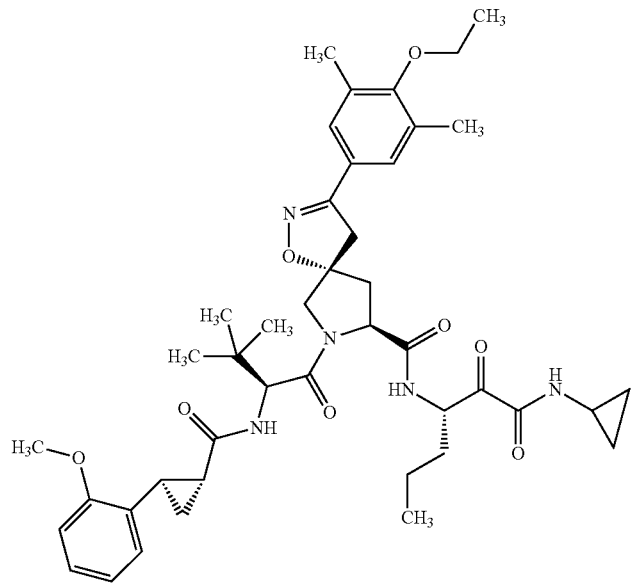
979
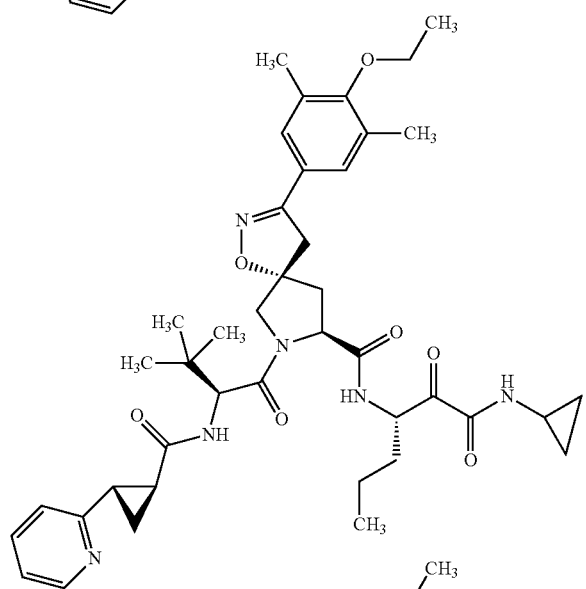
980
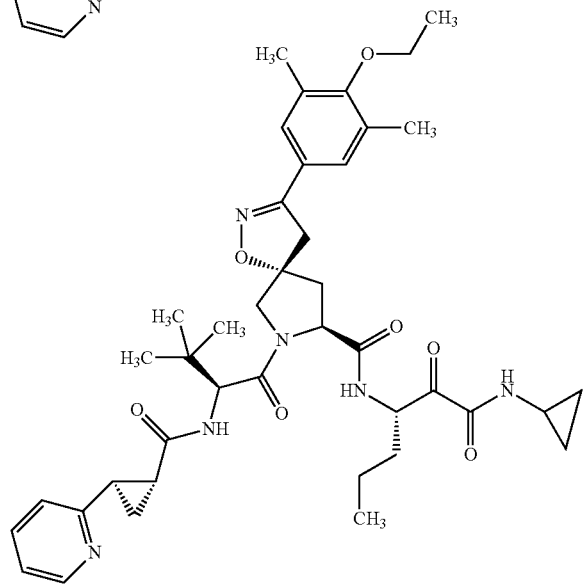
981

982
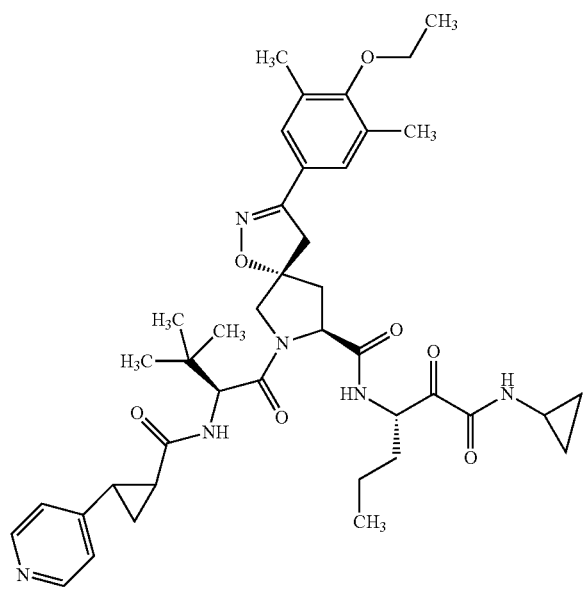
983
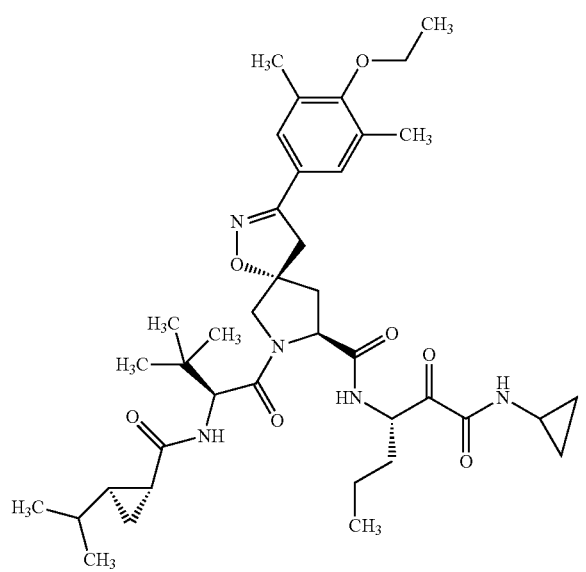

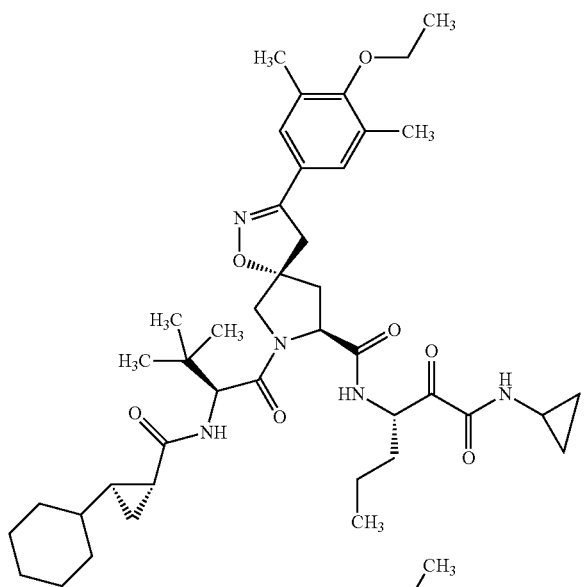
984
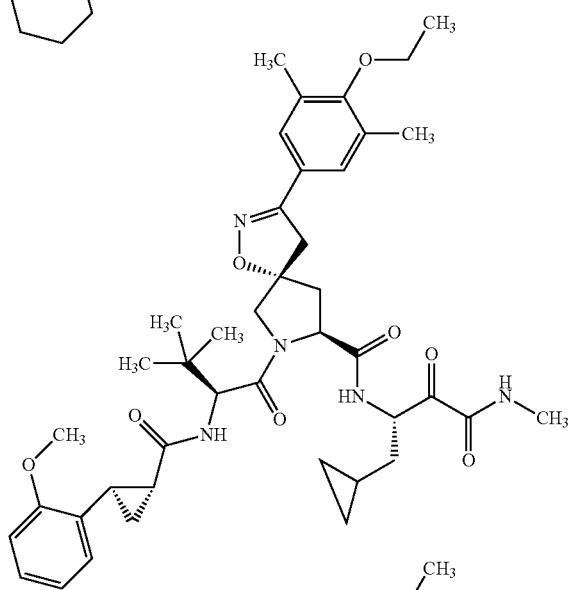
985
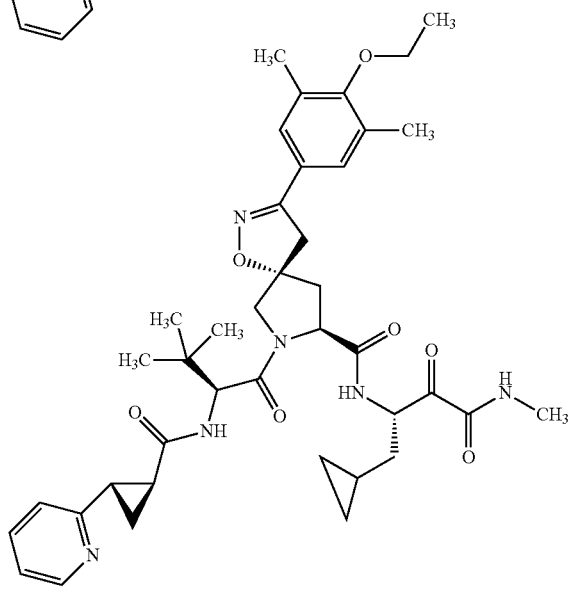
986

| 1243 | 1244 |
|---|---|
| -continued | |
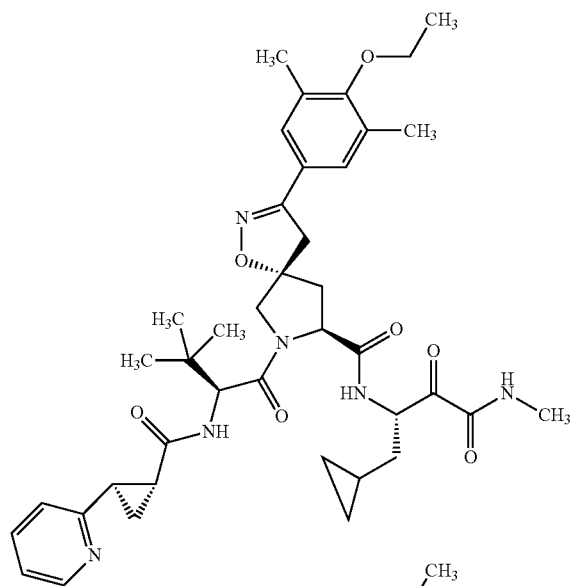
987
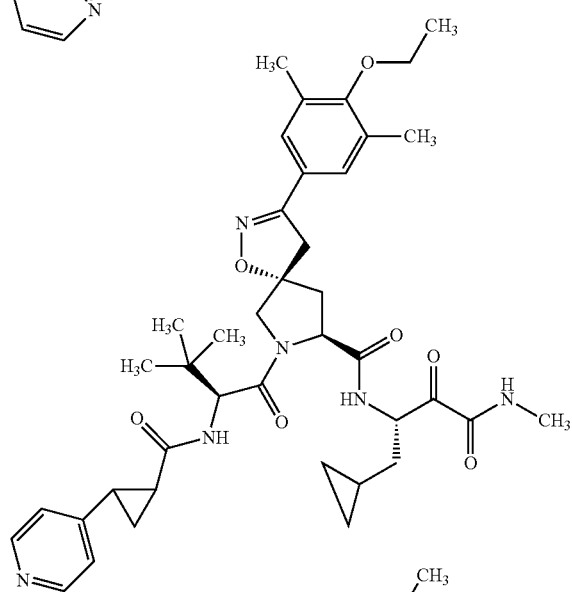
988
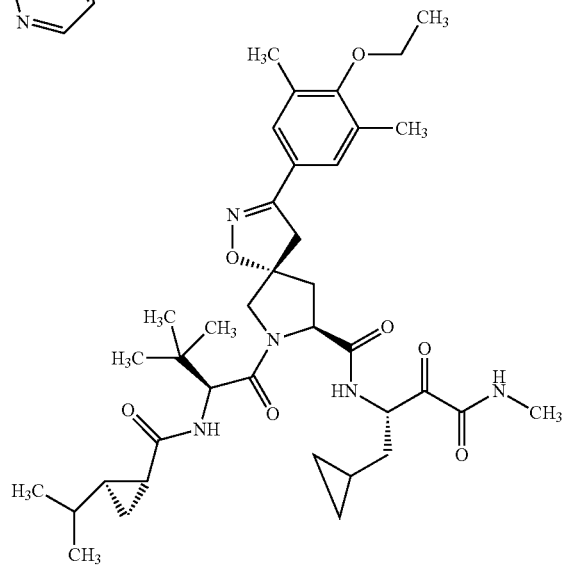
989

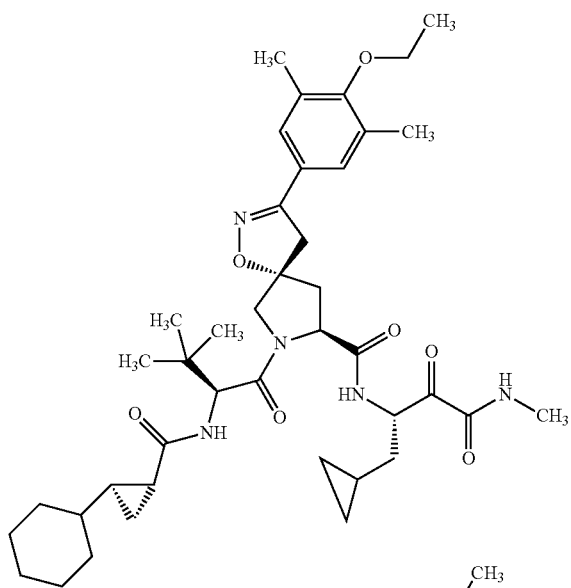
990
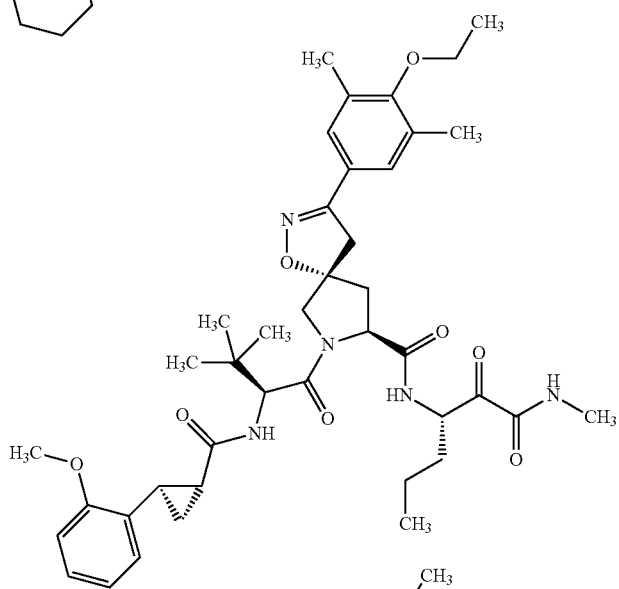
991
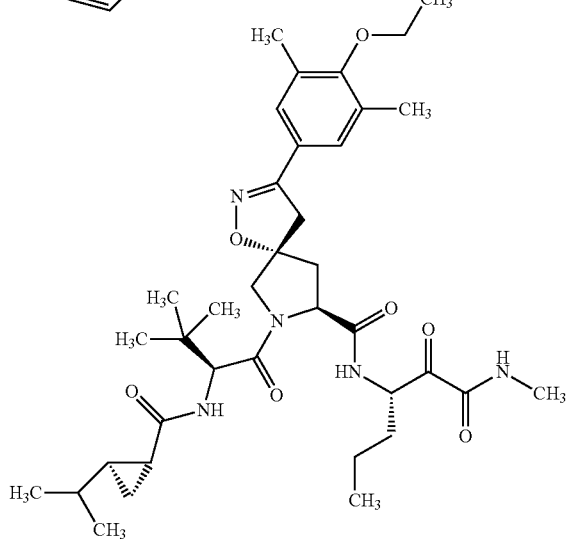
992

-continued
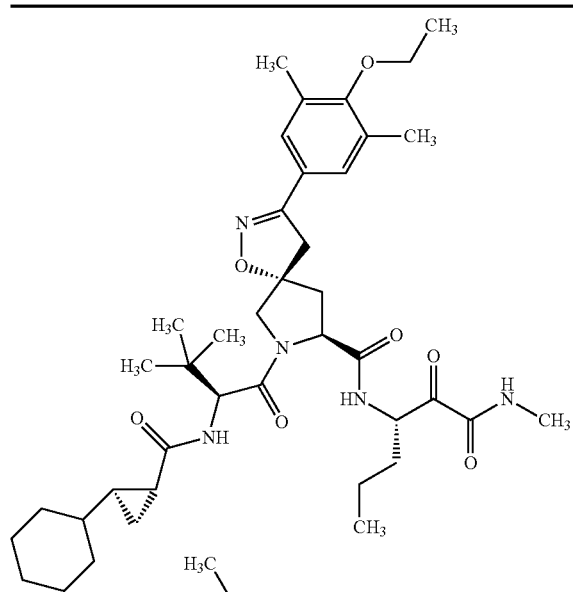
993
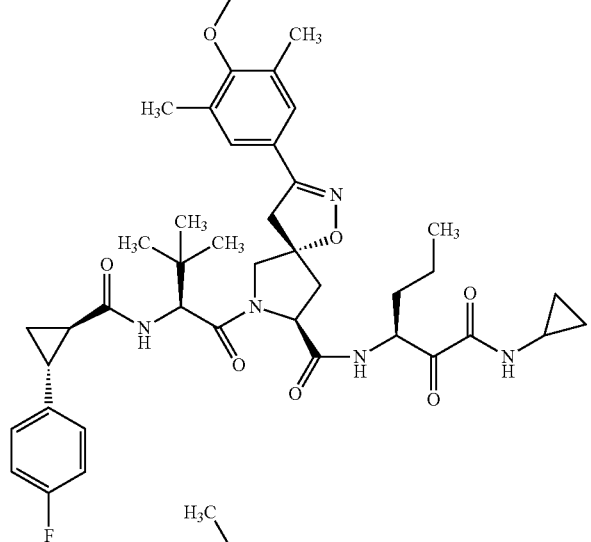
994
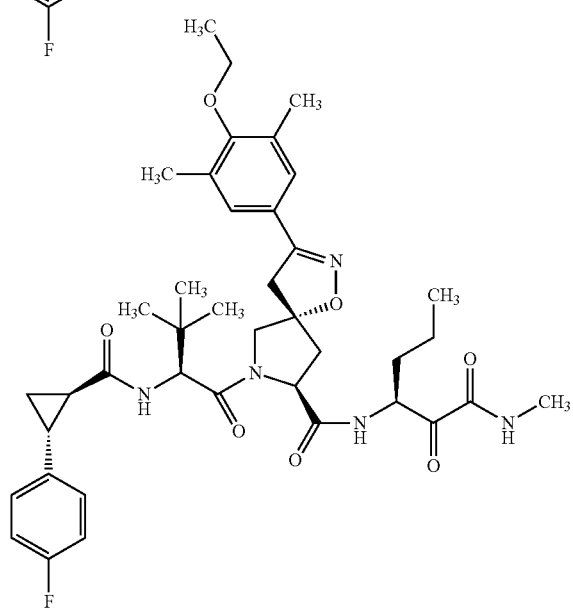
995

| | |
|---|---|
| 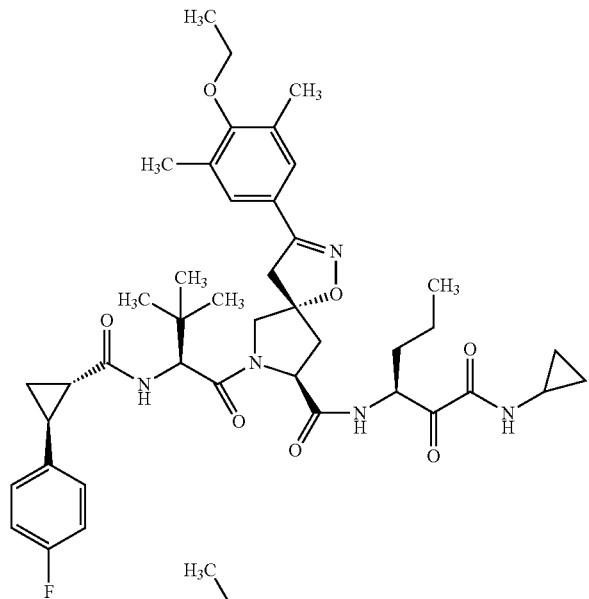 | 996 |
| 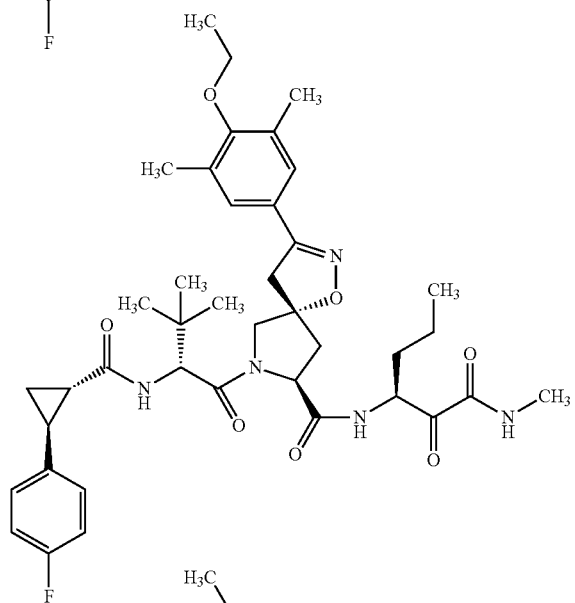 | 997 |
| 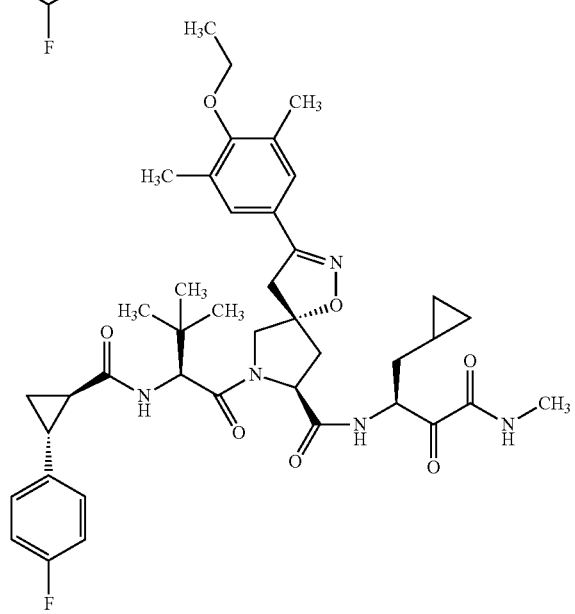 | 998 |

| | |
|---|---|
| 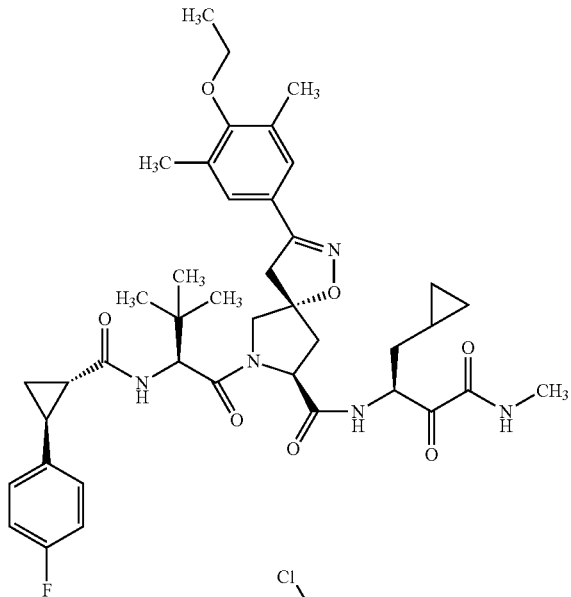 | 999 |
| 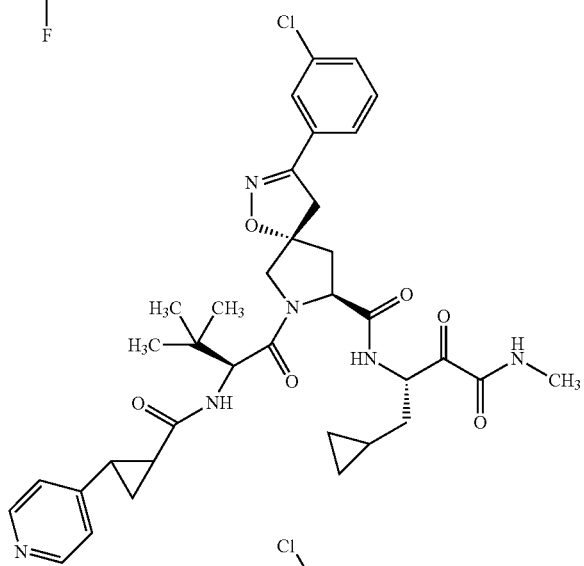 | 1000 |
| 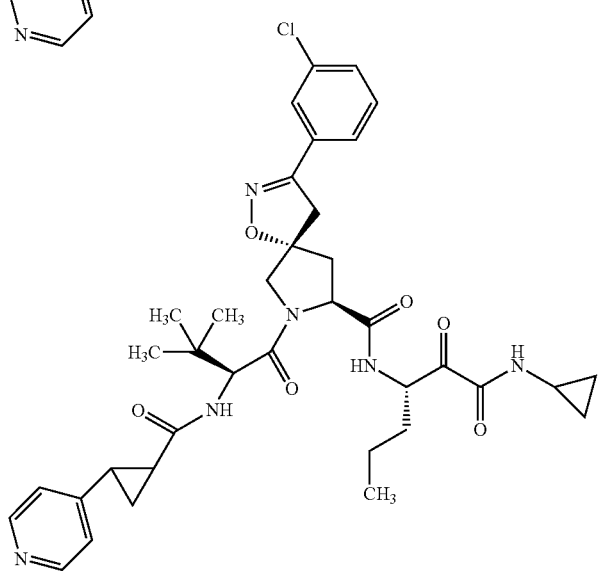 | 1001 |

-continued
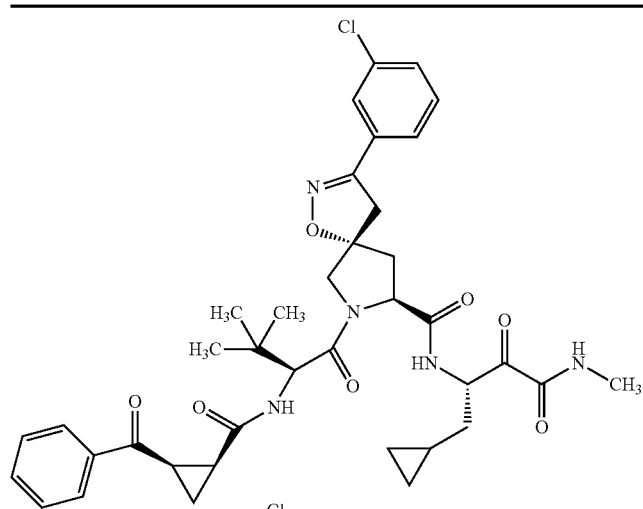
1002
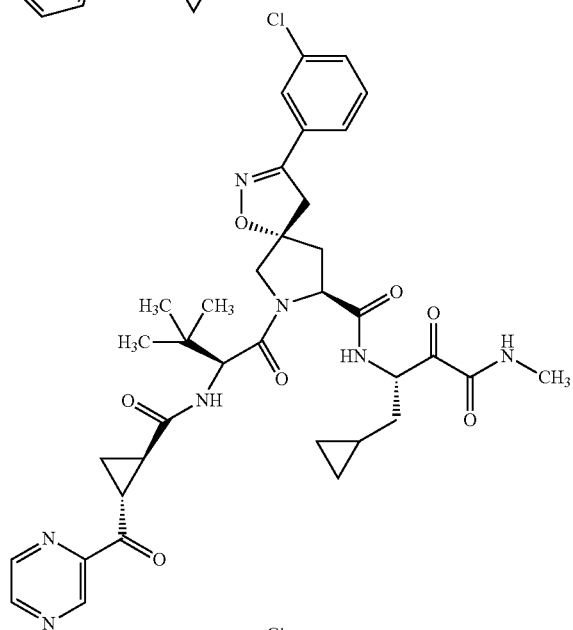
1003
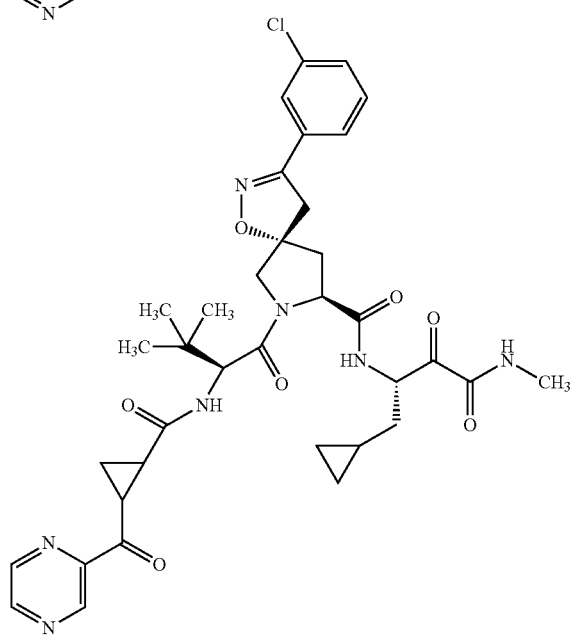
1004

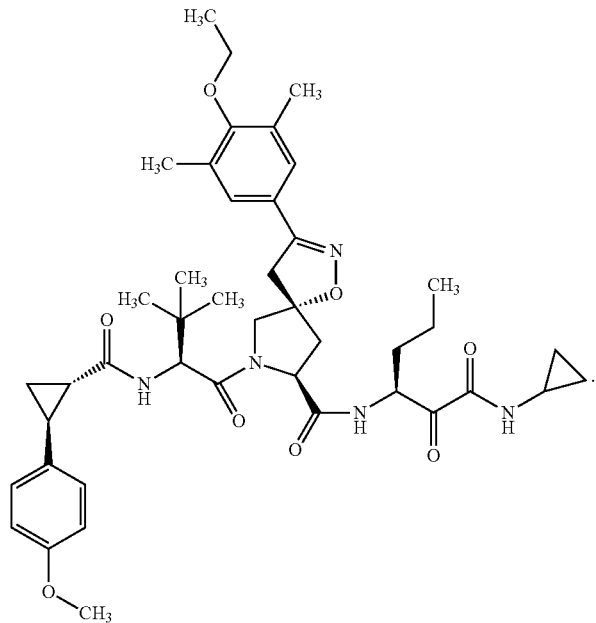

1005.

24. A pharmaceutical composition comprising a compound of claim 1, or a pharmaceutically acceptable salt thereof, and a pharmaceutically acceptable carrier, adjuvant or vehicle.

25. The composition according to claim 24, further comprising an agent selected from an immunomodulatory agent; an antiviral agent; an inhibitor of HCV protease; an inhibitor of the HCV life cycle; and a cytochrome P-450 inhibitor.

26. The composition according to claim 25, wherein said immunomodulatory agent is α-, β-, or γ-interferon or thymosin; said antiviral agent is ribavirin, amantadine, or telbivudine; and said inhibitor of the HCV life cycle is an inhibitor of HCV helicase, polymerase, or metalloprotease.

27. The composition according to claim 25, wherein said cytochrome P450 inhibitor is ritonavir.

* * * * *